(12) United States Patent
Choi et al.

(10) Patent No.: US 11,963,439 B2
(45) Date of Patent: Apr. 16, 2024

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Eun-Joung Choi, Gyeonggi-do (KR); Young-Kwang Kim, Gyeonggi-do (KR); Su-Hyun Lee, Gyeonggi-do (KR); So-Young Jung, Gyeonggi-do (KR); YeJin Jeon, Gyeonggi-do (KR); Hong-Se Oh, Gyeonggi-do (KR); Dong-Hyung Lee, Gyeonggi-do (KR); Jin-Man Kim, Gyeonggi-do (KR); Hyun-Woo Kang, Gyeonggi-do (KR); Mi-Ja Lee, Gyeonggi-do (KR); Hee-Ryong Kang, Gyeonggi-do (KR); Hyo-Nim Shin, Gyeonggi-do (KR); Jeong-Hwan Jeon, Gyeonggi-do (KR); Sang-Hee Cho, Gyeonggi-do (KR)

(73) Assignee: Rohm and Haas Electronic Materials Korea Ltd. (KR)

( * ) Notice: Subject to any disclaimer, the term of this patent is extended or adjusted under 35 U.S.C. 154(b) by 0 days.

(21) Appl. No.: 17/894,700

(22) Filed: Aug. 24, 2022

(65) Prior Publication Data
US 2023/0157156 A1 May 18, 2023

(30) Foreign Application Priority Data

Sep. 1, 2021 (KR) .......................... 10-2021-0116109
Jul. 29, 2022 (KR) .......................... 10-2022-0094454

(51) Int. Cl.
| | | |
|---|---|---|
| C09K 11/06 | (2006.01) |
| C07C 211/61 | (2006.01) |
| C07D 209/08 | (2006.01) |
| C07D 209/86 | (2006.01) |
| C07D 213/38 | (2006.01) |
| C07D 239/26 | (2006.01) |
| C07D 265/38 | (2006.01) |
| C07D 307/79 | (2006.01) |
| C07D 307/91 | (2006.01) |
| C07D 333/76 | (2006.01) |
| C07D 345/00 | (2006.01) |
| C07D 403/14 | (2006.01) |
| C07D 405/14 | (2006.01) |
| C07D 409/14 | (2006.01) |
| C07D 491/048 | (2006.01) |
| C07D 495/04 | (2006.01) |
| H10K 85/60 | (2023.01) |
| H10K 50/15 | (2023.01) |

(52) U.S. Cl.
CPC .......... H10K 85/633 (2023.02); C07C 211/61 (2013.01); C07D 307/91 (2013.01); C07D 345/00 (2013.01); C09K 11/06 (2013.01); H10K 85/636 (2023.02); C07C 2603/18 (2017.05); C07C 2603/52 (2017.05); C09K 2211/1007 (2013.01); C09K 2211/1011 (2013.01); C09K 2211/1014 (2013.01); C09K 2211/1018 (2013.01); H10K 50/156 (2023.02); H10K 85/623 (2023.02); H10K 85/626 (2023.02); H10K 85/657 (2023.02); H10K 85/6574 (2023.02)

(58) Field of Classification Search
CPC ............. H10K 85/6574; H10K 85/657; H10K 85/626; H10K 85/623; H10K 85/633; H10K 85/636; H10K 50/156; H10K 2101/10; H10K 2101/90; C07C 211/61; C07C 2603/18; C07C 2603/52; C07C 2603/26; C07C 2603/42; C07C 2603/48; C07C 2603/94; C07D 307/79; C07D 307/91; C07D 345/00; C07D 403/14; C07D 405/14; C07D 409/14; C07D 491/048; C07D 495/04; C07D 209/08; C07D 209/86; C07D 213/38; C07D 239/26; C07D 265/38; C07D 333/76; C09K 11/06; C09K 2211/1007; C09K 2211/1011; C09K 2211/1014; C09K 2211/1018; C09K 2211/1022; C09K 2211/1088; C09K 2211/1092

See application file for complete search history.

(56) References Cited

U.S. PATENT DOCUMENTS

2021/0269445 A1    9/2021    Kang et al.

FOREIGN PATENT DOCUMENTS

KR    20120116881 A    10/2012

OTHER PUBLICATIONS

Je et al., caplus an 2012:1561061 (2012).*
RN 1409959-13-2, registry database compound (2012).*

* cited by examiner

*Primary Examiner* — Sun Jae Yoo
(74) *Attorney, Agent, or Firm* — G. Creston Campbell

(57) ABSTRACT

The present disclosure relates to an organic electroluminescent compound and an organic electroluminescent device comprising the same. By comprising the compound according to the present disclosure, it is possible to produce an organic electroluminescent device having improved driving voltage, power efficiency, and/or lifetime properties compared to the conventional organic electroluminescent devices.

13 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer (see Appl. Phys. Lett. 51, 913, 1987).

An organic electroluminescent device (OLED) changes electric energy into light by applying electricity to an organic electroluminescent material, and commonly comprises an anode, a cathode, and an organic layer between the two electrodes. The organic layer of the OLED may comprise a hole injection layer, a hole transport layer, a hole auxiliary layer, a light-emitting auxiliary layer, an electron blocking layer, a light-emitting layer, an electron buffer layer, a hole blocking layer, an electron transport layer, an electron injection layer, etc., if necessary. The materials used in the organic layer can be classified into a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc., depending on their functions. In the OLED, holes from the anode and electrons from the cathode are injected into a light-emitting layer by the application of electric voltage, and excitons having high energy are produced by the recombination of the holes and electrons. The organic light-emitting compound moves into an excited state by the energy and emits light from the energy when the organic light-emitting compound returns to the ground state from the excited state.

The selection of the compound comprised in the hole transport layer, etc. has been recognized as a means for improving device properties such as hole transport efficiency to the light-emitting layer, luminous efficiency, and lifetime. Recently, the development of the organic electroluminescent device having high efficiency and long lifetime has emerged as an urgent task. In particular, the development of highly excellent material over conventional light-emitting materials is urgently required, considering the level of EL properties required for medium- and large-sized OLED panels.

Meanwhile, International Patent Publication No. 2019/235725 discloses a compound in which an amino group is attached to a naphthocarbazole derivative. In addition, Korean Patent Application Laid-Open No. 2012-0116881 discloses a compound in which two amino groups are attached to a naphthofluorene derivative. However, the aforementioned references do not specifically disclose that a compound in which one amino group is attached to naphthalene-fused fluoren can improve the performance of an organic electroluminescent device.

DISCLOSURE OF INVENTION

Technical Problem

The objective of the present disclosure is to provide an organic electroluminescent compound effective for producing an organic electroluminescent device having low driving voltage, high power efficiency, and/or improved lifetime properties.

Solution to Problem

The present inventors have found that the above objective can be achieved by an organic electroluminescent compound represented by the following formula 1.

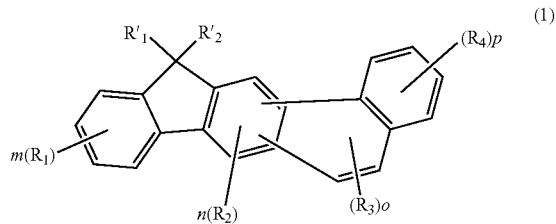

In formula 1, $R'_1$ and $R'_2$, each independently, represent a substituted or unsubstituted (C1-C30)alkyl, a substituted or unsubstituted (C6-C30)aryl, or a substituted or unsubstituted (3- to 30-membered)heteroaryl; or $R'_1$ and $R'_2$ may be linked to each other to form a ring(s), in which $R'_1$ and $R'_2$ may be the same as or different from each other;

$R_1$ to $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or $-L_1$-N—$(Ar_1)(Ar_2)$; or may be linked to an adjacent substituent to form a ring(s);

with the proviso that any one of $R_1$'s to $R_4$'s represents $-L_1$-N—$(Ar_1)(Ar_2)$;

$L_1$ represents a single bond, a substituted or unsubstituted (C6-C30)arylene, or a substituted or unsubstituted (3- to 30-membered)heteroarylene:

$Ar_1$ and $Ar_2$, each independently, represent a substituted or unsubstituted (C1-C30)alkyl, a substituted or unsubstituted (C2-C30)alkenyl, a substituted or unsubstituted fused ring group of a (C3-C30) aliphatic ring(s) and a (C6-C30) aromatic ring(s), a substituted or unsubstituted (C6-C30) aryl, or a substituted or unsubstituted (3- to 30-membered) heteroaryl; and m and p, each independently, represent an integer of 4; n and o, each independently, represent an integer of 2; and each of $R_1$ to each of $R_4$ may be the same or different.

Advantageous Effects of Invention

The organic electroluminescent compound according to the present disclosure is possible to provide an organic electroluminescent device having low driving voltage, high power efficiency, and/or improved lifetime properties.

MODE FOR THE INVENTION

Hereinafter, the present disclosure will be described in detail. However, the following description is intended to explain the disclosure, and is not meant in any way to restrict the scope of the disclosure.

The term "an organic electroluminescent compound" in the present disclosure means a compound that may be used in an organic electroluminescent device. If necessary, the organic electroluminescent compound may be comprised in any layers constituting an organic electroluminescent device.

The term "an organic electroluminescent material" in the present disclosure means a material that may be used in an organic electroluminescent device, and may comprise at least one compound. If necessary, the organic electroluminescent material may be comprised in any layers constituting an organic electroluminescent device. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

Herein, the term "(C1-C30)alkyl" is meant to be a linear or branched alkyl having 1 to 30 carbon atoms constituting the chain, in which the number of carbon atoms is preferably 1 to 10, and more preferably 1 to 6. The above alkyl may include methyl, ethyl, n-propyl, isopropyl, n-butyl, isobutyl, tert-butyl, sec-butyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered)heterocycloalkyl" is meant to be a cycloalkyl having 3 to 7 ring backbone atoms, and including at least one heteroatom selected from the group consisting of B, N, O, S, Si, P, Te, and Se, and preferably the group consisting of O, S, N, Te, and Se. The above heterocycloalkyl may include tetrahydrofuran, pyrrolidine, thiolan, tetrahydropyran, etc. The term "(C6-C30)aryl" or "(C6-C30)arylene" is meant to be a monocyclic or fused ring radical derived from an aromatic hydrocarbon having 6 to 30 ring backbone carbon atoms. The above aryl(ene) may be partially saturated, and may comprise a spiro structure. The above aryl may include phenyl, biphenyl, terphenyl, naphthyl, binaphthyl, phenylnaphthyl, naphthylphenyl, fluorenyl, phenylfluorenyl, diphenylfluorenyl, benzofluorenyl, dibenzofluorenyl, phenanthrenyl, phenylphenanthrenyl, benzophenanthrenyl, anthracenyl, indenyl, triphenylenyl, pyrenyl, tetracenyl, perylenyl, chrysenyl, naphthacenyl, fluoranthenyl, spirobifluorenyl, spiro[fluorene-benzofluoren]yl, spiro[cyclopentenfluoren]yl, spiro[dihydroinden-fluoren]yl, azulenyl, tetramethyldihydrophenanthrenyl, etc. Specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-tert-butylphenyl, p-(2-phenylpropyl)phenyl, 4'-methylbiphenyl, 4"-tert-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered)heteroaryl" or "(3- to 30-membered)heteroarylene" in the present disclosure is meant to be an aryl(ene) having 3 to 30 ring backbone atoms and including at least one heteroatom(s) selected from the group consisting of B, N, O, S, Si, P, Te, and Se. The number of heteroatoms is preferably 1 to 4. The above heteroaryl (ene) may be a monocyclic ring or a fused ring condensed with at least one benzene ring; may be partially saturated; may be one formed by linking at least one heteroaryl or aryl group to a heteroaryl(ene) group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolyl, benzofuroquinazolinyl, benzofuronaphthyridinyl, benzofuropyrimidinyl, naphthofuropyrimidinyl, benzothienoquinolyl, benzothienoquinazolinyl, naphthyridinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, benzoquinazolinyl, quinoxalinyl, benzoquinoxalinyl, carbazolyl, benzocarbazolyl, dibenzocarbazolyl, phenoxazinyl, phenanthridinyl, benzodioxolyl, dihydroacridinyl, benzotriazolyl, phenazinyl, imidazopyridyl, chromenoquinazolinyl, thiochromenoquinazolinyl, dimethylbenzoperimidinyl, indolocarbazolyl, indenocarbazolyl, etc. More specifically, the heteroaryl may include 1-pyrrolyl, 2-pyrrolyl, 3-pyrrolyl, pyrazinyl, 2-pyridyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridyl, 3-imidazopyridyl, 5-imidazopyridyl, 6-imidazopyridyl, 7-imidazopyridyl, 8-imidazopyridyl, 3-pyridyl, 4-pyridyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-tert-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-tert-butyl-1-indolyl, 4-tert-butyl-1-indolyl, 2-tert-butyl-3-indolyl, 4-tert-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. In the present disclosure, the term "halogen" includes F, Cl, Br, and I.

In addition, "ortho (o-)," "meta (m-)," and "para (p-)" are prefixes, which represent the relative positions of substituents respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent, and also includes that the hydrogen atom is replaced with a group formed by a linkage of two or more substituents of the above substituents. For example, the "group formed by a linkage of two or more substituents" may be pyridine-triazine. That is, pyridine-triazine may be interpreted as a heteroaryl substituent, or as substituents in which two heteroaryl substituents are linked. Herein, the substituent(s) of the substituted alkyl, the substituted alkenyl, the substituted alkynyl, the substituted aryl, the substituted arylene, the substituted heteroaryl, the substituted heteroarylene, the substituted cycloalkyl, the substituted alkoxy, the substituted trialkylsilyl, the substituted dialkylarylsilyl, the substituted alkyldiarylsilyl, the substituted triarylsilyl, the substituted fused ring group of an aliphatic ring(s) and an aromatic ring(s), the substituted alkylarylamino, the substituted mono- or di-alkylamino, the substituted mono- or di-arylamino, the substituted mono- or di-heteroarylamino, and the substituted arylheteroarylamino, each independently, are at least one selected from the group consisting of deuterium; a halogen; a cyano; a carboxyl; a nitro; a hydroxyl; a phosphineoxide; a (C1-C30)alkyl; a halo(C1-C30)alkyl; a (C2-C30)alkenyl unsubstituted or substituted with a (C6-C30)aryl(s); a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with at least one of deuterium and a (C6-C30)aryl(s); a (C6-C30)aryl unsubstituted or substituted with at least one of deuterium, a halogen(s), a cyano(s), a (C1-C30)alkyl(s), a (C6-C30)aryl(s), (3- to 30-membered) heteroaryl(s), a tri(C6-C30)arylsilyl(s), and a tri(C6-C30) arylgermanyl(s); a tri(C1-C30)alkylsilyl; a tri(C6-C30)arylsilyl; a di(C1-C30)alkyl(C6-C30)arylsilyl; a (C1-C30) alkyldi(C6-C30)arylsilyl; a tri(C1-C30)alkylgermanyl; a tri (C6-C30)arylgermanyl; a di(C1-C30)alkyl(C6-C30) arylgermanyl; a (C1-C30)alkyldi(C6-C30)arylgermanyl; a fused ring group of a (C3-C30) aliphatic ring(s) and a (C6-C30) aromatic ring(s); an amino; a mono- or di-(C1-C30)alkylamino; a mono- or di-(C2-C30)alkenylamino; a mono- or di-(C6-C30)arylamino unsubstituted or substituted with a (C1-C30)alkyl(s); a mono- or di-(3- to 30-membered) heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30) alkoxycarbonyl; a (C6-C30)arylcarbonyl; a (C6-C30) arylphosphinyl; a di(C6-C30)arylboronyl; a di(C1-C30) alkylboronyl; a (C1-C30)alkyl(C6-C30)arylboronyl; a (C6-C30)aryl(C1-C30)alkyl; and a (C1-C30)alkyl(C6-C30)aryl, or the combination thereof. According to one embodiment of the present disclosure, the substituent(s), each independently, are at least one selected from the group consisting of deuterium; a halogen; a cyano; a (C1-C20)alkyl; a (C2-C20) alkenyl unsubstituted or substituted with a (C6-C25)aryl(s); a (C6-C25)aryl unsubstituted or substituted with at least one of deuterium, a halogen(s), a cyano(s), a (C1-C20)alkyl(s), a (C6-C25)aryl(s), a (5- to 20-membered)heteroaryl(s), a tri(C6-C18)arylsilyl(s), and a tri(C6-C18)arylgermanyl(s); a (5- to 25-membered)heteroaryl unsubstituted or substituted with at least one of deuterium and a (C6-C25)aryl(s); a tri(C6-C18)arylsilyl; a tri(C6-C18)arylgermanyl; and a (C6-C25)aryl(C1-C20)alkyl. According to another embodiment of the present disclosure, the substituent(s), each independently, are at least one selected from the group consisting of deuterium; a cyano; a (C1-C10)alkyl; a (C2-C10)alkenyl unsubstituted or substituted with a (C6-C18)aryl(s); a (C6-C25)aryl unsubstituted or substituted with at least one of deuterium, a halogen(s), a cyano(s), a (C1-C10)alkyl(s), a (C6-C18)aryl(s), (5- to 20-membered)heteroaryl(s), a tri (C6-C18)arylsilyl(s), and a tri(C6-C18)arylgermanyl(s); a (5- to 20-membered)heteroaryl unsubstituted or substituted with at least one of deuterium and a (C6-C18)aryl(s); a tri(C6-C18)arylsilyl; a tri(C6-C18)arylgermanyl; and a (C6-C18)aryl(C1-C10)alkyl. For example, the substituent(s), each independently, may be any one selected from the group consisting of deuterium, a cyano, a methyl, a tert-butyl, a ethylene substituted with a phenyl(s), a substituted or unsubstituted phenyl, a substituted or unsubstituted naphthyl, a biphenyl; a phenanthrenyl, a terphenyl, a chrysenyl, a benzo [c]phenanthryl, a triphenylenyl, a dimethylfluorenyl, a diphenylfluorenyl, a dimethylbenzofluorenyl, a spirobifluorenyl, a pyridyl, a pyrimidinyl, a triazinyl substituted with a phenyl(s), an indolyl, a dibenzofuranyl unsubstituted or substituted with at least one of deuterium and a phenyl(s), a dibenzothiophenyl, a carbazolyl unsubstituted or substituted with at least one of a phenyl(s) and a biphenyl(s), a phenylpropyl, a dibenzotelluriumyl, a dibenzoselenophenyl, a benzonaphthofuranyl, a benzonaphthothiophenyl, a phenanthrooxazolyl substituted with a phenyl(s), a triphenylsilyl, and a triphenylgermanyl, or the combination thereof. The substituent(s) of the substituted phenyl may be at least one selected from the group consisting of deuterium, a cyano, a fluoro, a methyl, a naphthyl, a carbazolyl, a triphenylsilyl, a triphenylgermanyl, and a dibenzotellurumyl. The substituent(s) of the substituted naphthyl may be at least one selected from the group consisting of a phenyl, a biphenyl, and a chrysenyl.

Herein, a ring formed by a linkage of adjacent substituents means that at least two adjacent substituents are linked to or fused with each other to form a substituted or unsubstituted, mono- or polycyclic, (3- to 30-membered) alicyclic or aromatic ring, or the combination thereof. Preferably, the ring may be a substituted or unsubstituted, mono- or polycyclic, (3- to 26-membered) alicyclic or aromatic ring, or the combination thereof. More preferably, the ring may be a mono- or polycyclic, (5- to 25-membered) aromatic ring unsubstituted or substituted with at least one of a (C1-C6) alkyl(s), a (C6-C18)aryl(s) and a (3- to 20-membered) heteroaryl(s). In addition, the formed ring may contain at least one heteroatom selected from B, N, O, S, Si, P, Te, and Se, and preferably at least one heteroatom selected from N, O, S, Te, and Se. For example, the ring may be a benzene ring, a cyclopentane ring, an indene ring, an indane ring, a fluorene ring, a phenanthrene ring, an indole ring, a benzofuran ring unsubstituted or substituted with a phenyl(s), a benzothiophene ring unsubstituted or substituted with a phenyl(s), a xanthene ring, etc. The ring may also form a spiro ring(s).

Herein, heteroaryl, heteroarylene, and heterocycloalkyl, each independently, may contain at least one heteroatom selected from the group consisting of B, N, O, S, Si, P, Te, and Se. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, and a substituted or unsubstituted (C6-C30)aryl(3- to 30-membered)heteroarylamino.

In formula 1, $R'_1$ and $R'_2$, each independently, represent a substituted or unsubstituted (C1-C30)alkyl, a substituted or unsubstituted (C6-C30)aryl, or a substituted or unsubstituted (3- to 30-membered)heteroaryl; or $R'_1$ and $R'_2$ may be linked to each other to form a ring(s). $R'_1$ and $R'_2$ may be the same as or different from each other. According to one embodiment of the present disclosure, $R'_1$ and $R'_2$, each independently, represent a substituted or unsubstituted (C1-C20)alkyl, a substituted or unsubstituted (C6-C25)aryl, or a substituted or unsubstituted (5- to 25-membered)heteroaryl; or $R'_1$ and $R'_2$ may be linked to each other to form a ring(s). According to another embodiment of the present disclosure, $R'_1$ and $R'_2$, each independently, represent an unsubstituted (C1-C10)alkyl, an unsubstituted (C6-C18)aryl, or an unsubstituted (5- to 20-membered)heteroaryl; or $R'_1$ and $R'_2$ may be linked to each other to form a spiro ring. For example, $R'_1$ and $R'_2$, each independently, represent a methyl, an ethyl, a propyl, a phenyl, a naphthyl, a pyridyl, etc.; or $R'_1$ and $R'_2$ may be linked to each other to form a spirofluorene ring or a spiroindane ring, etc.

In formula 1, m and p, each independently, represent an integer of 4; n and o, each independently, represent an integer of 2; and each of $R_1$ to each of $R_4$ may be the same or different.

In formula 1, $R_1$ to $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or -$L_1$-N—(Ar$_1$)(Ar$_2$); or may be linked to an adjacent substituent to form a ring(s); with the proviso that any one of $R_1$'s to $R_4$'s represents -$L_1$-N—(Ar$_1$)(Ar$_2$). According to one embodiment of the present disclosure, $R_1$ to $R_4$, each independently, represent hydrogen, or -$L_1$-N—(Ar$_1$)(Ar$_2$).

$L_1$ represents a single bond, a substituted or unsubstituted (C6-C30)arylene, or a substituted or unsubstituted (3- to 30-membered)heteroarylene. According to one embodiment of the present disclosure, $L_1$ represents a single bond, a substituted or unsubstituted (C6-C25)arylene, or a substituted or unsubstituted (5- to 25-membered)heteroarylene. According to another embodiment of the present disclosure, $L_1$ represents a single bond, a (C6-C18)arylene unsubstituted or substituted with a (C6-C18)aryl(s), or an unsubstituted (5- to 20-membered)heteroarylene. For example, $L_1$ may be a single bond, a phenylene unsubstituted or substituted with a phenyl(s), a naphthylene, a biphenylene, a dibenzothiophenylene, a dibenzofuranylene, etc.

Ar$_1$ and Ar$_2$, each independently, represent a substituted or unsubstituted (C1-C30)alkyl, a substituted or unsubstituted (C2-C30)alkenyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl. Ar$_1$ and Ar$_2$ may be the same or different. According to one embodiment of the present disclosure, Ar$_1$ and Ar$_2$, each independently, represent a substituted or unsubstituted (C6-C25)aryl, or a substituted or unsubstituted (5- to 25-membered)heteroaryl. According to another embodiment of the present disclosure, Ar$_1$ and Ar$_2$, each independently, represent a substituted or unsubstituted (C6-C24)aryl, or a (5- to 20-membered)heteroaryl unsubstituted or substituted with a (C6-C18)aryl(s). The substituent(s) of the substituted aryl may be any one selected from the group consisting of a (C1-C10)alkyl, a (C2-C10)alkenyl, a (C6-C18)aryl, a (5- to 15-membered)heteroaryl, and a (C6-C18)aryl(C1-C10)alkyl; or the combination thereof. For example, Ar$_1$ and Ar$_2$, each independently, may be a substituted or unsubstituted phenyl, a naphthyl, a phenylnaphthyl, a naphthylphenyl, a biphenyl, a phenanthrenyl, a terphenyl, a quaterphenyl, a triphenylenyl, a chrysenyl, a dimethylfluorenyl, a diphenylfluorenyl, a benzofuranyl, a benzothiophenyl, a dibenzofuranyl unsubstituted or substituted with a phenyl(s), a dibenzothiophenyl unsubstituted or substituted with a phenyl(s), a dibenzoselenophenyl unsubstituted or substituted with a phenyl(s), a phenylcarbazolyl, a phenoxazinyl substituted with a phenyl(s), etc. The substituent(s) of the phenyl may be at least one selected from the group consisting of a methyl, a tert-butyl, a triphenylethylenyl, a dimethylfluorenyl, a dibenzofuranyl, a dibenzothiophenyl, an indolyl, a pyridyl, a pyrimidinyl, a carbazolyl, and a phenylpropyl, etc.

The formula 1 may be represented by the following formula 1-1.

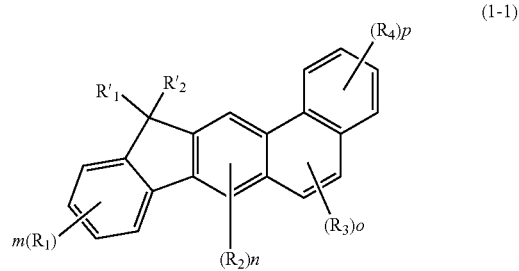

(1-1)

In formula 1-1, $R'_1$, $R'_2$, $R_1$ to $R_4$, and m to p are as defined in formula 1 above.

The formula 1 may be represented by any one of the following formulas 1-1-1 to 1-1-4.

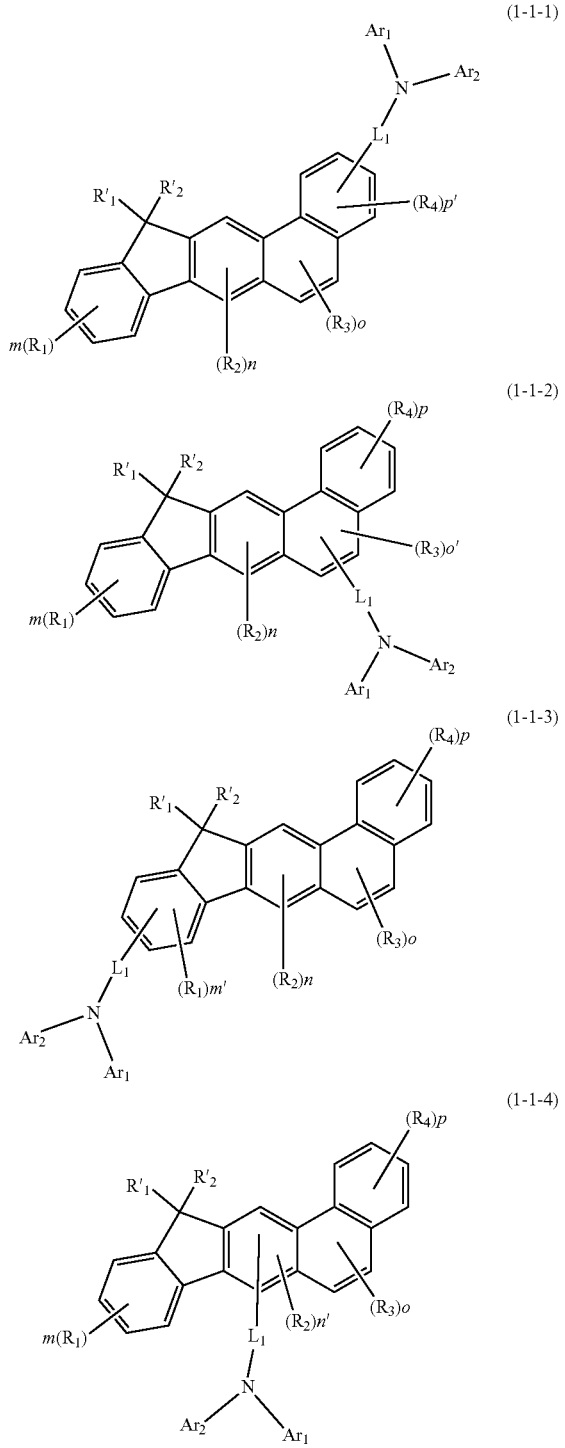

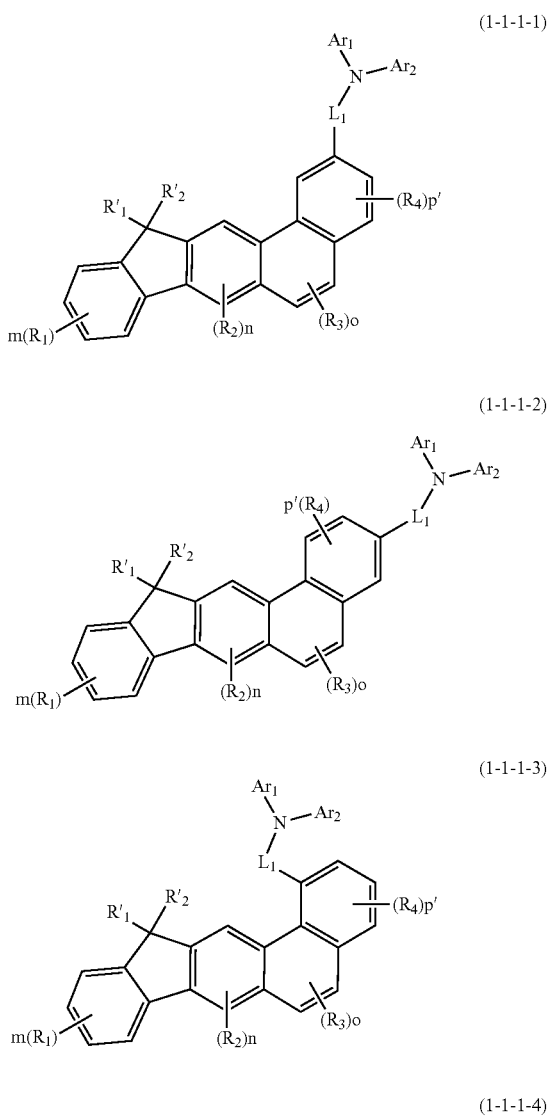

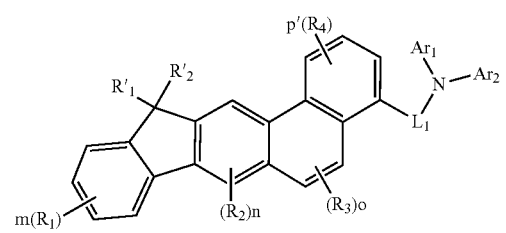

tuted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl (C6-C30)arylsilyl, a substituted or unsubstituted (C1-C30)alkyldi(C6-C30)arylsilyl, a substituted or unsubstituted tri(C6-C30)arylsilyl, or a substituted or unsubstituted fused ring group of a (C3-C30) aliphatic ring(s) and a (C6-C30) aromatic ring(s); or may be linked to an adjacent substituent to form a ring(s). For example, $R_1$ to $R_4$ may be hydrogen.

The formula 1 may be represented by any one of the following formulas 1-1-1-1 to 1-1-1-12.

In formulas 1-1-1 to 1-1-4, $R'_1$, $R'_2$, $L_1$, $Ar_1$, $Ar_2$, and m to p are as defined in formula 1 above.

In formulas 1-1-1 to 1-14, m' and p', each independently, represent an integer of 3; and n' and o', each independently, represent an integer of 1.

In formulas 1-1-1 to 1-14, $R_1$ to $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubsti-

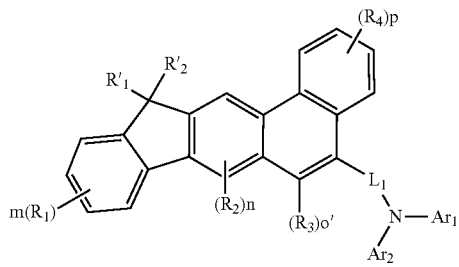
(1-1-1-5)

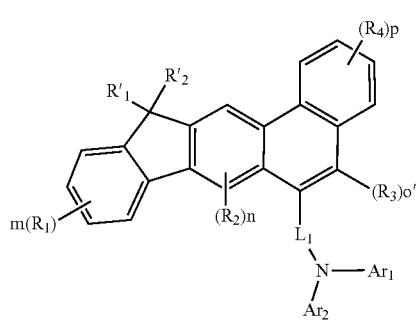
(1-1-1-6)

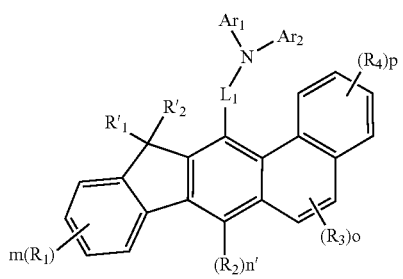
(1-1-1-7)

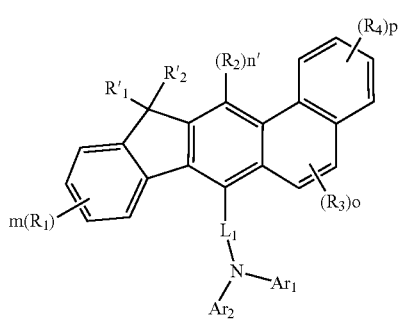
(1-1-1-8)

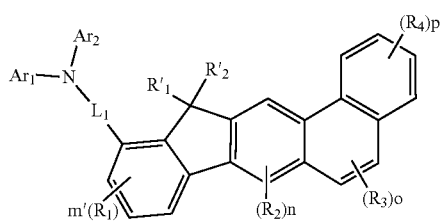
(1-1-1-9)

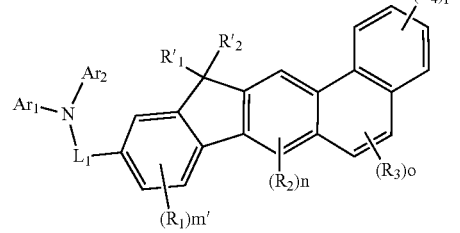
(1-1-1-10)

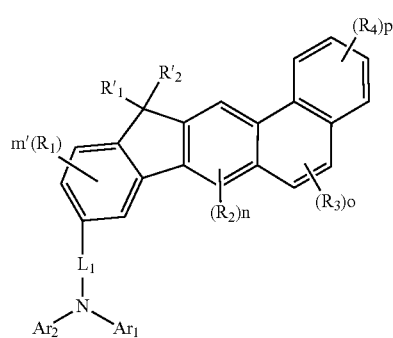
(1-1-1-11)

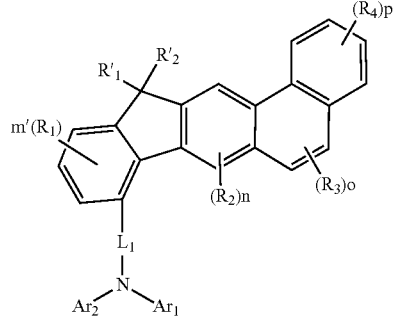
(1-1-1-12)

In formulas 1-1-1-1 to 1-1-1-12, $R'_1$, $R'_2$, $L_1$, $Ar_1$, $Ar_2$, and m to p are as defined in formula 1 above.

In formulas 1-1-1-1 to 1-1-1-12, m' and p', each independently, represent an integer of 3; and n' and o', each independently, represent an integer of 1.

In formulas 1-1-1-1 to 1-1-1-12, $R_1$ to $R_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl (C6-C30)arylsilyl, a substituted or unsubstituted (C1-C30)alkyldi(C6-C30)arylsilyl, a substituted or unsubstituted tri (C6-C30)arylsilyl, or a substituted or unsubstituted fused ring group of a (C3-C30) aliphatic ring(s) and a (C6-C30) aromatic ring(s); or may be linked to an adjacent substituent to form a ring(s). For example, $R_1$ to $R_4$ may be hydrogen.

The compound represented by formula 1 may be at least one selected from the group consisting of the following compounds, but is not limited thereto.

C-1
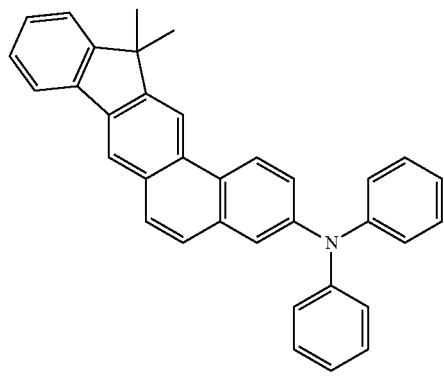
C-2
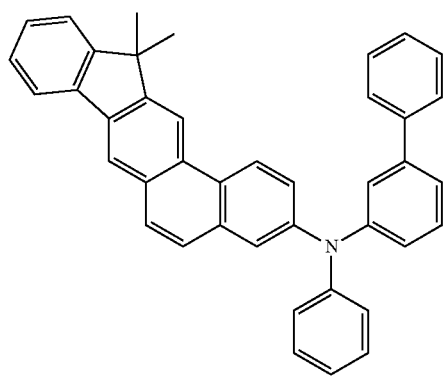
C-3
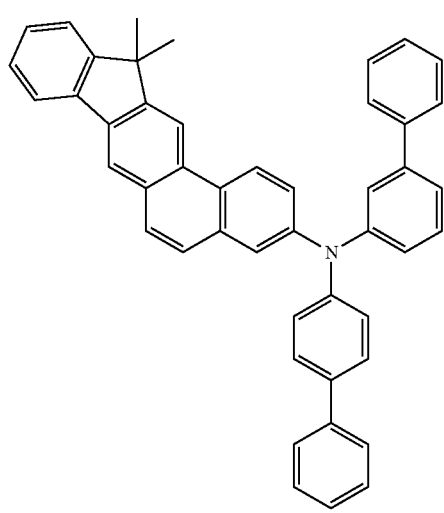
C-4
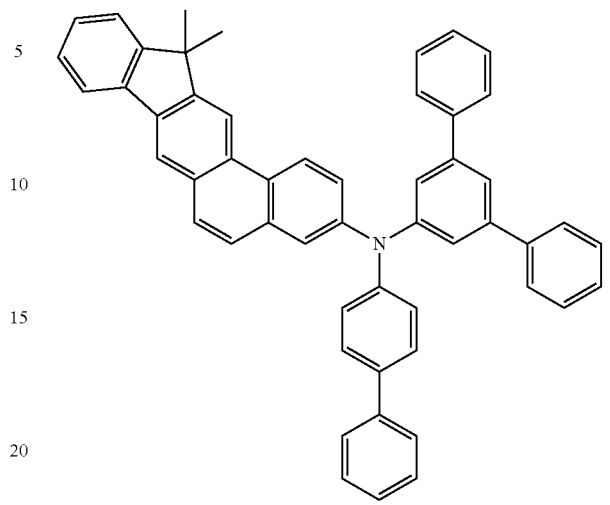
C-5
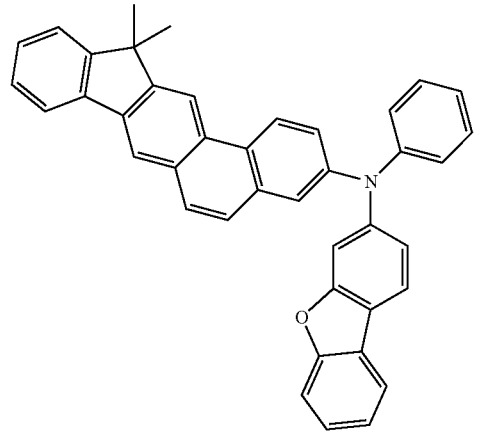
C-6
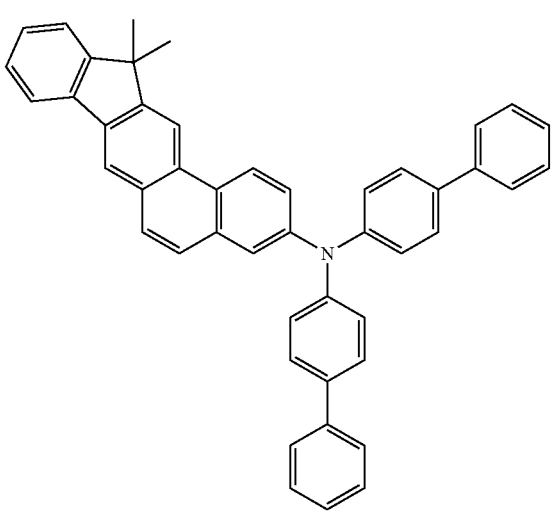

C-7
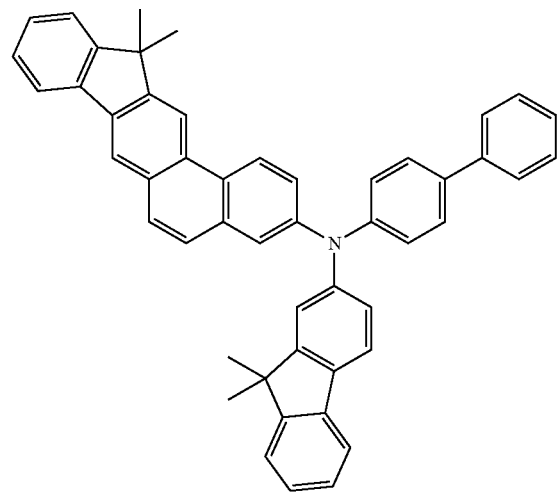
C-8
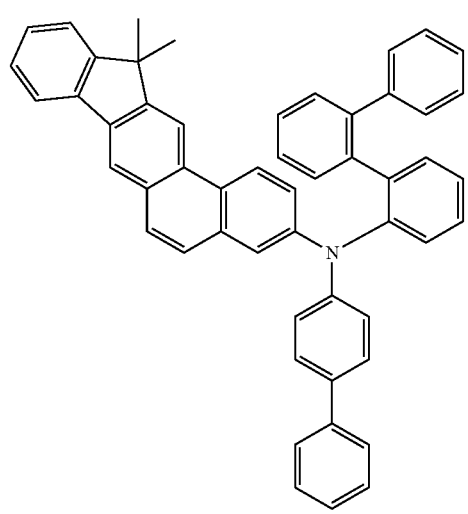
C-9
C-10
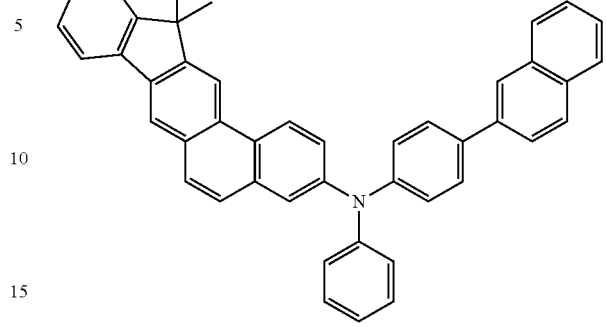
C-11
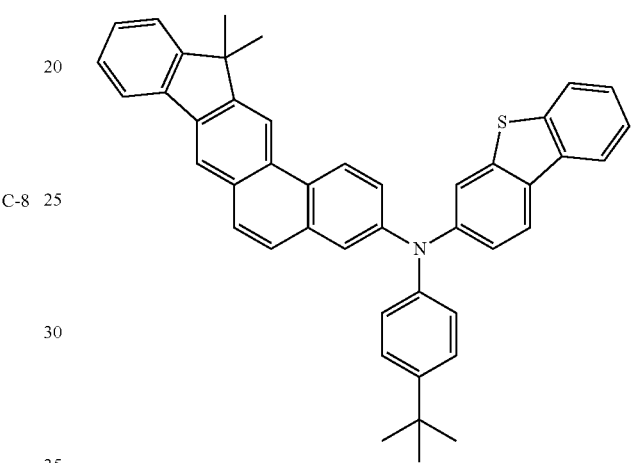
C-12
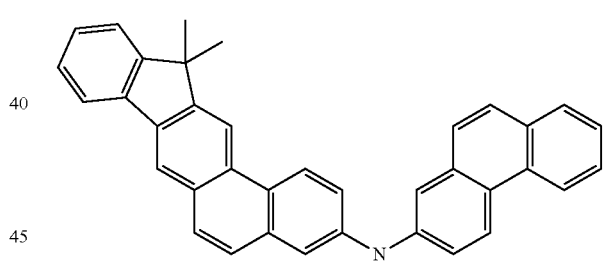
C-13
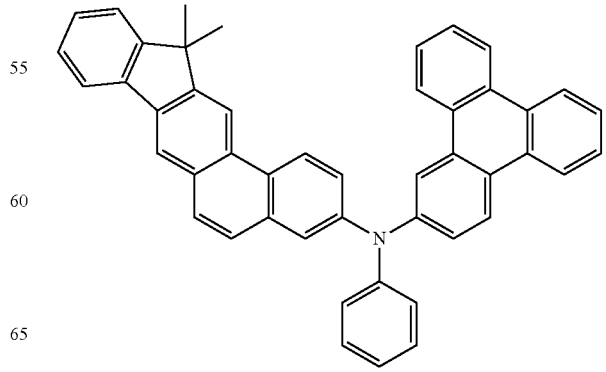

-continued
C-14
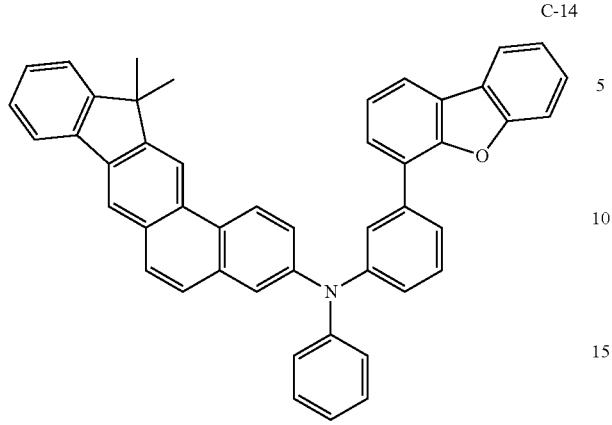
C-15
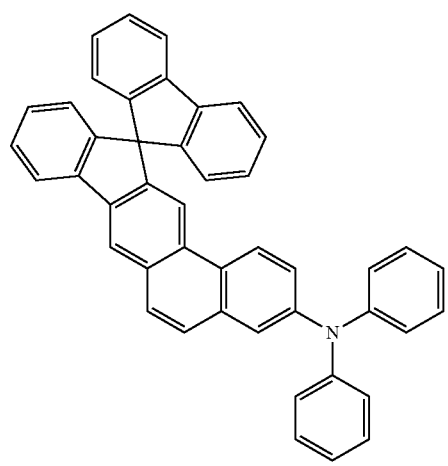
C-16
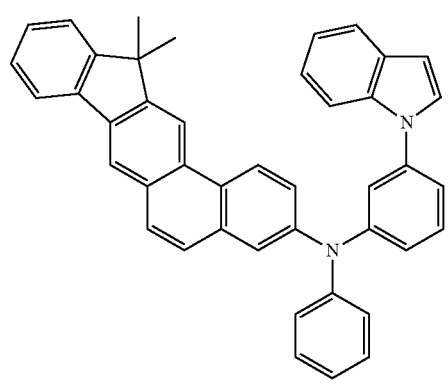
C-17
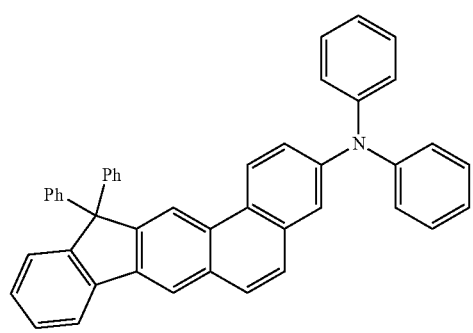
-continued
C-18
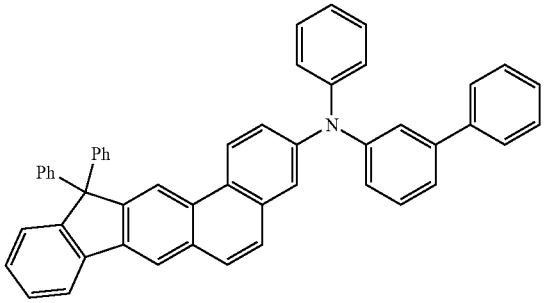
C-19
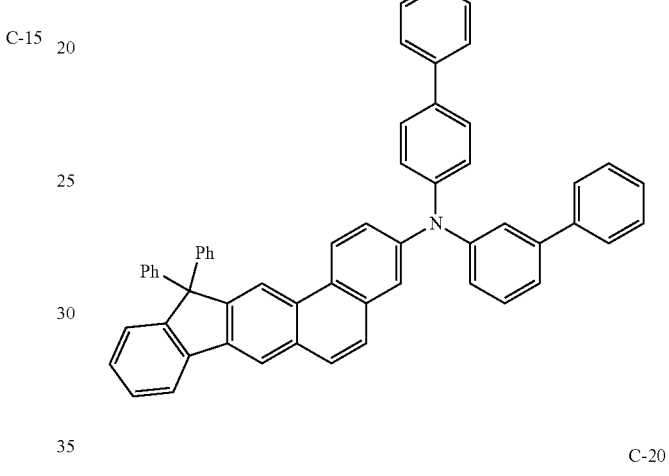
C-20
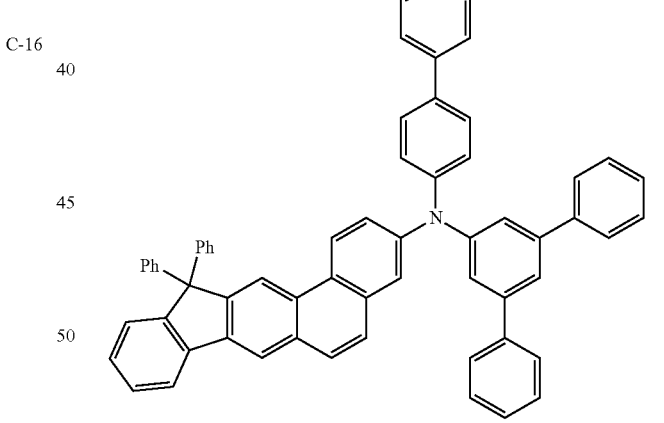
C-21
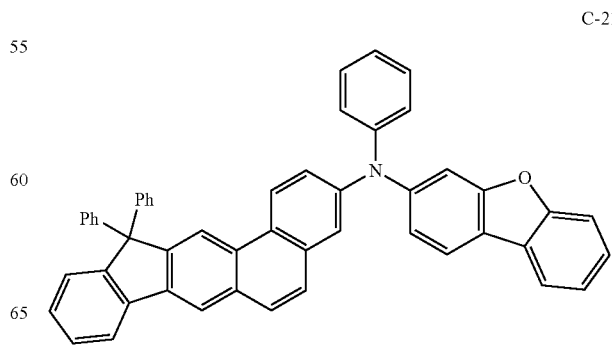

C-22
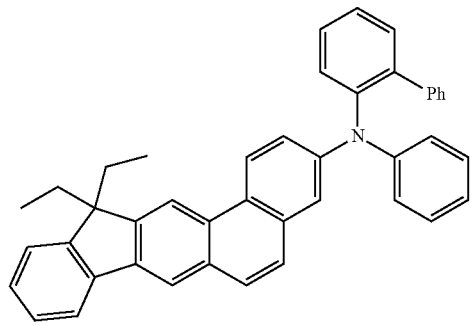
C-23
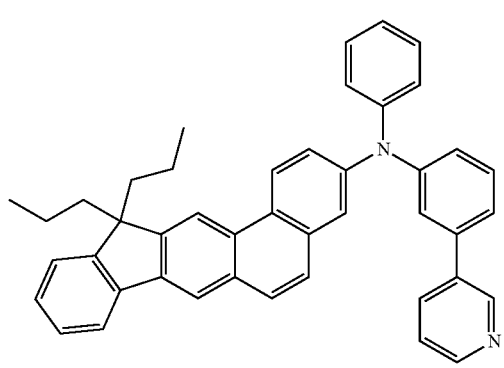
C-24
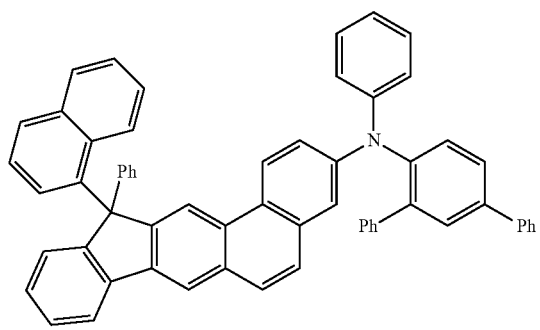
C-25
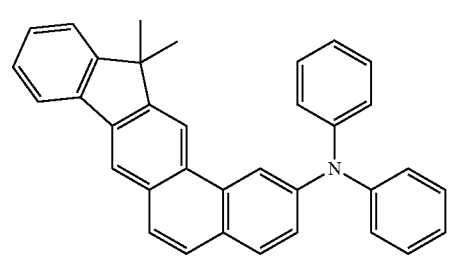
C-26
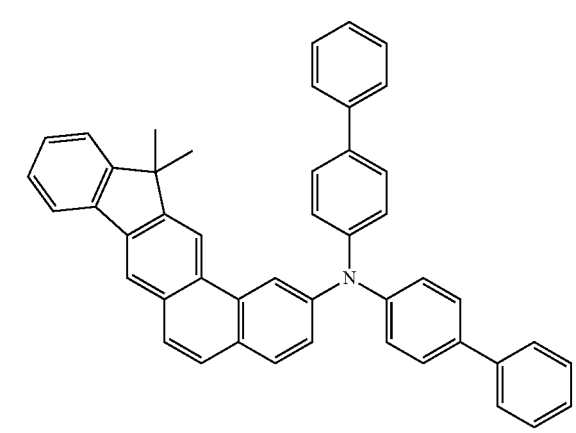
C-27
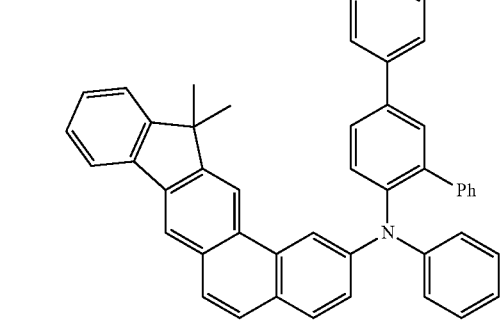
C-28
C-29
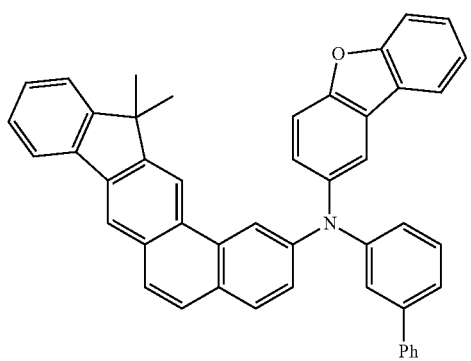

C-30 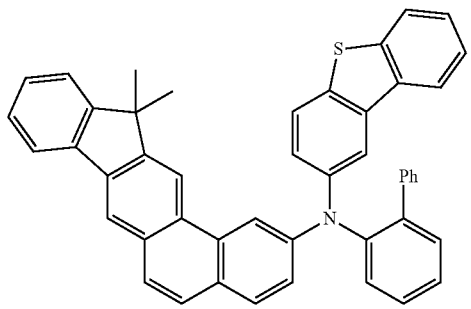
C-31 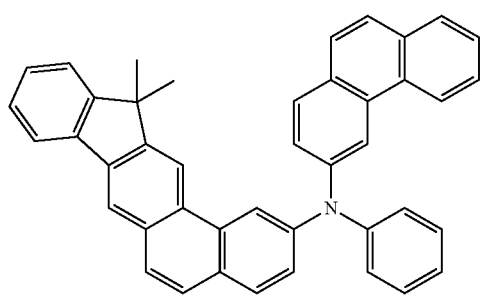
C-32 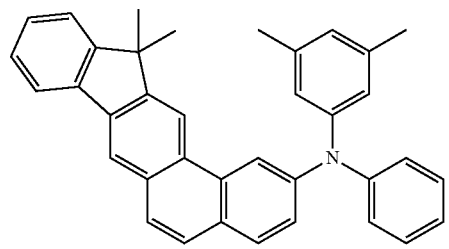
C-33 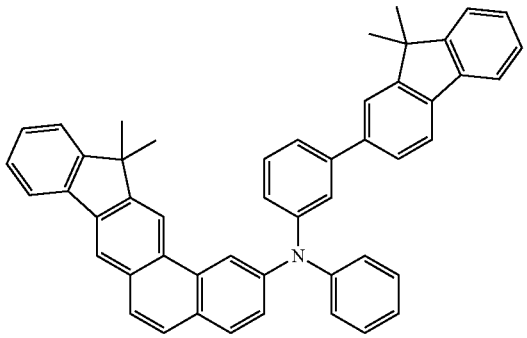
C-34 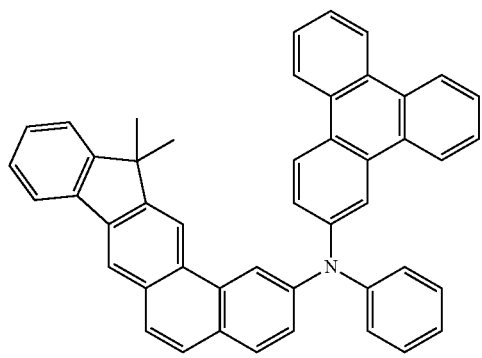
C-35 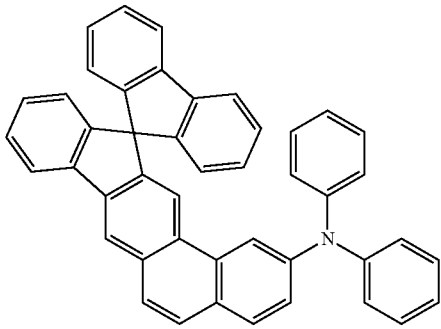
C-36 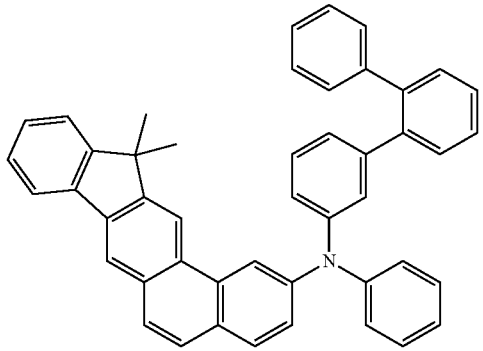
C-37 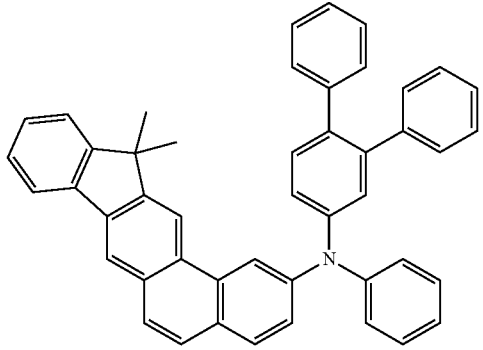
C-38 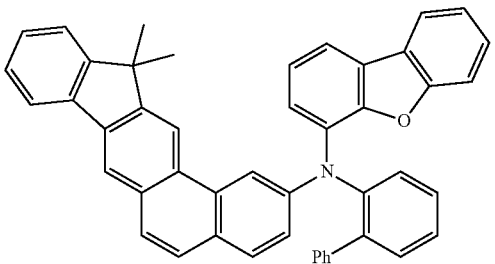

C-39
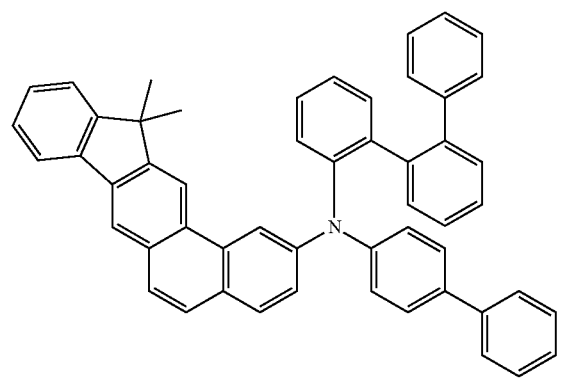
C-40
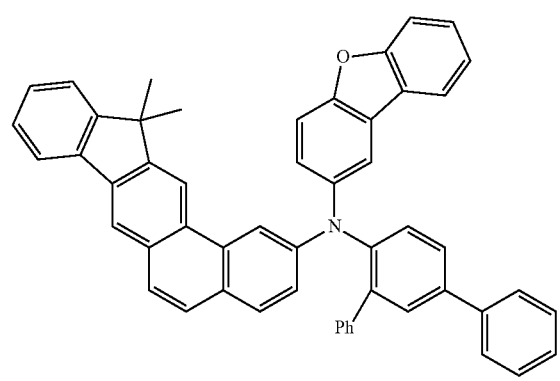
C-41
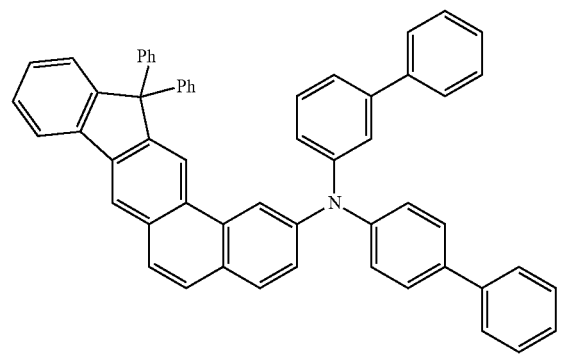
C-42
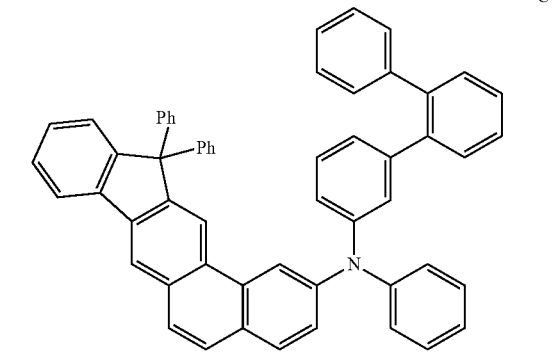
C-43
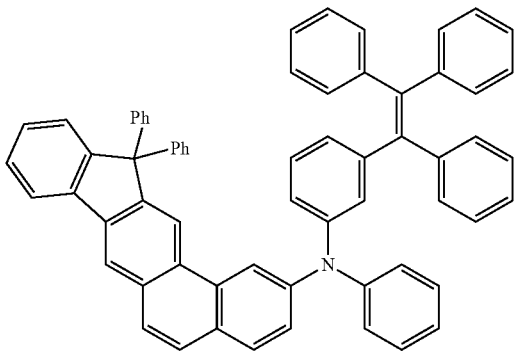
C-44
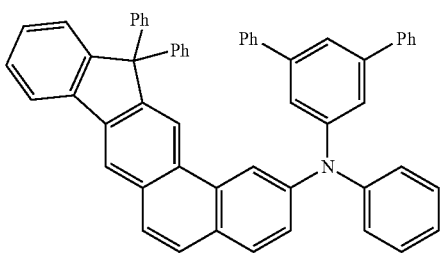
C-45
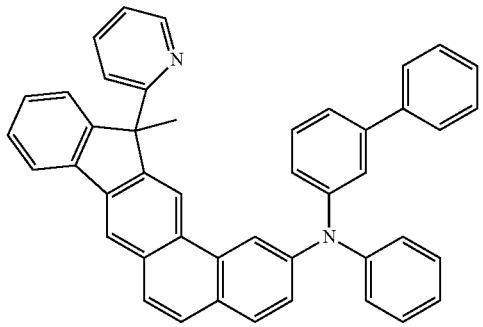
C-46
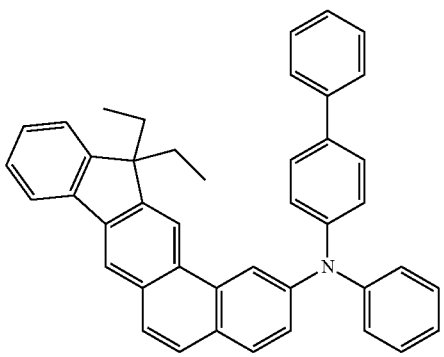

C-47
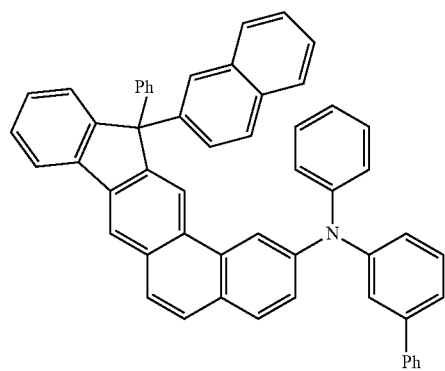
C-48
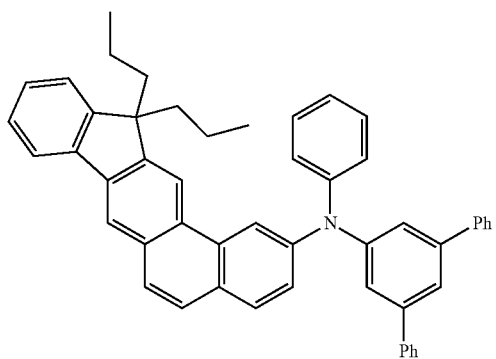
C-49
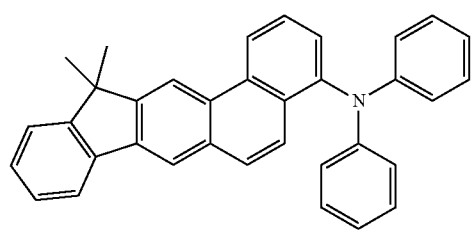
C-50
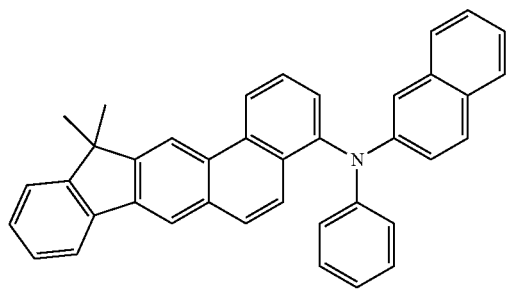
C-51
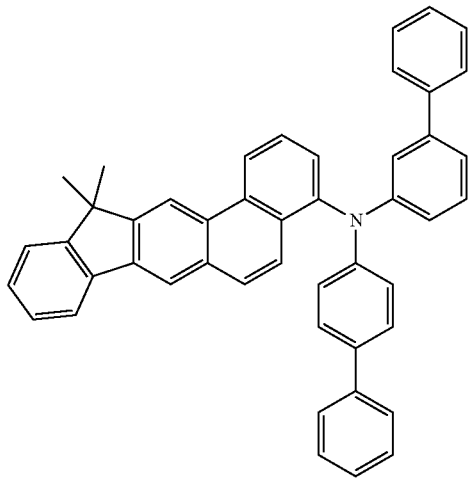
C-52
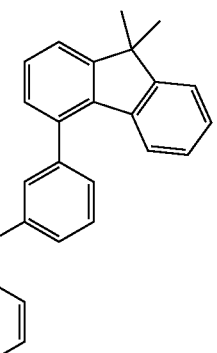
C-53
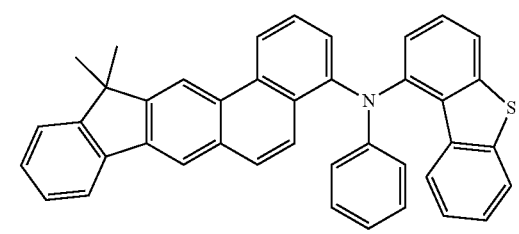
C-54
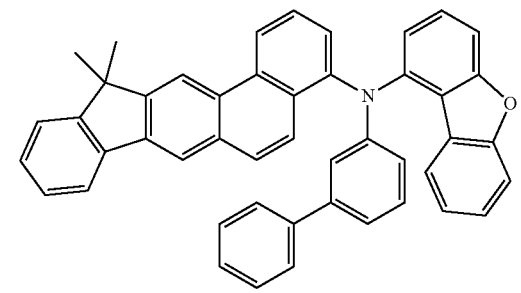

C-55
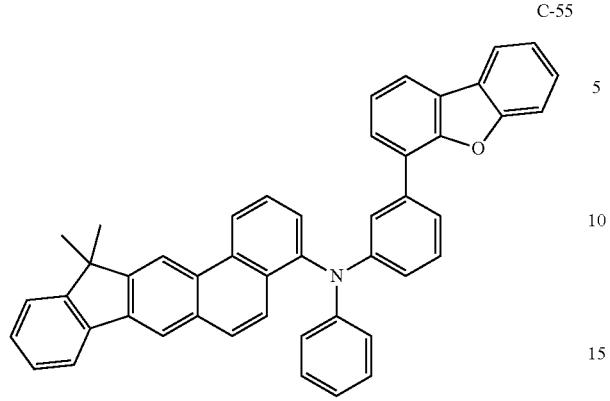
C-56
C-59
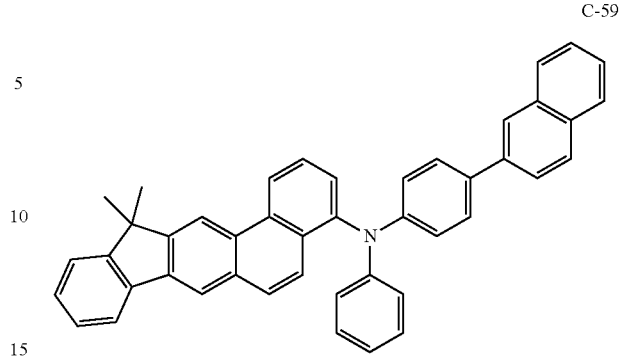
C-57
C-60
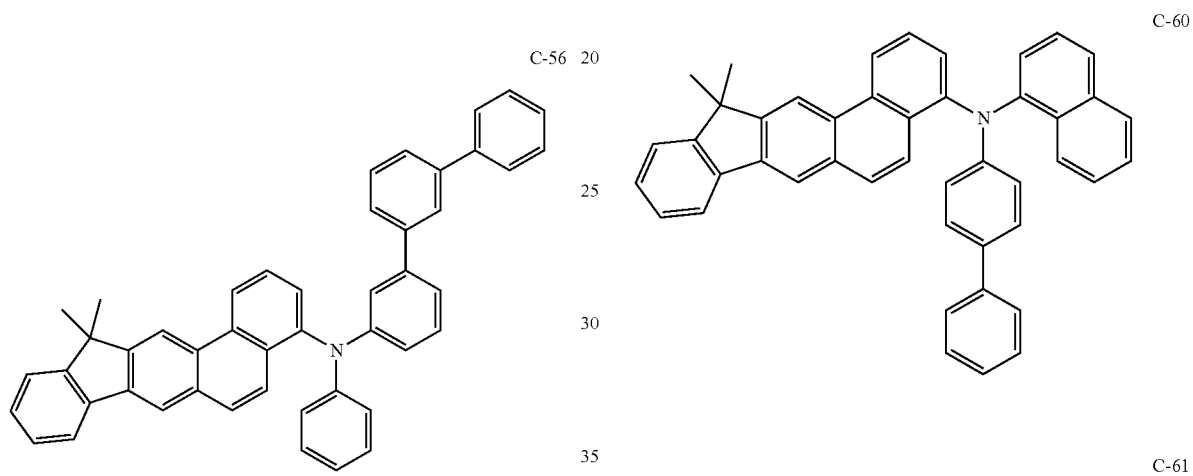
C-58
C-61
C-62
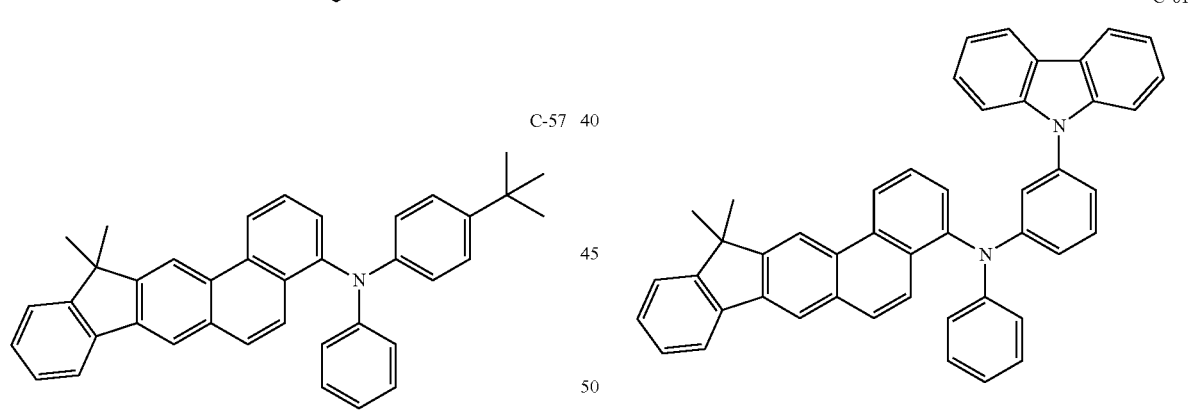
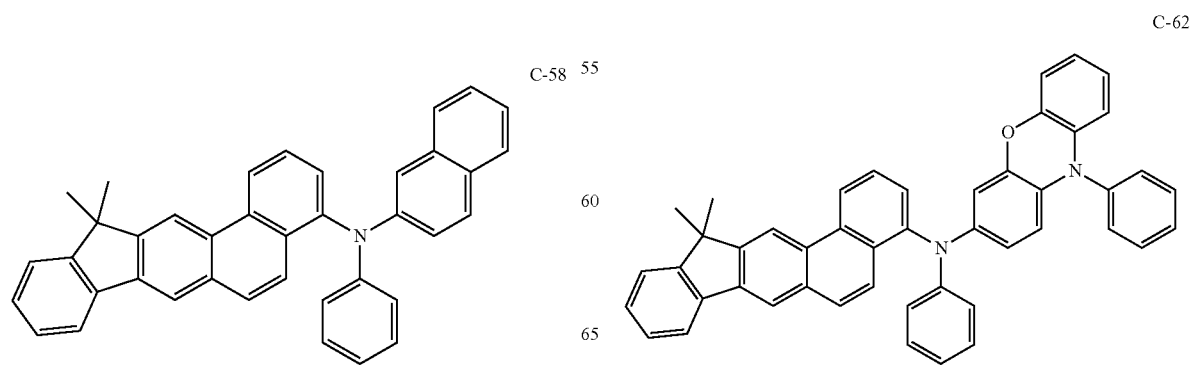

C-63
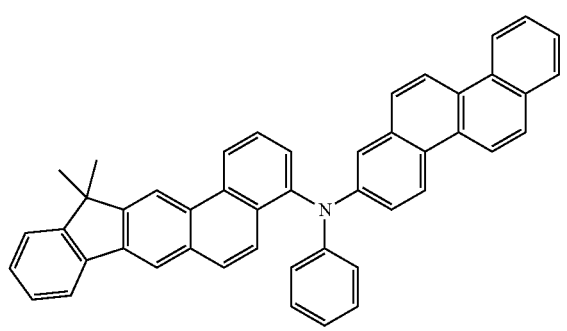
C-64
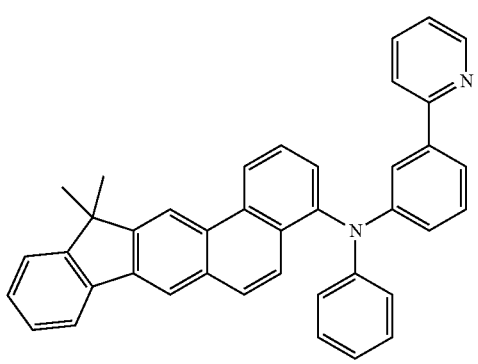
C-65
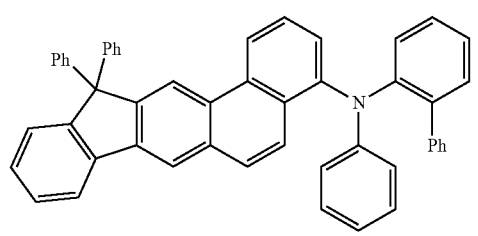
C-66
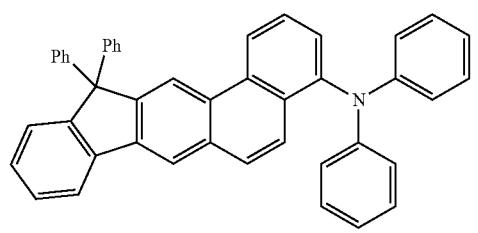
C-67

C-68
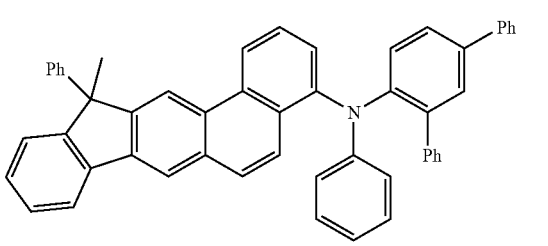
C-69
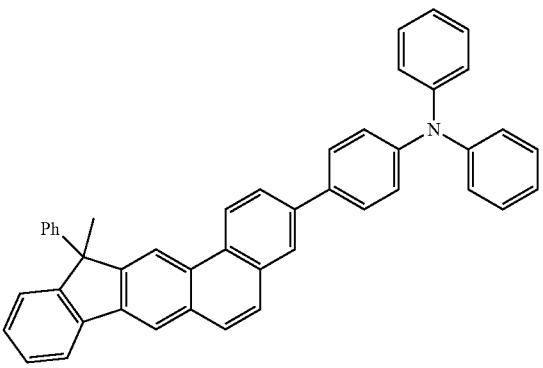
C-70
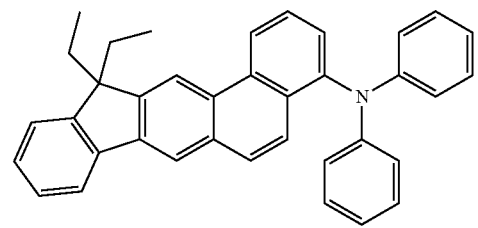
C-71
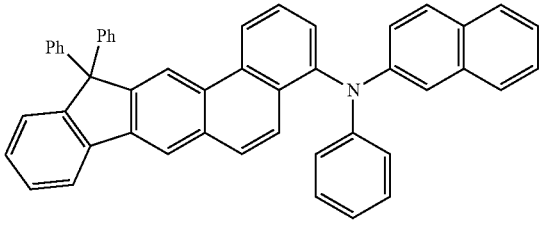
C-72
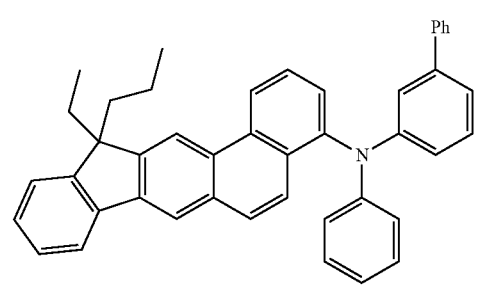

C-73
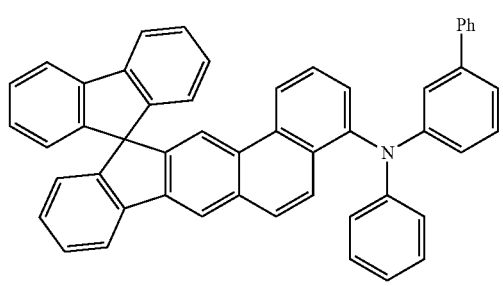
C-74
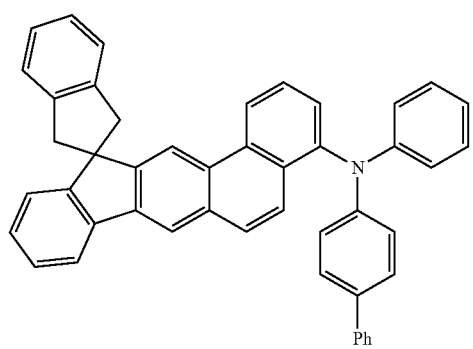
C-75
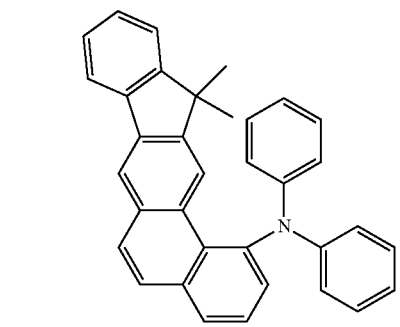
C-76
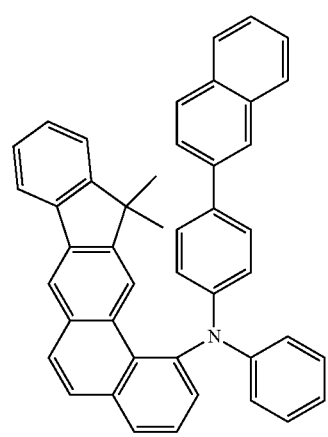
C-77
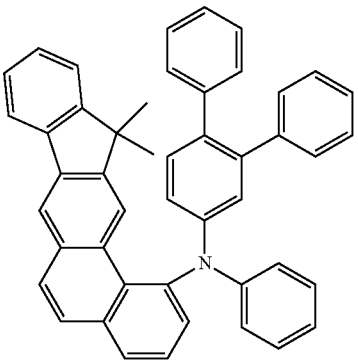
C-78
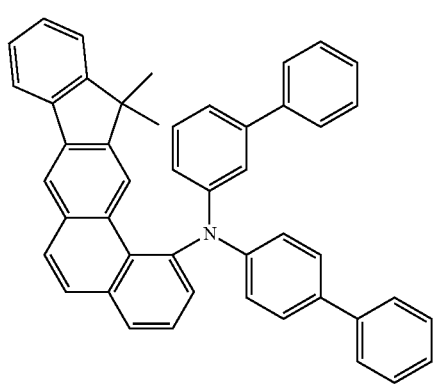
C-79
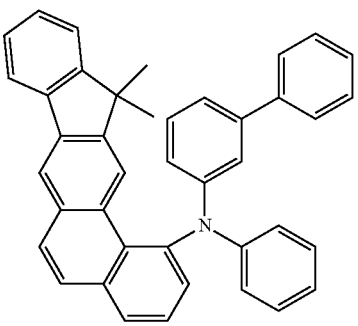
C-80
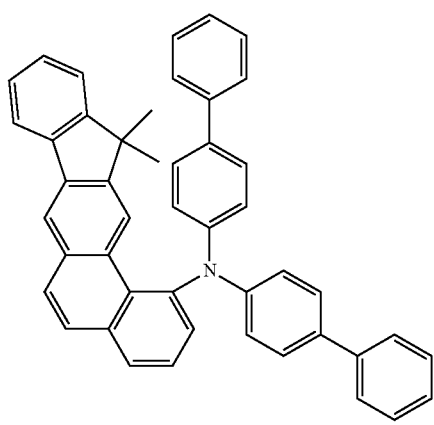

-continued
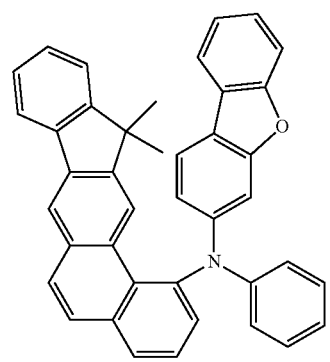
C-81
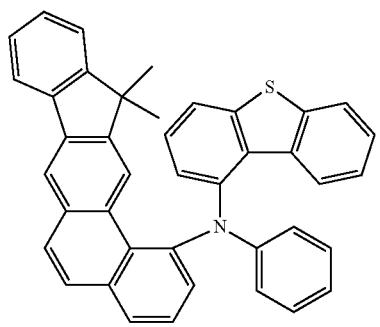
C-82
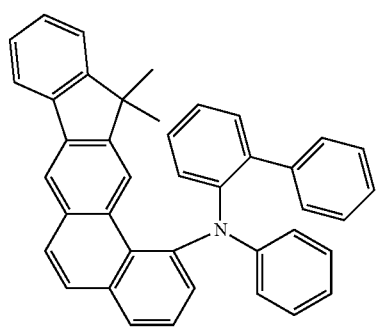
C-83
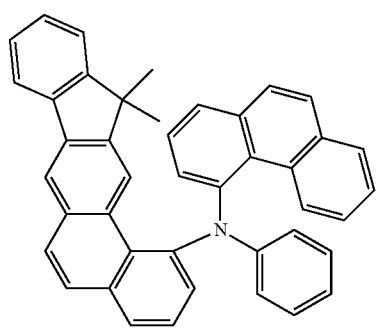
C-84
-continued
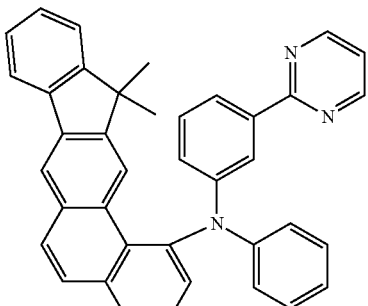
C-85
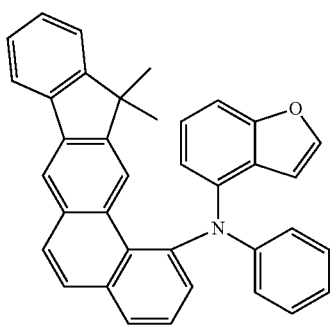
C-86
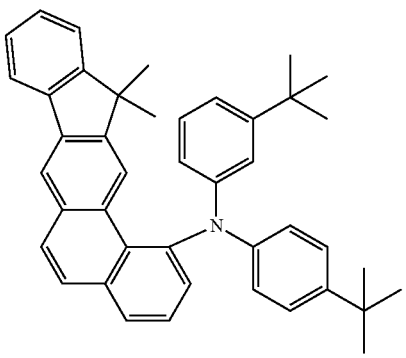
C-87
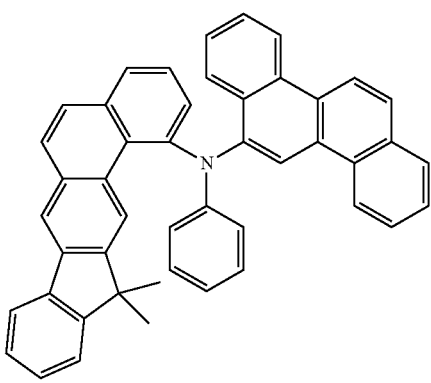
C-88

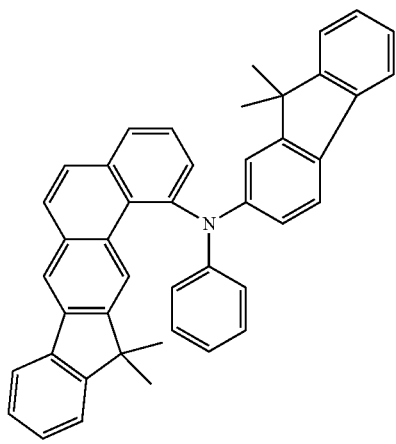
C-89
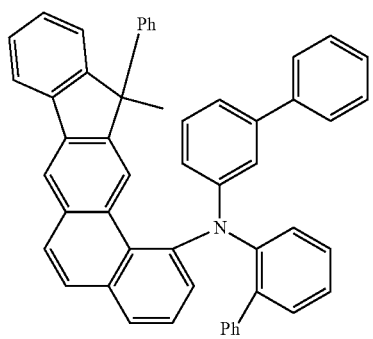
C-93
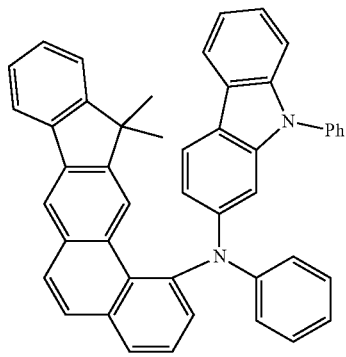
C-94
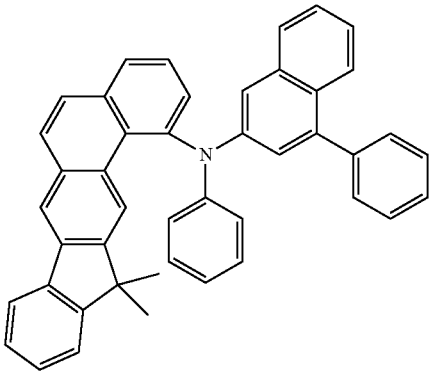
C-95
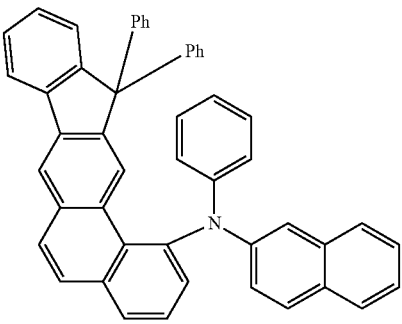
C-96

-continued
C-97
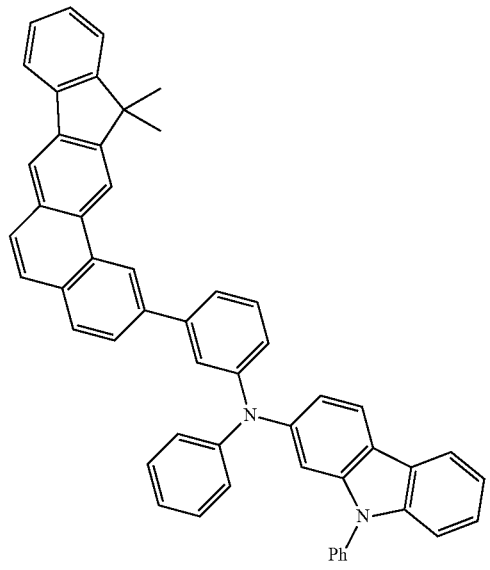
C-98
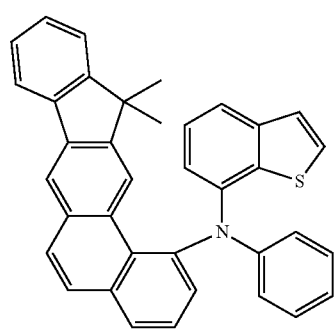
C-99
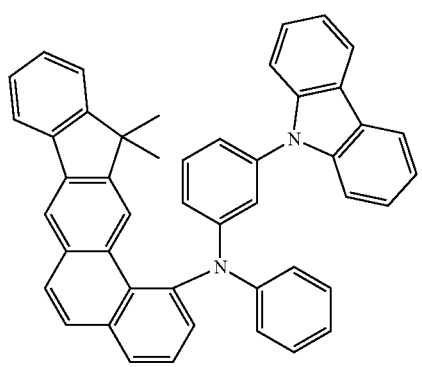
C-100
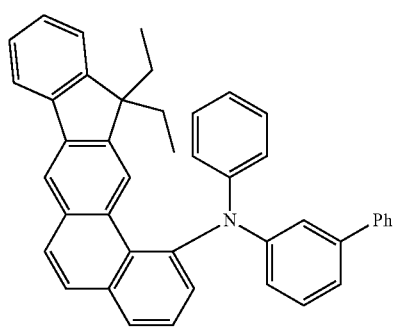
C-101
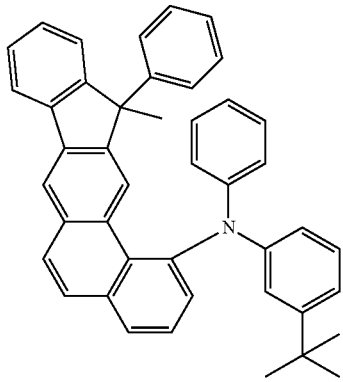
C-102
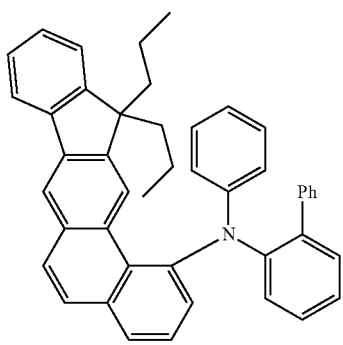
C-103
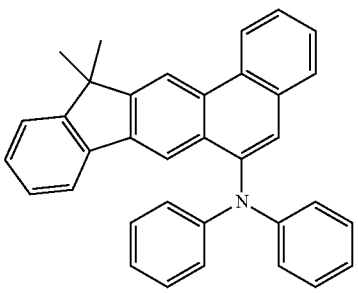
C-104
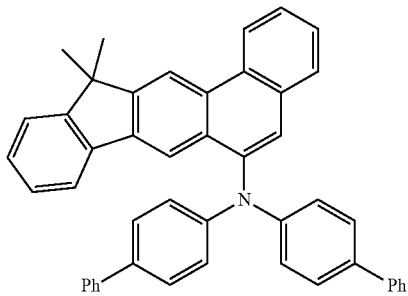

C-105
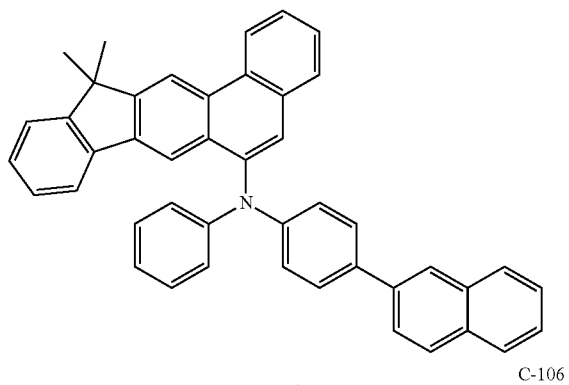
C-106
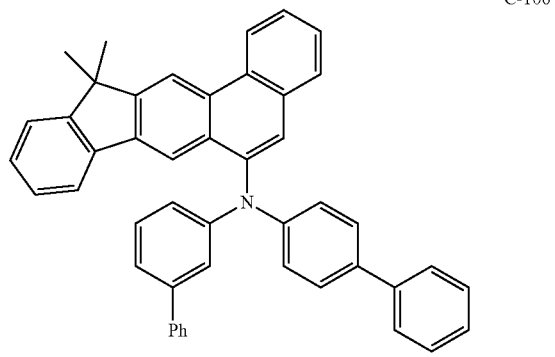
C-107
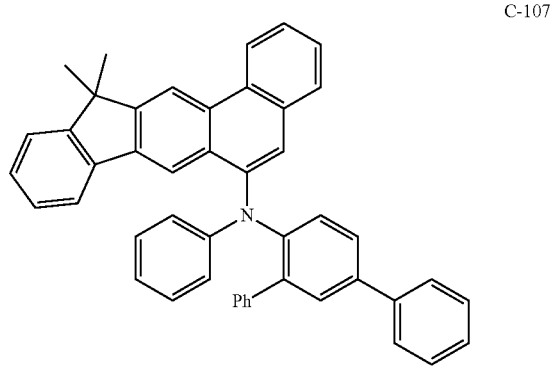
C-108
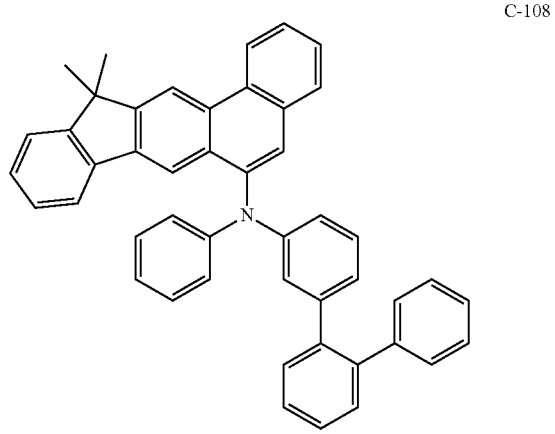
C-109
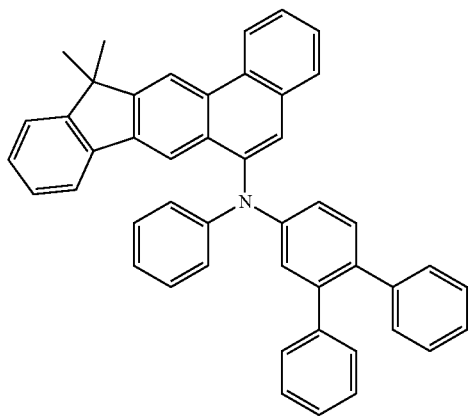
C-110
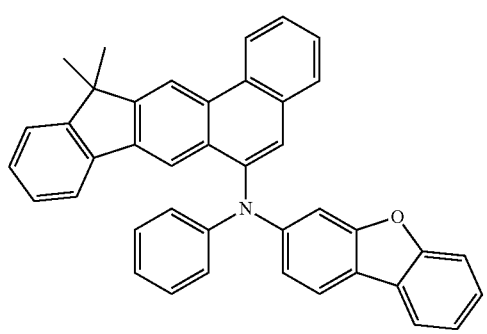
C-111
C-112
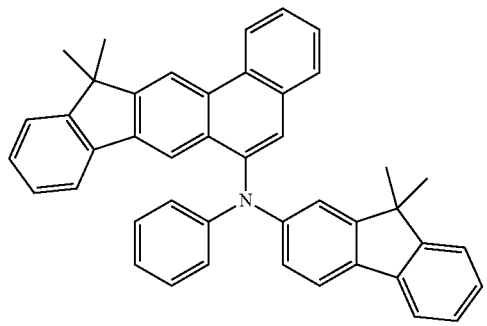

C-113
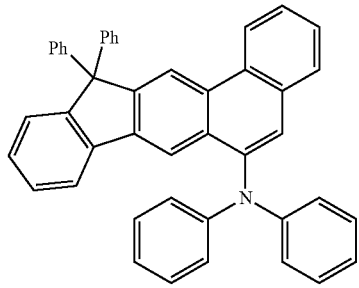
C-118
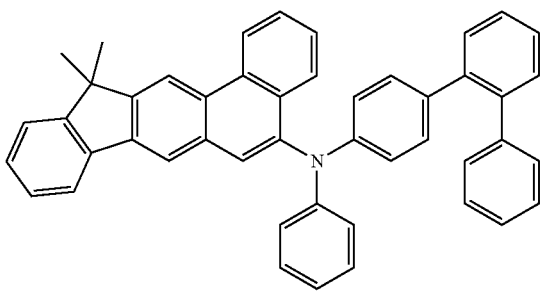
C-114
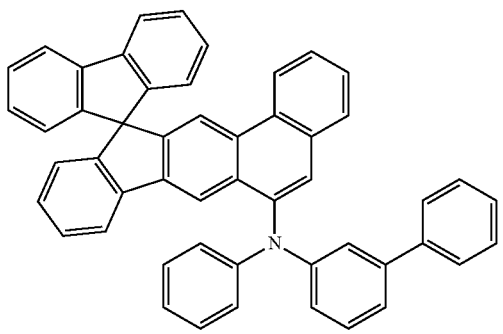
C-119
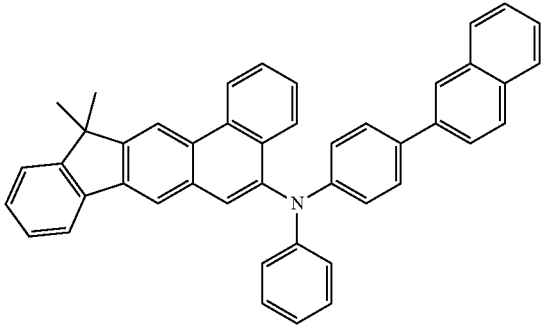
C-115
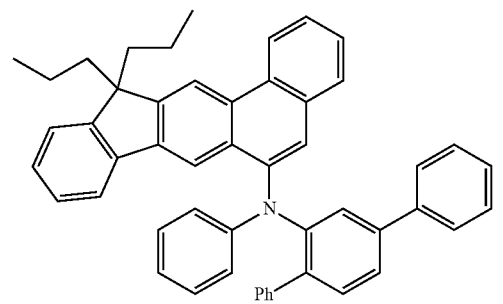
C-120
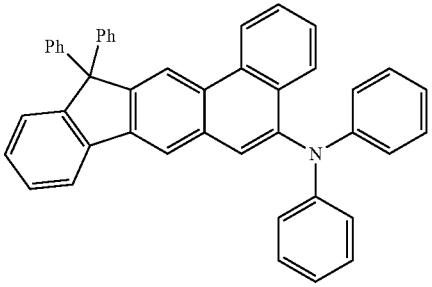
C-116
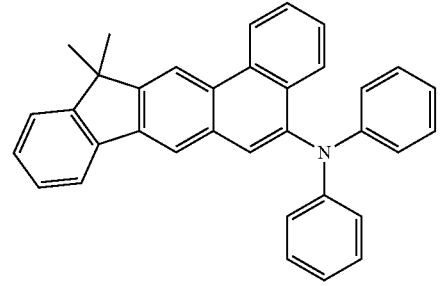
C-121
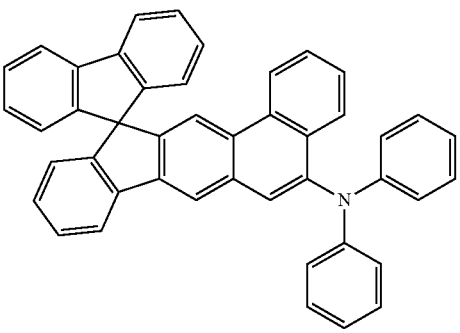
C-117
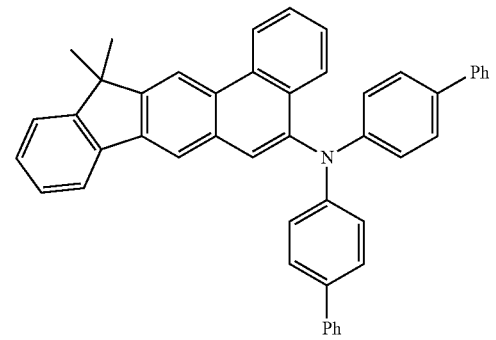
C-122
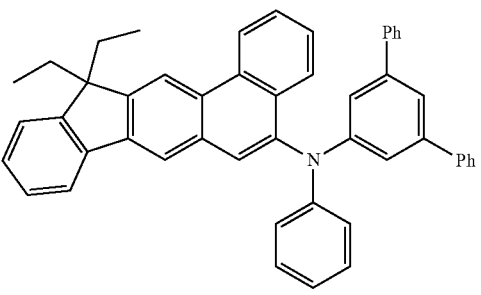

C-123
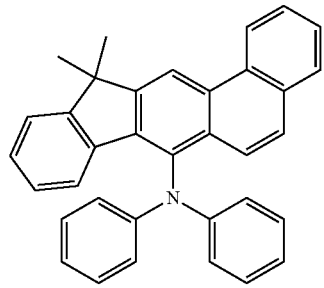
C-124
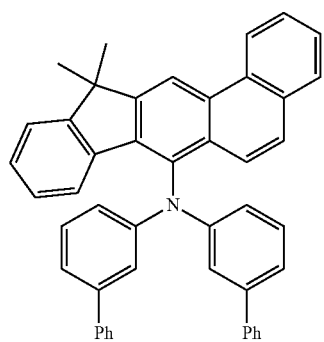
C-125
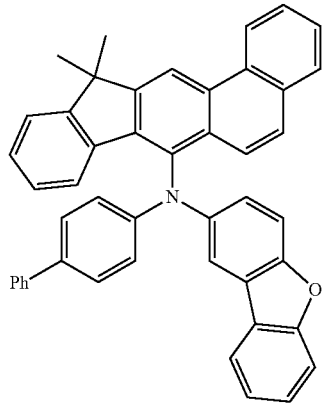
C-126
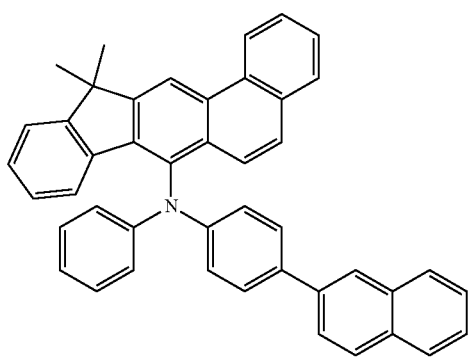
C-127
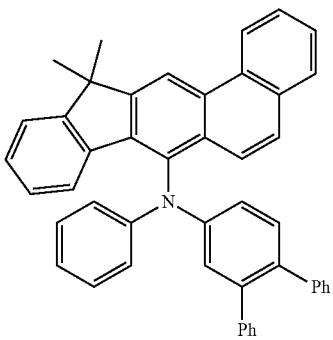
C-128
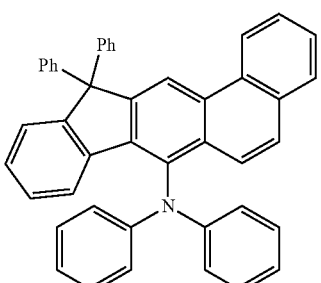
C-129
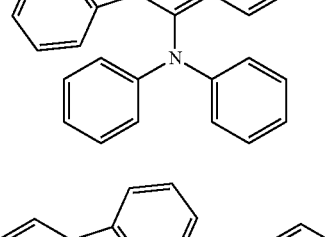
C-130
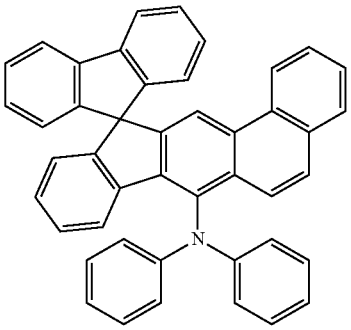
C-131
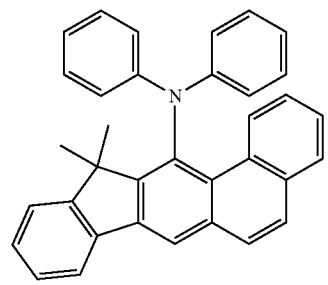

C-132 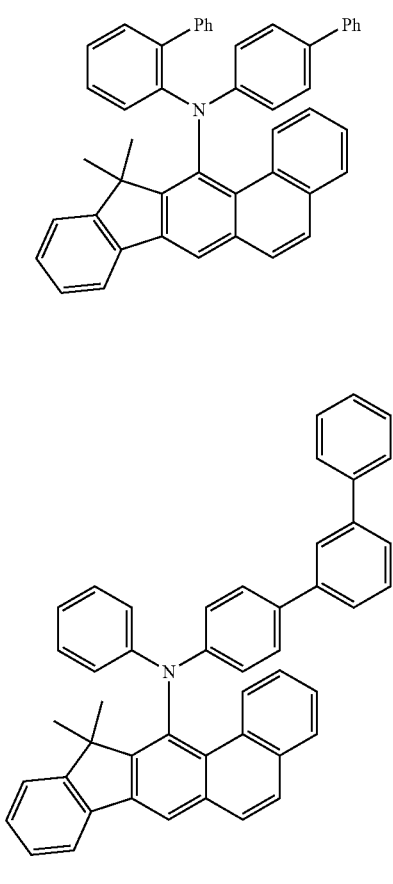
C-133 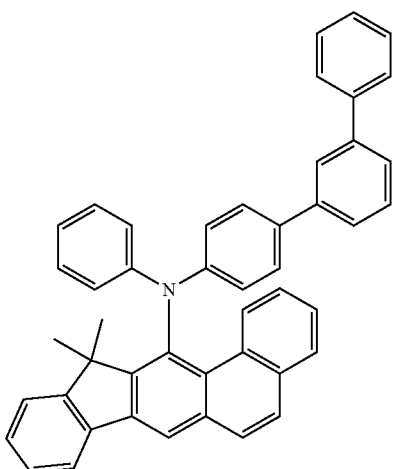
C-134 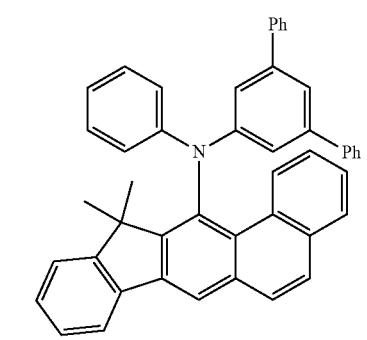
C-135 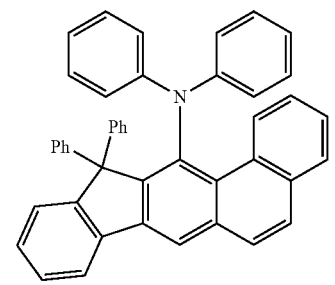
C-136 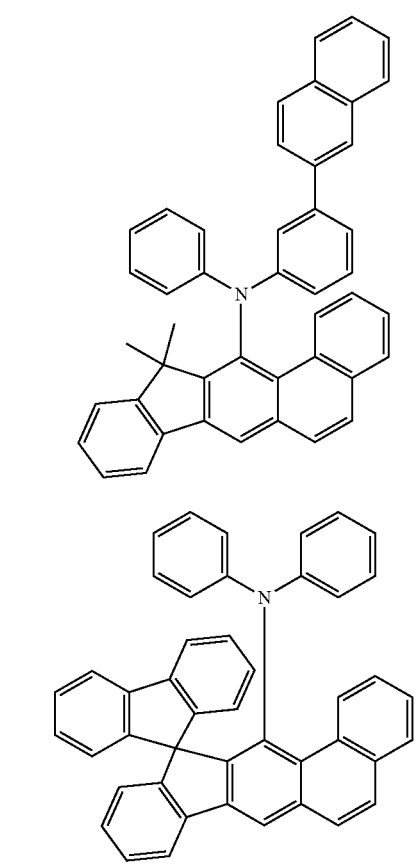
C-137 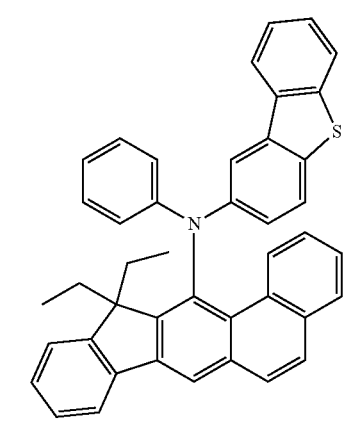
C-138
C-139 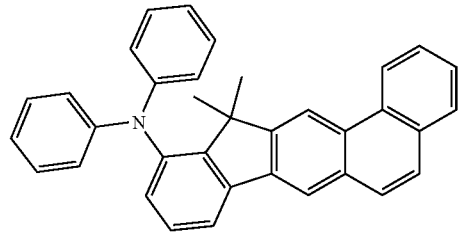

C-140
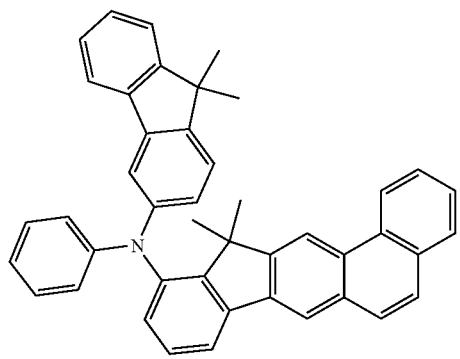
C-145
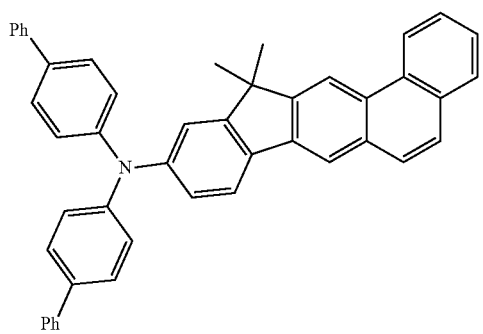
C-141
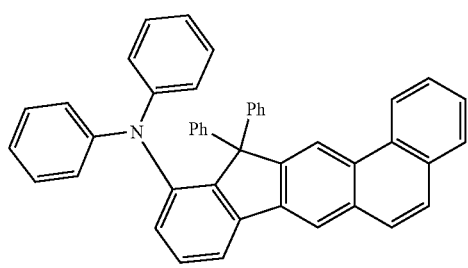
C-146
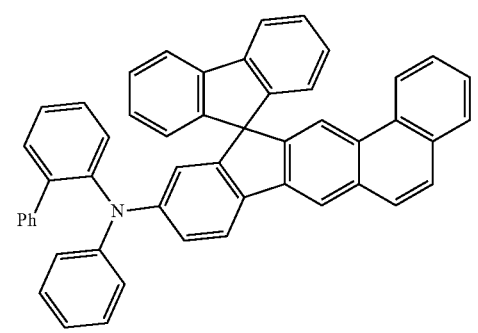
C-142
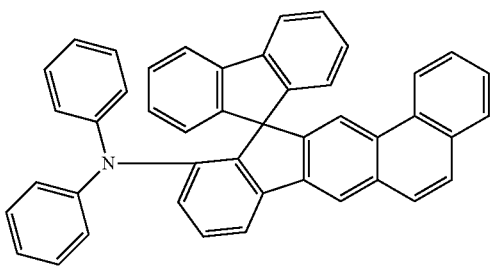
C-147
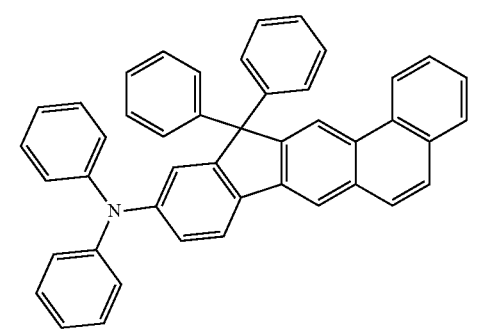
C-143
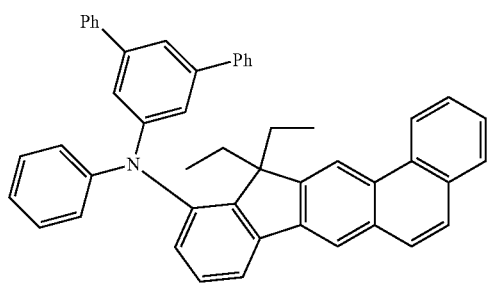
C-148
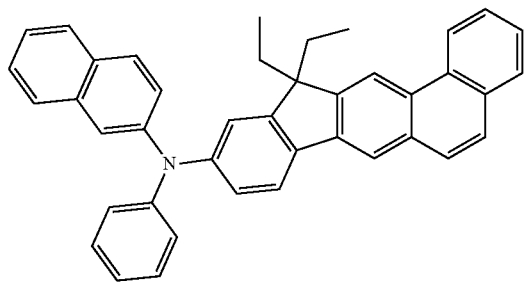
C-144
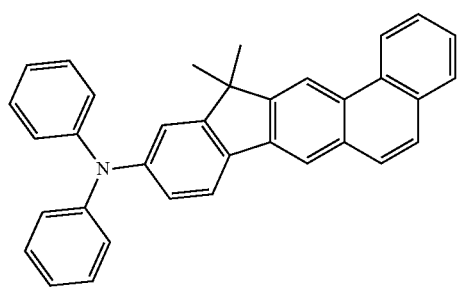
C-149
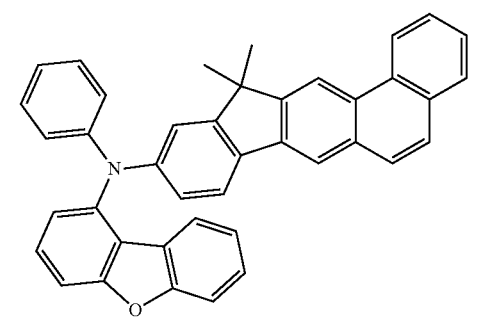

C-150
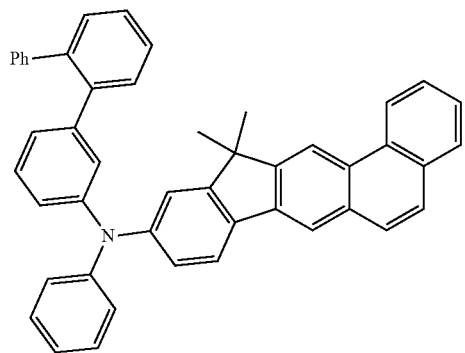
C-151
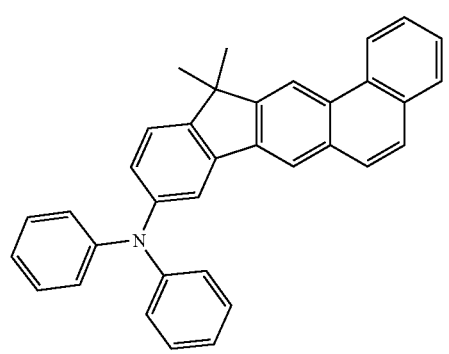
C-152
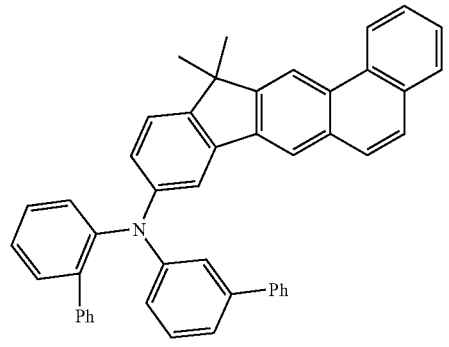
C-153
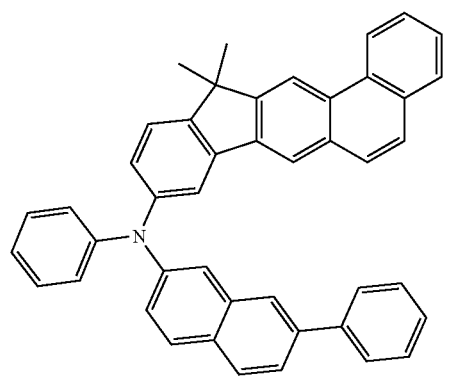
C-154
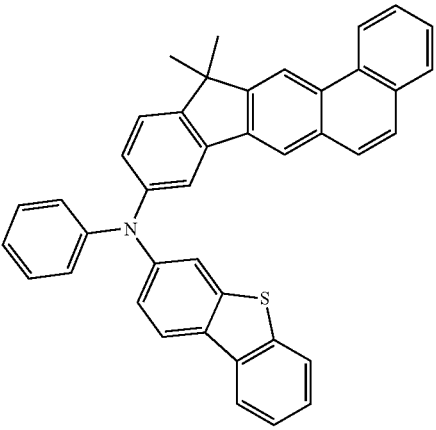
C-155
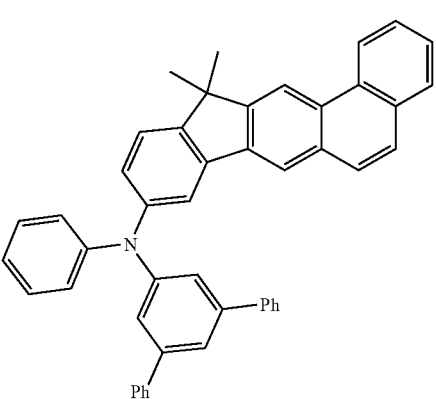
C-156
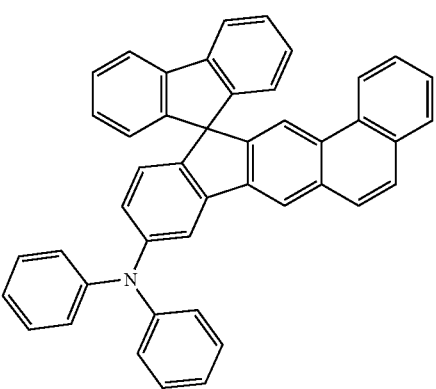
C-157
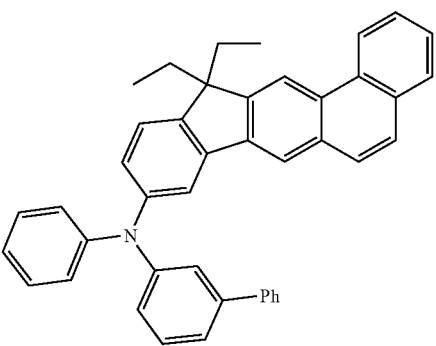

-continued
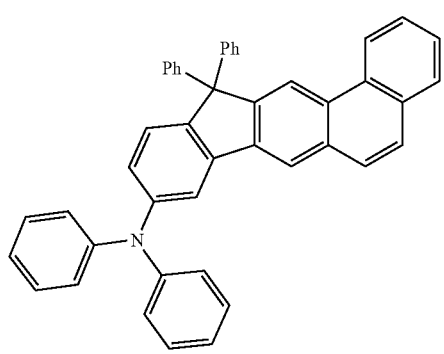
C-158
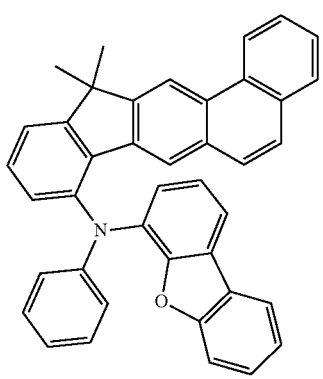
C-162
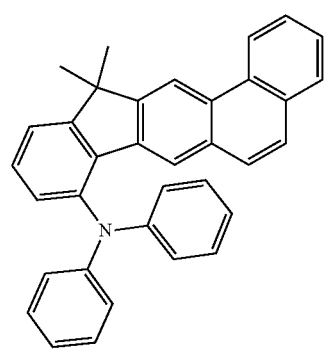
C-159
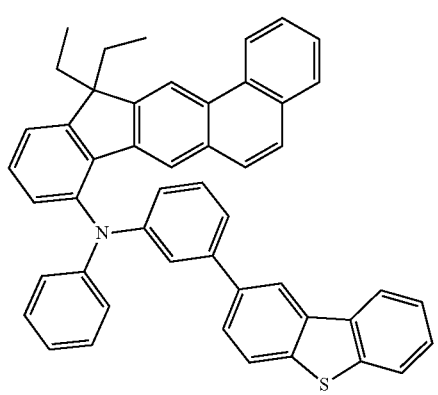
C-163
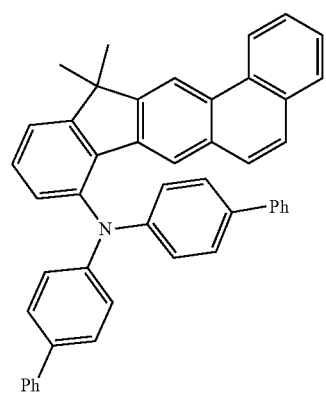
C-160
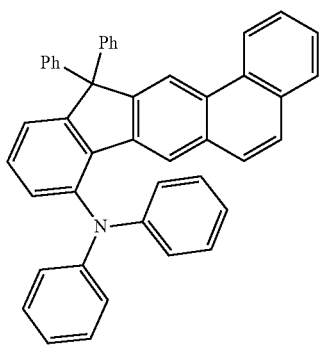
C-164
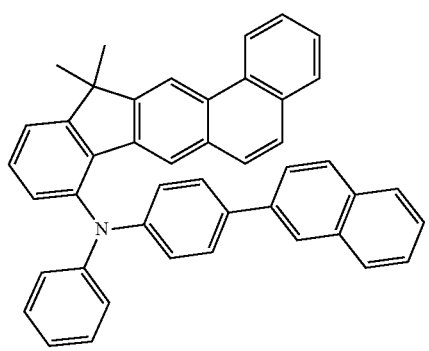
C-161
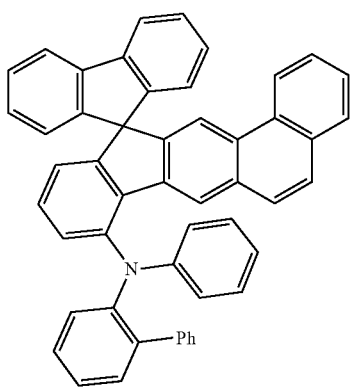
C-165

C-166
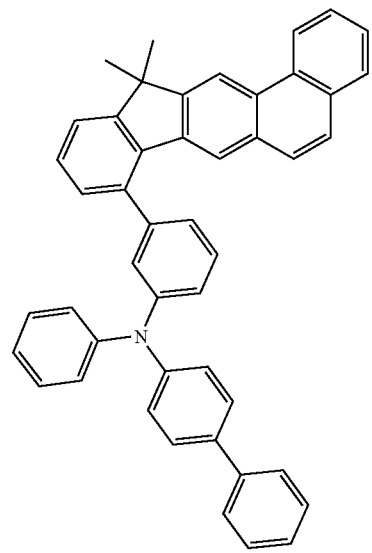
C-167
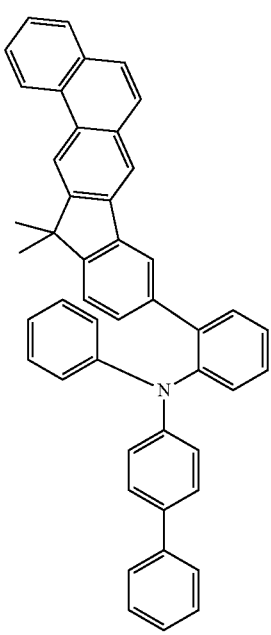
C-168
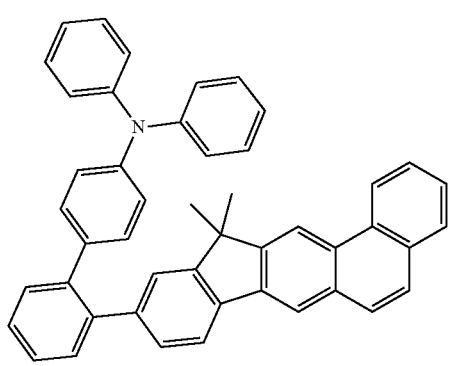
C-169
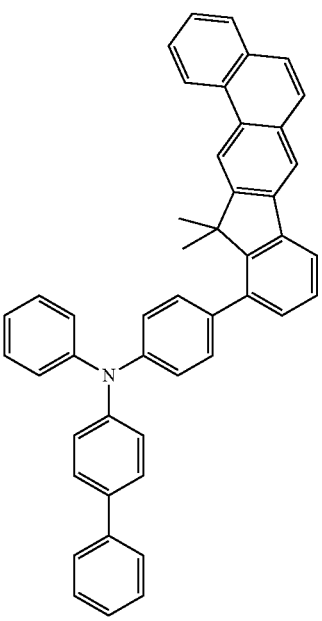
C-170
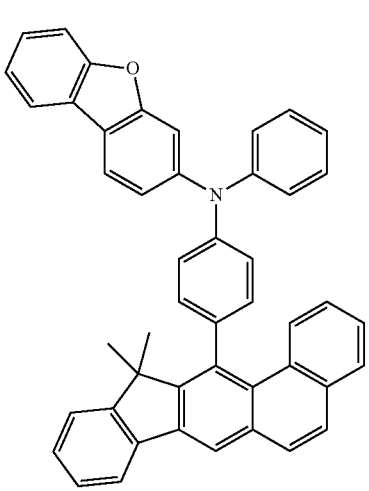
C-171
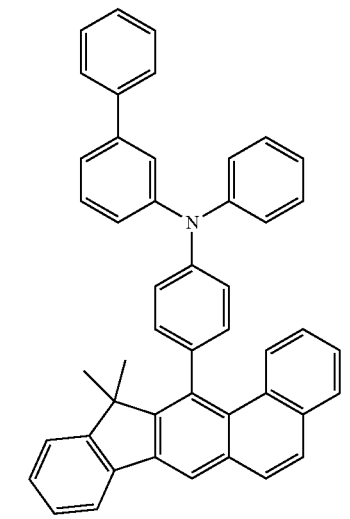

C-172
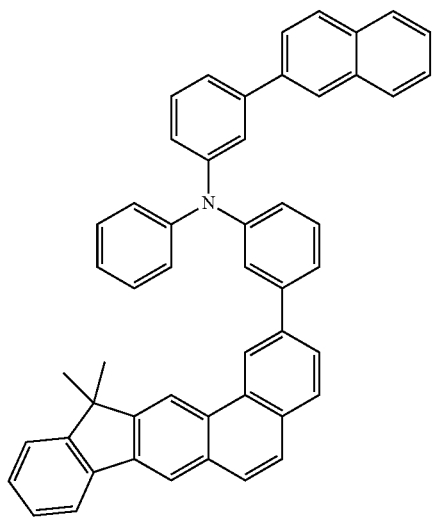
C-173
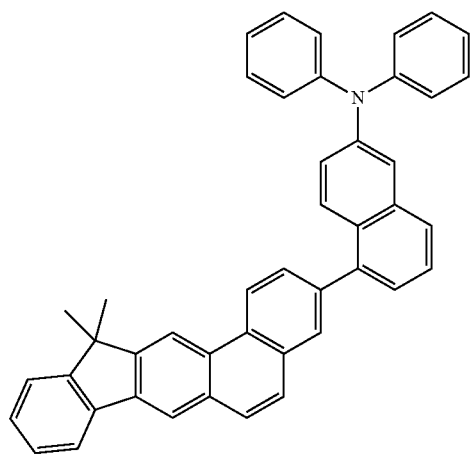
C-174
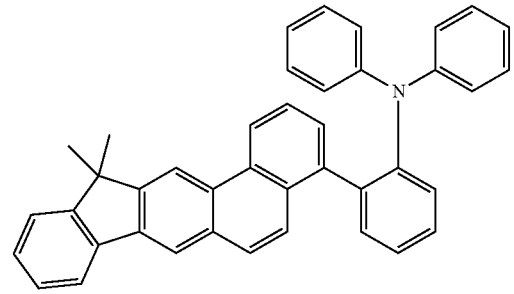
C-175
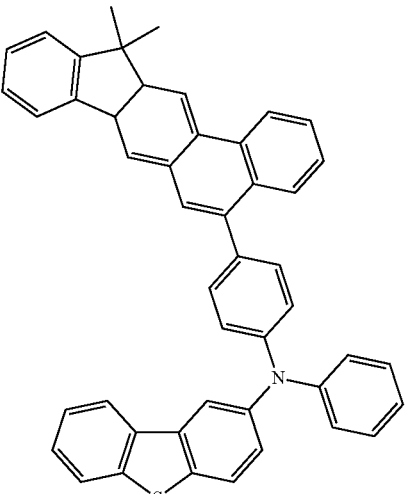
C-176
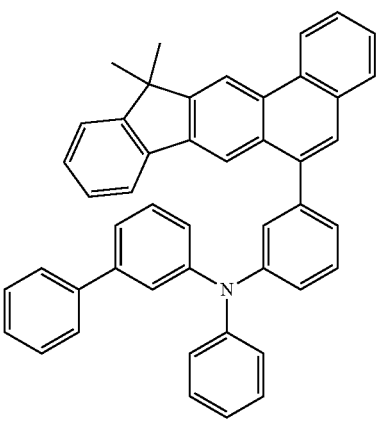
C-177
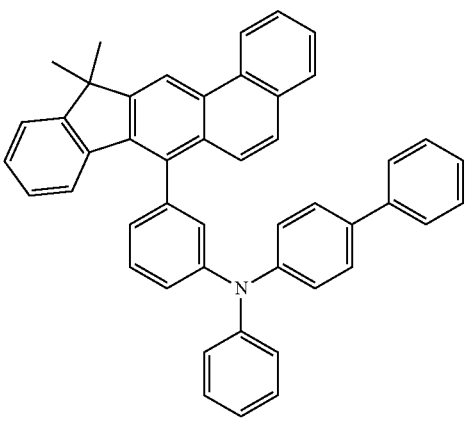

C-178
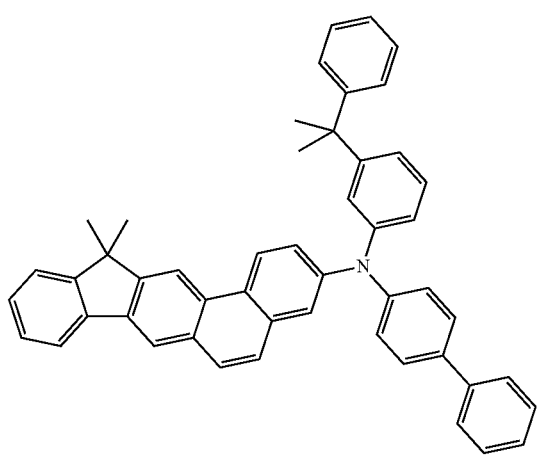
C-182
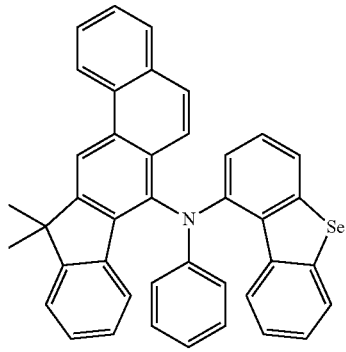
C-179
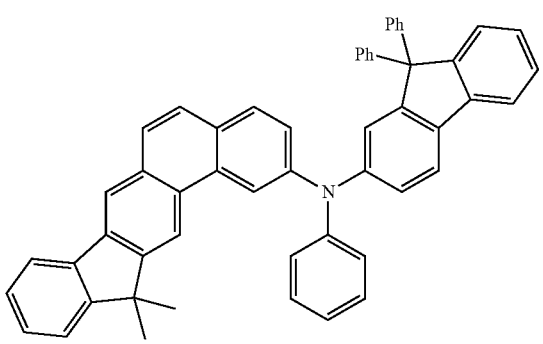
C-183
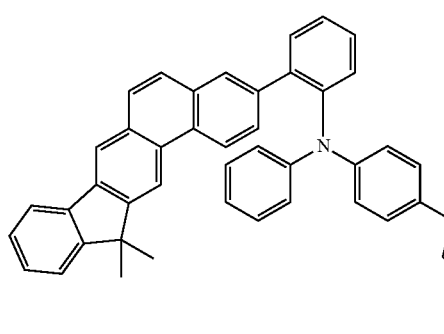
C-180
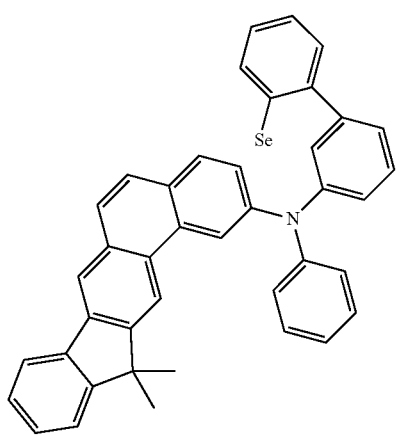
C-184
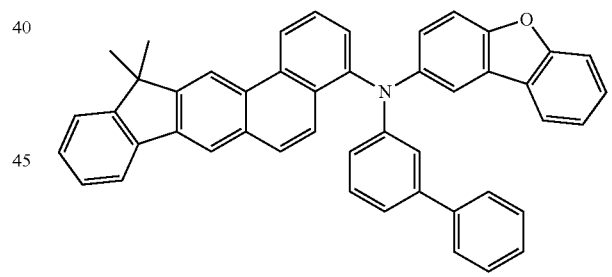
C-181
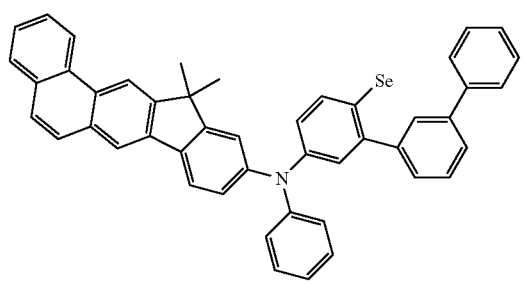
C-185
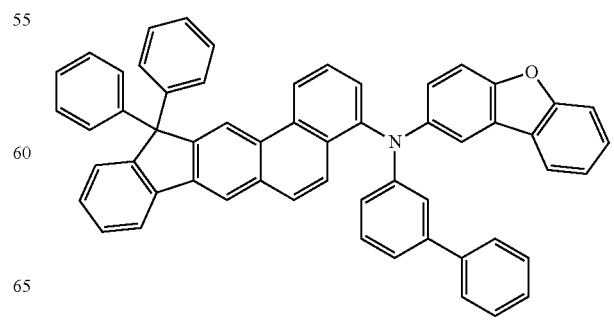

-continued
C-186
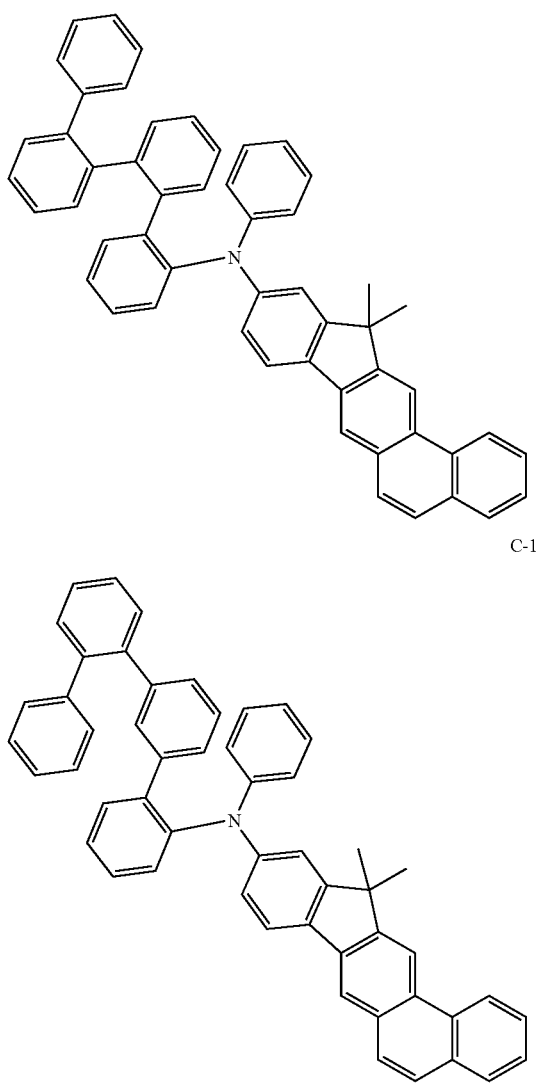
C-187
The organic electroluminescent compound of the present disclosure may be produced by a synthetic method known to one skilled in the art, and for example, by referring to the following reaction schemes 1 to 4, but is not limited thereto.
[Reaction Scheme 1]
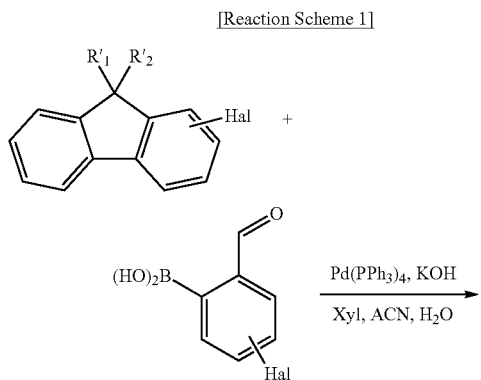
-continued
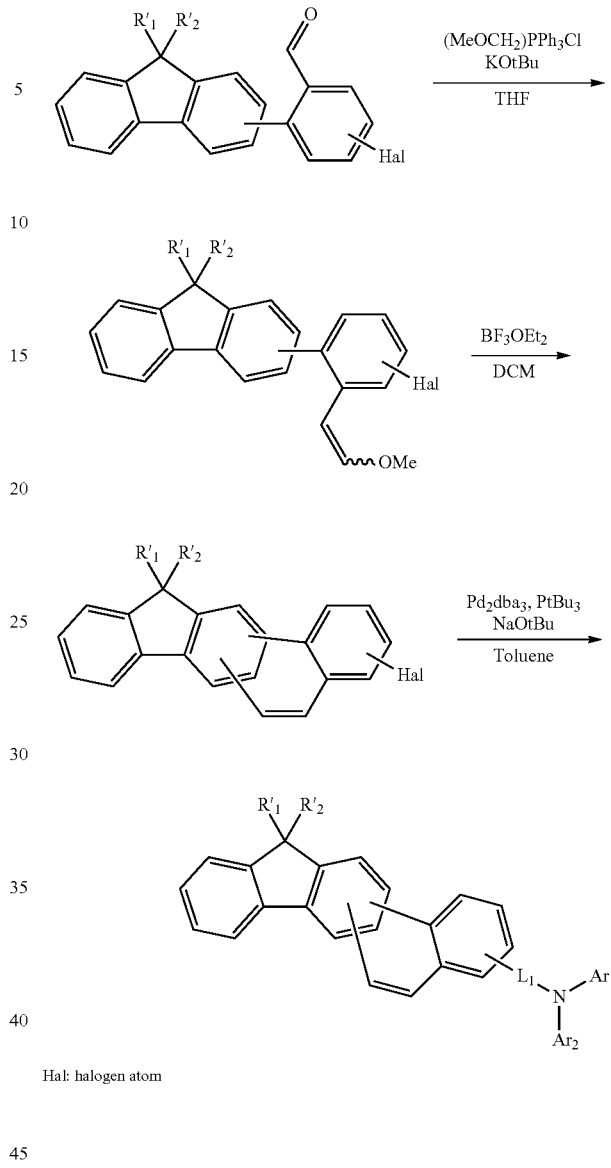
Hal: halogen atom
[Reaction Scheme 2]
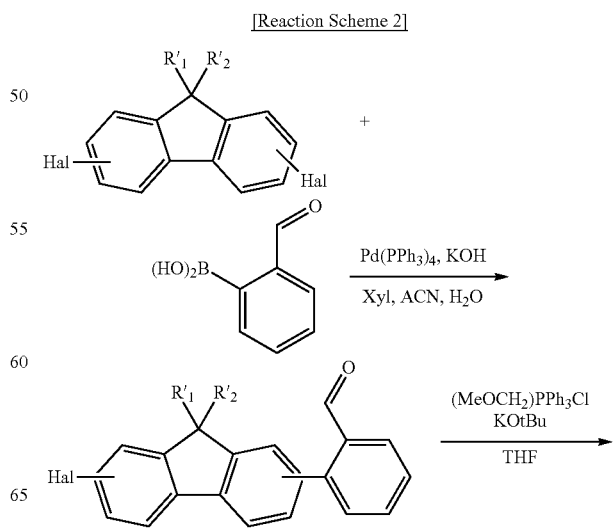

-continued
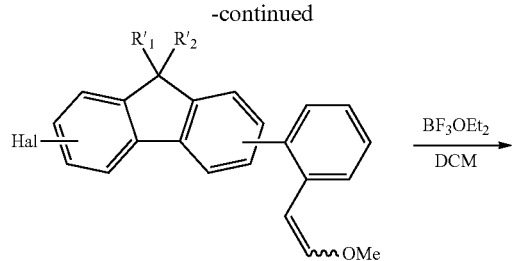
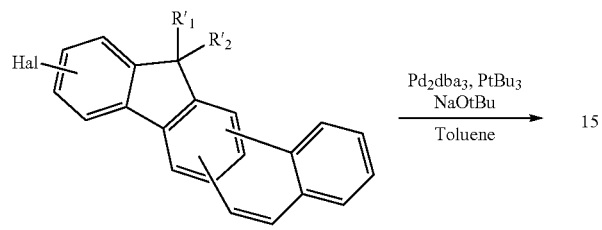
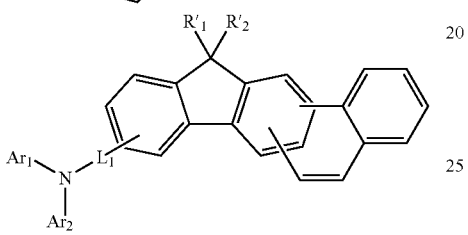
Hal: halogen atom
[Reaction Scheme 3]
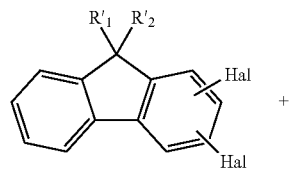
+
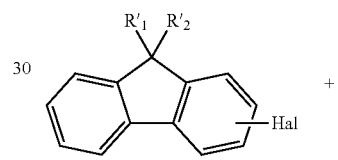
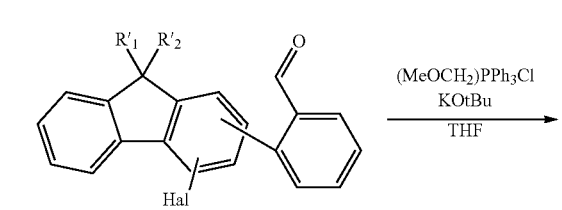
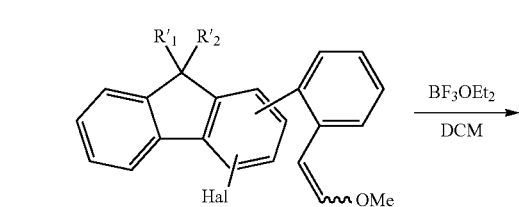
-continued
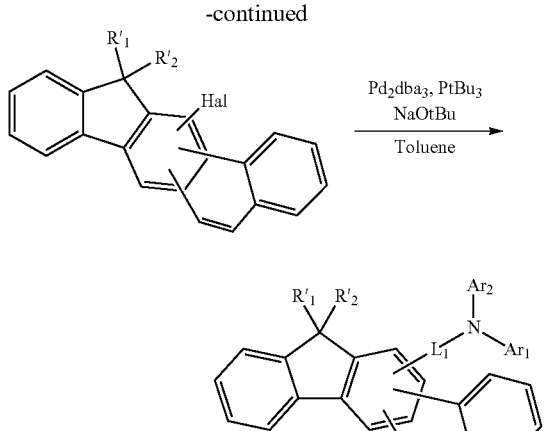
Hal: halogen atom
[Reaction Scheme 4]
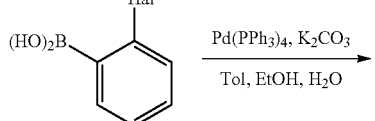
+
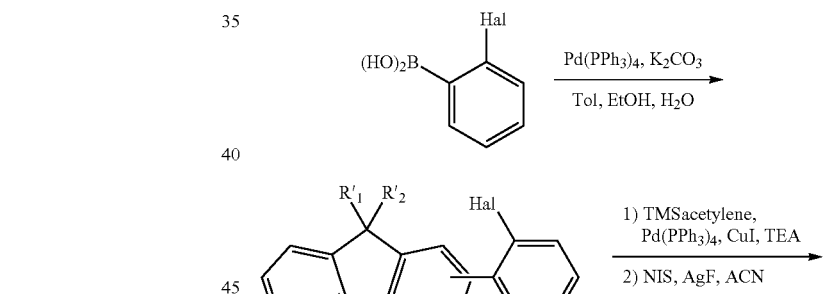
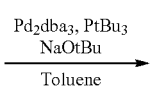

-continued

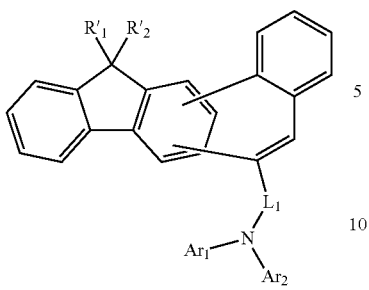

Hal: halogen atom

In reaction schemes 1 to 4, $R'_1$, $R'_2$, $L_1$, $Ar_1$, and $Ar_2$ are as defined in formula 1.

Although illustrative synthesis examples of the compound represented by formula 1 are described above, one skilled in the art will be able to readily understand that all of them are based on a Buchwald-Hartwig cross-coupling reaction, an N-arylation reaction, a H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, and a Phosphine-mediated reductive cyclization reaction, etc., and the reactions above proceed even when substituents which are defined in formula 1 above, but are not specified in the specific synthesis examples, are bonded.

A host compound, which can be used in combination with the compound of the present disclosure, includes a compound represented by any one of the following formulas 11 to 15, but is not limited thereto.

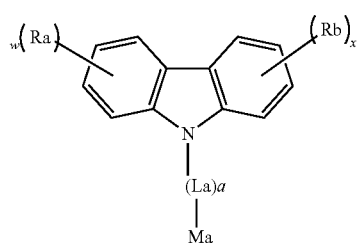 (11)

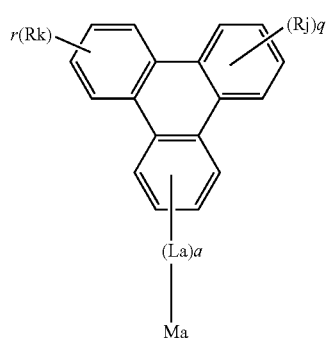 (12)

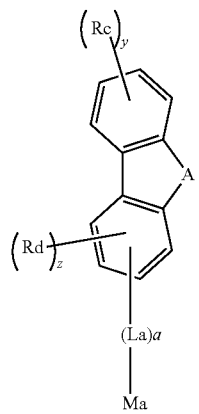 (13)

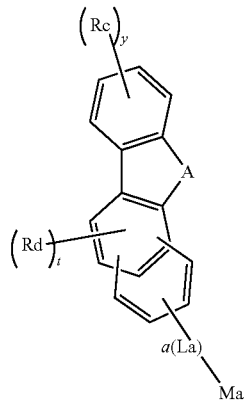 (14)

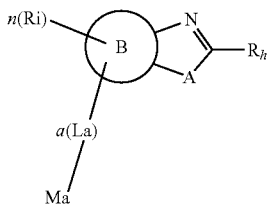 (15)

In formulas 11 to 15,

Ma represents a substituted or unsubstituted (C6-C30) aryl, a substituted or unsubstituted mono- or di-(C6-C30) arylamino, a substituted or unsubstituted mono- or di-(3- to 30-membered)heteroarylamino, a substituted or unsubstituted (C6-C30)aryl(3- to 30-membered)heteroarylamino, or a substituted or unsubstituted (3- to 30-membered)heteroaryl;

La represents a single bond, a substituted or unsubstituted (C6-C30)arylene, or a substituted or unsubstituted (3- to 30-membered)heteroarylene;

A represents S, O, N(Re), C(Rf)(Rg), Te, or Se;

ring B represents a naphthalene ring or a phenanthrene ring;

Ra to Rd, and Rh to Rk, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30) alkynyl, a substituted or unsubstituted (C3-C30)cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di-(C1-C30)alkylamino, a substituted or unsubstituted (C1-C30)alkyl(C6-C30)arylamino, or a substituted or unsubstituted mono- or di-(C6-C30)arylamino; or may be linked to an adjacent substituent to form a ring(s);

Re to Rg, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; and Rf and Rg may be linked to each other to form a ring(s);

w to y, q, and r, each independently, represent an integer of 1 to 4; z represents an integer of 1 to 3; and a and t, each independently, represent an integer of 1 or 2; n represents an integer of 1 to 9; and each of Ra to each of Rd, each of Ri to each of Rk, and each of La may be the same or different; and the heteroaryl(ene) comprises at least one heteroatom selected from the group consisting of B, N, O, S, Si, P, Te, and Se.

According to one embodiment, Ma represents a substituted or unsubstituted phenyl, a substituted or unsubstituted pyridyl, a substituted or unsubstituted pyrimidinyl, a substituted or unsubstituted triazinyl, a substituted or unsubstituted quinazolinyl, a substituted or unsubstituted quinoxalinyl, a substituted or unsubstituted benzoquinazolinyl, a substituted or unsubstituted benzoquinoxalinyl, a substituted or unsubstituted dibenzofuranyl, a substituted or unsubstituted dibenzothiophenyl, a substituted or unsubstituted dibenzotellurumyl, a substituted or unsubstituted benzofuranopyrimidinyl, a substituted or unsubstituted benzothienopyrimidinyl, a substituted or unsubstituted benzoxazolyl, etc.; and the substituent(s) thereof, each independently, may be any one selected from the group consisting of a substituted or unsubstituted phenyl, a substituted or unsubstituted naphthyl, a biphenyl, a phenanthrenyl, a terphenyl, a chrysenyl, a benzo[c]phenanthryl, a triphenylenyl, a dimethylfluorenyl, a diphenylfluorenyl, a dimethylbenzofluorenyl, a spirobifluorenyl, a pyridyl, a pyrimidinyl, a triazinyl substituted with a phenyl(s), a dibenzofuranyl unsubstituted or substituted with deuterium and/or a phenyl(s), a dibenzothiophenyl, a carbazolyl unsubstituted or substituted with a phenyl(s) and/or a biphenyl(s), a dibenzotelluriumyl, a dibenzoselenophenyl, a benzonaphthofuranyl, a benzonaphthothiophenyl, a phenanthrooxazolyl substituted with a phenyl(s), a triphenylsilyl, and a triphenylgermanyl; or the combination thereof. The substituent(s) of the substituted phenyl may be at least one selected from the group consisting of deuterium, a cyano, a fluoro, a methyl, a naphthyl, a carbazolyl, a triphenylsilyl, a triphenylgermanyl, and a dibenzotelluriumyl. The substituent(s) of the substituted naphthyl may be at least one selected from the group consisting of a phenyl, a biphenyl, and a chrysenyl.

According to one embodiment, La represents a single bond; a (C6-C25)arylene unsubstituted or substituted with at least one selected from the group consisting of deuterium, a (C1-C30)alkyl, and a (C6-C30)aryl; or a (5- to 25-membered)heteroarylene unsubstituted or substituted with a (C6-C30)aryl(s). For example, La may be a single bond; a phenylene unsubstituted or substituted with at least one of deuterium and a phenyl(s); a naphthylene unsubstituted or substituted with deuterium; a biphenylene unsubstituted or substituted with a phenyl(s); a phenanthrenylene; a terphenylene; a dimethylfluorenylene; a pyridylene; a dibenzofuranylene; a dibenzothiophenylene; a phenylcarbazolylene; a quinoxalinylene substituted with a phenyl(s); or a quinazolinylene, etc.

According to one embodiment, Ra to Rd, and Rh to Rk, each independently, represent hydrogen, deuterium, a cyano, a substituted or unsubstituted (C1-C20)alkyl, a substituted or unsubstituted (C6-C30)aryl, or a substituted or unsubstituted (5- to 20-membered)heteroaryl; or may be linked to an adjacent substituent to form a substituted or unsubstituted, mono- or polycyclic, (3- to 30-membered) alicyclic or aromatic ring, or the combination thereof. For example, Ra to Rd, and Ri to Rk, each independently, may be hydrogen, deuterium, a cyano, a methyl, a phenyl, a naphthyl, a biphenyl unsubstituted or substituted with deuterium, a phenylnaphthyl, a naphthylphenyl, a phenanthrenyl, a dimethylfluorenyl, a dibenzofuranyl unsubstituted or substituted with a phenyl(s), a dibenzothiophenyl unsubstituted or substituted with a phenyl(s), or a carbazolyl unsubstituted or substituted with a phenyl(s), etc.; or may be linked to an adjacent substituent to form a benzene ring, a benzofuran ring unsubstituted or substituted with a phenyl(s), or a benzothiophene ring unsubstituted or substituted with a phenyl(s), etc. For example, Rh may be a substituted phenyl, a naphthyl unsubstituted or substituted with a diphenyltriazinyl(s), a biphenyl, a phenanthrenyl, a dimethylfluorenyl, a pyridyl unsubstituted or substituted with a phenyl(s), a dibenzothiophenyl, a dibenzofuranyl, a phenylcarbazolyl, etc. The substituent(s) of the substituted phenyl may be at least one selected from the group consisting of deuterium, a cyano, a triazinyl substituted with a phenyl(s), a triphenylsilyl, and a triphenylgermanyl.

According to one embodiment, Re to Rg, each independently, represent an unsubstituted (C1-C20)alkyl, an unsubstituted (C6-C25)aryl, or an unsubstituted (5- to 20-membered)heteroaryl; and Rf and Rg may be linked to each other to form a substituted or unsubstituted, mono- or polycyclic, (3- to 30-membered) alicyclic or aromatic ring, or the combination thereof. For example, Re may be a phenyl or a dibenzotelluriumyl. For example, Rf and Rg, each independently, may be a methyl or a phenyl, etc.; or Rf and Rg may be linked to each other to form a spirofluorene ring.

The compound represented by formula 11 may be at least one selected from the group consisting of the following compounds, but is not limited thereto.

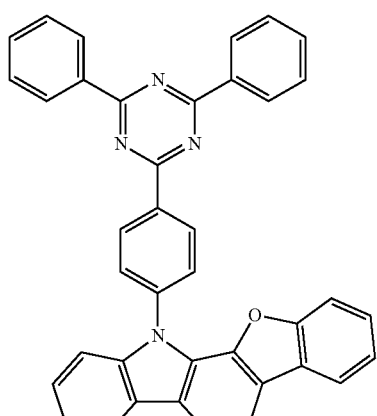
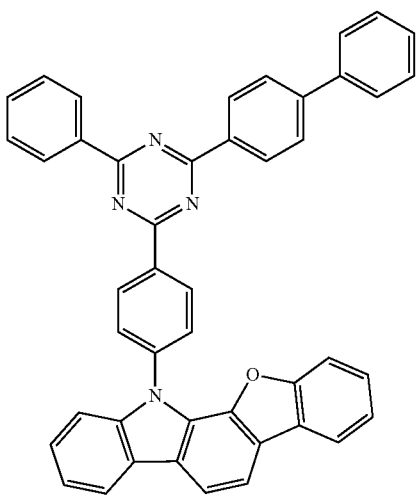
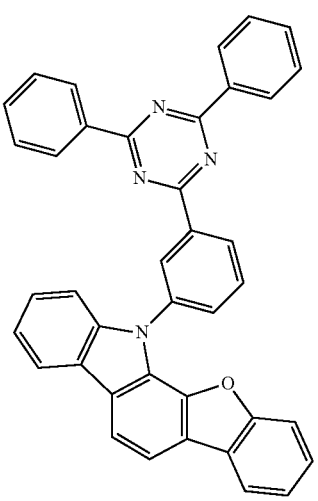
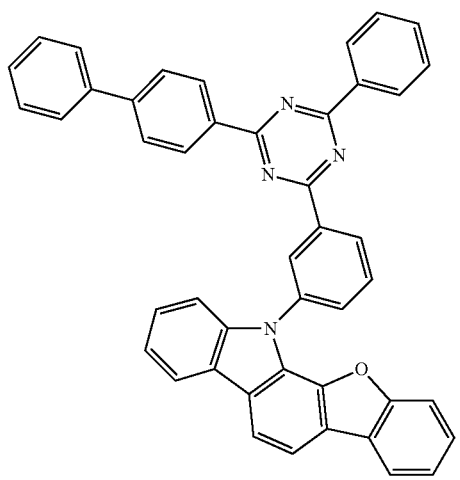
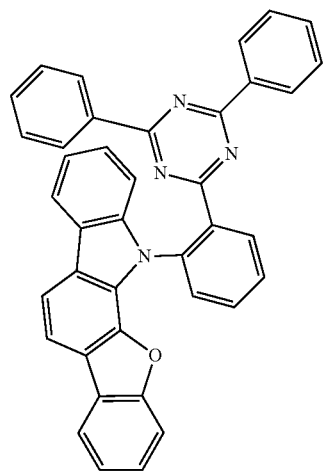
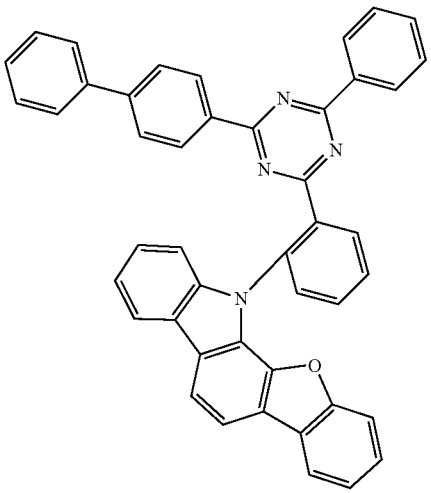
-continued 71
-continued
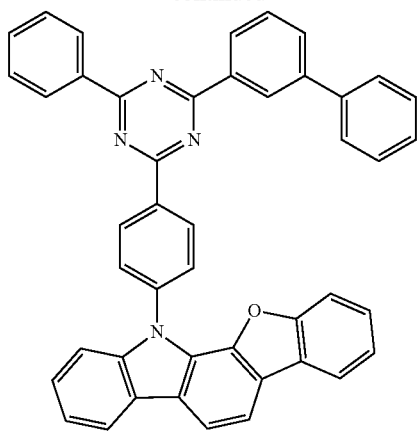
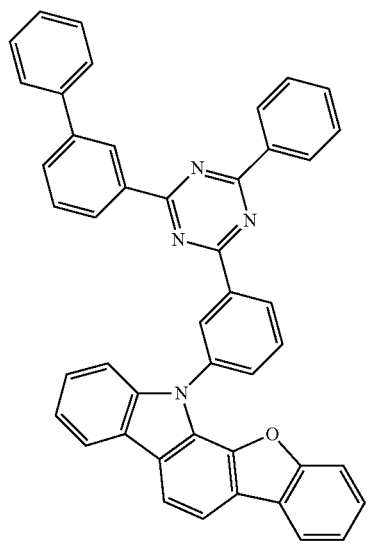
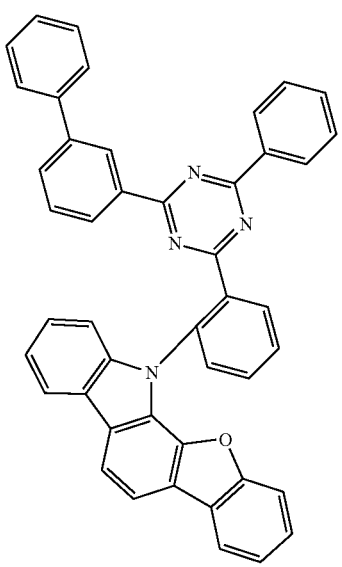
72
-continued
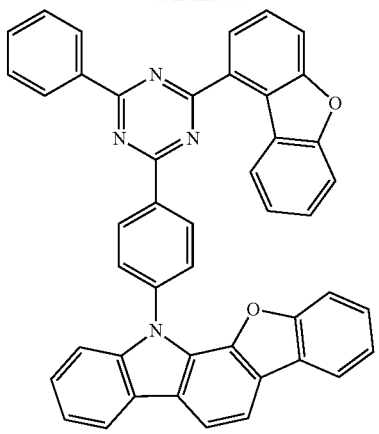
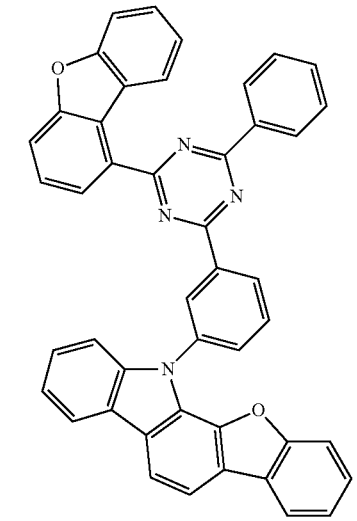
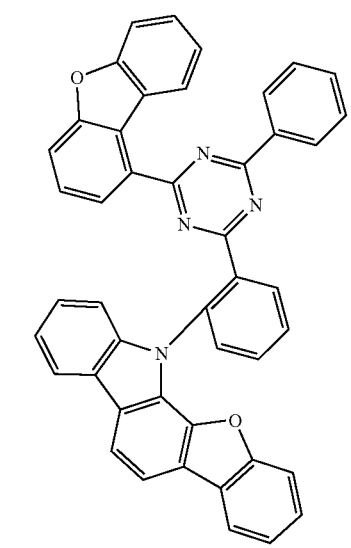

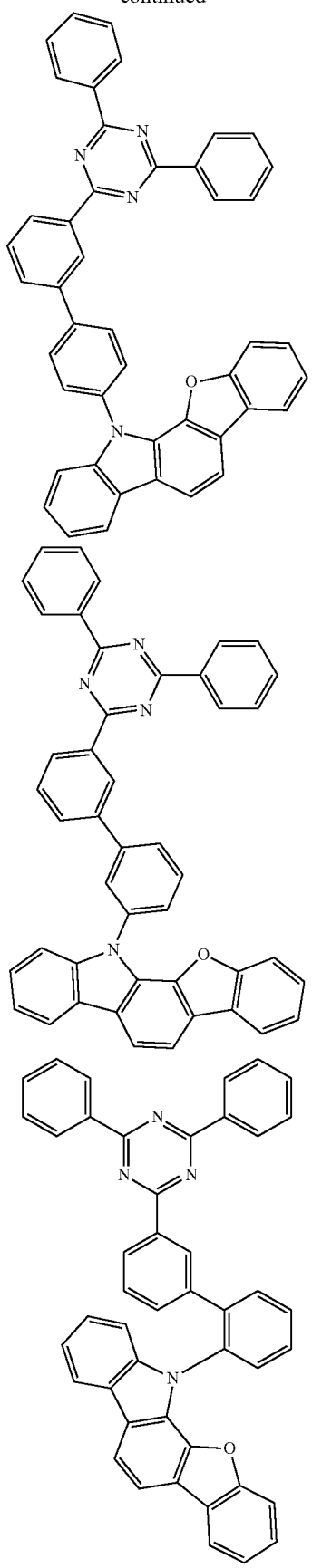
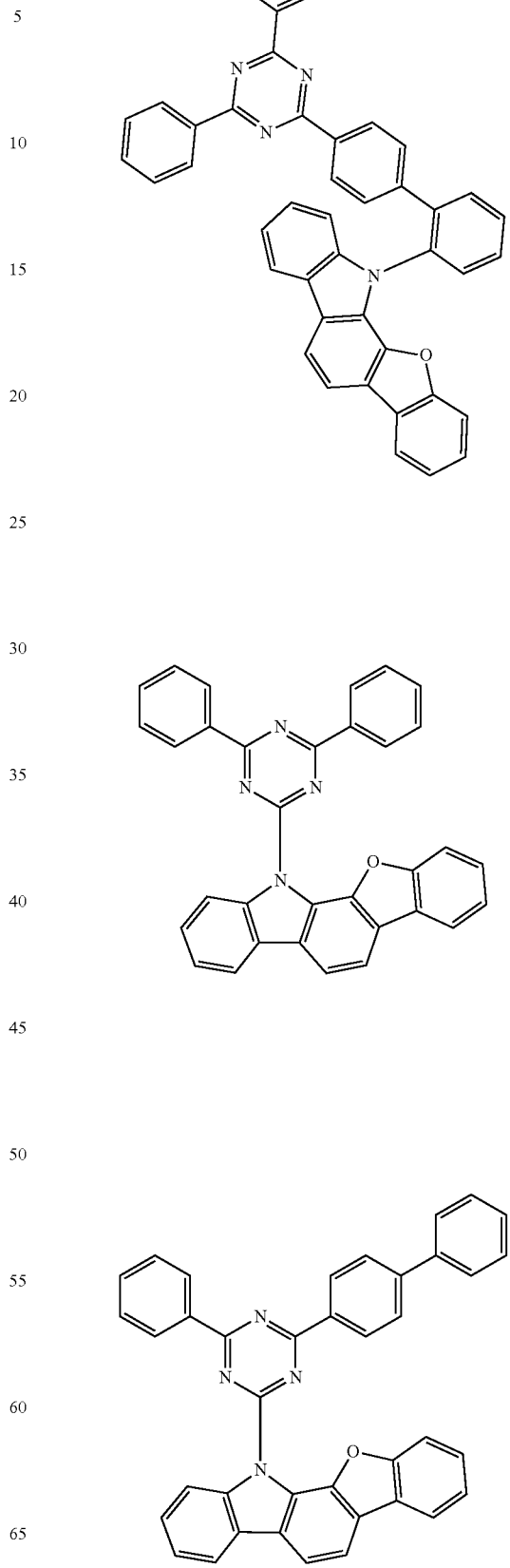

75
-continued
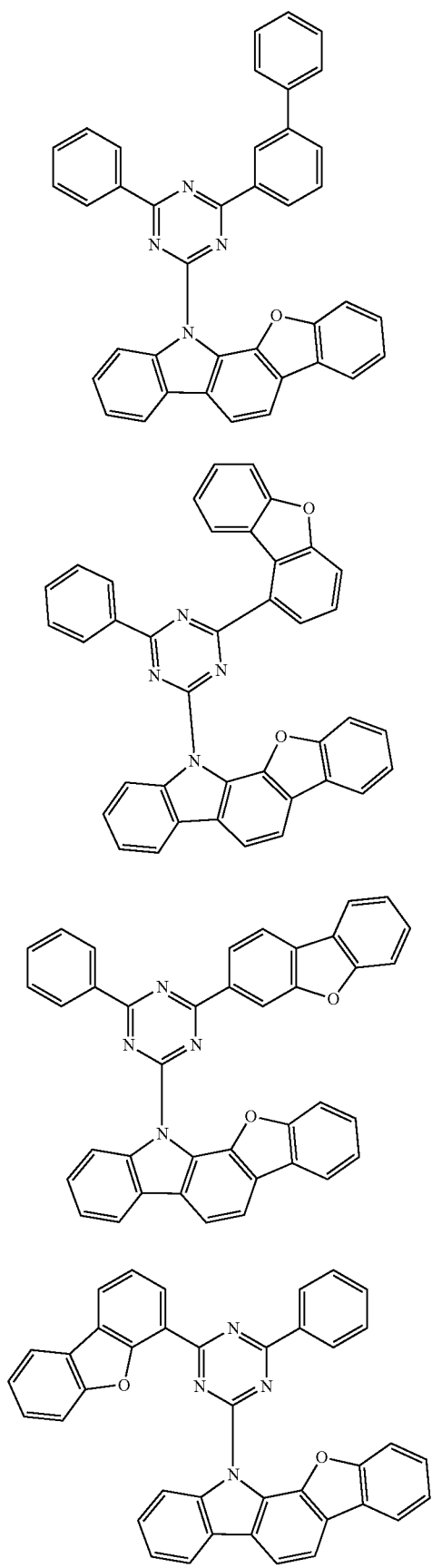
76
-continued
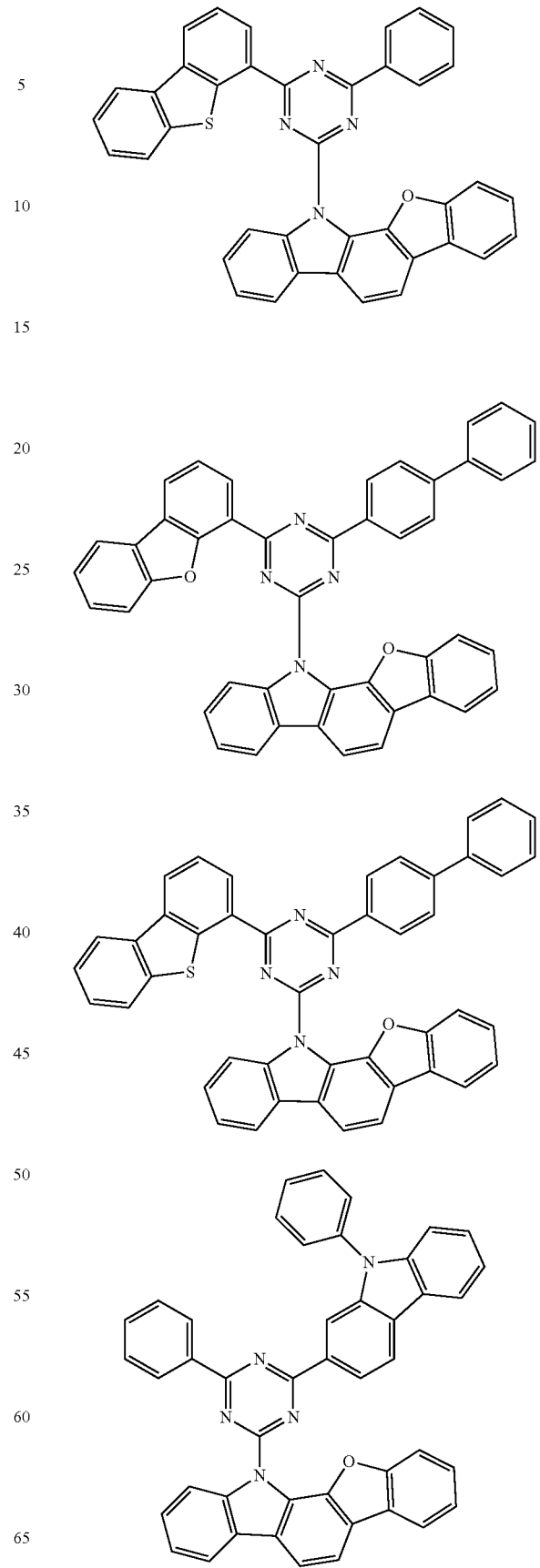

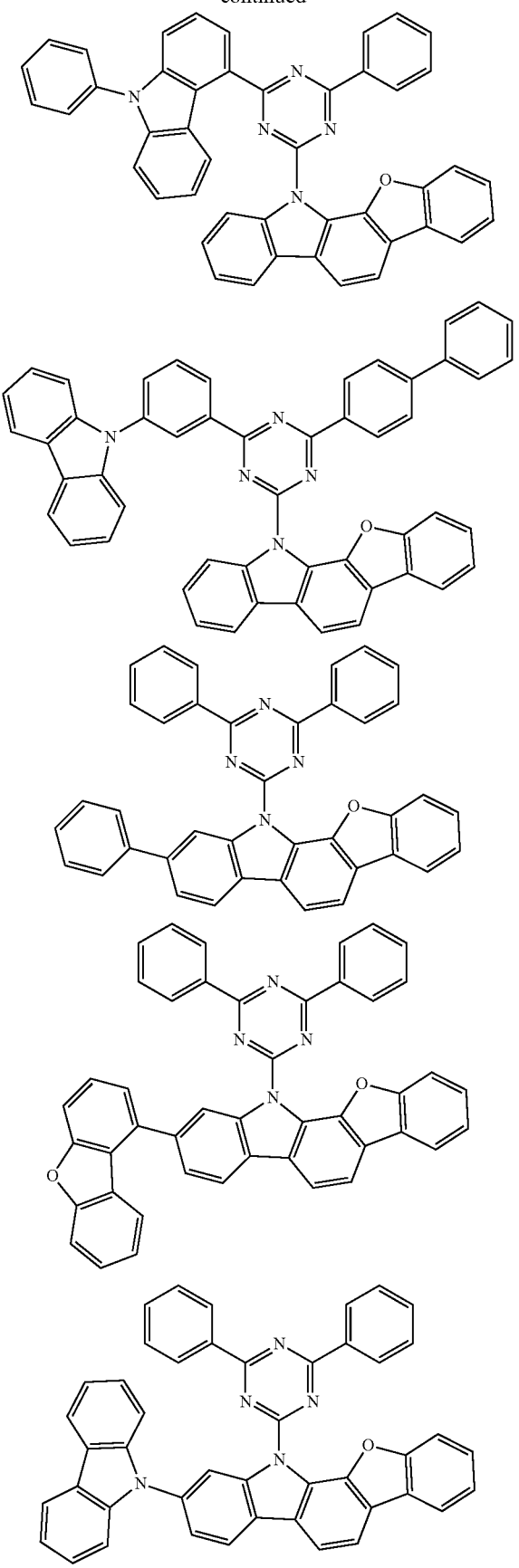
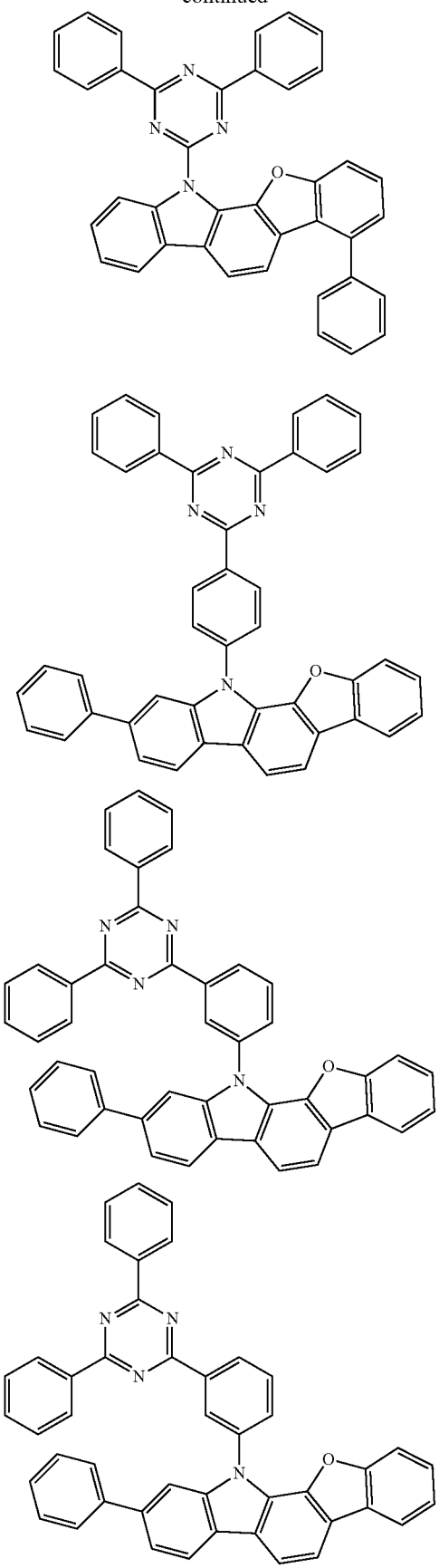

79
-continued
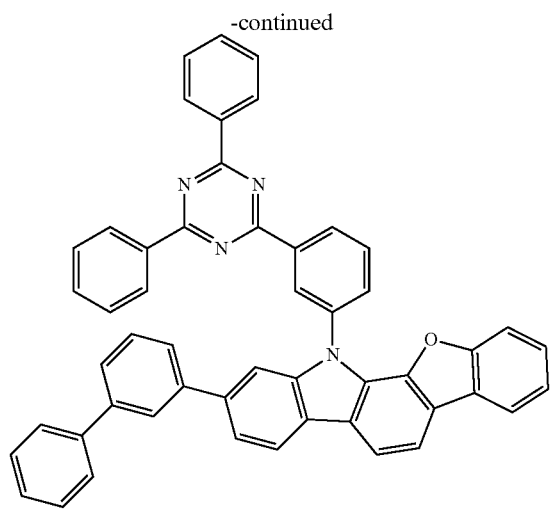
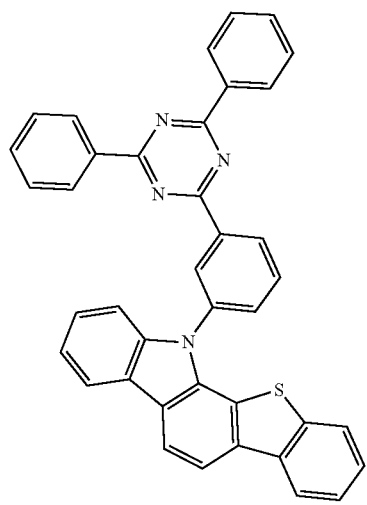
80
-continued
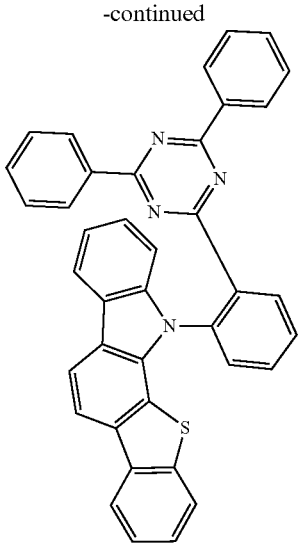
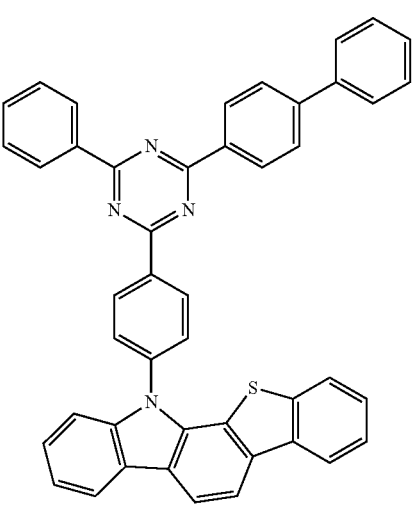
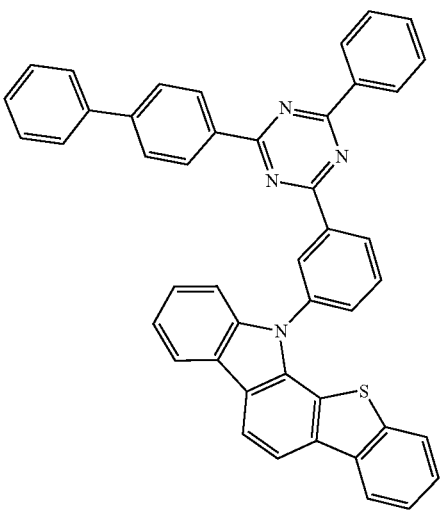

-continued
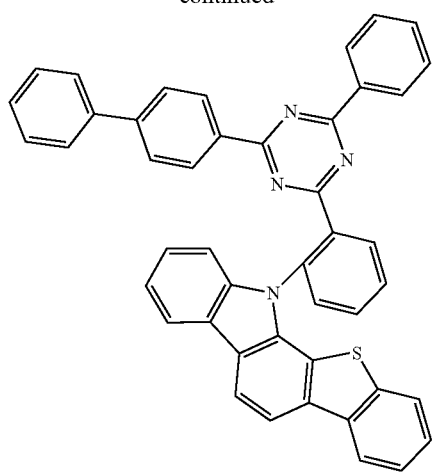
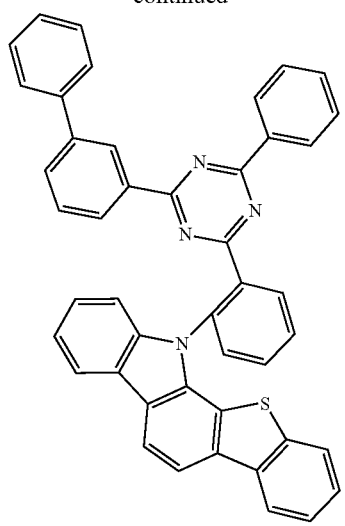
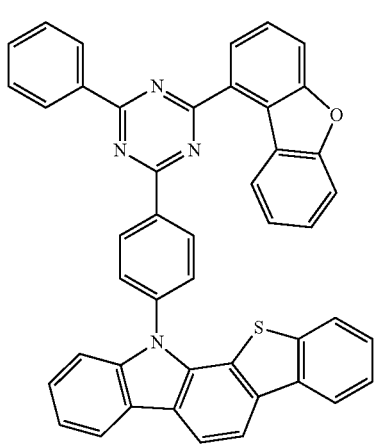
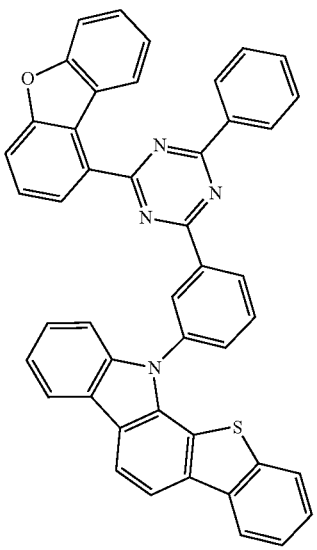

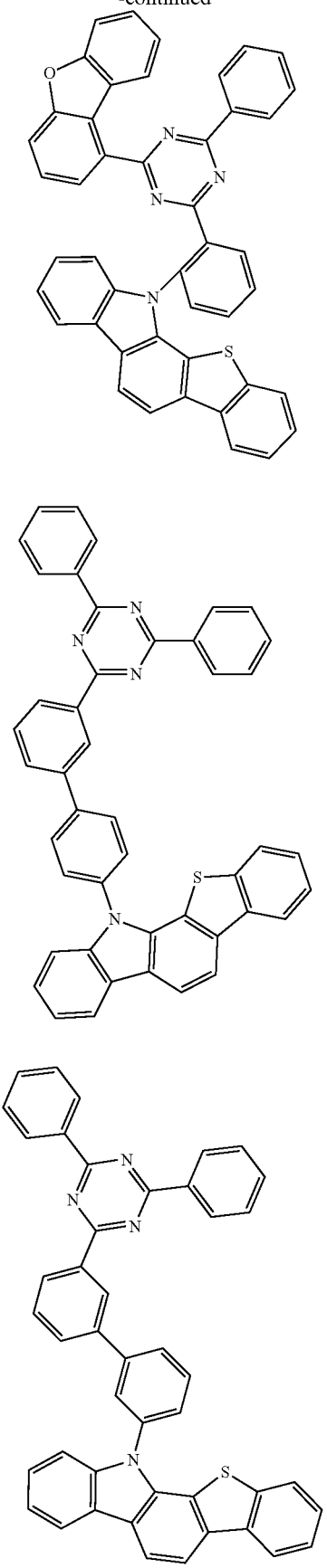
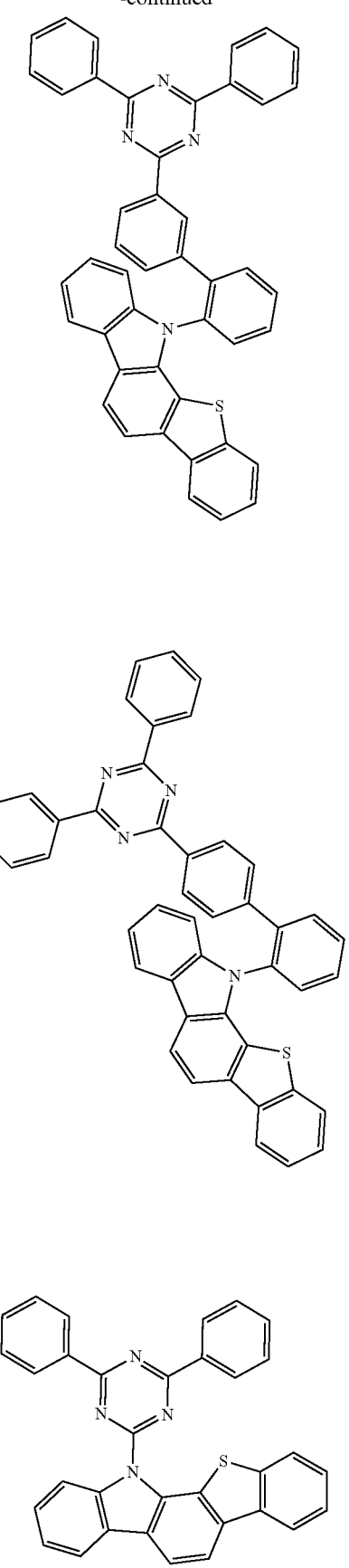

85
-continued
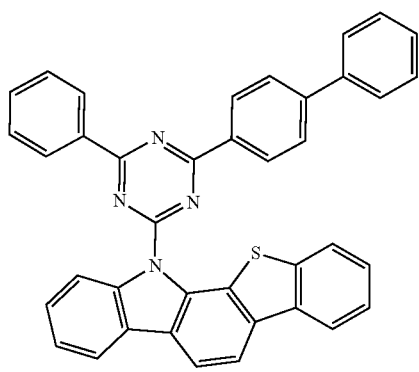
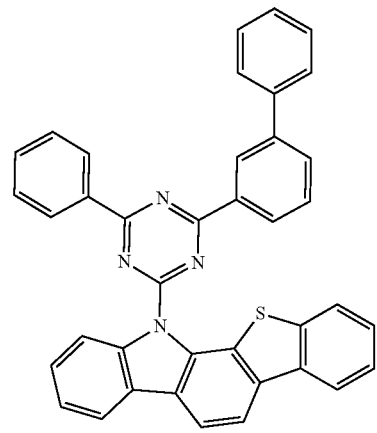
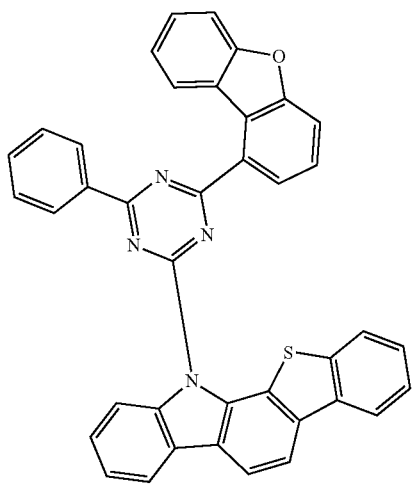
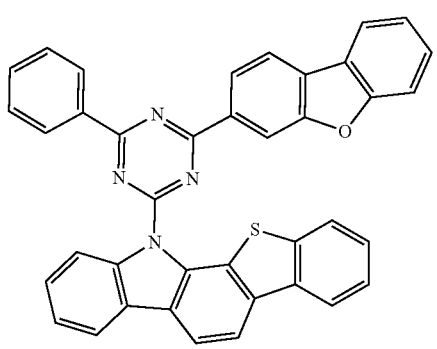
86
-continued
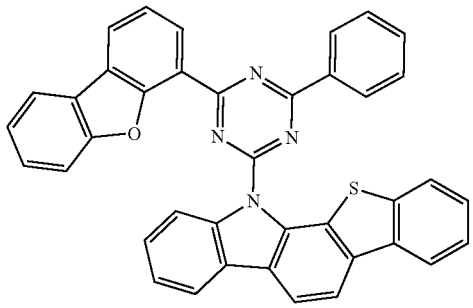
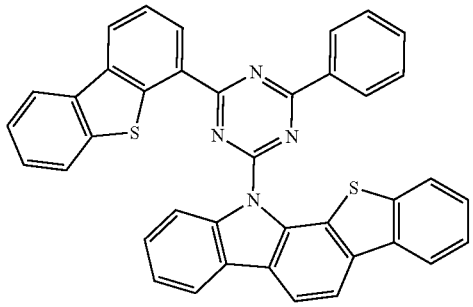
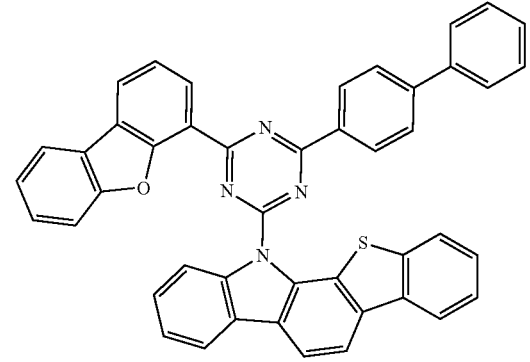
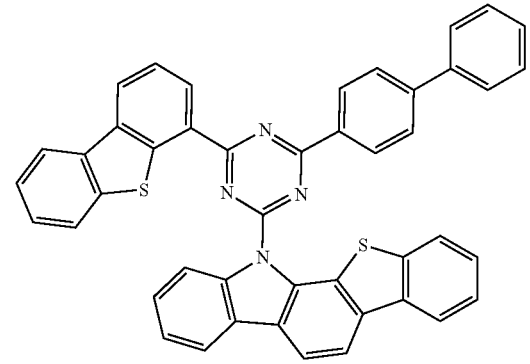

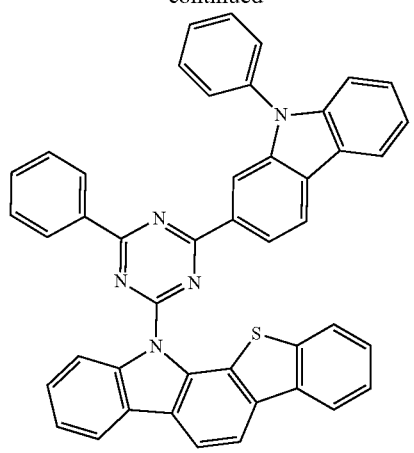
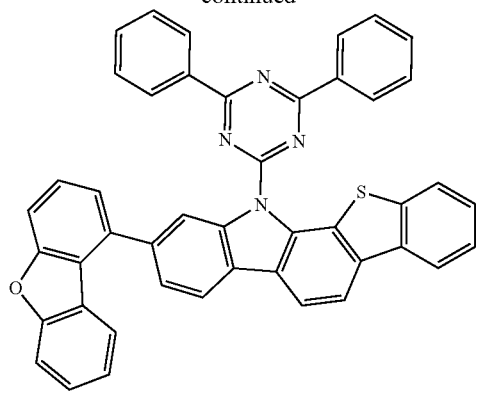
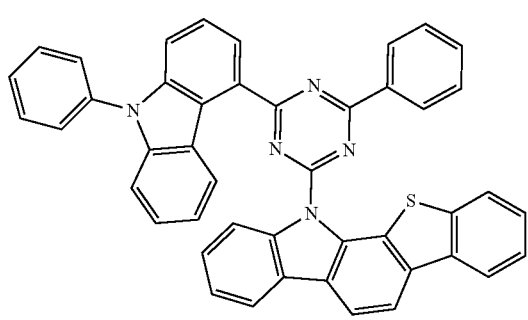
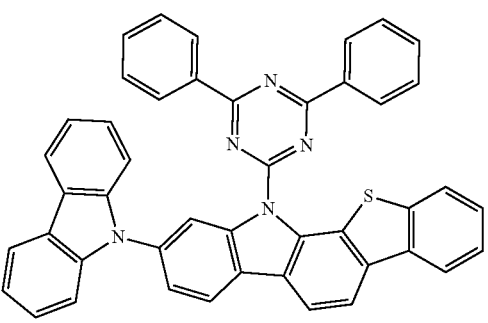
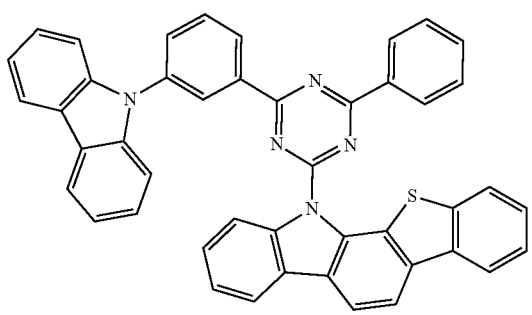
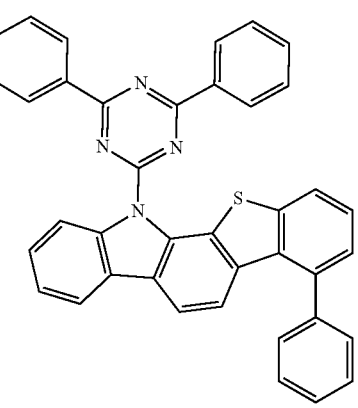
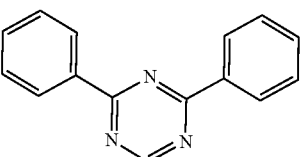
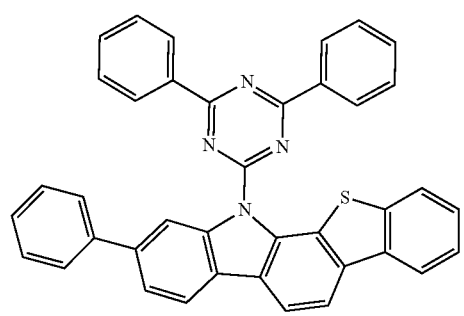
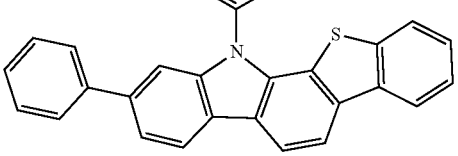

89
-continued
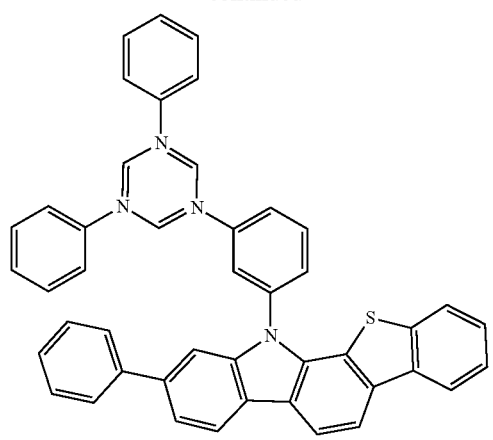
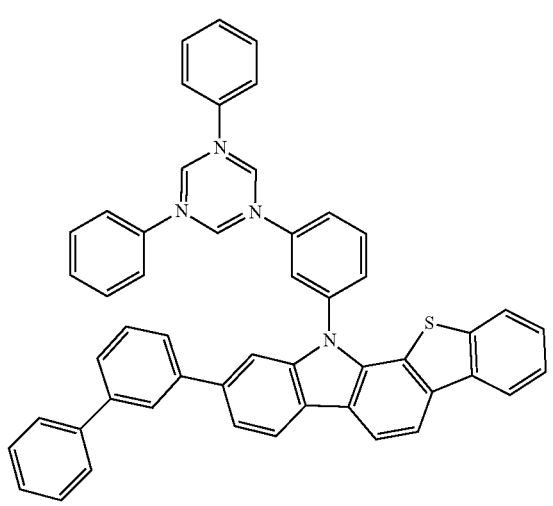
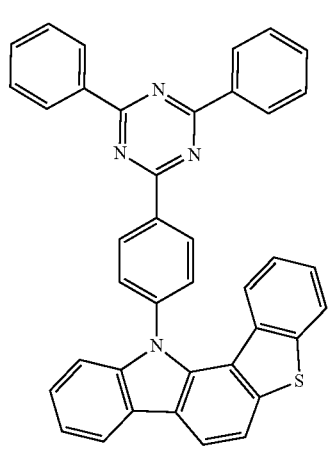
90
-continued
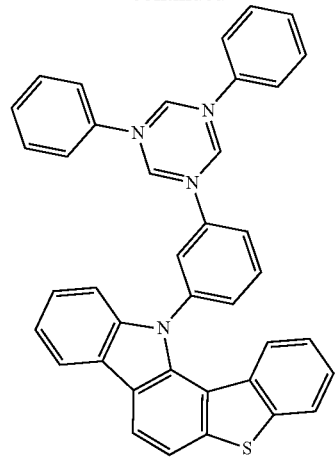
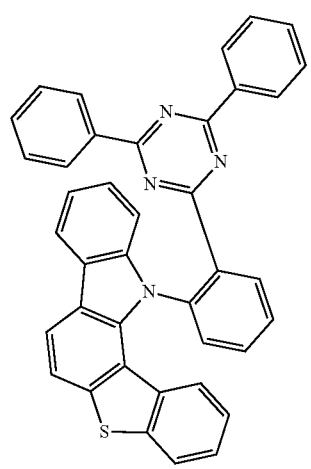
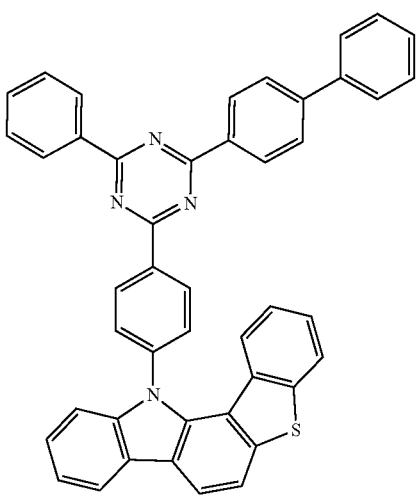

-continued
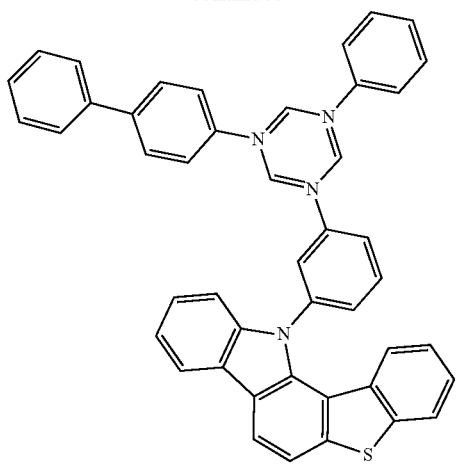
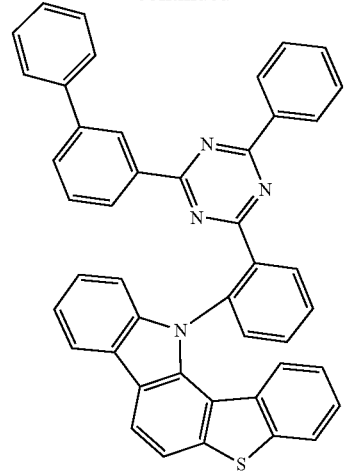
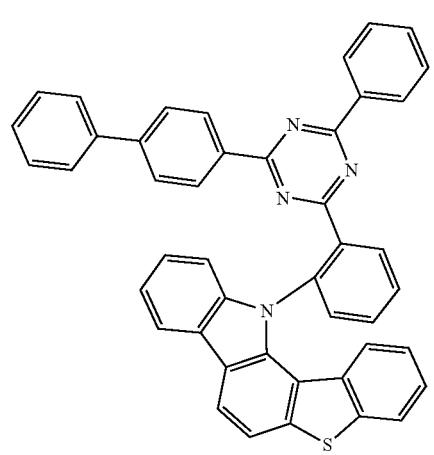
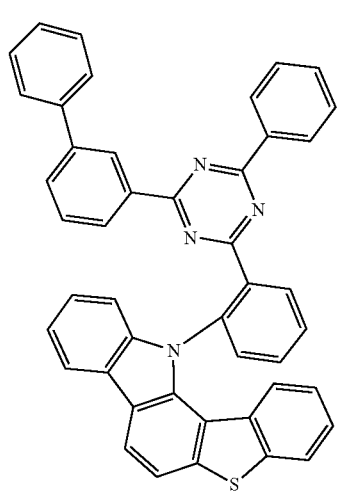
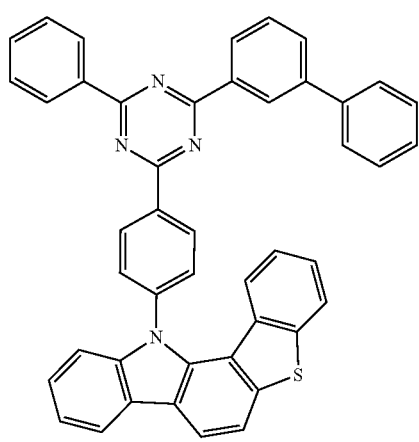
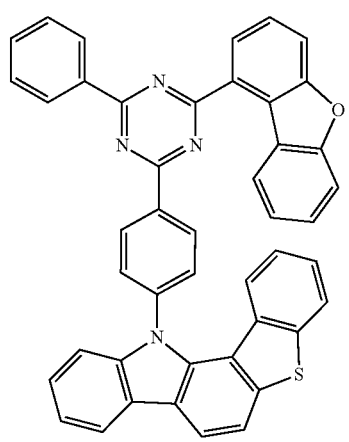

-continued
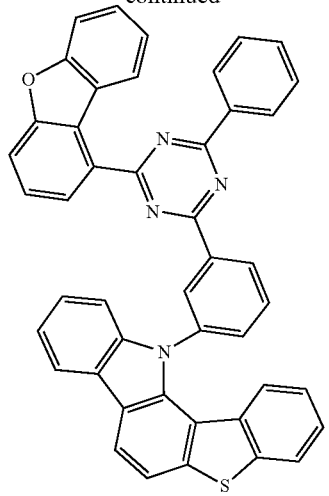
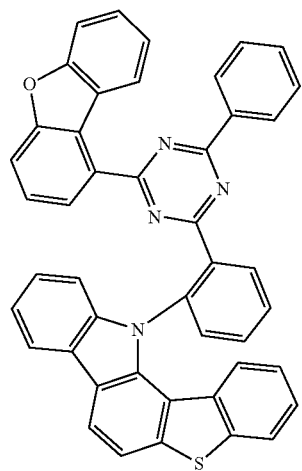
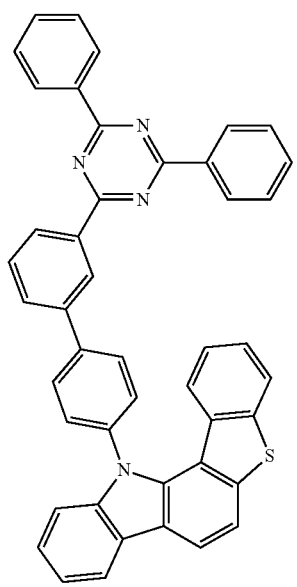
-continued
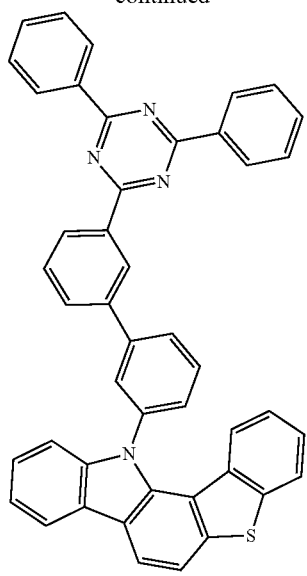
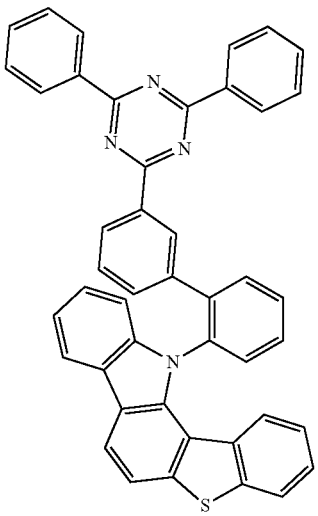
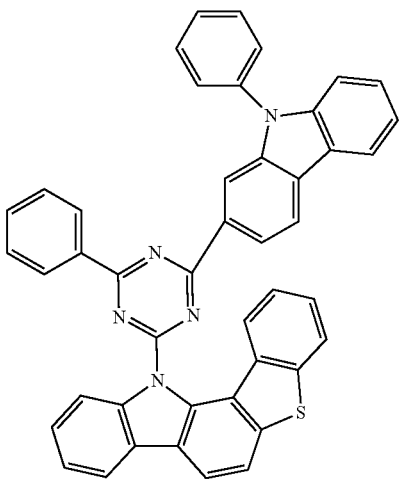

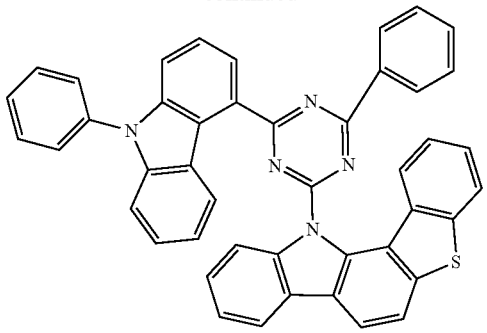
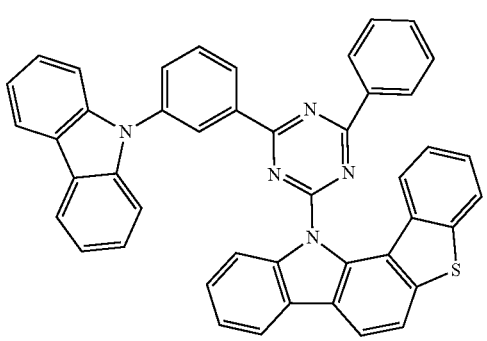
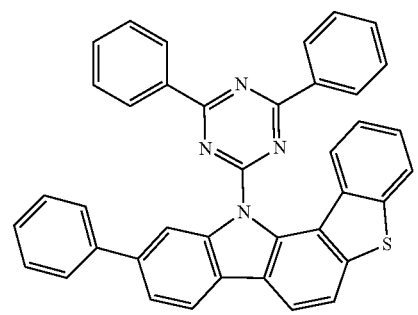
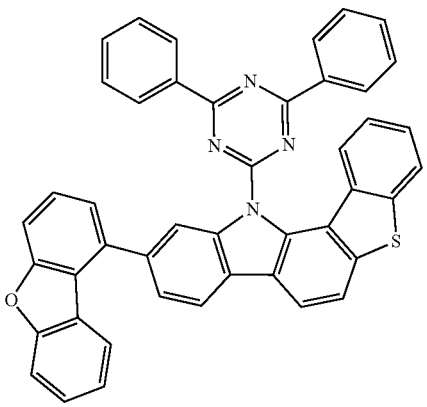
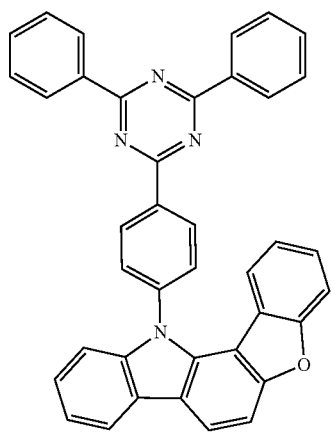
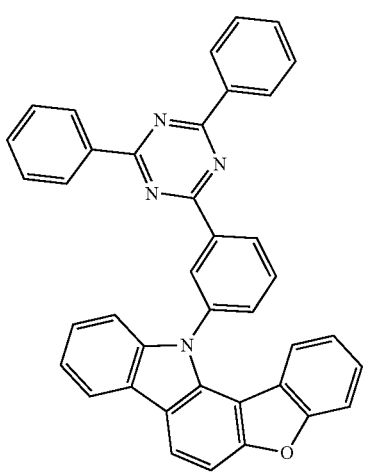
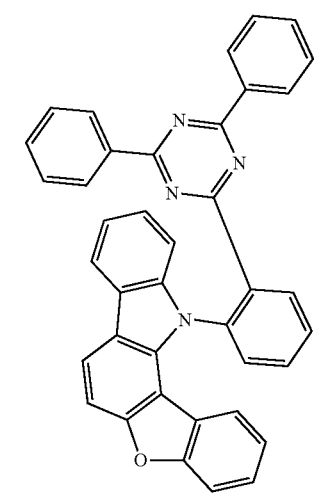

97
-continued
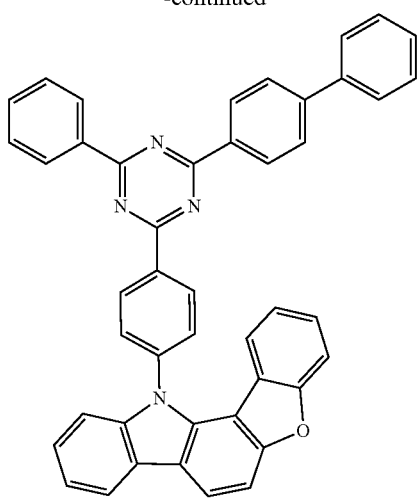
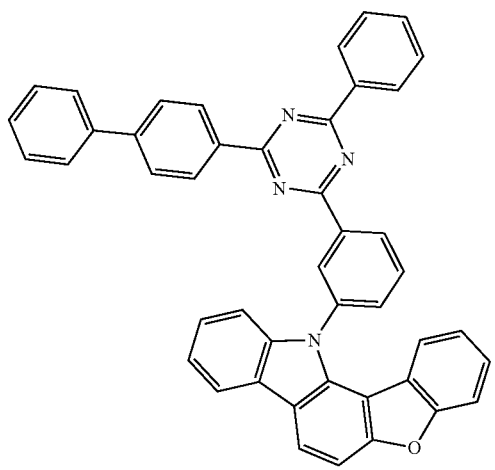
98
-continued
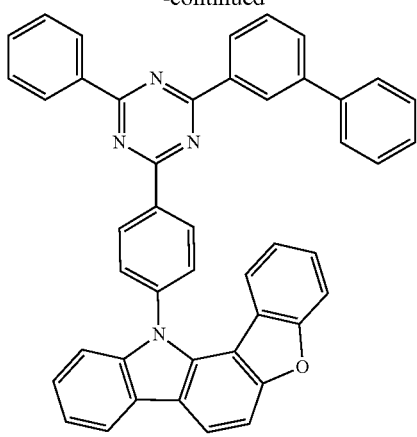
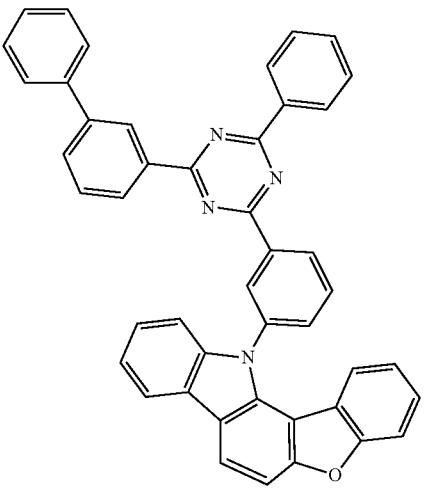
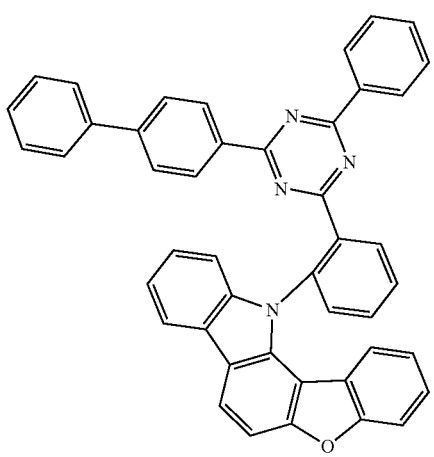
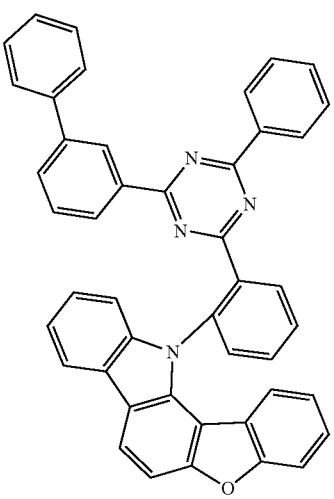

99
-continued
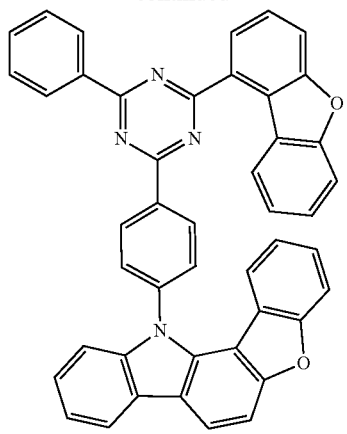
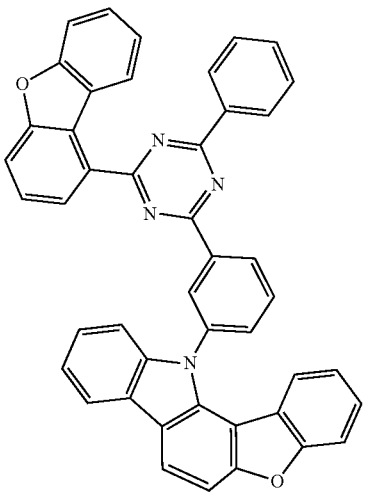
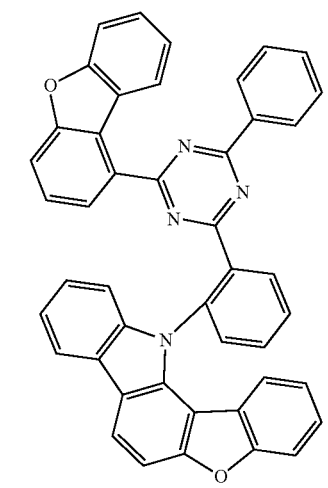
100
-continued
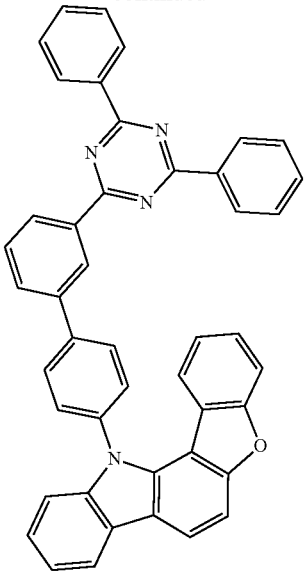
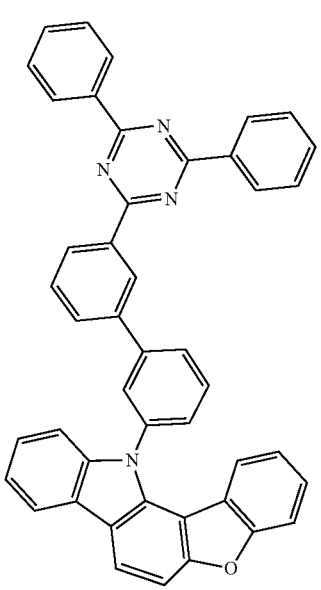
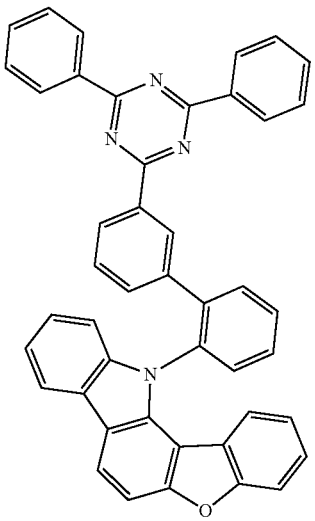

101
-continued
102
-continued
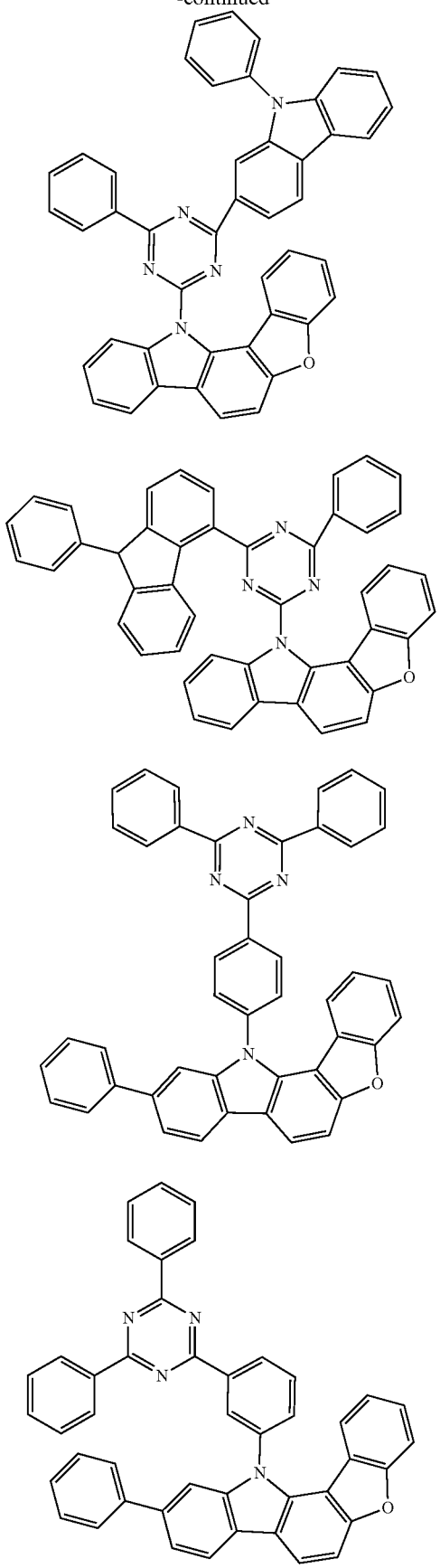
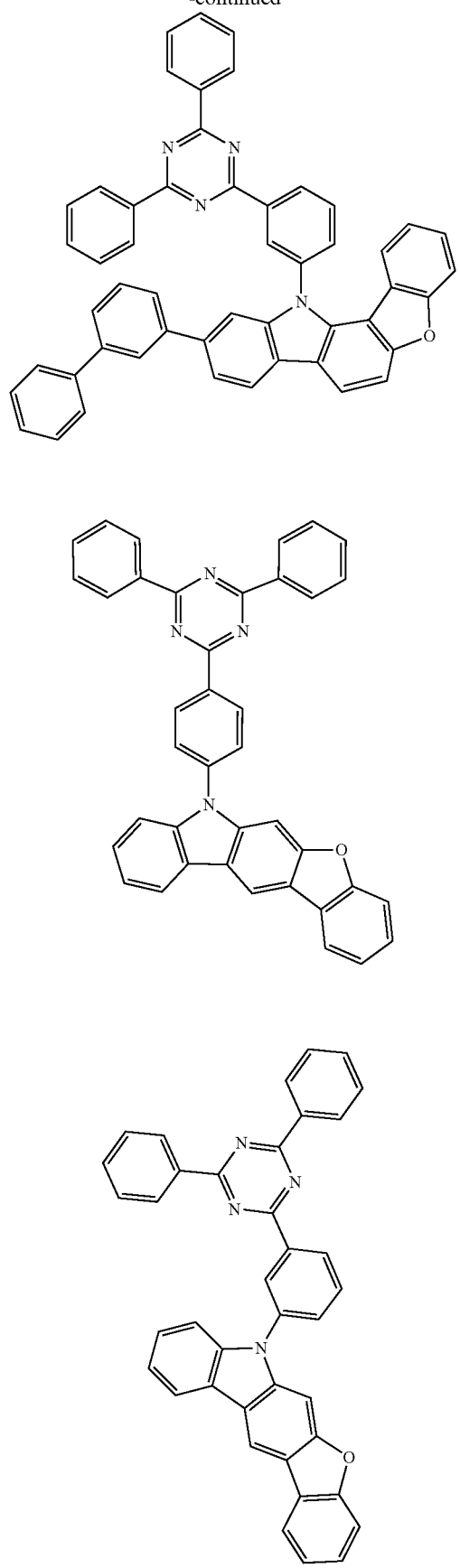

103
-continued
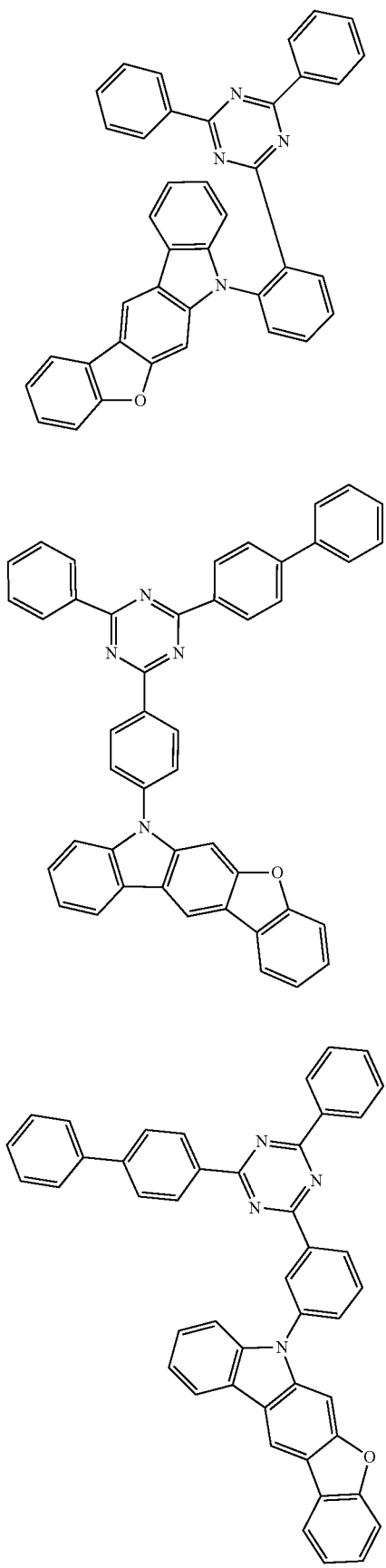
104
-continued
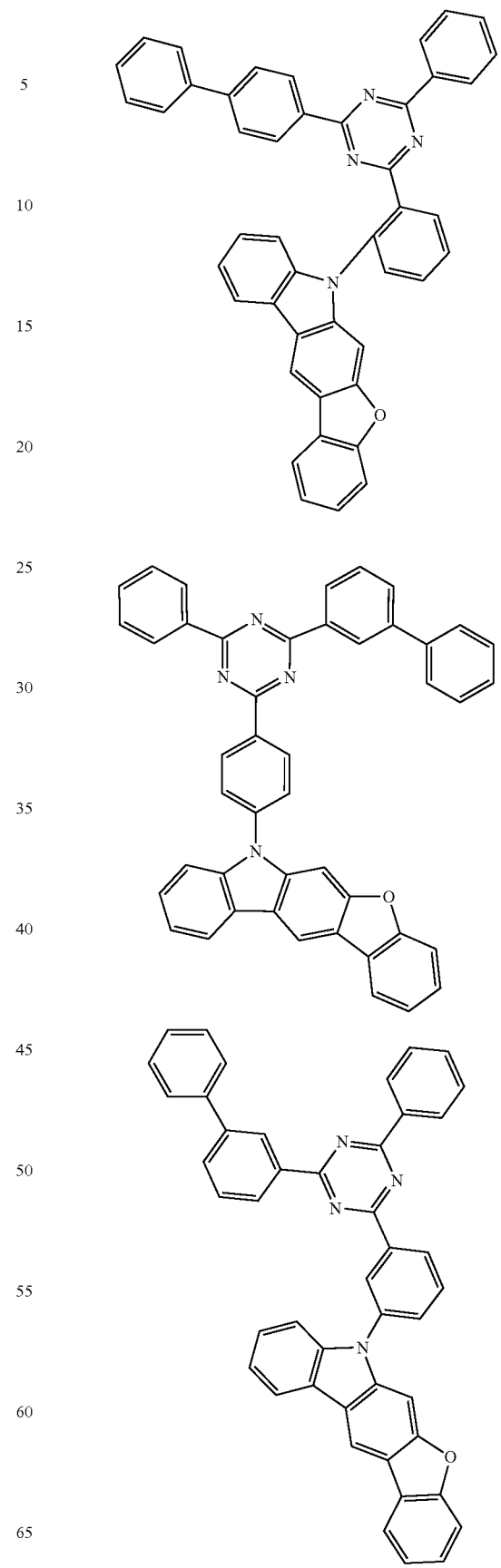

105
-continued
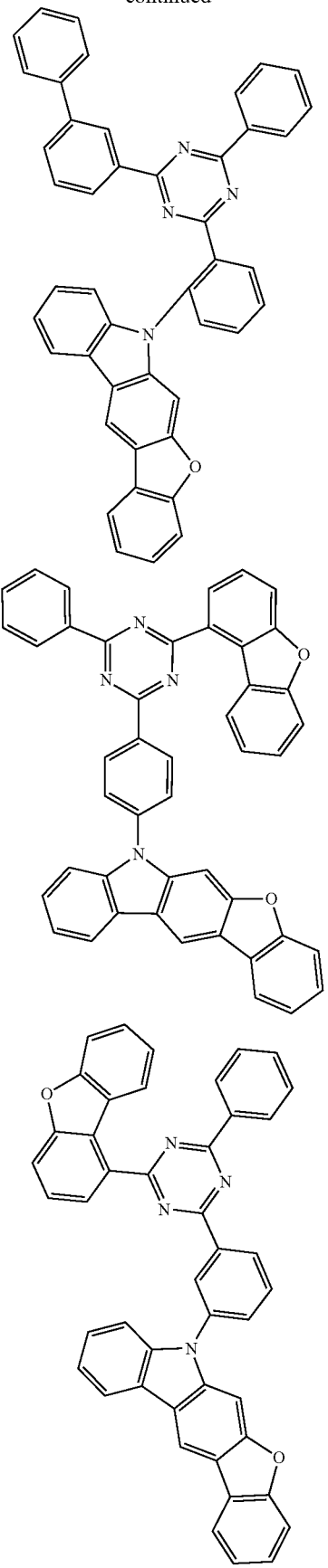
106
-continued
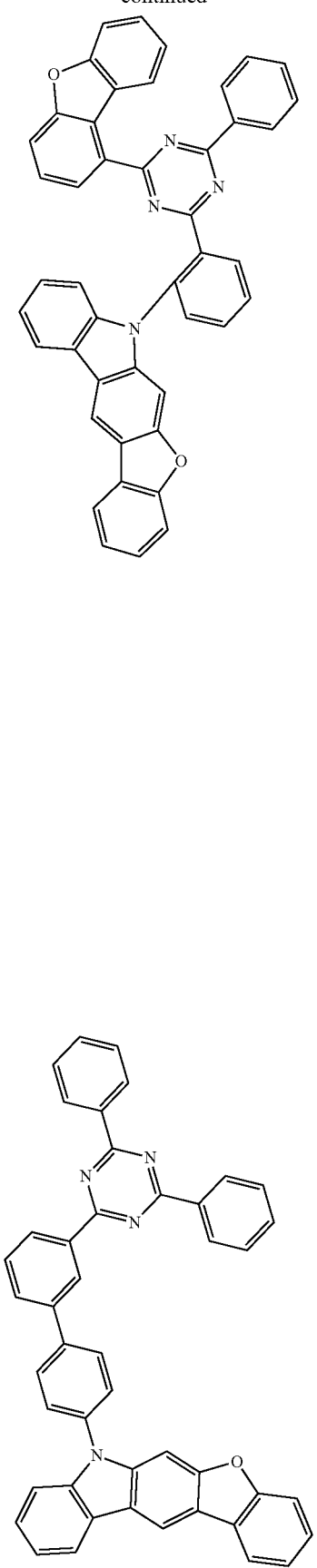

107
-continued
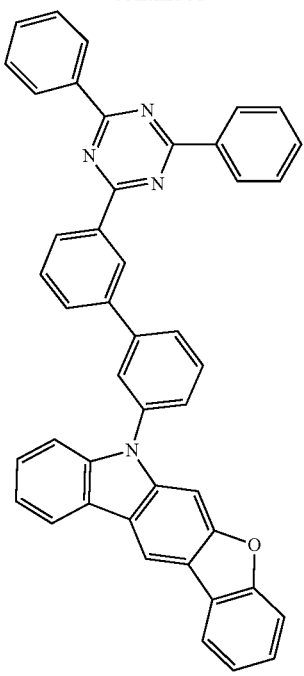
108
-continued
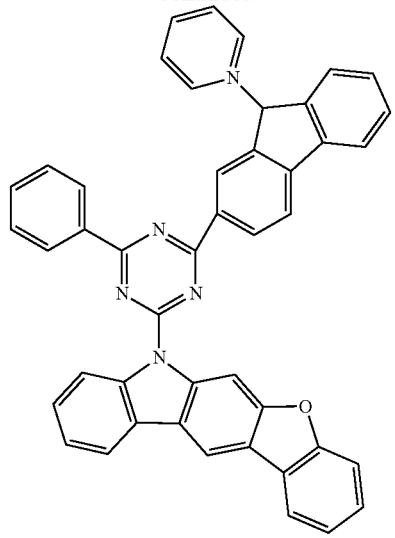
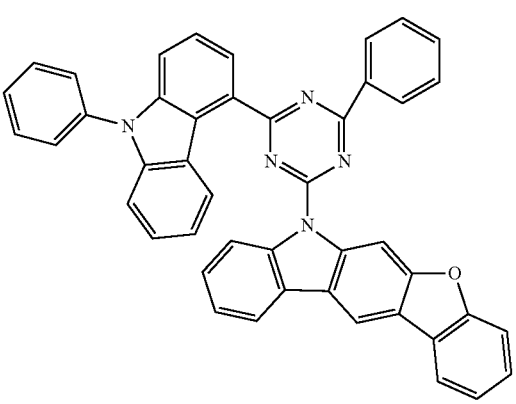
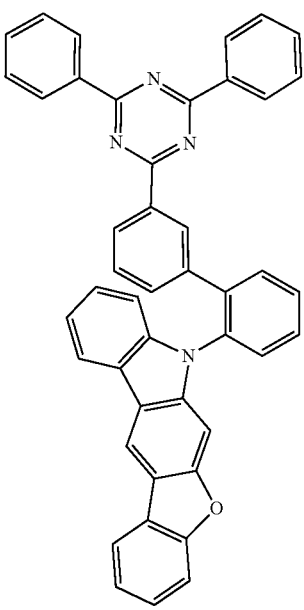

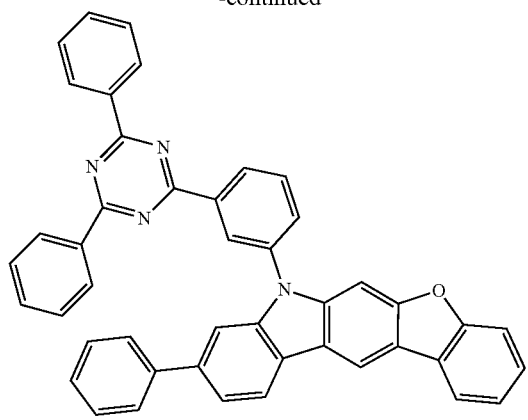
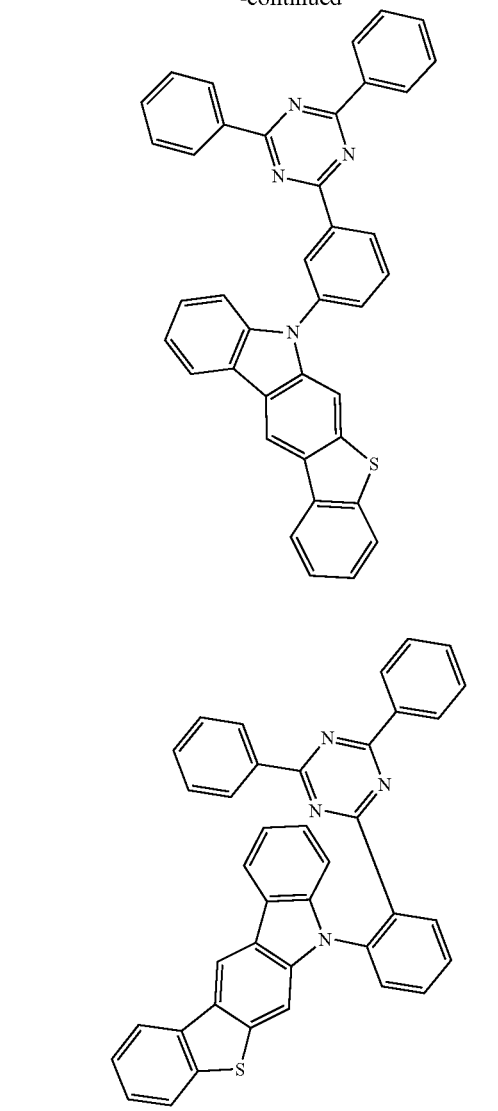
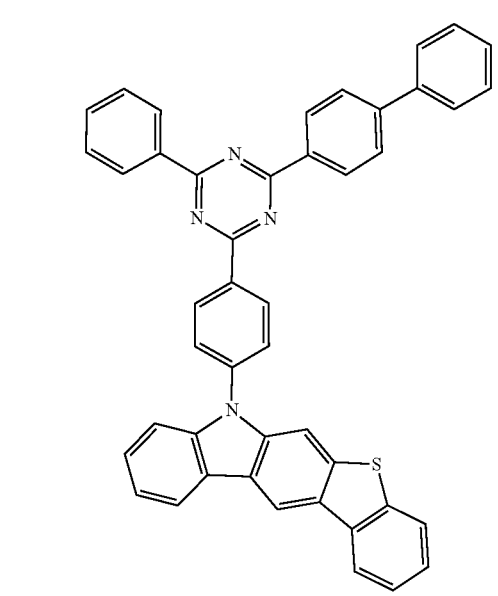

111
-continued
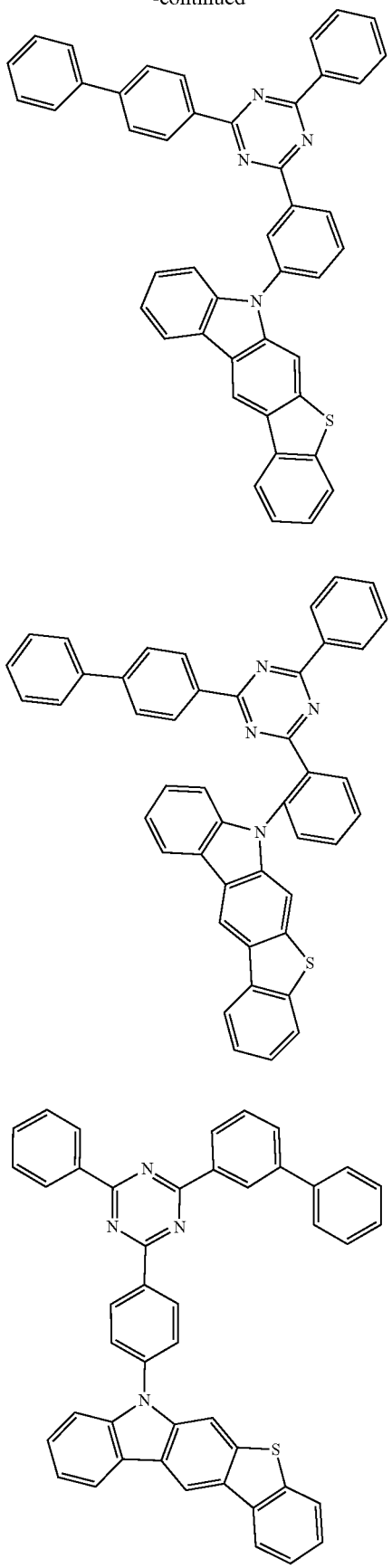
112
-continued
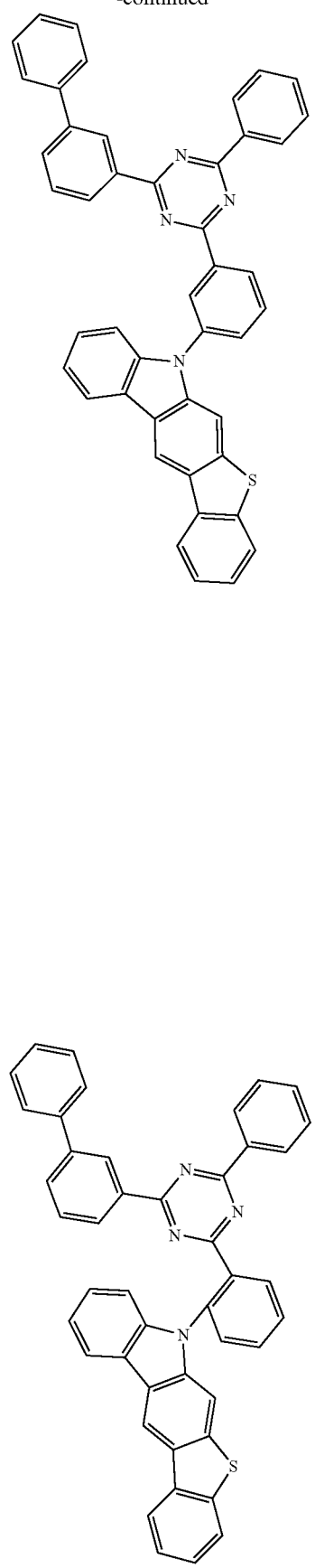

113
-continued
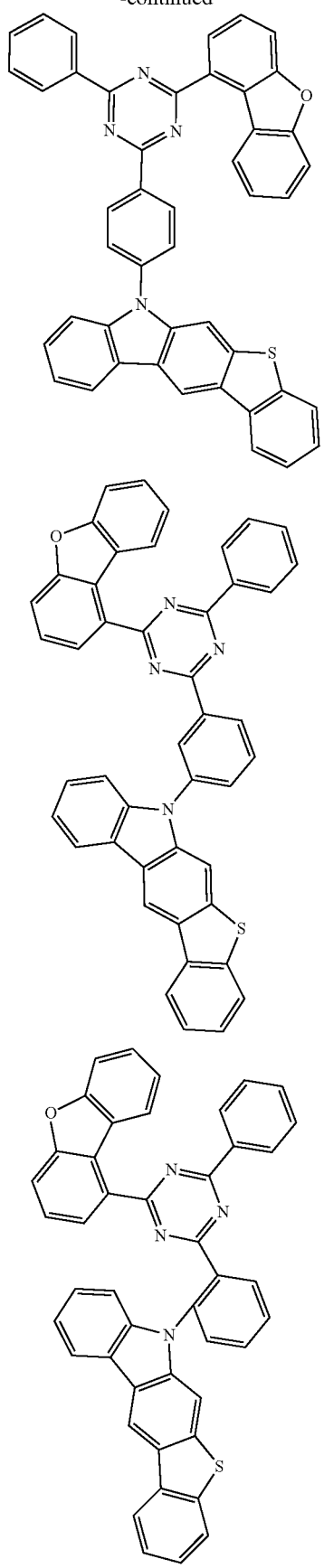
114
-continued
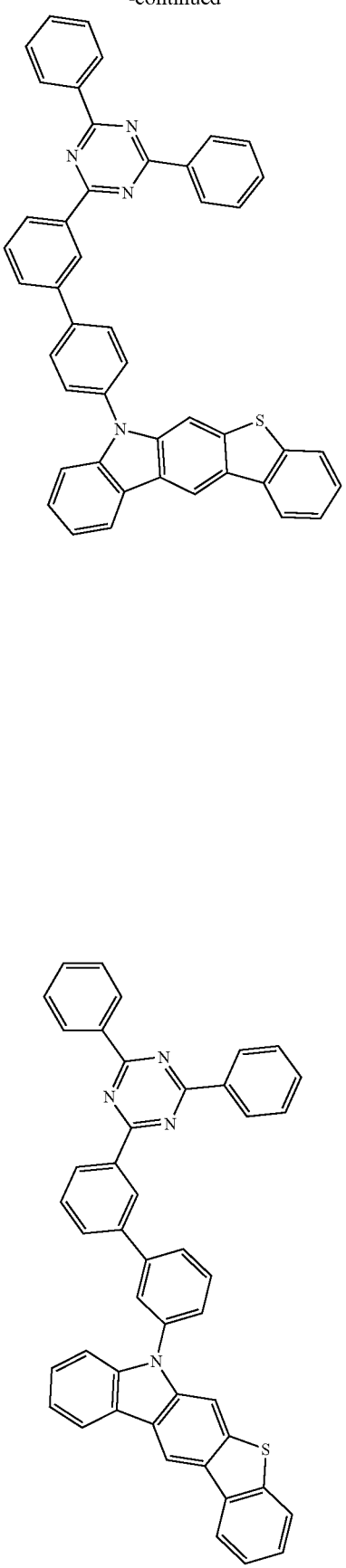

115
-continued
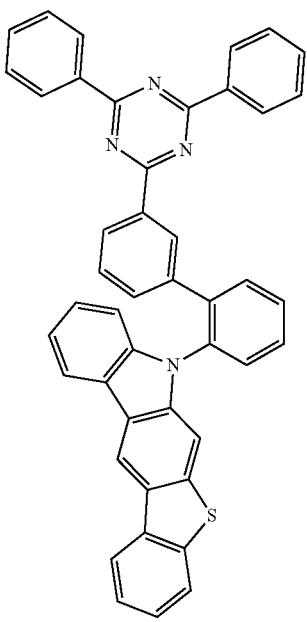
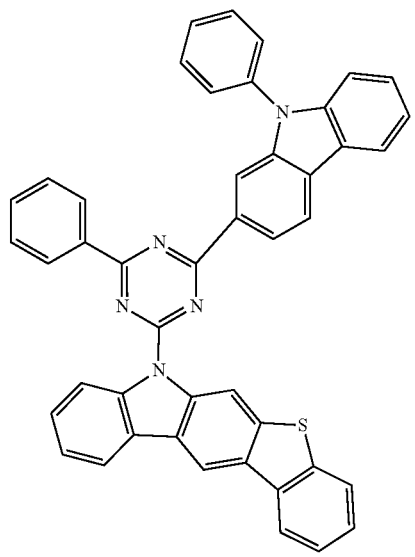
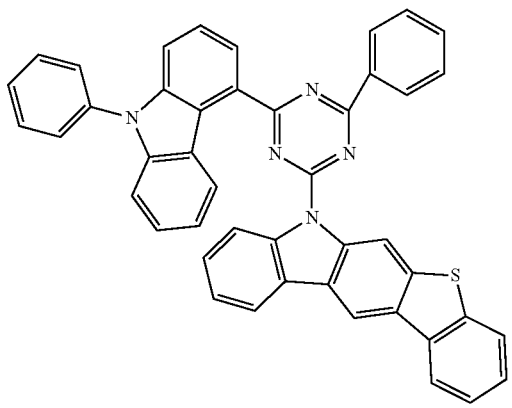
116
-continued
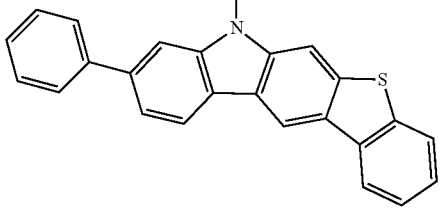
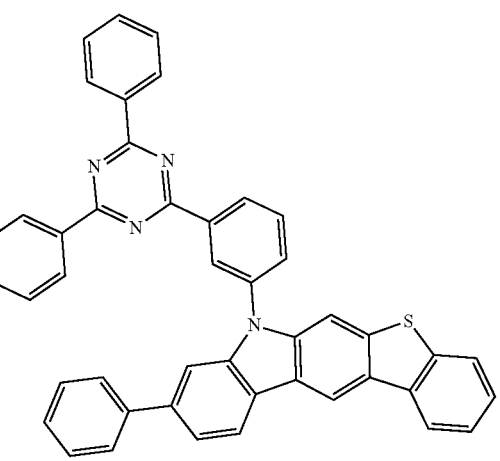
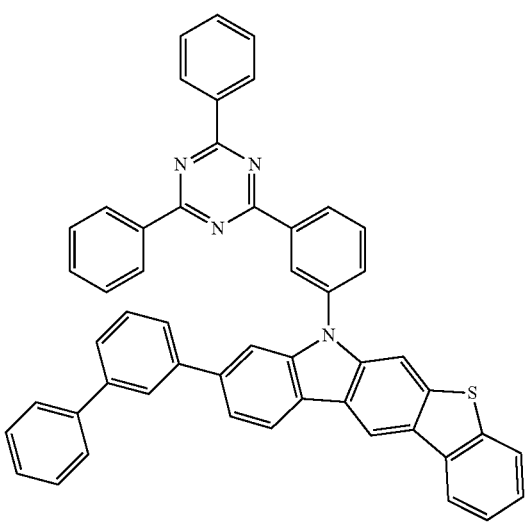

117
-continued
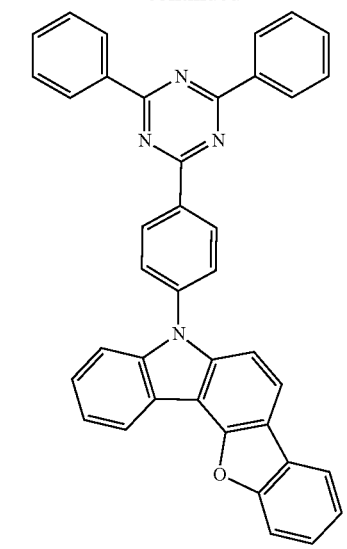
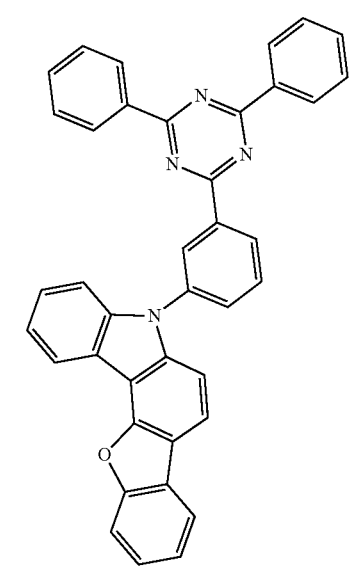
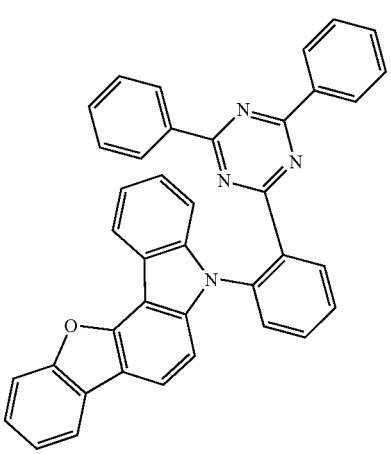
118
-continued
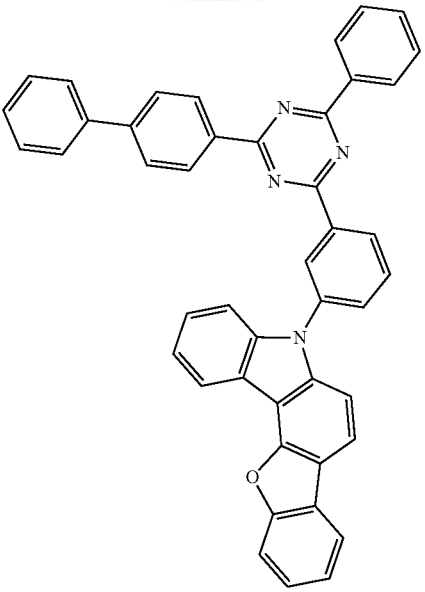
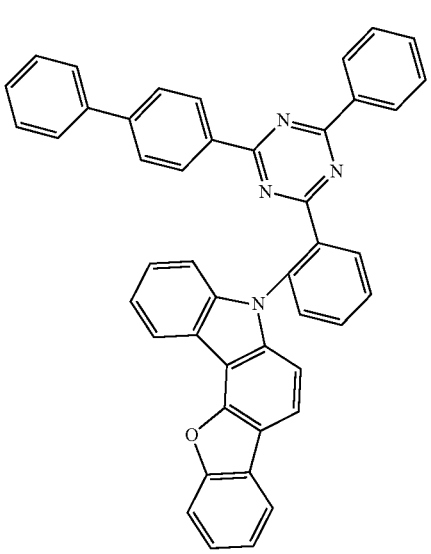
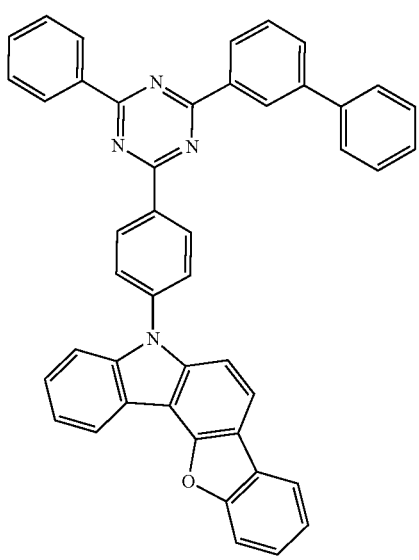

119
-continued
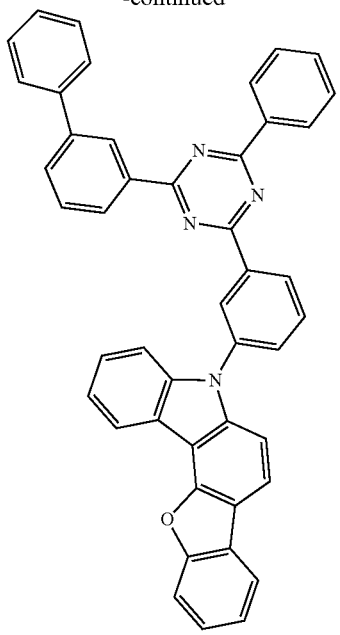
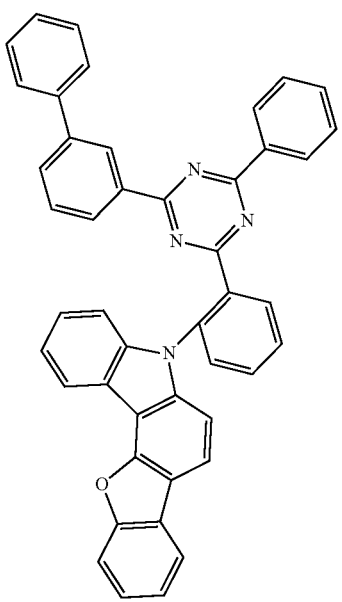
120
-continued
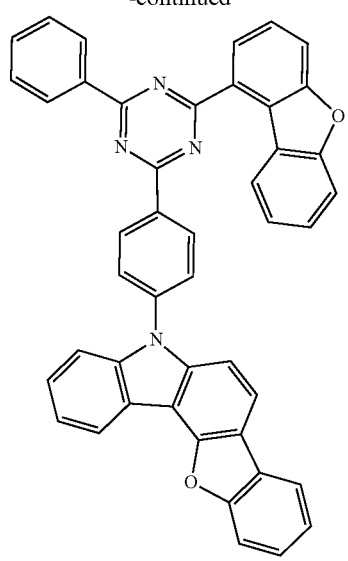
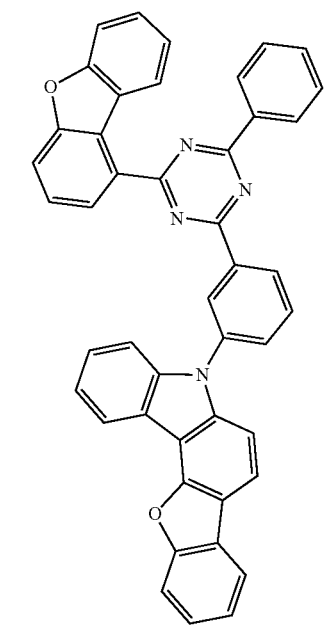

121
-continued
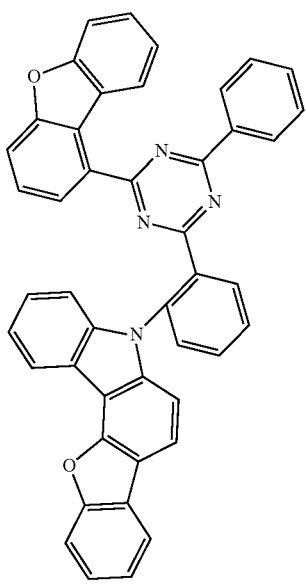
122
-continued
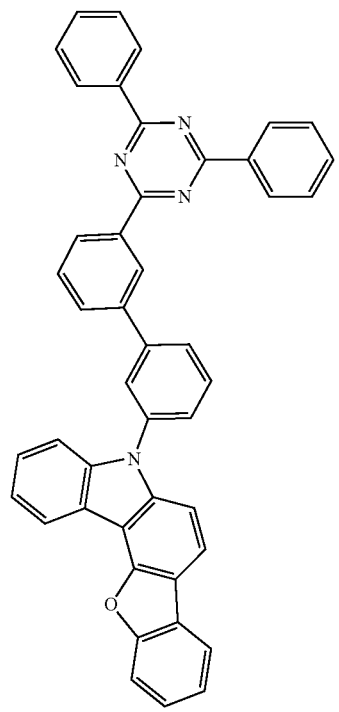
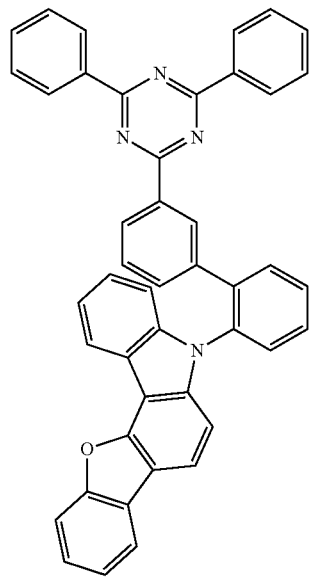
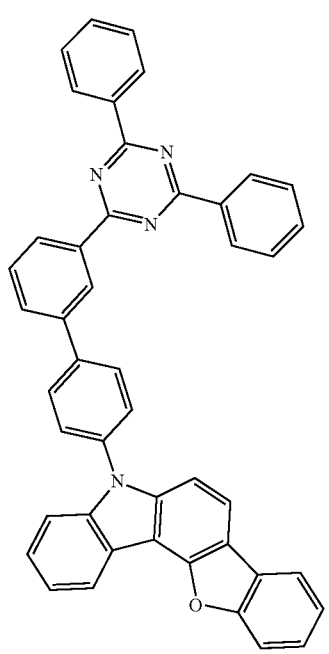
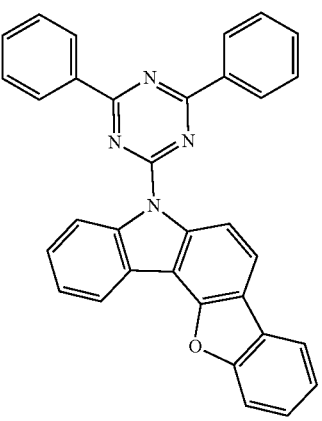

123
-continued
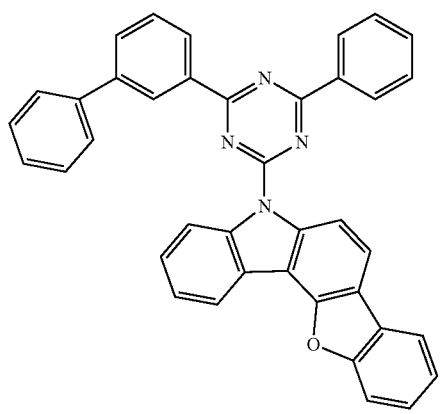
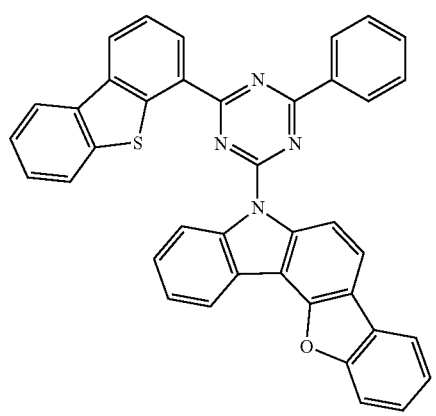
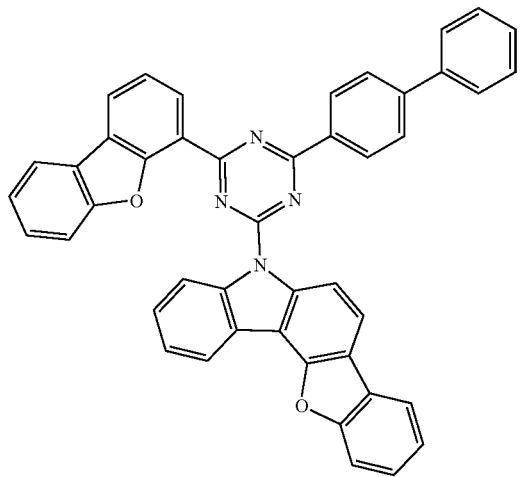
124
-continued
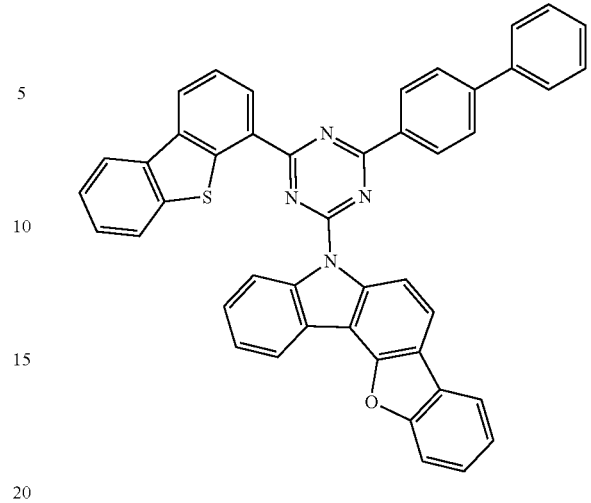
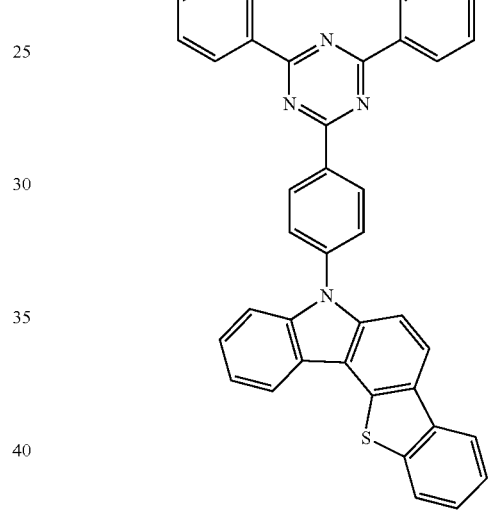
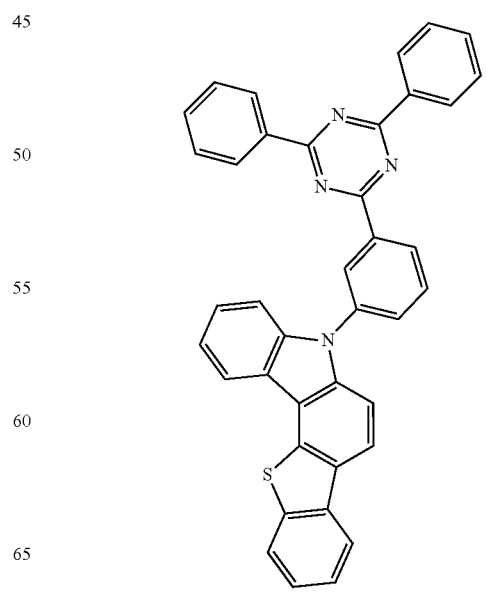

125
-continued
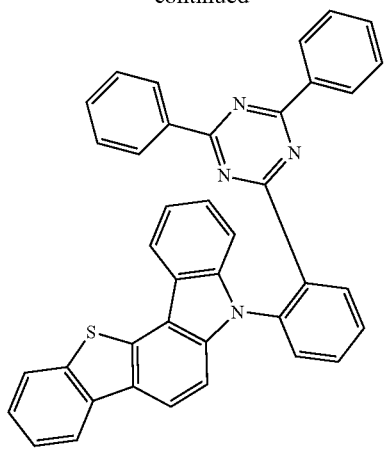
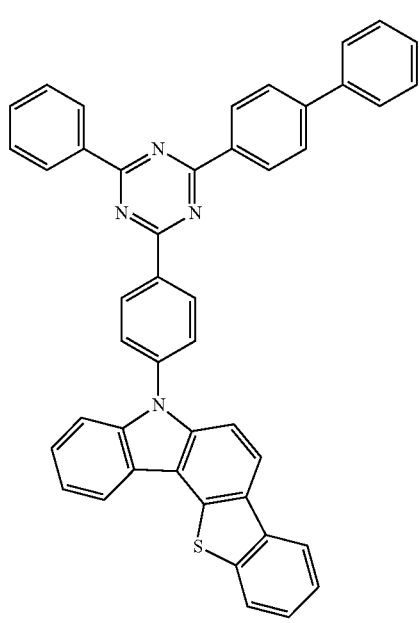
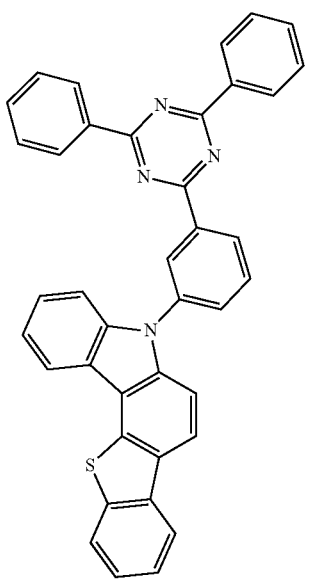
126
-continued
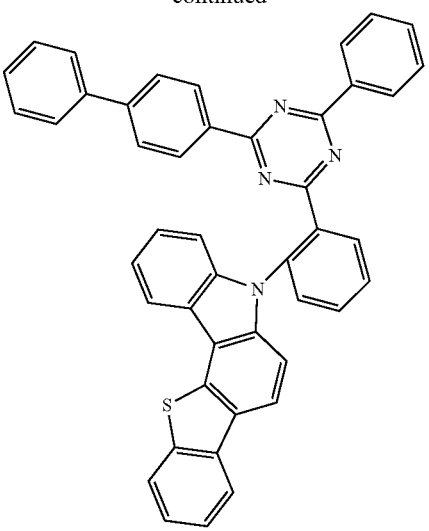
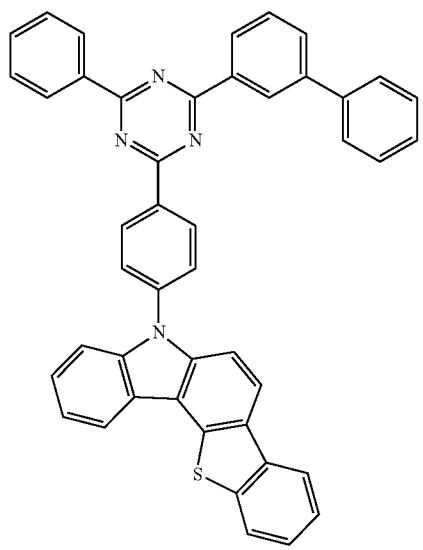
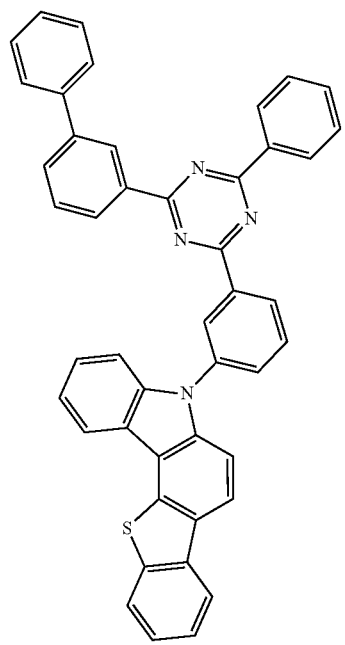

127
-continued
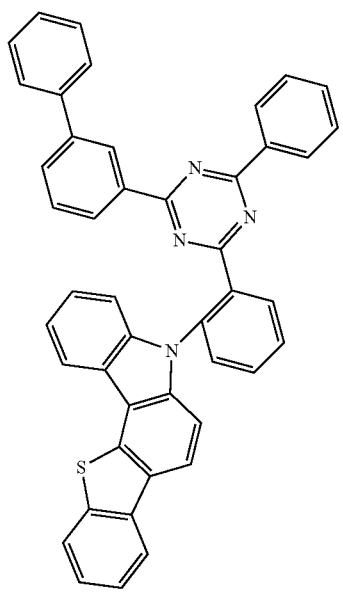
128
-continued
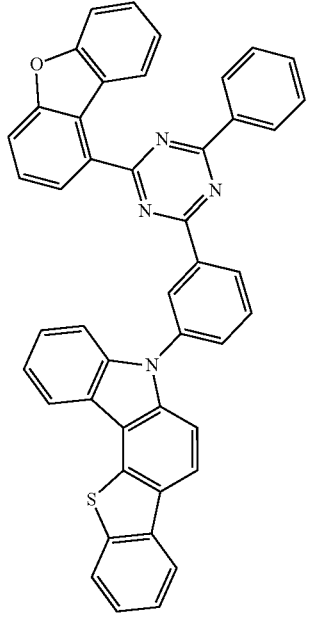
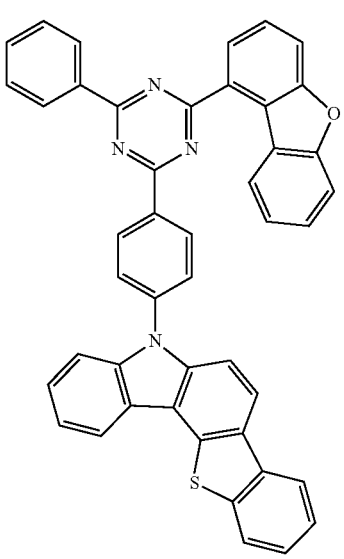
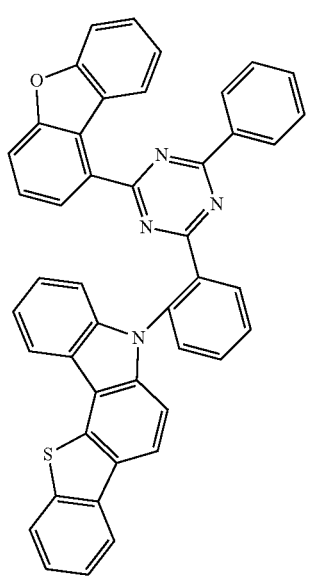

129
-continued
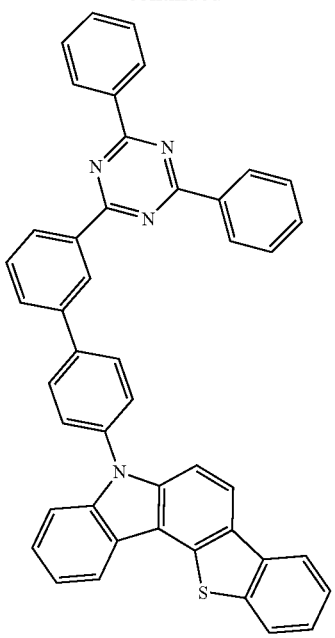
130
-continued
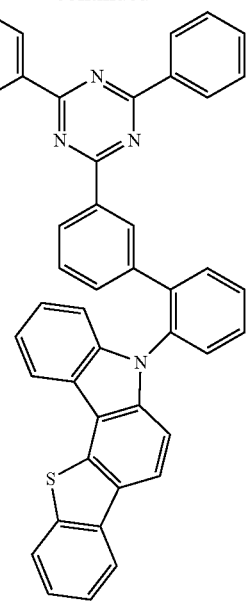
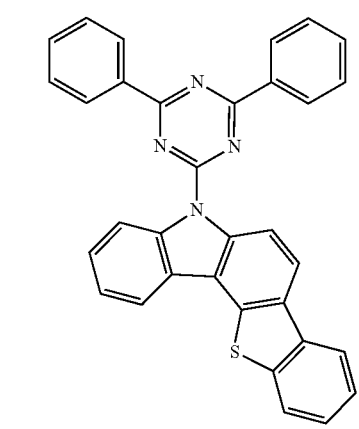
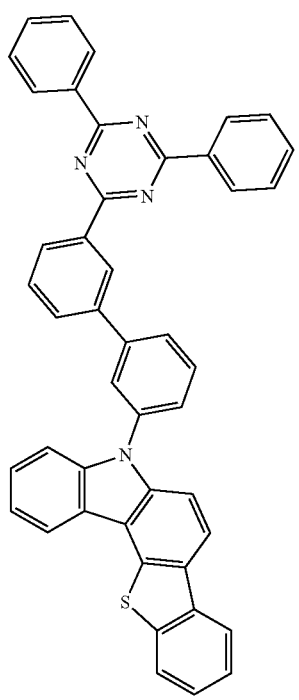
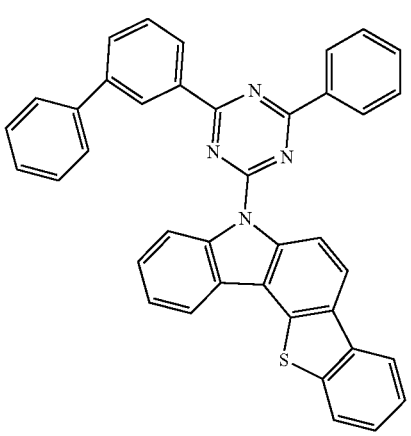

131
-continued
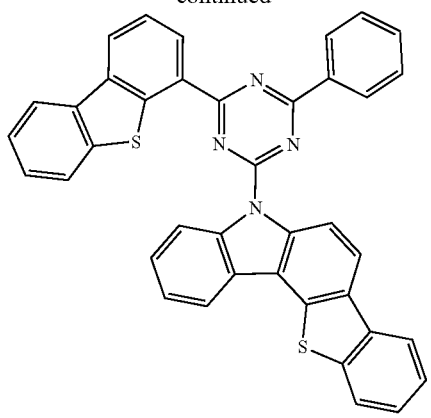
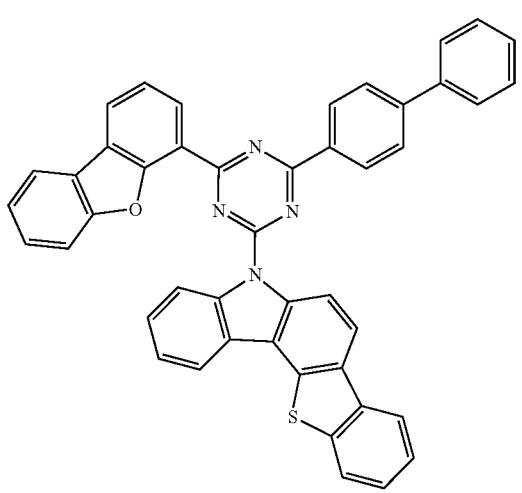
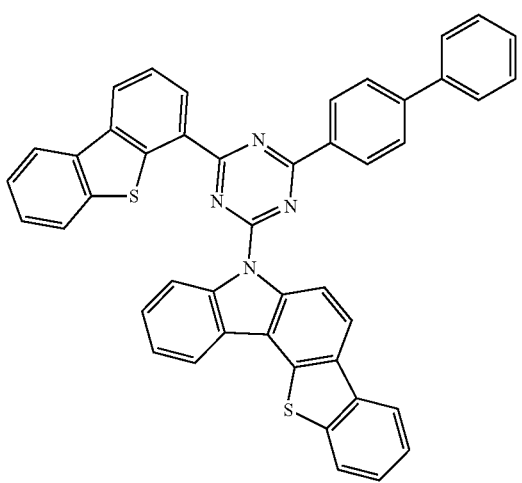
132
-continued
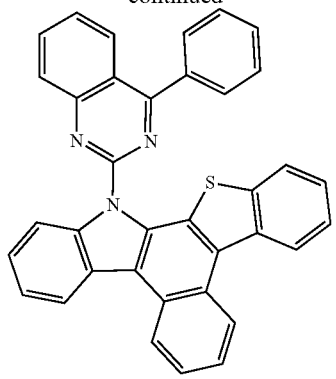
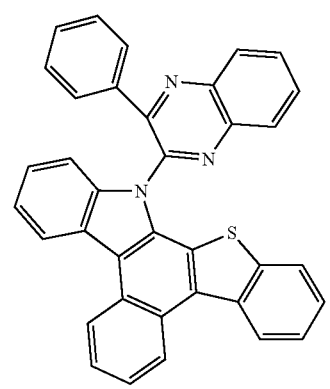
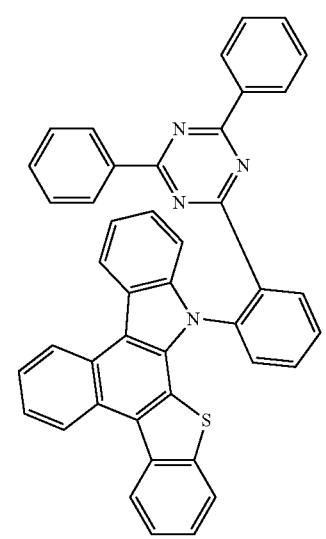

133
-continued
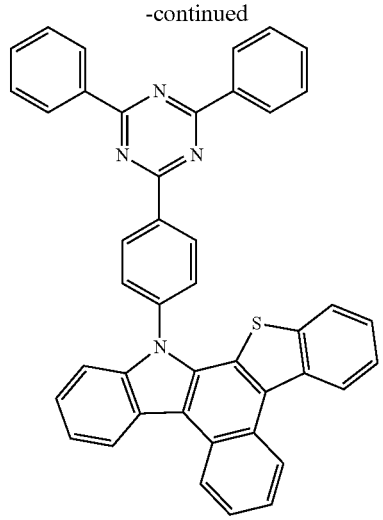
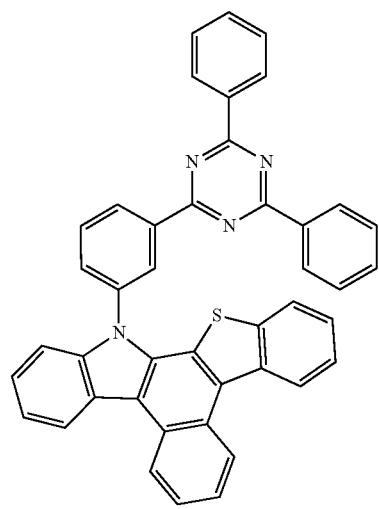
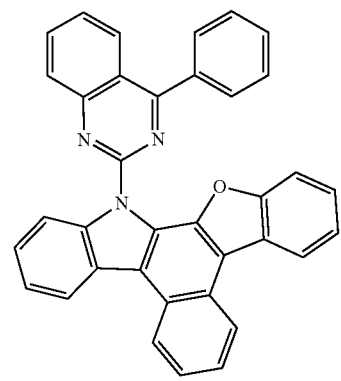
134
-continued
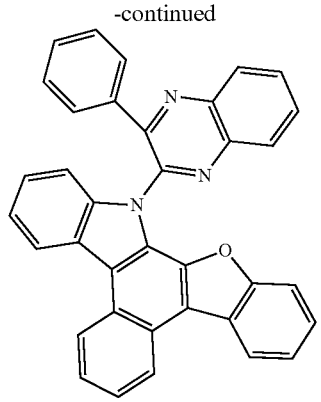
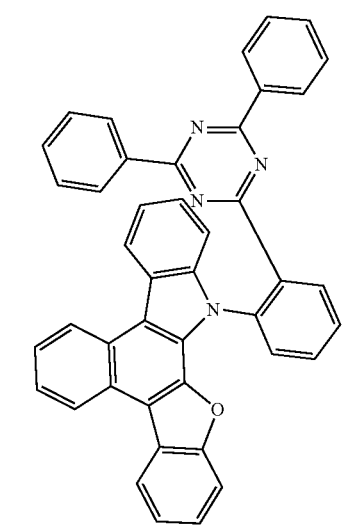
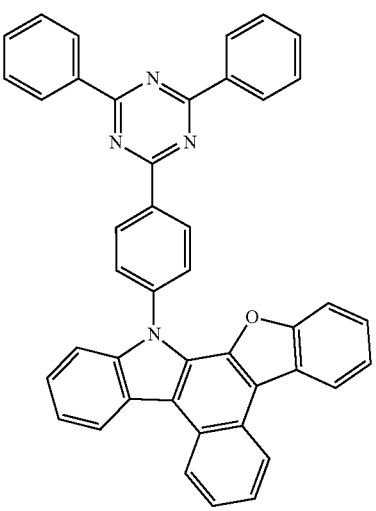

135
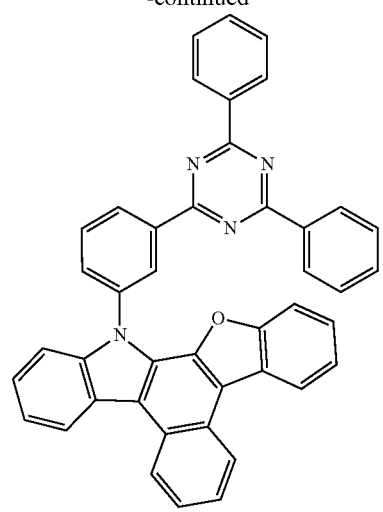
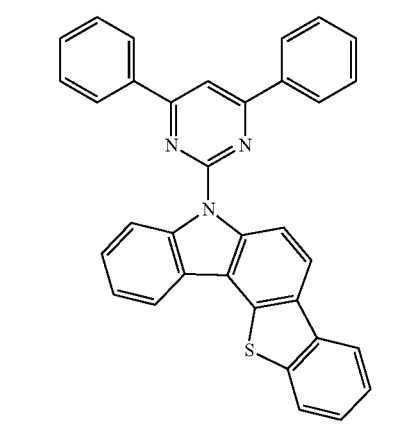
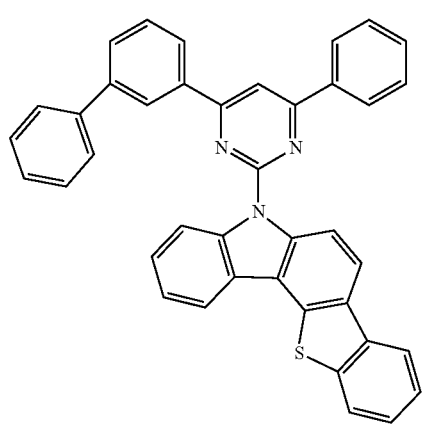
136
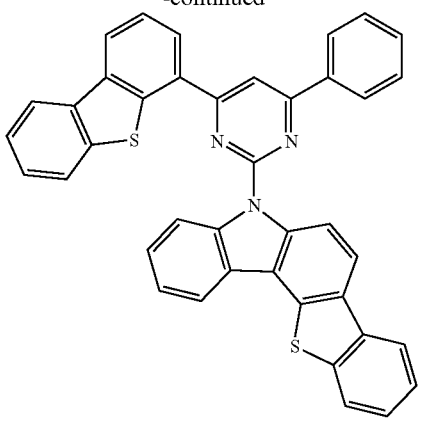
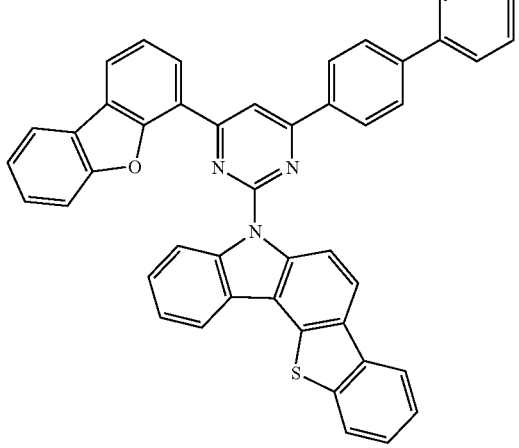
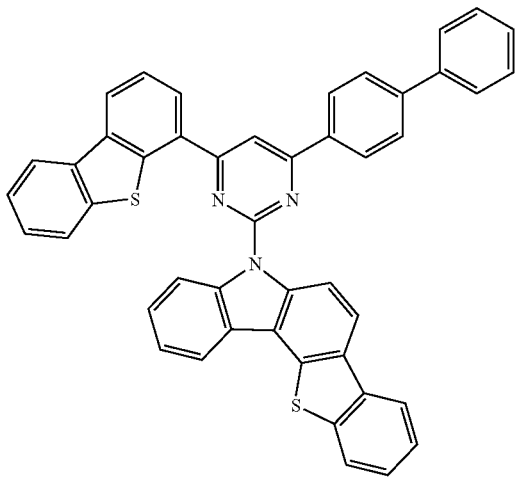
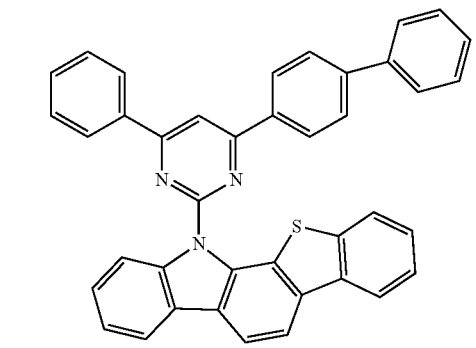

137
-continued
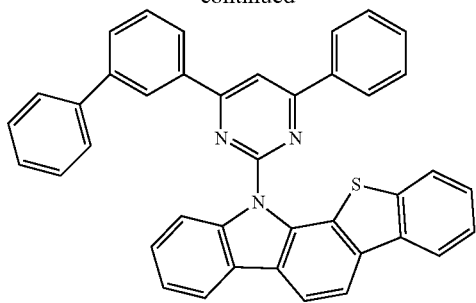
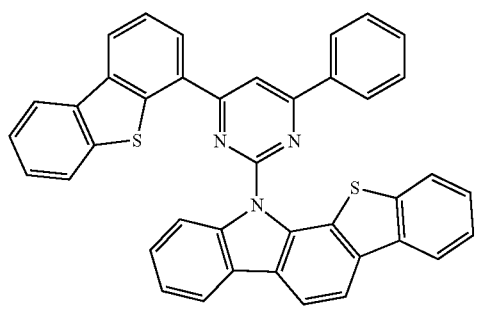
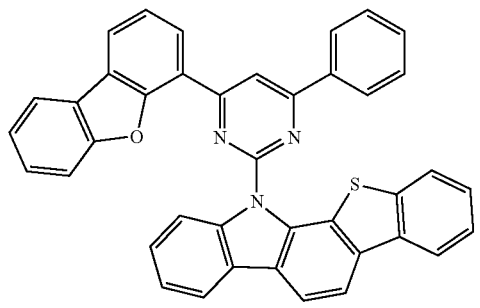
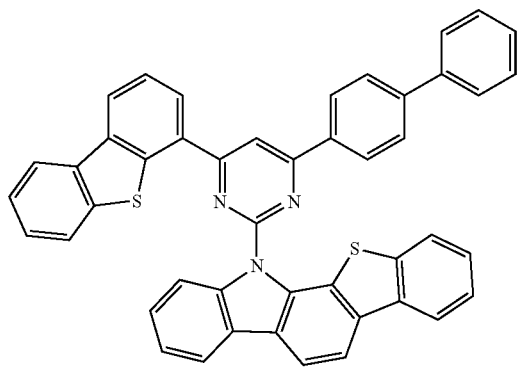
138
-continued
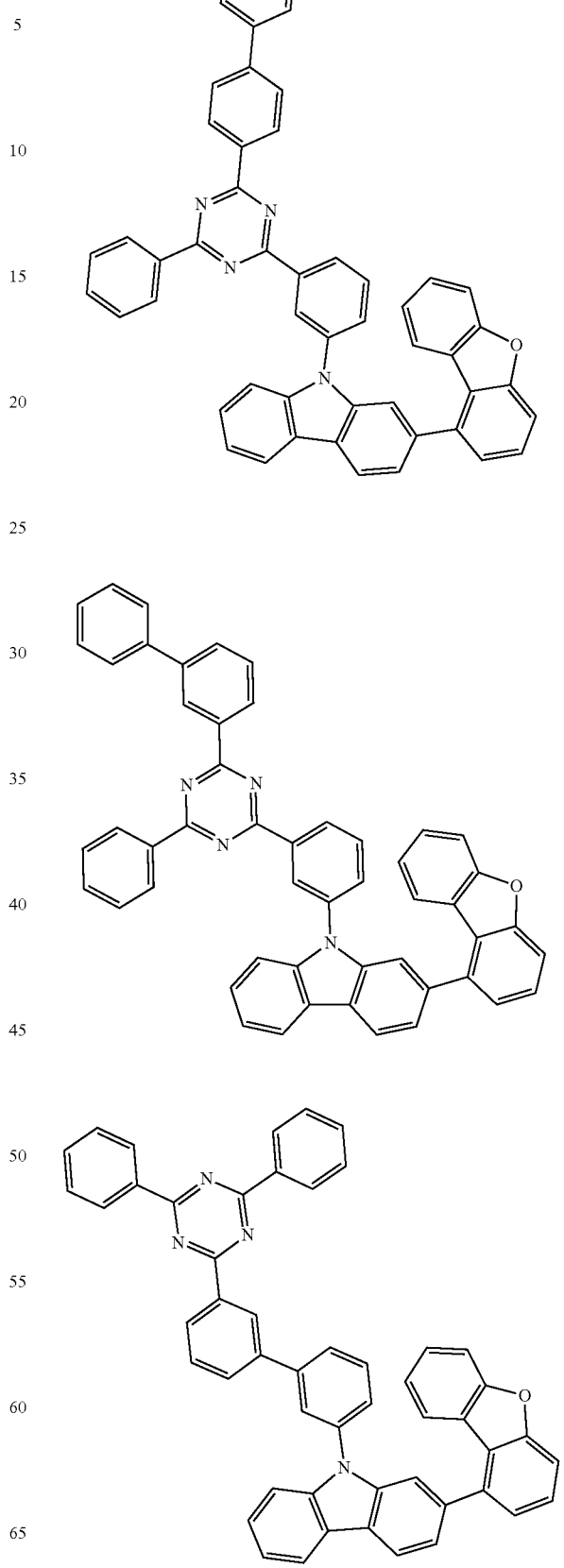

139
-continued
140
-continued
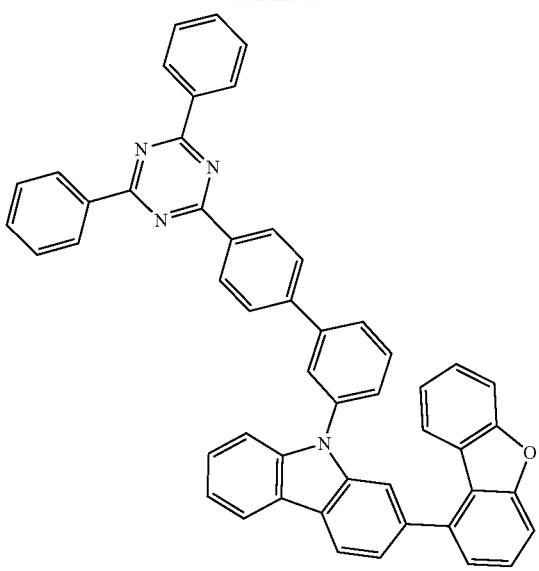
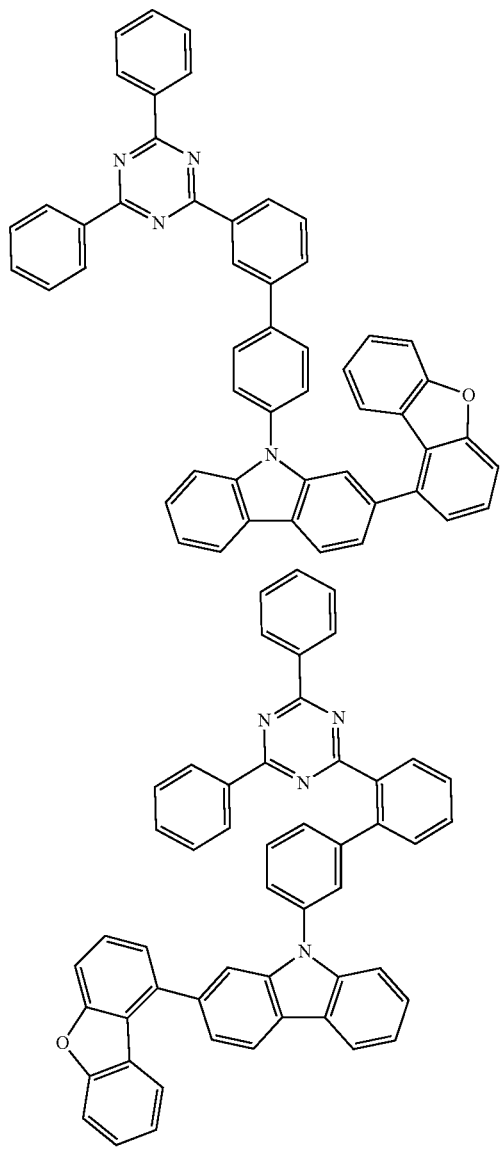
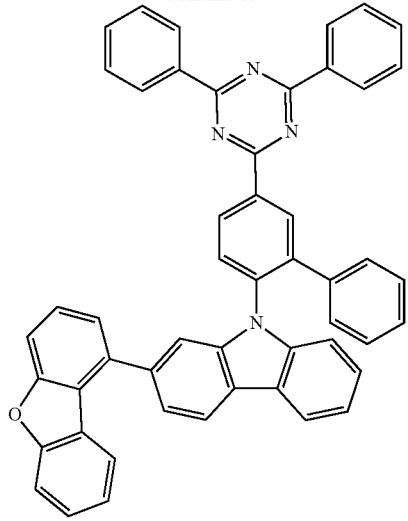
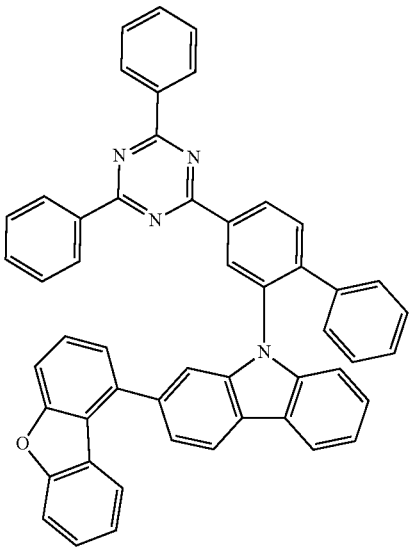
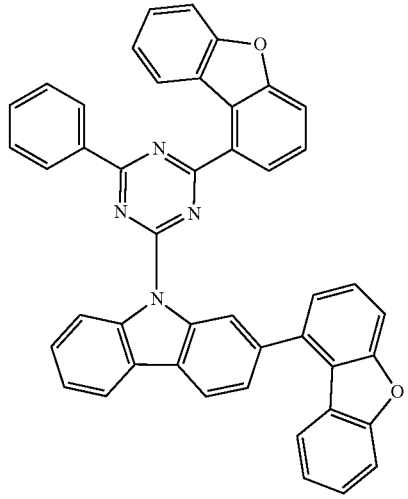

141
-continued
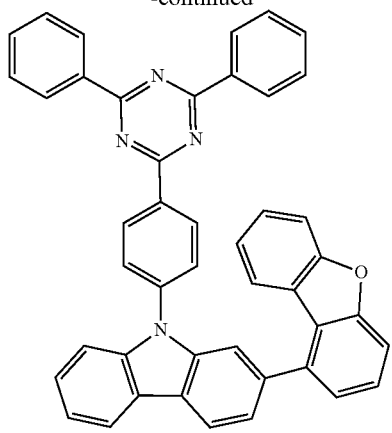
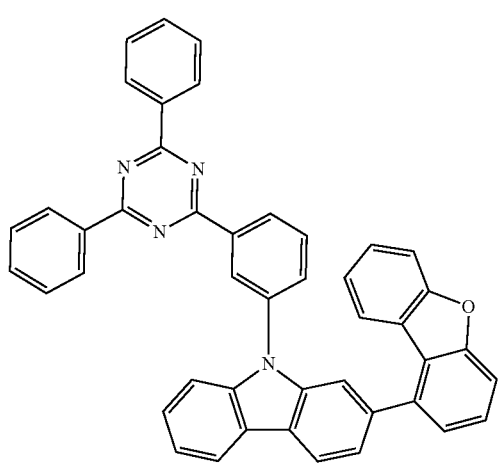
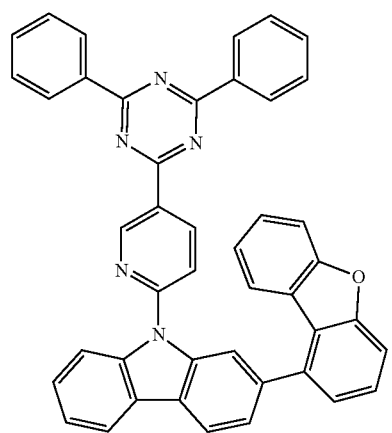
142
-continued
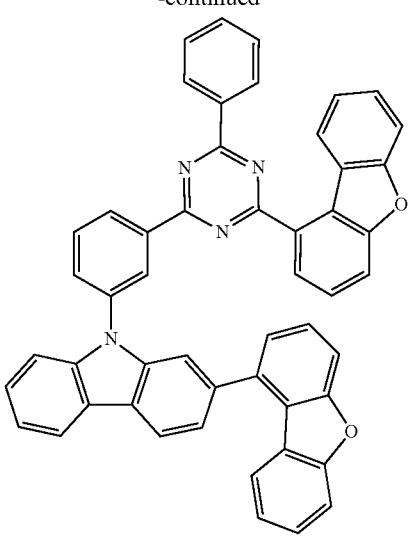
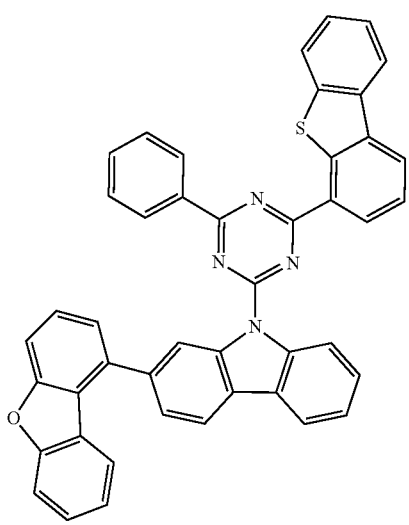

143
-continued
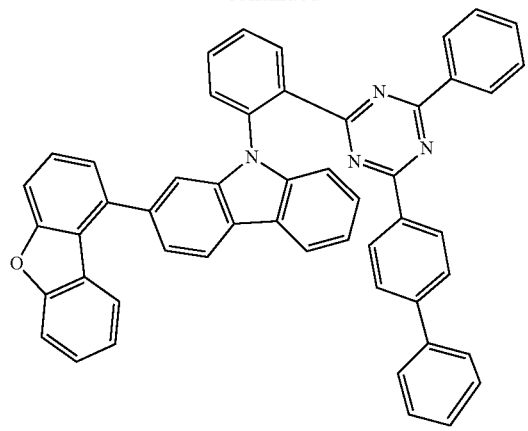
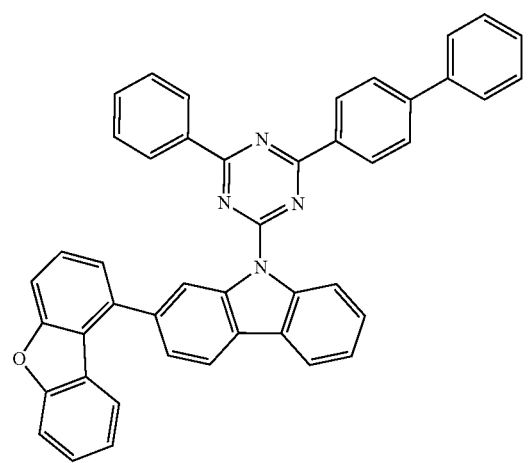
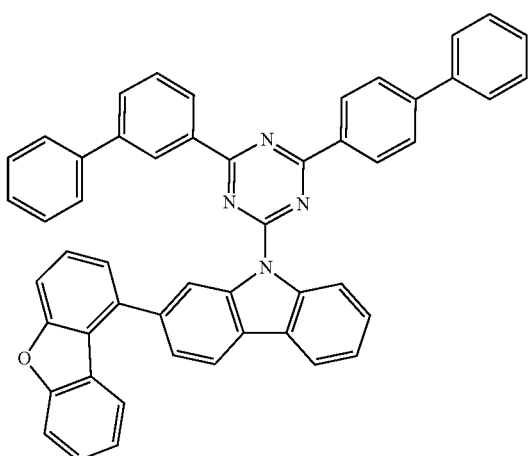
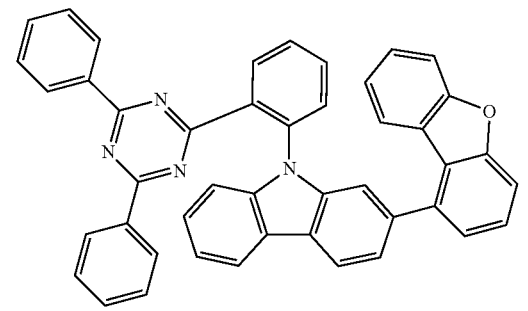
144
-continued
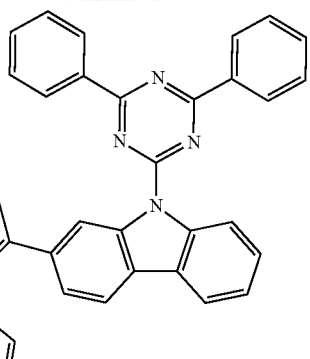
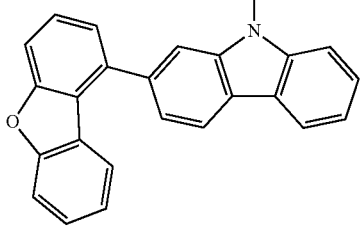
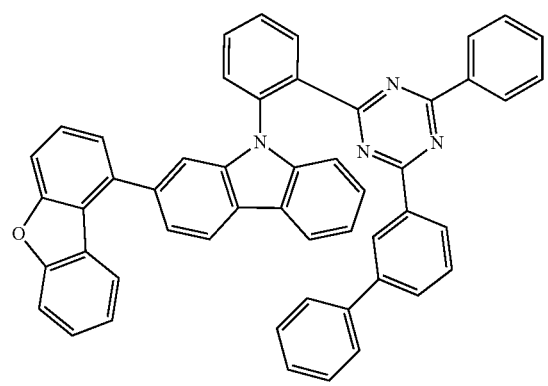
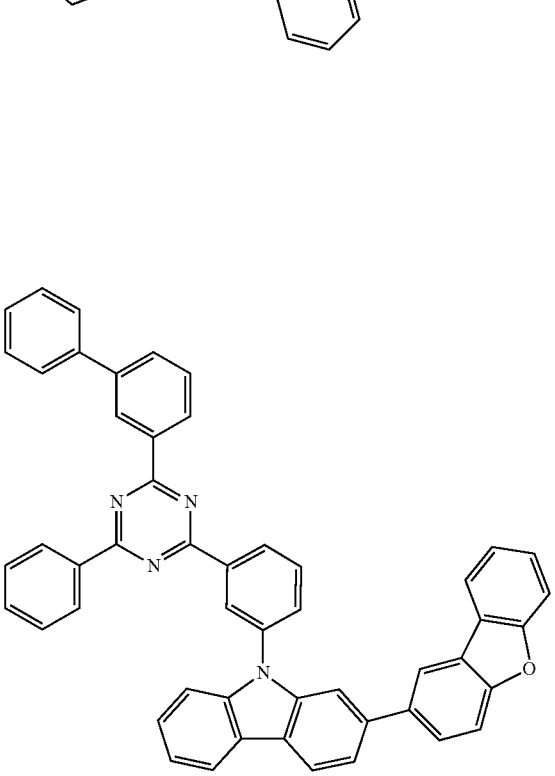

145
-continued
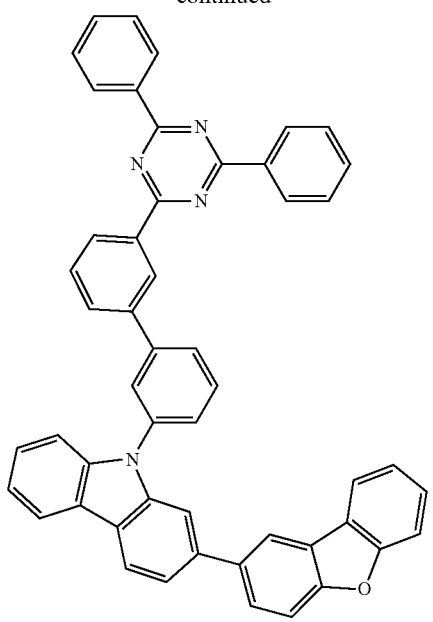
146
-continued
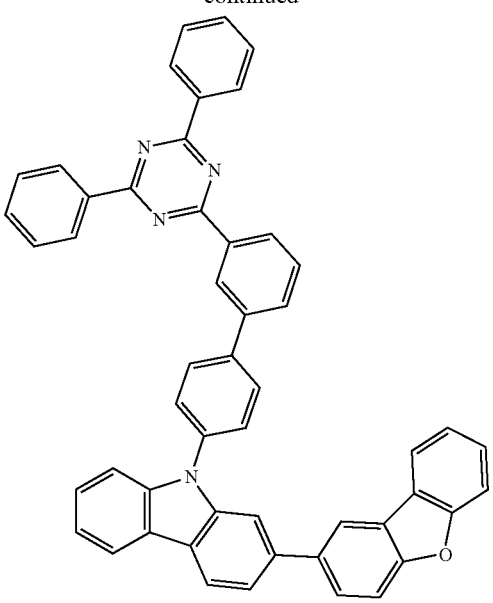
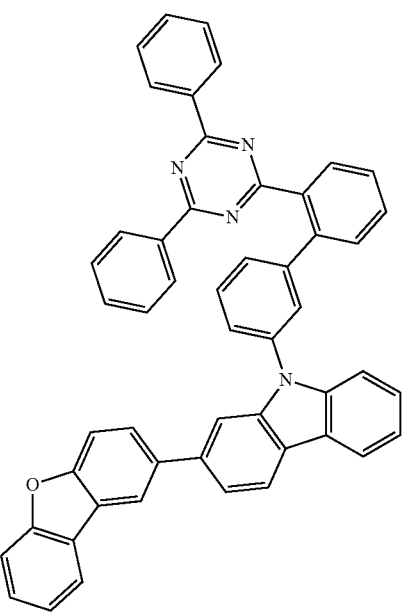

147
-continued
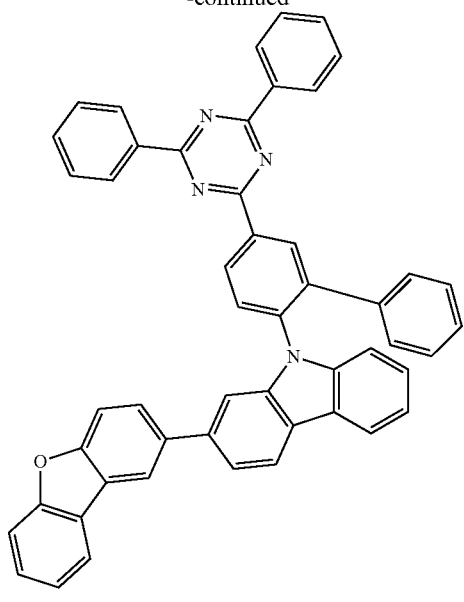
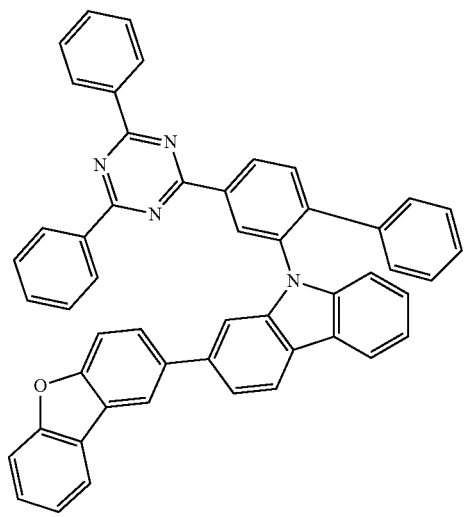
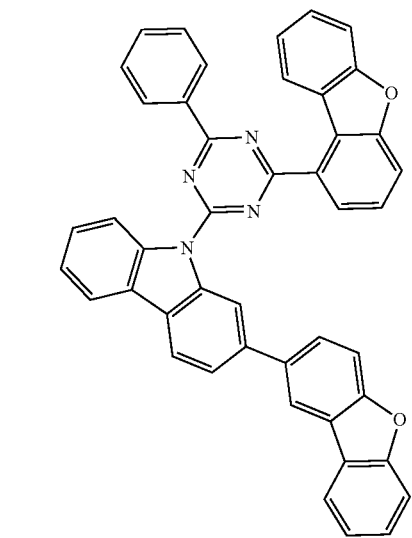
148
-continued
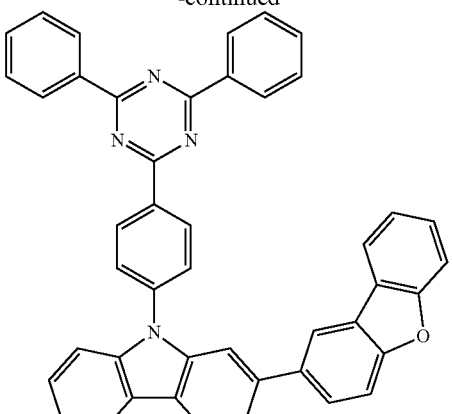
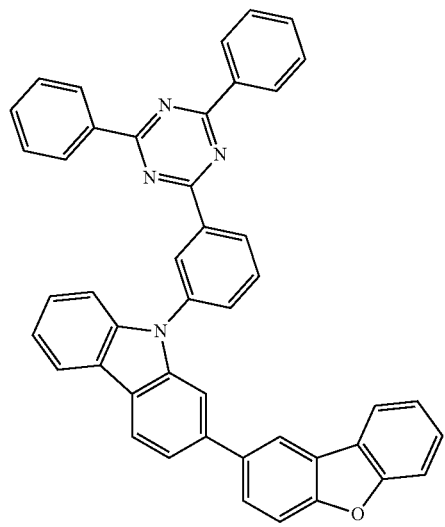
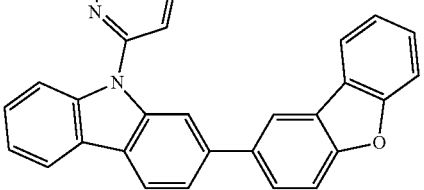

149
-continued
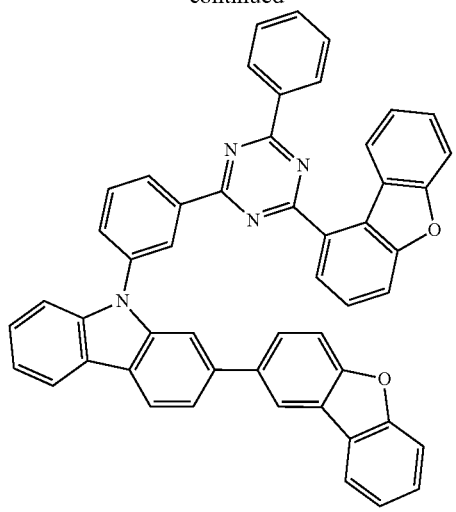
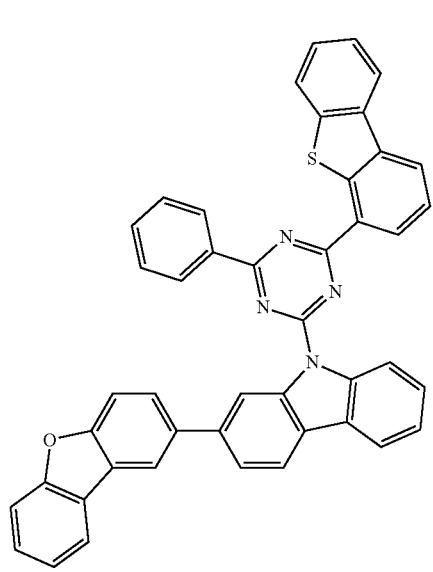
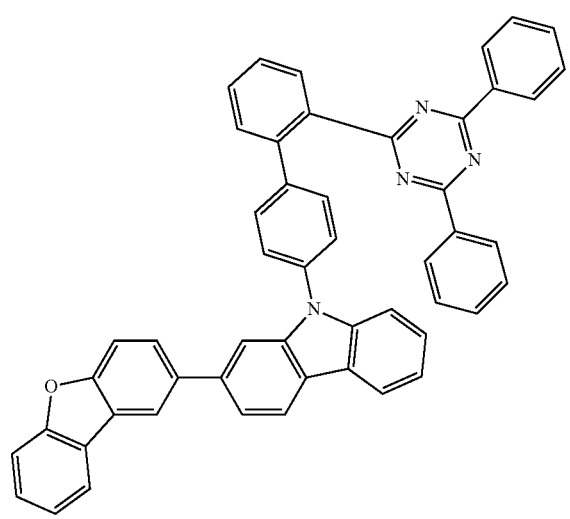
150
-continued
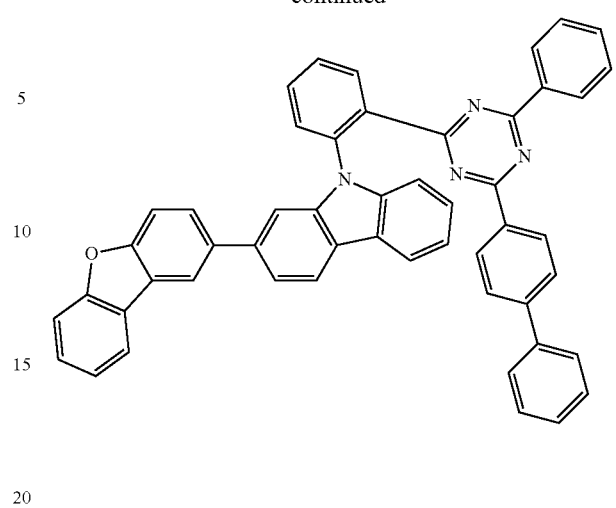
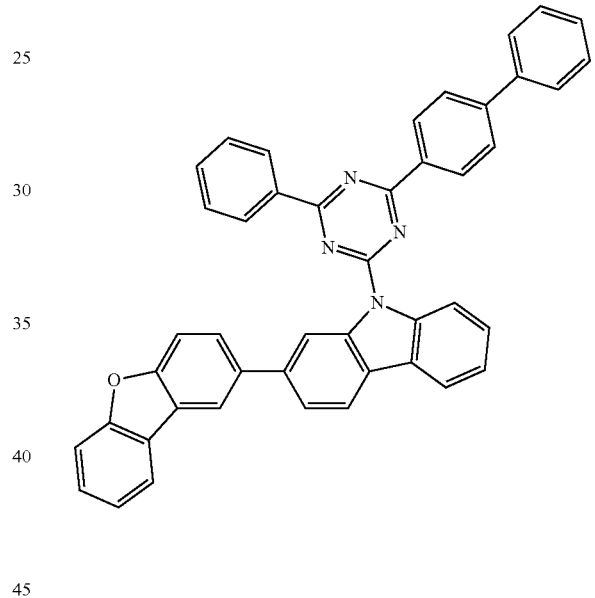
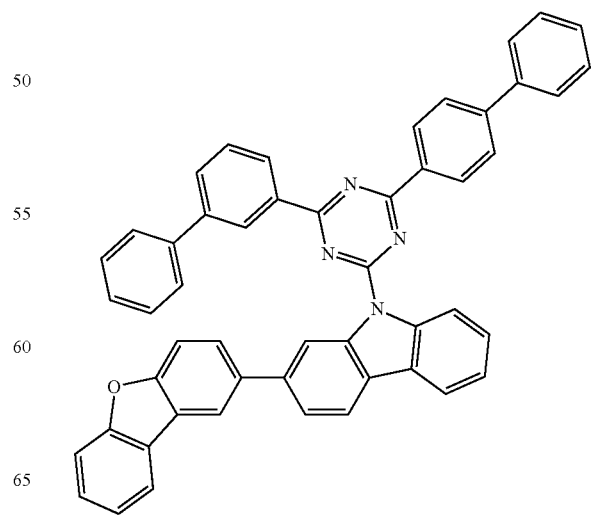

151
-continued
152
-continued
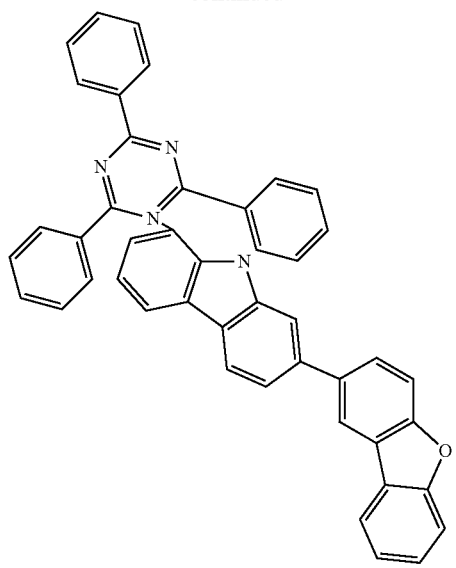
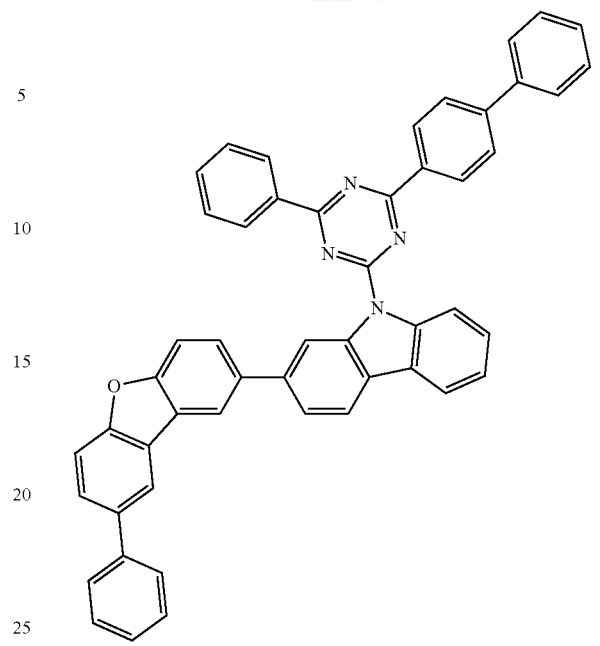
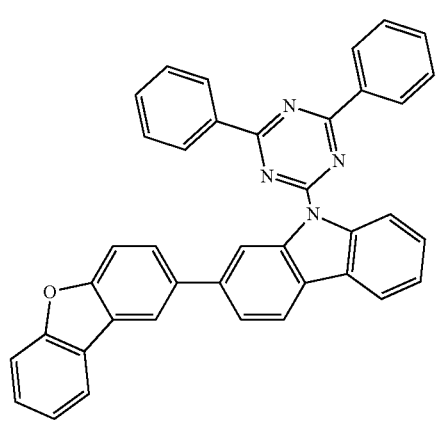
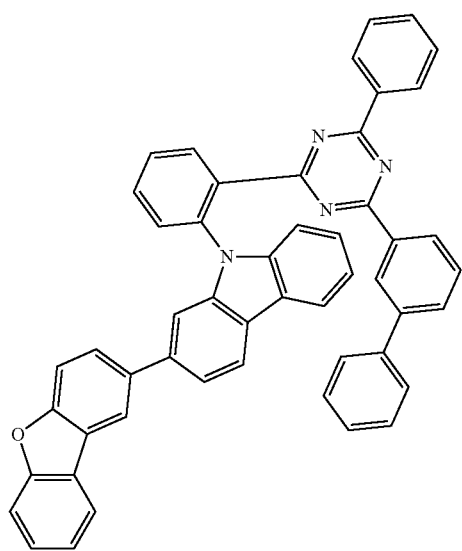

153
-continued
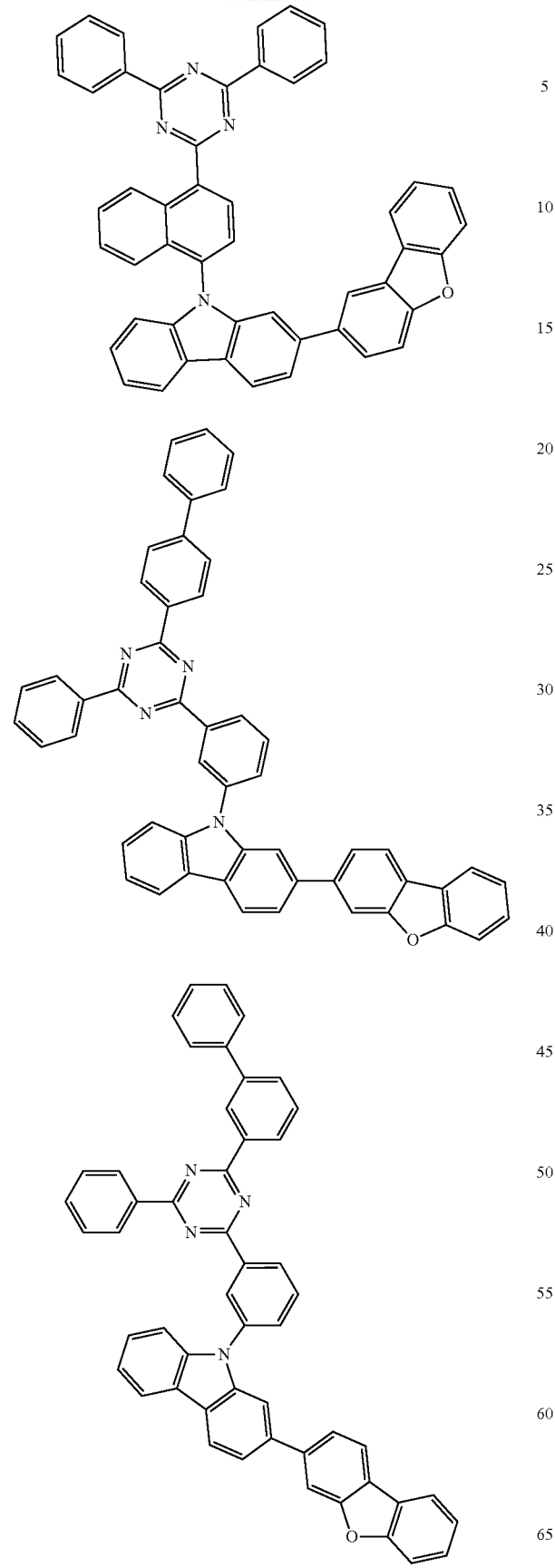
154
-continued
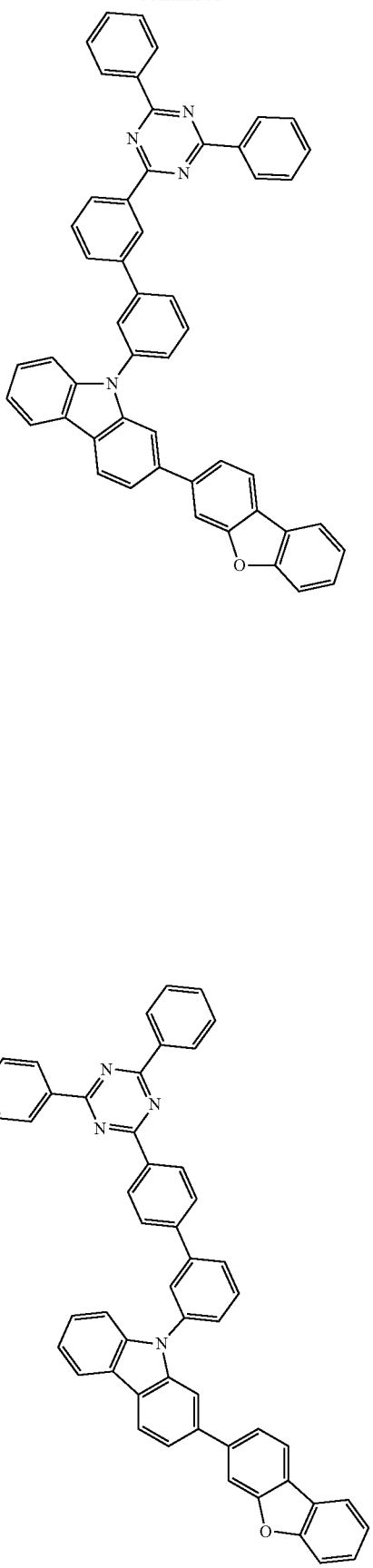

155
-continued
156
-continued
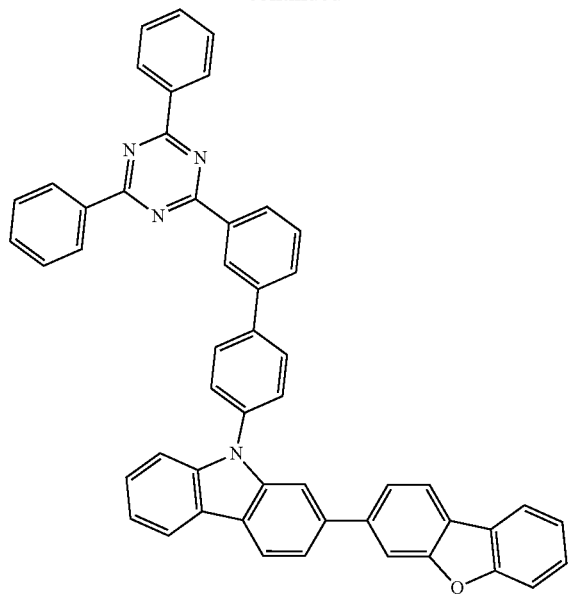
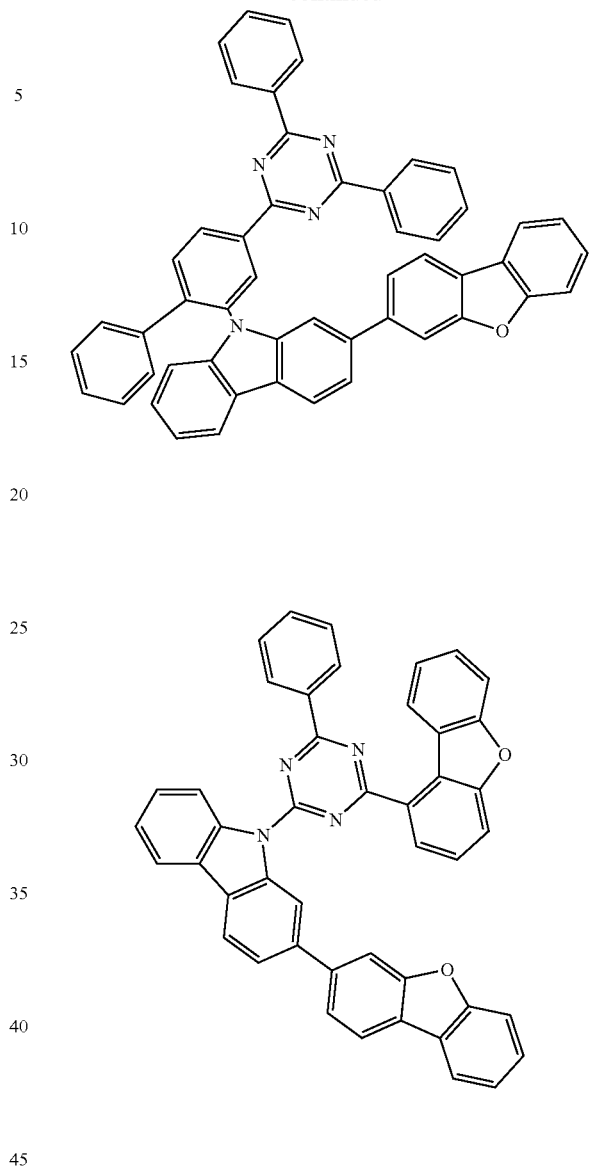
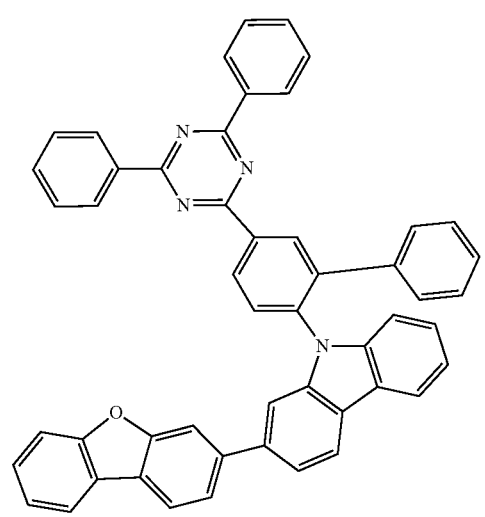

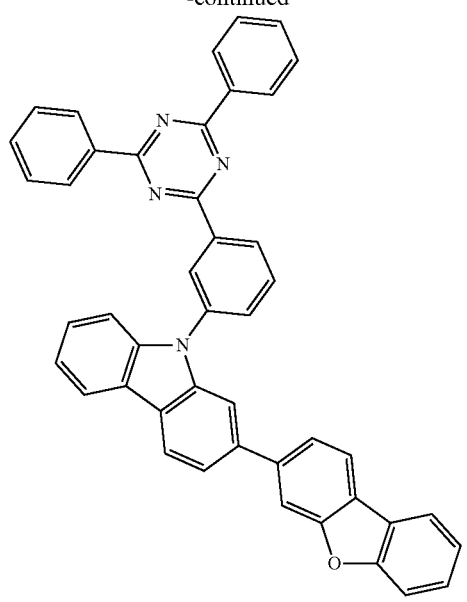
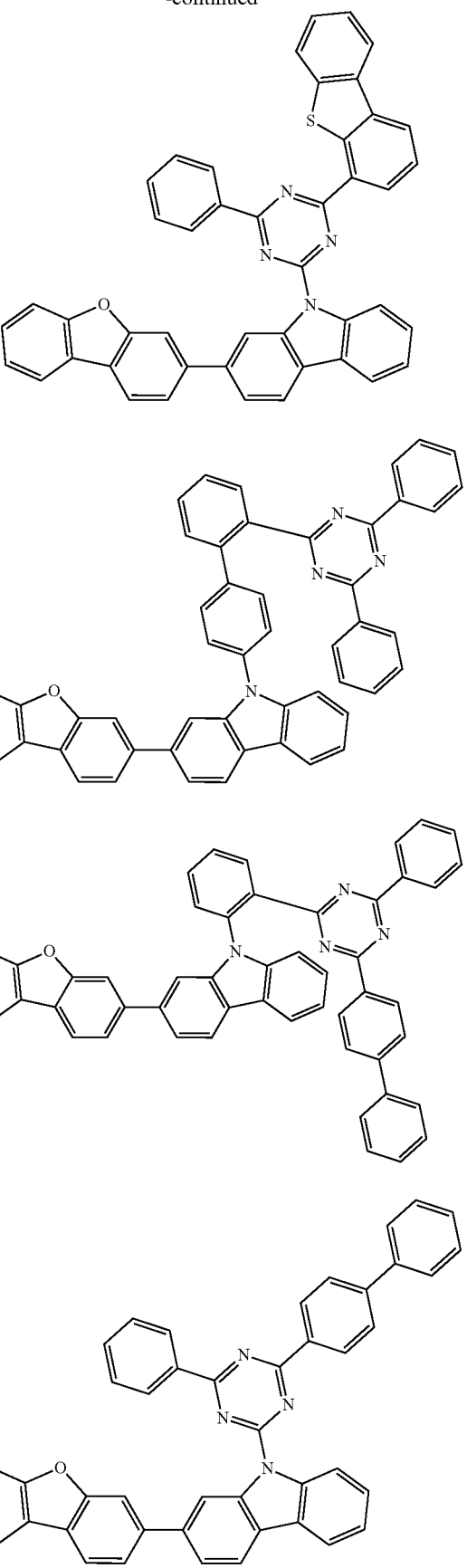

159
-continued
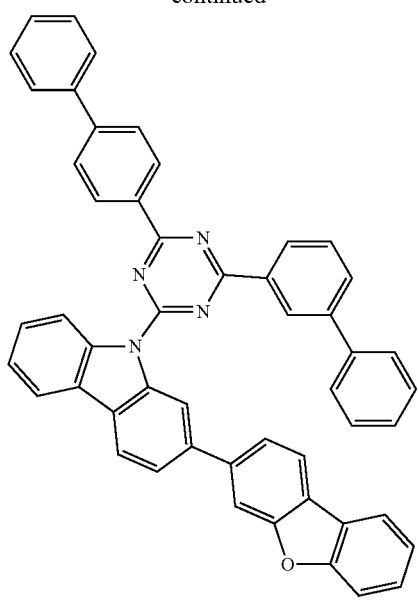
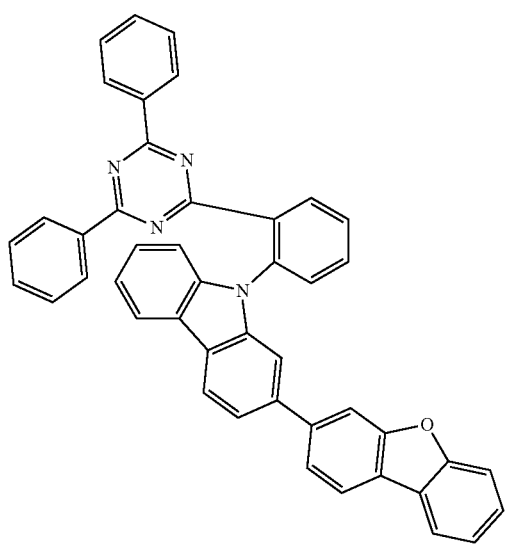
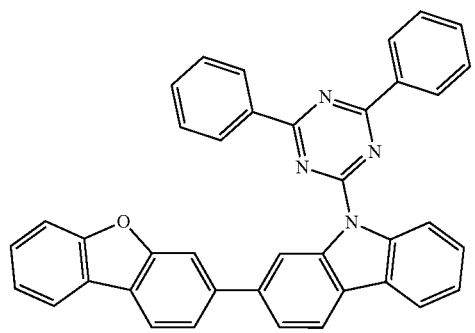
160
-continued
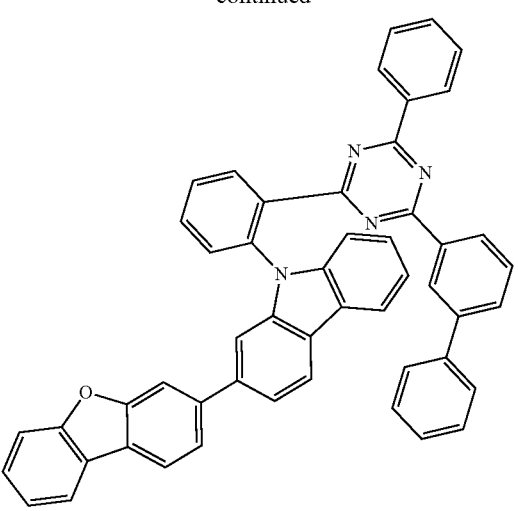
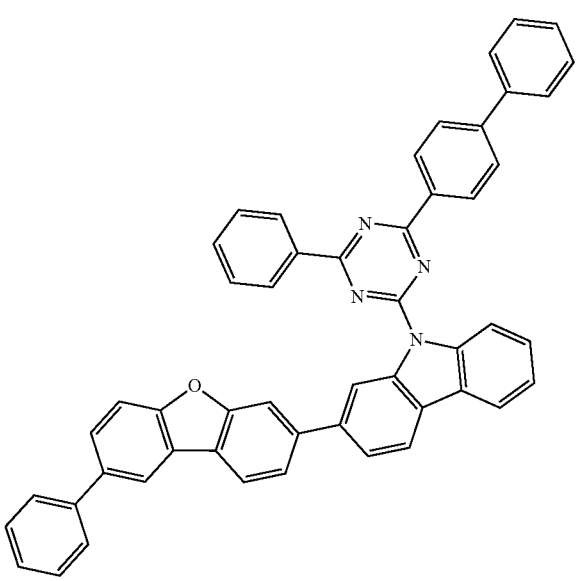

161
-continued
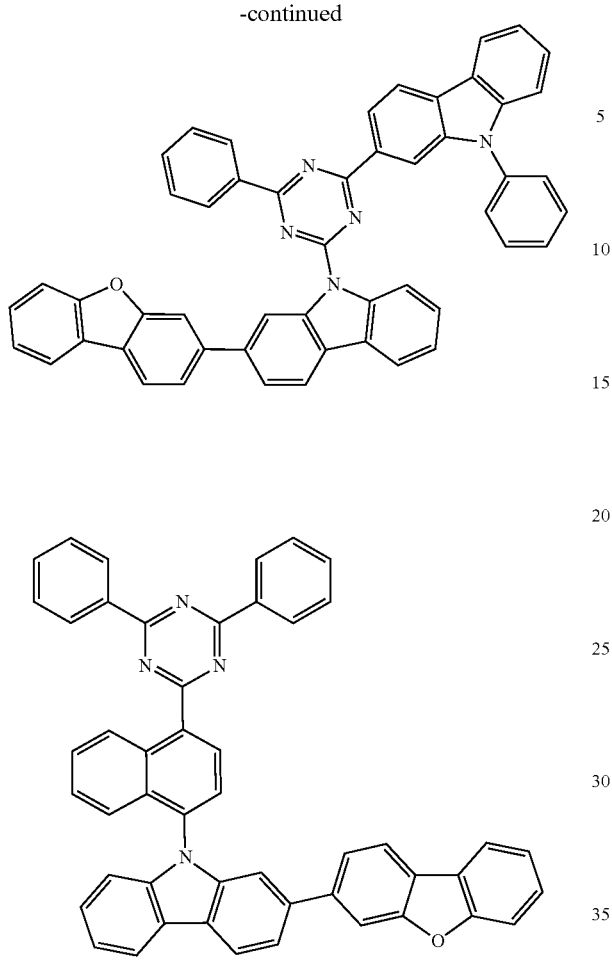
162
-continued
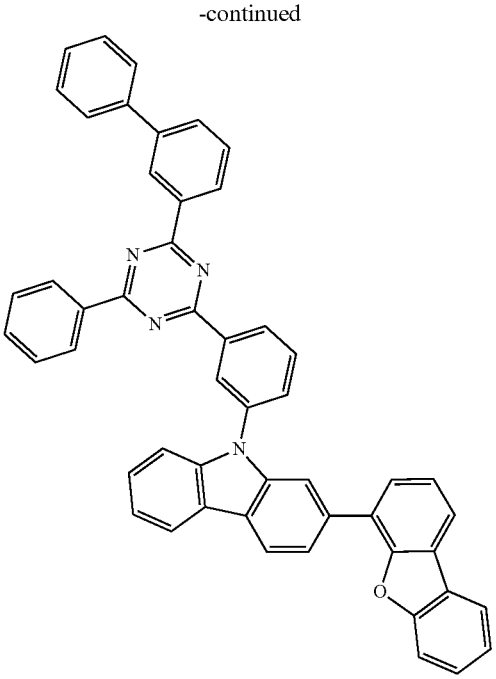

163
-continued
164
-continued
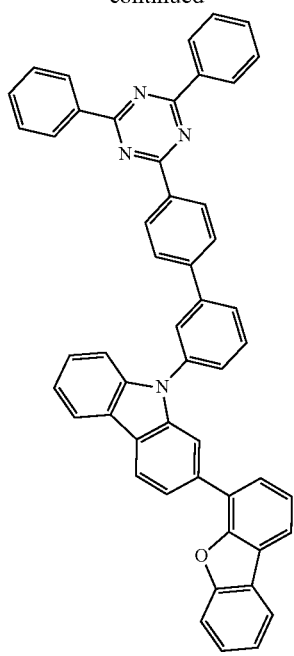
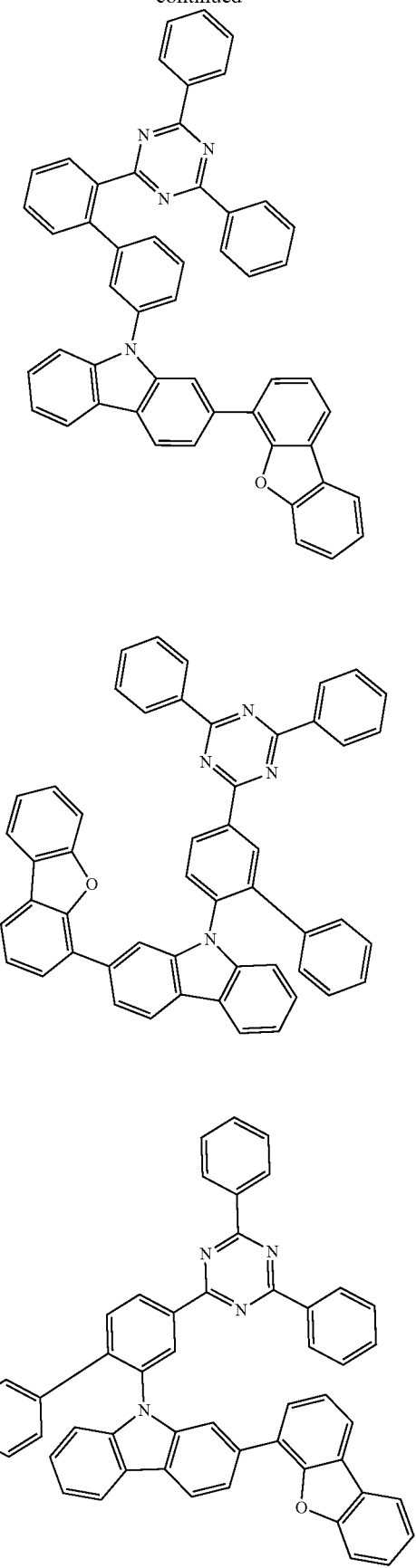

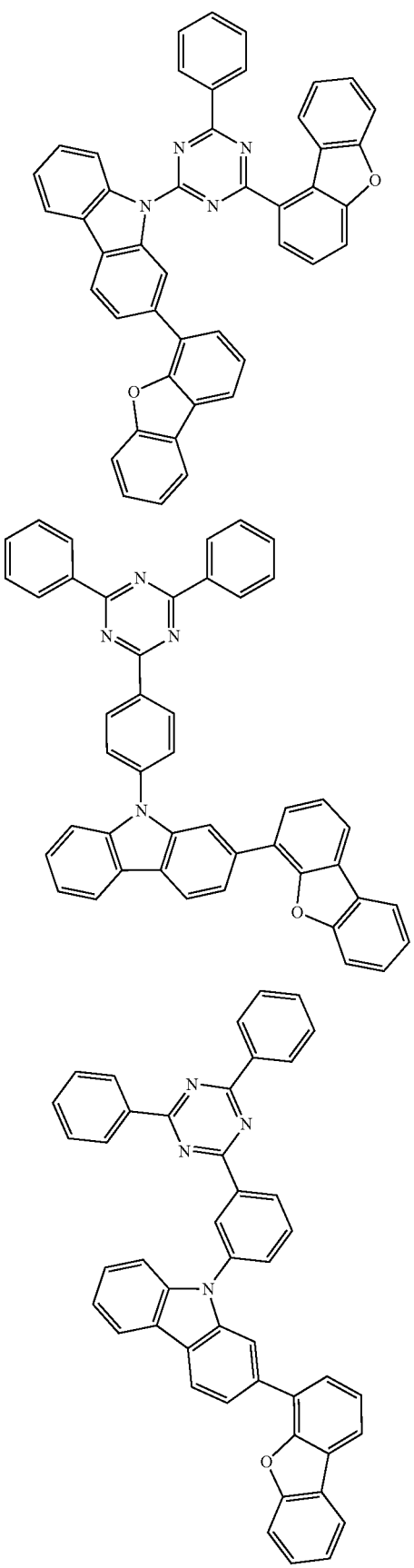
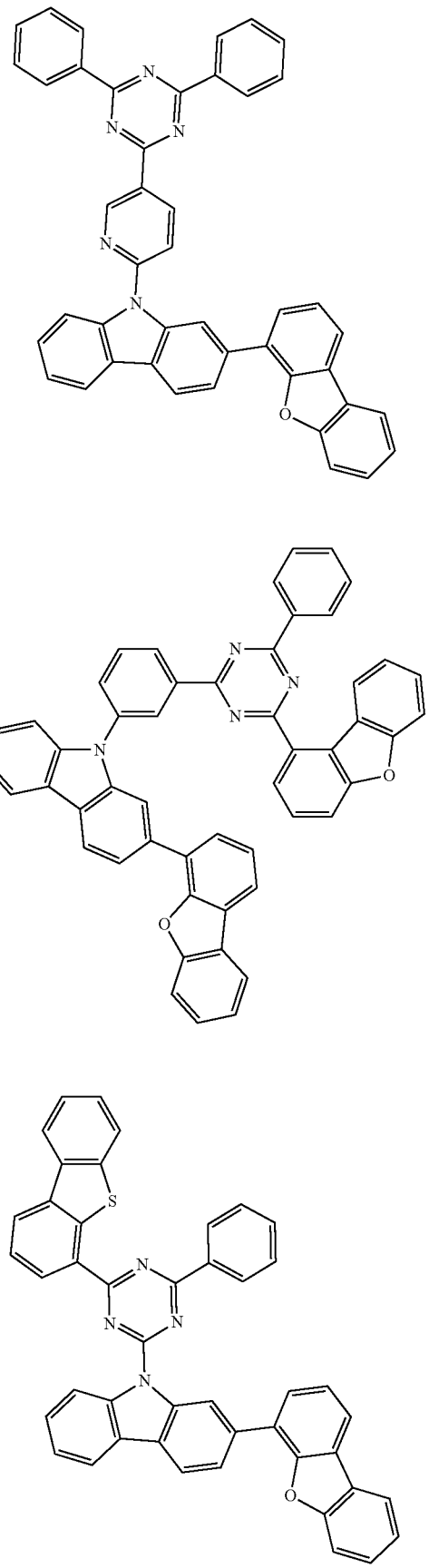

167
-continued
168
-continued
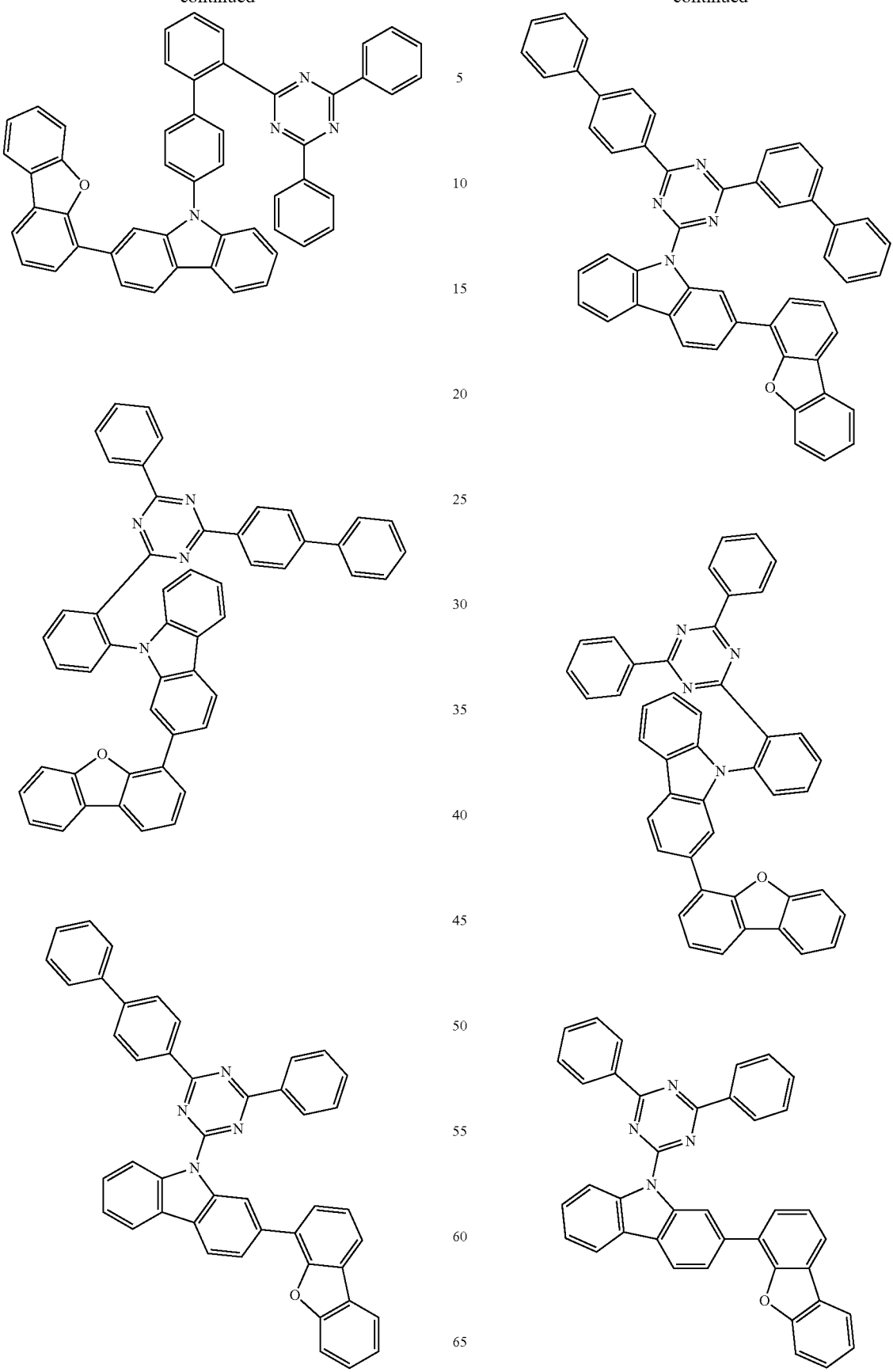

169
-continued
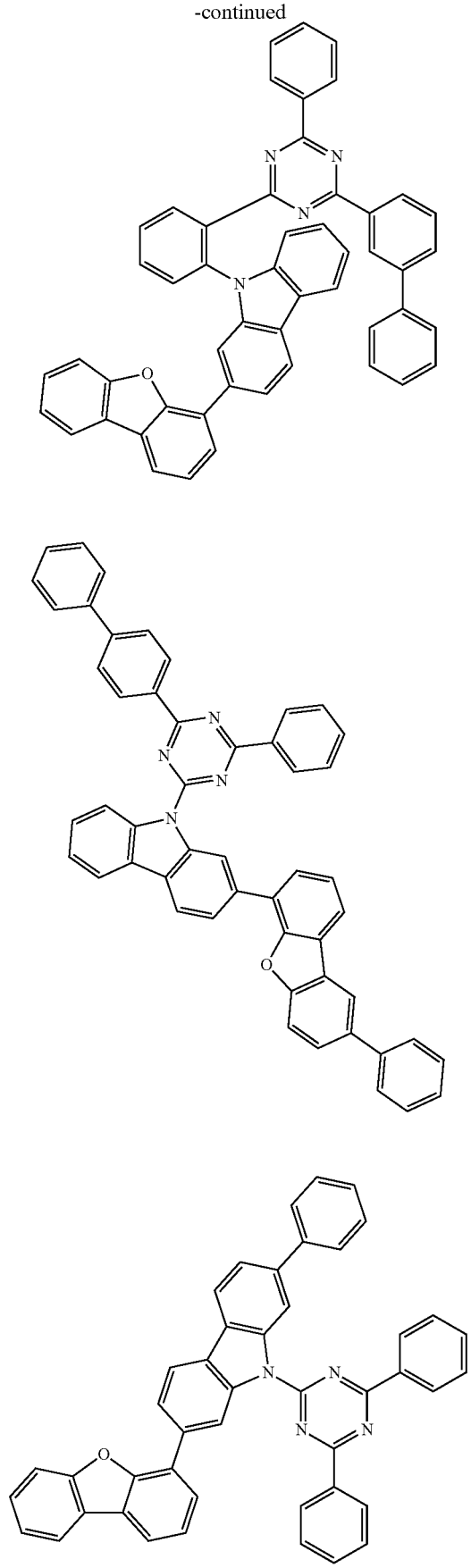
170
-continued
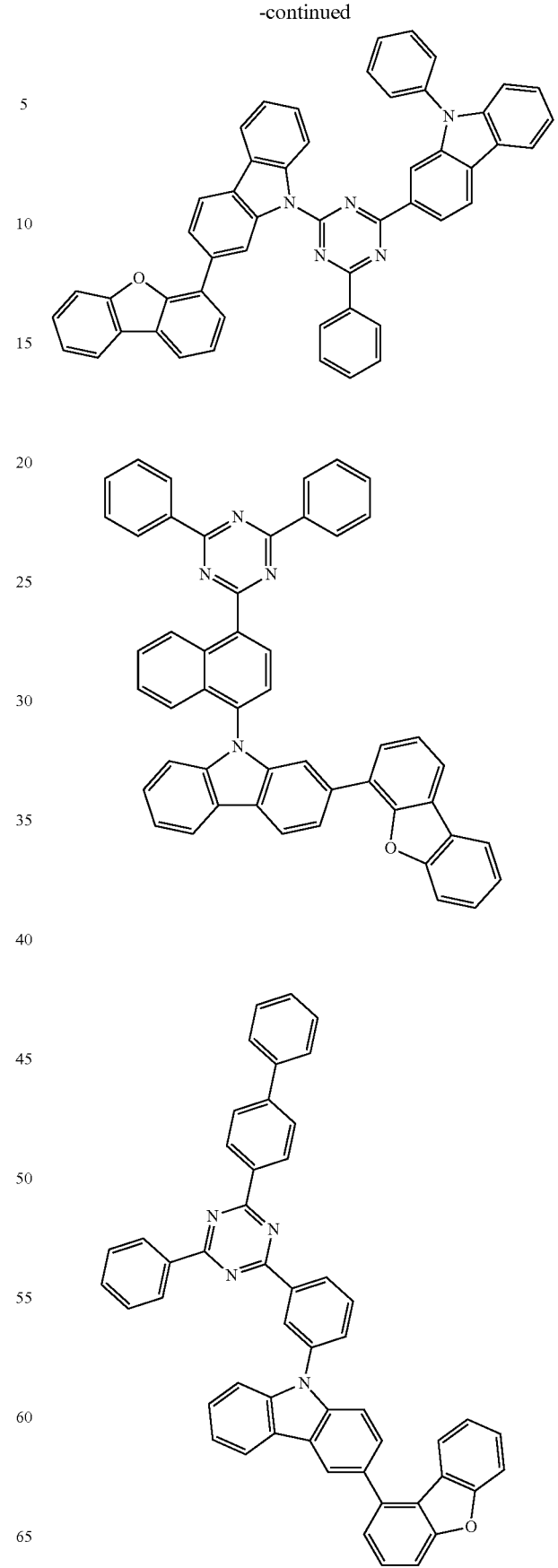

171
-continued
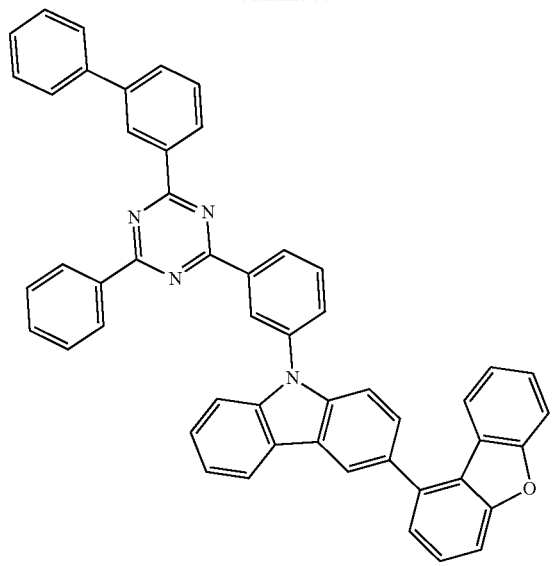
172
-continued
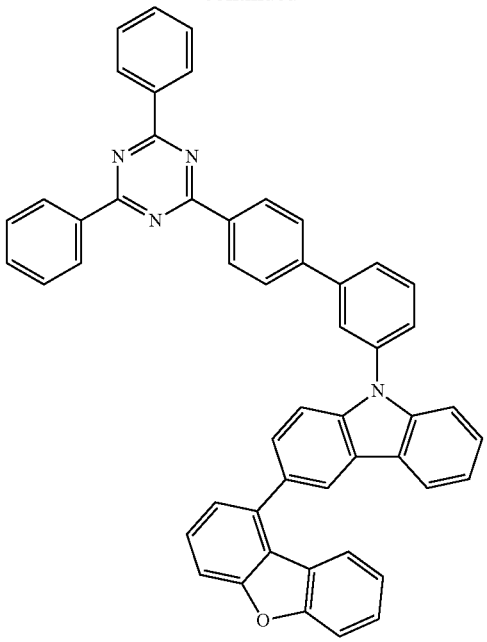
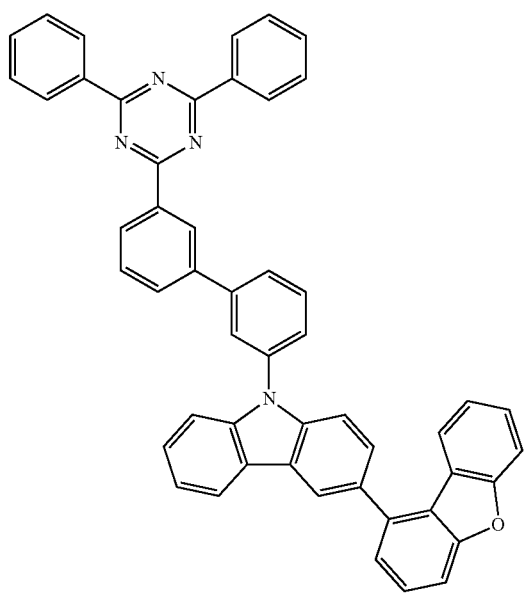
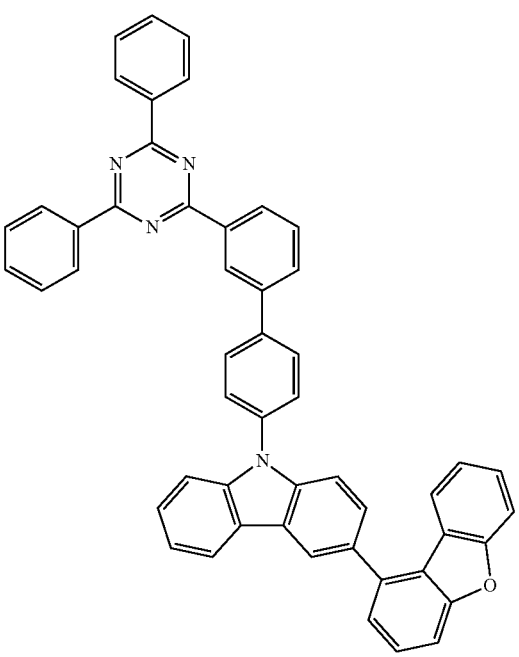

173
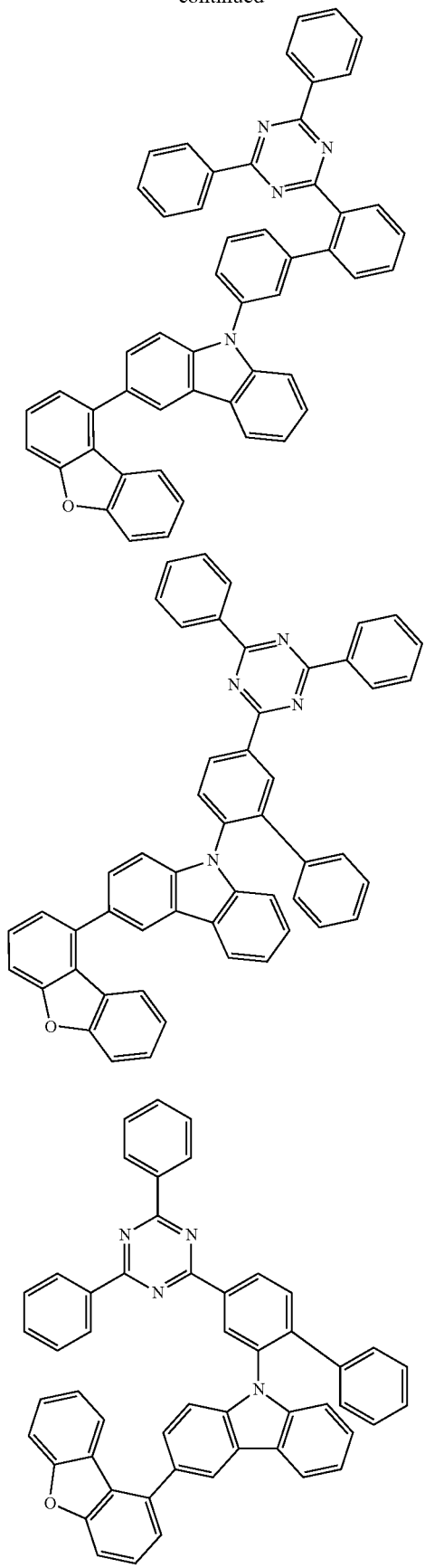
174
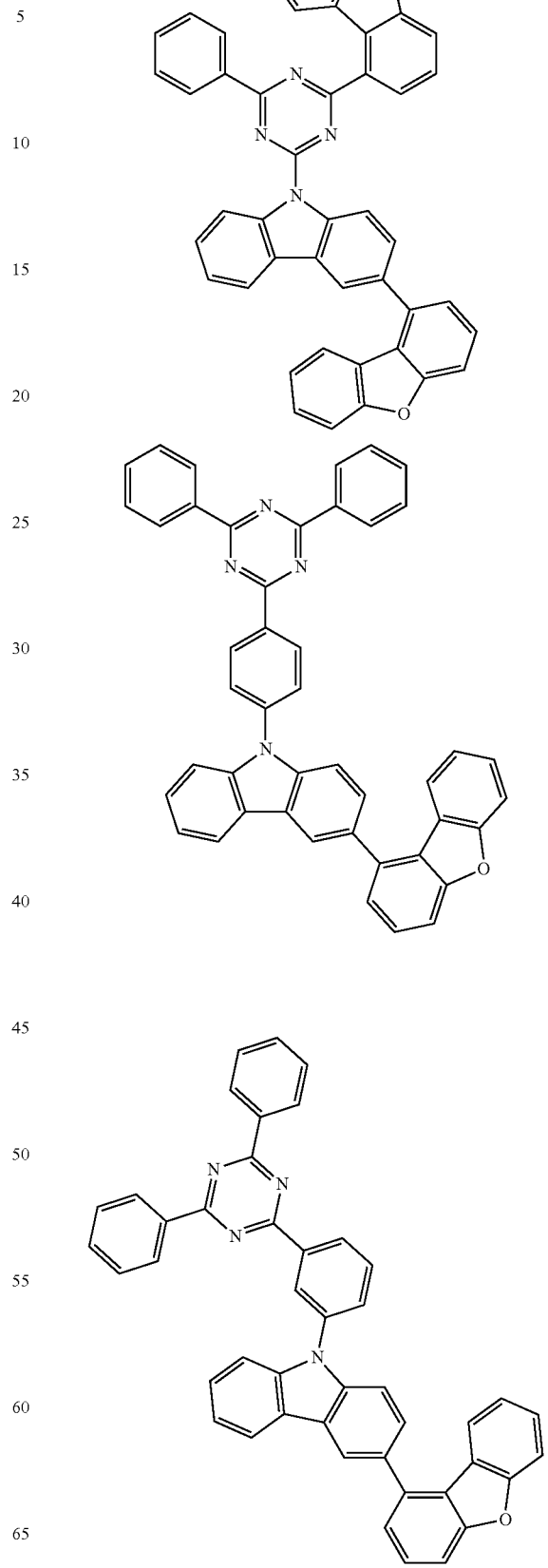

175
-continued
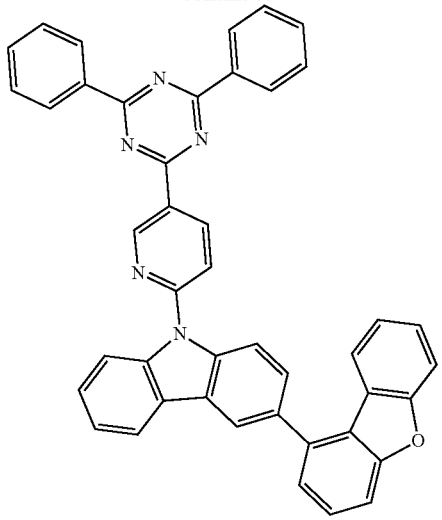
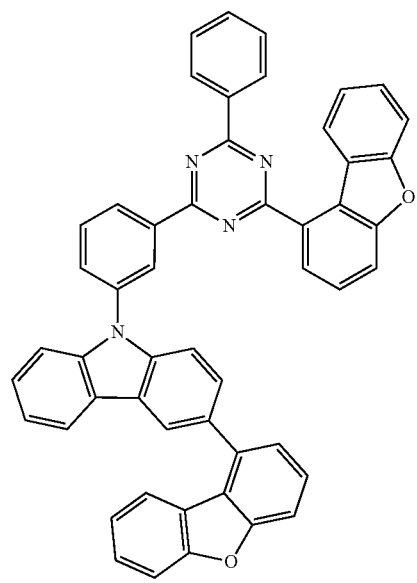
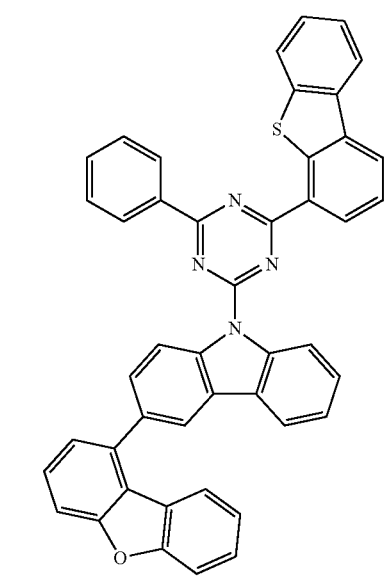
176
-continued
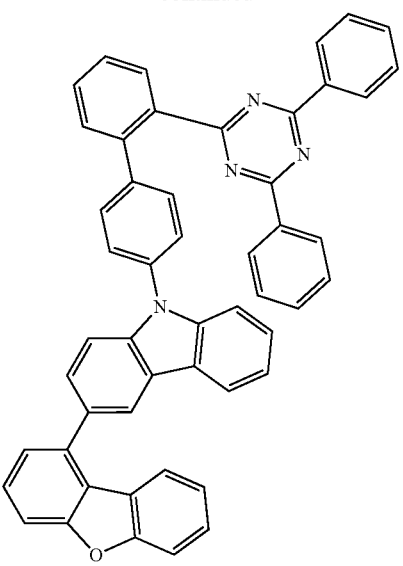
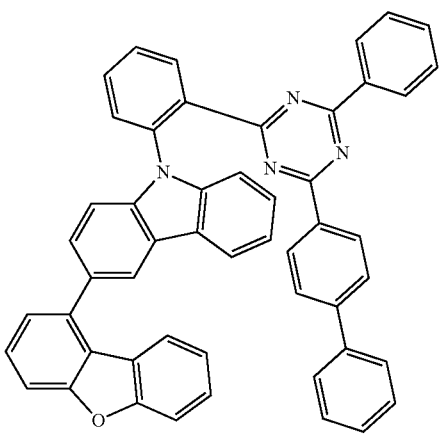
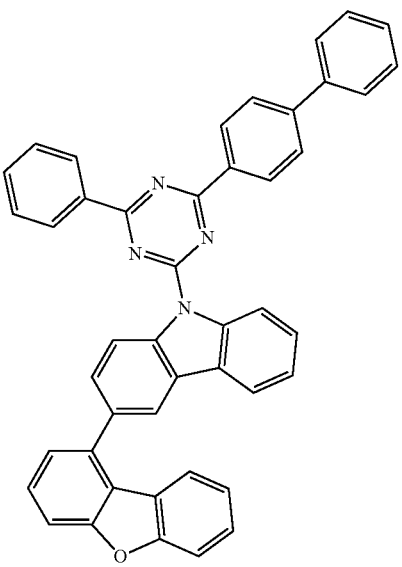

177
-continued
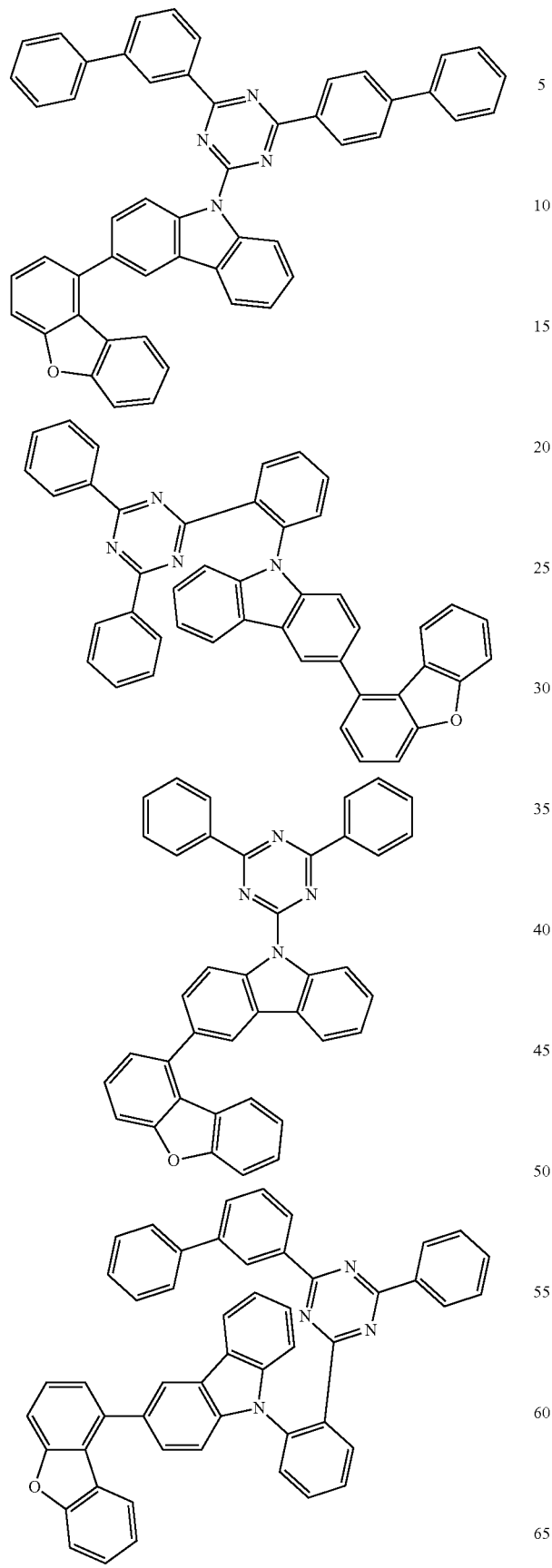
178
-continued
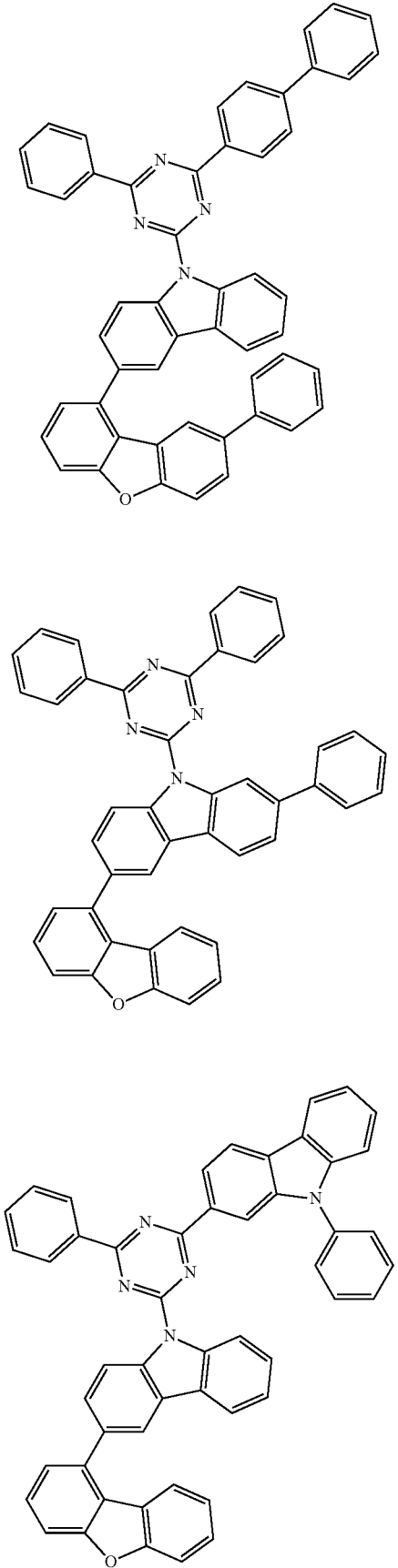

179
-continued
180
-continued
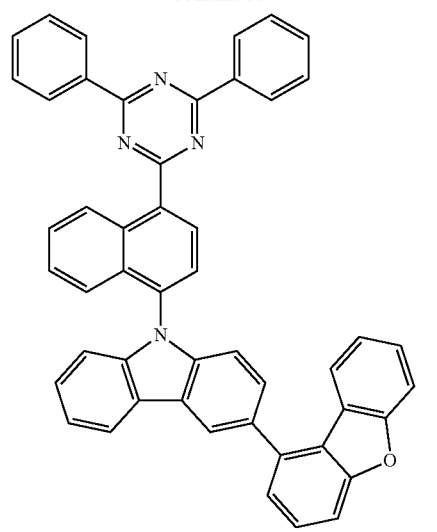
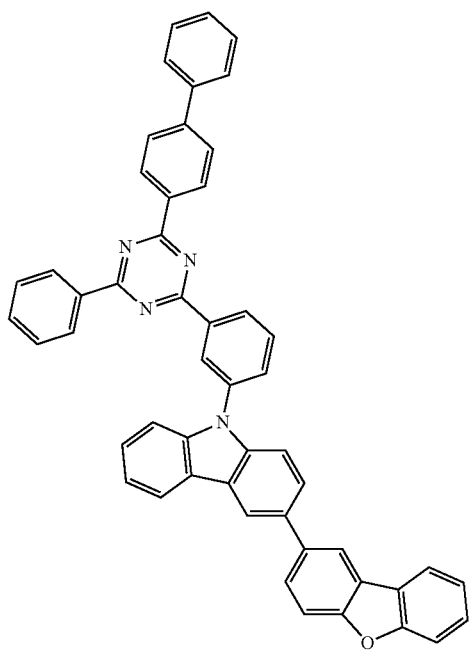
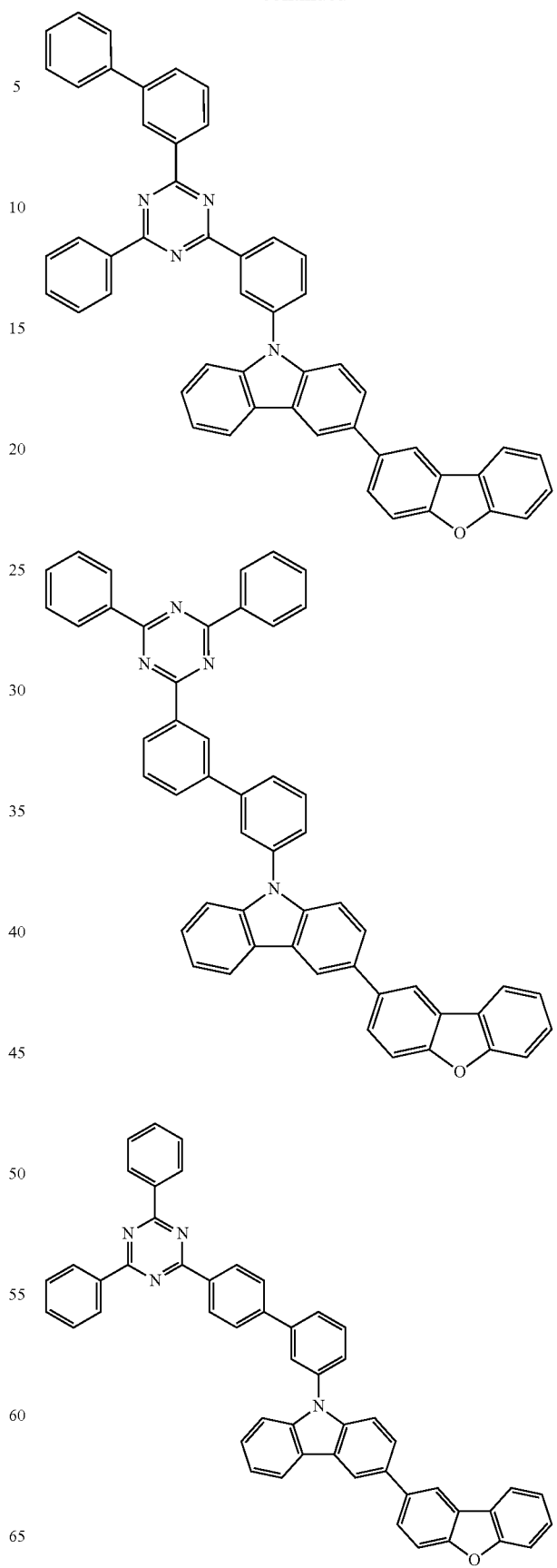

181
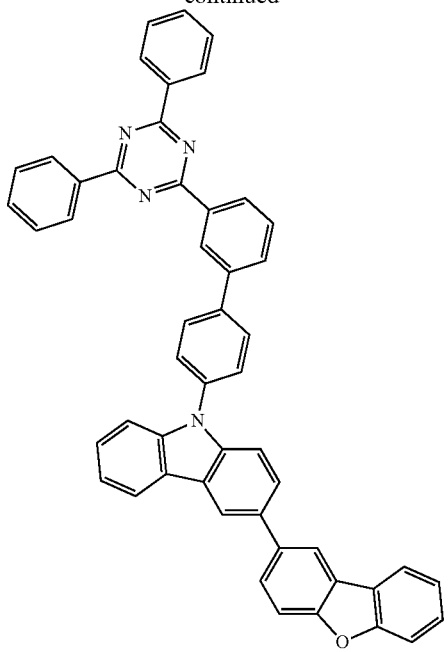
182
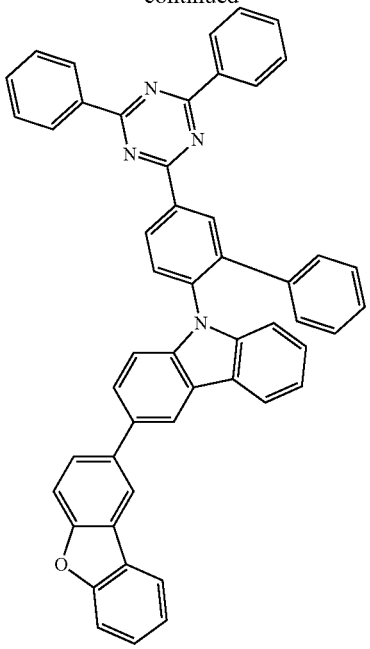

183
-continued
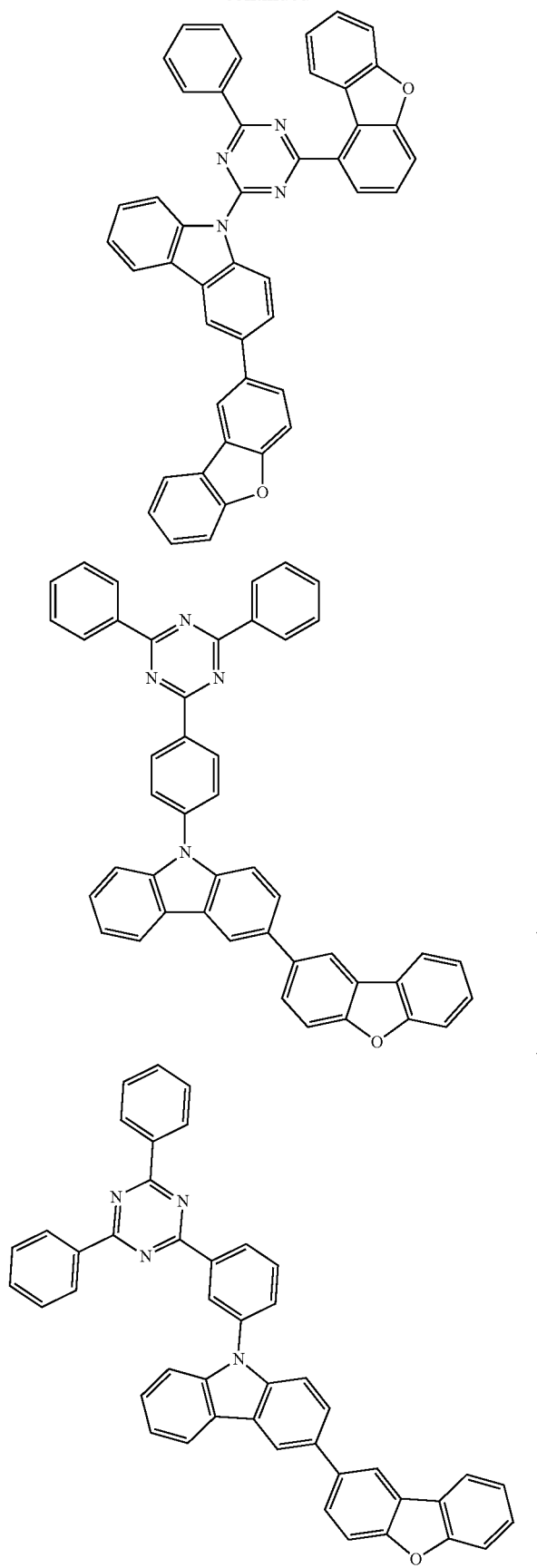
184
-continued
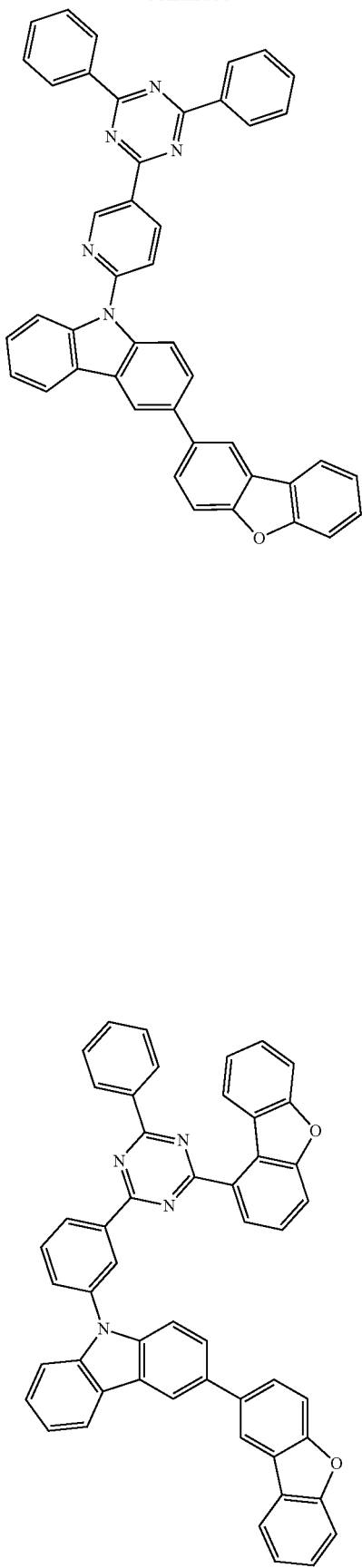

185
-continued
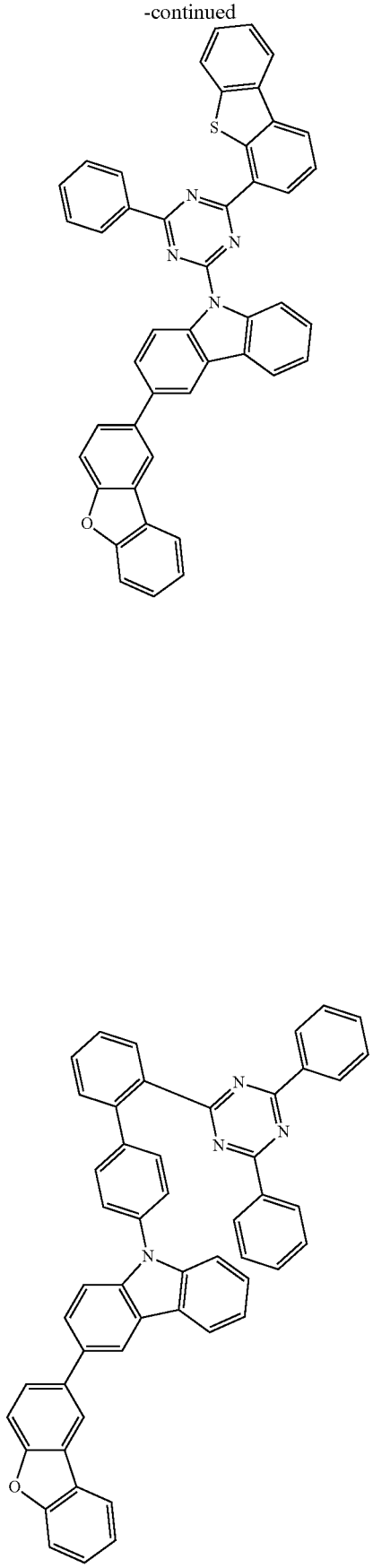
186
-continued
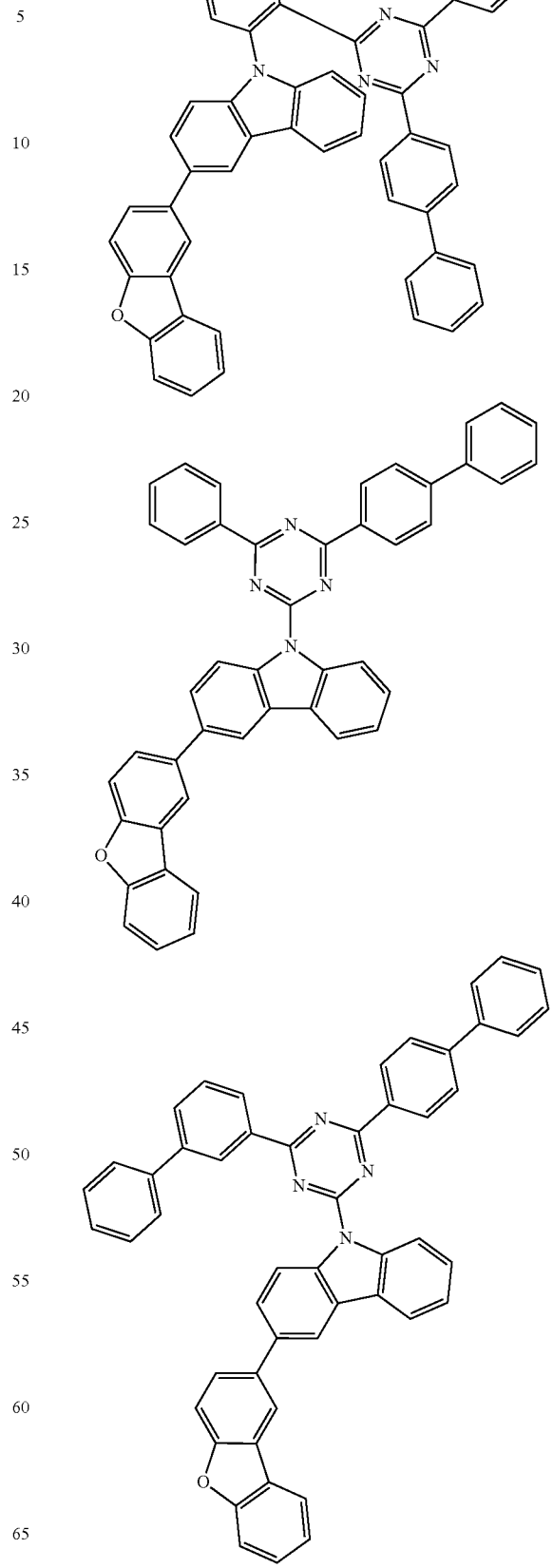

187
-continued
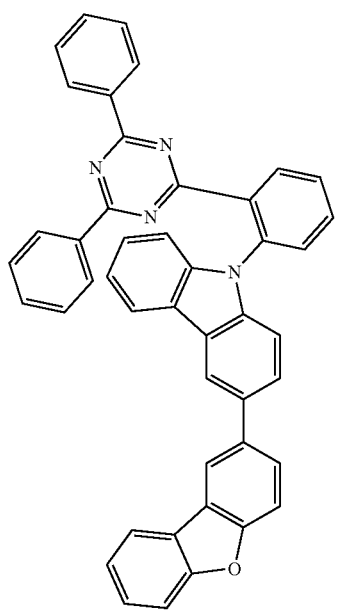
188
-continued
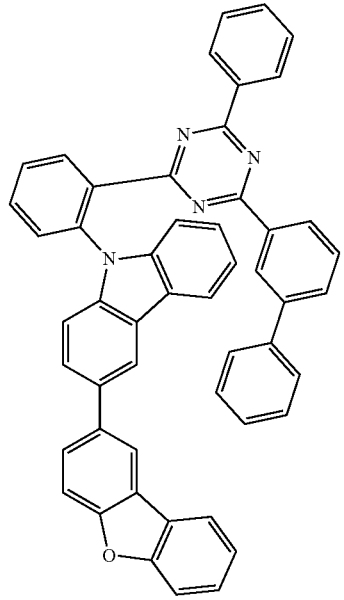
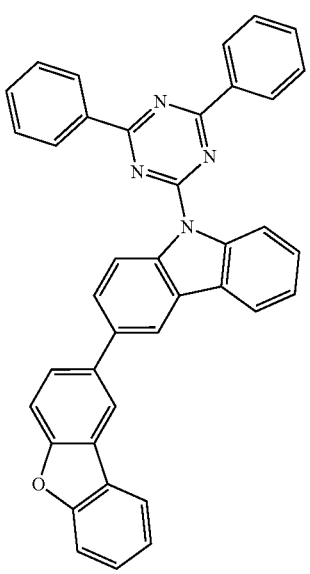
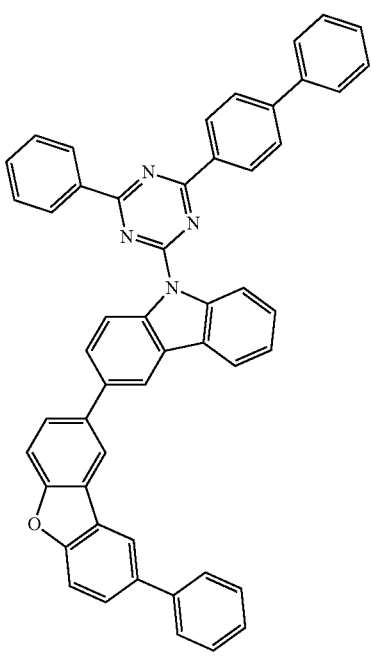

189
-continued
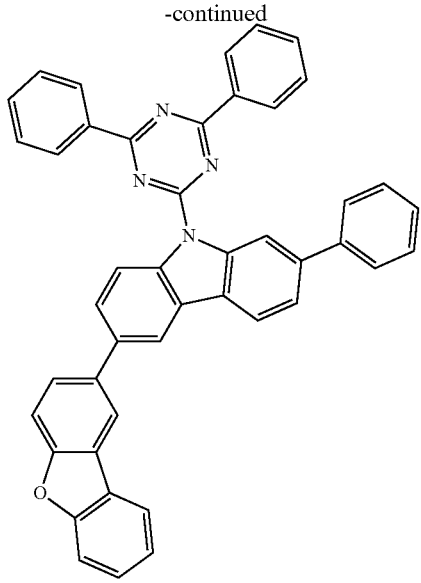
190
-continued
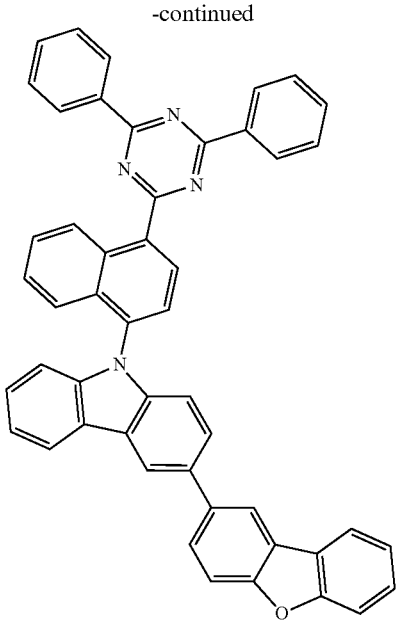
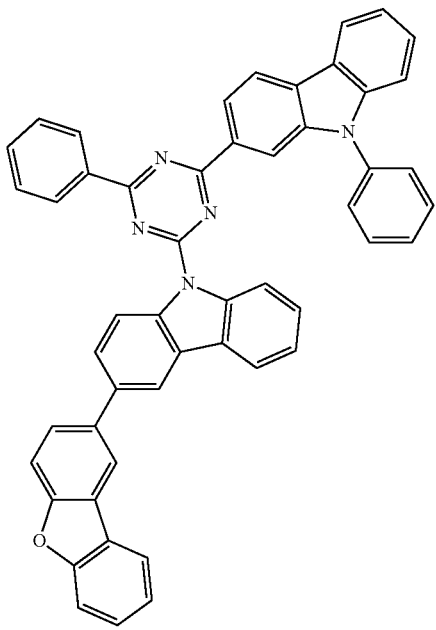
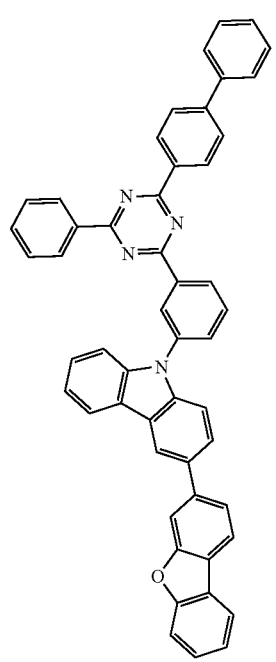

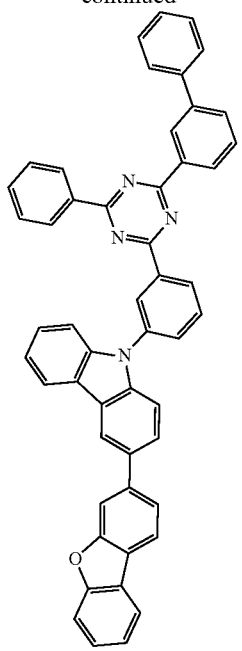
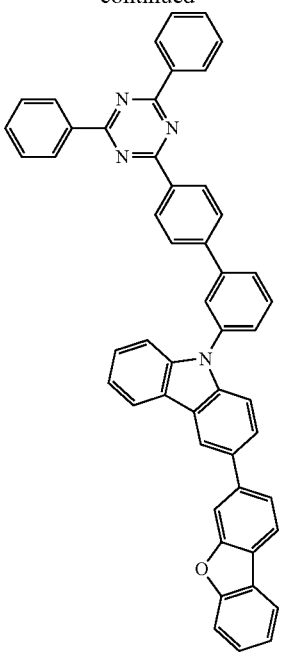
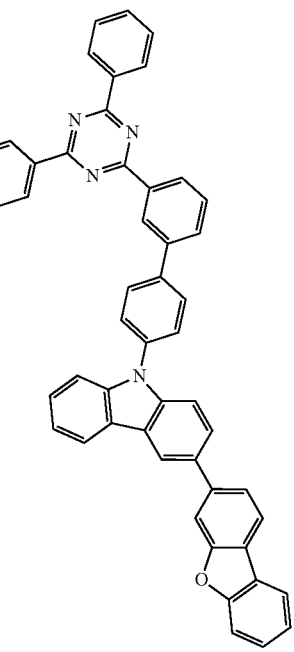

193
-continued
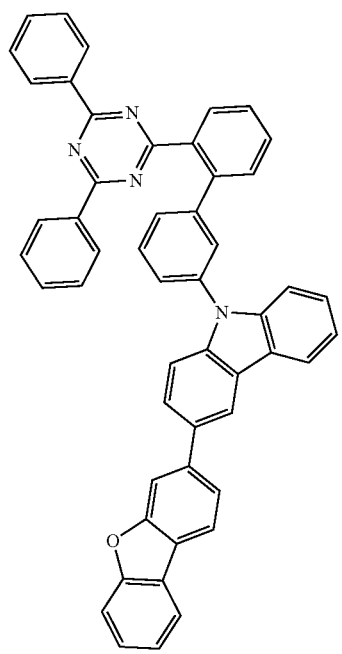
194
-continued
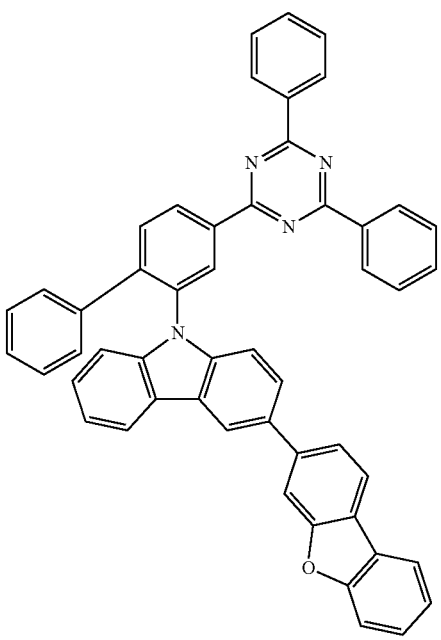
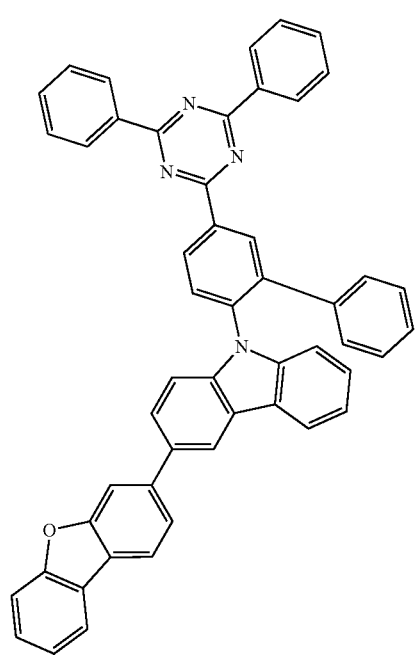
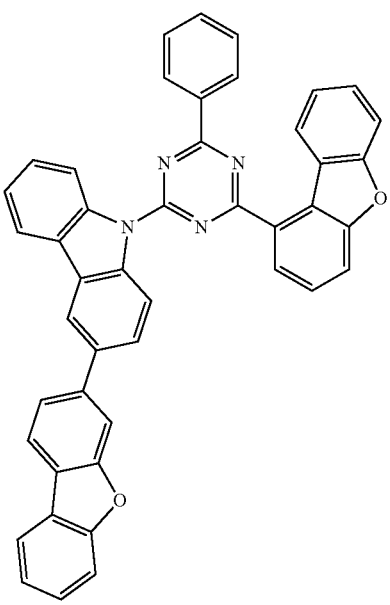

195
-continued
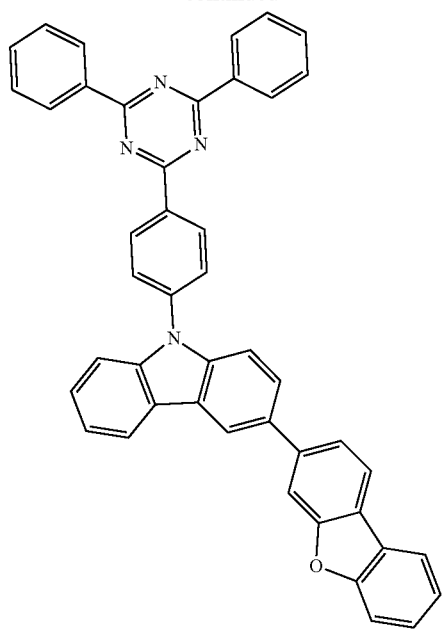
196
-continued
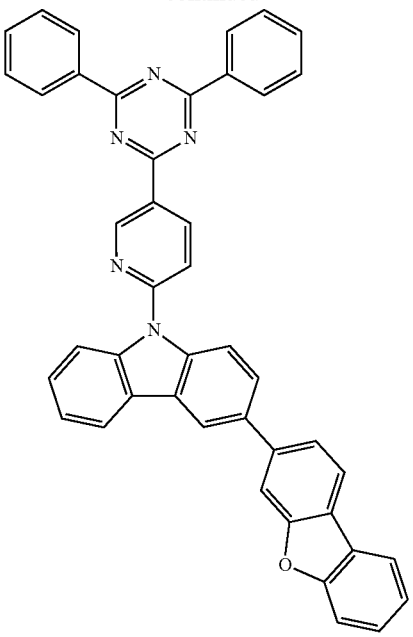
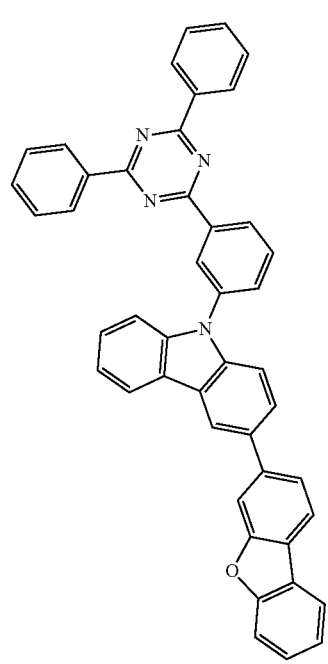
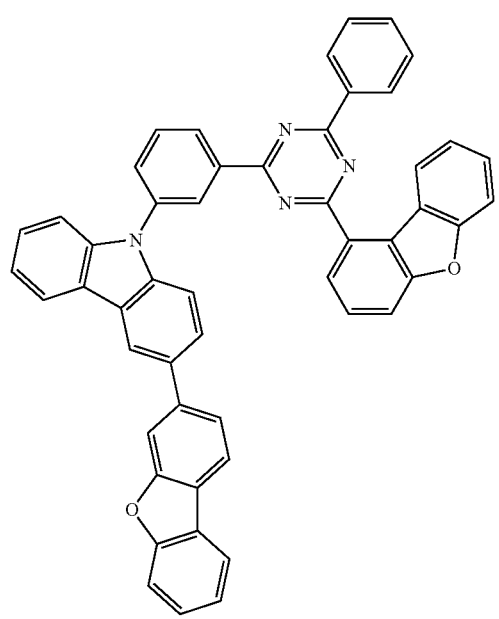

197
-continued
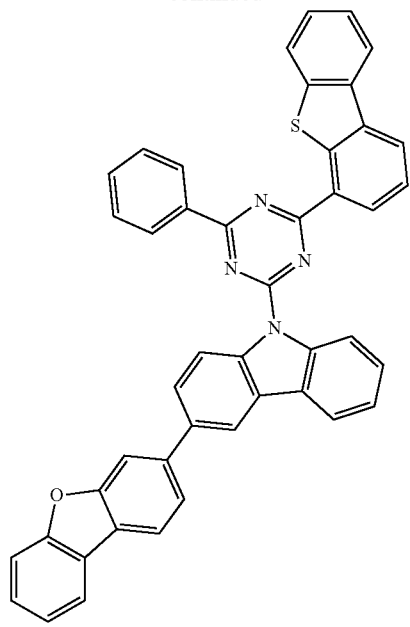
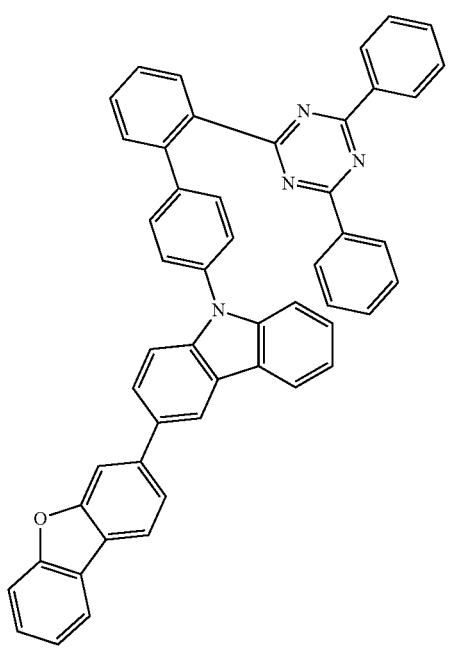
198
-continued
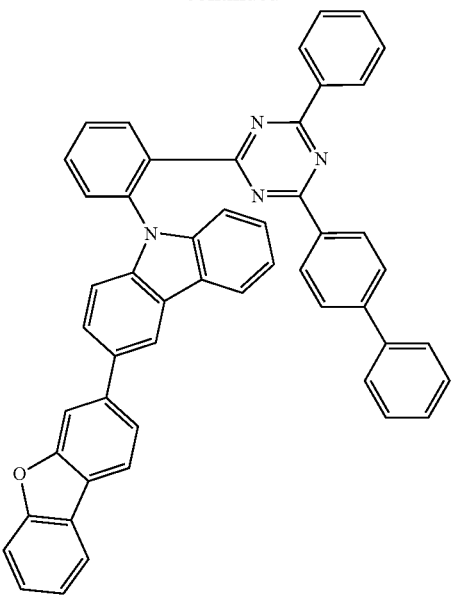
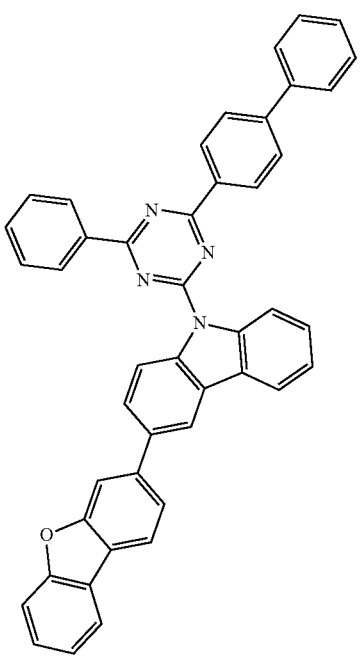

199
-continued
200
-continued
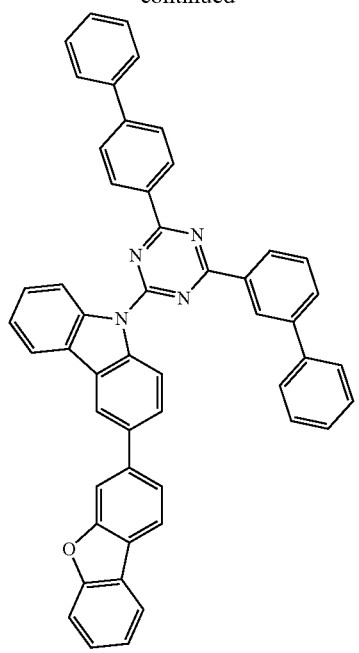
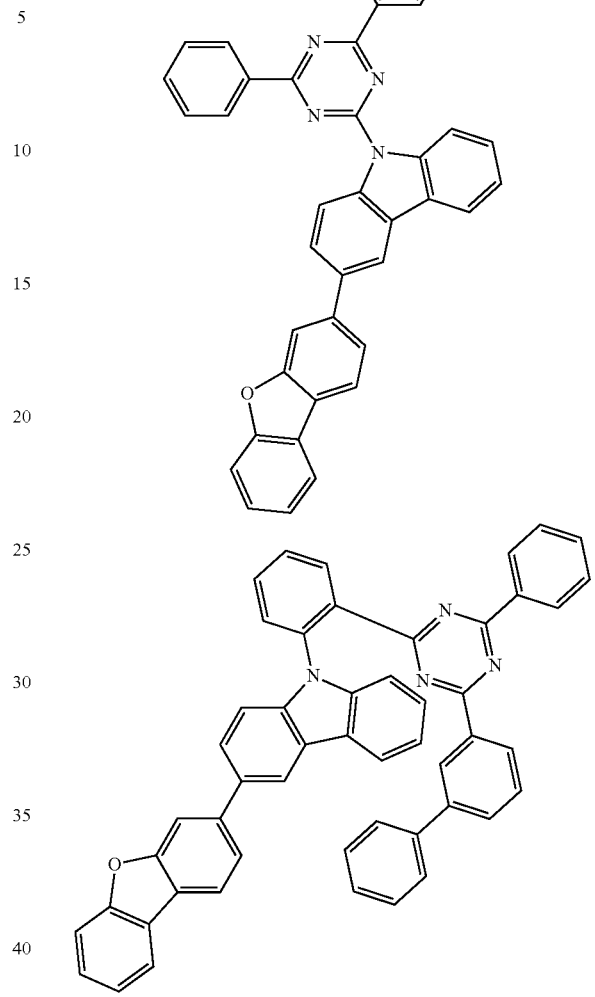
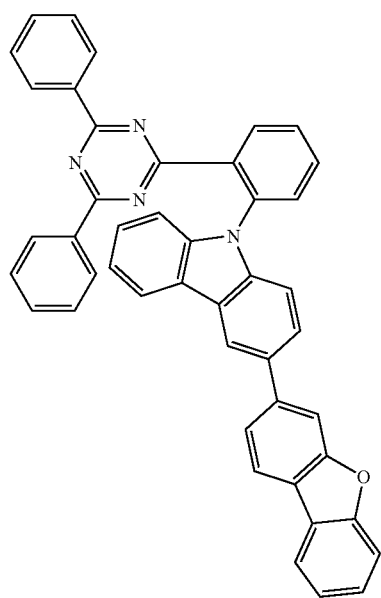

201
-continued
202
-continued
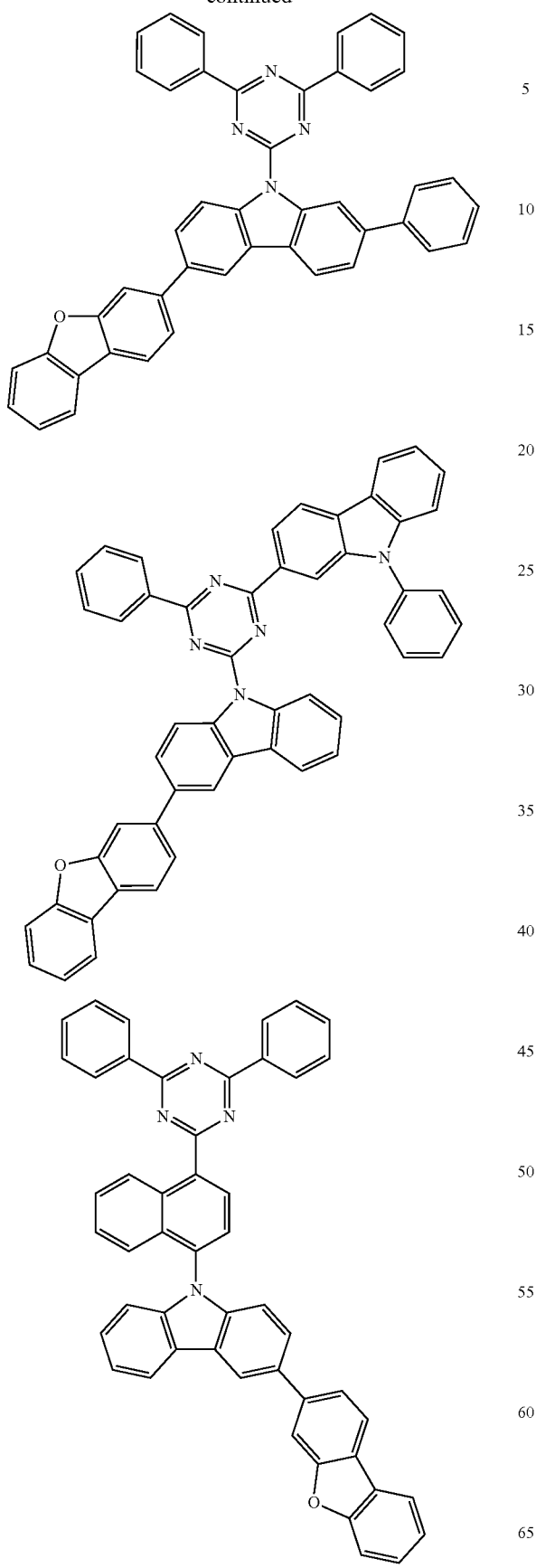
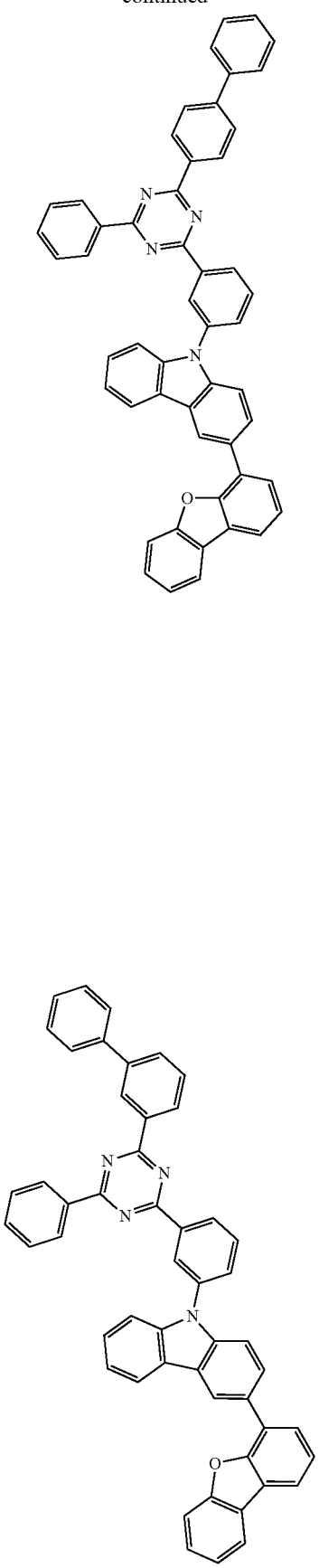

203
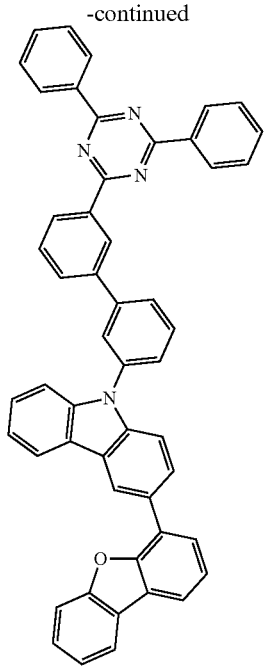
204
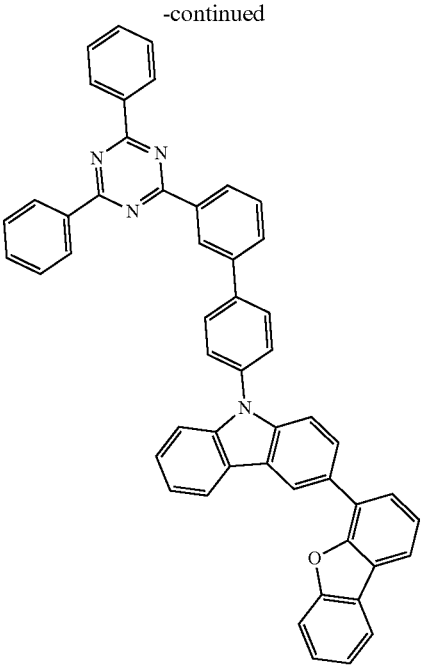
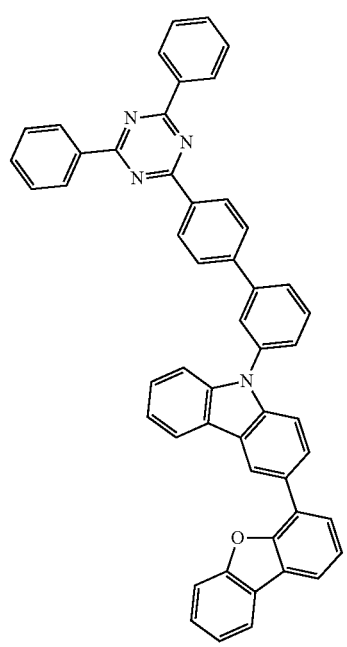
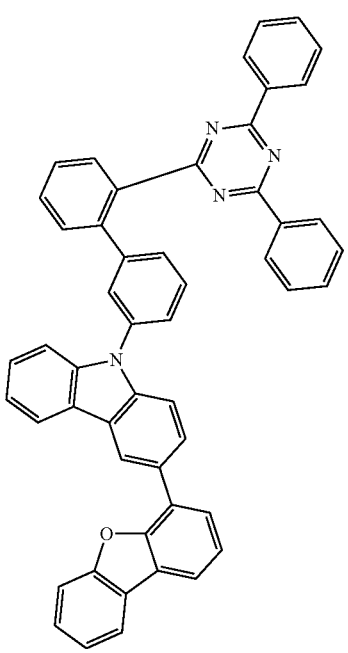

205
-continued
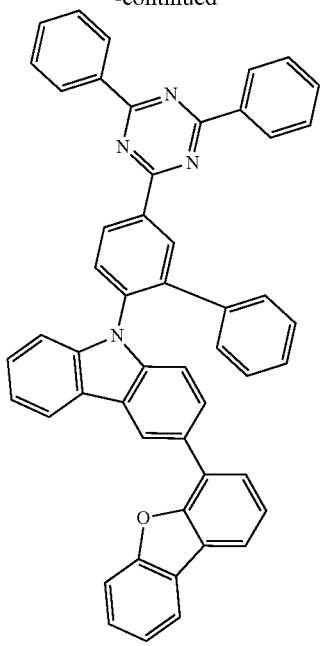
206
-continued
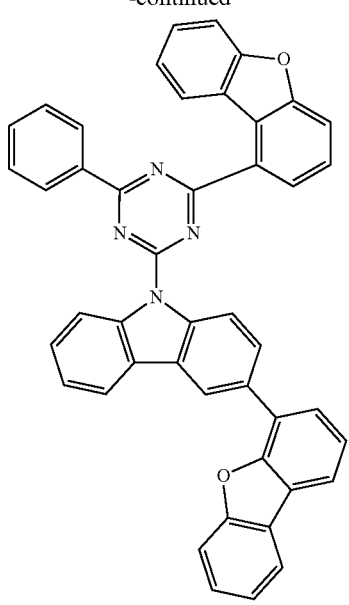
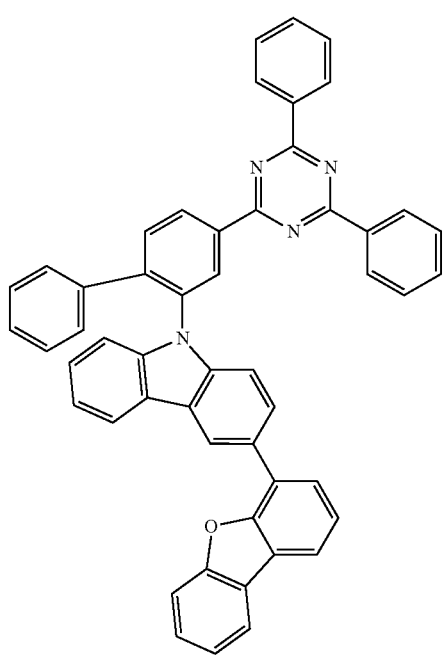

207
-continued
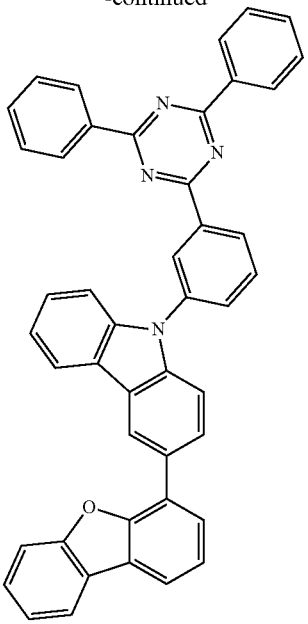
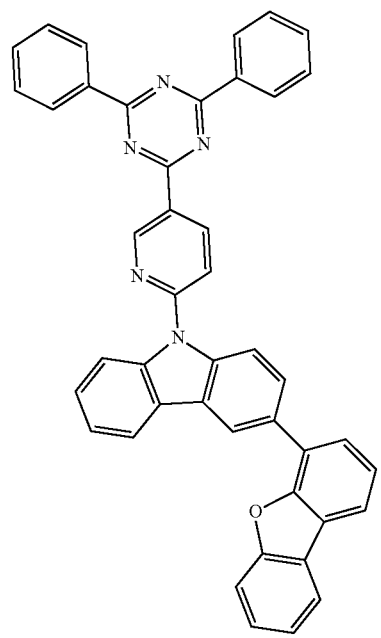
208
-continued
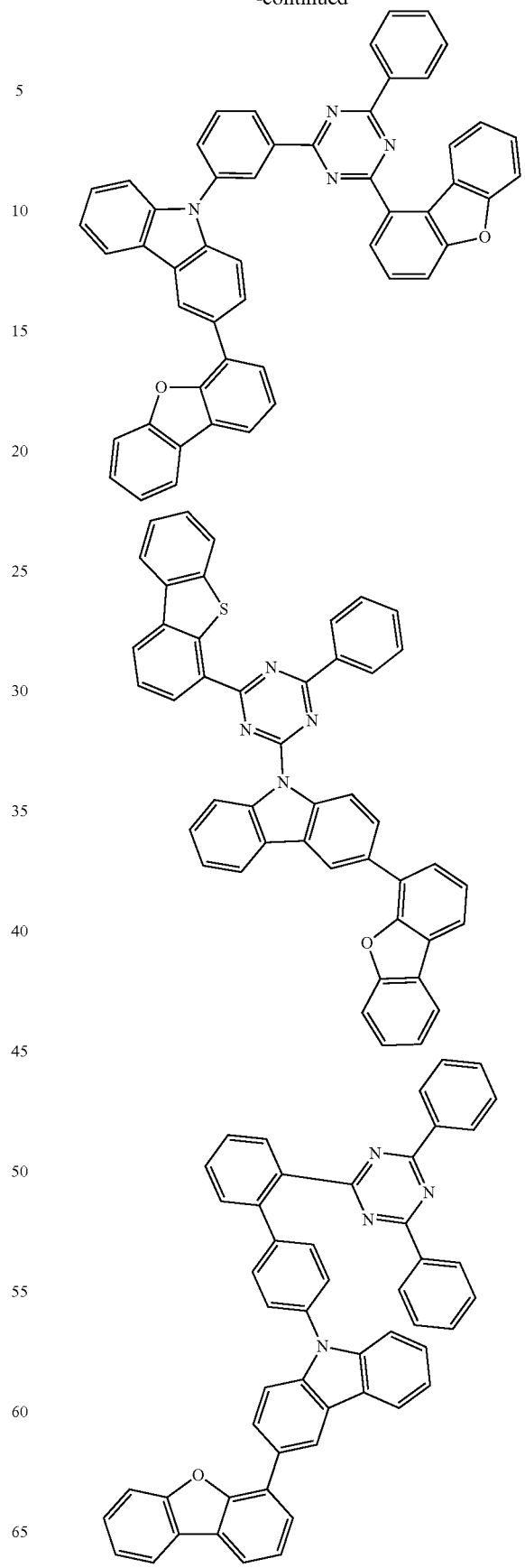

209
-continued
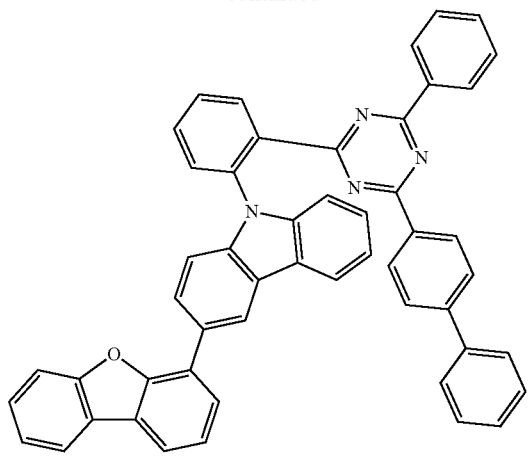
210
-continued
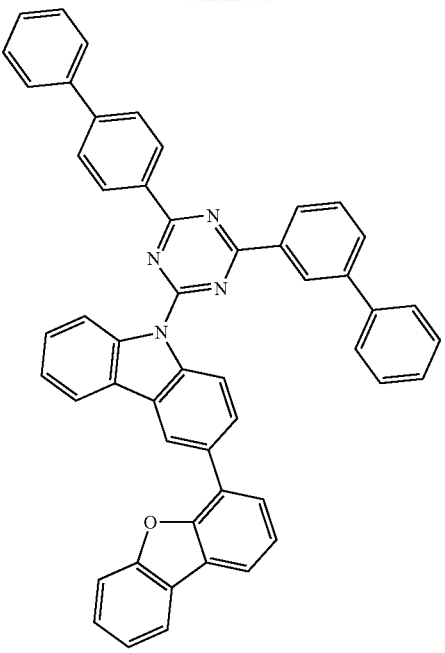
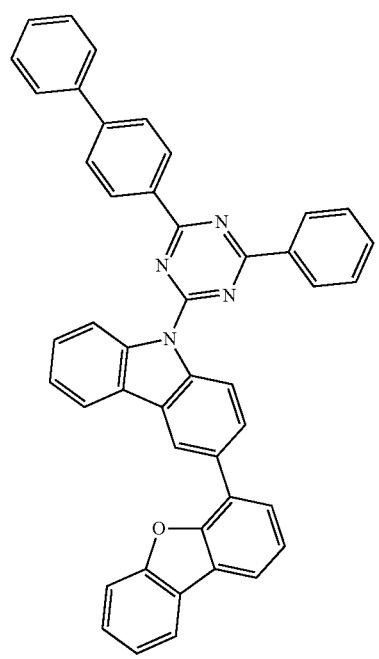
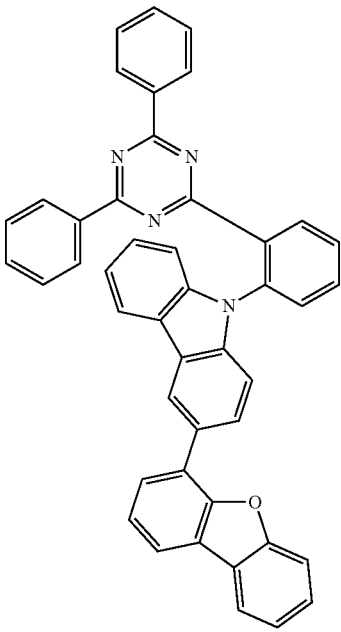

211
-continued
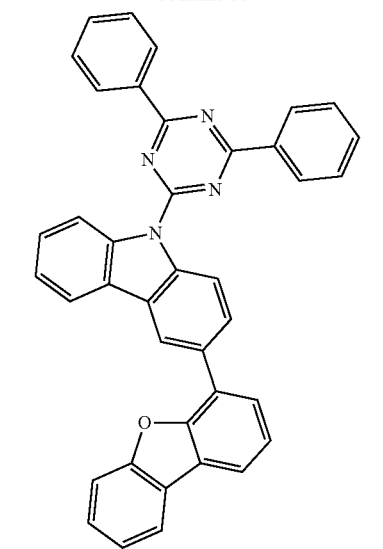
212
-continued
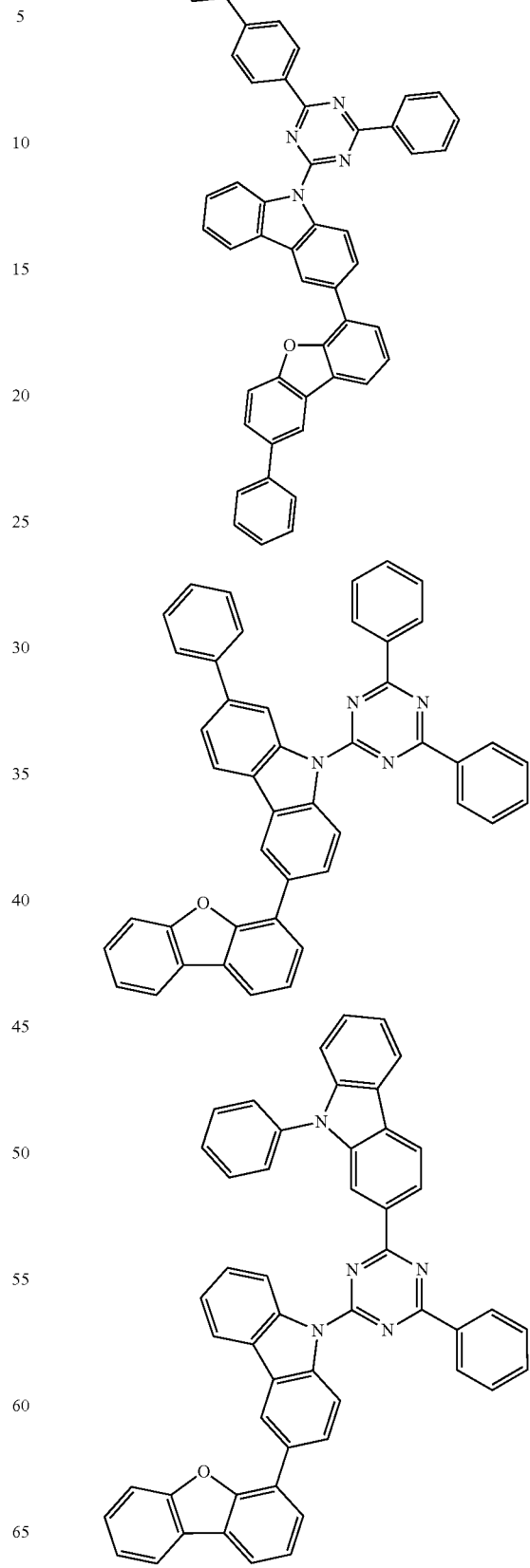
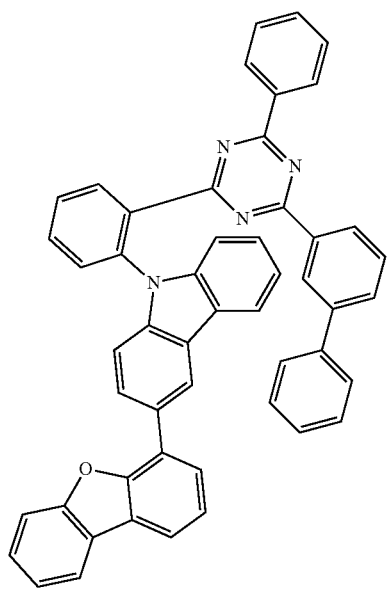

213
-continued
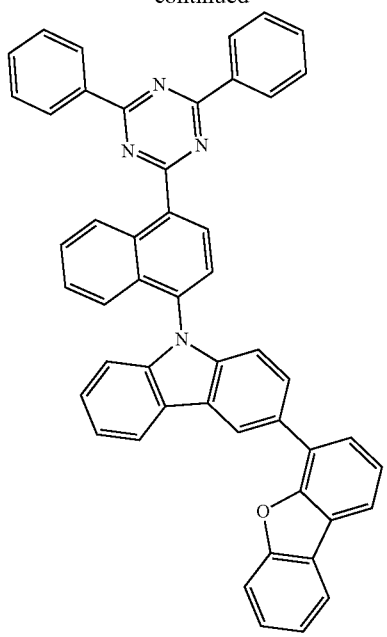
214
-continued
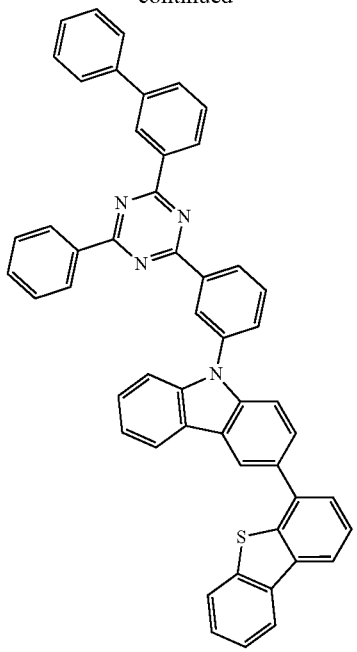

215
-continued
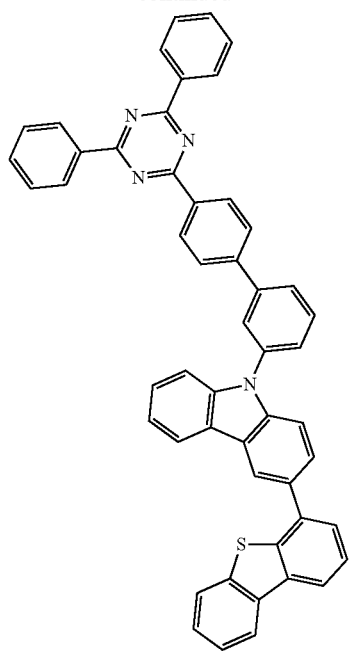
216
-continued
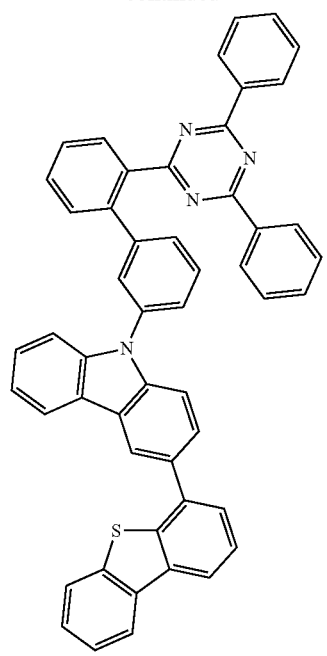
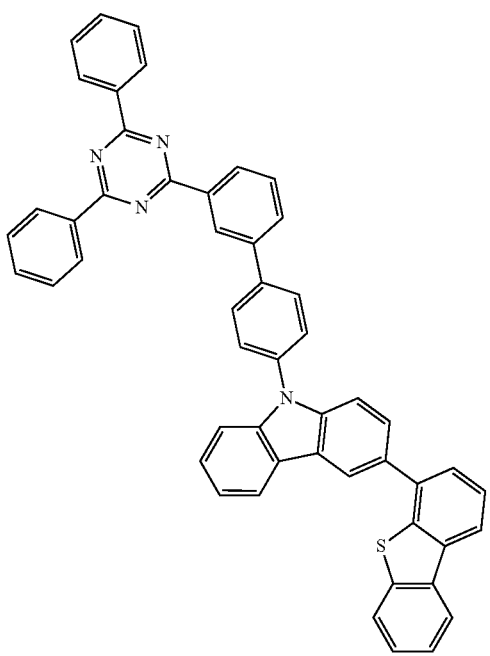
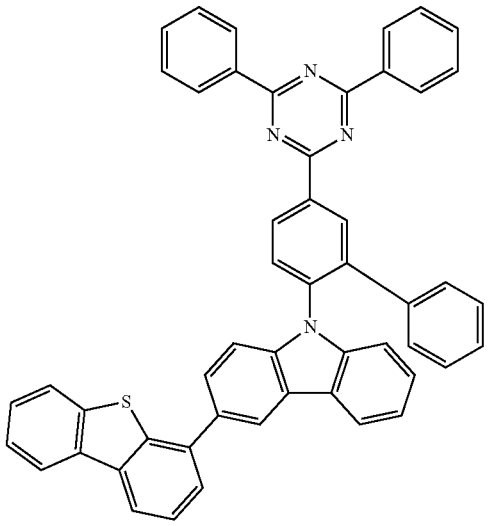

217
-continued

218
-continued

219
-continued
220
-continued
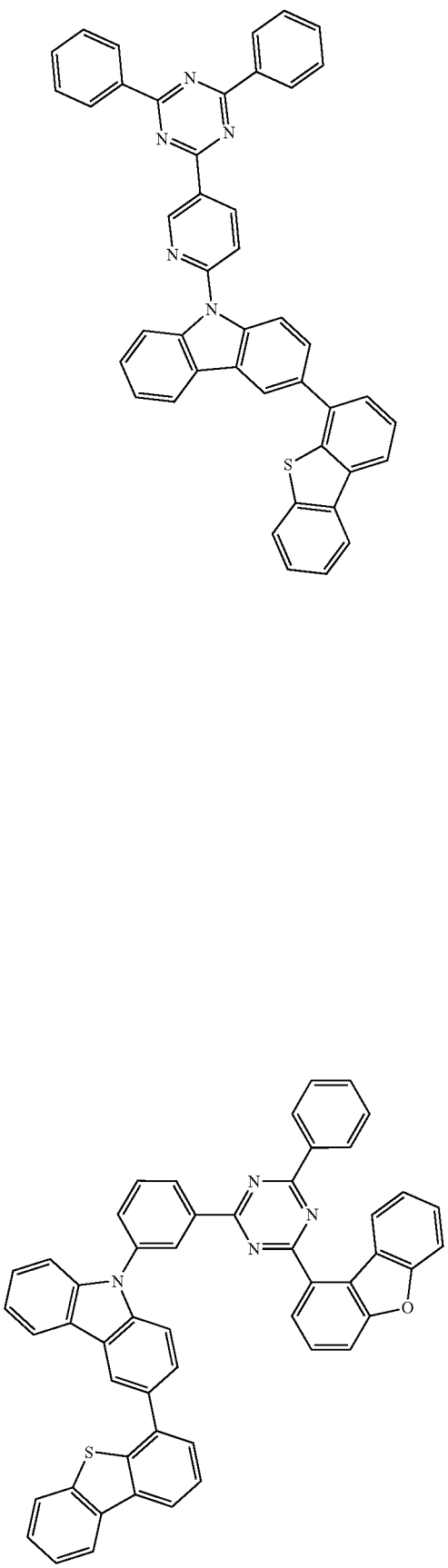
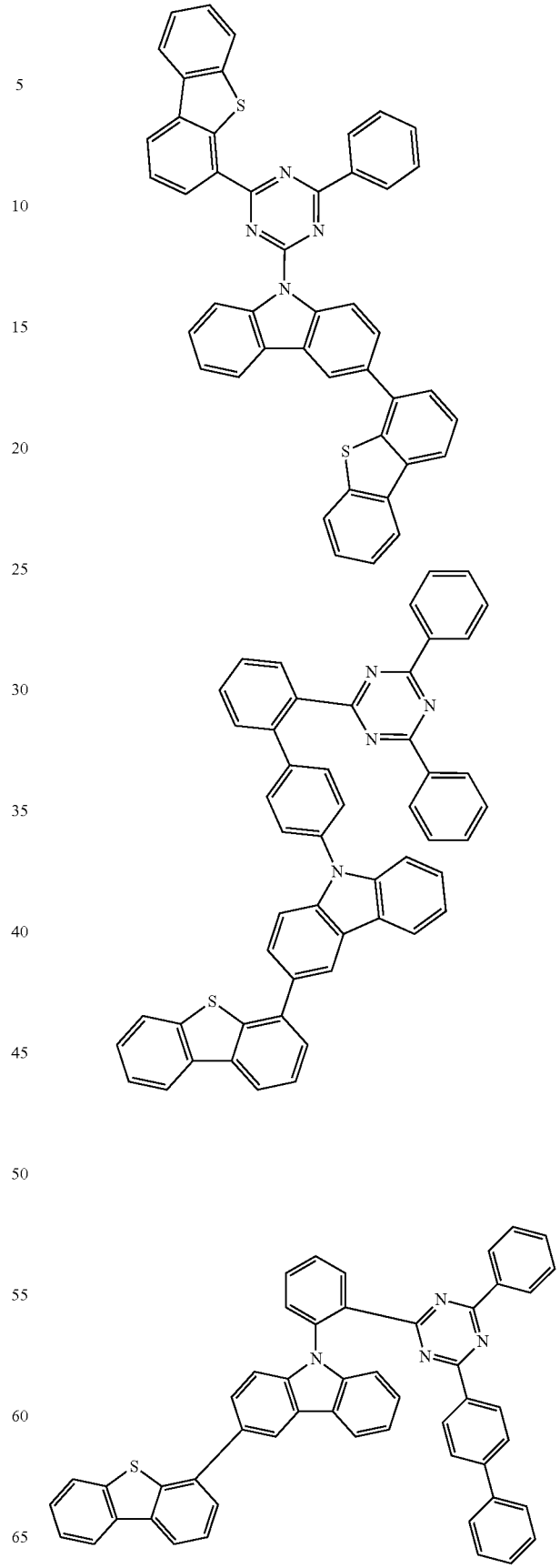

221
-continued
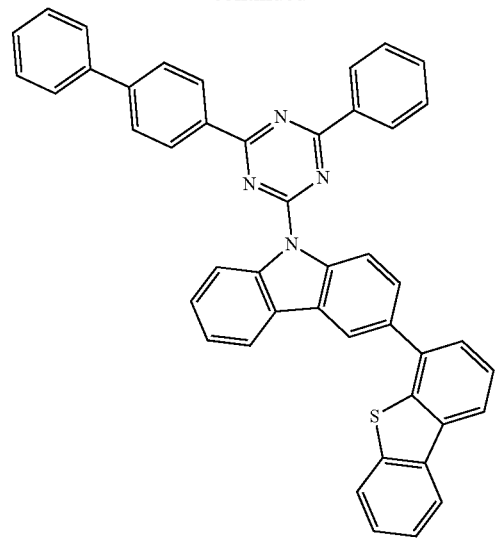
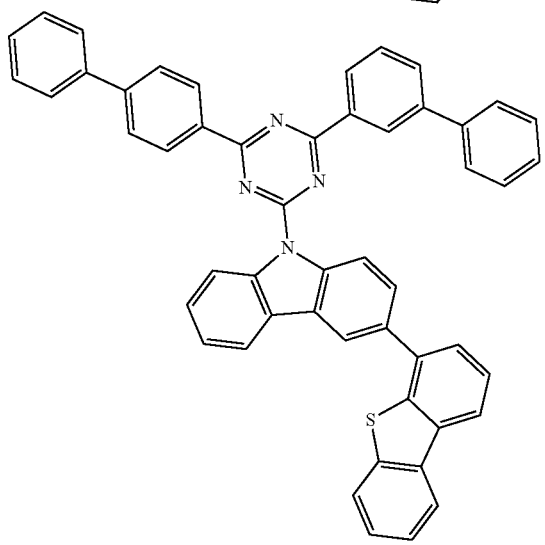
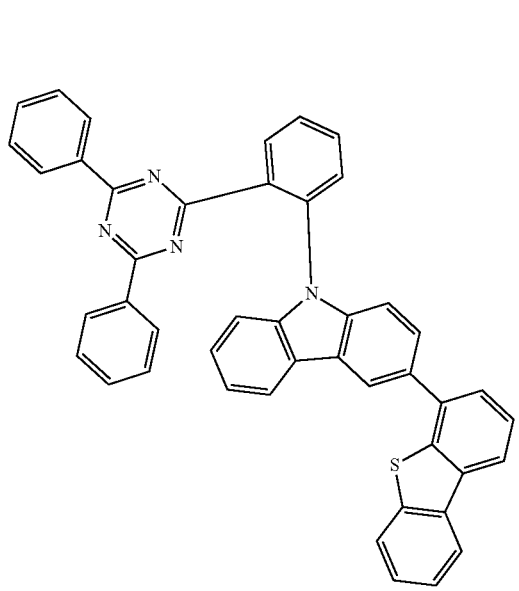
222
-continued
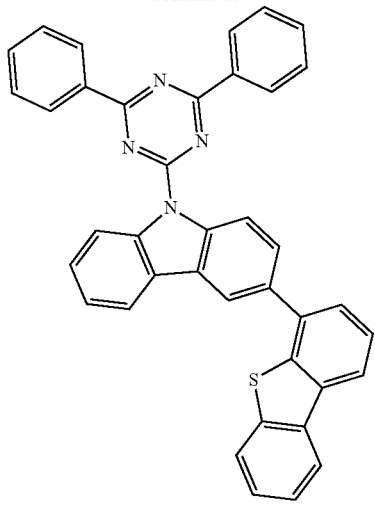
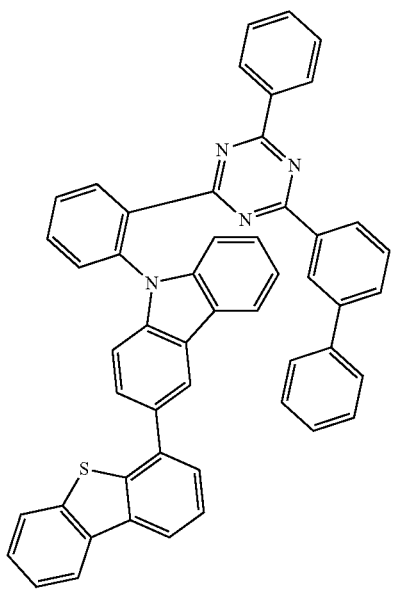

223
-continued
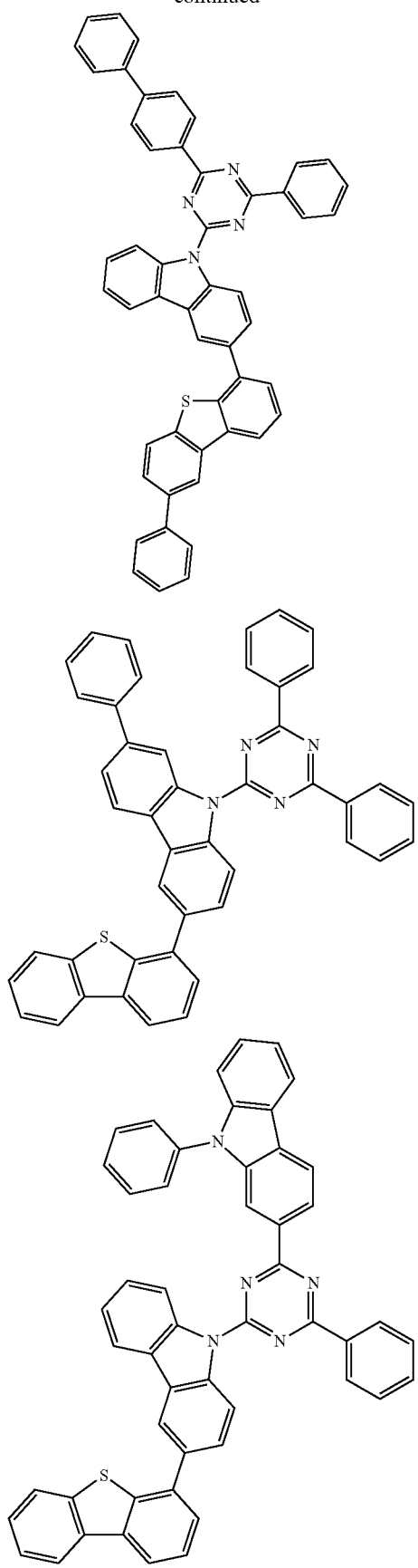
224
-continued
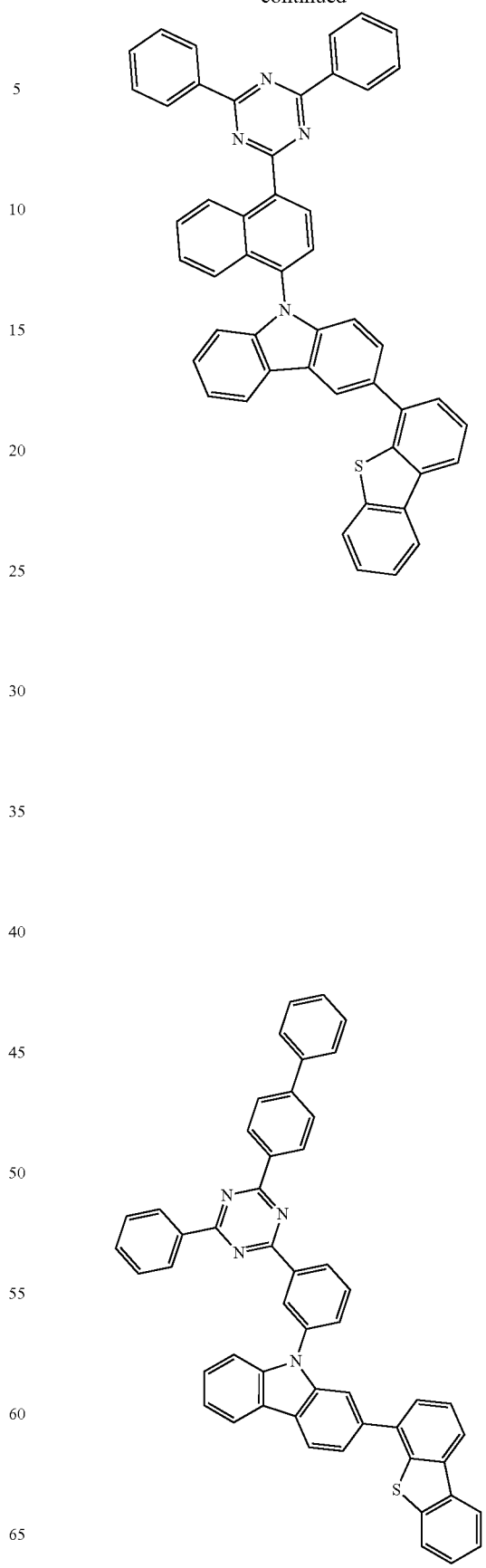

225
-continued
226
-continued
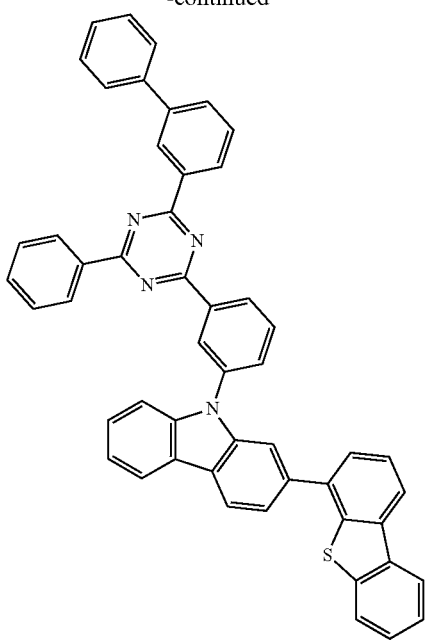
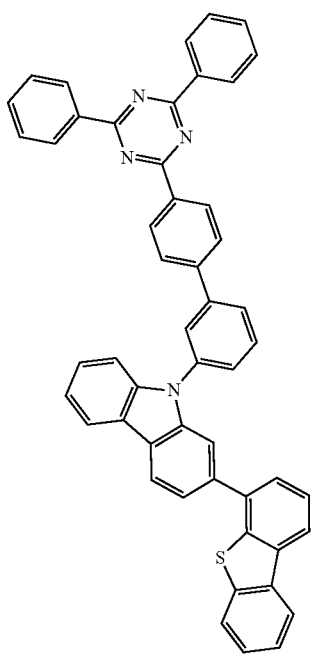

227
-continued
228
-continued
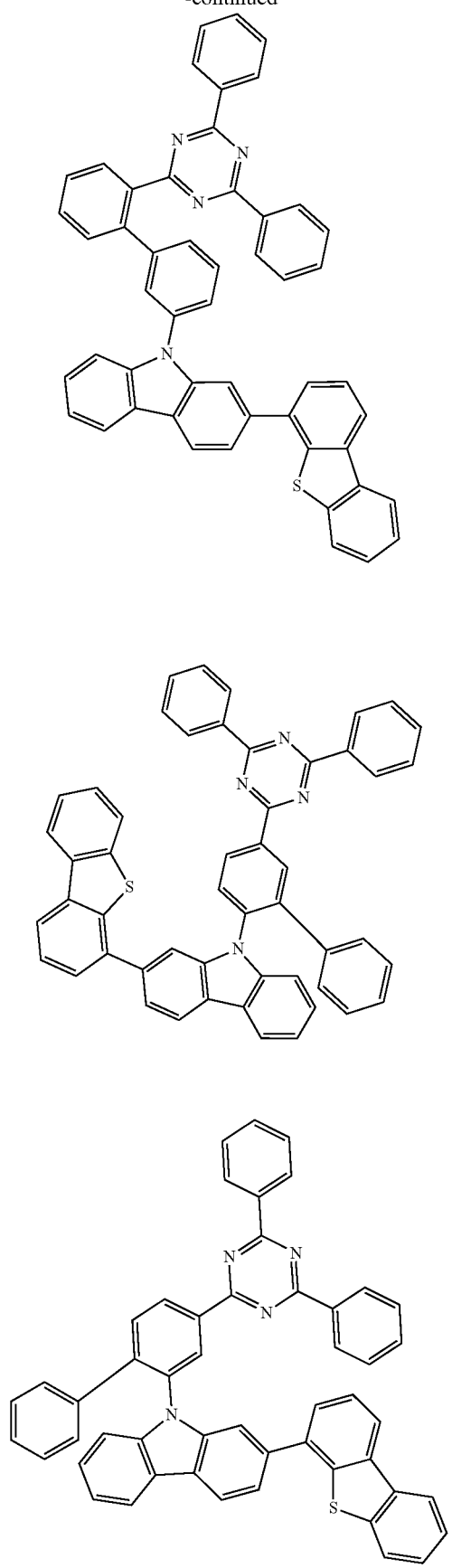
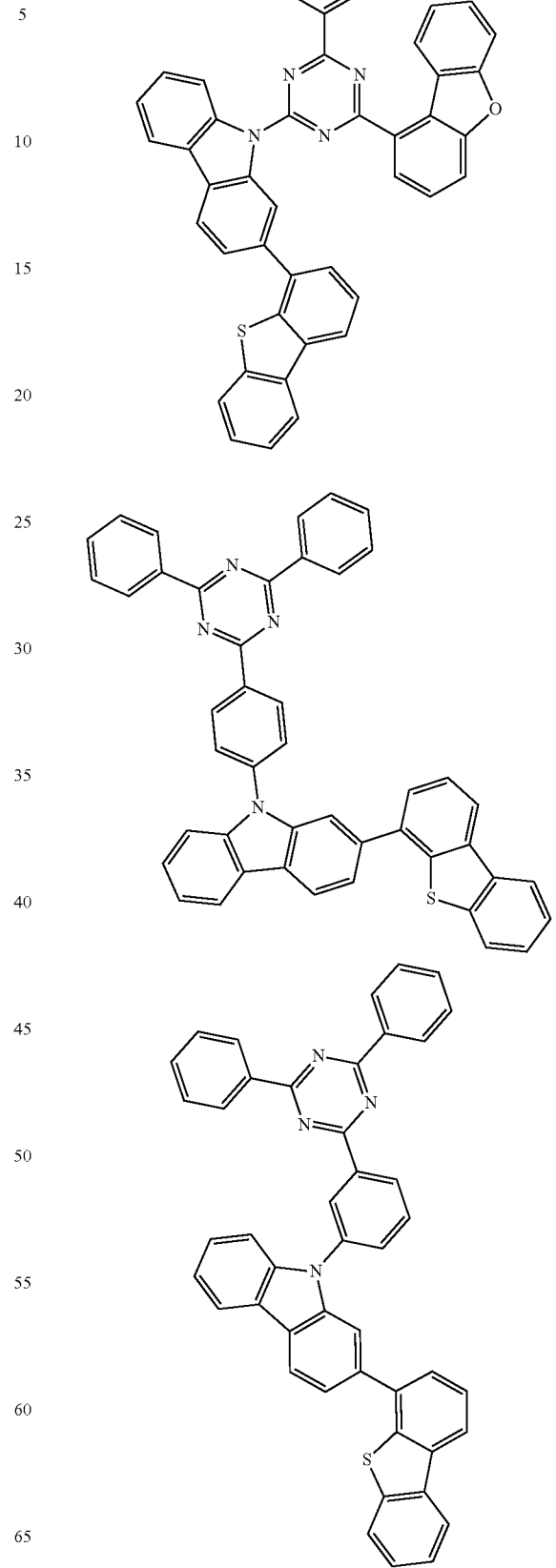

229
-continued
230
-continued
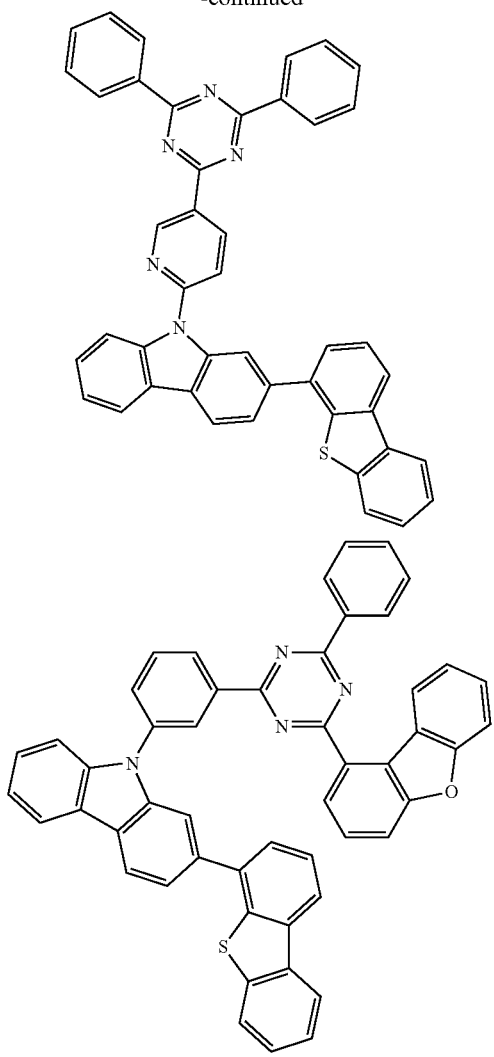
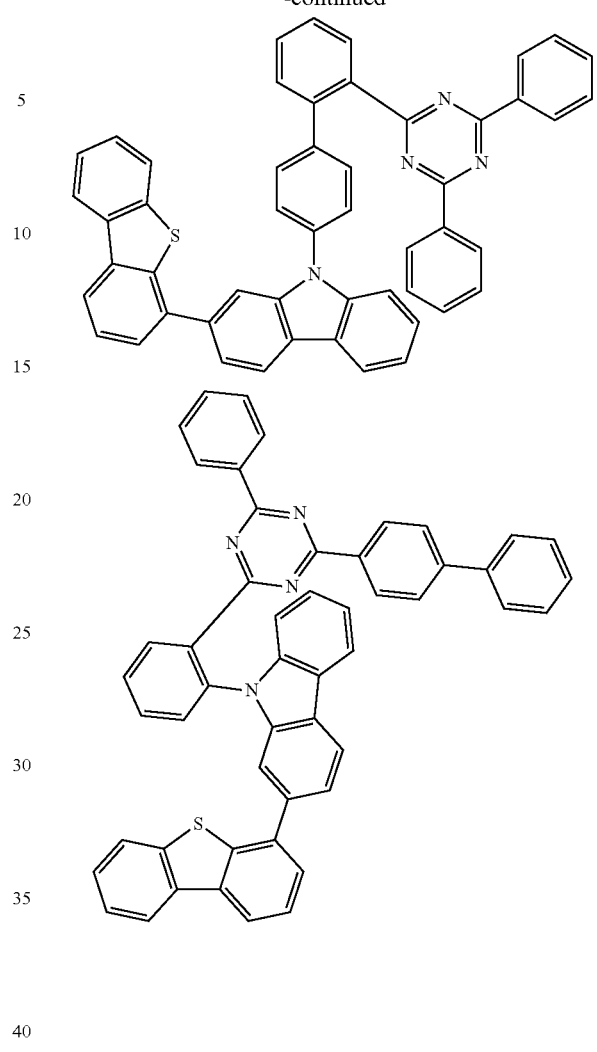
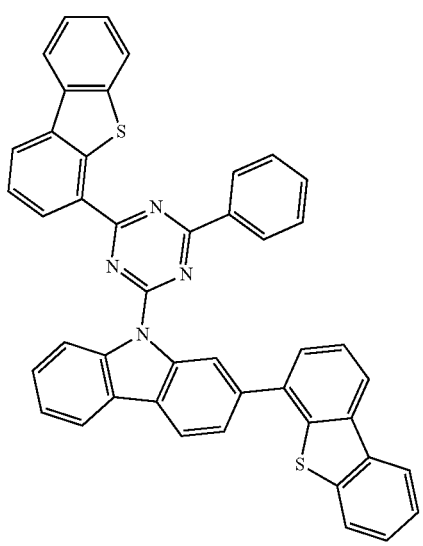
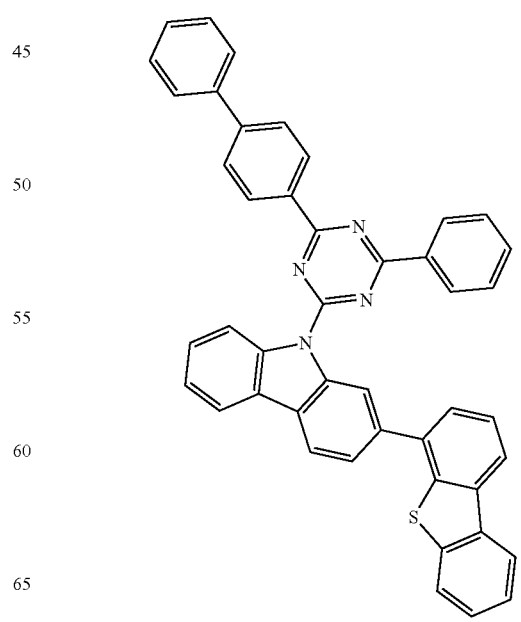

231
-continued
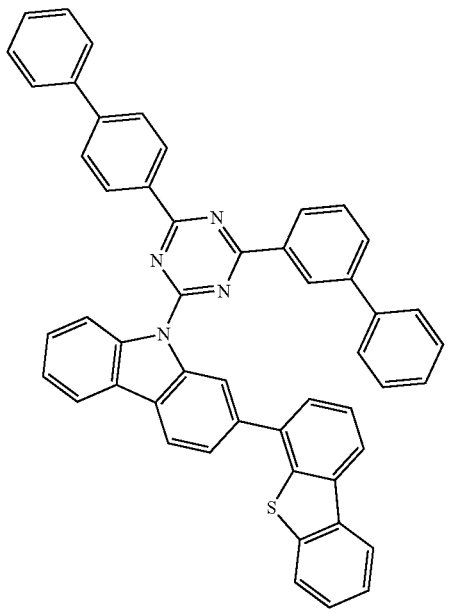
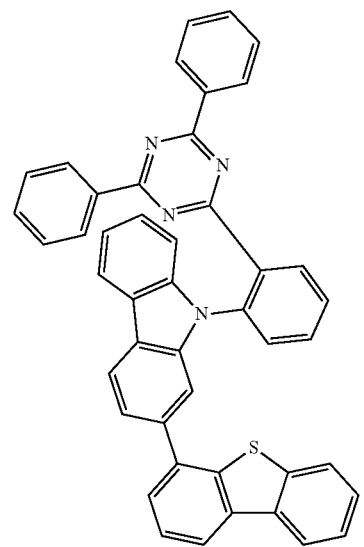
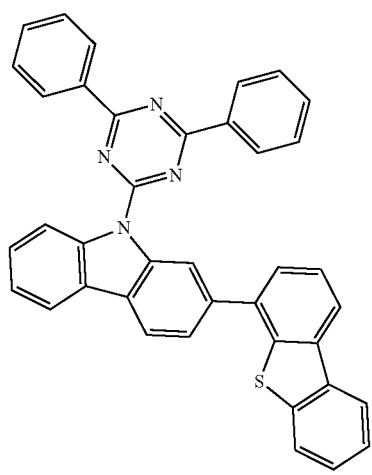
232
-continued
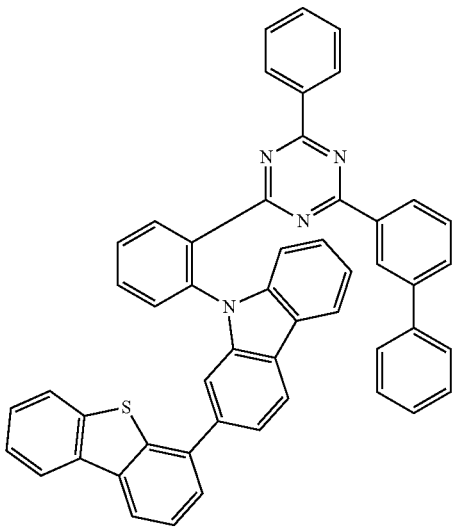
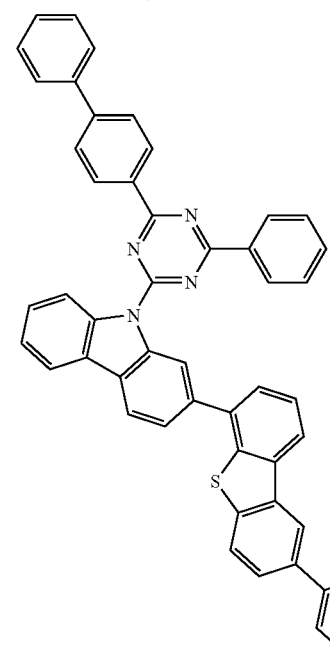
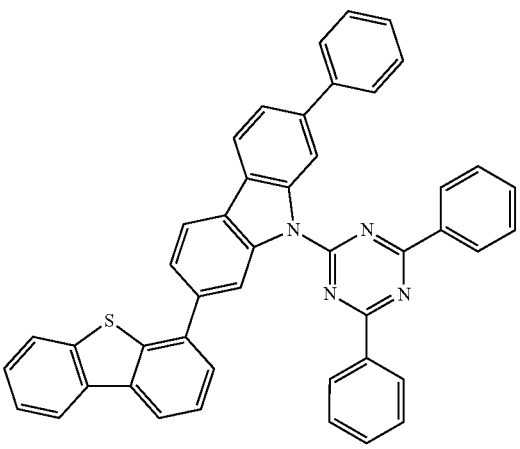

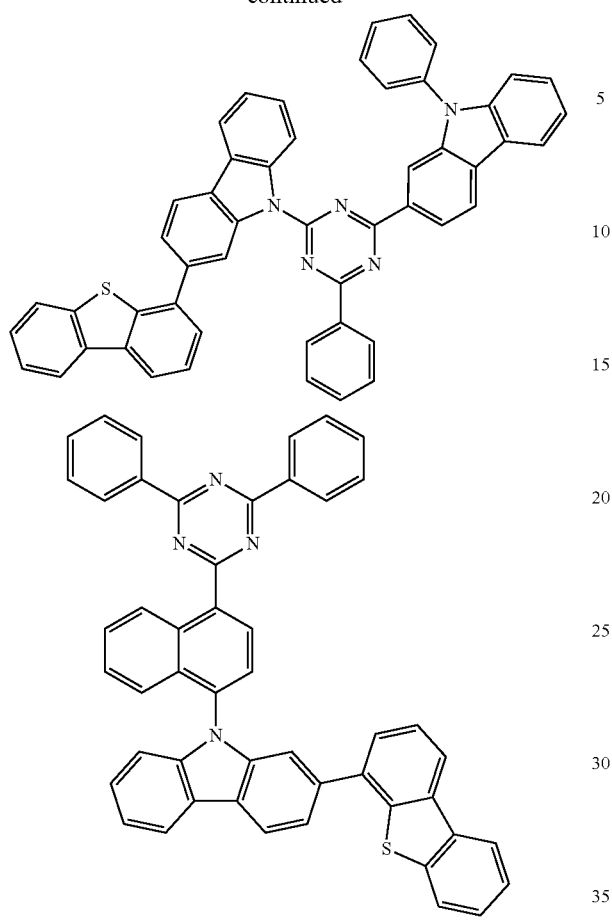
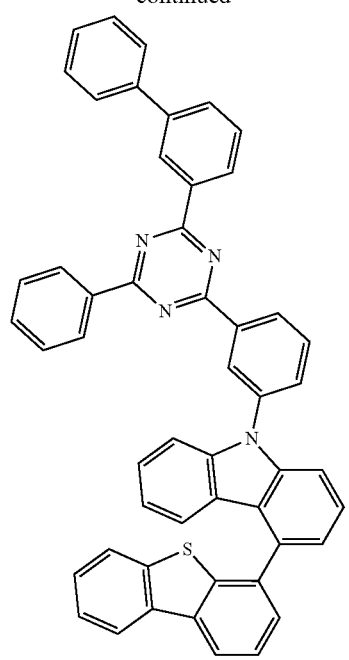

235
-continued
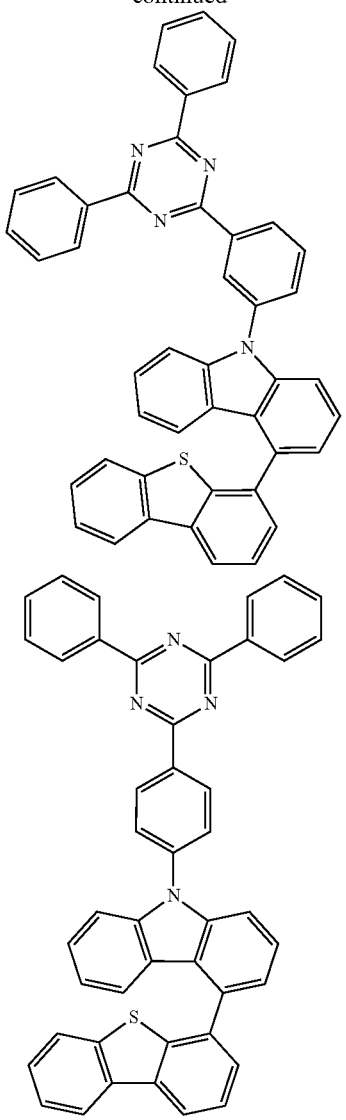
236
-continued
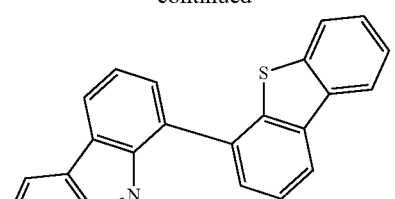
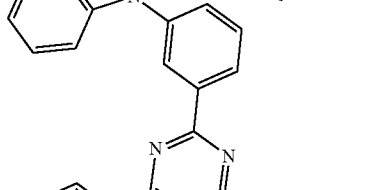
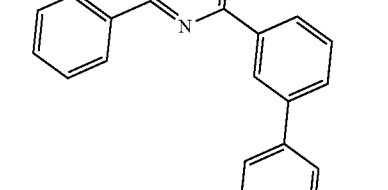
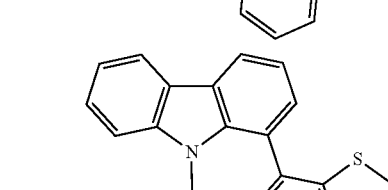
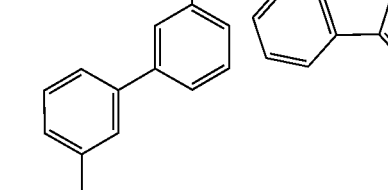
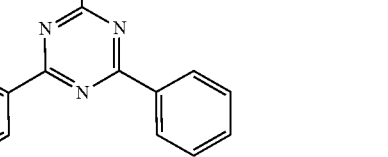

237
-continued
238
-continued

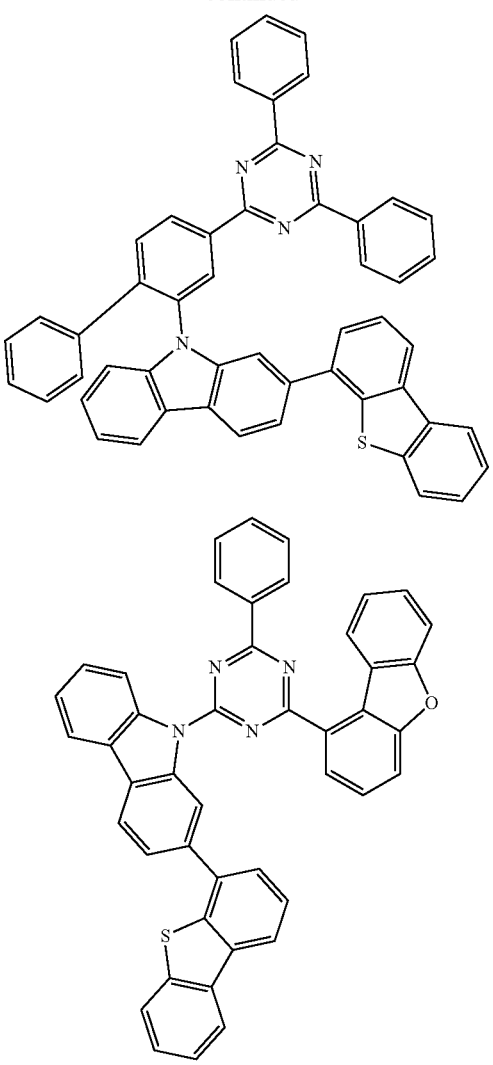
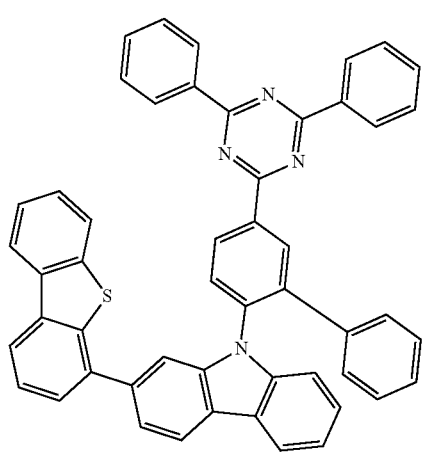
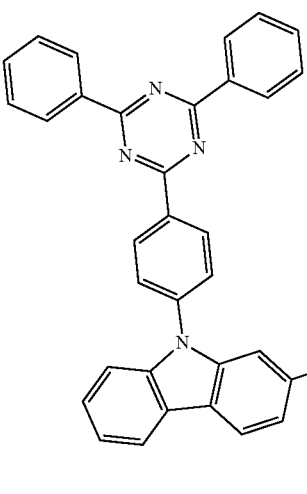

239
-continued
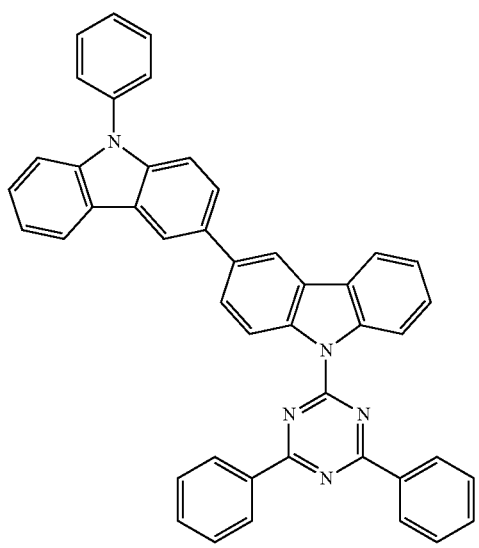
240
-continued
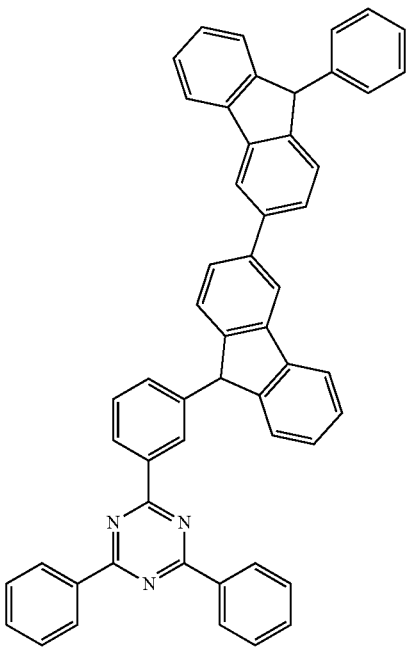
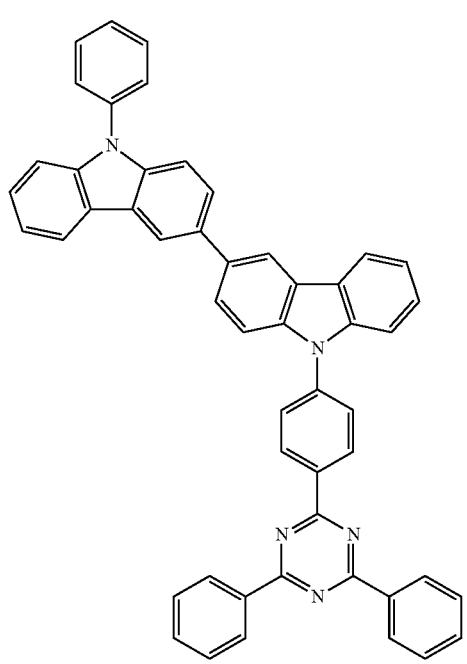
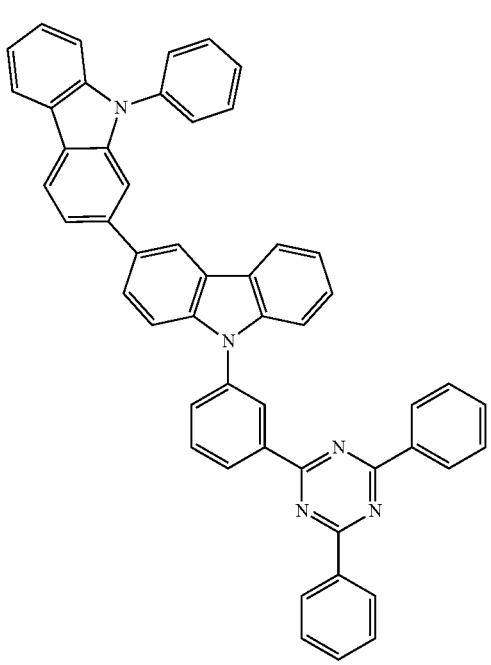

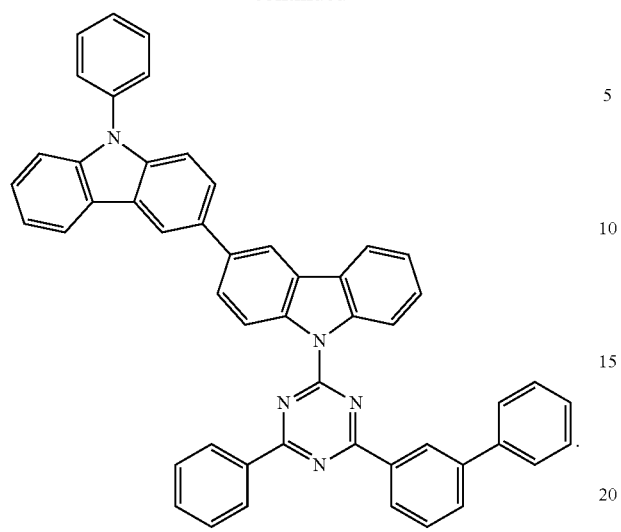
The compound represented by formula 12 may be at least one selected from the group consisting of the following compounds, but is not limited thereto.
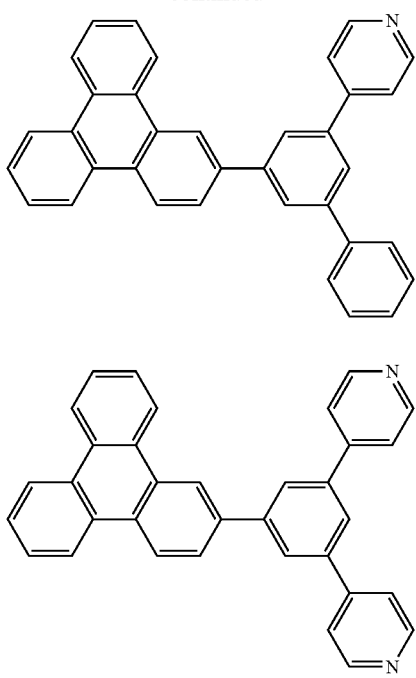
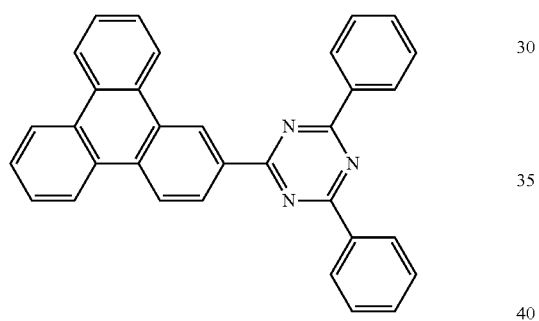
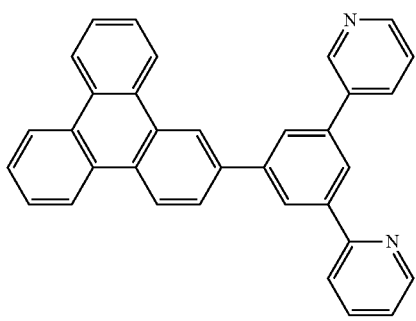
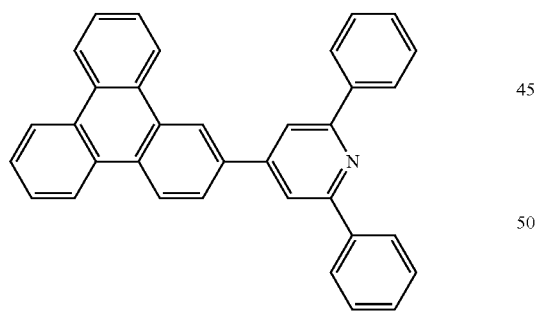
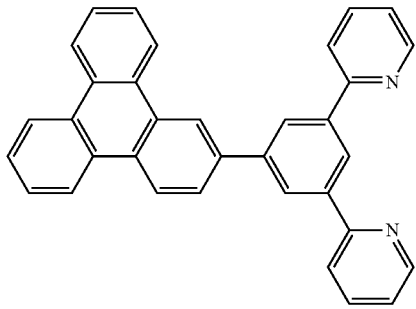
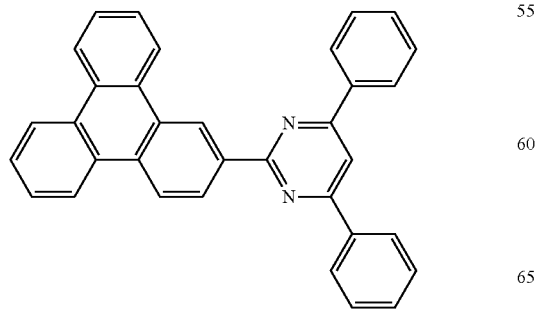
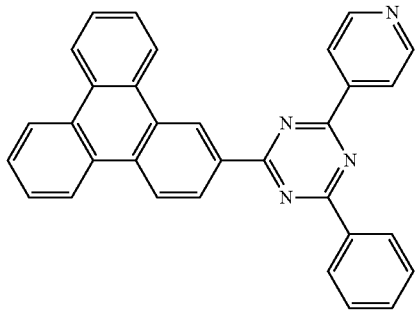

243
-continued
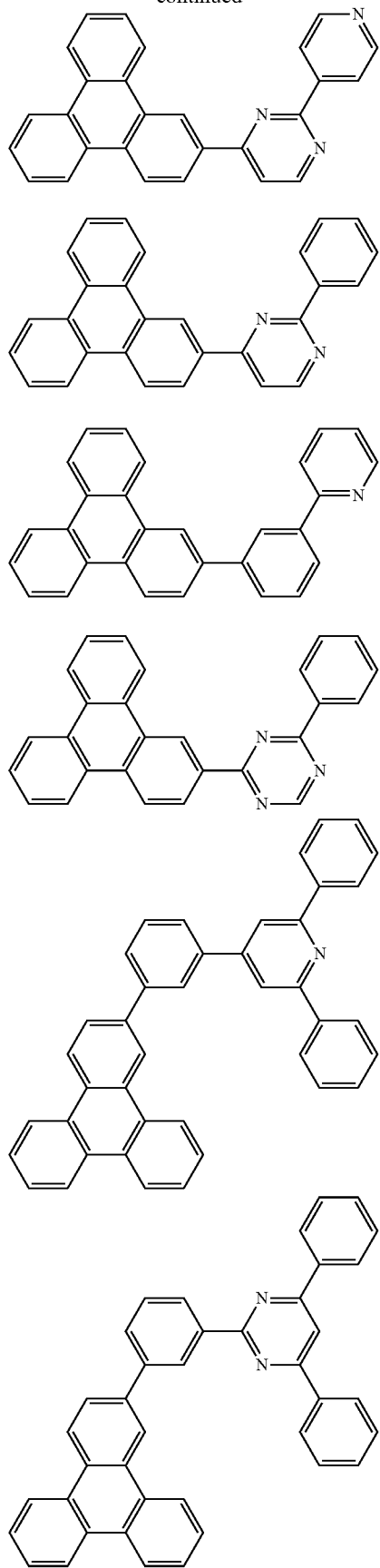
244
-continued
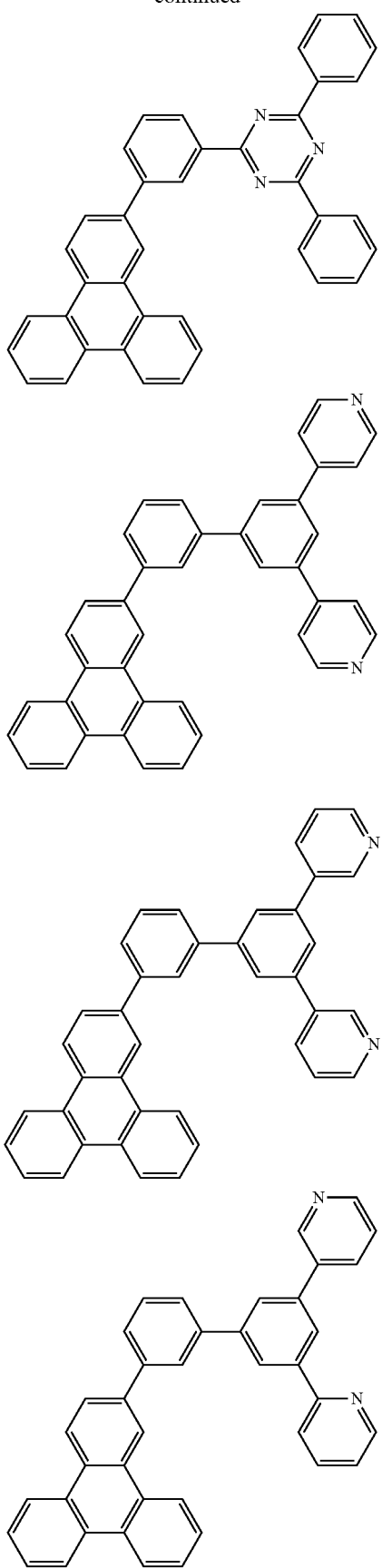

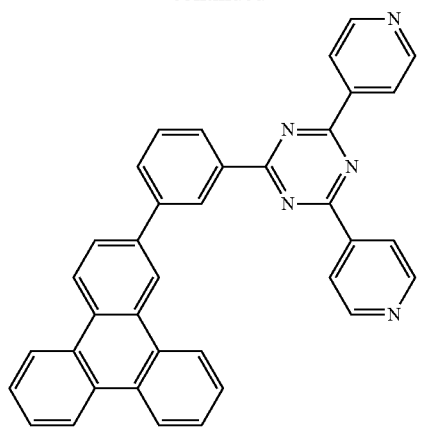
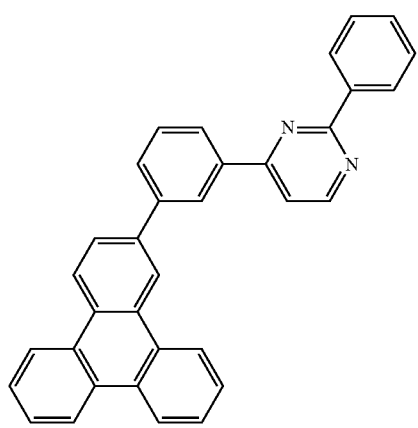
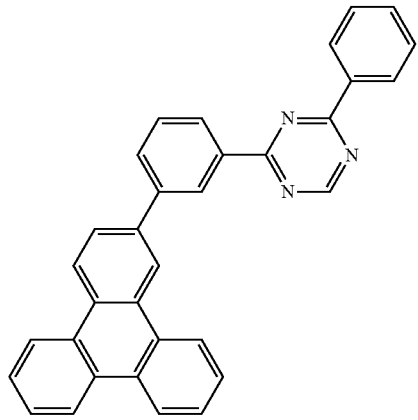
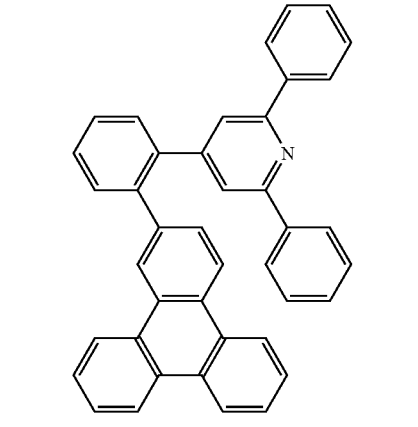
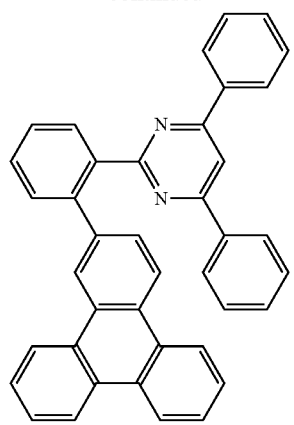

247
-continued
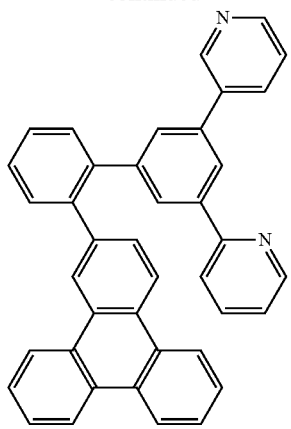
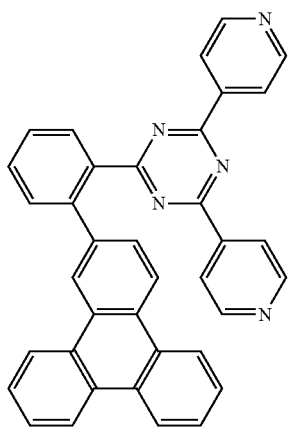
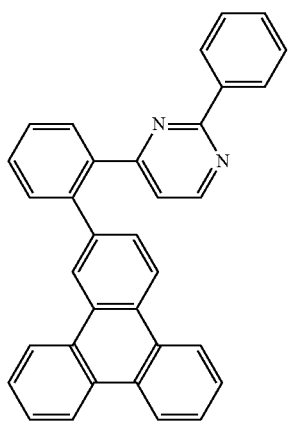
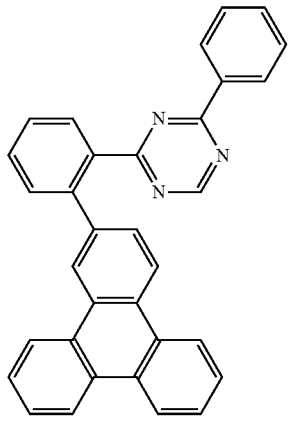
248
-continued
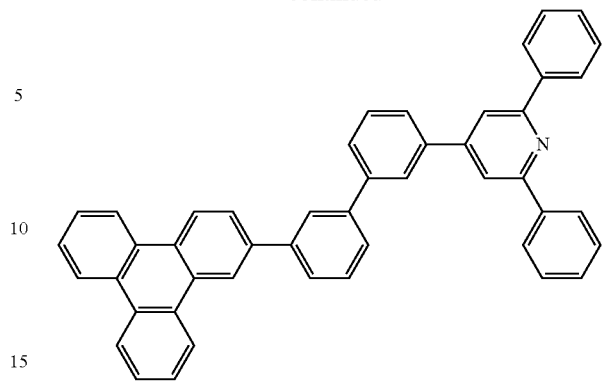
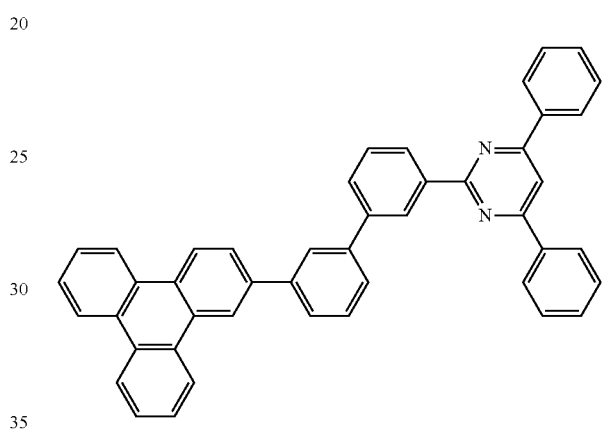
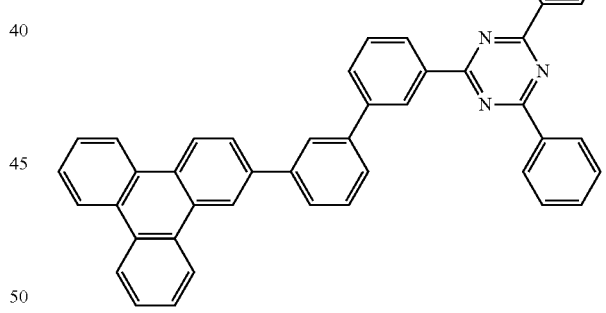
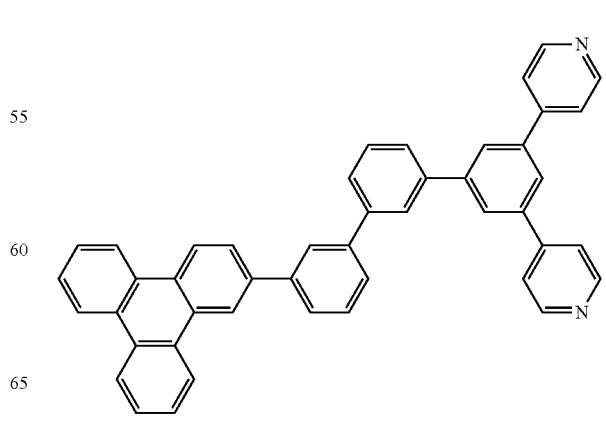

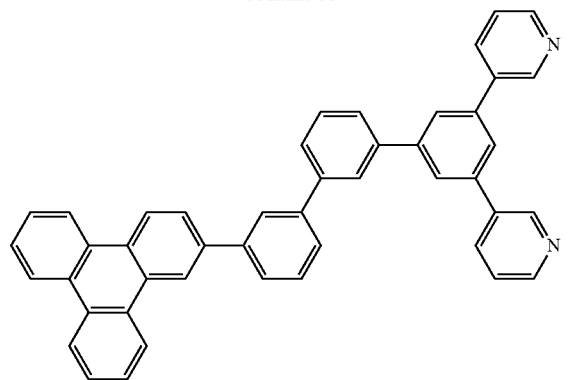
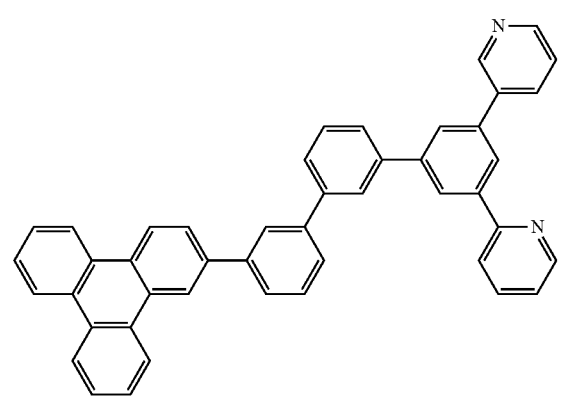

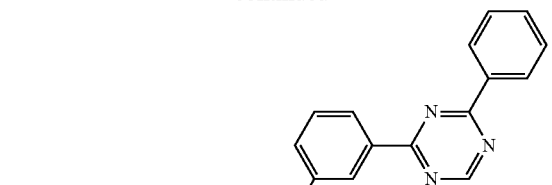
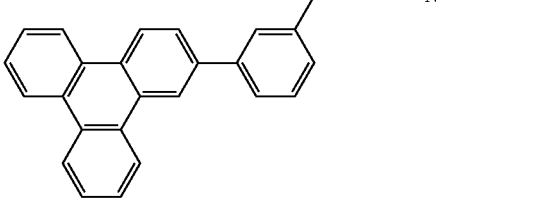
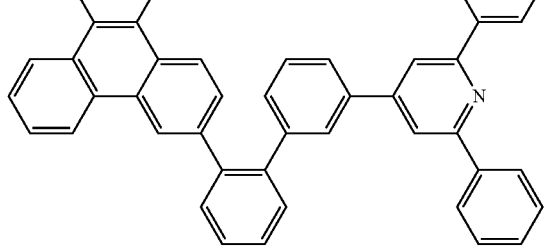
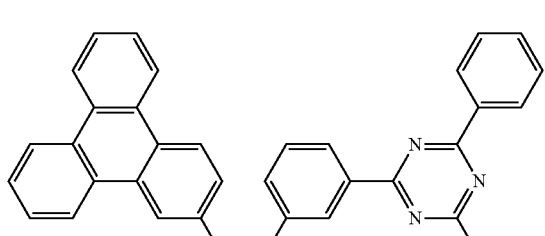
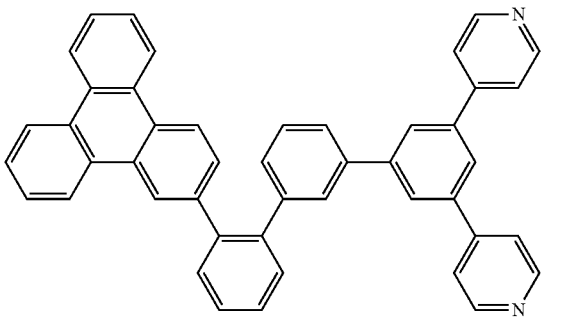

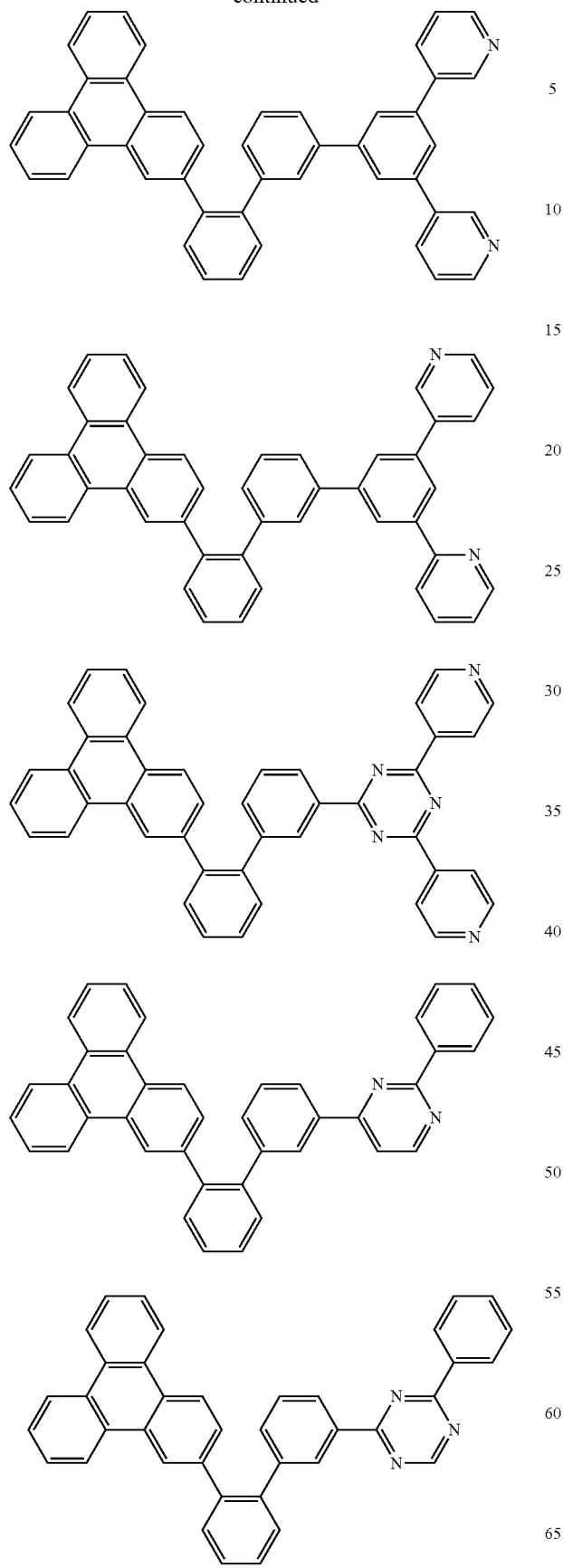
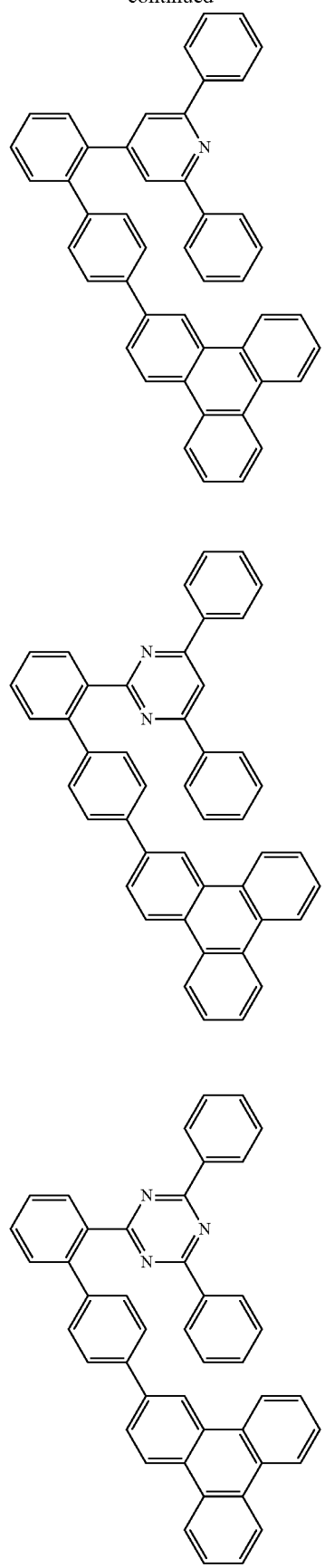

-continued
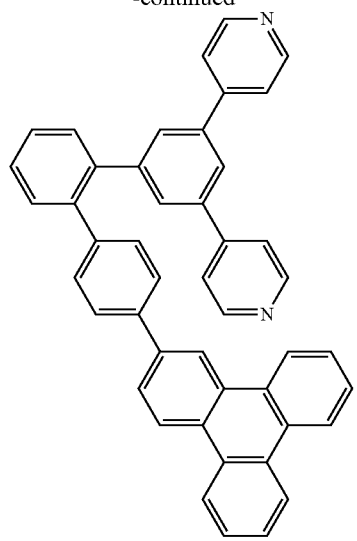
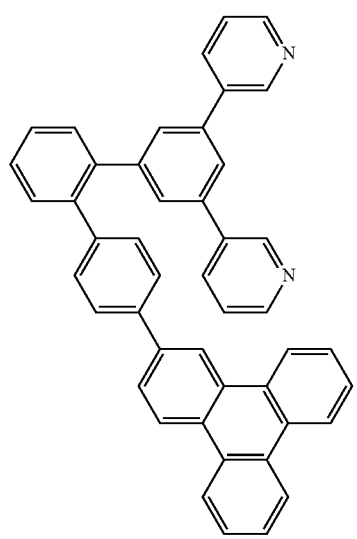
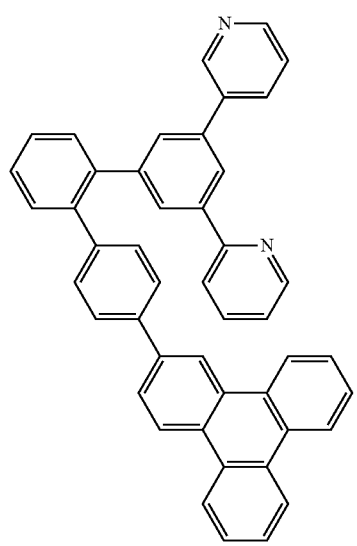
-continued
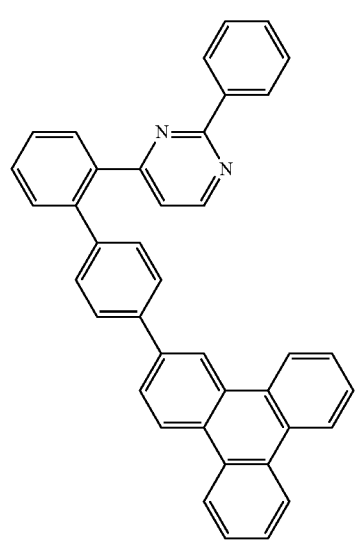
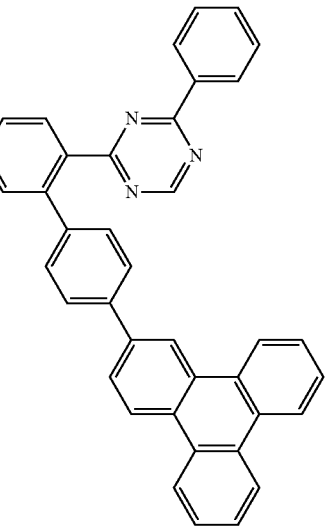

255
-continued
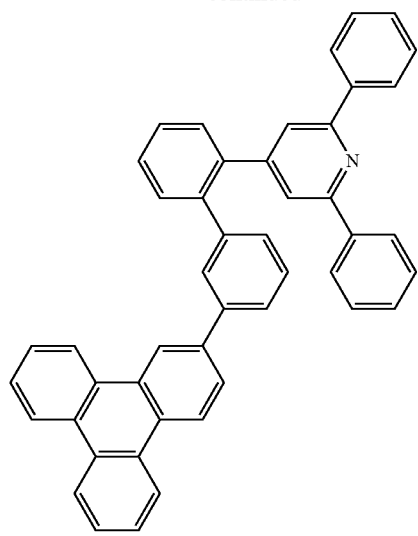
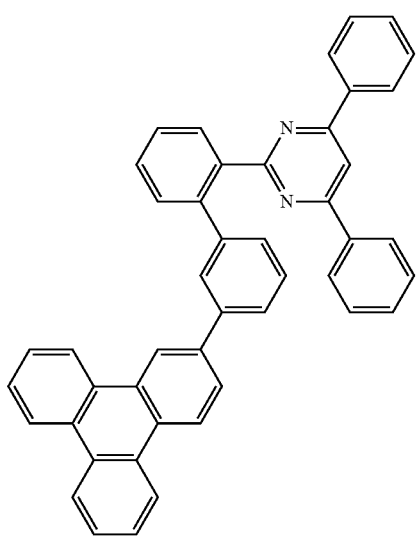
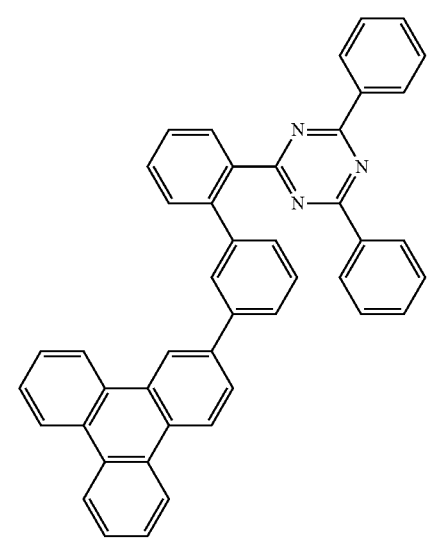
256
-continued
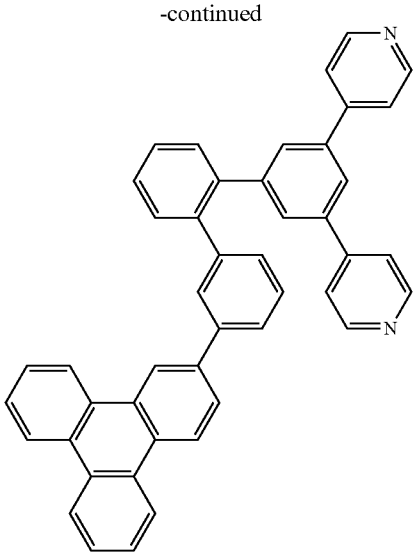
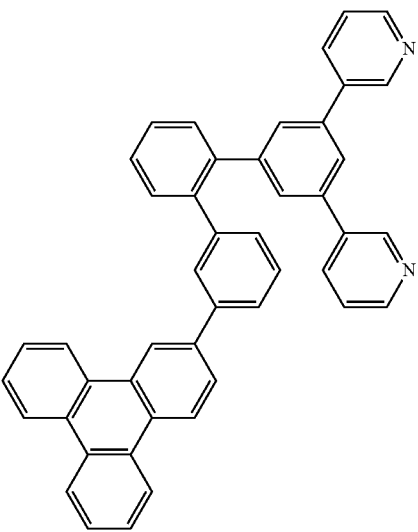
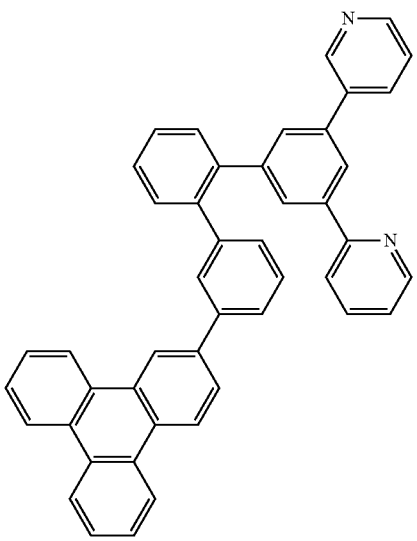

257
258
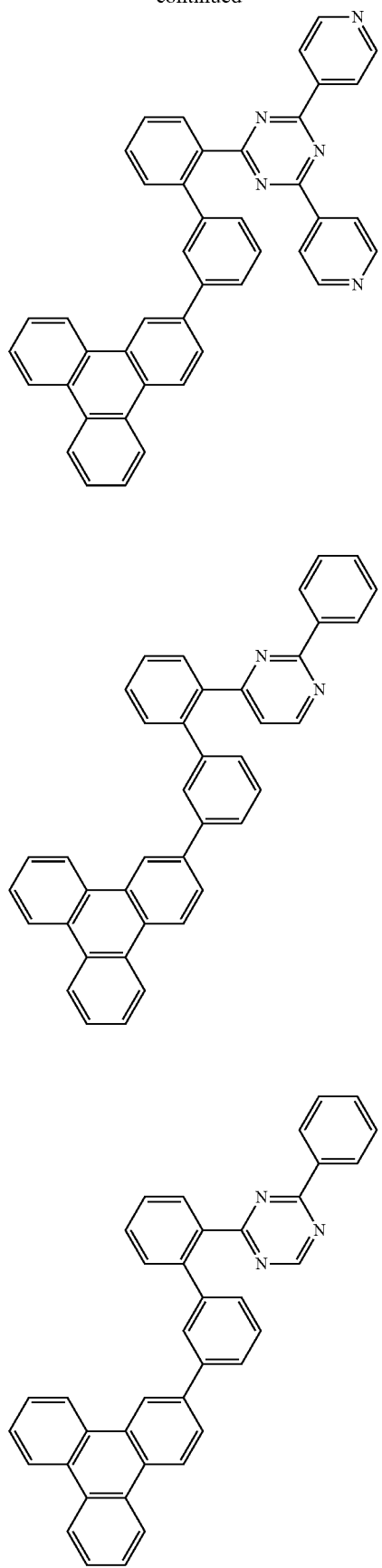
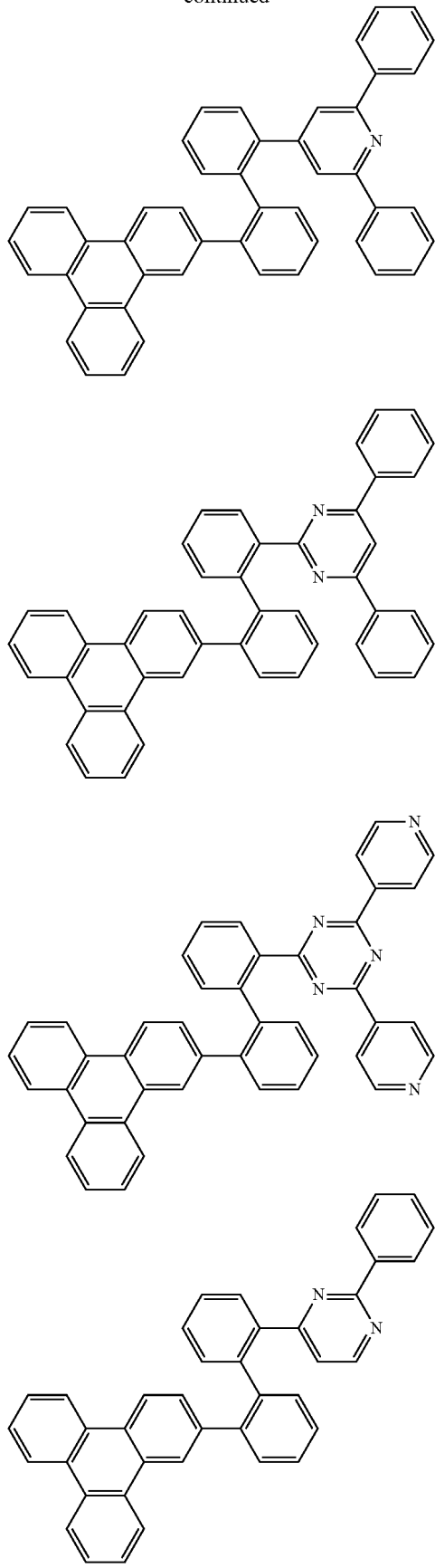

259
-continued
260
-continued
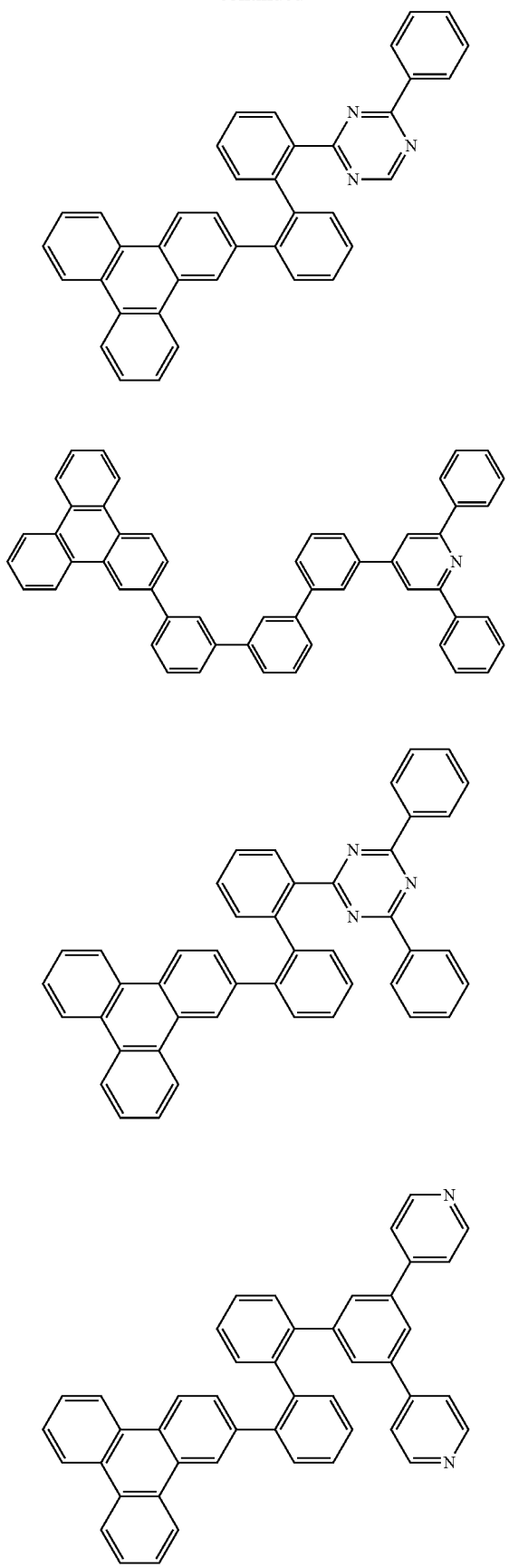
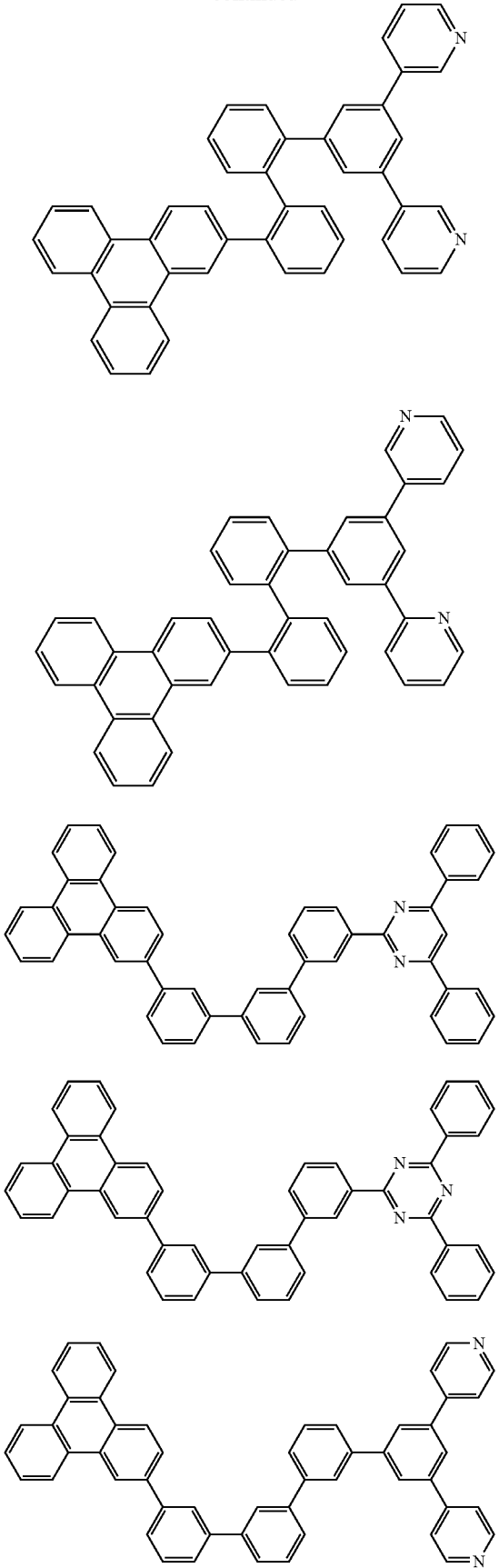

261
-continued
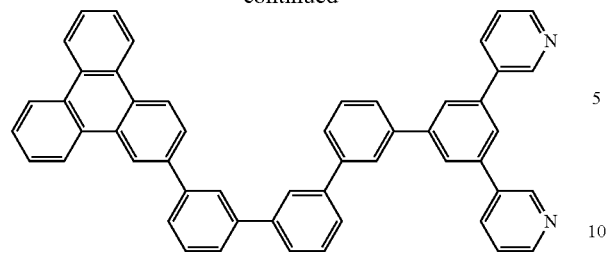
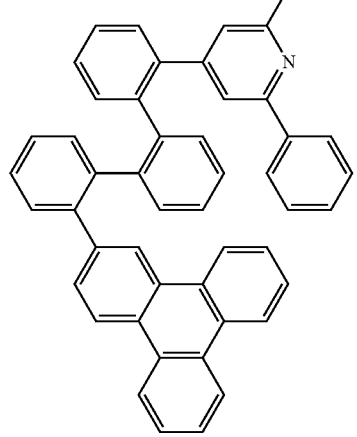
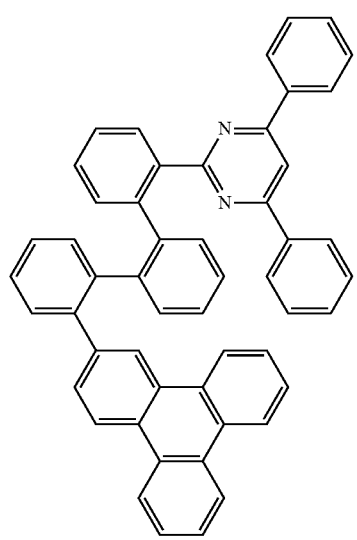
262
-continued
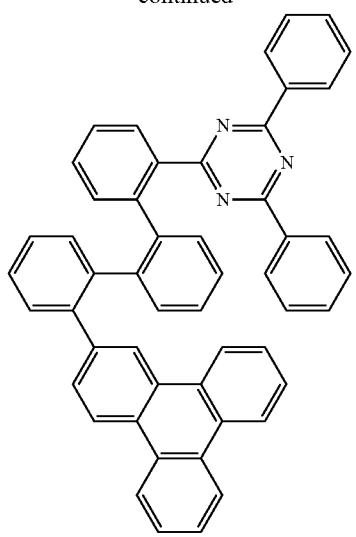
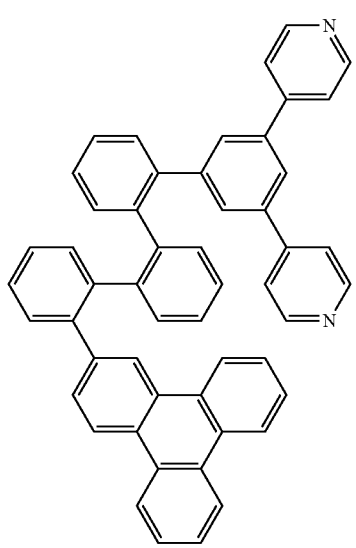
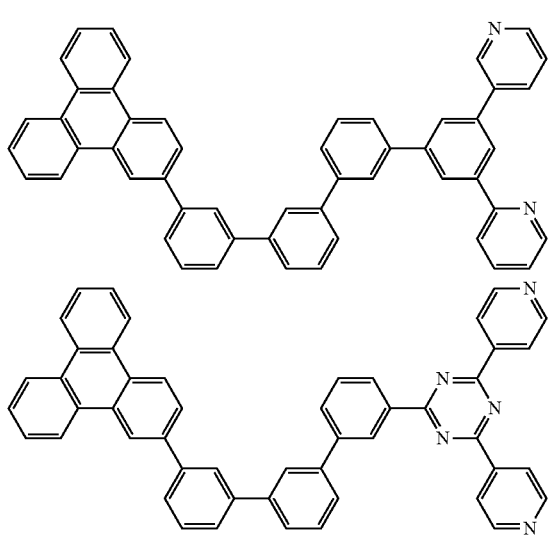

263
-continued
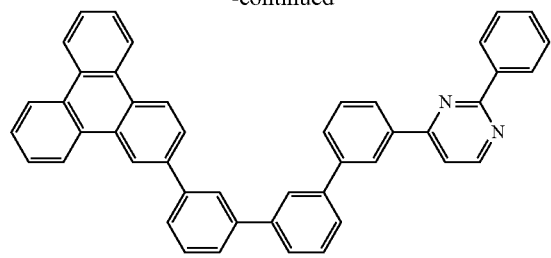
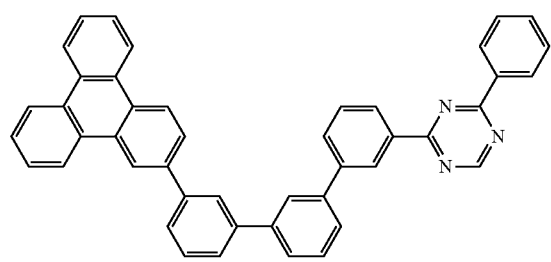
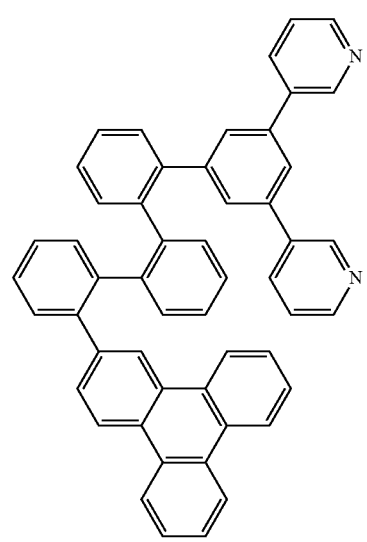
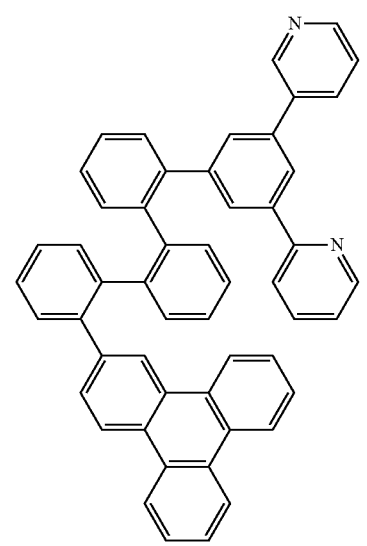
264
-continued
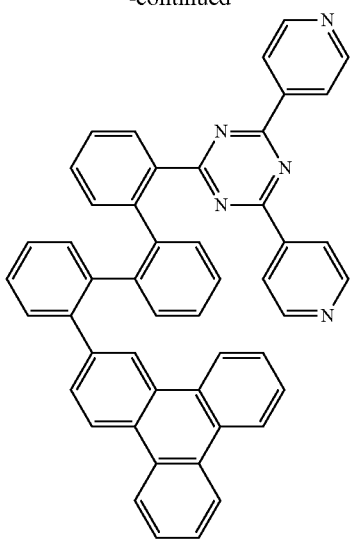
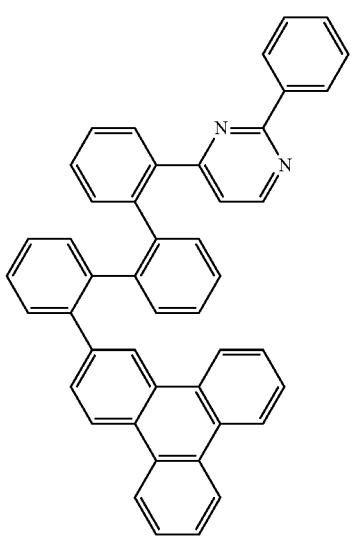
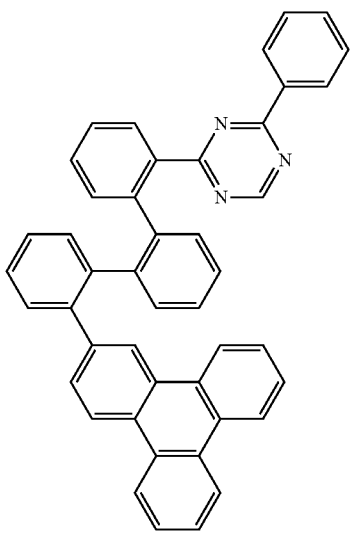

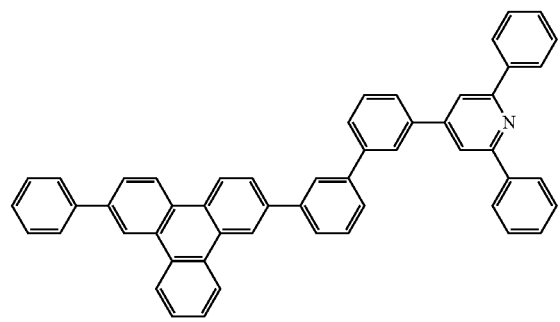
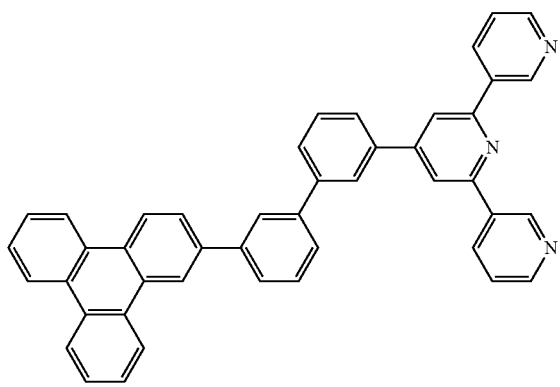
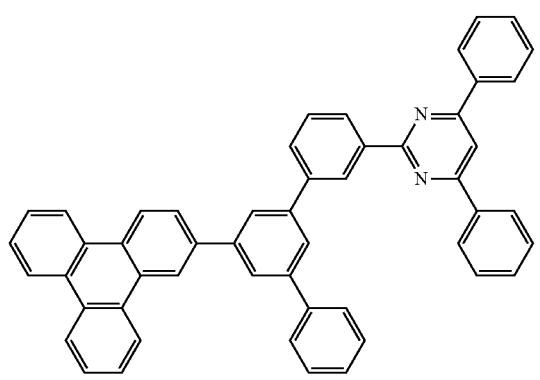
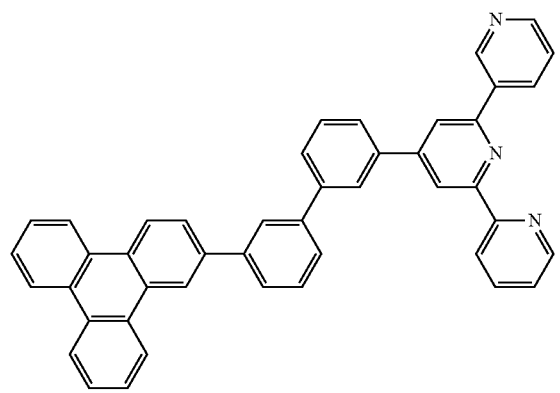
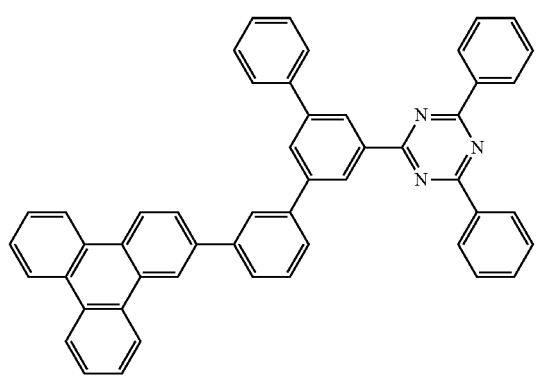
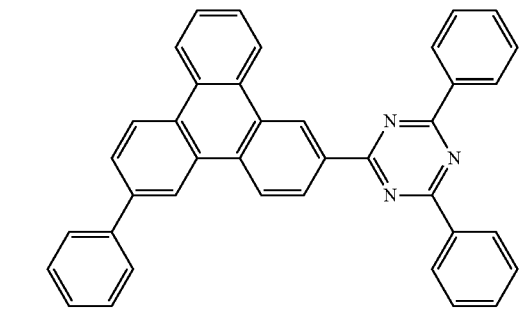
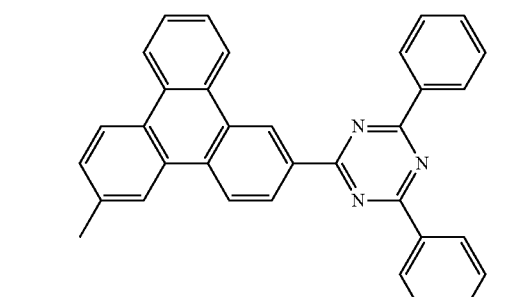
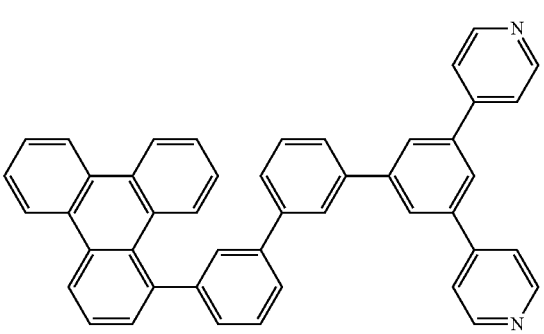
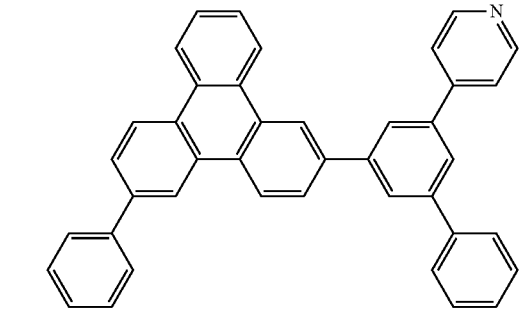

267
-continued
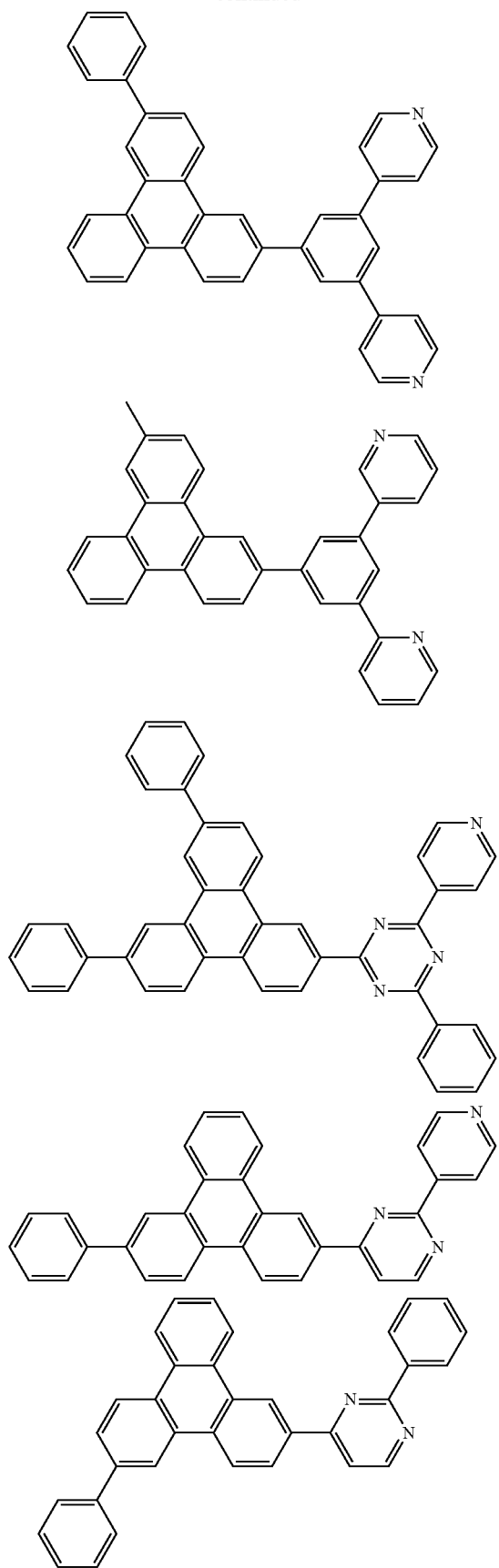
268
-continued
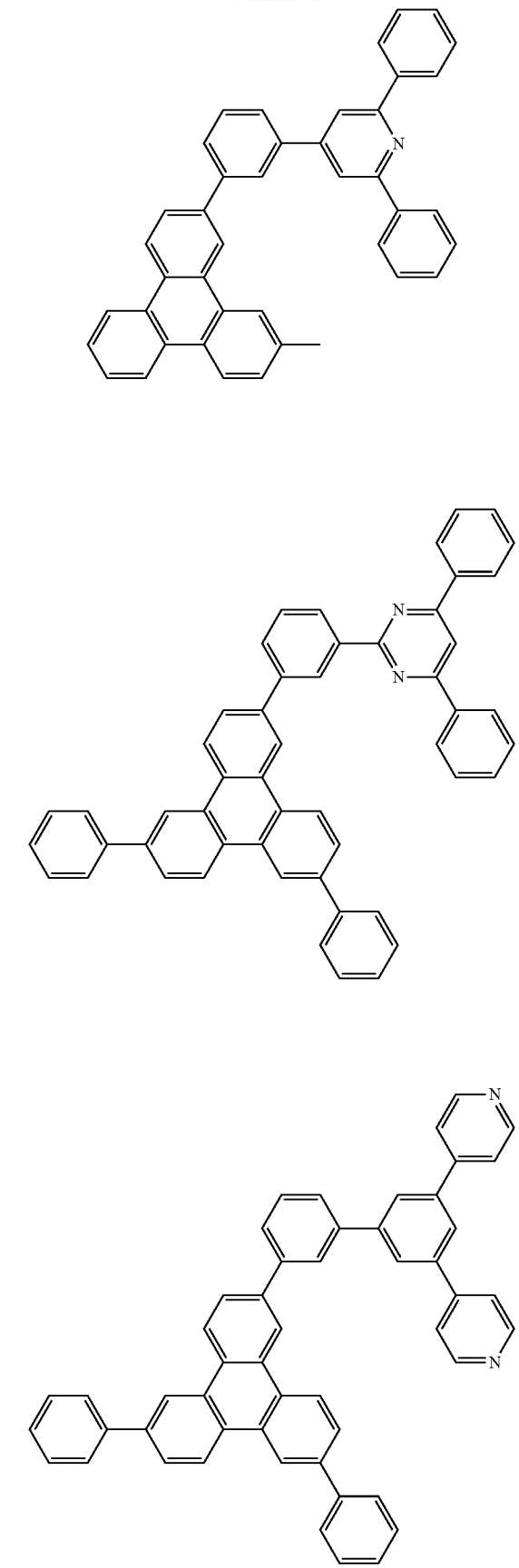

269
-continued
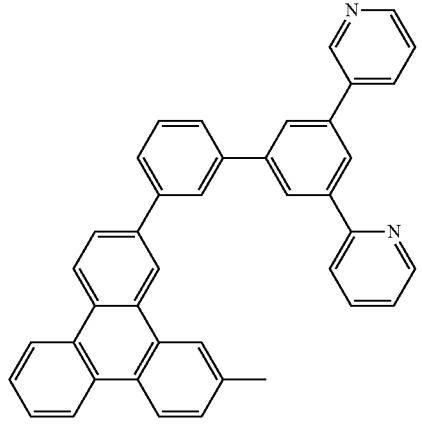
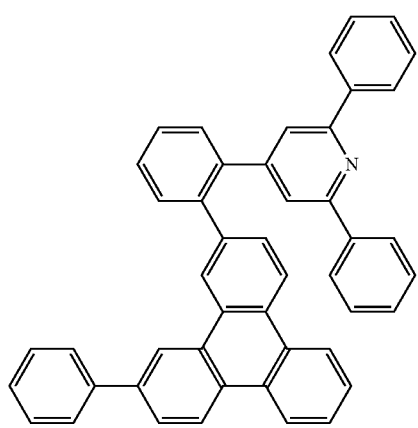
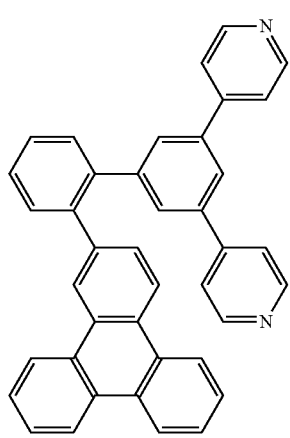
270
-continued
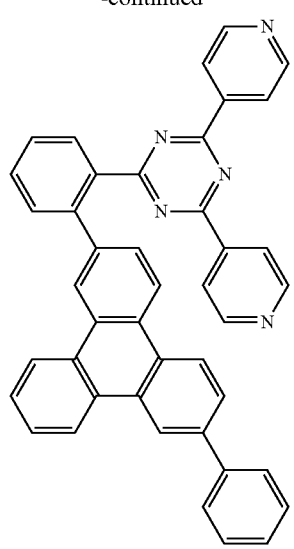
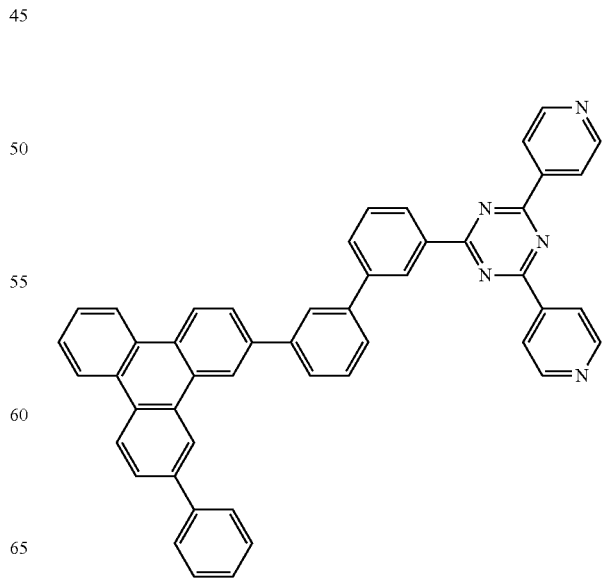

271
-continued
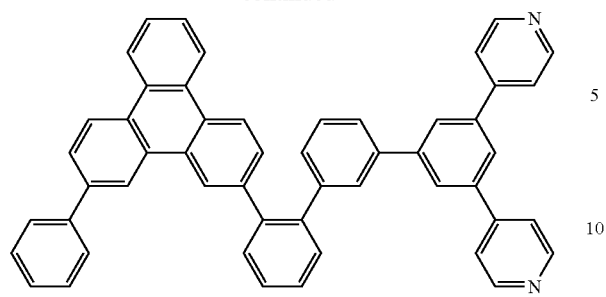
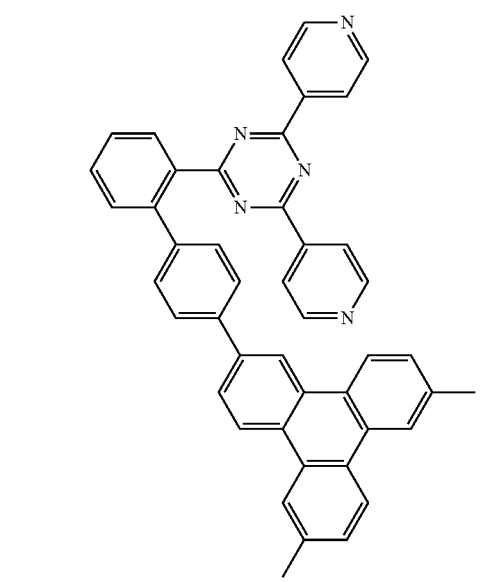
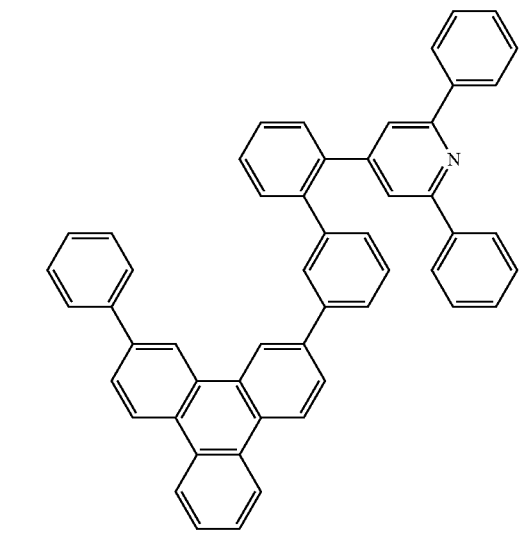
272
-continued
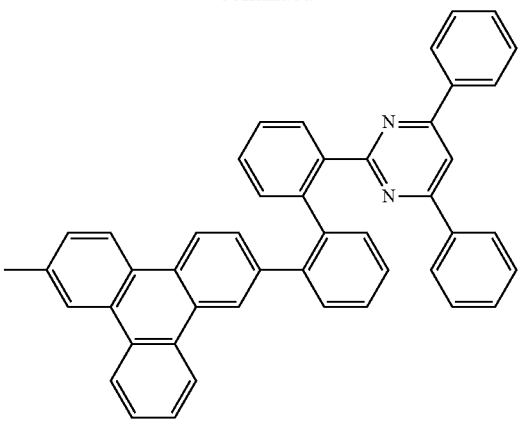
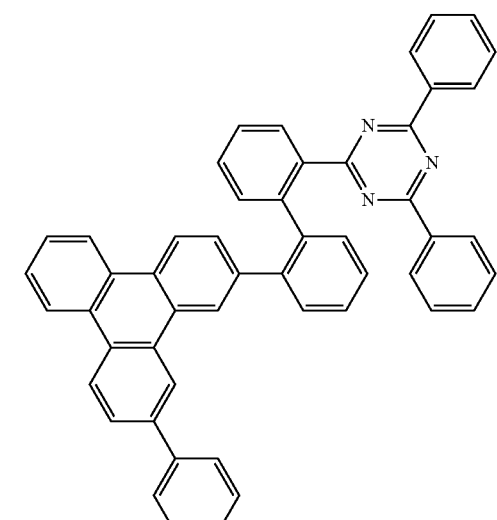
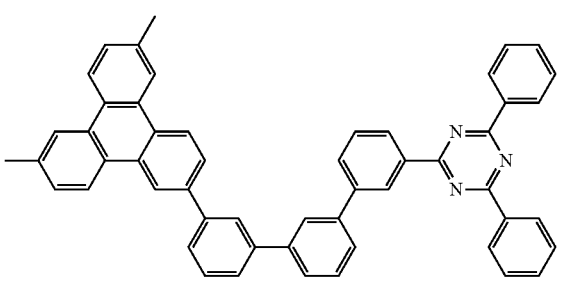

-continued
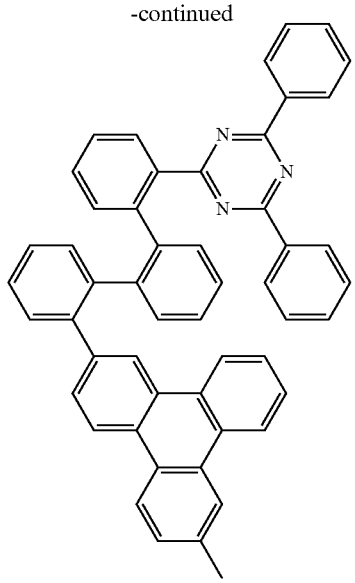
-continued
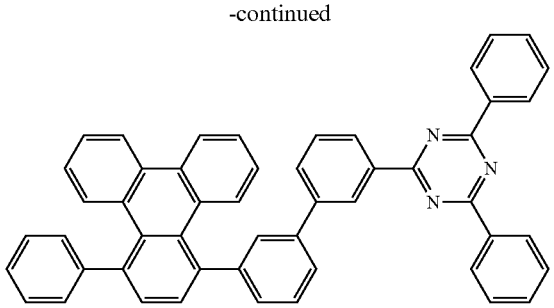
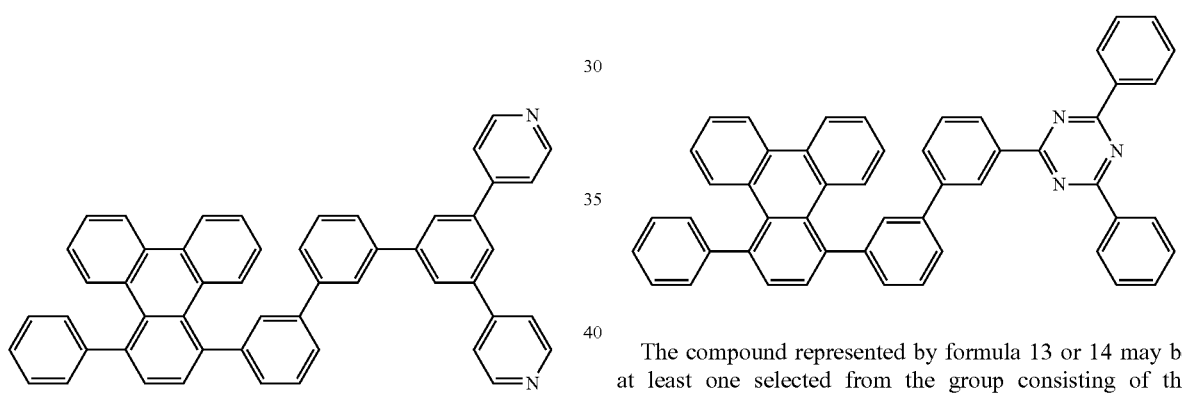
The compound represented by formula 13 or 14 may be at least one selected from the group consisting of the following compounds, but is not limited thereto.
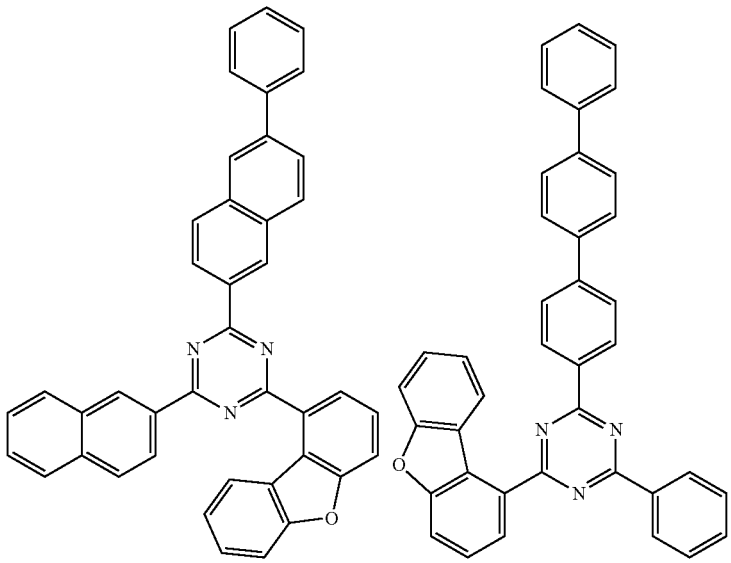

-continued
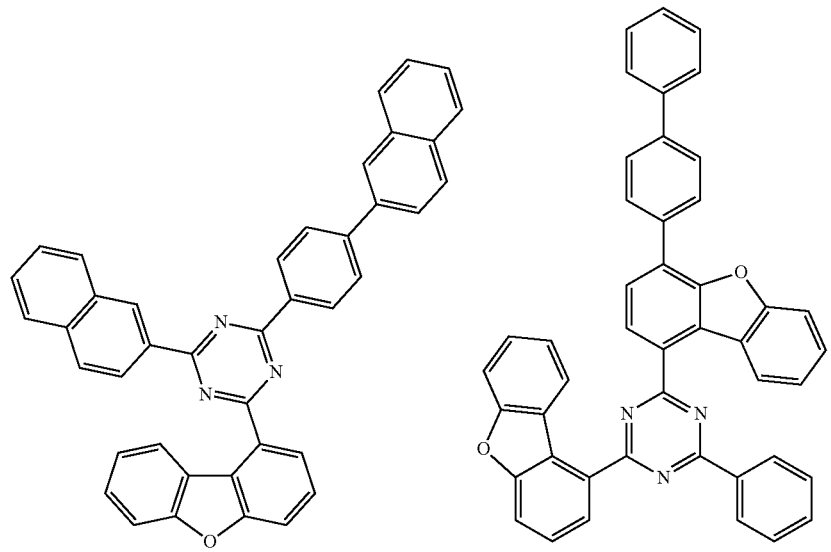
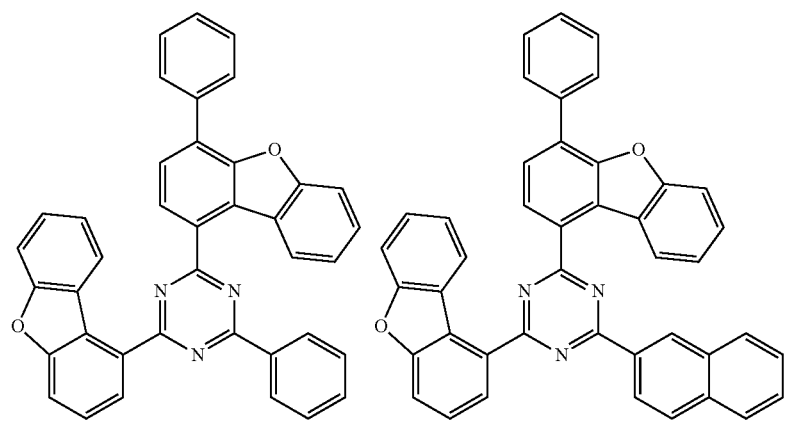
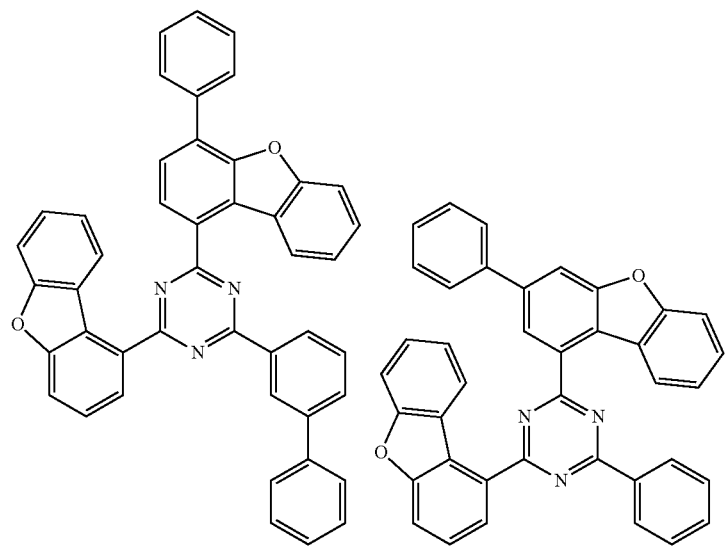

-continued
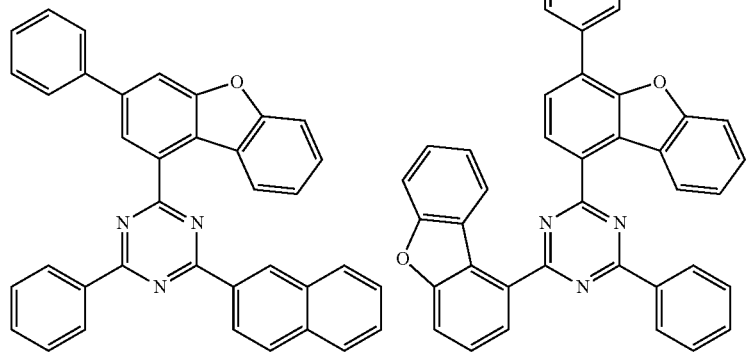
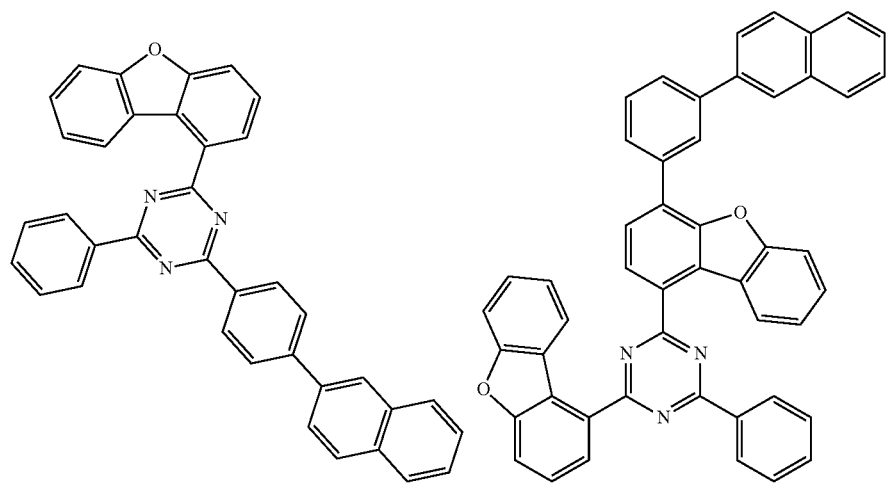
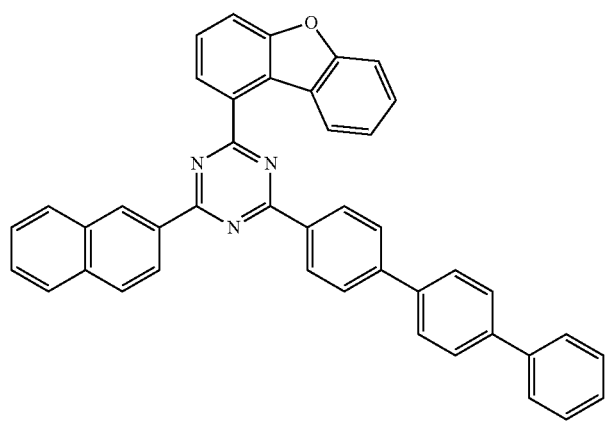

-continued
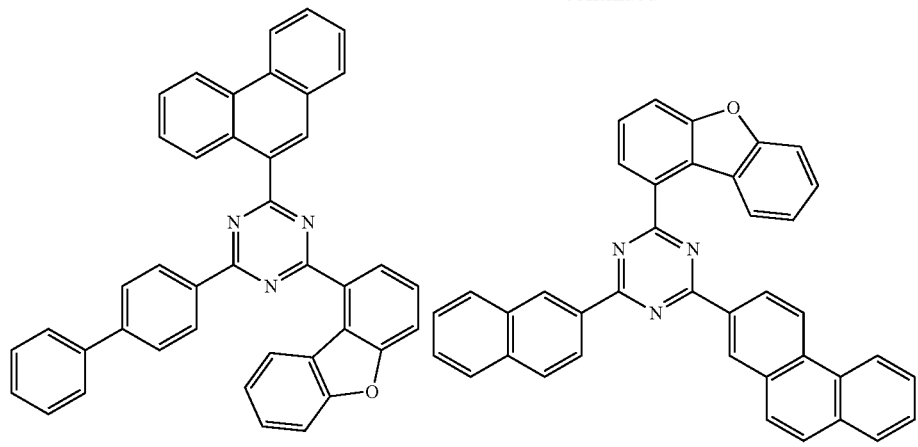
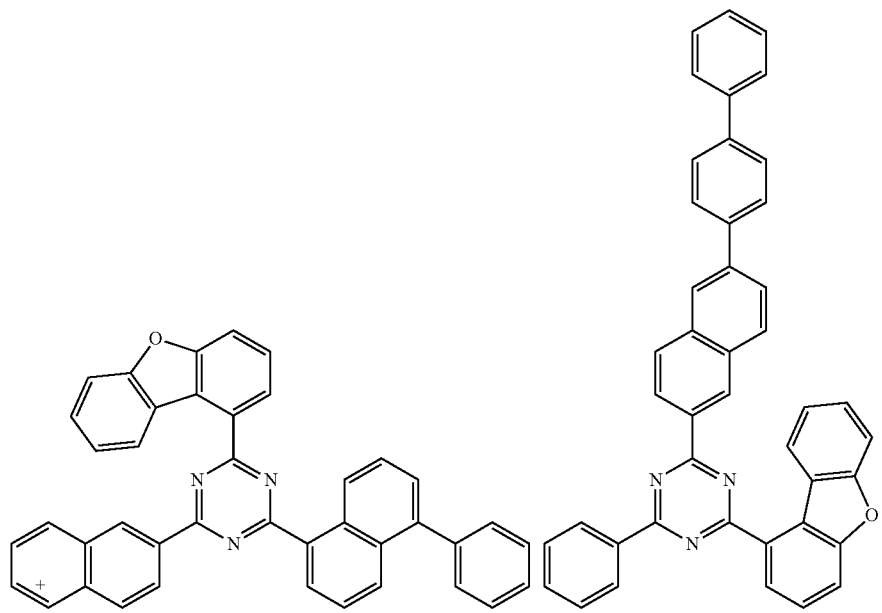
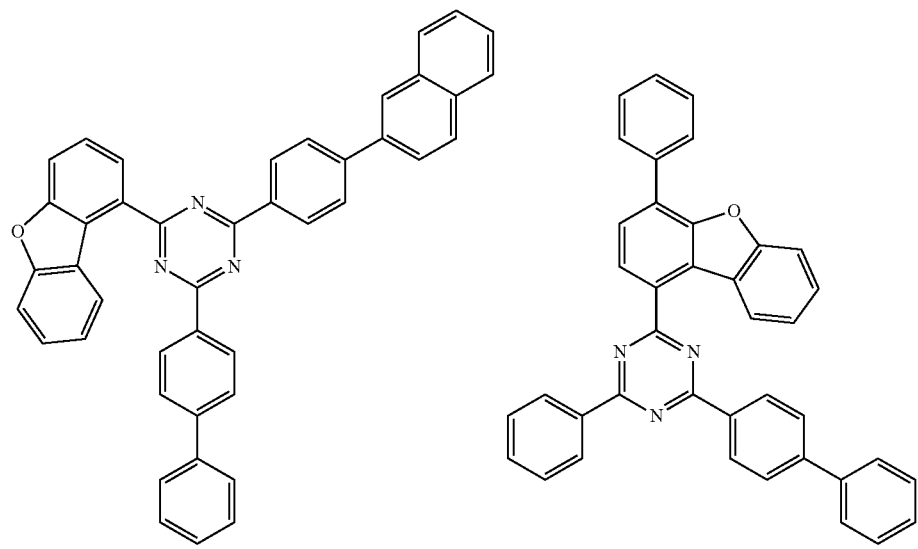

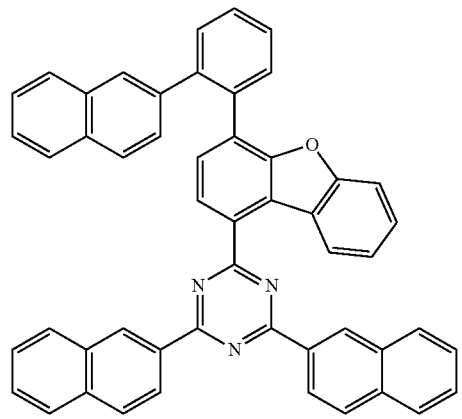
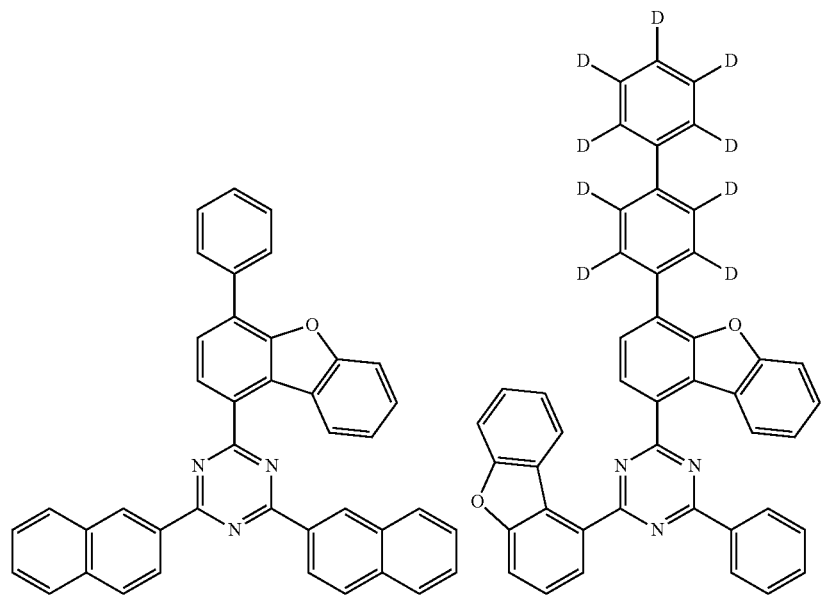
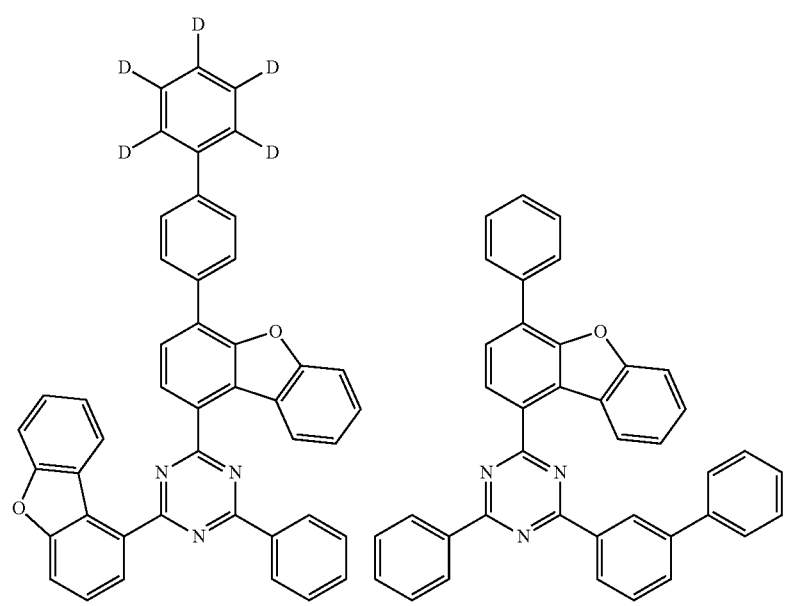

-continued
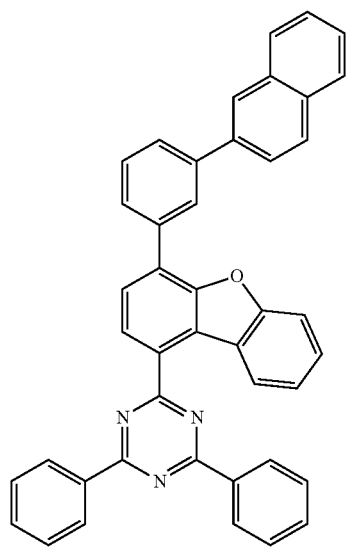
283
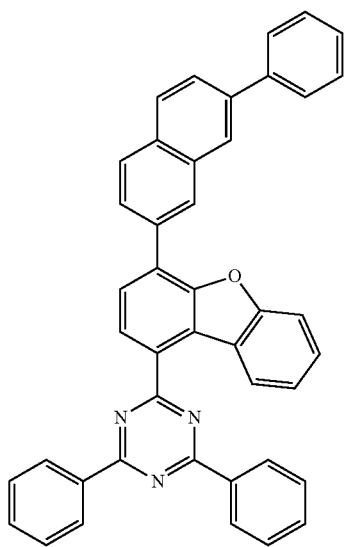
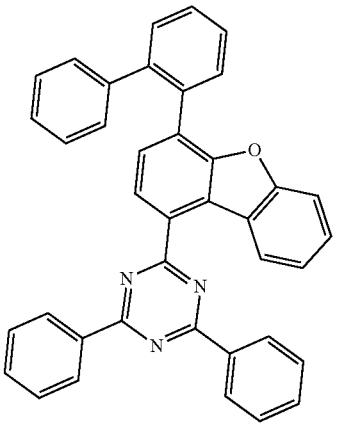
284
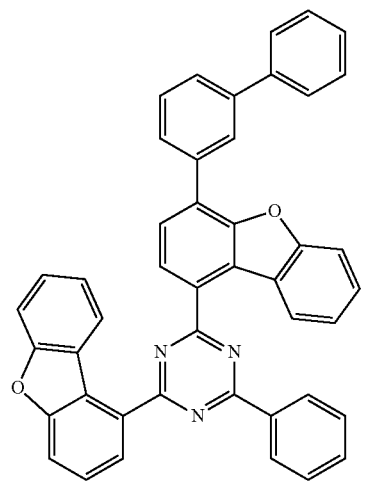
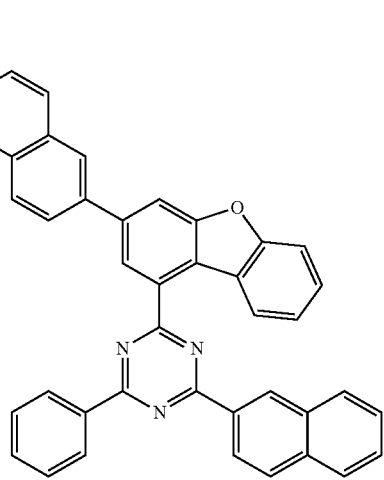
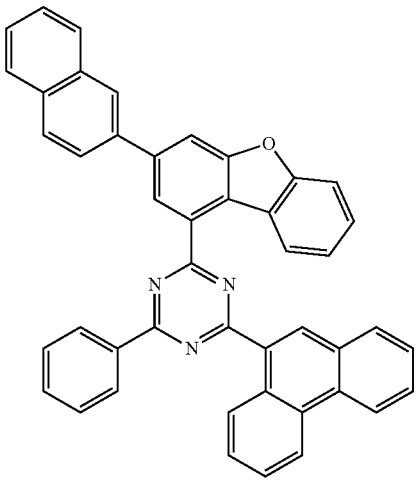
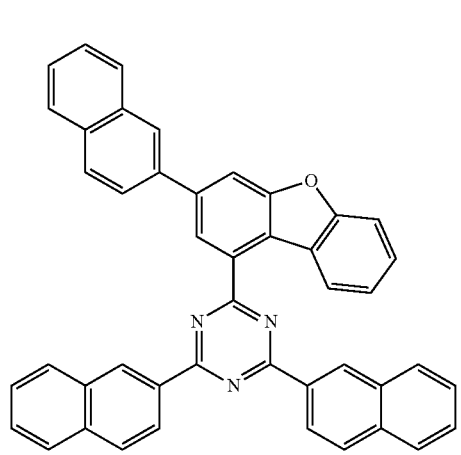
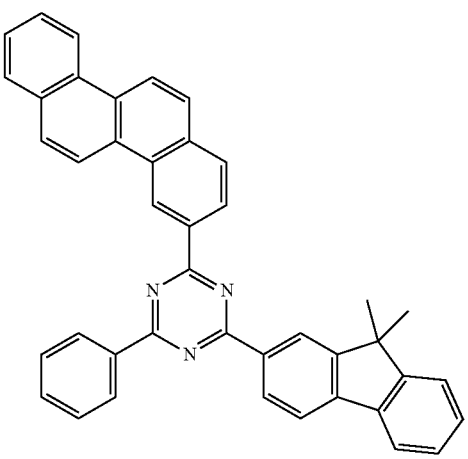

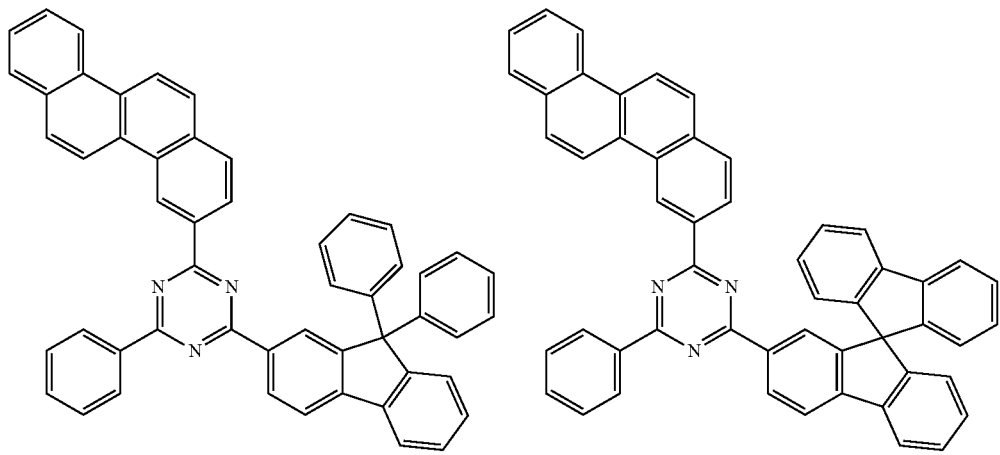
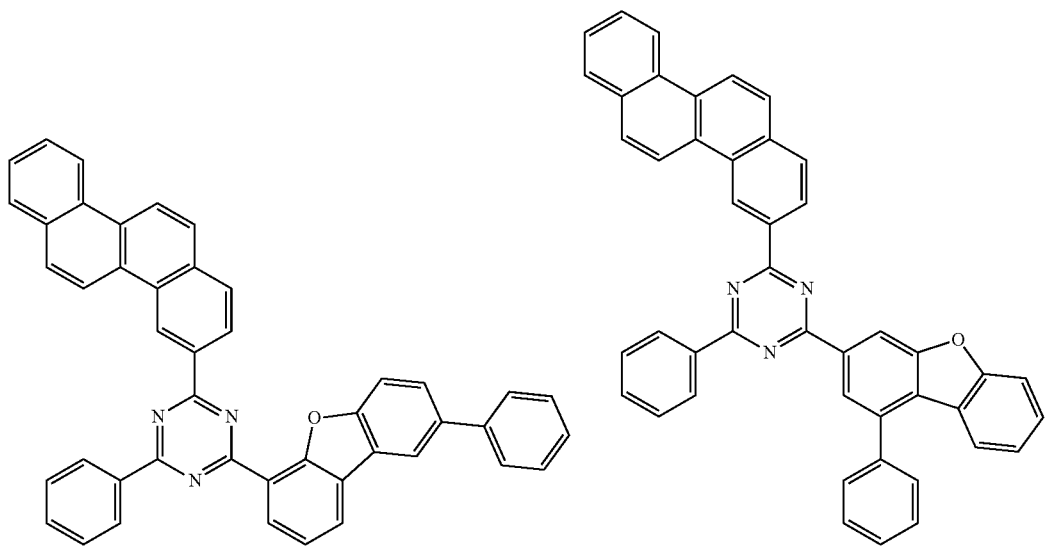

287 288
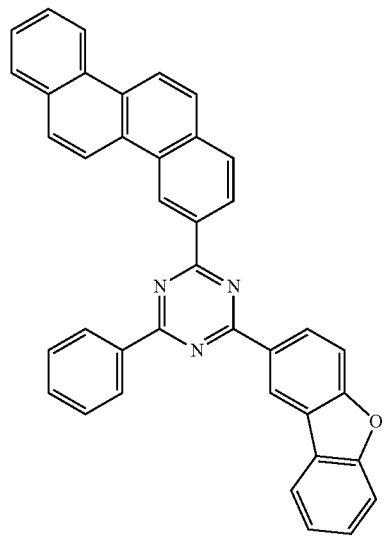 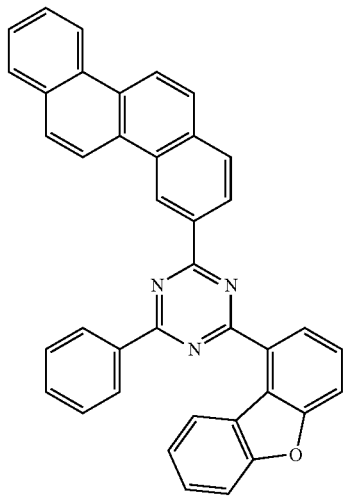 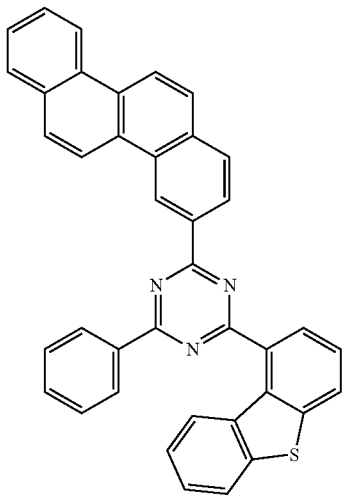
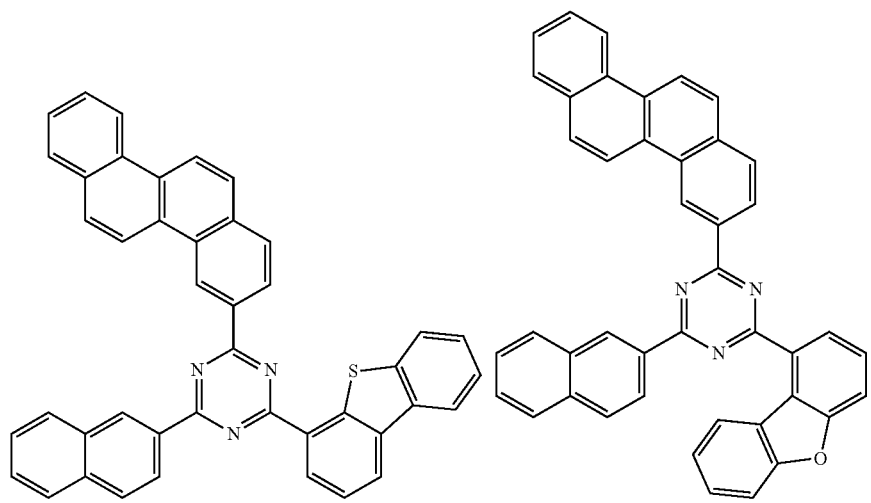
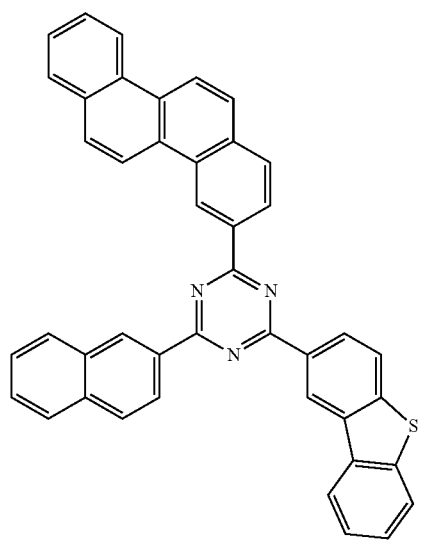

-continued
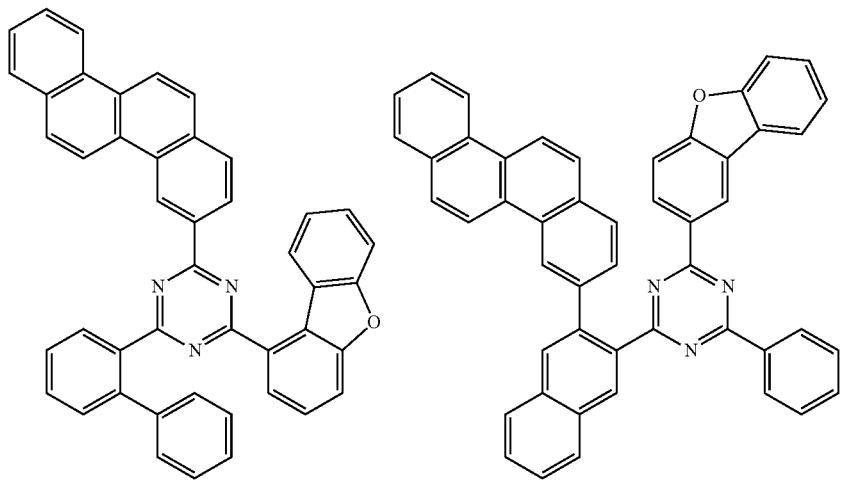
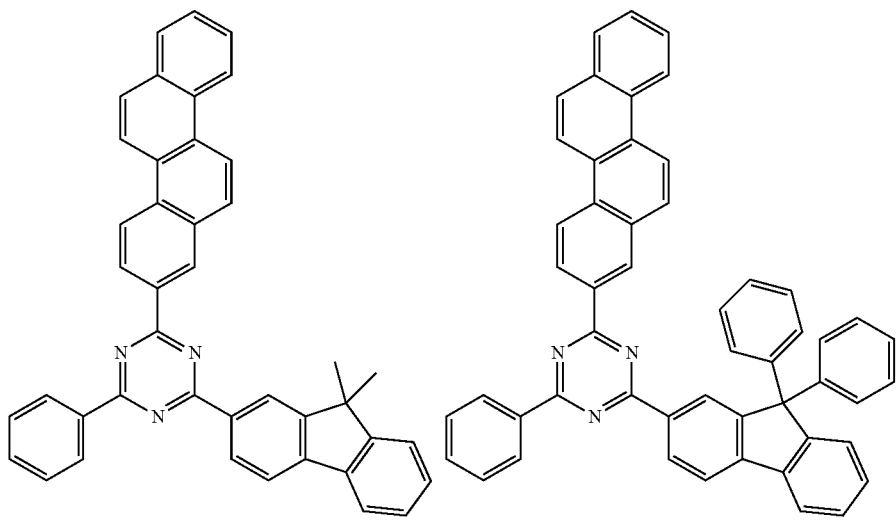
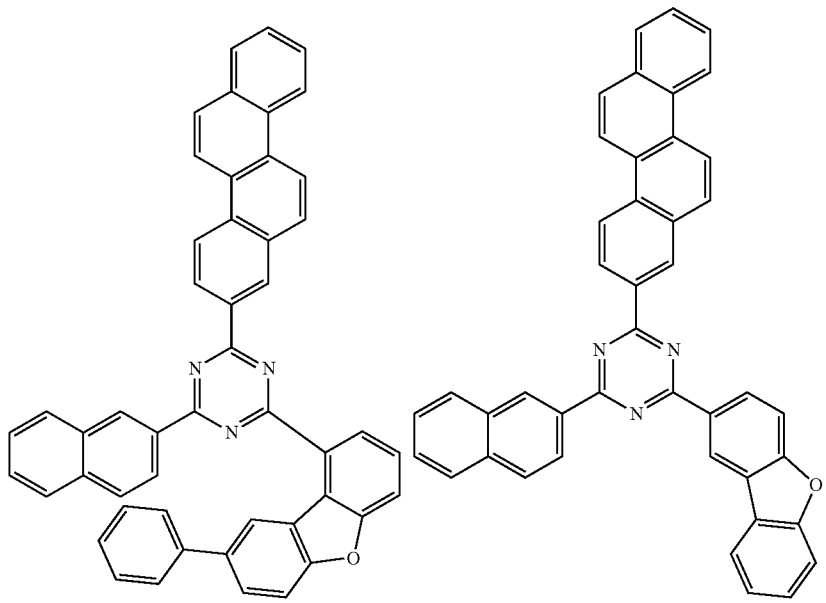

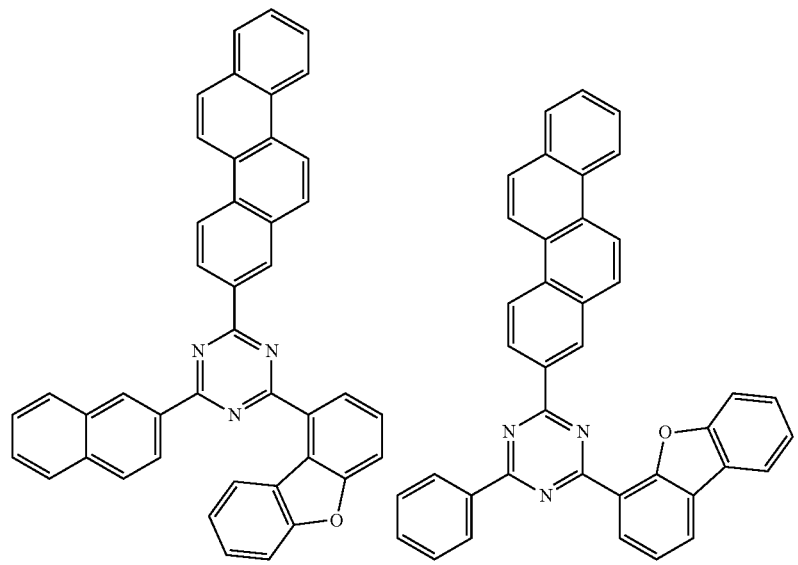
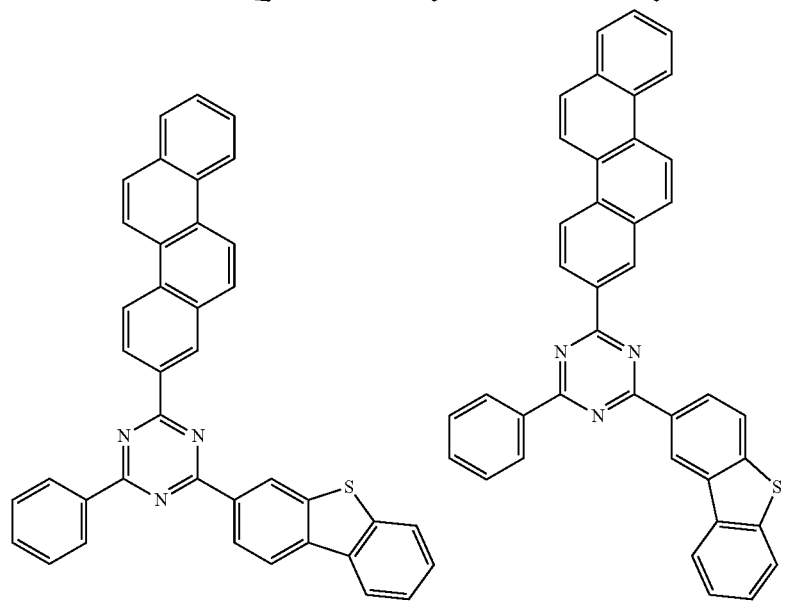
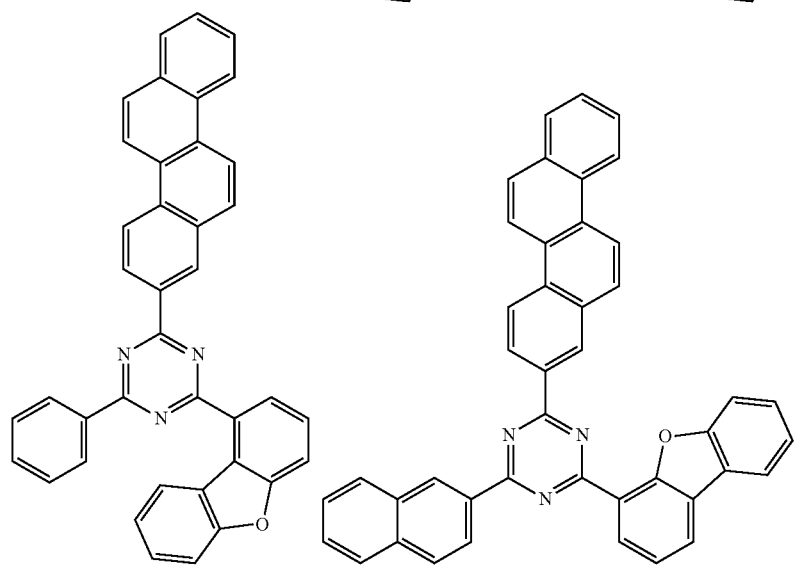

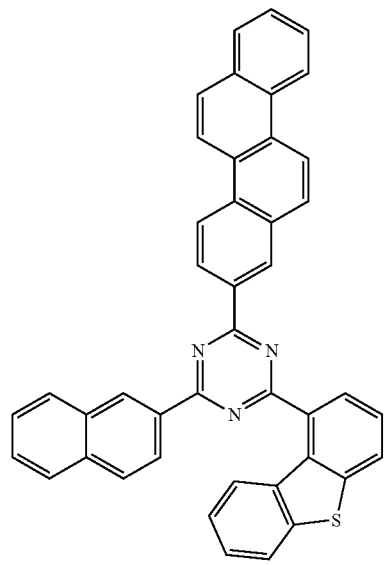
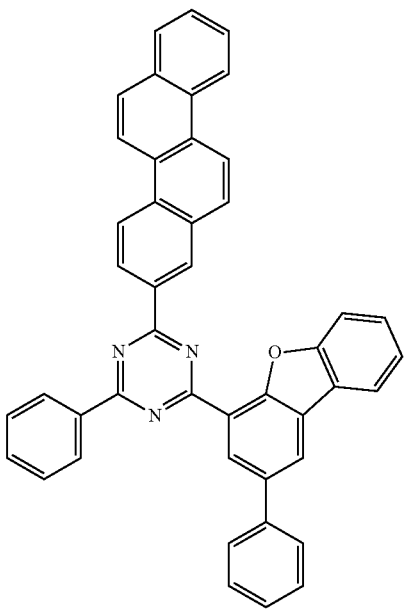
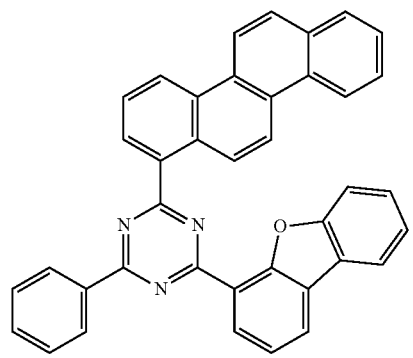
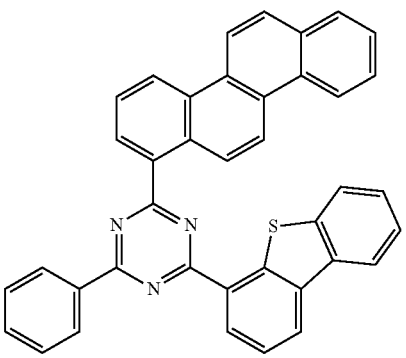
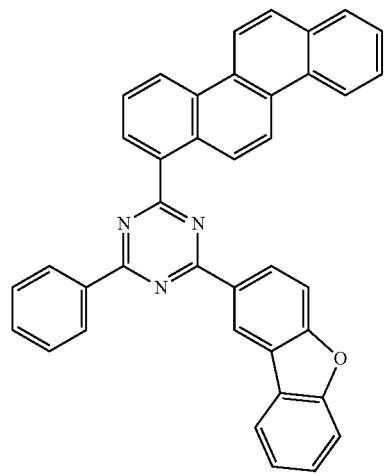
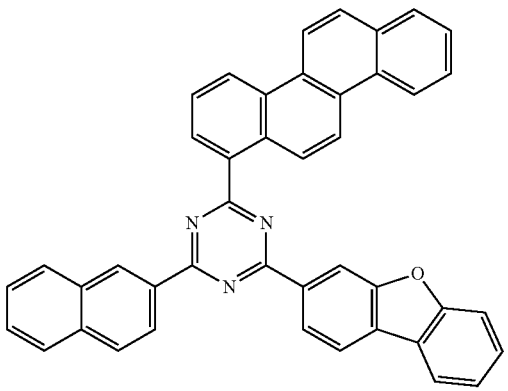

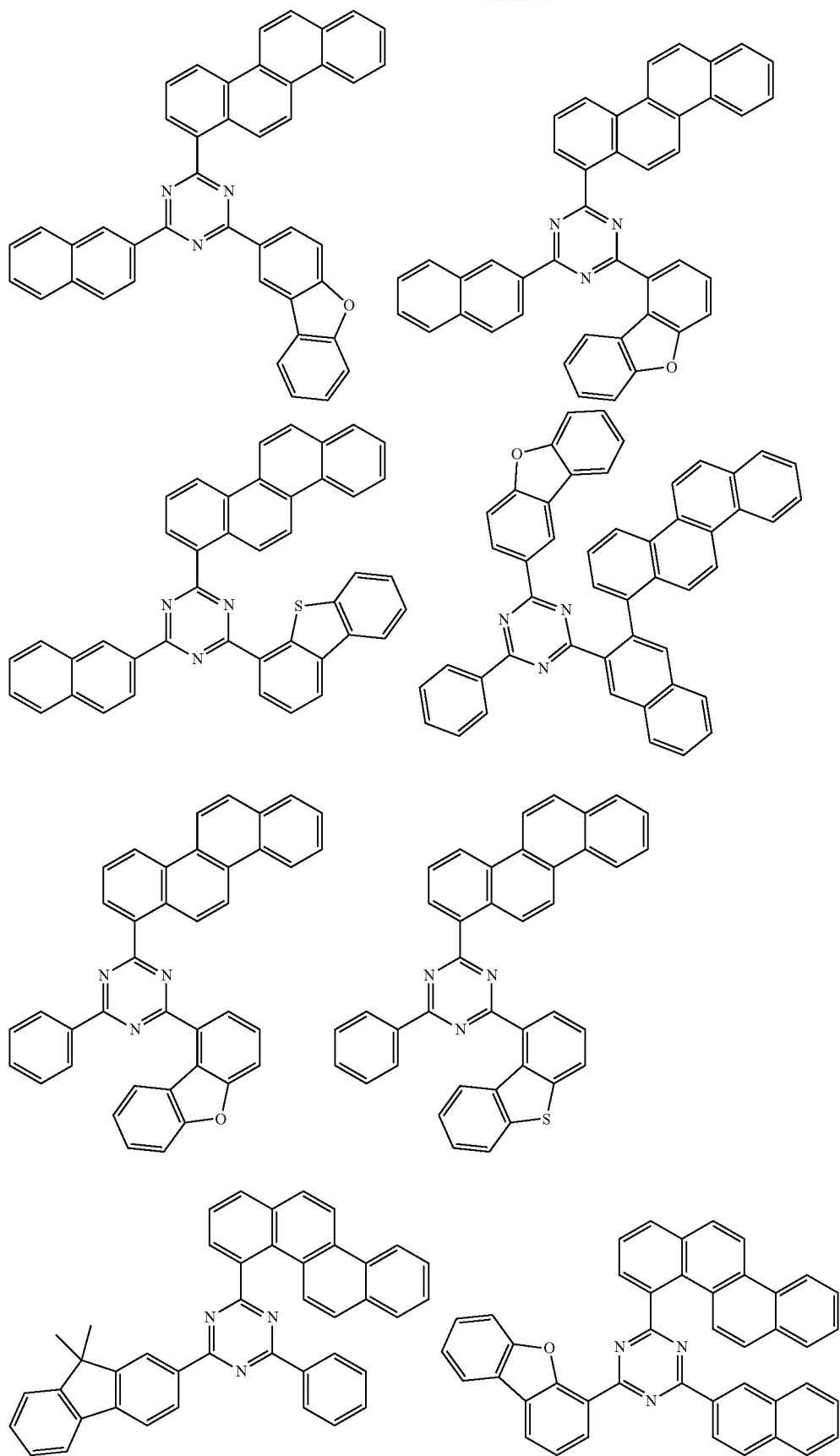

297 298
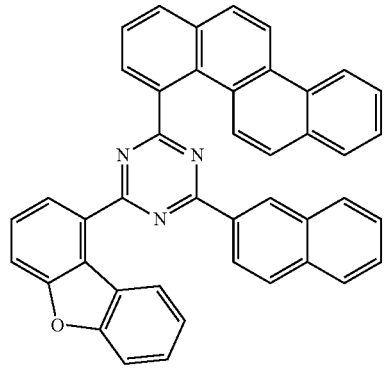 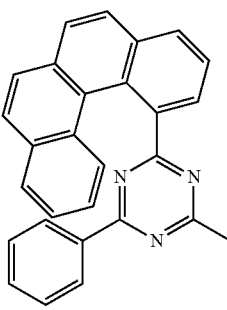 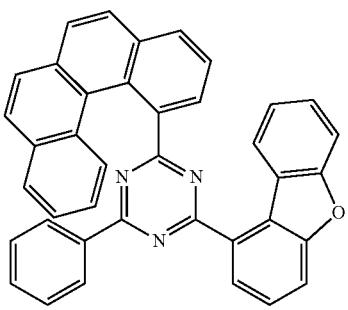
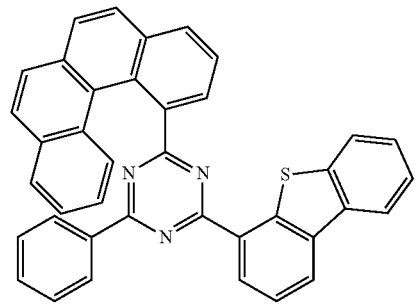 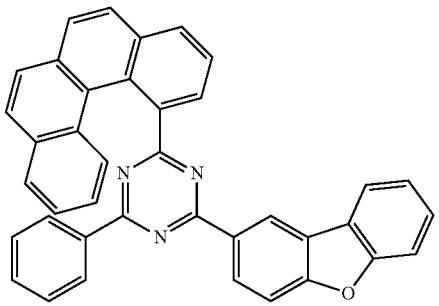
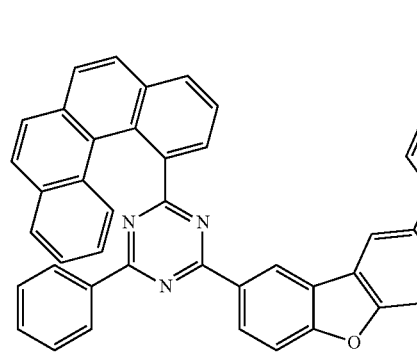 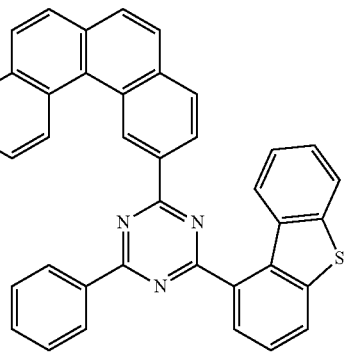
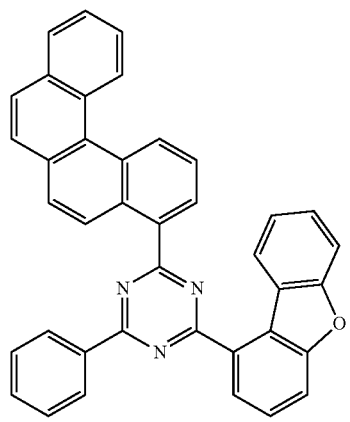 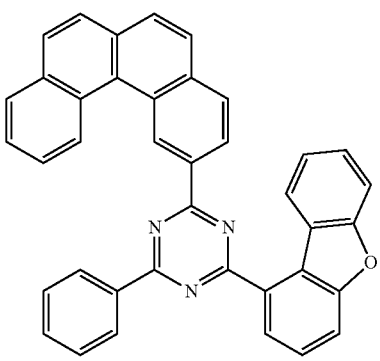

-continued
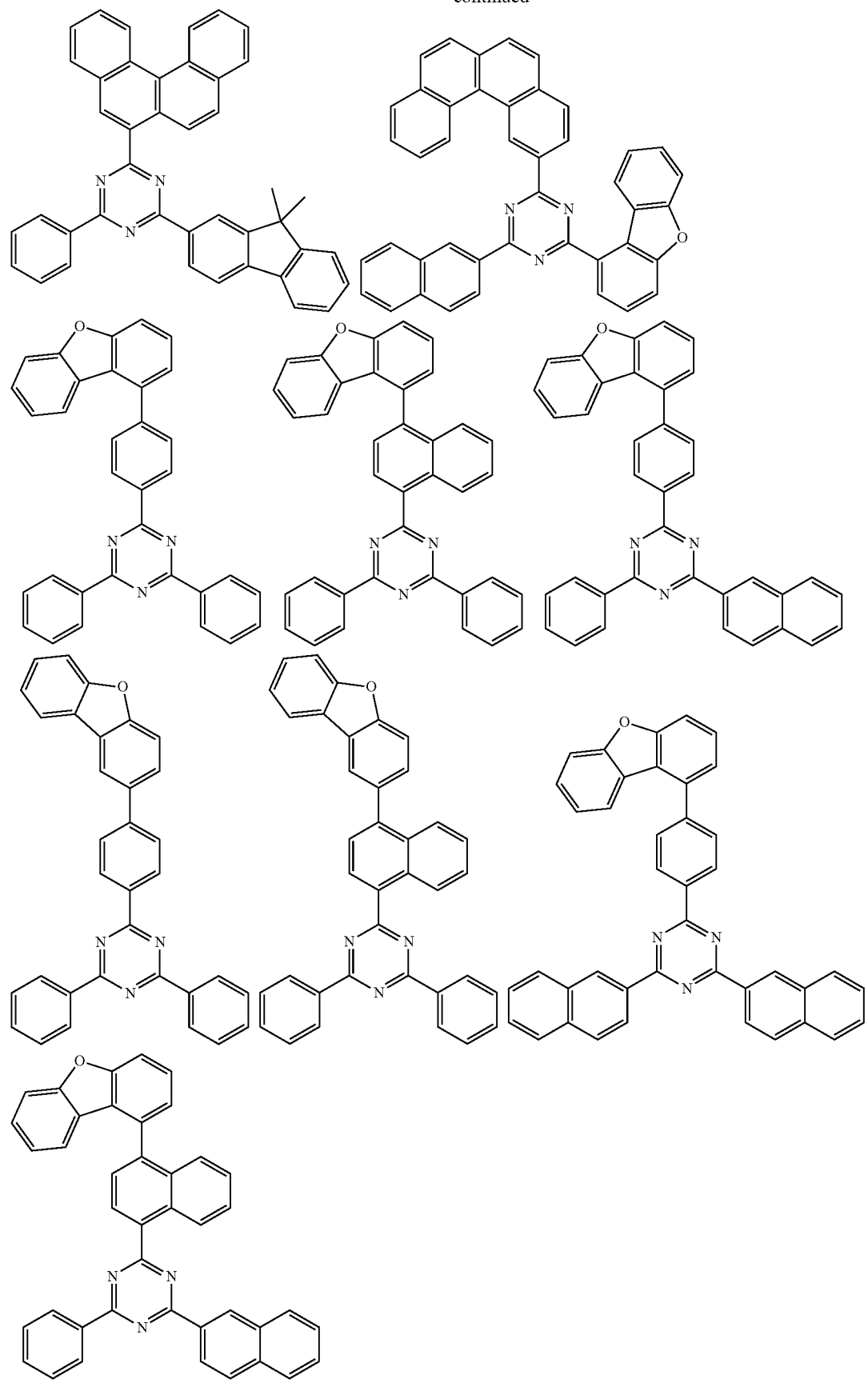

-continued
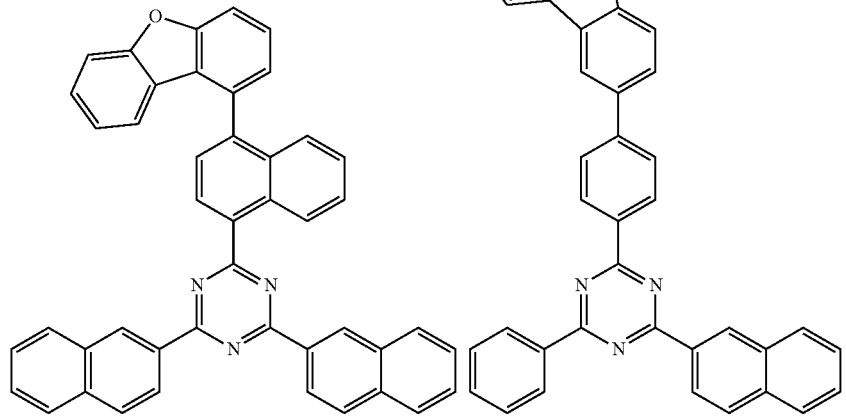
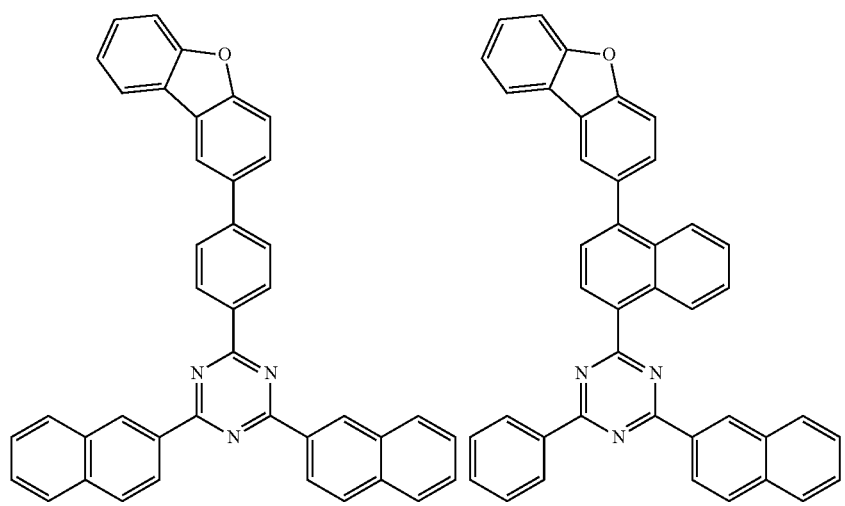
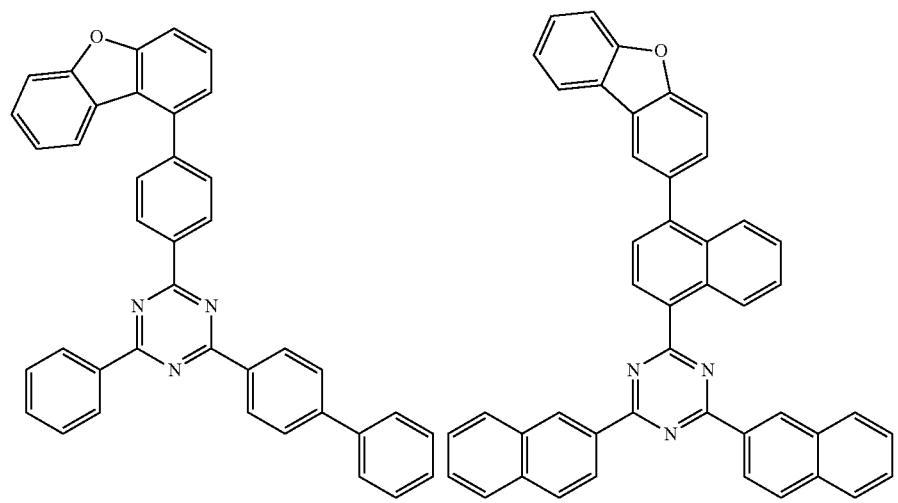

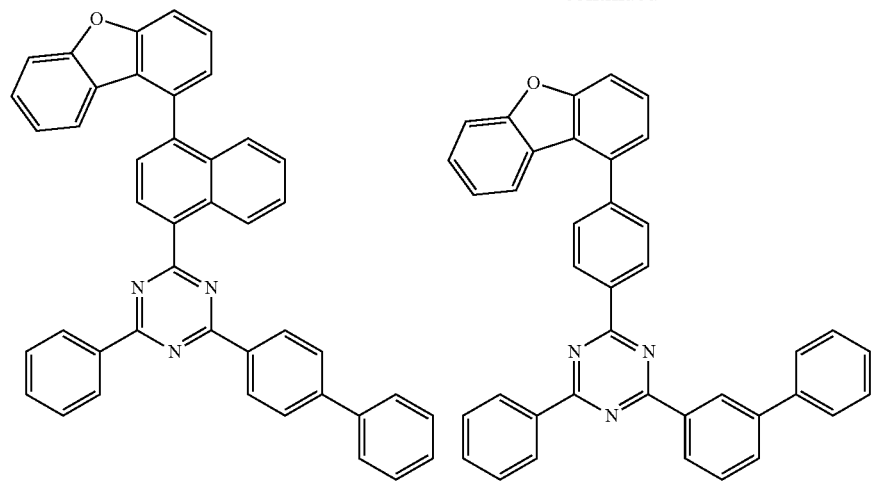
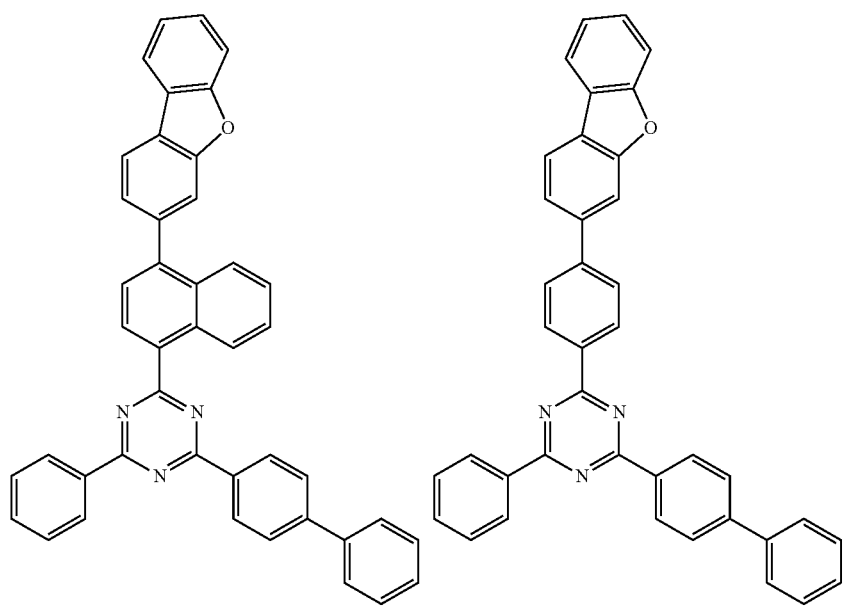
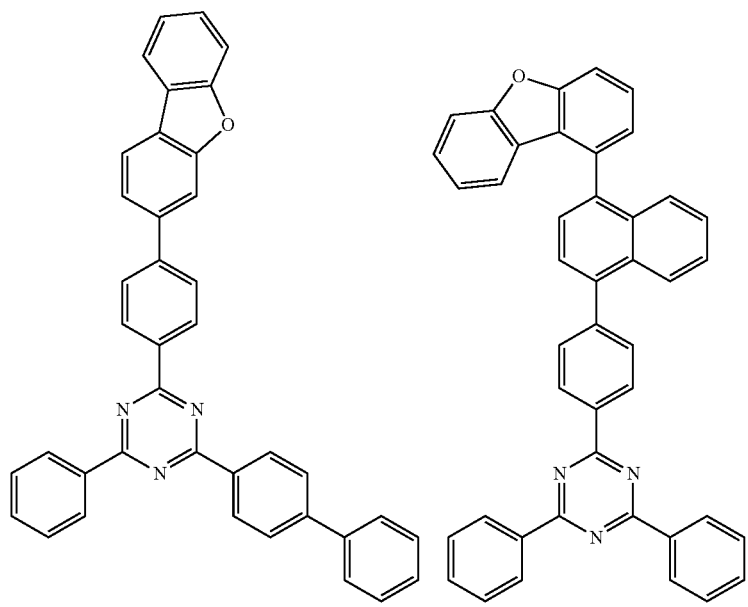

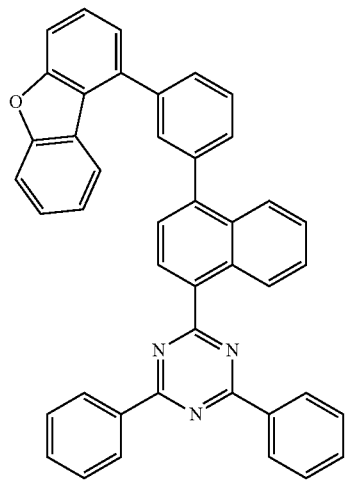 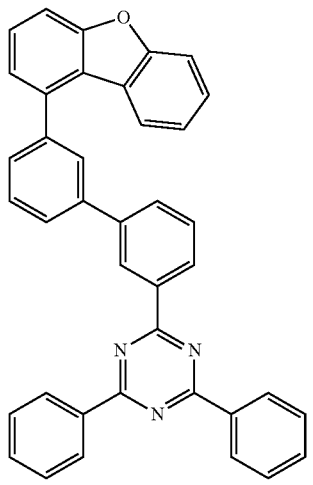 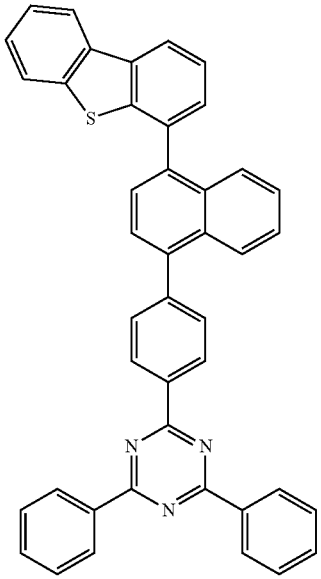
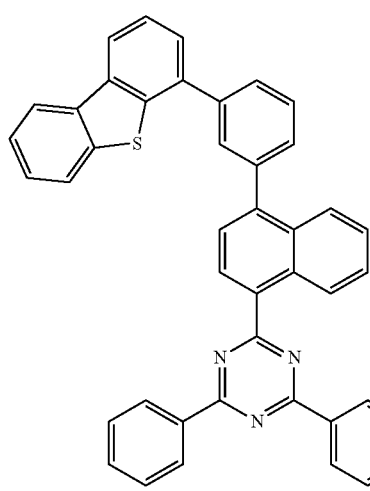 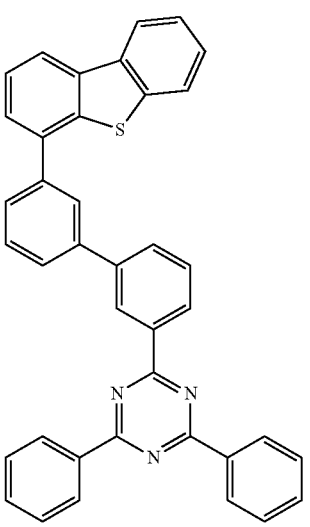
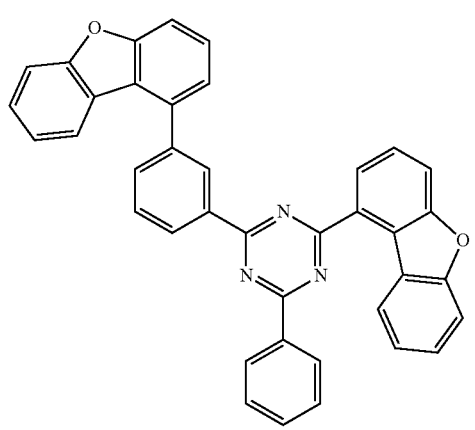 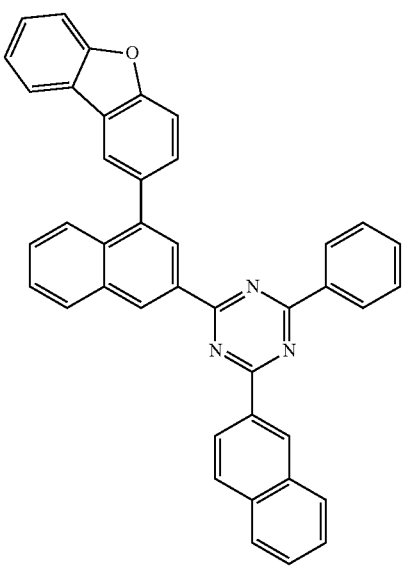

307 308
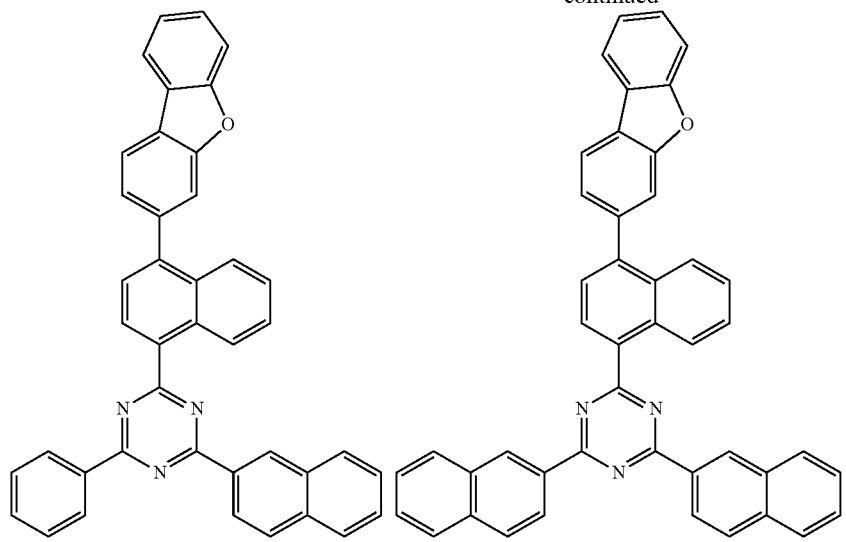
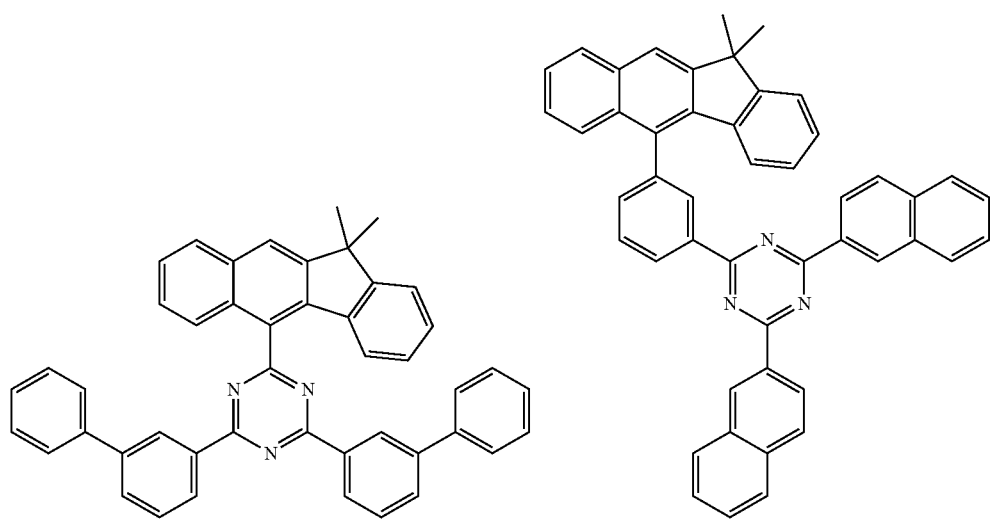
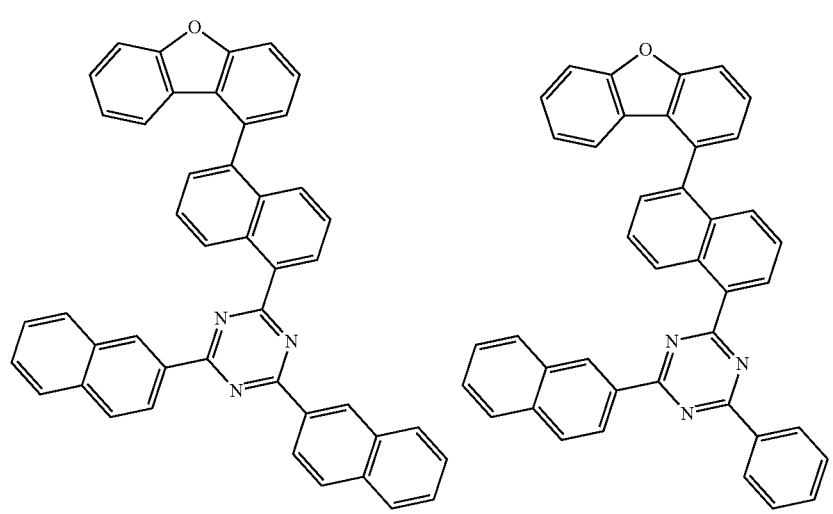

309 310
-continued
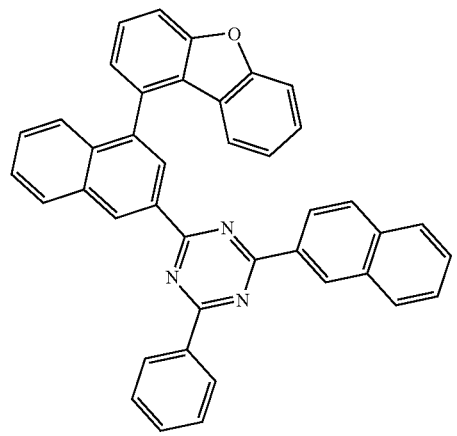
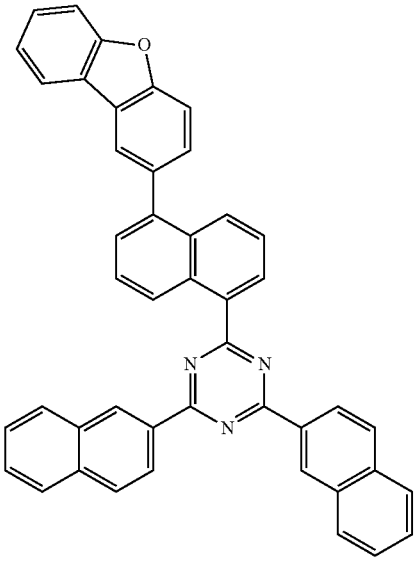
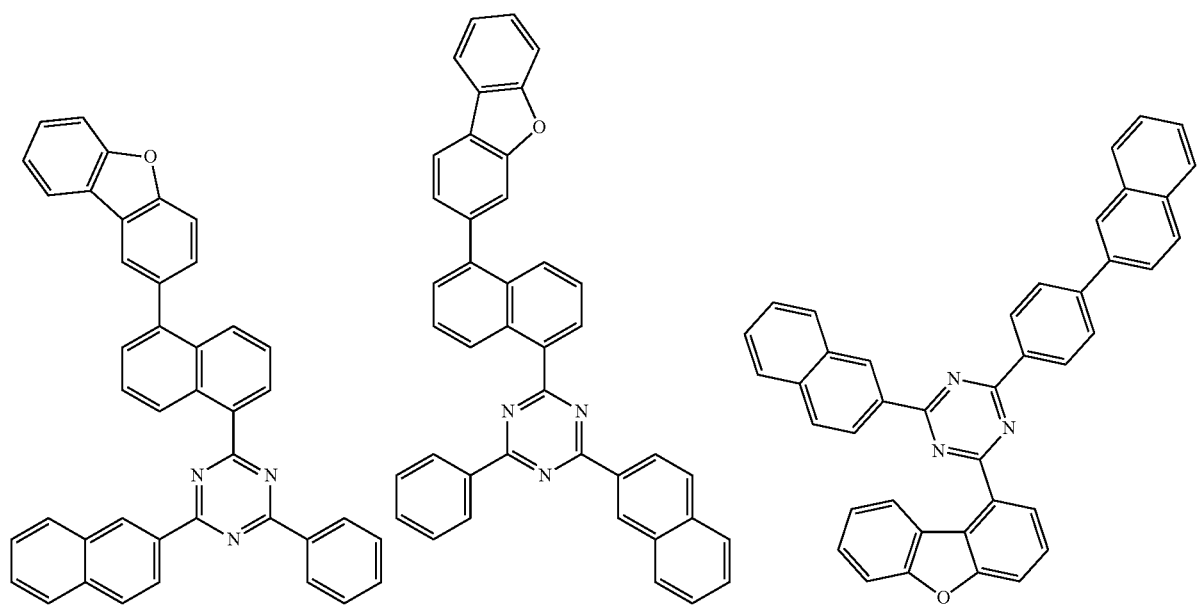
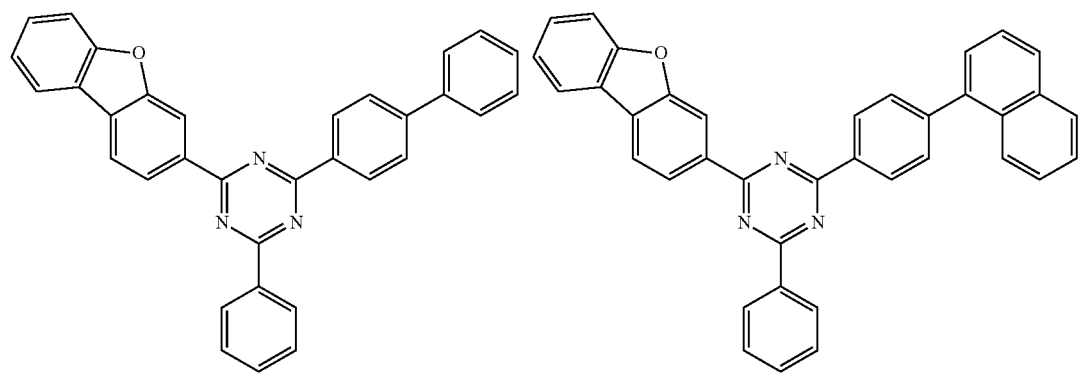

311
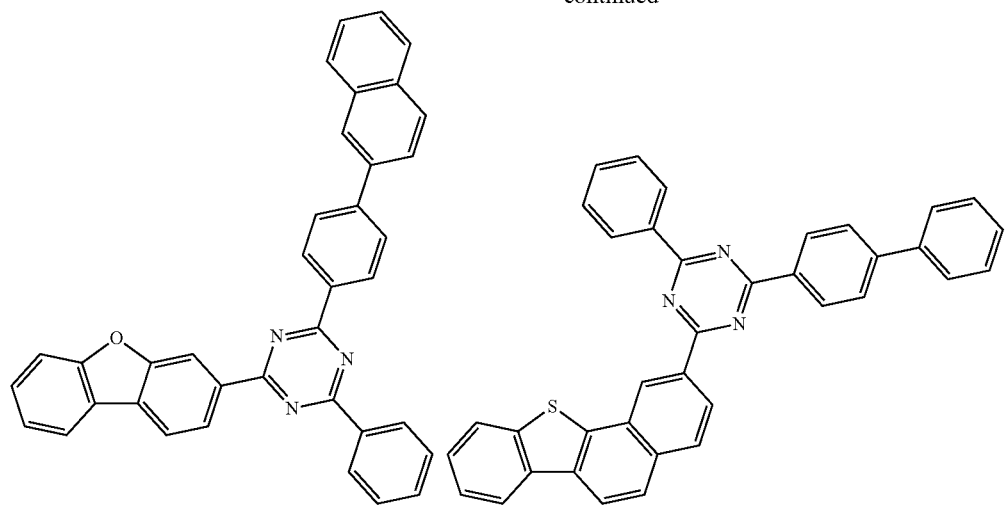
312
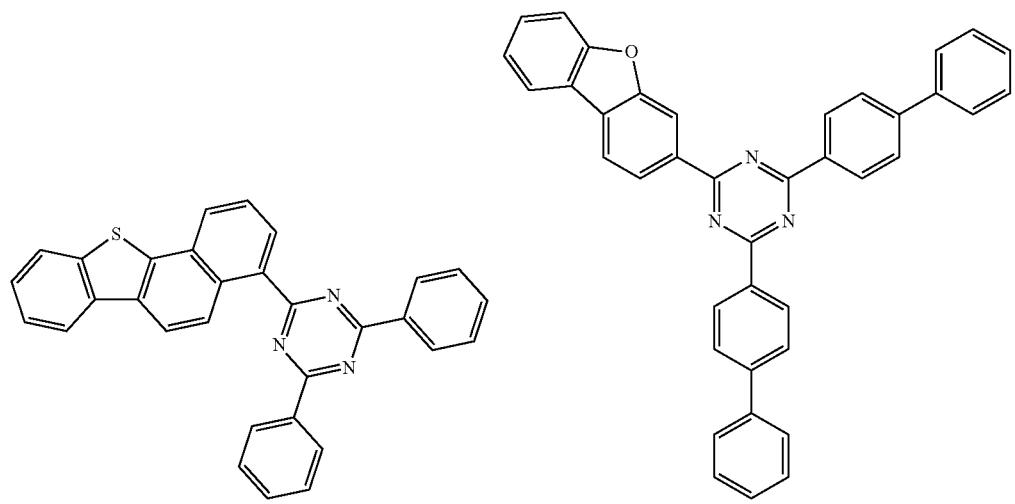
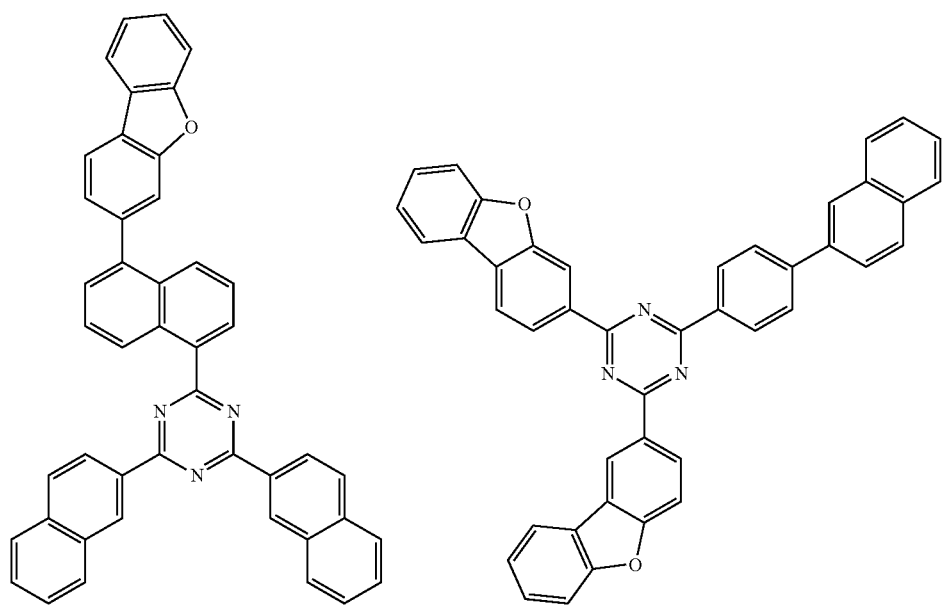

-continued
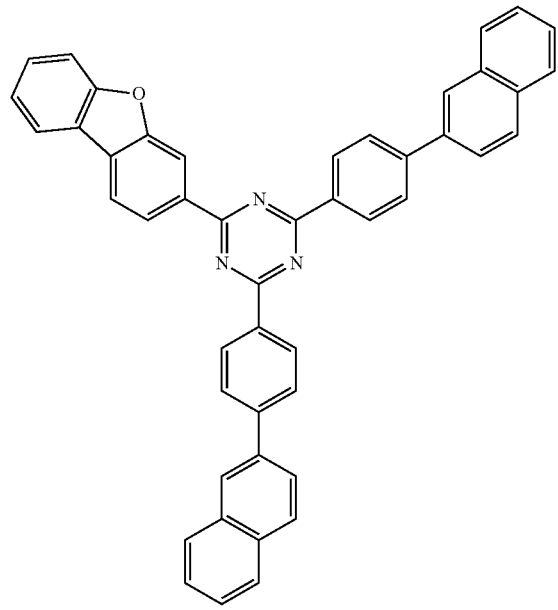
313
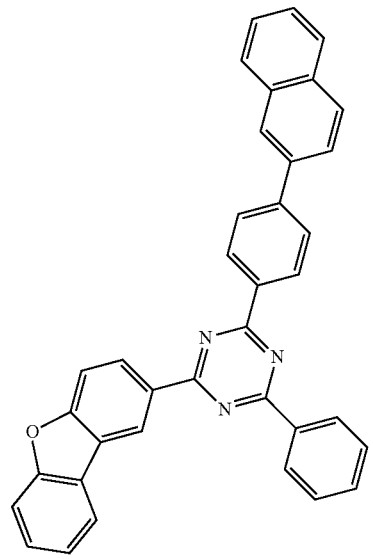
314
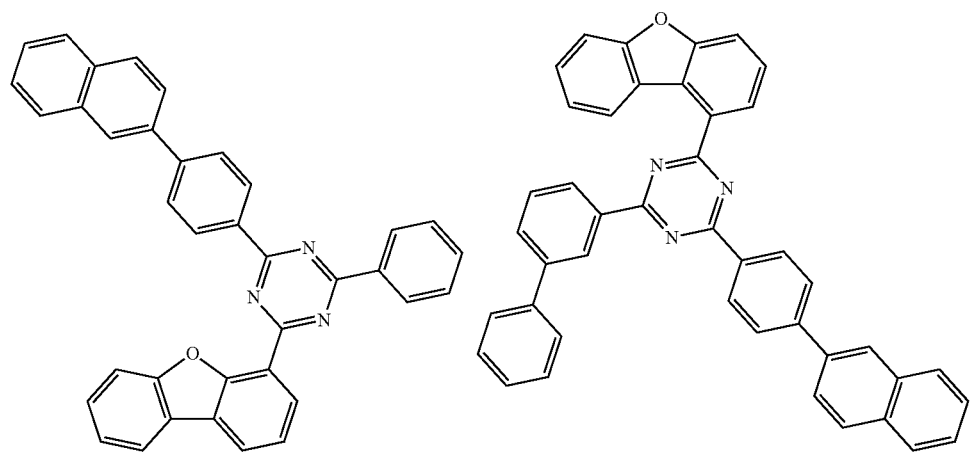
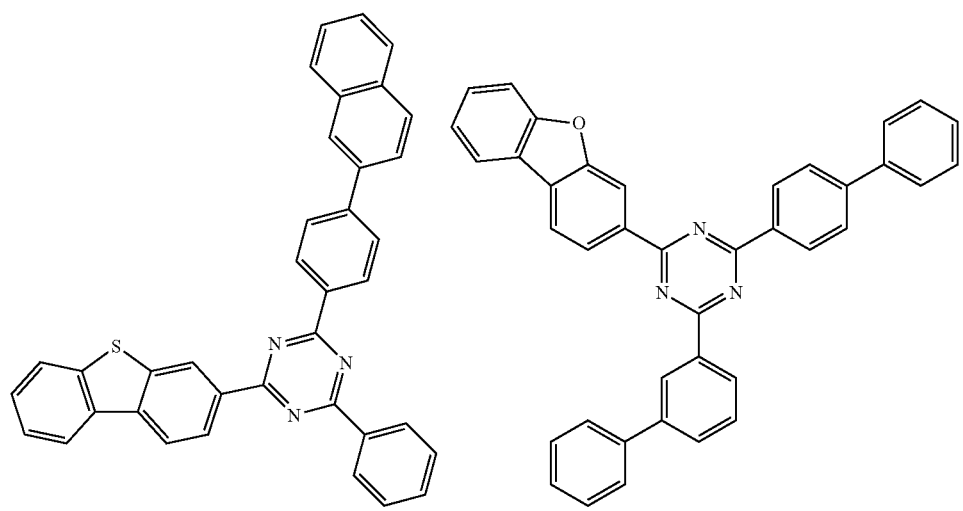

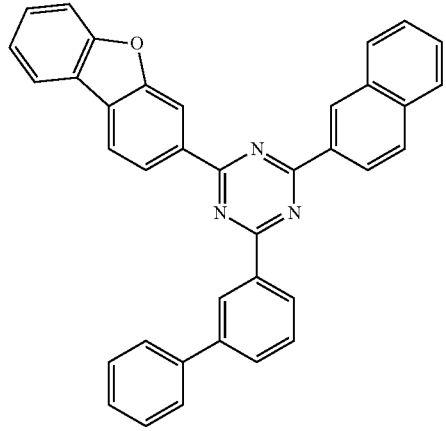
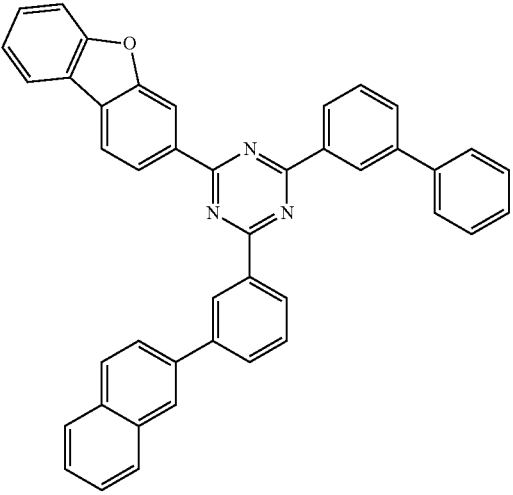
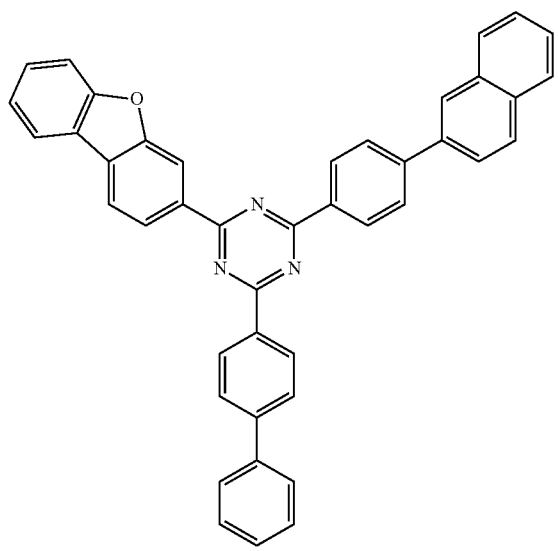
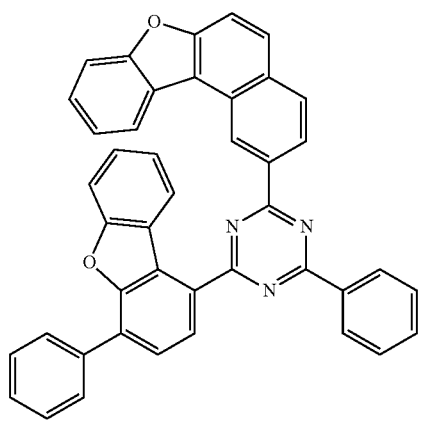
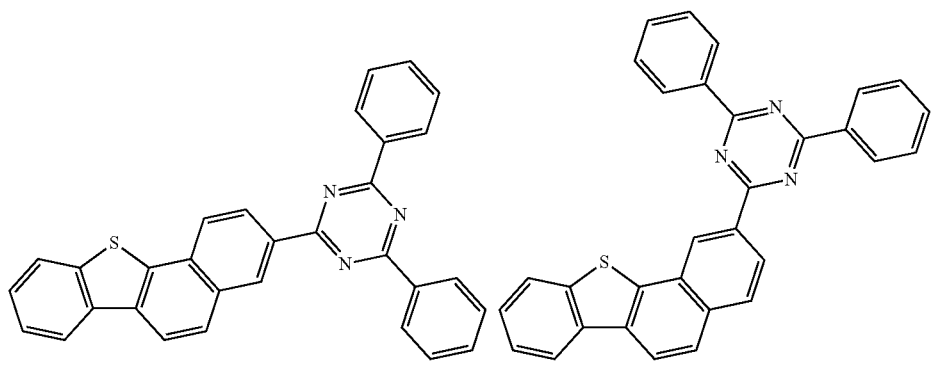

-continued
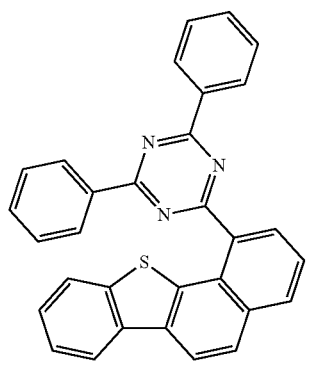
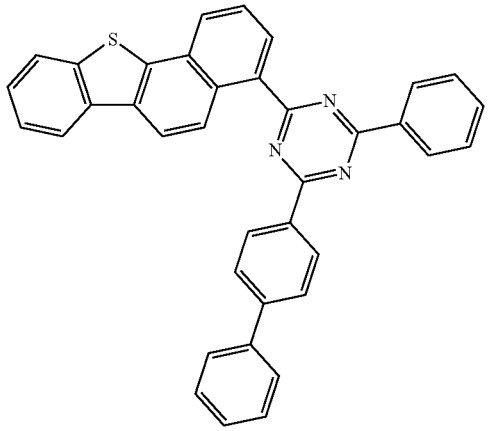
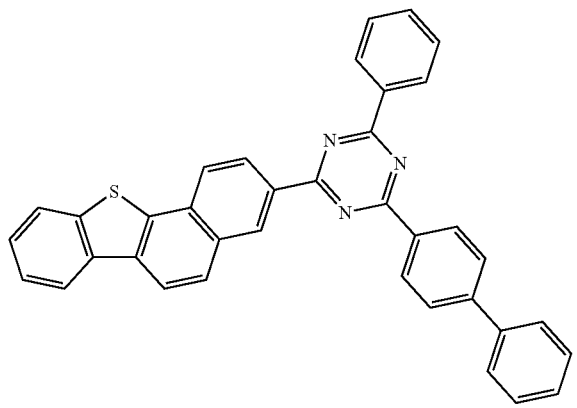
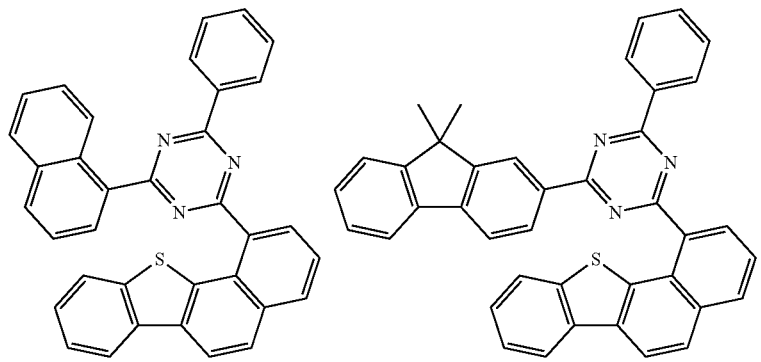
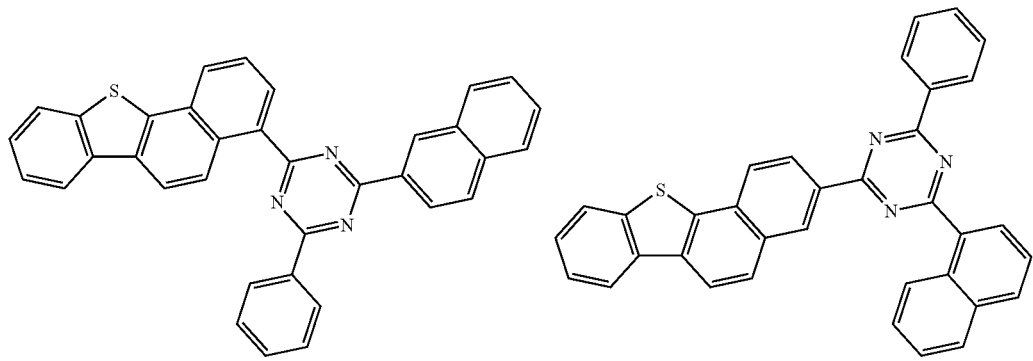

-continued
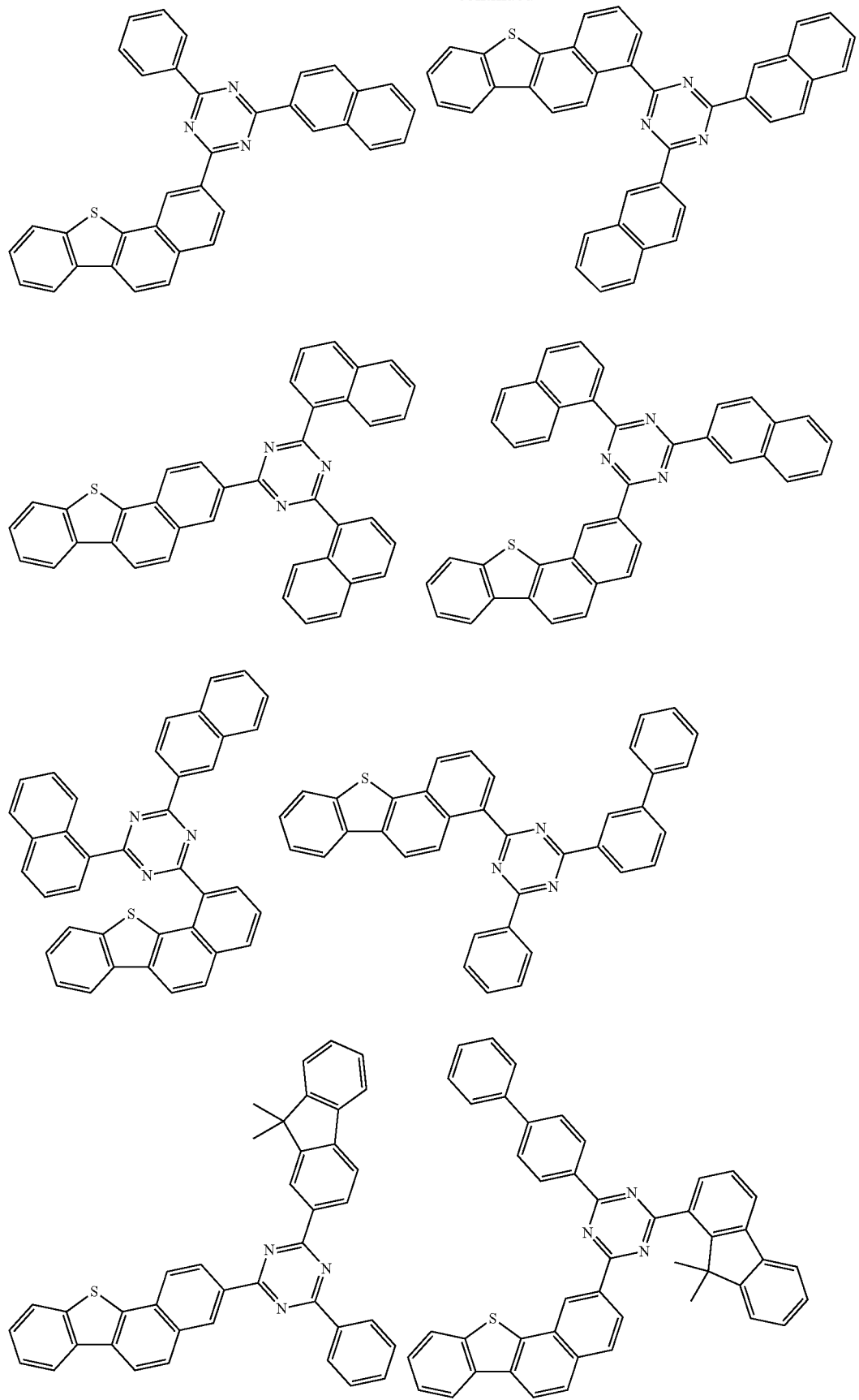

-continued
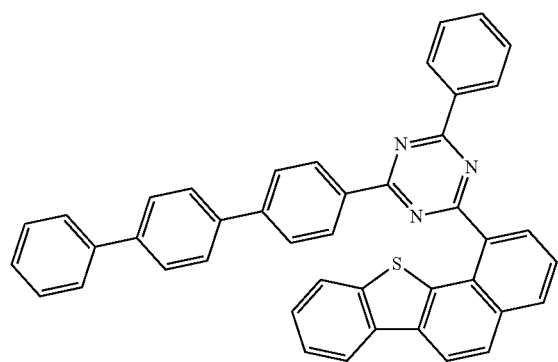
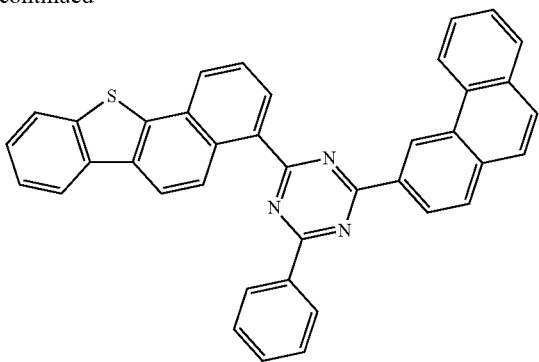
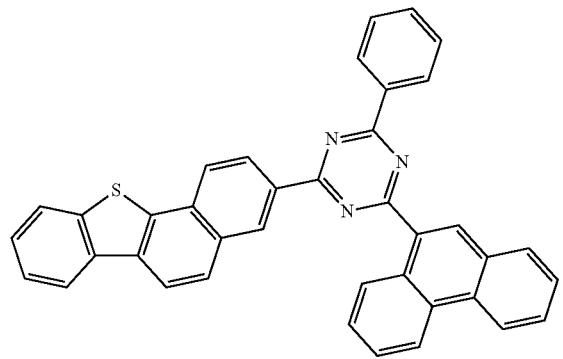
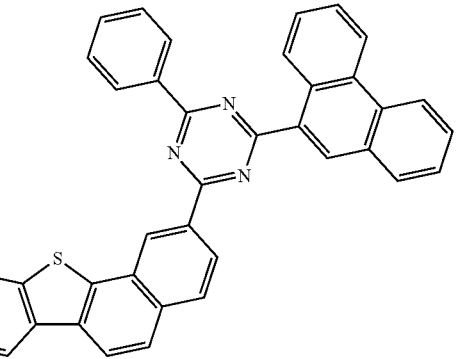
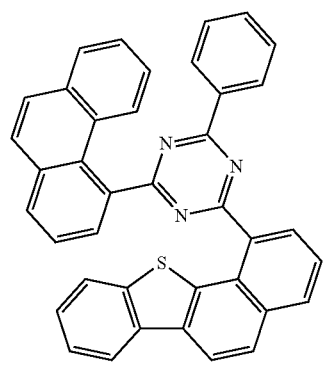
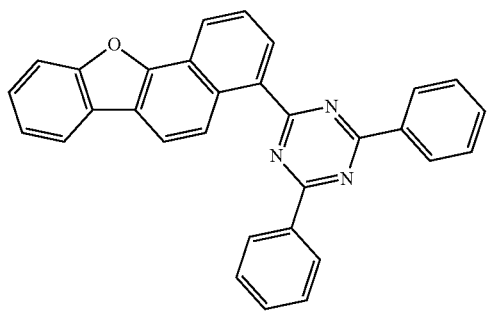
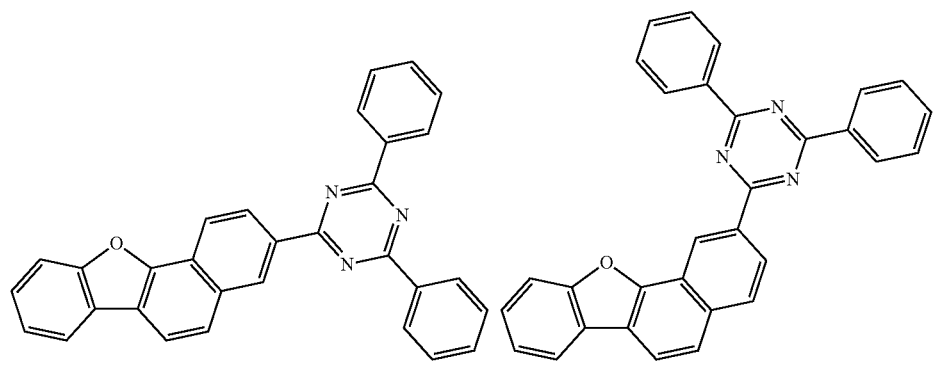

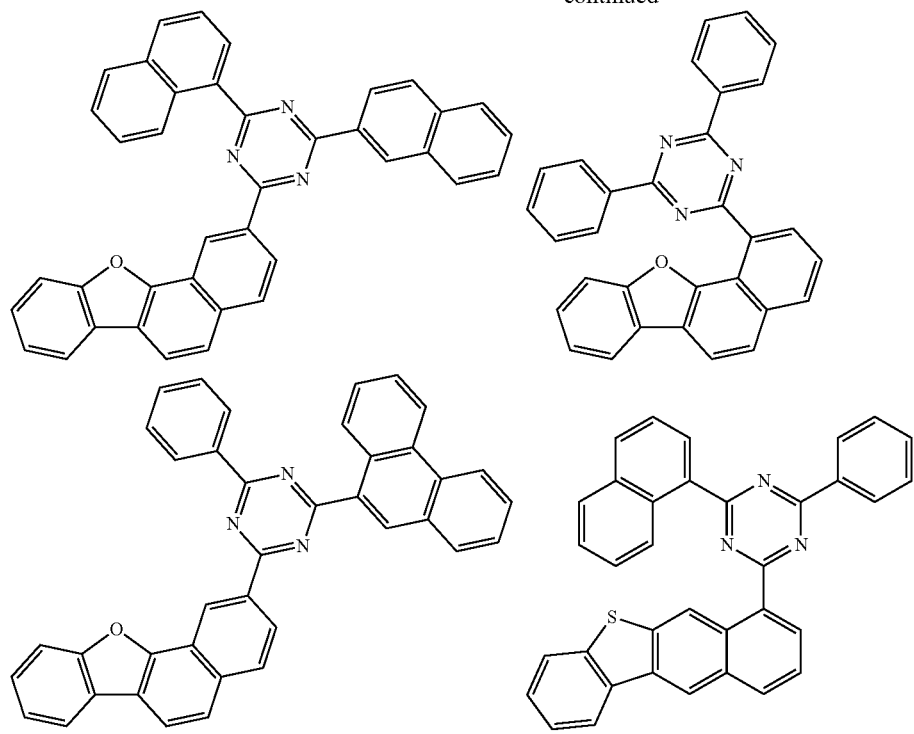
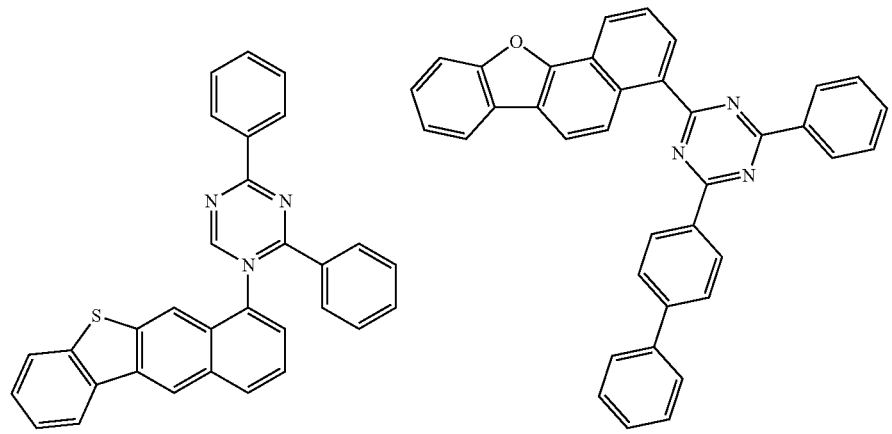
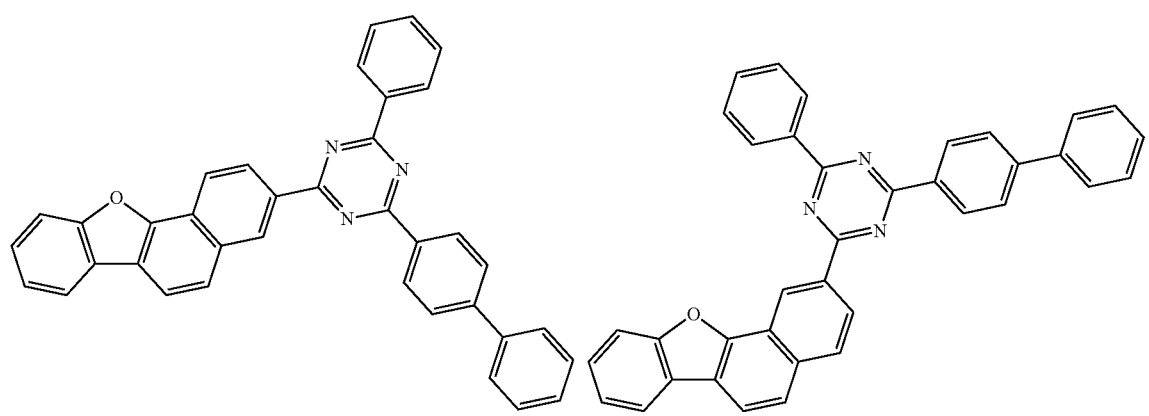

325
326
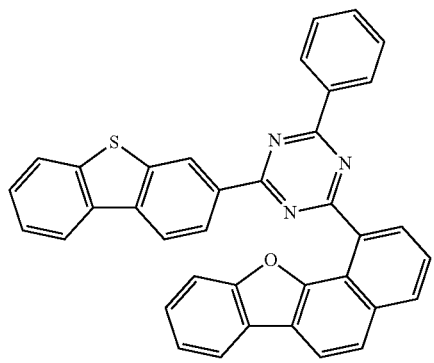
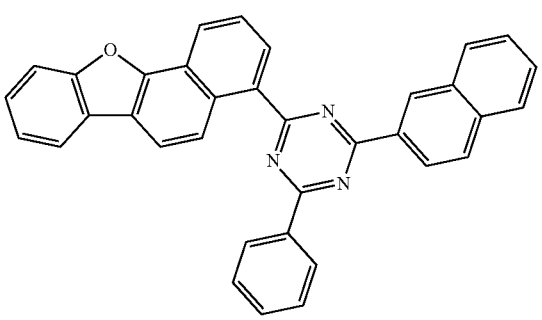
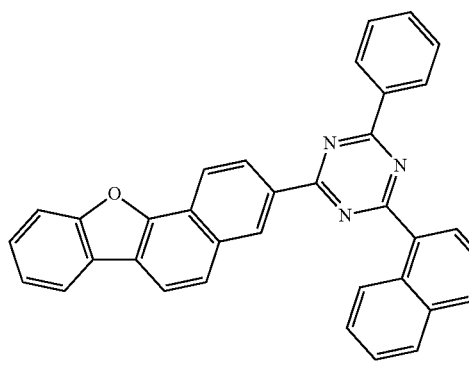
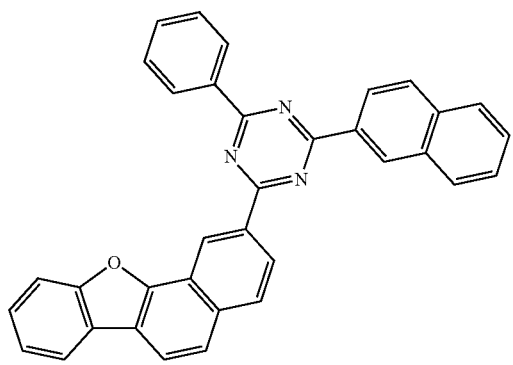
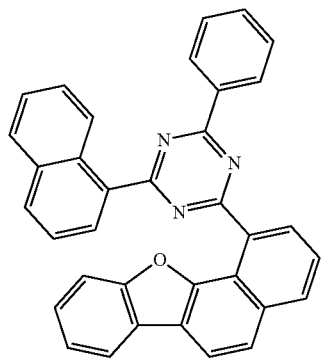
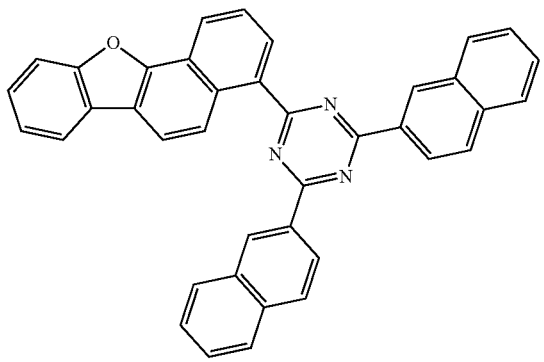
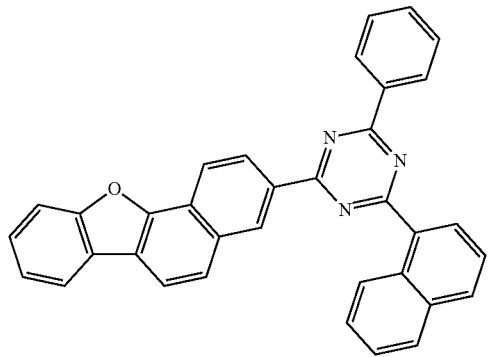
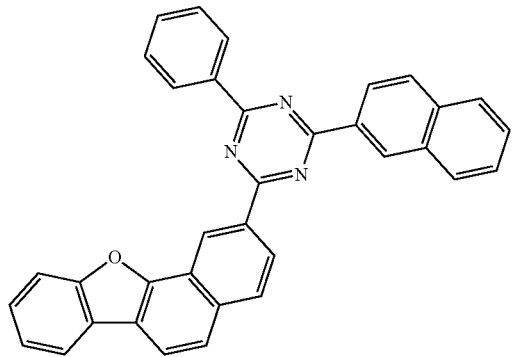

-continued
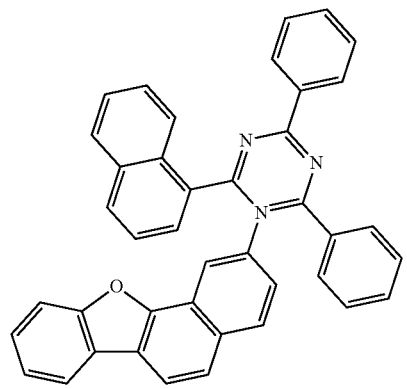
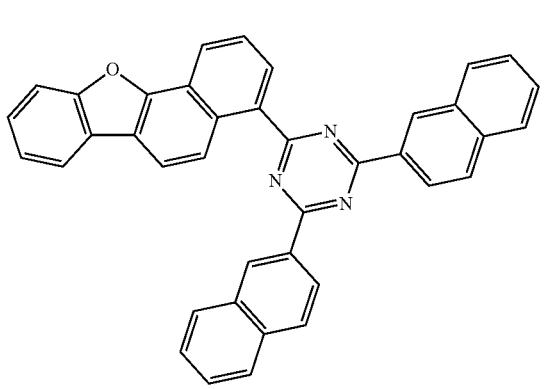
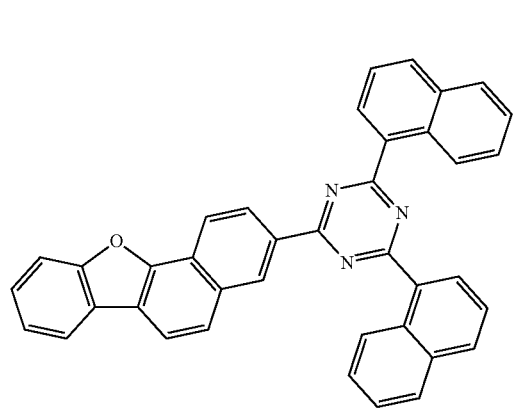
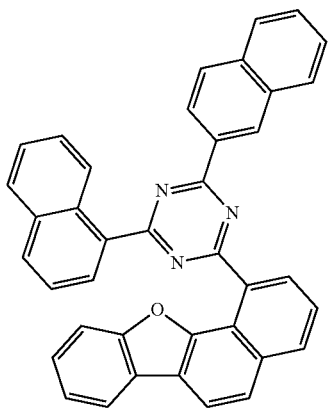
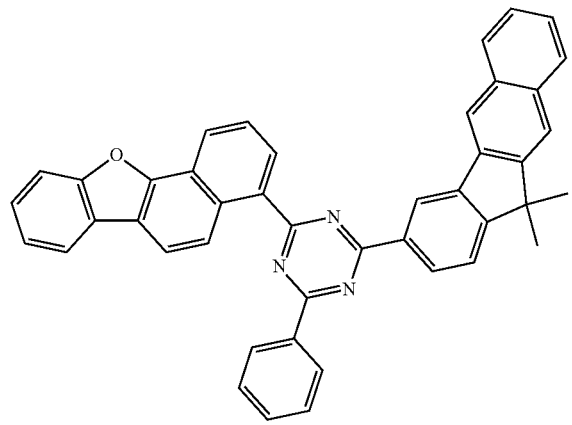
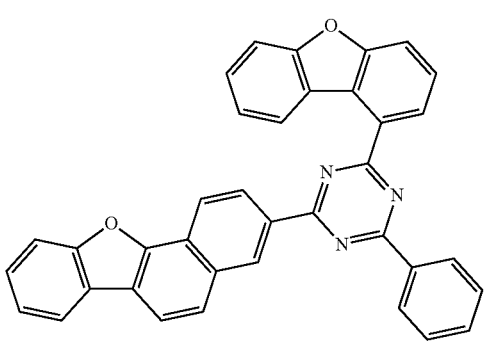
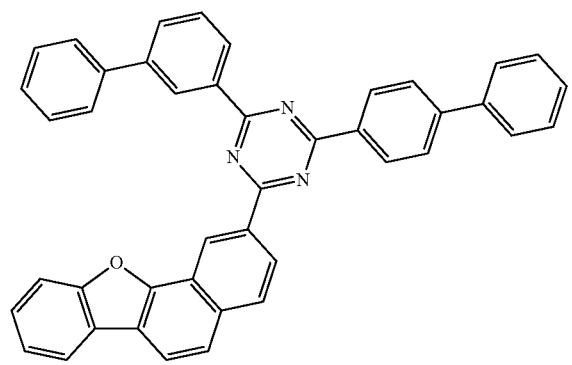
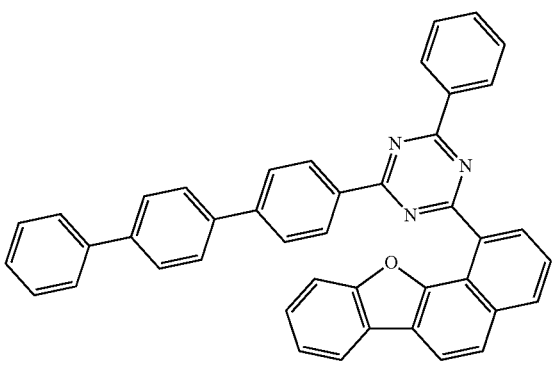

-continued
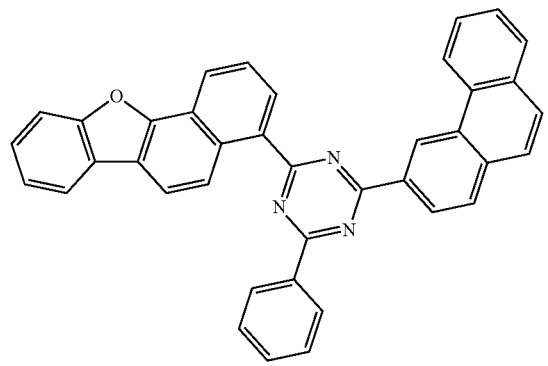
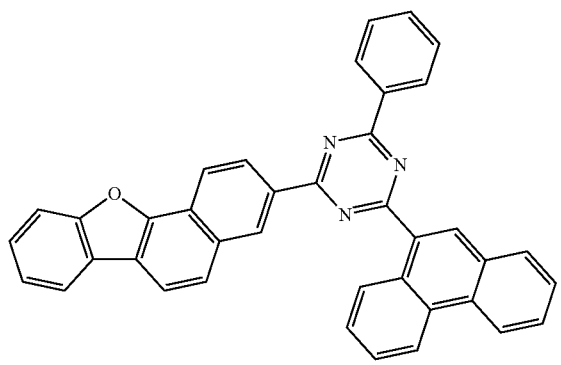
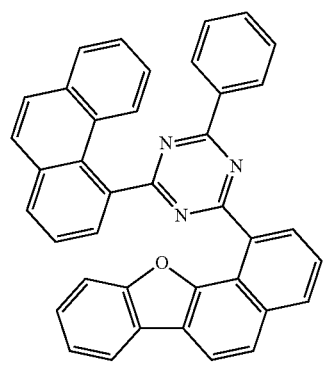
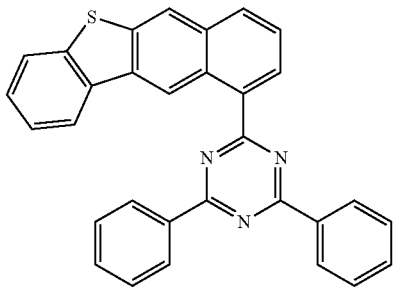
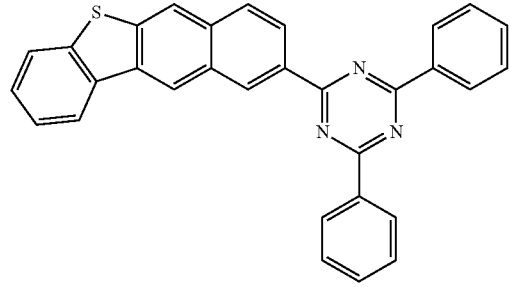
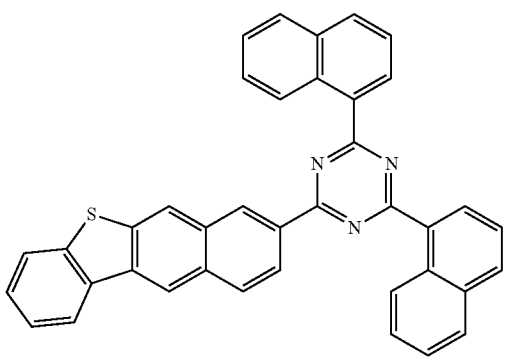
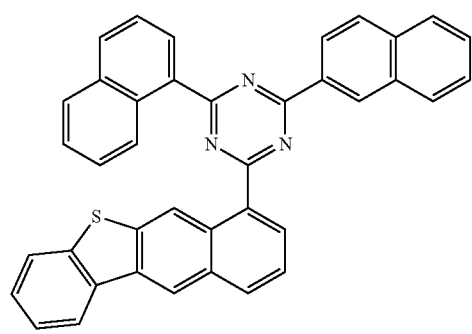

-continued
331
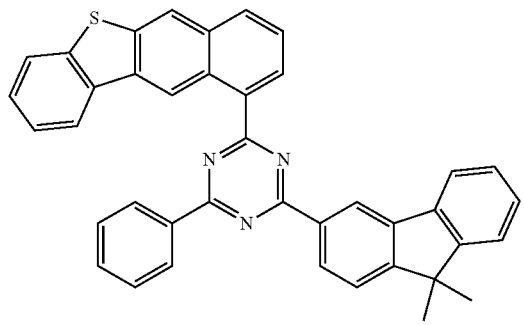
332
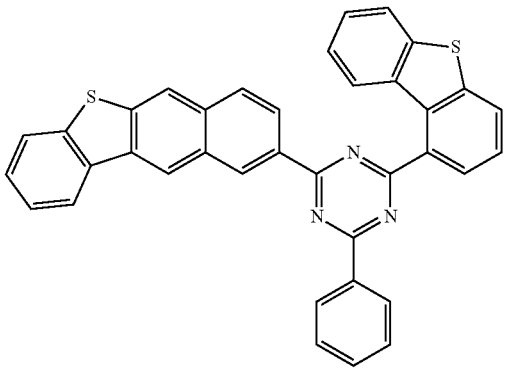
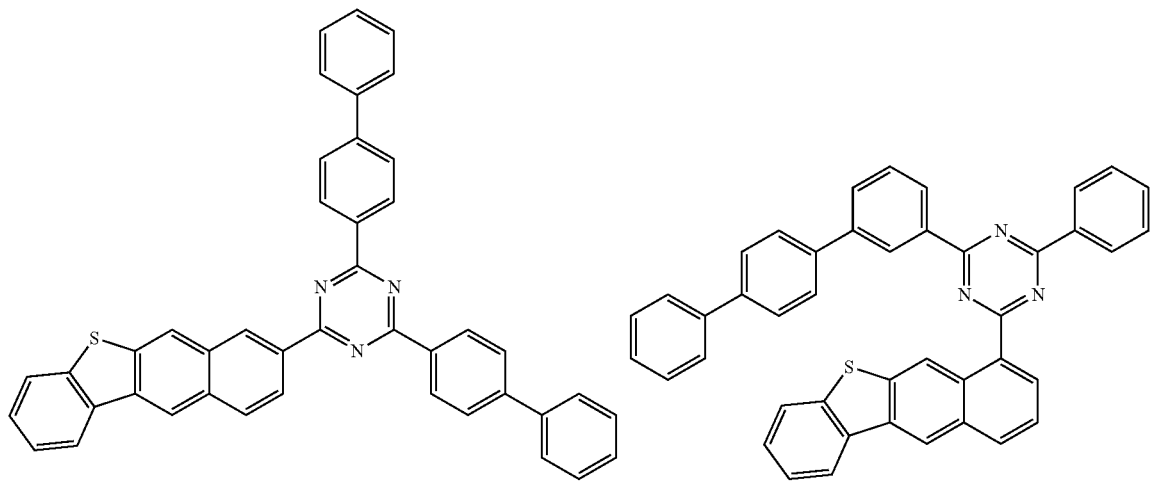
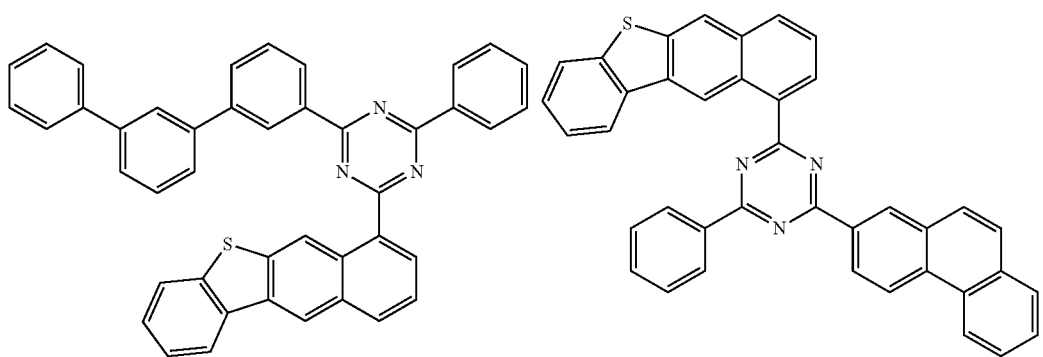
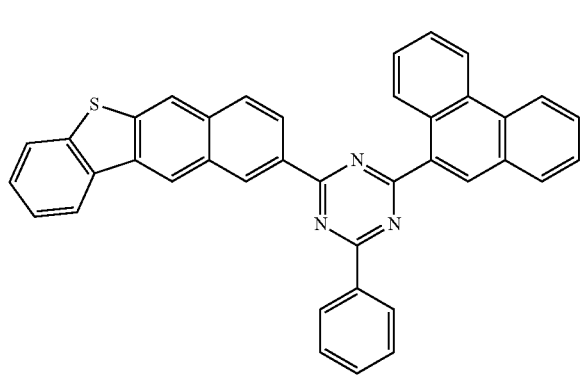
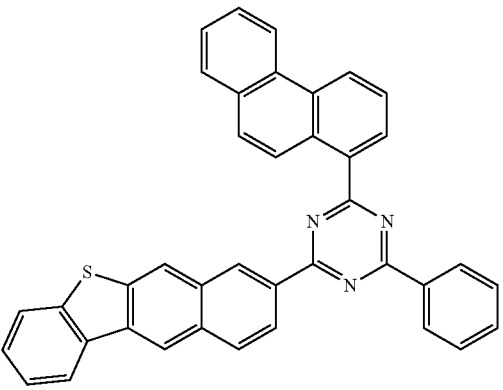

333
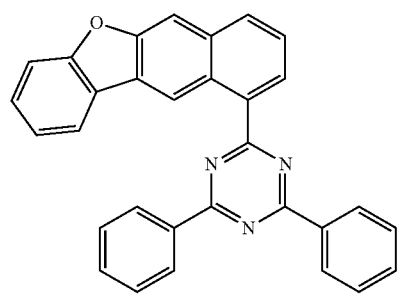
334
-continued
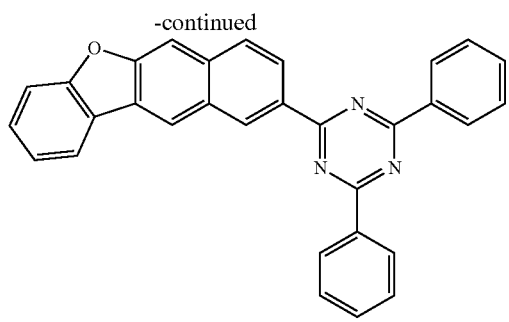
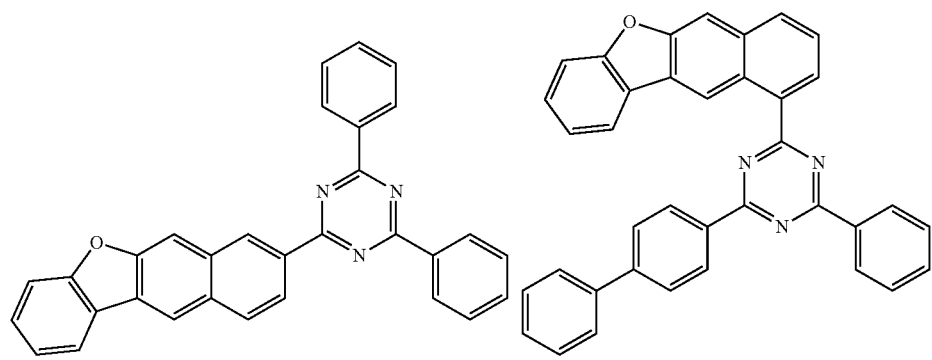
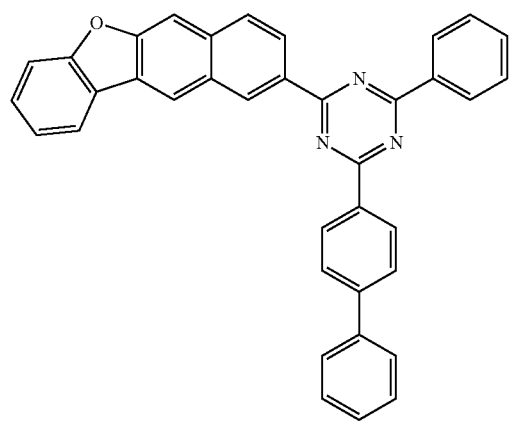
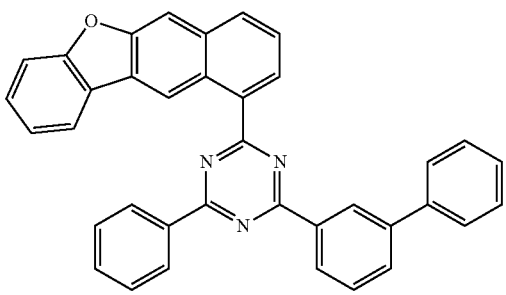
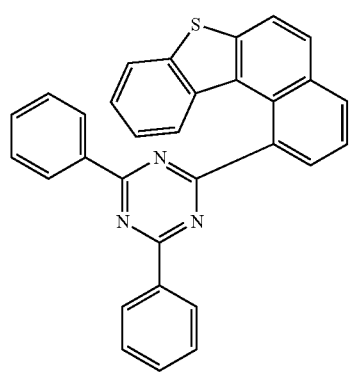
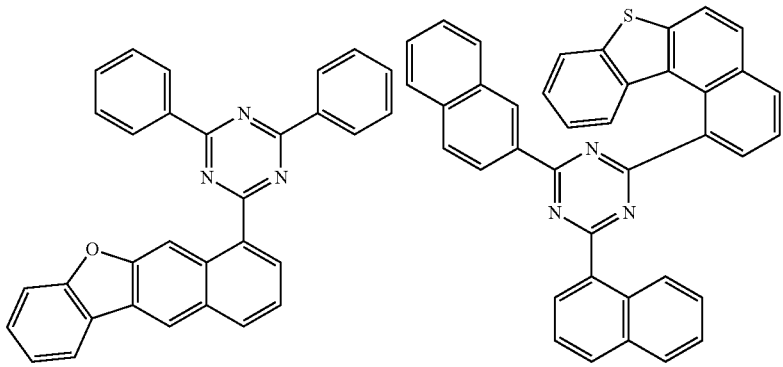

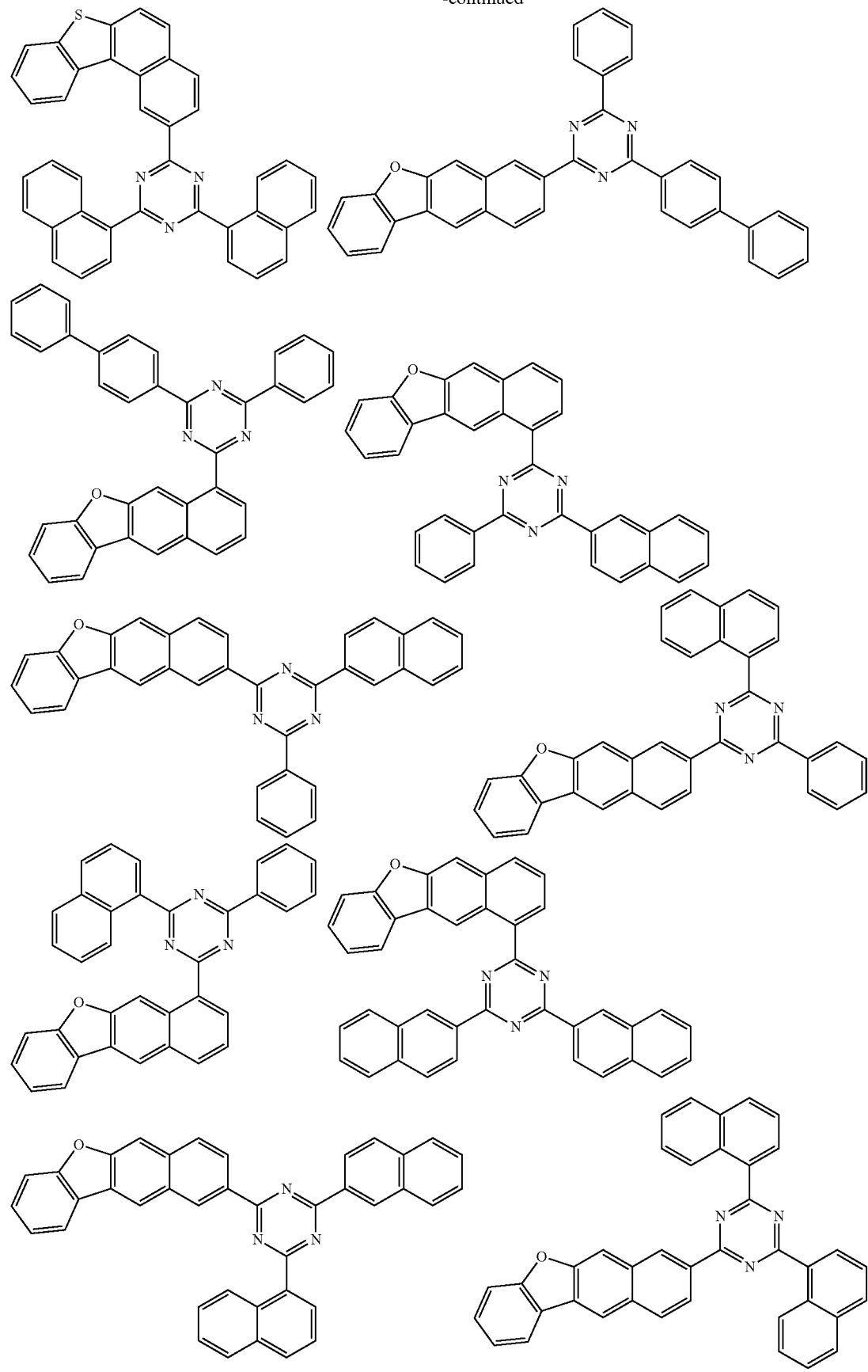

337 338
-continued
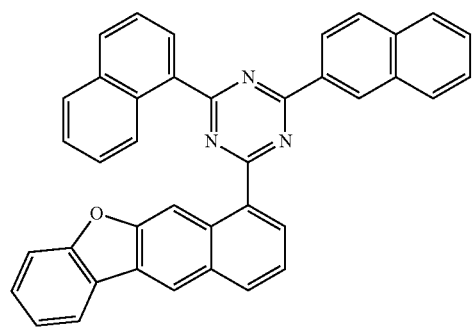
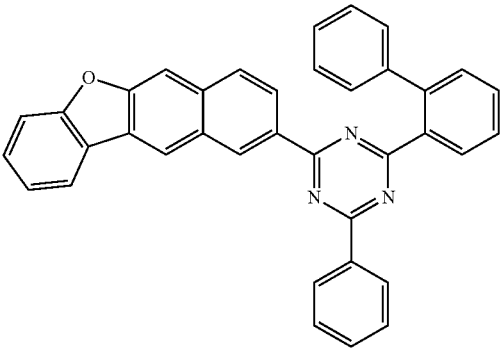
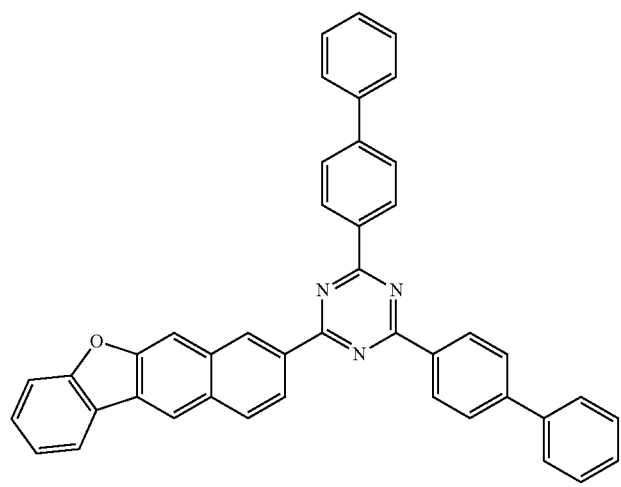
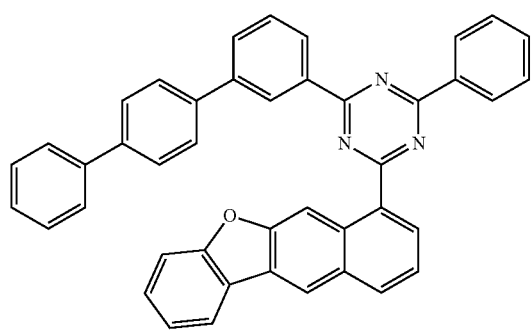
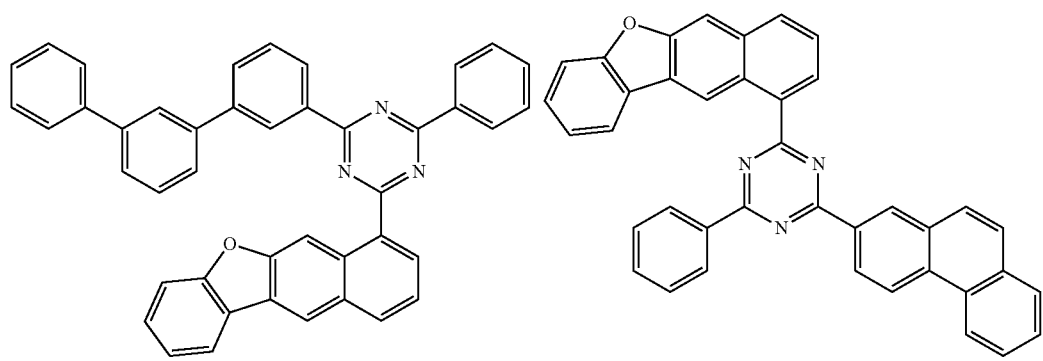

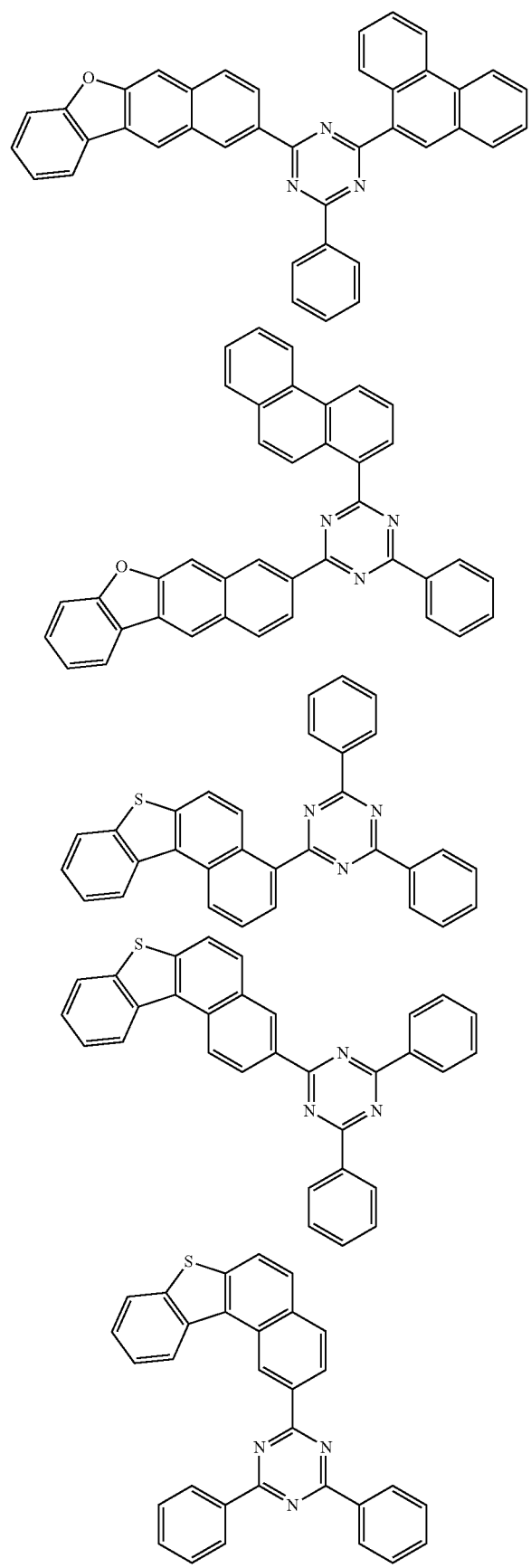
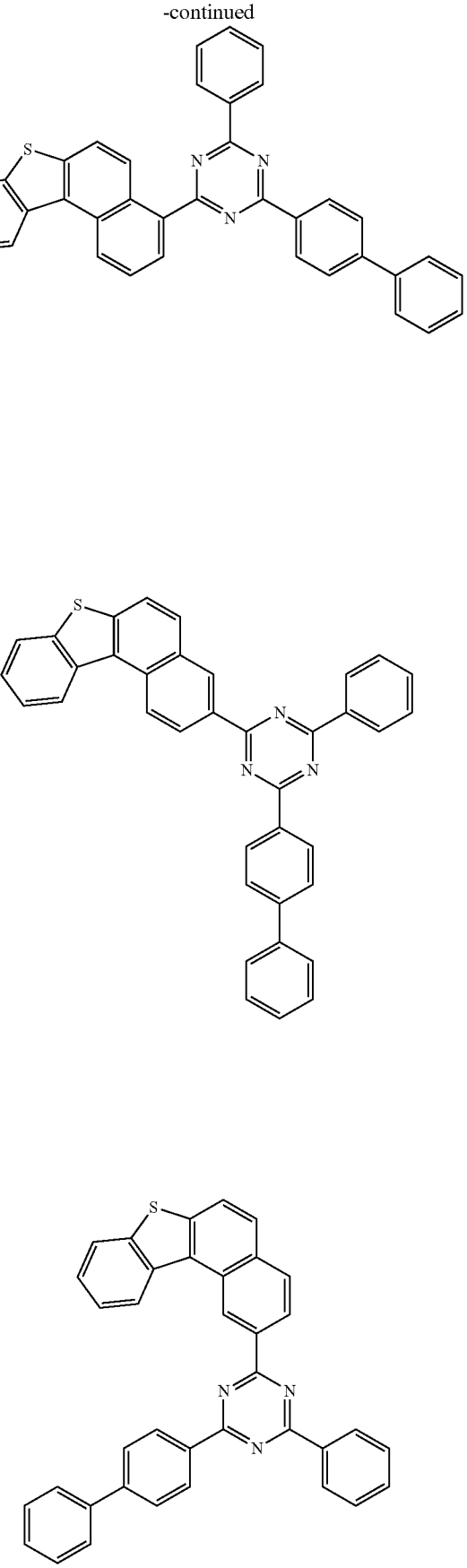

341
-continued
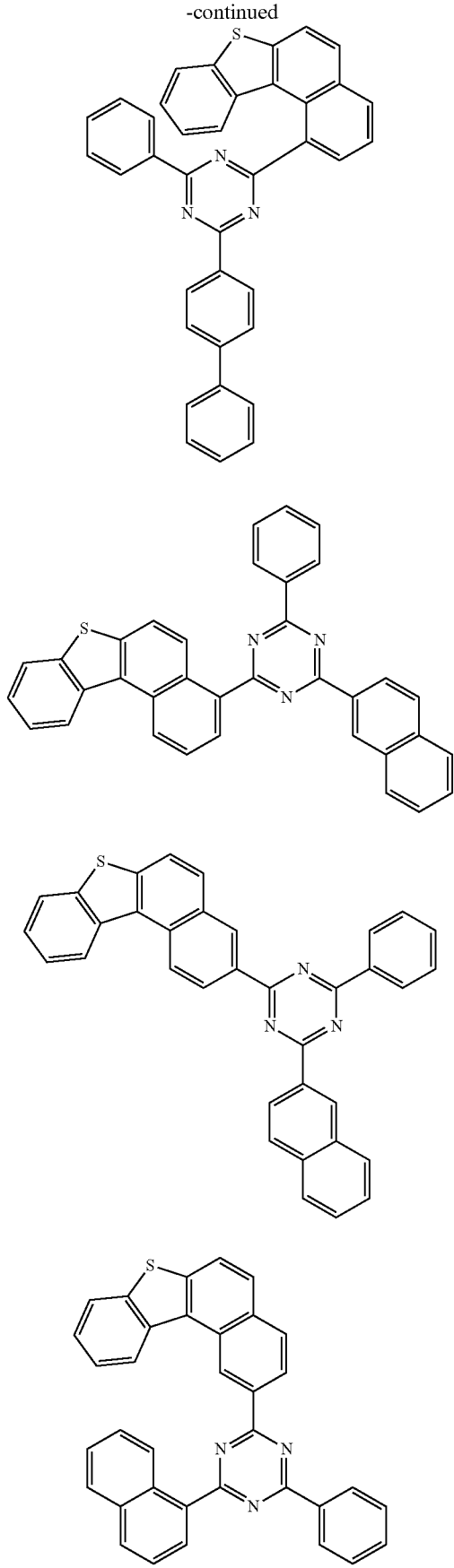
342
-continued
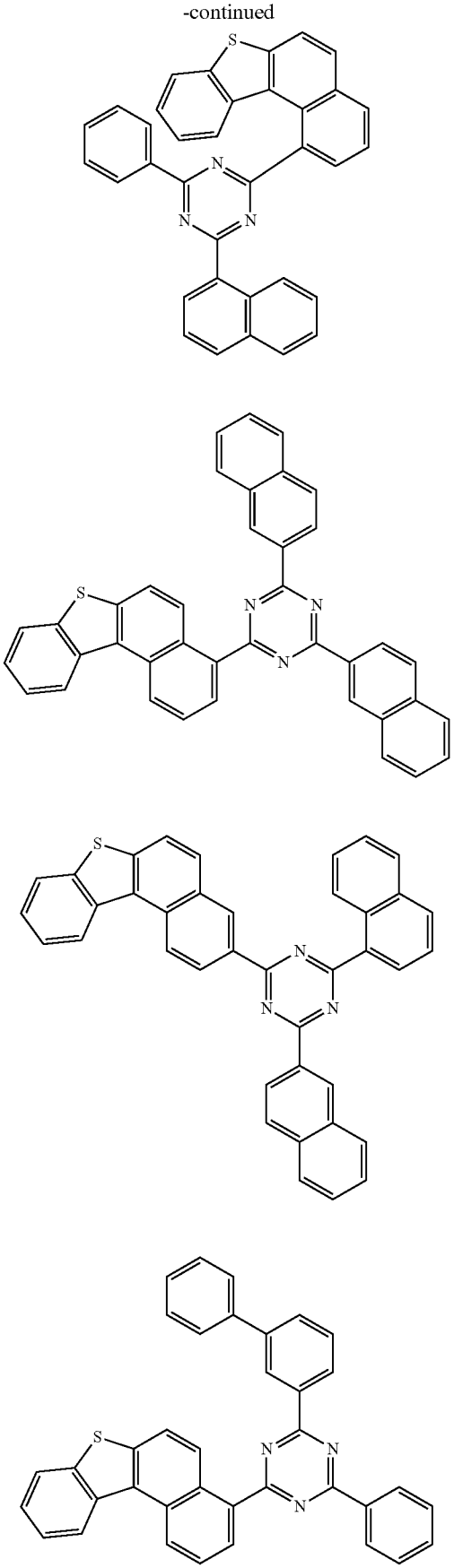

343
-continued
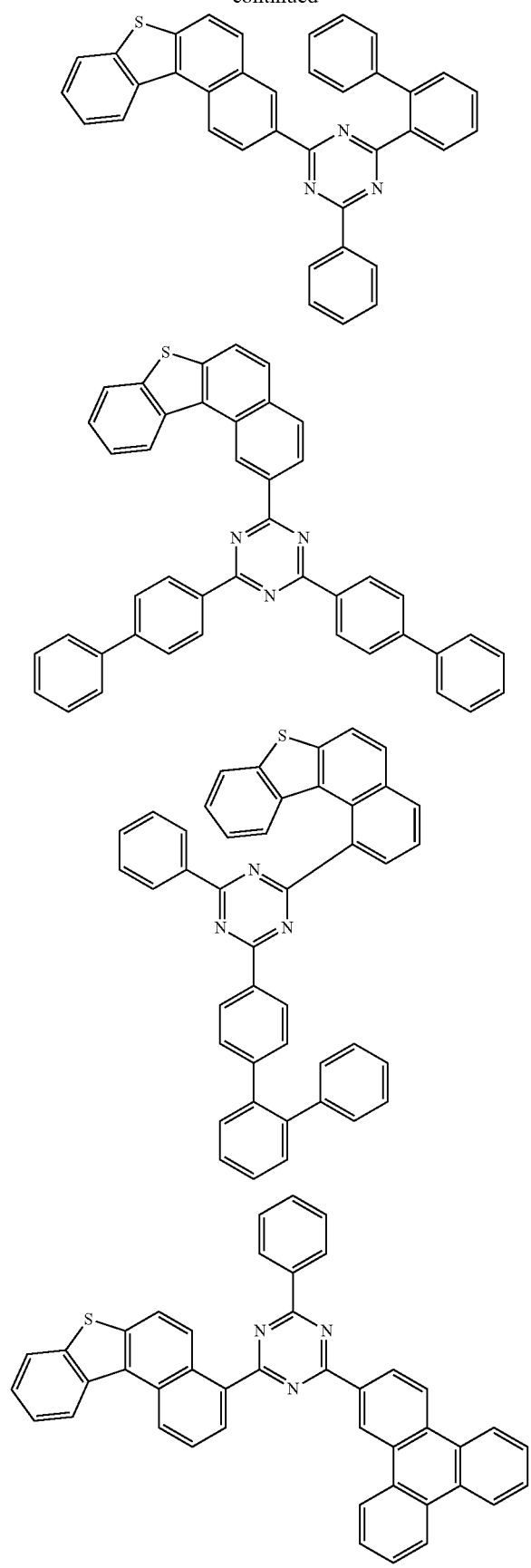
344
-continued
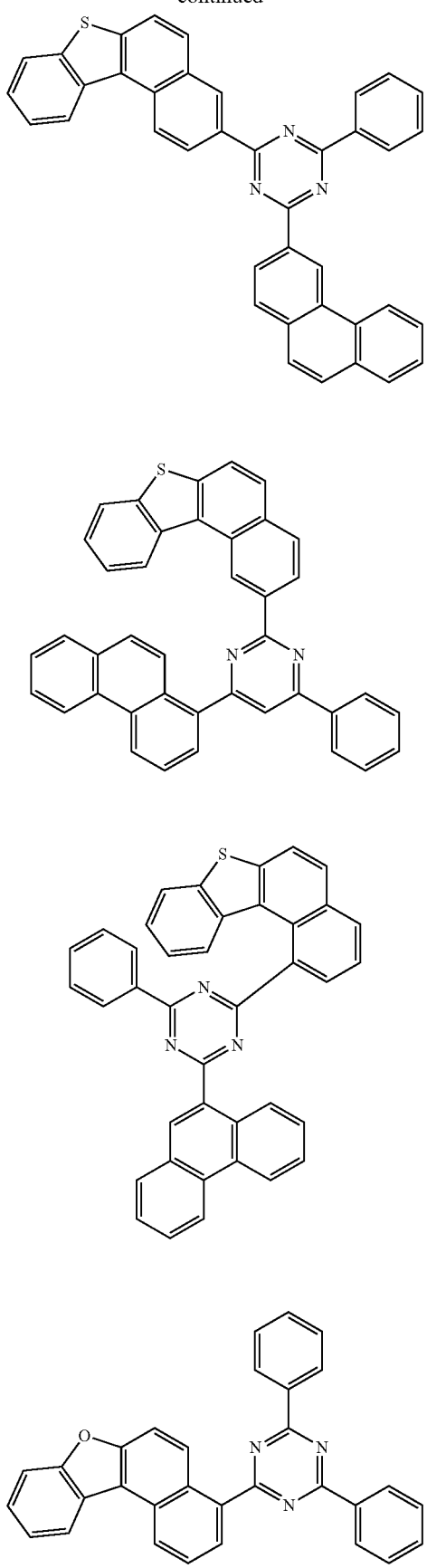

345
-continued
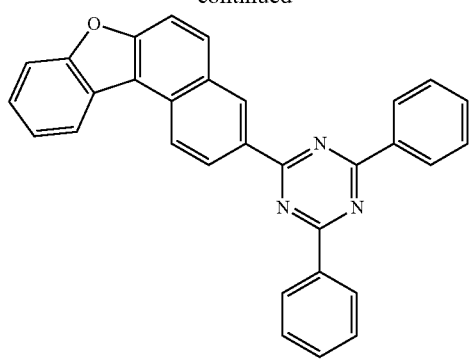
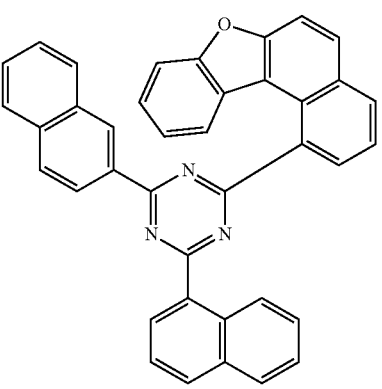
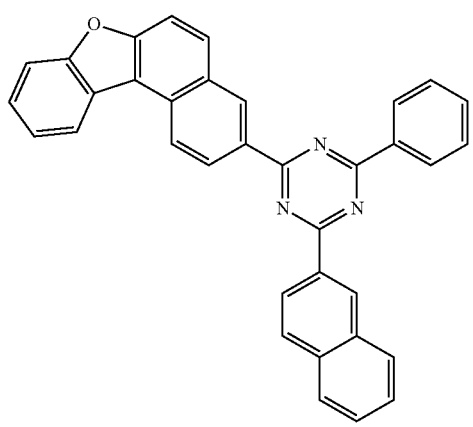
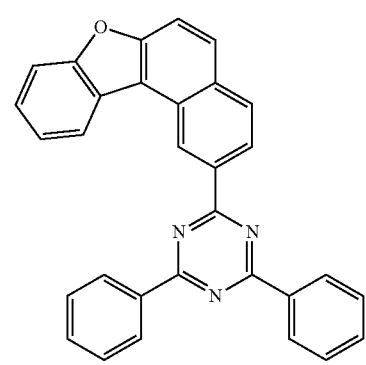
346
-continued
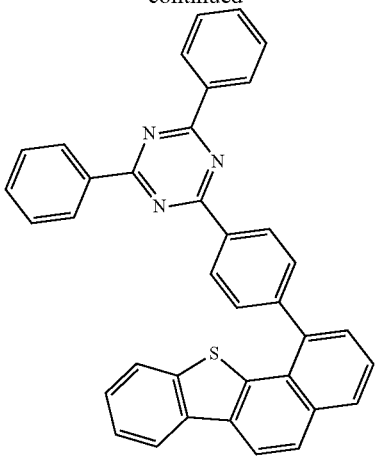
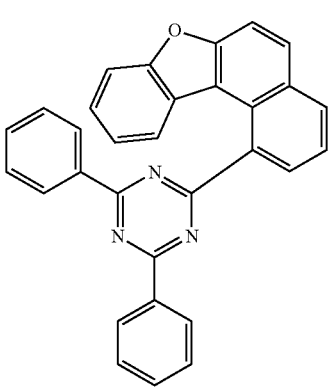

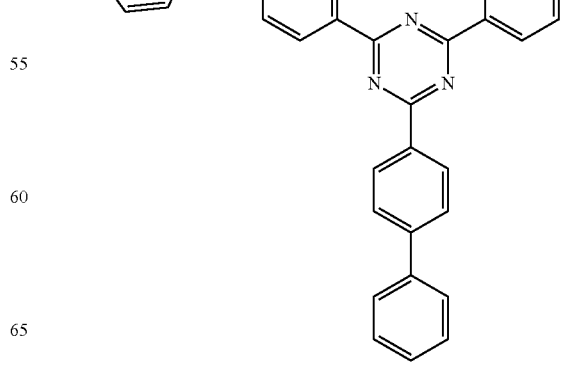

347
-continued
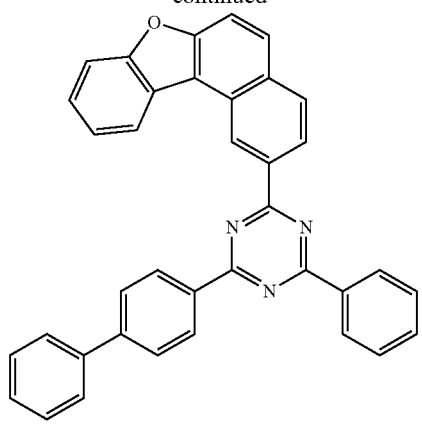
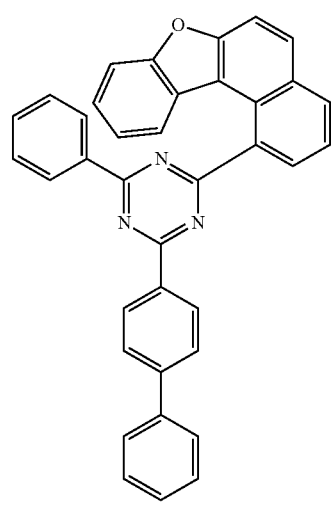
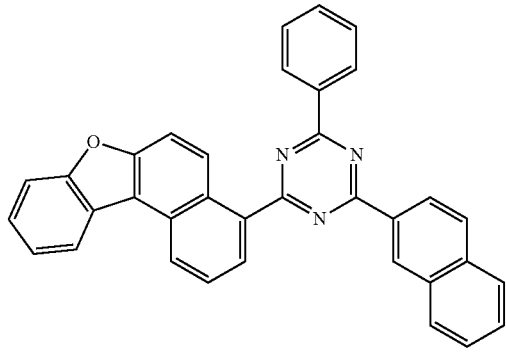
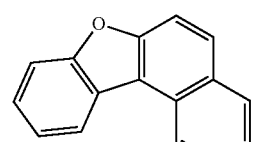
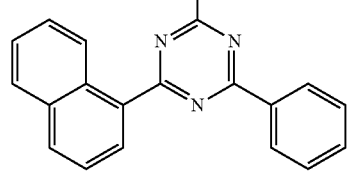
348
-continued
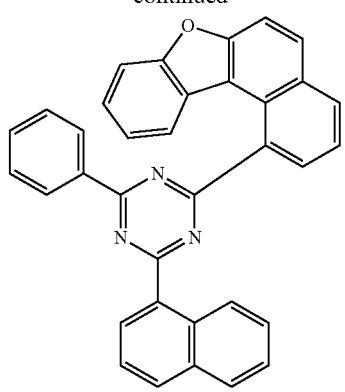
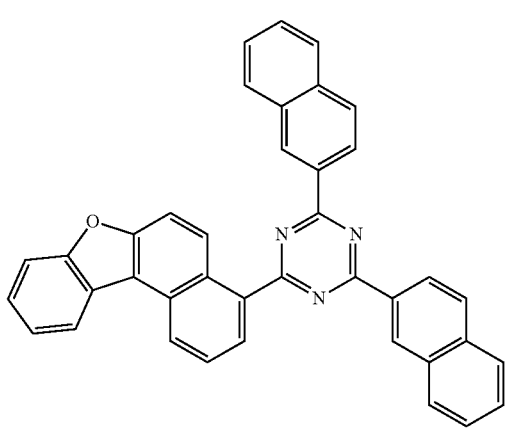
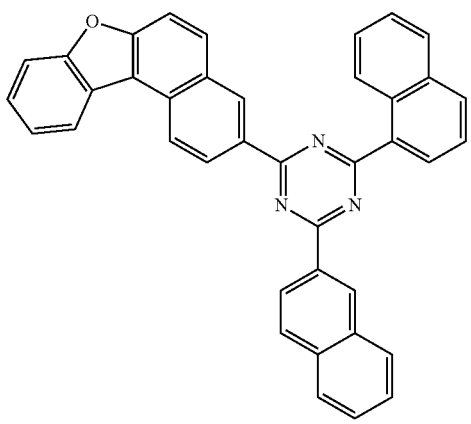
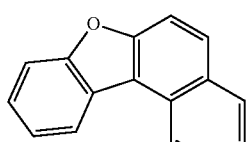
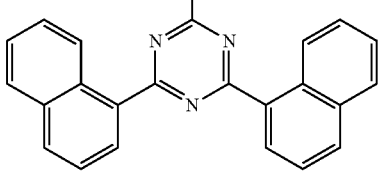

349
-continued
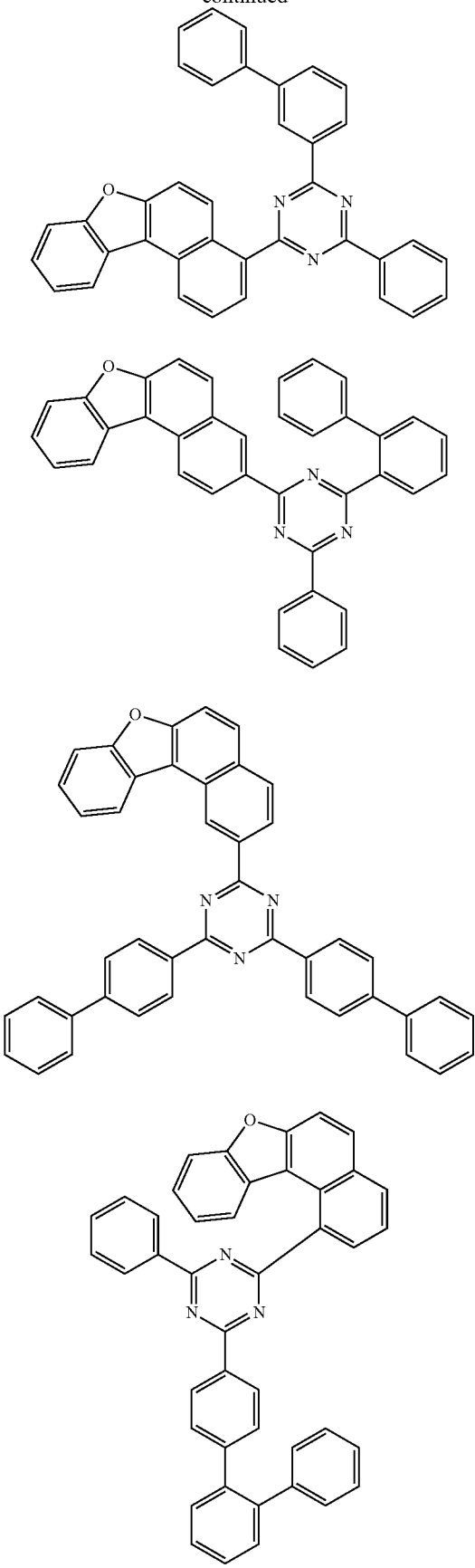
350
-continued
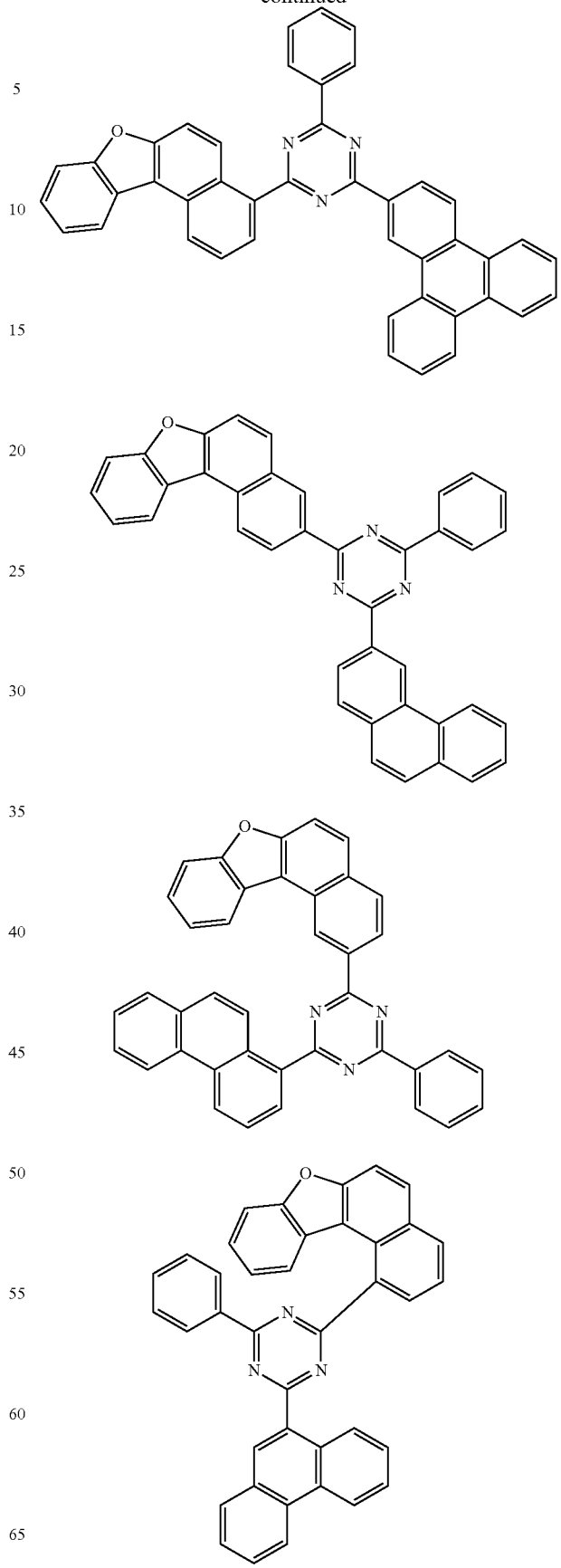

351
-continued
352
-continued
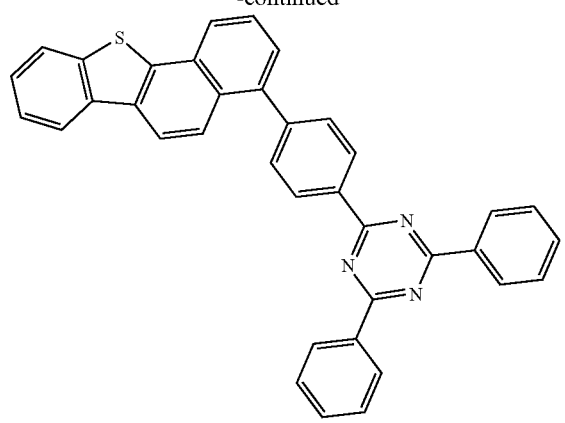
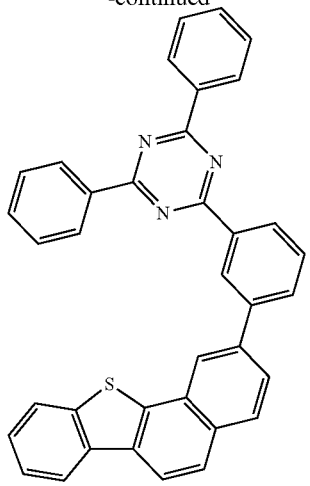
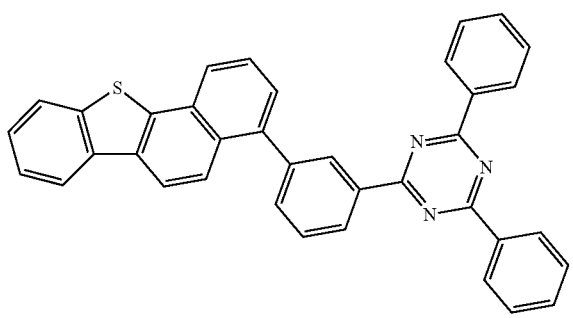
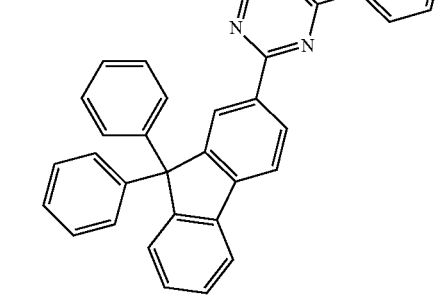
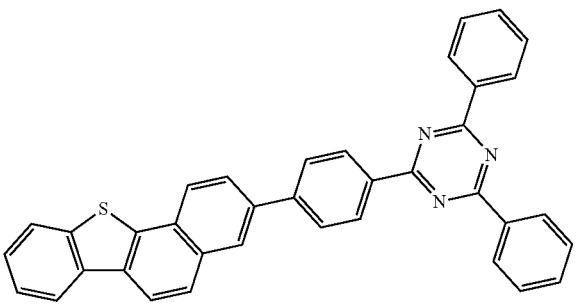
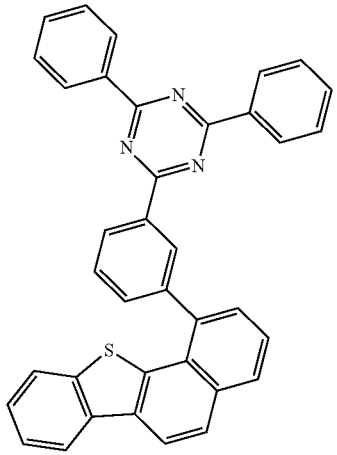

353
-continued
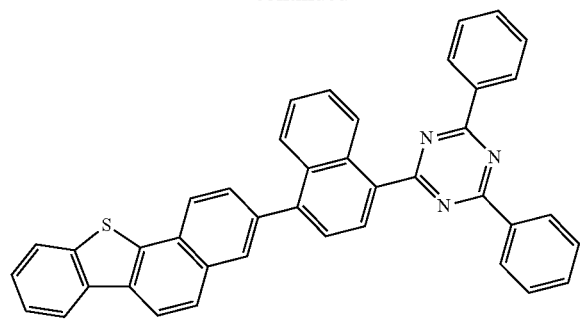
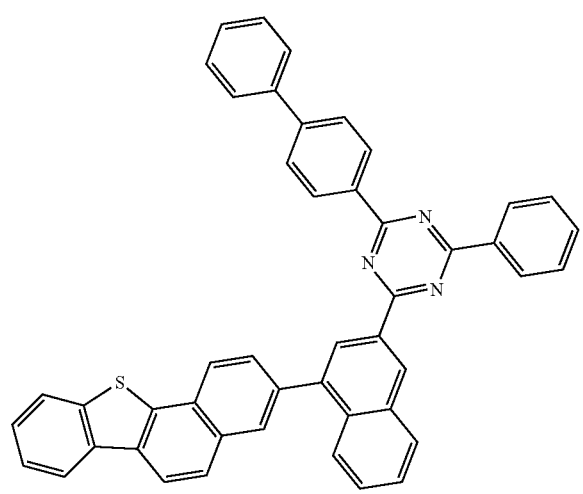
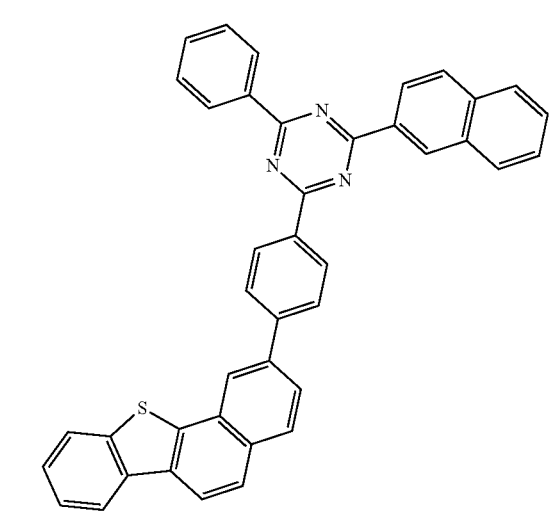
354
-continued
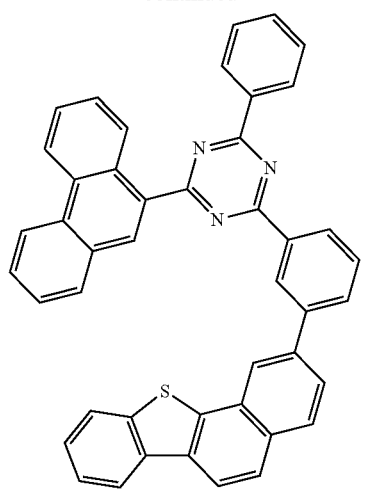
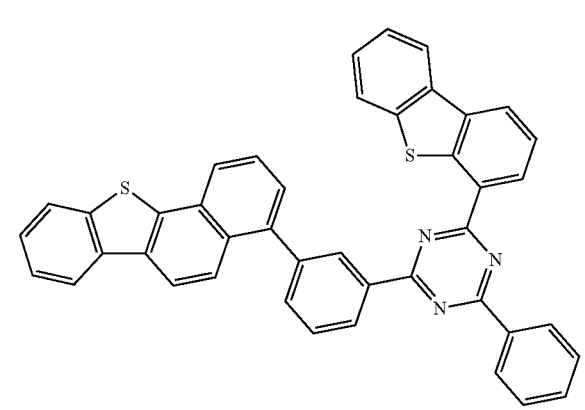
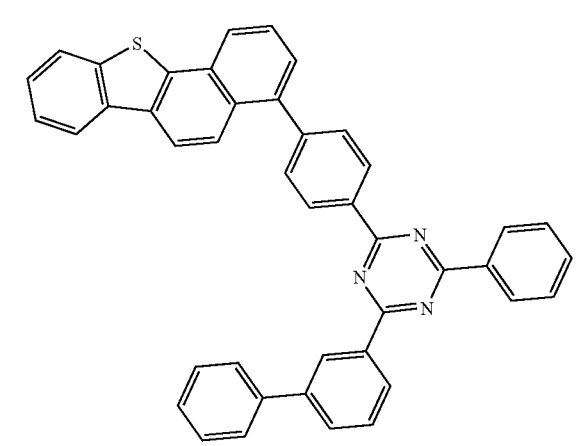
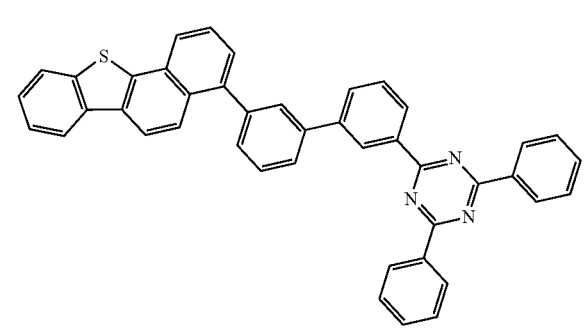

355
-continued
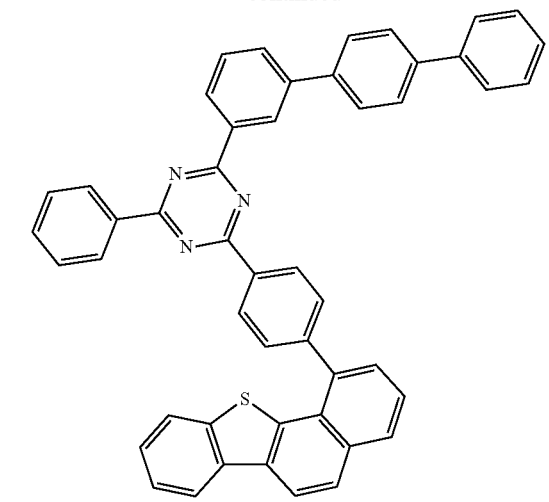
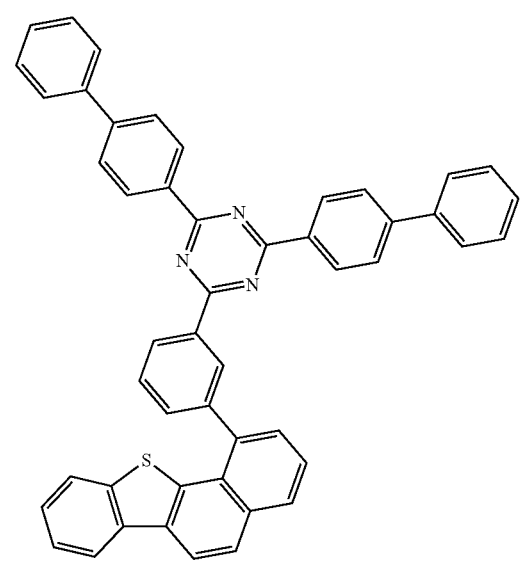
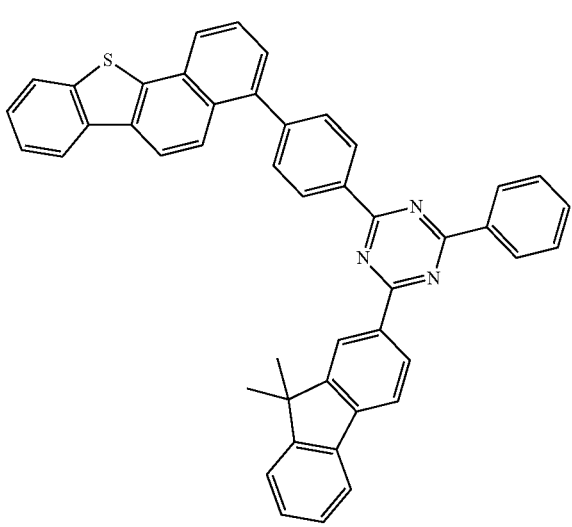
356
-continued
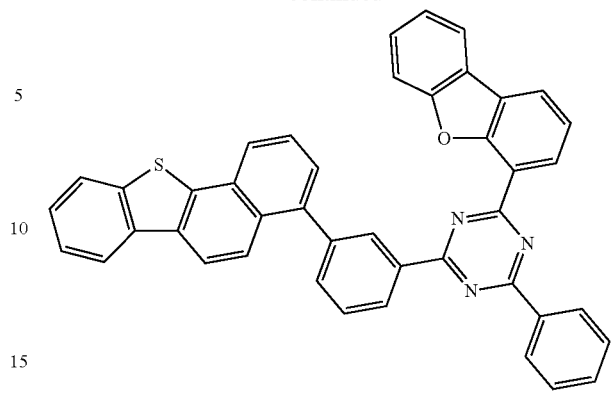
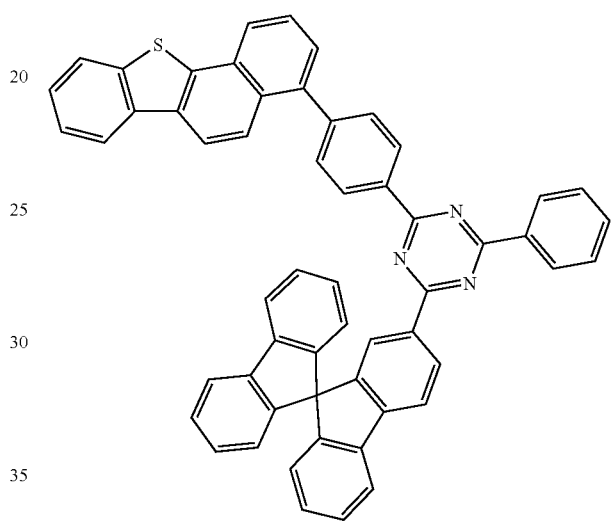
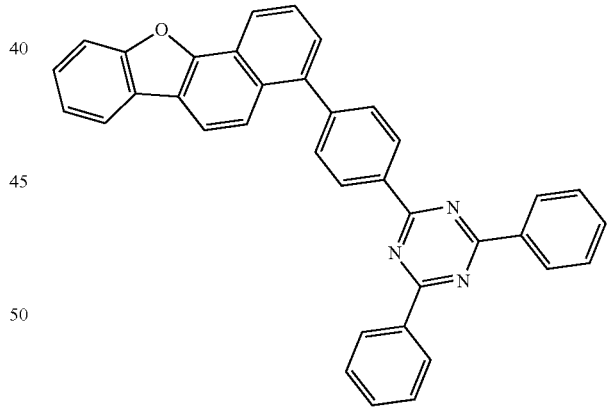
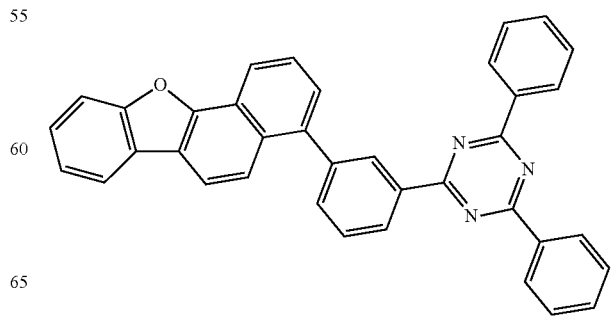

357
-continued
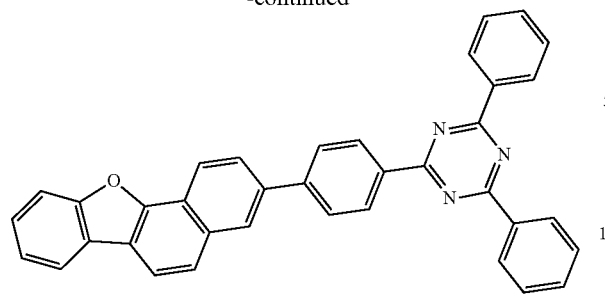
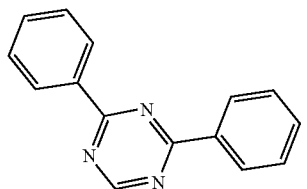
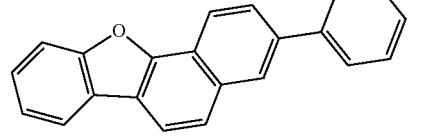
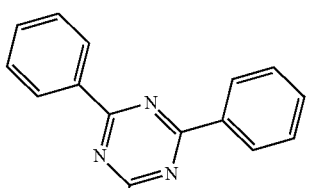
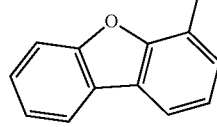
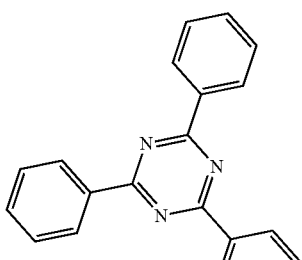
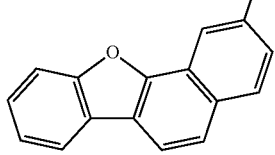
358
-continued
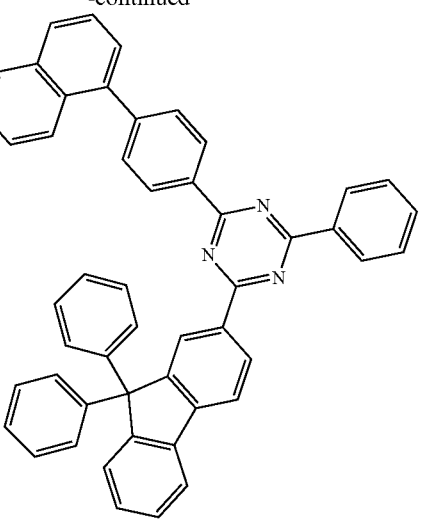
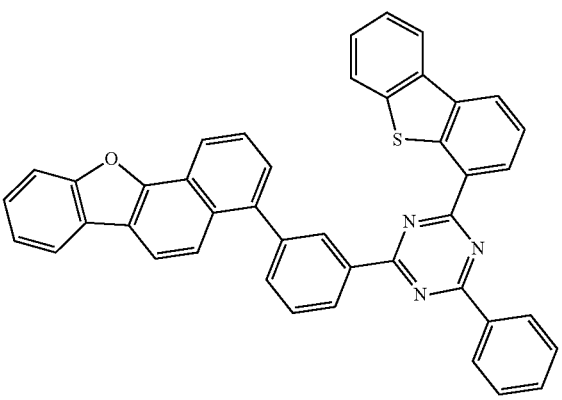
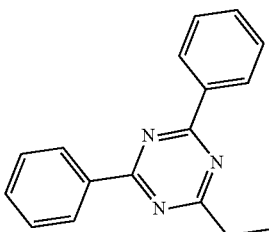
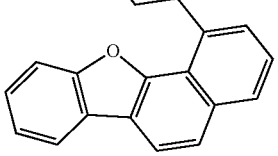

359
-continued
360
-continued
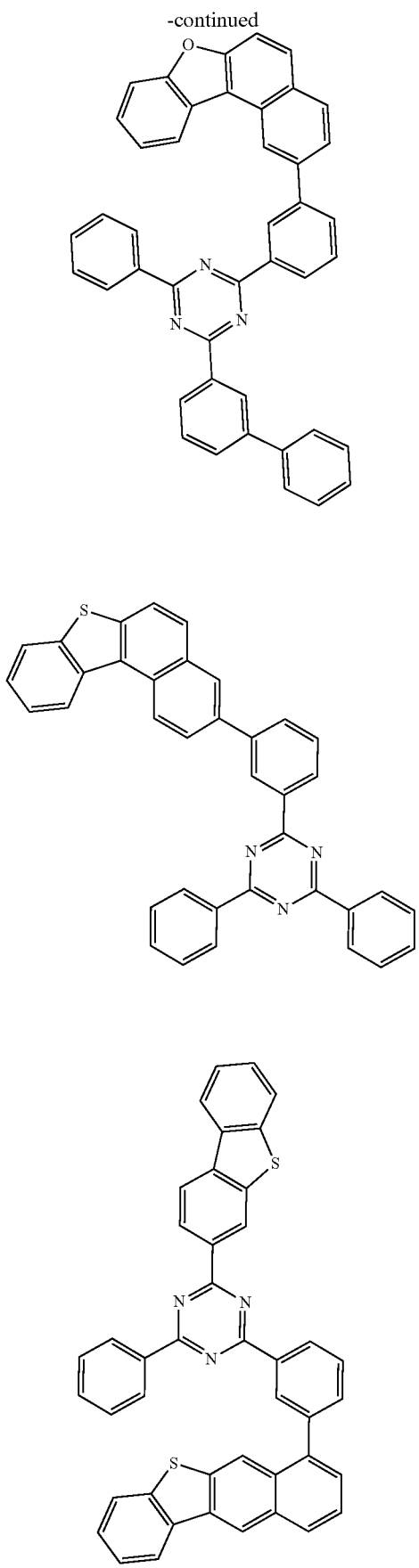
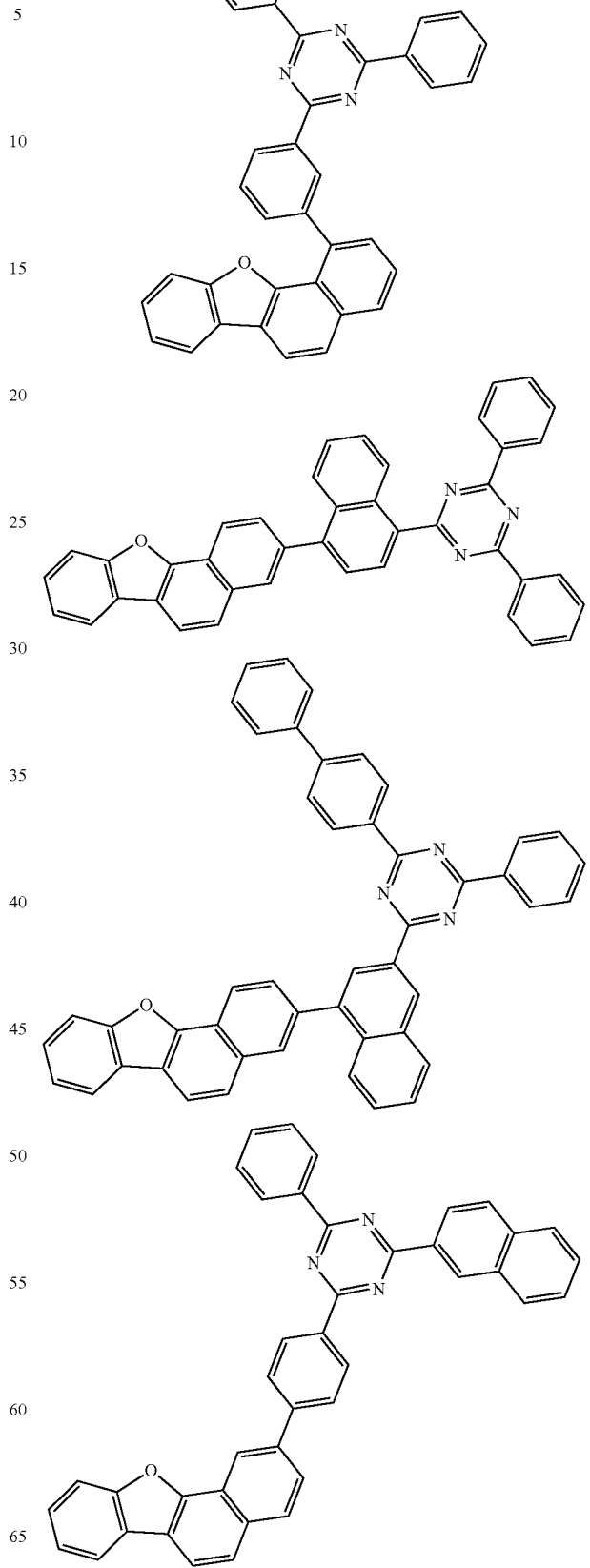

361
-continued
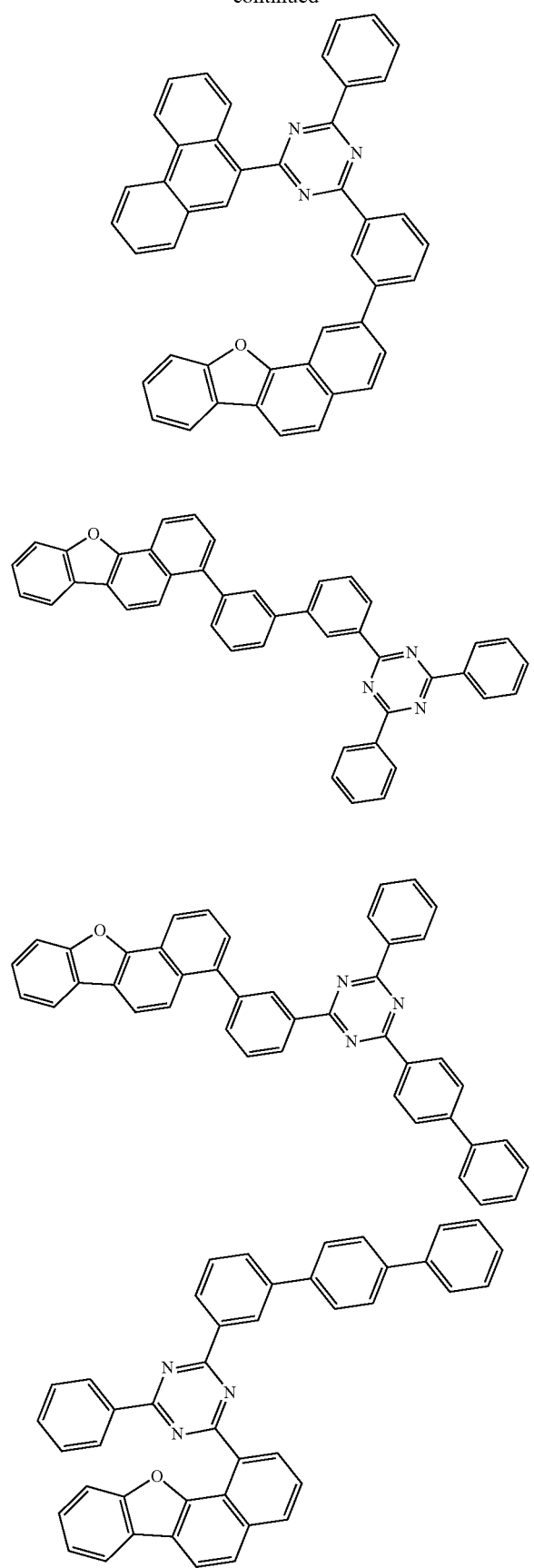
362
-continued
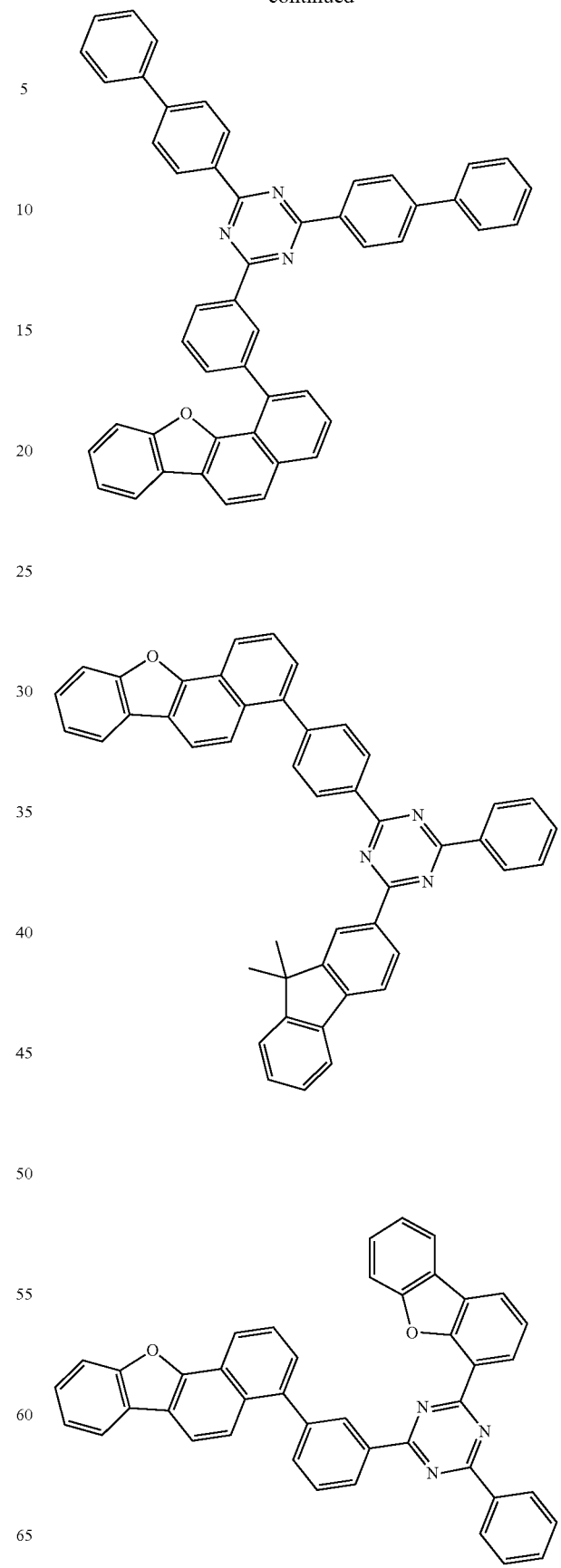

363
-continued
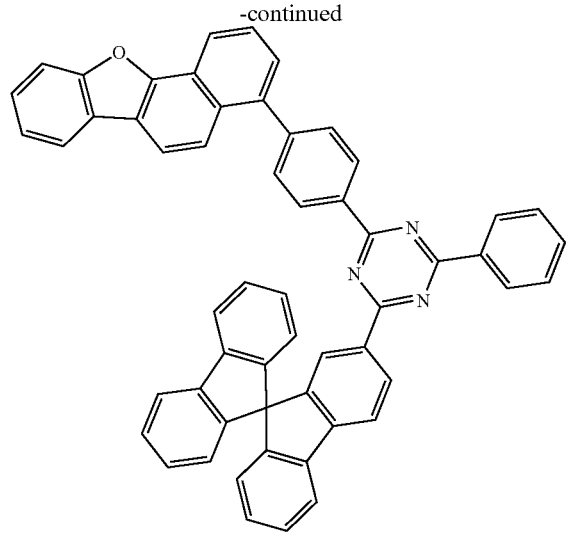
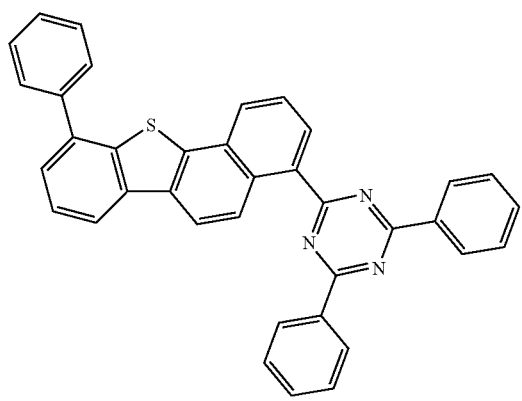
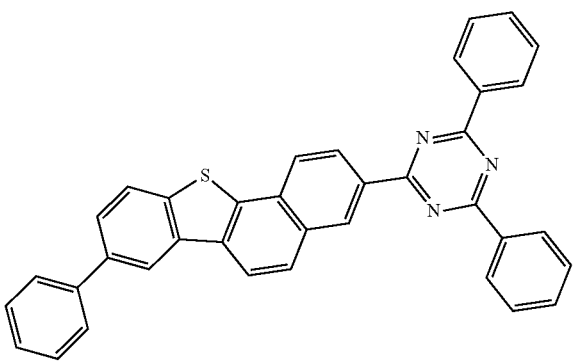
364
-continued
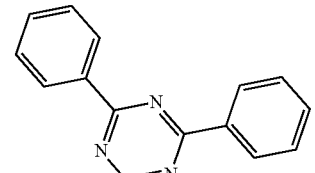
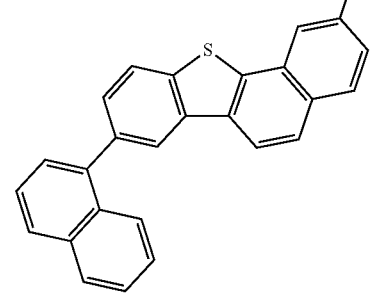
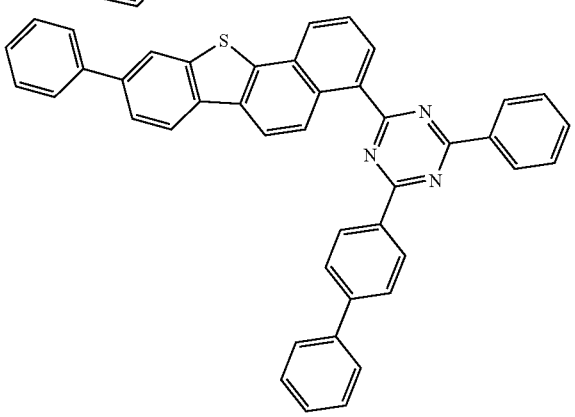
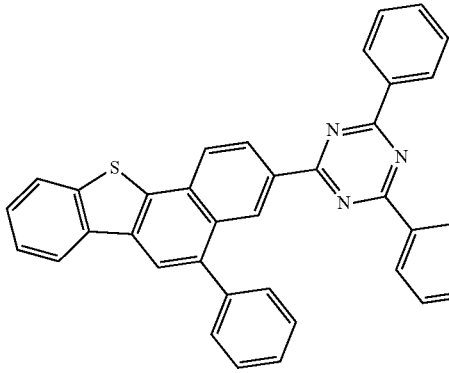
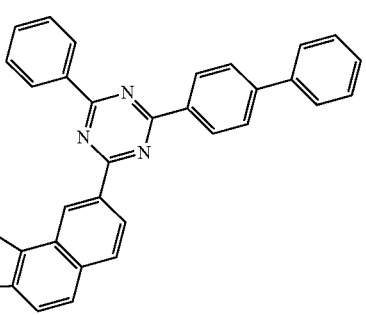

365
-continued
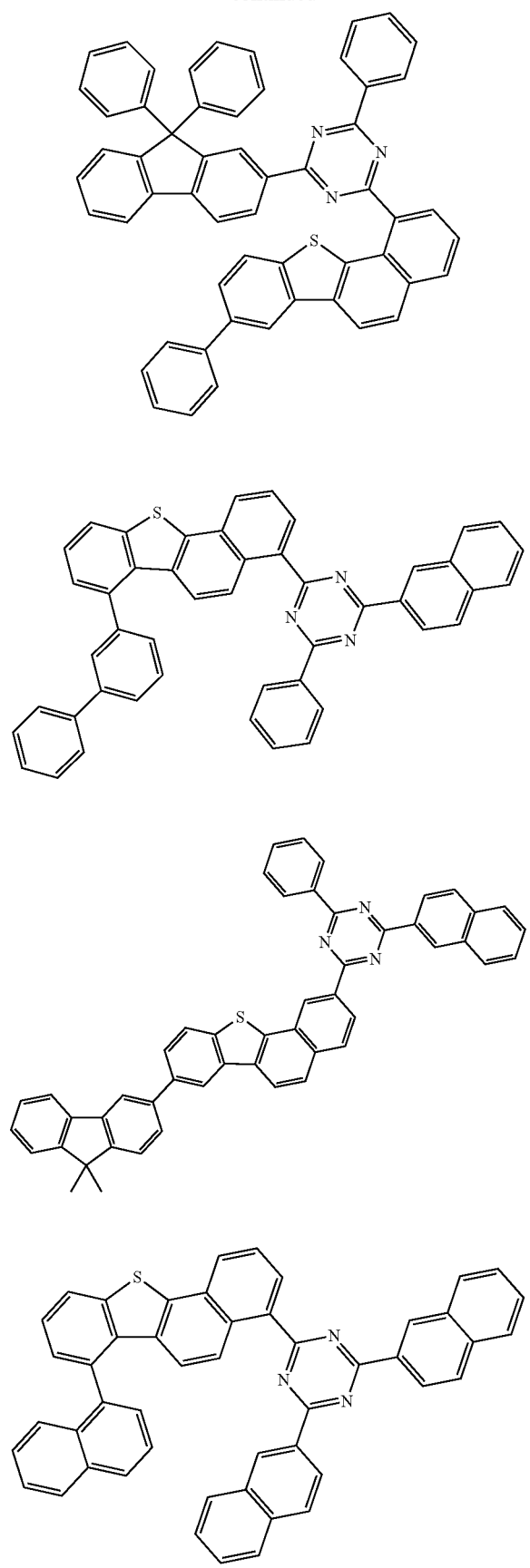
366
-continued
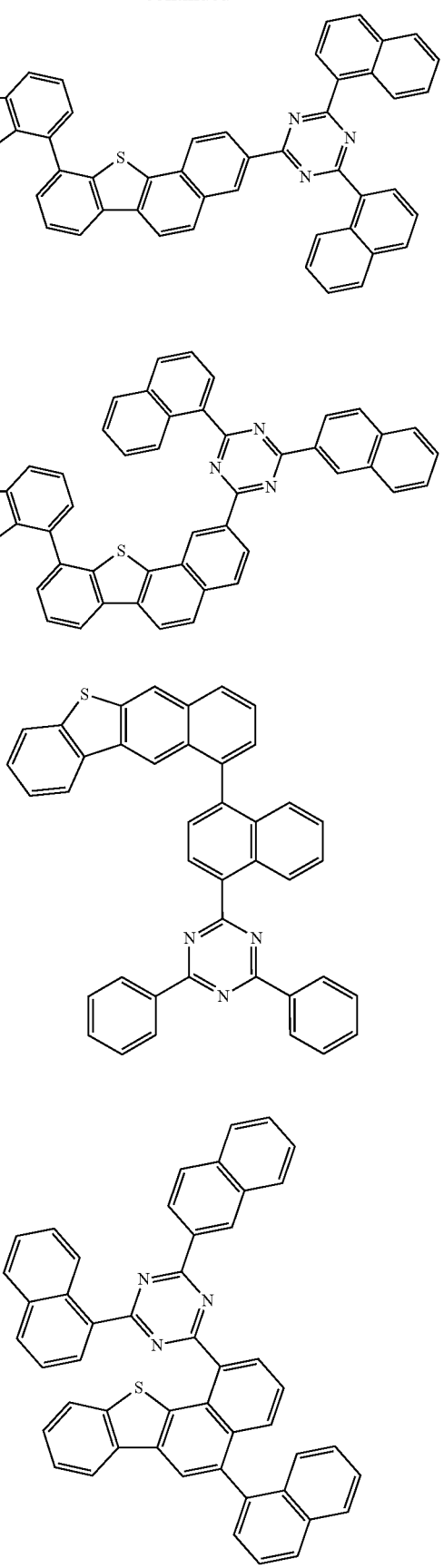

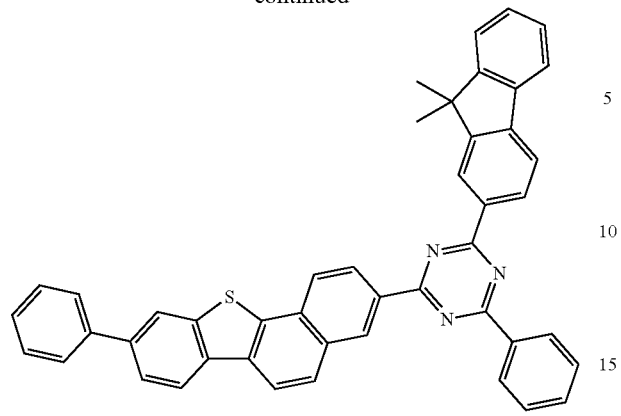
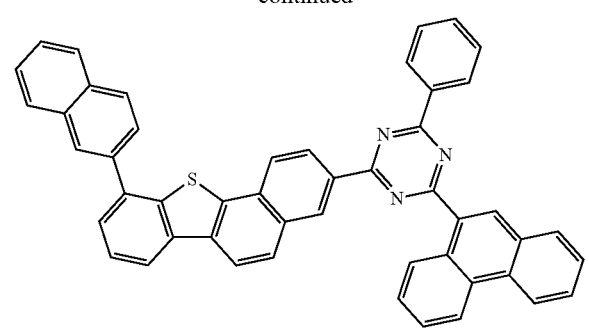
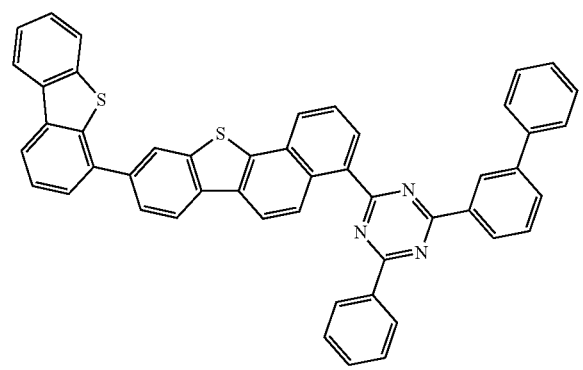
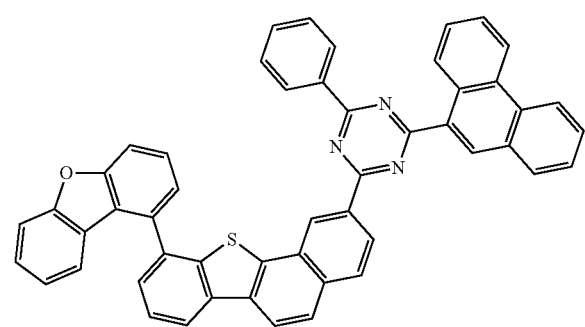
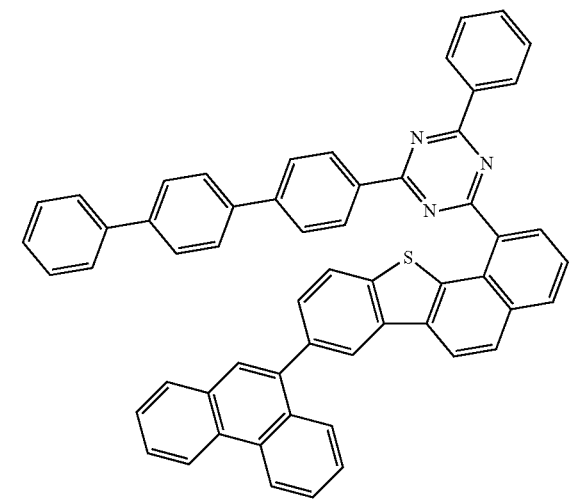
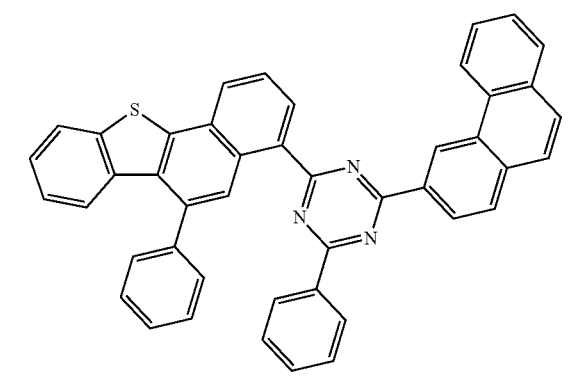
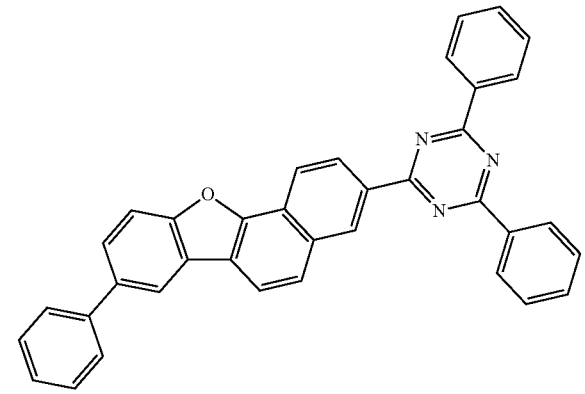

369
-continued
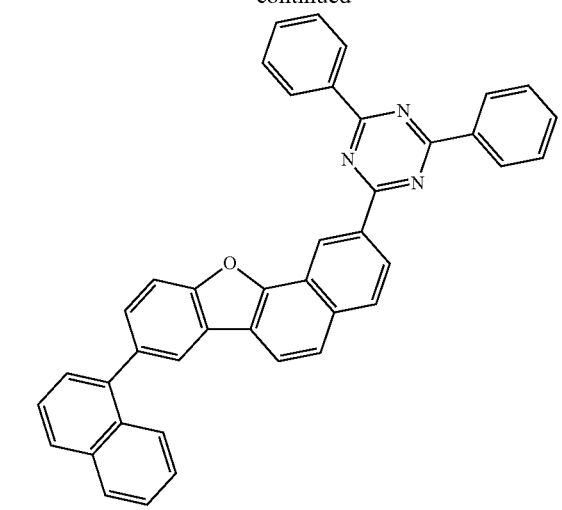
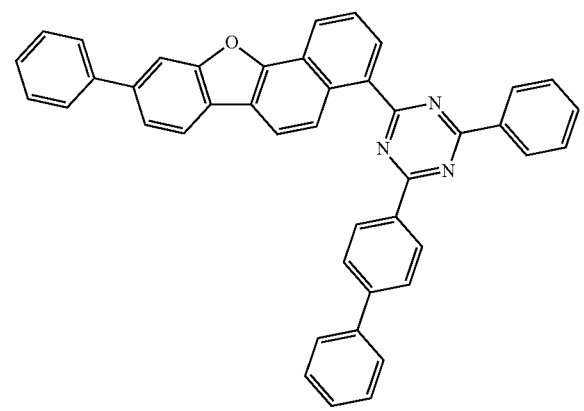
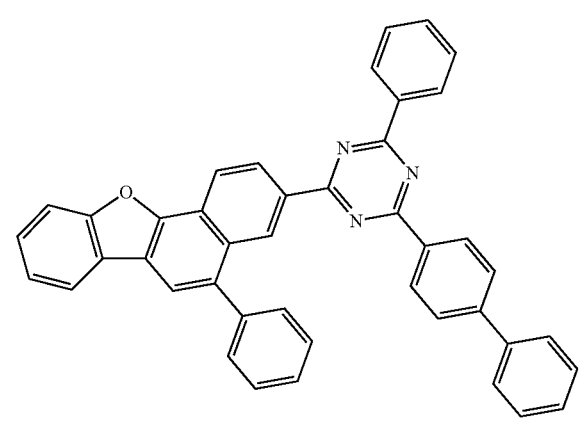
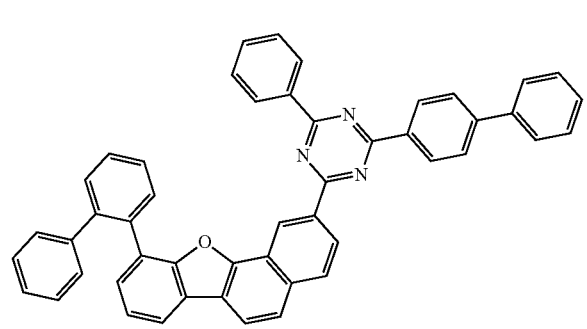
370
-continued
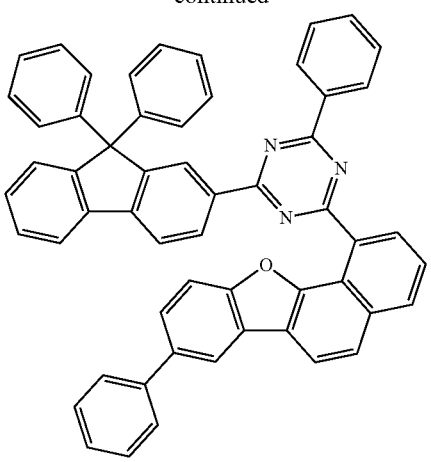

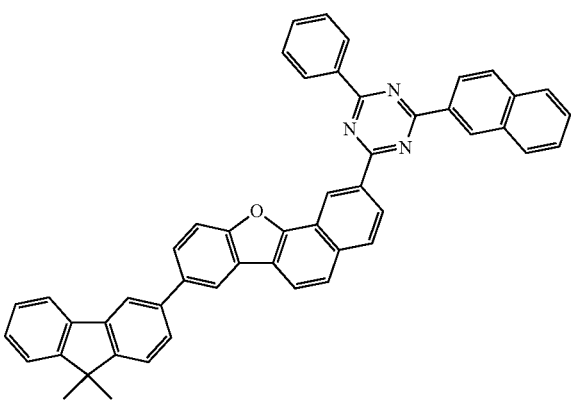
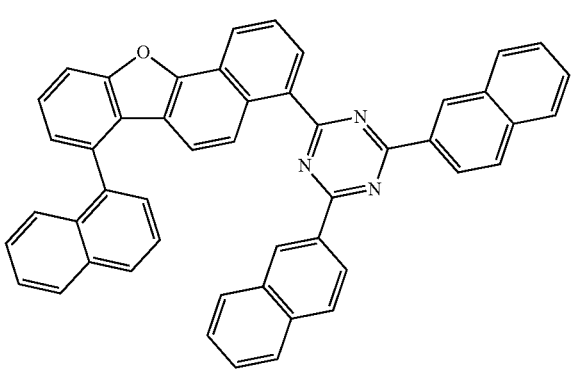

371
-continued
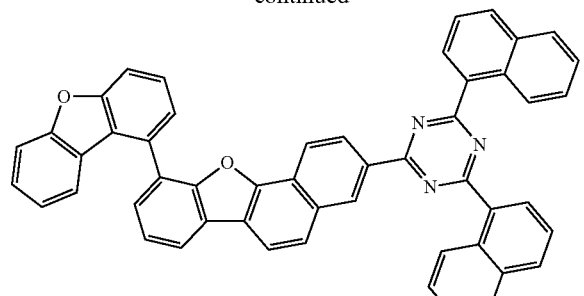
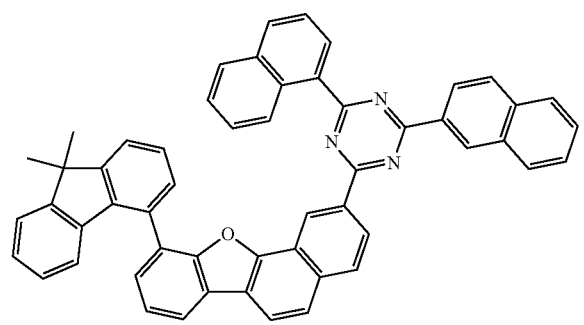
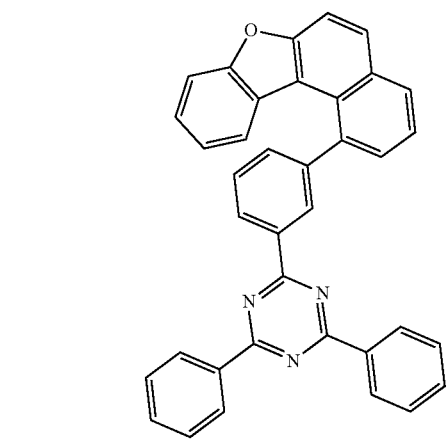
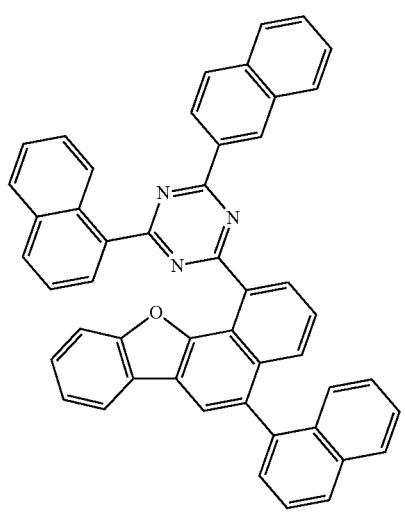
372
-continued
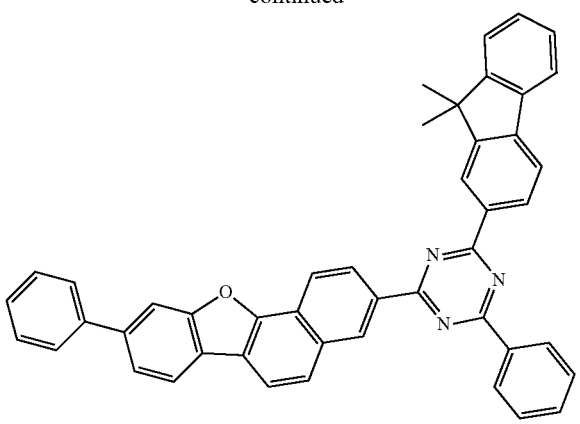
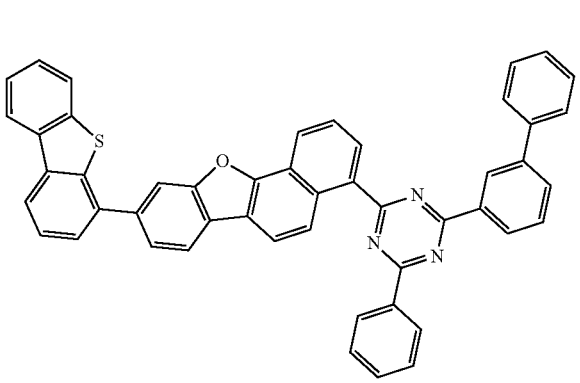
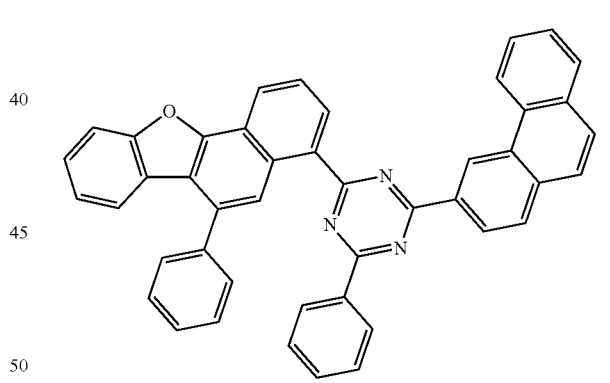
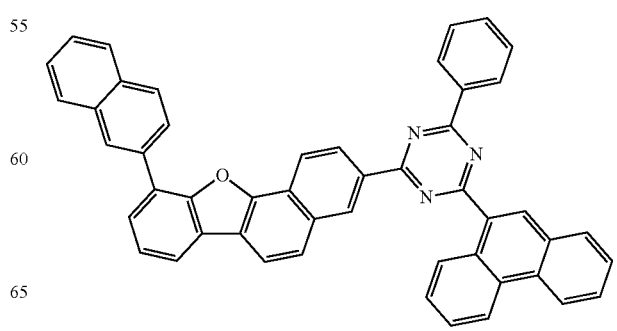

373
-continued
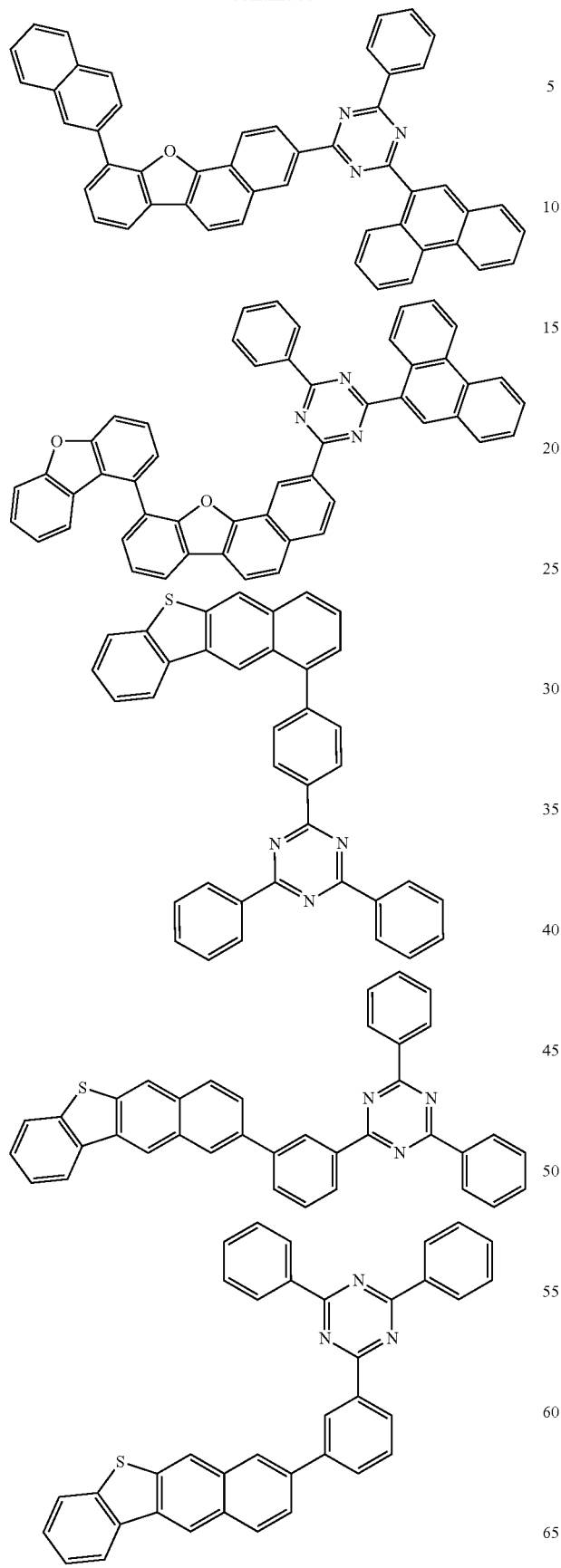
374
-continued
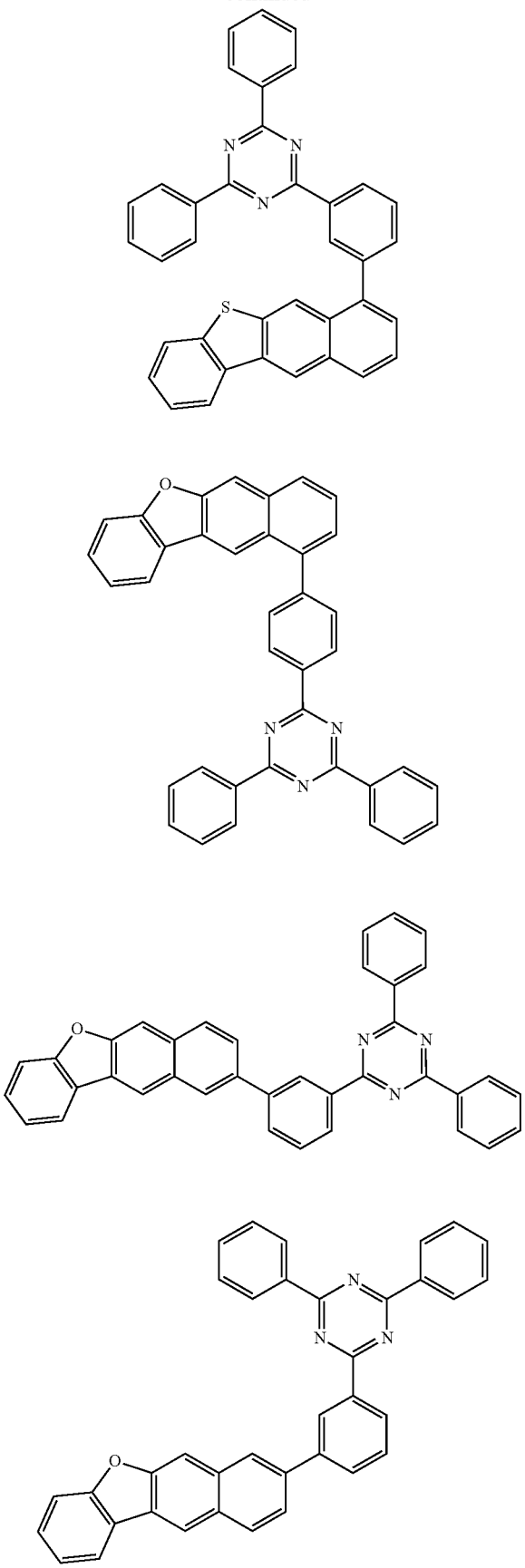

375
-continued
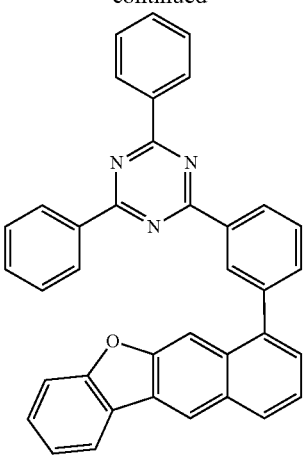
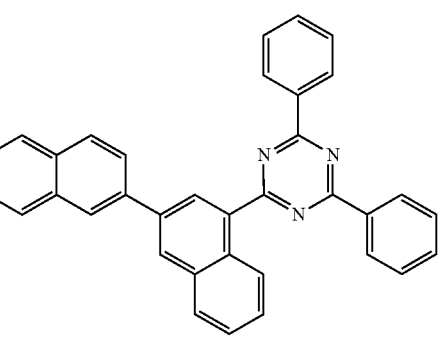
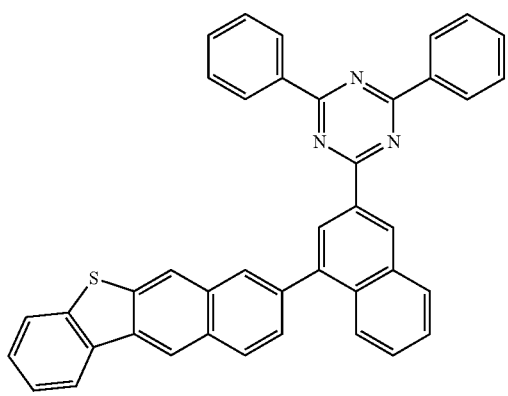
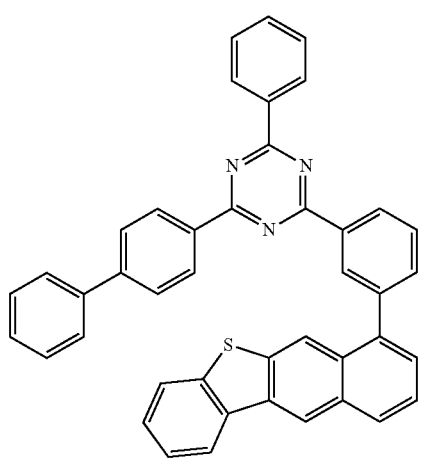
376
-continued
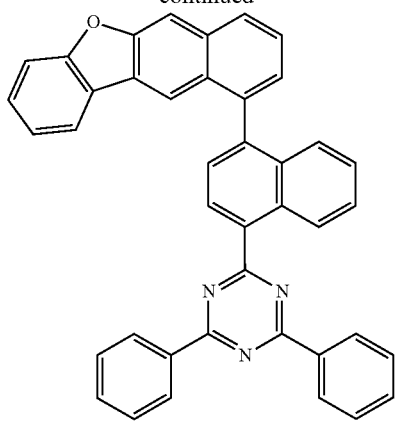
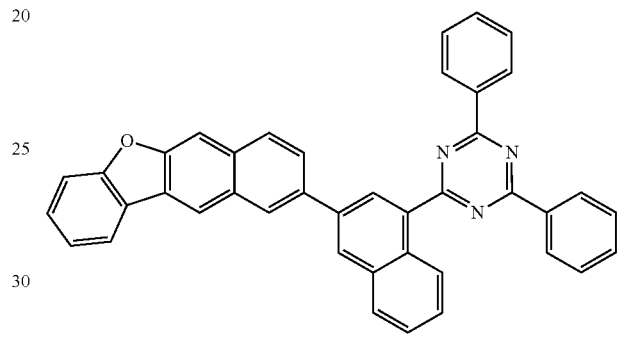
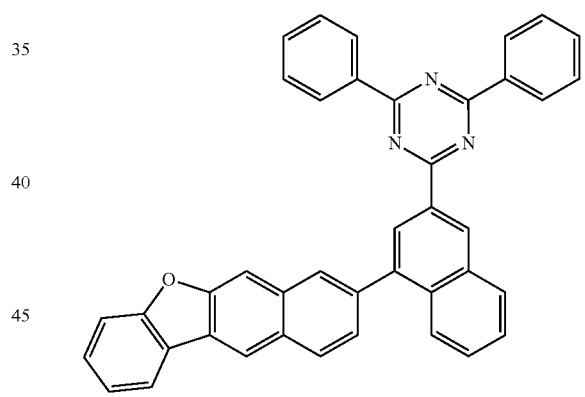
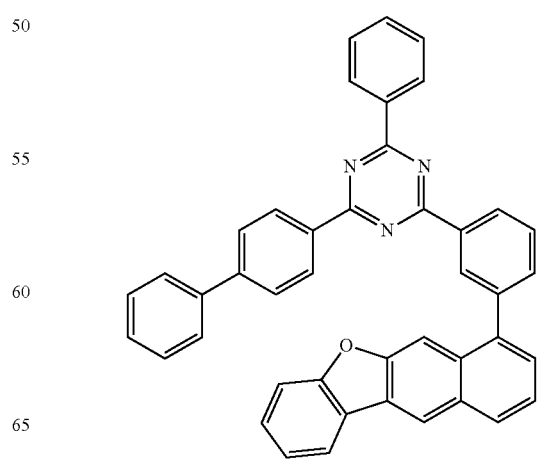

-continued
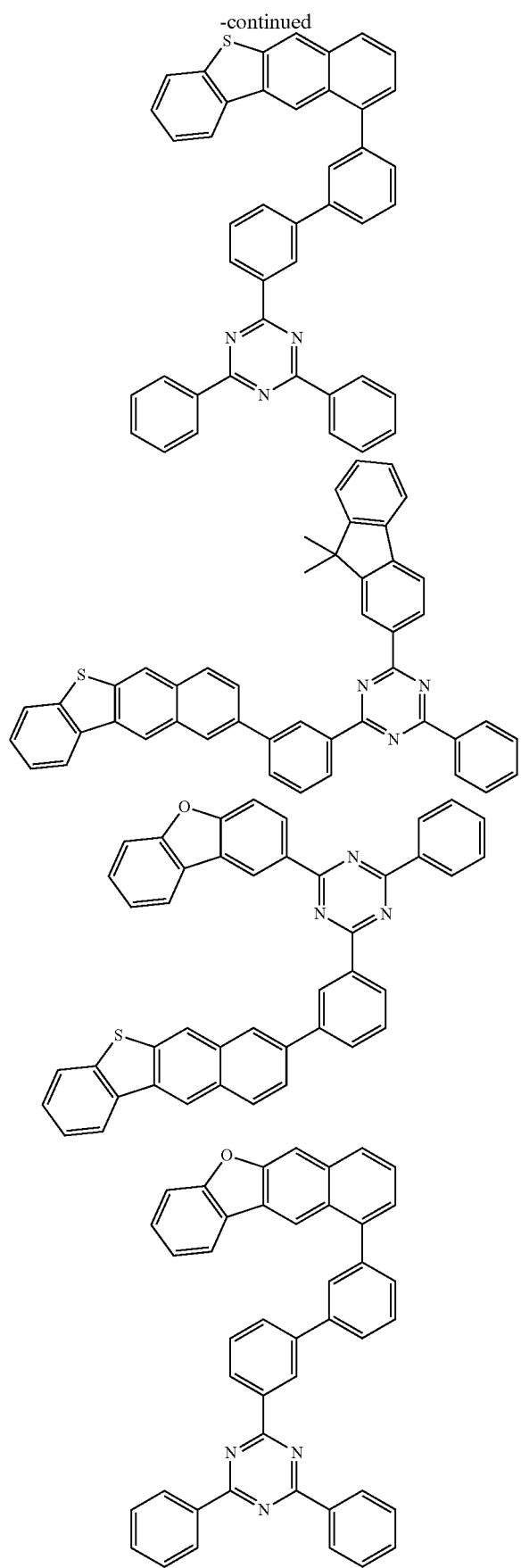
-continued
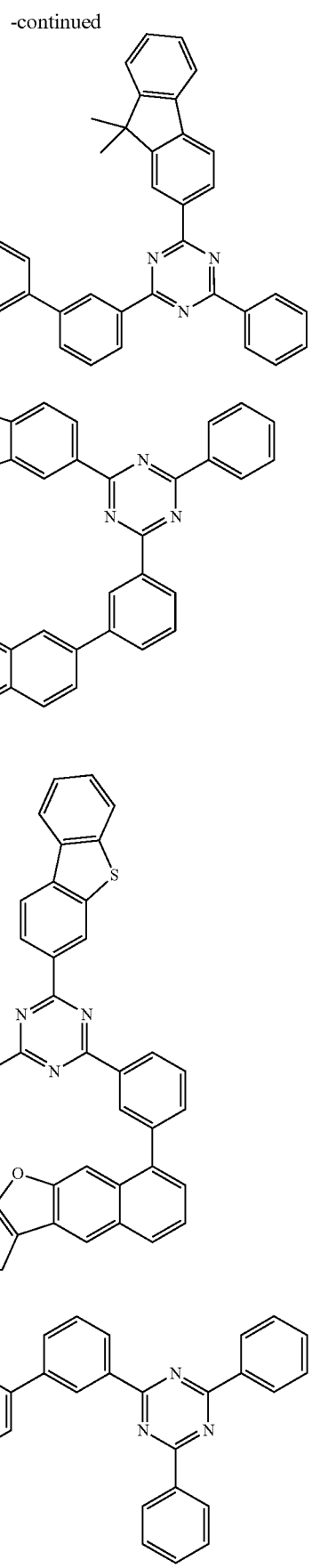

379
-continued
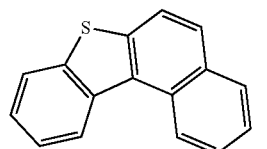
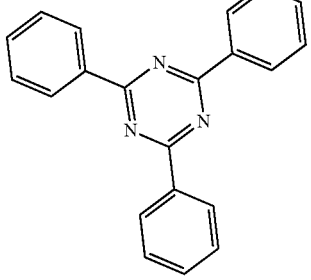
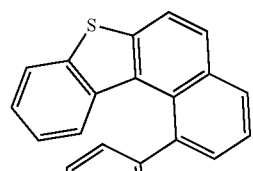
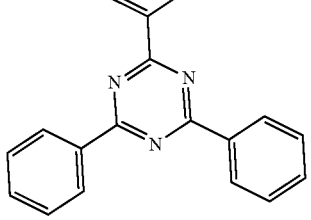
380
-continued
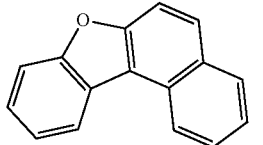
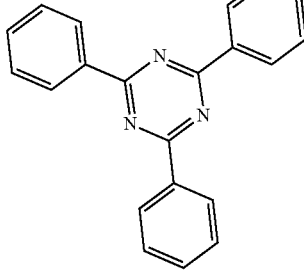
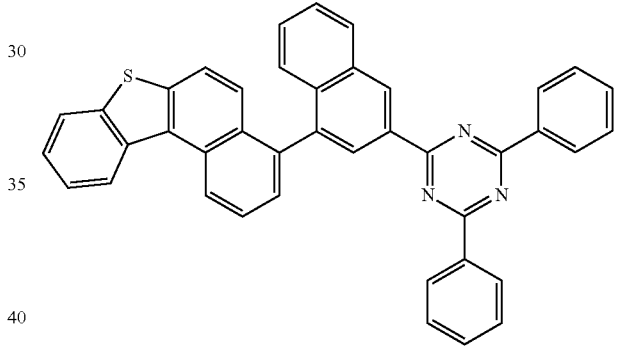
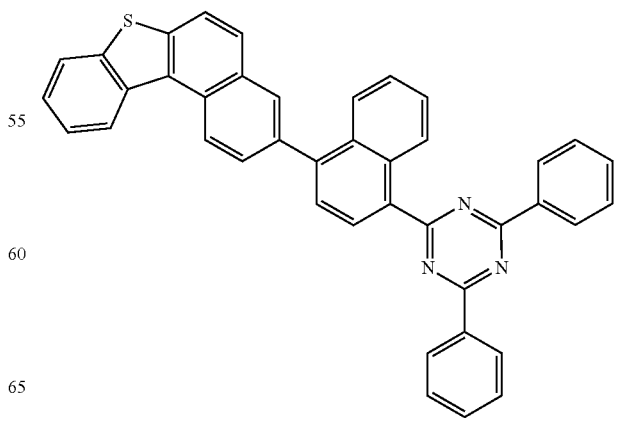

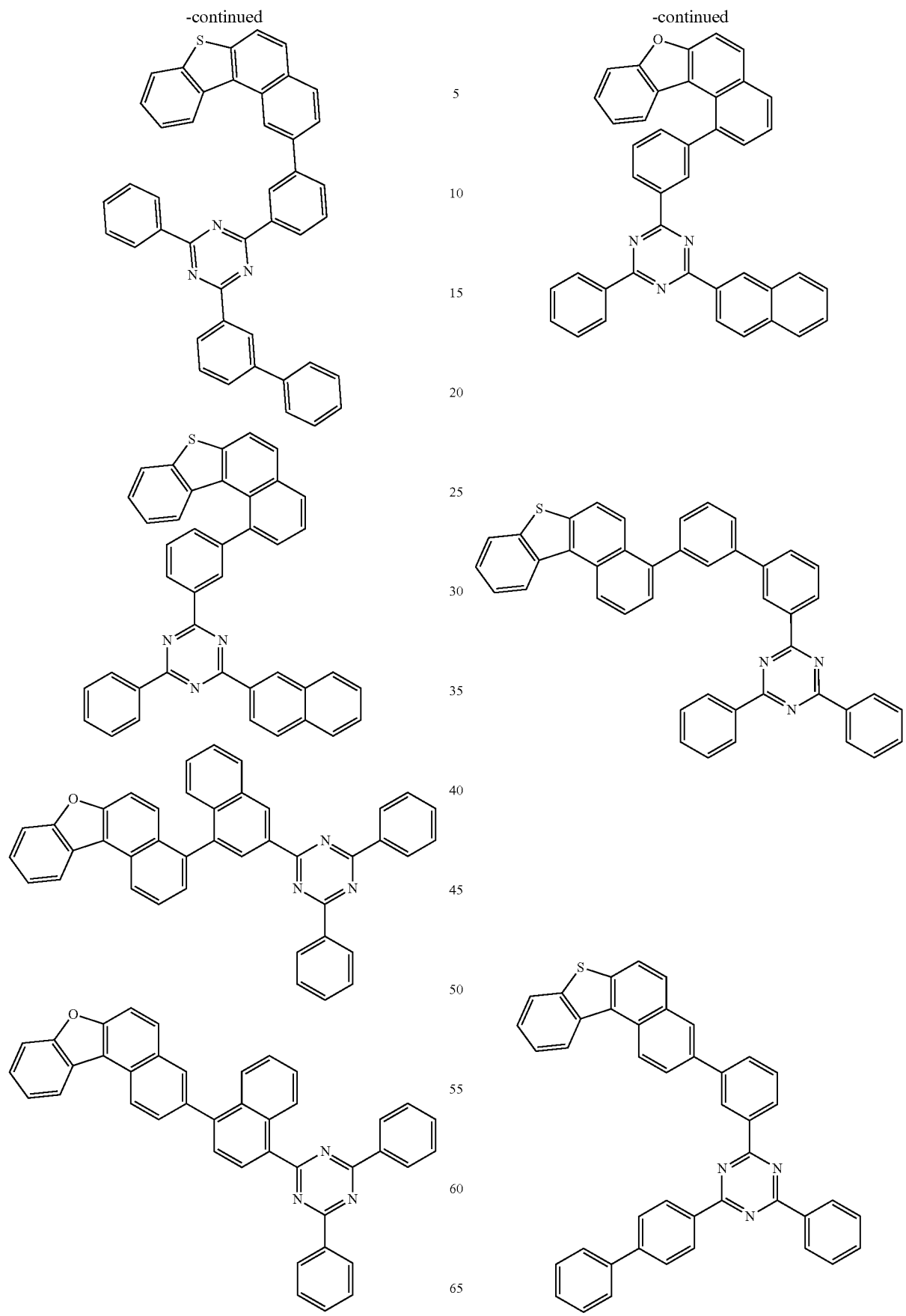

383
-continued
384
-continued
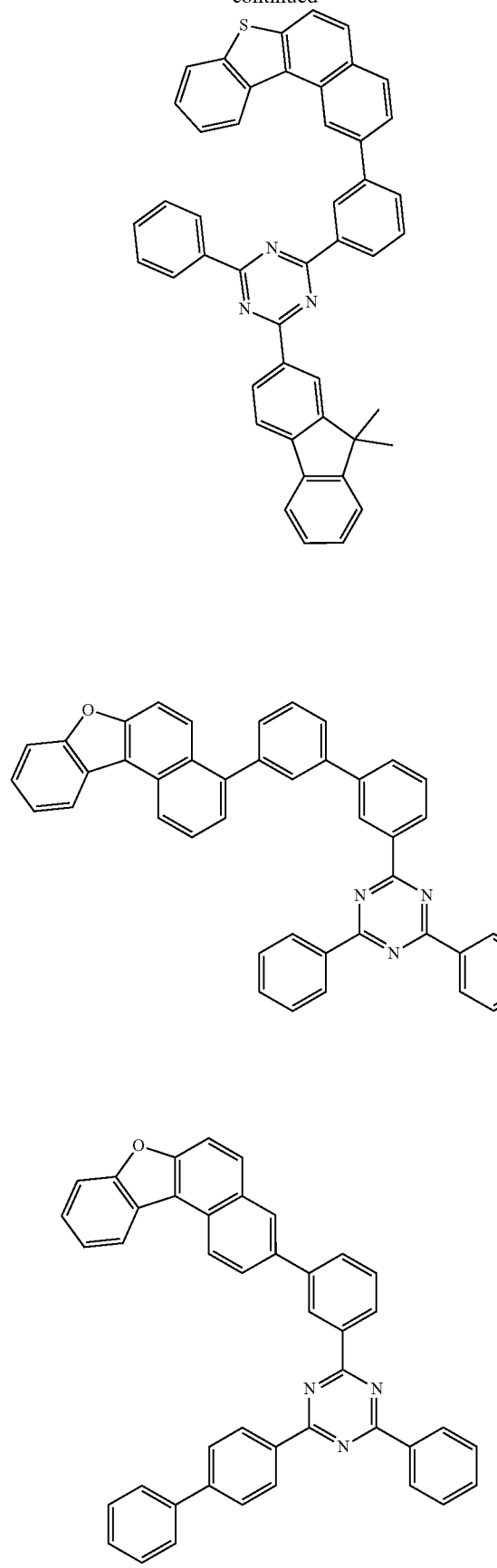
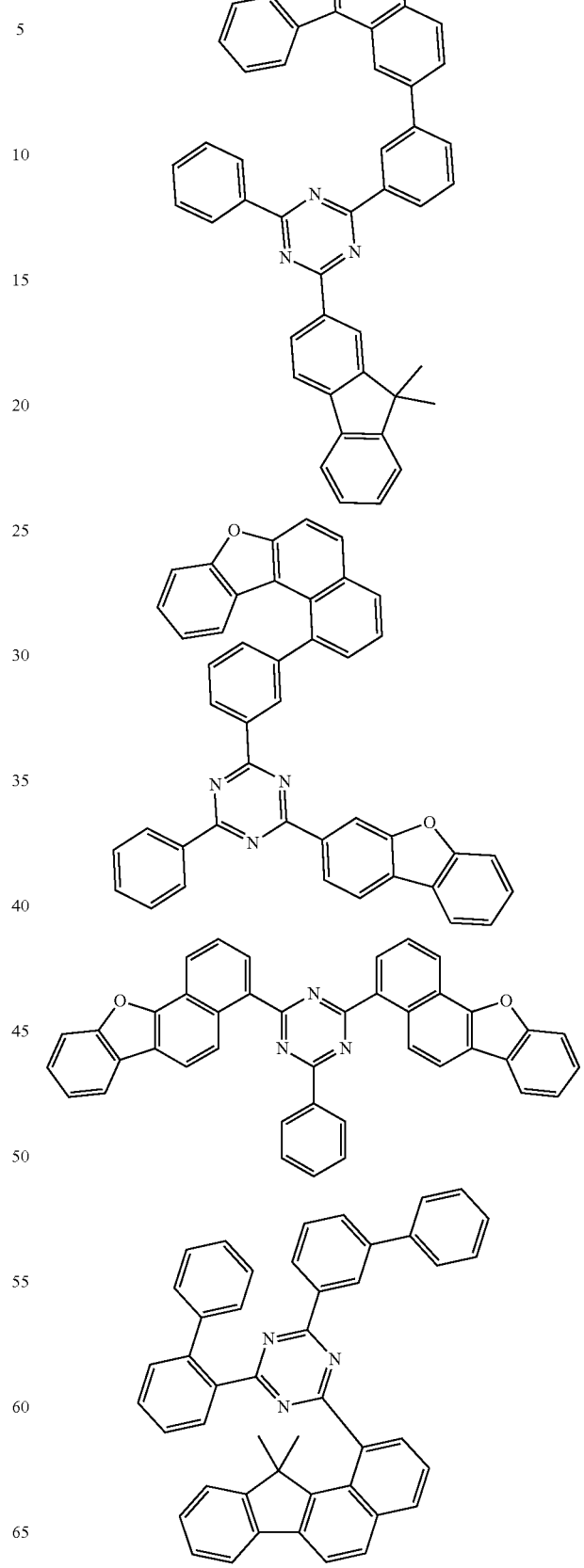

385
-continued
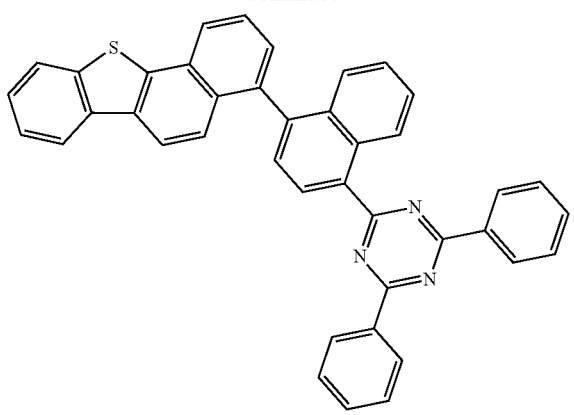
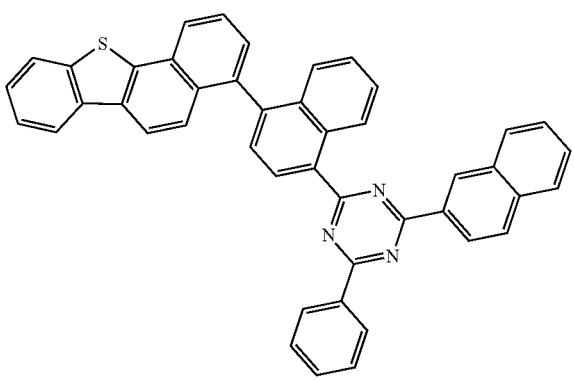
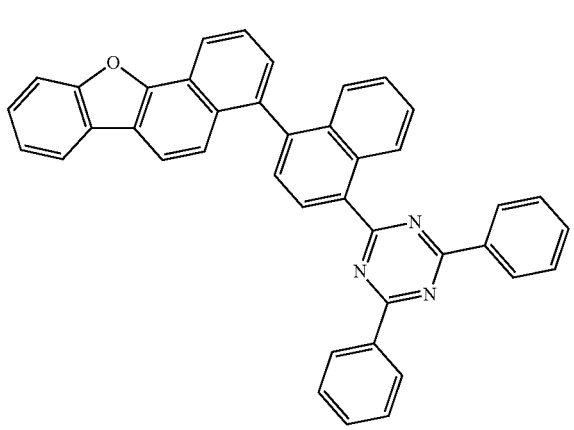
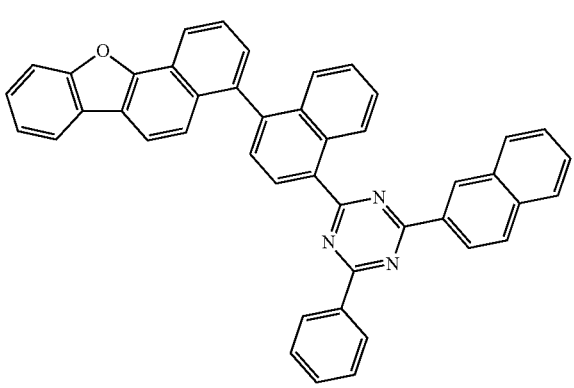
386
-continued
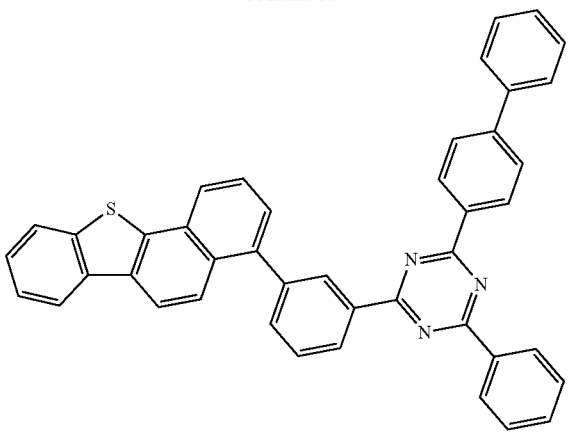
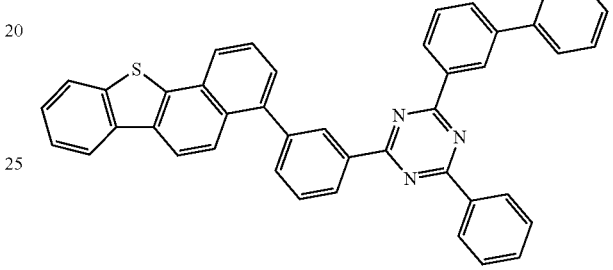
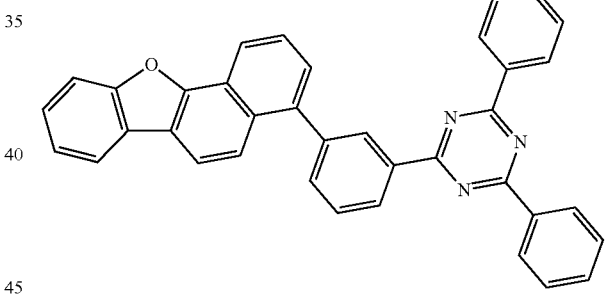
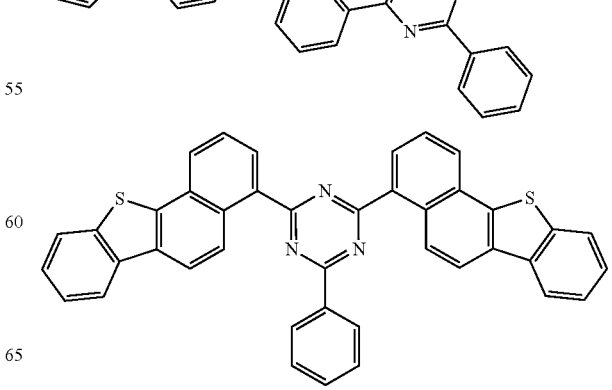

387
-continued
388
-continued
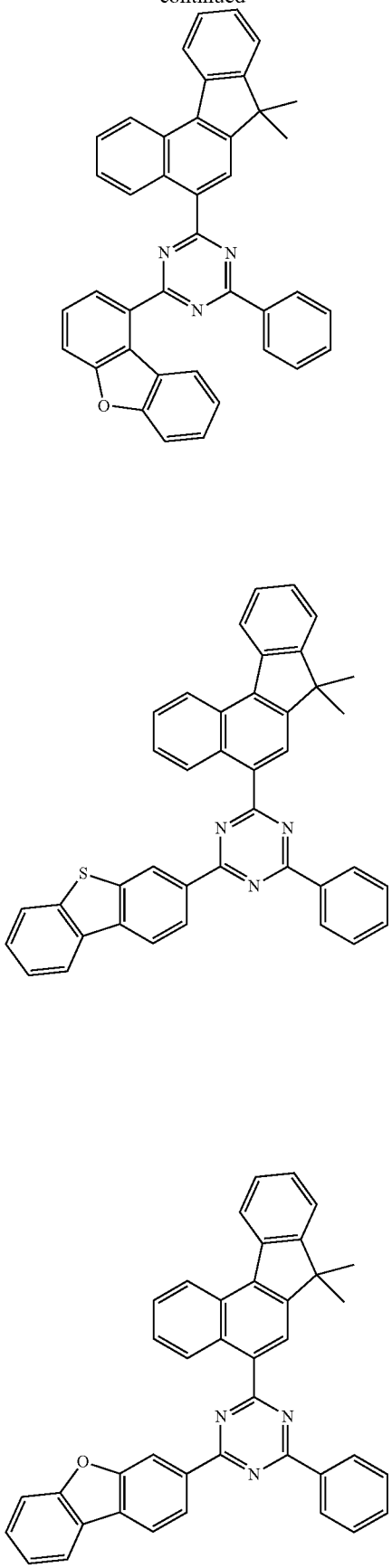
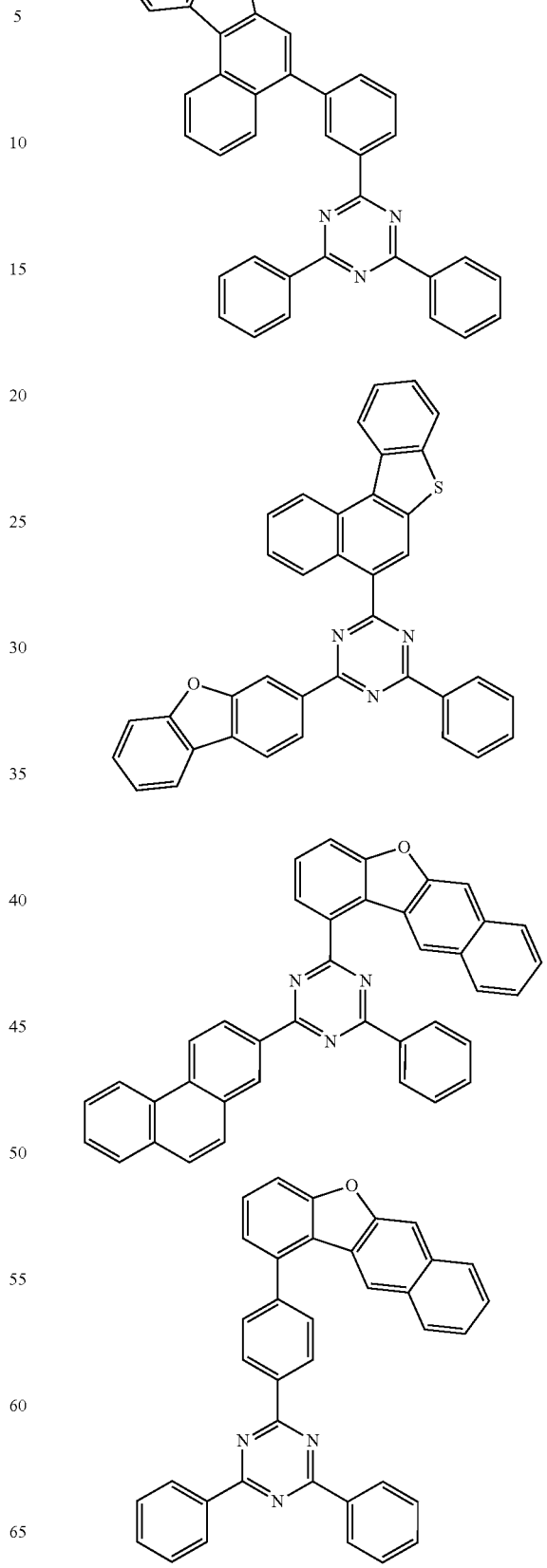

389
-continued
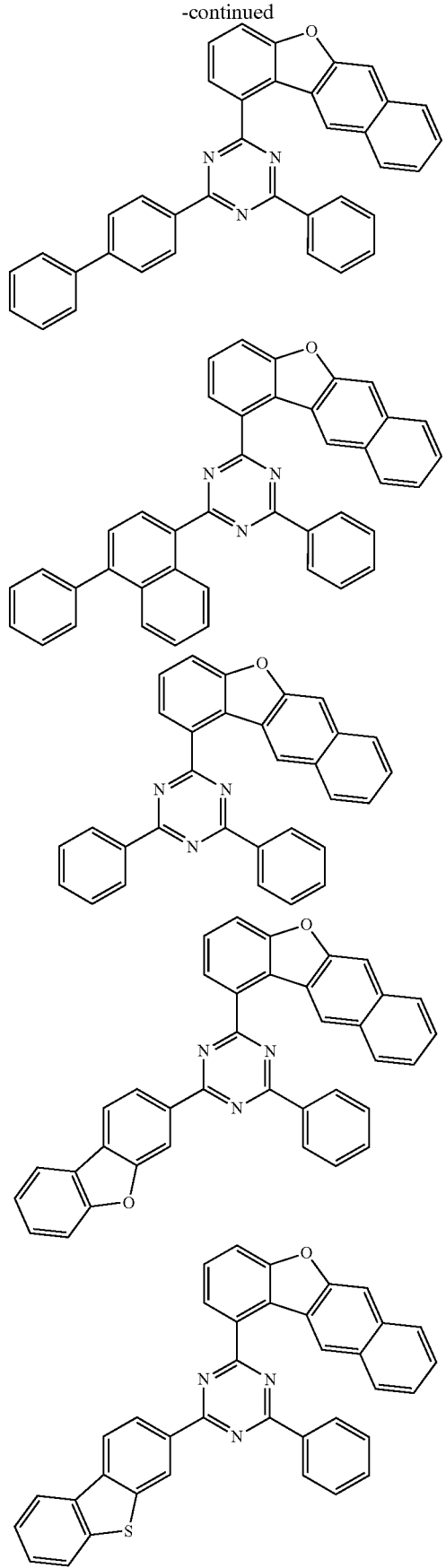
390
-continued
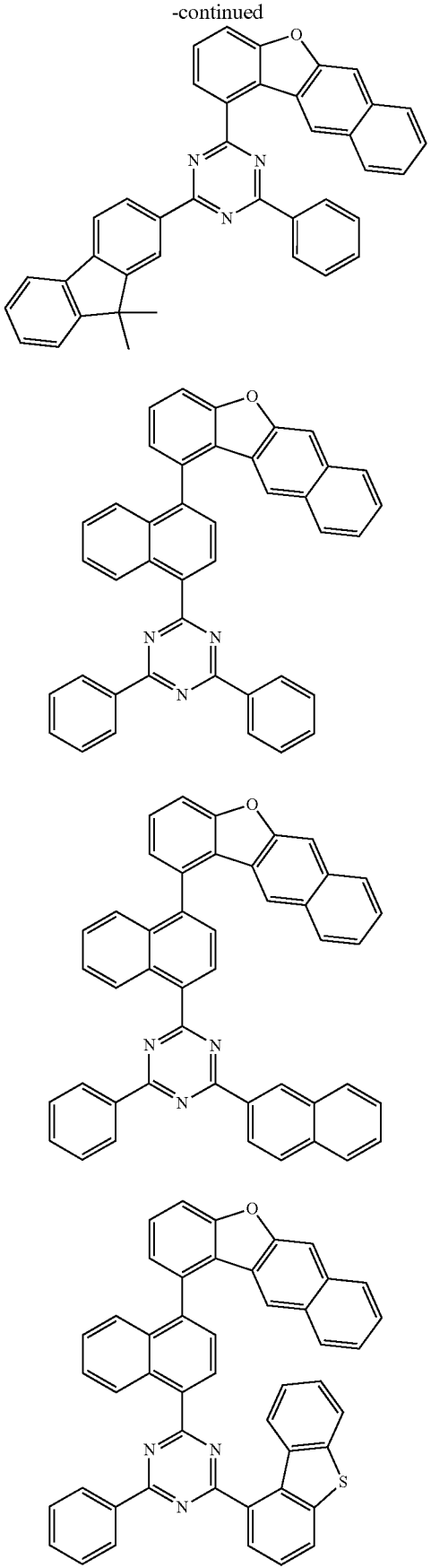

391
-continued
392
-continued
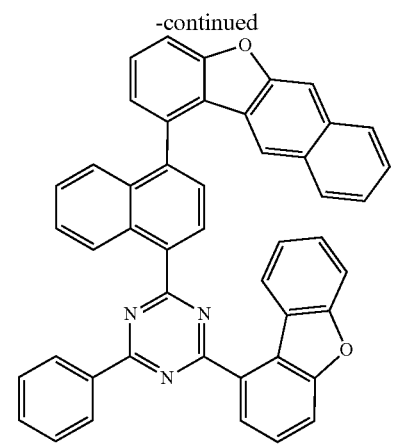
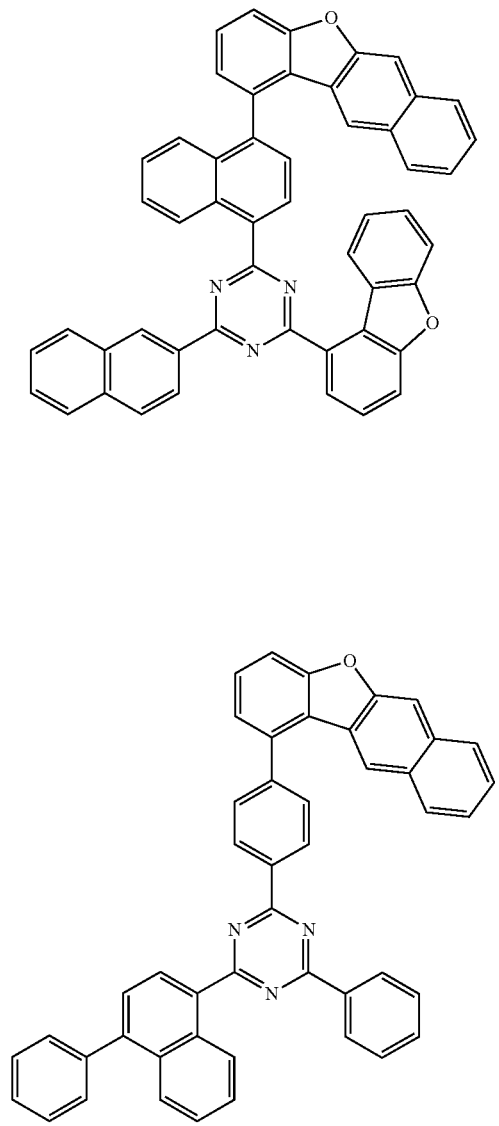
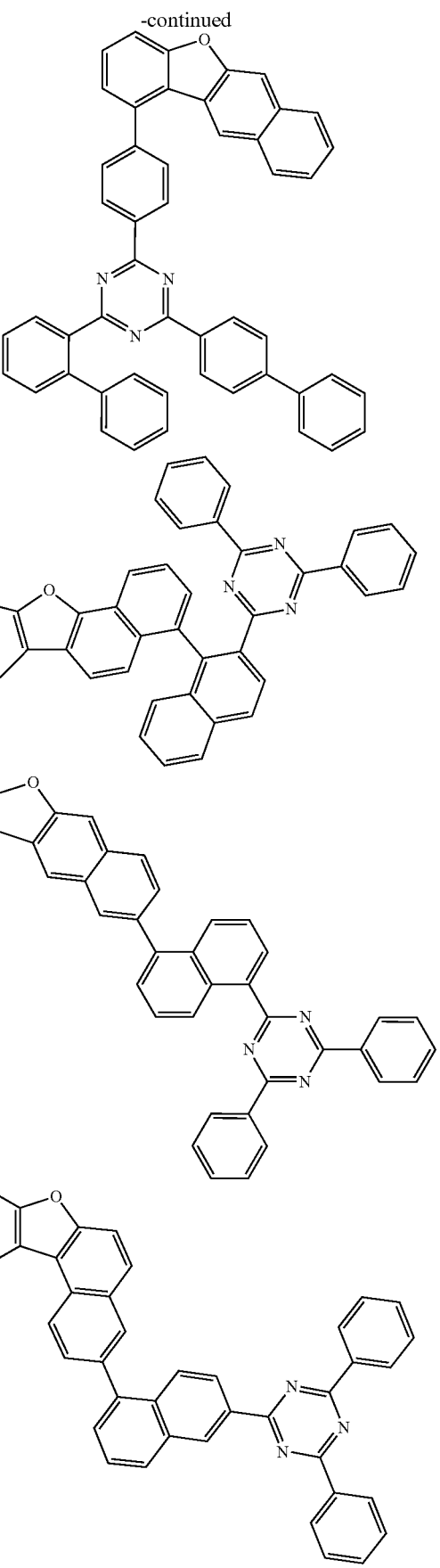

393
-continued
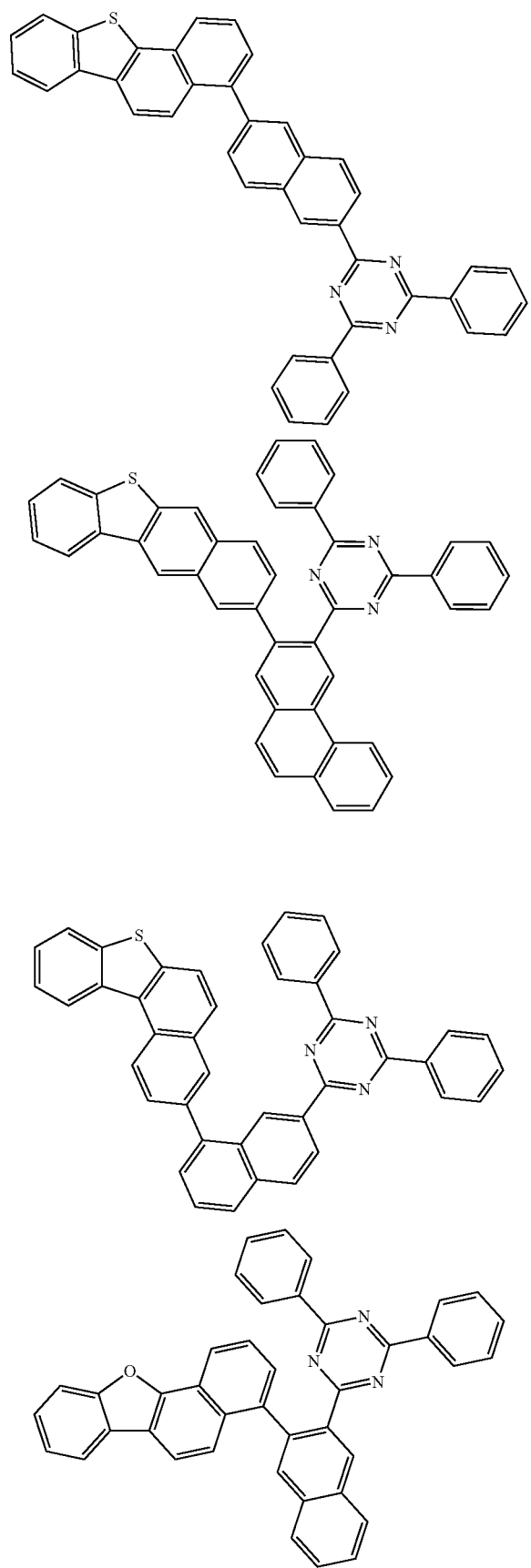
394
-continued
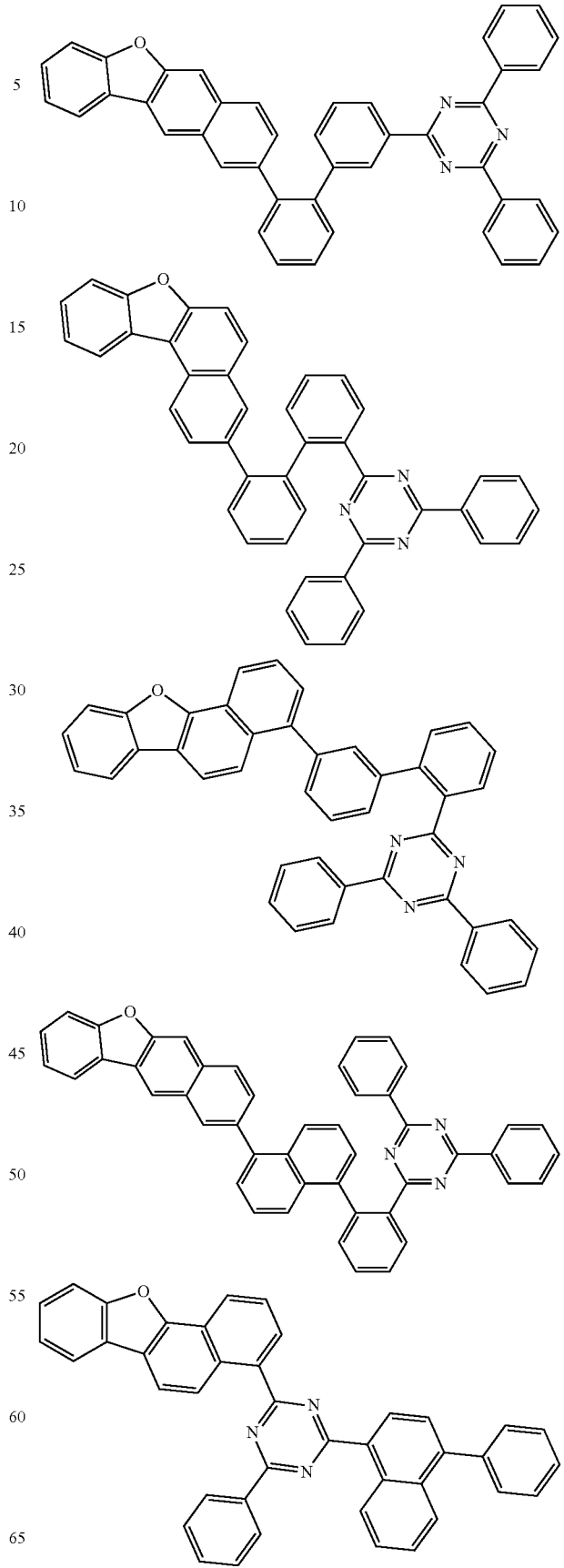

395
-continued
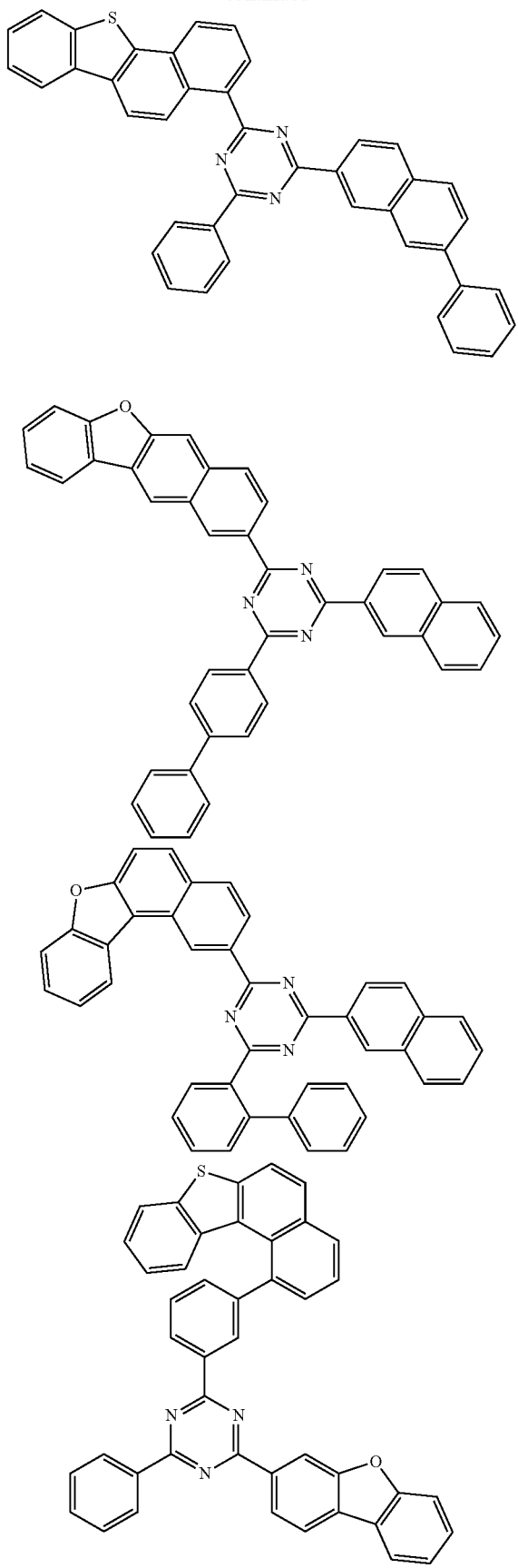
396
-continued
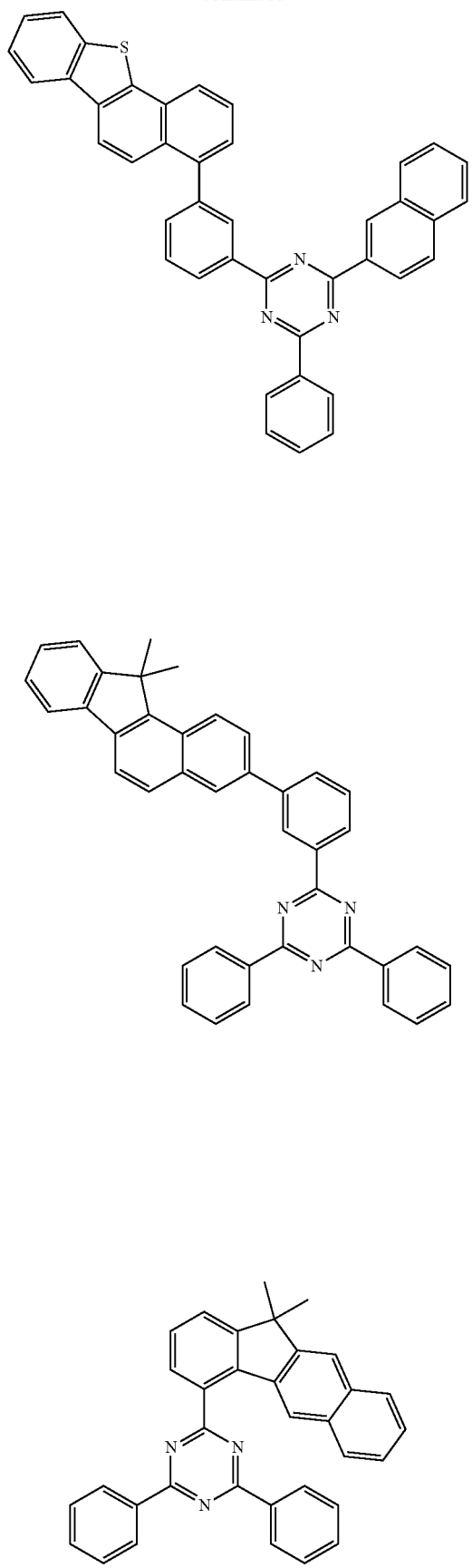

397
-continued
398
-continued
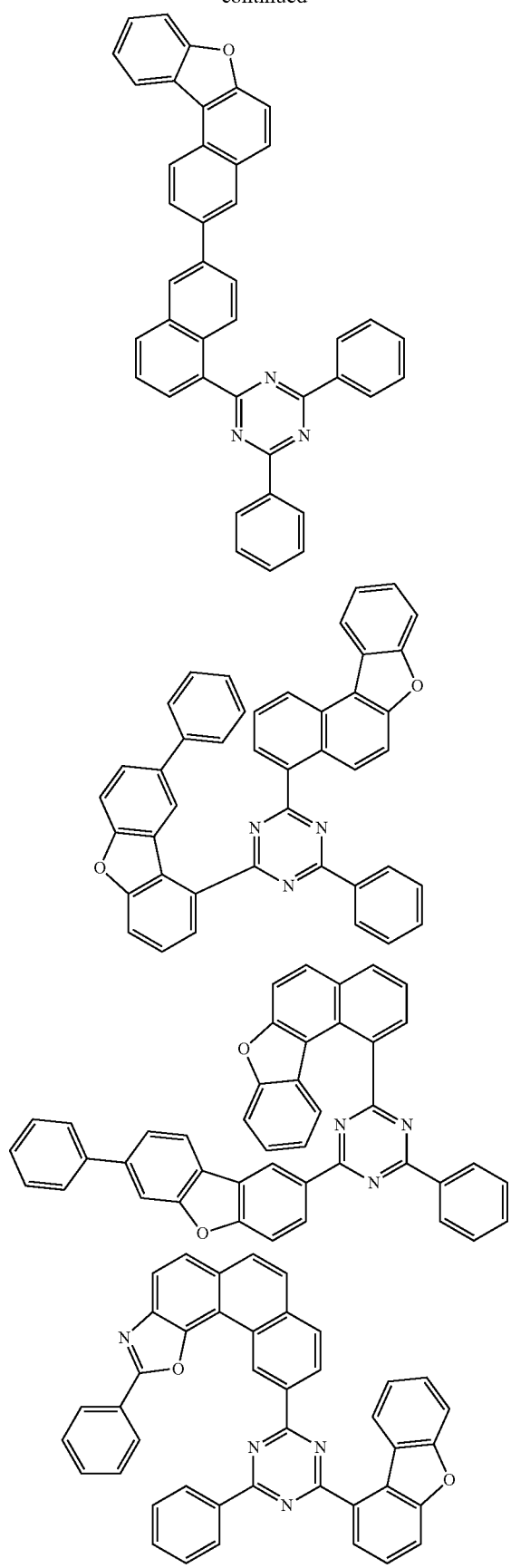
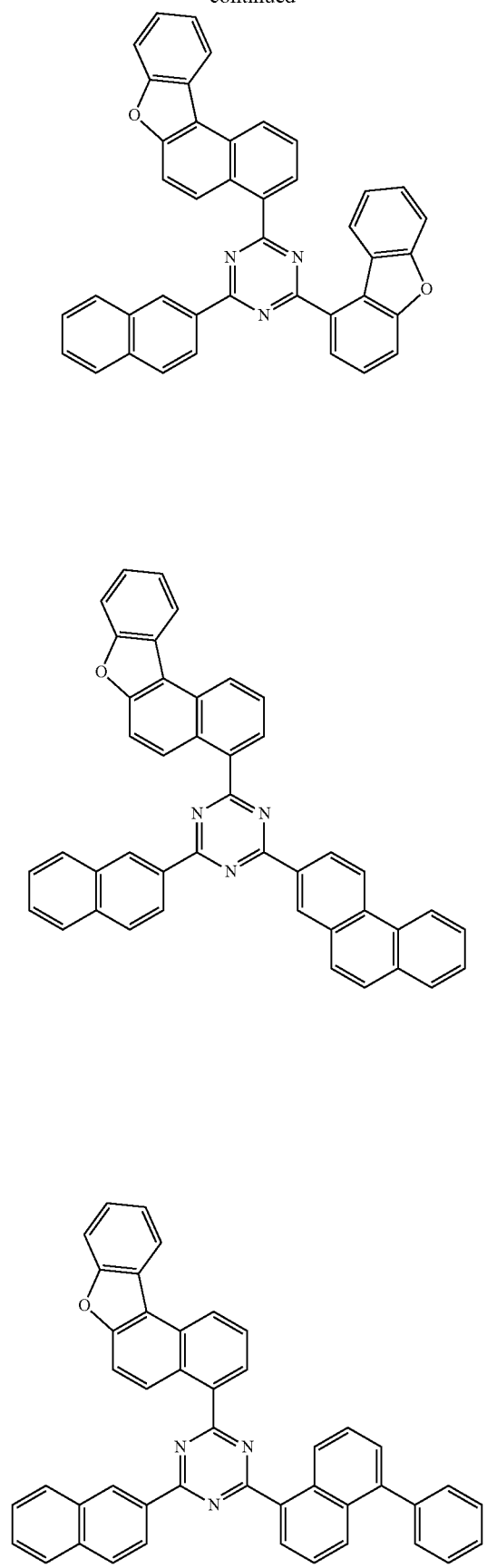

399
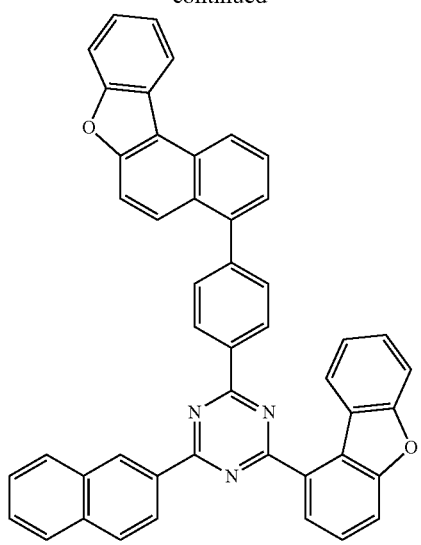
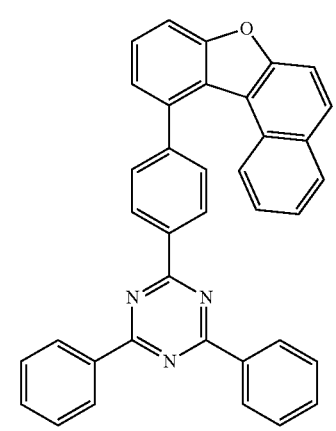
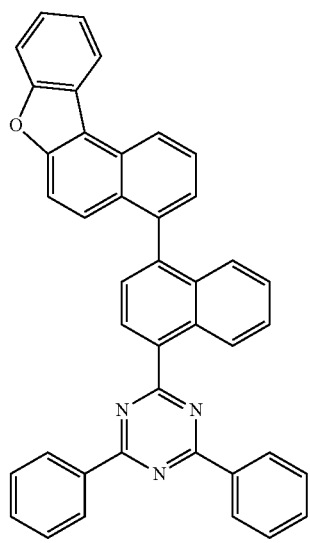
400
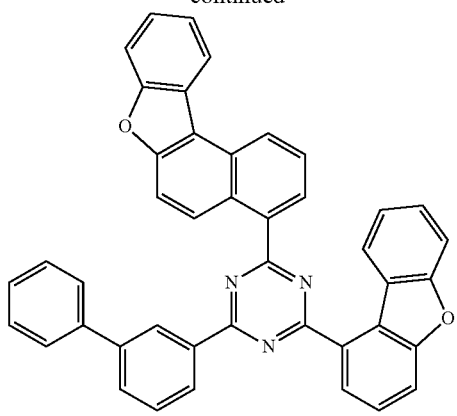
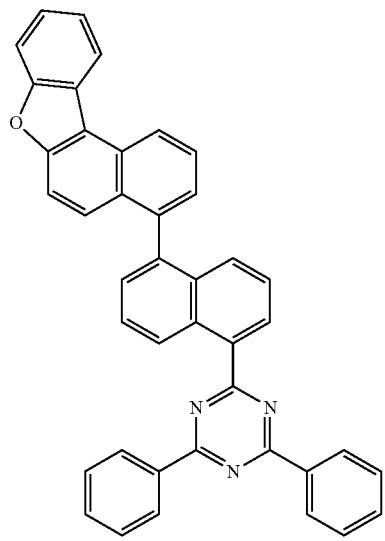
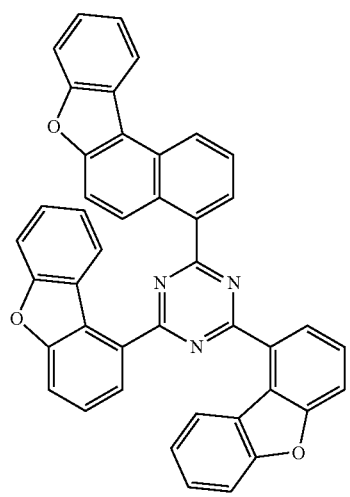

401
-continued
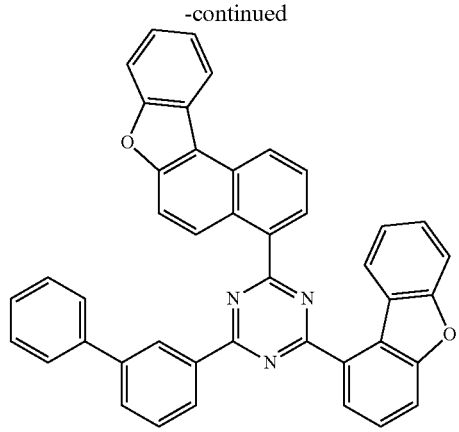
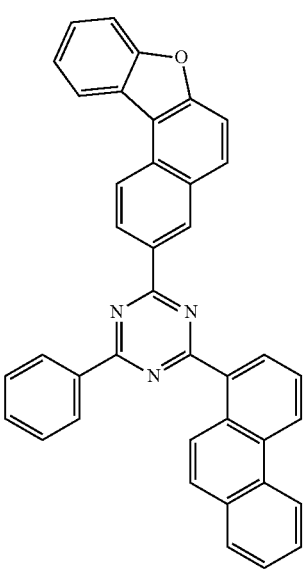
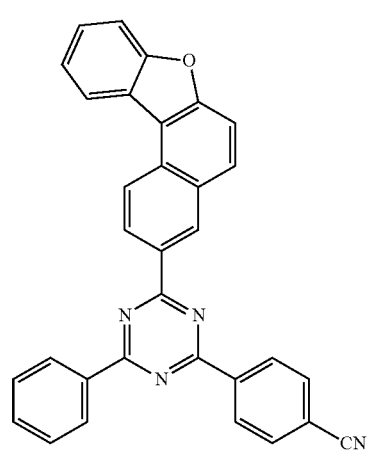
402
-continued
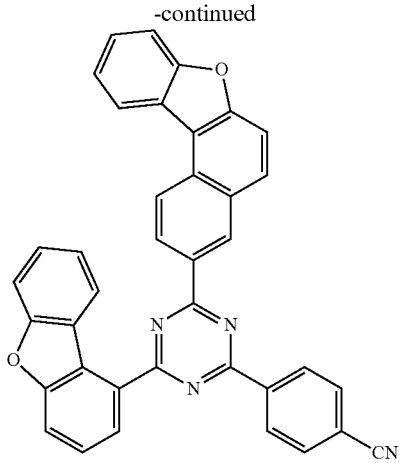
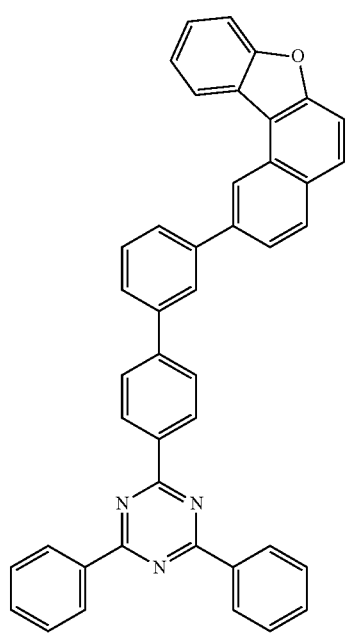
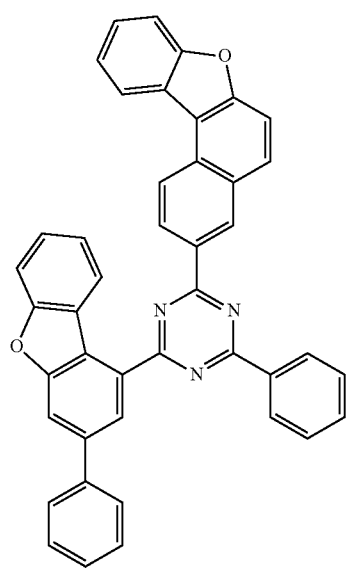

403
-continued
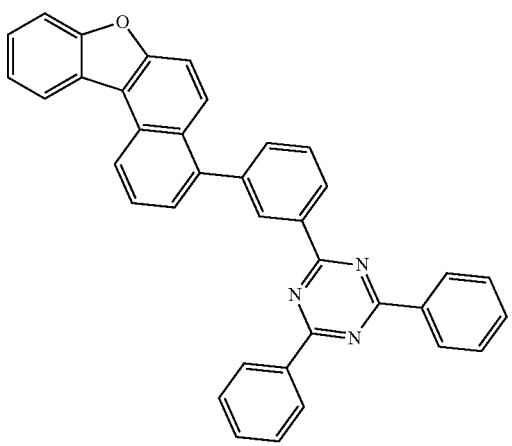
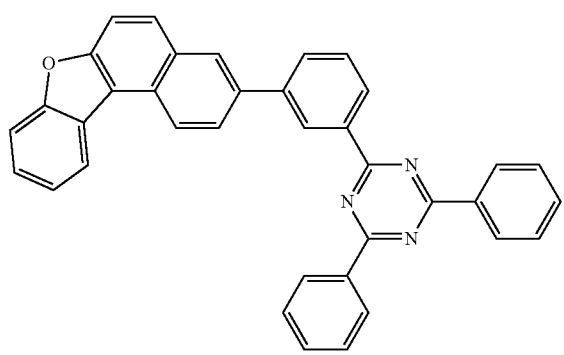
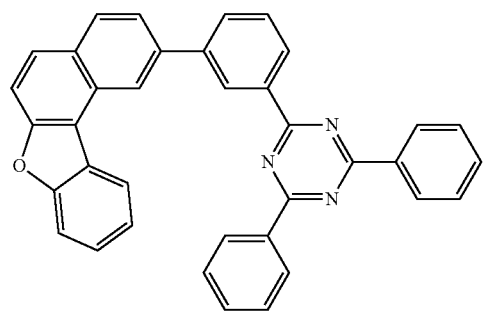
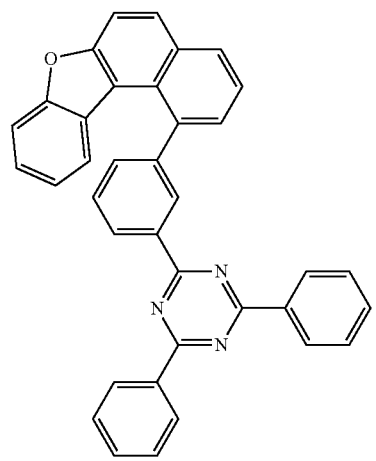
404
-continued
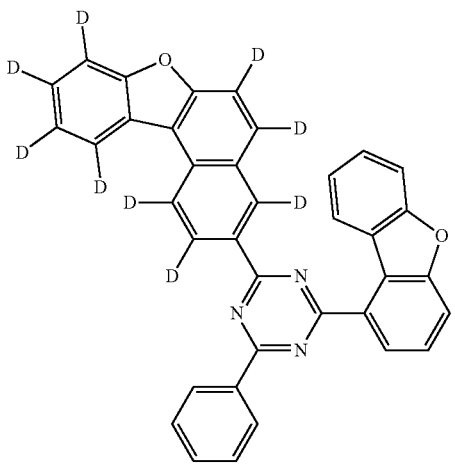 [SMILES: [2H]c1c([2H])c([2H])c2c(oc3c([2H])c([2H])c4c([2H])c(-c5nc(-c6ccccc6)nc(-c6cccc7oc8ccccc8c67)n5)c([2H])c([2H])c4c32)c1[2H]]
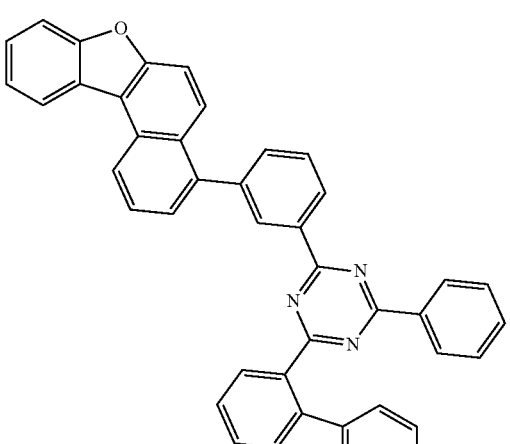
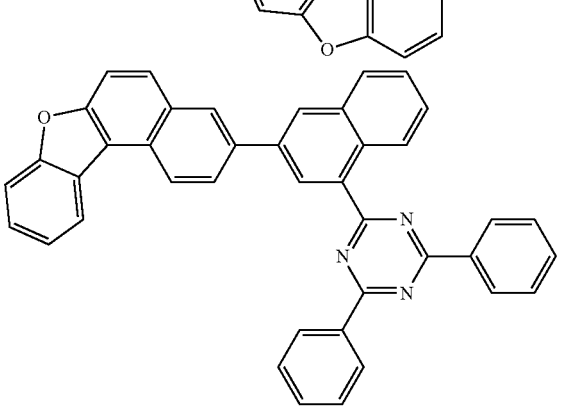
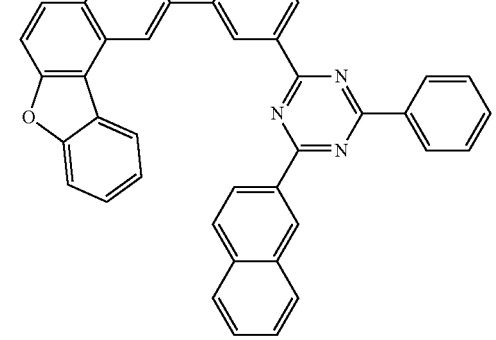

405
-continued
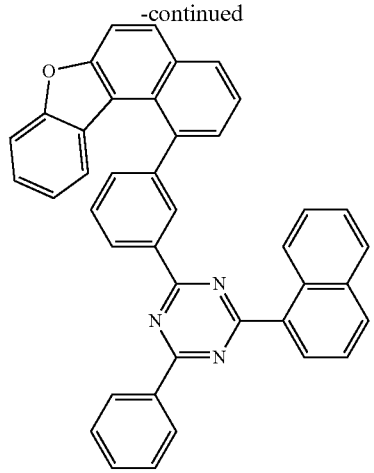
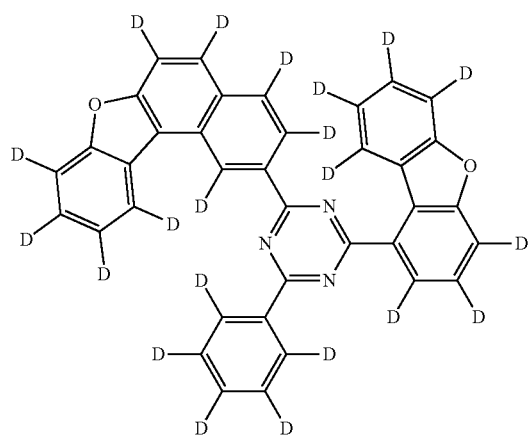 [SMILES: [2H]c1c([2H])c([2H])c(-c2nc(-c3c([2H])c([2H])c4c([2H])c([2H])c5oc6c([2H])c([2H])c([2H])c([2H])c6c5c4c3[2H])nc(-c3c([2H])c([2H])c([2H])c4oc5c([2H])c([2H])c([2H])c([2H])c5c34)n2)c([2H])c1[2H]]
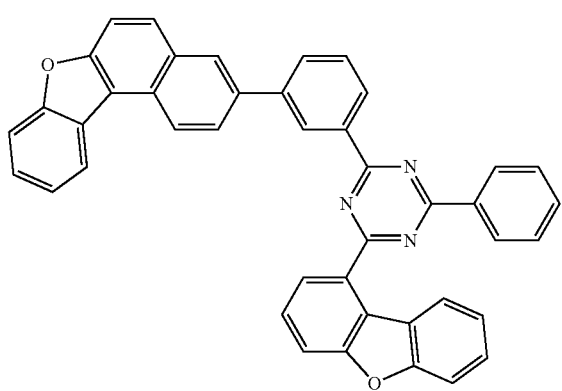
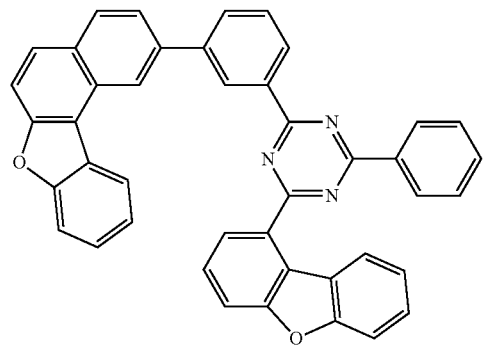
406
-continued
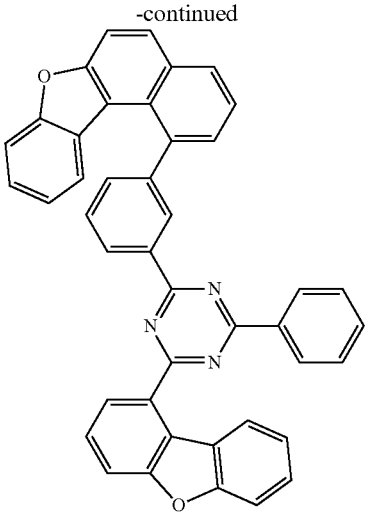
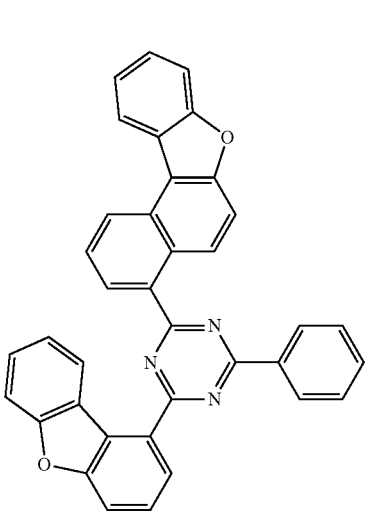
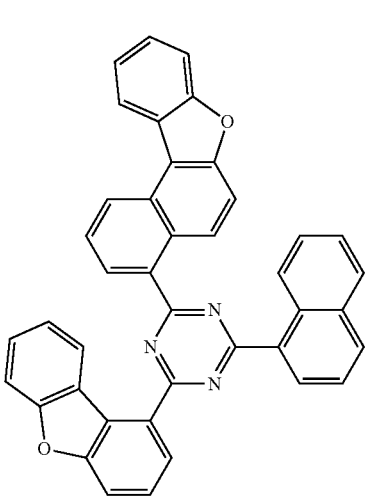

407
-continued
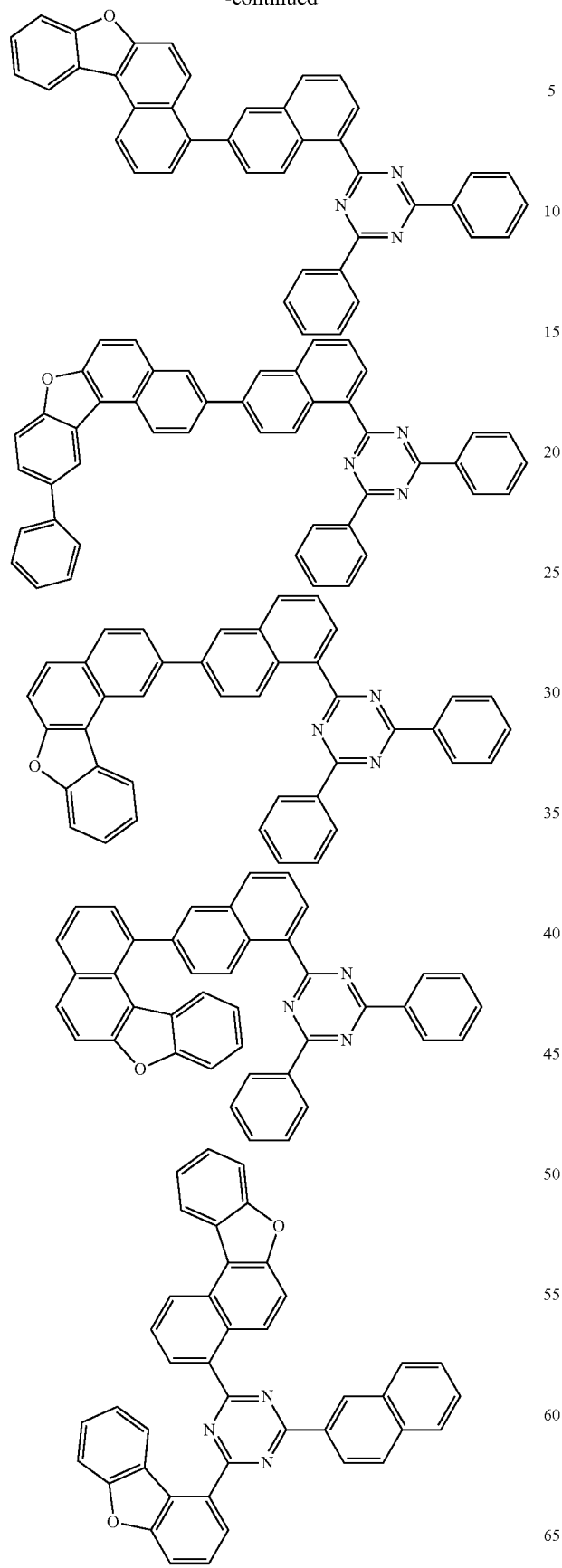
408
-continued
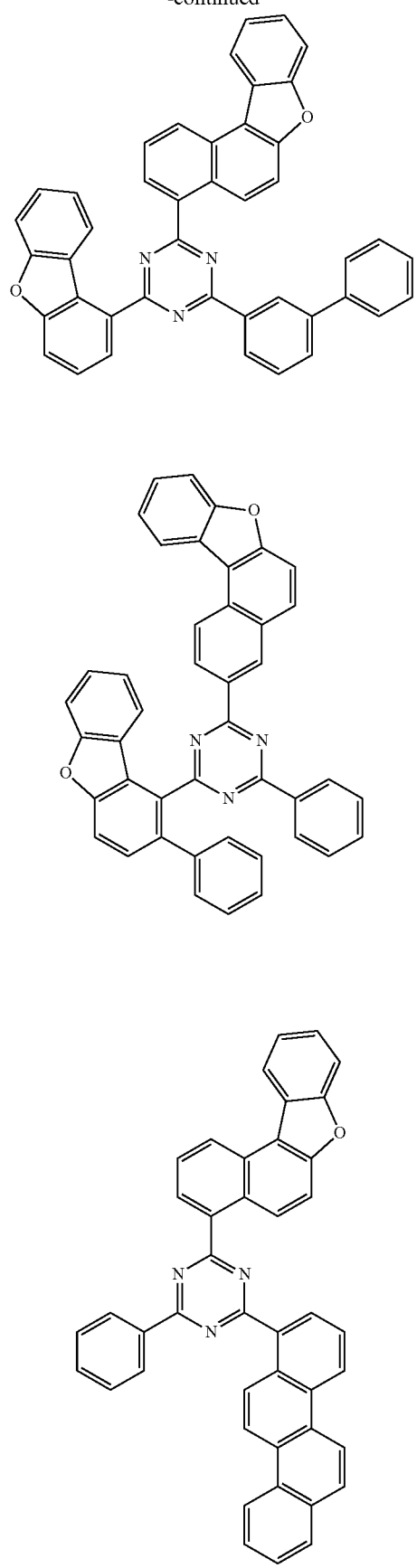

409
-continued
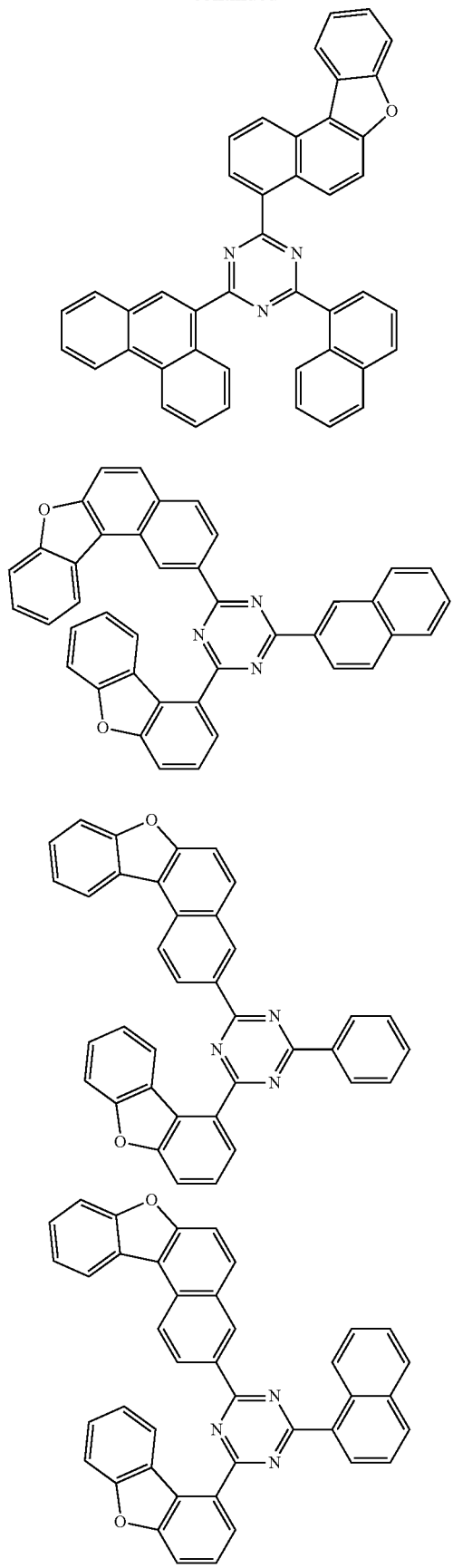
410
-continued
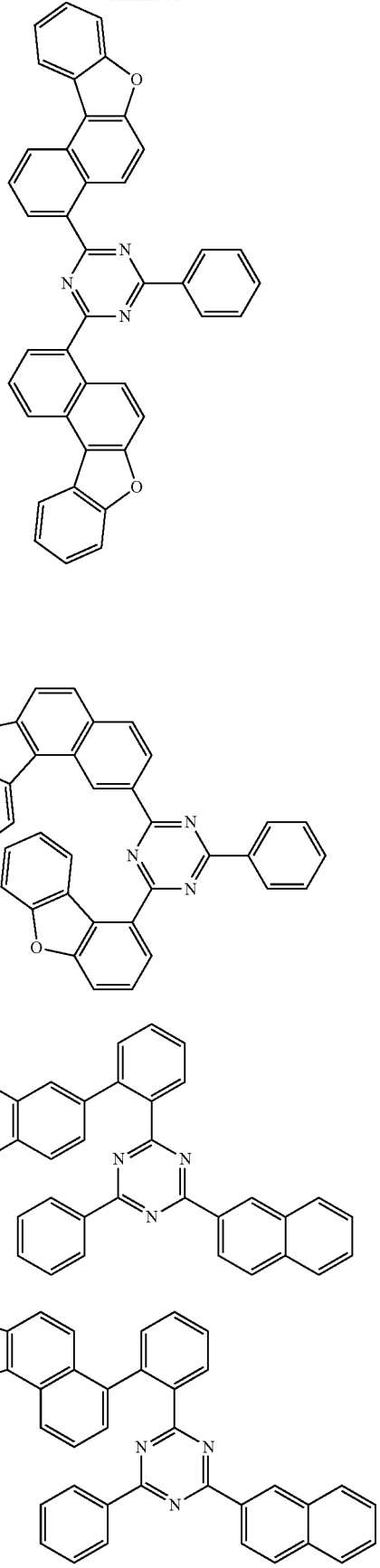

411 -continued
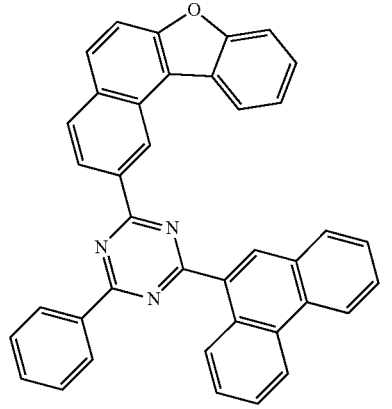
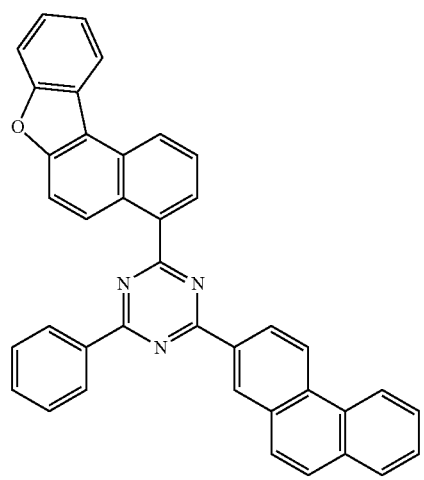
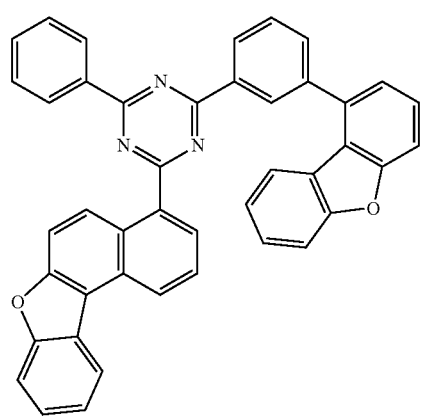
412 -continued
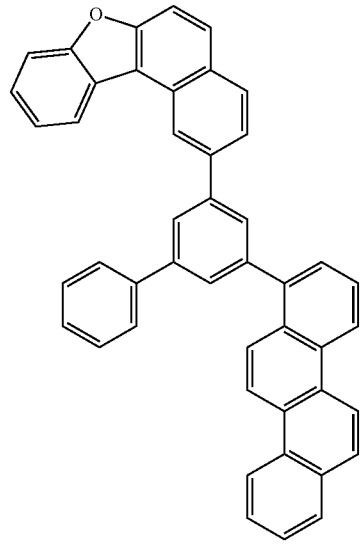
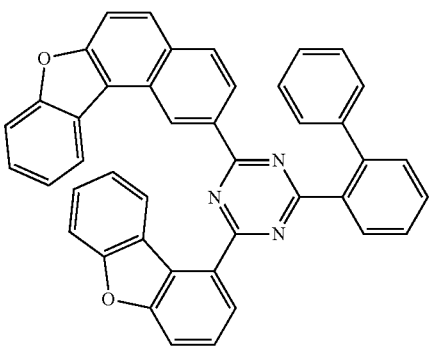
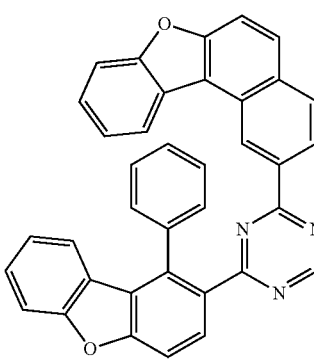
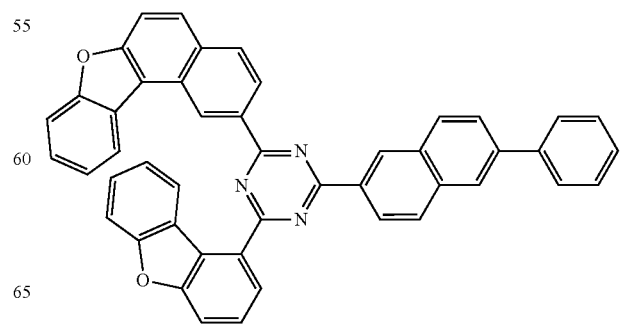

413
-continued
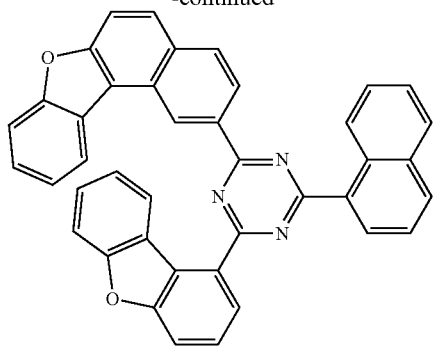
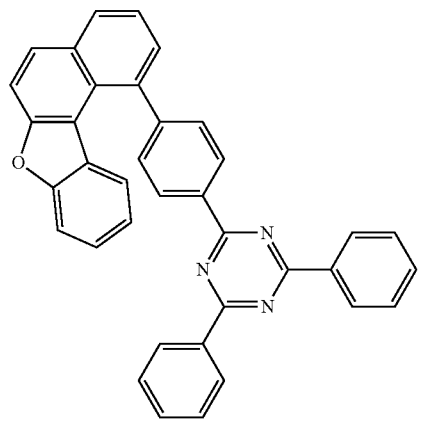 [SMILES: c1ccc(-c2nc(-c3ccccc3)nc(-c3ccc(-c4cccc5ccc6oc7ccccc7c6c45)cc3)n2)cc1]
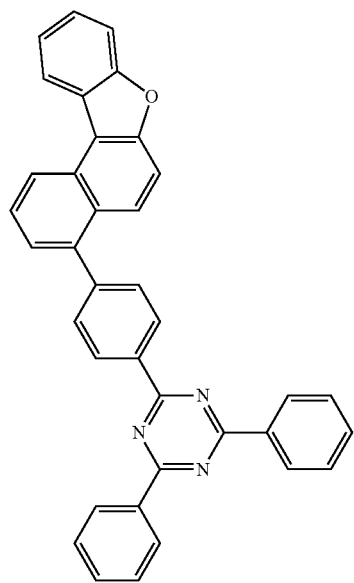
414
-continued
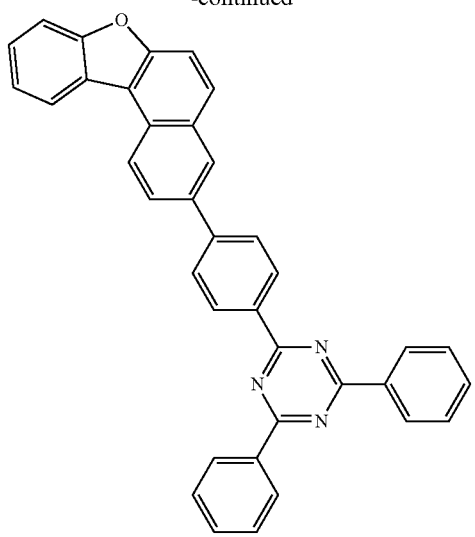
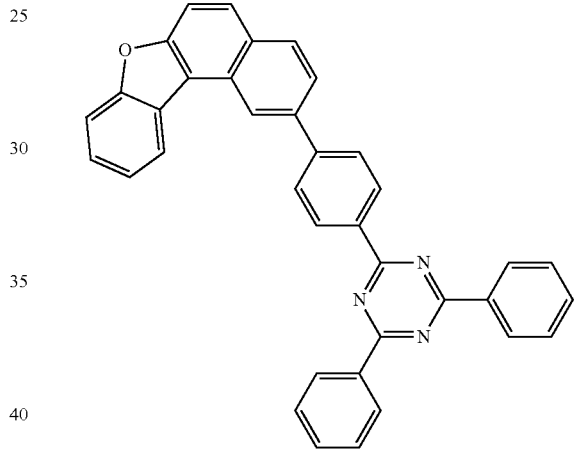
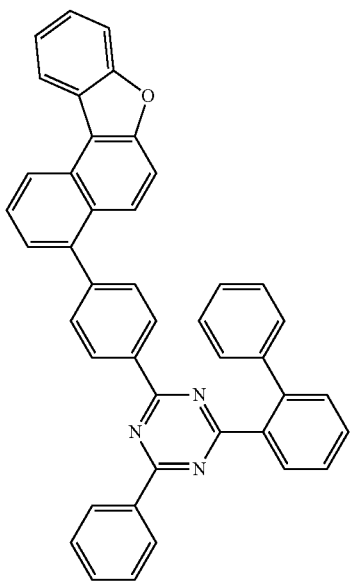

415
-continued

416
-continued

417
-continued
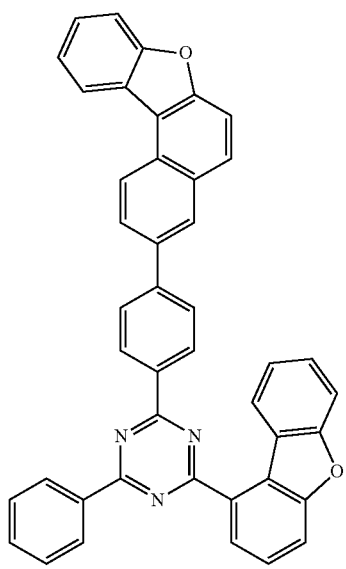
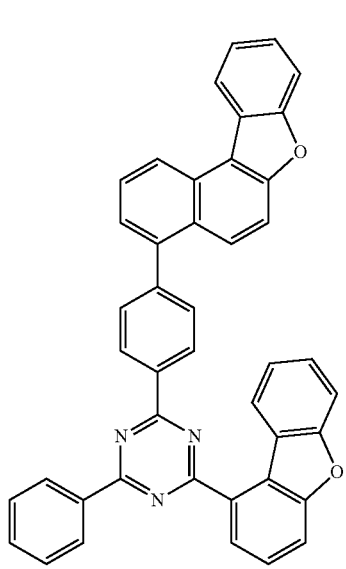
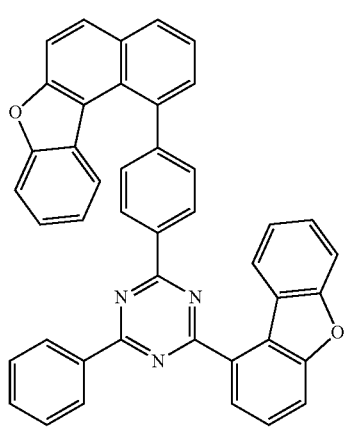
418
-continued
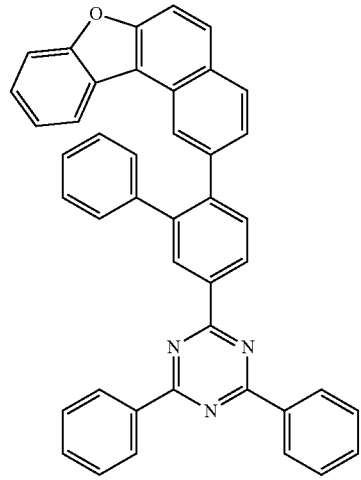
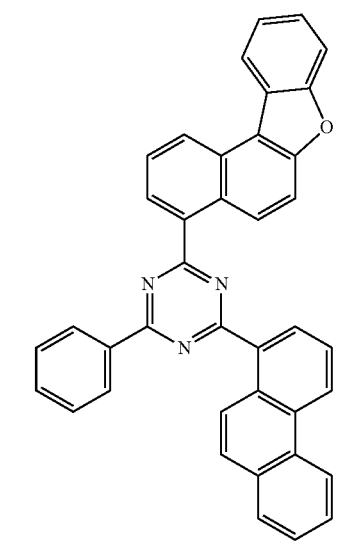
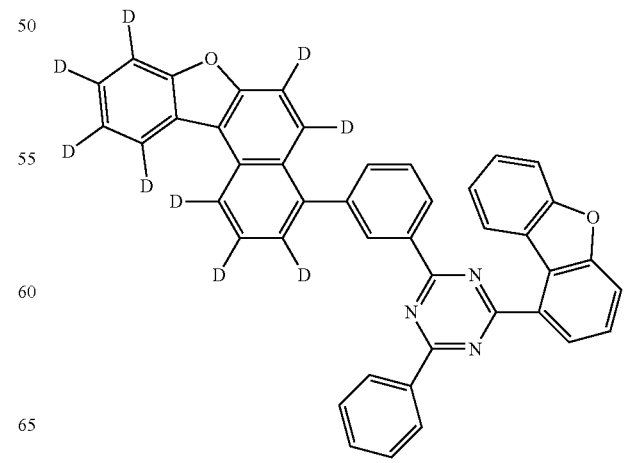

419
-continued
420
-continued
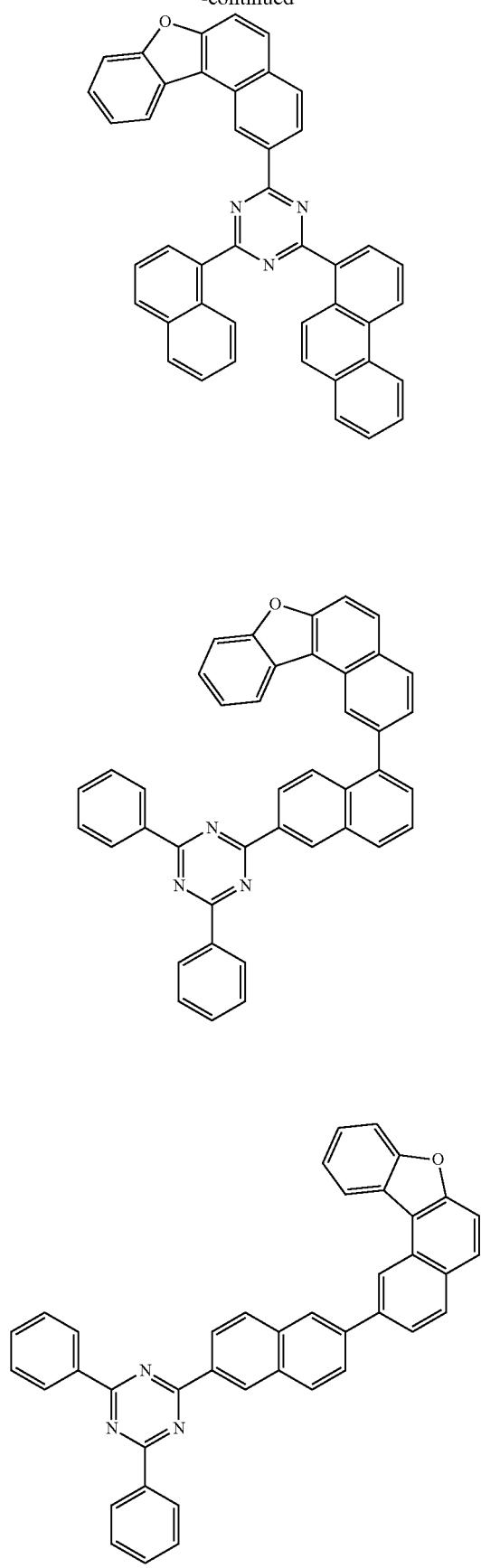

421
-continued
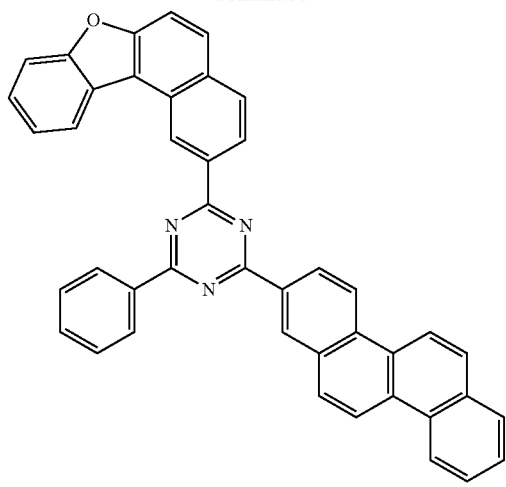
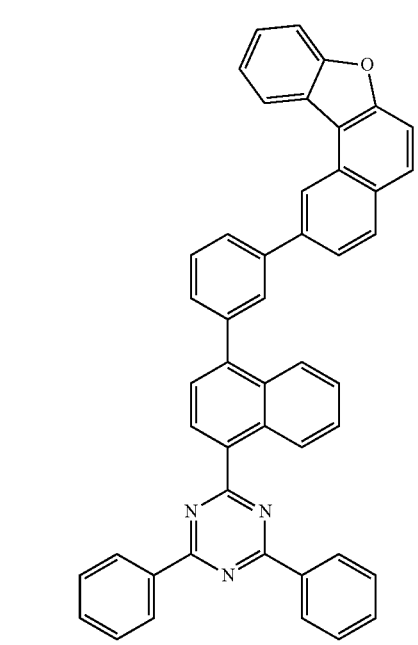
422
-continued
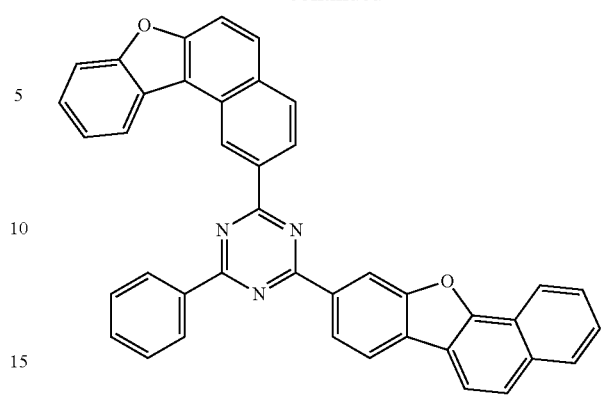
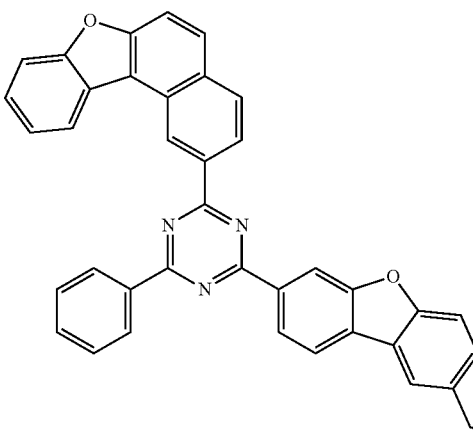
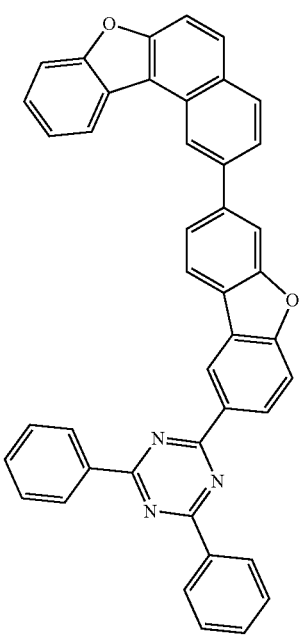

423
-continued
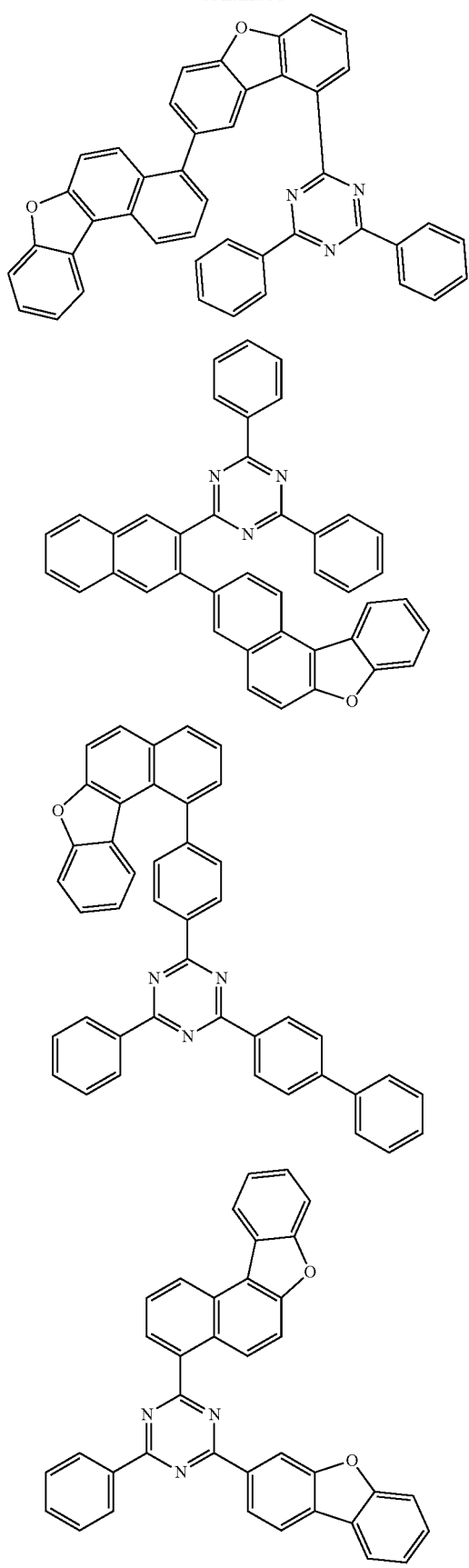
424
-continued
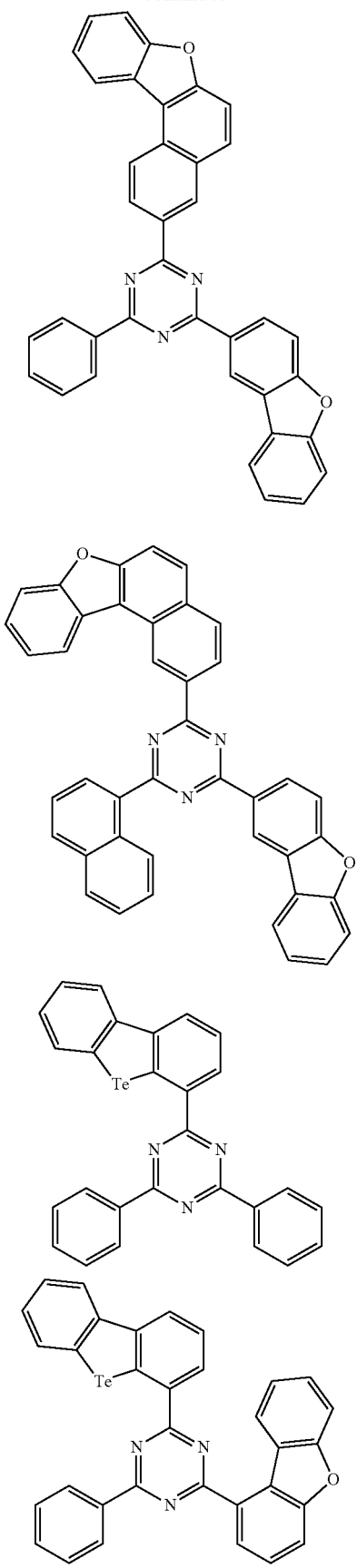

425
-continued
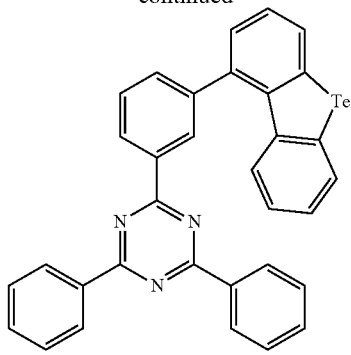
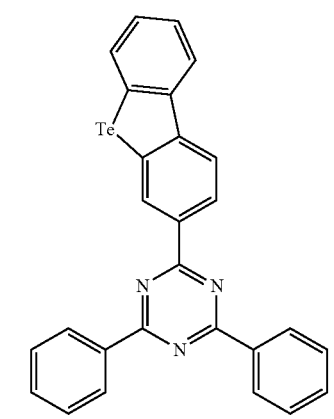
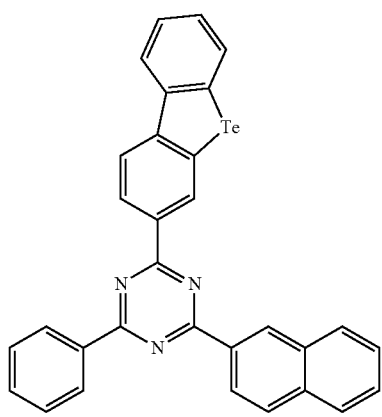
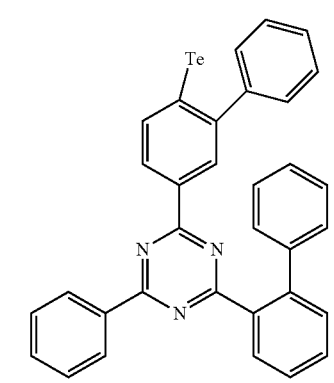
426
-continued
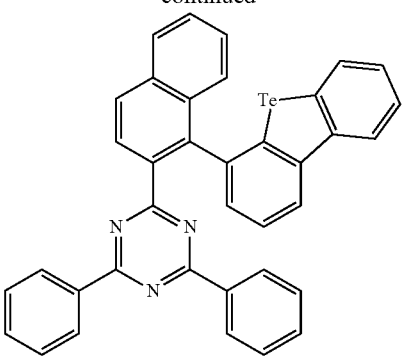
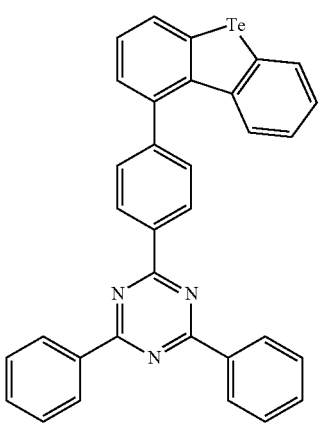
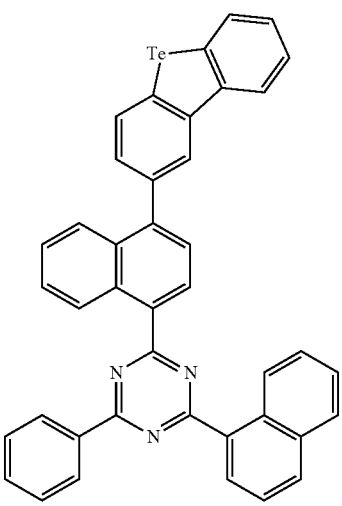
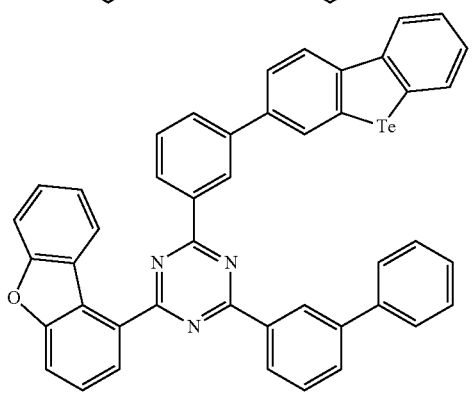

427
-continued
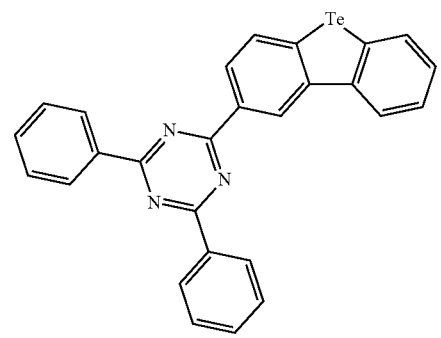
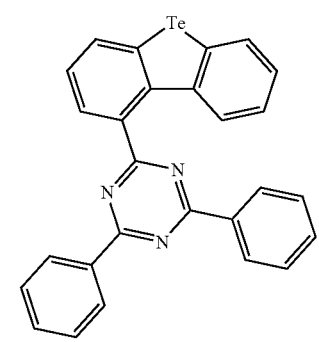
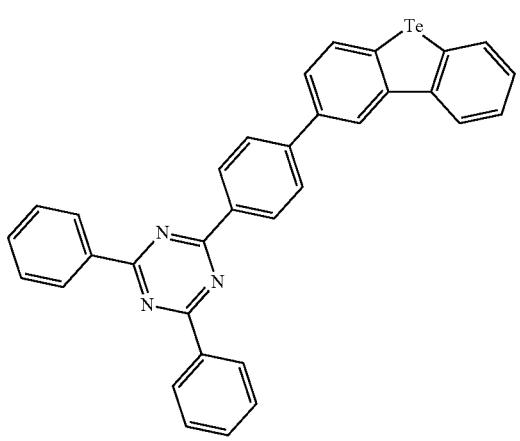
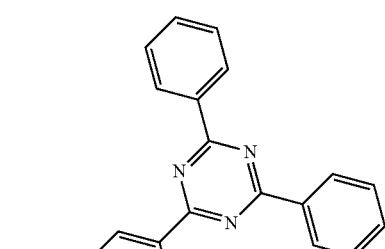
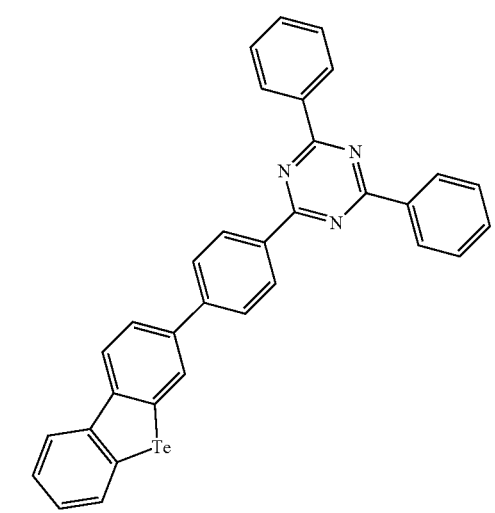
428
-continued
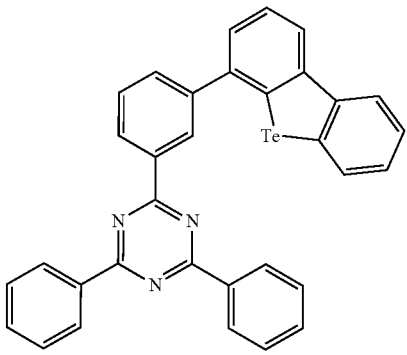
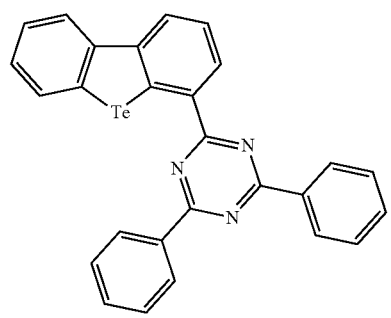
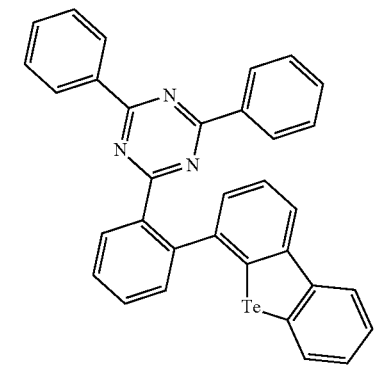

429
-continued
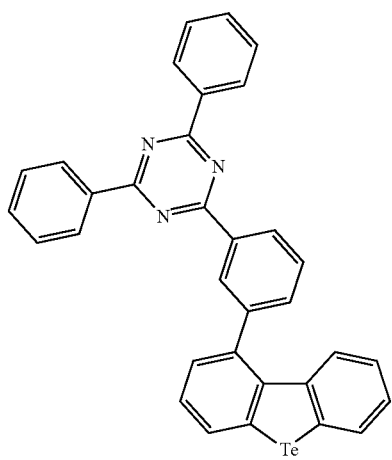
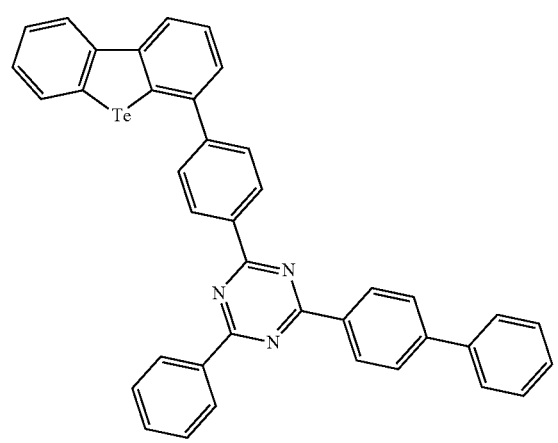
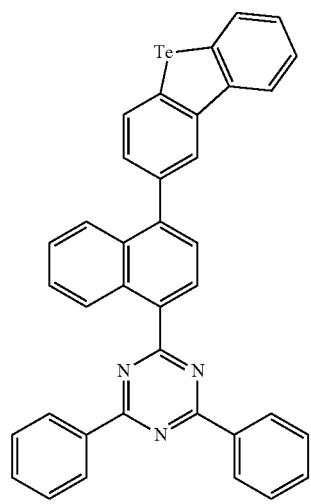
430
-continued
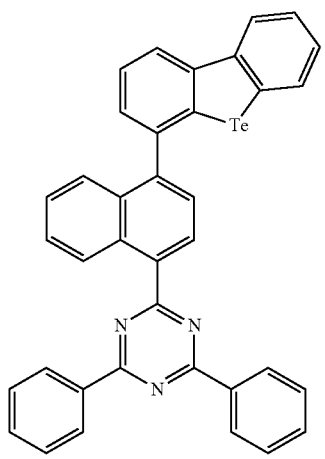
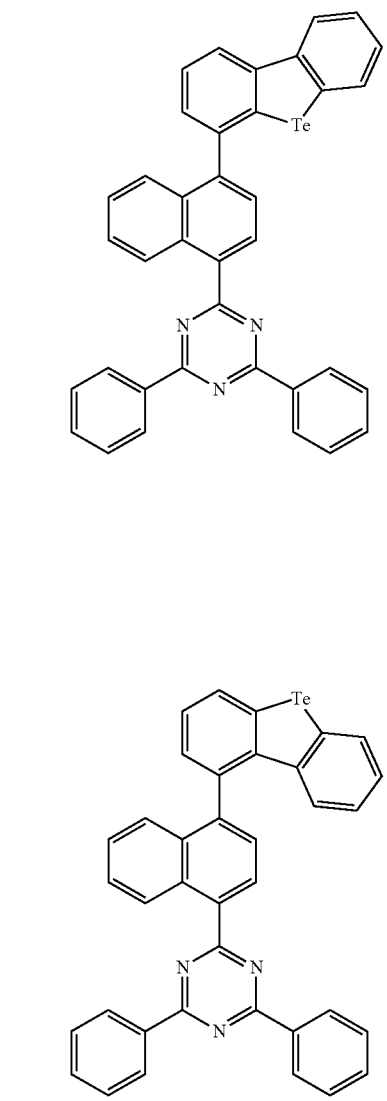
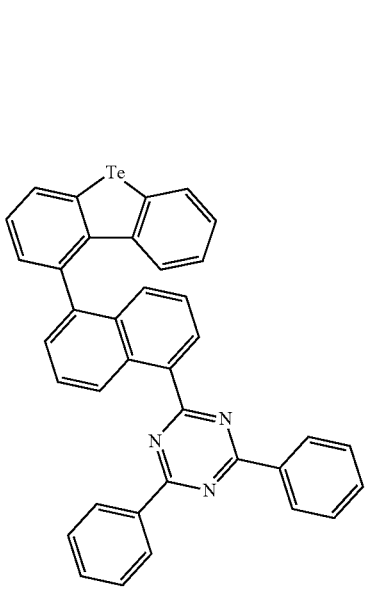

431
-continued
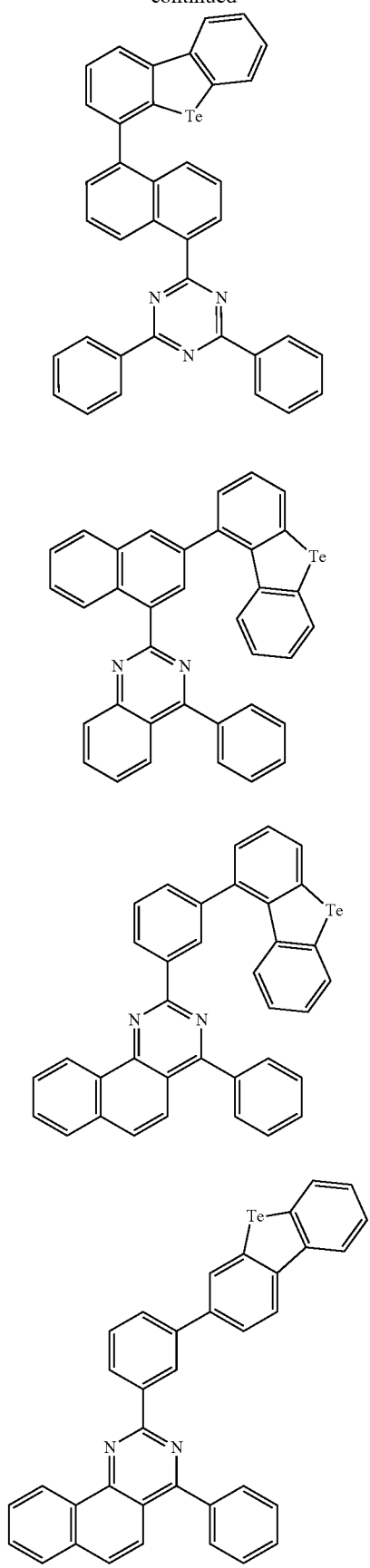
432
-continued
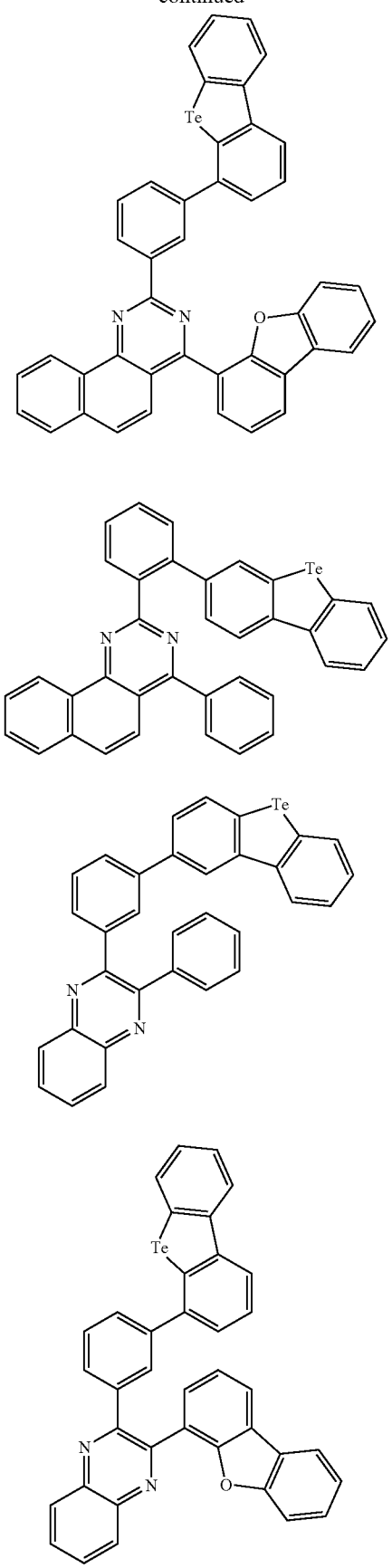

433
-continued
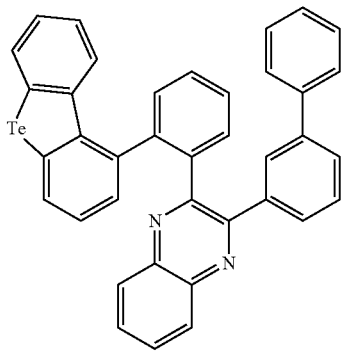
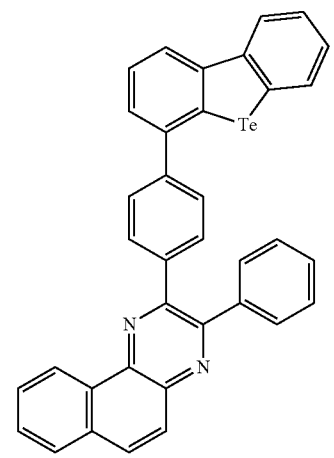
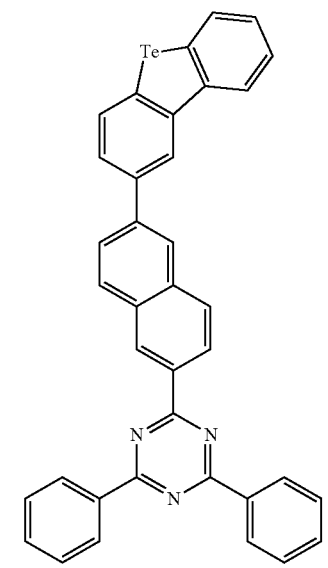
434
-continued
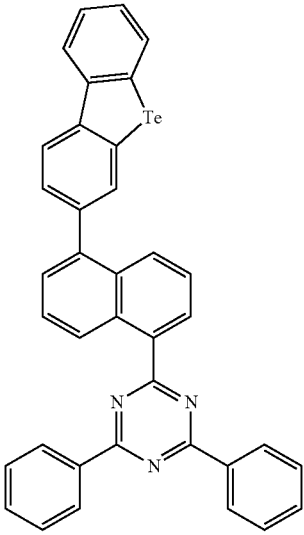
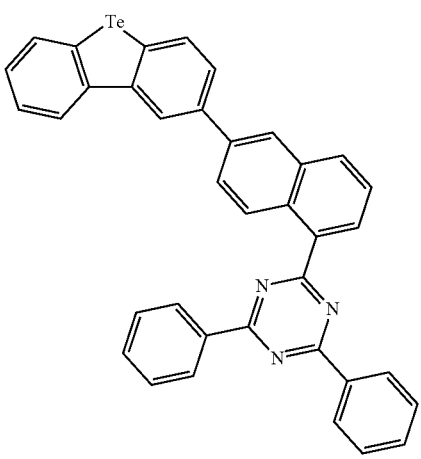
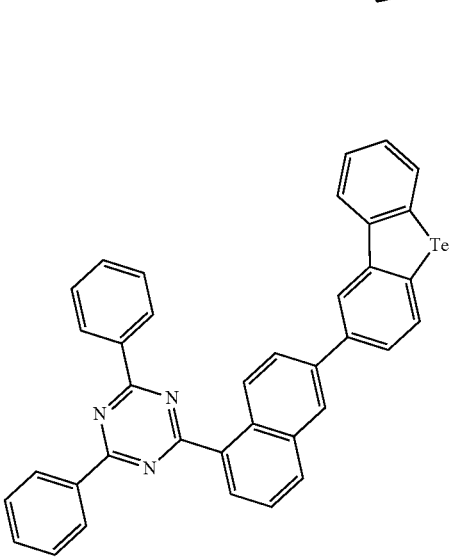

435
-continued
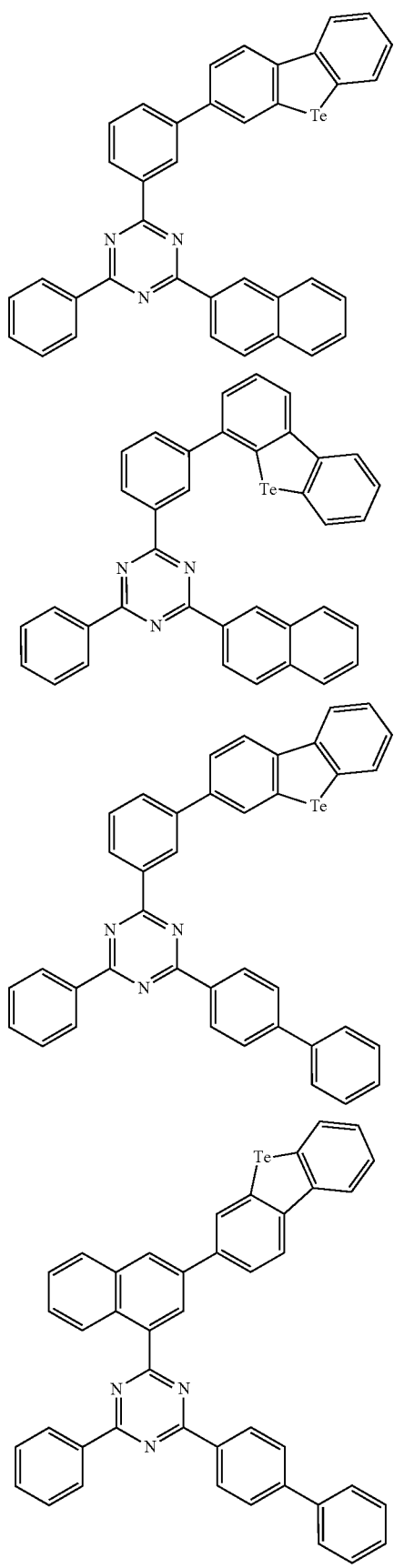
436
-continued
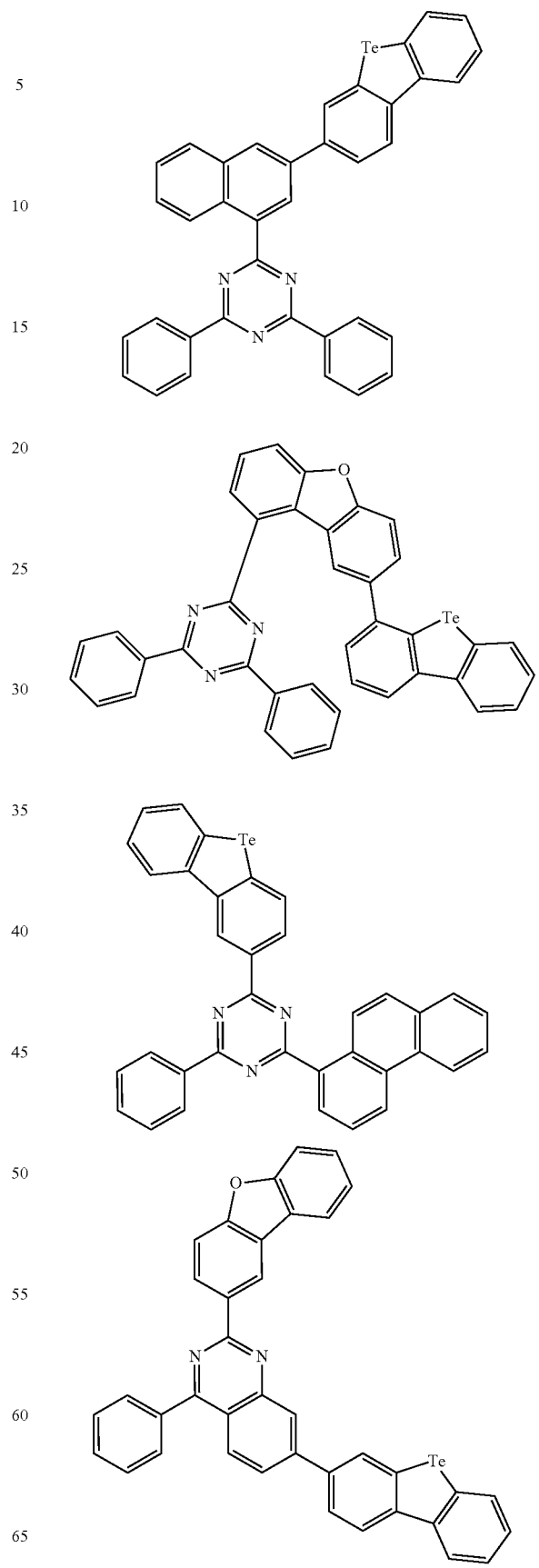

437
-continued
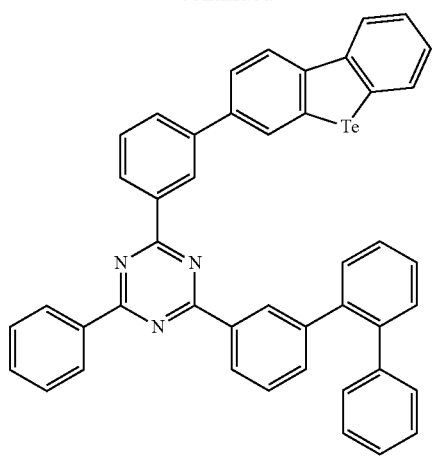
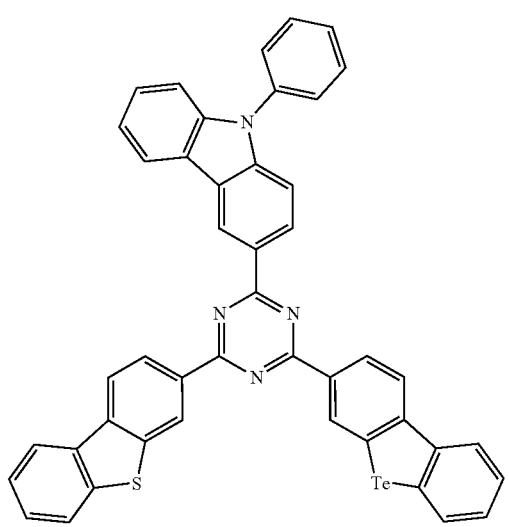
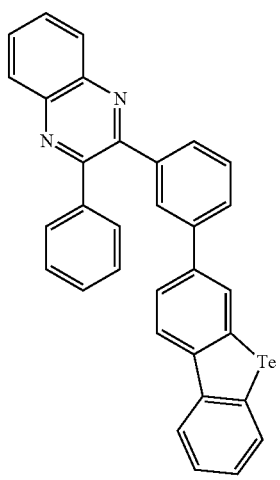
438
-continued
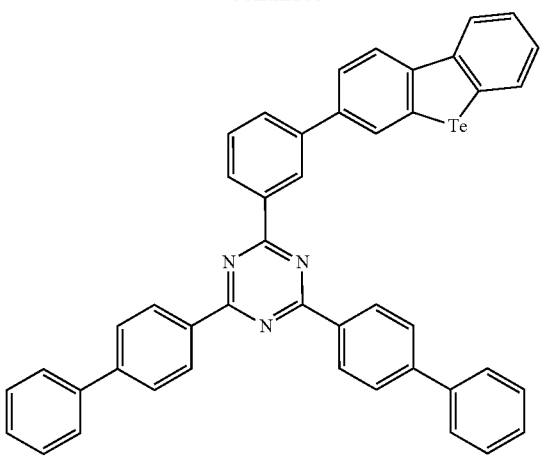
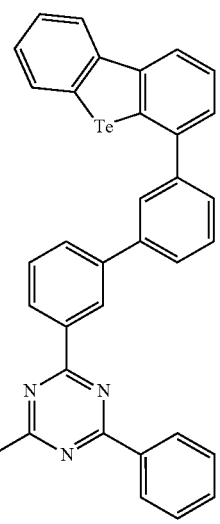
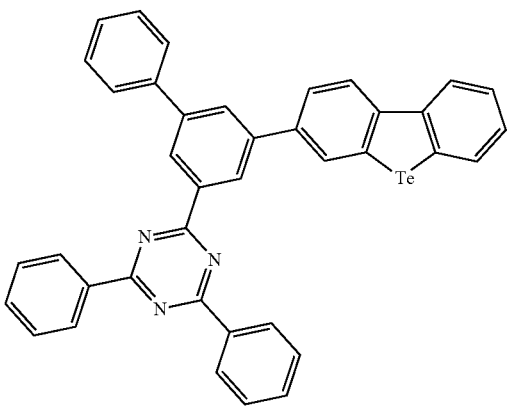

439
-continued
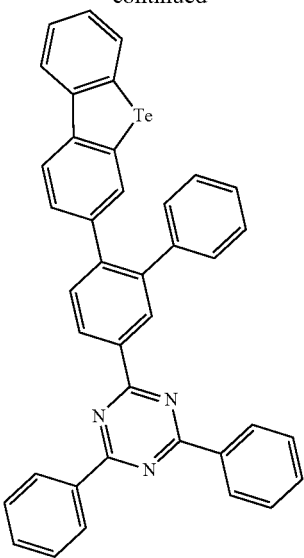
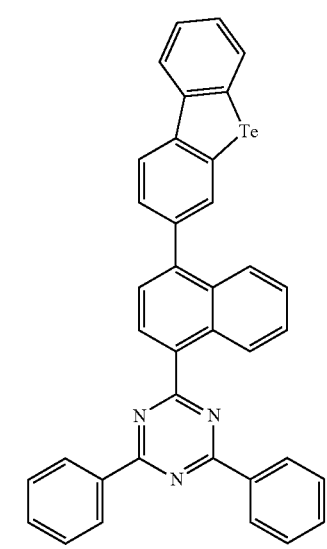
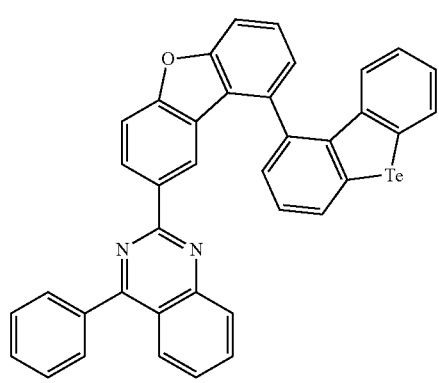
440
-continued
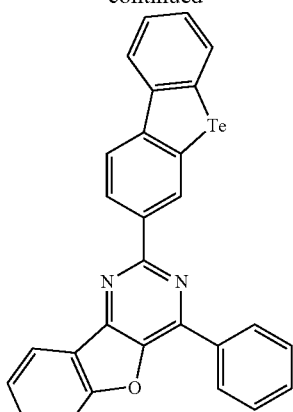
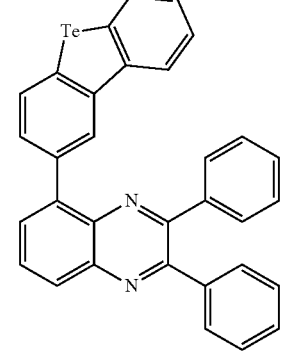
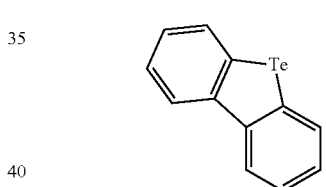
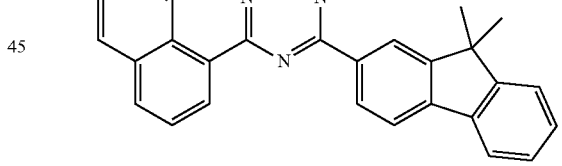
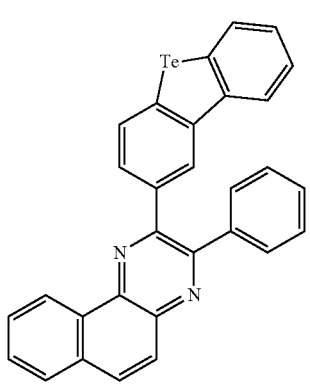

441
-continued
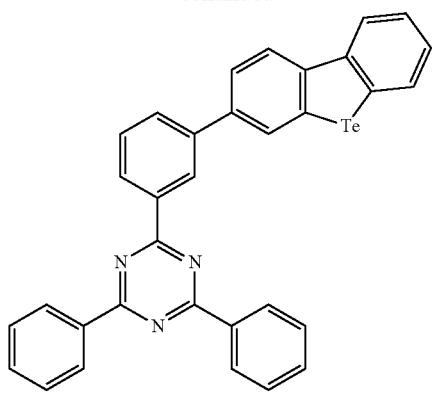
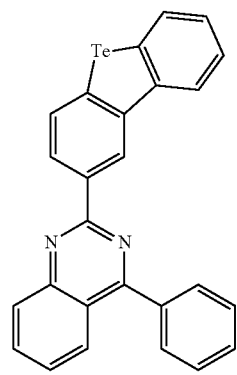
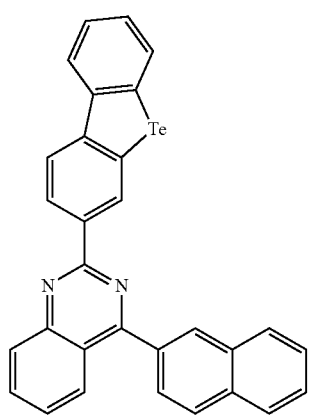
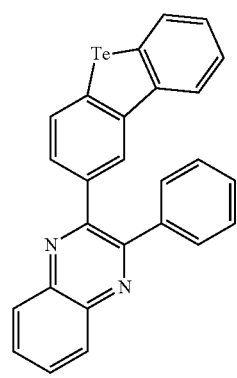
442
-continued
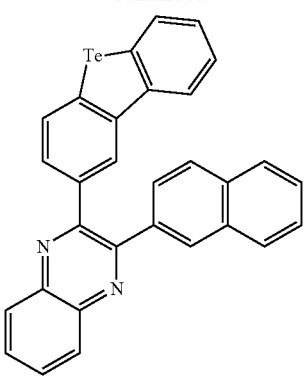
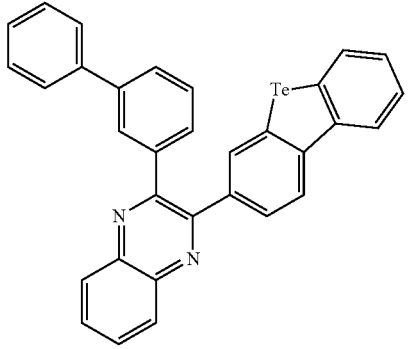
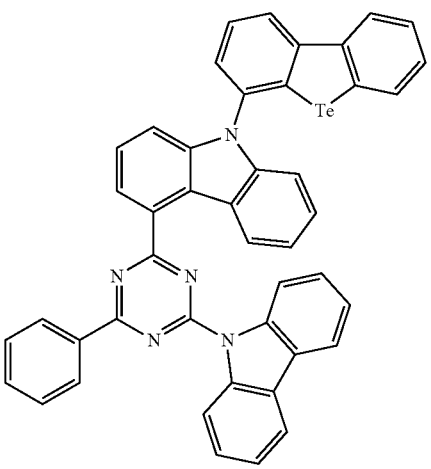
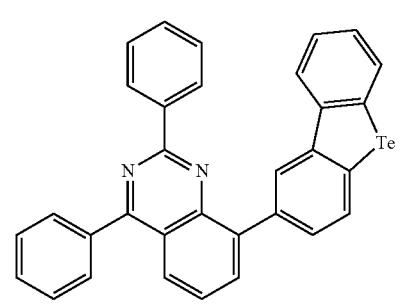

443
-continued
444
-continued
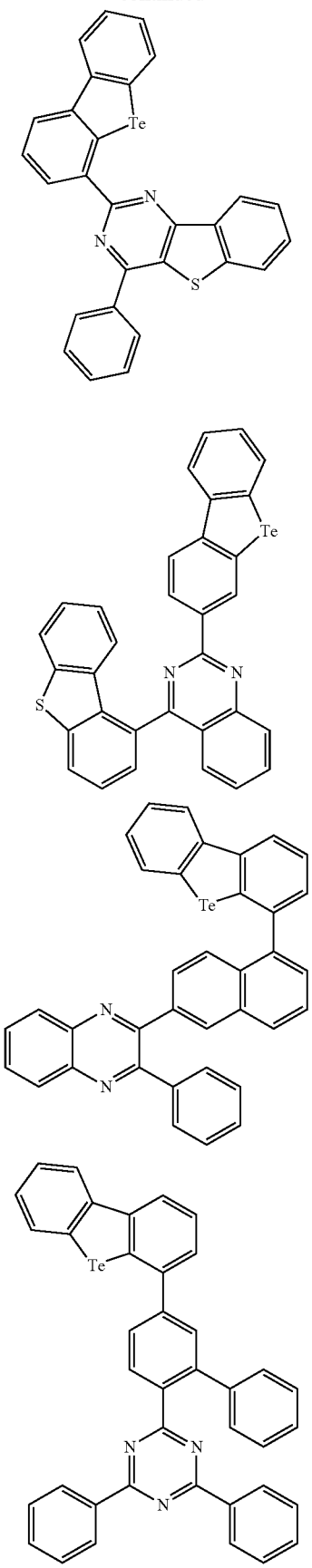
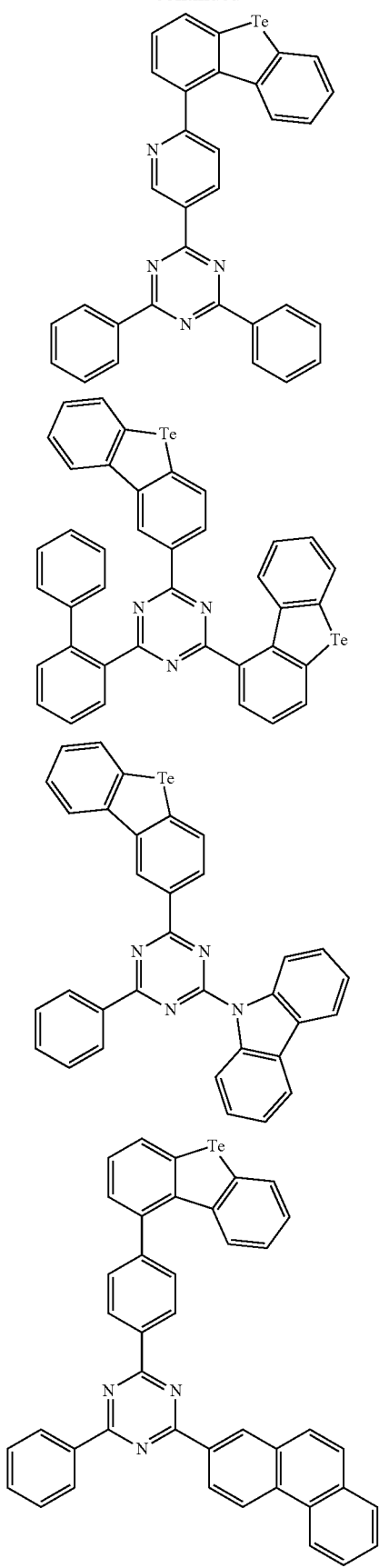

445
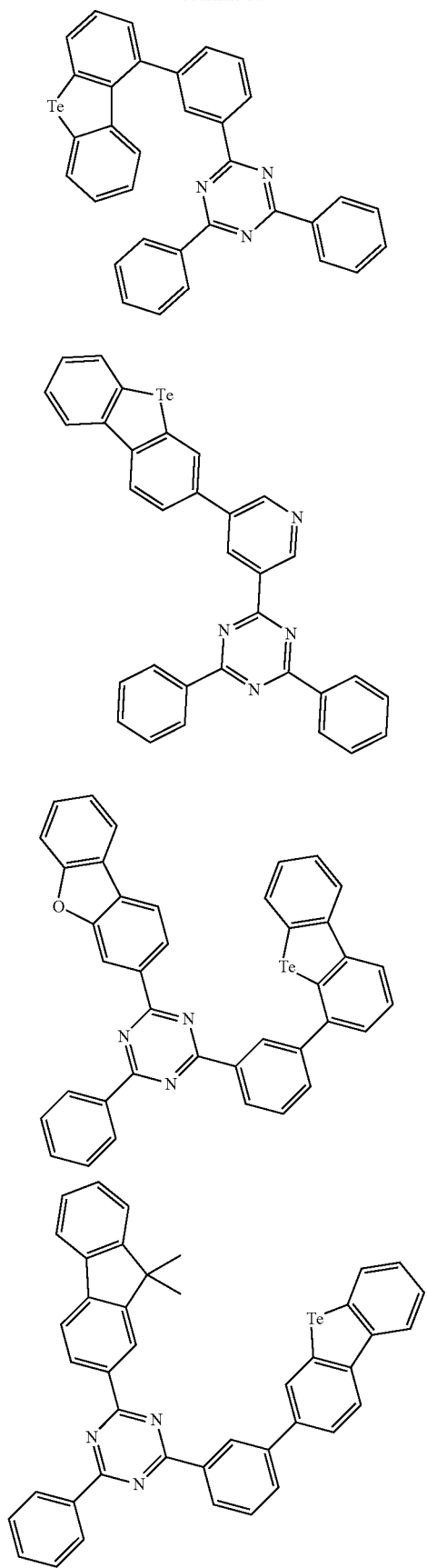
446
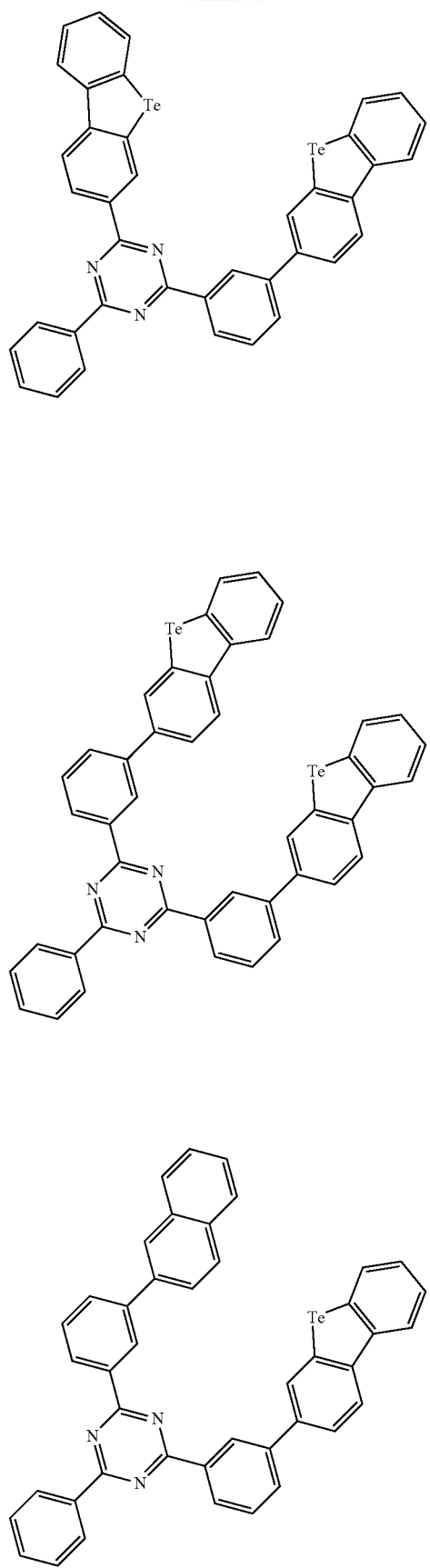

447
-continued
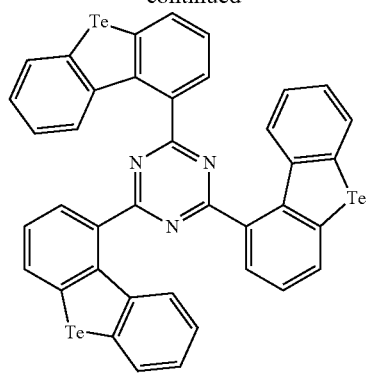
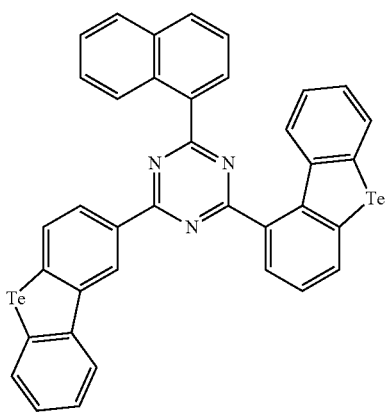
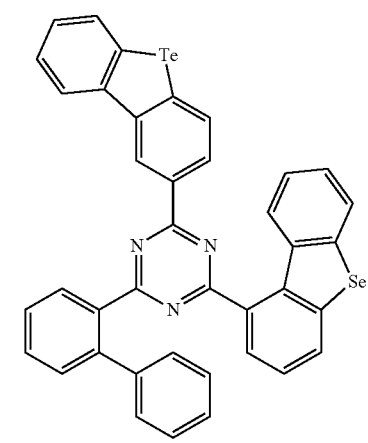
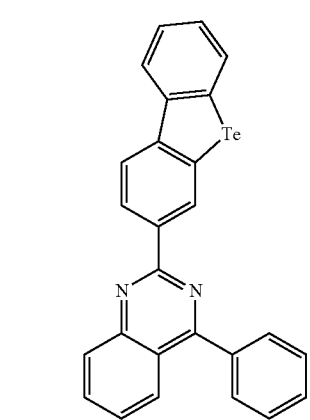
448
-continued
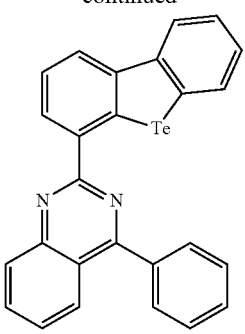

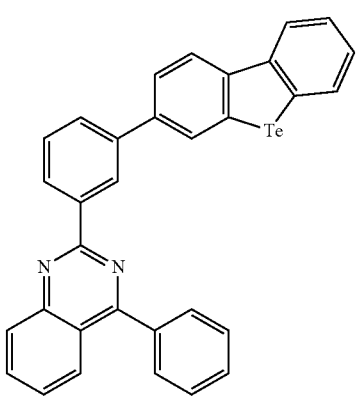

449
-continued
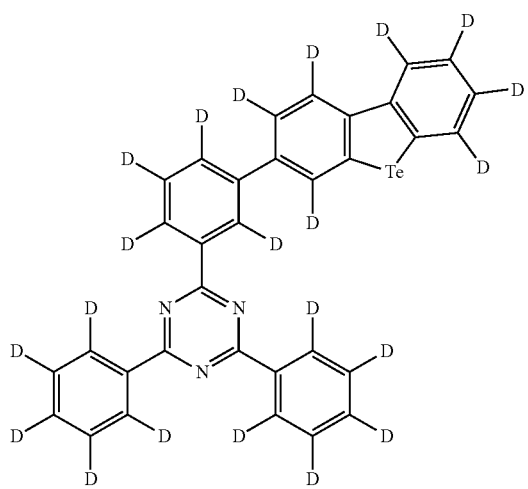
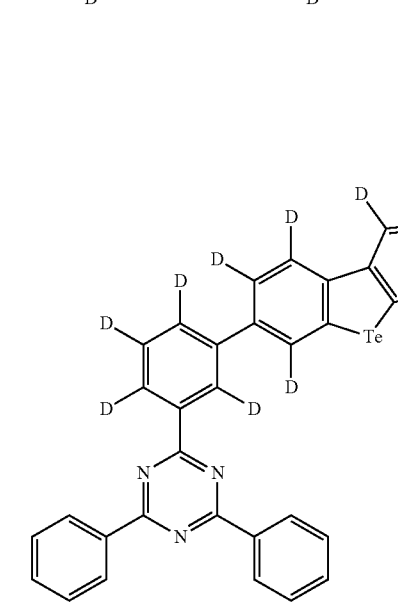
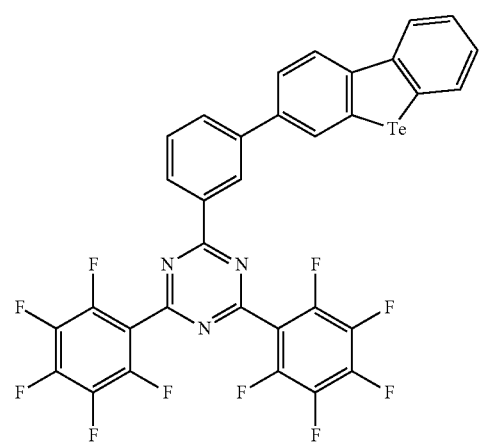
450
-continued
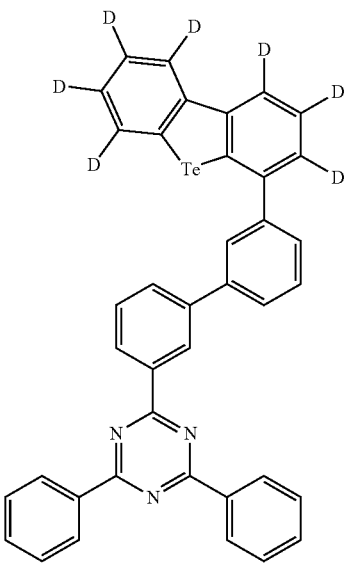
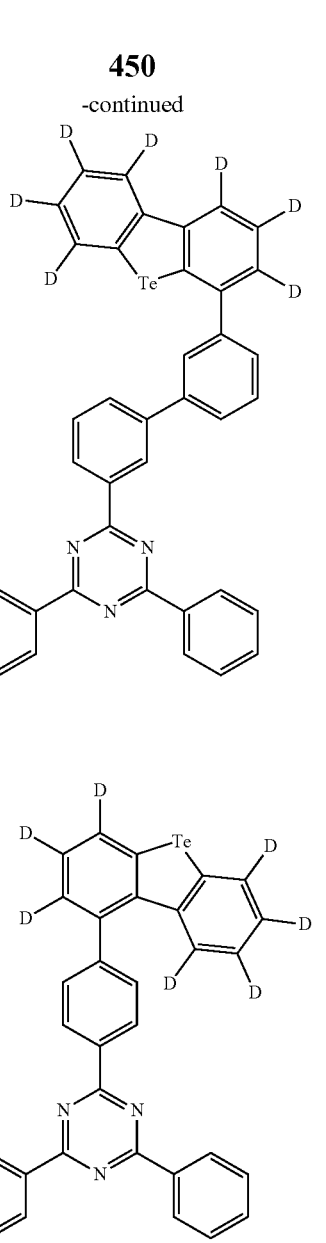
The compound represented by formula 15 may be at least one selected from the group consisting of the following compounds, but is not limited thereto.
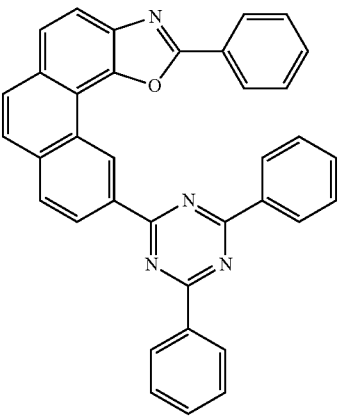

451
-continued
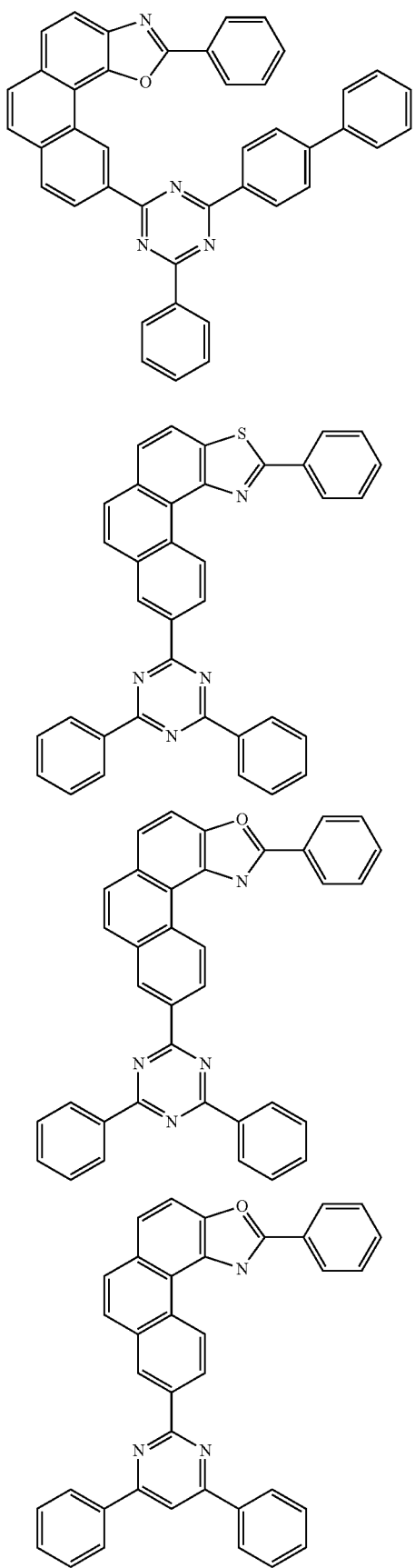
452
-continued
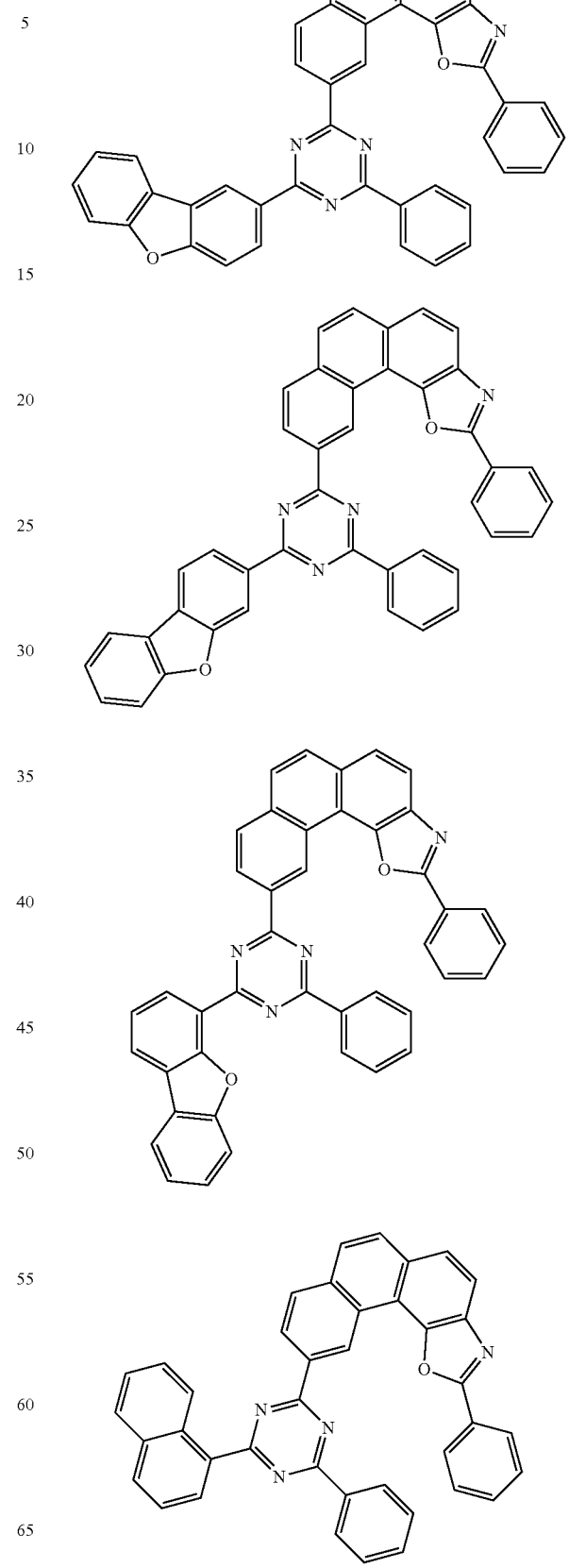

453
-continued
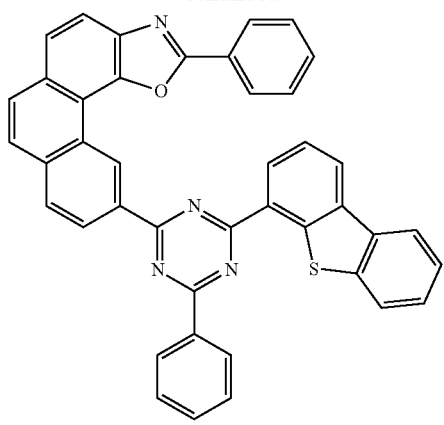
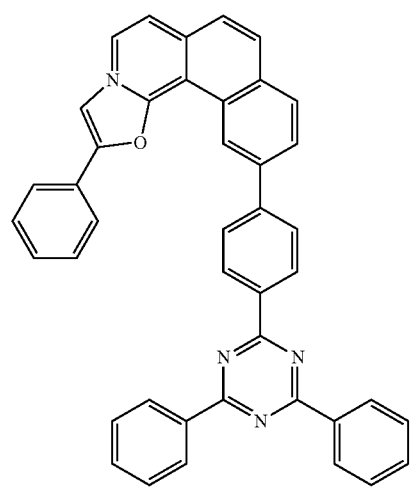
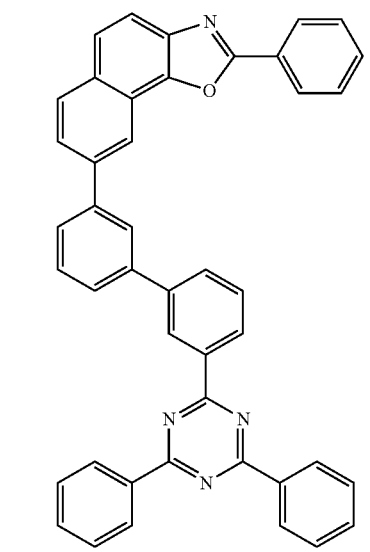
454
-continued
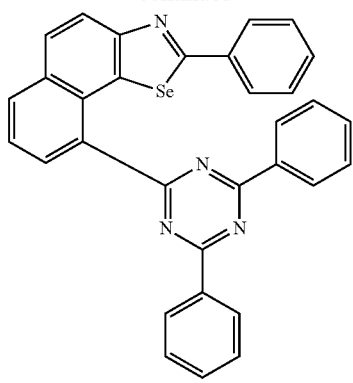
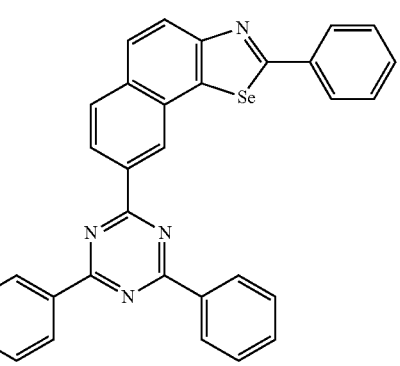
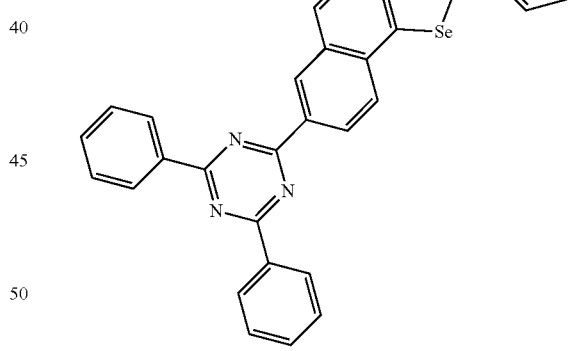
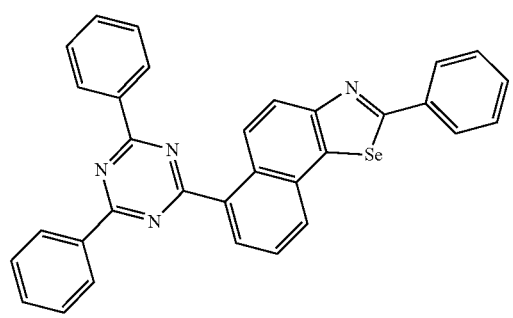

455
-continued
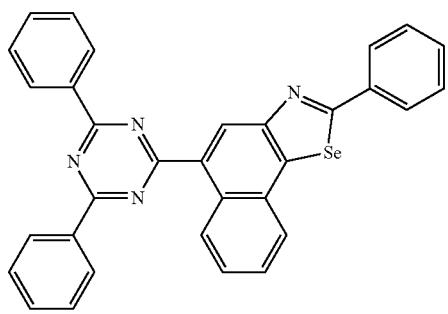
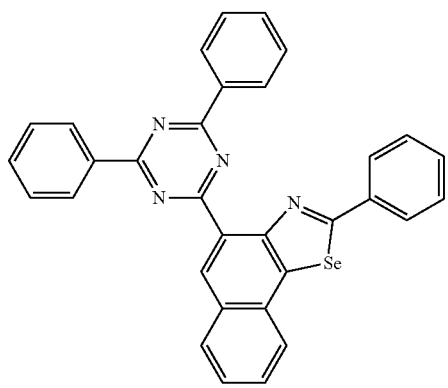
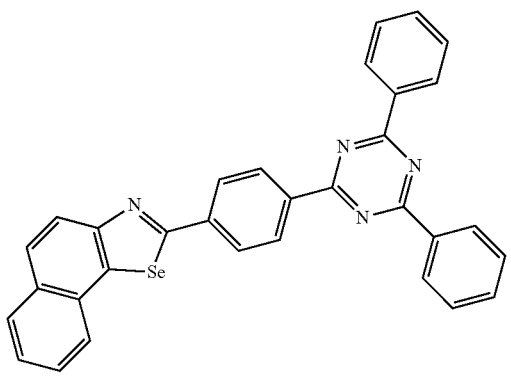
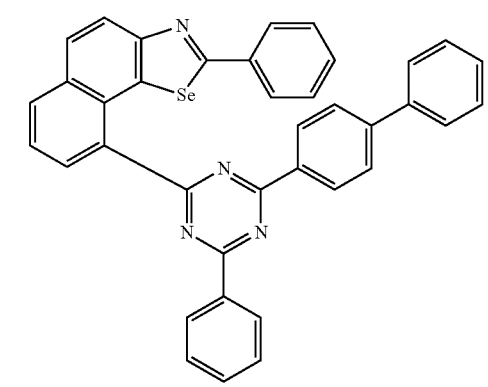
456
-continued
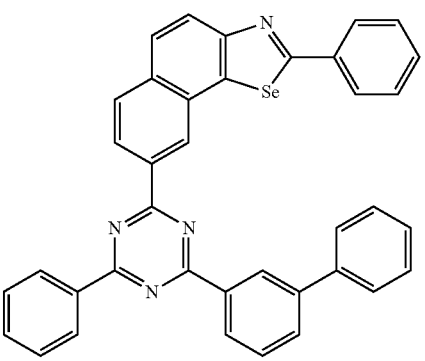
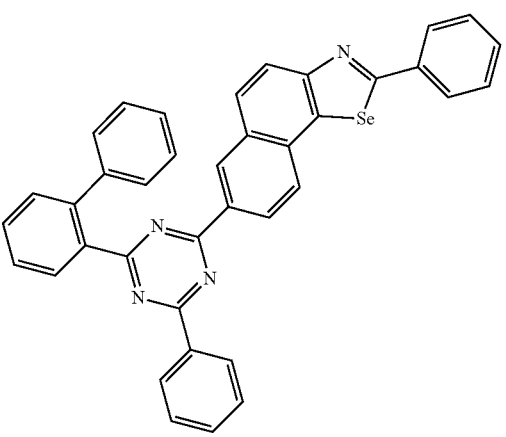
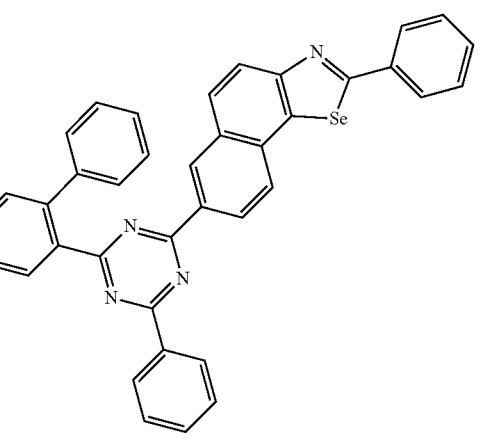
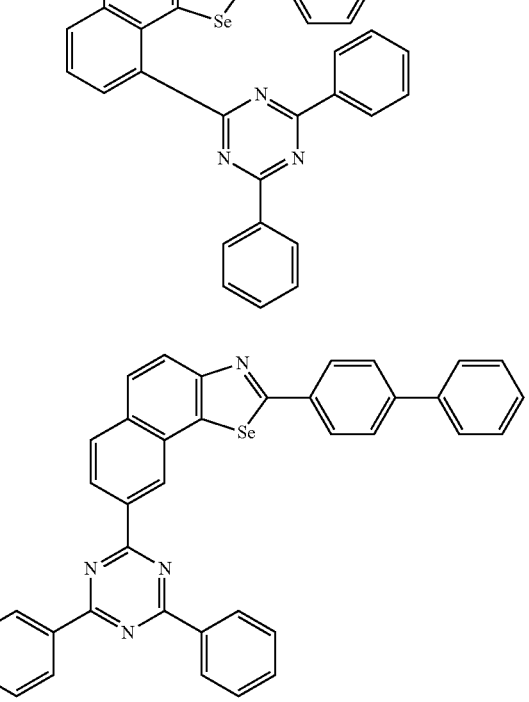

457
-continued
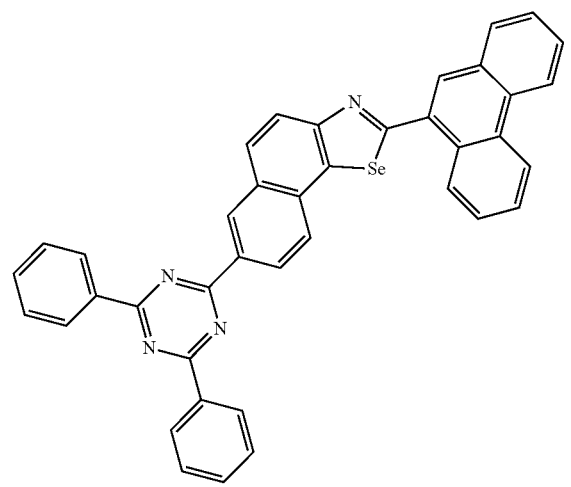
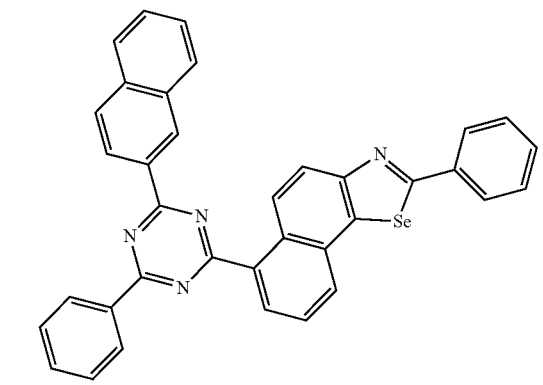
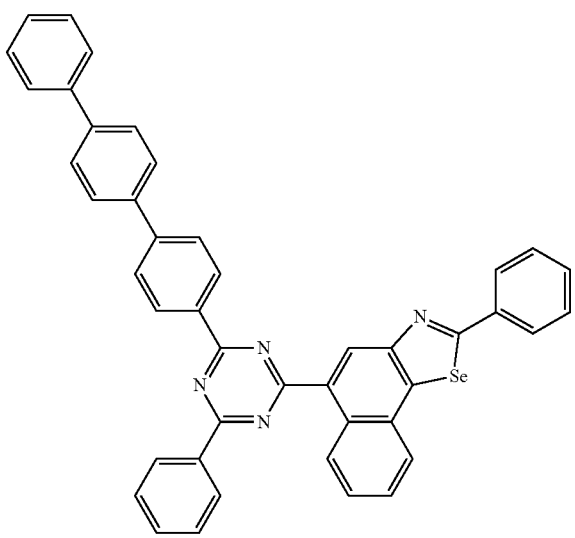
458
-continued
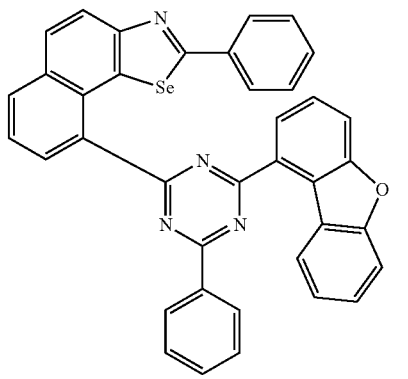
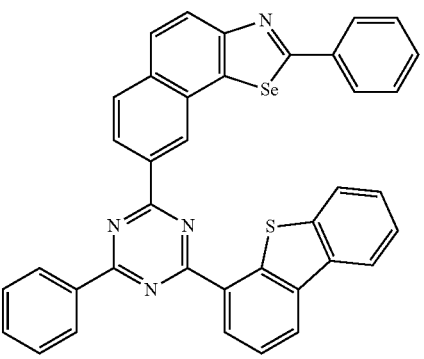
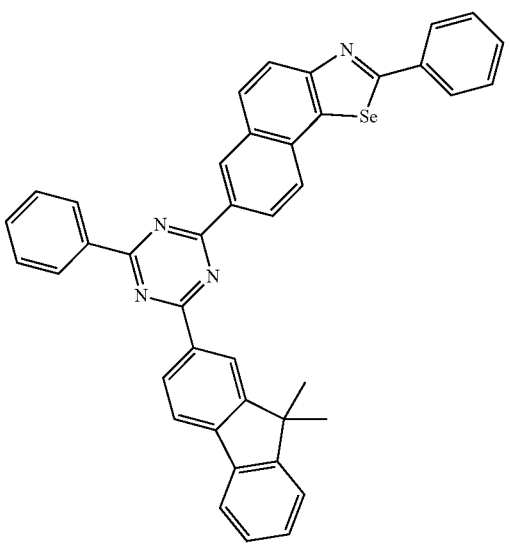
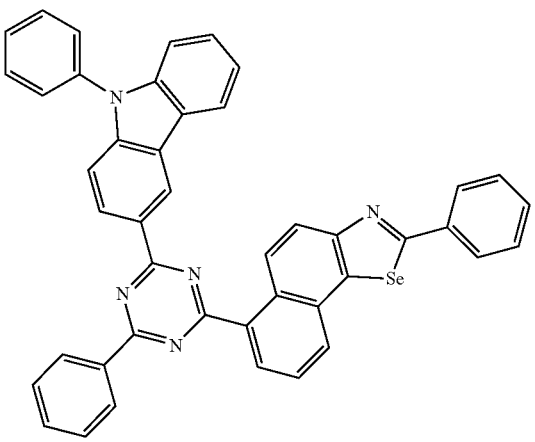

459
-continued
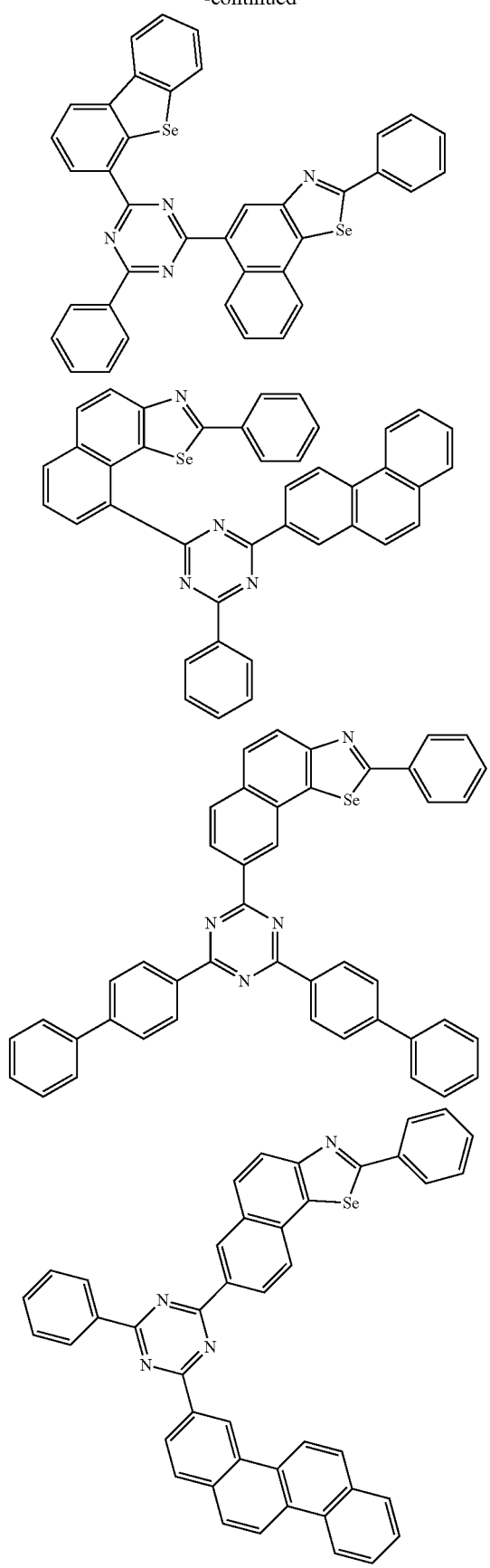
460
-continued
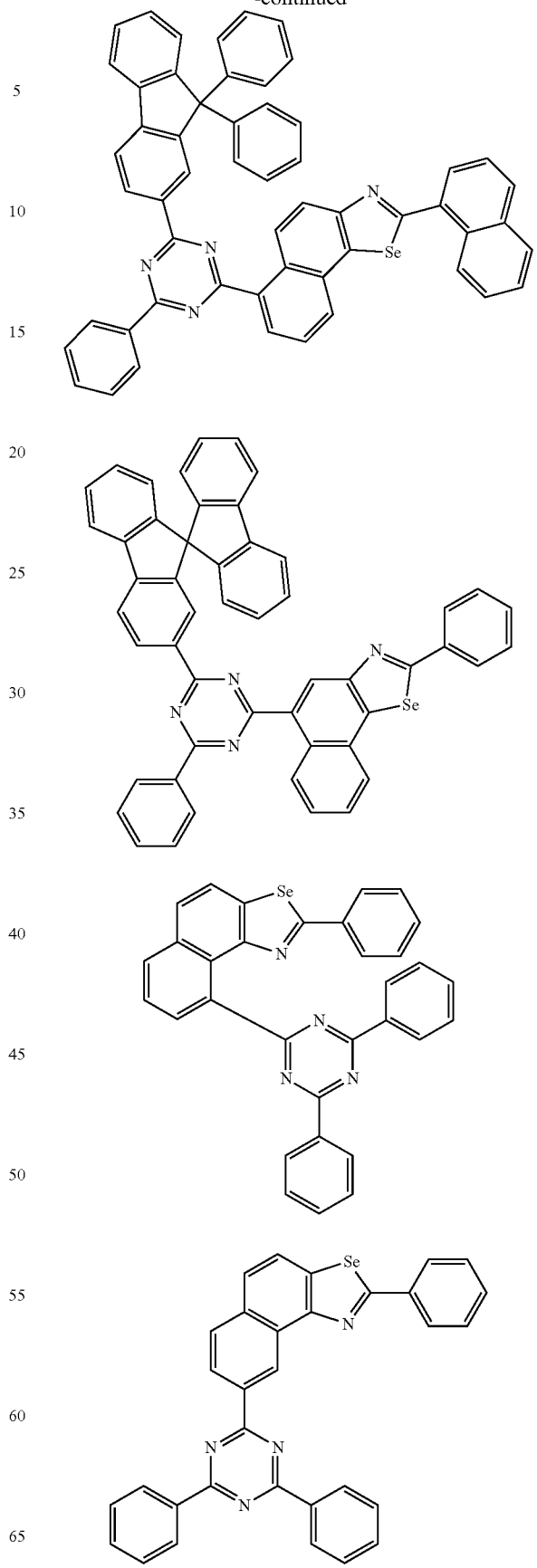

| 461 | 462 |
|---|---|
| -continued | -continued |
| 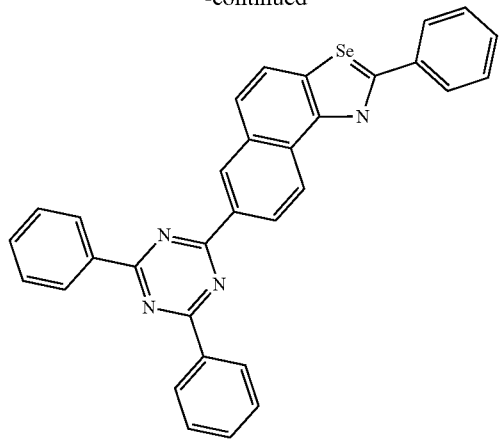 | 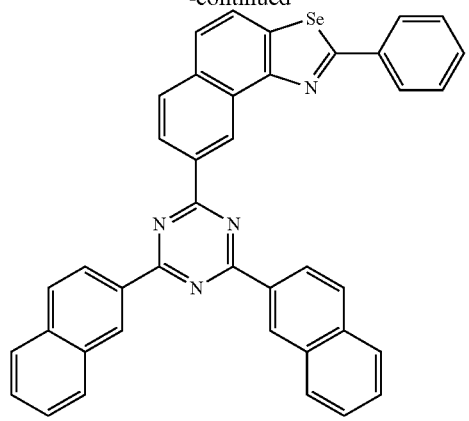 |
| 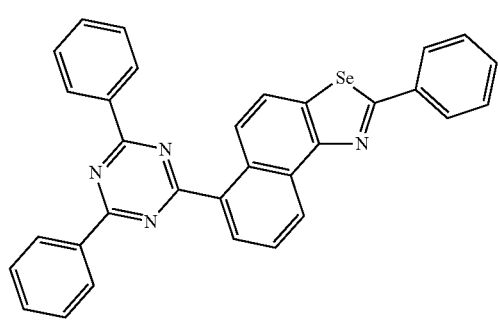 | 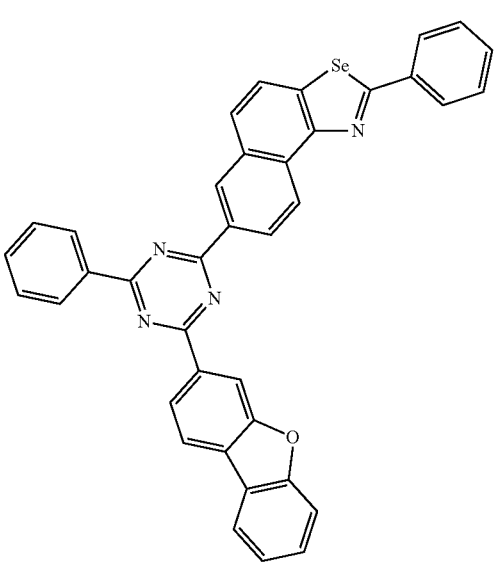 |
| 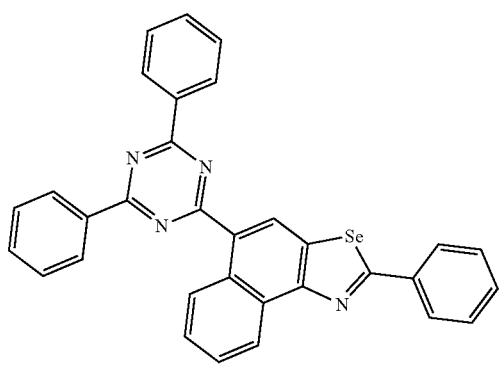 | |
| 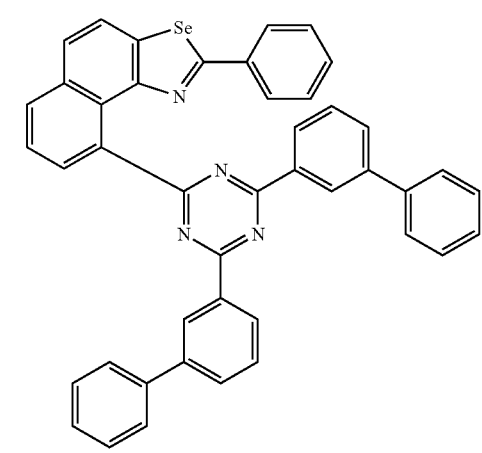 | 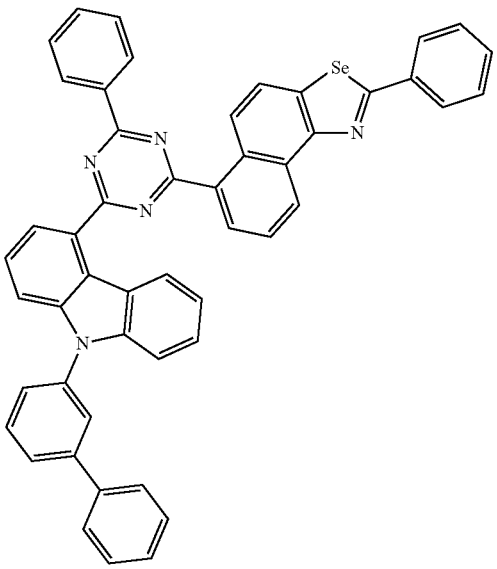 |

463
-continued
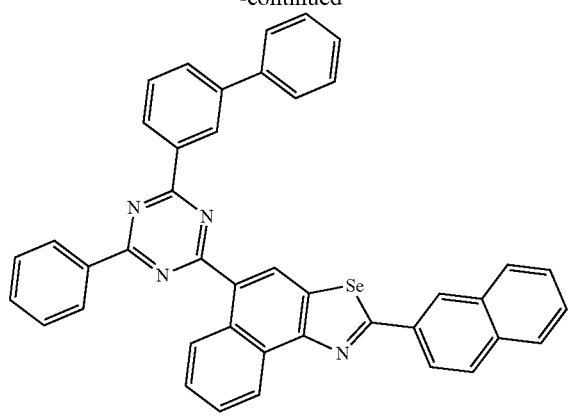
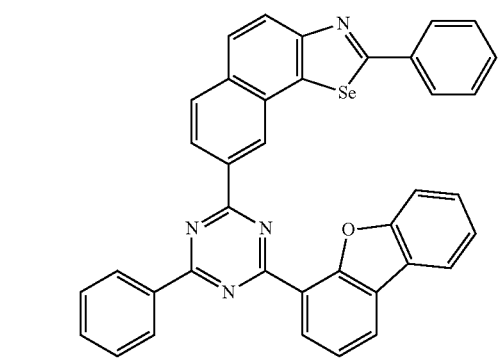
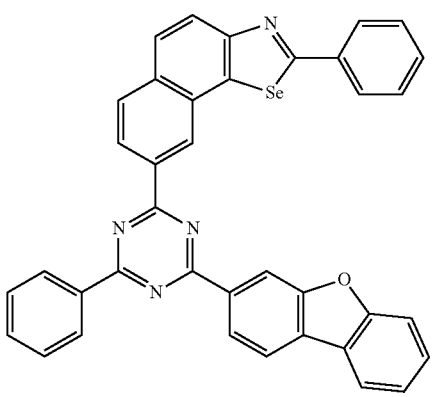

464
-continued
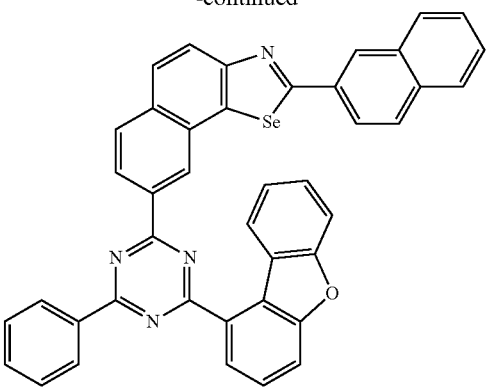
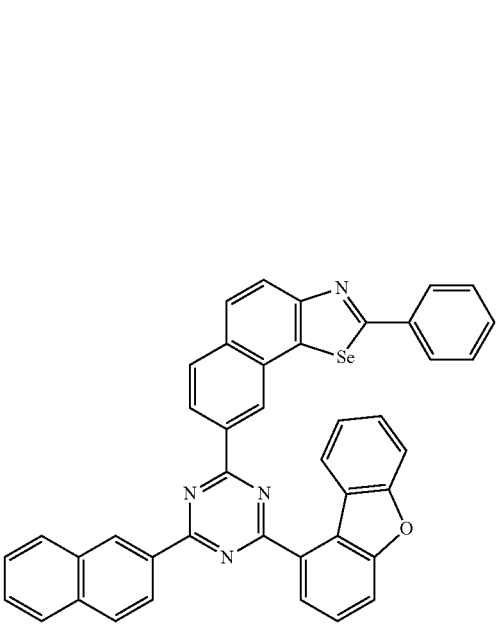
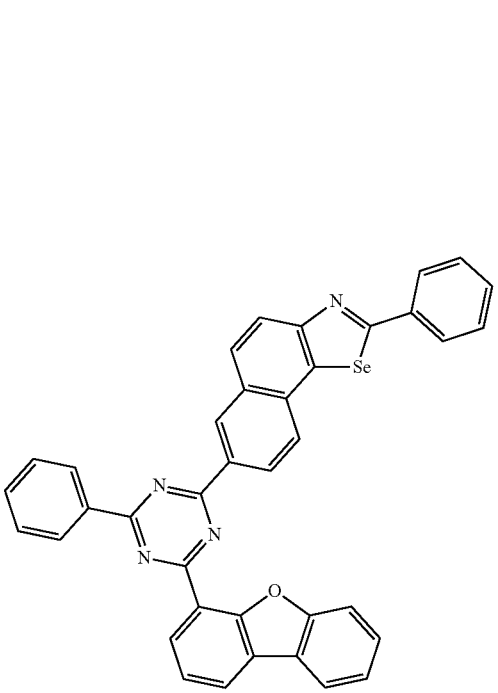

465
-continued
466
-continued
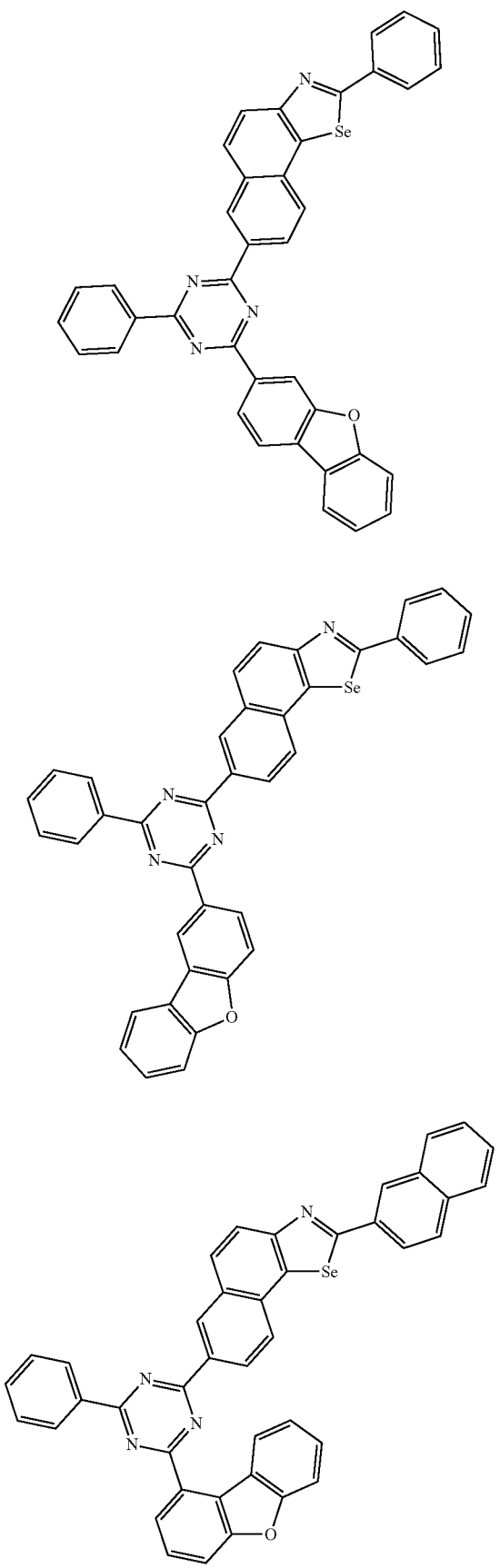
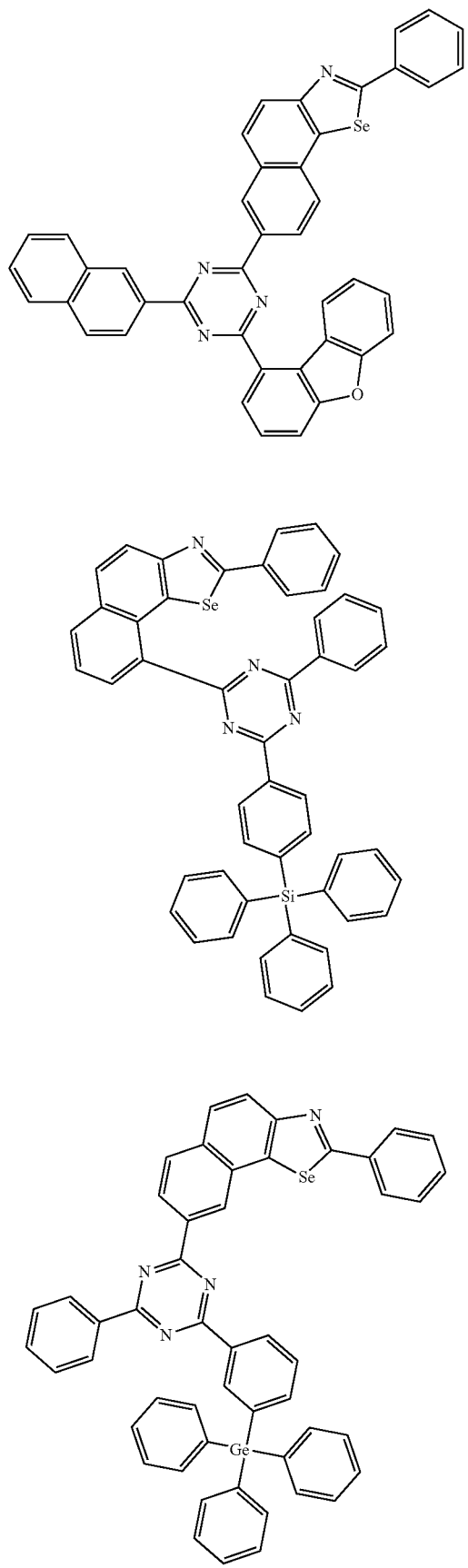

467
-continued
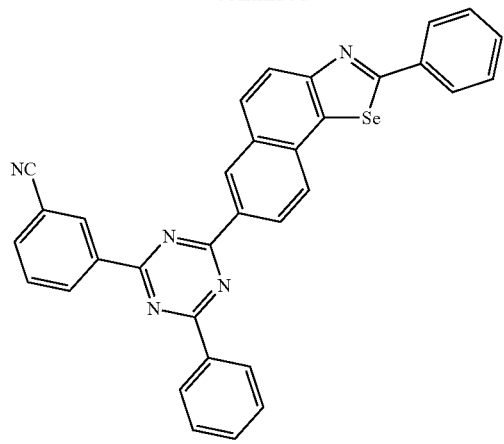
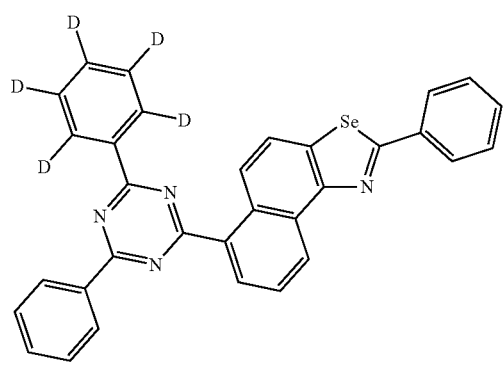
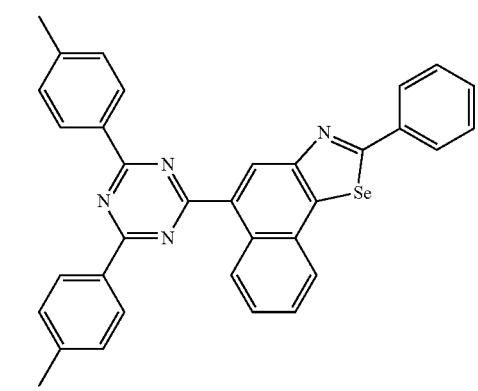
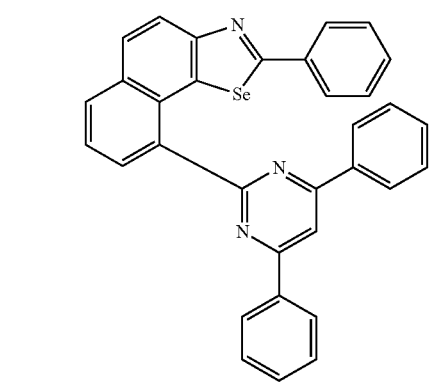
468
-continued
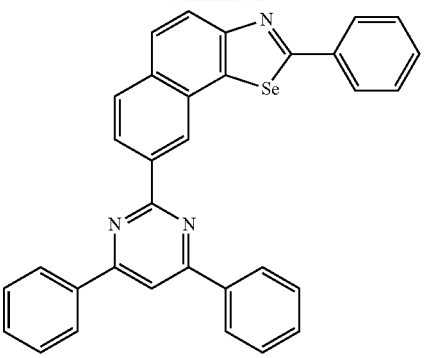
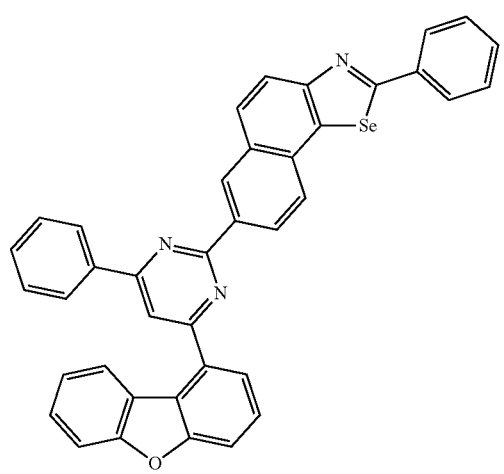
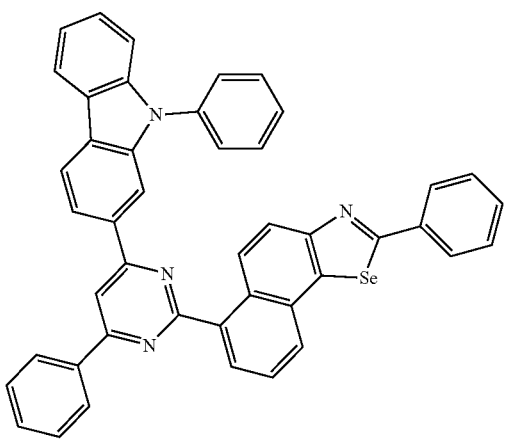

| 469 -continued | 470 -continued |
|---|---|
| 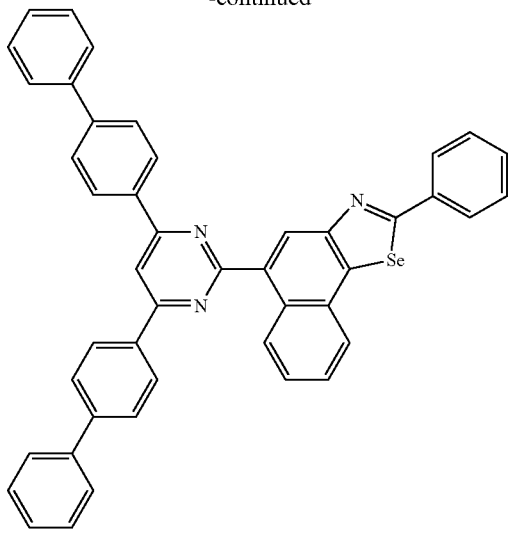 | 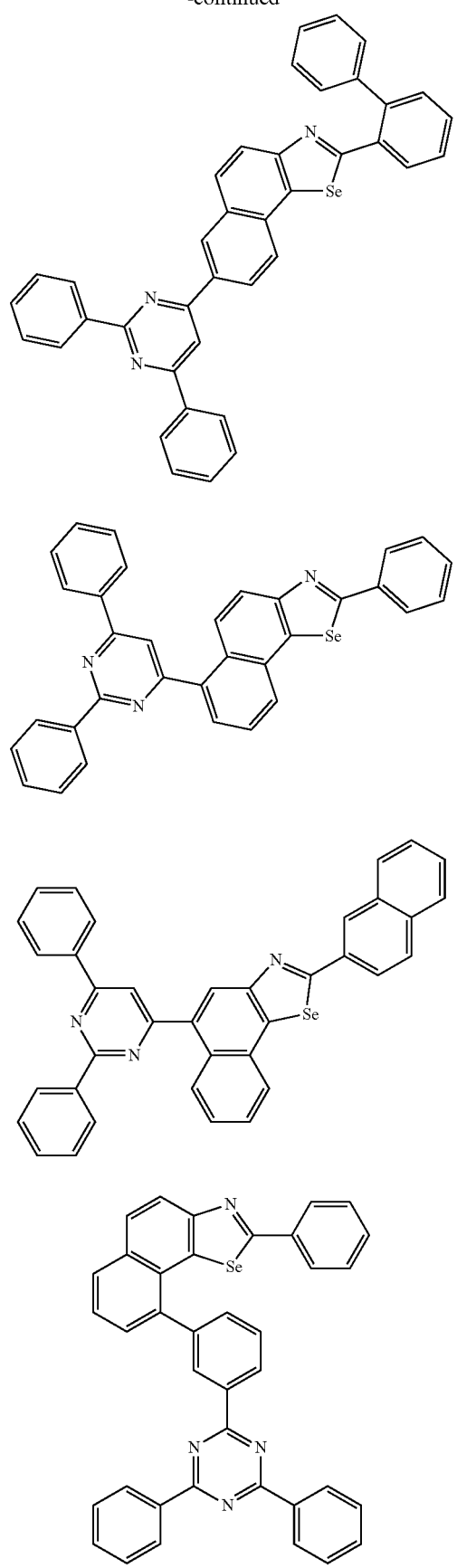 |

471
-continued
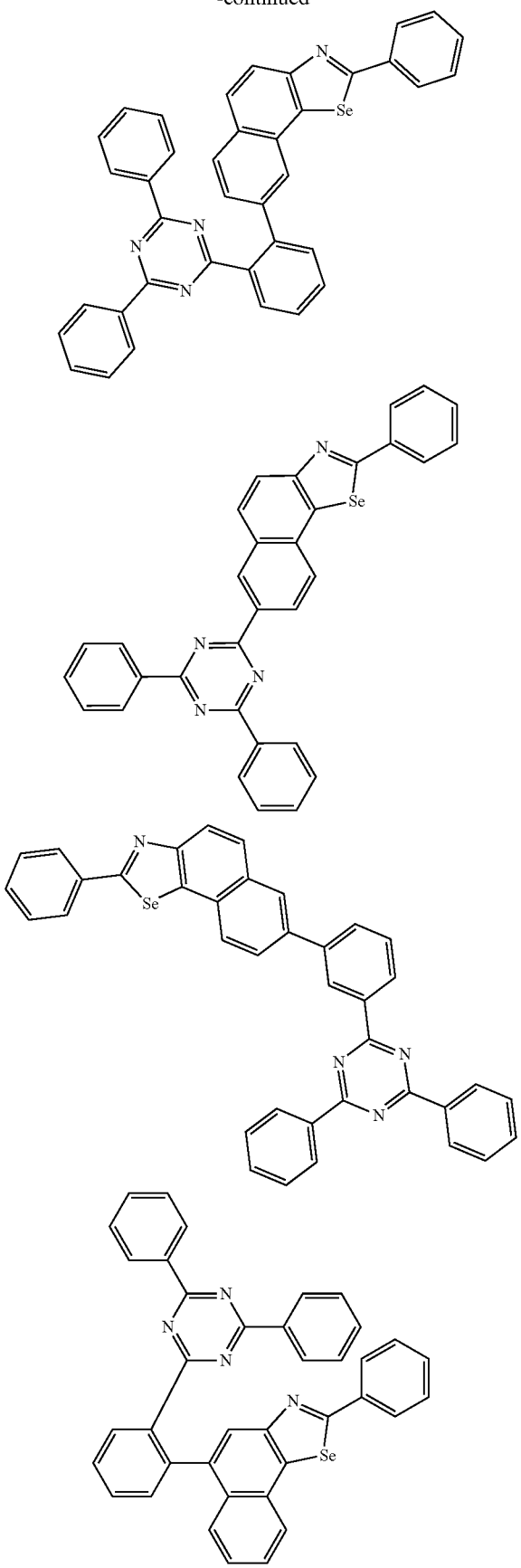
472
-continued
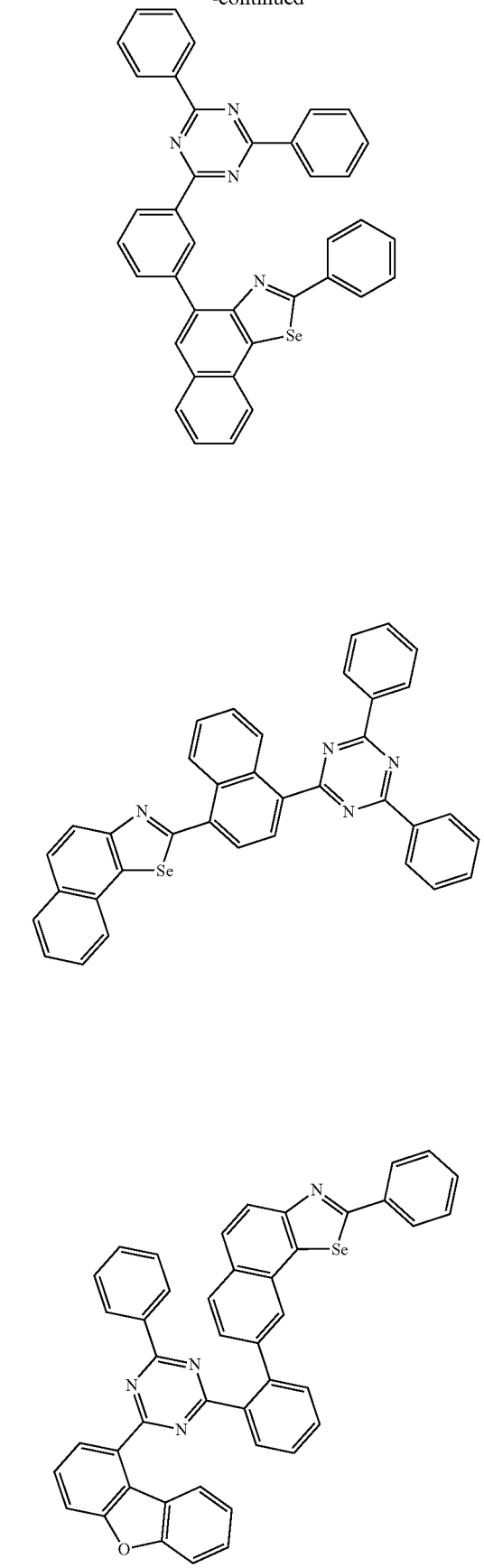

473
-continued
474
-continued
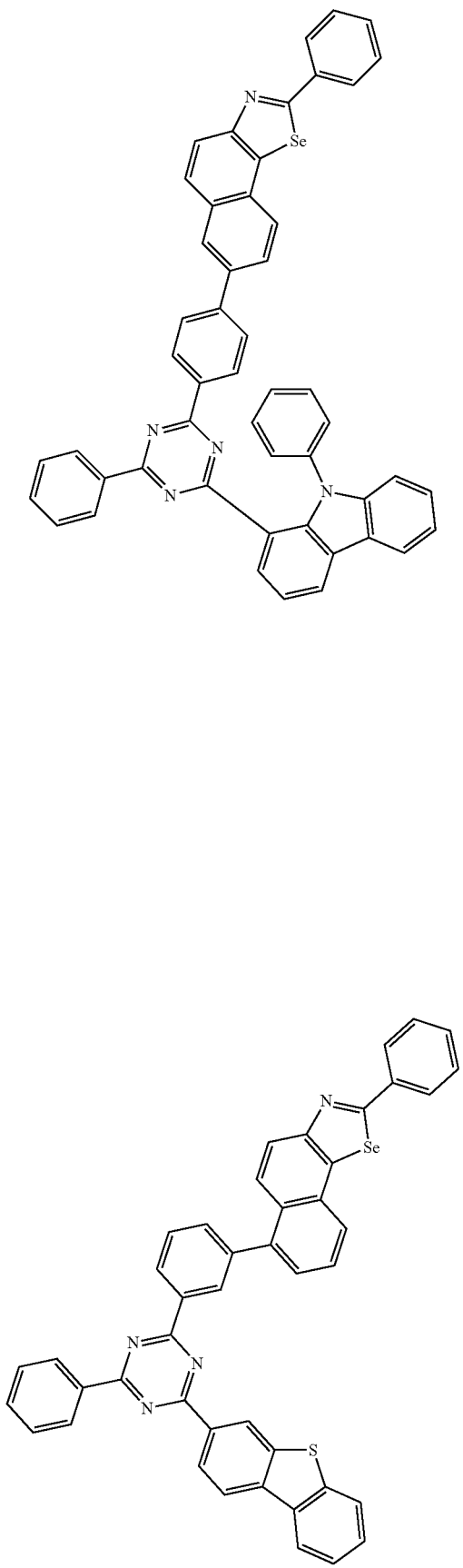
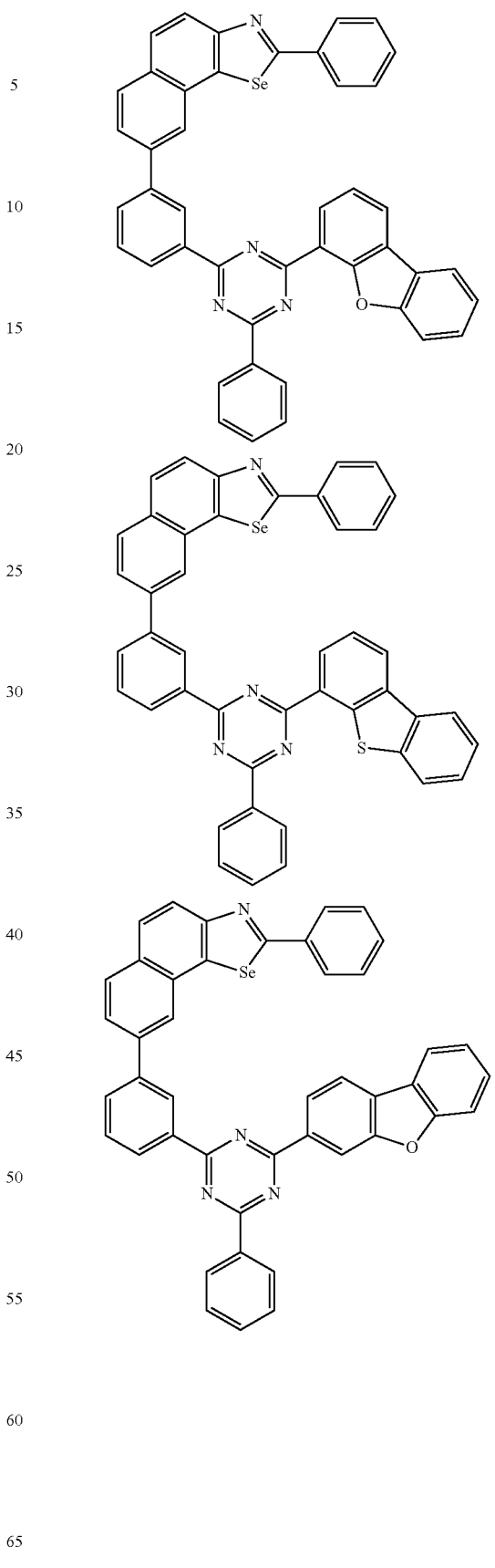

475
-continued
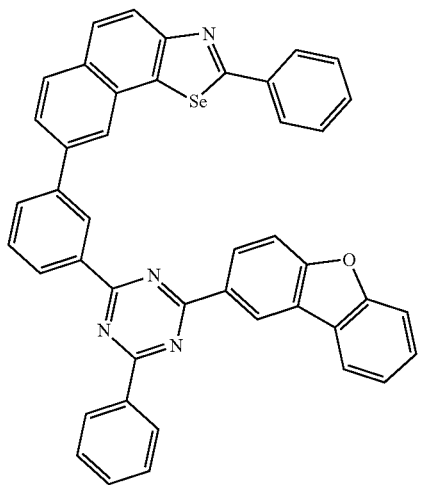
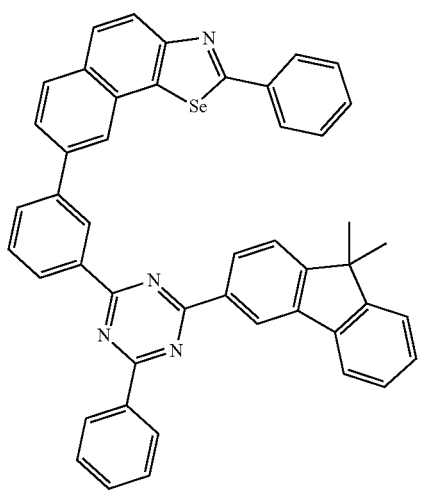
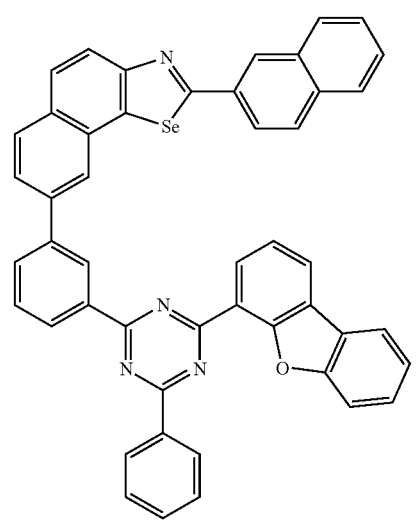
476
-continued
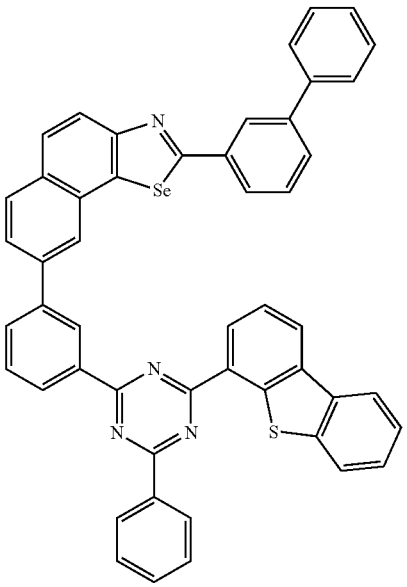
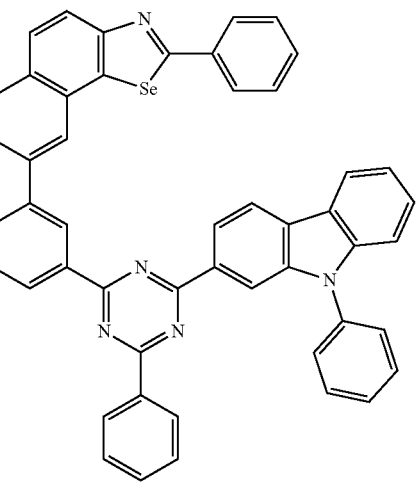
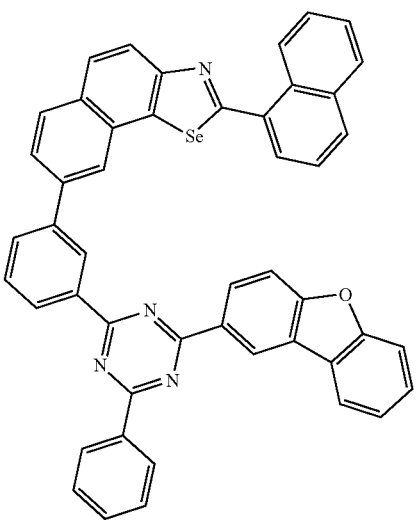

477
-continued
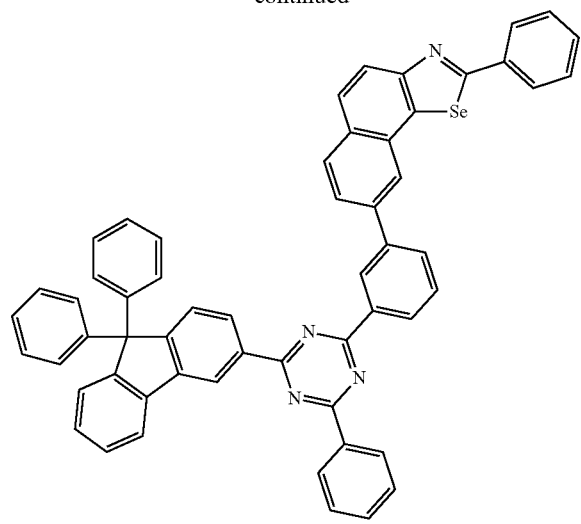
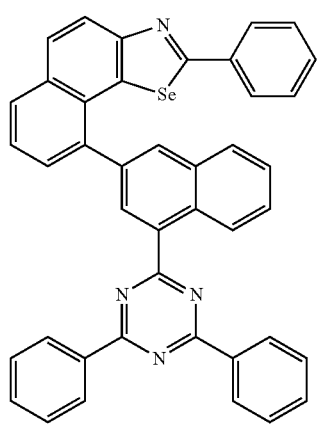
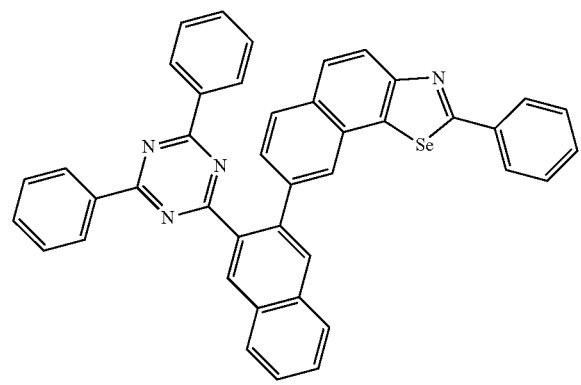
478
-continued
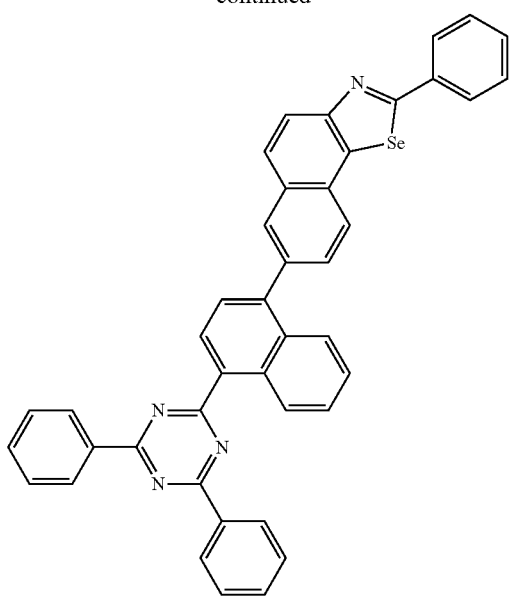
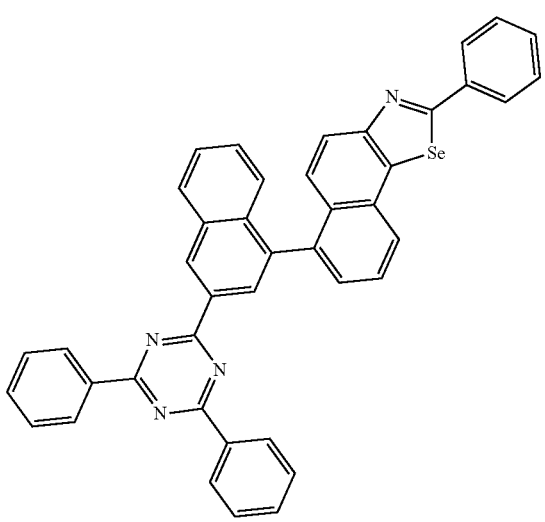
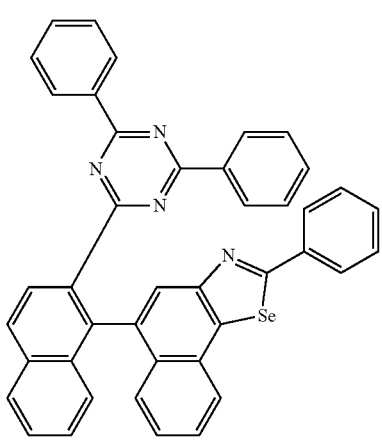

479
-continued
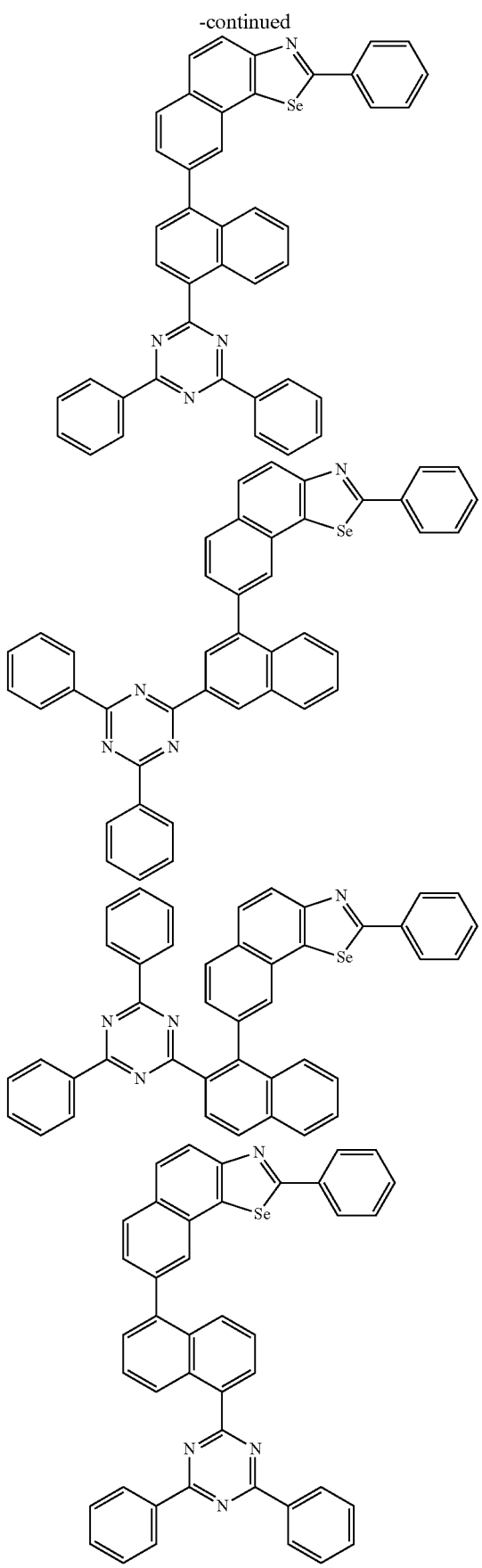
480
-continued
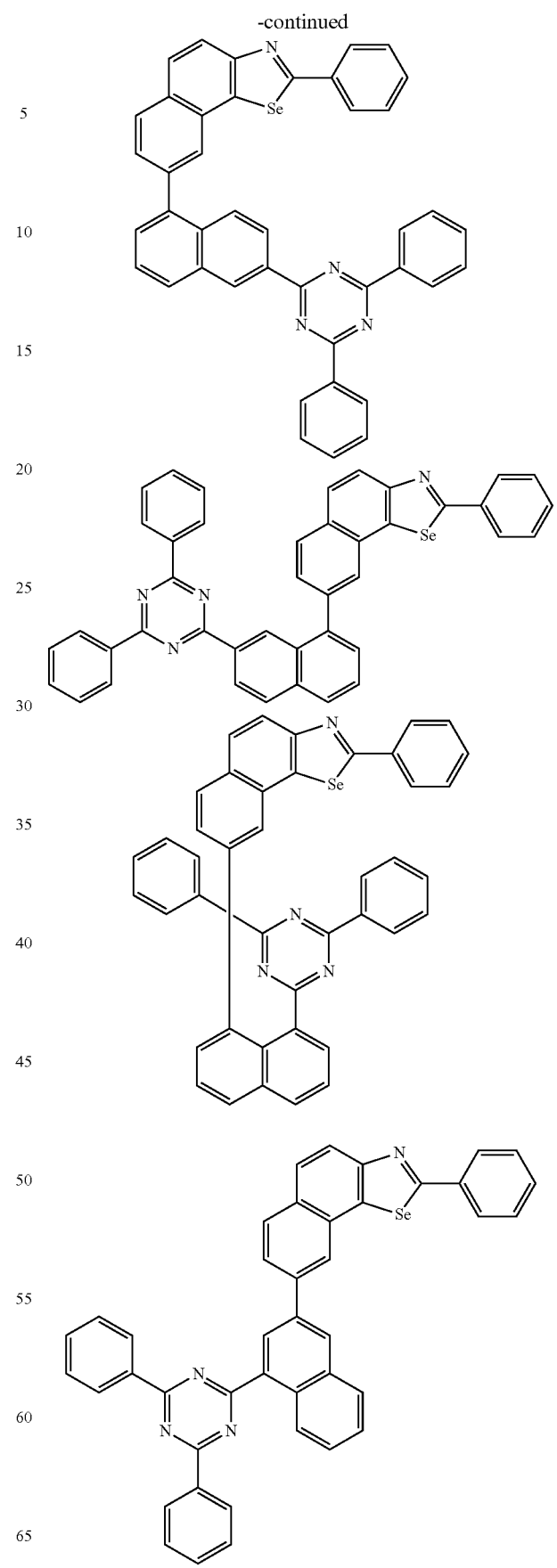

481
-continued
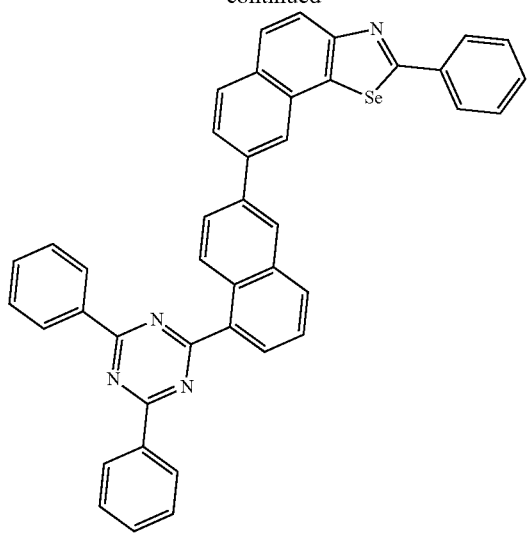
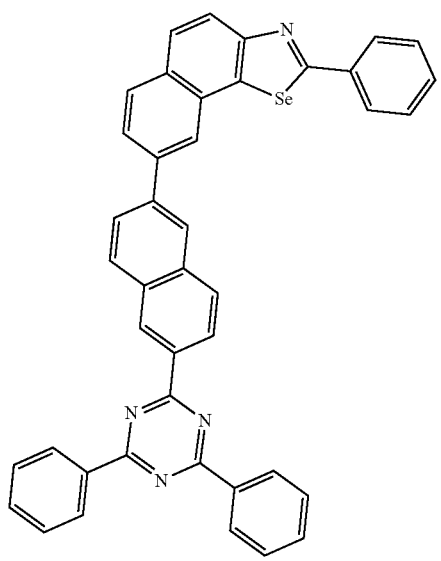
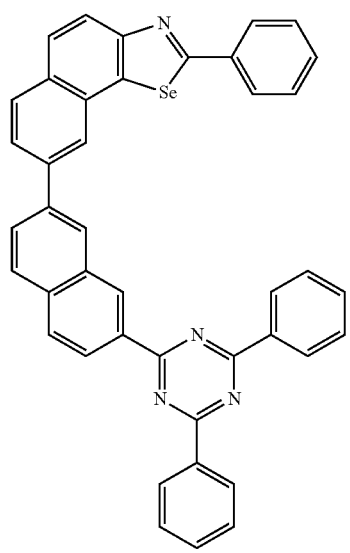
482
-continued
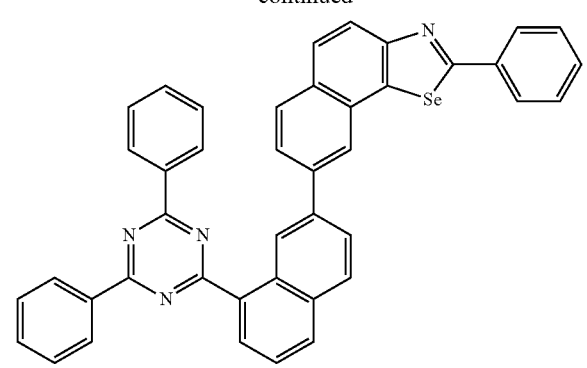
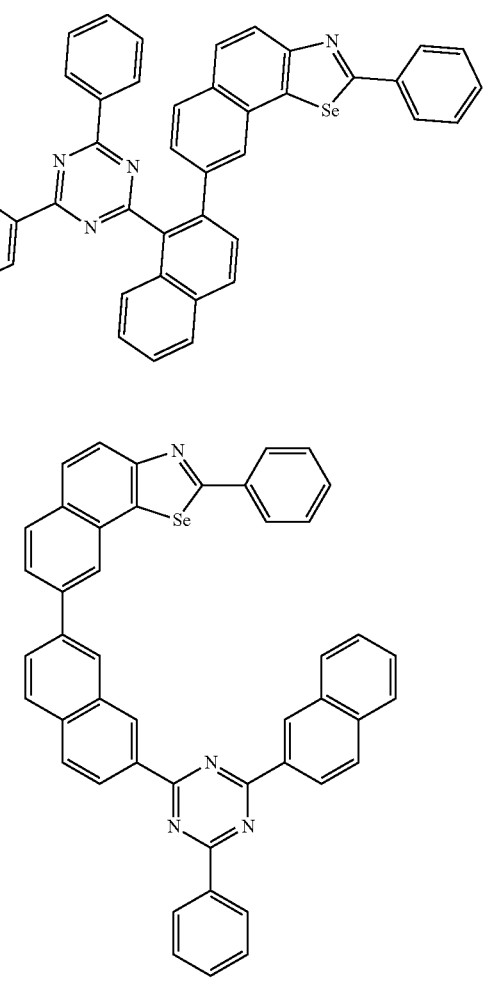

483
-continued
484
-continued
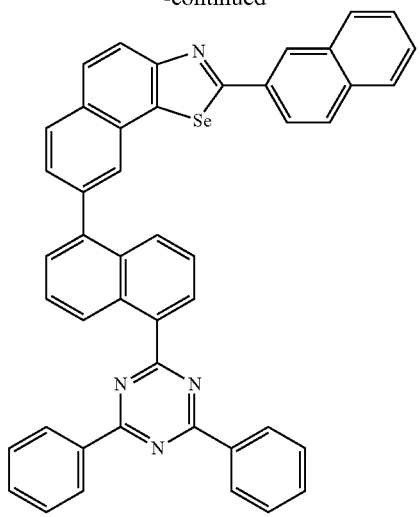
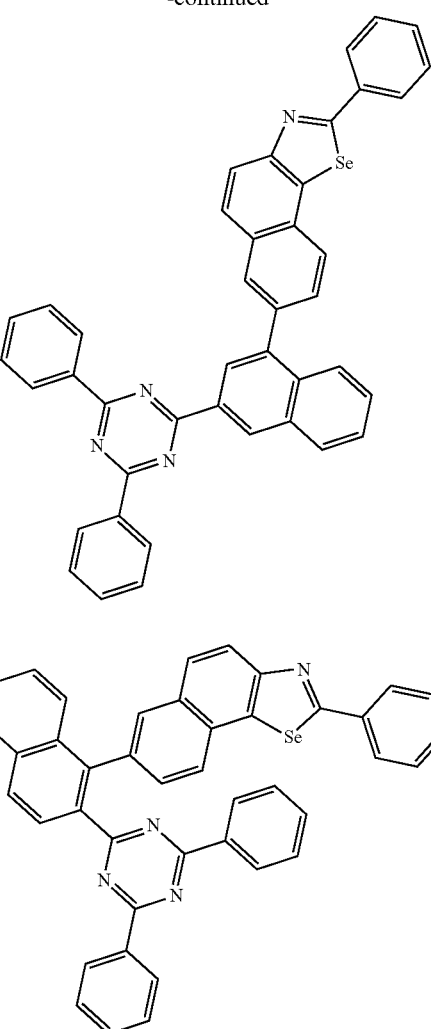
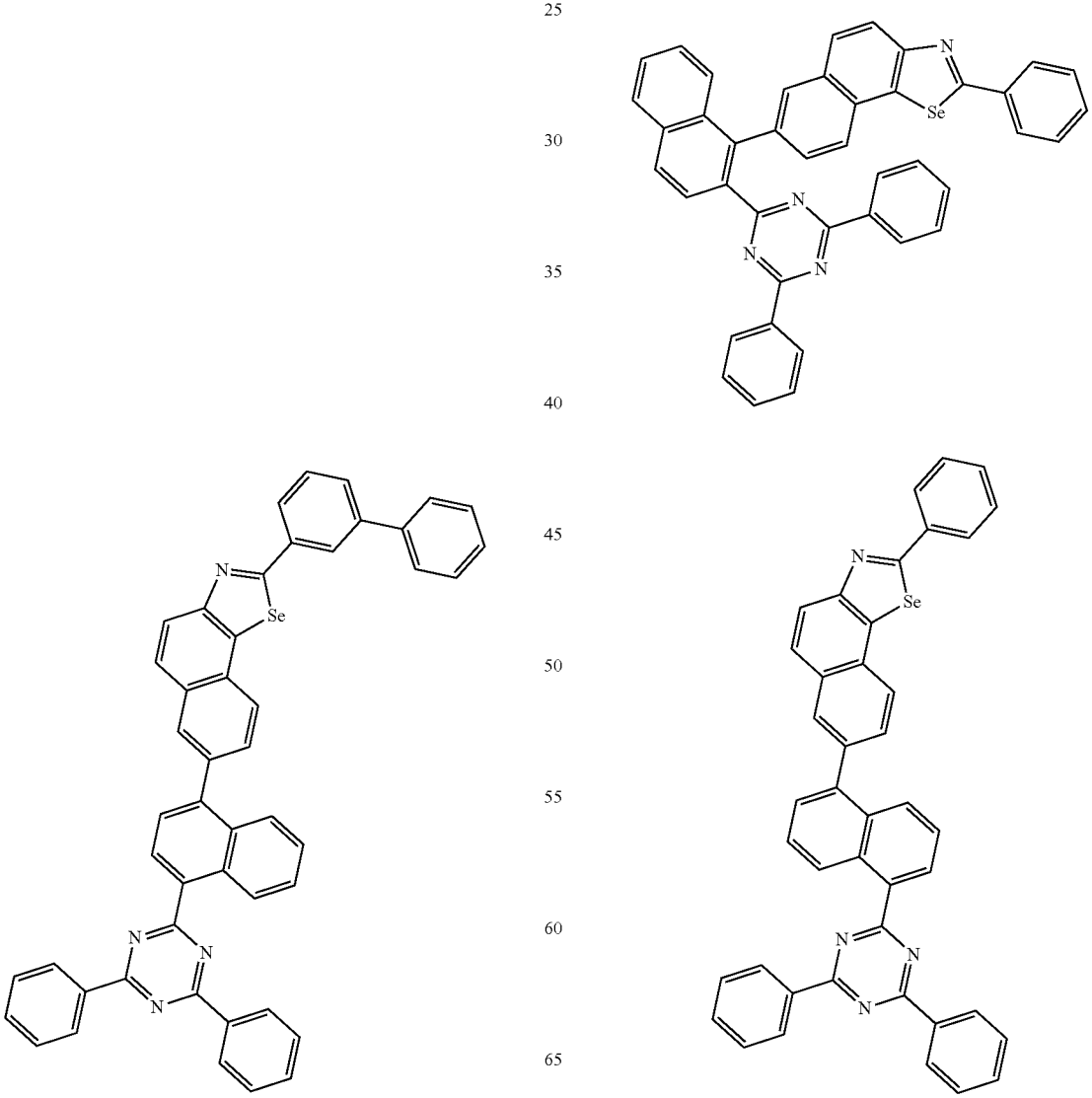
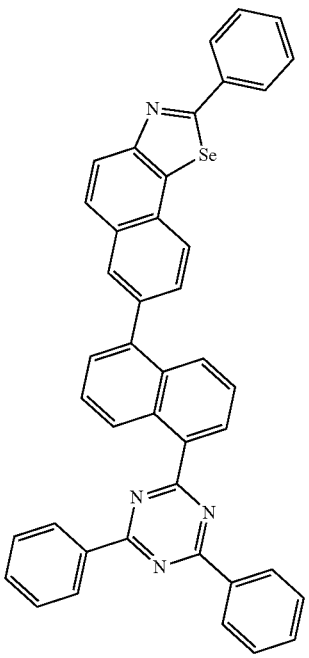

485
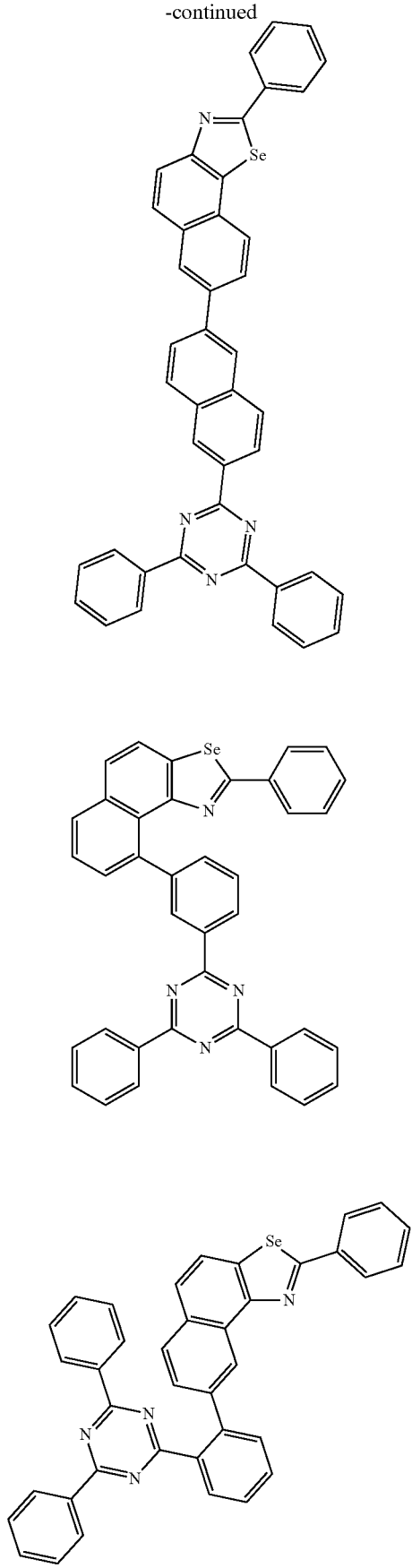
486

487
-continued
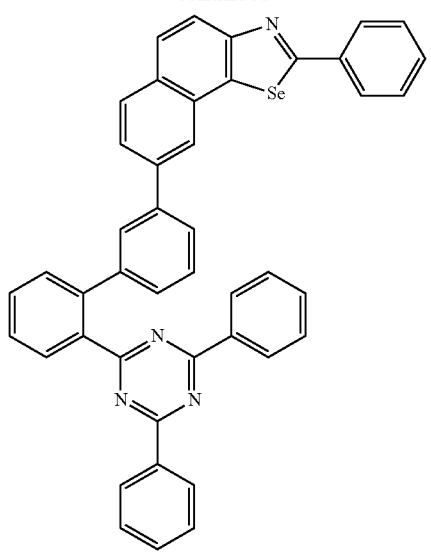
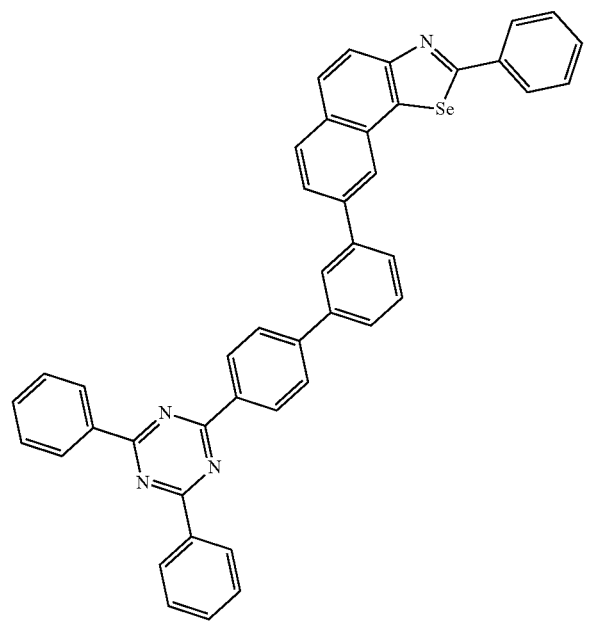
488
-continued
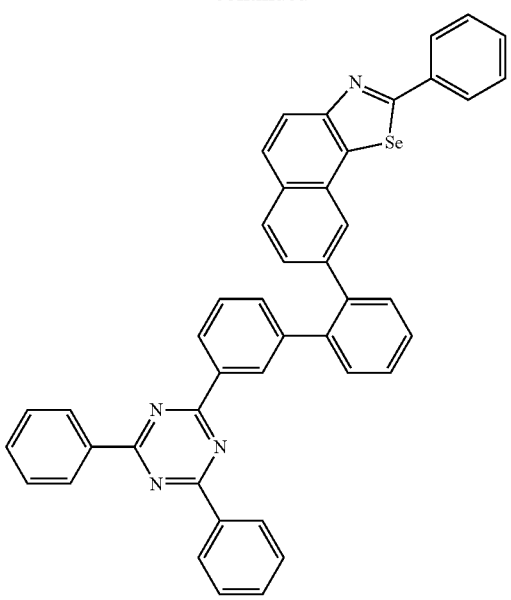
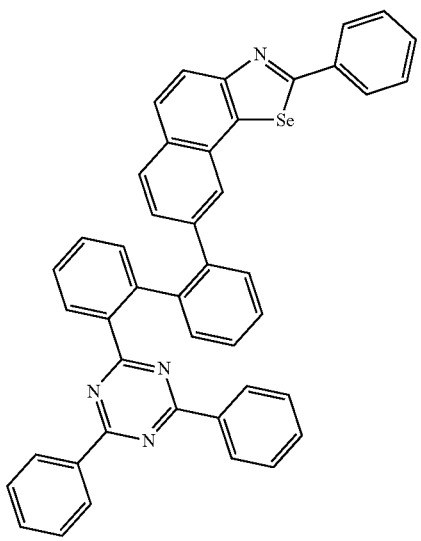

489
-continued
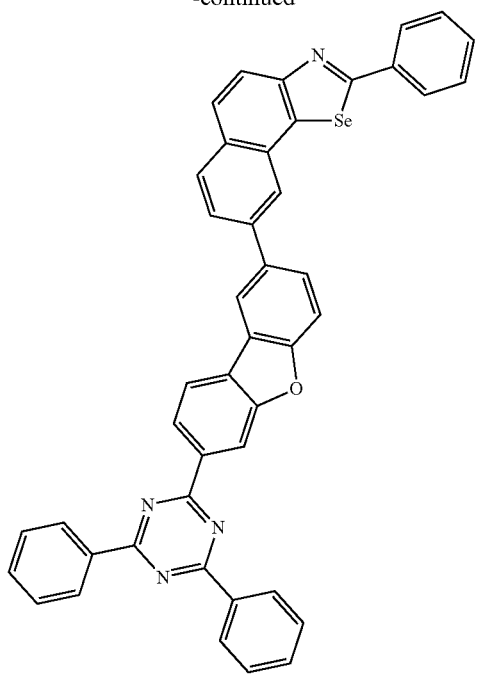
490
-continued
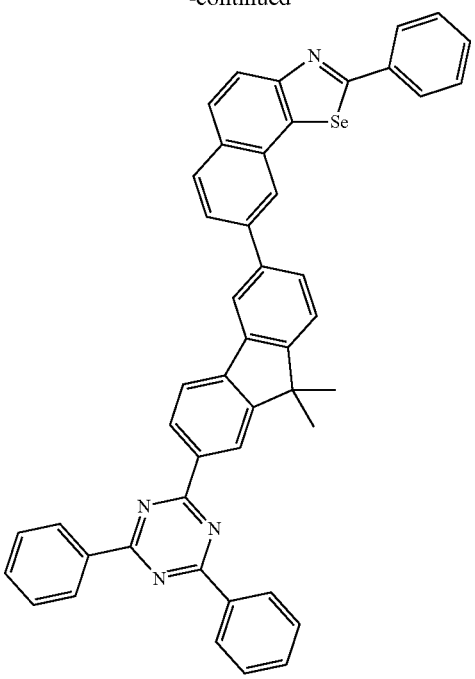
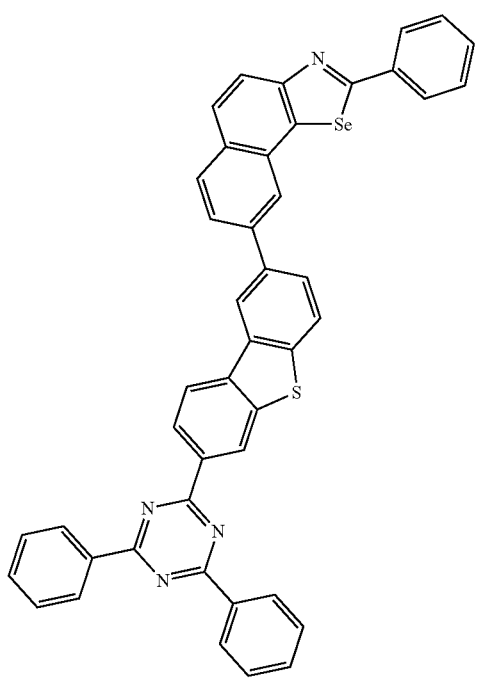

491
-continued
492
-continued
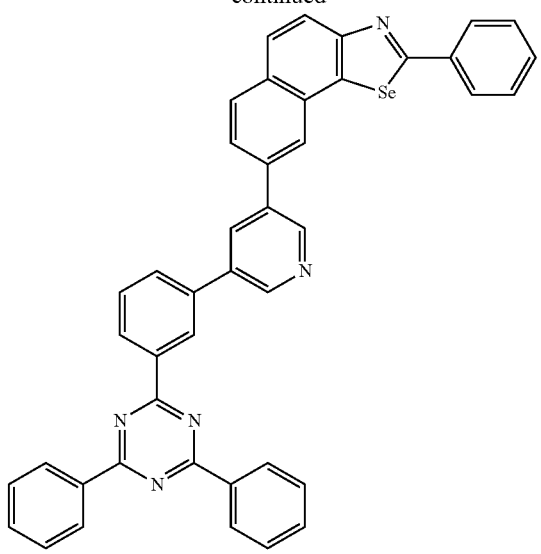
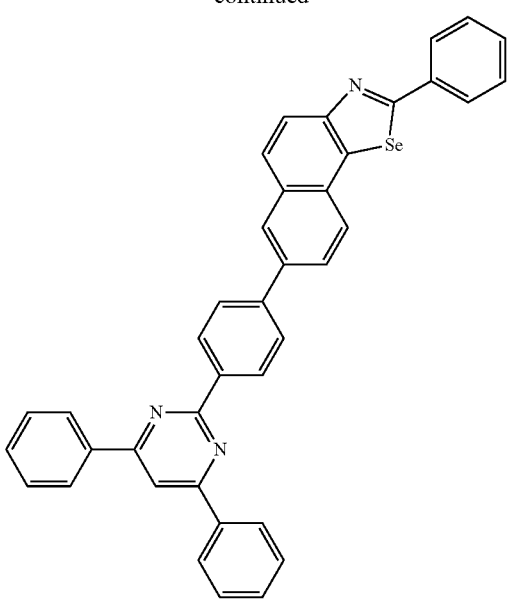
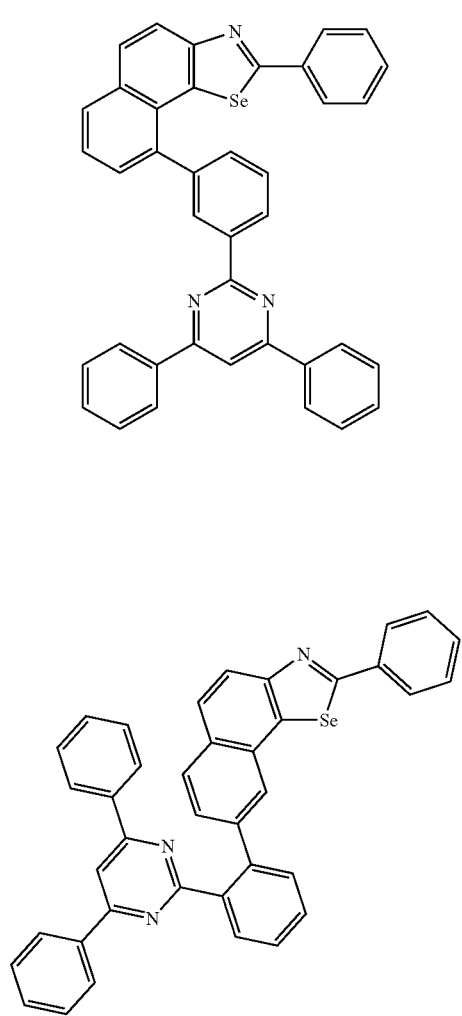

493
-continued
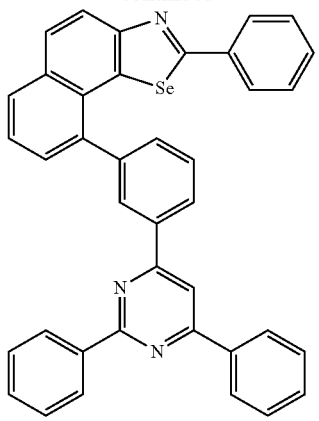
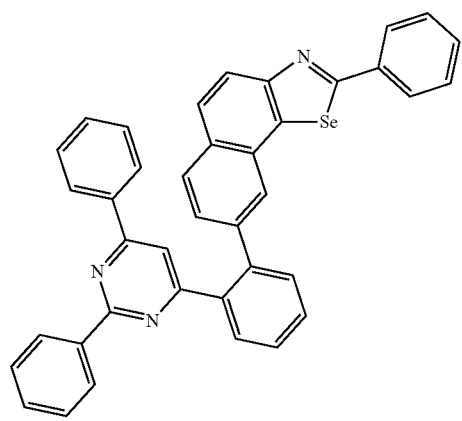
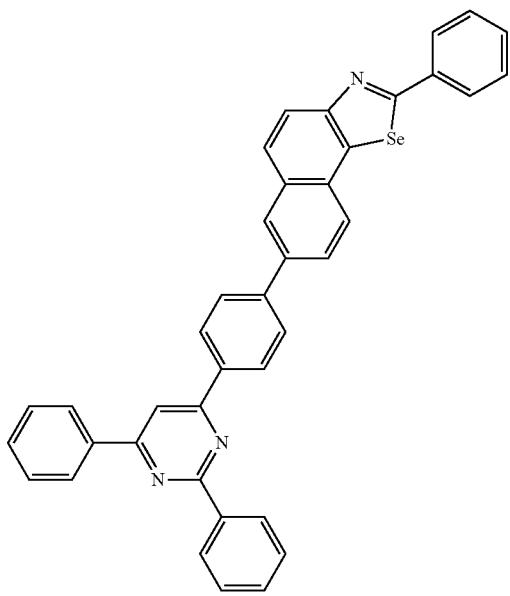
494
-continued
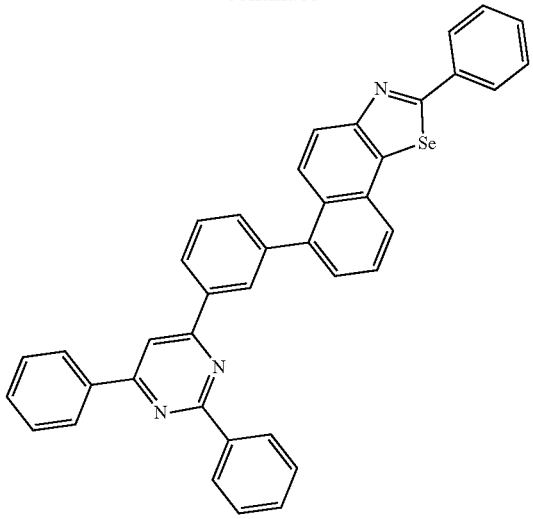
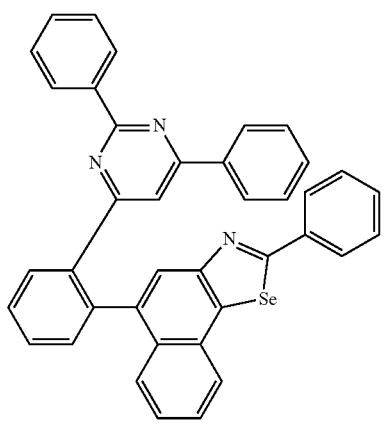
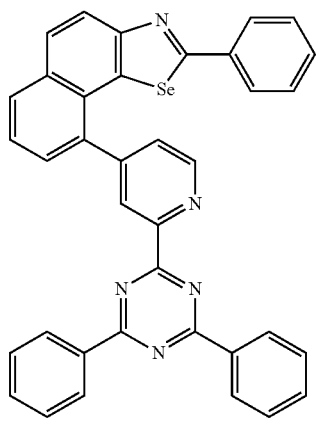

495
-continued
496
-continued
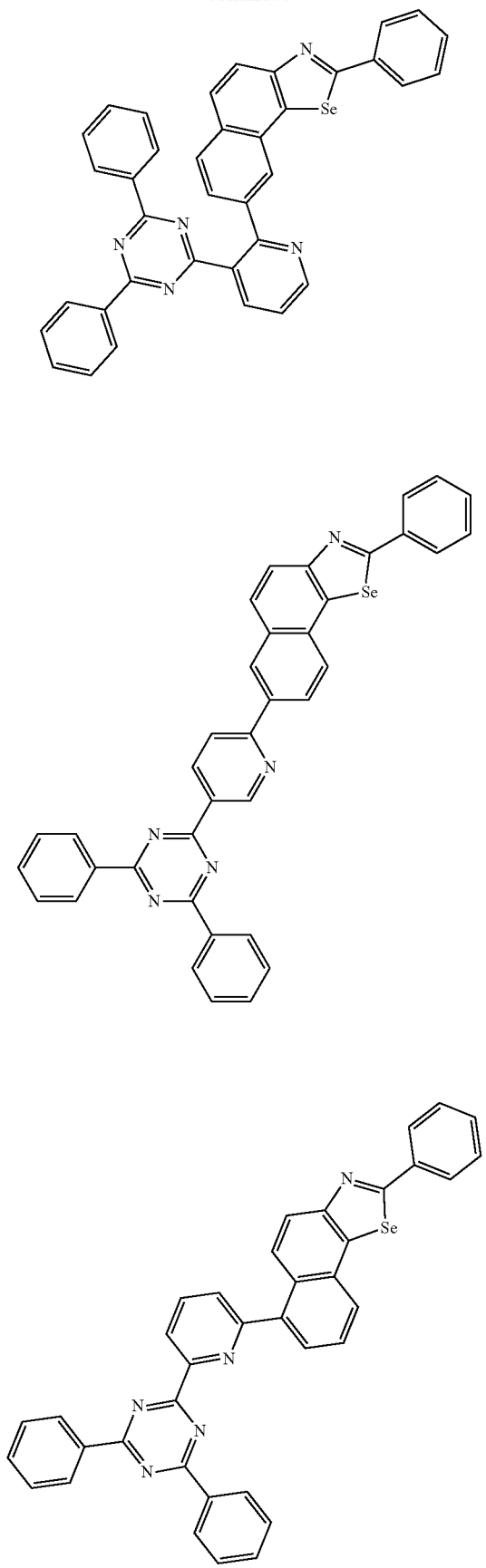
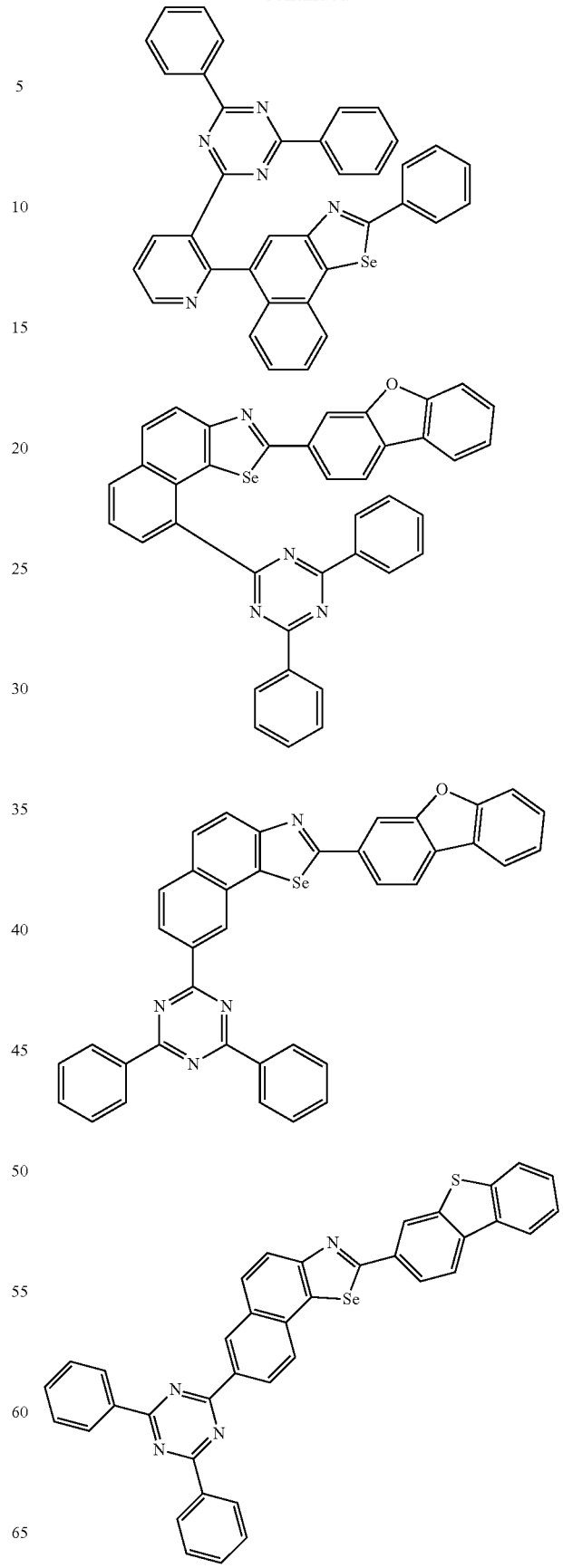

497
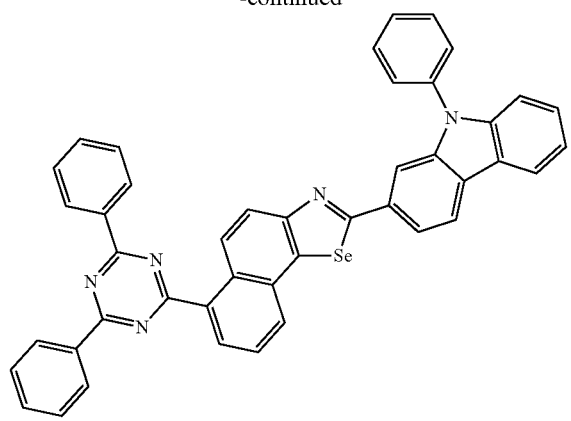
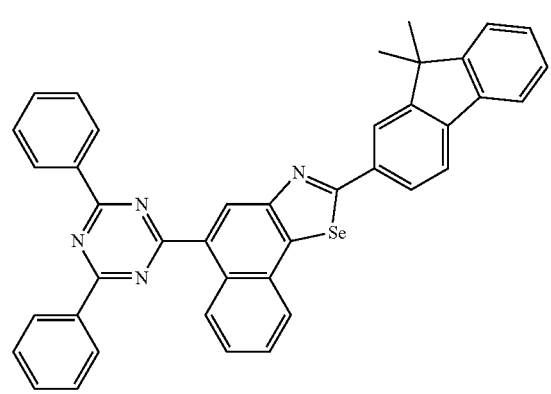
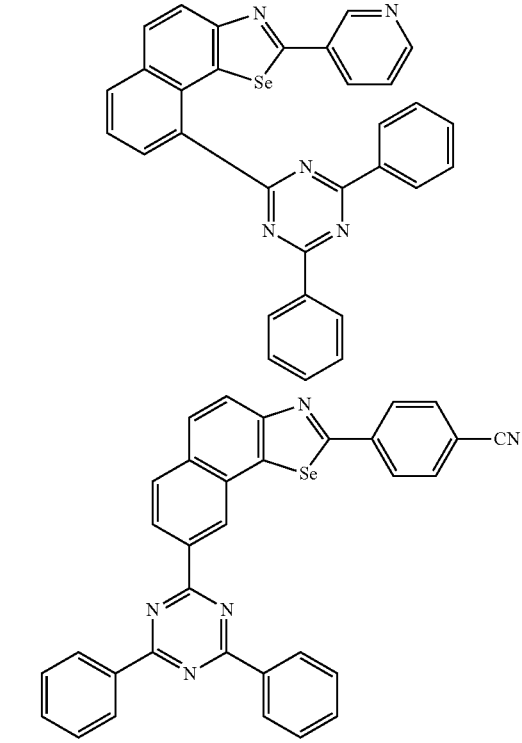
498
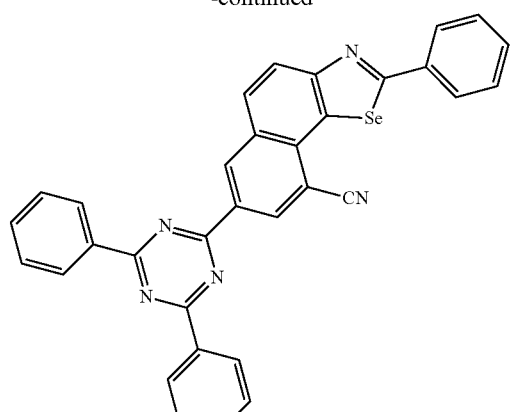
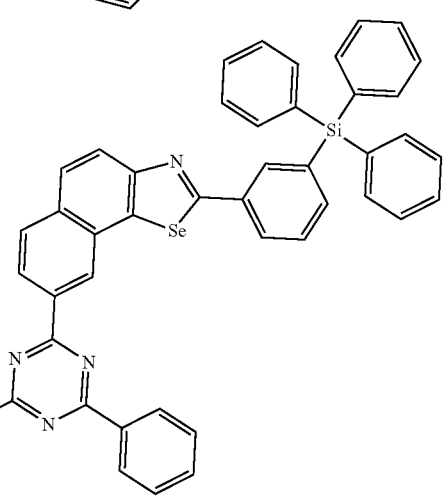

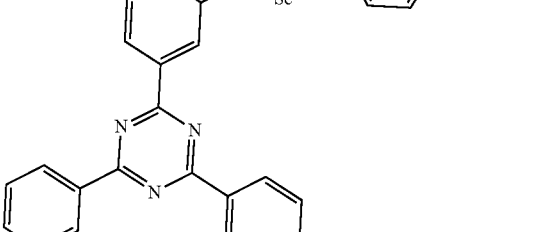
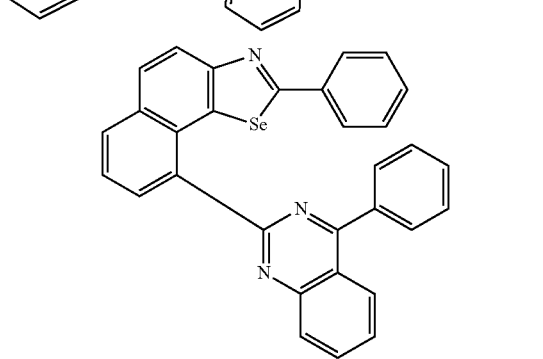

499
-continued
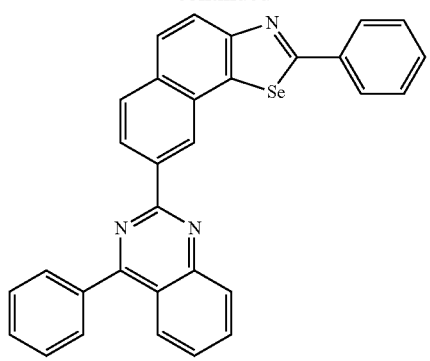
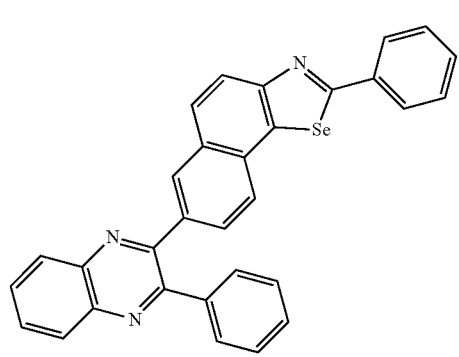
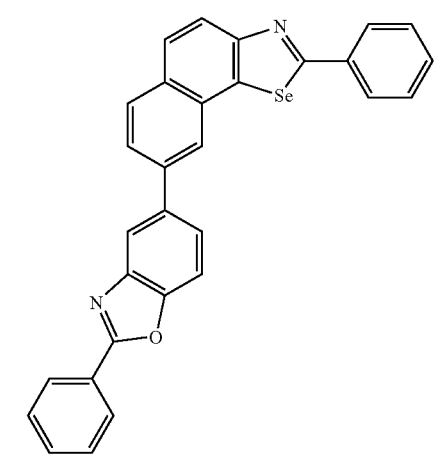
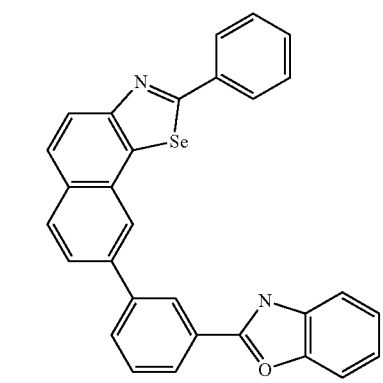
500
-continued
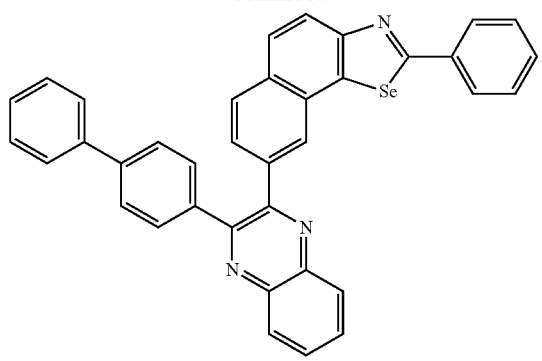
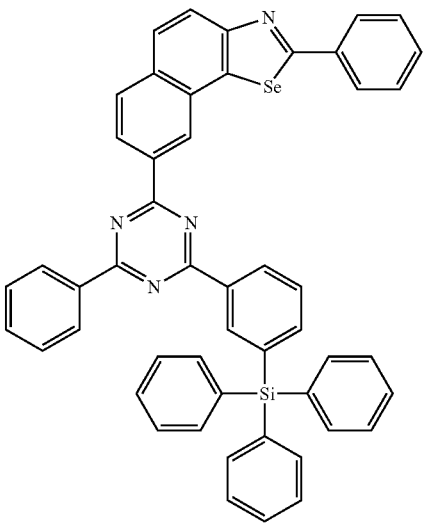
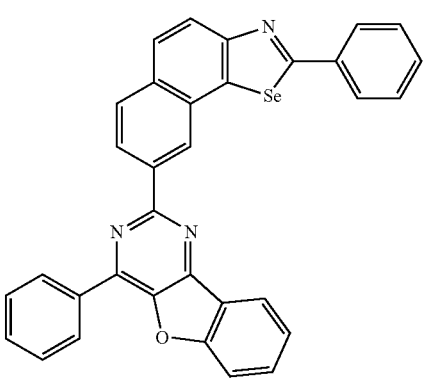
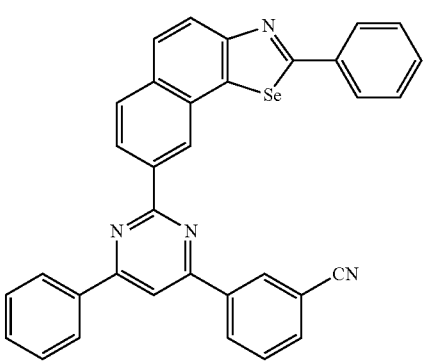

501
-continued
502
-continued
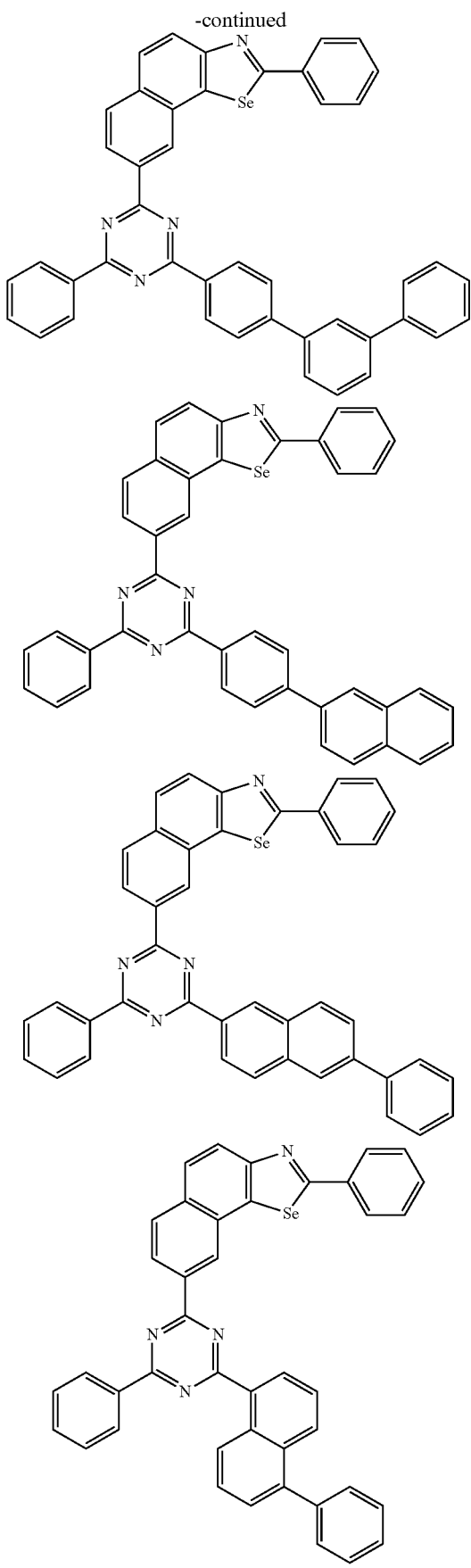
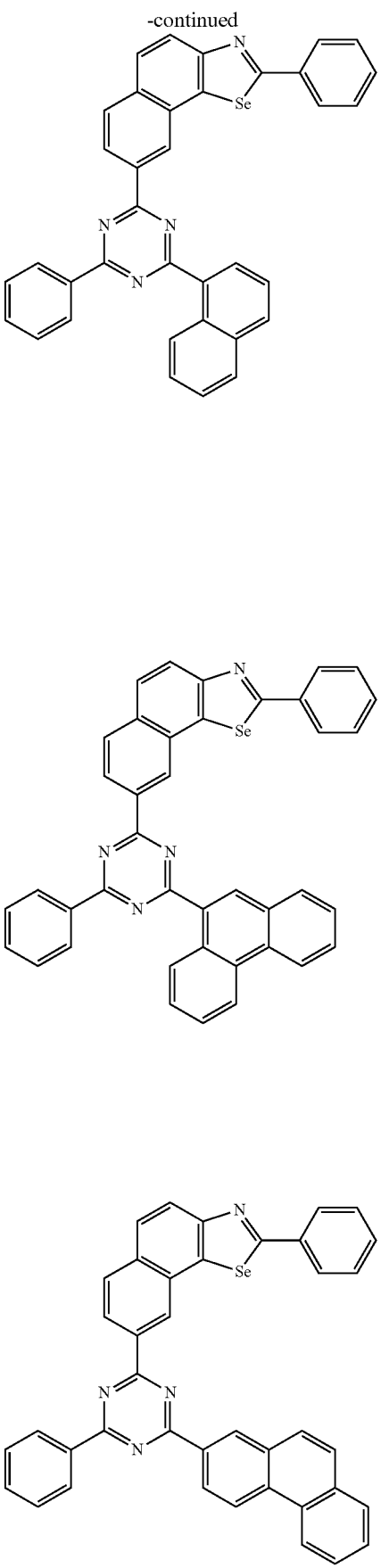

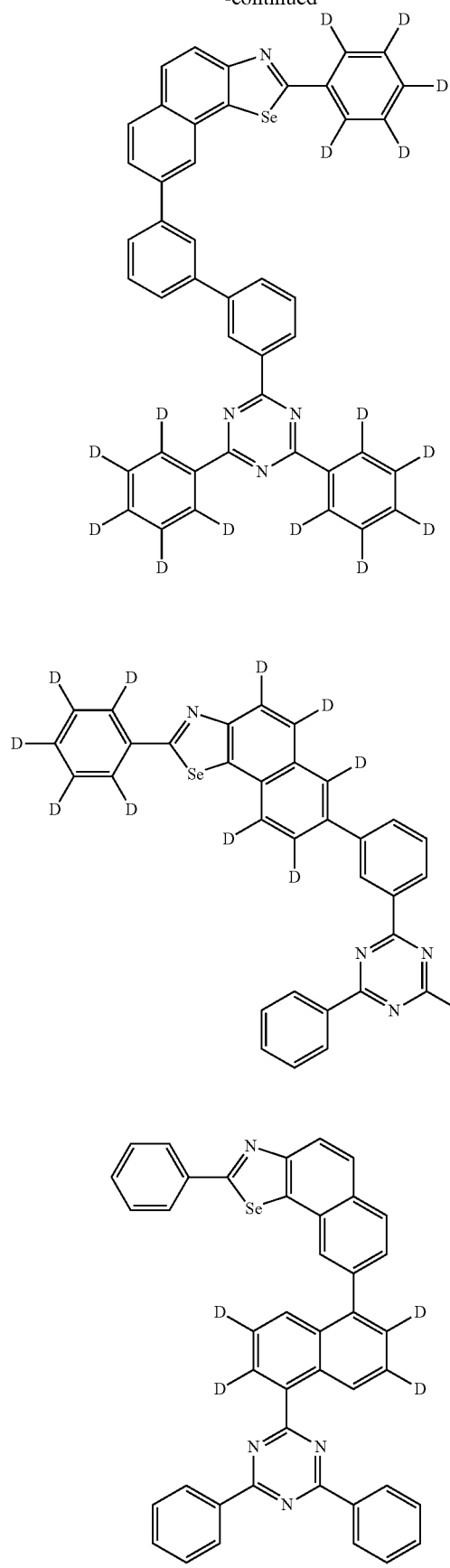

505
-continued
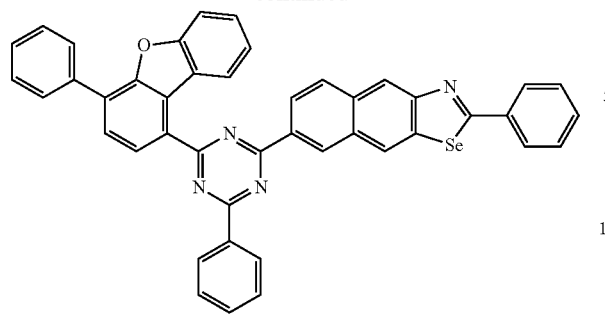
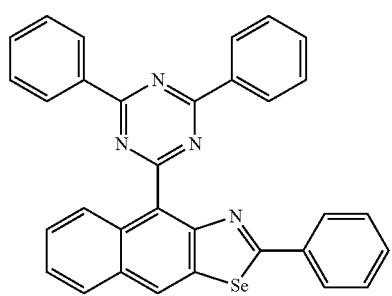
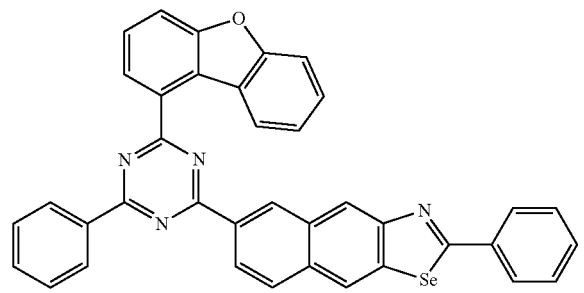
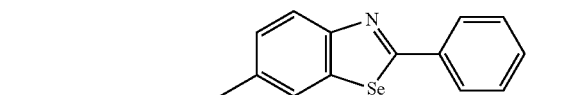

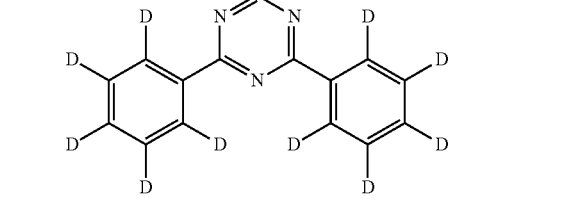
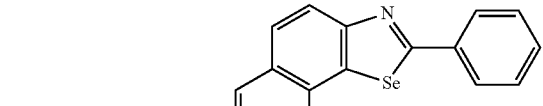
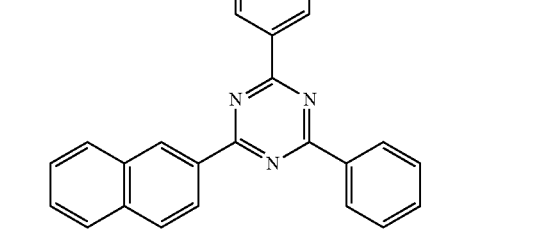
506
-continued
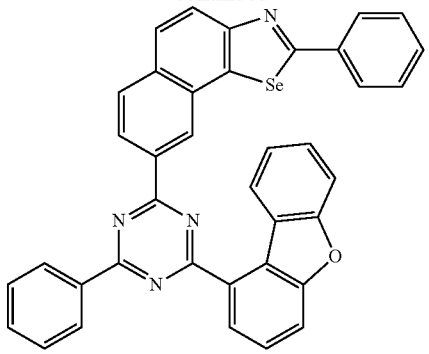
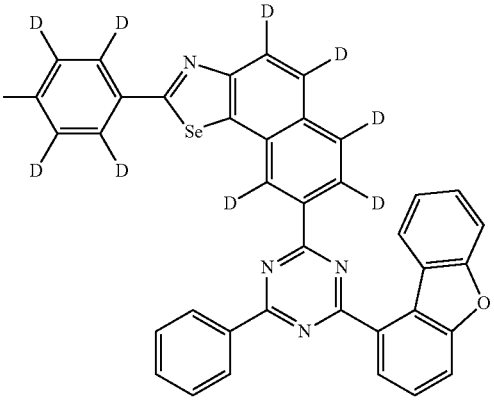
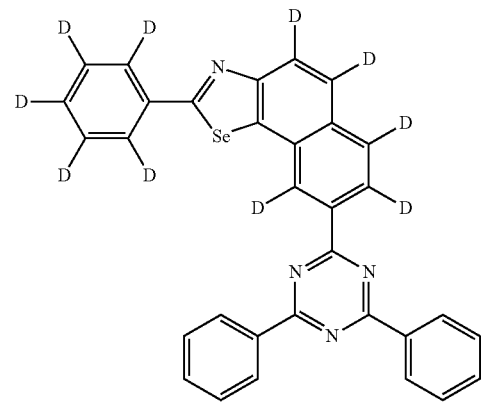

507
-continued

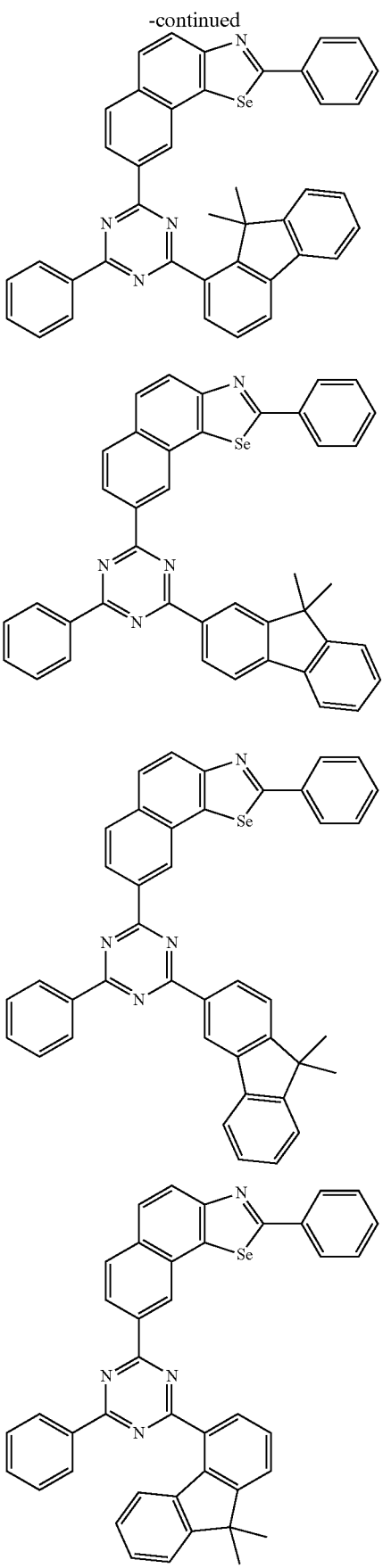

508
-continued

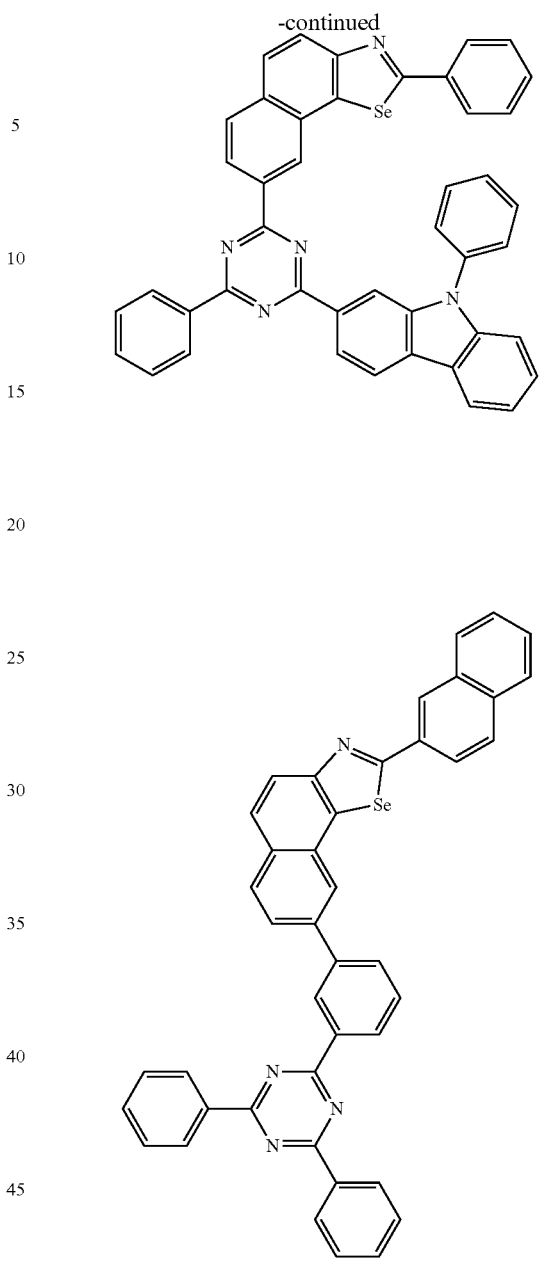

The dopant comprised in the organic electroluminescent device of the present disclosure may be at least one phosphorescent or fluorescent dopant, and is preferably a phosphorescent dopant. The phosphorescent dopant material applied to the organic electroluminescent device of the present disclosure is not particularly limited, but may be preferably selected from the group consisting of the metallated complex compounds of iridium (Ir), osmium (Os), copper (Cu), and platinum (Pt), more preferably selected from the group consisting of ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may be a compound represented by the following formula 101, but is not limited thereto.

(101)

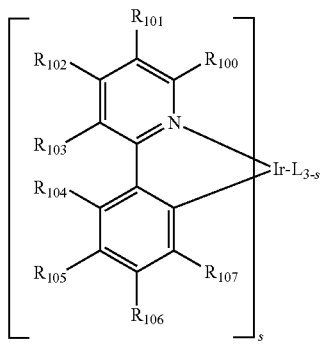

In formula 101,

L is any one selected from the following structures 1 to 3:

[Structure 1]

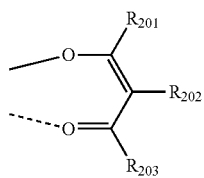

[Structure 2]

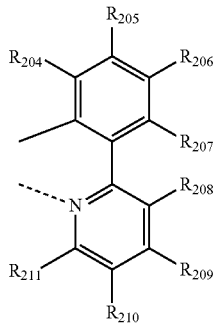

[Structure 3]

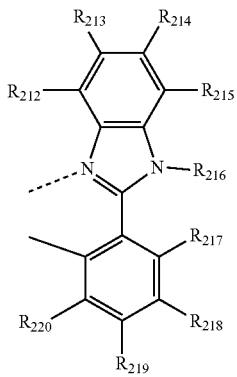

$R_{100}$ to $R_{103}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, benzofuropyridine, benzothienopyridine, indenopyridine, benzofuroquinoline, benzothienoquinoline, or indenoquinoline ring, together with pyridine;

$R_{104}$ to $R_{107}$, each independently, represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring(s), e.g., a substituted or unsubstituted, naphthalene, fluorene, dibenzothiophene, dibenzofuran, indenopyridine, benzofuropyridine, or benzothienopyridine ring, together with benzene;

$R_{201}$ to $R_{220}$, each independently, represent hydrogen, deuterium, a halogen, a (C1-C30)alkyl unsubstituted or substituted with deuterium and/or a halogen(s), a substituted or unsubstituted (C3-C30)cycloalkyl, or a substituted or unsubstituted (C6-C30)aryl; or may be linked to an adjacent substituent to form a substituted or unsubstituted ring(s); and s represents an integer of 1 to 3.

The specific examples of the dopant compound are as follows, but are not limited thereto.

D-1

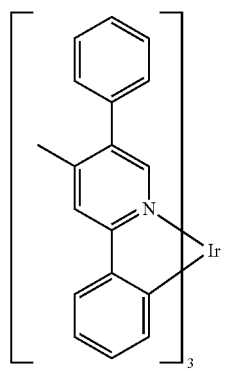

D-2

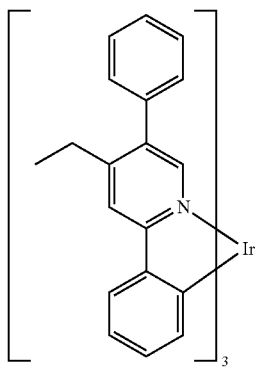

-continued
D-3
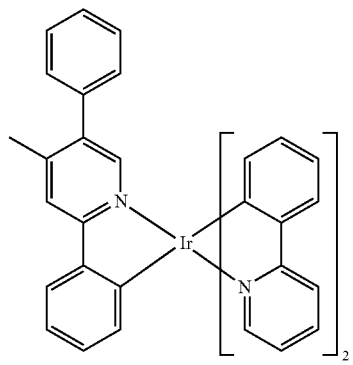
D-4
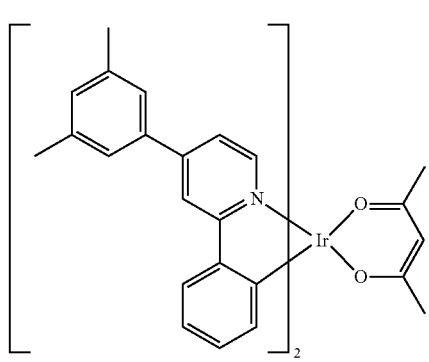
D-5
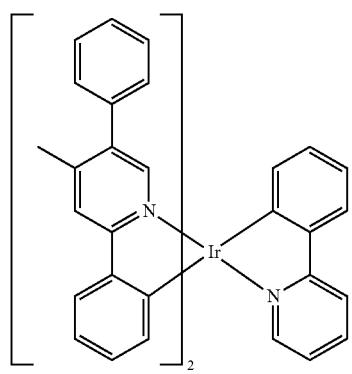
D-6
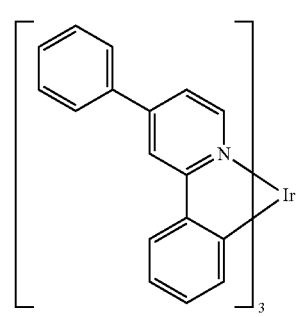
-continued
D-7
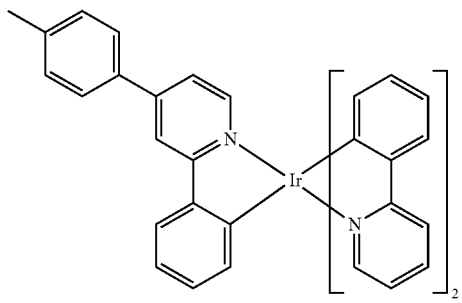
D-8
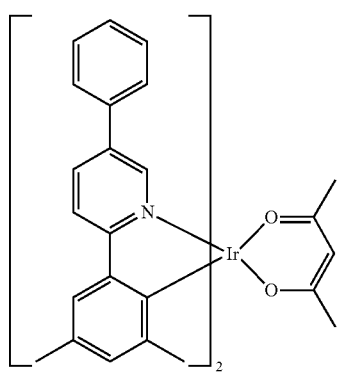
D-9
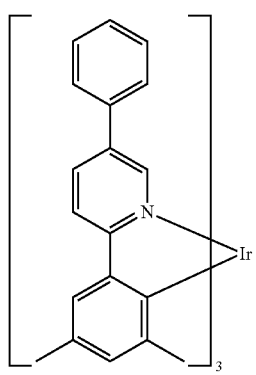
D-10
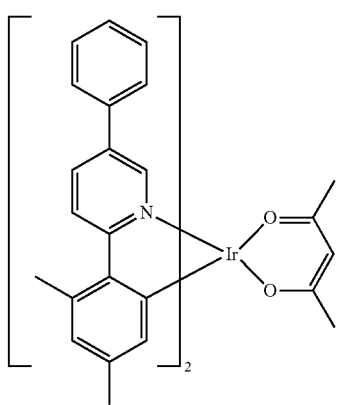

-continued
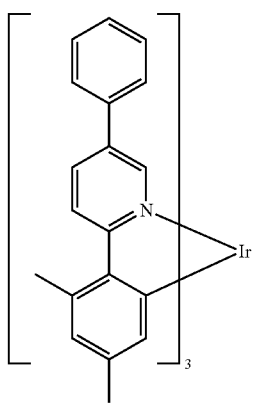
D-11
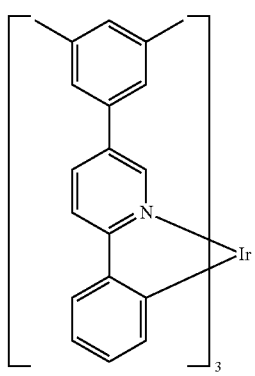
D-12
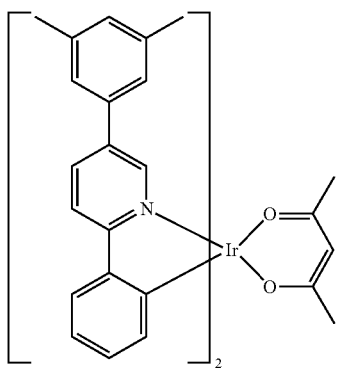
D-13
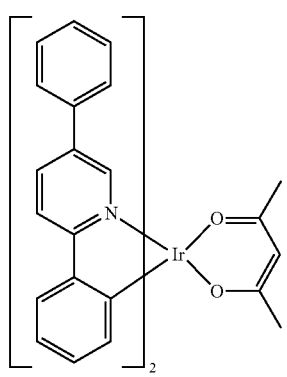
D-14
-continued
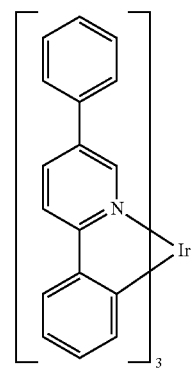
D-15
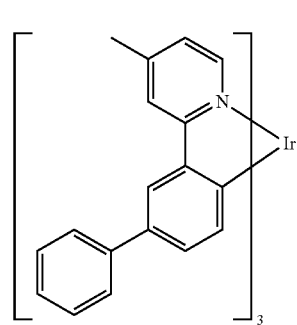
D-16
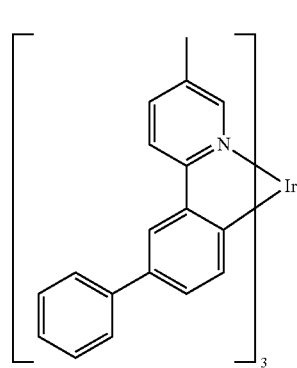
D-17
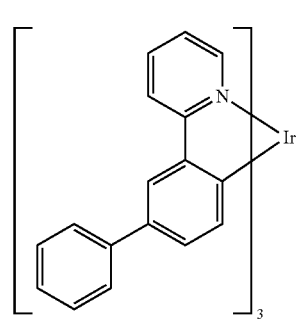
D-18

-continued
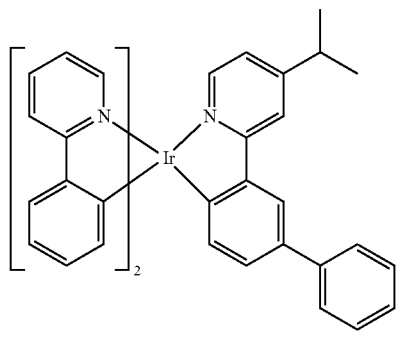
D-19
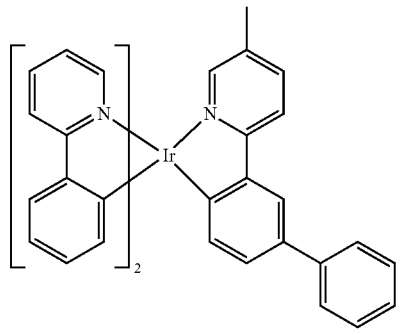
D-23
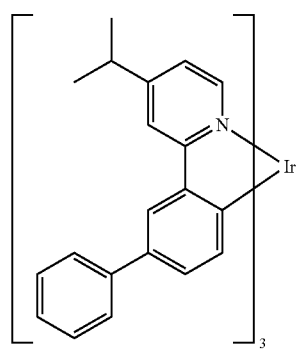
D-20
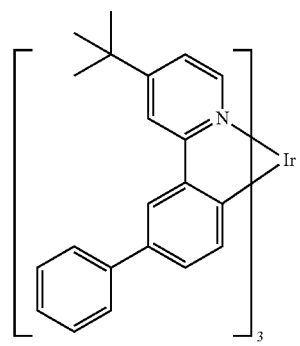
D-24
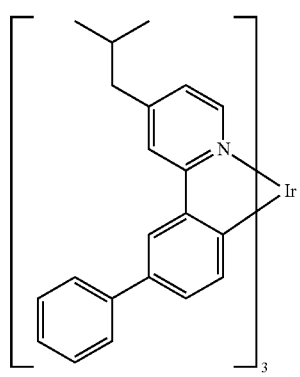
D-21
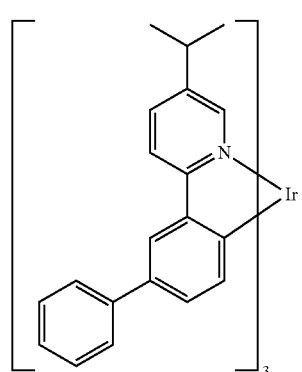
D-25
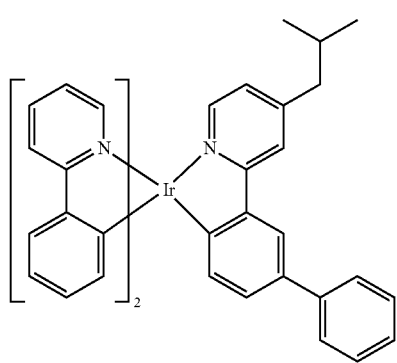
D-22
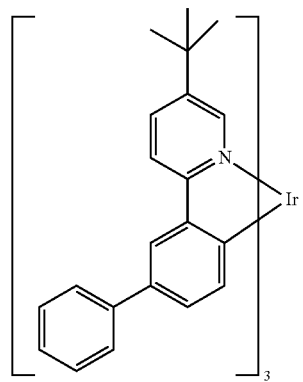
D-26

-continued
D-27
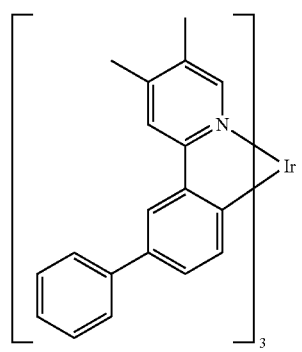
D-28
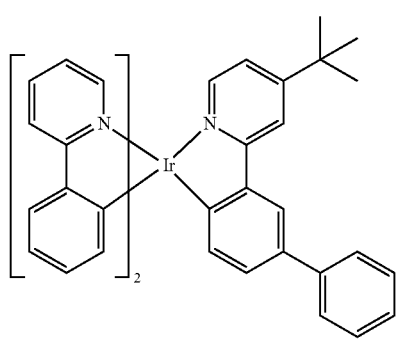
D-29
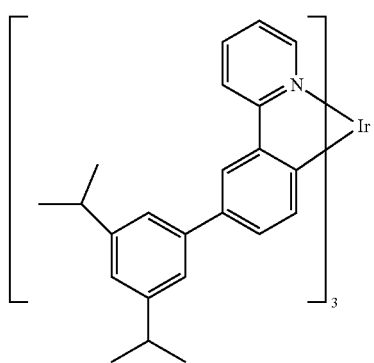
D-30
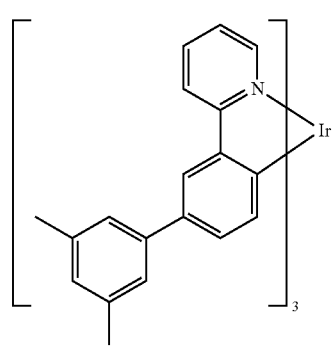
D-31
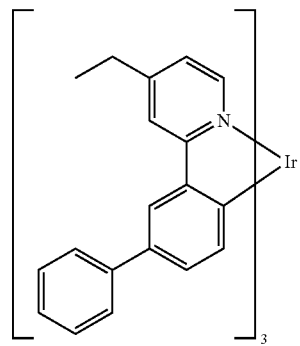
D-32
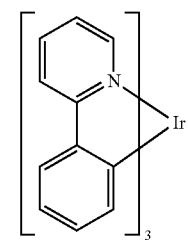
D-33
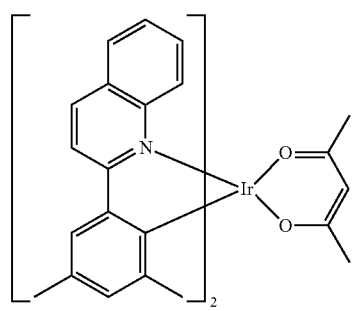
D-34
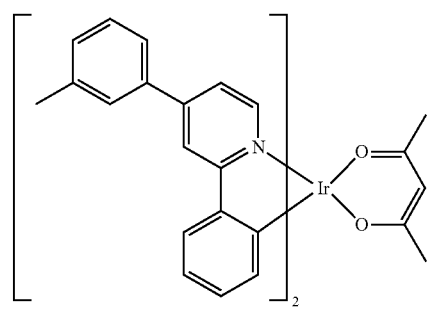
D-35
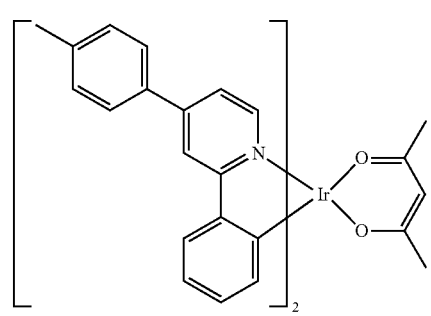

-continued
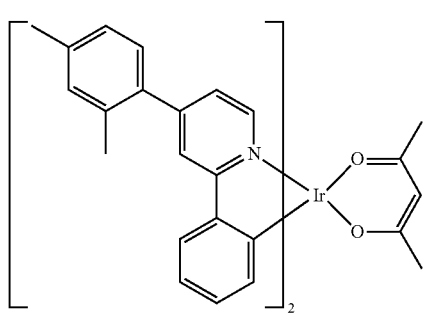
D-36
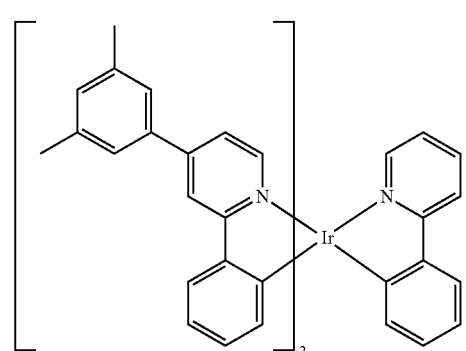
D-40
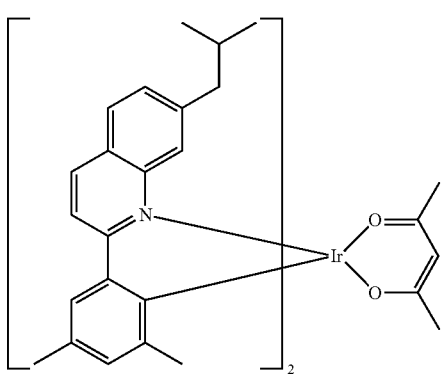
D-37
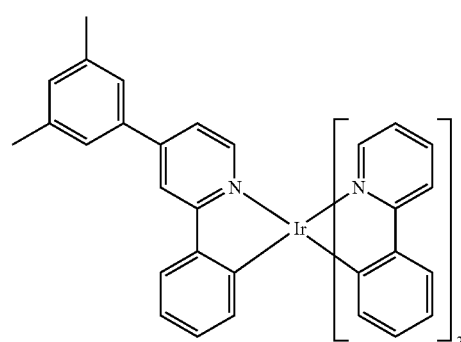
D-41
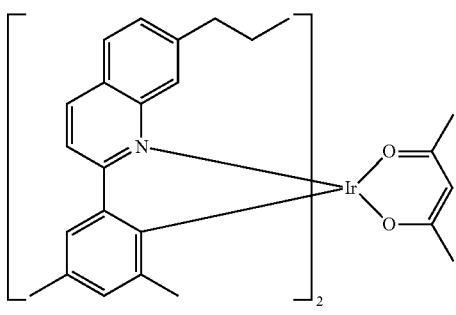
D-38
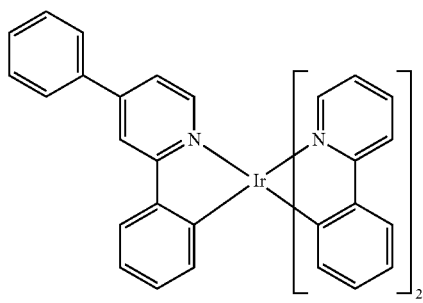
D-42
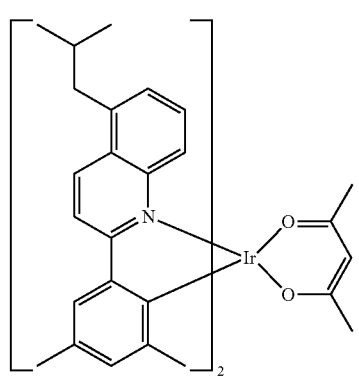
D-39
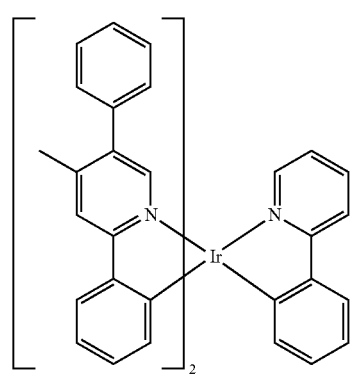
D-43

D-44
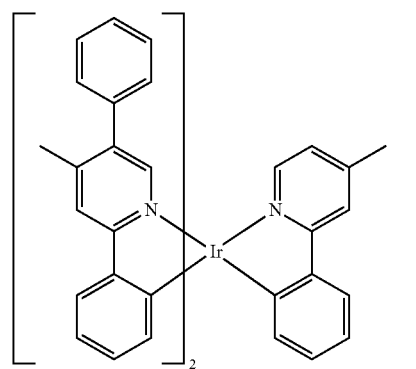
D-45
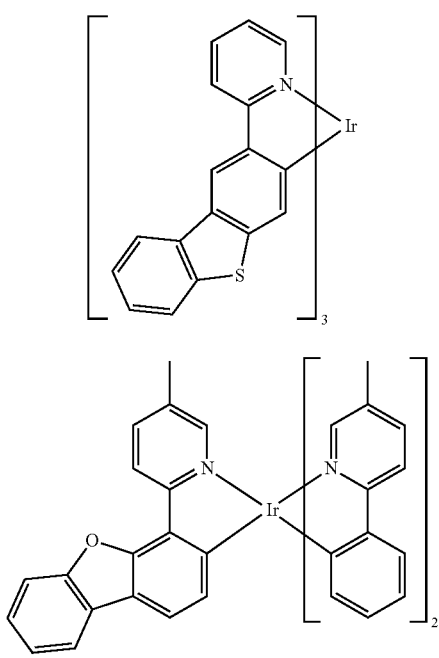
D-46
D-47
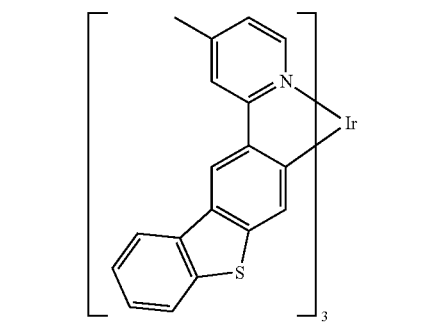
D-48
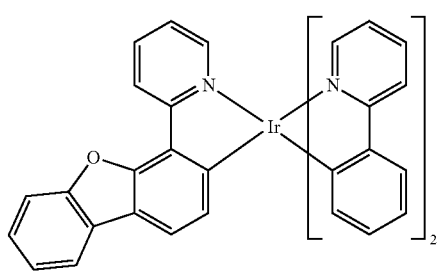
D-49
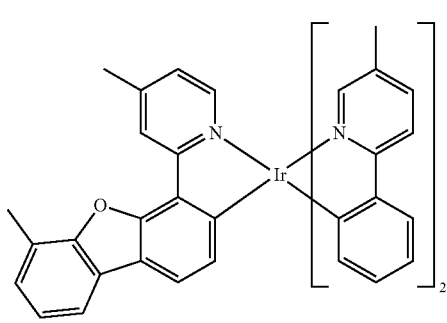
D-50
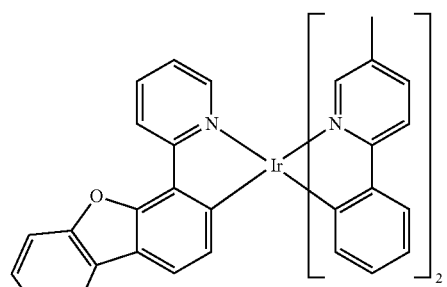
D-51
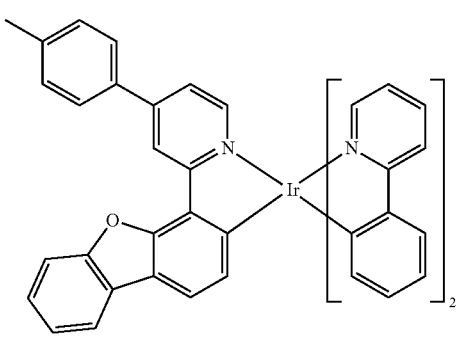
D-52
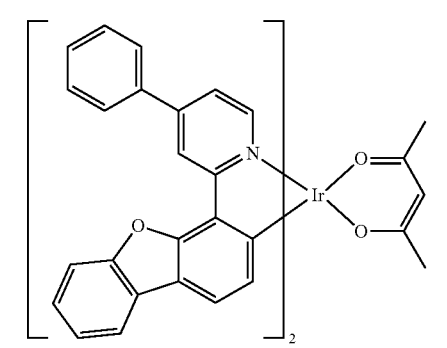
D-53
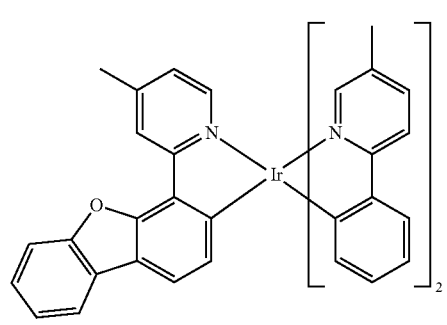

D-54
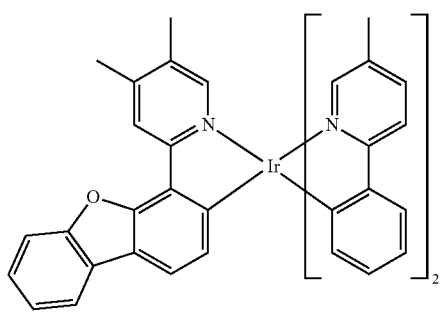
D-55
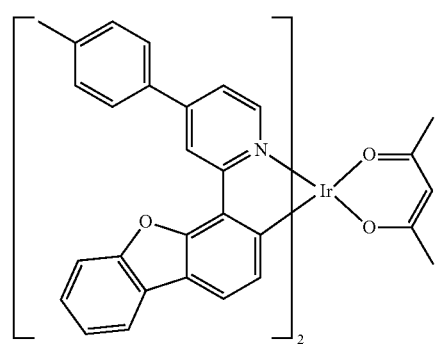
D-56
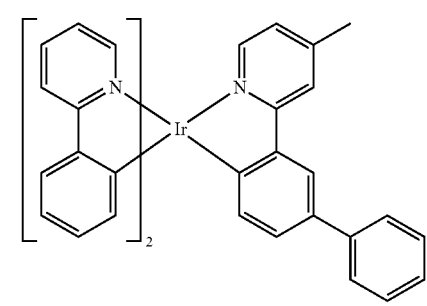
D-57
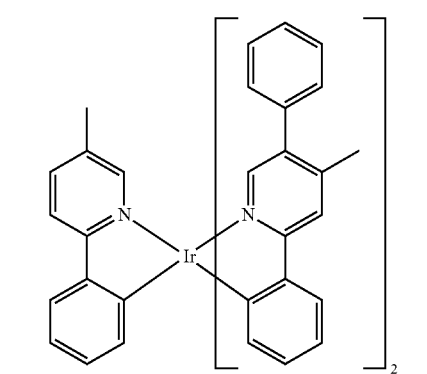
D-58
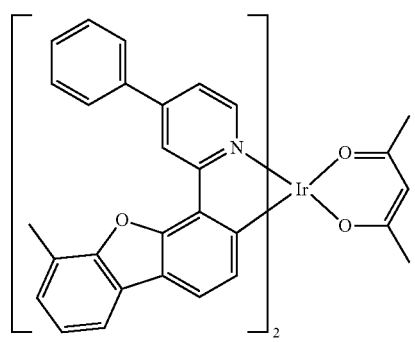
D-59
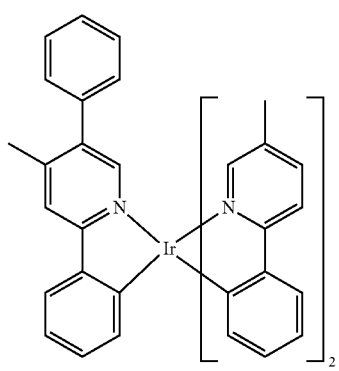
D-60
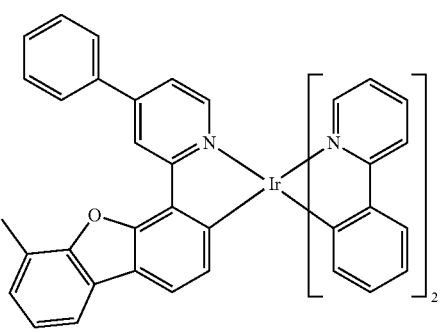
D-61
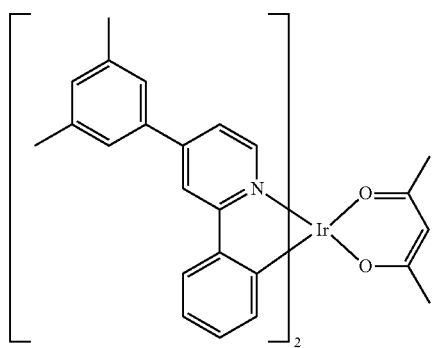

D-62
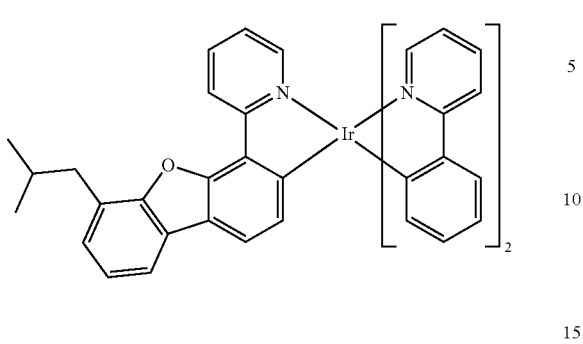
D-63
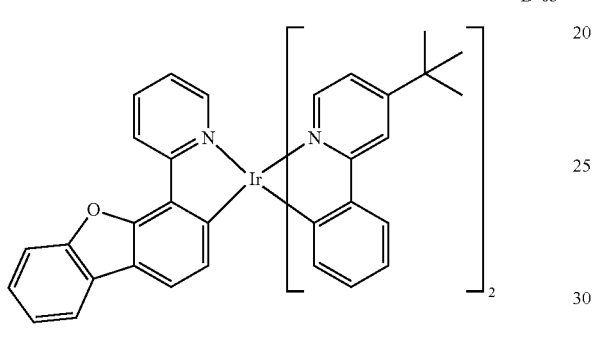
D-64
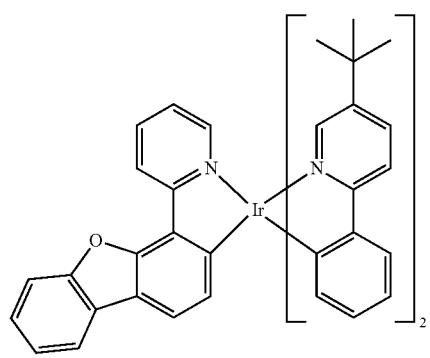
D-65
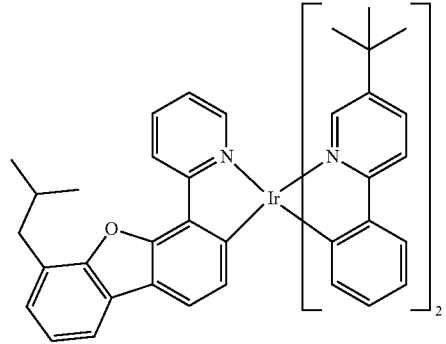
D-66
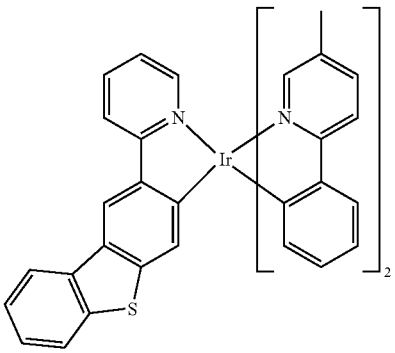
D-67
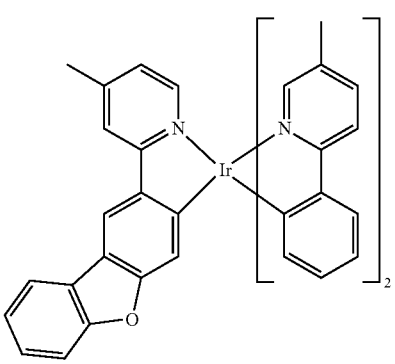
D-68
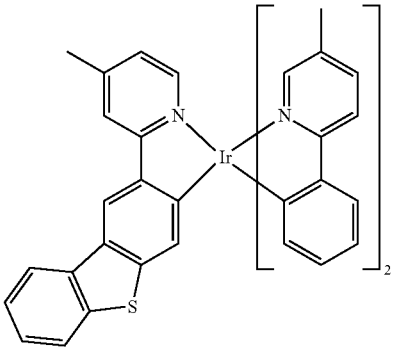
D-69
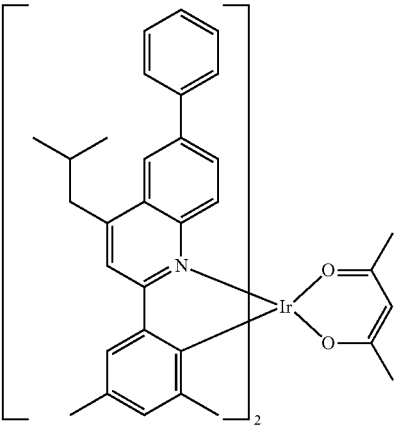

-continued
D-70
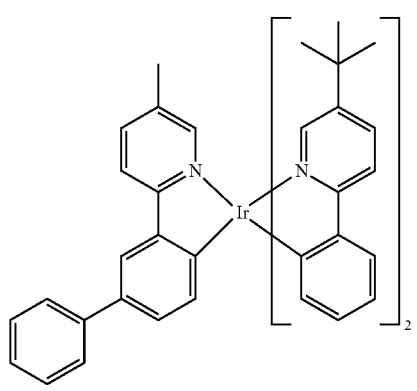
D-71
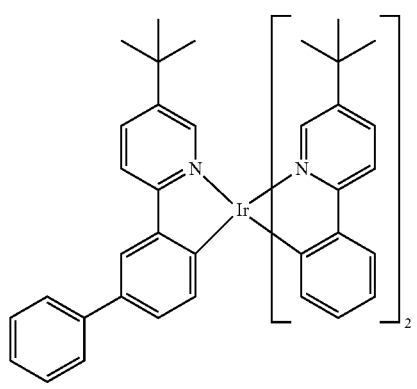
D-72
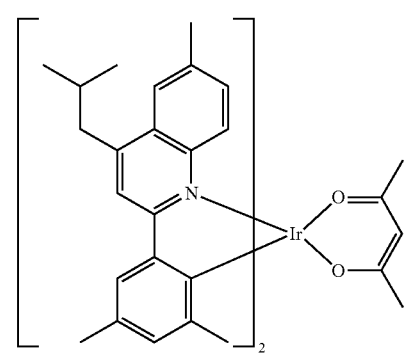
D-73
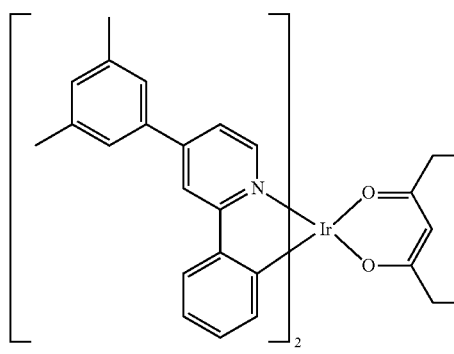
-continued
D-74
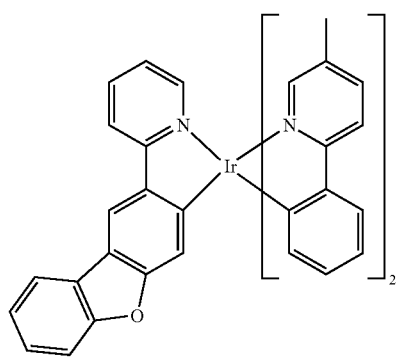
D-75
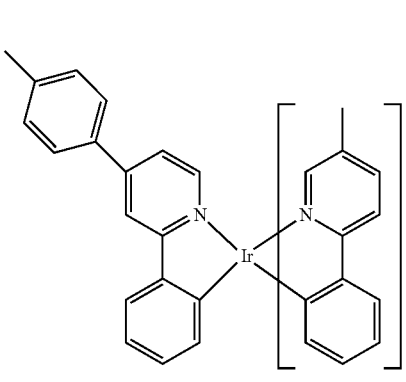
D-76
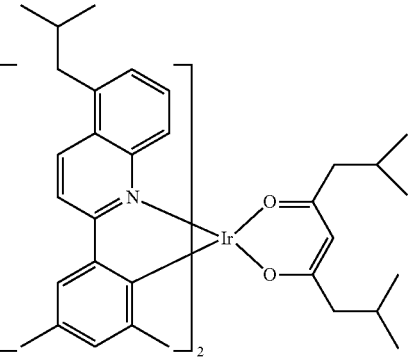
D-77
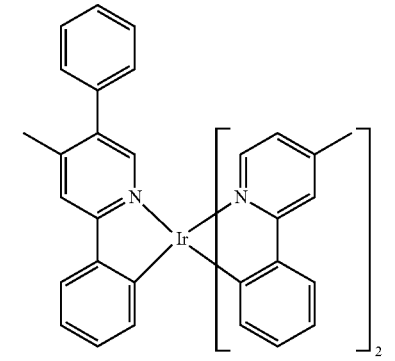

-continued
D-78
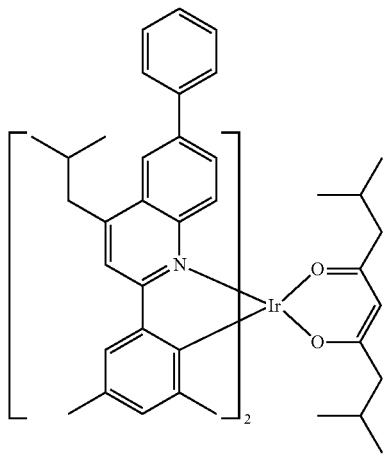
D-79
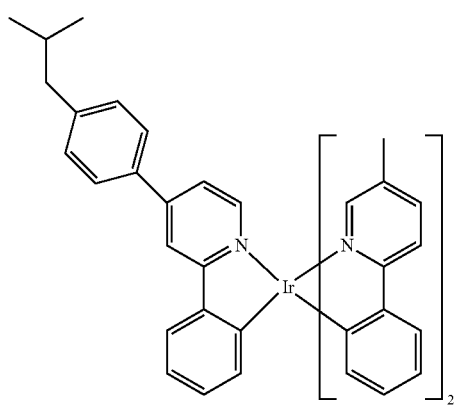
D-80
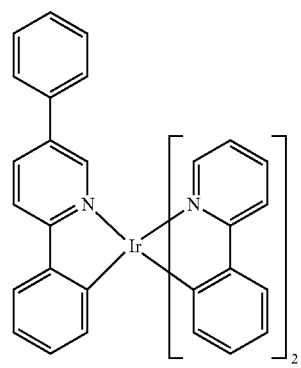
-continued
D-81
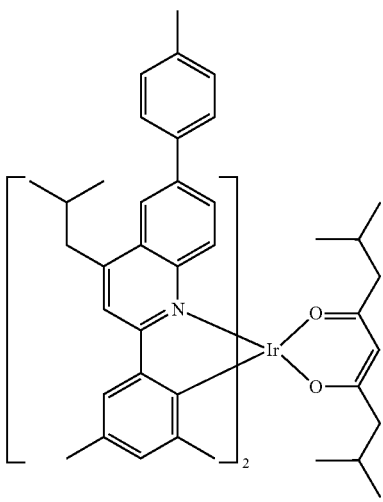
D-82
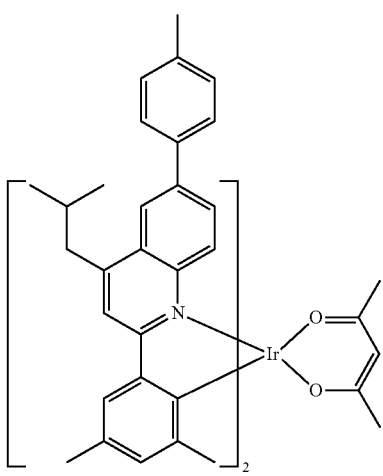
D-83
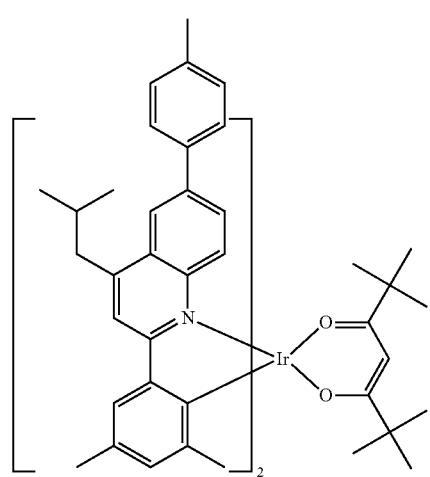

-continued
D-84
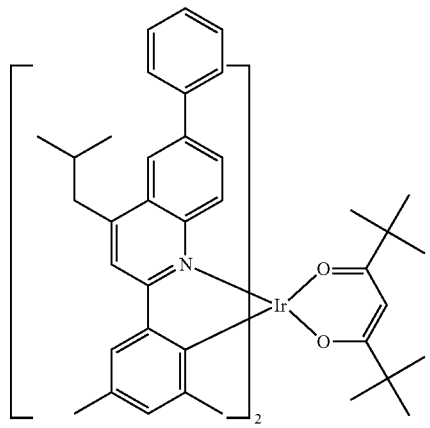
D-85
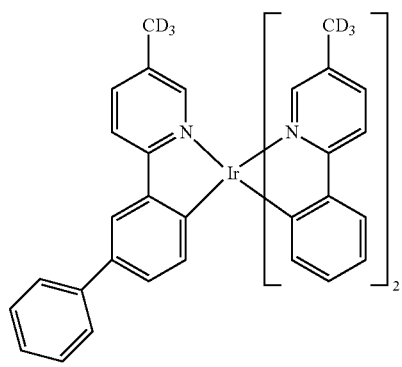
D-86
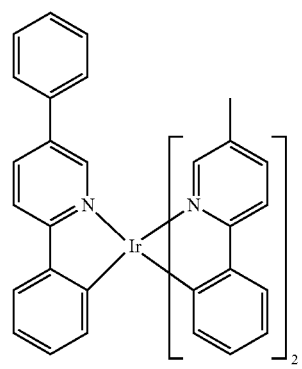
D-87
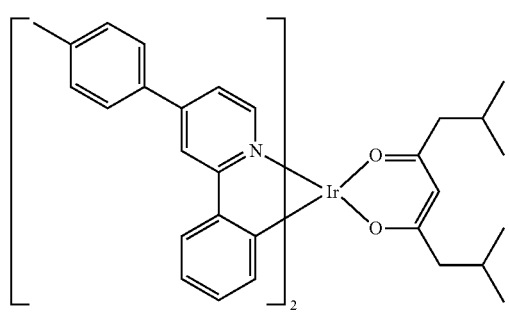
-continued
D-88
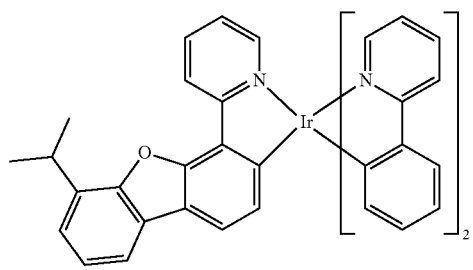
D-89
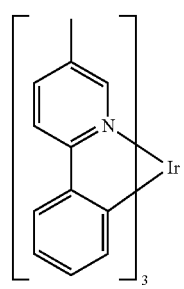
D-90
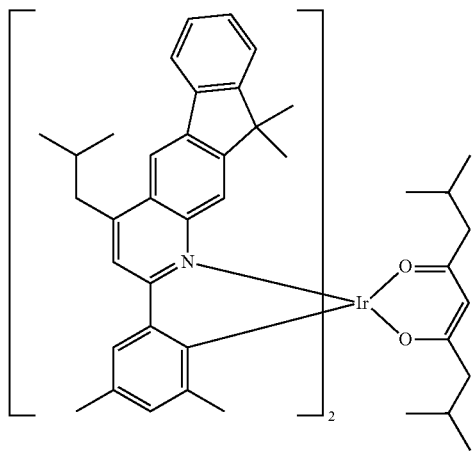
D-91
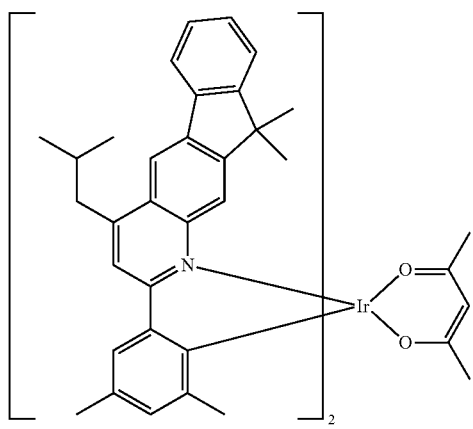

D-92 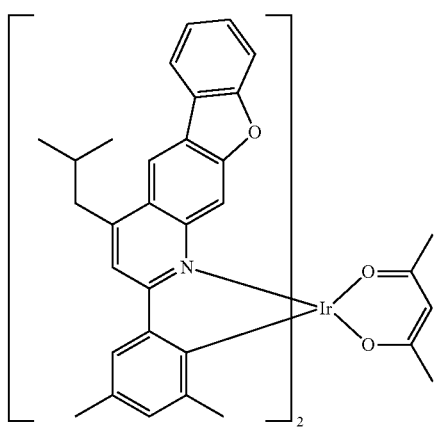
D-93 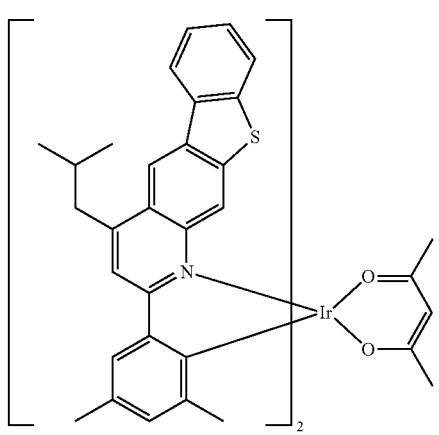
D-94 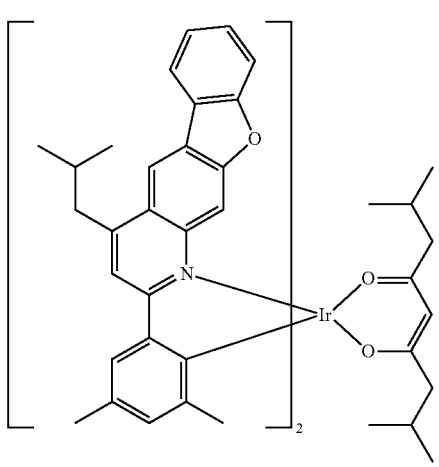
D-95 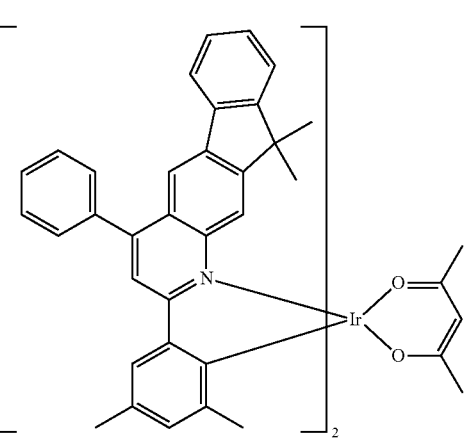
D-96 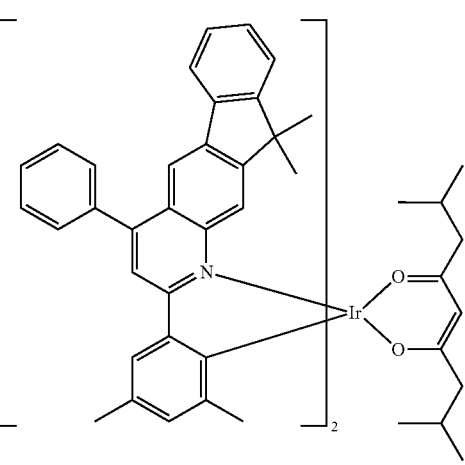
D-97 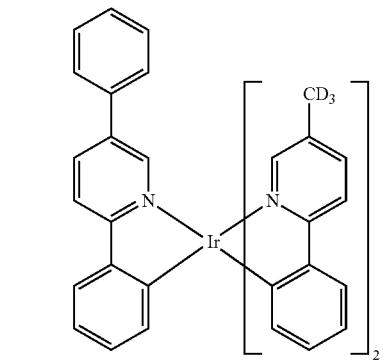
D-98 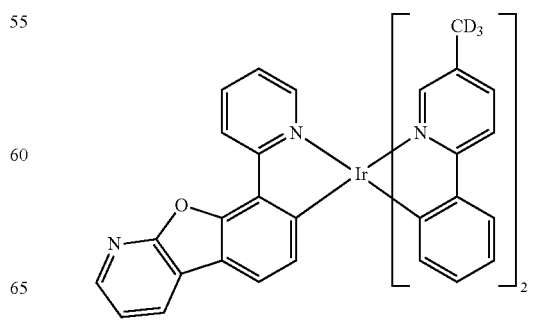

D-99
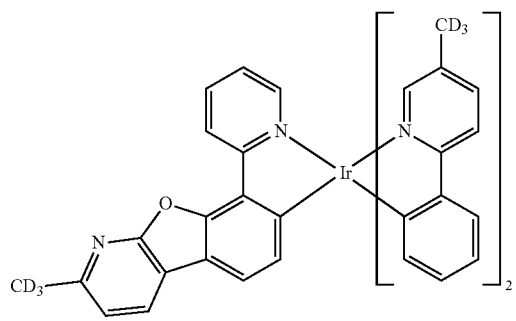
D-100
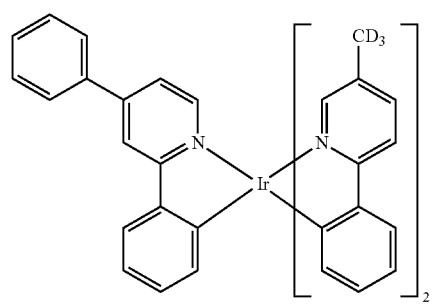
D-101
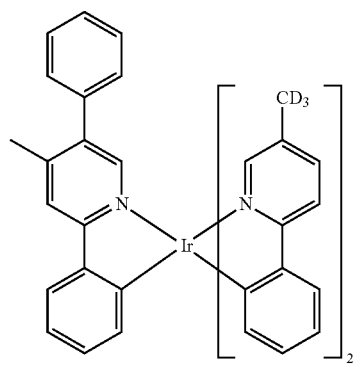
D-102
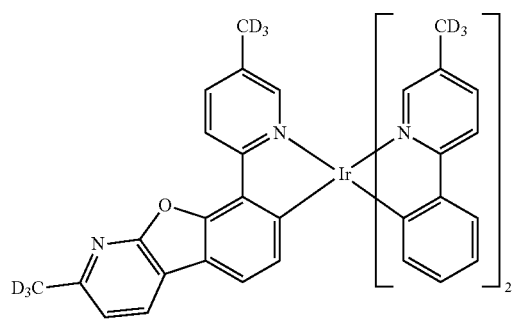
D-103
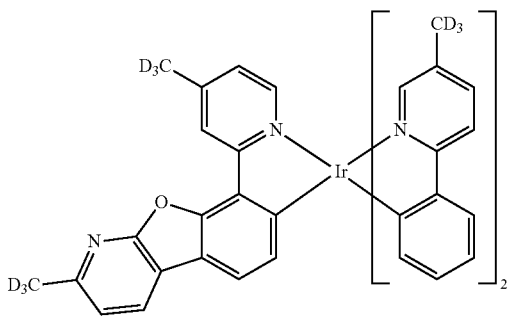
D-104
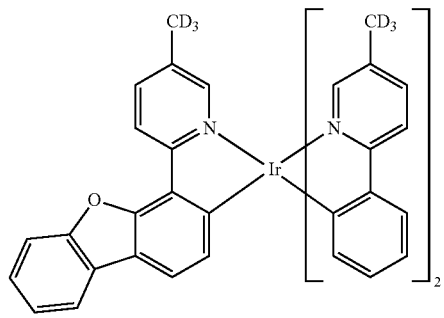
D-105
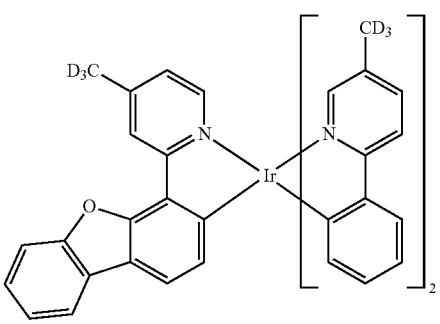
D-106
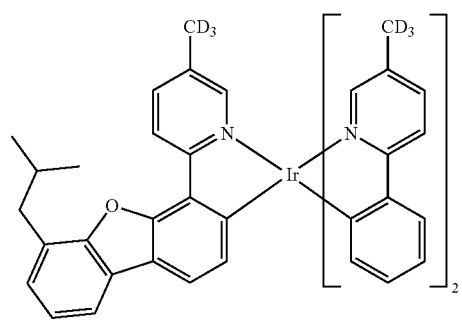

D-107
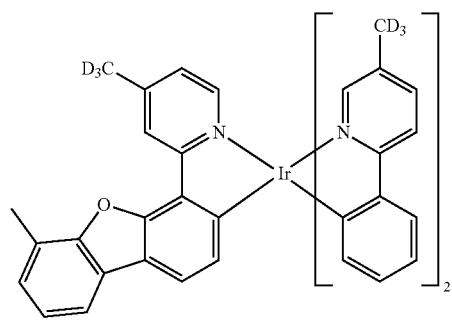
D-108
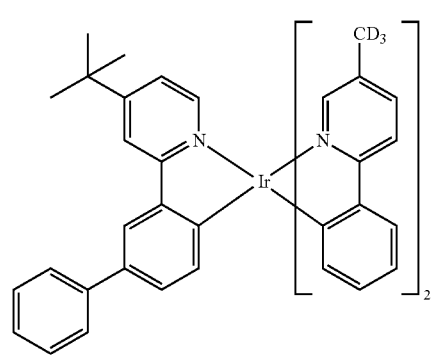
D-109
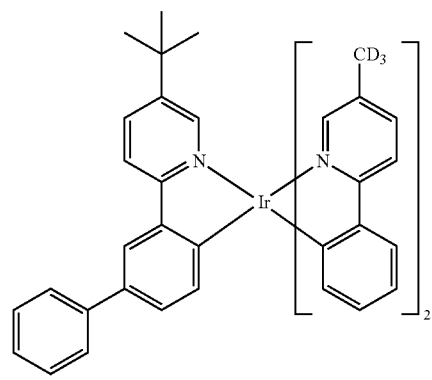
D-110
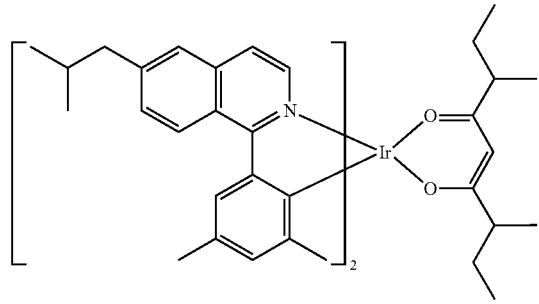
D-111
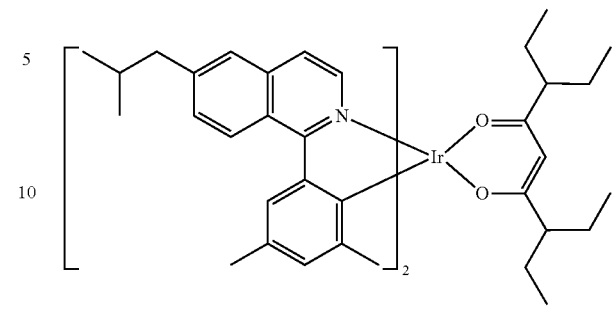
D-112
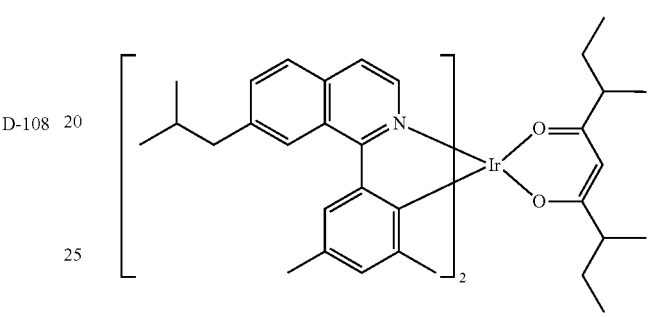
D-113
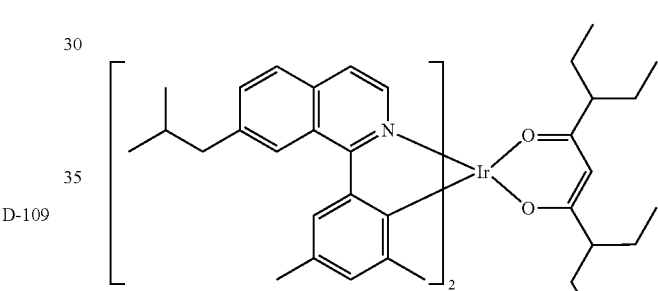
D-114
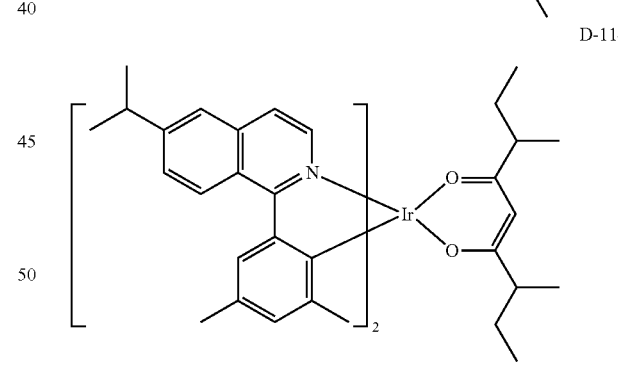
D-115
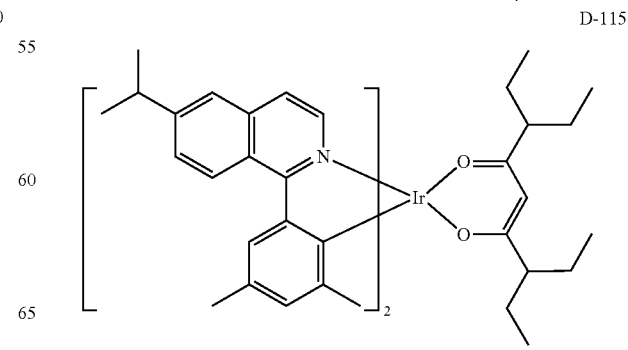

-continued
D-116
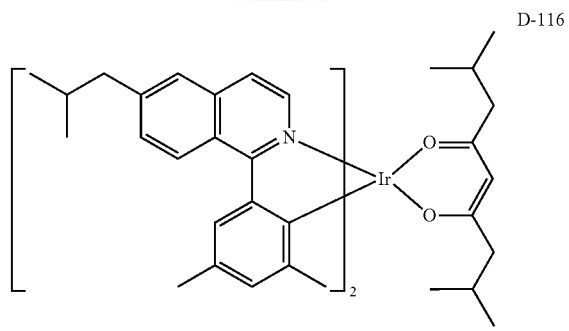
D-117
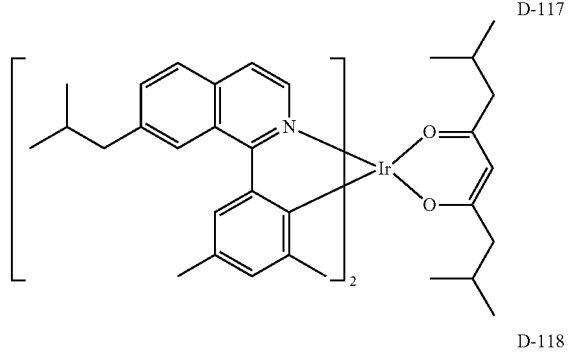
D-118
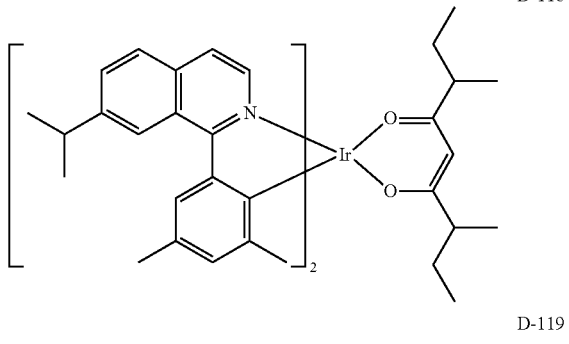
D-119
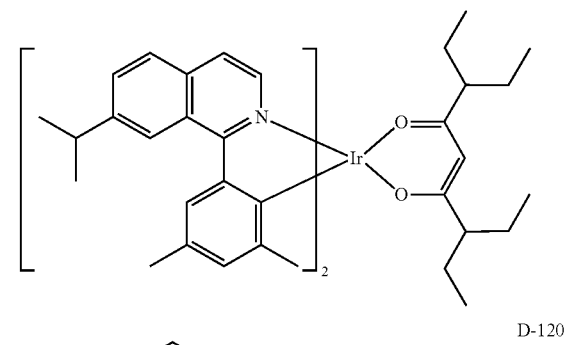
D-120
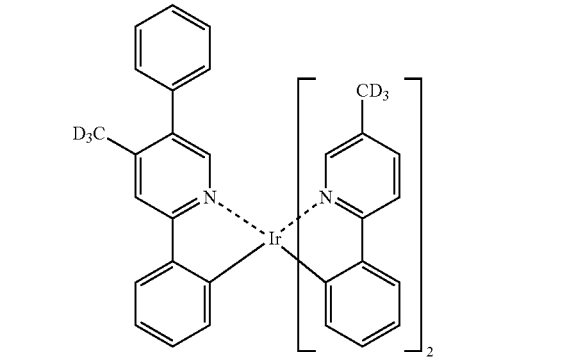
-continued
D-121
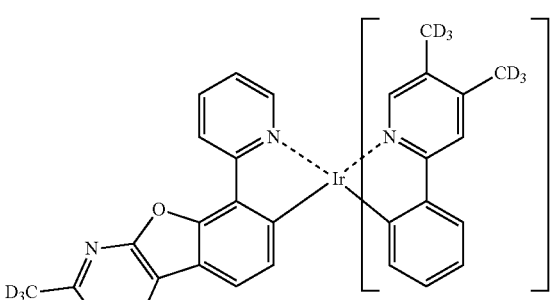
D-122
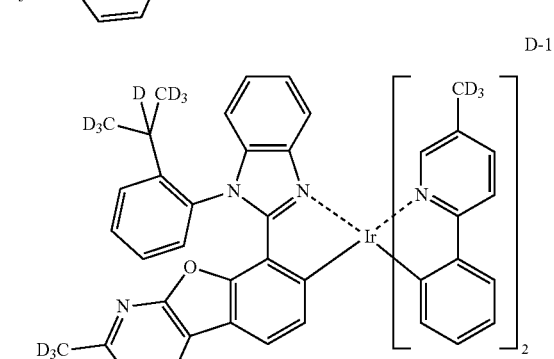
D-123
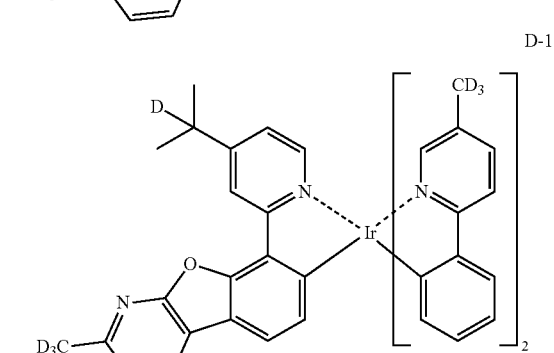
D-124
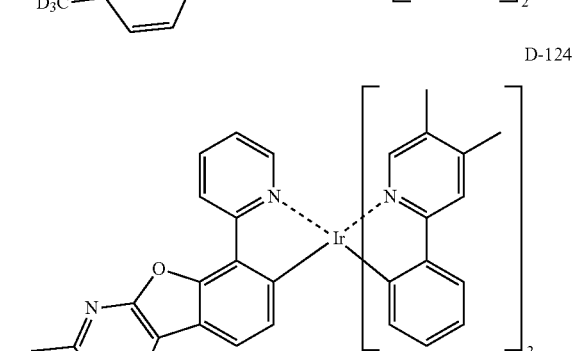
D-125
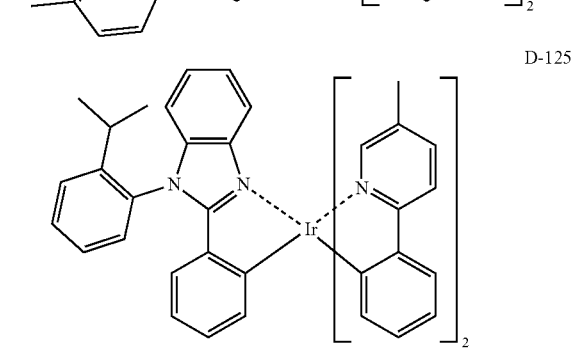

D-126 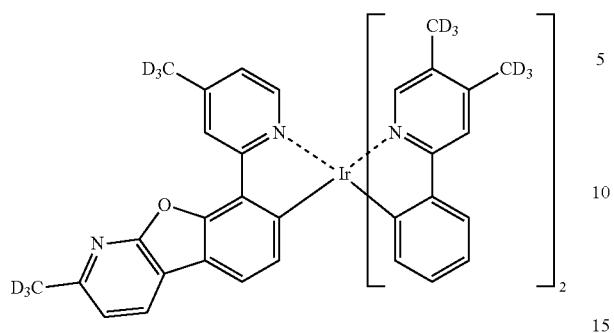
D-130 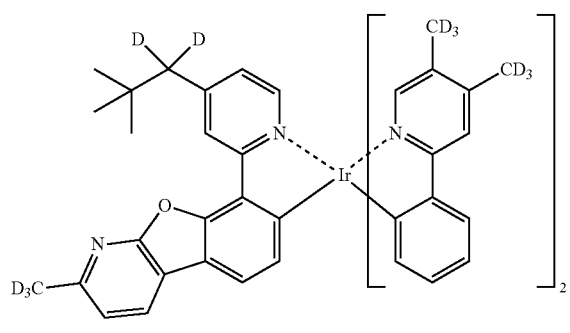
D-127 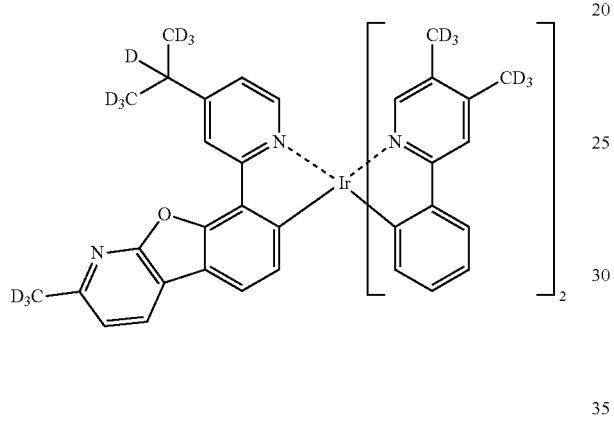
D-131 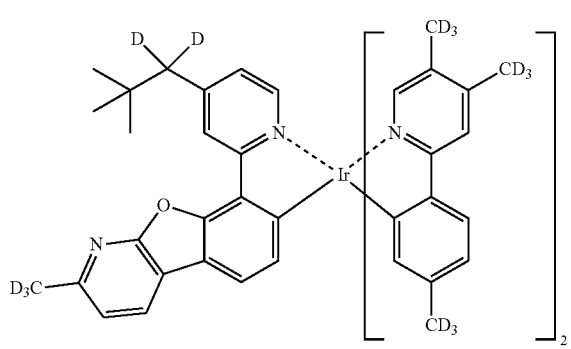
D-128 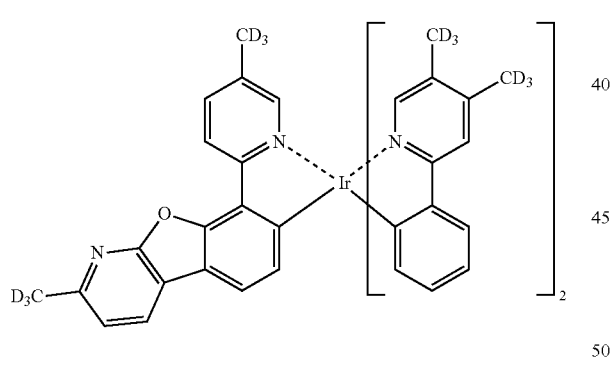
D-132 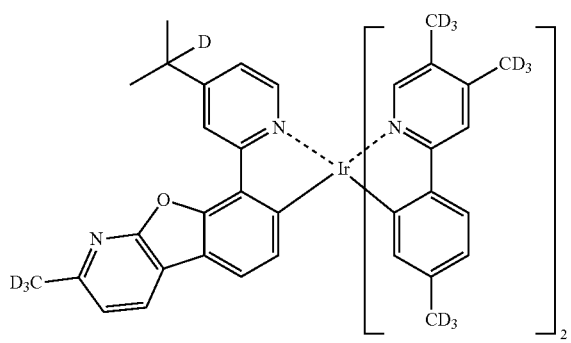
D-129 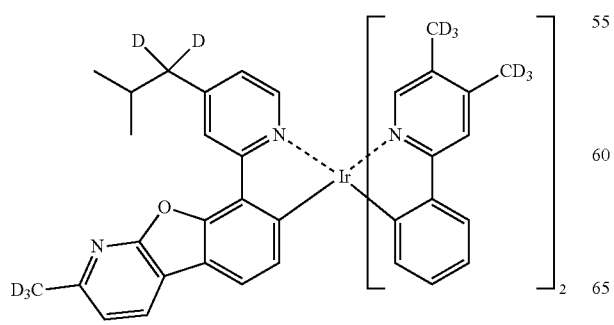
D-133 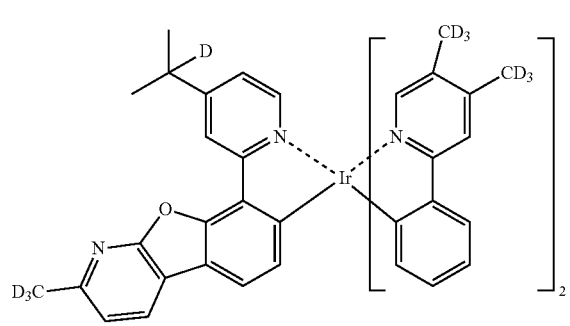

D-134
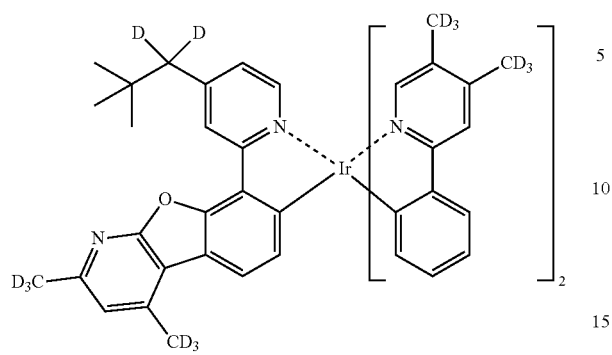
D-138
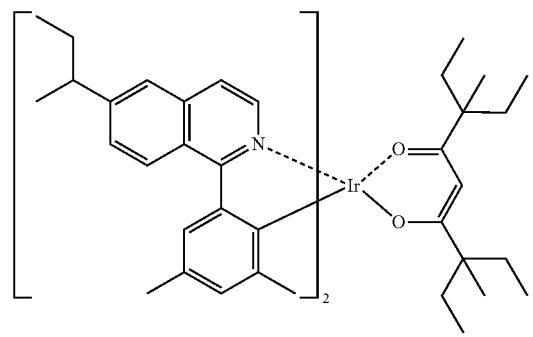
D-135
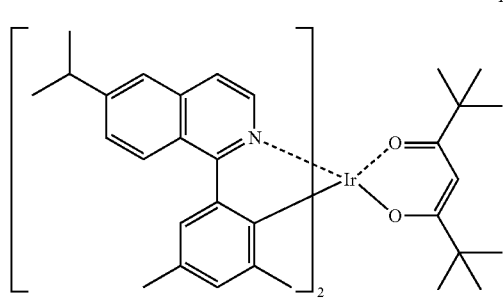
D-139
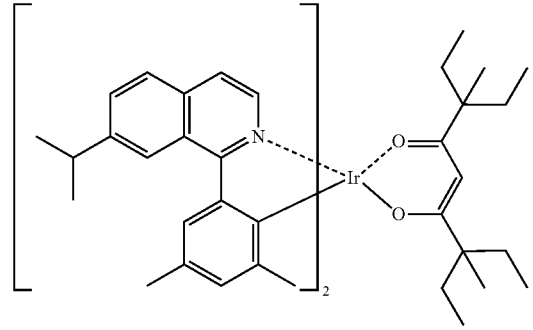
D-136
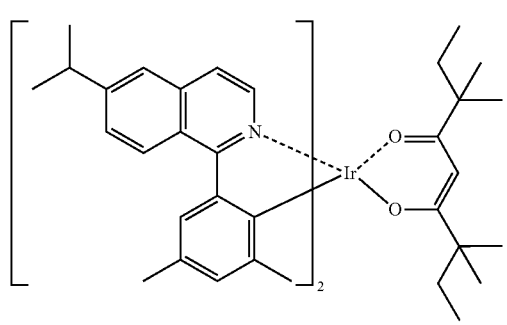
D-140
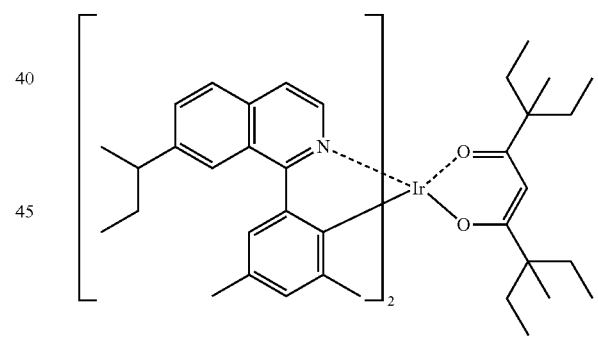
D-137
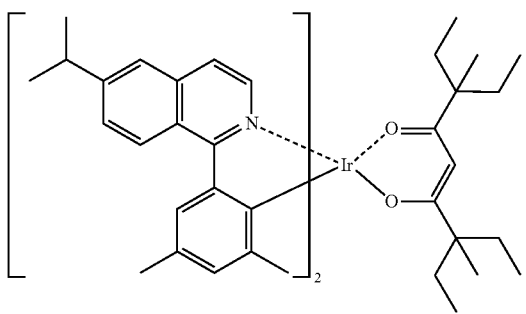
D-141
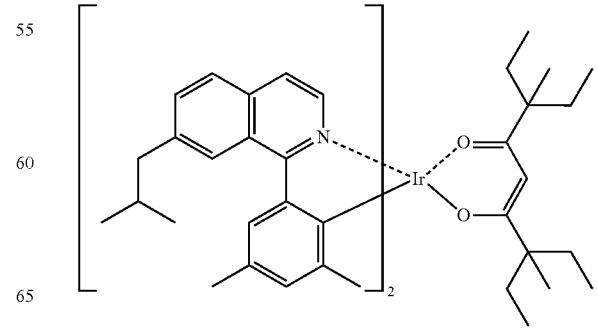

D-142
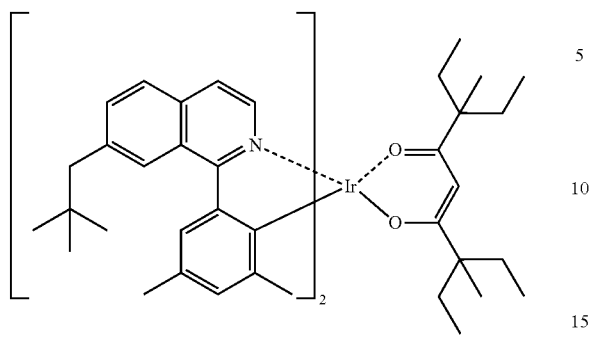
D-143
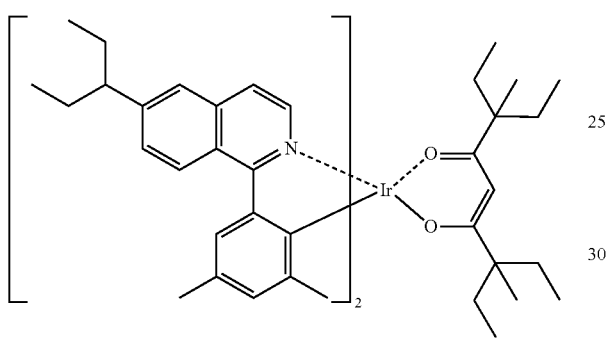
D-144
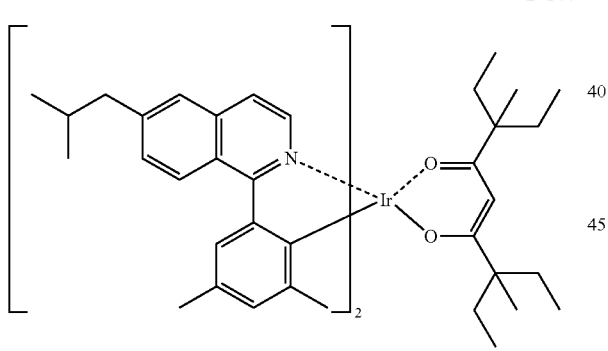
D-145
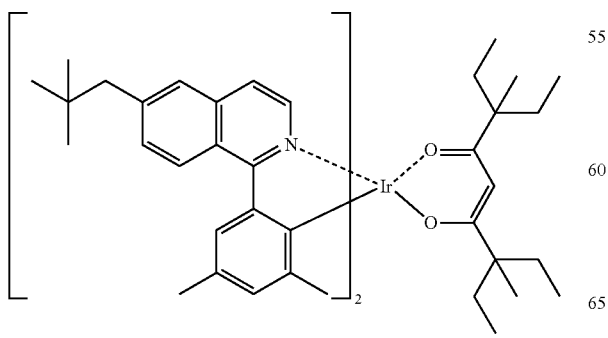
D-146
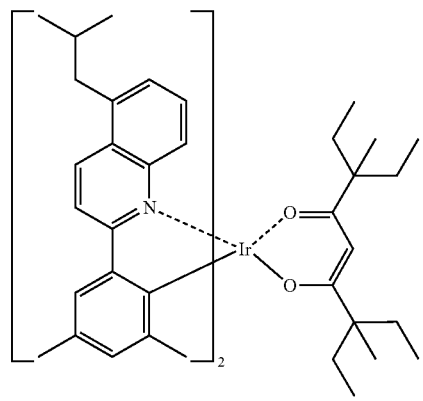
D-147
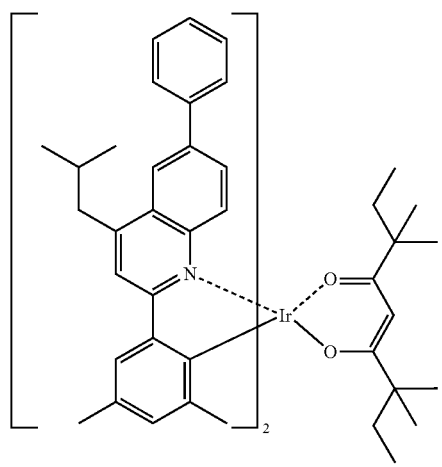
D-148
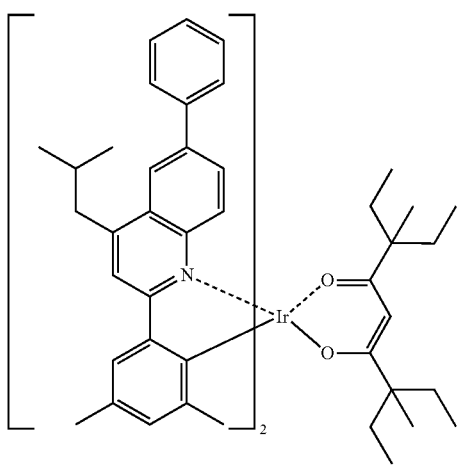

-continued

D-149

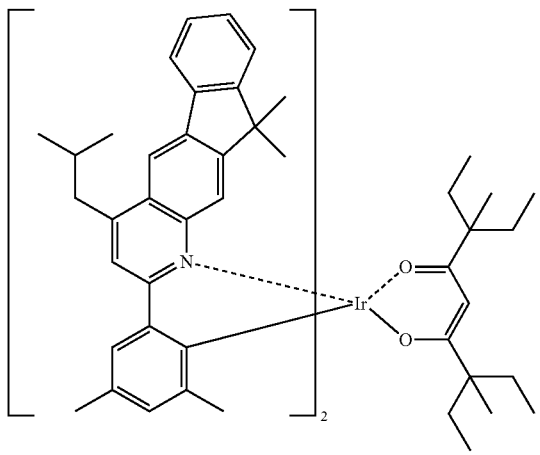

The compound represented by formula 1 of the present disclosure may be comprised in one or more layers constituting the organic electroluminescent device, for example, at least one layer selected from the group consisting of a hole injection layer, a hole transport layer, a hole auxiliary layer, a light-emitting auxiliary layer, a light-emitting layer, an electron transport layer, an electron buffer layer, an electron injection layer, an interlayer, a hole blocking layer, and an electron blocking layer. Each of the layers may be further configured as a plurality of layers.

In addition, the compound represented by formula 1 of the present disclosure may be comprised in the hole transport zone and/or the light-emitting layer, but is not limited thereto. The compound represented by formula 1 of the present disclosure may be comprised in the hole transport zone as at least one of a hole injection material, a hole transport material, a hole auxiliary material, a light-emitting auxiliary layer material, and an electron blocking material, e.g., as a hole transport material. Furthermore, the compound represented by formula 1 of the present disclosure may be comprised in the light-emitting layer as a host, and may be used as a host having hole transport properties among hosts.

The present disclosure may comprise a hole transport zone between an anode and a light-emitting layer, and the hole transport zone may comprise at least one of a hole injection layer, a hole transport layer, a hole auxiliary layer, a light-emitting auxiliary layer and an electron blocking layer. The hole injection layer, the hole transport layer, the hole auxiliary layer, the light-emitting auxiliary layer and the electron blocking layer, respectively, may be a single layer or a plurality of layers in which two or more layers are stacked. The hole injection layer may be multi-layers in order to lower the hole injection barrier (or hole injection voltage) from the anode to the hole transport layer or the electron blocking layer, wherein two compounds may be used simultaneously in each of the multi-layers. The electron blocking layer may be placed between the hole transport layer (or the hole injection layer) and the light-emitting layer, and can confine the excitons within the light-emitting layer by blocking the overflow of electrons from the light-emitting layer to prevent a light-emitting leakage.

In addition, the hole transport zone may comprise a p-doped hole injection layer, a hole transport layer, and a light-emitting auxiliary layer. Herein, the p-doped hole injection layer means a hole injection layer doped with a p-dopant. The p-dopant is a material capable of imparting p-type semiconductor properties. The p-type semiconductor properties mean the properties of injecting or transporting holes at the HOMO (highest occupied molecular orbital) energy level, i.e., the properties of a material having a high hole conductivity.

The organic electroluminescent material of the present disclosure, e.g., at least one of a hole injection material, a hole transport material, a hole auxiliary material, a light-emitting auxiliary material, an electron blocking material, a light-emitting material, an electron buffer material, a hole blocking material, an electron transport material, an electron injection material and a light-emitting material (host material) may comprise a compound represented by formula 1. The organic electroluminescent material may be a hole transport material and/or a light-emitting material. The organic electroluminescent material may consist of the compound represented by formula 1 alone, or may further comprise conventional materials included in the organic electroluminescent material. For example, the organic electroluminescent material of the present disclosure may further comprise at least one compound represented by any one of formulas 11 to 15. When two or more materials are comprised in one layer, they may be mixture-evaporated to form a layer, or may be separately co-evaporated at the same time to form a layer.

The organic electroluminescent device of the present disclosure may comprise a first electrode, a second electrode, and at least one organic layer between the first and second electrodes. One of the first and second electrodes may be an anode, and the other may be a cathode. The organic layer may comprise at least one light-emitting layer, and may further comprise at least one layer selected from the group consisting of a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The first electrode and the second electrode may each be formed with a transmissive conductive material, a transflective conductive material, or a reflective conductive material. The organic electroluminescent device may be a top emission type, a bottom emission type, or both-sides emission type depending on the type of the material forming the first electrode and the second electrode. In addition, the hole injection layer may be further doped with a p-dopant, and the electron injection layer may be further doped with an n-dopant.

The organic electroluminescent device of the present disclosure may comprise the compound represented by formula 1, and may further comprise conventional materials included in the organic electroluminescent material. The organic electroluminescent device comprising the organic electroluminescent compound represented by formula 1 of the present disclosure may exhibit low driving voltage and/or high power efficiency.

In addition, the organic electroluminescent material according to one embodiment of the present disclosure may be used as a light-emitting material for a white organic light-emitting device. The white organic light-emitting device has been suggested to have various structures such as a side-by-side structure or a stacking structure depending on the arrangement of R (red), G (green) or YG (yellow green), and B (blue) light-emitting parts, or color conversion material (CCM) method, etc. The present disclosure may also be applied to such a white organic light-emitting device. The organic electroluminescent material according to one embodiment of the present disclosure may also be used in an organic electroluminescent device comprising a quantum dot (QD).

Furthermore, the present disclosure may provide a display system using the compound represented by formula 1. In other words, it is possible to produce a display system or a lighting system by using the compound of the present disclosure. Specifically, it is possible to produce a display system, e.g., a display system for smart phones, tablets, notebooks, PCs, TVs, or cars; or a lighting system, e.g., an outdoor or indoor lighting system, by using the compound of the present disclosure.

Hereinafter, the preparation method of the compounds according to the present disclosure, the properties thereof, and the properties of the OLED comprising the organic electroluminescent compound according to the present disclosure will be explained in detail with reference to the representative compounds of the present disclosure. The following examples only describe the properties of the compound and the OLED comprising the same according to the present disclosure, but the present disclosure is not limited to the following examples.

Example 1: Preparation of Compound C-6

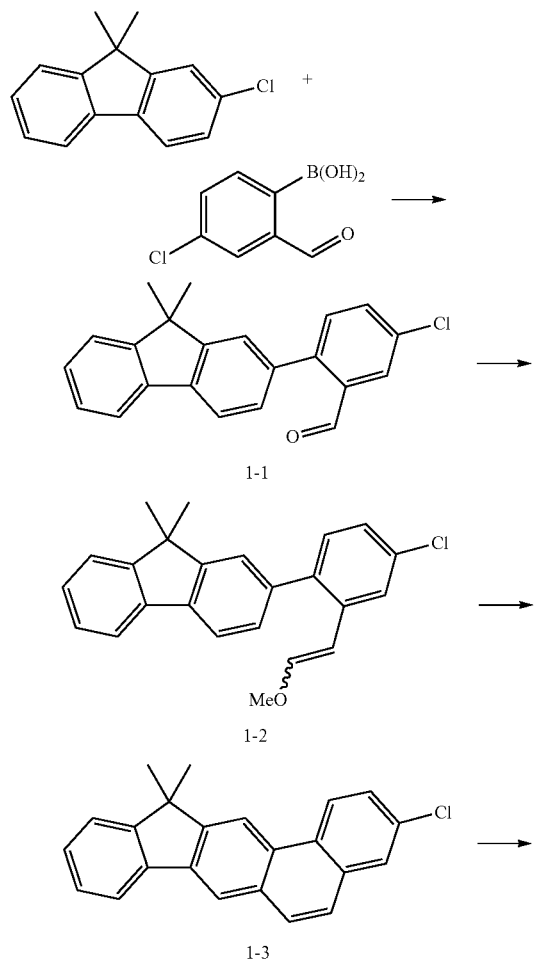

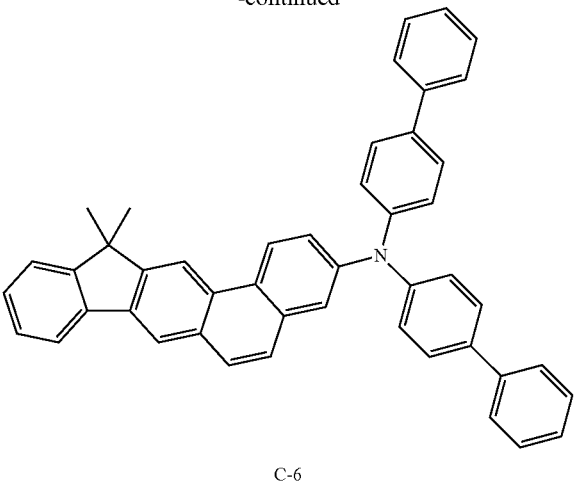

C-6

Synthesis of Compound 1-1

In a flask, 2-chloro-9,9-dimethyl-9H-fluorene (40.0 g, 150.0 mmol), (4-chloro-2-formylphenyl)boronic acid (55.3 g, 300.0 mmol), tetrakis(triphenylphosphine)palladium(0) (Pd(PPh$_3$)$_4$) (12.1 g, 10.50 mmol), and KOH (18.5 g, 330 mmol) were dissolved in 410 mL of o-xylene, 82 mL of acetonitrile, and 164 mL of distilled water, and the mixture was refluxed at 160° C. for 16 hours. After completion of the reaction, an organic layer was extracted with ethyl acetate. The residual moisture was removed with magnesium sulfate. The residue was dried and separated by column chromatography to obtain compound 1-1 (18.9 g, yield: 56.8%).

Synthesis of Compound 1-2

(Methoxymethyl)triphenylphosphonium chloride (25.9 g, 75.5 mmol) and compound 1-1 (18.9 g, 56.8 mmol) were dissolved in 280 mL of tetrahydrofuran (THF). Thereafter, potassium tert-butoxide (tBuOK) (26.7 g, 237.6 mmol) was added at 0° C., and the temperature was raised, and then the mixture was stirred at room temperature for 3 hours. After completion of the reaction, an organic layer was extracted with ethyl acetate. The residual moisture was removed with magnesium sulfate. The residue was dried and separated by column chromatography to obtain compound 1-2 (20.3 g, yield: 99.0%).

Synthesis of Compound 1-3

Compound 1-2 (20.3 g, 56.3 mmol) was dissolved in 284 mL of dichloromethane (DCM). Thereafter, boron trifluoride etherate (21.4 mL, 170.4 mmol) was added at 0° C., the temperature was raised, and the mixture was stirred at room temperature for 12 hours. After completion of the reaction, an aqueous NaHCO$_3$ solution was added, and an organic layer was extracted with dichloromethane. The residual moisture was removed with magnesium sulfate. The residue was distilled under reduced pressure and separated by column chromatography to obtain compound 1-3 (18.2 g, yield: 98.3%).

Synthesis of Compound C-6

Compound 1-3 (4.93 g, 15.0 mmol), bis(4-biphenylyl)amine (4.82 g, 15.0 mmol), tris(dibenzylideneacetone)dipalladium(0) (687 mg, 0.75 mmol), tributylphosphine (0.728 mL, 1.50 mmol), and sodium tert-butoxide (NaOtBu) (4.32 g, 45.0 mmol) were dissolved in 75 mL of toluene, and the mixture was refluxed at 145° C. for 3 hours. After completion of the reaction, the mixture was distilled under reduced pressure and separated by column chromatography to obtain compound C-6 (4.7 g, yield: 54.7%).

| | MW | M.P. (° C.) |
|---|---|---|
| C-6 | 613.80 | 275.3 |

Example 2: Preparation of Compound C-7

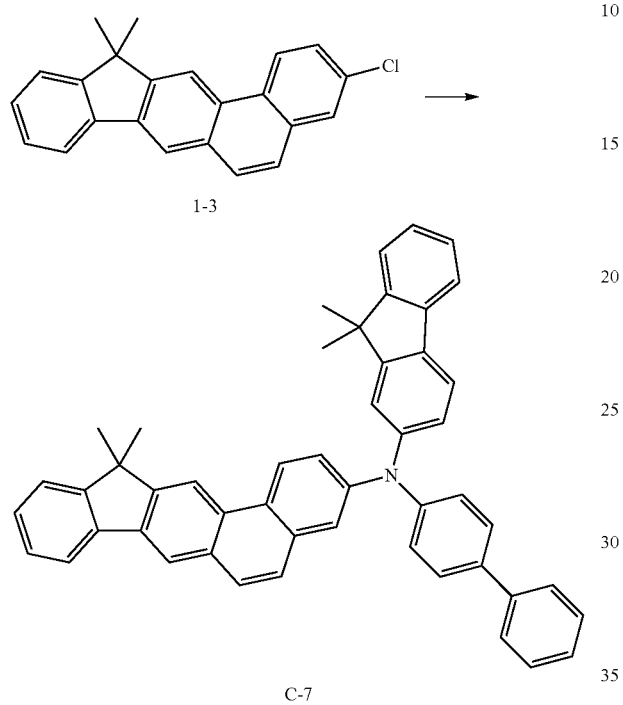

Compound 1-3 (4.93 g, 15.0 mmol), N-([1,1'-biphenyl]4-yl)-9,9-dimethyl-9H-fluoren-2-amine (5.42 g, 15.0 mmol), tris(dibenzylideneacetone)dipalladium(0) (687 mg, 0.75 mmol), tributylphosphine (0.728 mL, 1.50 mmol), and NaOtBu (4.32 g, 45.0 mmol) were dissolved in 75 mL of toluene, and the mixture was refluxed at 145° C. for 3 hours. After completion of the reaction, the mixture was distilled under reduced pressure and separated by column chromatography to obtain compound C-7 (7.1 g, yield: 72.4%).

| | MW | M.P. (° C.) |
|---|---|---|
| C-7 | 653.87 | 173.2 |

Example 3: Preparation of Compound C-39

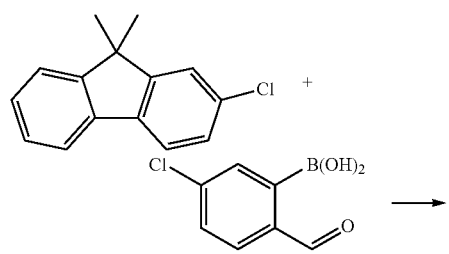

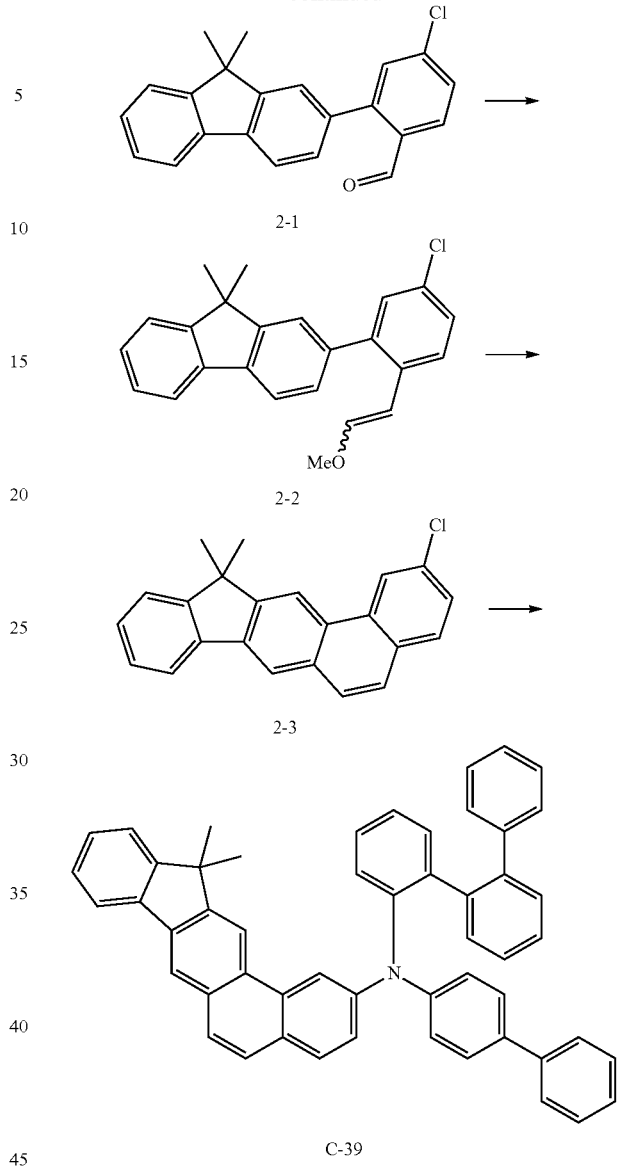

Synthesis of Compound 2-1

In a flask, 2-chloro-9,9-dimethyl-9H-fluorene (40.0 g, 150.0 mmol), (5-chloro-2-formylphenyl)boronic acid (55.3 g, 300.0 mmol), Pd(PPh$_3$)$_4$ (12.1 g, 10.50 mmol), and KOH (18.5 g, 330 mmol) were dissolved in 410 mL of o-xylene, 82 mL of acetonitrile, and 164 mL of distilled water, and the mixture was refluxed at 160° C. for 16 hours. After completion of the reaction, an organic layer was extracted with ethyl acetate. The residual moisture was removed with magnesium sulfate. The residue was dried and separated by column chromatography to obtain compound 2-1 (44.3 g, yield: 88.7%).

Synthesis of Compound 2-2

(Methoxymethyl)triphenylphosphonium chloride (60.1 g, 175.4 mmol) and compound 2-1 (43.9 g, 132.0 mmol) were dissolved in 528 mL of THF. Thereafter, potassium tert-butoxide (tBuOK) (26.7 g, 237.6 mmol) was added at 0° C., and the temperature was raised, and then the mixture was stirred at room temperature for 3 hours. After completion of the reaction, an organic layer was extracted with ethyl acetate. The residual moisture was removed with magnesium sulfate. The residue was dried and separated by column chromatography to obtain compound 2-2 (39.5 g, yield: 82.9%).

Synthesis of Compound 2-3

Compound 2-2 (39.5 g, 109.5 mmol) was dissolved in 545 mL of DCM. Thereafter, boron trifluoride etherate (41.3 mL, 328.5 mmol) was added at 0° C., the temperature was raised, and the mixture was stirred at room temperature for 12 hours. After completion of the reaction, an aqueous NaHCO₃ solution was added, and an organic layer was extracted with dichloromethane. The residual moisture was removed with magnesium sulfate. The residue was distilled under reduced pressure and solidified with hexane to obtain compound 2-3 (30.4 g, yield: 84.4%).

Synthesis of Compound C-39

Compound 2-3 (4.34 g, 13.2 mmol), N-([1,1'-biphenyl]4-yl)-[1,1':2',1"-terphenyl]-2-amine (5.00 g, 12.6 mmol), tris(dibenzylideneacetone)dipalladium(0) (691 mg, 0.755 mmol), tributylphosphine (0.733 mL, 1.51 mmol), and NaOtBu (3.63 g, 37.7 mmol) were dissolved in 63 mL of toluene, and the mixture was refluxed at 145° C. for 16 hours. After completion of the reaction, the mixture was distilled under reduced pressure and separated by column chromatography to obtain compound C-39 (4.9 g, yield: 56.5%).

|      | MW     | M.P. (° C.) |
|------|--------|-------------|
| C-39 | 689.90 | 289.3       |

Example 4: Preparation of Compound C-40

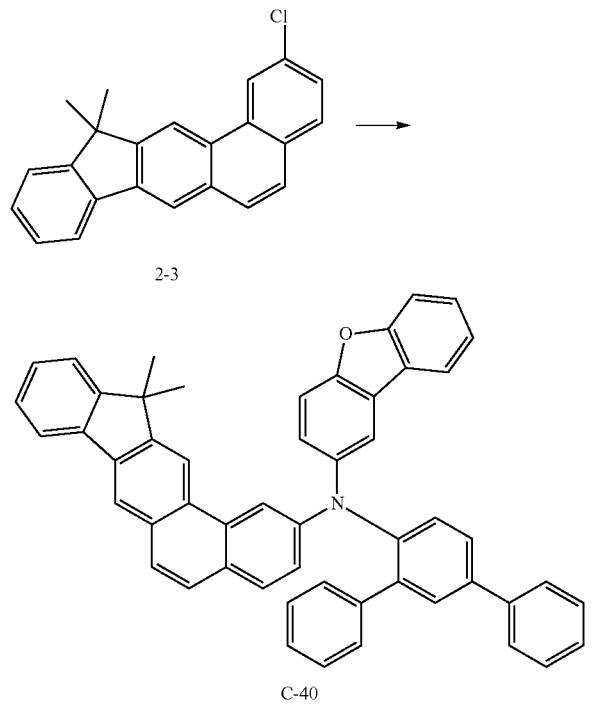

Compound 2-3 (4.34 g, 13.2 mmol), N-([1,1':3',1"-terphenyl]-4'-yl)dibenzo[b,d]furan-2-amine (5.18 g, 12.6 mmol), tris(dibenzylideneacetone)dipalladium(0) (691 mg, 0.755 mmol), tributylphosphine (0.733 mL, 1.51 mmol), and NaOtBu (3.63 g, 37.7 mmol) were dissolved in 63 mL of toluene, and the mixture was refluxed at 145° C. for 3 hours. After completion of the reaction, the mixture was distilled under reduced pressure and separated by column chromatography to obtain compound C-40 (6.4 g, yield: 72.3%).

|      | MW     | M.P. (° C.) |
|------|--------|-------------|
| C-40 | 703.88 | 171.7       |

Example 5: Preparation of Compound C-26

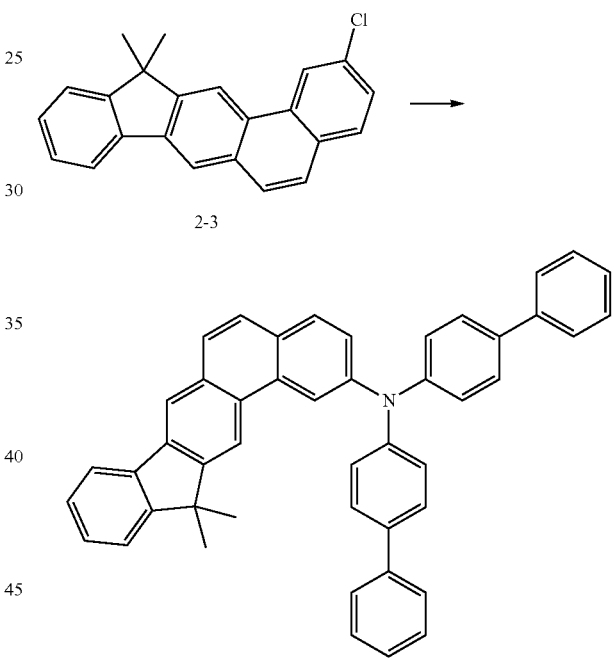

Compound 2-3 (4.6 g, 14.0 mmol), bis(4-biphenylyl)amine (4.5 g, 14.0 mmol), tris(dibenzylideneacetone)dipalladium(0) (641 mg, 0.7 mmol), tributylphosphine (0.680 mL, 1.40 mmol), and NaOtBu (4.04 g, 42.0 mmol) were dissolved in 75 mL of toluene, and the mixture was refluxed at 145° C. for 4 hours. After completion of the reaction, the mixture was distilled under reduced pressure and separated by column chromatography to obtain compound C-26 (4.2 g, yield: 48.9%).

|      | MW     | M.P. (° C.) |
|------|--------|-------------|
| C-26 | 613.80 | 221.2       |

Example 6: Preparation of Compound C-178

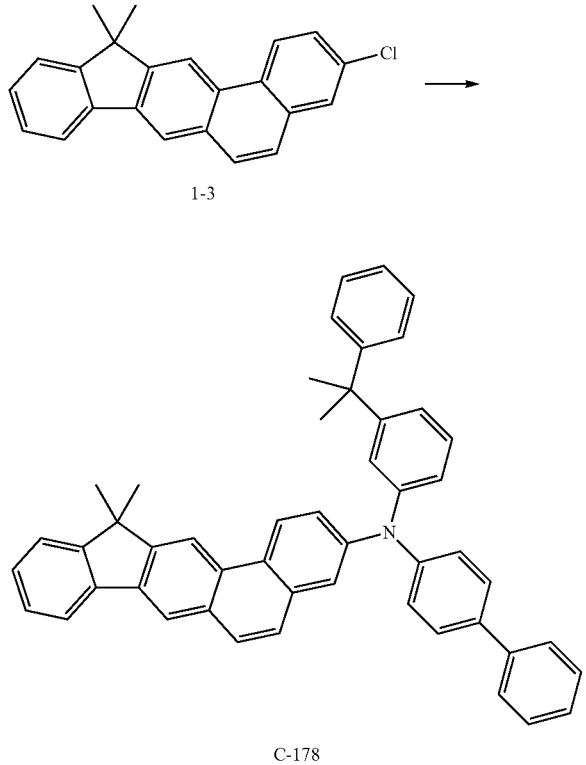 [SMILES: CC1(C)c2ccccc2-c2cc3ccc4cc(Cl)ccc4c3cc21 ; CC(C)(c1ccccc1)c1cccc(N(c2ccc(-c3ccccc3)cc2)c2ccc3c(ccc4cc5c(cc43)C(C)(C)c3ccccc3-5)c2)c1]

Compound 1-3 (5.06 g, 15.4 mmol), N-(3-(2-phenylpropan-2-yl)-phenyl)-[1,1'-biphenyl]-4-amine (5.09 g, 14.0 mmol), tris(dibenzylideneacetone)dipalladium(0) (641 mg, 0.70 mmol), tributylphosphine (0.680 mL, 1.40 mmol), and NaOtBu (4.04 g, 42.0 mmol) were dissolved in 70 mL of toluene, and the mixture was refluxed at 145° C. for 3 hours. After completion of the reaction, the mixture was distilled under reduced pressure and separated by column chromatography to obtain compound C-178 (7.3 g, yield: 79.5%).

|   | MW | M.P. (° C.) |
|---|---|---|
| C-178 | 655.88 | 273.8 |

Example 7: Preparation of Compound C-179

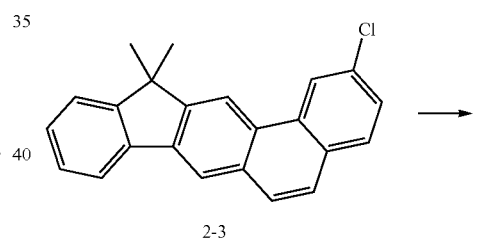

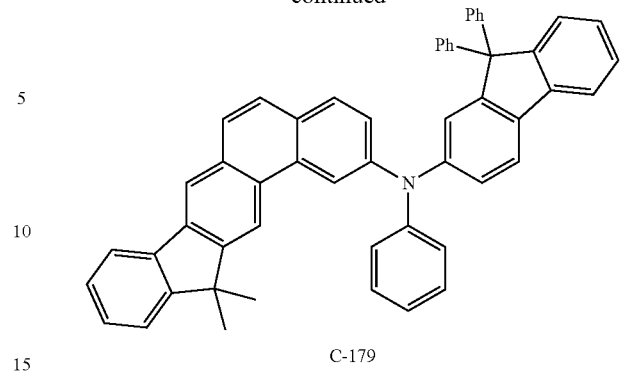

Compound 2-3 (5.06 g, 15.4 mmol), 9,9-diphenyl-N-phenyl-9H-fluoren-2-amine (5.73 g, 14.0 mmol), tris(dibenzylideneacetone)dipalladium(0) (641 mg, 0.700 mmol), tributylphosphine (0.680 mL, 1.40 mmol), and NaOtBu (4.04 g, 42.0 mmol) were dissolved in 70 mL of toluene, and the mixture was refluxed at 145° C. for 4 hours. After completion of the reaction, the mixture was distilled under reduced pressure and separated by column chromatography to obtain compound C-179 (8.0 g, yield: 81.4%).

|   | MW | M.P. (° C.) |
|---|---|---|
| C-179 | 701.91 | 243.0 |

Example 8: Preparation of Compound C-180

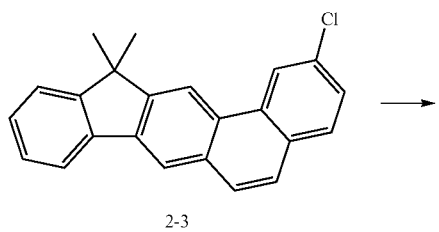

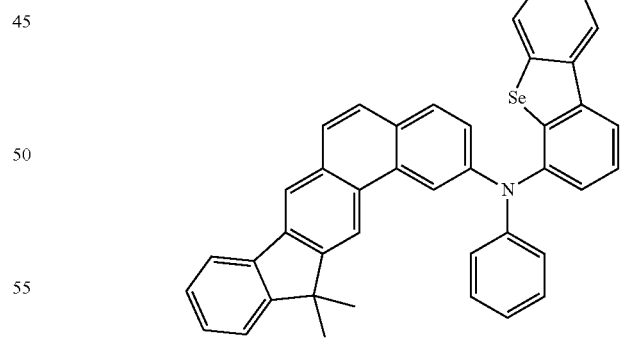

Compound 2-3 (6.04 g, 18.4 mmol), N-phenyldibenzo[b,d]selenophen-4-amine (5.64 g, 17.5 mmol), tris(dibenzylideneacetone)dipalladium(0) (801 mg, 0.875 mmol), tributylphosphine (0.850 mL, 1.75 mmol), and NaOtBu (5.05 g, 52.5 mmol) were dissolved in 88 mL of toluene, and the mixture was refluxed at 145° C. for 2 hours. After completion of the reaction, the mixture was distilled under reduced pressure and separated by column chromatography to obtain compound C-180 (9.0 g, yield: 83.6%).

| | MW | M.P. (° C.) |
|---|---|---|
| C-180 | 614.65 | 170.7 |

Example 9: Preparation of Compound C-183

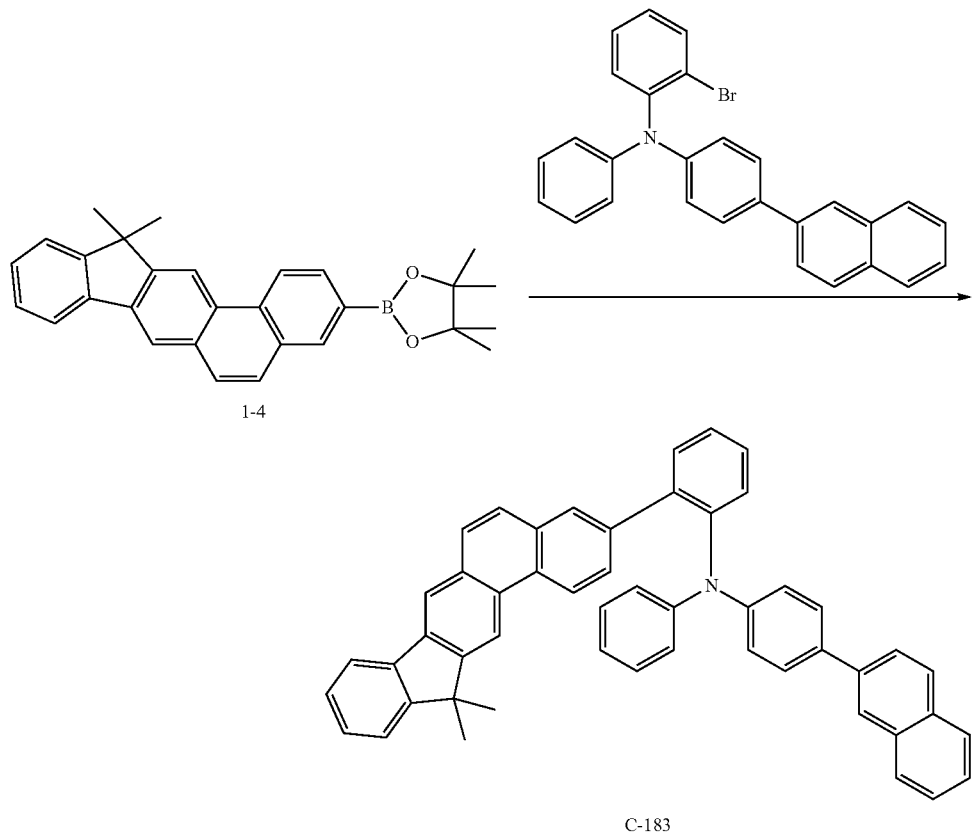

In a flask, compound 1-4 (0.25 g, 0.5 mmol), 2-bromo-N-(4-(naphthalen-2-yl)phenyl)-N-phenyl aniline (0.23 g, 0.55 mmol), PdCl$_2$(Amphos) (0.017 g, 0.025 mmol), Na$_2$CO$_3$ (0.1 g, 1.0 mmol), Aliquot 336 (0.01 g, 0.025 mmol), 5 mL of toluene, 1 mL of H$_2$O were added, and the mixture was stirred at 120° C. for 18 hours. After completion of the reaction, the mixture was cooled to room temperature, and distilled under reduced pressure, and then separated by column chromatography to obtain compound C-183 (0.1 g, yield: 29%).

| | MW |
|---|---|
| C-183 | 663.86 |

Example 10: Preparation of Compound C-185

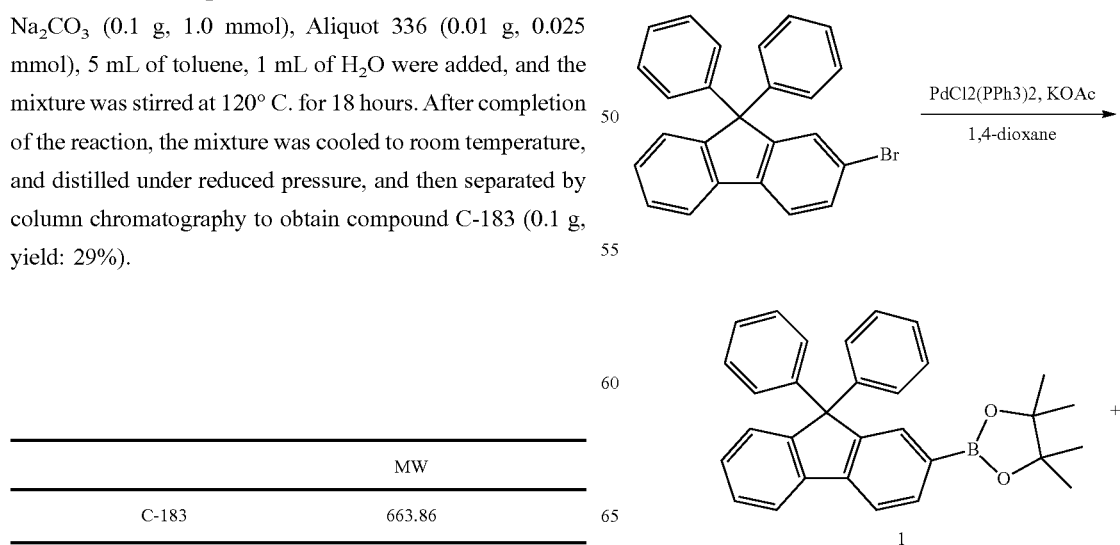

-continued

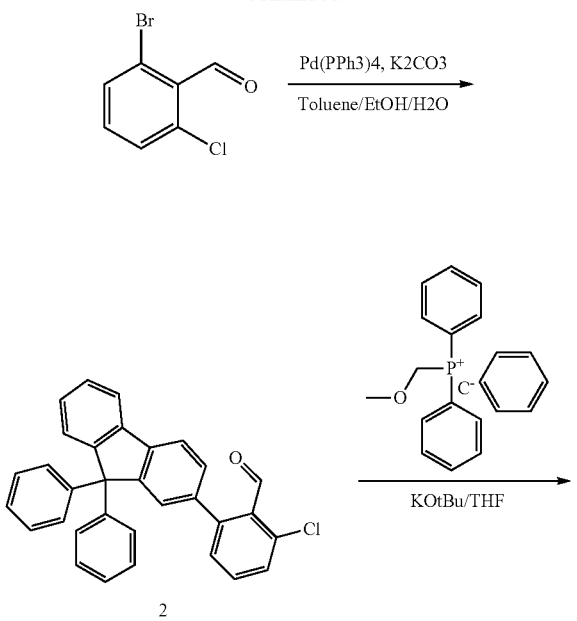

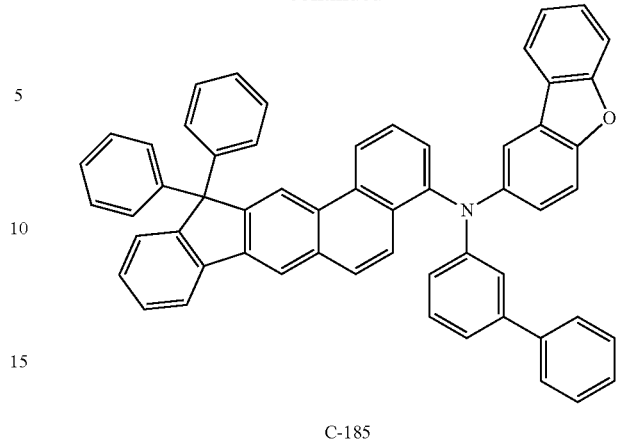

C-185

Synthesis of Compound 1

In a flask, 2-bromo-9,9-diphenyl-9H-fluorene (30 g, 75.5 mmol), 4,4,4',4',5,5,5',5'-octamethyl-2,2'-bi(1,3,2-dioxaborolane) (28 g, 113.2 mmol), KOAc (14.8 g, 151 mmol), and $PdCl_2(PPh_3)_2$ (4.3 g, 3.77 mmol) were dissolved in 500 mL of 1,4-dioxane, and the mixture was stirred under reflux at 150° C. for 3 hours. After completion of the reaction, an organic layer was extracted with ethyl acetate and the residual moisture was removed with magnesium sulfate. The residue was dried and separated by column chromatography to obtain compound 1 (35 g, yield: 100%).

Synthesis of Compound 2

In a flask, compound 1 (35 g, 78.7 mmol), 2-bromo-6-chlorobenzaldehyde (17 g, 78.7 mmol), $Pd(PPh_3)_4$ (4.5 g, 3.93 mmol), $K_2CO_3$ (21 g, 154.8 mmol), 546 mL of toluene, 273 mL of EtOH, and 273 mL of $H_2O$ were added, and the mixture was stirred under reflux at 130° C. for 3 hours. After completion of the reaction, methanol and water were added and stirred, and the solvent was removed by filtration under reduced pressure. After separation by column chromatography, methanol was added to produce a solid. The resulting solid was filtered under reduced pressure to obtain compound 2 (30 g, yield: 83.4%).

Synthesis of Compound 3

In a flask, compound 2 (30 g, 65.6 mmol), (methoxymethyl)triphenylphosphonium chloride (33 g, 98.5 mmol), and KOtBu (15.1 g, 98.5 mmol) were dissolved in 326 mL of THF, and the mixture was stirred at room temperature for 2 hours. After completion of the reaction, MeOH and water were added and stirred, and the solvent was removed by filtration under reduced pressure. After separation by column chromatography, MeOH was added to produce a solid. The resulting solid was filtered under reduced pressure to obtain compound 3 (40 g, yield: over yield %).

Synthesis of Compound 4

In a flask, compound 3 (40 g, 82.4 mmol) was dissolved in 500 mL of methylene chloride, and TfOH (trifluoromethane sulfonic acid) (7.2 mL, 82.4 mmol) was slowly added dropwise, followed by stirring at room temperature for 1 hour. After completion of the reaction, MeOH and water were added and stirred, and the solvent was removed by filtration under reduced pressure. After separation by column chromatography, MeOH was added to produce a solid. The resulting solid was filtered under reduced pressure to obtain compound 4 (24 g, yield: 64%).

Synthesis of Compound C-185

In a flask, compound 4 (5 g, 15.21 mmol), compound 5 (5.4 g, 16.73 mmol), NaOtBu (2.9 g, 30.42 mmol), S-Phos (499 mg, 1.21 mmol), and Pd$_2$(dba)$_3$ (696 mg, 0.76 mmol) were dissolved in 76 mL of xylene, and the mixture was stirred under reflux at 130° C. for 12 hours. After completion of the reaction, an organic layer was extracted with ethyl acetate. The residual moisture was removed with magnesium sulfate. The residue was dried and separated by column chromatography to obtain compound C-185 (3.5 g, yield: 37.1%).

|  | MW | M.P. (° C.) |
|---|---|---|
| C-185 | 751.93 | 309 |

Device Examples 1 to 7: Producing a Red OLED Comprising the Organic Electroluminescent Compound According to the Present Disclosure OLEDs according to the present disclosure were produced. A transparent electrode indium tin oxide (ITO) thin film (10 Ω/sq) on a glass substrate for an OLED (GEO-MATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 as a hole injection compound was introduced into a cell of the vacuum vapor deposition apparatus, and compound HT-1 as a hole transport compound was introduced into another cell of the vacuum vapor deposition apparatus. The two materials were evaporated at different rates, and compound HI-1 was deposited in a doping amount of 3 wt % based on the total amount of compound HI-1 and compound HT-1 to form a hole injection layer having a thickness of 10 nm on the ITO substrate. Next, compound HT-1 was deposited on the hole injection layer to form a first hole transport layer having a thickness of 90 nm. The compound of the second hole transport layer shown in Table 1 below was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: Compound RH-1 and compound RH-2 were introduced into two cells of the vacuum vapor deposition apparatus as hosts, and compound D-39 was introduced into another cell as a dopant. Compound RH-1 and compound RH-2 as hosts were evaporated at a rate of 5:5 and the dopant material was simultaneously evaporated at a different rate, and the dopant was deposited in a doping amount of 2 wt % based on the total amount of the hosts and the dopant to form a light-emitting layer having a thickness of 40 nm on the second hole transport layer. Next, compound HBL was deposited as an electron buffer layer having a thickness of 5 nm on the light-emitting layer. Thereafter, compound ETL-1 and compound EIL-1 were evaporated in a weight ratio of 5:5 to deposit an electron transport layer having a thickness of 30 nm on the electron buffer layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

Comparative Example 1: Producing a Red OLED Comprising a Comparative Compound

An OLED was produced in the same manner as in Device Example 1, except that compound A was used as the second hole transport layer.

The driving voltage, power efficiency, and CIEx,y (1931) chromaticity coordinates at a luminance of 1,000 nit of the OLEDs produced in Device Examples 1 to 7, and Comparative Example 1 are provided in Table 1 below.

TABLE 1

| | Second Hole Transport Layer | Driving Voltage [V] | Power Efficiency [lm/W] | CIE Chromaticity Coordinates (x, y) |
|---|---|---|---|---|
| Device Example 1 | C-6 | 2.8 | 33.1 | (0.661, 0.339) |
| Device Example 2 | C-7 | 2.8 | 30.1 | (0.657, 0.342) |
| Device Example 3 | C-39 | 2.9 | 28.1 | (0.656, 0.343) |
| Device Example 4 | C-40 | 2.8 | 33.0 | (0.658, 0.341) |
| Device Example 5 | C-178 | 3.0 | 26.8 | (0.656, 0.343) |
| Device Example 6 | C-180 | 3.0 | 26.0 | (0.654, 0.344) |
| Device Example 7 | C-179 | 2.8 | 34.5 | (0.656, 0.343) |
| Comparative Example 1 | A | 4.2 | 21.4 | (0.662, 0.338) |

From Table 1 above, it can be confirmed that the organic electroluminescent device comprising the compound according to the present disclosure as a hole transport layer material exhibits superior properties, particularly lower driving voltage and/or higher power efficiency compared to the organic electroluminescent device using the conventional compound.

Without being limited by theory, it is understood that the excellent effect of the compound of the present disclosure as described above is due to the following properties. The indeno[1,2-b]phenanthrene compound of the present disclosure may exhibit sufficient triplet energy in the hole transport layer due to the high triplet energy of phenanthrene. In addition, indeno[1,2-b]phenanthrene core does not contain a heteroatom, which has additional lone pairs that can possibly interrupt hole transition, thereby allowing the hole flow to be properly regulated. Thus, the performance of the device including the same can be improved. Furthermore, indeno[1,2-b]phenanthrene may show a high glass transition temperature (Tg) and/or a high refractive index, which is advantageous in terms of morphological stability, since heat generation cannot be avoided during OLED device operation.

Device Examples 8 to 10: Producing a Red OLED Comprising the Organic Electroluminescent Compound According to the Present Disclosure OLEDs according to the present disclosure were produced. A transparent electrode indium tin oxide (ITO) thin film (10 Ω/sq) on a glass substrate for an OLED (GEO-MATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 was introduced into a cell of the vacuum vapor deposition apparatus, and compound HT-2 was introduced into another cell of the vacuum vapor deposition apparatus. The two materials were evaporated at different rates, and compound HI-1 was deposited in a doping amount of 3 wt % based on the total amount of compound HI-1 and compound HT-2 to form a hole injection layer having a thickness of 10 nm on the ITO substrate. Next, compound HT-2 was deposited on the hole injection layer to form a first hole transport layer having a thickness of 80 nm. Compound HT-3 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: the first and second host compounds shown in Table 2 below were introduced into two cells of the vacuum vapor deposition apparatus as hosts, and compound D-39 was introduced into another cell as a dopant. The two host materials were evaporated at a rate of 1:1 and the dopant material was simultaneously evaporated at a different rate, and the dopant was deposited in a doping amount of 3 wt % based on the total amount of the hosts and the dopant to form a light-emitting layer having a thickness of 40 nm on the second hole transport layer. Thereafter, compound ETL-2 and compound EIL-1 were evaporated in a weight ratio of 50:50 to deposit an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the materials used for producing the OLED were purified by vacuum sublimation at $10^{-6}$ torr.

Comparative Example 2: Producing an OLED Comprising a Comparative Compound as a Single Host An OLED was produced in the same manner as in Device Example 8, except that compound RH-2 was used as a single host of the light-emitting layer.

Comparative Example 3: Producing an OLED Comprising a Comparative Compound as the First Host An OLED was produced in the same manner as in Device Example 8, except that the first host compound shown in Table 2 below was used as the first host of the light-emitting layer.

The driving voltage, luminous efficiency, and light-emitting color at a luminance of 1,000 nit, and the time taken for luminance to decrease from 100% to 95% (lifetime; T95) at a luminance of 10,000 nit of the OLEDs produced in Device Examples 8 to 10, and Comparative Examples 2 and 3 are provided in Table 2 below.

TABLE 2

|  | First Host | Second Host | Driving Voltage [V] | Luminous Efficiency [cd/A] | Light-Emitting Color | Lifetime (T95) [hr] |
|---|---|---|---|---|---|---|
| Device Example 8 | C-26 | RH-2 | 3.0 | 35.1 | Red | 120 |
| Device Example 9 | C-6 | RH-2 | 3.0 | 33.0 | Red | 293 |
| Device Example 10 | C-179 | RH-2 | 3.0 | 34.6 | Red | 142 |
| Comparative Example 2 | — | RH-2 | 3.5 | 31.8 | Red | 18 |
| Comparative Example 3 | A | RH-2 | 3.4 | 33.1 | Red | 113 |

From Table 2 above, it can be confirmed that the organic electroluminescent device comprising the compound according to the present disclosure as a host material exhibits superior properties, particularly low driving voltage, high luminous efficiency, and/or long lifetime properties compared to the organic electroluminescent device using the conventional compound.

The compounds used in the Device Examples and the Comparative Examples are shown in Table 3 below.

TABLE 3

| Hole Injection Layer/ Hole Transport Layer | |
|---|---|

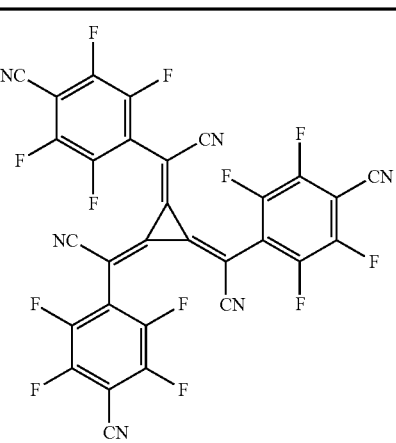

HI-1

TABLE 3-continued
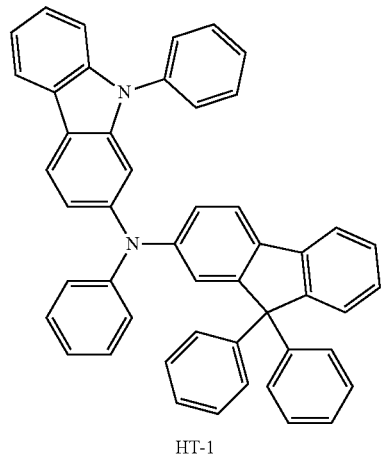
HT-1
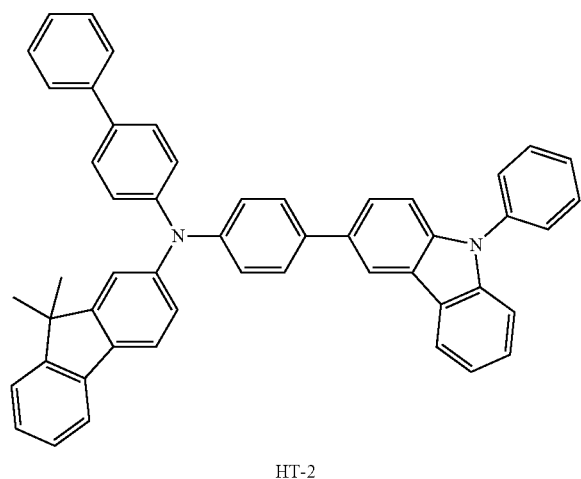
HT-2
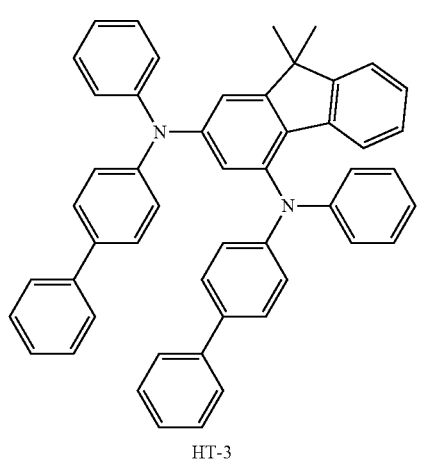
HT-3

TABLE 3-continued
Second Hole Transport Layer
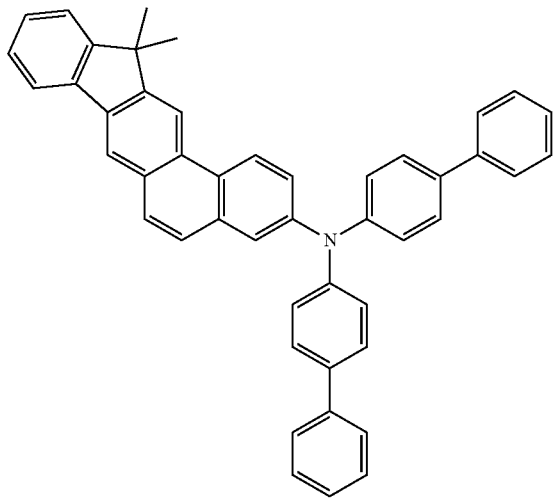
C-6
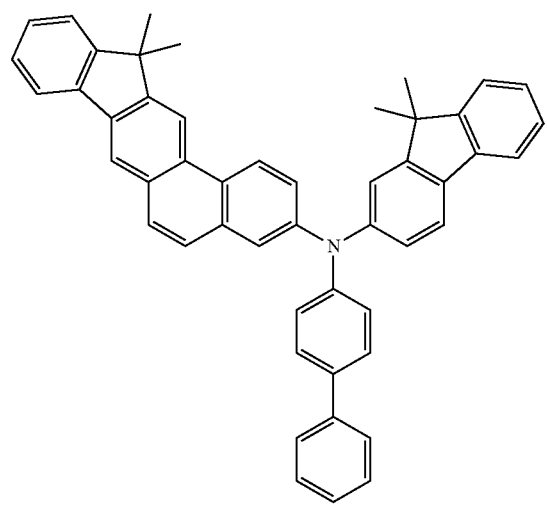
C-7
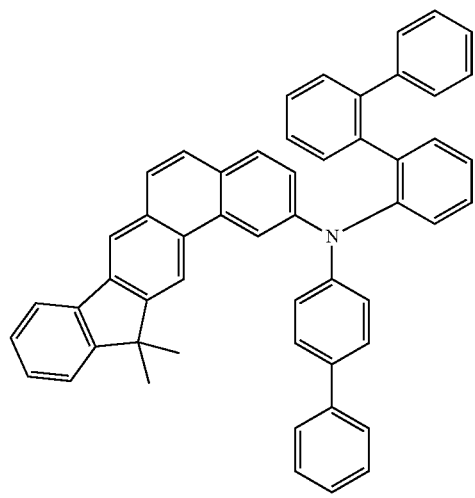
C-39

TABLE 3-continued
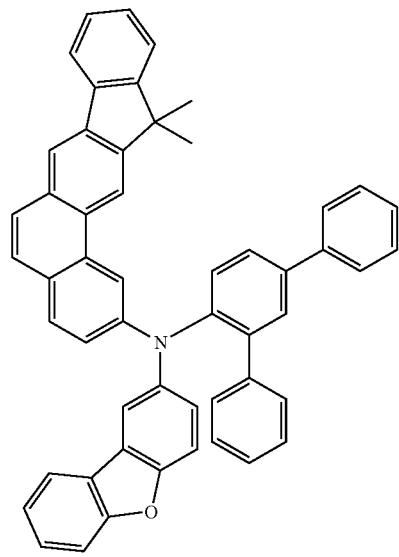
C-40
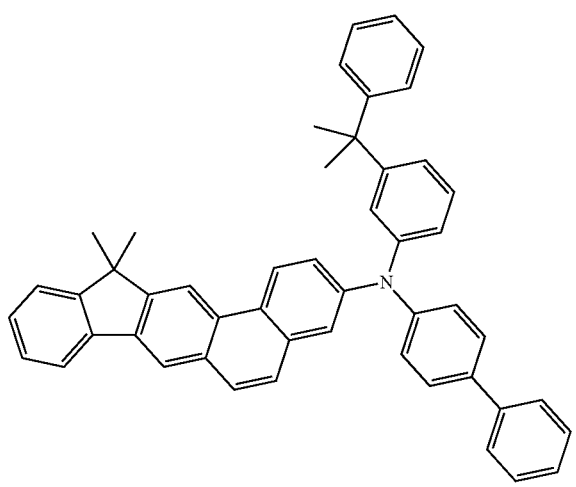
C-178
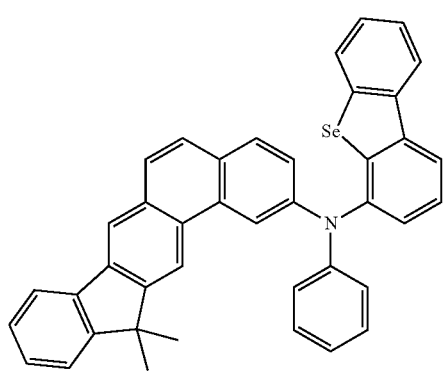
C-180

TABLE 3-continued
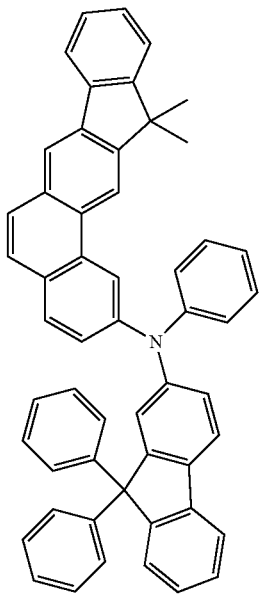
C-179
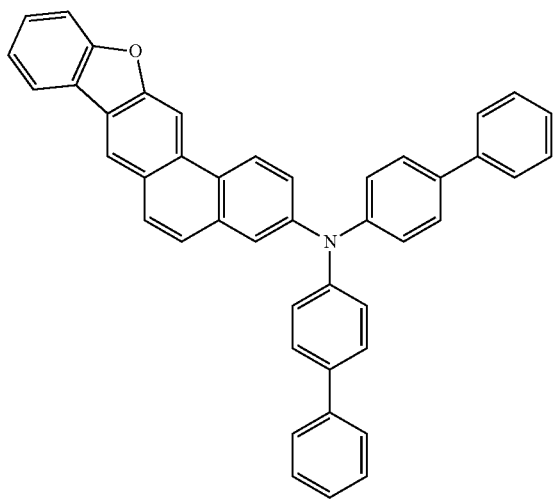
A
Light-Emitting
Layer
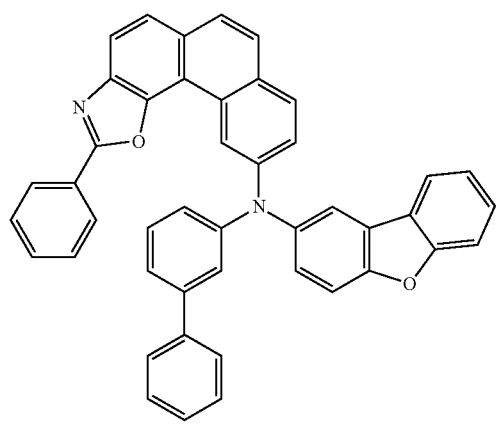
RH-1

TABLE 3-continued
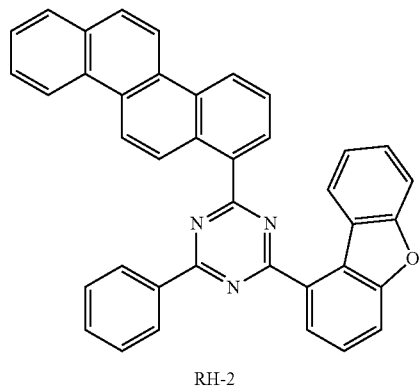 [SMILES: c1ccc(-c2nc(-c3cccc4c3ccc3c5ccccc5ccc43)nc(-c3cccc4oc5ccccc5c34)n2)cc1]
RH-2
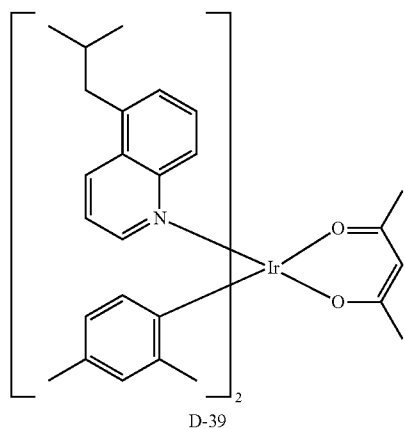
D-39
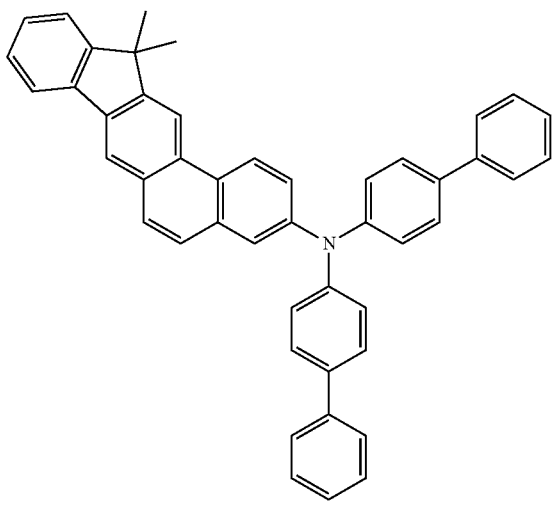
C-6

TABLE 3-continued
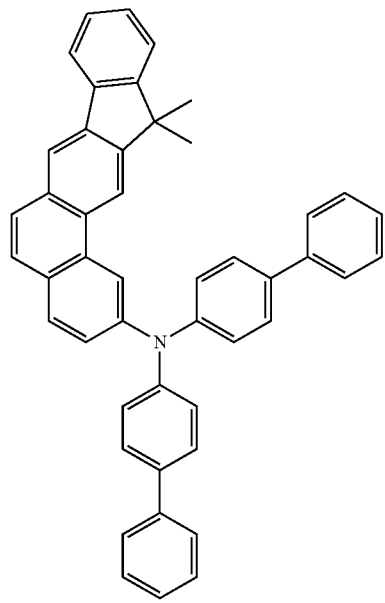
C-26
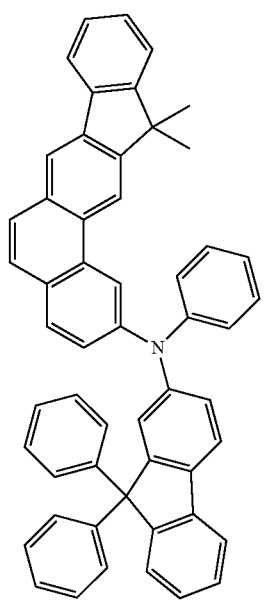
C-179

TABLE 3-continued
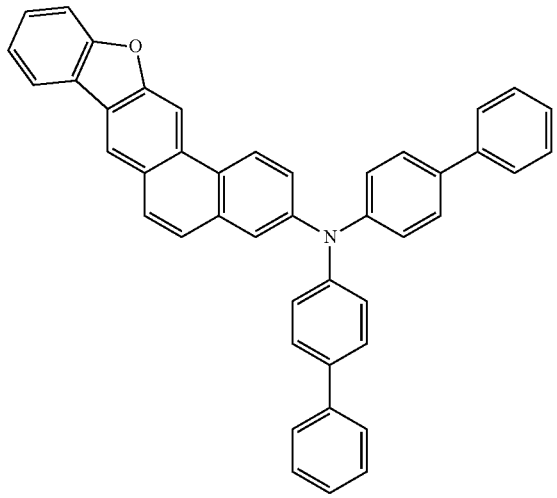
A
Electron Buffer Layer
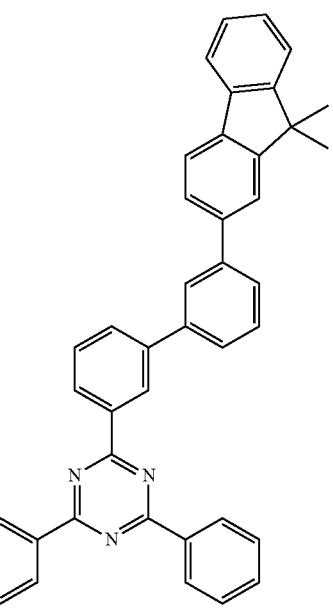
HBL
Electron Transport Layer/Electron Injection Layer
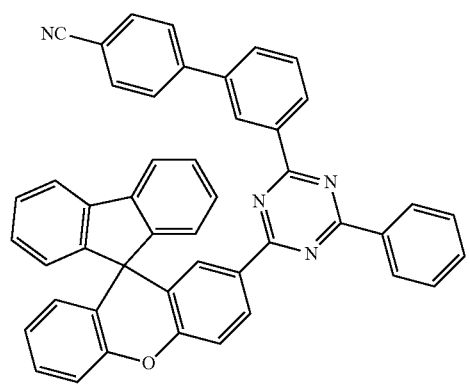
ETL-1

TABLE 3-continued

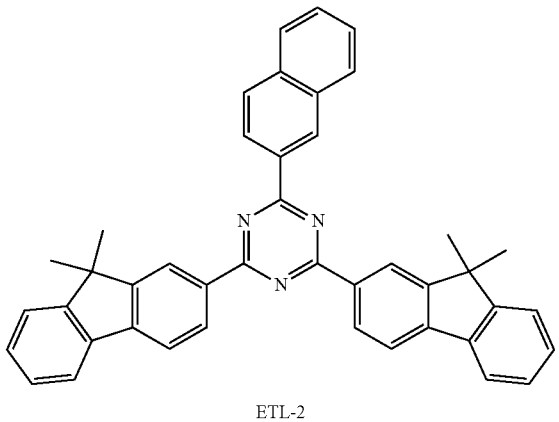 [SMILES: CC1(C)c2ccccc2-c2ccc(-c3nc(-c4ccc5c(c4)C(C)(C)c4ccccc4-5)nc(-c4ccc5ccccc5c4)n3)cc21]

ETL-2

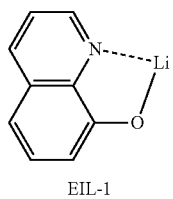

EIL-1

The invention claimed is:

1. An organic electroluminescent compound represented by the following formula 1:

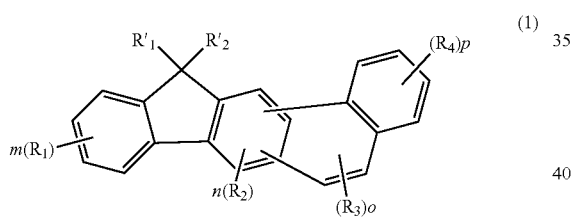

in formula 1,

R'$_1$ and R'$_2$, each independently, represent a substituted or unsubstituted (C1-C30)alkyl, a substituted or unsubstituted (C6-C30)aryl, or a substituted or unsubstituted (3- to 30-membered)heteroaryl; or R'$_1$ and R'$_2$ may be linked to each other to form a ring(s), in which R'$_1$ and R'$_2$ may be the same as or different from each other;

R$_1$ to R$_4$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30) alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or -L$_1$-N—(Ar$_1$)(Ar$_2$); or may be linked to an adjacent substituent to form a ring(s);

with the proviso that any one of R$_1$'s to R$_4$'s represents -L$_1$-N—(Ar$_1$)(Ar$_2$);

L$_1$ represents a single bond, a substituted or unsubstituted (C6-C30)arylene, or a substituted or unsubstituted (3- to 30-membered)heteroarylene;

Ar$_1$ and Ar$_2$, each independently, represent a substituted or unsubstituted (C1-C30)alkyl, a substituted or unsubstituted (C2-C30)alkenyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl; and m and p, each independently, represent an integer of 4; n and o, each independently, represent an integer of 2; and each of R$_1$ to each of R$_4$ may be the same or different.

2. The organic electroluminescent compound according to claim 1, wherein formula 1 is represented by the following formula 1-1:

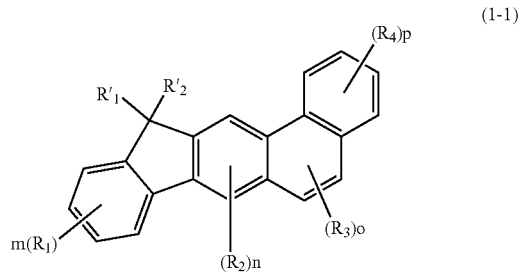

in formula 1-1, R'$_1$, R'$_2$, R$_1$ to R$_4$, and m to p are as defined in claim 1.

3. The organic electroluminescent compound according to claim 1, wherein formula 1 is represented by any one of the following formulas 1-1-1 to 1-1-4:

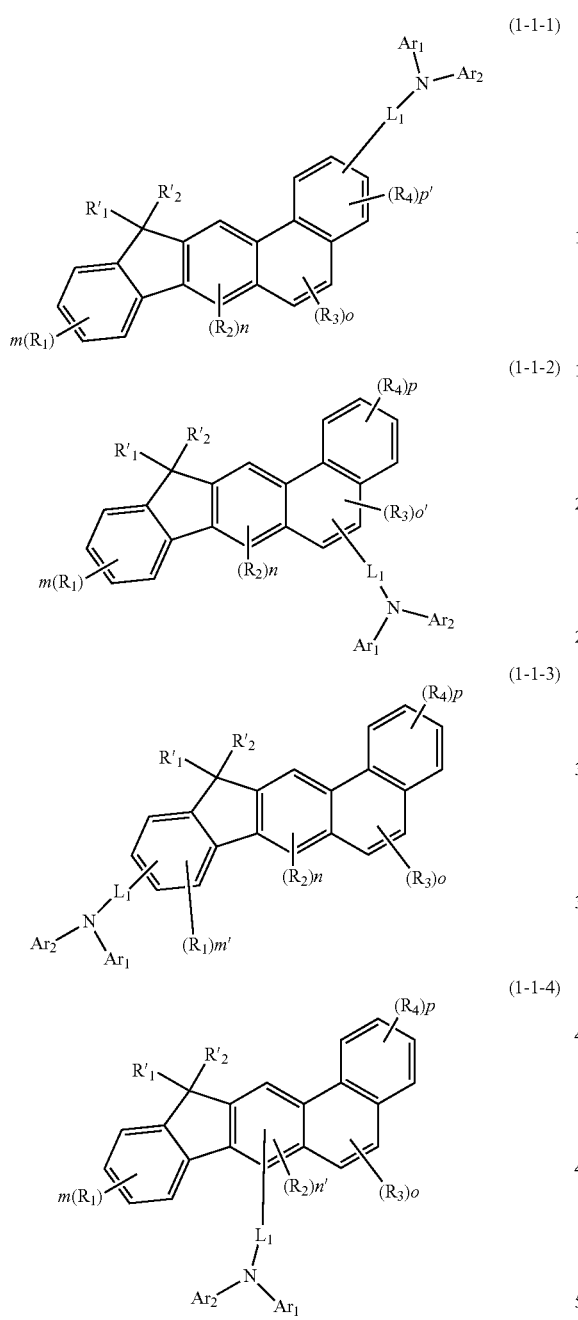

(1-1-1)

(1-1-2)

(1-1-3)

(1-1-4)

in formulas 1-1-1 to 1-1-4,

R'$_1$, R'$_2$, L$_1$, Ar$_1$, Ar$_2$, and m to p are as defined in claim 1;

m' and p', each independently, represent an integer of 3;
n' and o', each independently, represent an integer of 1; and R$_1$ to R$_4$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, or a substituted or unsubstituted fused ring group of a (C3-C30) aliphatic ring(s) and a (C6-C30) aromatic ring(s); or may be linked to an adjacent substituent to form a ring(s).

4. The organic electroluminescent compound according to claim 1, wherein formula 1 is represented by any one of the following formulas 1-1-1-1 to 1-1-1-12:

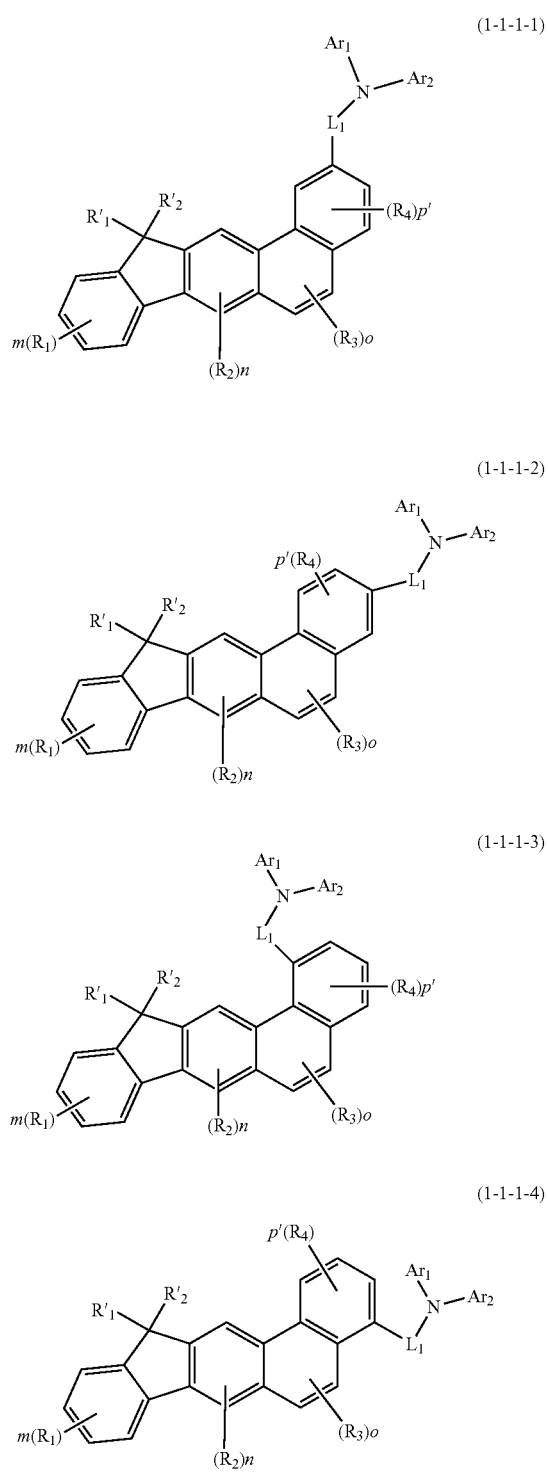

(1-1-1-1)

(1-1-1-2)

(1-1-1-3)

(1-1-1-4)

(1-1-1-5)
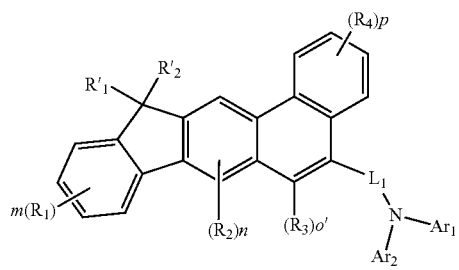

(1-1-1-6)
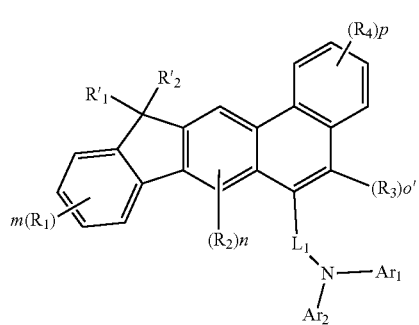

(1-1-1-7)
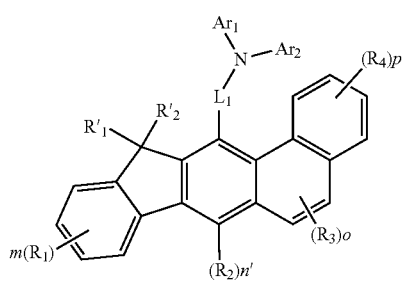

(1-1-1-8)
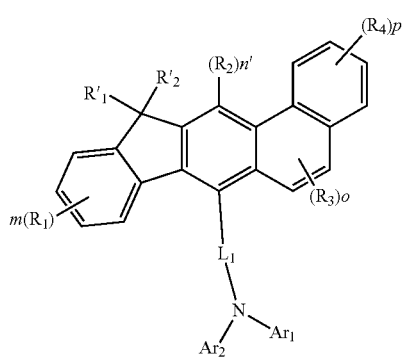

(1-1-1-9)
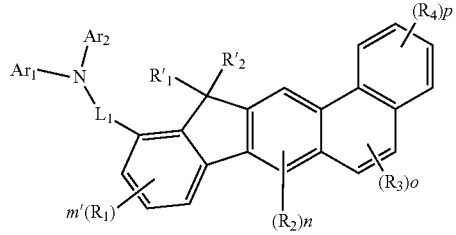

(1-1-1-10)
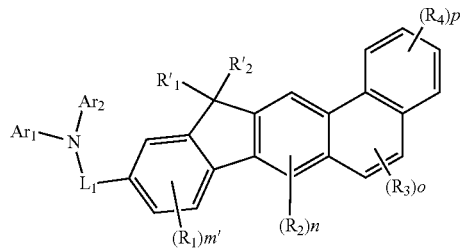

(1-1-1-11)
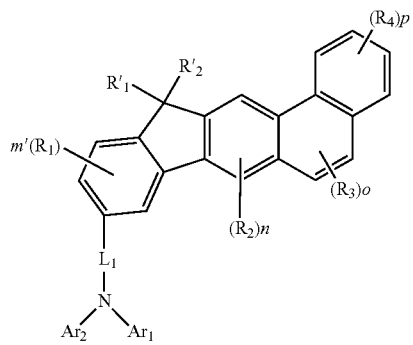

(1-1-1-12)
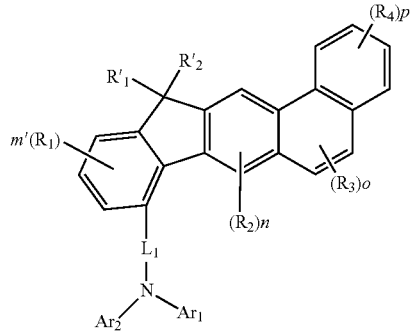

in formulas 1-1-1-1 to 1-1-1-12, $R'_1$, $R'_2$, $L_1$, $Ar_1$, $Ar_2$, and m to p are as defined in claim 1;

m' and p', each independently, represent an integer of 3; n' and o', each independently, represent an integer of 1; and $R_1$ to $R_4$, each independently, represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, or a substituted or unsubstituted fused ring group of a (C3-C30) aliphatic ring(s) and a (C6-C30) aromatic ring(s); or may be linked to an adjacent substituent to form a ring(s).

5. The organic electroluminescent compound according to claim 1, wherein the substituent(s) of the substituted alkyl, the substituted alkenyl, the substituted aryl, the substituted arylene, the substituted heteroaryl, the substituted heteroarylene, the substituted cycloalkyl, the substituted alkoxy, the substituted trialkylsilyl, the substituted dialkylarylsilyl, the substituted alkyldiarylsilyl, the substituted triarylsilyl, and the substituted fused ring group of an aliphatic ring(s) and an aromatic ring(s), each independently, are at least one selected from the group consisting of deuterium; a halogen; a cyano; a carboxyl; a nitro; a hydroxyl; a phosphineoxide; a (C1-C30)alkyl; a halo(C1-C30)alkyl; a (C2-C30)alkenyl unsubstituted or substituted with a (C6-C30)aryl(s); a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of a (C1-C30)alkyl(s) and (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; a fused ring group of a (C3-C30) aliphatic ring(s) and a (C6-C30) aromatic ring(s); a (C1-C30)alkylcarbonyl; a (C1-C30)alkoxycarbonyl; a (C6-C30)arylcarbonyl; a (C6-C30)arylphosphinyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

6. The organic electroluminescent compound according to claim 1, wherein the compound represented by formula 1 is selected from the group consisting of the following:

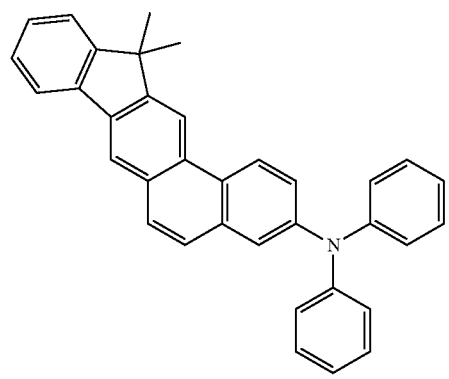

C-1

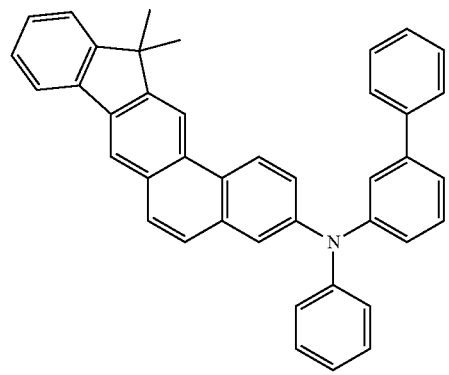

C-2

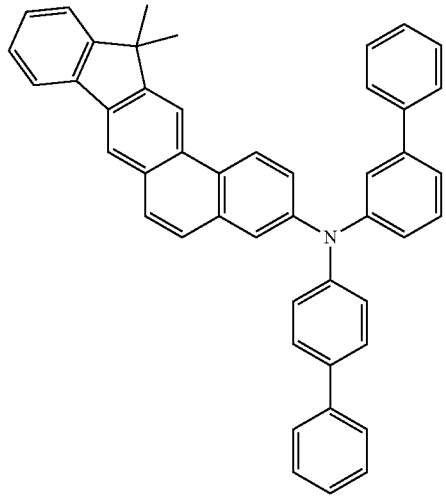

C-3

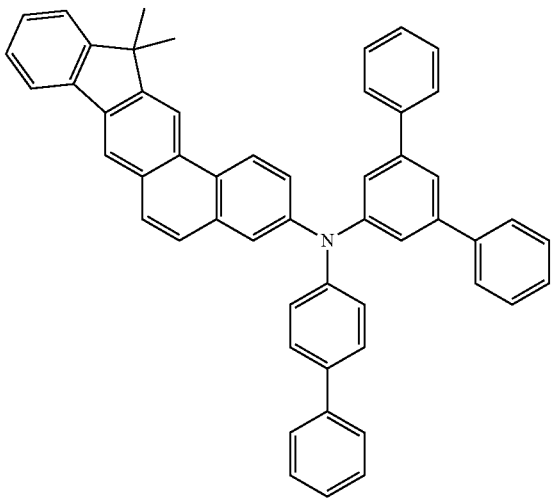

C-4

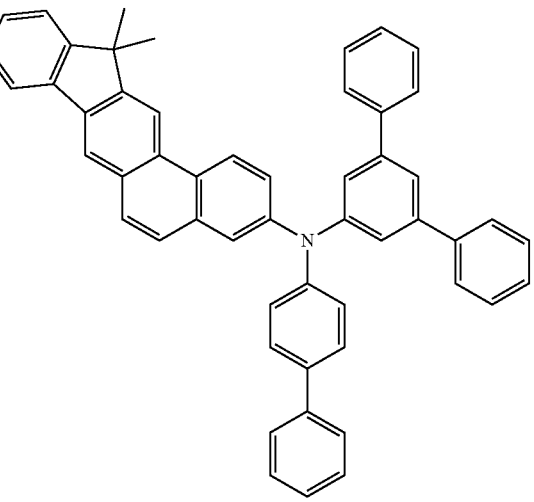

C-5

C-6
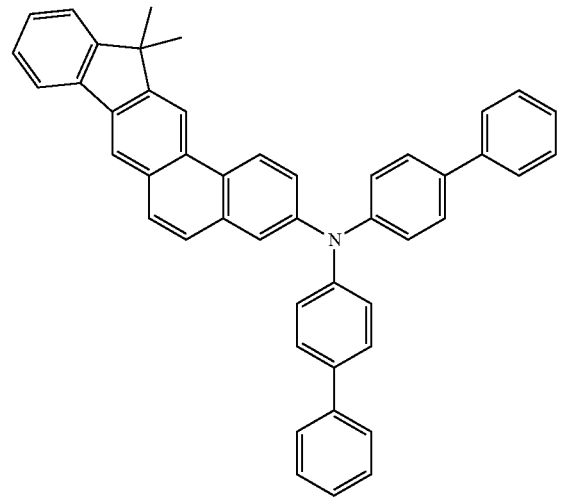
C-7
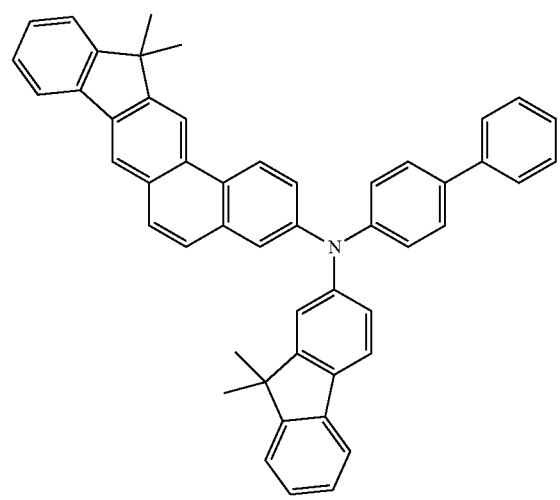
C-8
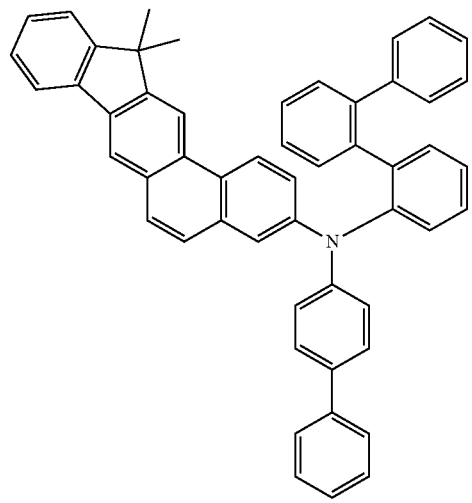
C-9
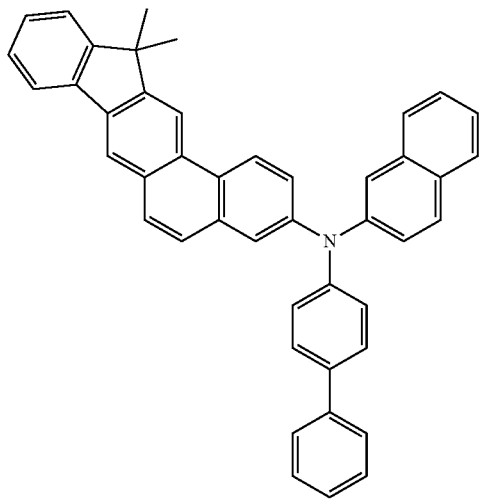
C-10
C-11
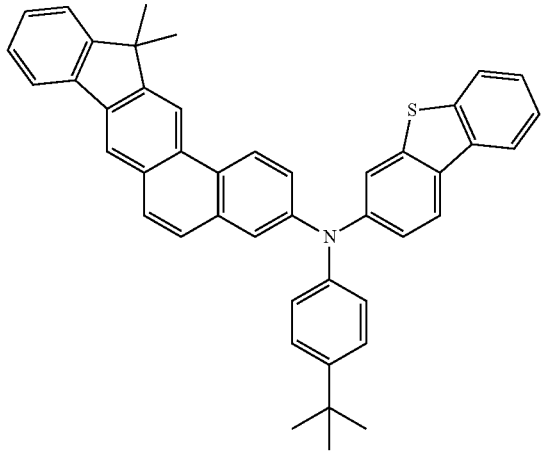

-continued
C-12
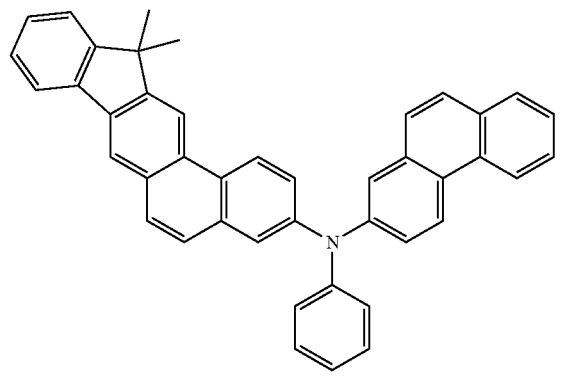
C-13
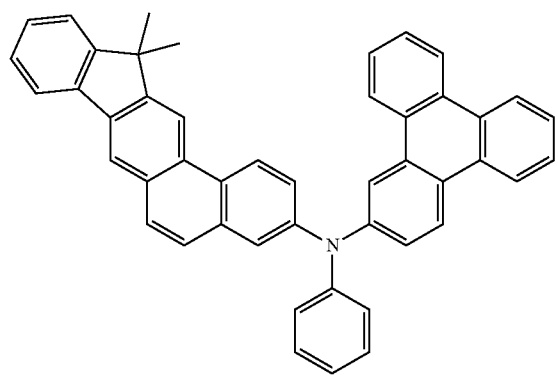
C-14
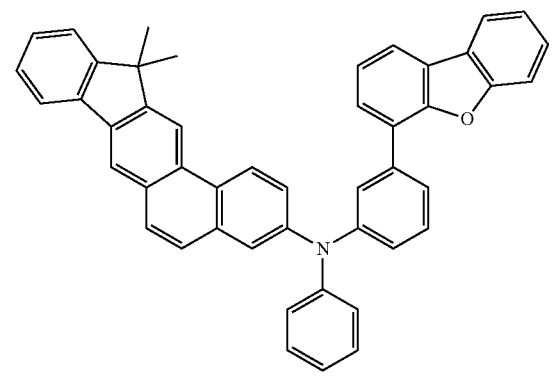
C-15
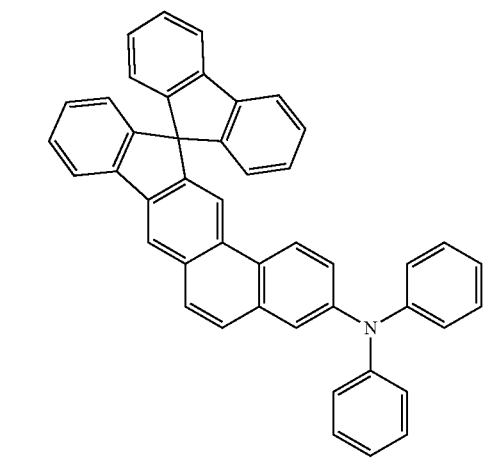
-continued
C-16
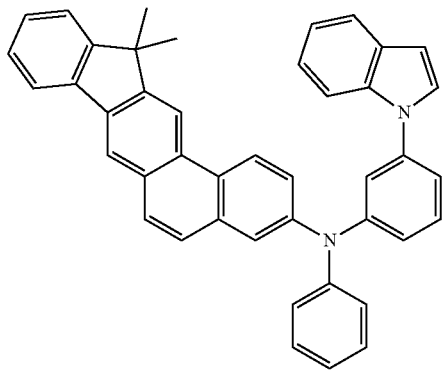
C-17
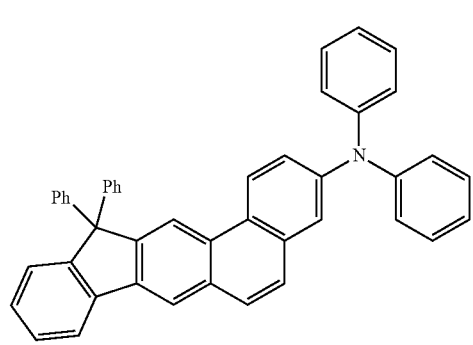
C-18
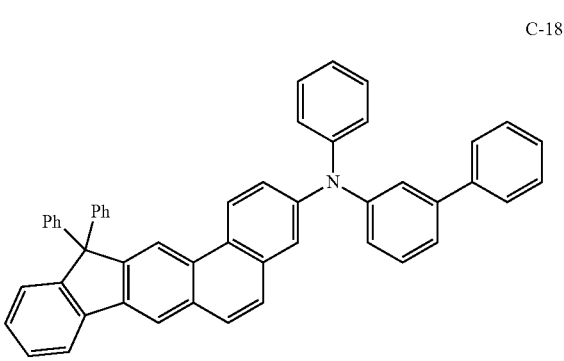
C-19
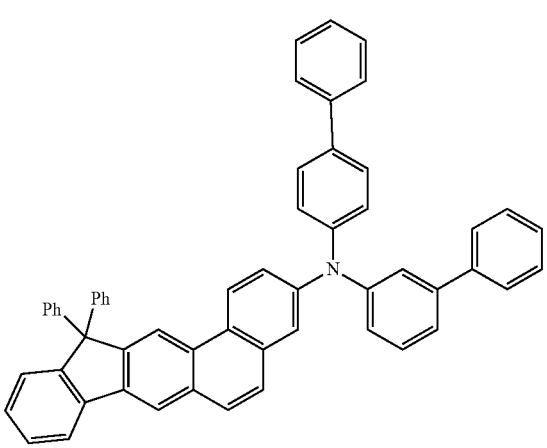

C-20
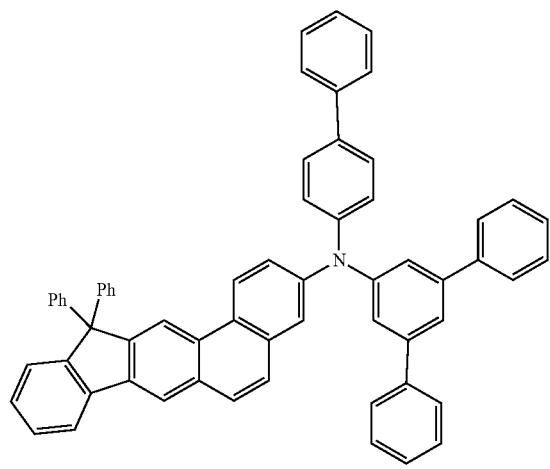
C-21
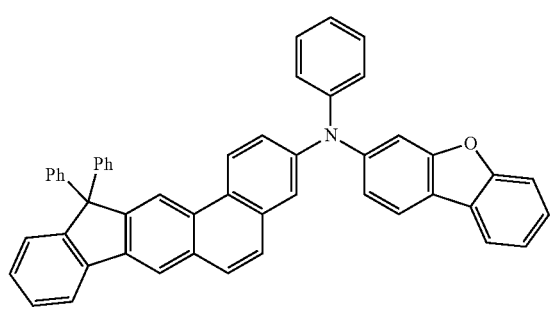
C-22
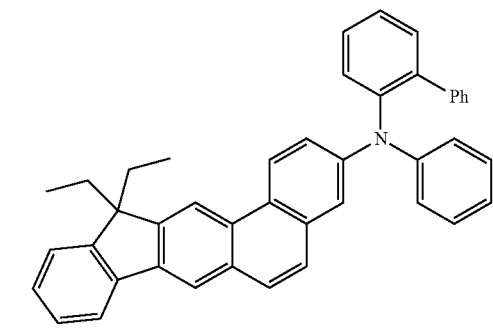
C-23
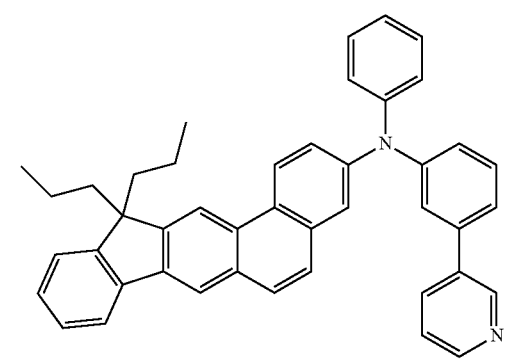
C-24
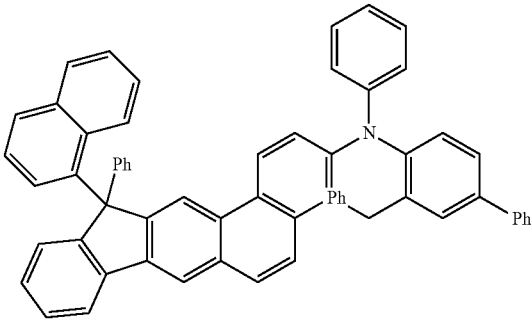
C-25
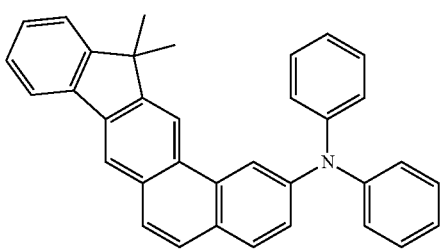
C-26
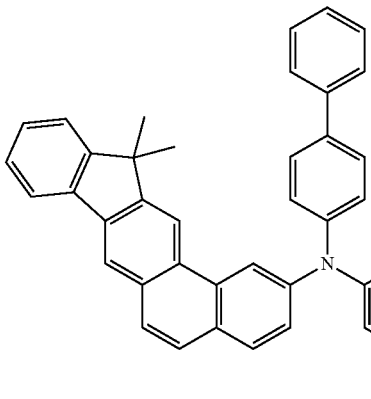
C-27
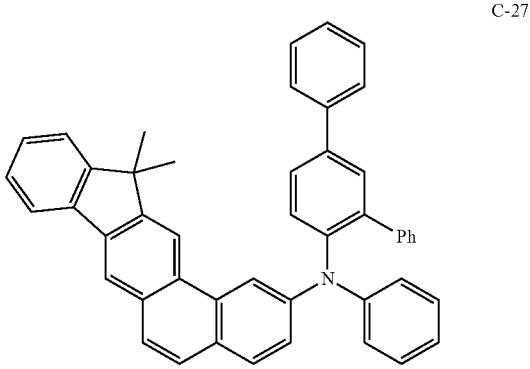

C-28
C-29
C-30
C-31
C-32
C-33
C-34
C-35
C-36

-continued
C-37
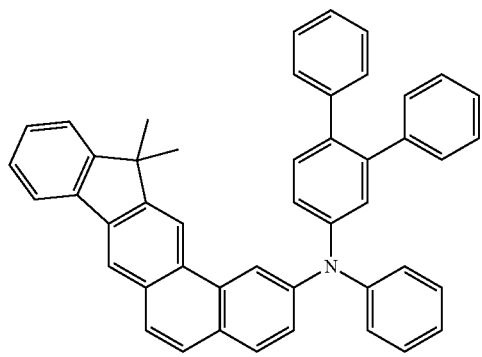
C-38
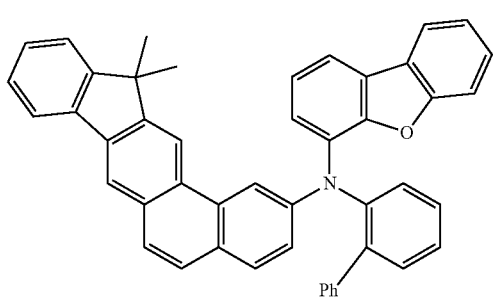
C-39
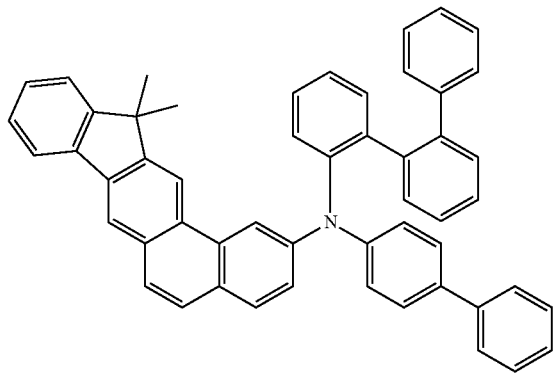
C-40
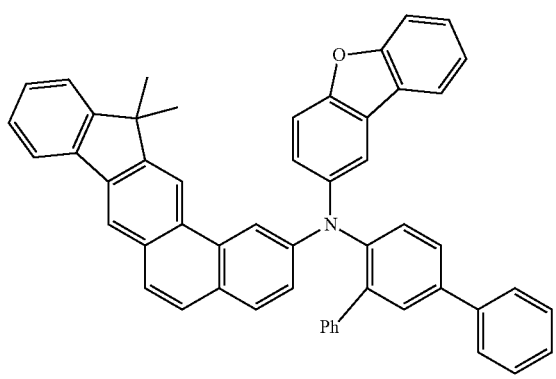
-continued
C-41
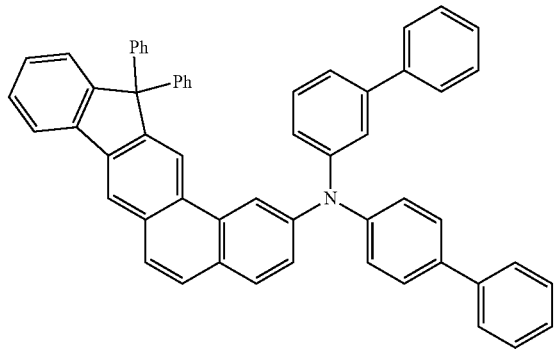
C-42
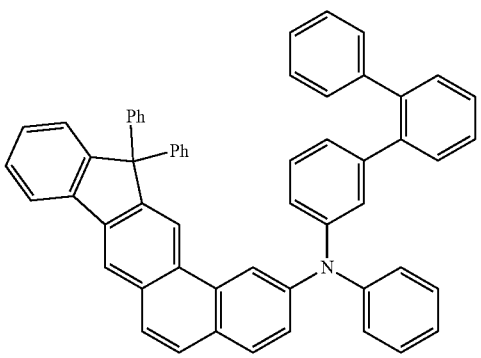
C-43
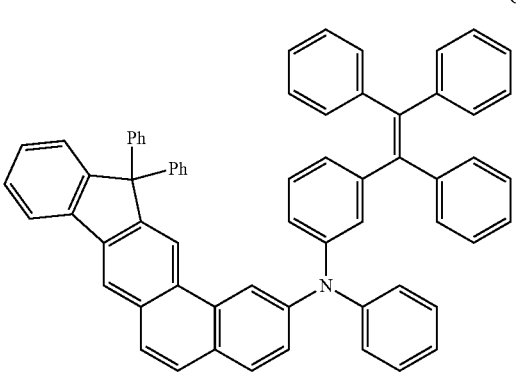
C-44
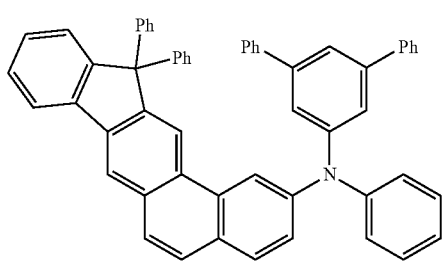

C-45
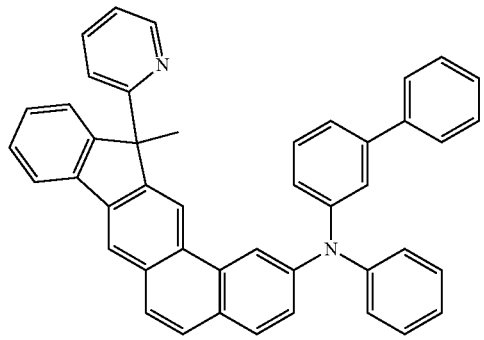
C-46
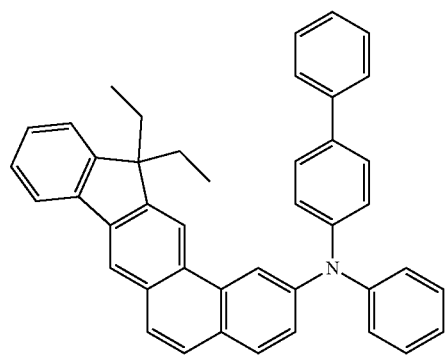
C-47
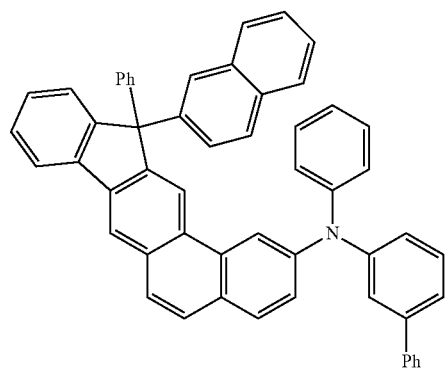
C-48
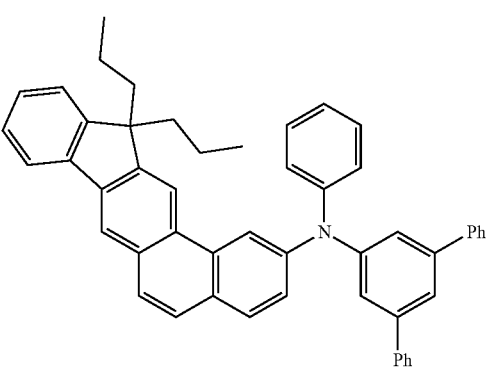
C-49
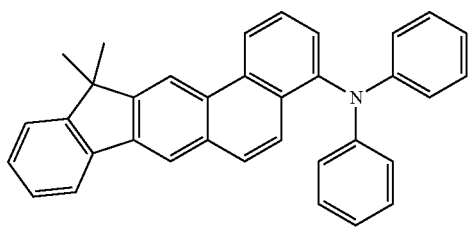
C-50
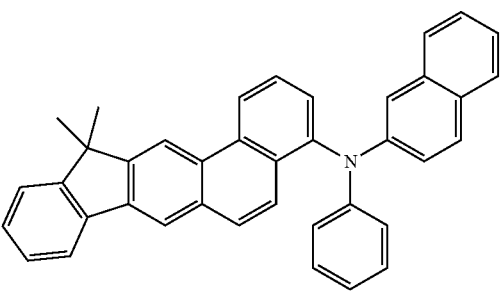
C-51
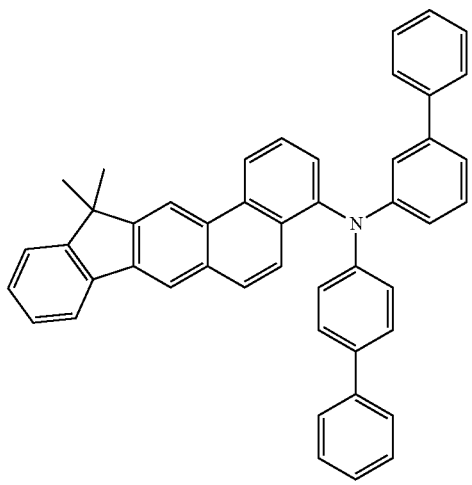
C-52
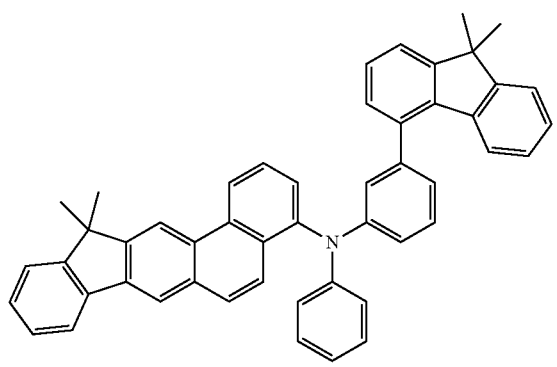

C-53
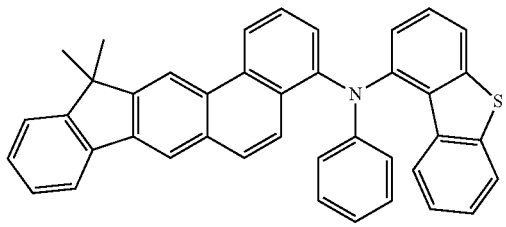
C-54
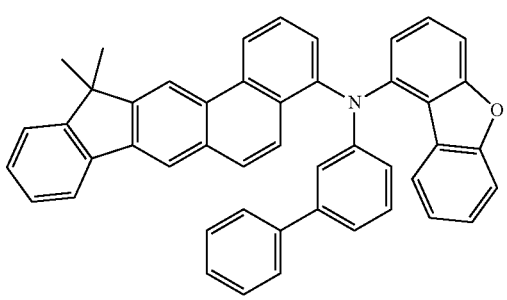
C-55
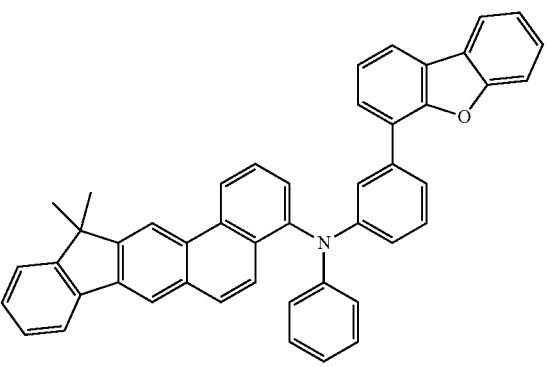
C-56
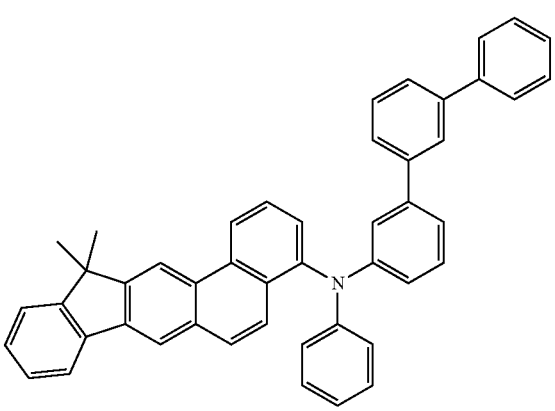
C-57
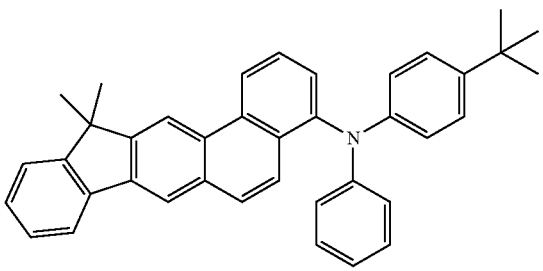
C-58
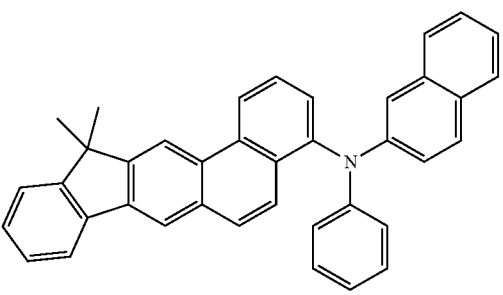
C-59
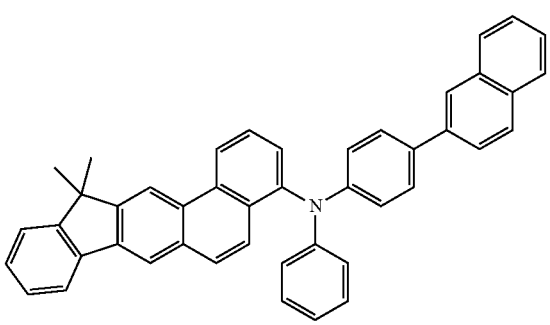
C-60
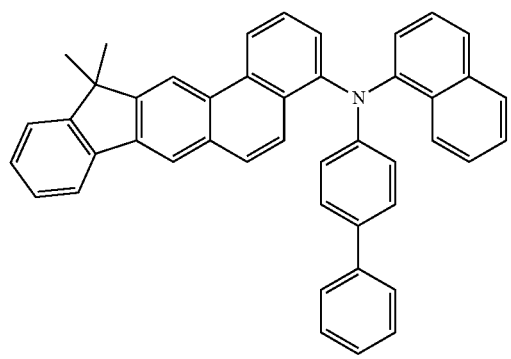

-continued
C-61
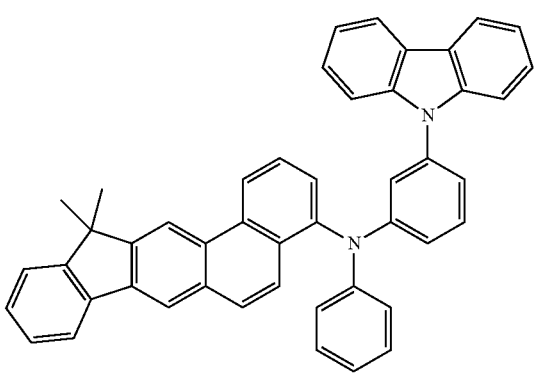
C-62
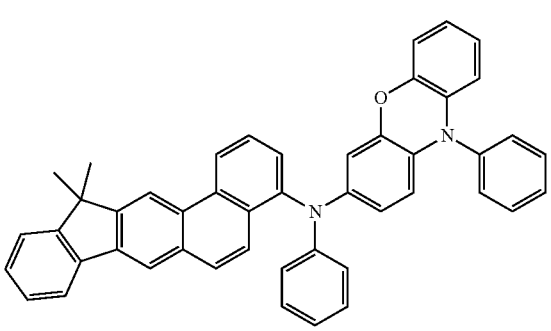
C-63
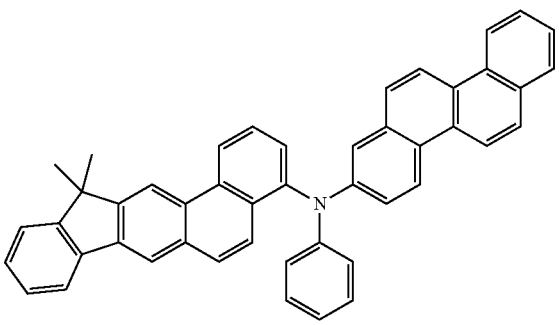
C-64
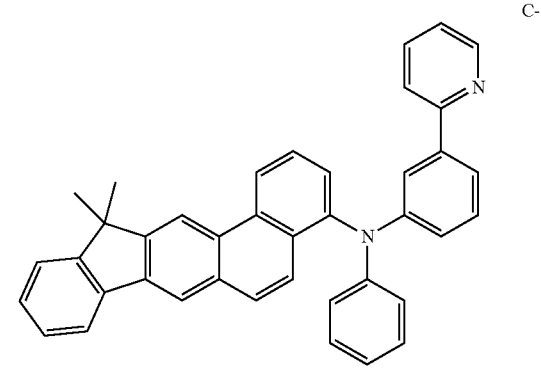
-continued
C-65
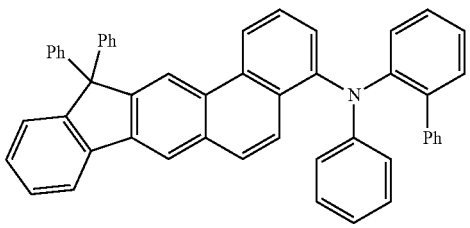
C-66
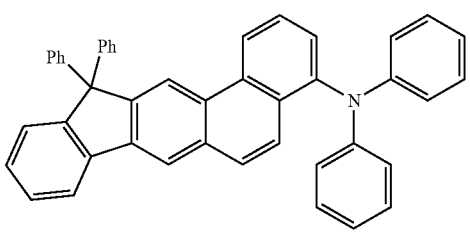
C-67
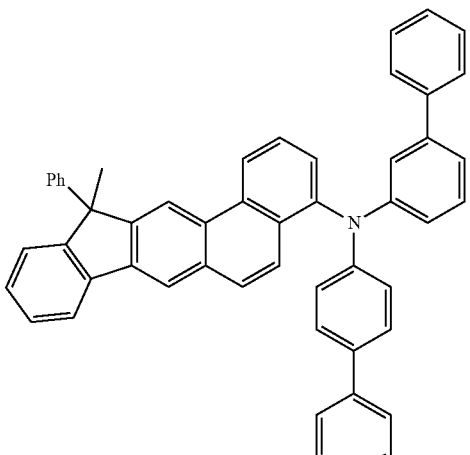
C-68
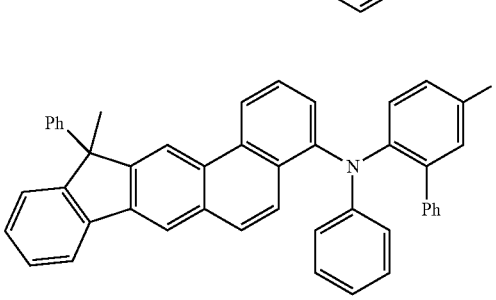
C-69
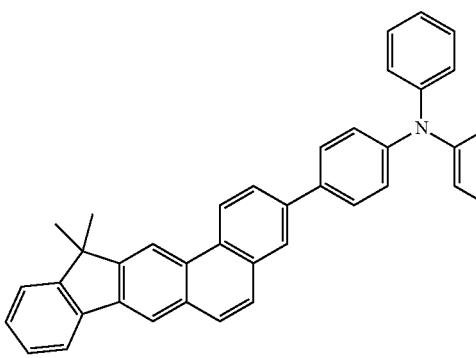

-continued
C-70
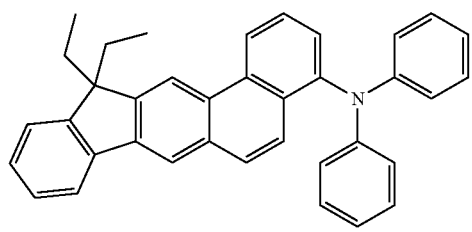
C-71
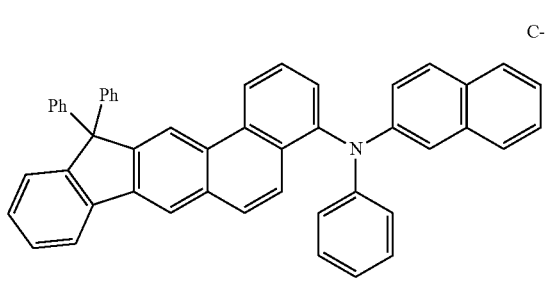
C-72
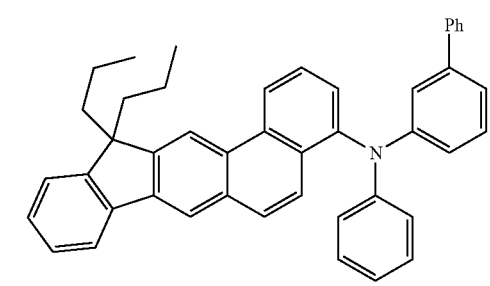
C-73
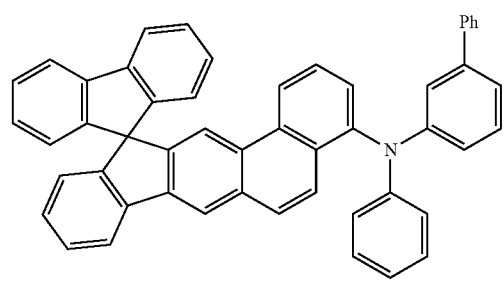
C-74
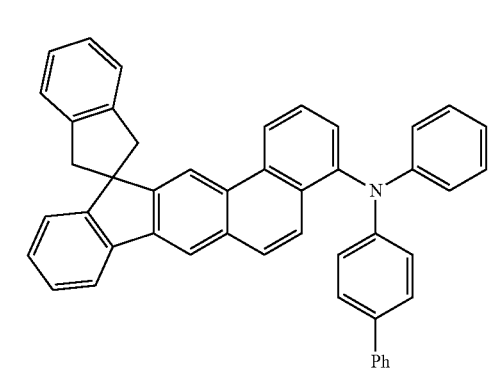
-continued
C-75
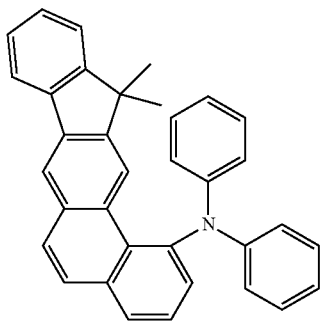
C-76
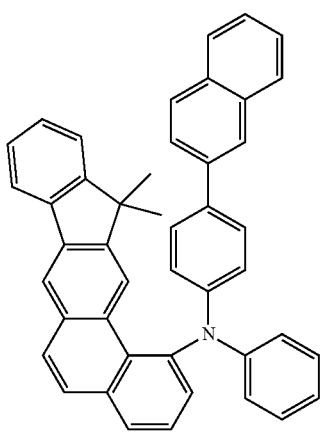
C-77
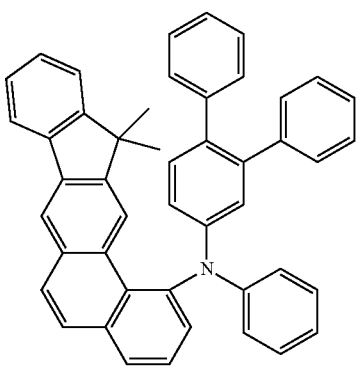
C-78
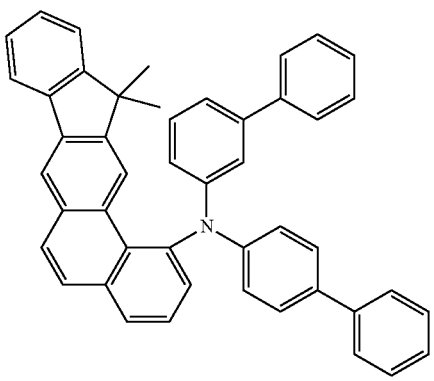

C-79
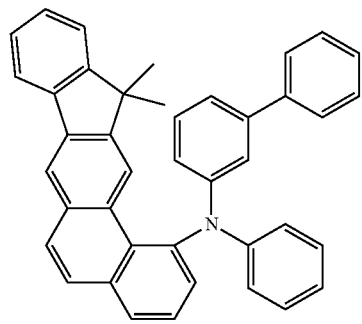
C-80
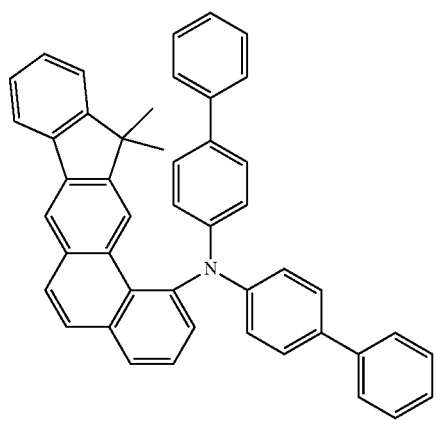
C-81
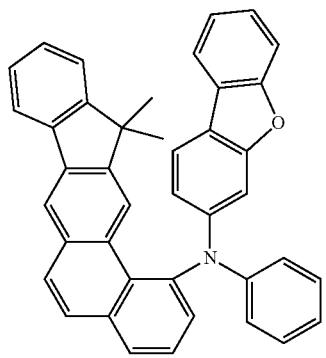
C-82
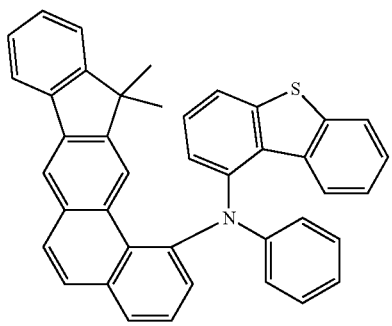
C-83
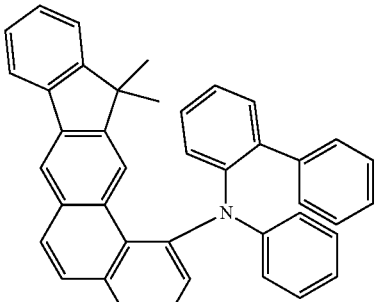
C-84
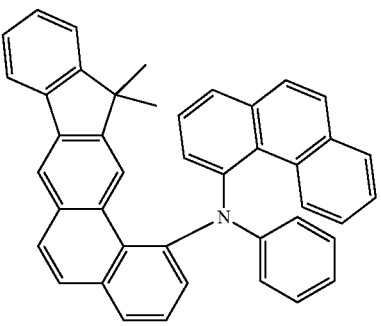
C-85
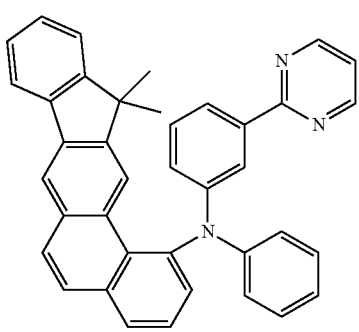
C-86
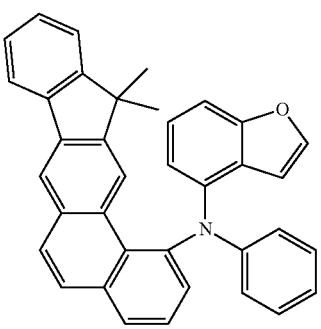

-continued
C-87
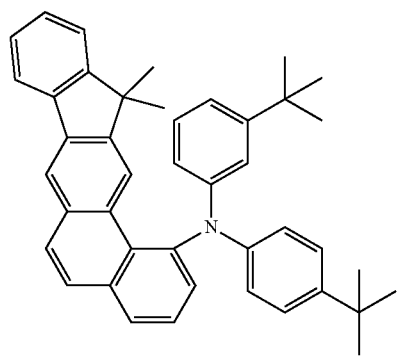
C-88
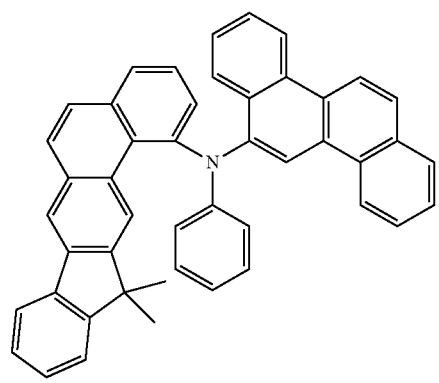
C-89
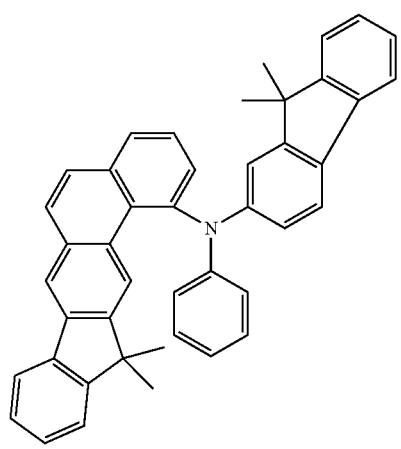
C-90
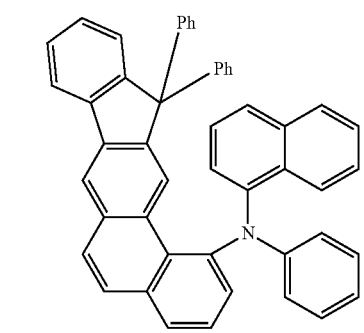
-continued
C-91
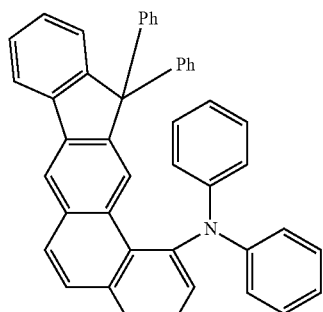
C-92
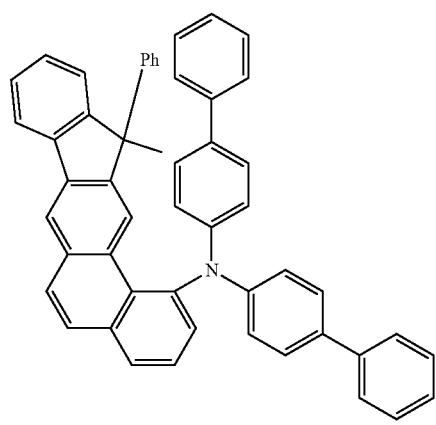
C-93
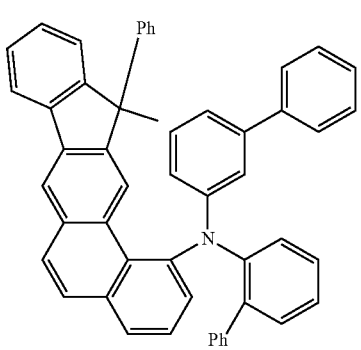
C-94
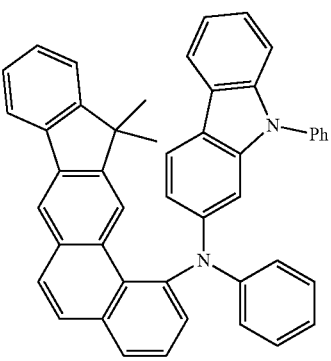

C-95 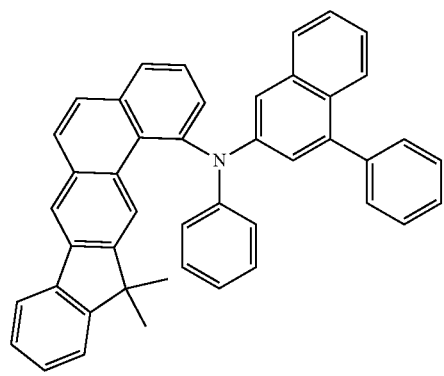
C-99 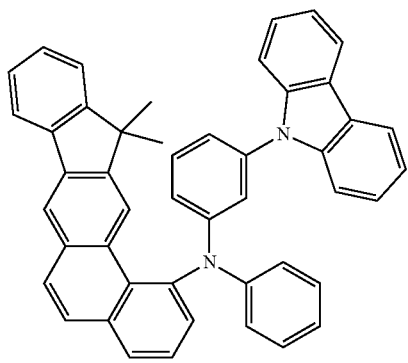
C-96 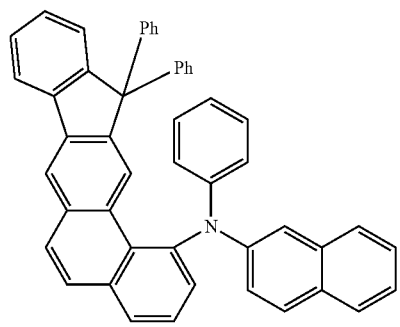
C-100 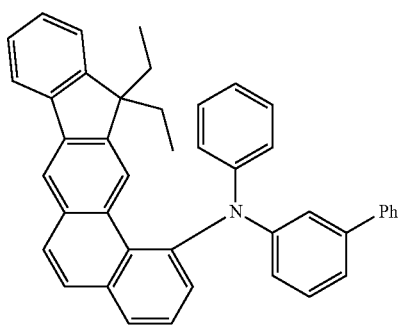
C-97 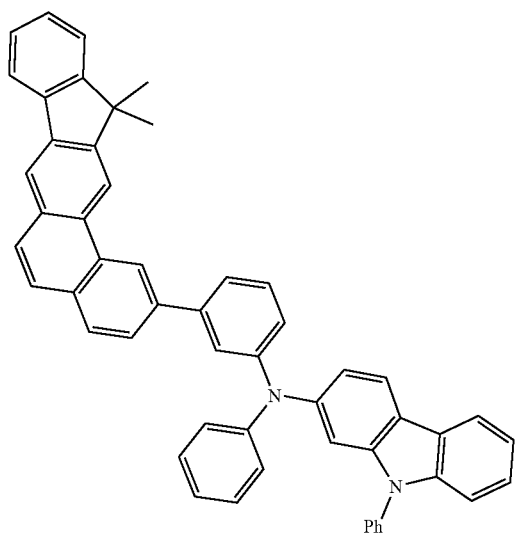
C-101 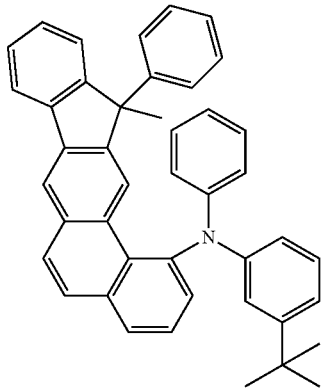
C-98 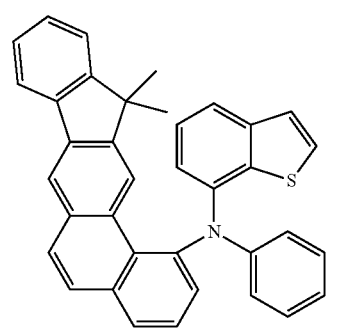
C-102 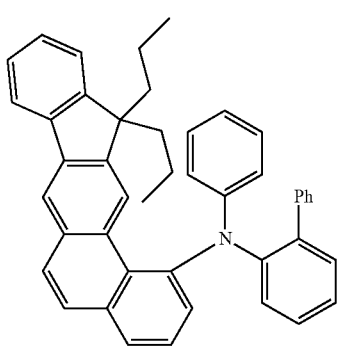

C-103
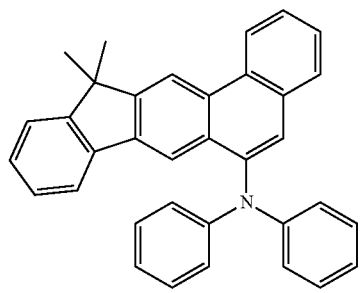
C-107
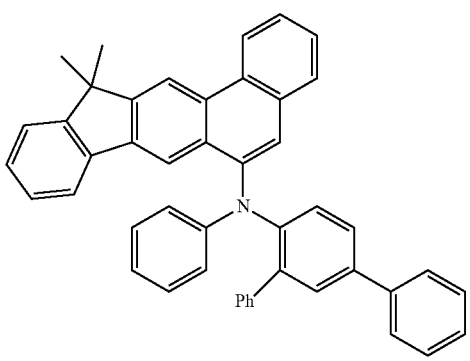
C-104
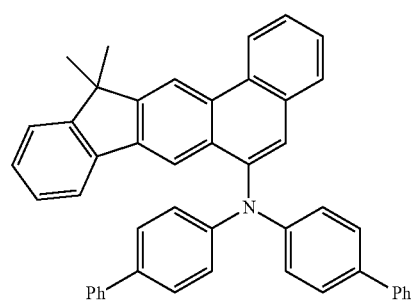
C-108
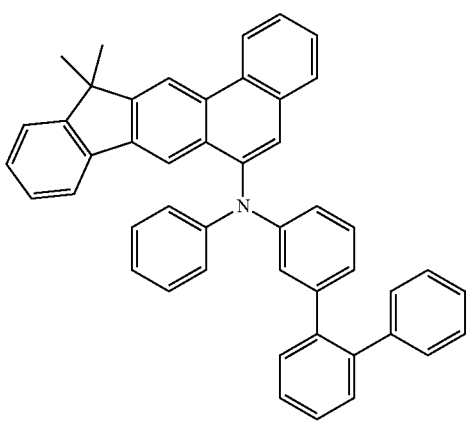
C-105
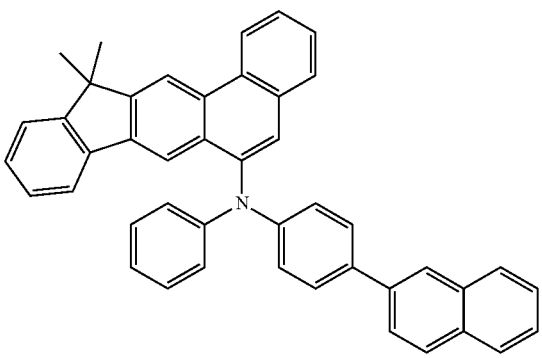
C-109
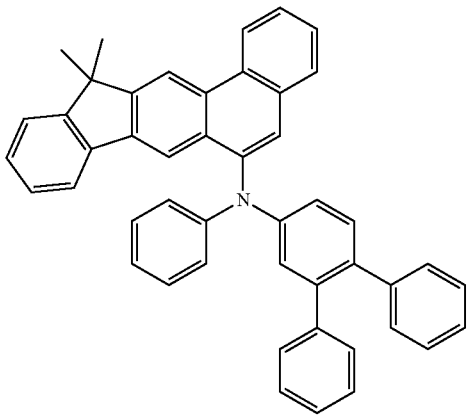
C-106
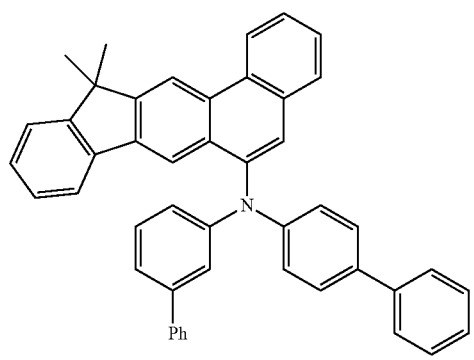
C-110
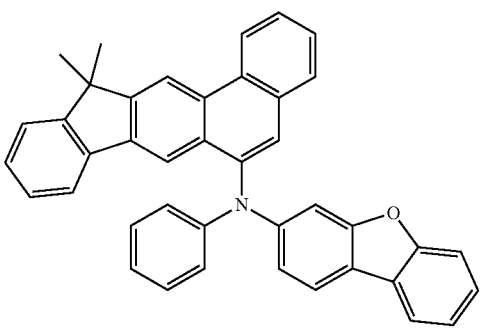

-continued
C-111
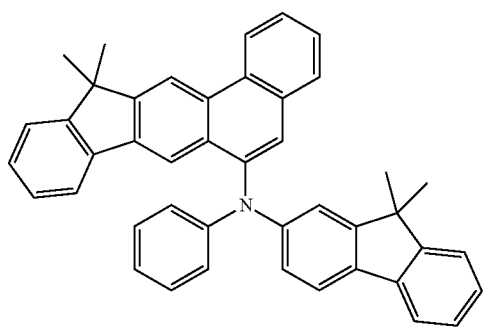
C-112
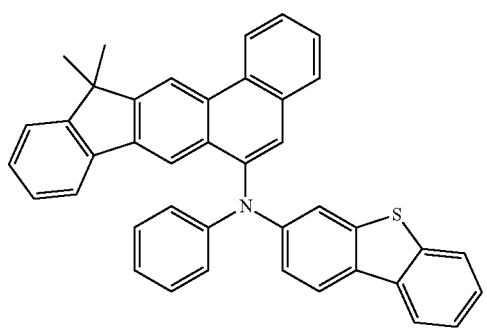
C-113
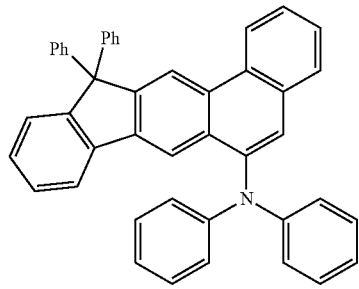
C-114
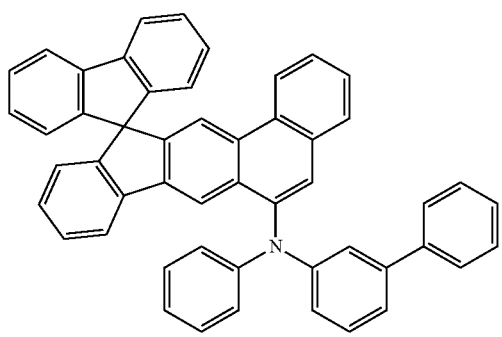
-continued
C-115
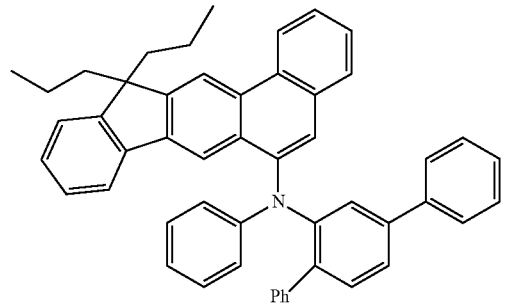
C-116
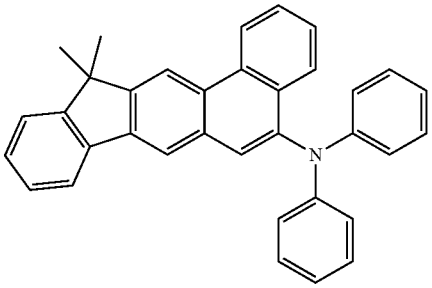
C-117
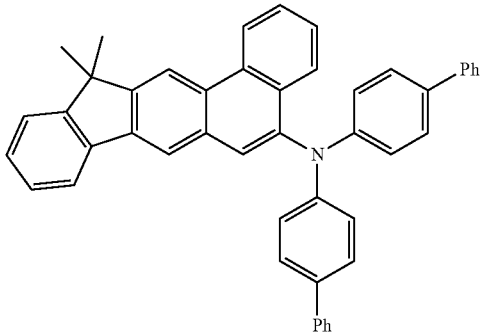
C-118
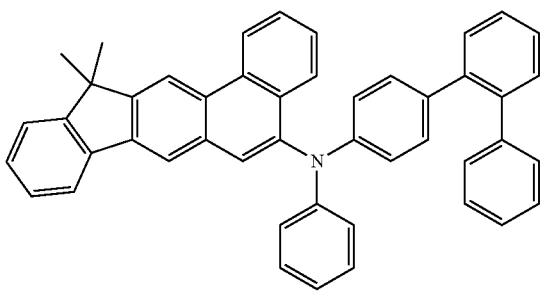

C-119
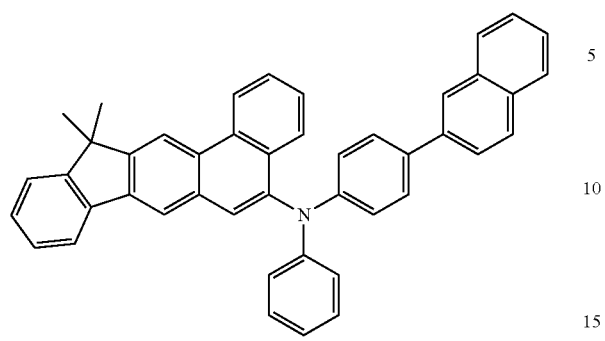
C-120
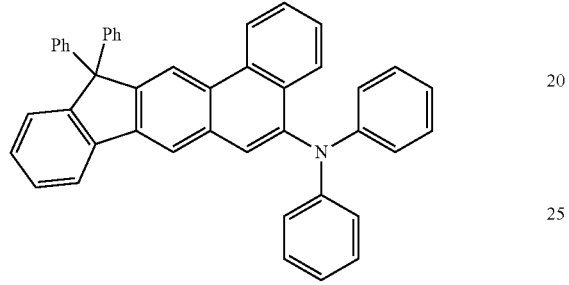
C-121
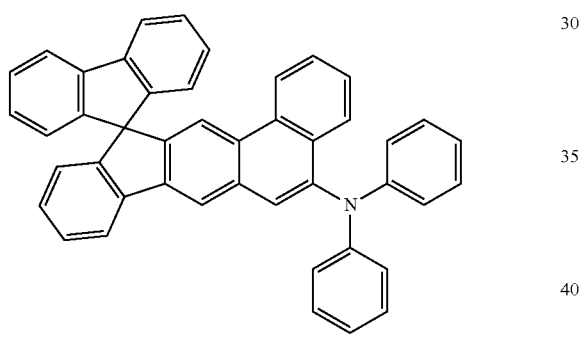
C-122
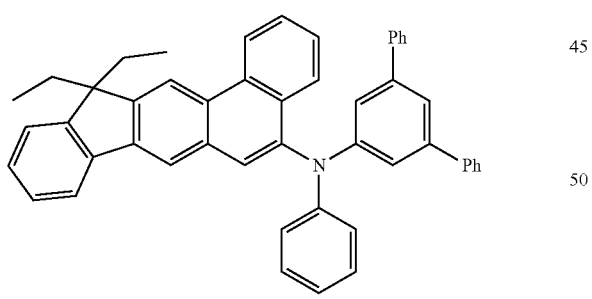
C-123
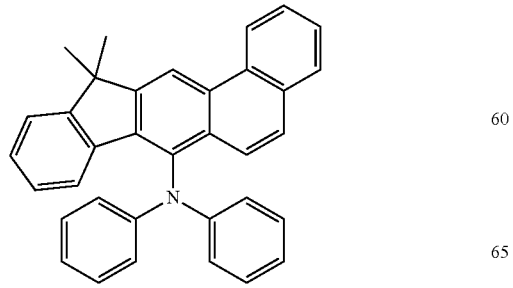
C-124
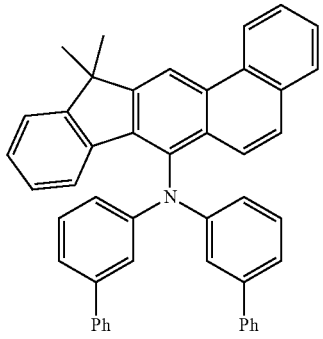
C-125
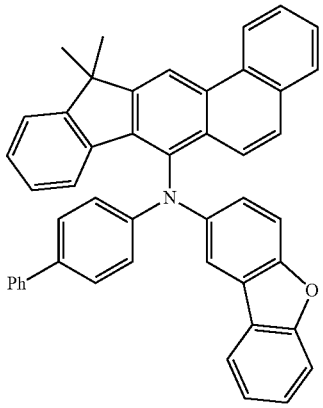
C-126
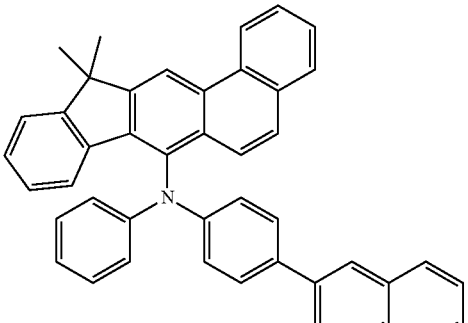
C-127
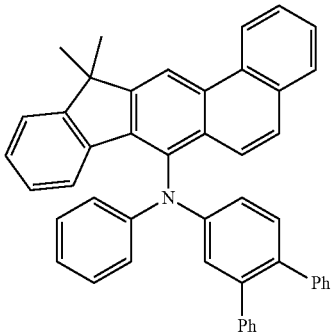

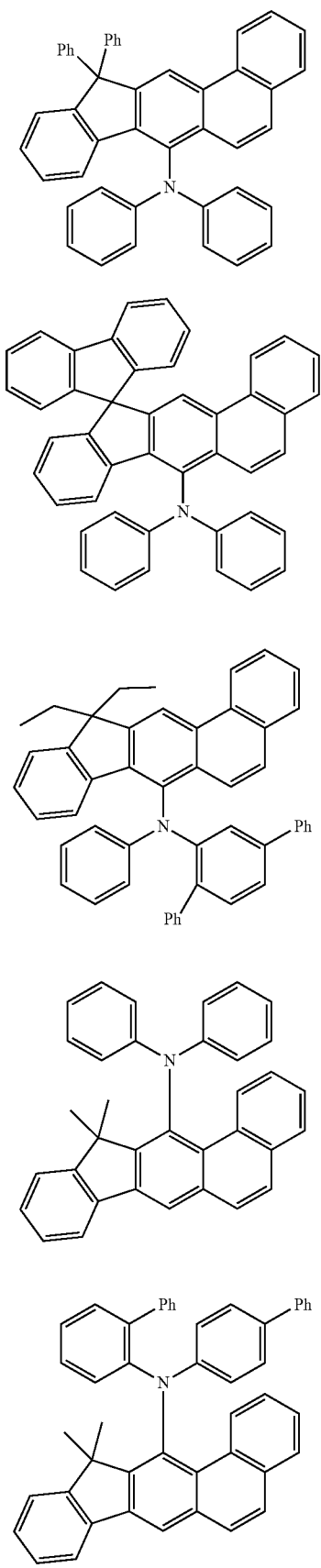
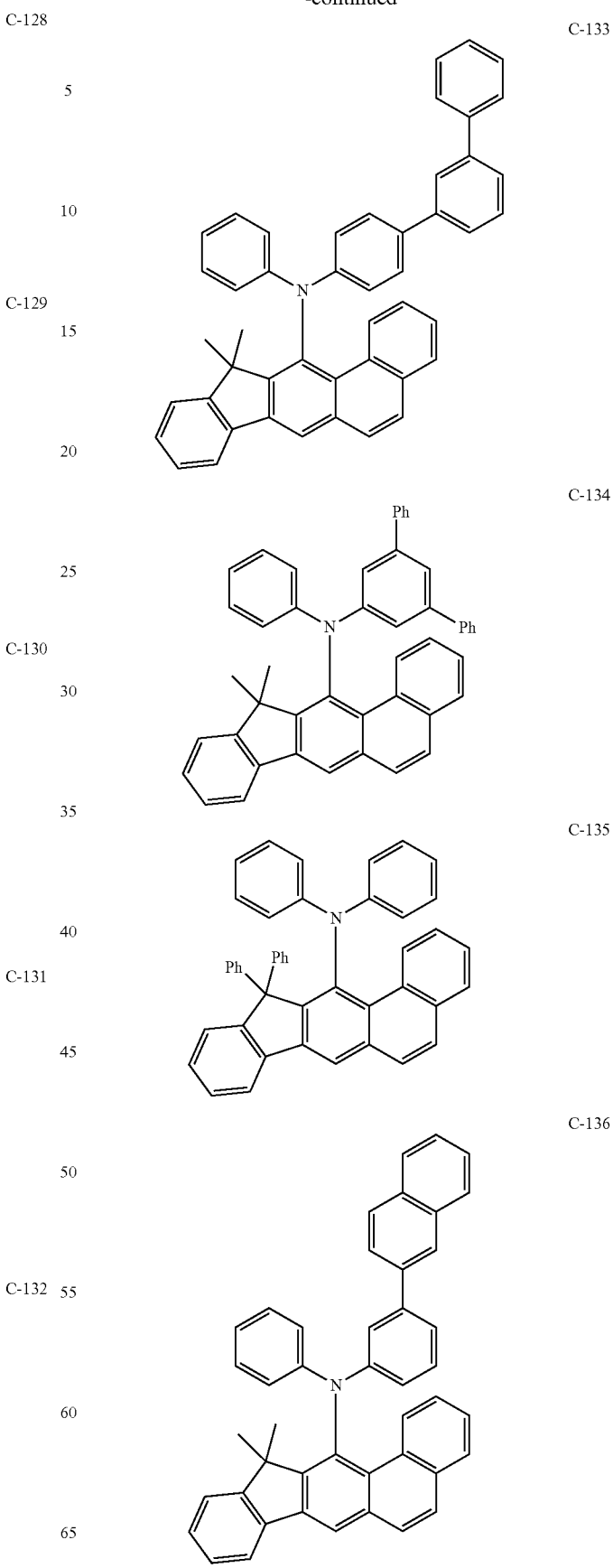

C-137
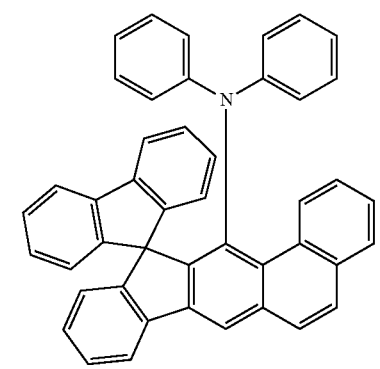
C-138
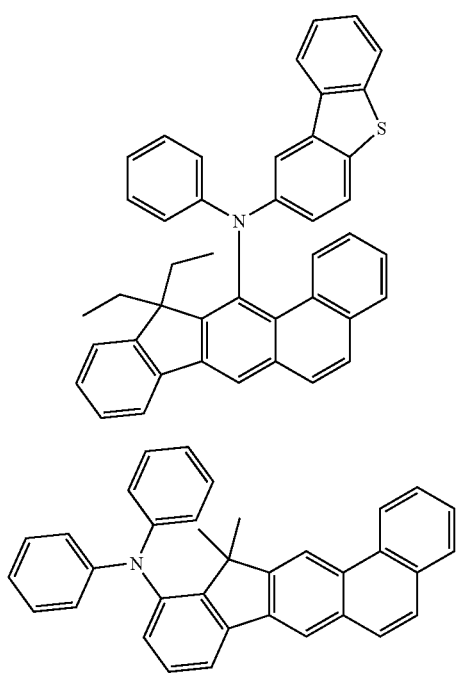
C-139
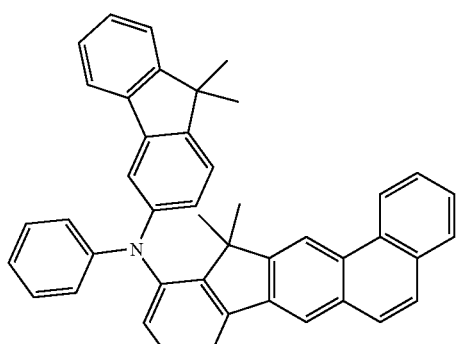
C-140
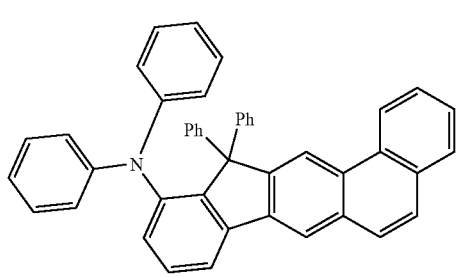
C-141
C-142
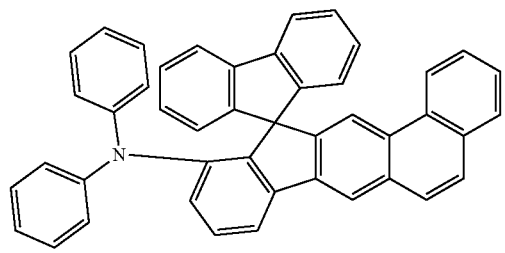
C-143
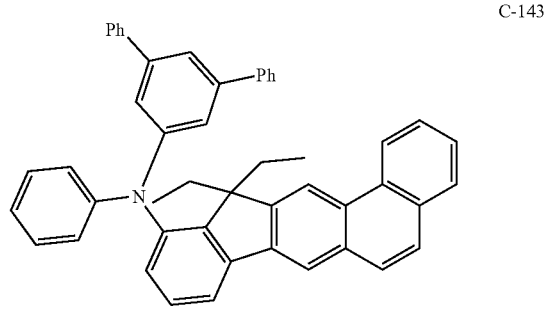
C-144
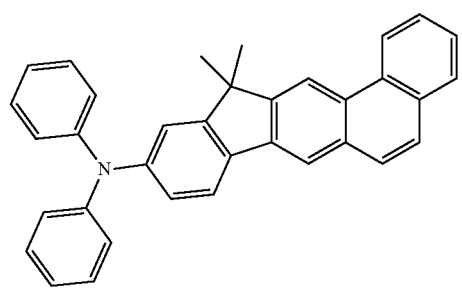
C-145
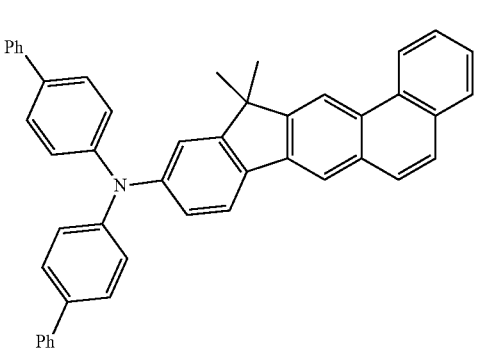
C-146
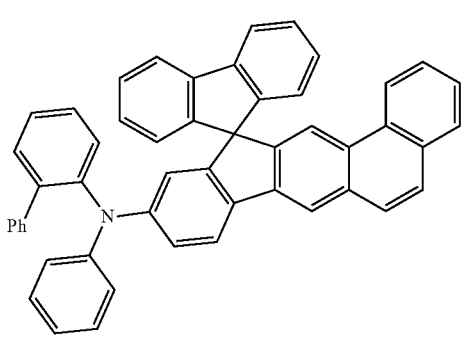

C-147
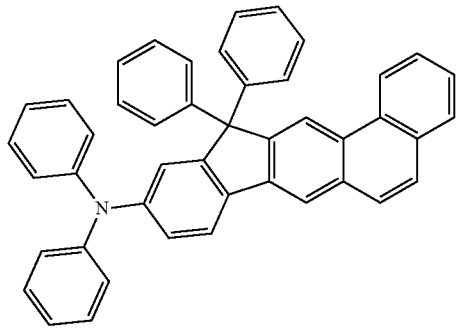
C-151
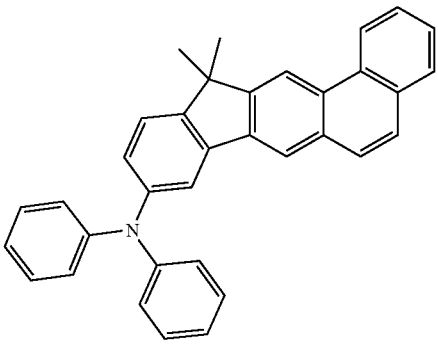
C-148
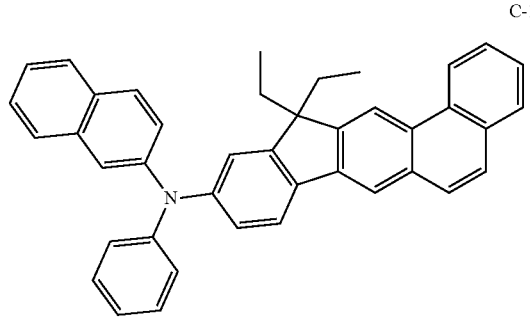
C-152
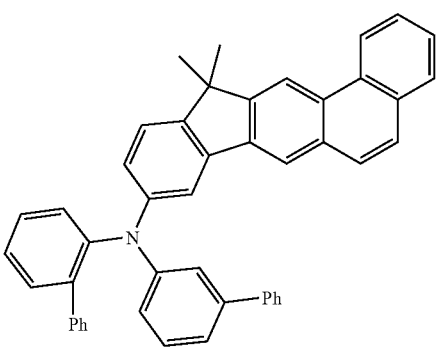
C-149
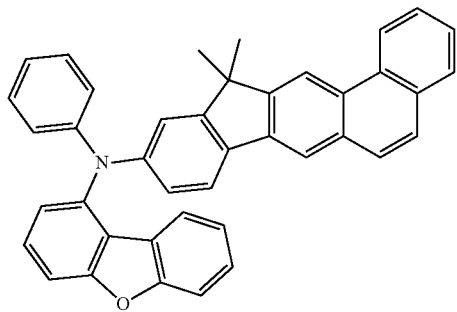
C-153
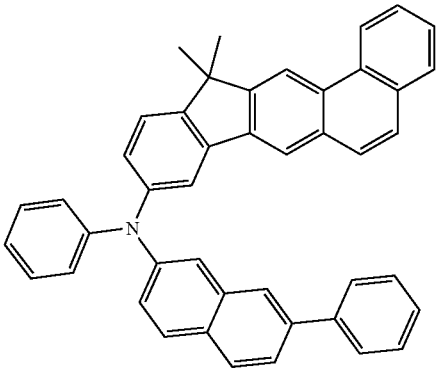
C-150
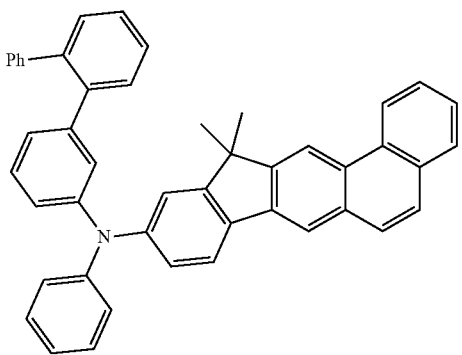
C-154
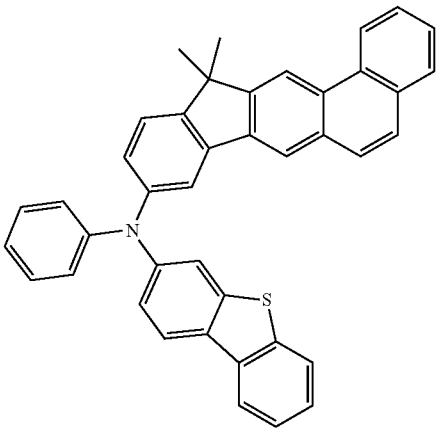

C-155
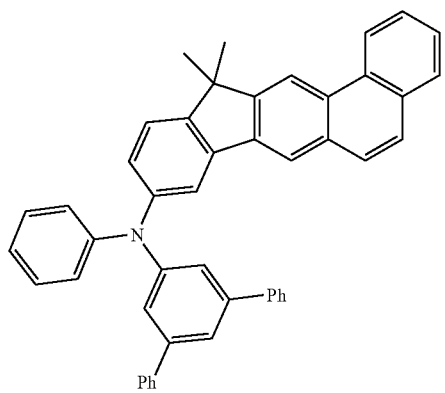
C-159
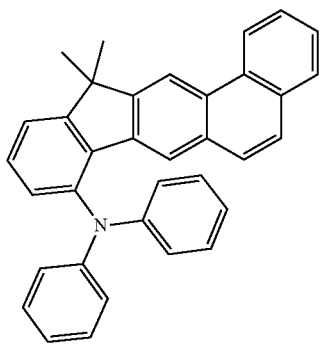
C-156
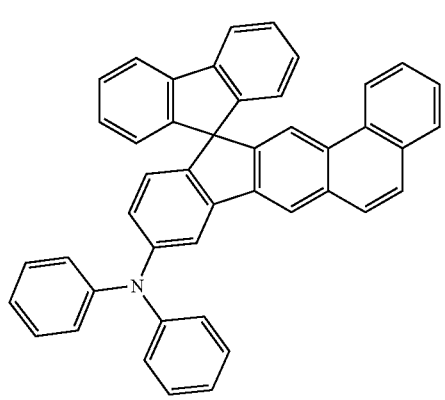
C-160
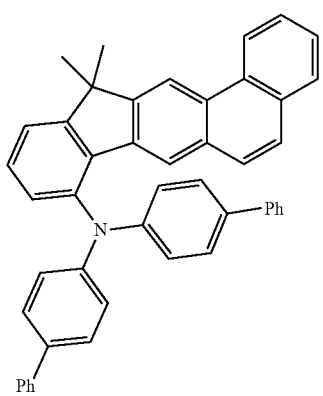
C-157
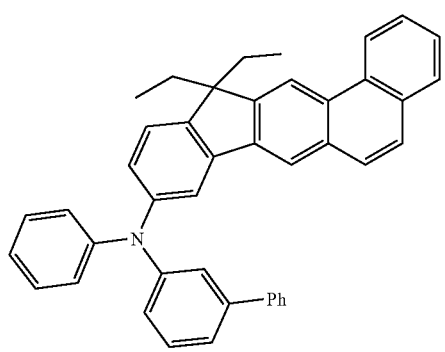
C-161
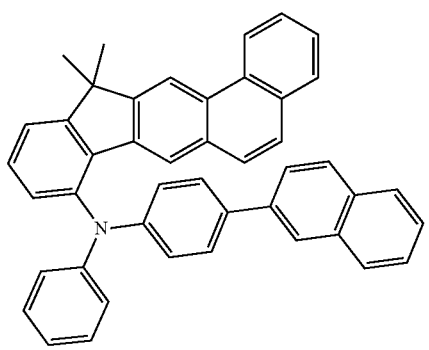
C-158
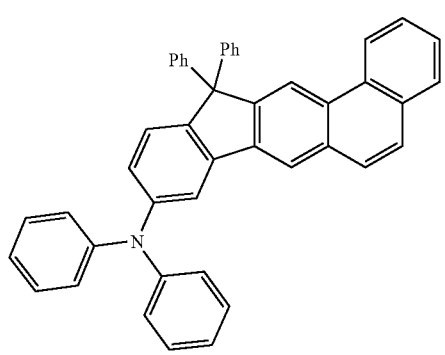
C-162
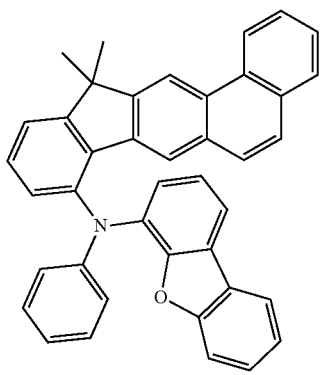

-continued
C-163
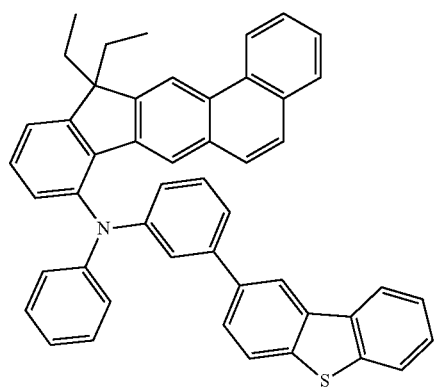
C-164
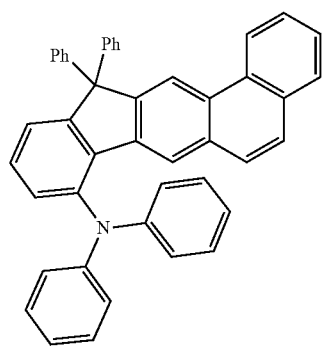
C-165
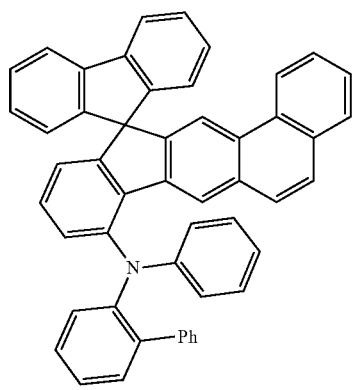
-continued
C-166
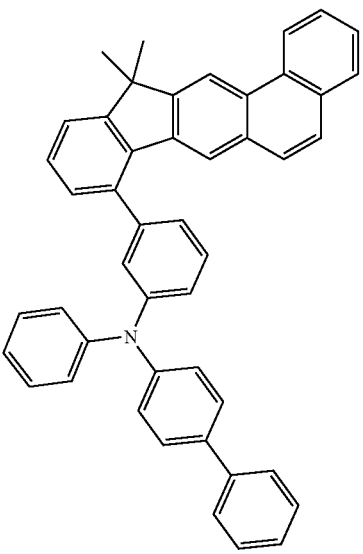
C-167
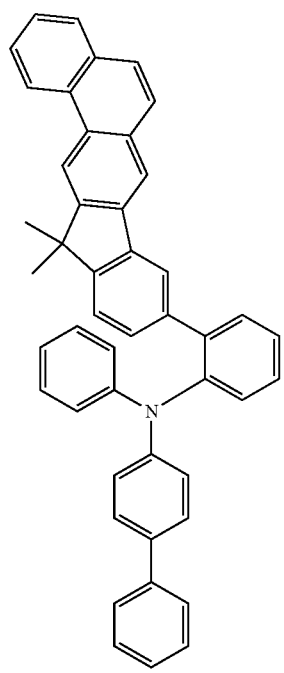
C-168
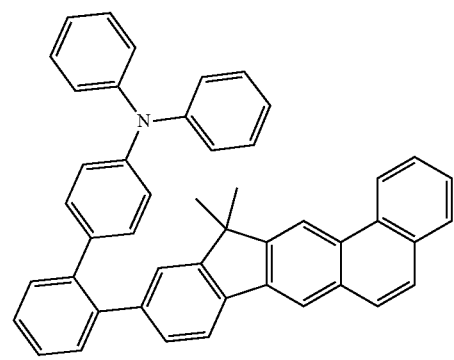

C-169
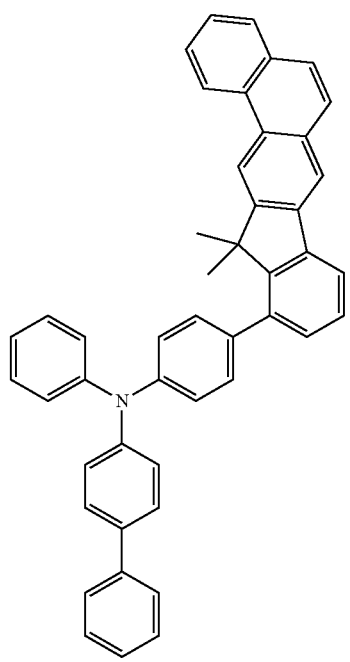
C-170
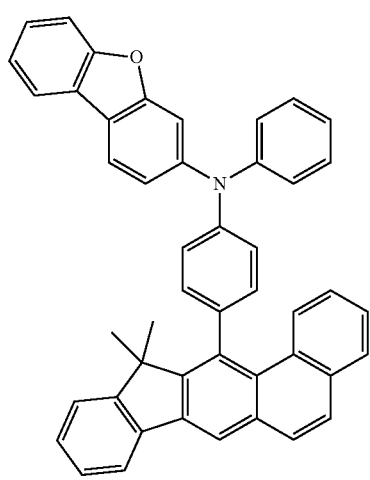
C-171
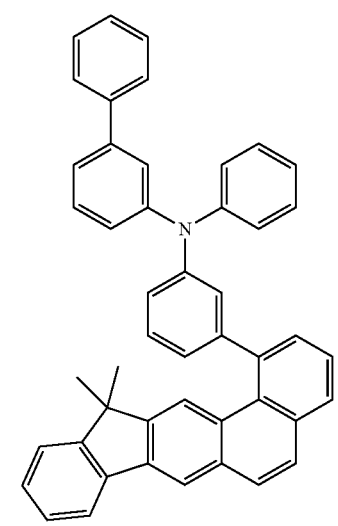
C-172
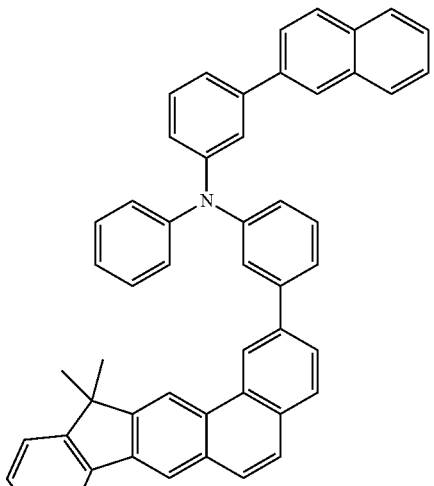
C-173
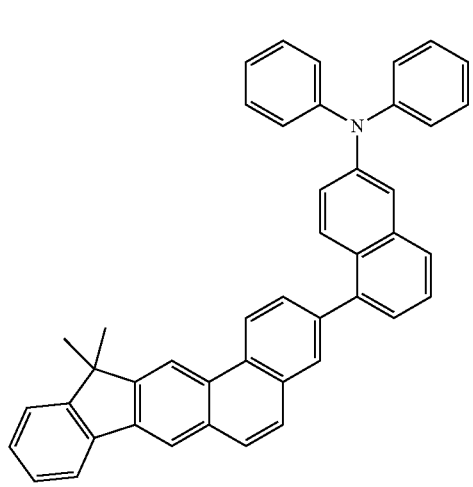
C-174
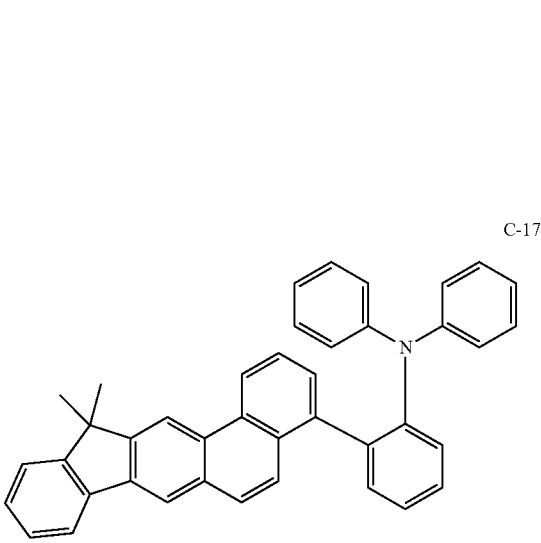

C-175
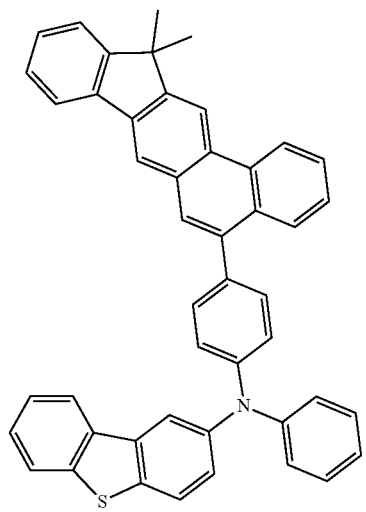
C-178
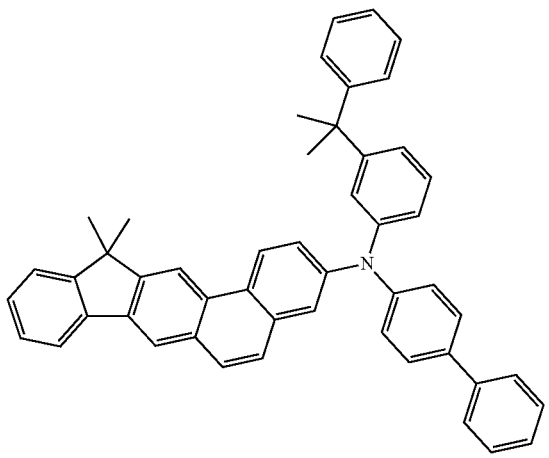
C-176
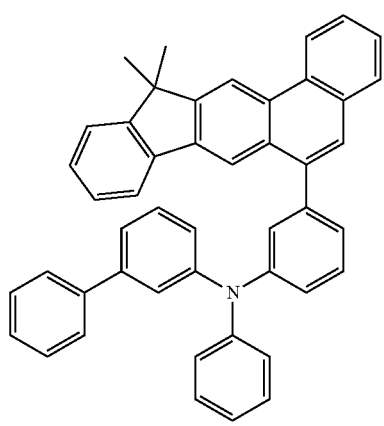
C-179
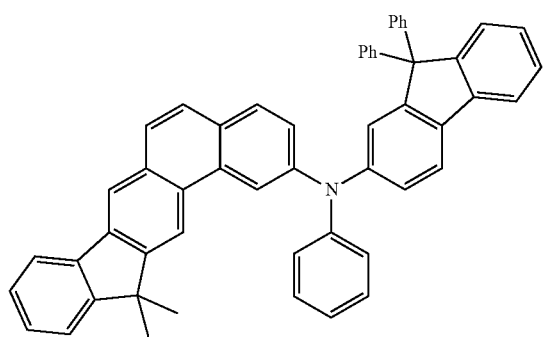
C-180
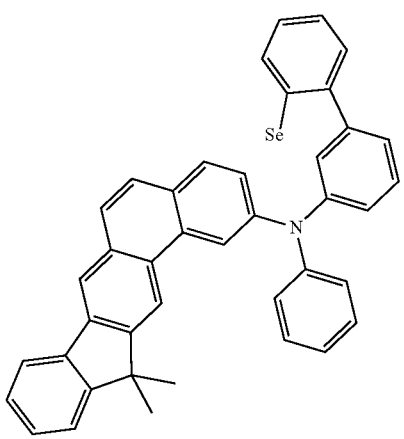
C-177
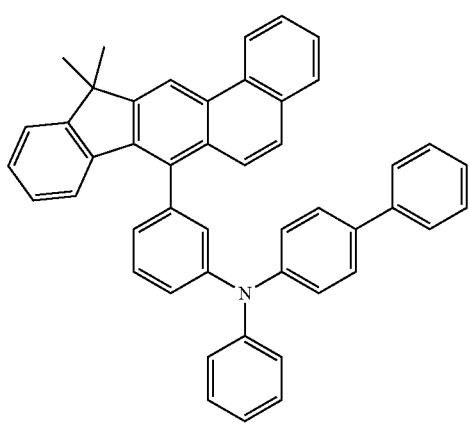
C-181
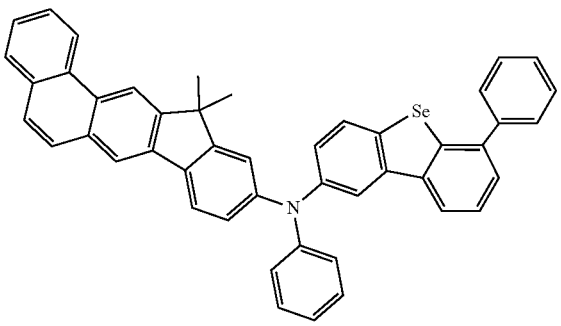

-continued
C-182
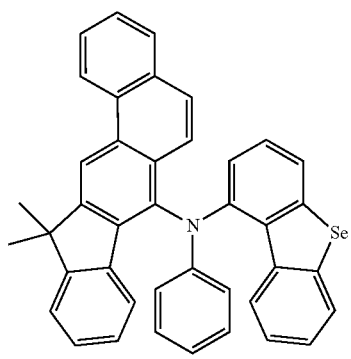
C-183
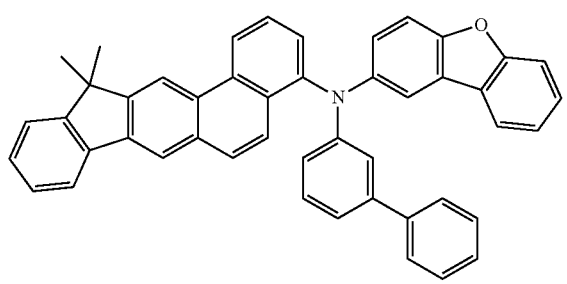
C-184
C-185
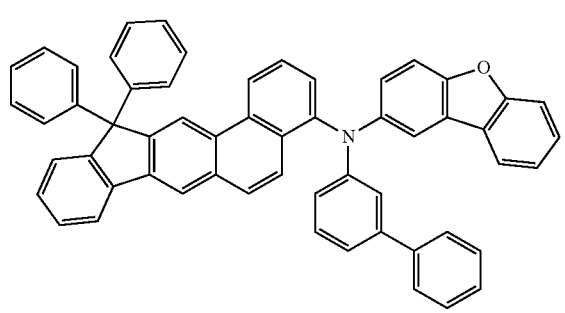
-continued
C-186
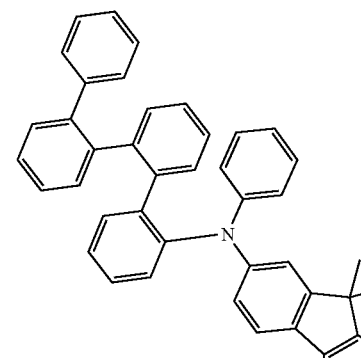
and
C-187
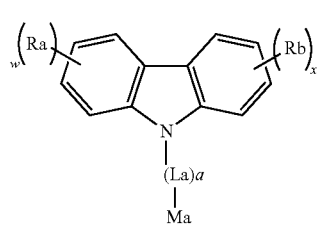
.
7. An organic electroluminescent material comprising the organic electroluminescent compound according to claim 1.
8. The organic electroluminescent material according to claim 7, further comprising at least one compound represented by any one of the following formulas 11 to 15:
(11)

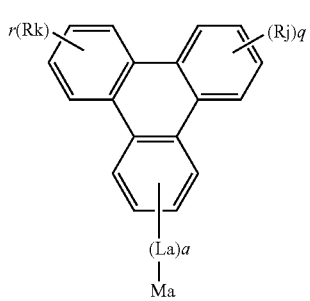

(12)

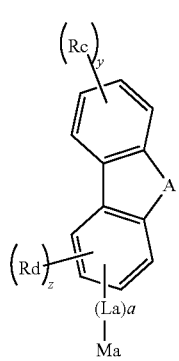

(13)

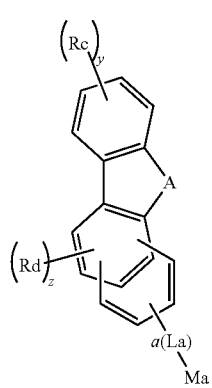

(14)

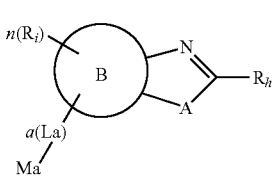

(15)

in formulas 11 to 15,
Ma represents a substituted or unsubstituted (C6-C30) aryl, a substituted or unsubstituted mono- or di- (C6-C30)arylamino, a substituted or unsubstituted mono- or di- (3- to 30-membered)heteroarylamino, a substituted or unsubstituted (C6-C30)aryl(3- to 30-membered)heteroarylamino, or a substituted or unsubstituted (3- to 30-membered)heteroaryl;
La represents a single bond, a substituted or unsubstituted (C6-C30)arylene, or a substituted or unsubstituted (3- to 30-membered)heteroarylene;
A represents S, O, N(Re), C(Rf)(Rg), Te, or Se;
ring B represents a naphthalene ring or a phenanthrene ring;

Ra to Rd, and Rh to Rk, each independently, represent hydrogen, deuterium, a halogen, a cyano, a substituted or unsubstituted (C1-C30)alkyl, a substituted or unsubstituted (C2-C30)alkenyl, a substituted or unsubstituted (C2-C30)alkynyl, a substituted or unsubstituted (C3-C30)cycloalkyl, a substituted or unsubstituted (C6-C30)aryl, a substituted or unsubstituted (3- to 30-membered)heteroaryl, a substituted or unsubstituted tri(C1-C30)alkylsilyl, a substituted or unsubstituted tri(C6-C30)arylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted mono- or di- (C1-C30) alkylamino, a substituted or unsubstituted (C1-C30)alkyl(C6-C30)arylamino, or a substituted or unsubstituted mono- or di- (C6-C30)arylamino; or may be linked to an adjacent substituent to form a ring(s);

Re to Rg, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C6-C30)arylamino, or a substituted or unsubstituted (C1-C30)alkyl(C6-C30)arylamino; and Rf and Rg may be linked to each other to form a ring(s);

w to y, q, and r, each independently, represents an integer of 1 to 4; z represents an integer of 1 to 3; and a and t, each independently, represent an integer of 1 or 2; n represents an integer of 1 to 9; and each of Rc, Ra to each of Rd, each of Ri to each of Rk, and each of La may be the same or different; and the heteroaryl(ene) comprises at least one heteroatom selected from the group consisting of B, N, O, S, Si, P, Te, and Se.

9. The organic electroluminescent material according to claim 8, wherein the compound represented by formula 11 is selected from the group consisting of the following:

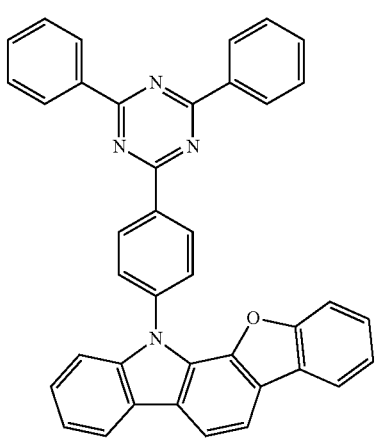

635
-continued
636
-continued
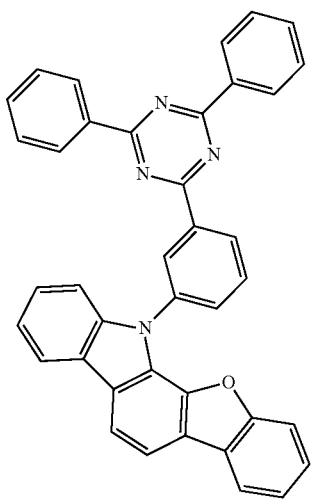
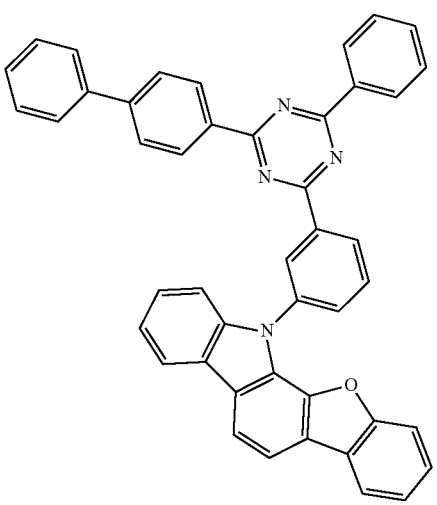
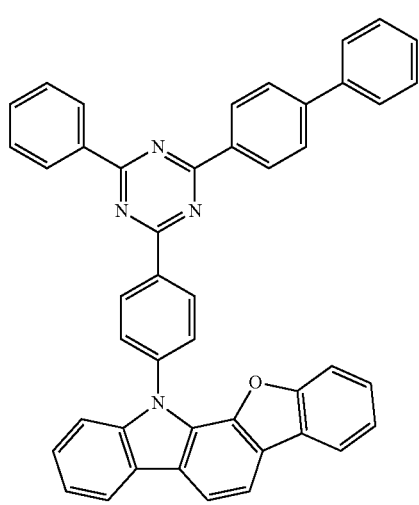

637
-continued
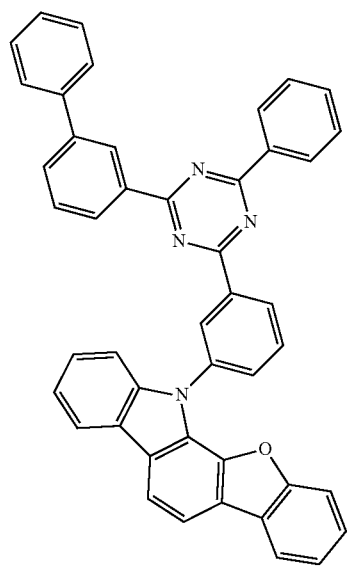
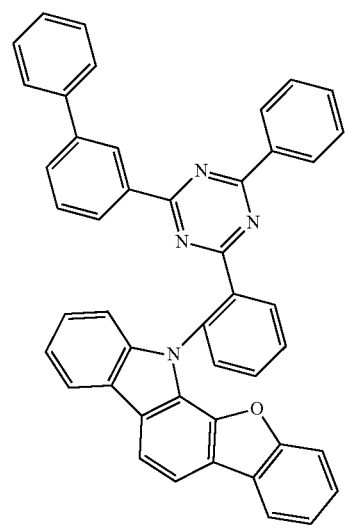
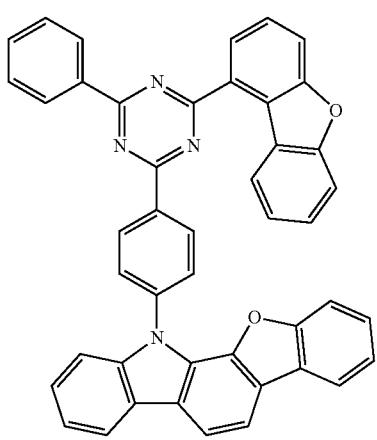
638
-continued
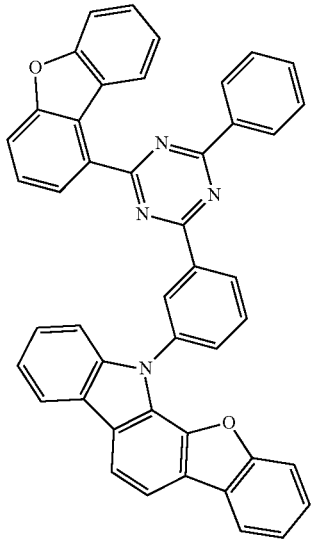
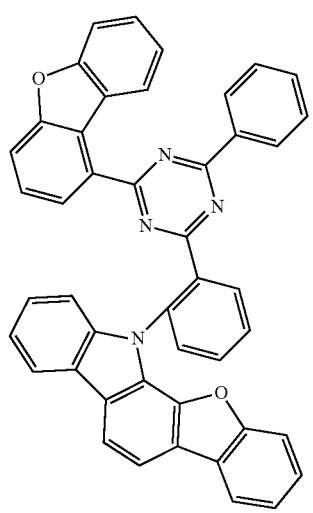
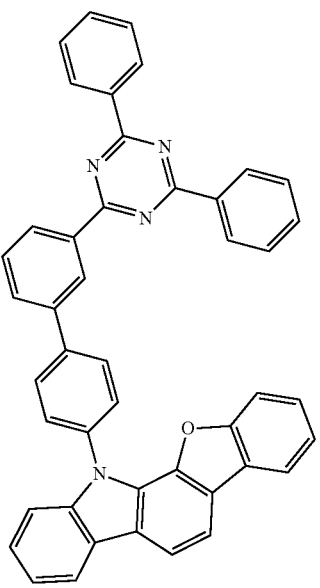

639
-continued
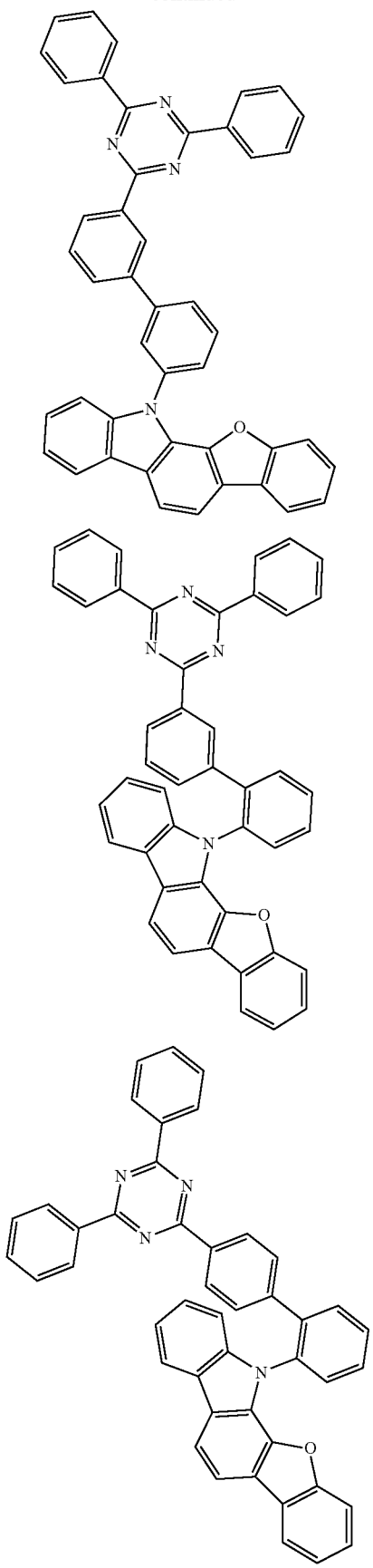
640
-continued
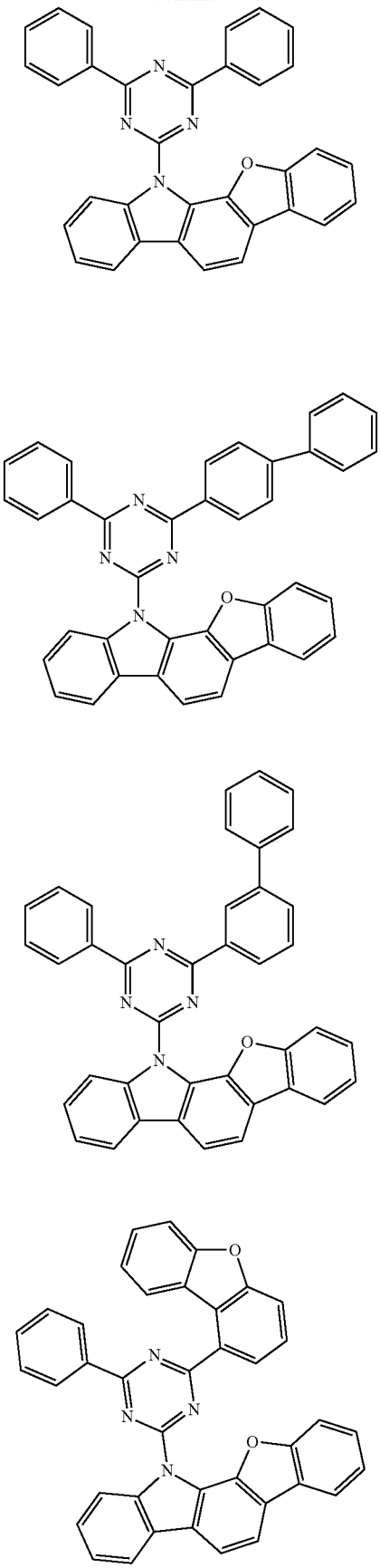

641
-continued
642
-continued
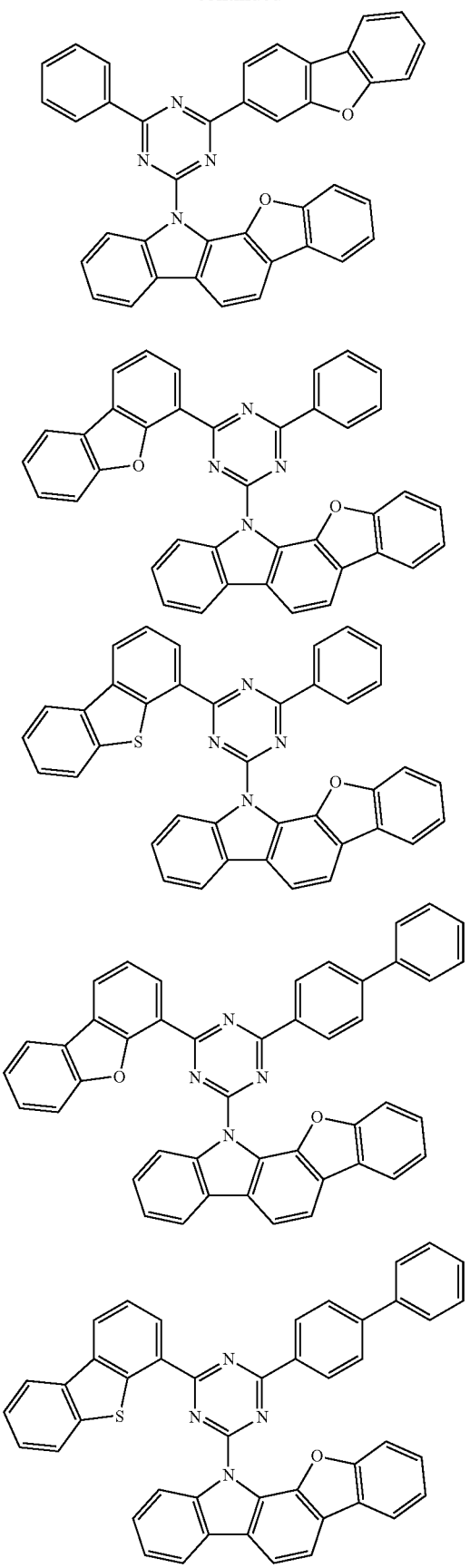
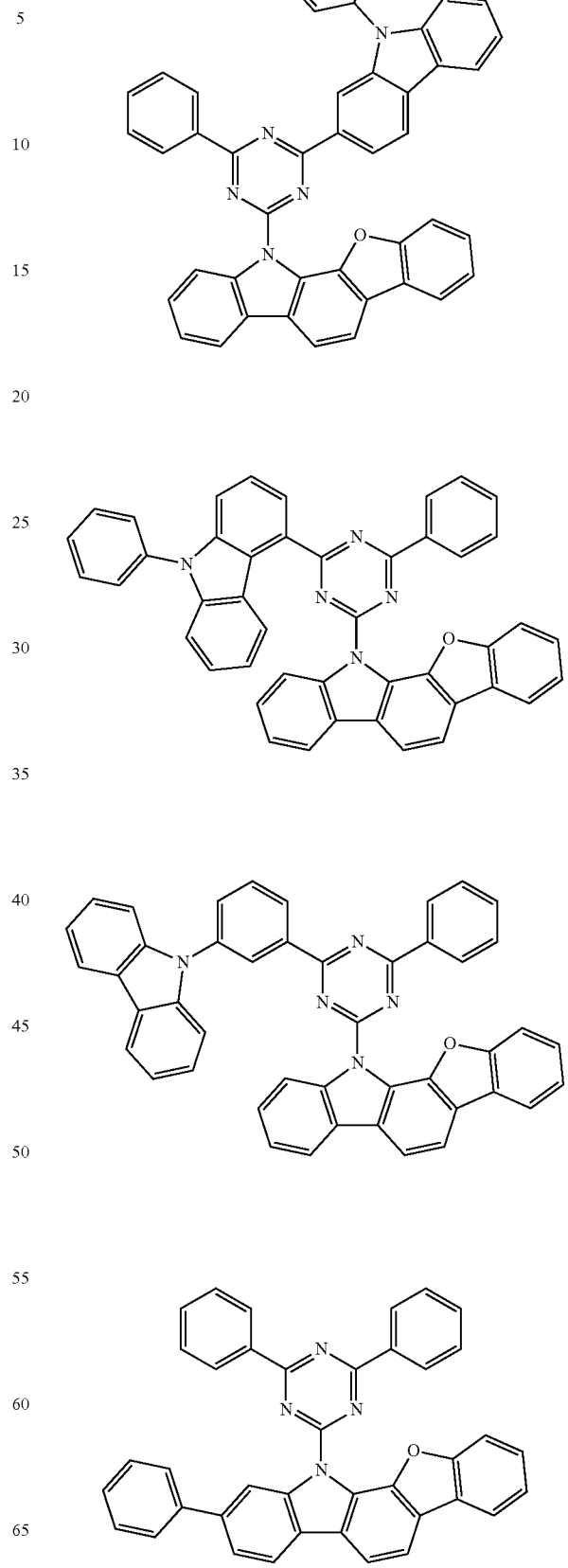

643
-continued
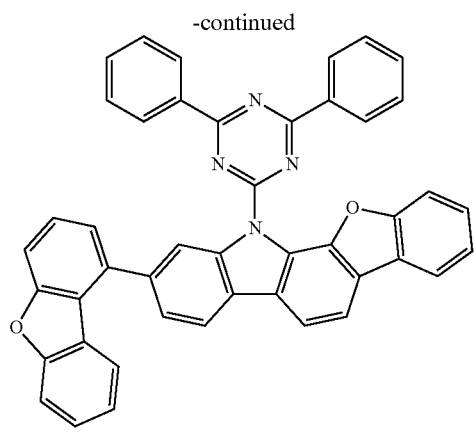
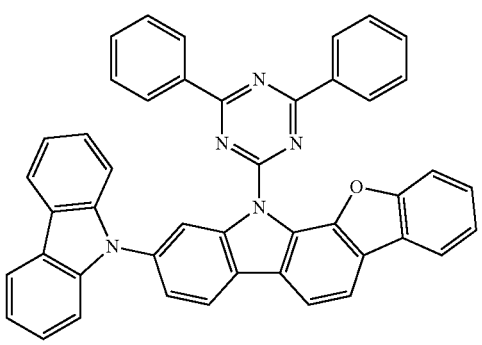
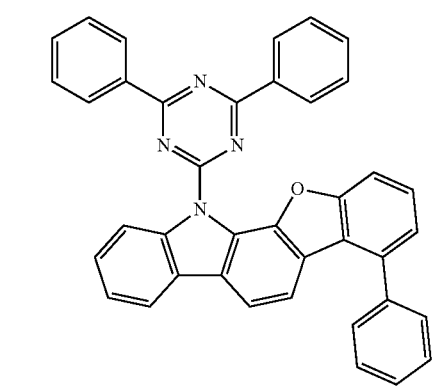
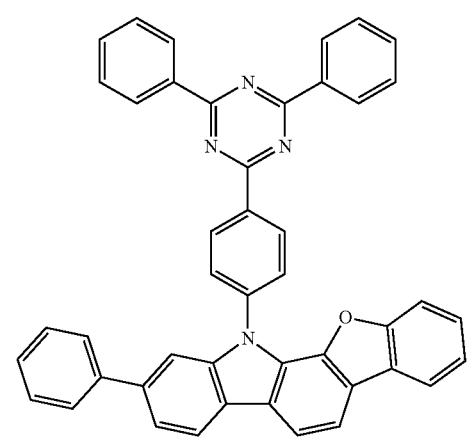
644
-continued
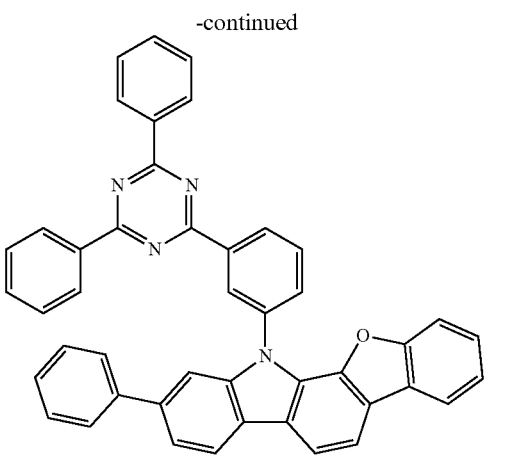
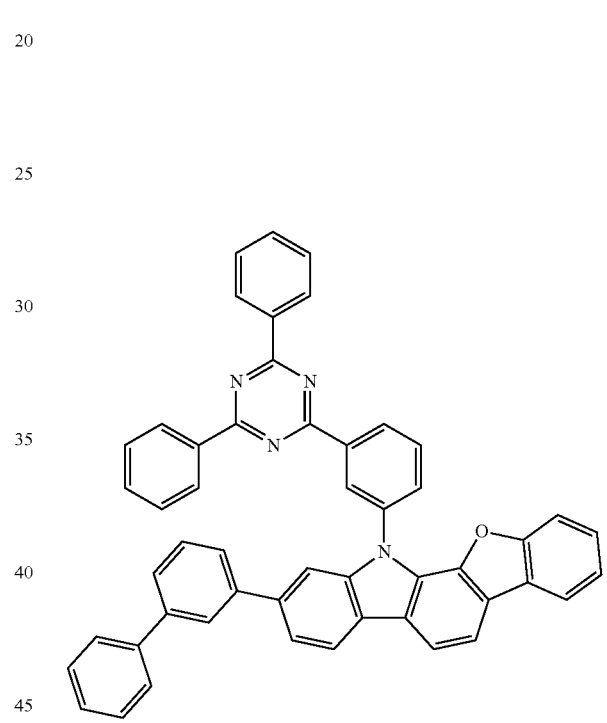
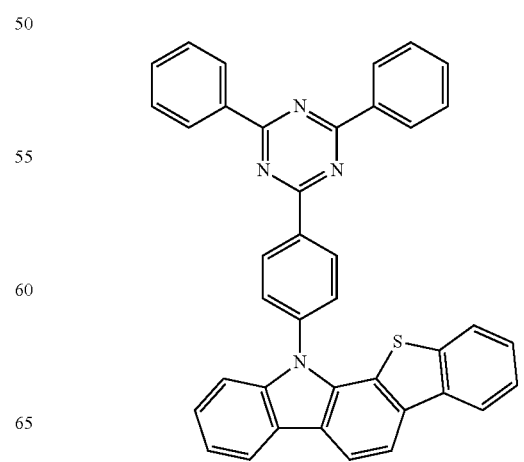

645
-continued
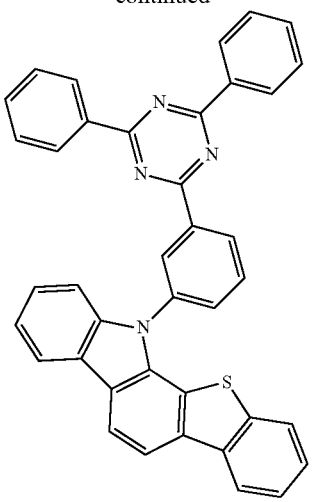
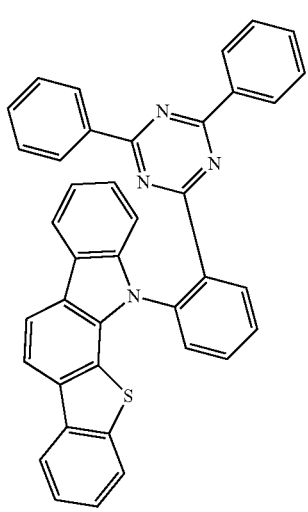
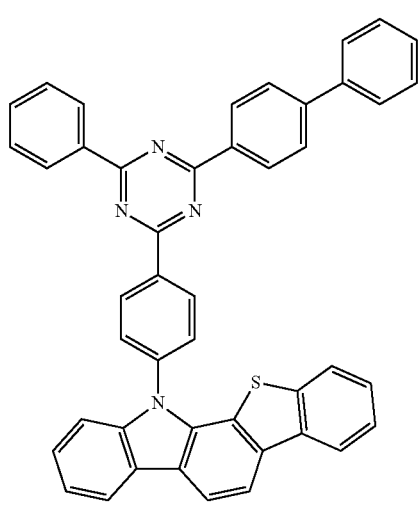
646
-continued
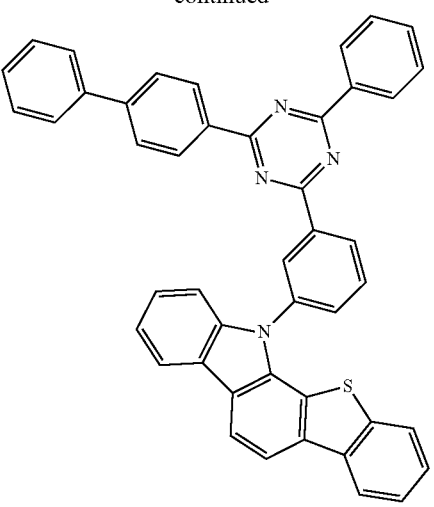
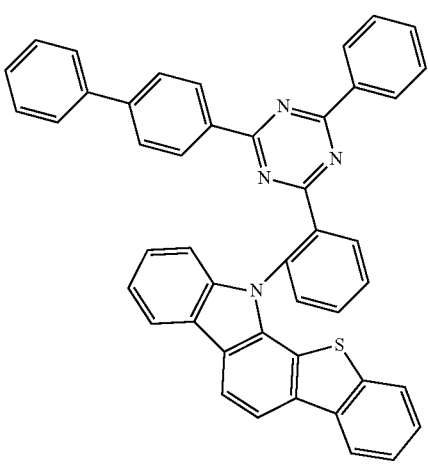

647
-continued
648
-continued
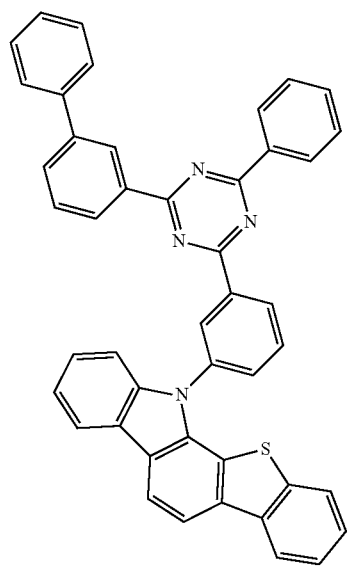
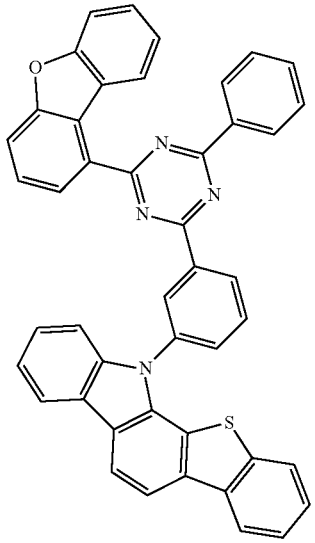
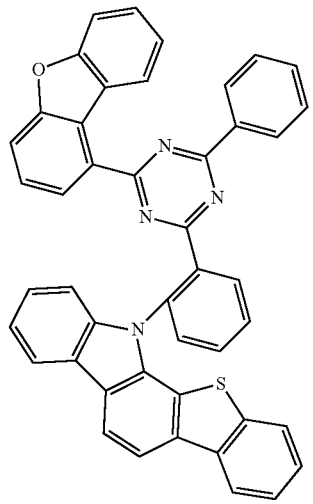
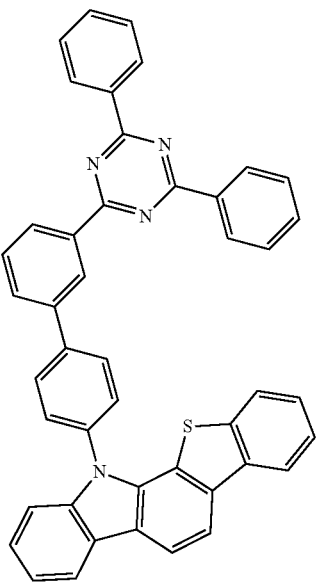

649
-continued
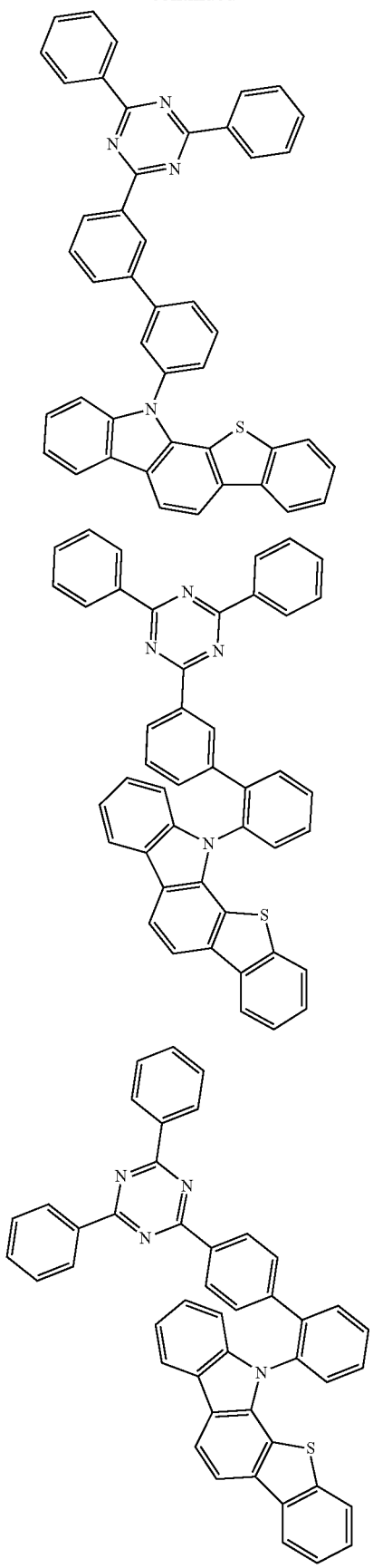
650
-continued
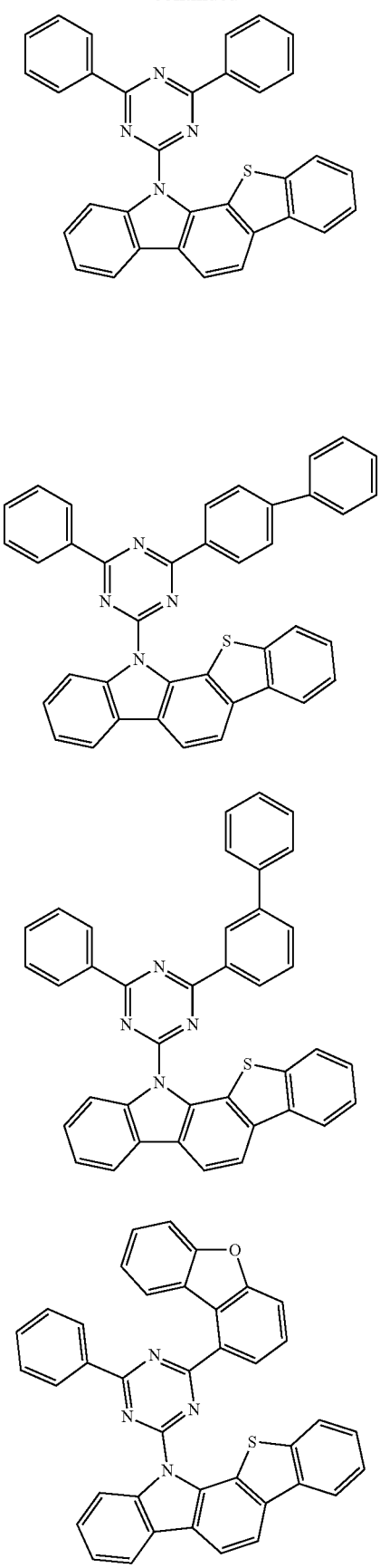

651
-continued
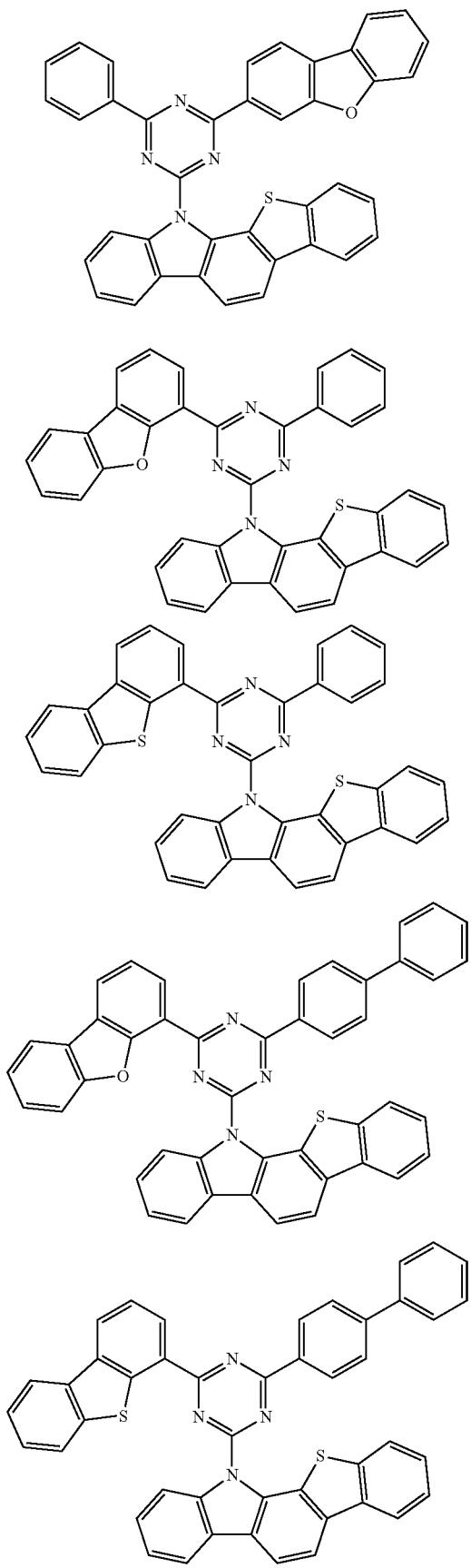
652
-continued
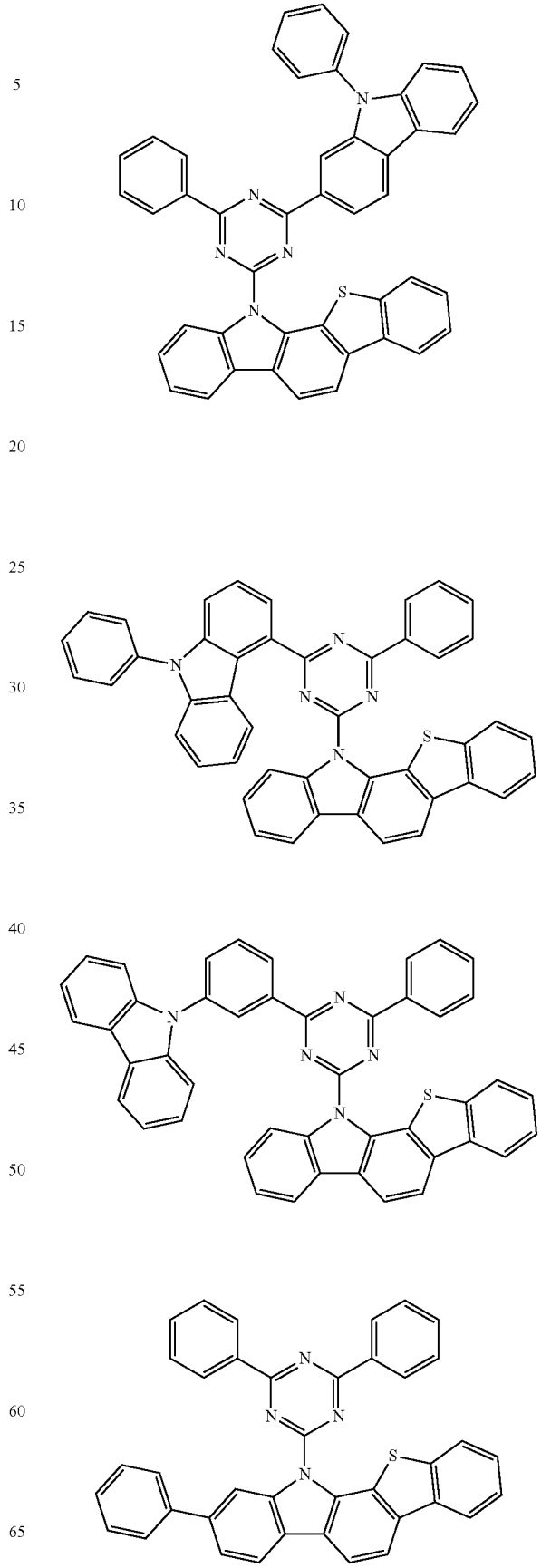

653
-continued
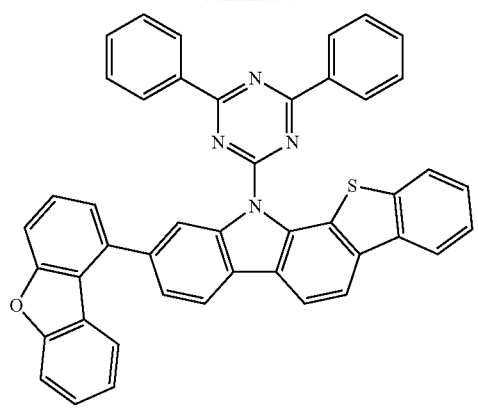
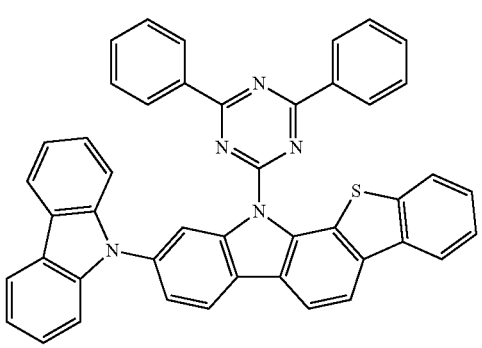
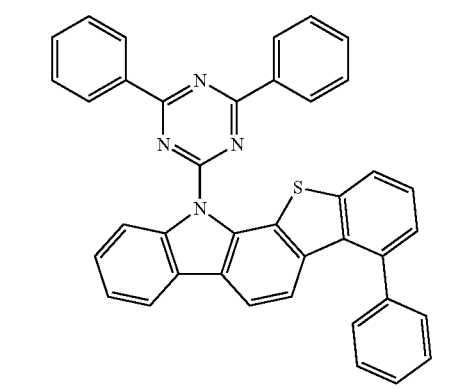
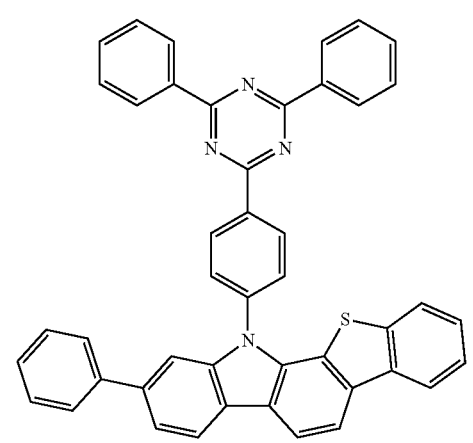
654
-continued
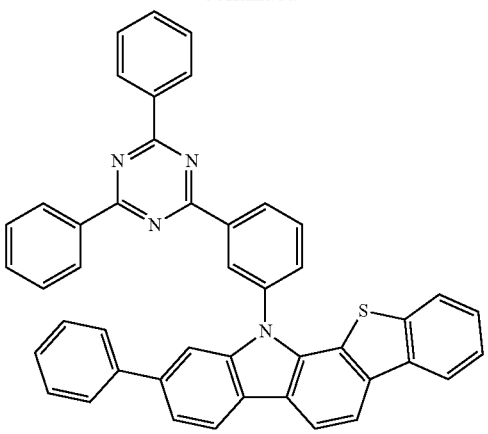
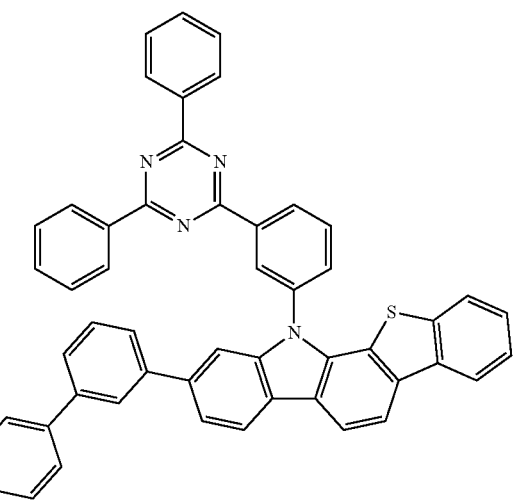
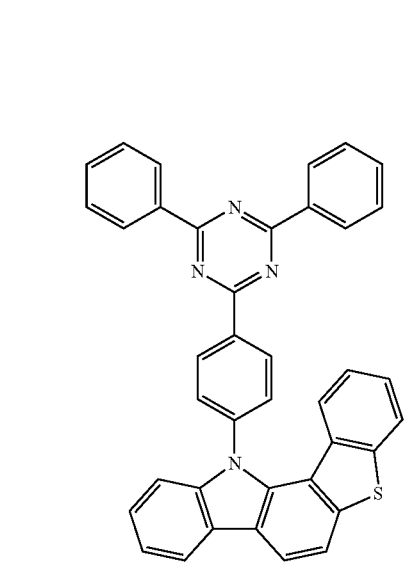

655
-continued
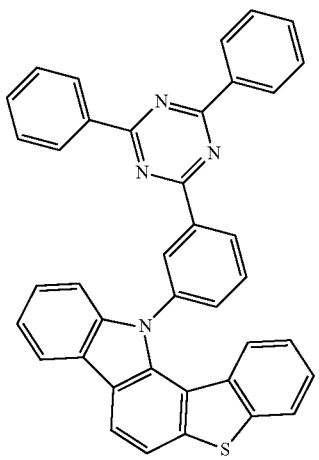
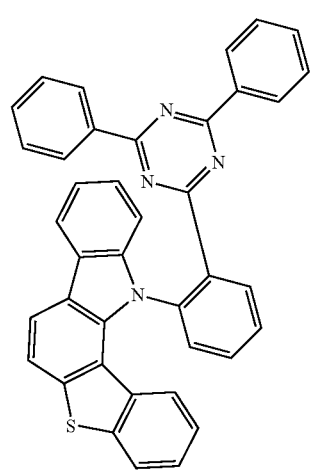
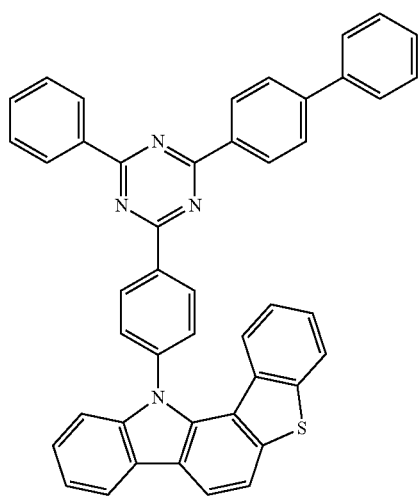
656
-continued
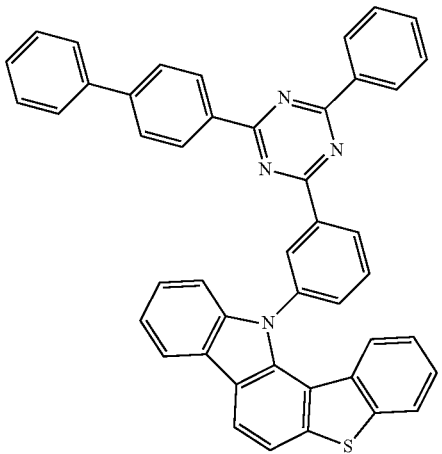
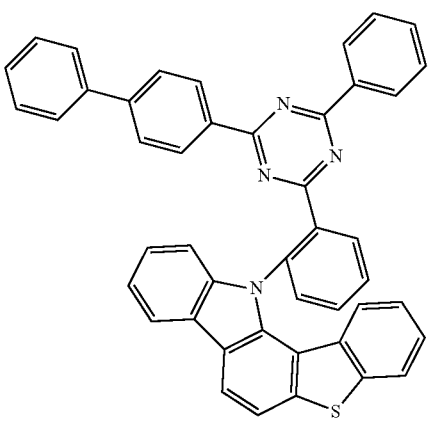
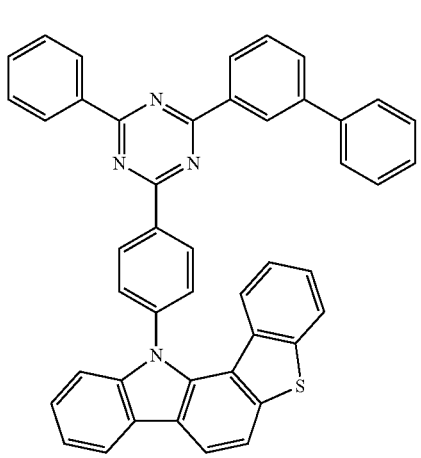

657
-continued
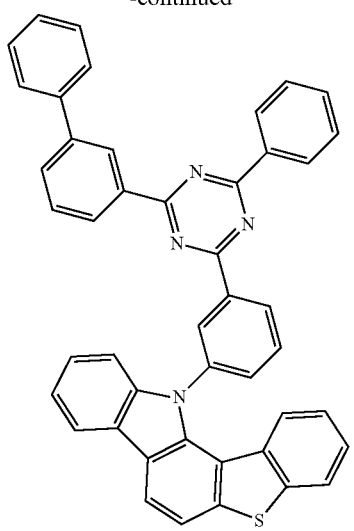
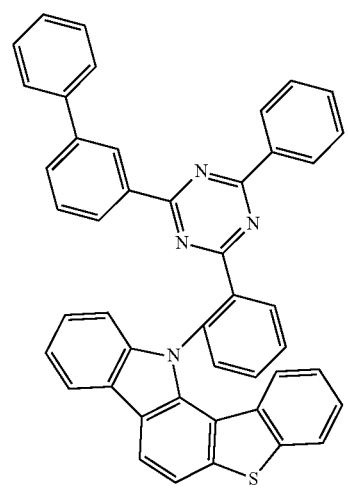
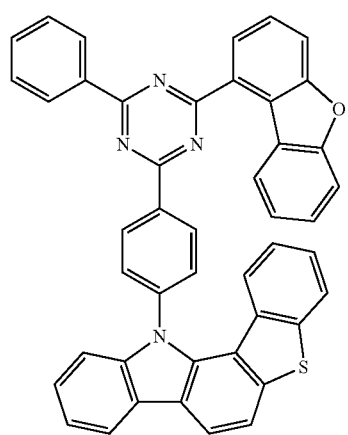
658
-continued
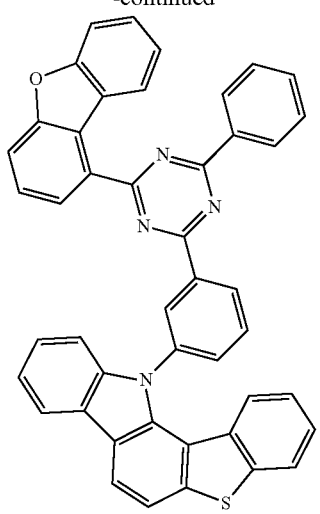
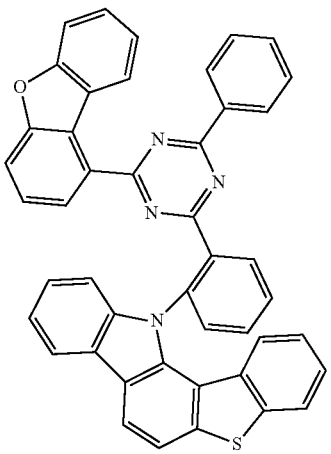
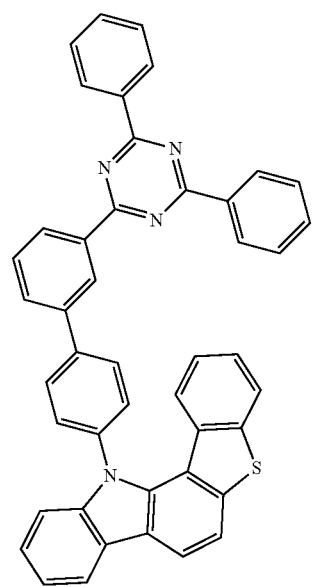

659
-continued
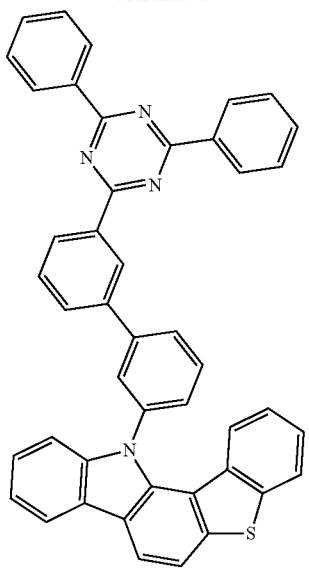
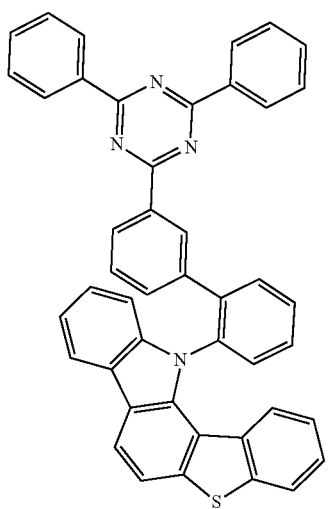
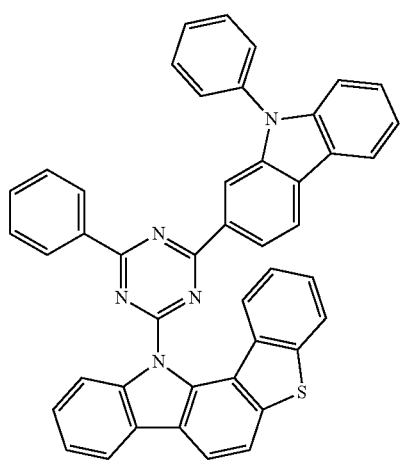
660
-continued
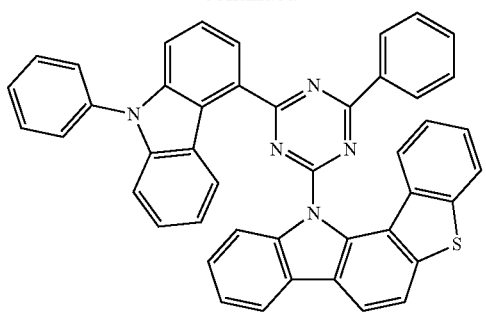
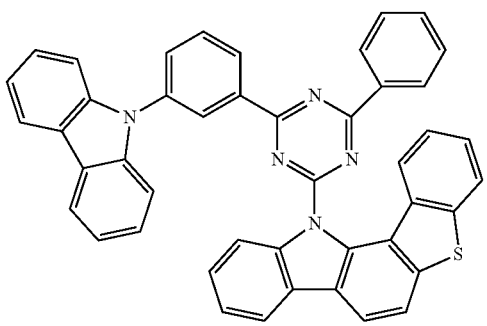
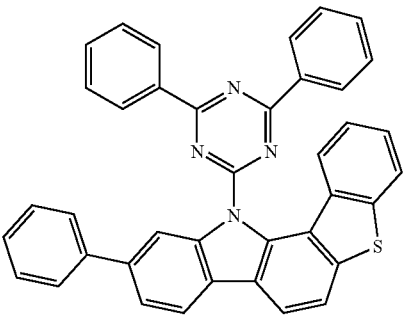
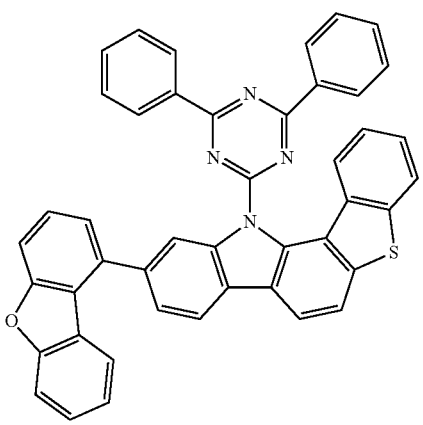

661
-continued
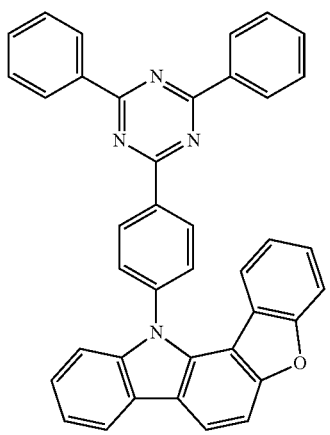
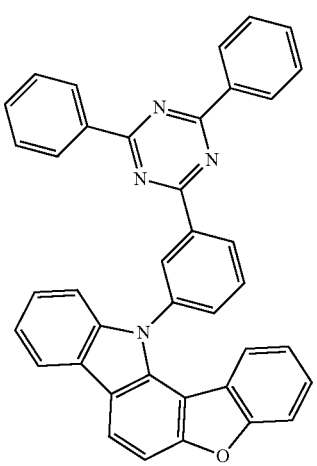
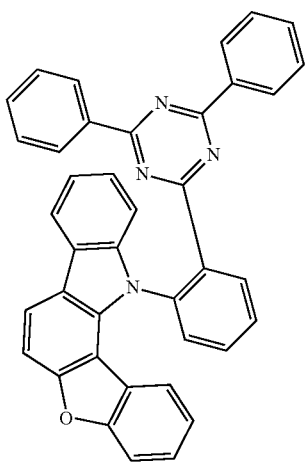
662
-continued
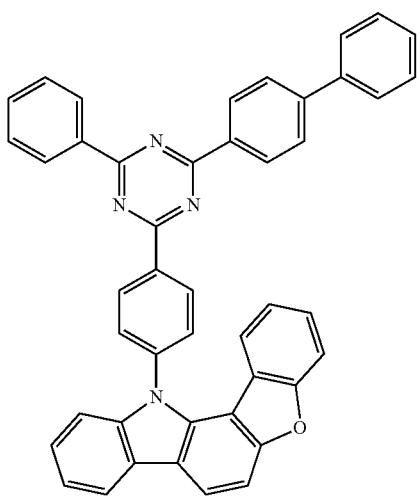
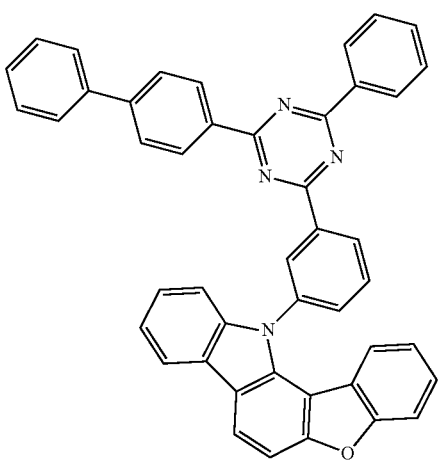
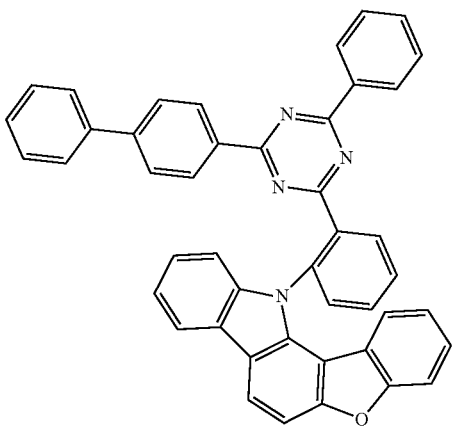

663
-continued
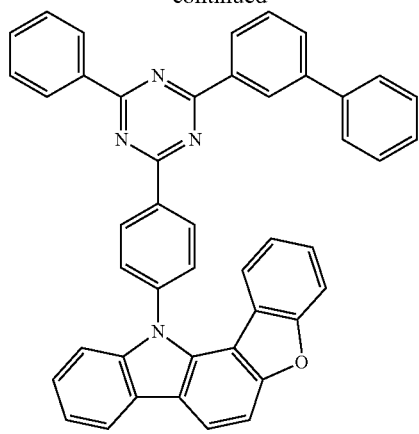
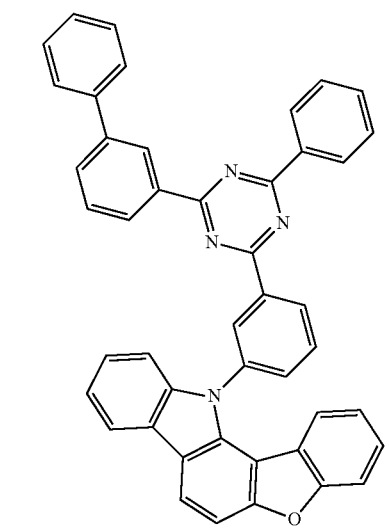
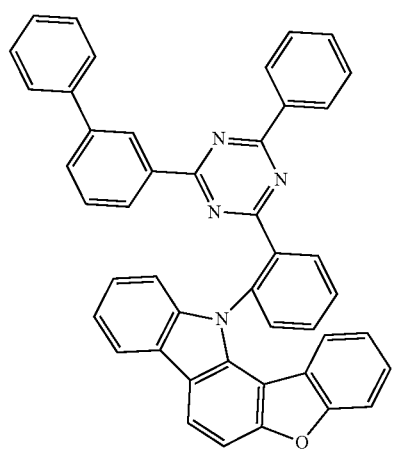
664
-continued
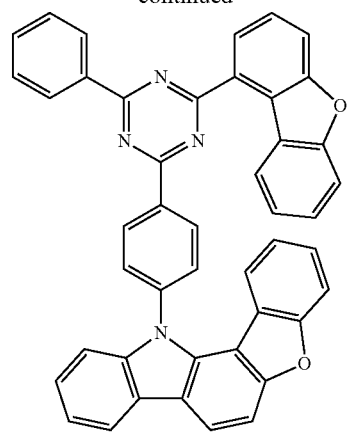
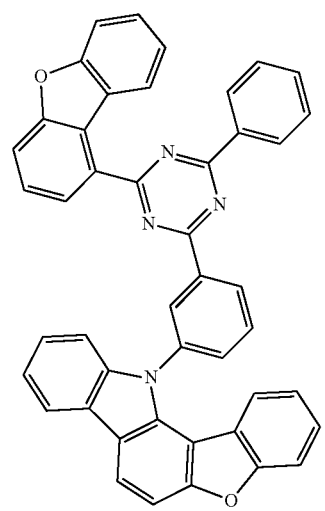
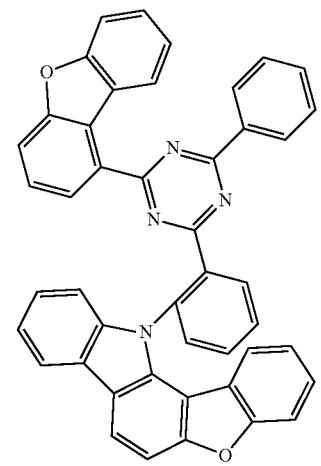

665
-continued
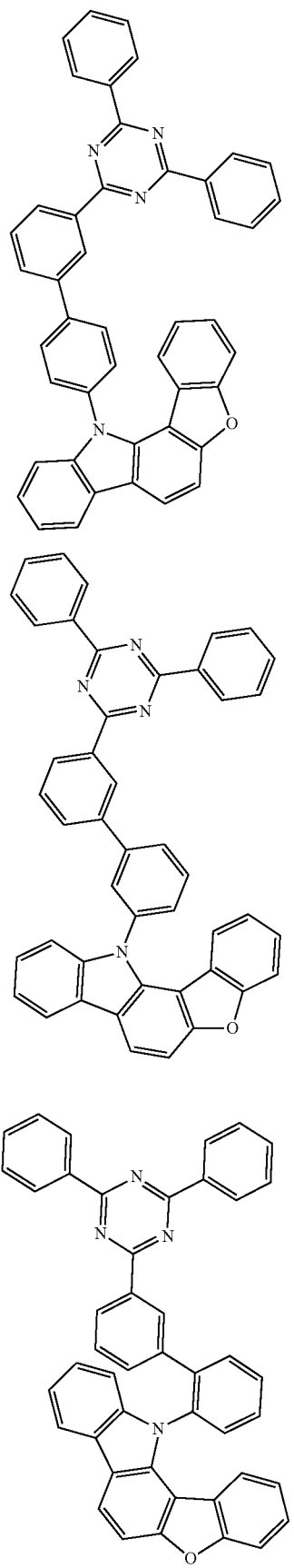
666
-continued
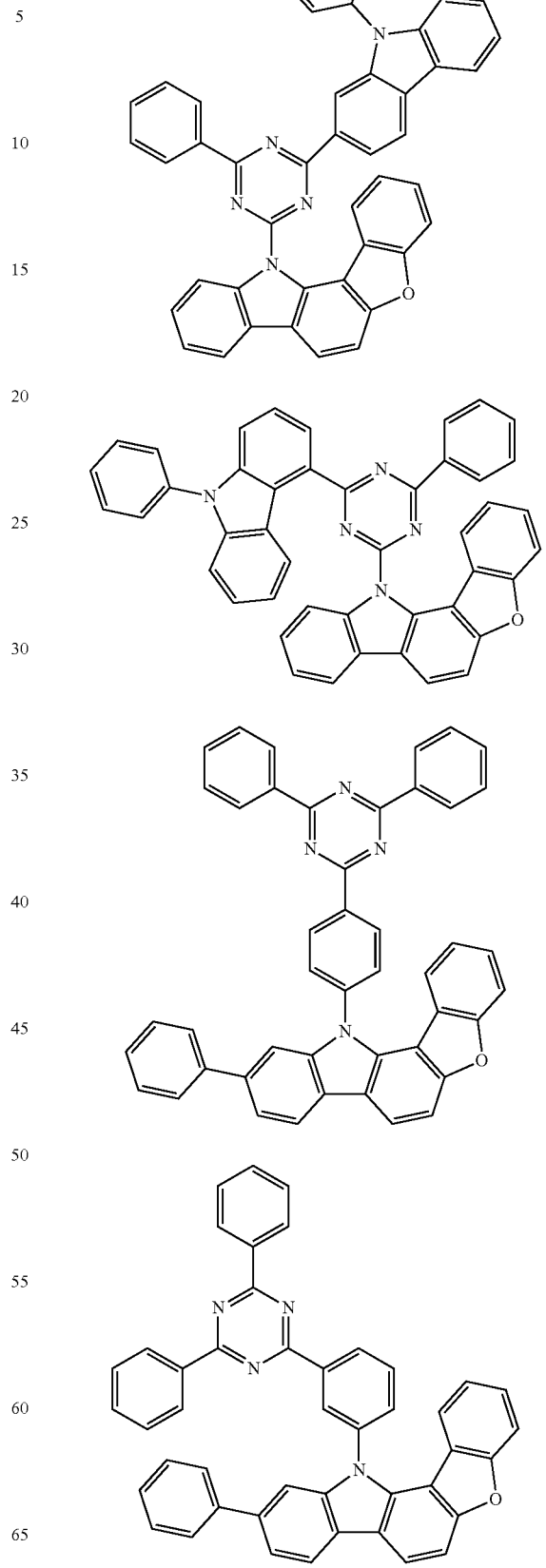

667
-continued
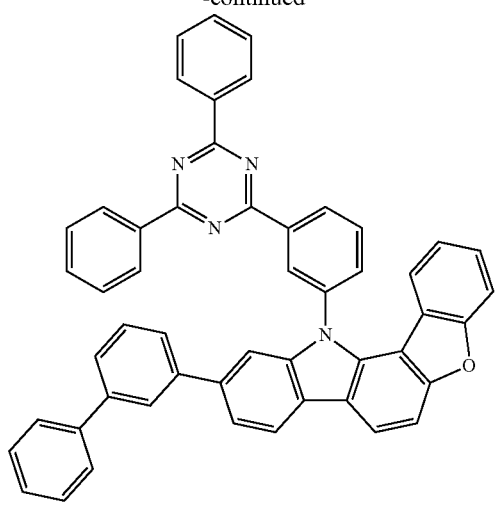
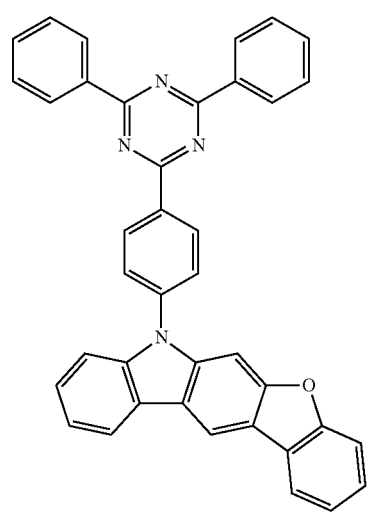
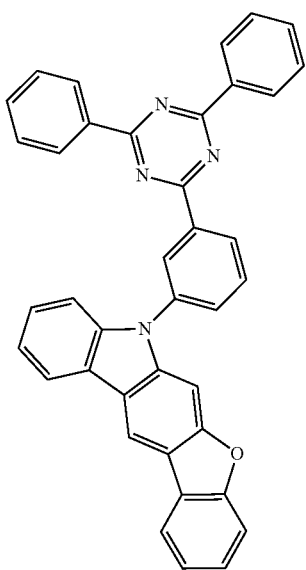
668
-continued
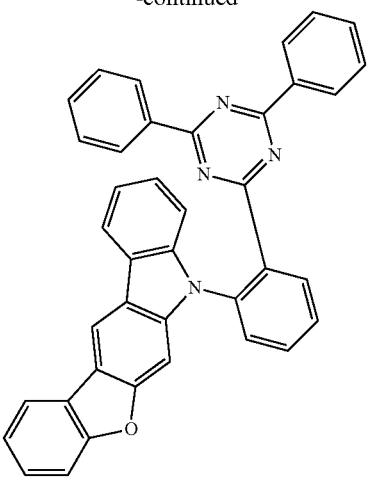
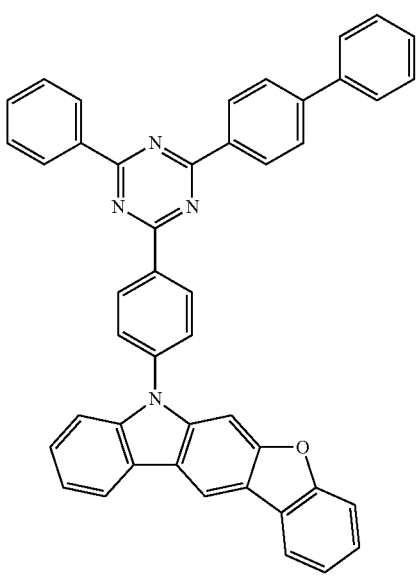
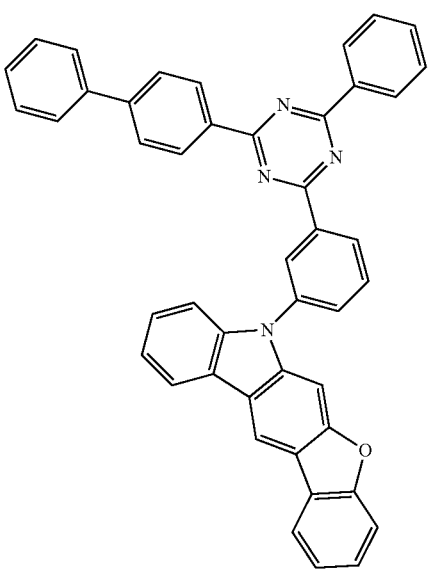

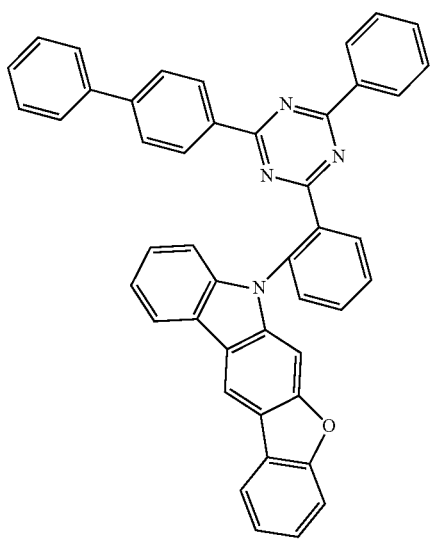
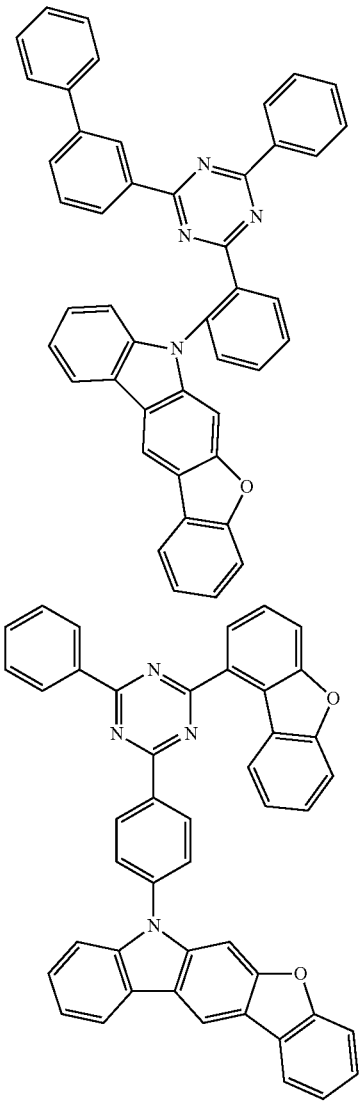

671
-continued
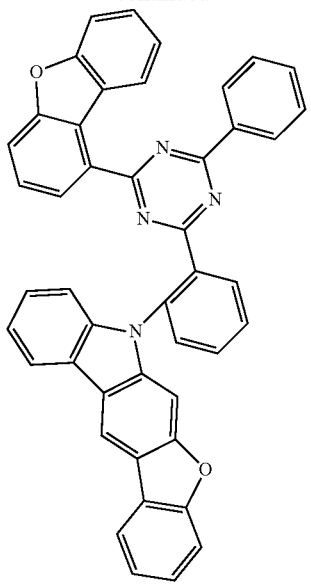
672
-continued
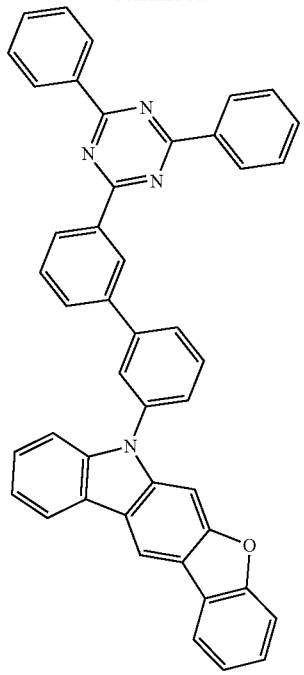
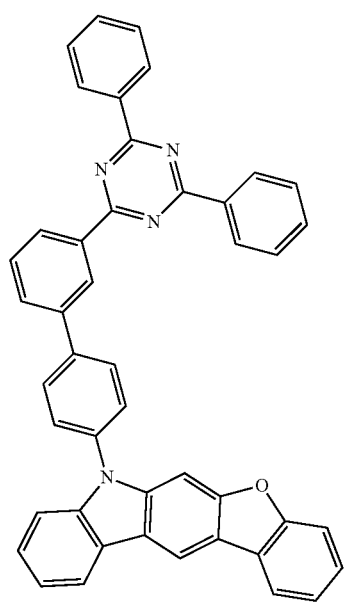
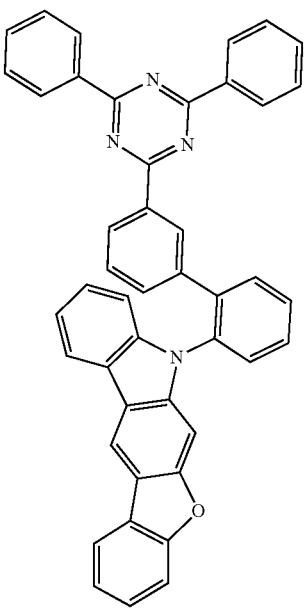

673
-continued
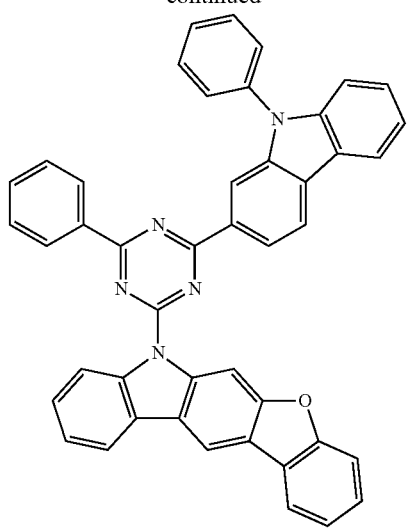
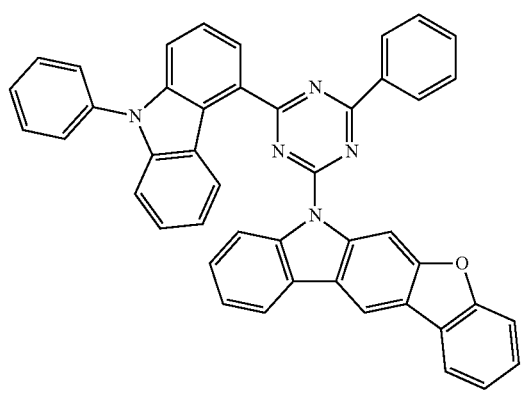
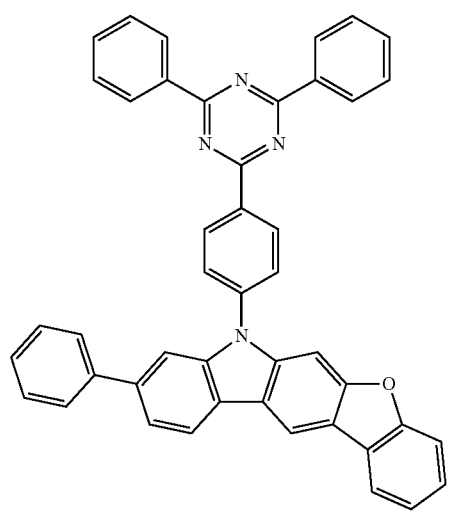
674
-continued
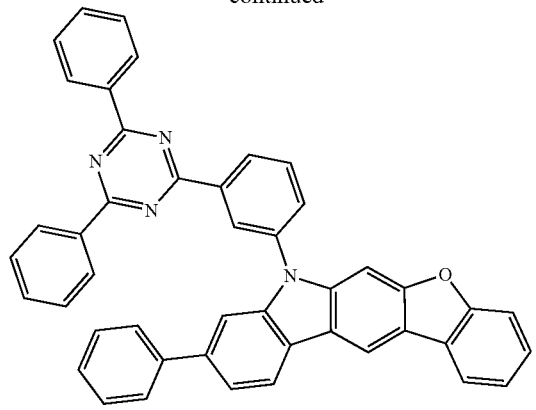
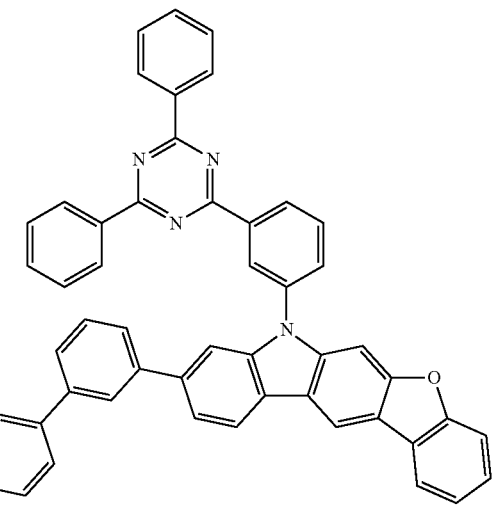
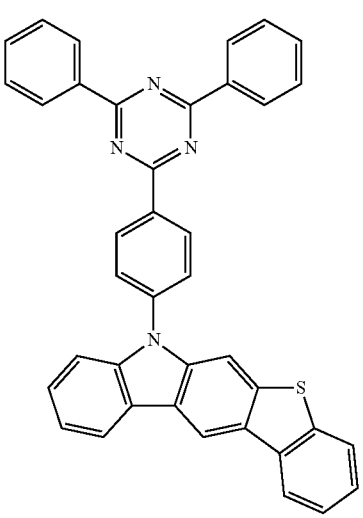

675
-continued
676
-continued
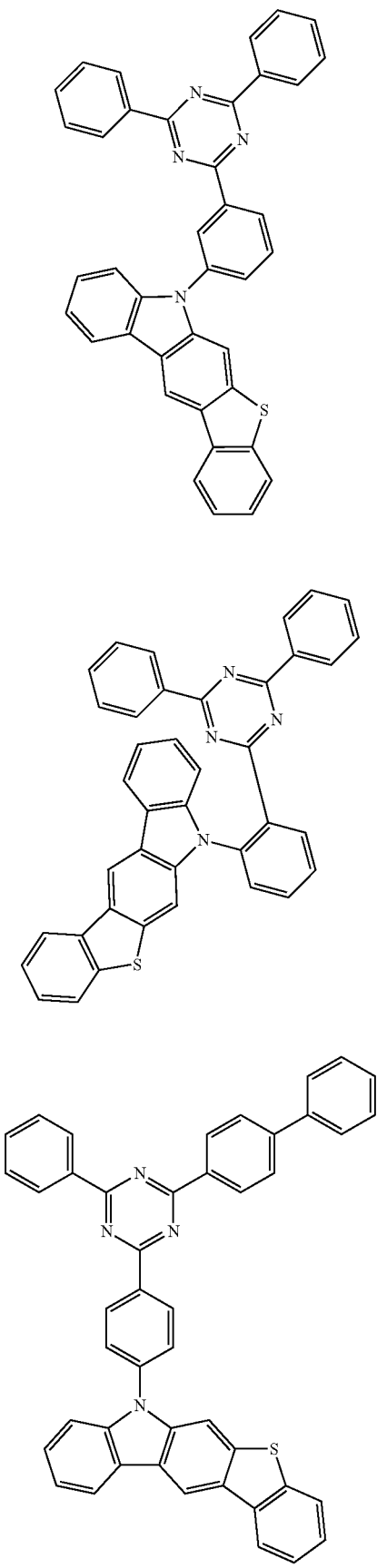
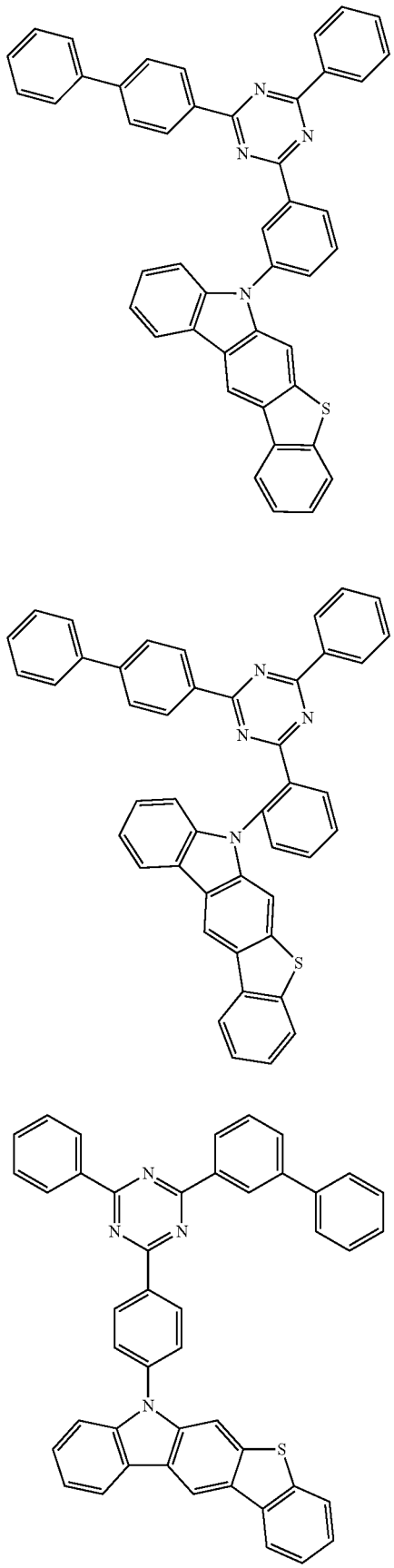

677
-continued
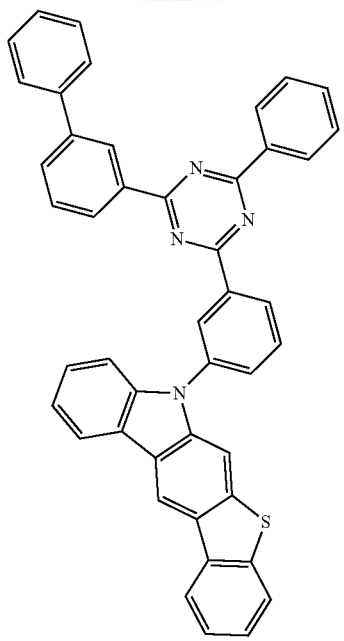
678
-continued
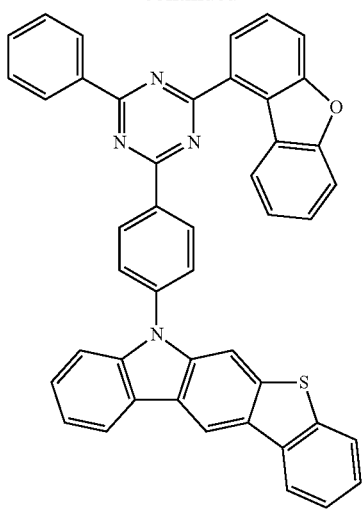
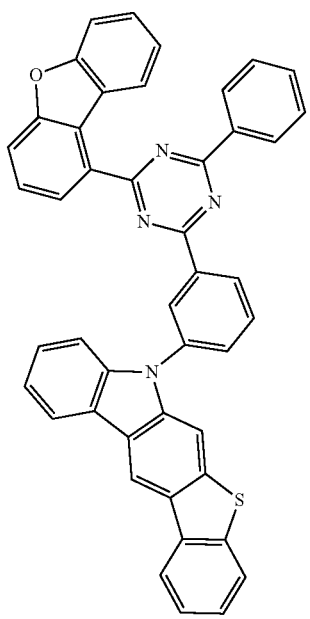
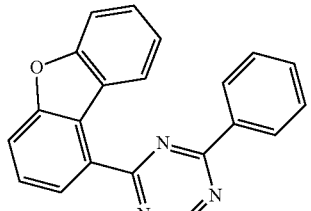
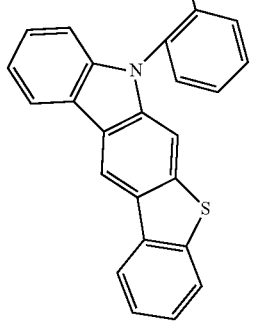

679
-continued
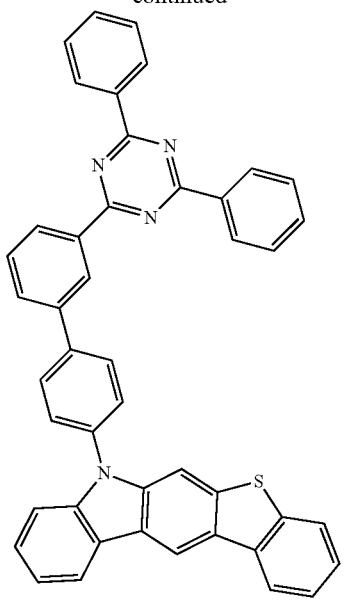
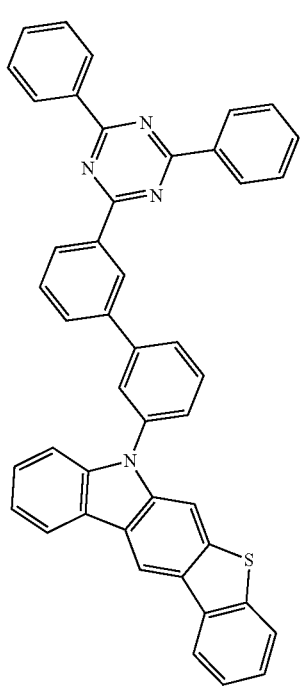
680
-continued
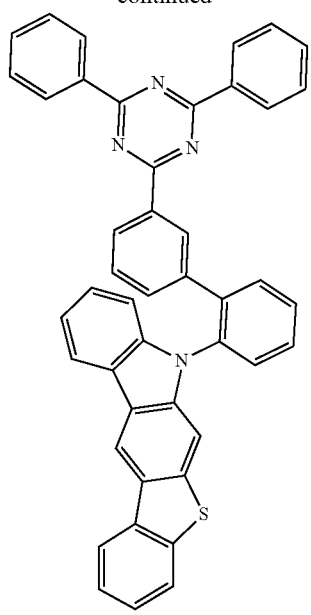

681
-continued
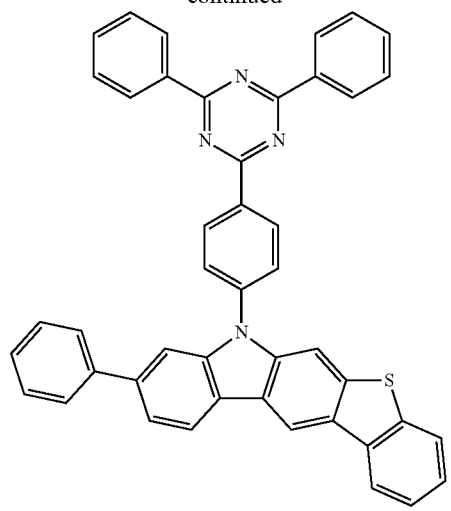
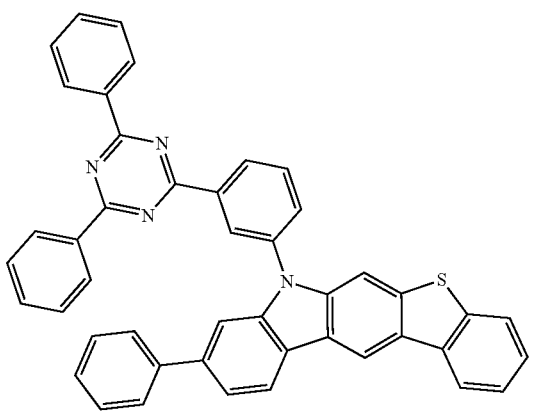
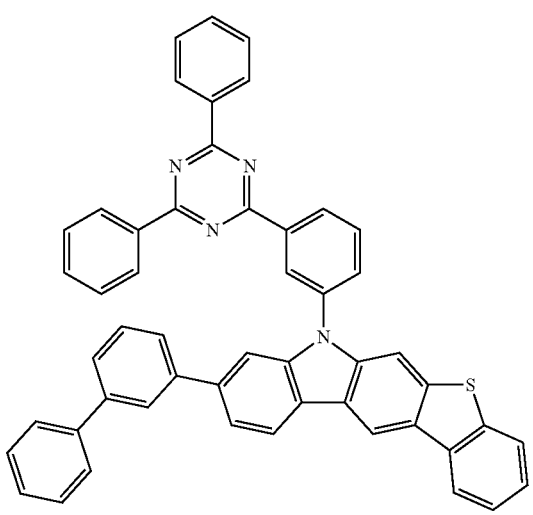
682
-continued
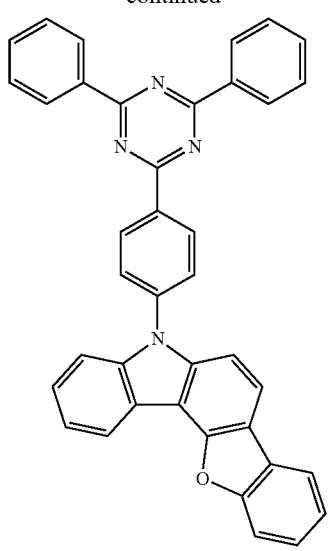
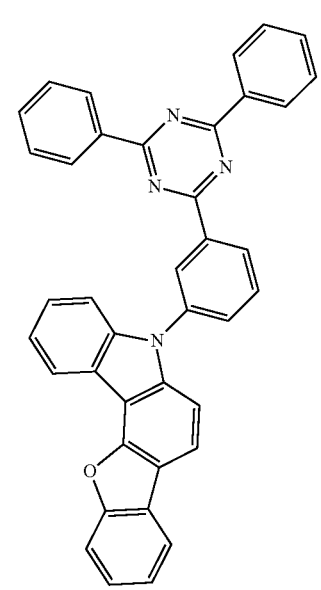
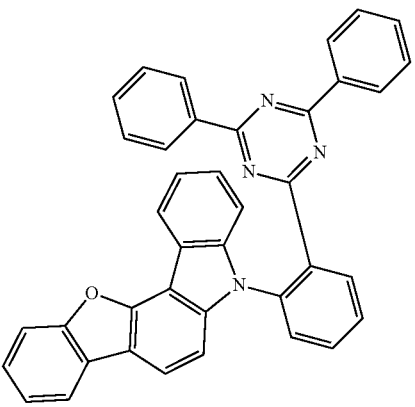

683
-continued
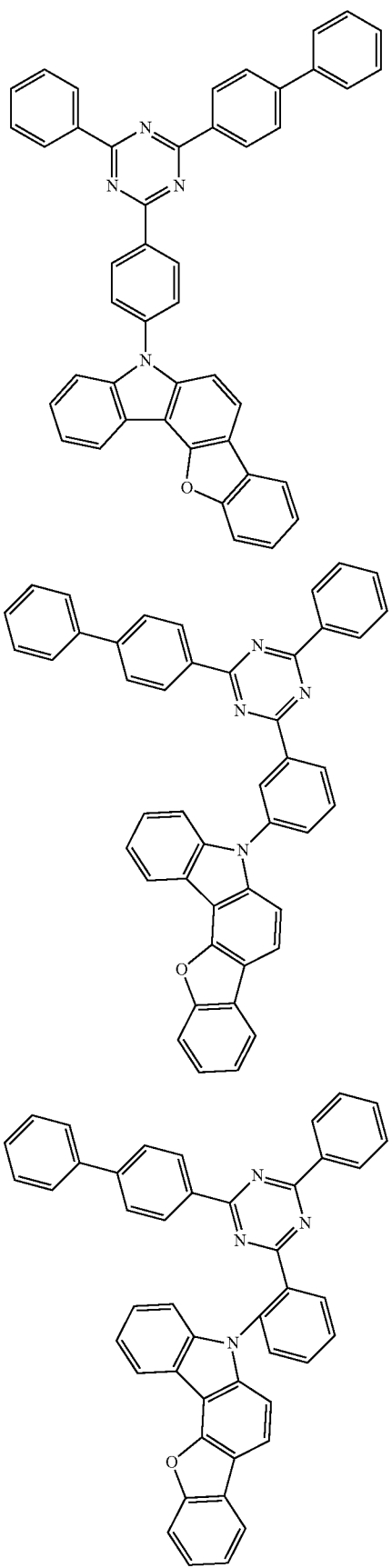
684
-continued
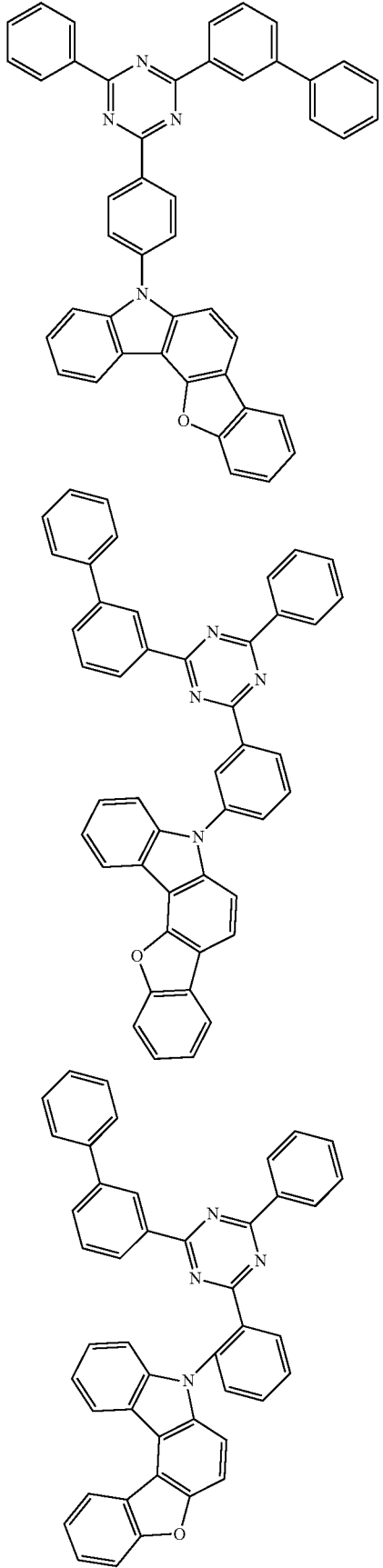

685
-continued
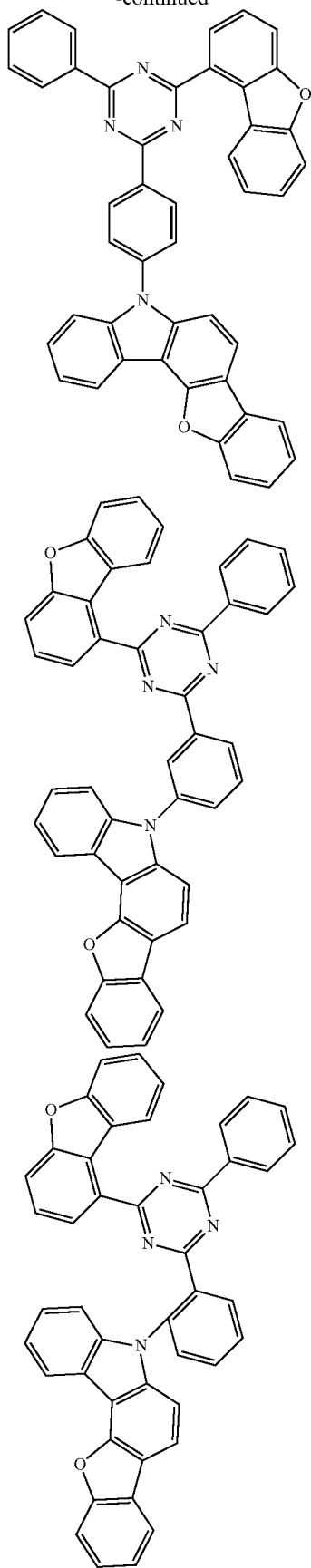
686
-continued

687
-continued
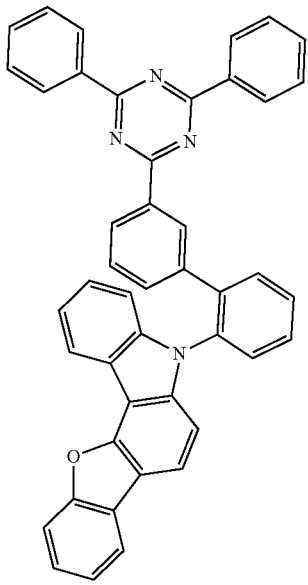
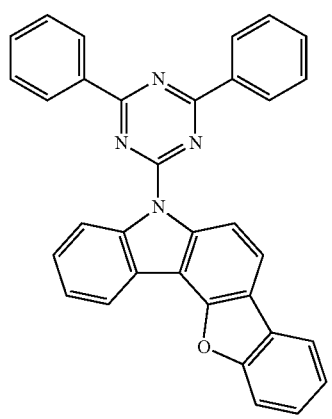
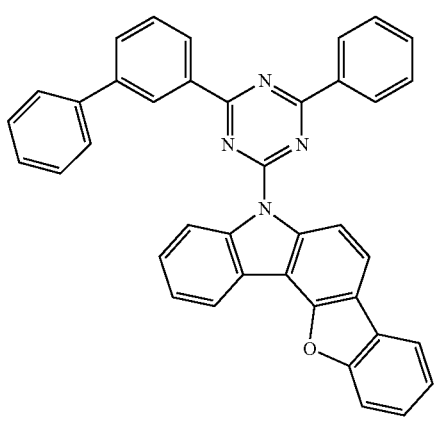
688
-continued
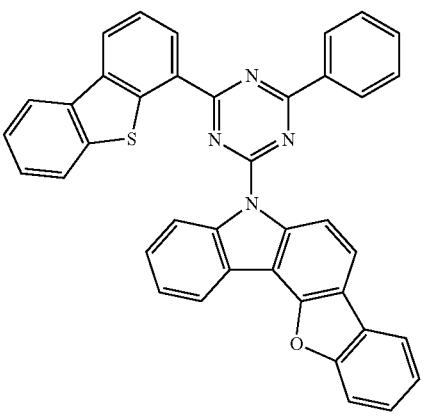
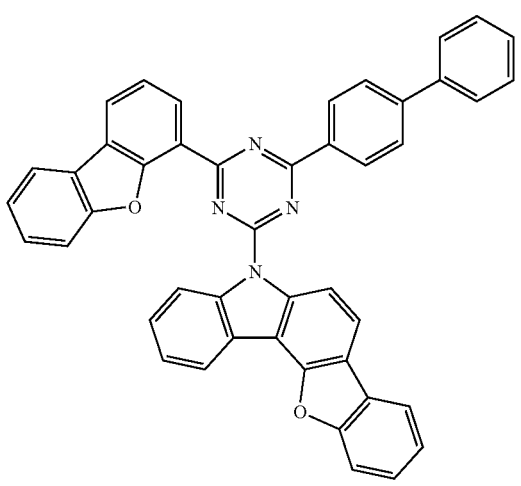
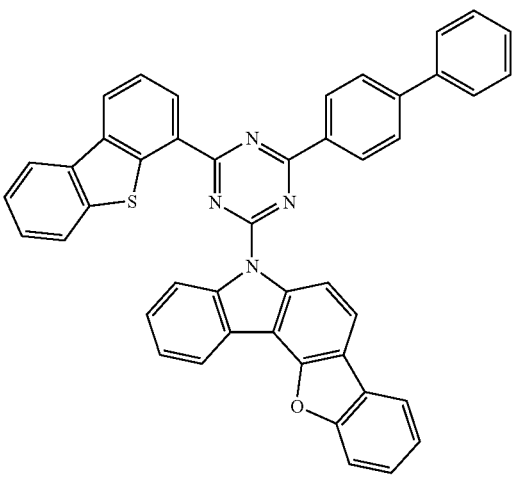

689
-continued
690
-continued
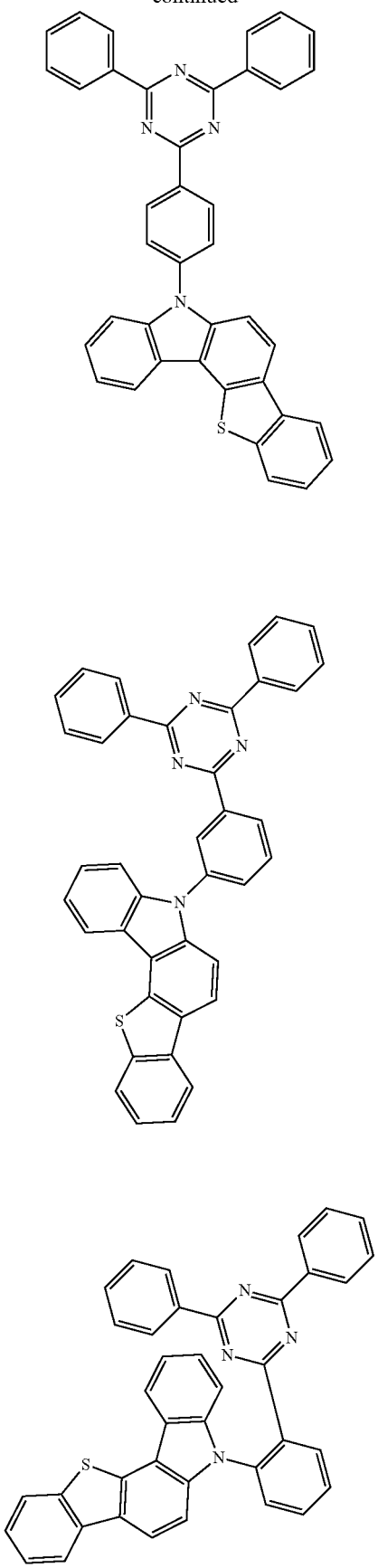
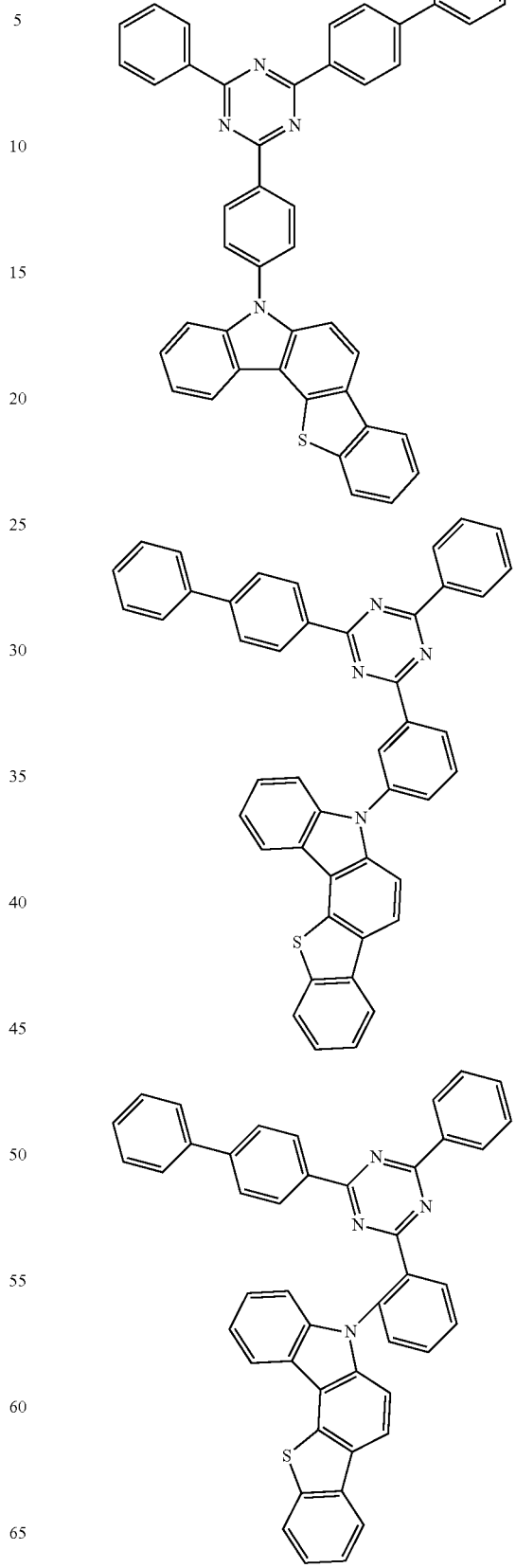

691
-continued
692
-continued
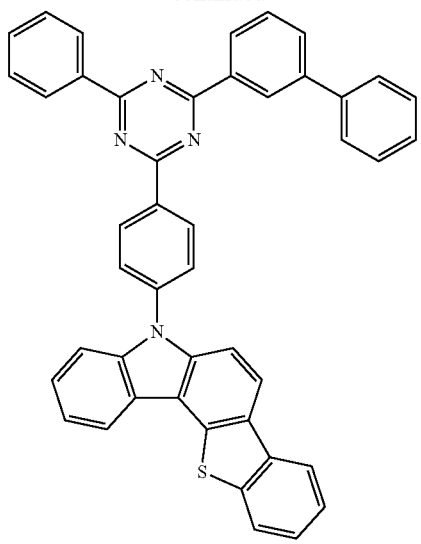
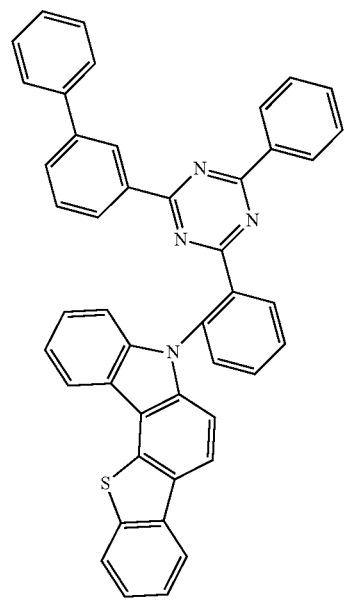

693
-continued
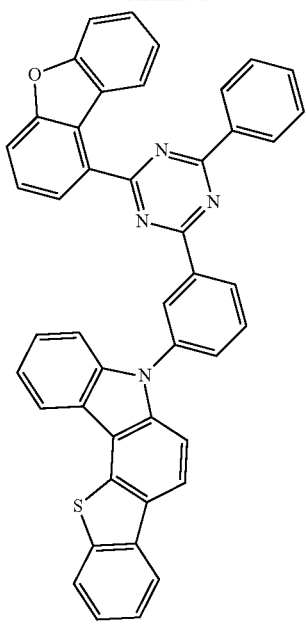
694
-continued
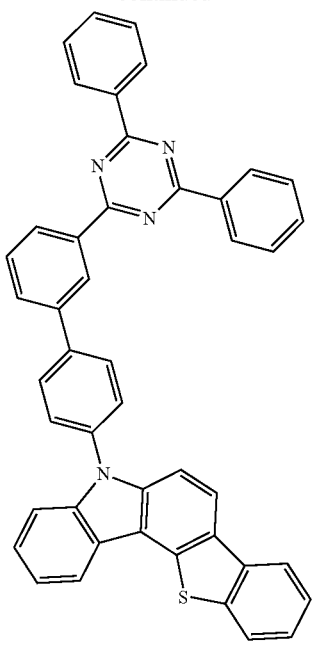
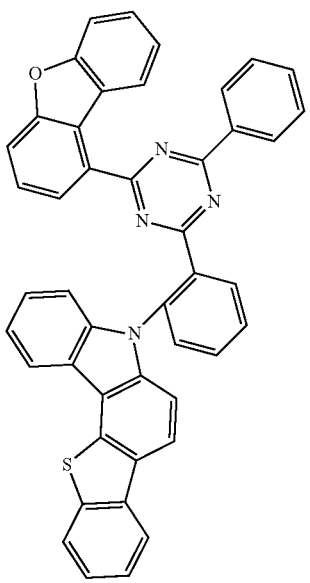

695
-continued
696
-continued
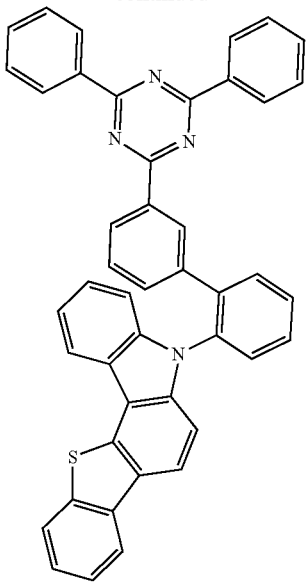
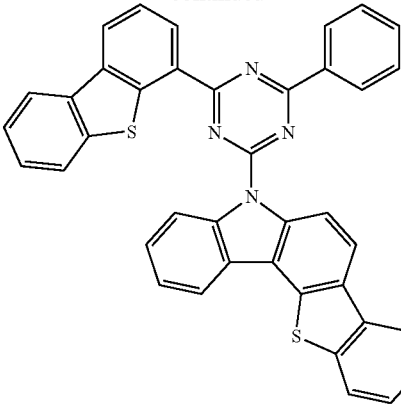
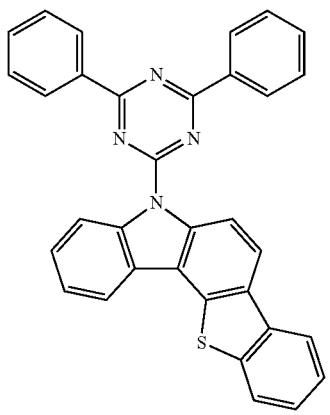
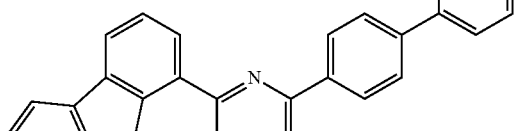
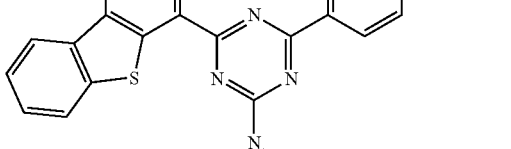
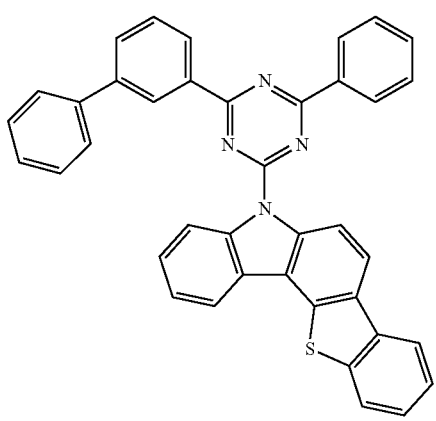
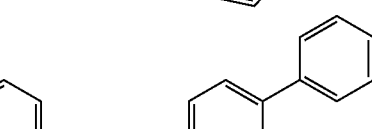
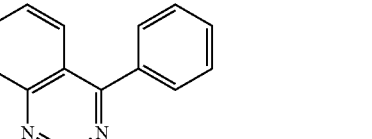

697
-continued
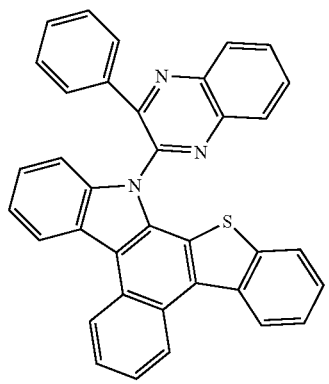
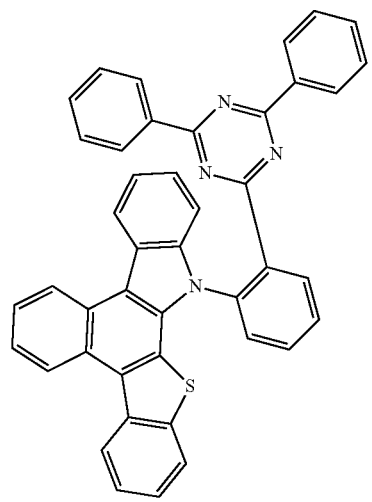
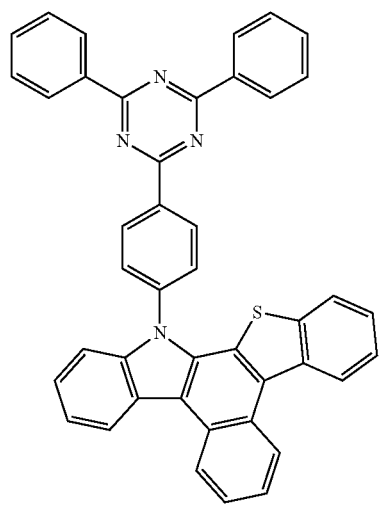
698
-continued
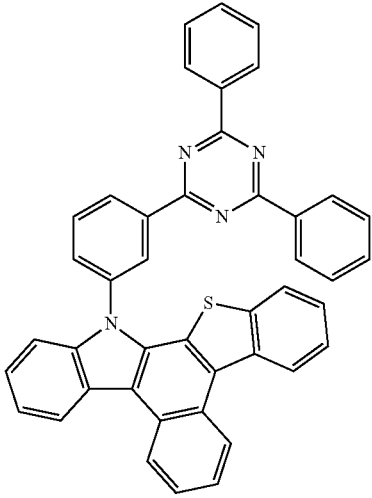
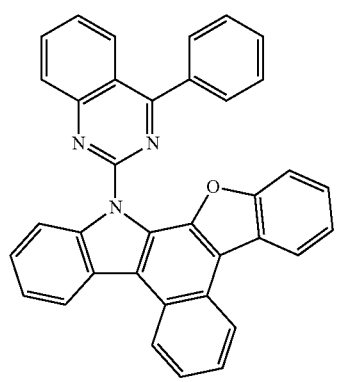
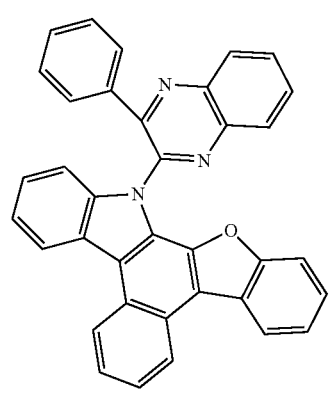

699
-continued
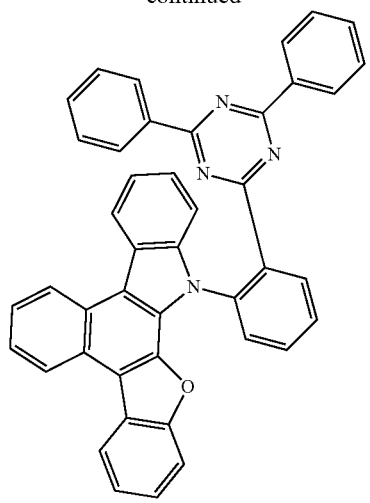
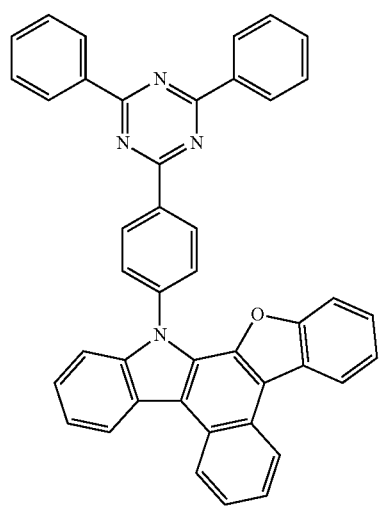
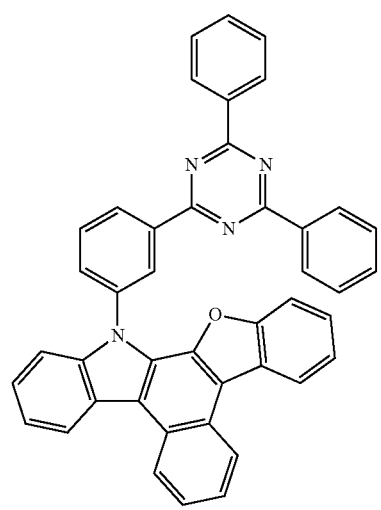
700
-continued
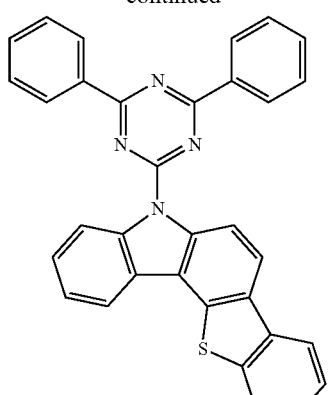
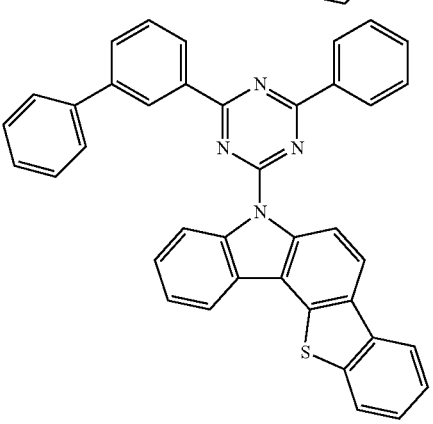
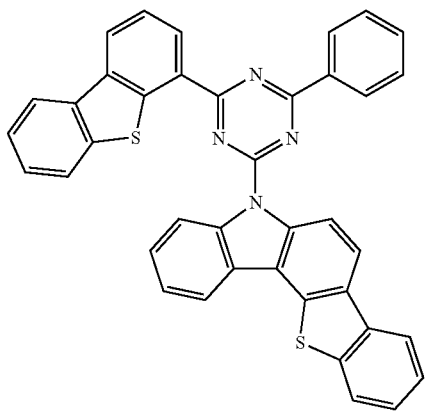
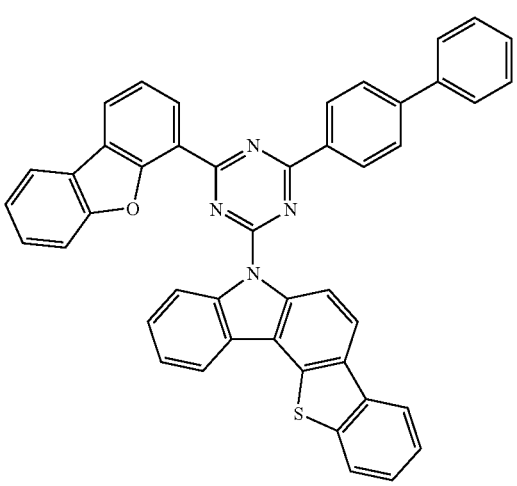

701
-continued
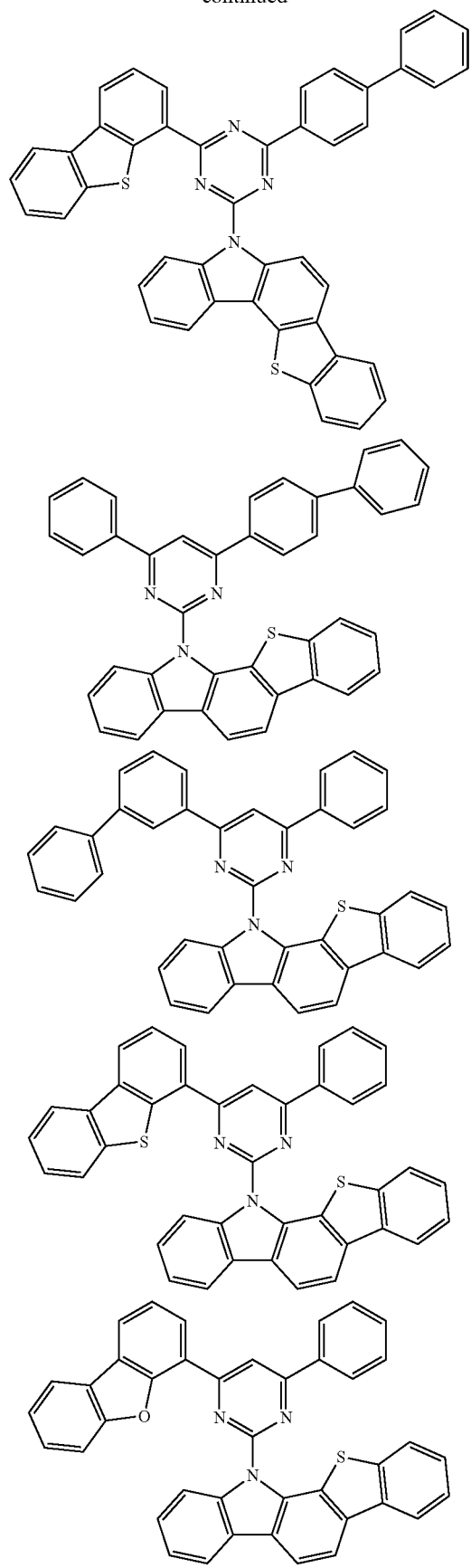
702
-continued
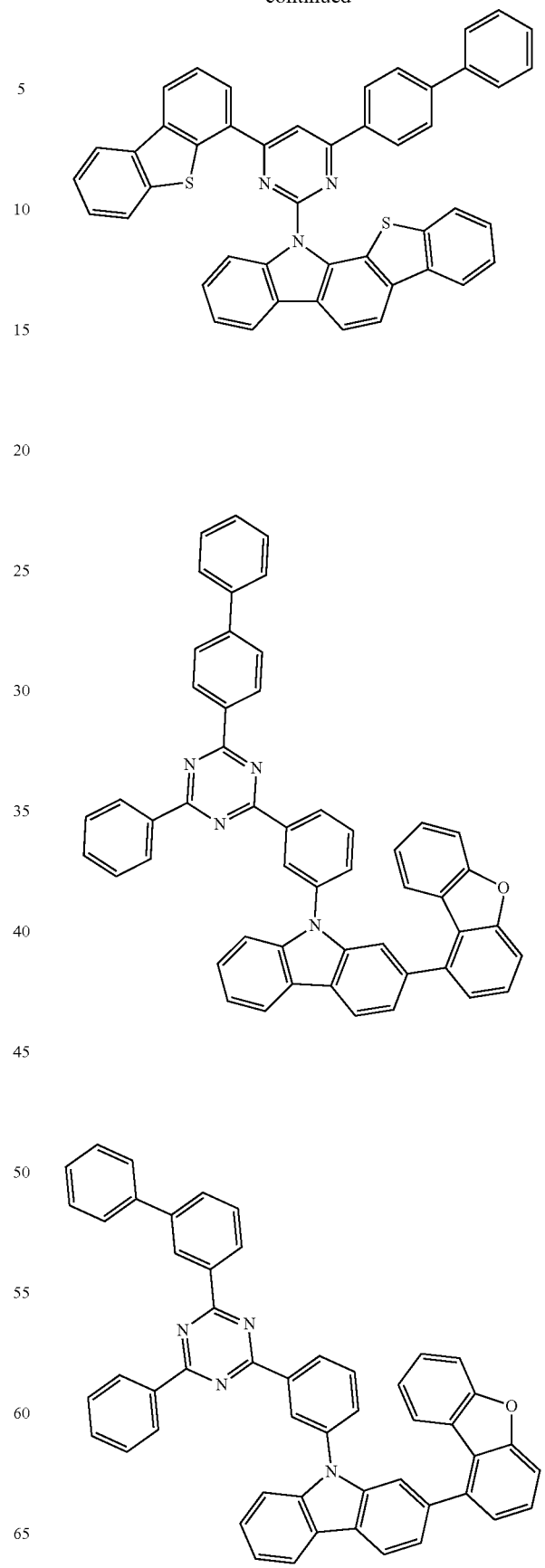

703
-continued
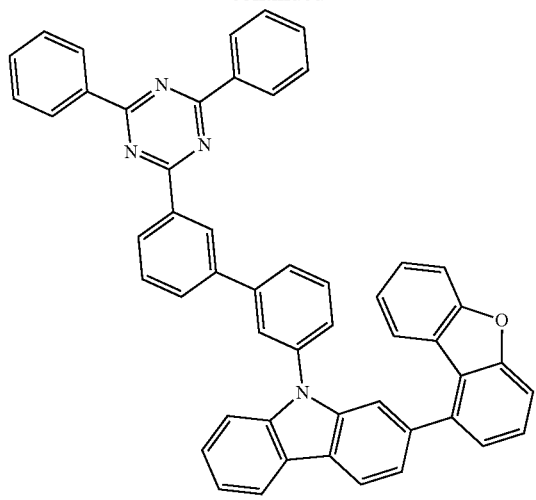
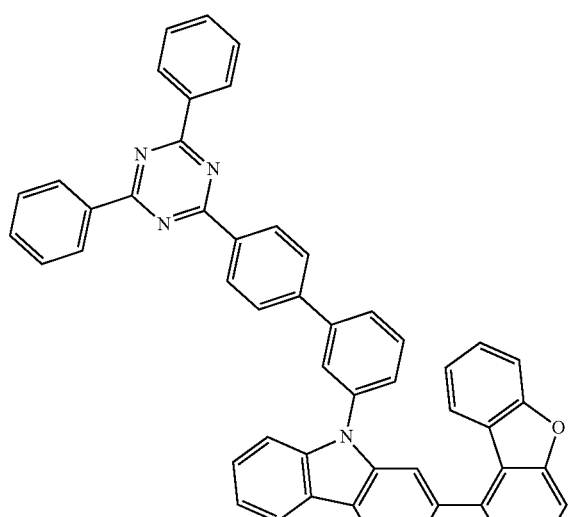
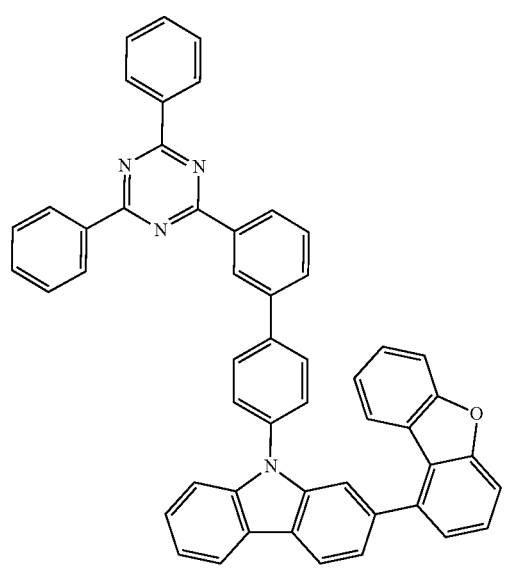
704
-continued
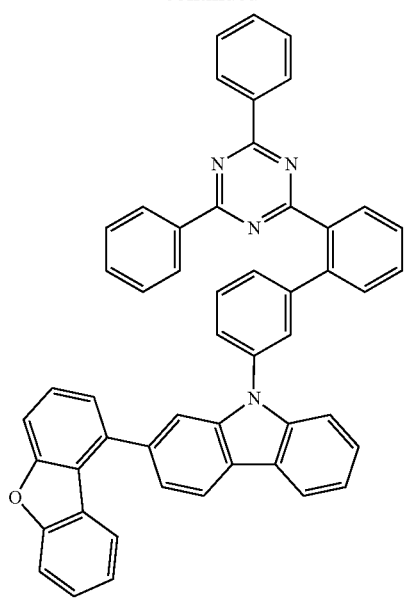
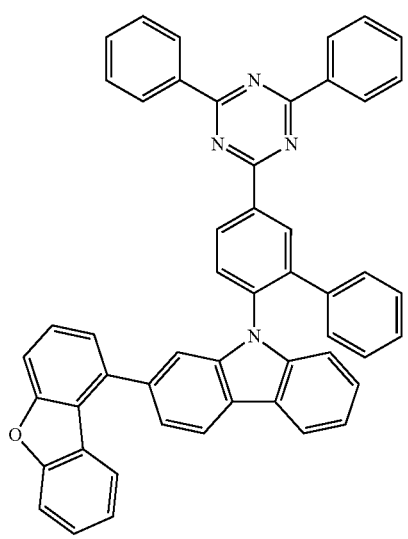
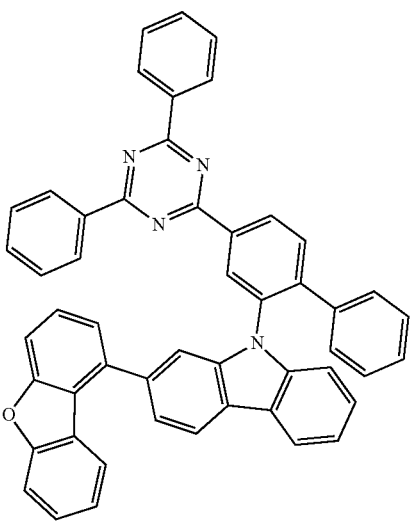

705
-continued
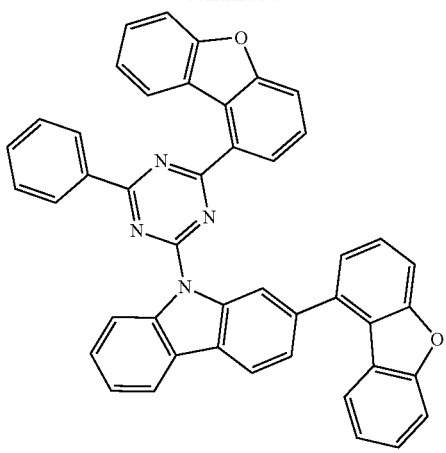
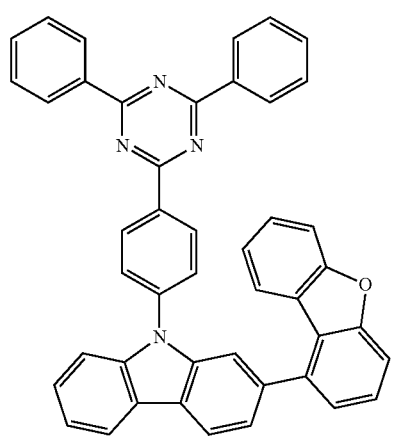
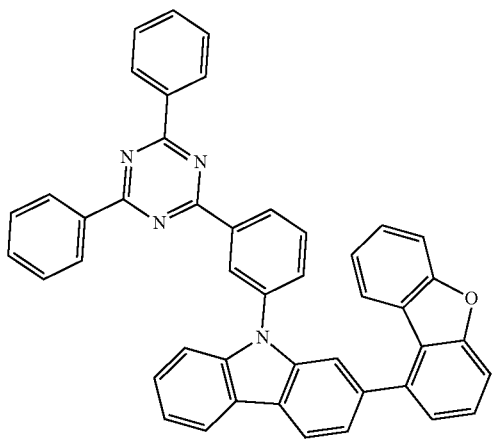
706
-continued
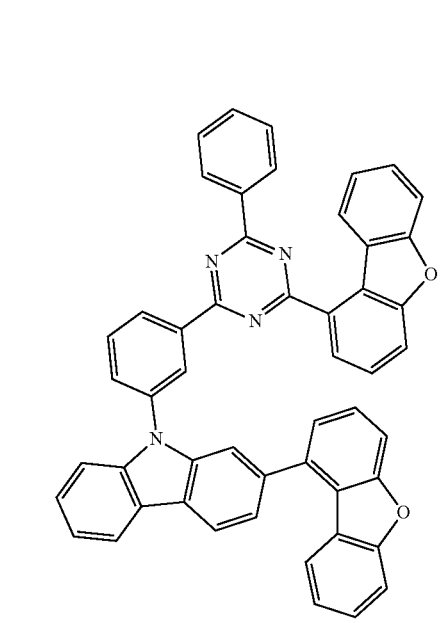
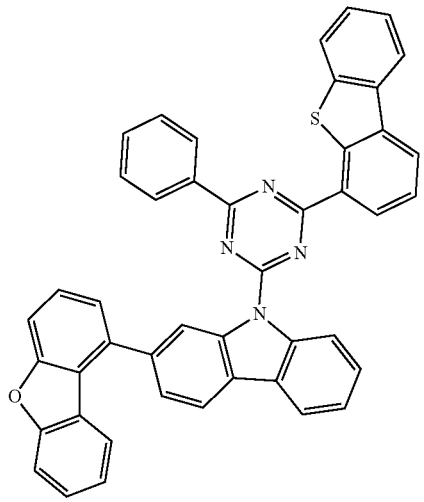

707
-continued
708
-continued
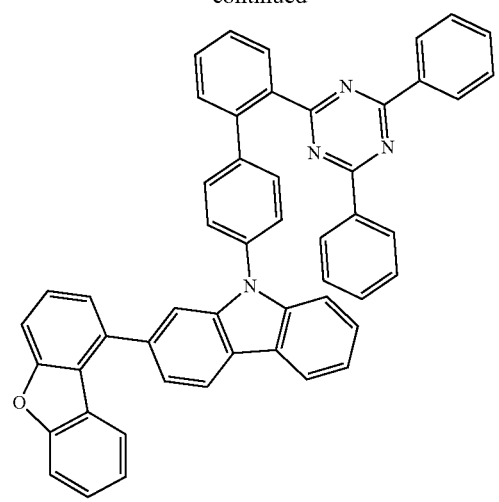
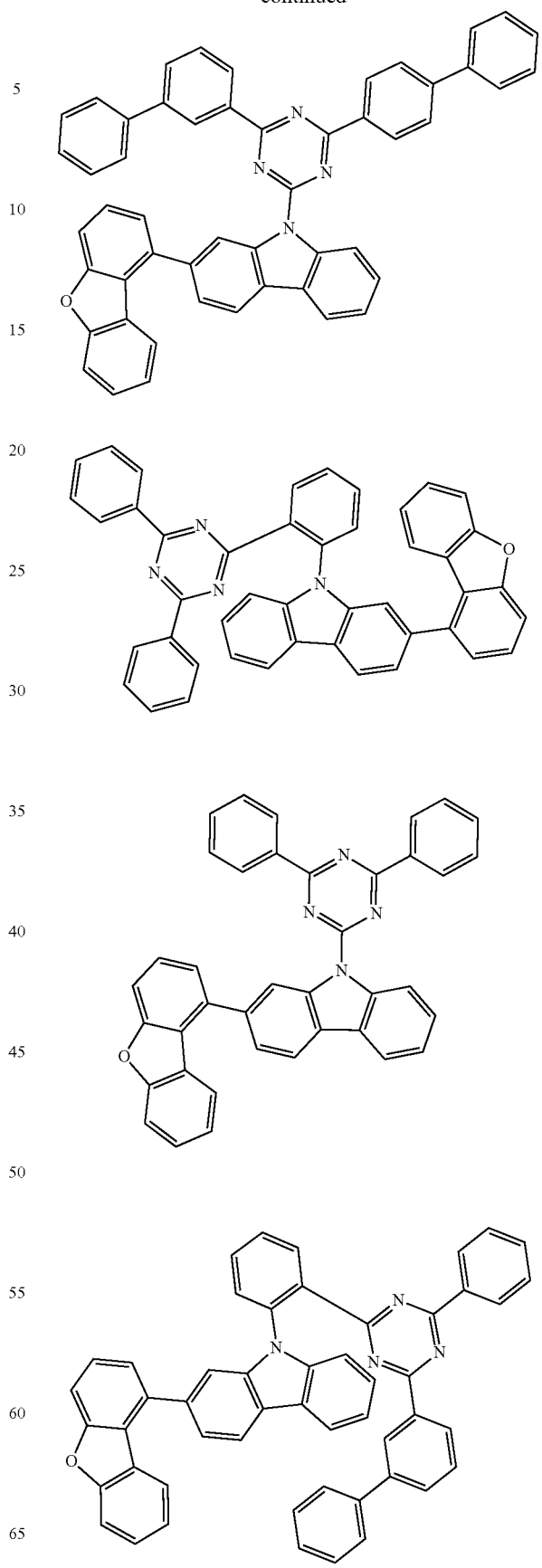

709
-continued
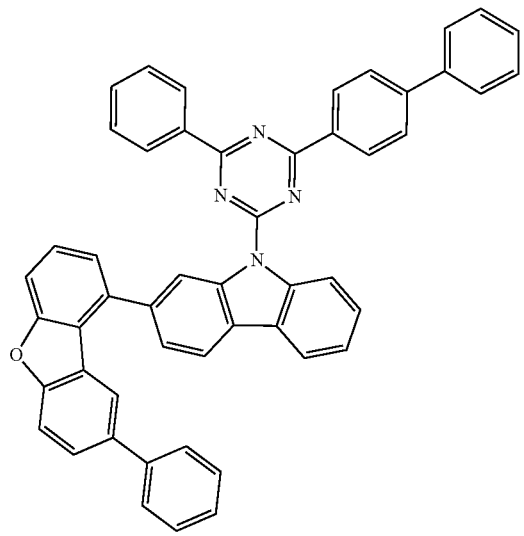
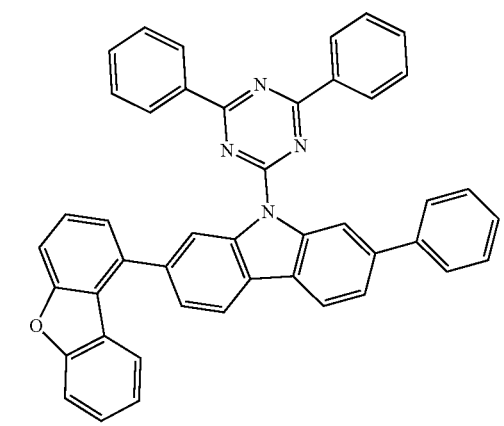
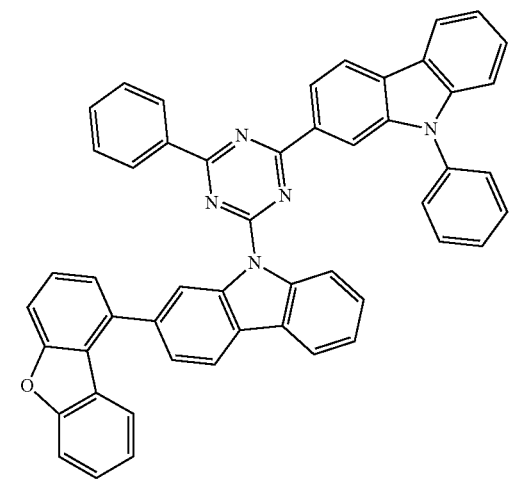
710
-continued
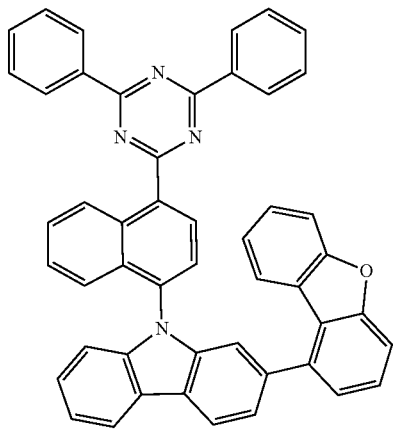
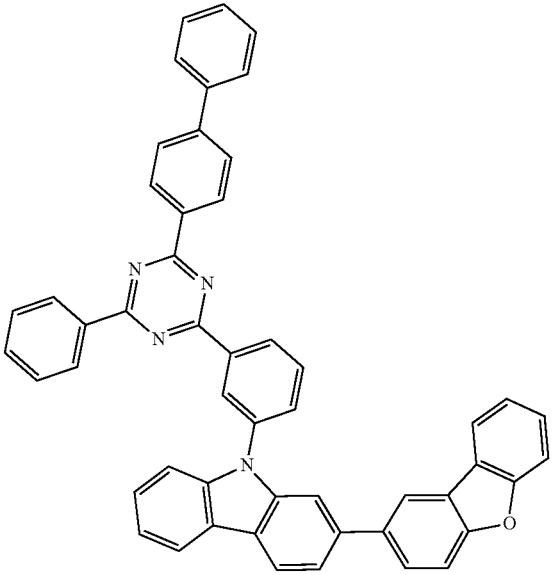
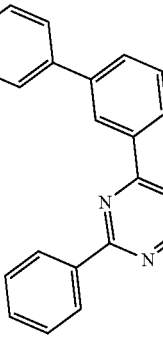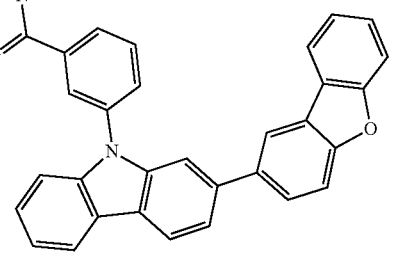

711
-continued
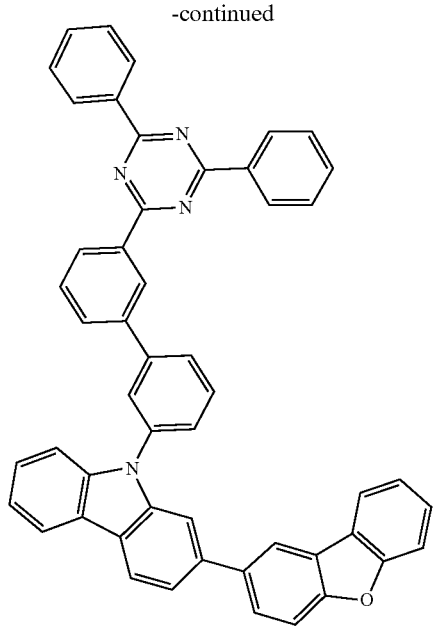
712
-continued
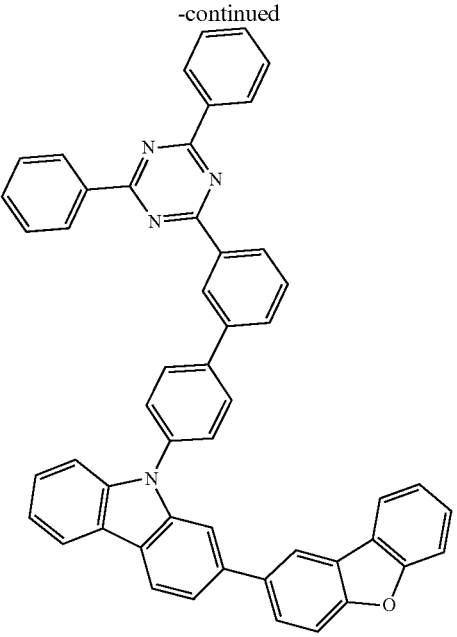
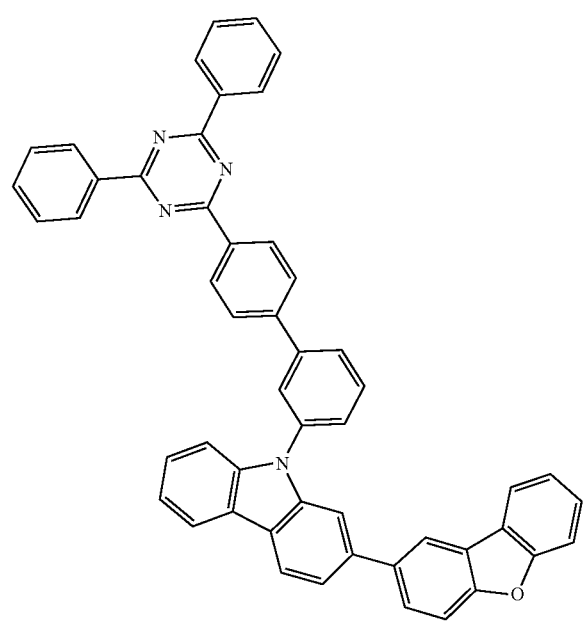
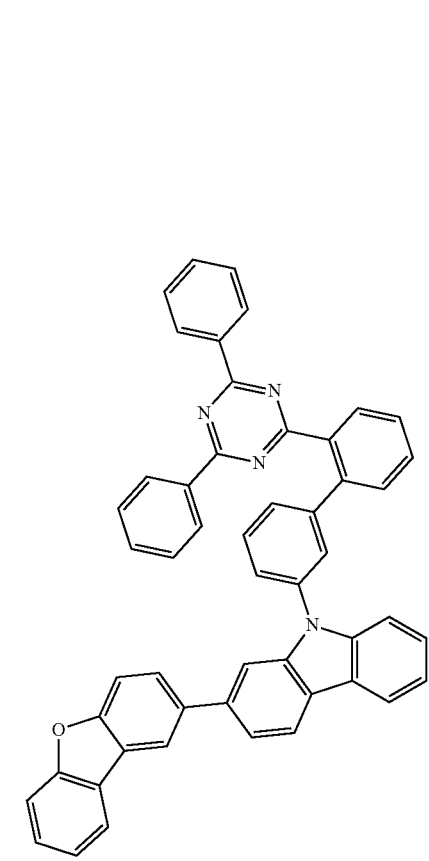

713
-continued
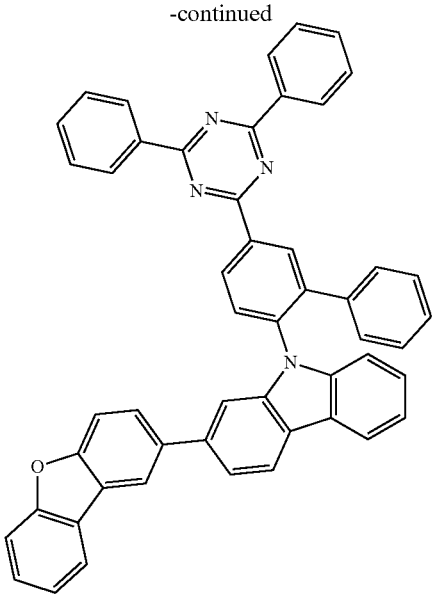
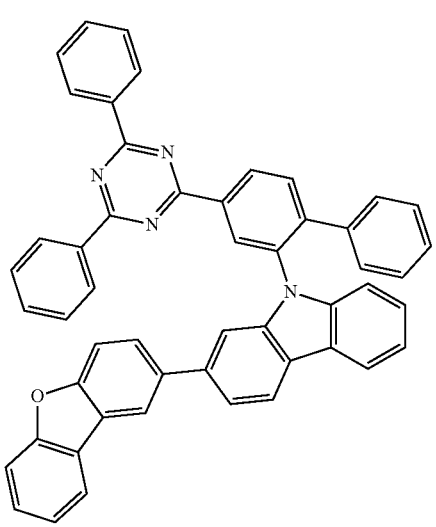
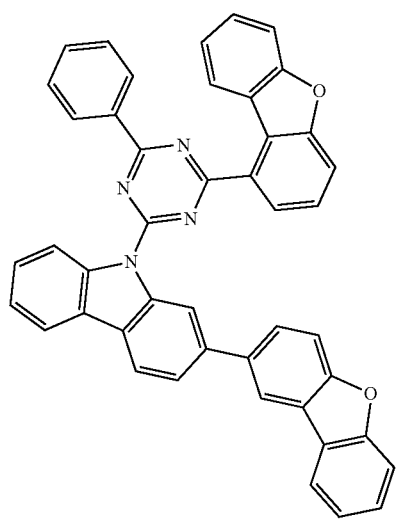
714
-continued
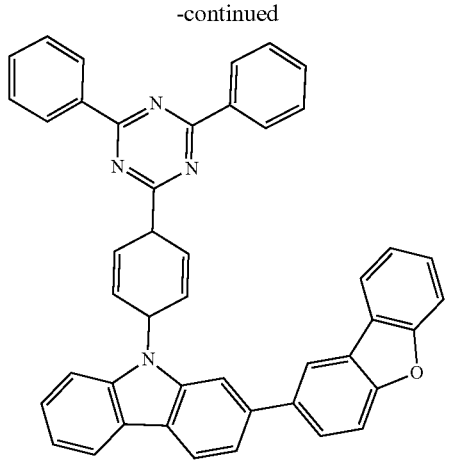
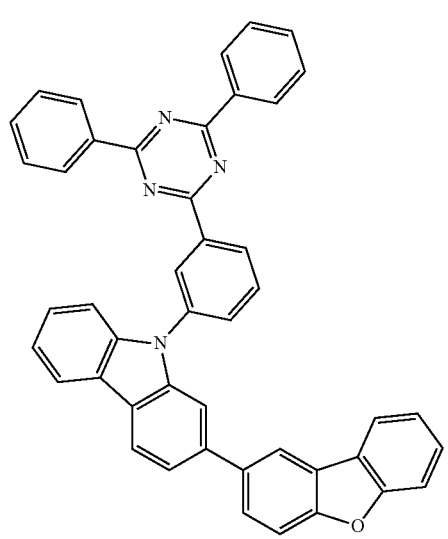
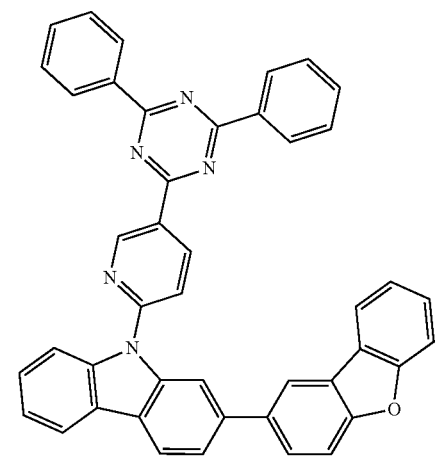

715
-continued
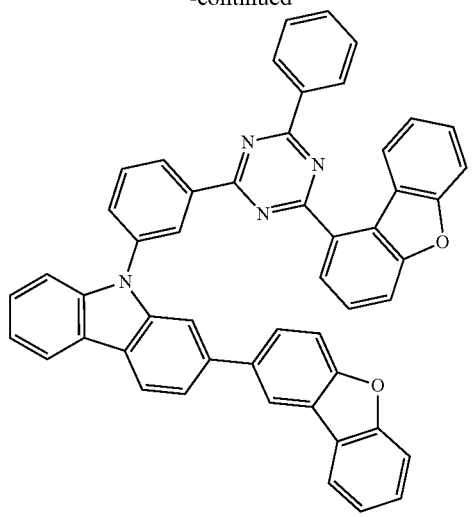
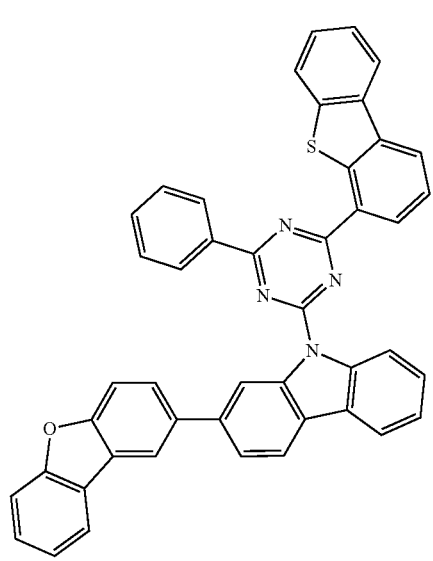
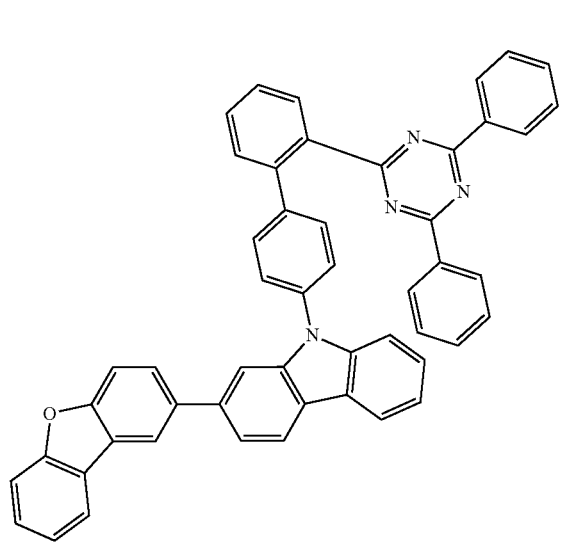
716
-continued
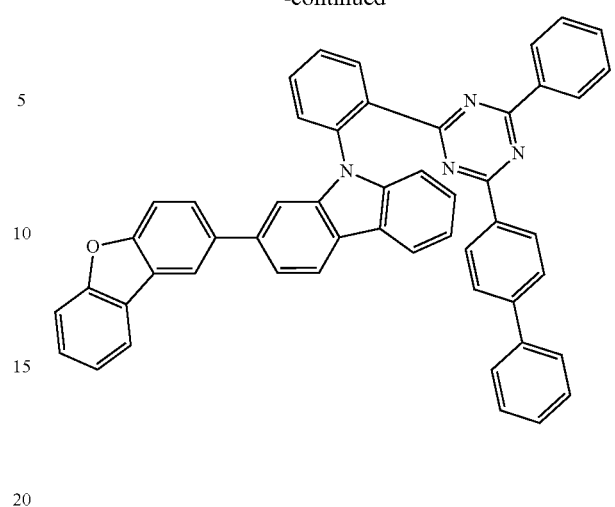
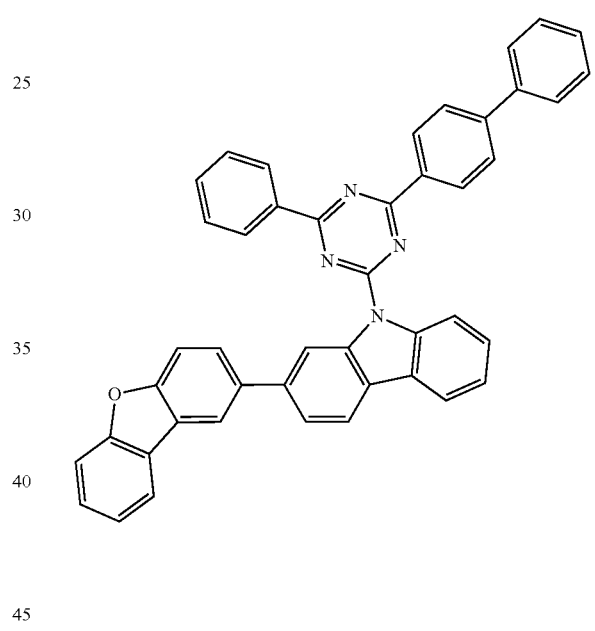
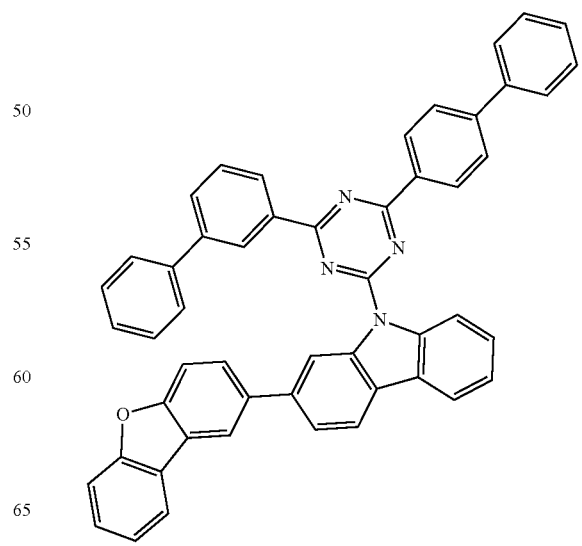

717
-continued
718
-continued
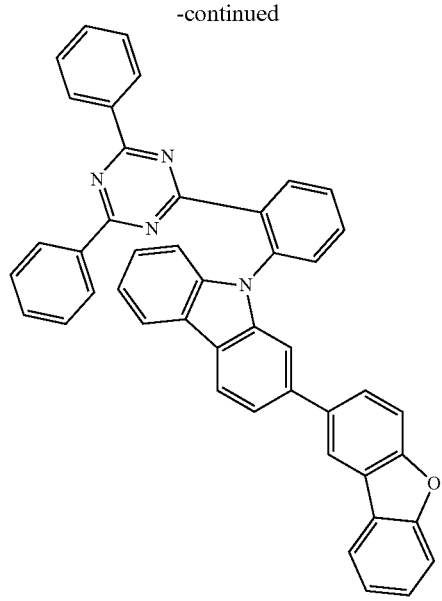
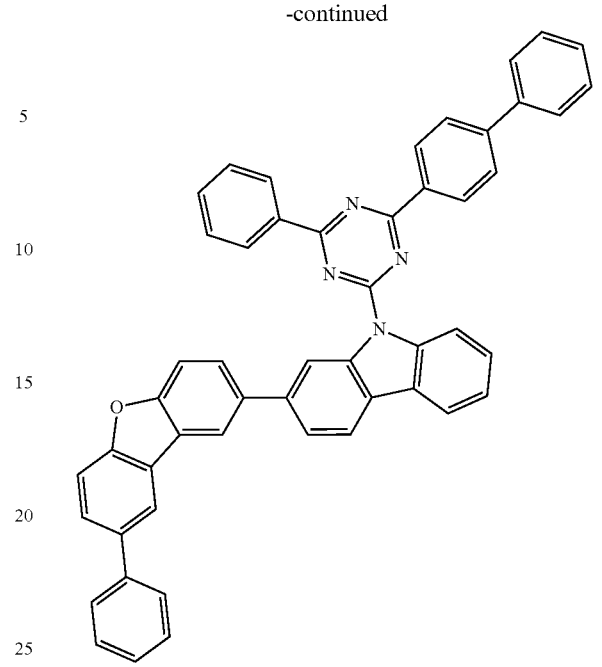
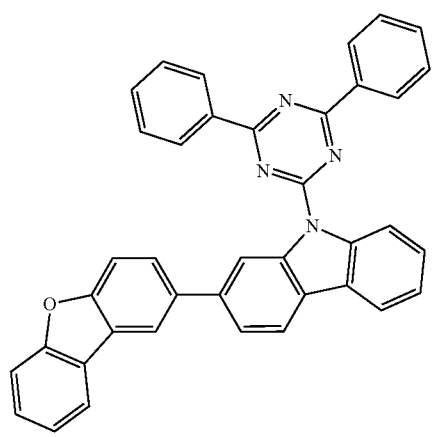
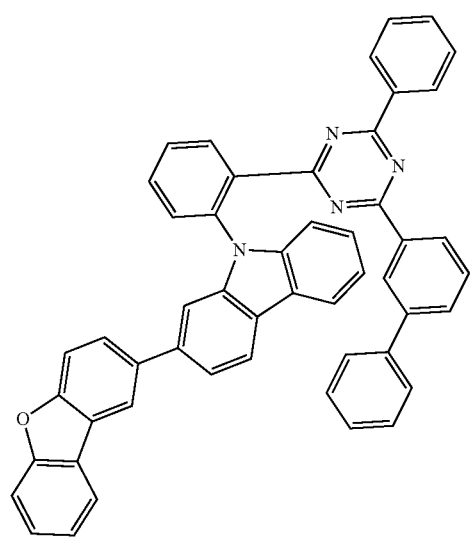

719
-continued
720
-continued
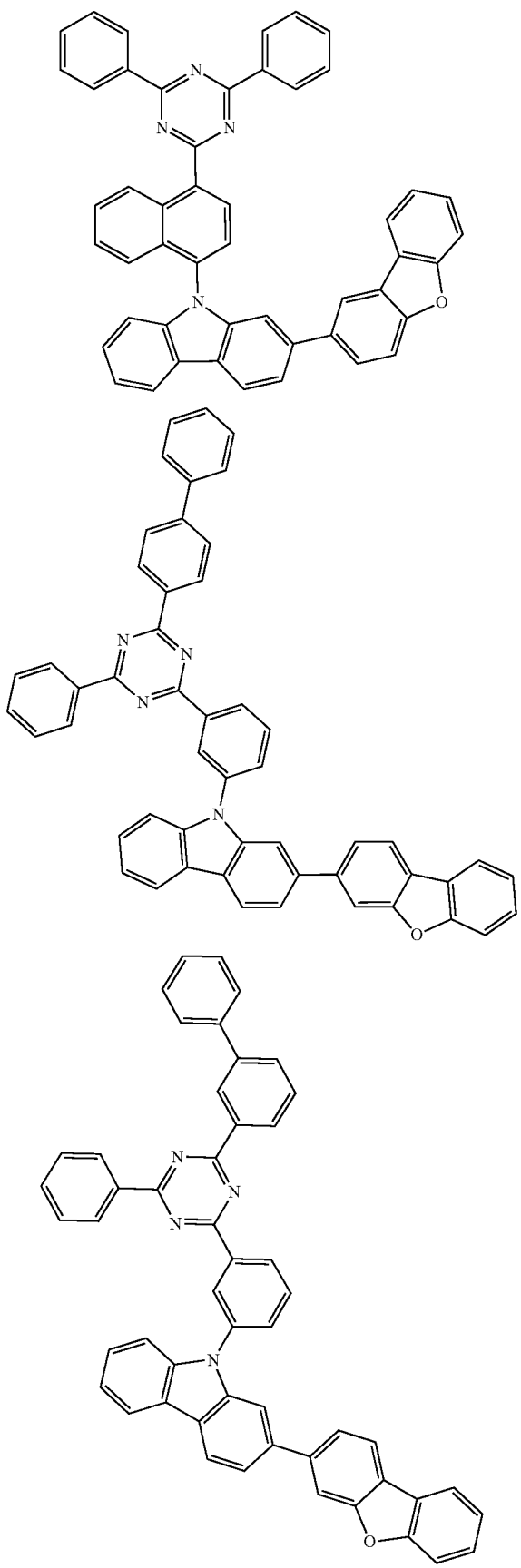
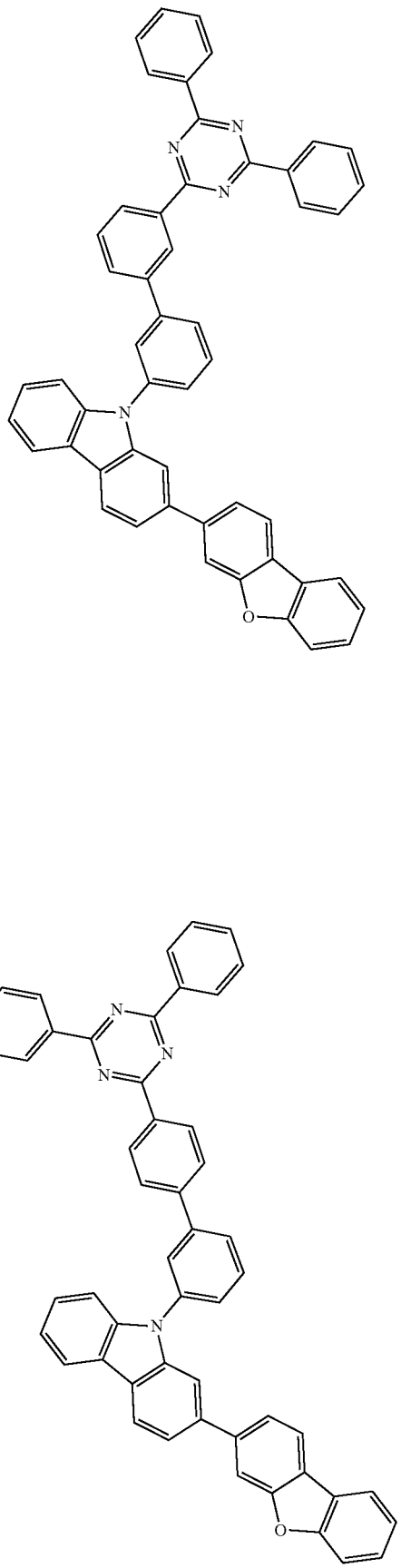

721
-continued
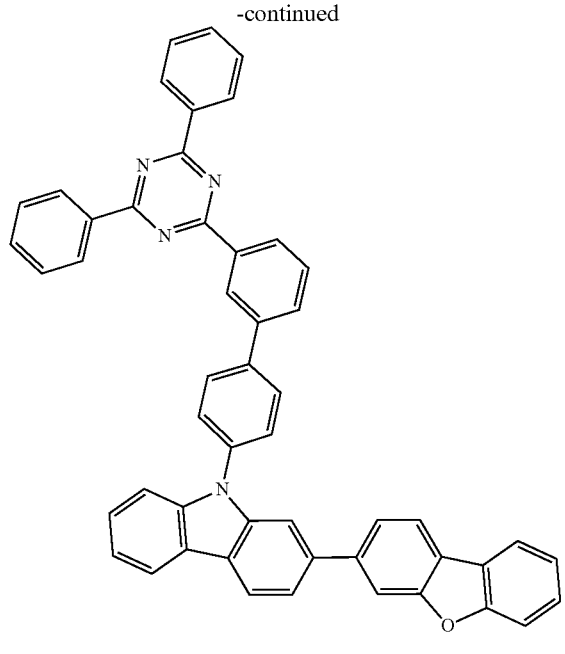
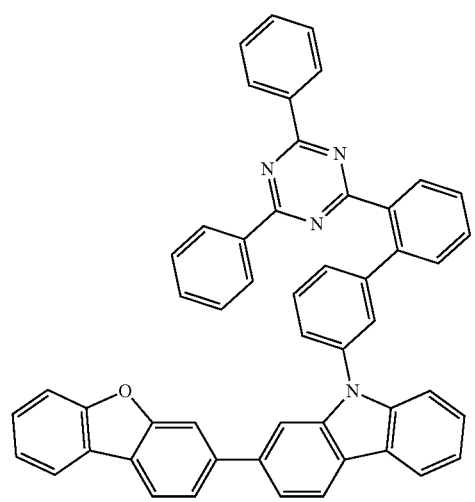
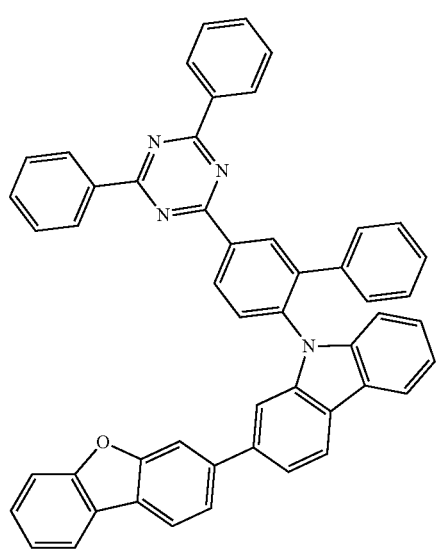
722
-continued
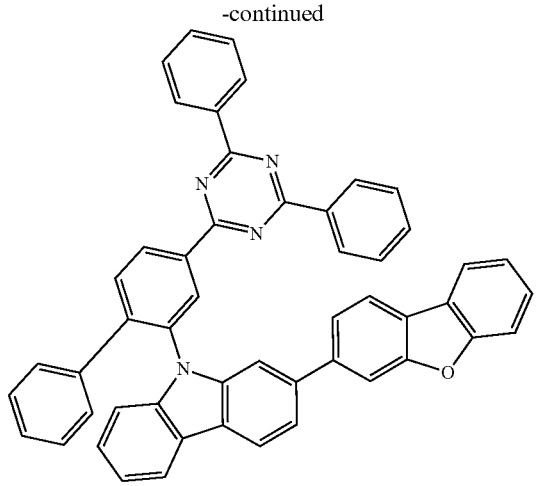
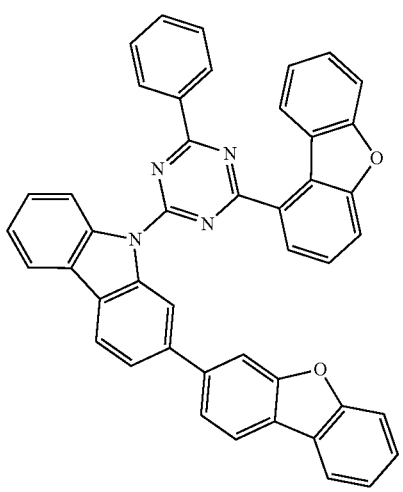
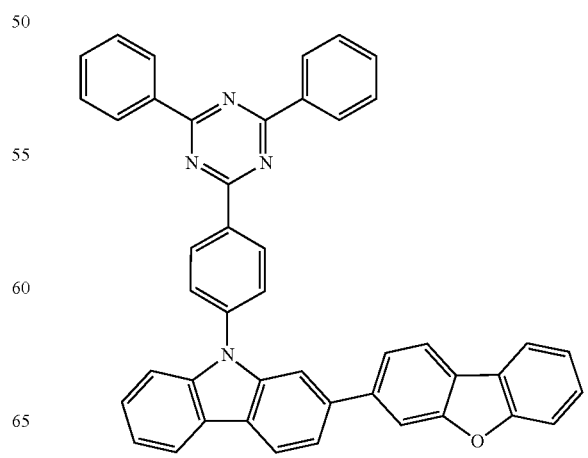

723
-continued
724
-continued
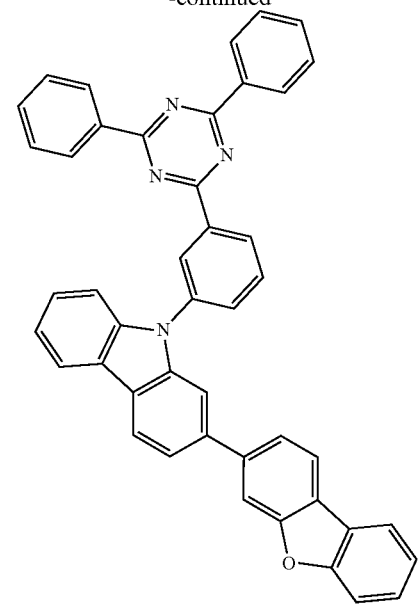
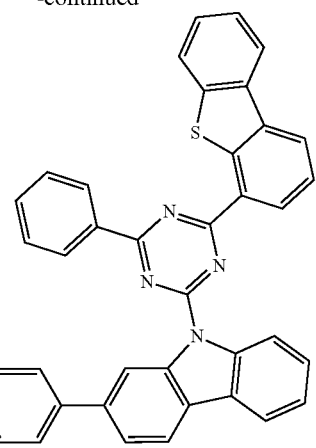
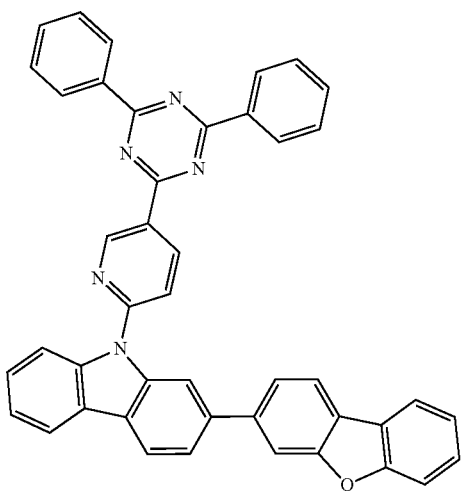
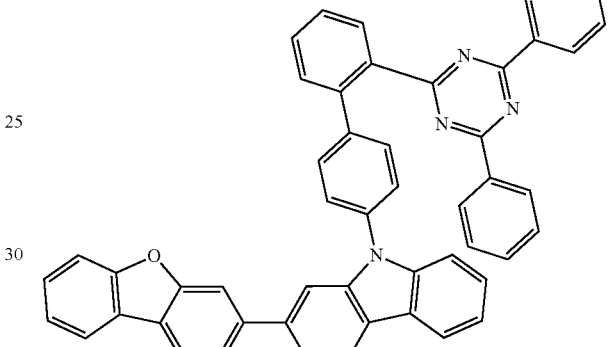
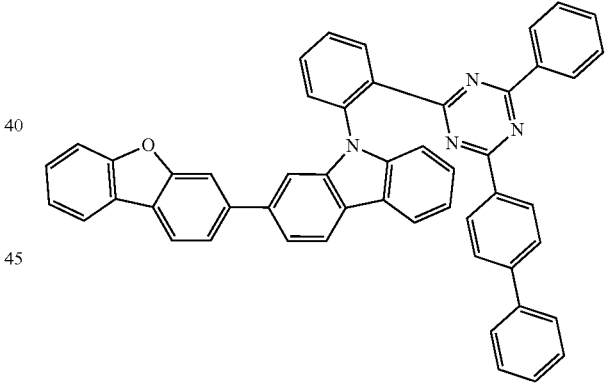
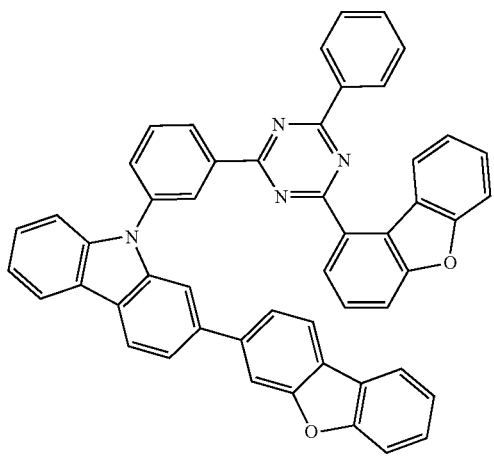
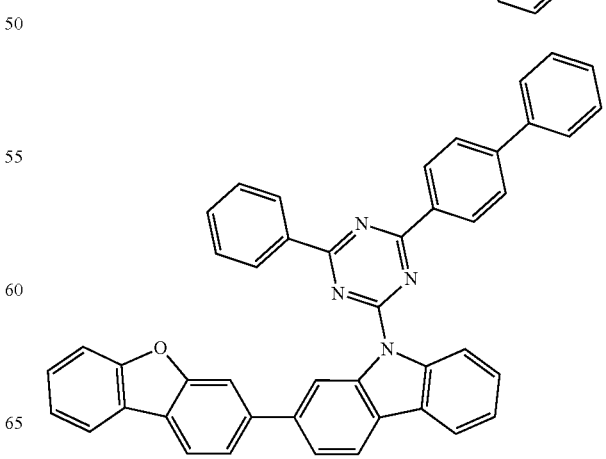

725
-continued
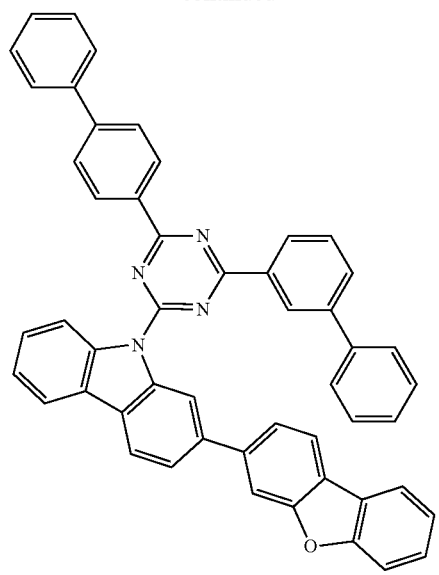
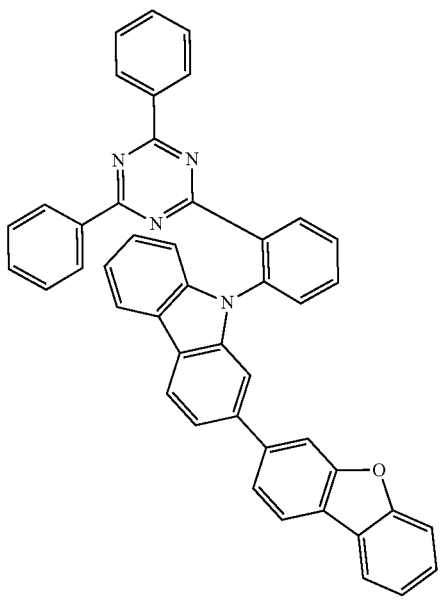
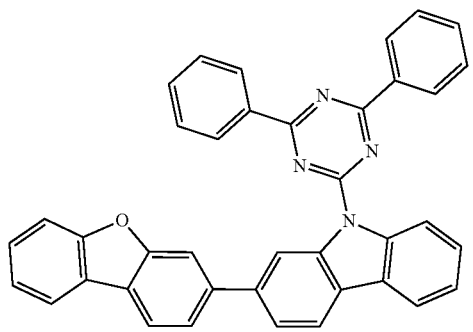
726
-continued
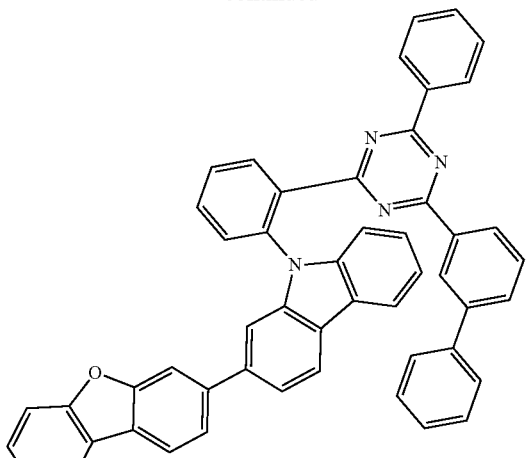
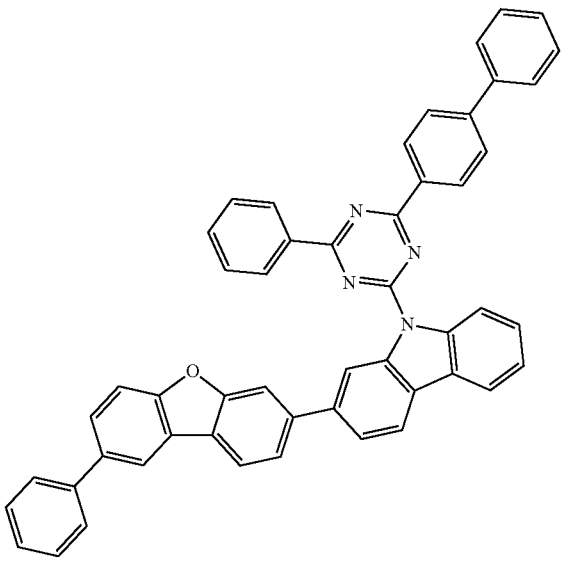
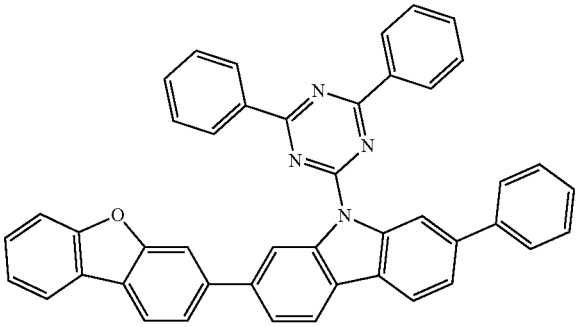

727
-continued
728
-continued
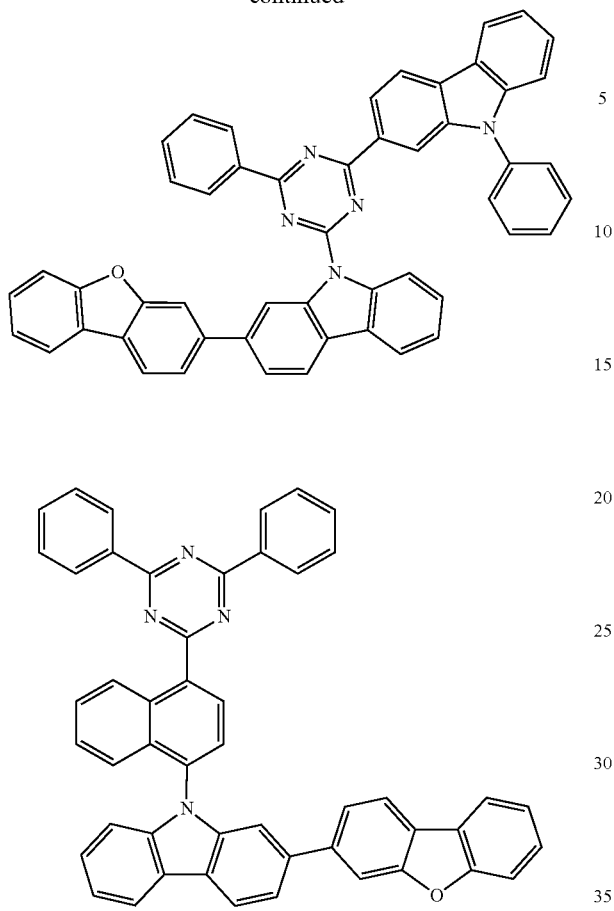
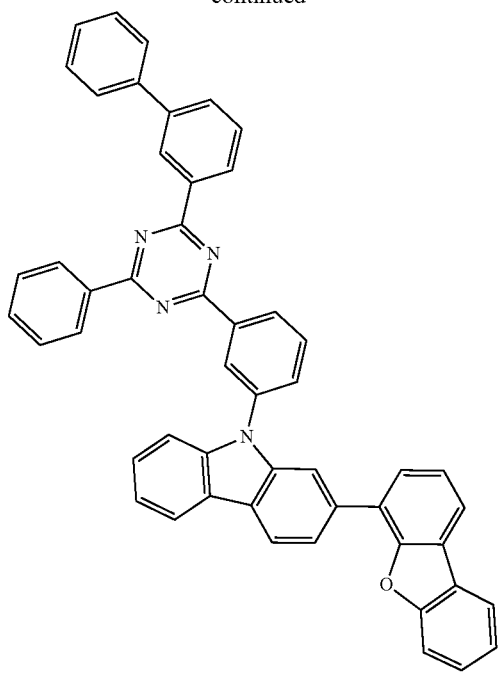
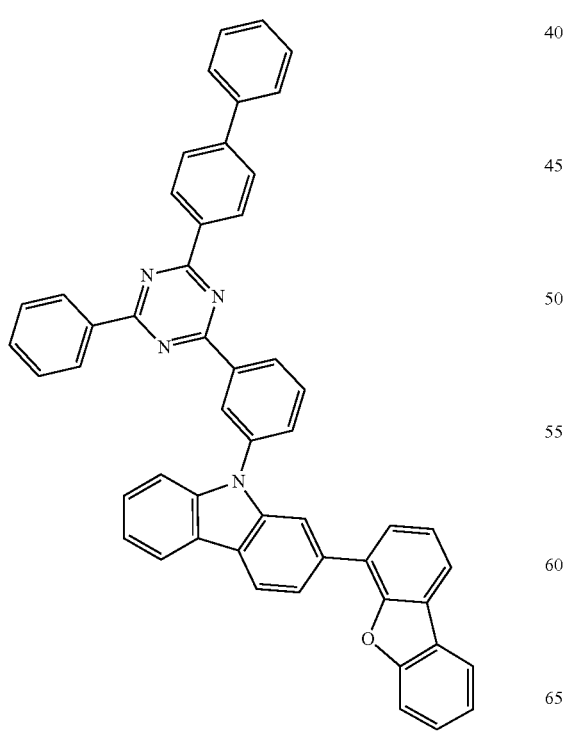
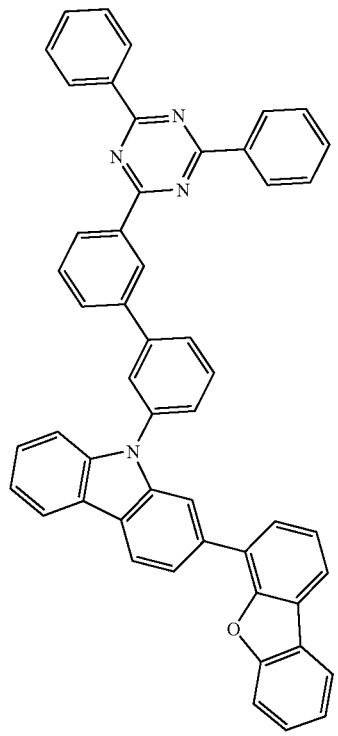

729
-continued
730
-continued
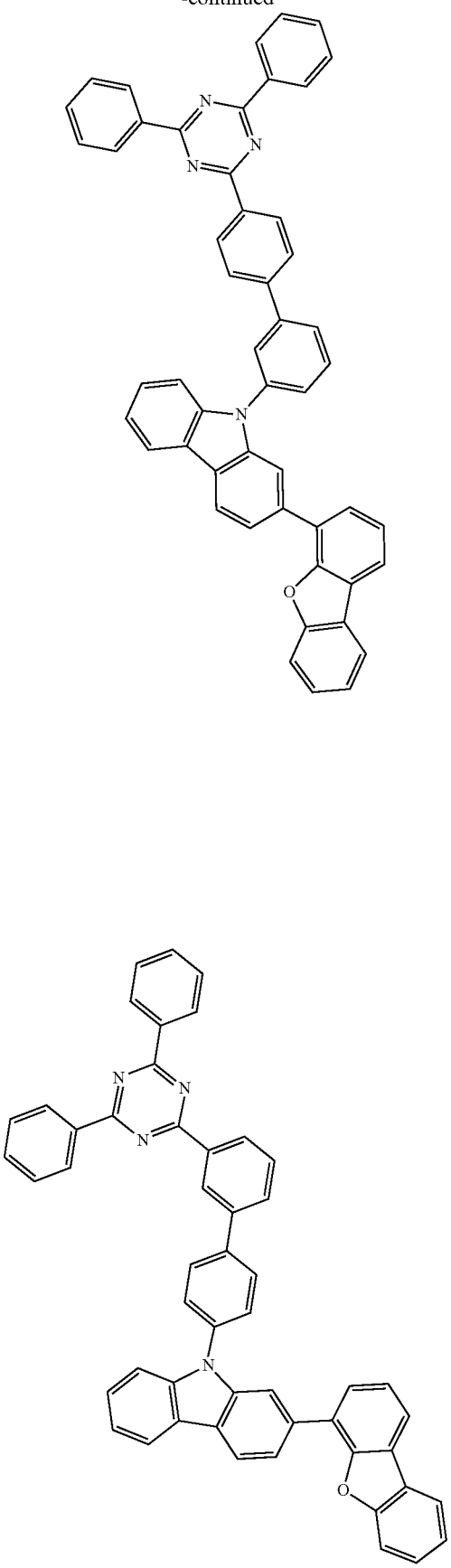
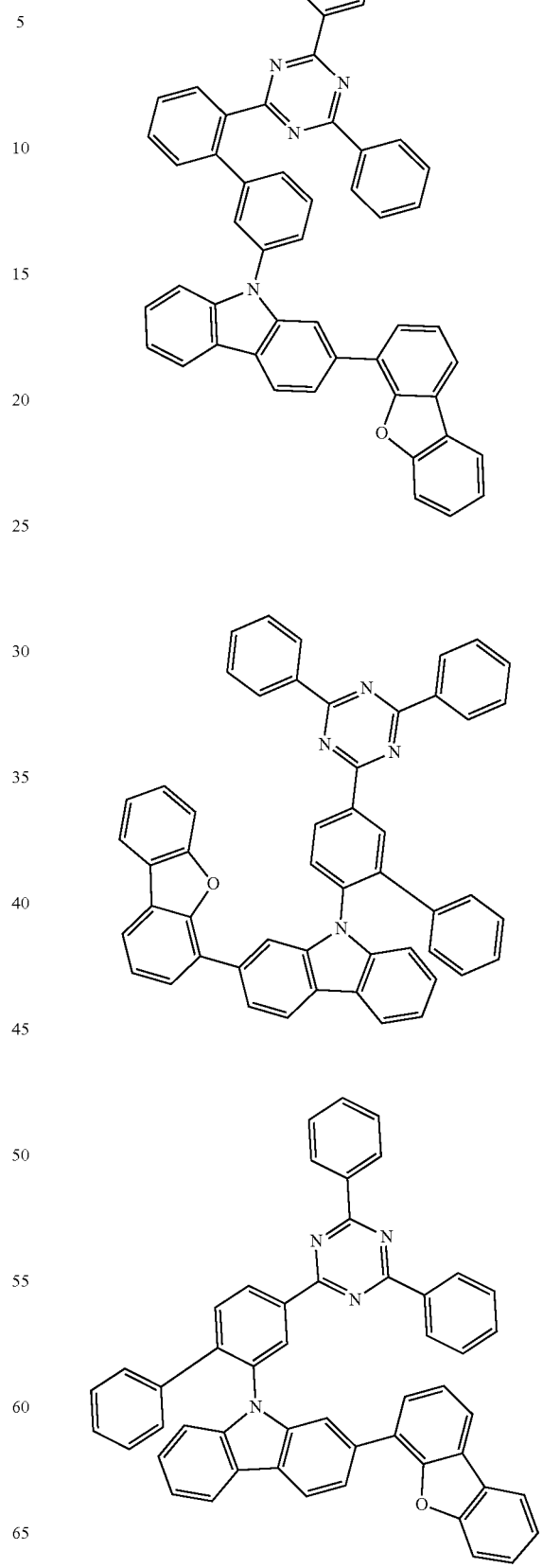

731
-continued
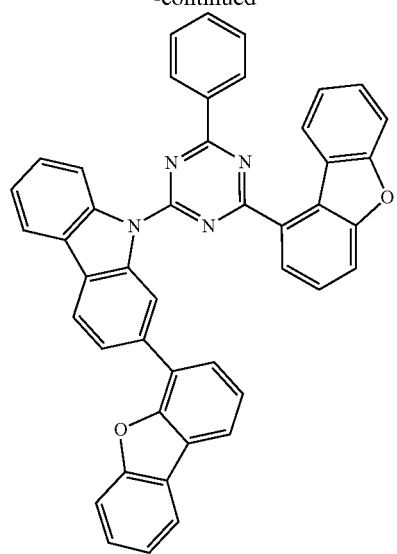
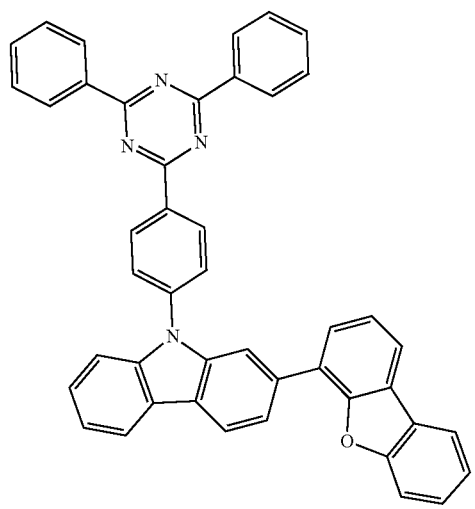
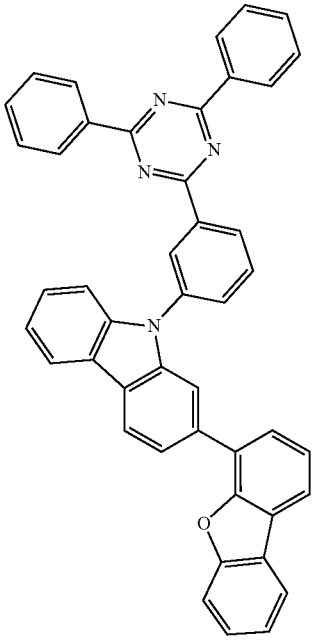
732
-continued
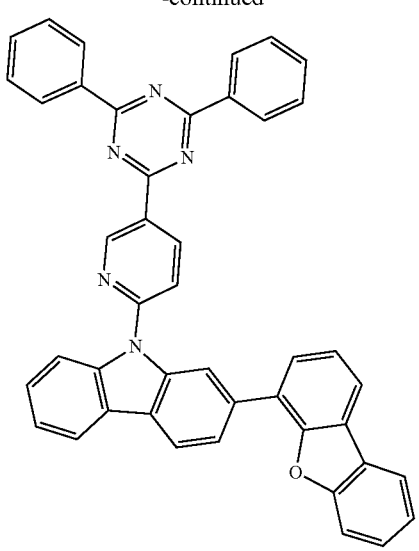
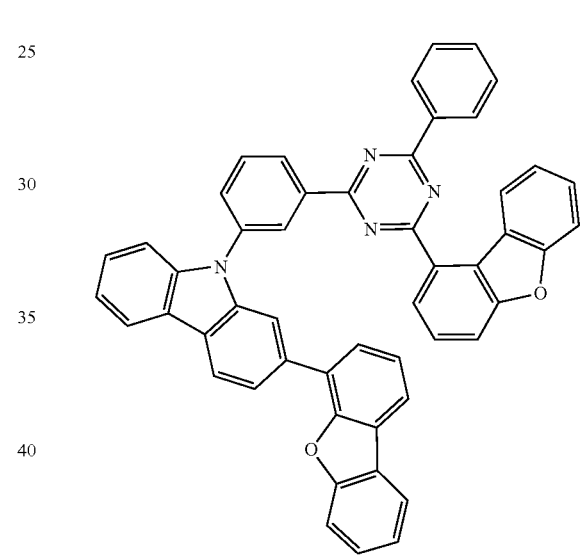
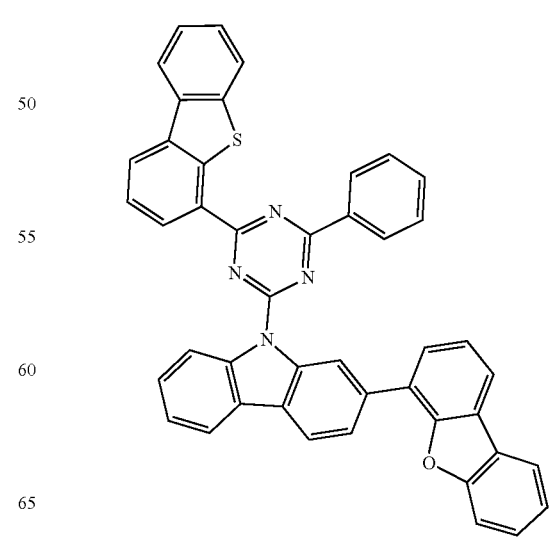

733
-continued
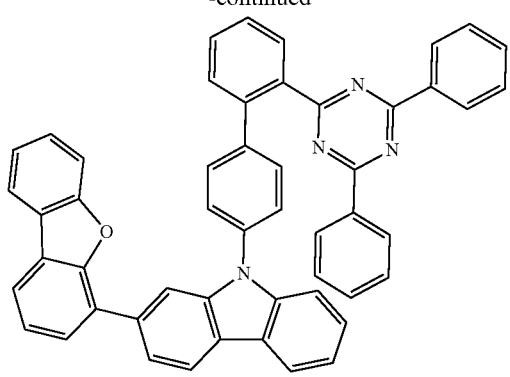
734
-continued
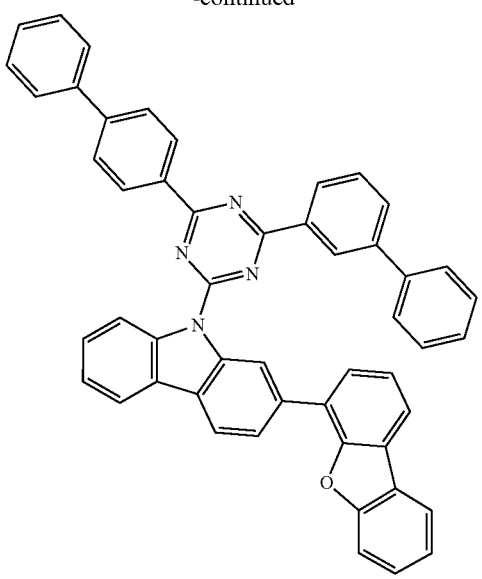
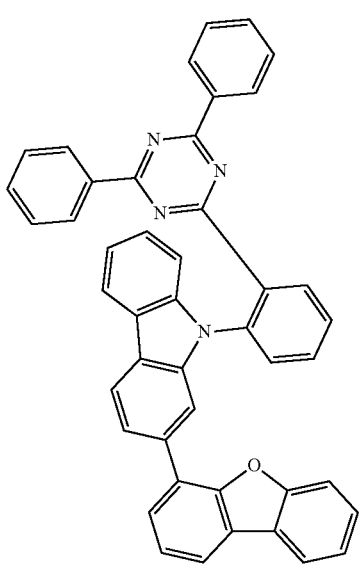
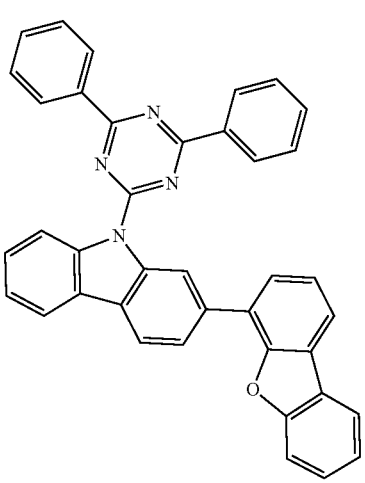

735
-continued
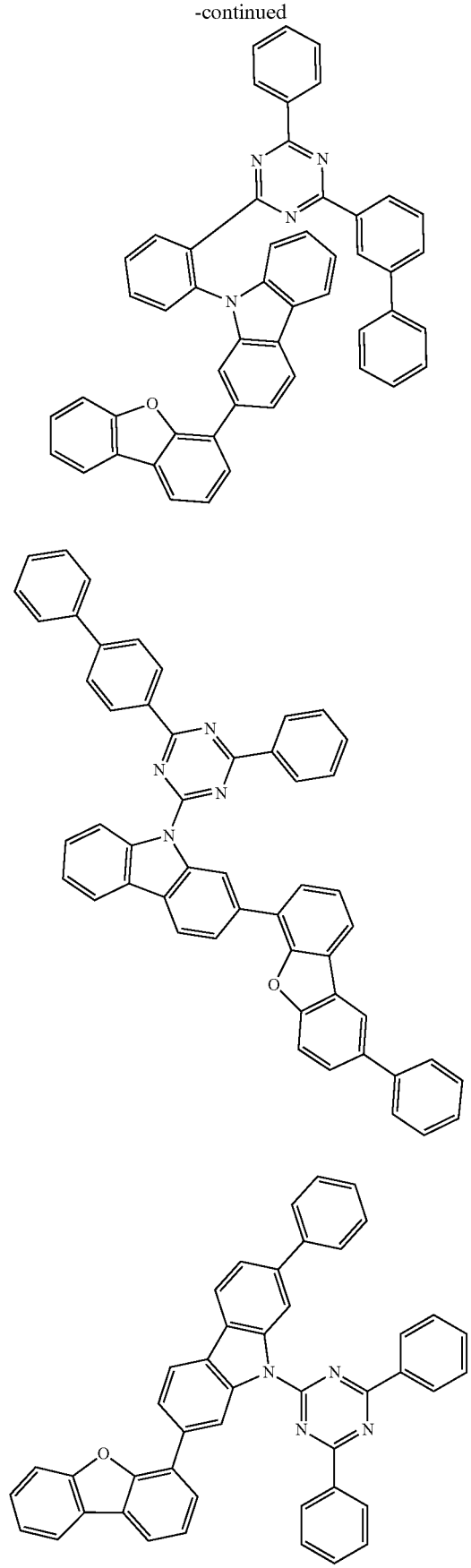
736
-continued
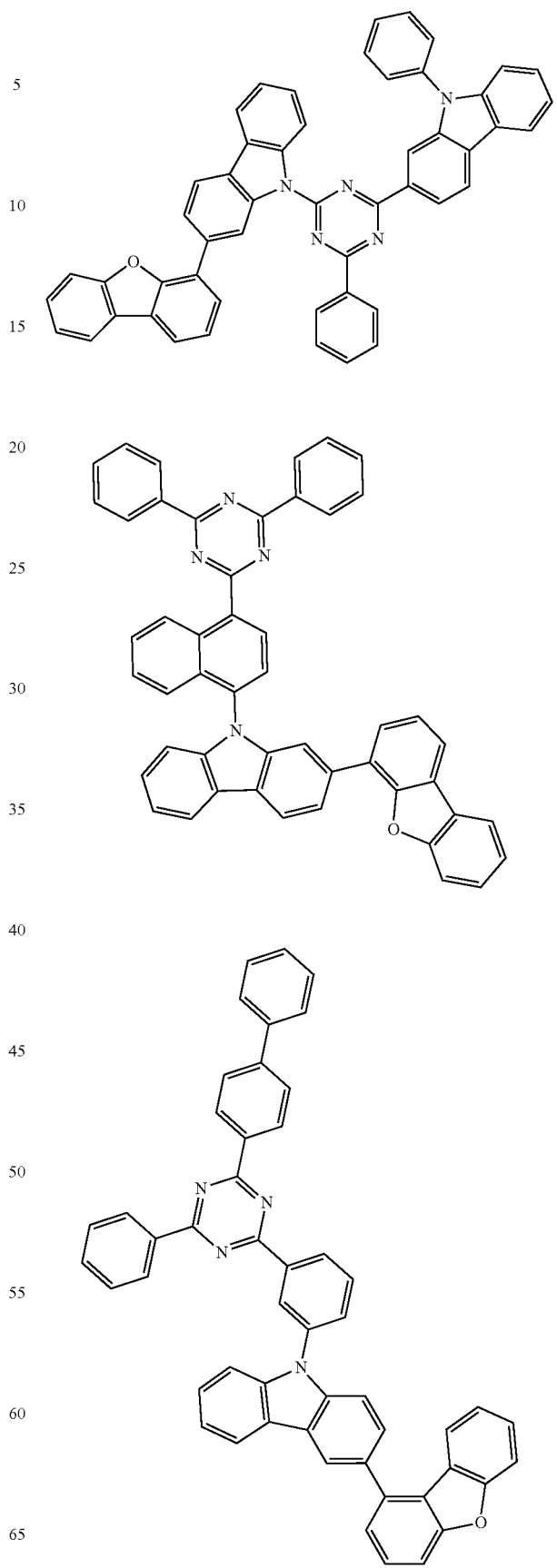

737
-continued
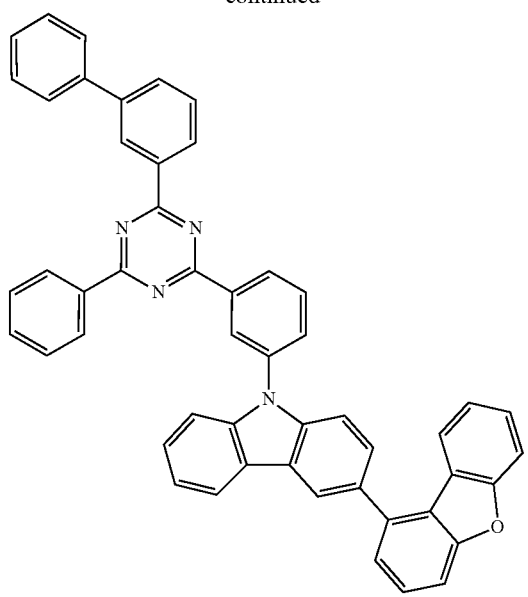
738
-continued
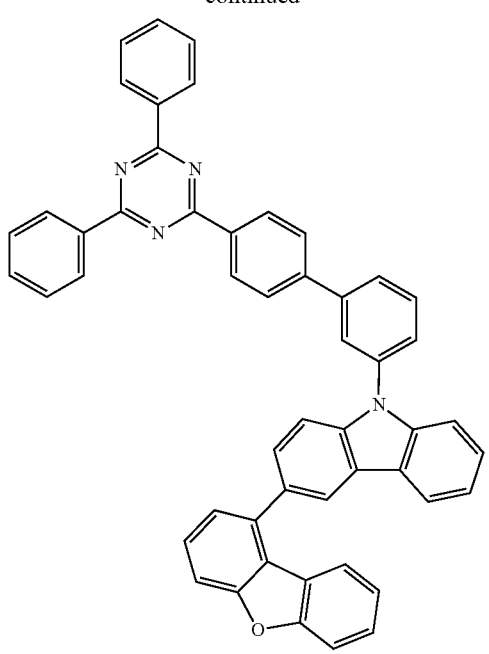
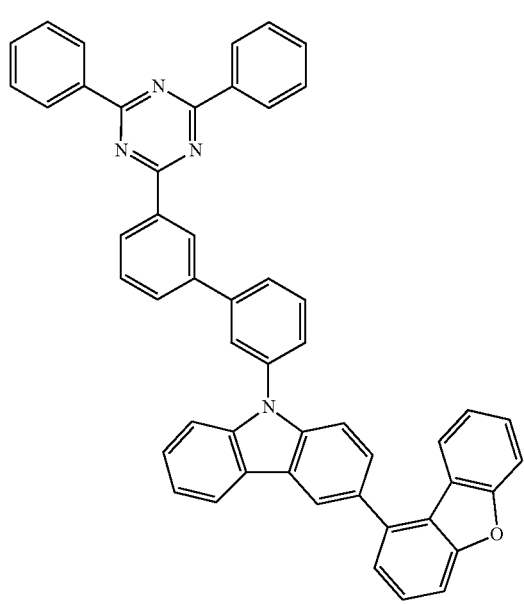
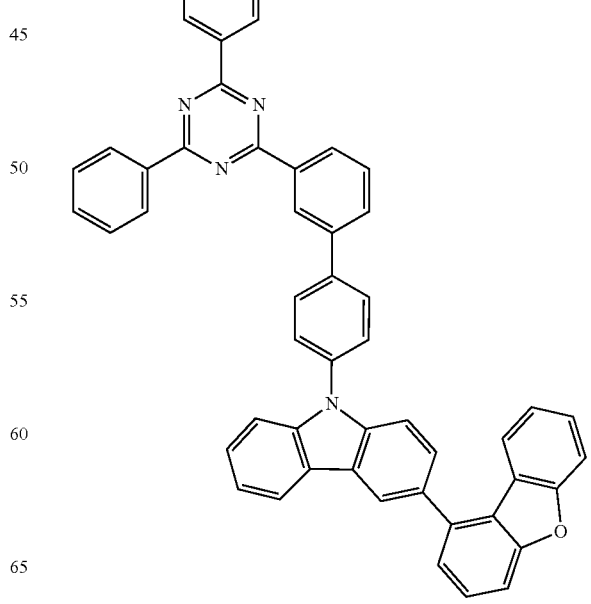

739
-continued
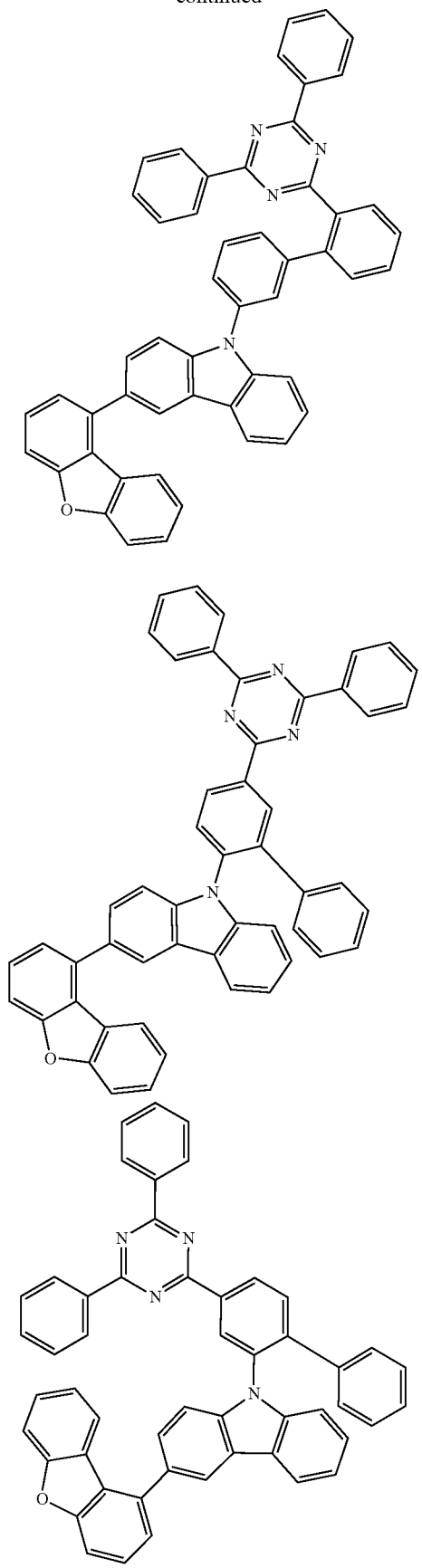
740
-continued
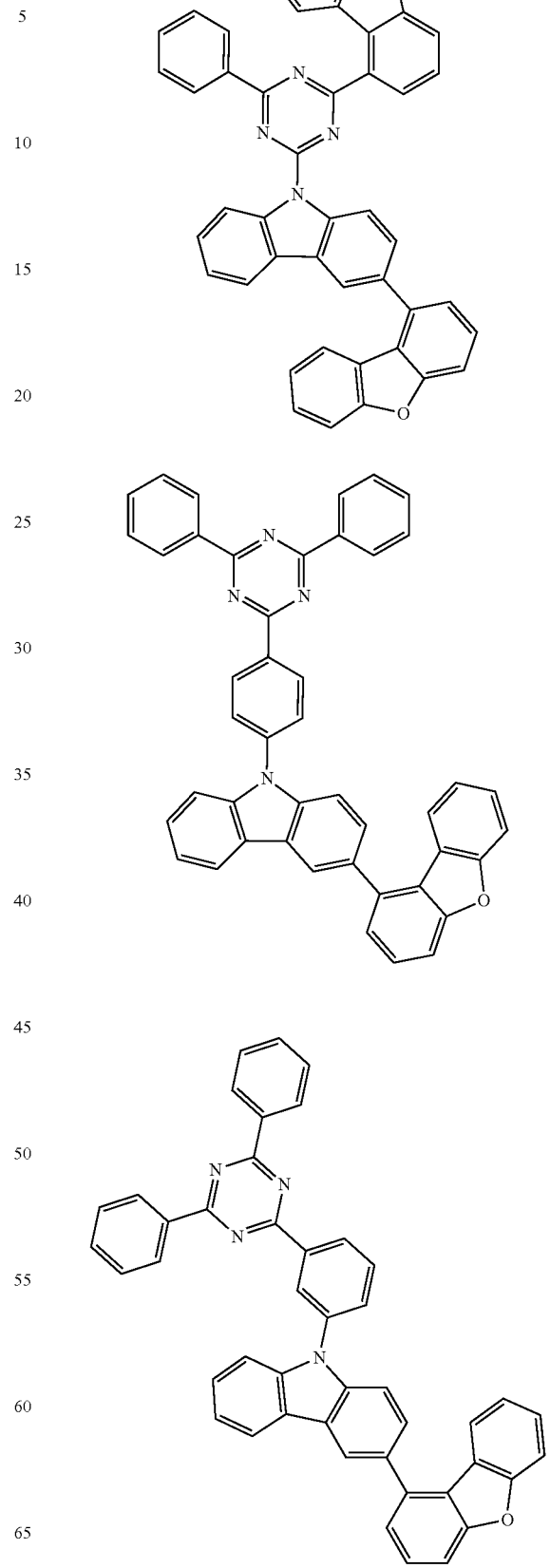

741
-continued
742
-continued
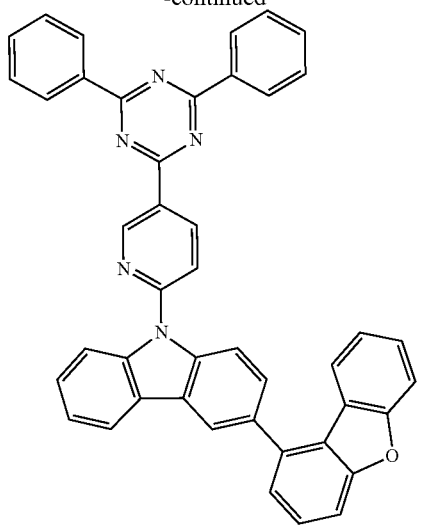
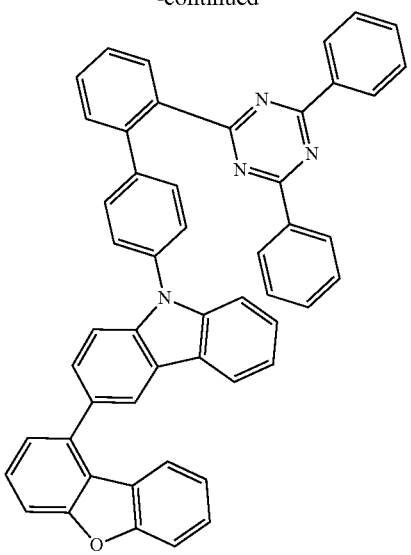

743
-continued
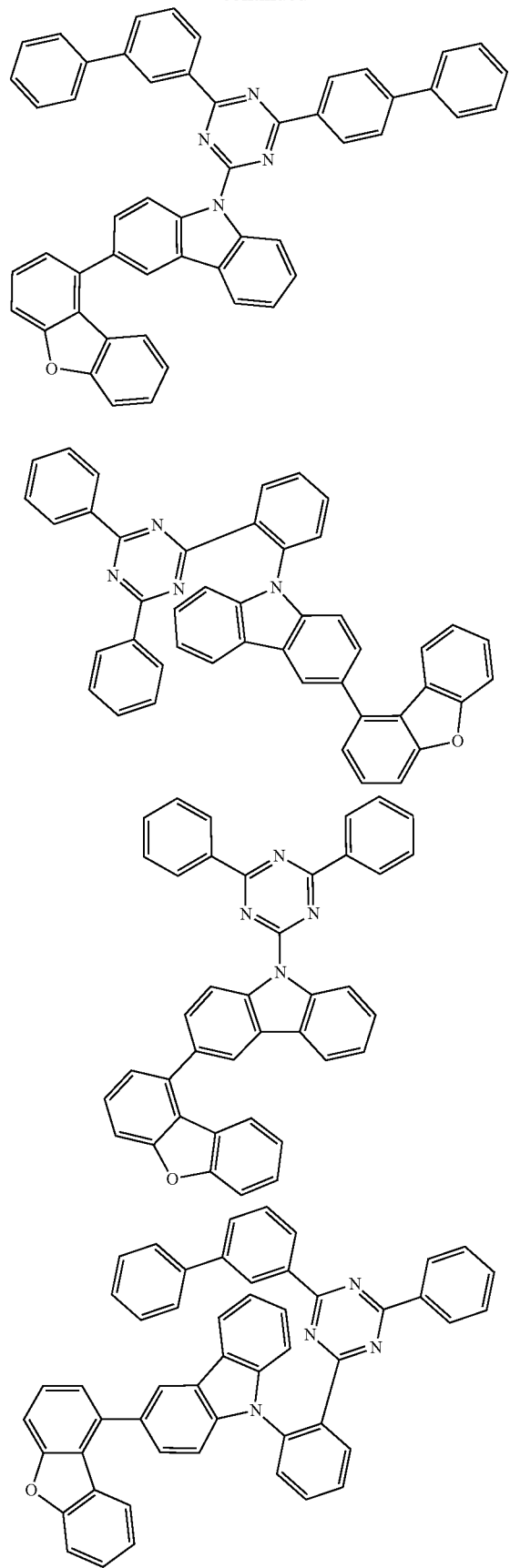
744
-continued
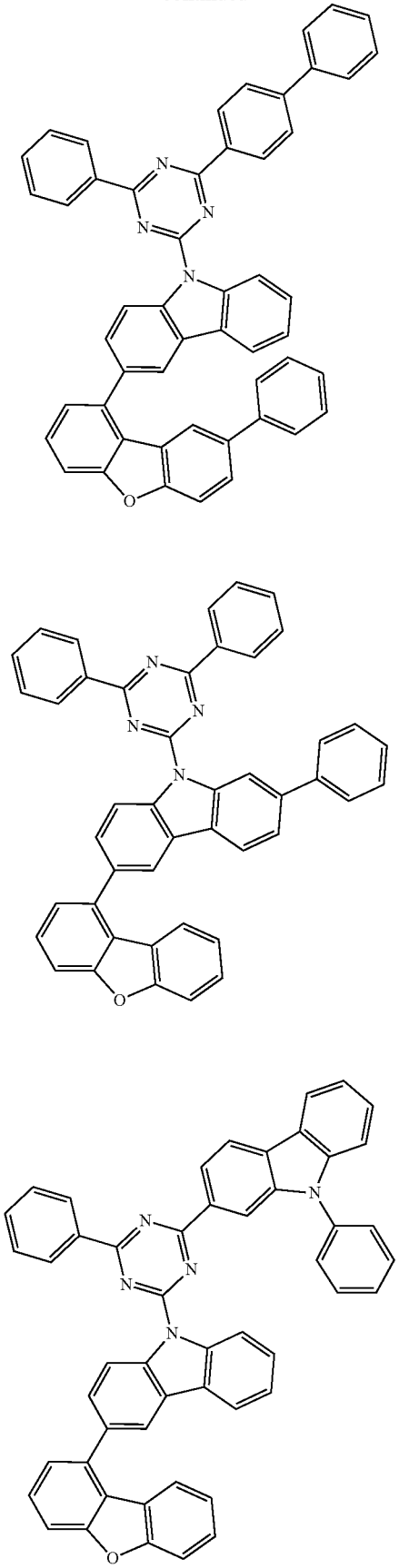 [SMILES: c1ccc(-c2ccc(-c3nc(-c4ccccc4)nc(-n4c5ccccc5c5cc(-c6cccc7oc8ccc(-c9ccccc9)cc8c67)ccc54)n3)cc2)cc1 ; c1ccc(-c2ccc3c4cc(-c5cccc6oc7ccccc7c56)ccc4n(-c4nc(-c5ccccc5)nc(-c5ccccc5)n4)c3c2)cc1 ; c1ccc(-c2nc(-c3ccc4c5ccccc5n(-c5ccccc5)c4c3)nc(-n3c4ccccc4c4cc(-c5cccc6oc7ccccc7c56)ccc43)n2)cc1]

745
-continued
746
-continued
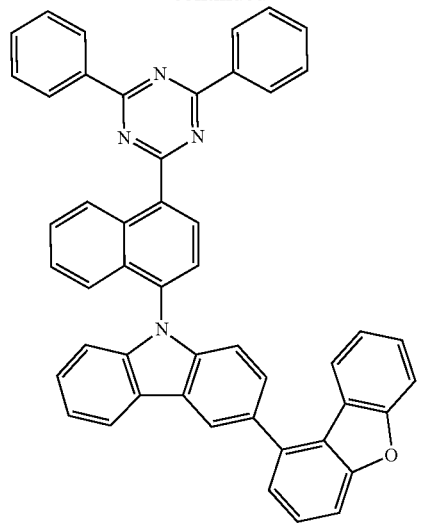
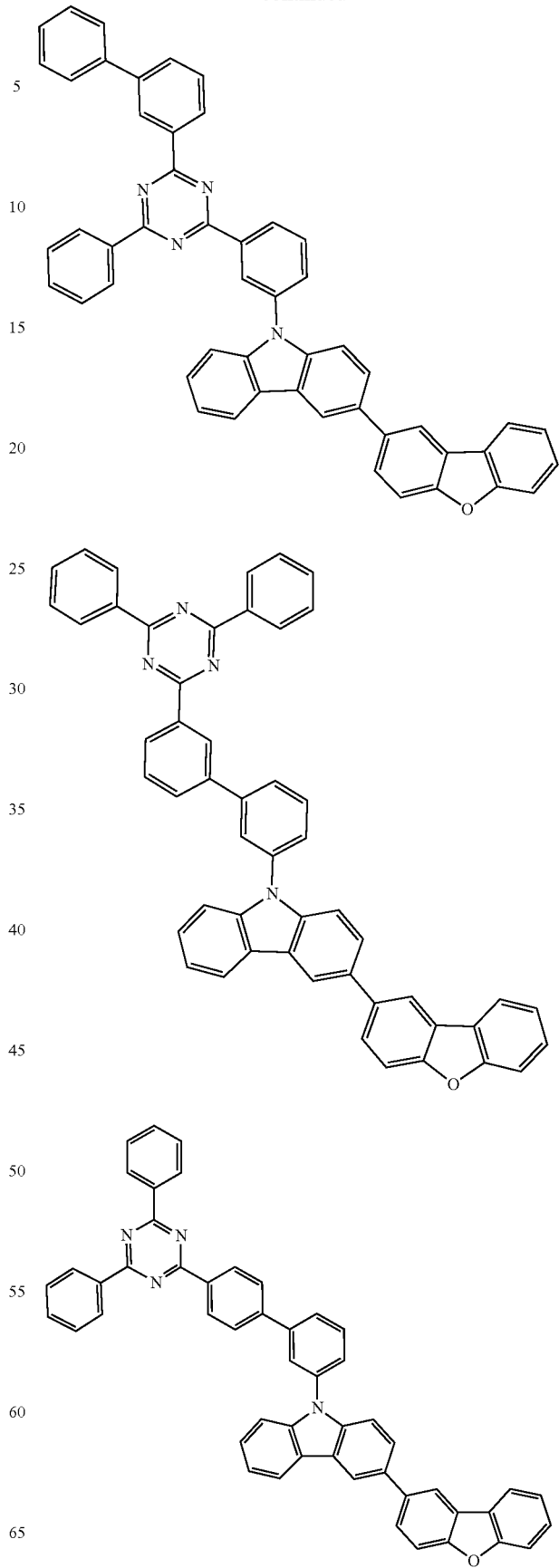

747
-continued
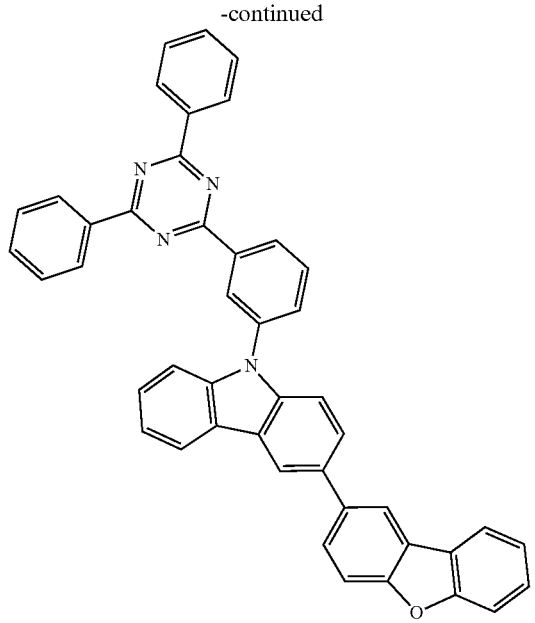
748
-continued
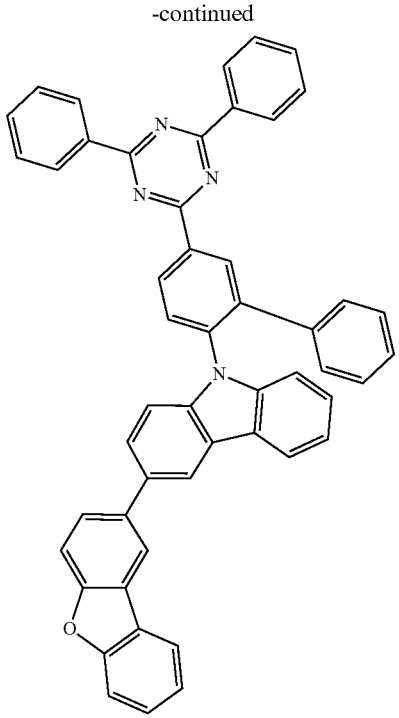
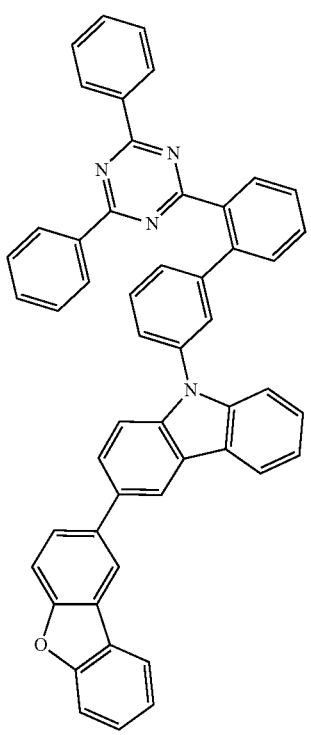
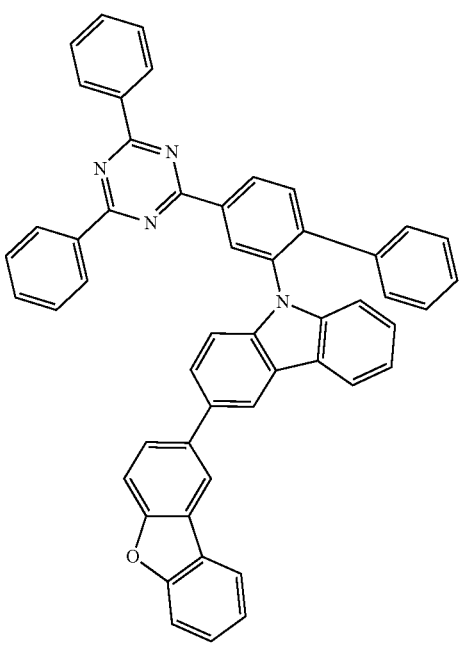

749
-continued
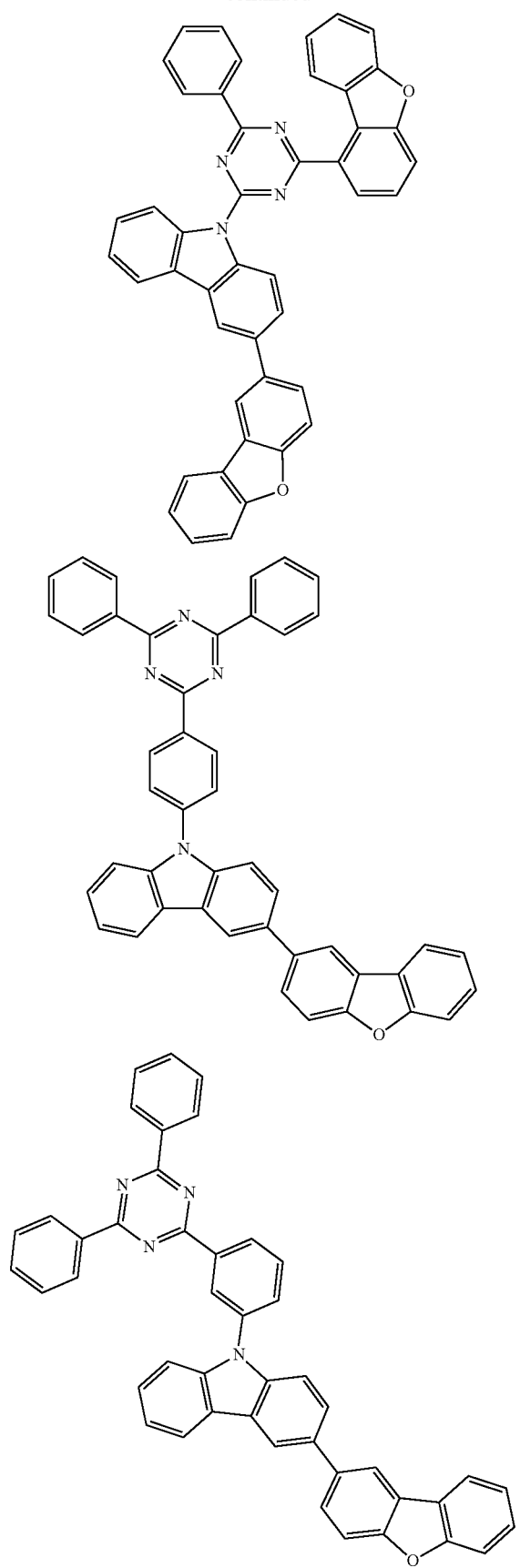
750
-continued
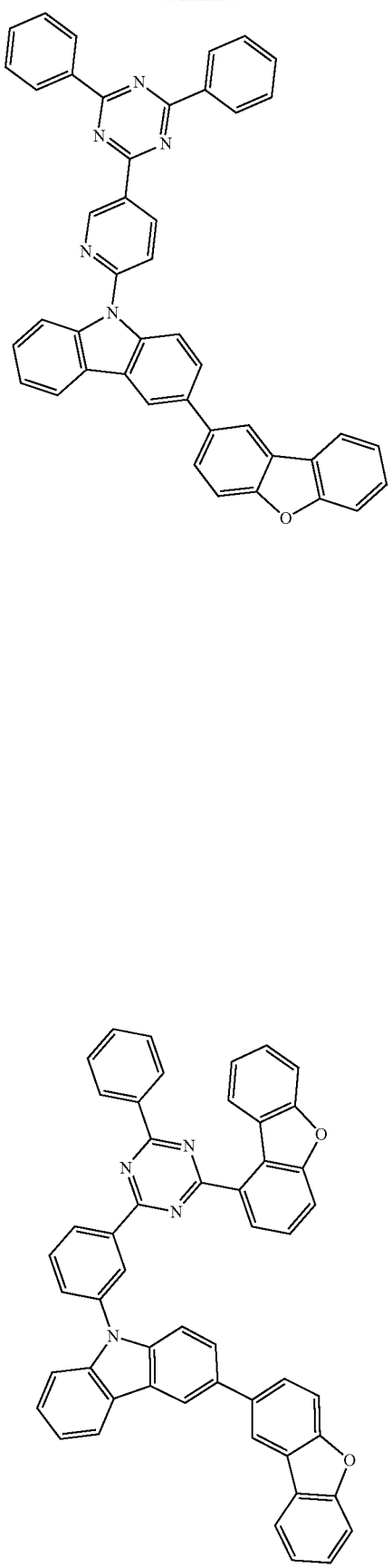

751
-continued
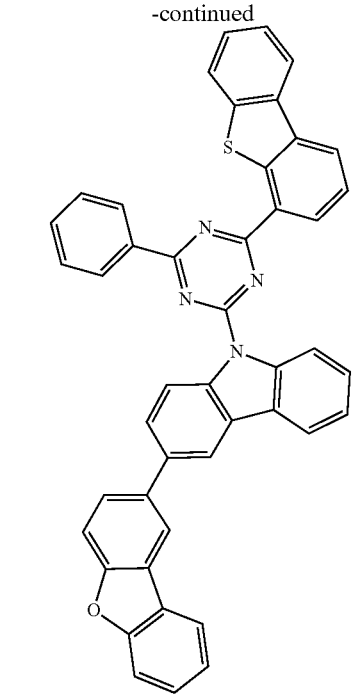
752
-continued
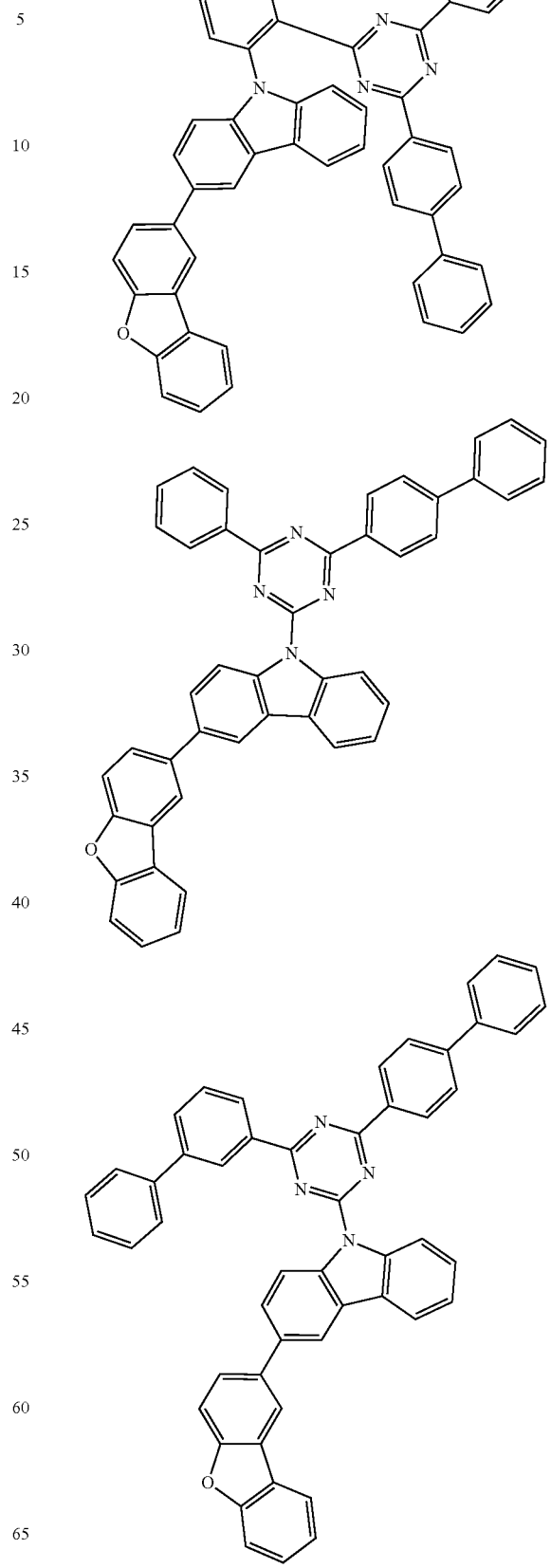
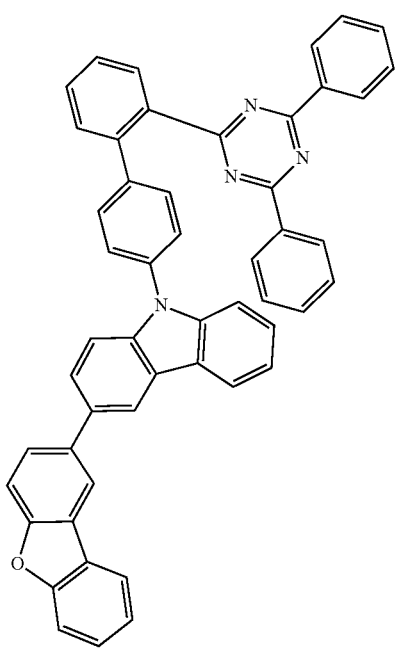

753
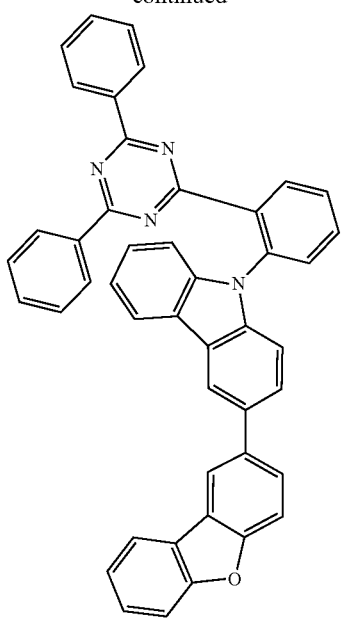
754
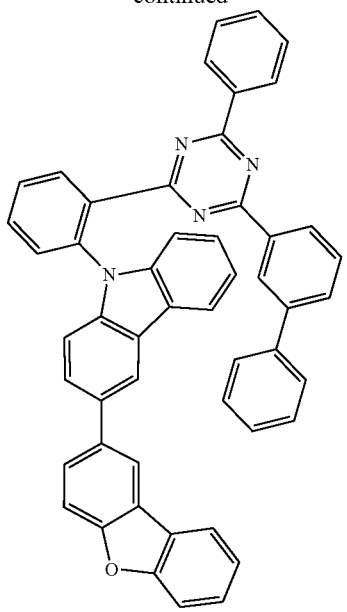
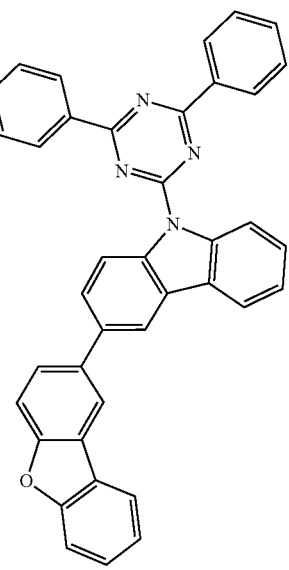
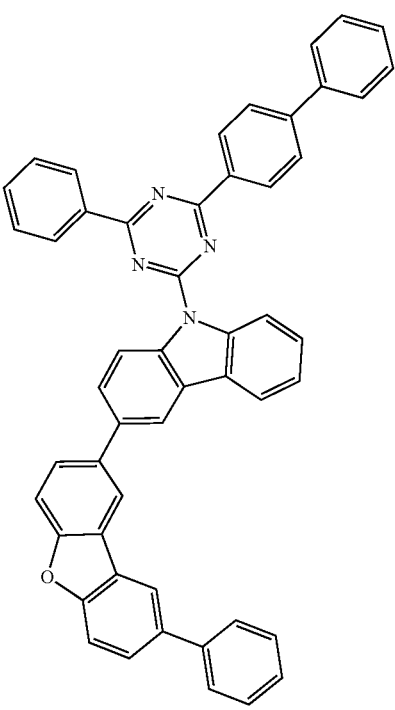

755
-continued
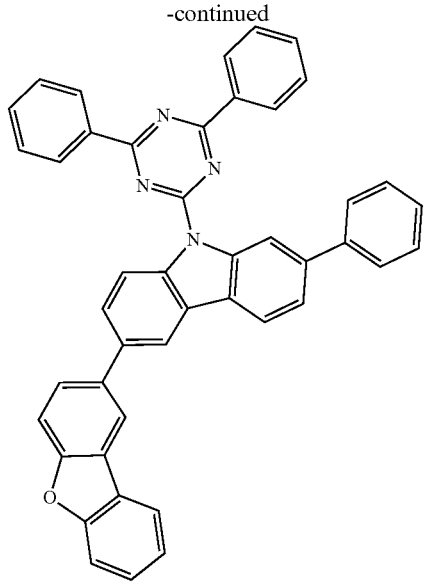
756
-continued
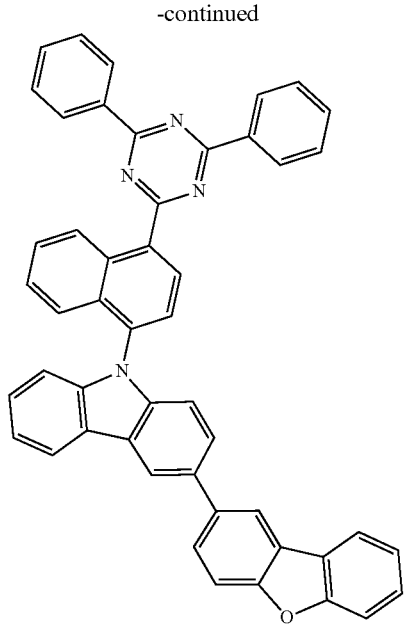
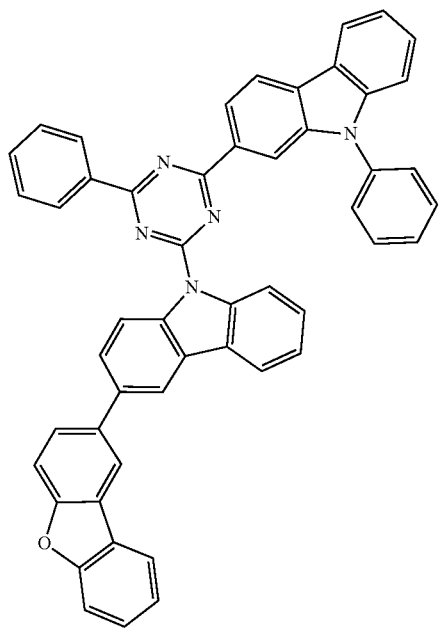
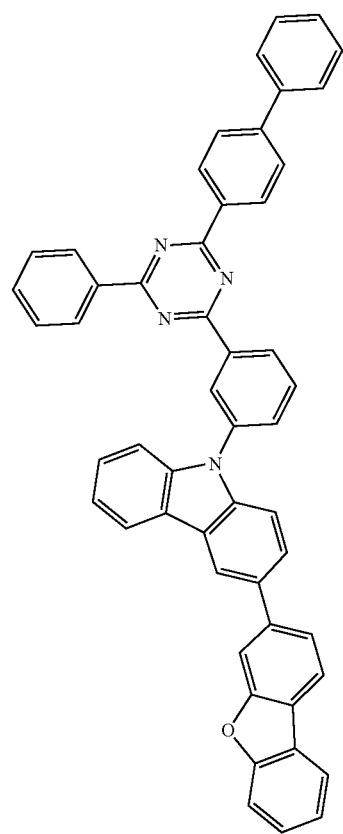

757
-continued
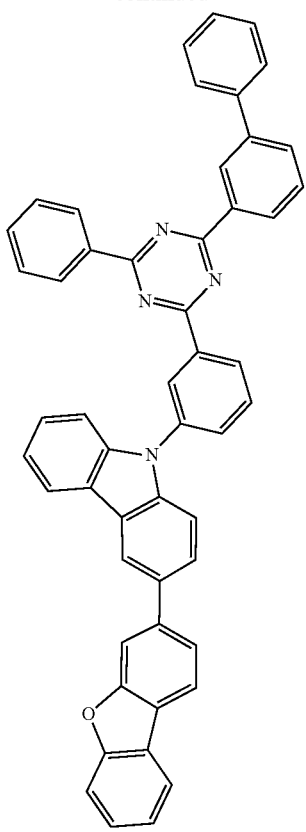
758
-continued
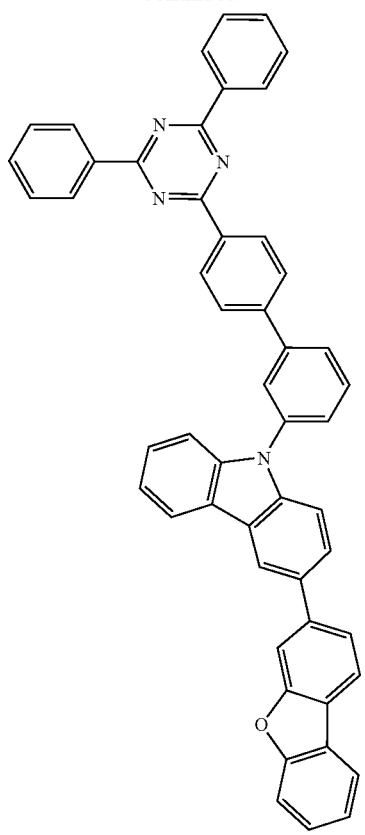
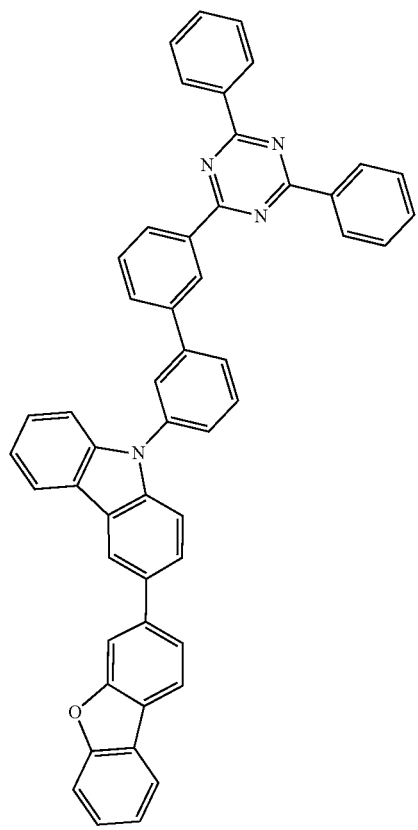

759
-continued
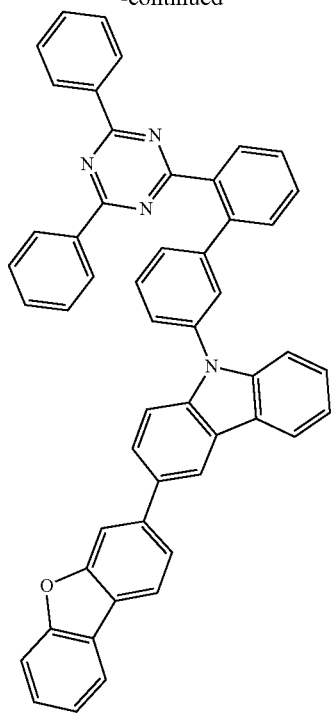
760
-continued
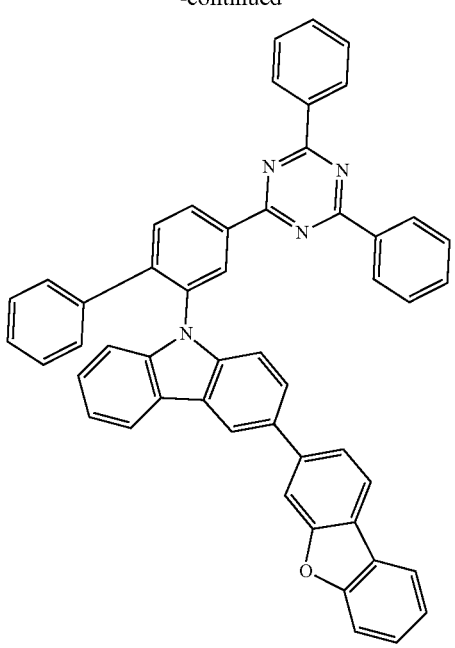
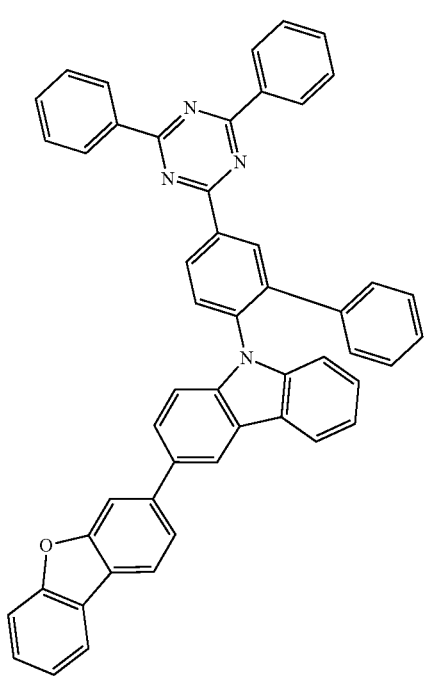
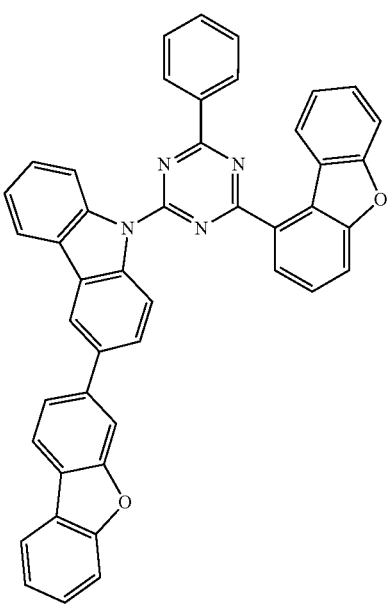

761
-continued
762
-continued
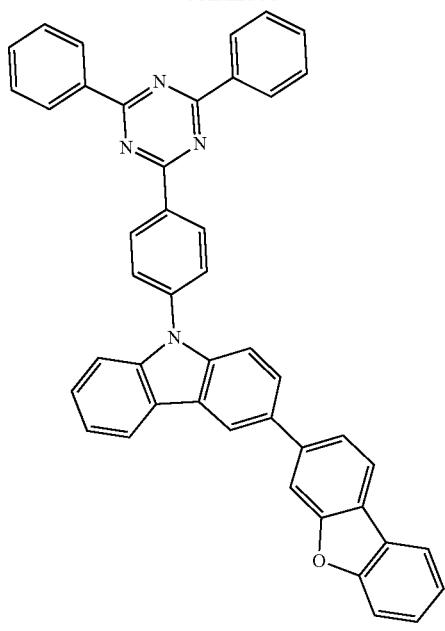
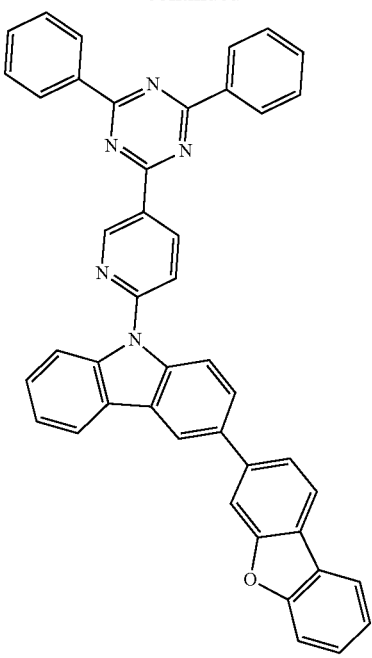

763
-continued
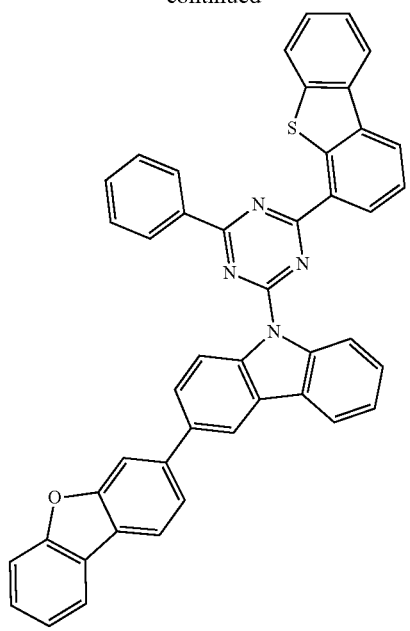
764
-continued
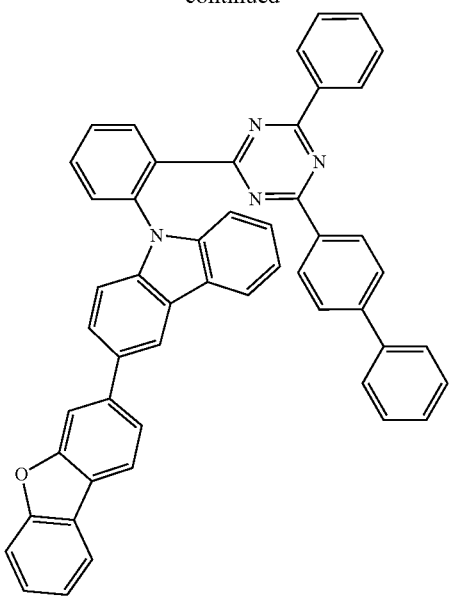
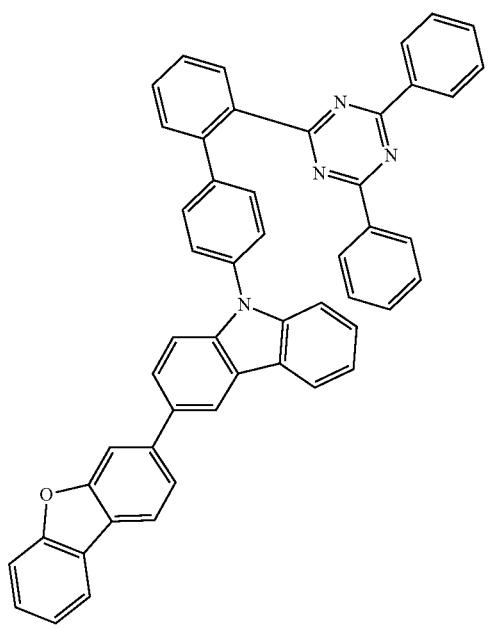
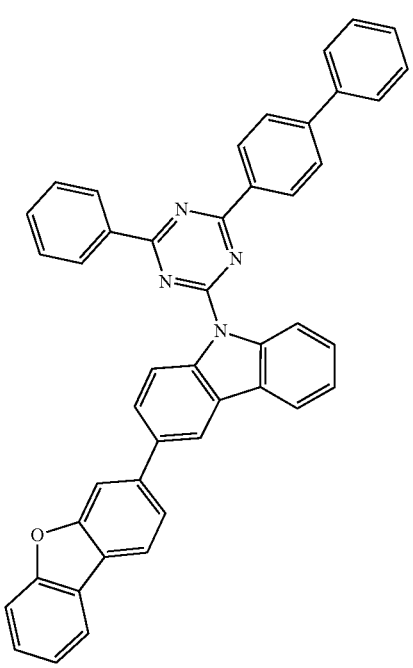

765
-continued
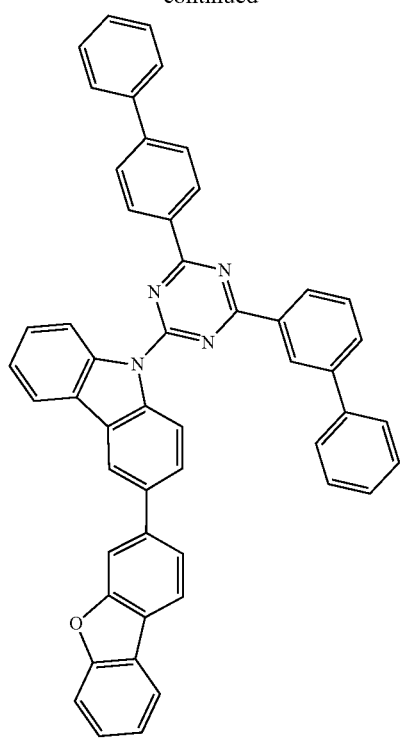
766
-continued
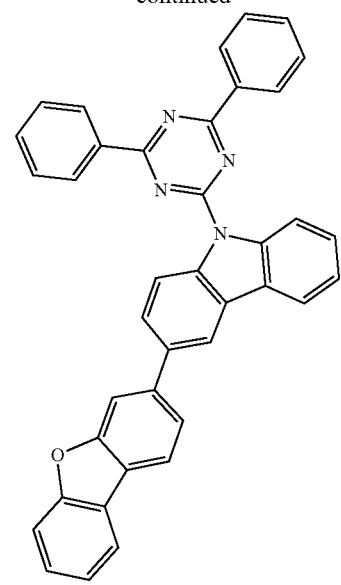
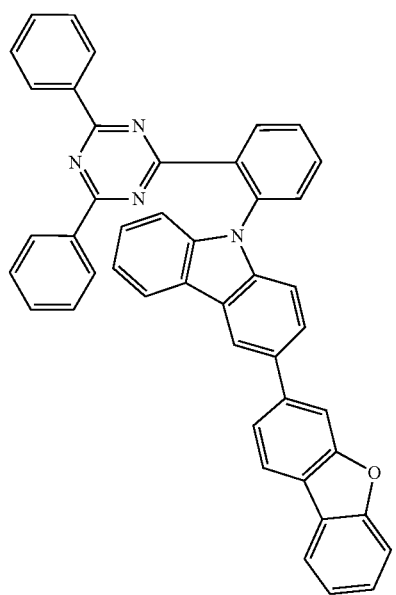
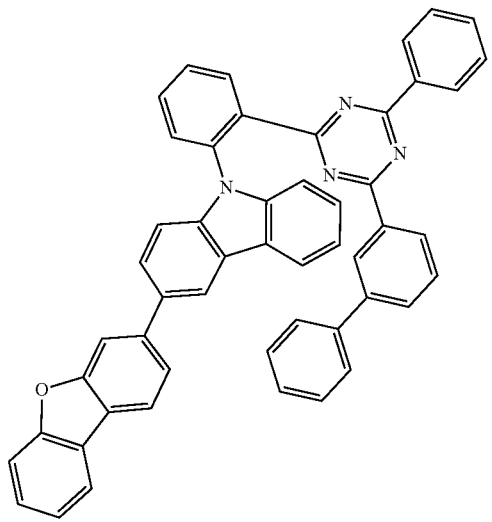

767
-continued
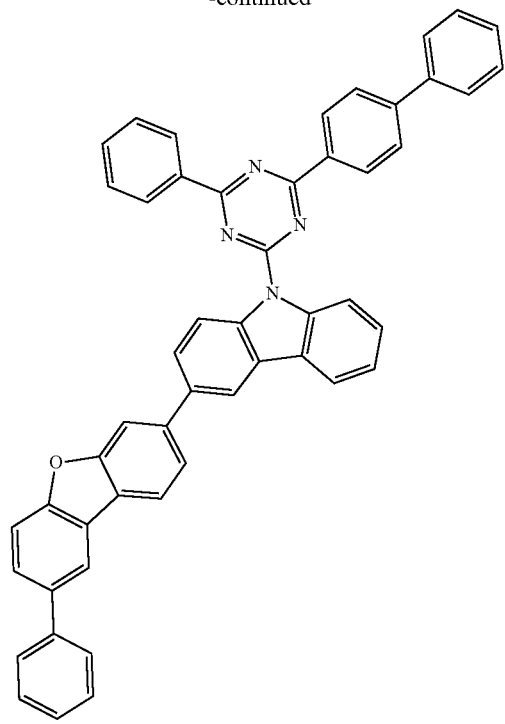
768
-continued
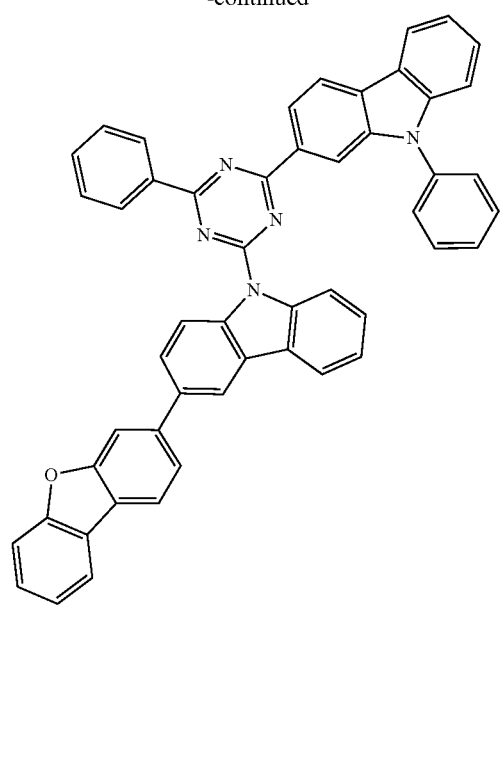
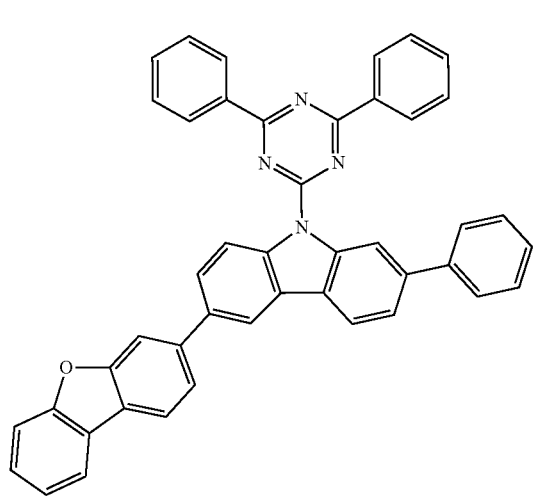
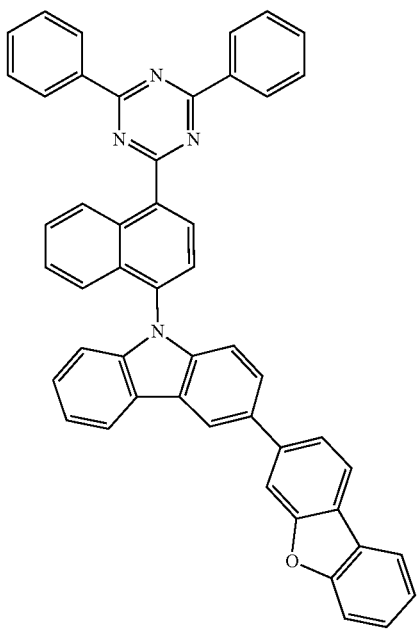

769
-continued
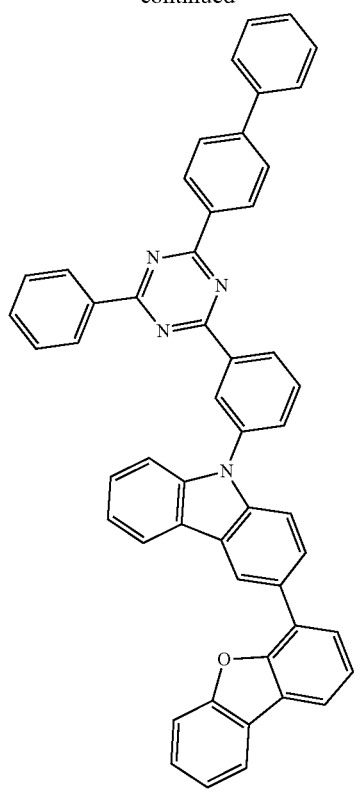
770
-continued
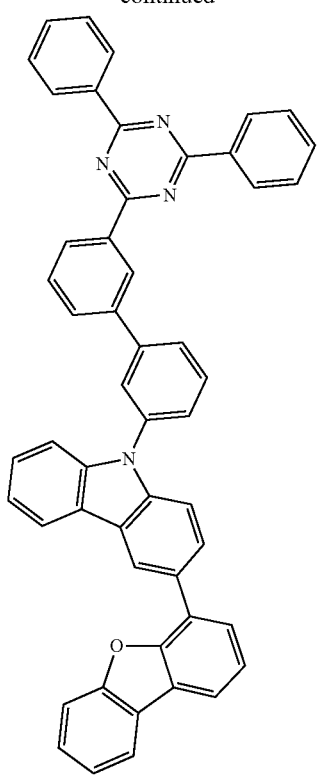
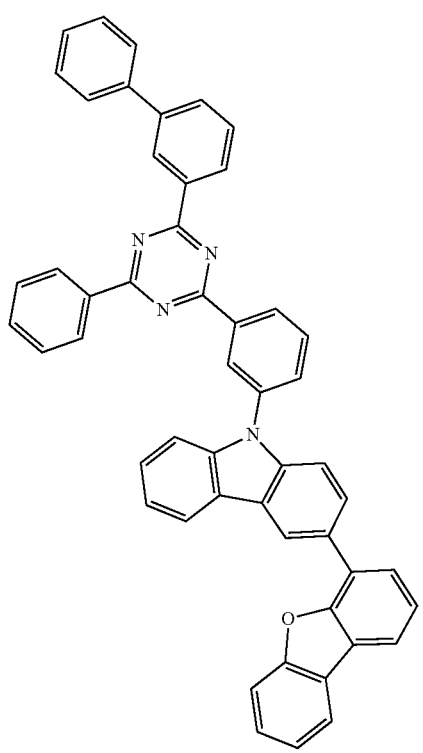
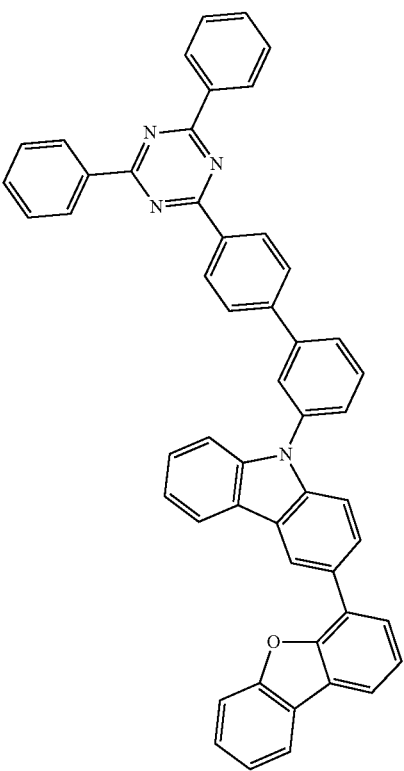

771
-continued
772
-continued
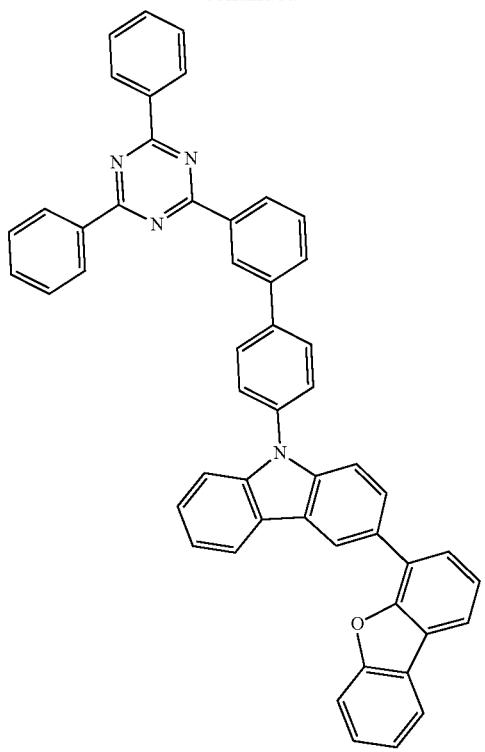
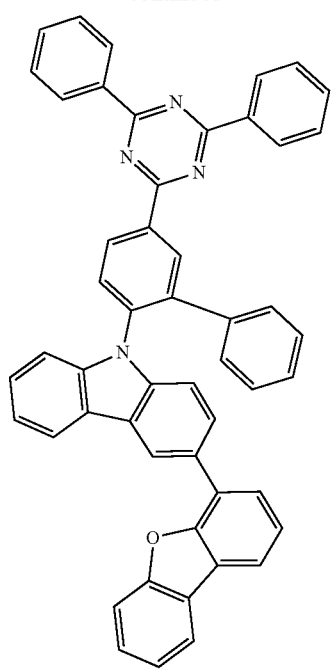

773
-continued
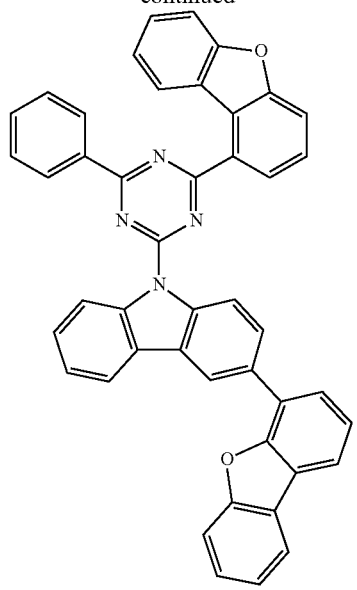
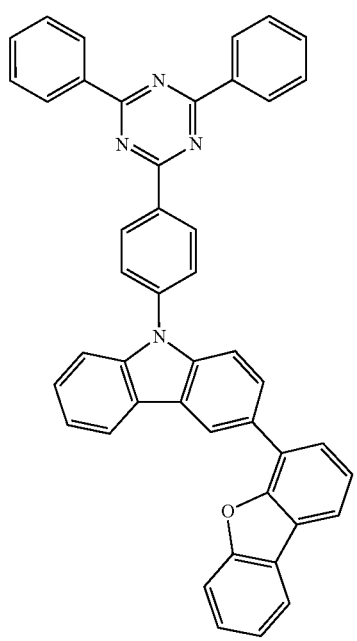
774
-continued
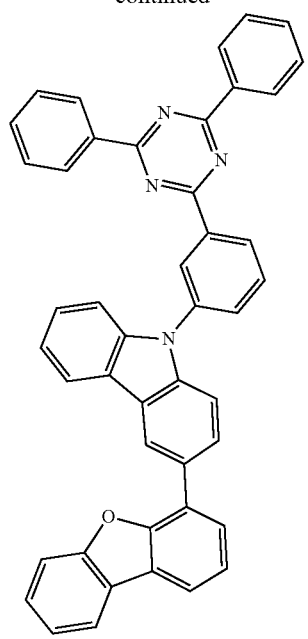
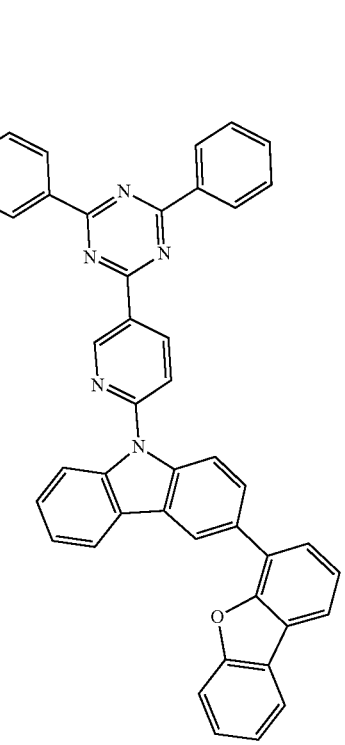

775
-continued
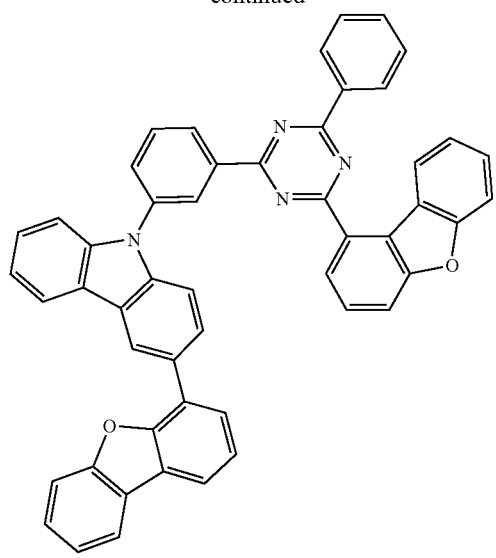
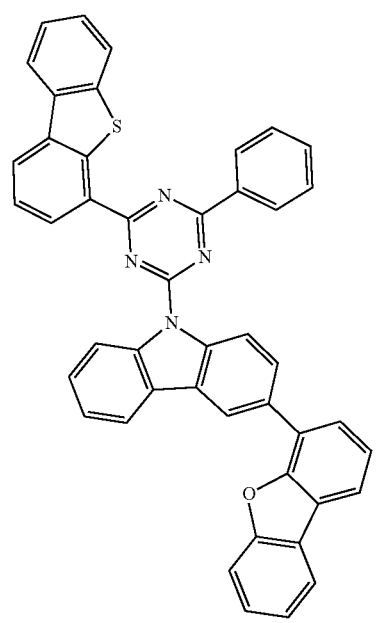
776
-continued
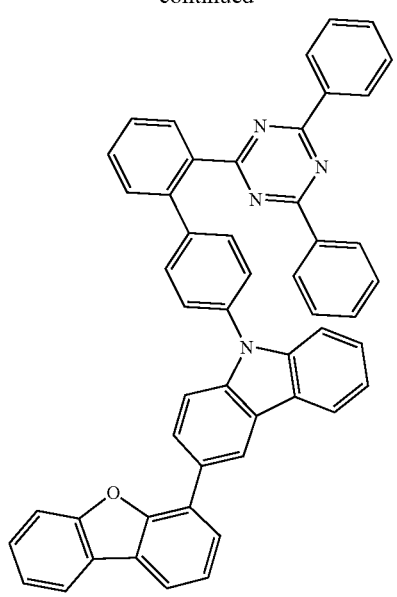
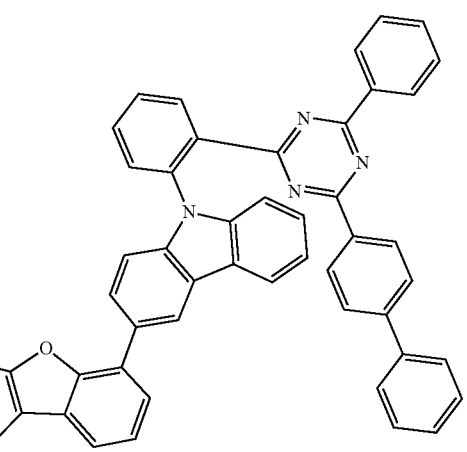

777
-continued
778
-continued
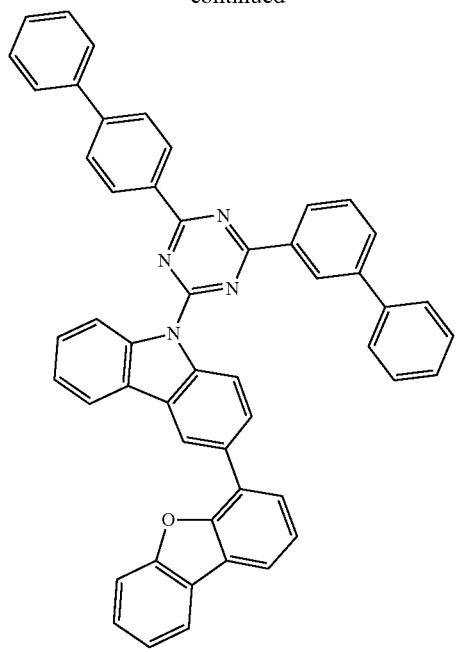
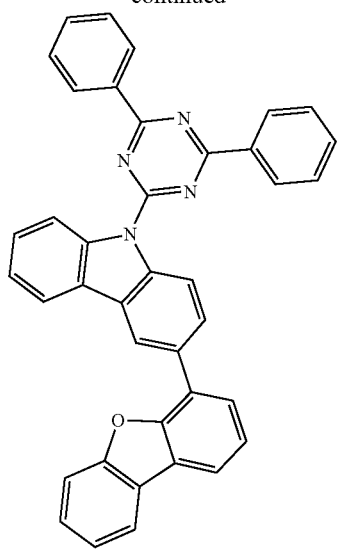

779
-continued
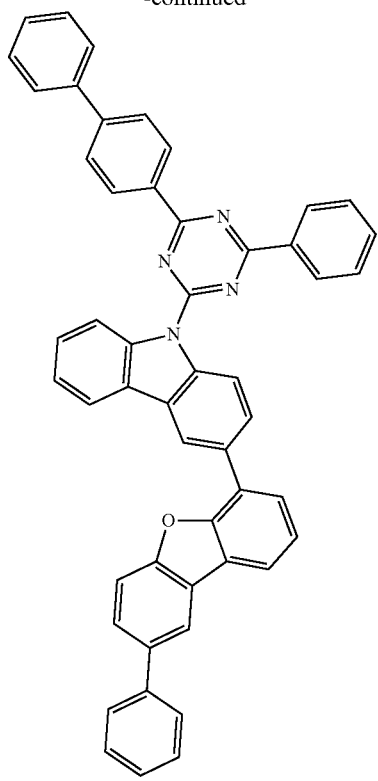
780
-continued
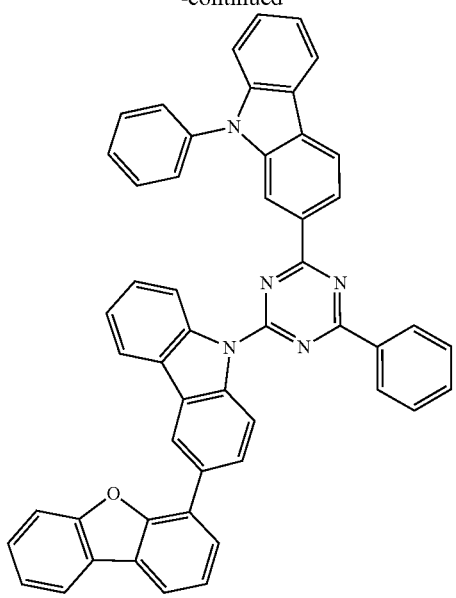
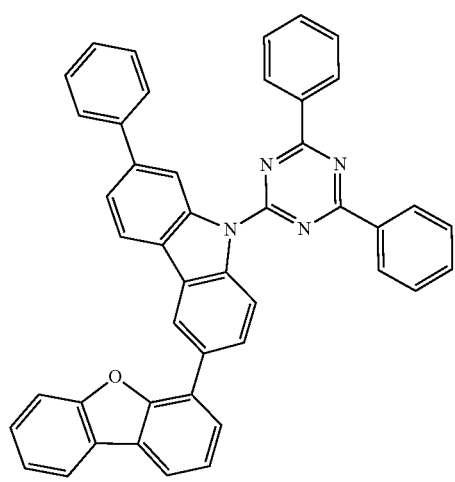

781
-continued
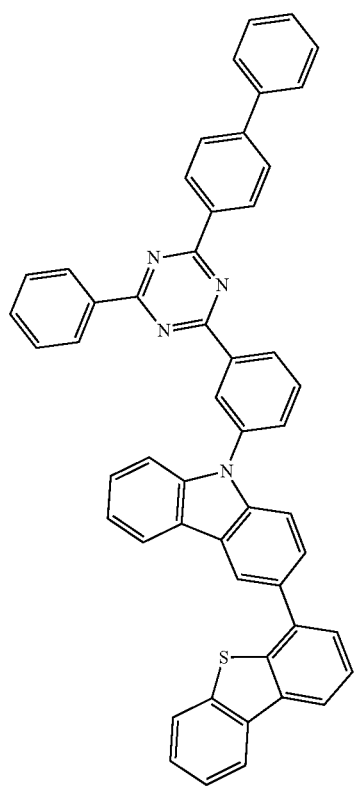
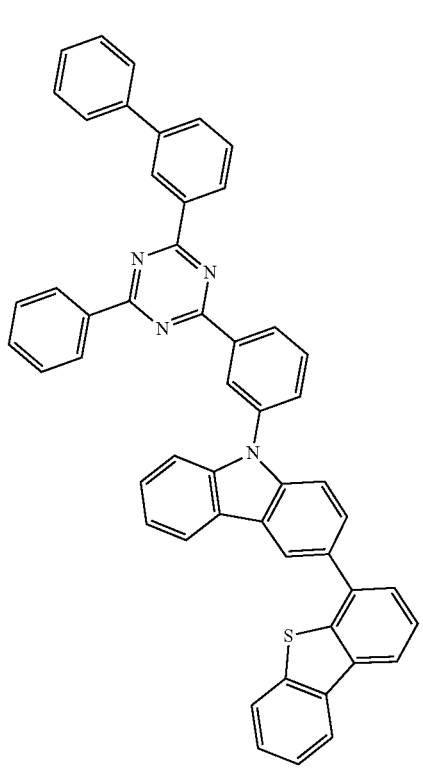
782
-continued
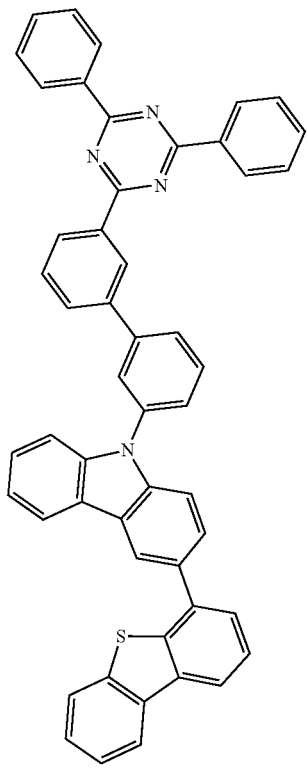
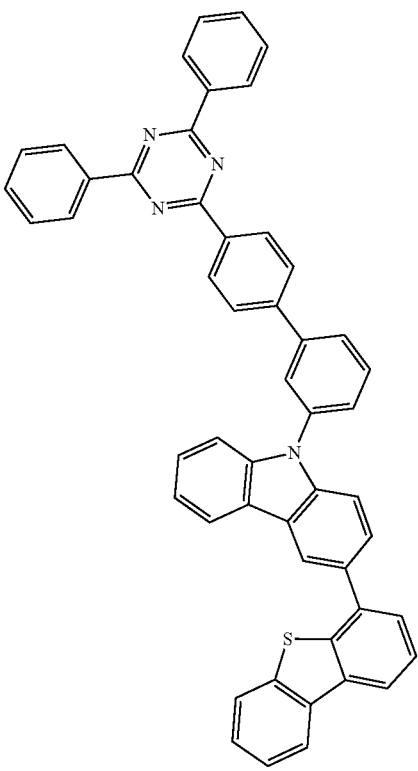

783
-continued
784
-continued
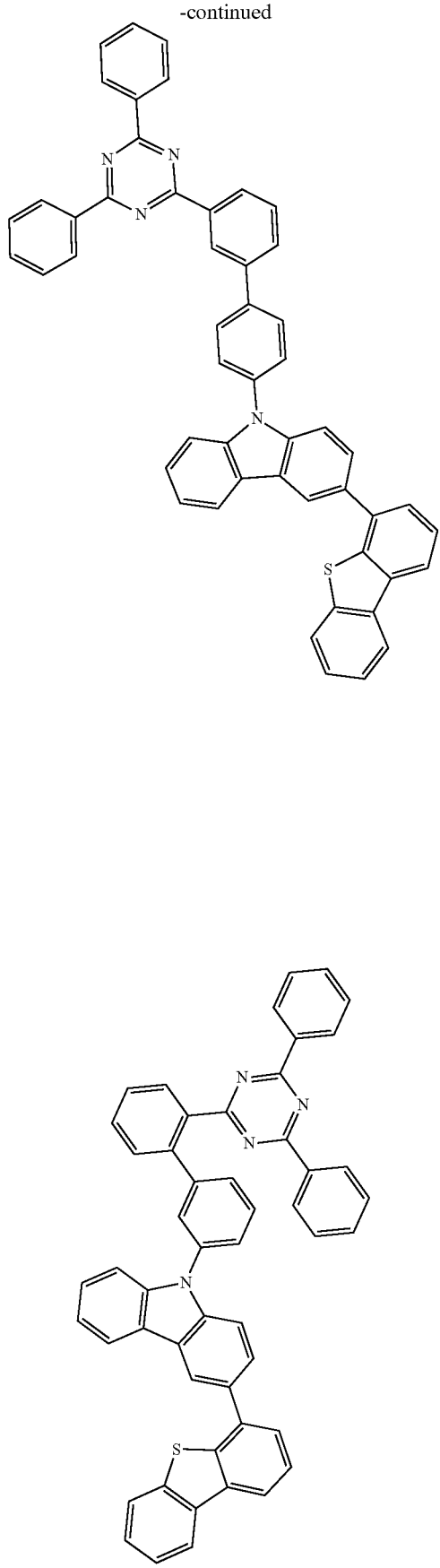
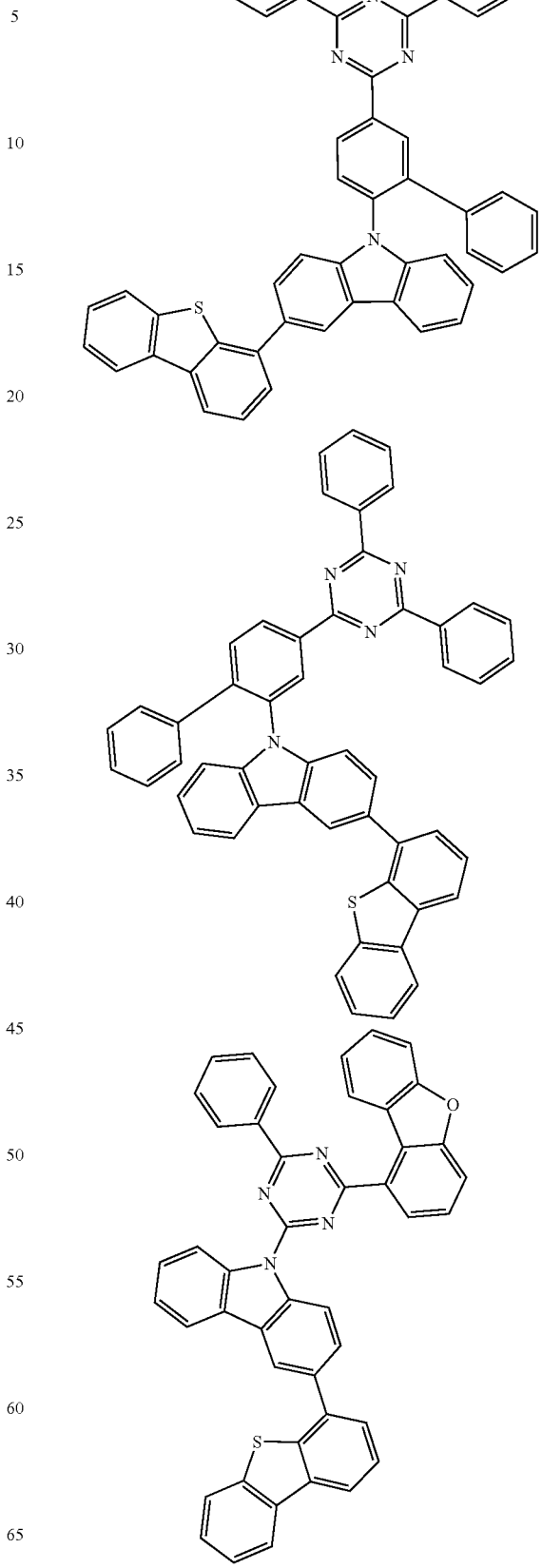

785
-continued
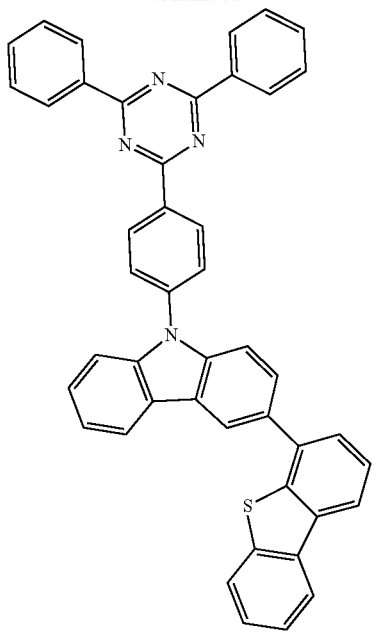
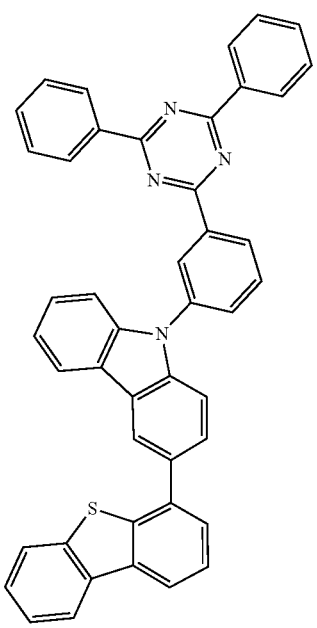
786
-continued
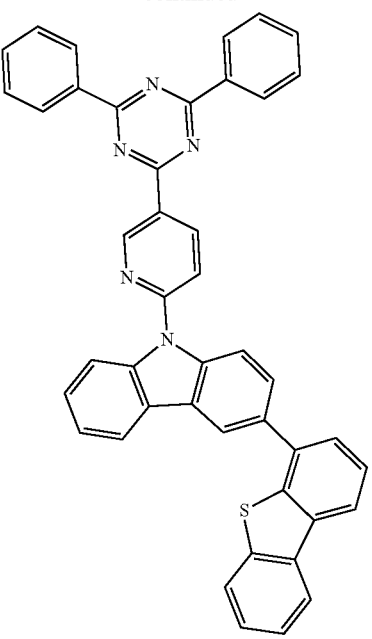
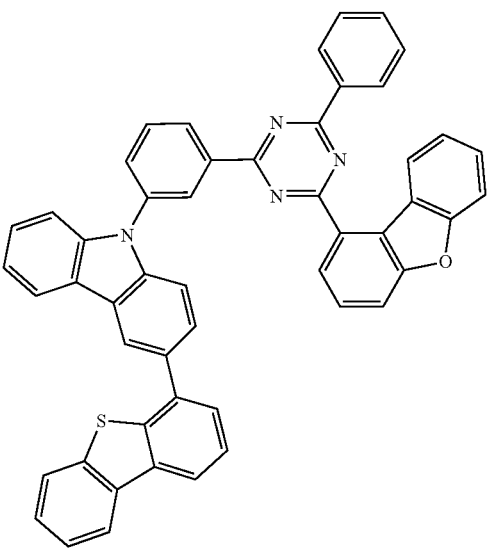

787
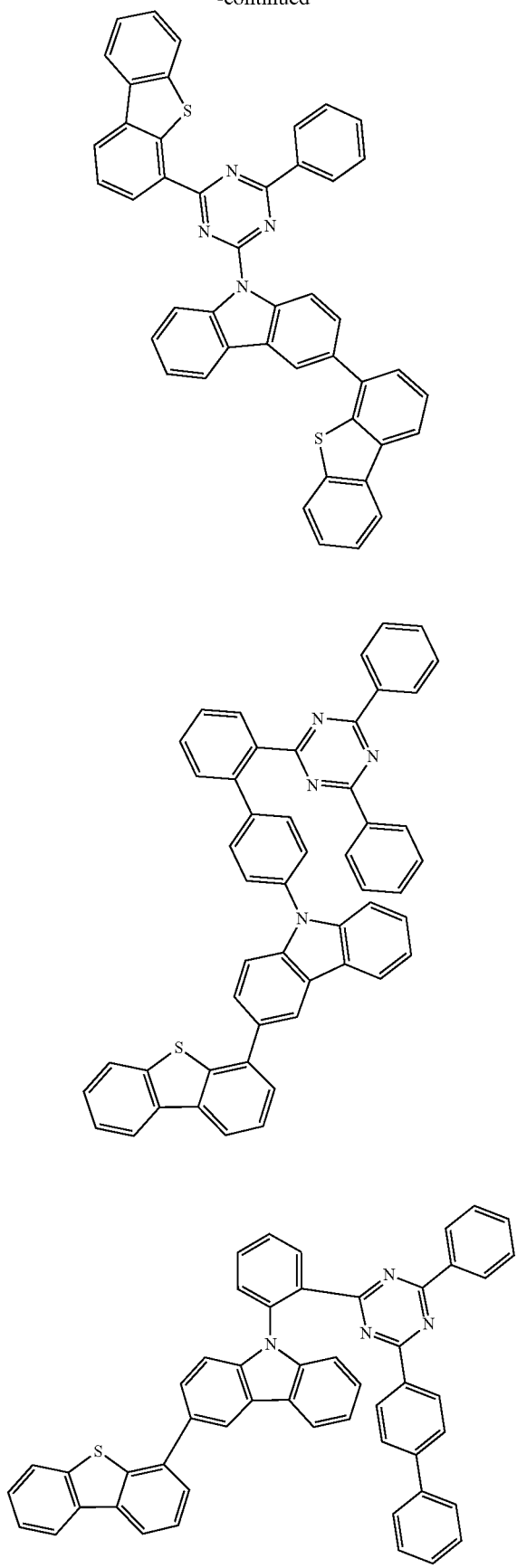
788
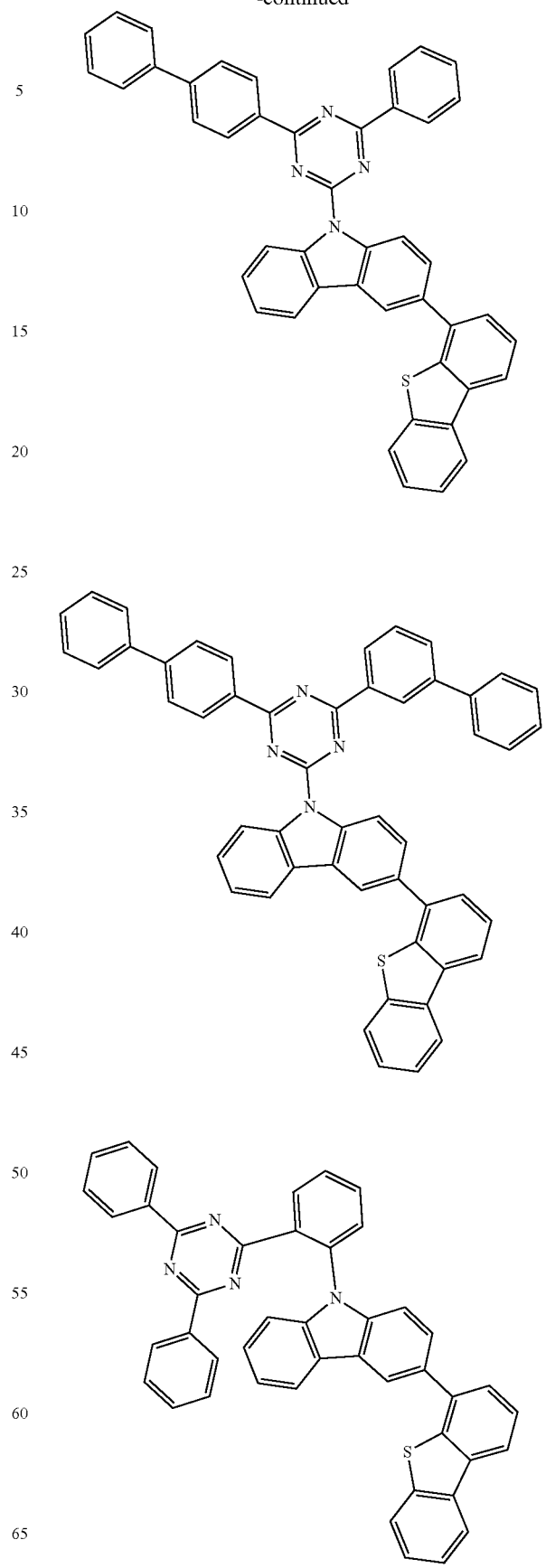

789
-continued
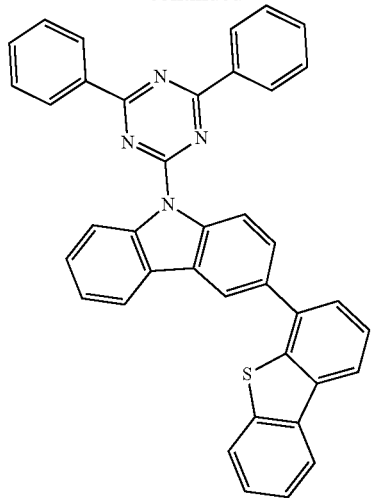
790
-continued
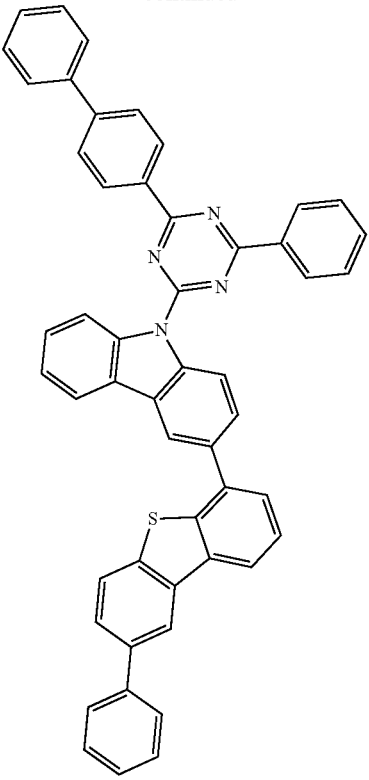
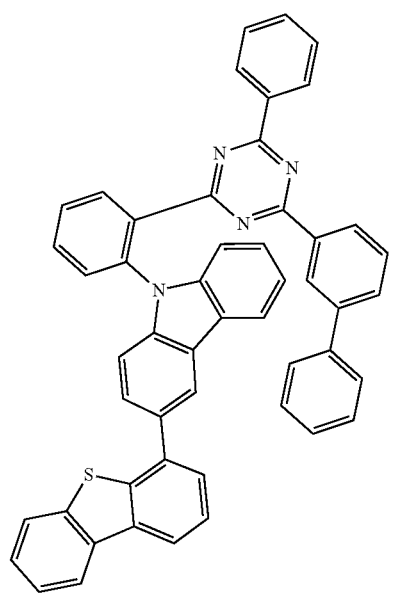
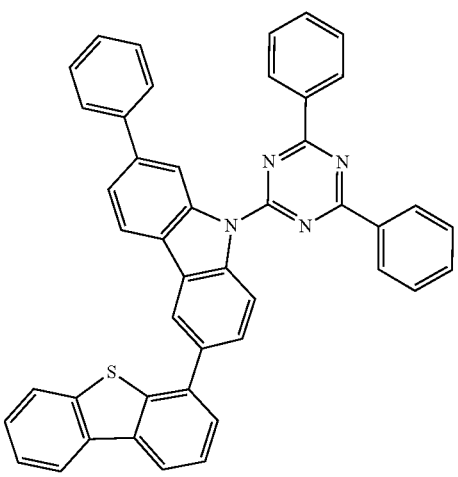

791
-continued
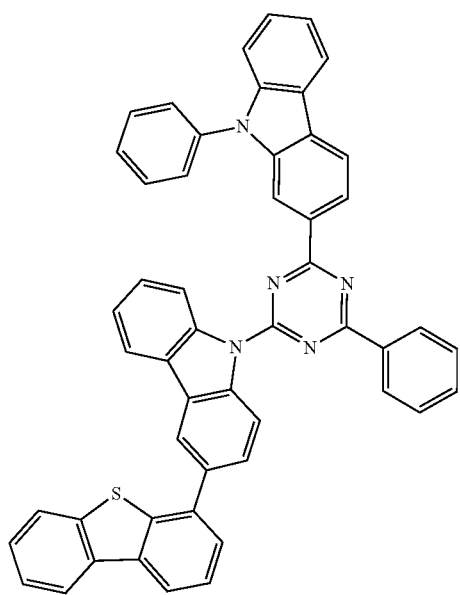
792
-continued
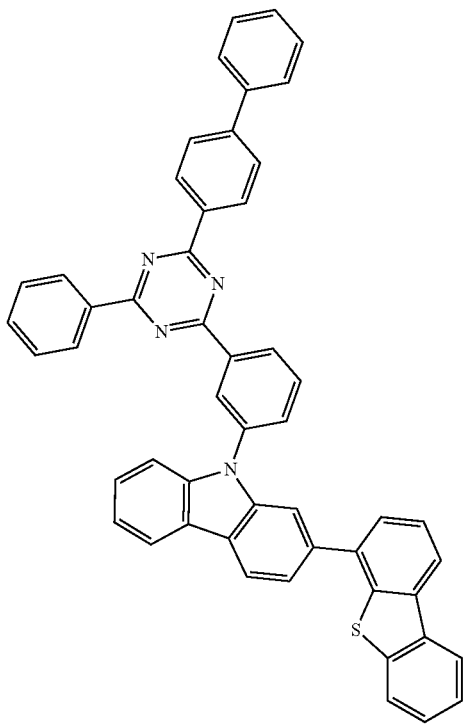
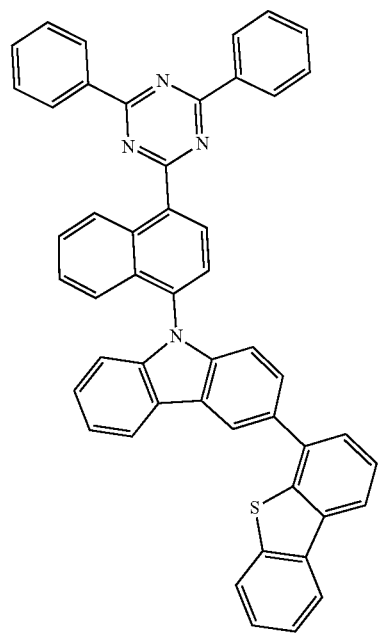

793
-continued
794
-continued
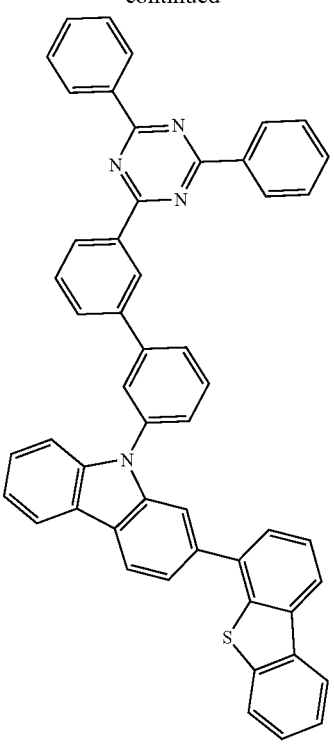
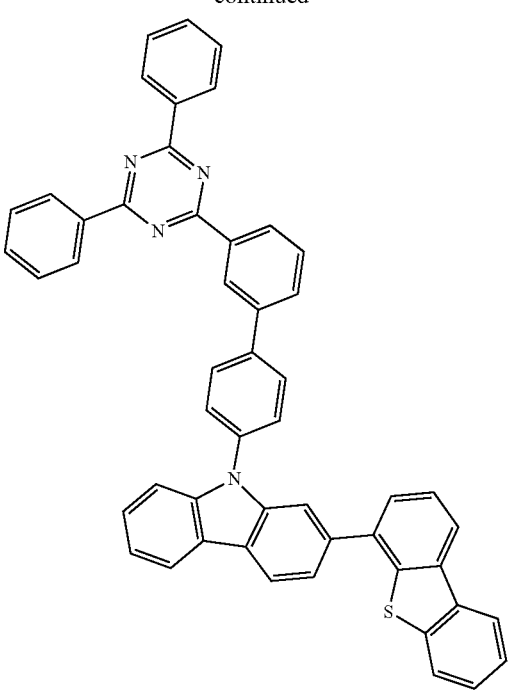
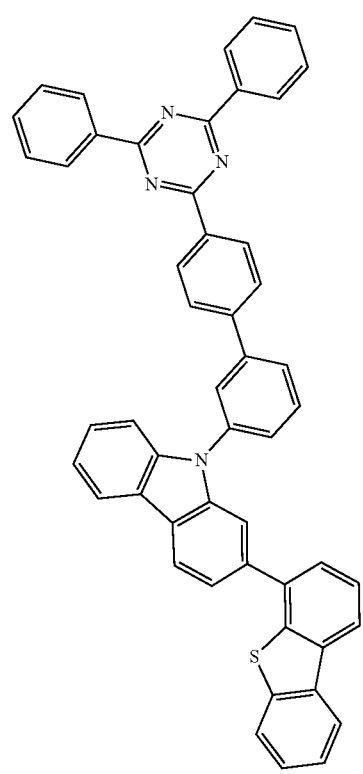

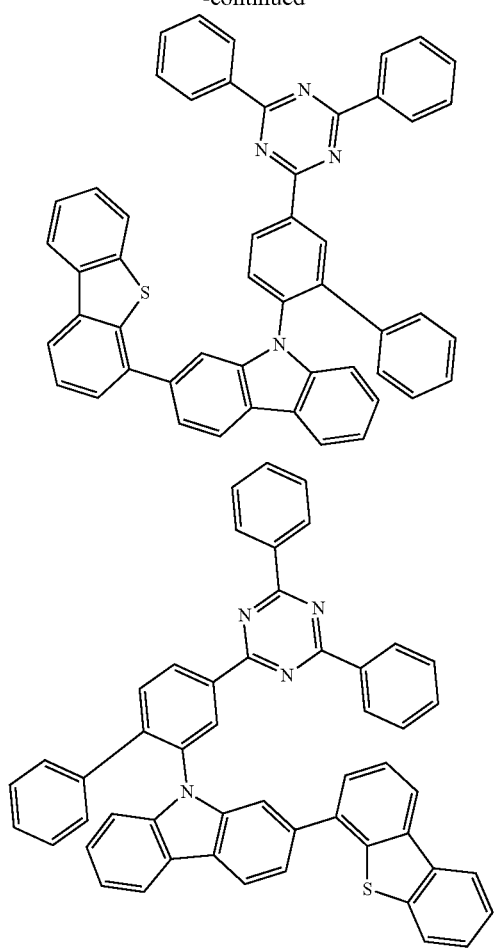
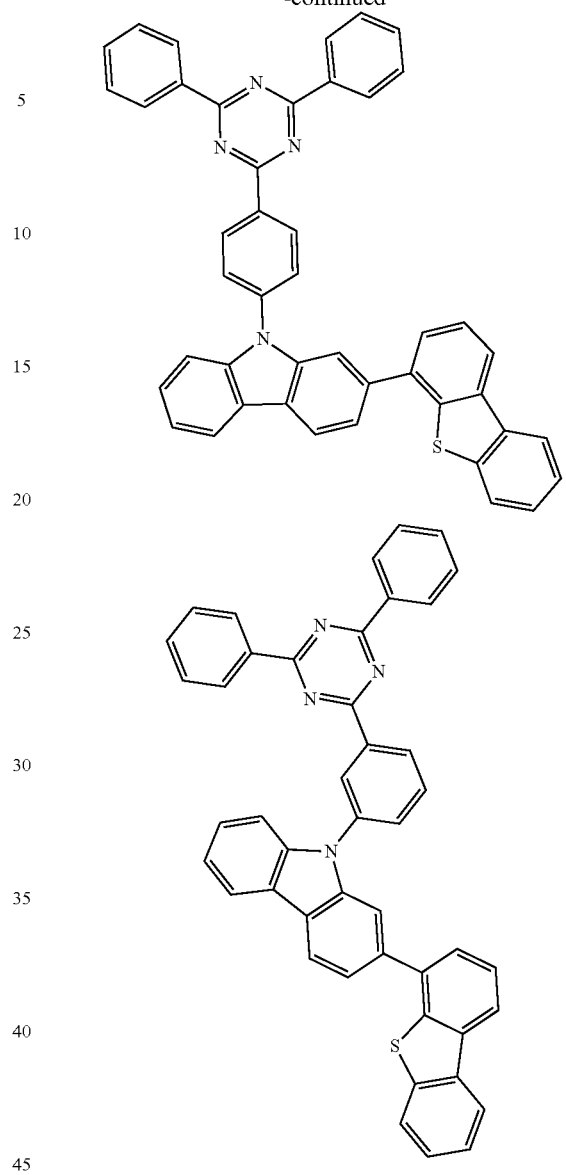
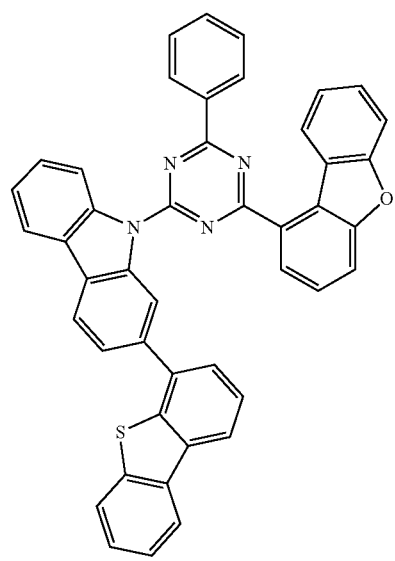
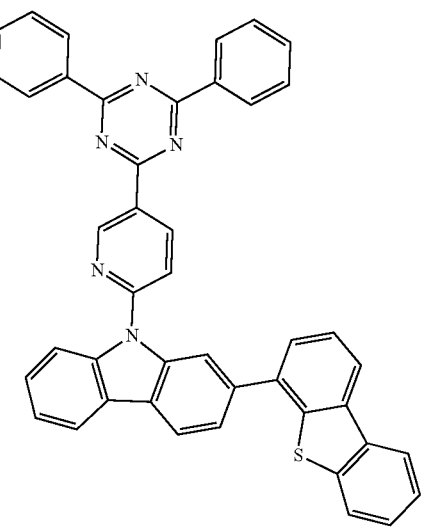

797
-continued
798
-continued
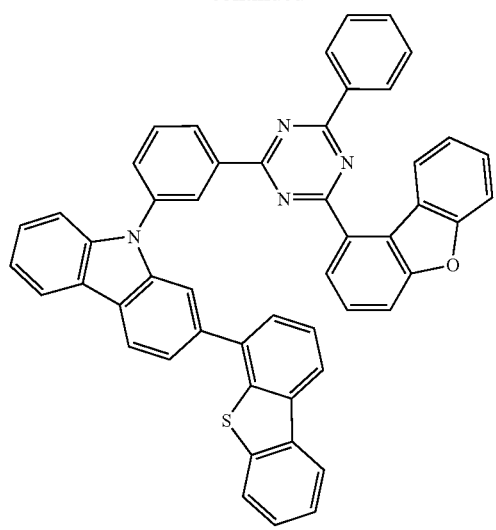
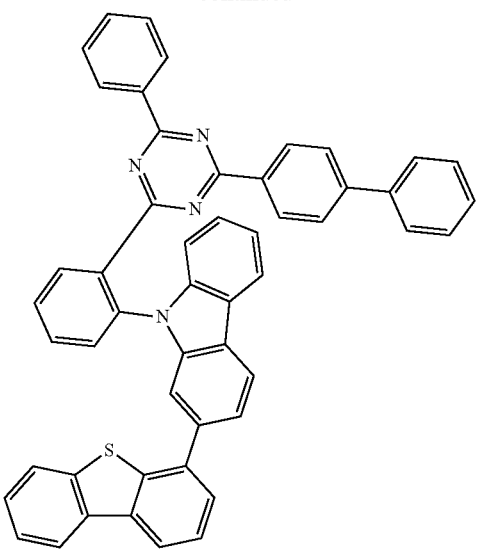

799
-continued
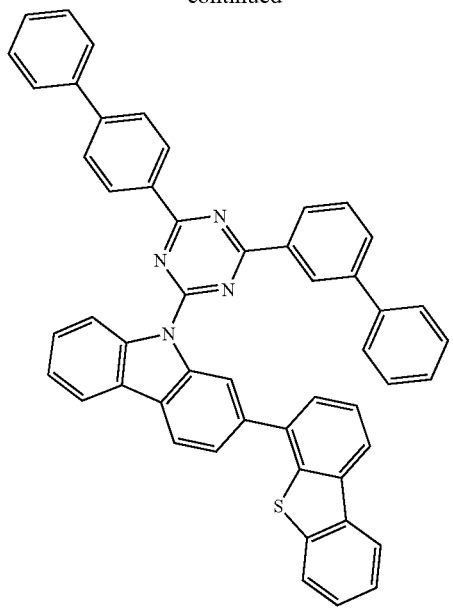
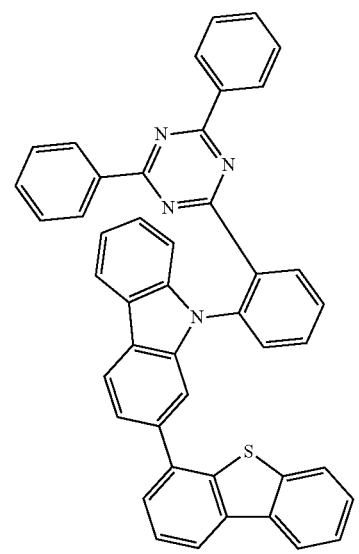
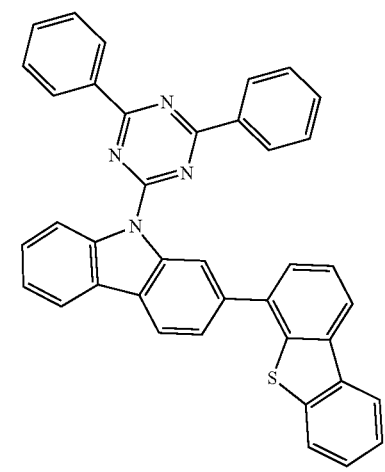
800
-continued
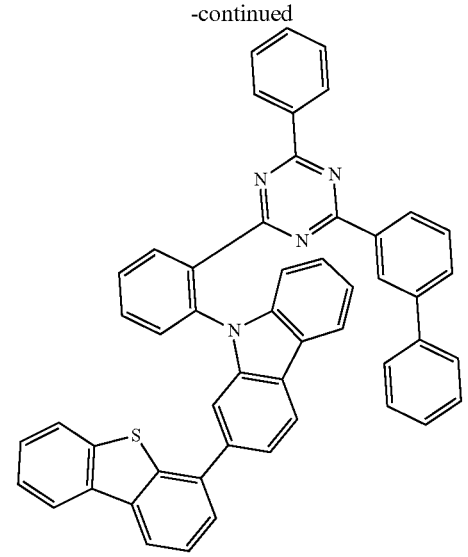
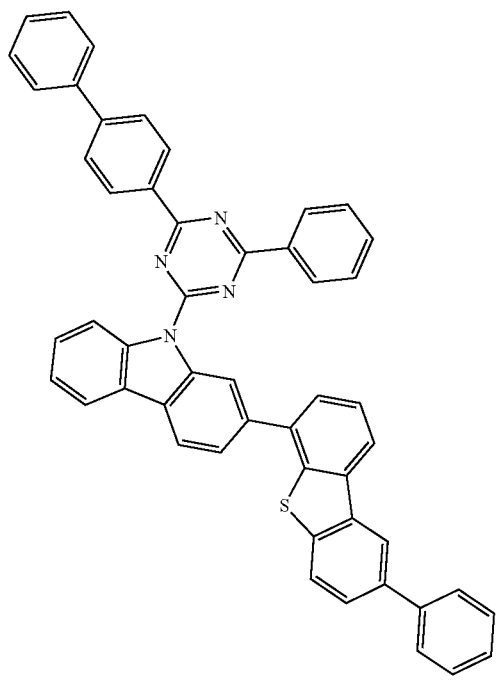
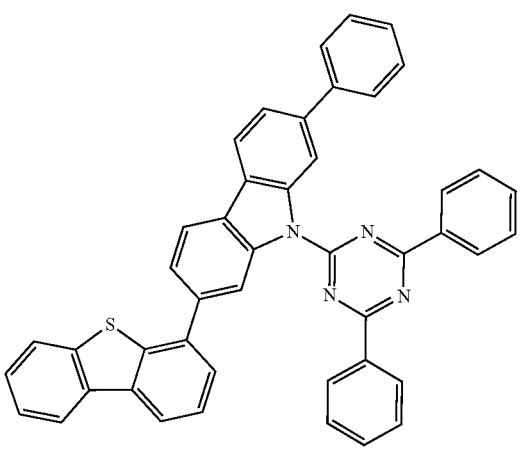

801
-continued
802
-continued
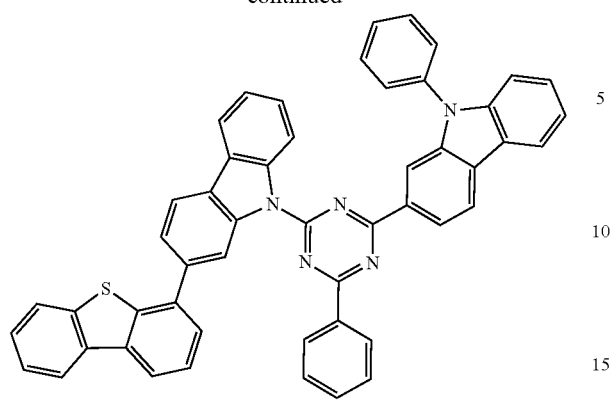
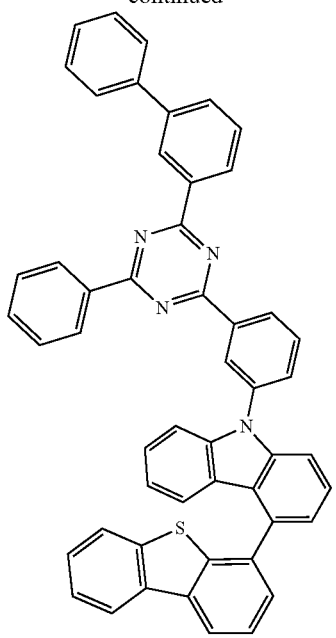

803
-continued
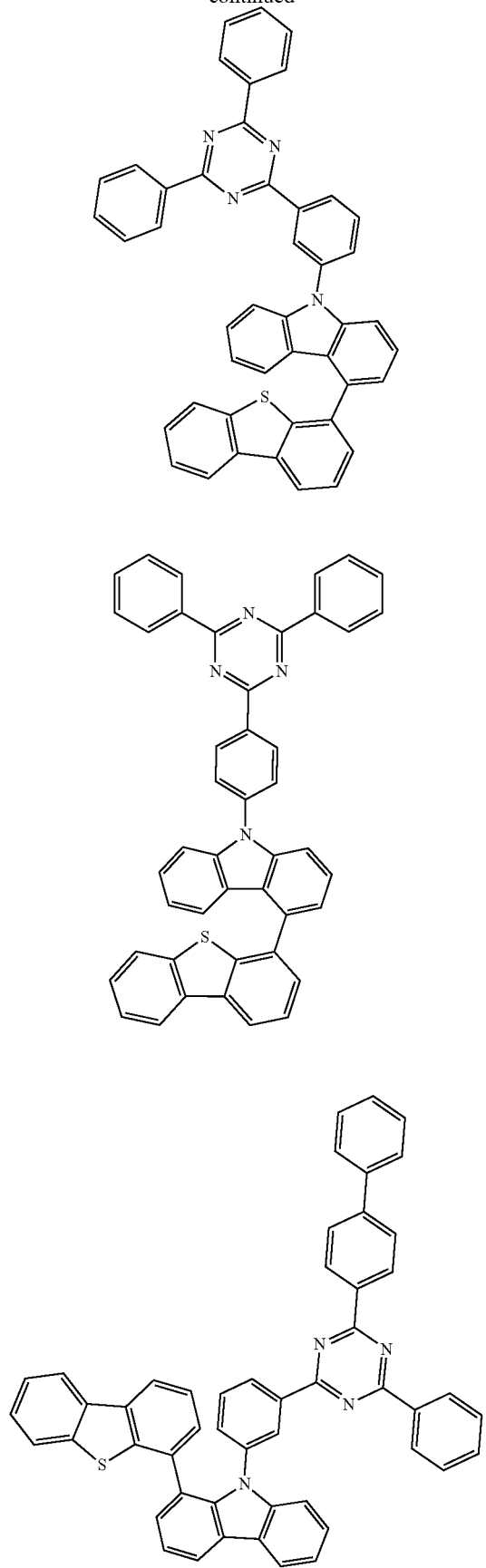
804
-continued
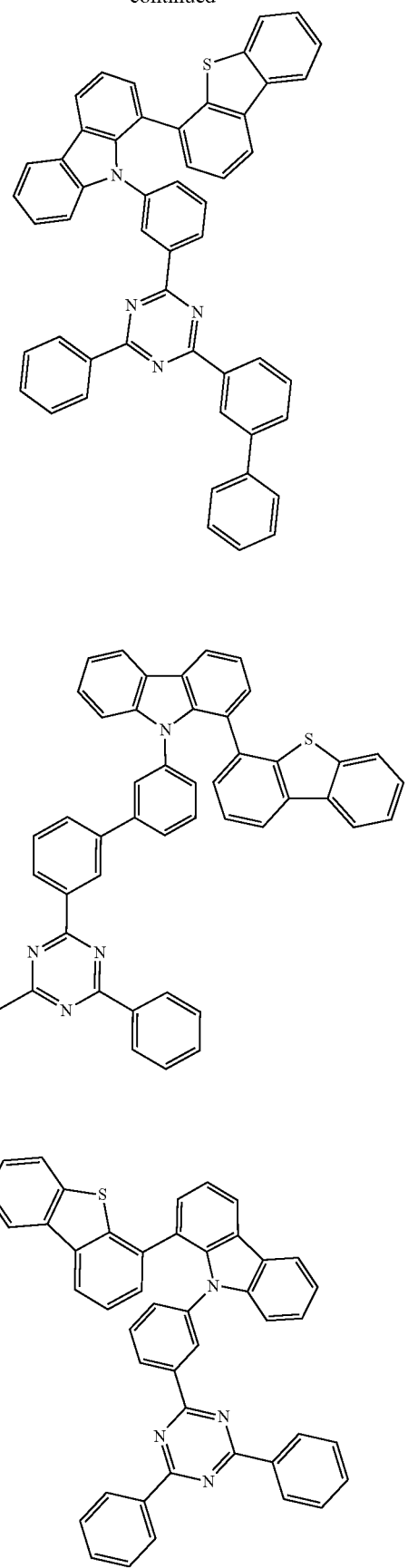

805
-continued
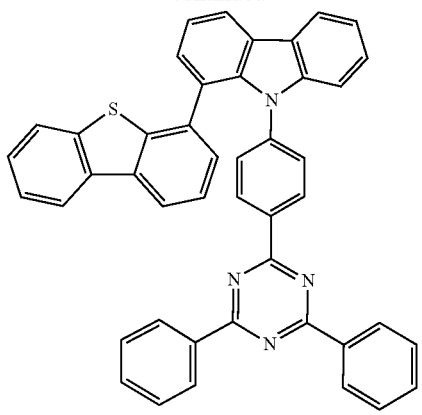
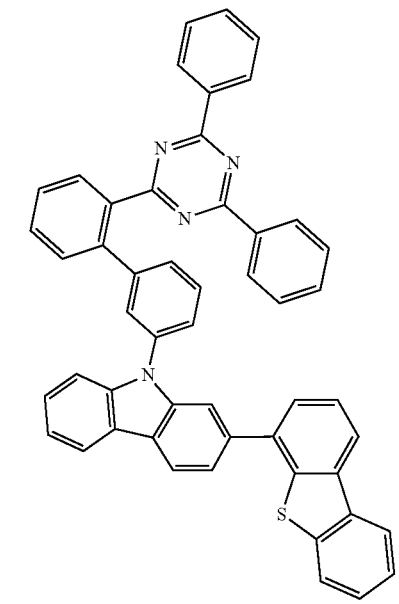
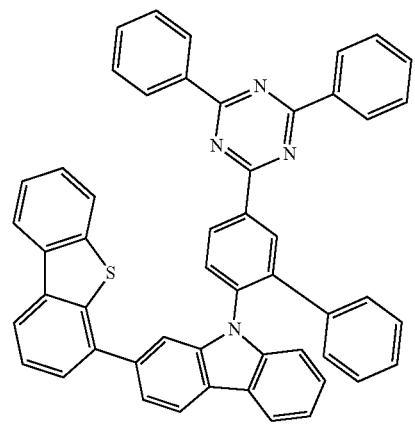
806
-continued
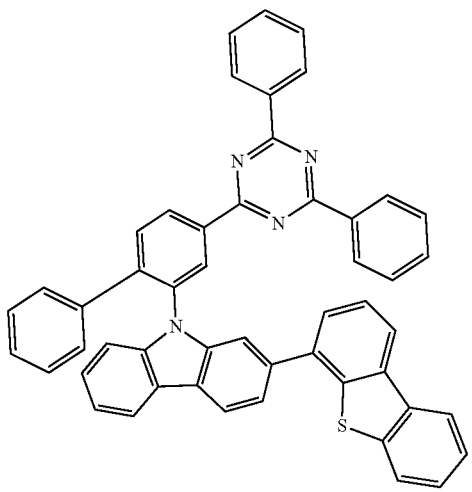
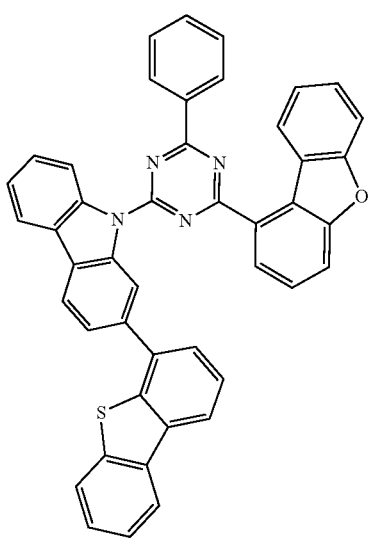
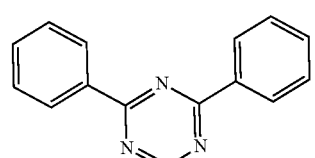
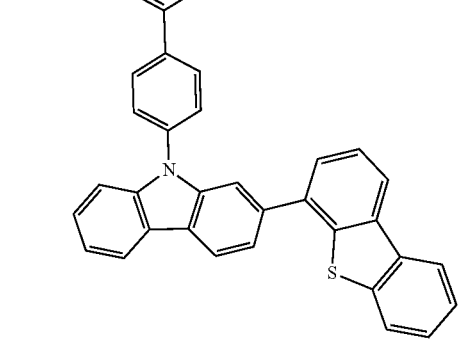

807
-continued
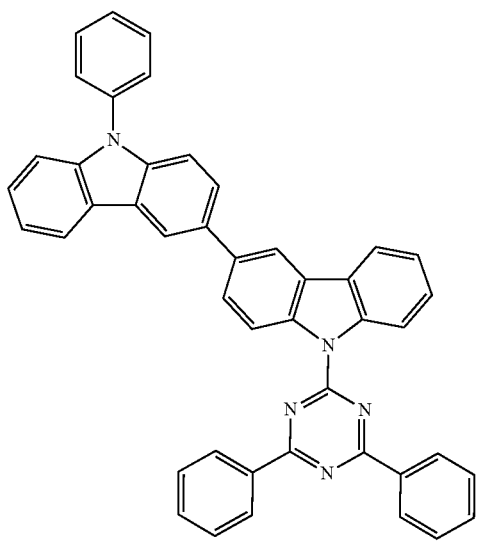
808
-continued
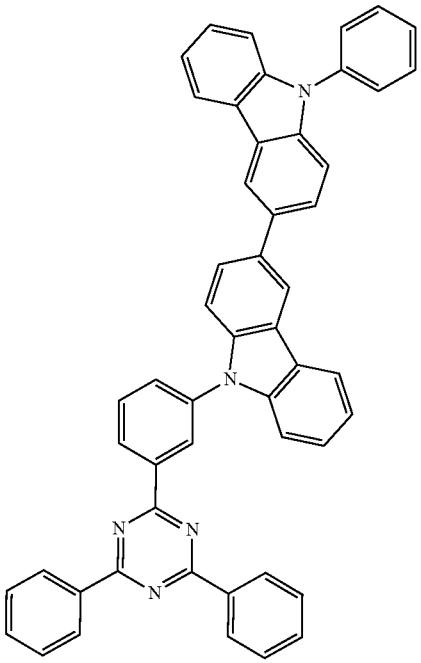
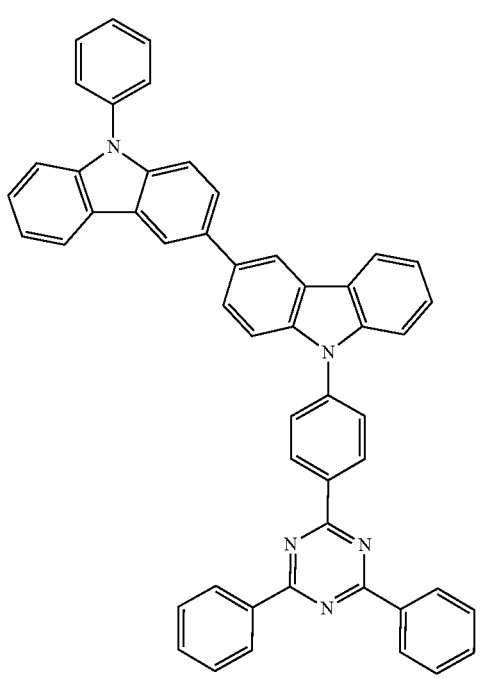
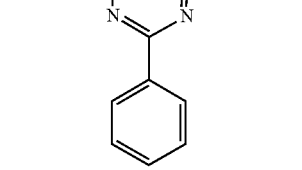
and 809
-continued
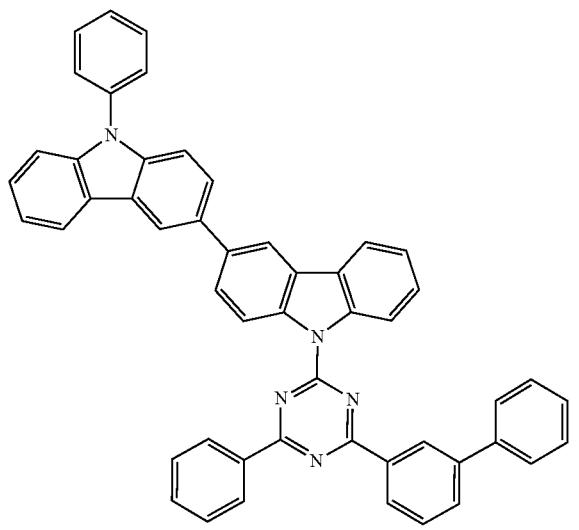 [SMILES: c1ccc(-c2cccc(-c3nc(-c4ccccc4)nc(-n4c5ccccc5c5cc(-c6ccc7c(c6)c6ccccc6n7-c6ccccc6)ccc54)n3)c2)cc1]
10. The organic electroluminescent material according to claim 8, wherein the compound represented by formula 12 is selected from the group consisting of the following:
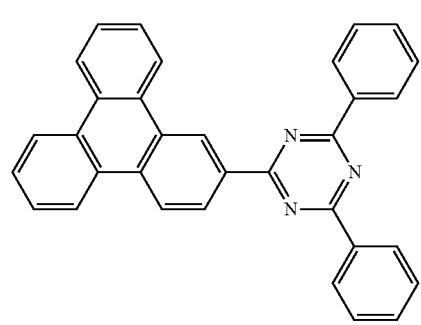
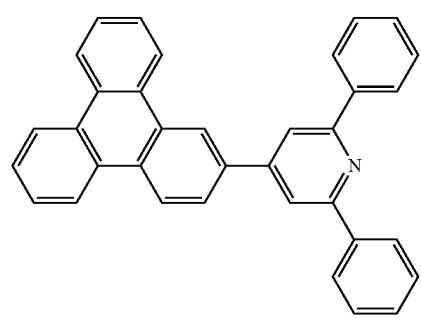
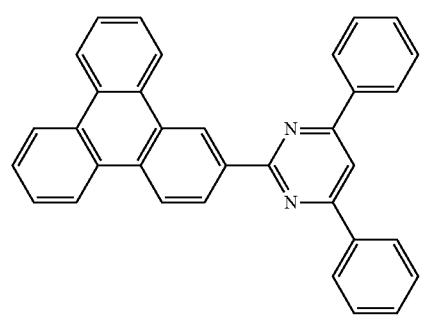
810
-continued
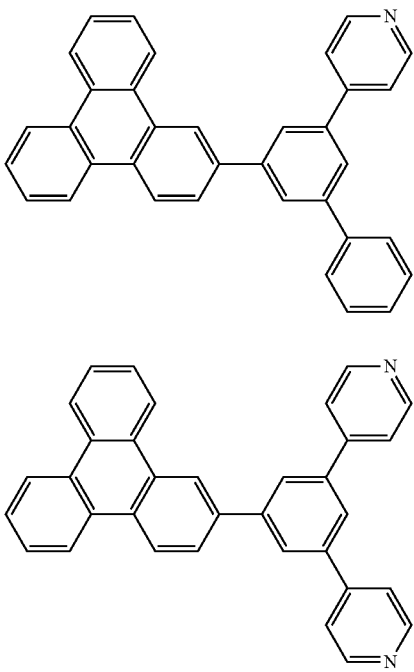
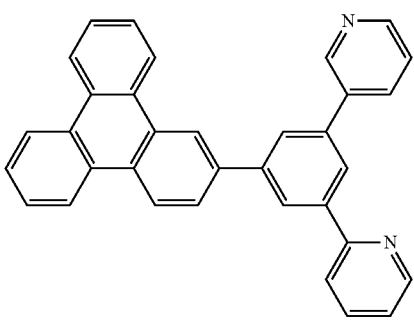
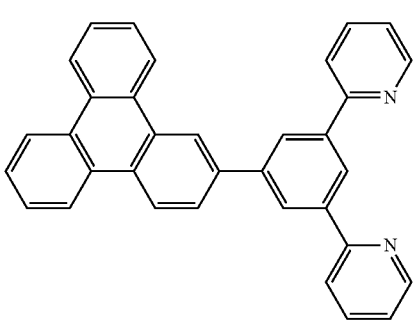
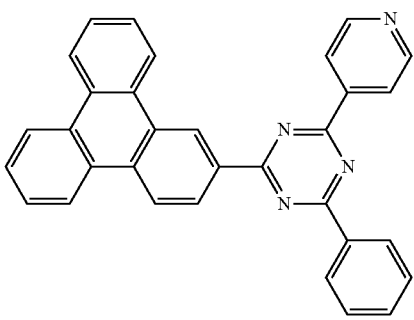

811
-continued
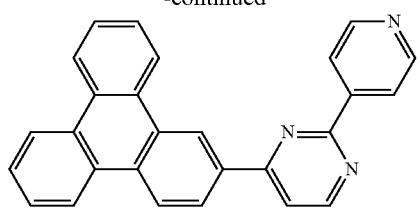
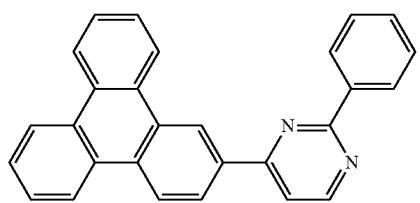
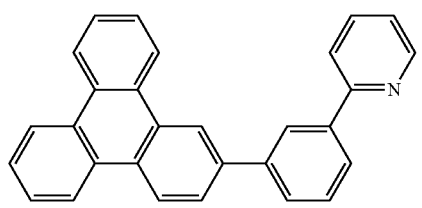
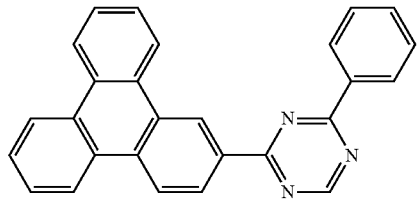
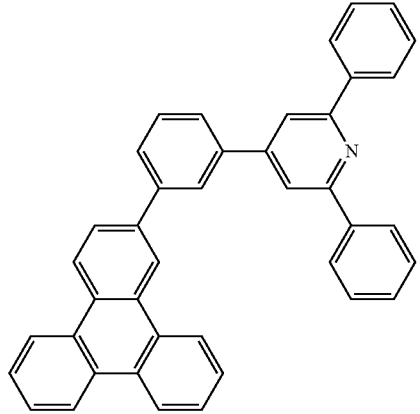
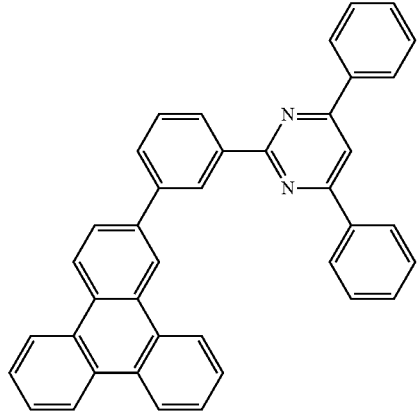
812
-continued
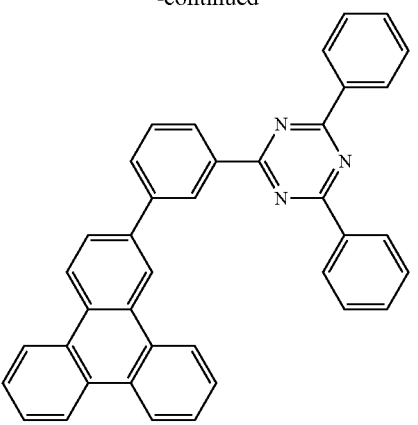
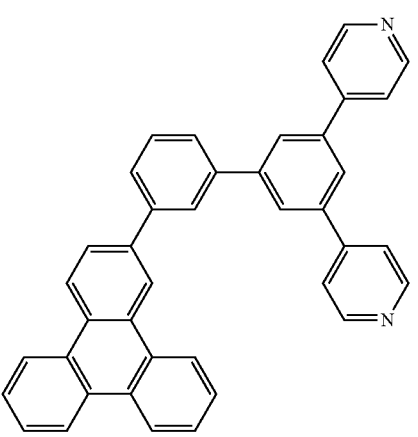
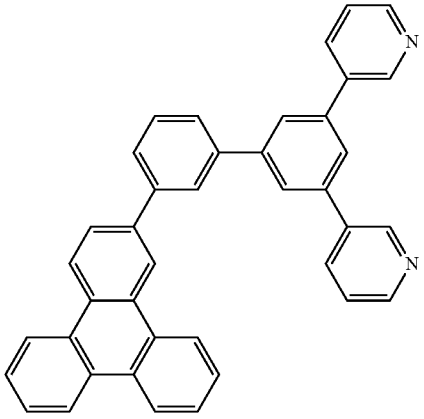
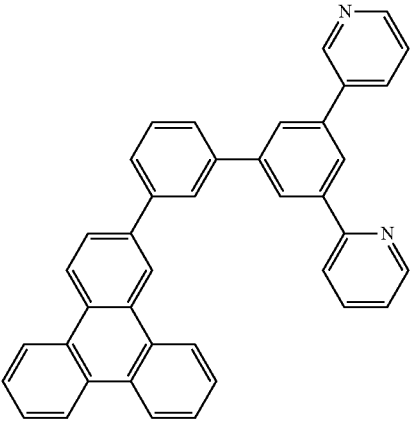

813
-continued
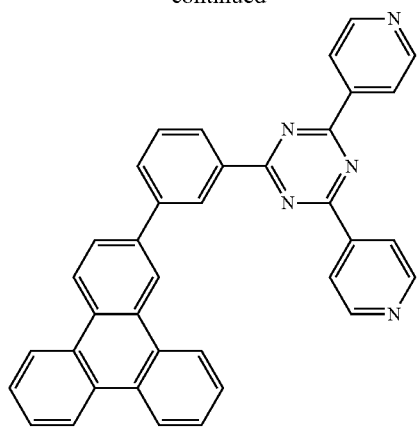
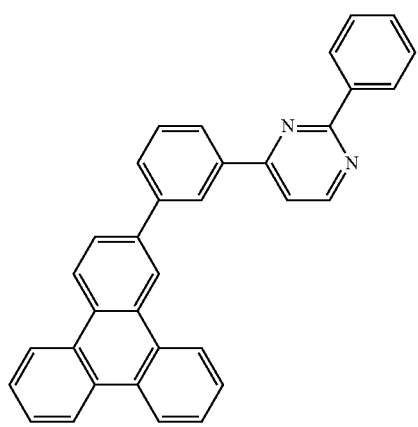
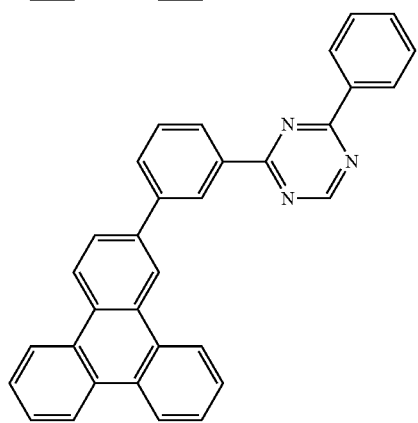
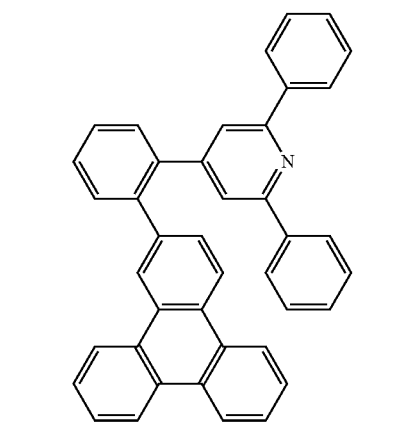
814
-continued
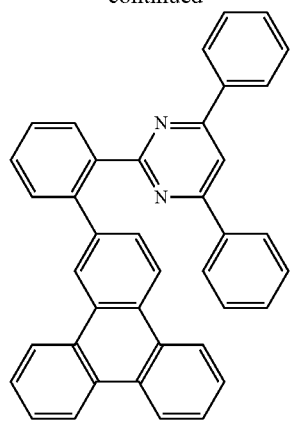
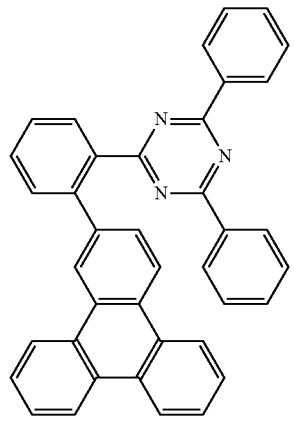
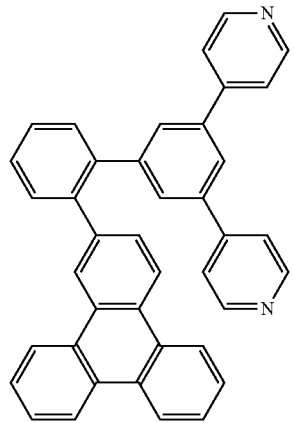
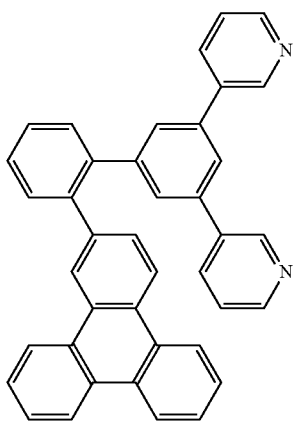

815
-continued
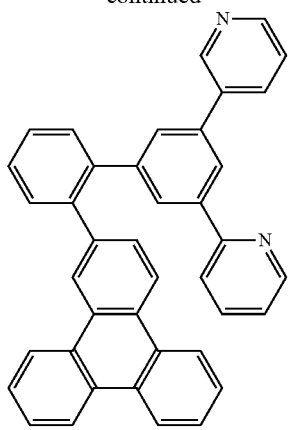
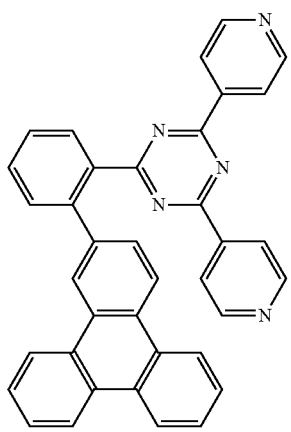
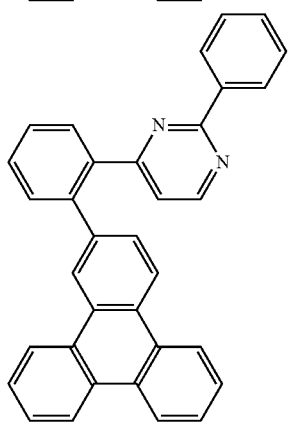
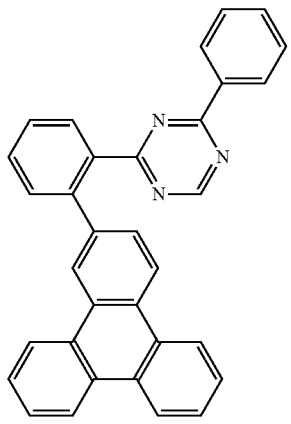
816
-continued
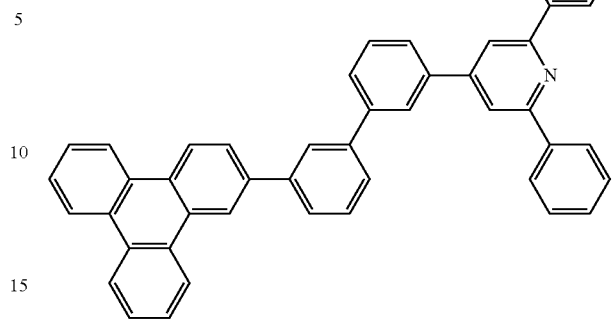
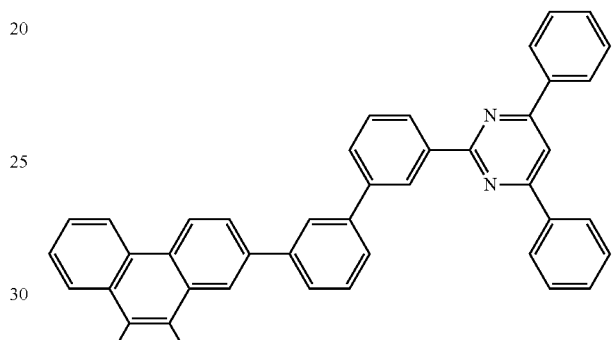
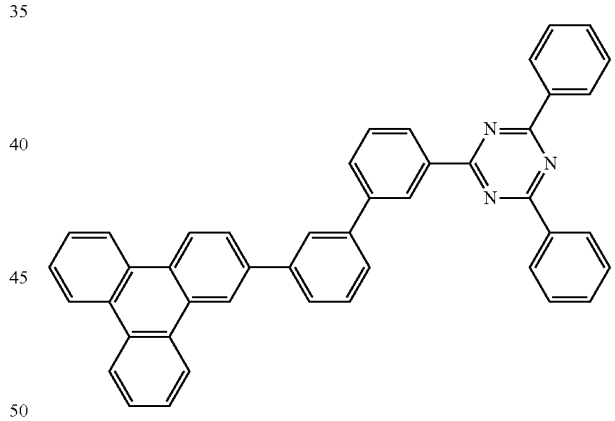
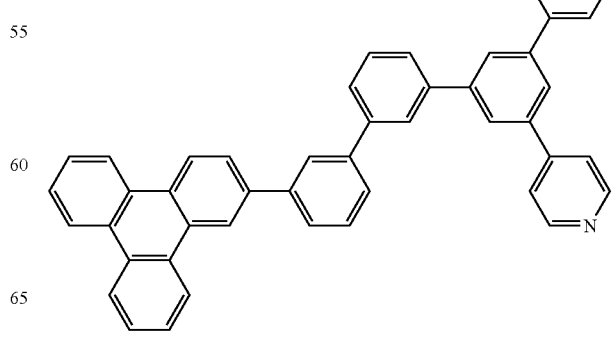

817
-continued
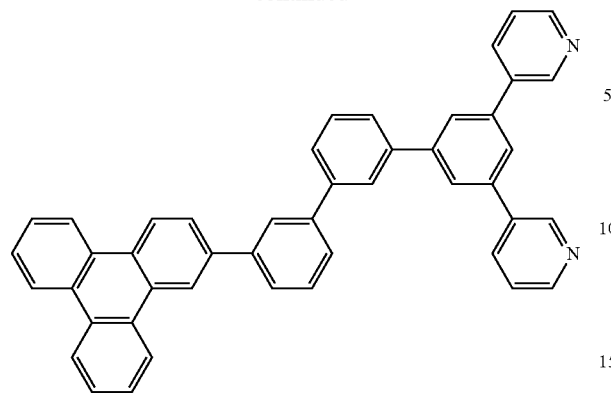
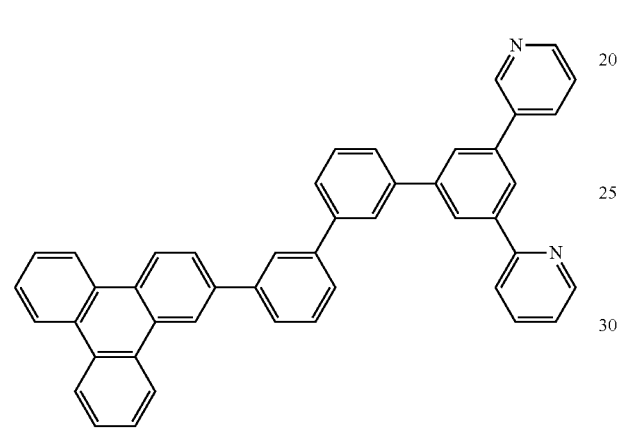
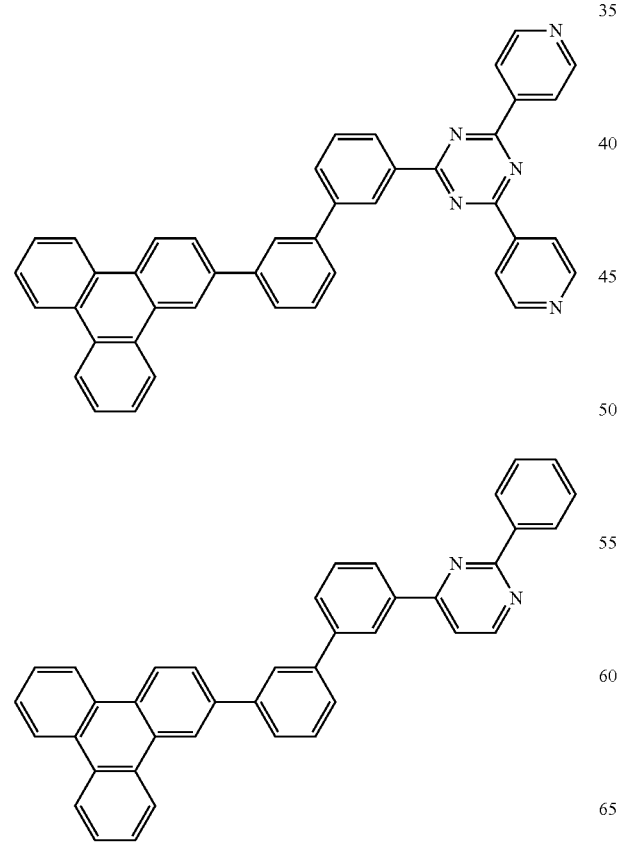
818
-continued
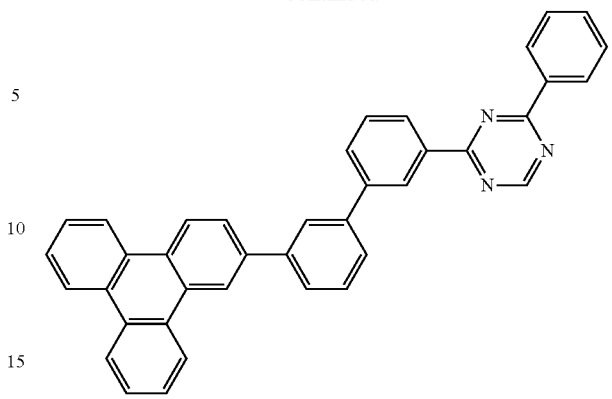
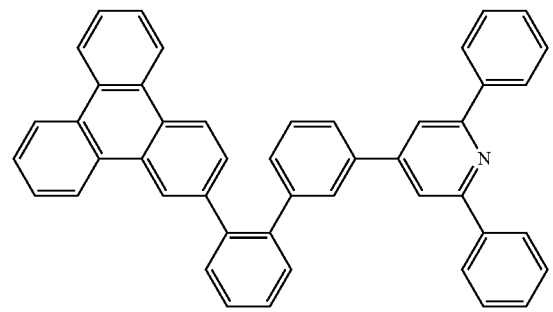
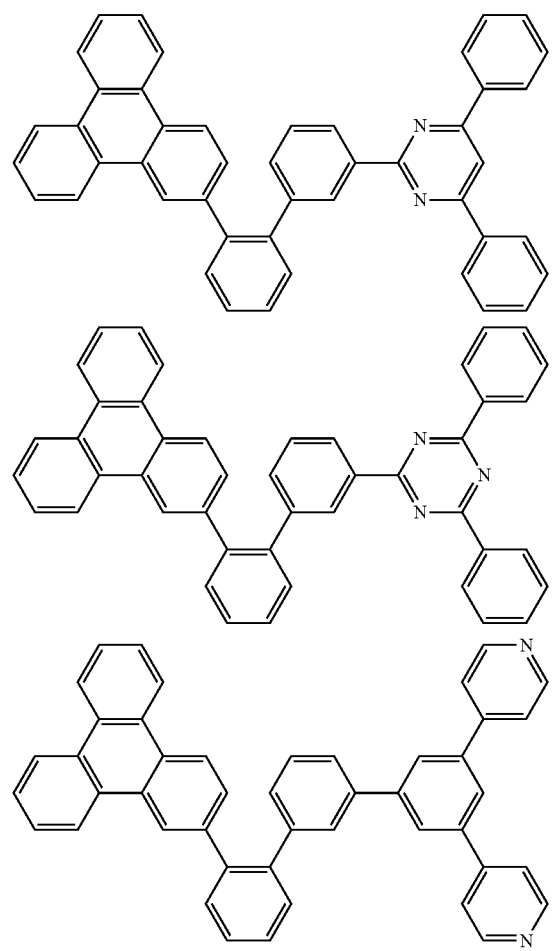

819
-continued
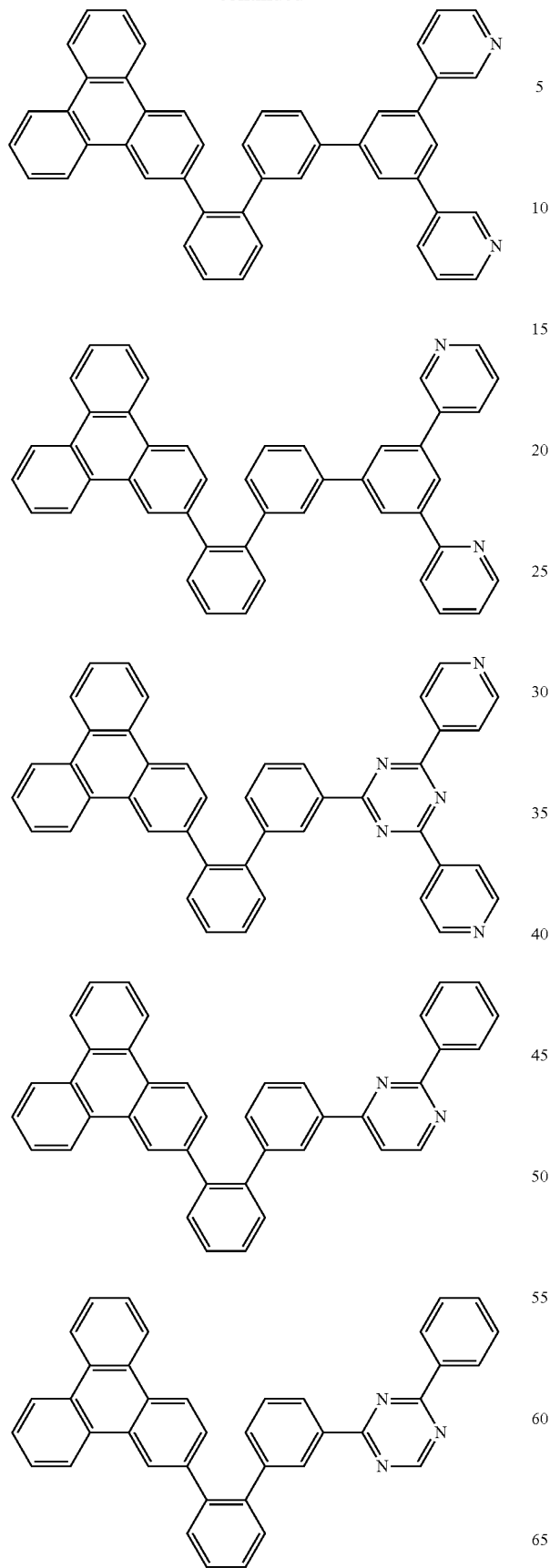
820
-continued
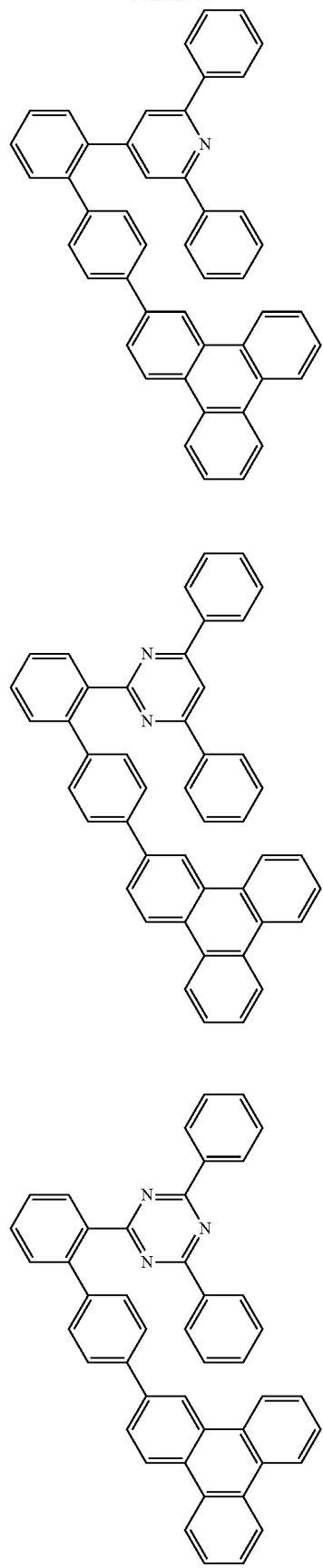

821
-continued
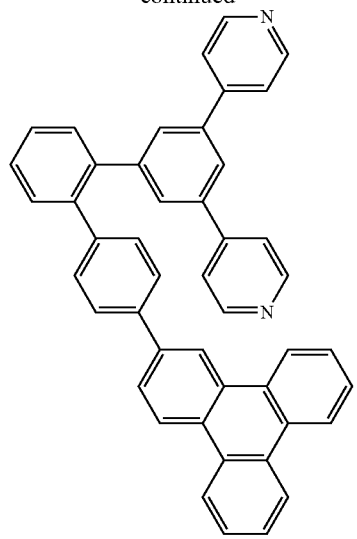
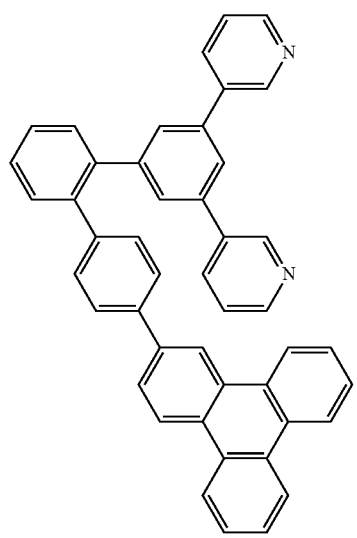
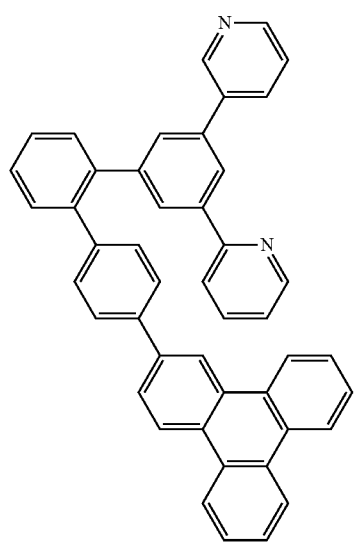
822
-continued
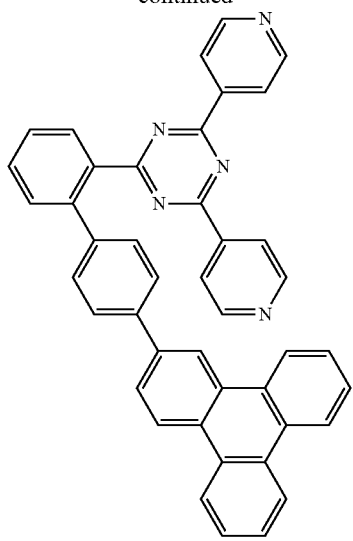
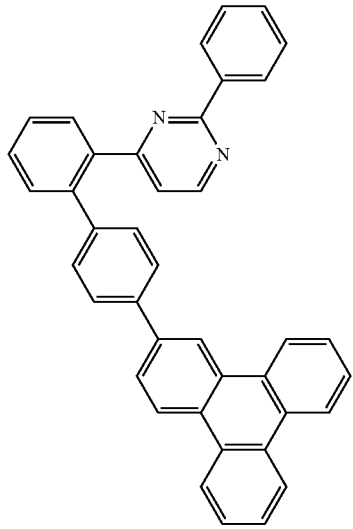
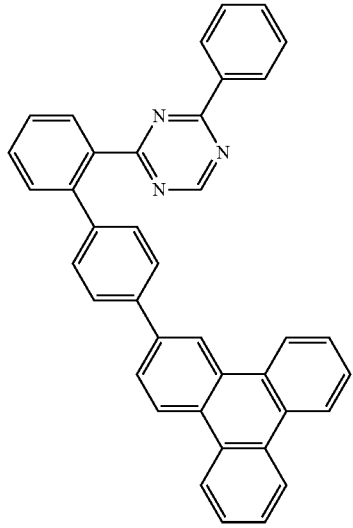

823
-continued
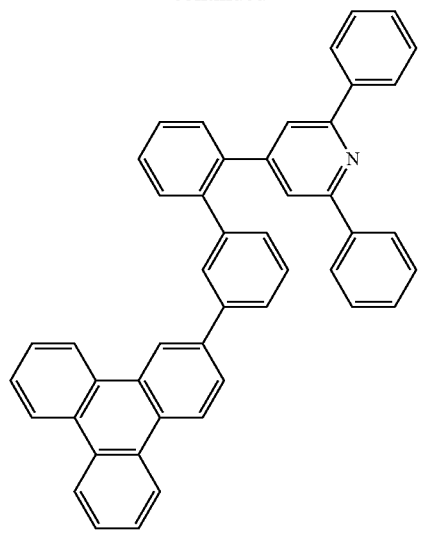
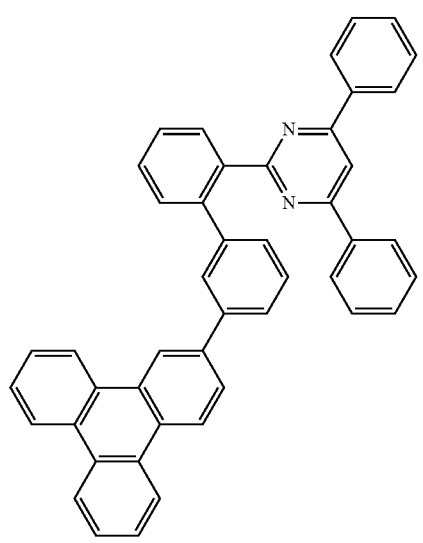
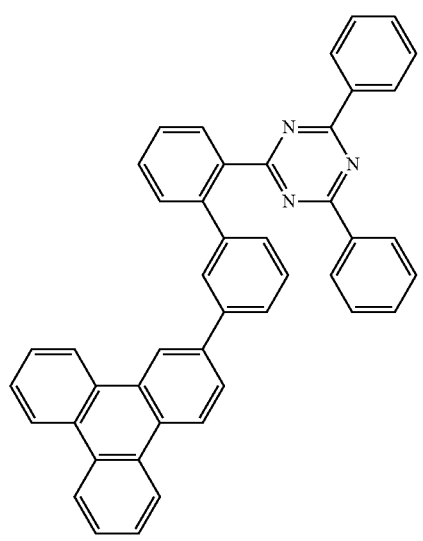
824
-continued
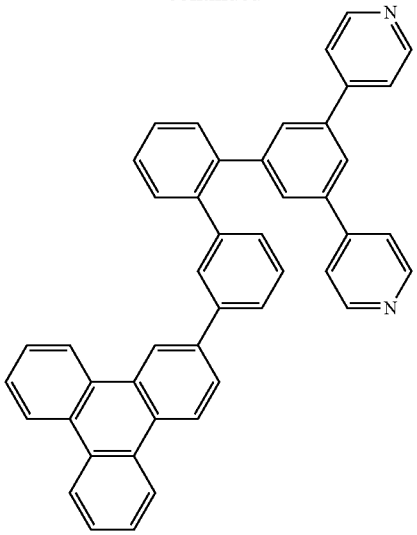
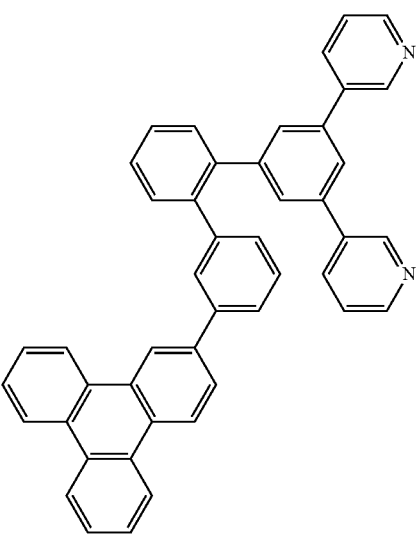
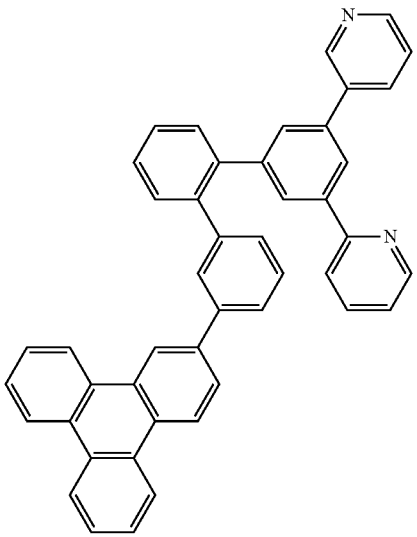

825
-continued
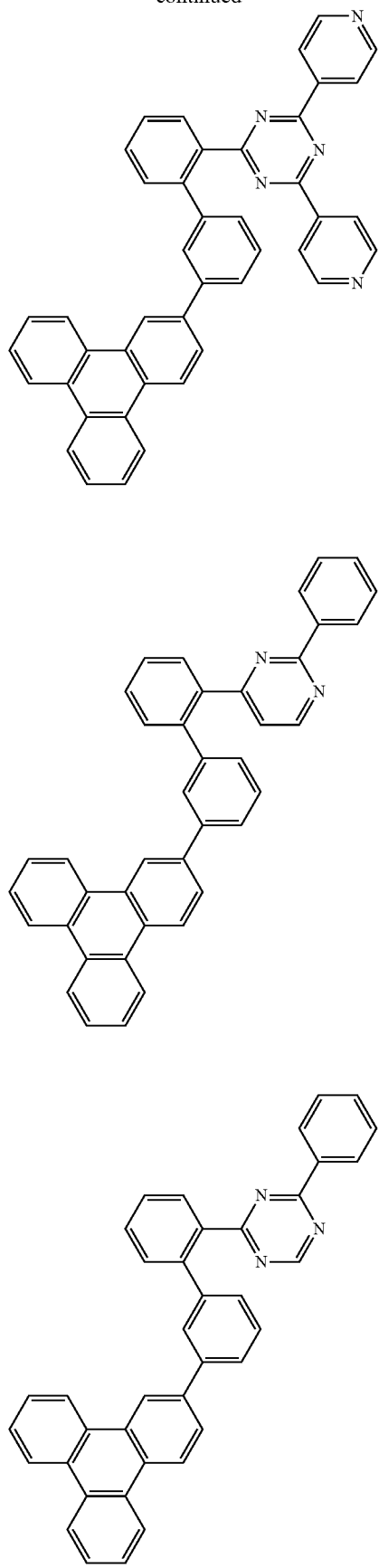
826
-continued
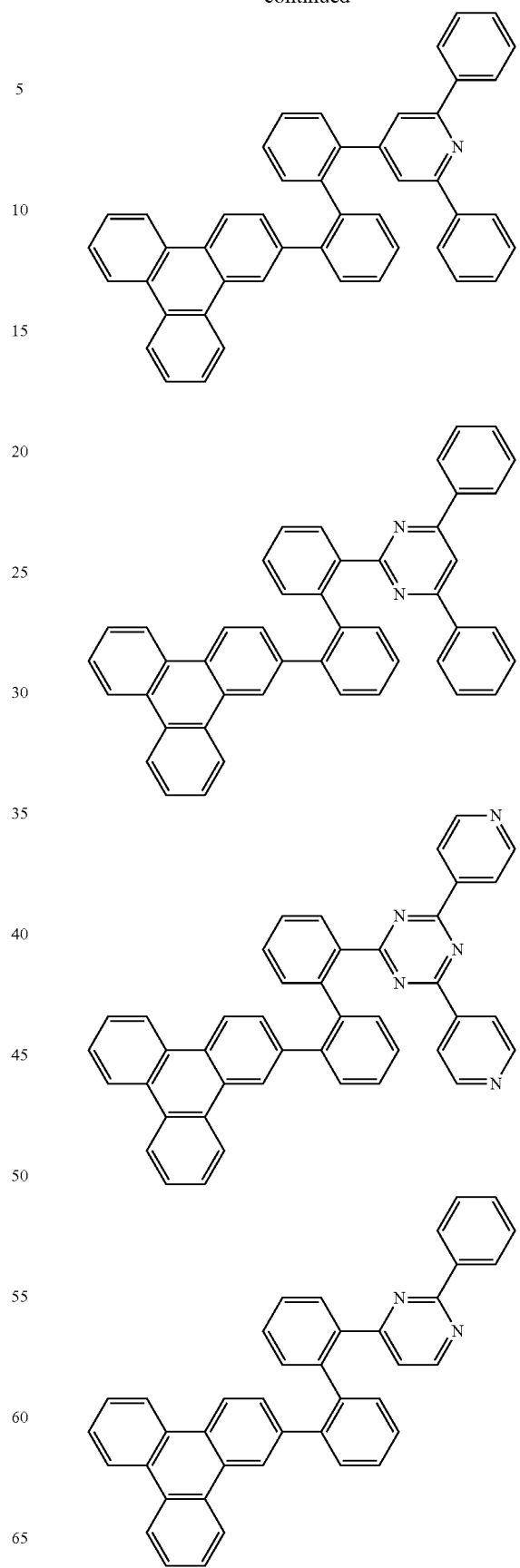

827
-continued
828
-continued
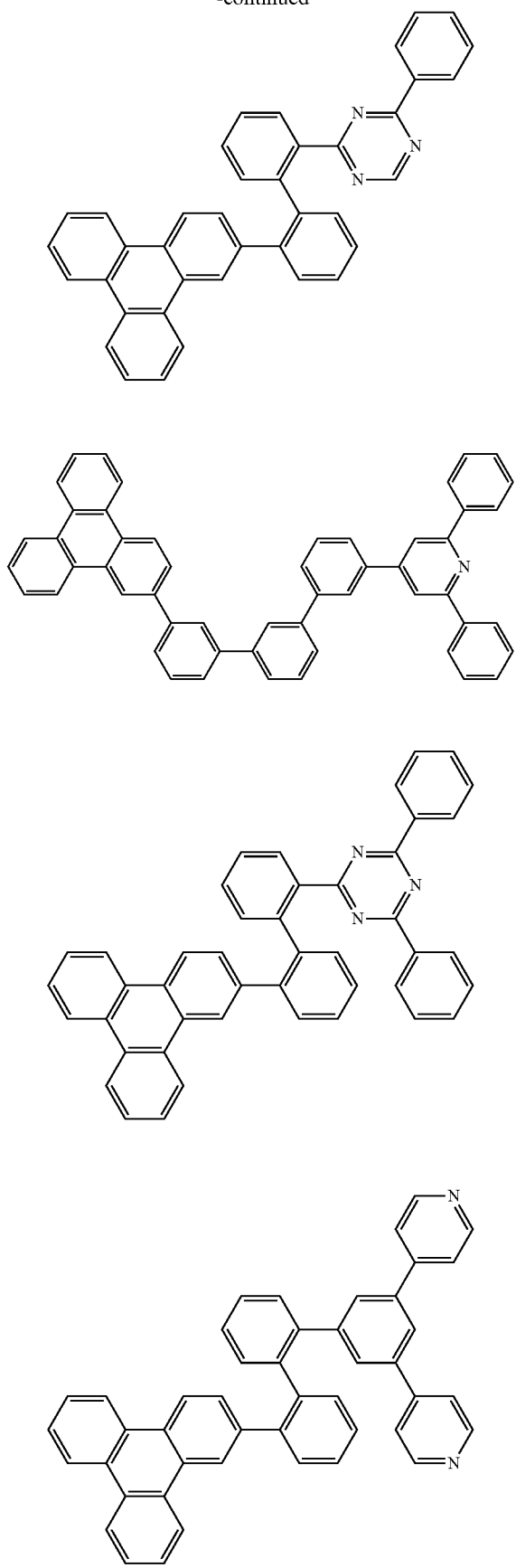
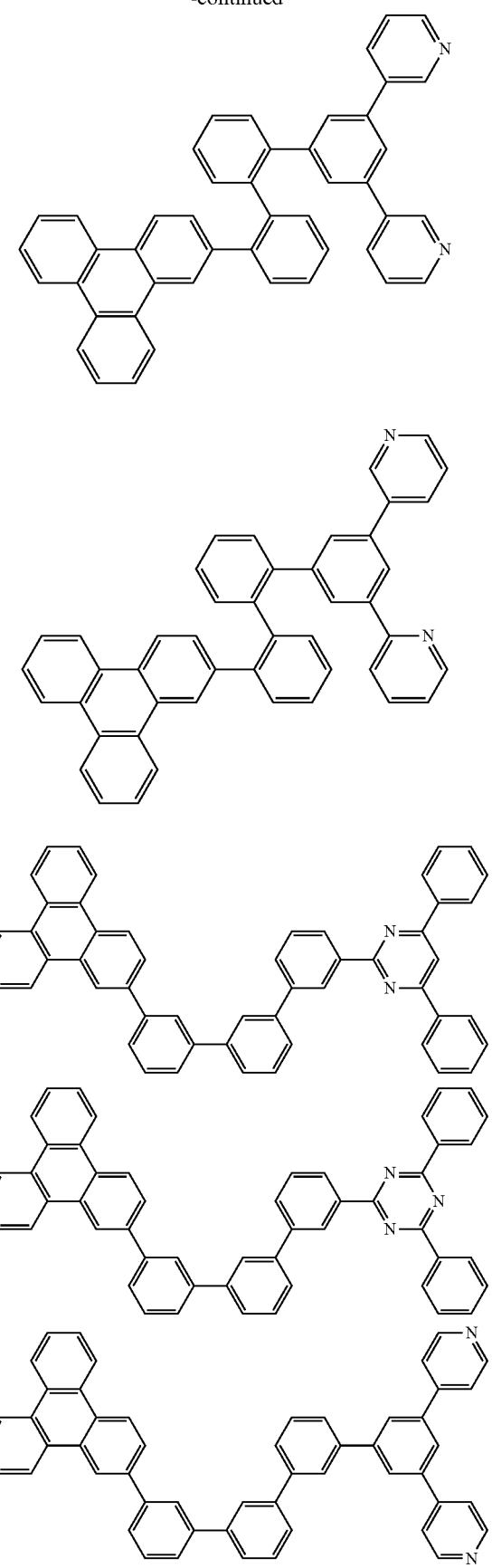

829
-continued
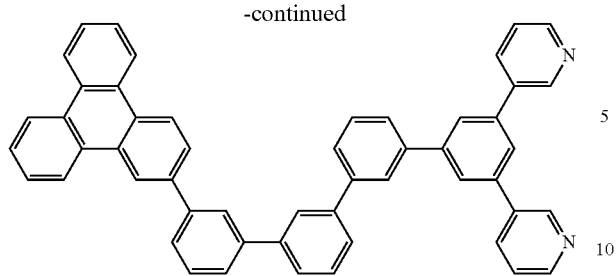
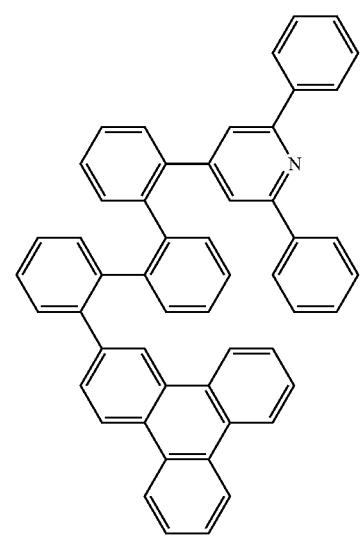
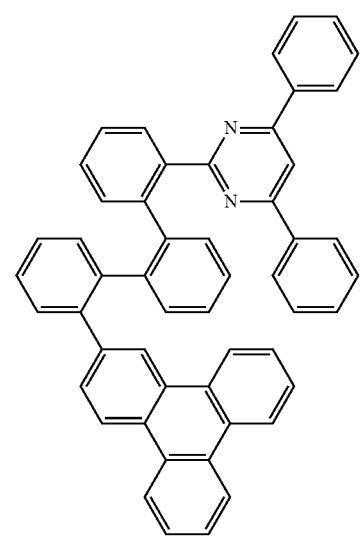
830
-continued
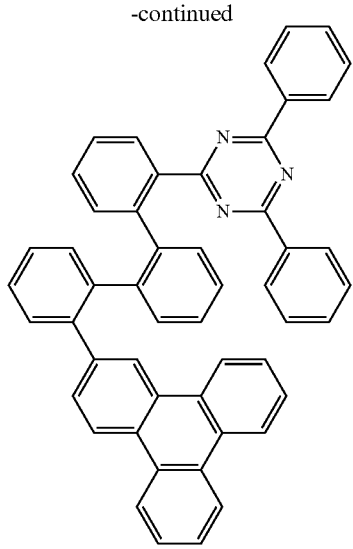
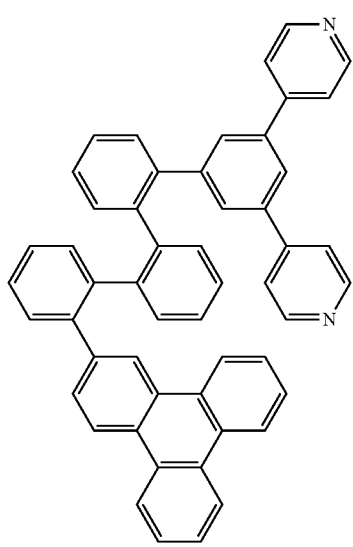
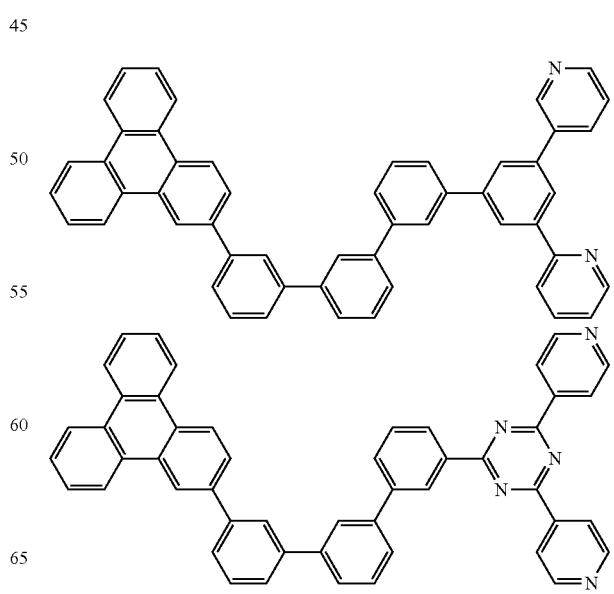

831
-continued
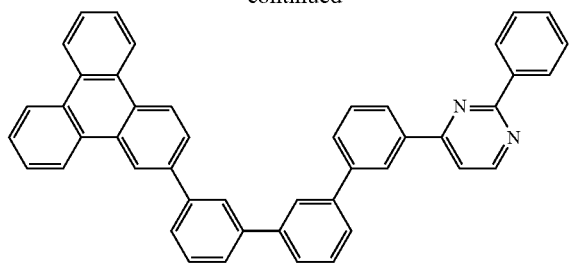
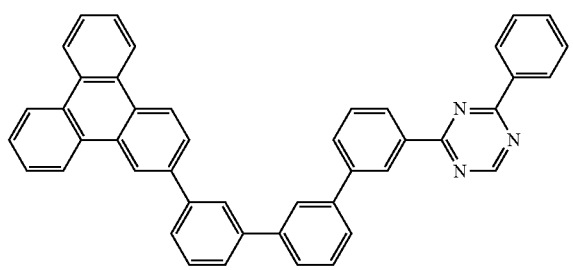
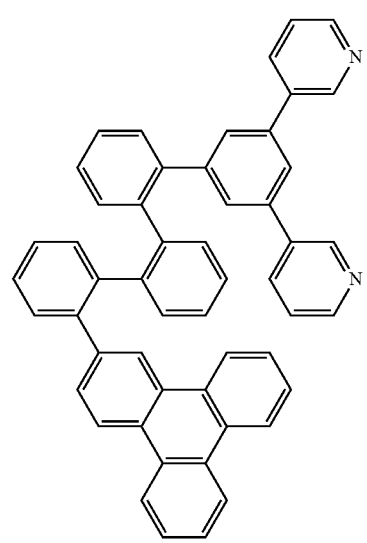
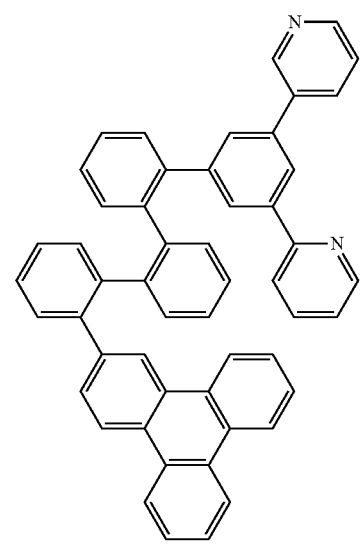
832
-continued
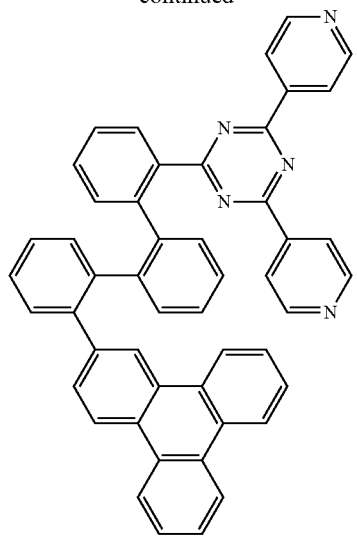
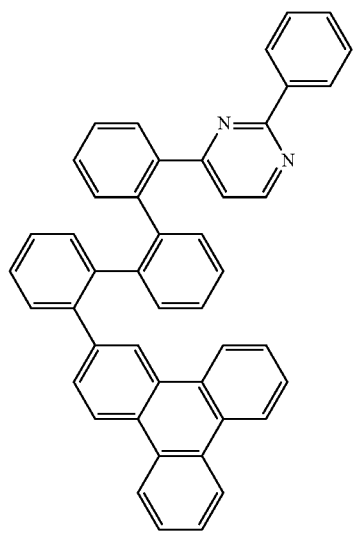
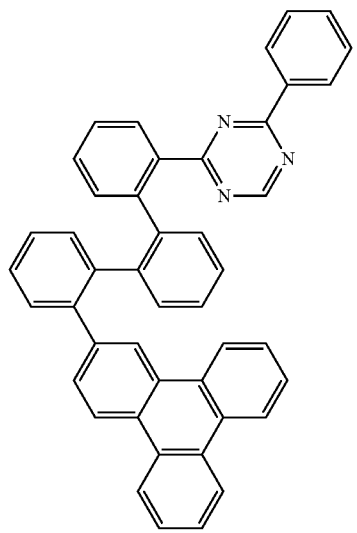

833
-continued
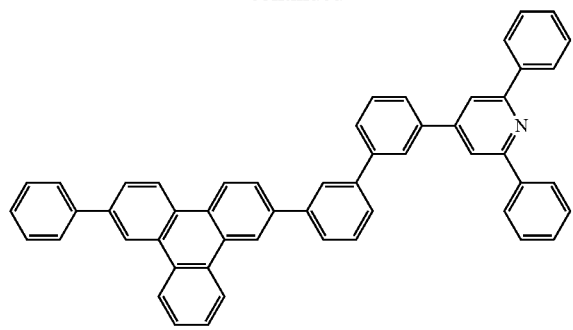
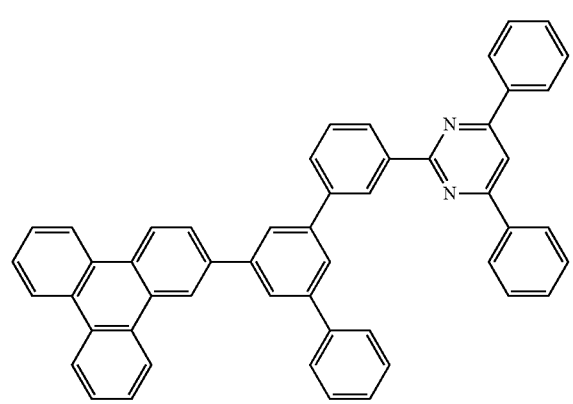
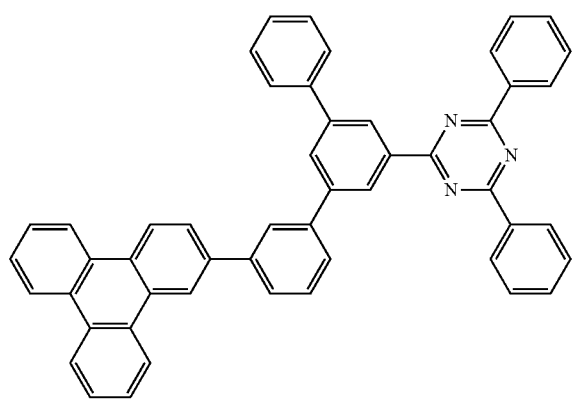
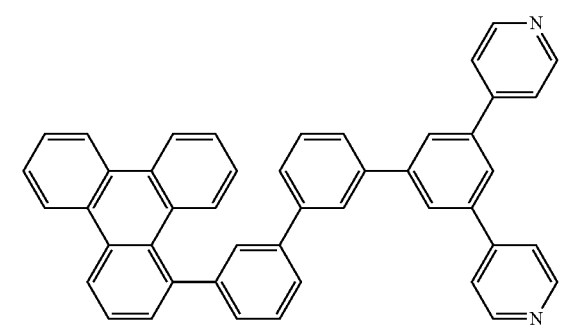
834
-continued
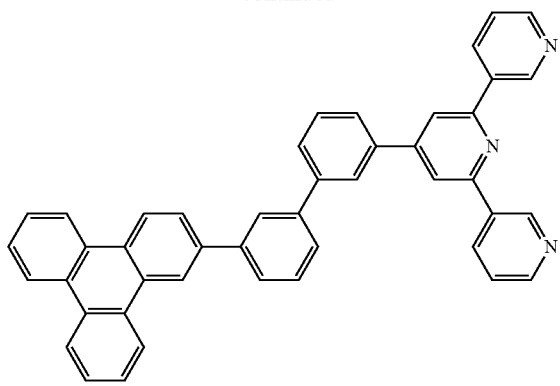
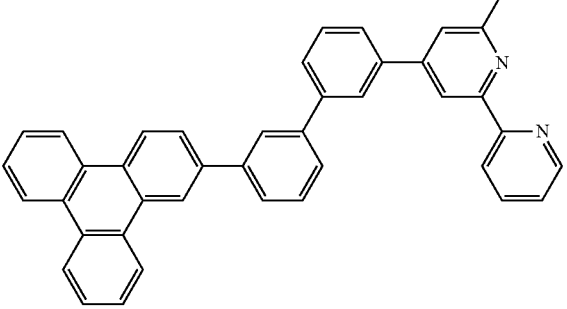
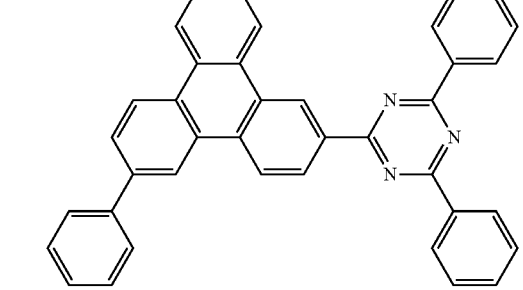

835
-continued
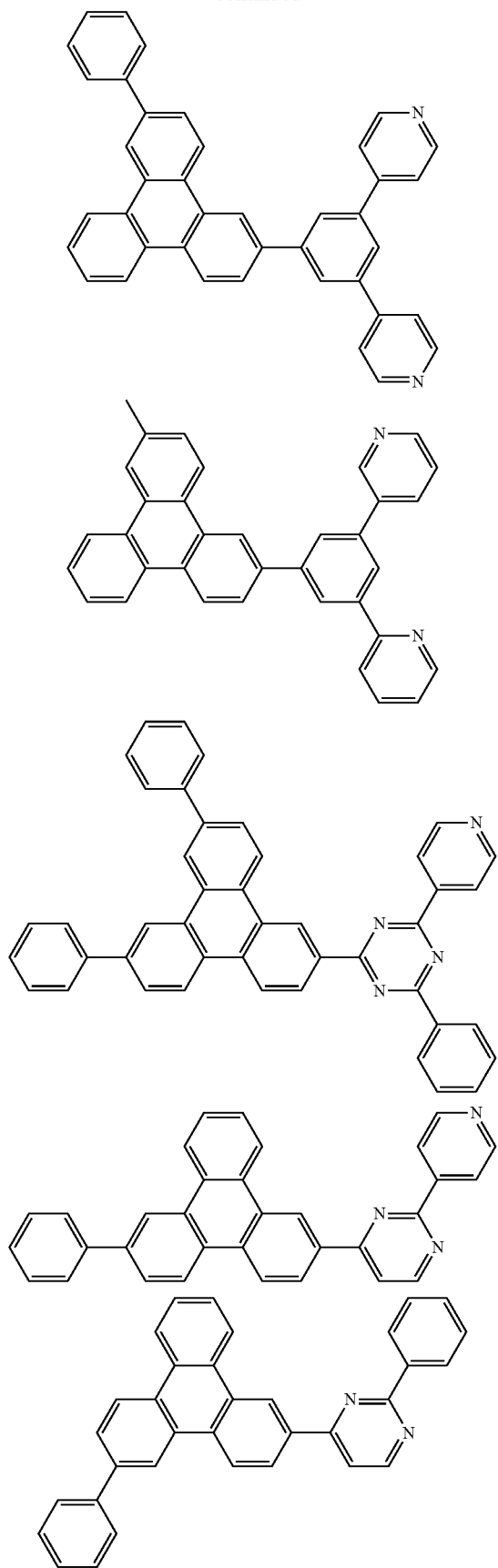
836
-continued
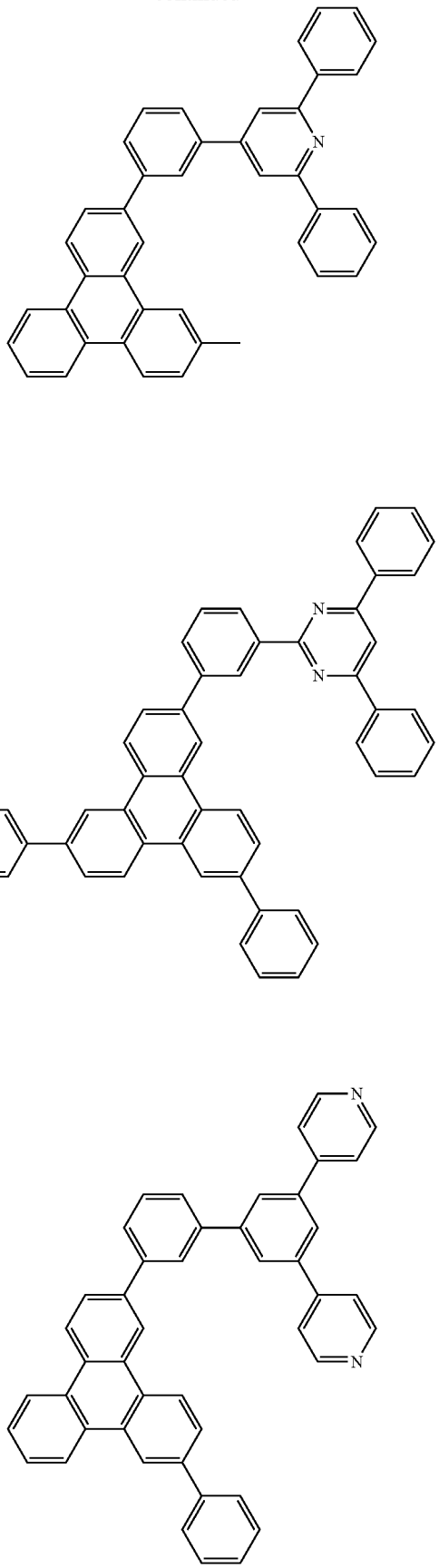

837
-continued
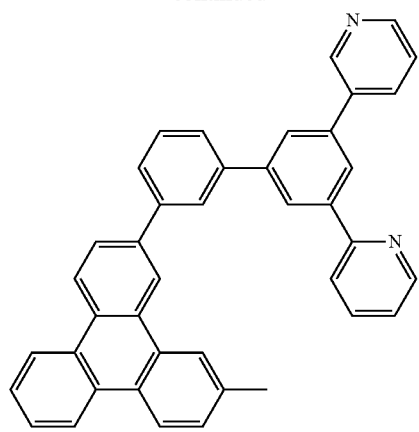
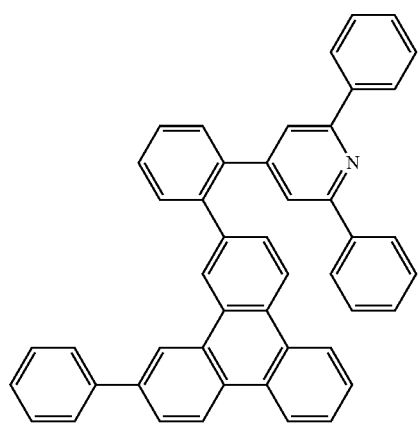
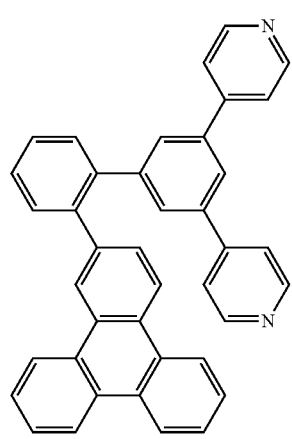
838
-continued
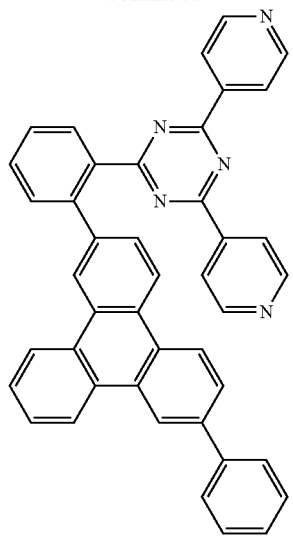
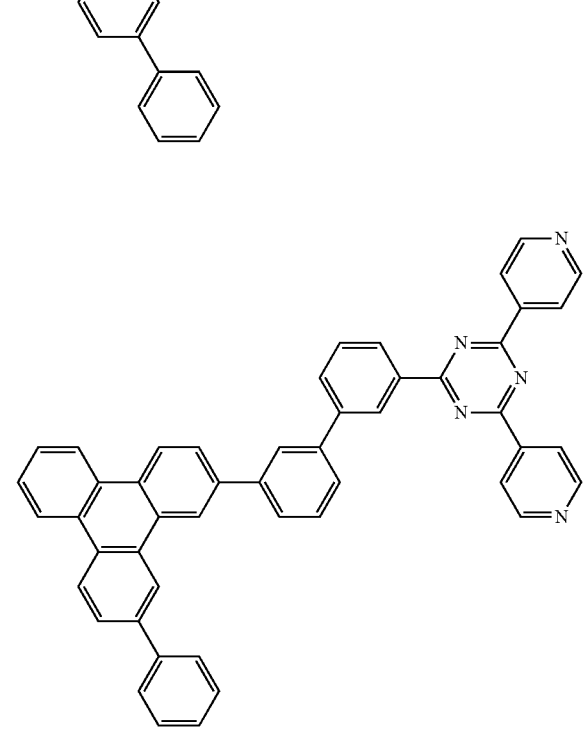

839
-continued
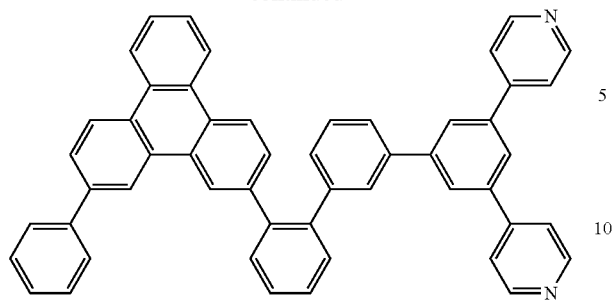
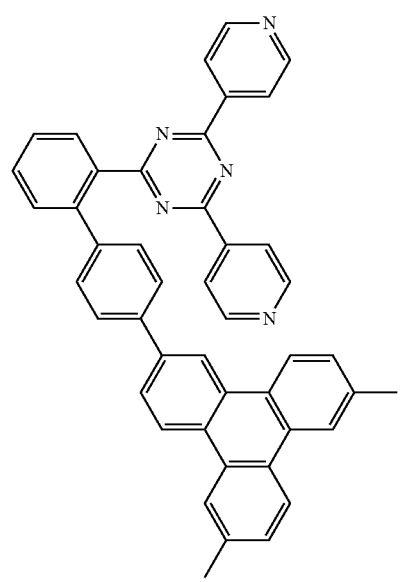
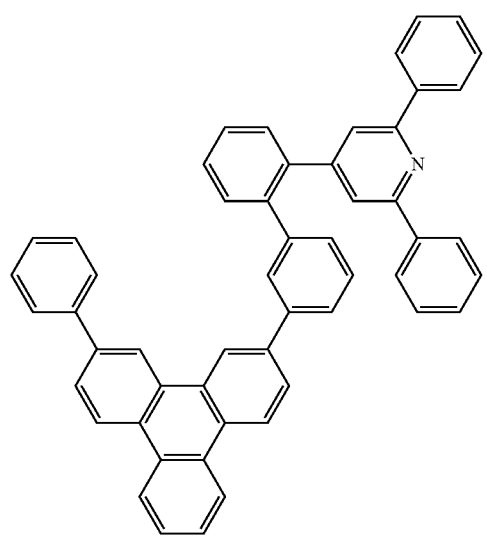
840
-continued
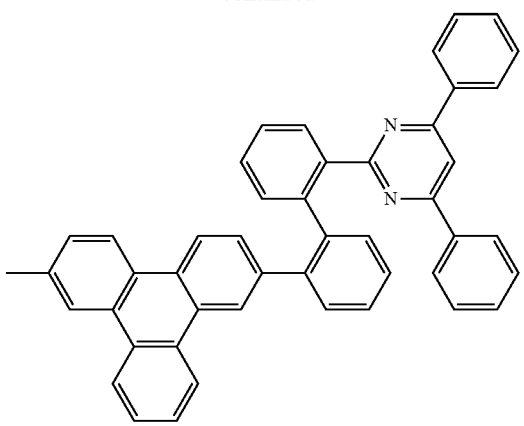
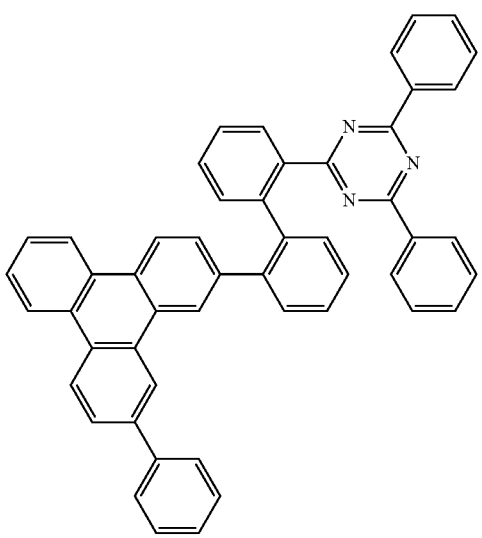
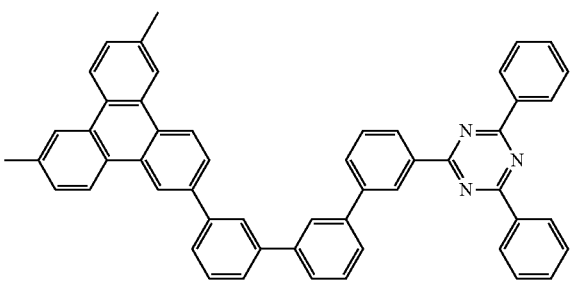

841
-continued
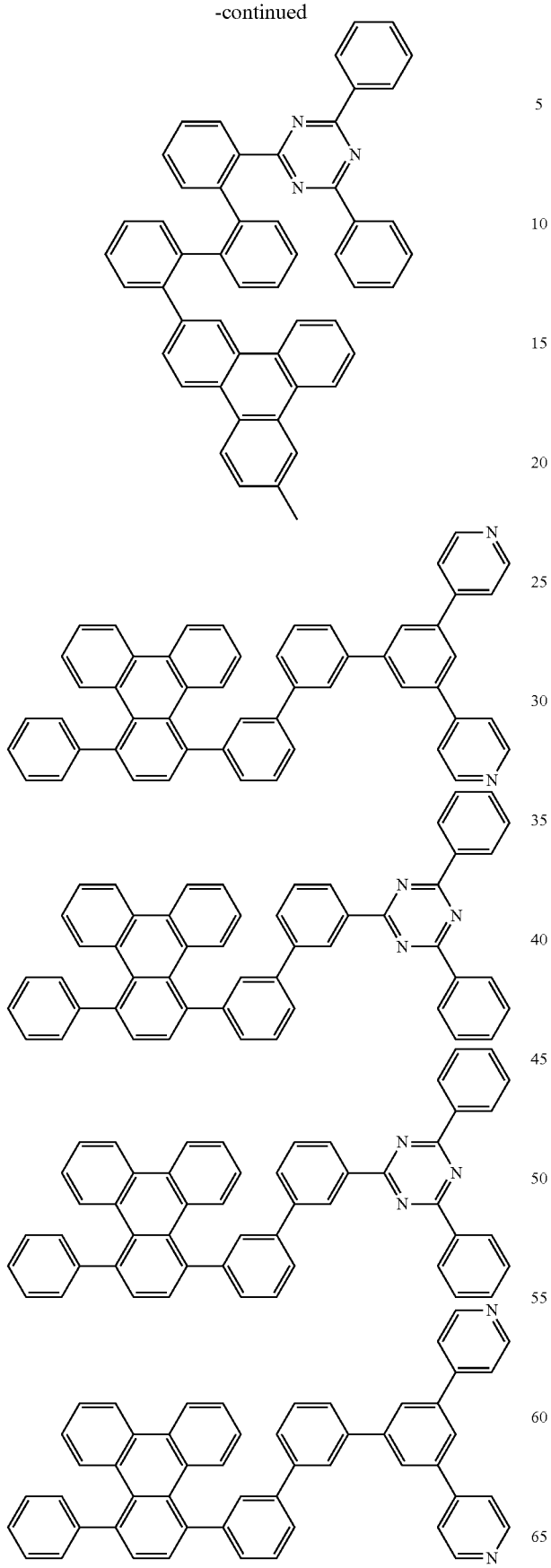
842
-continued
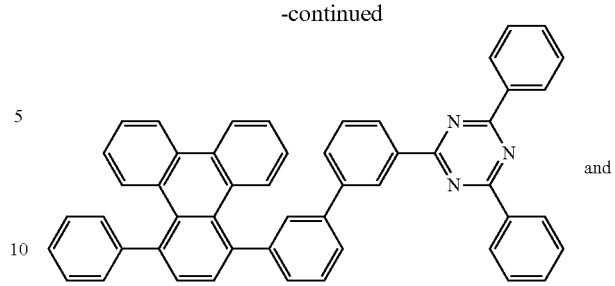
and
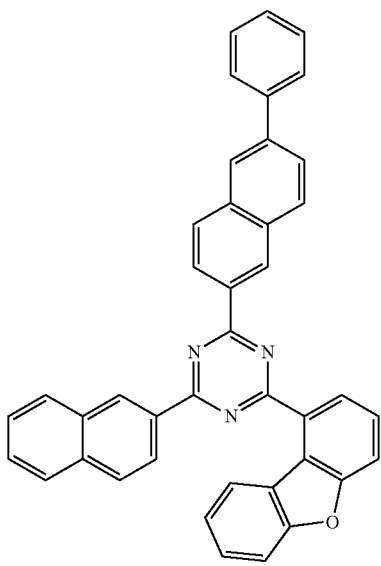
11. The organic electroluminescent material according to claim 8, wherein the compound represented by formula 13 or 14 is selected from the group consisting of the following:

843
-continued
844
-continued
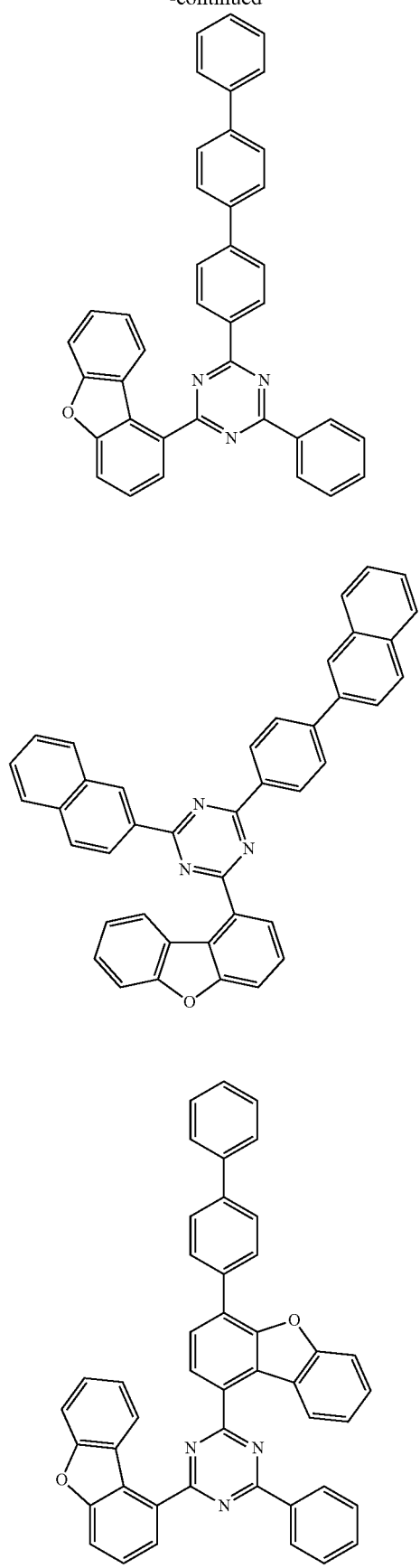
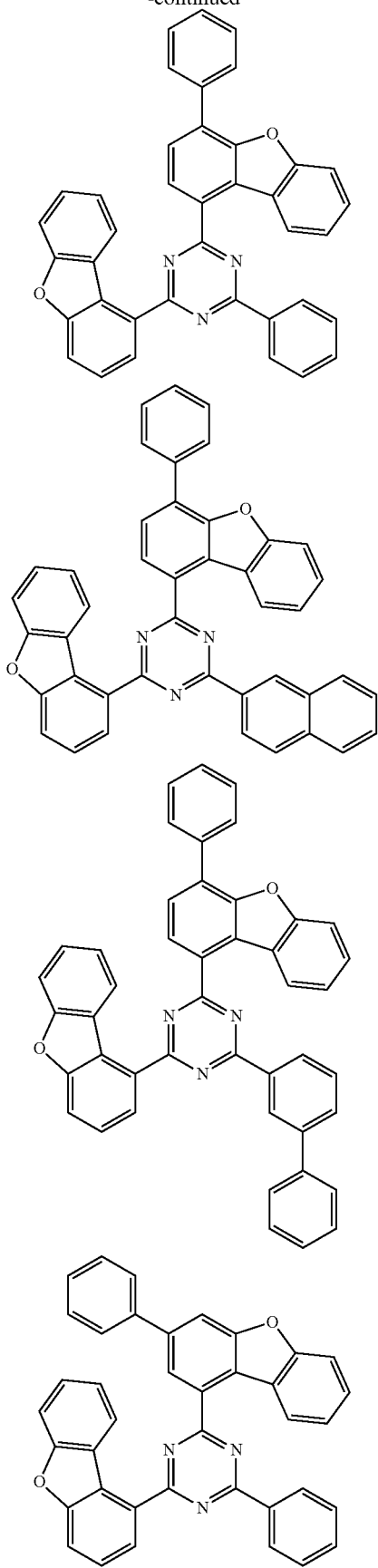

845
-continued
846
-continued
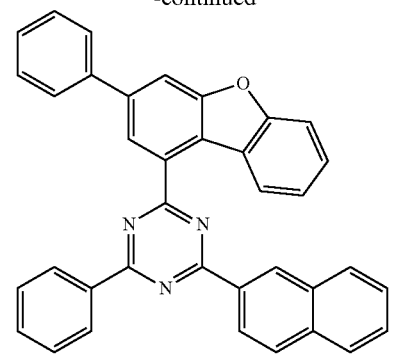
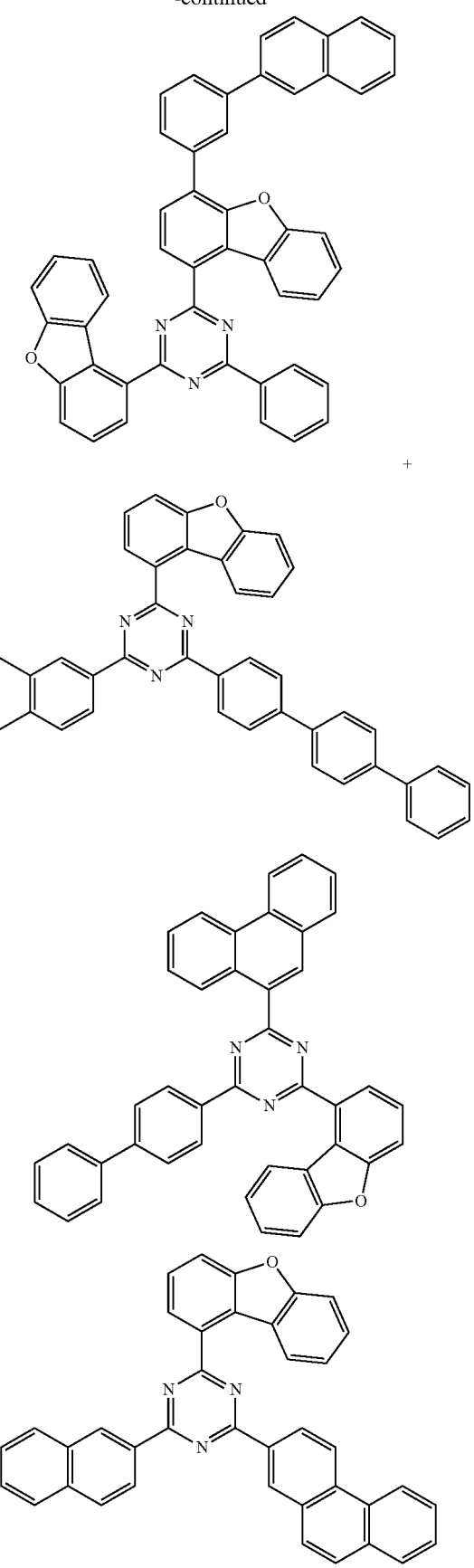

847
-continued
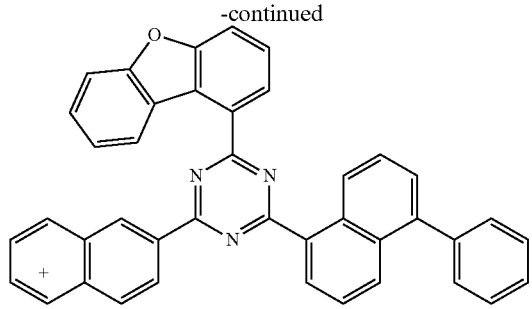
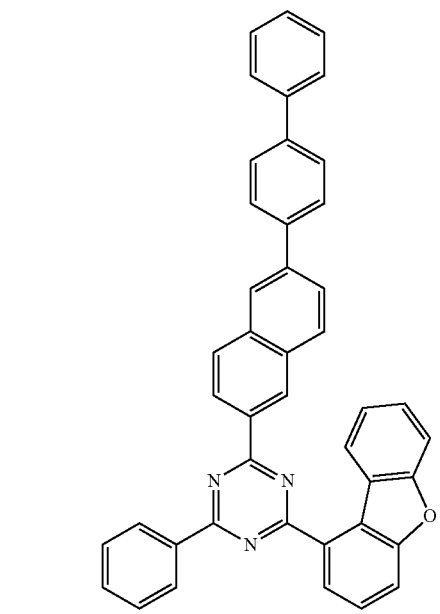
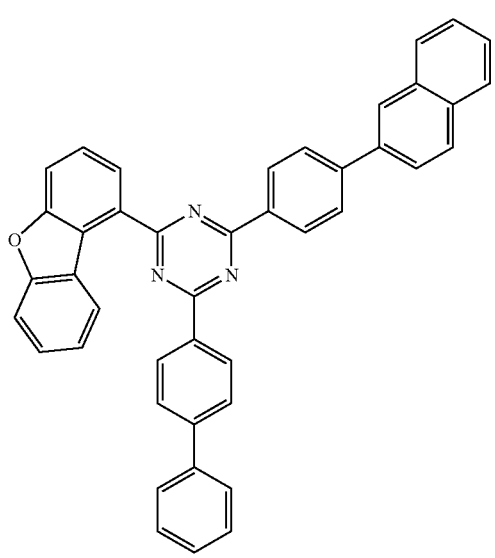
848
-continued
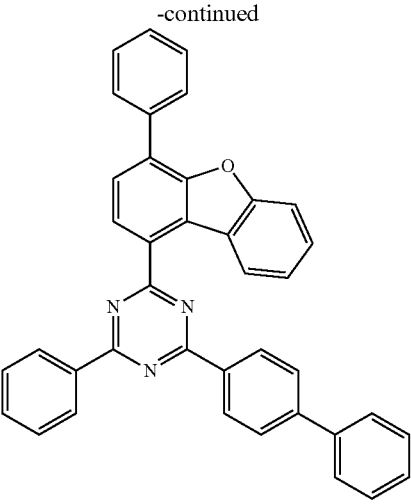
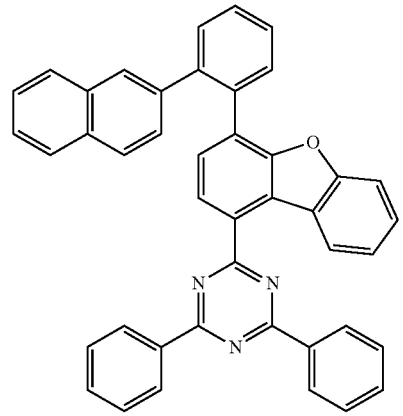
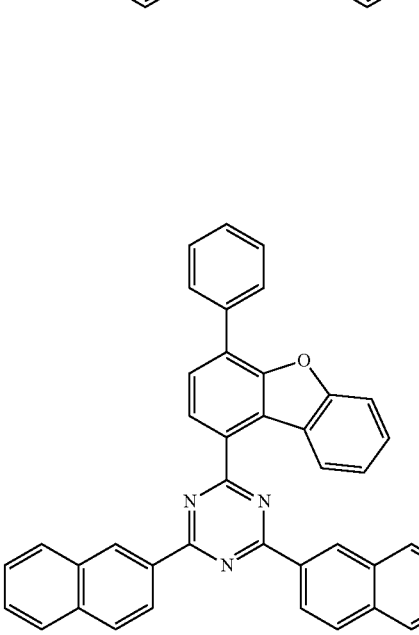

849
-continued
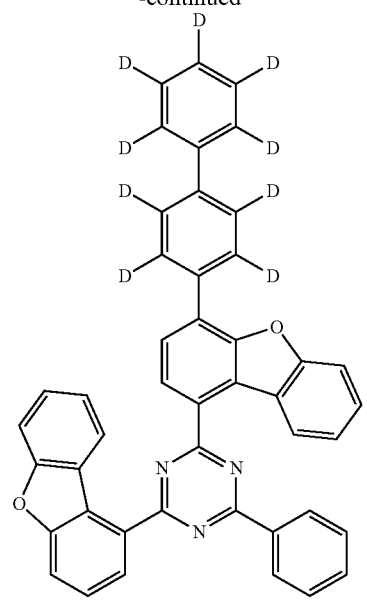
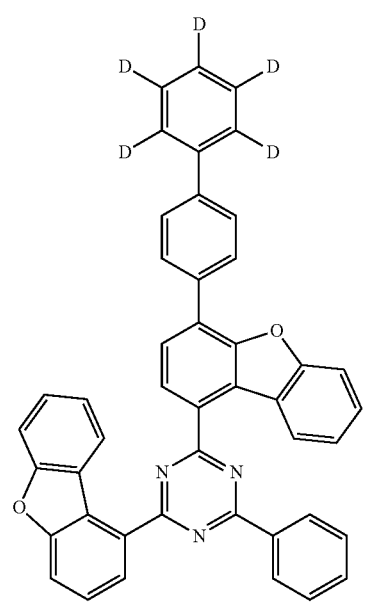
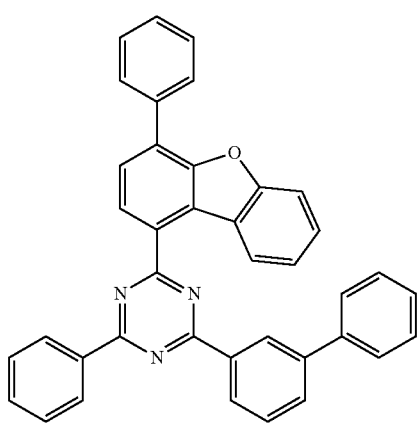
850
-continued
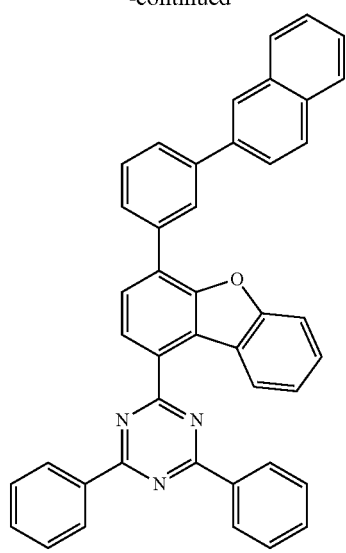
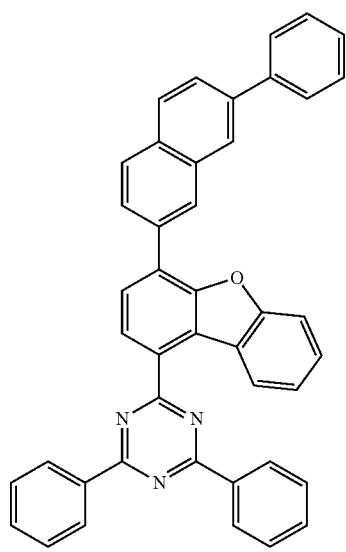
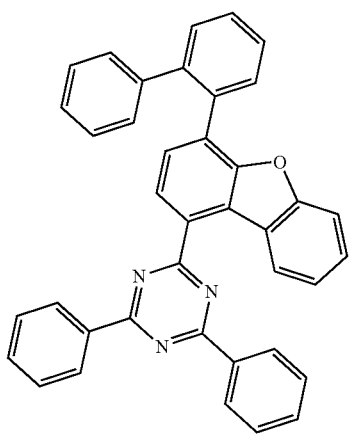

851
-continued
852
-continued
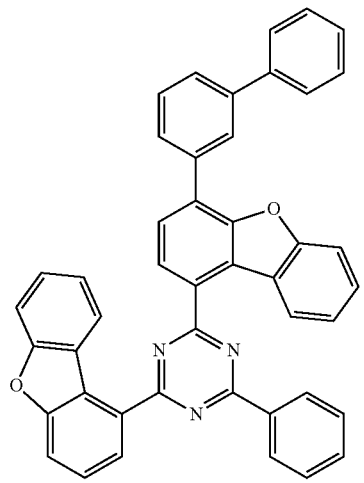
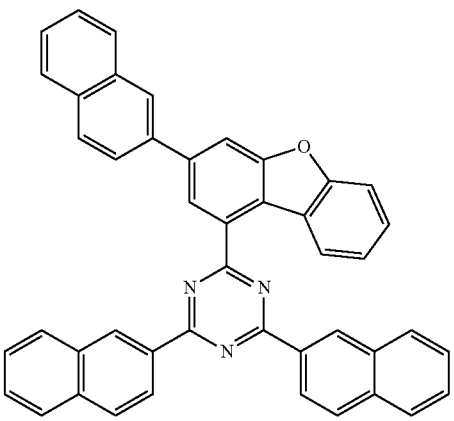
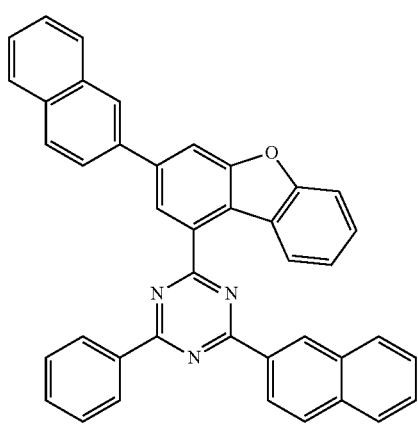
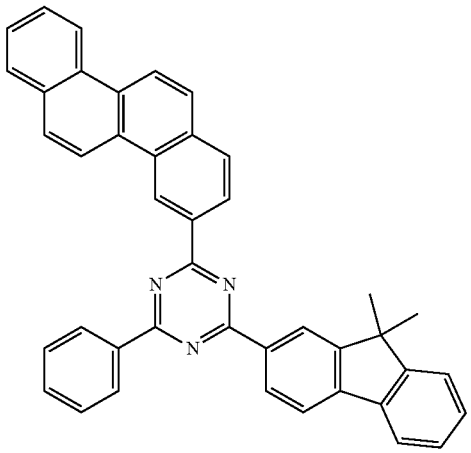
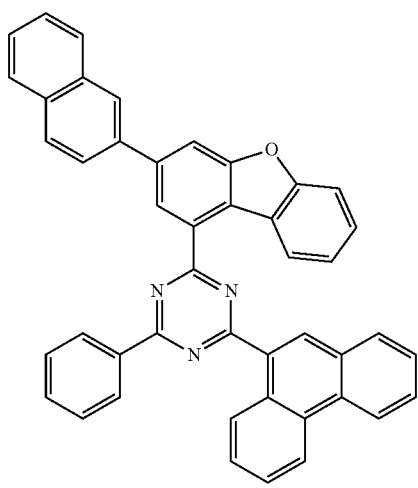
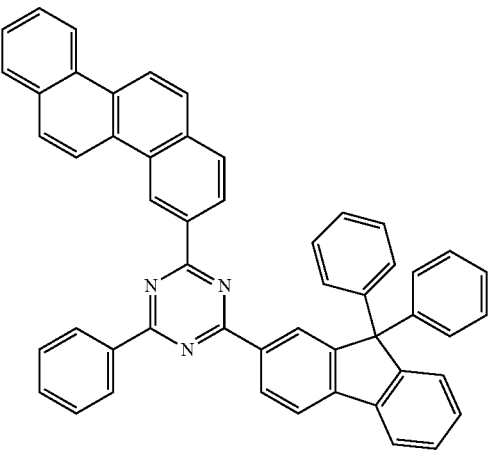

853
-continued
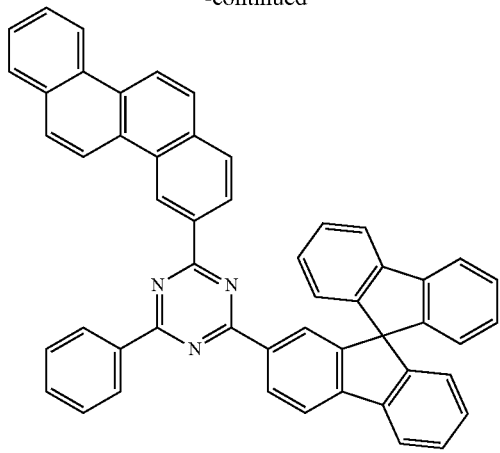
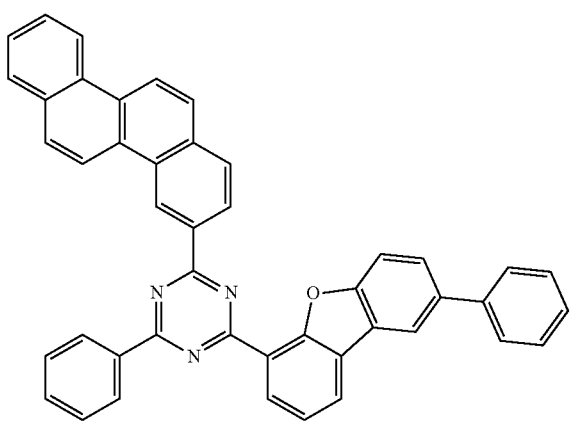
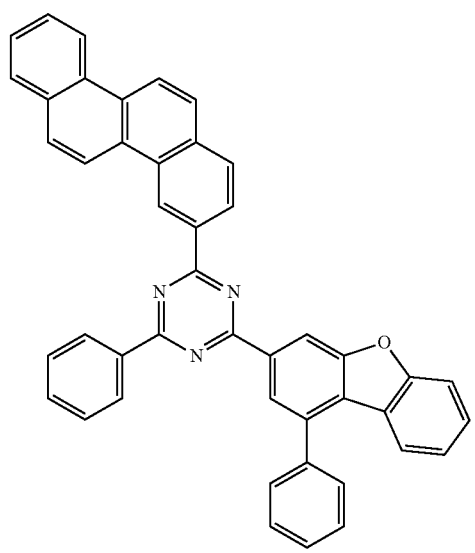
854
-continued
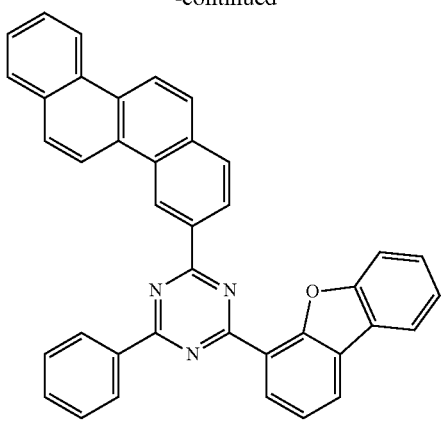
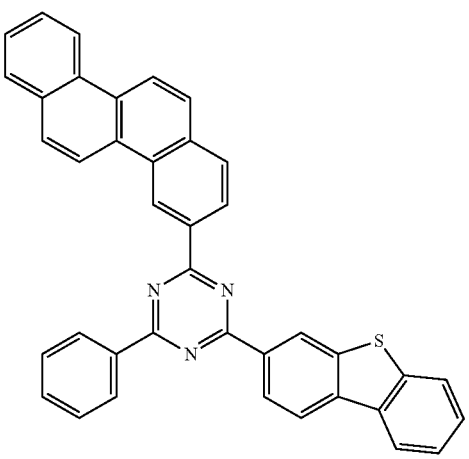
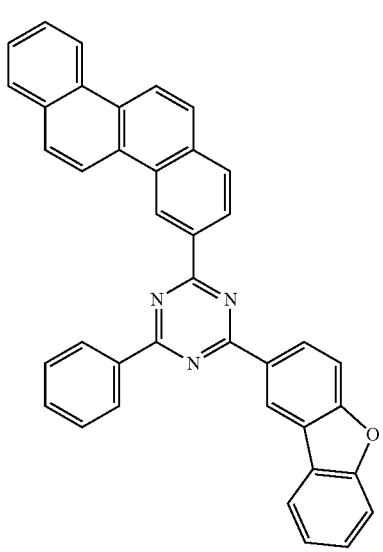

855
-continued
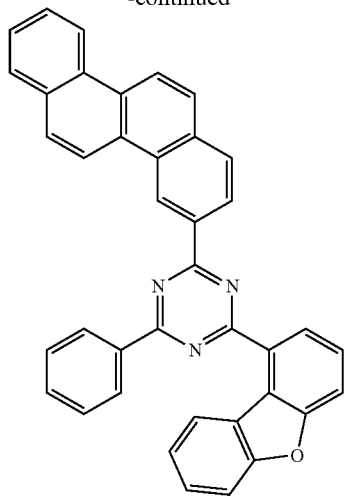
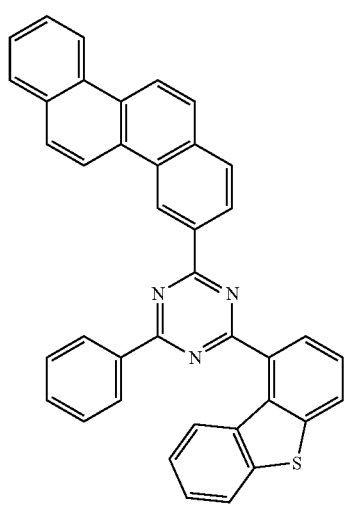
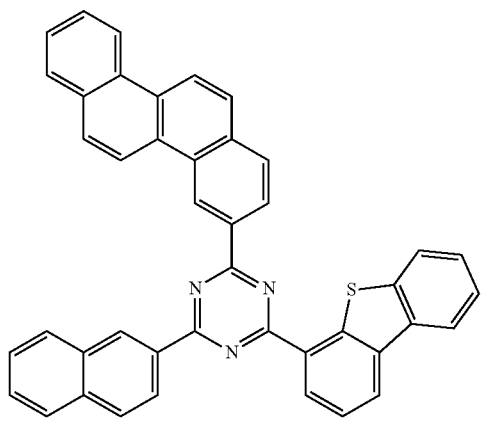
856
-continued
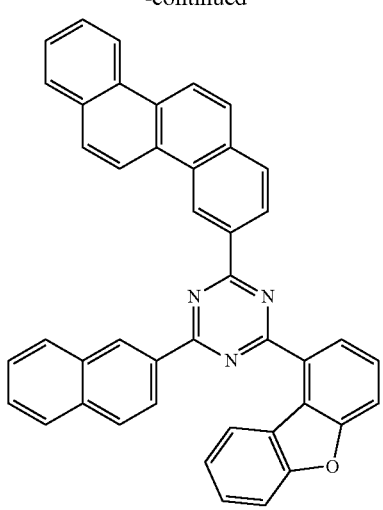
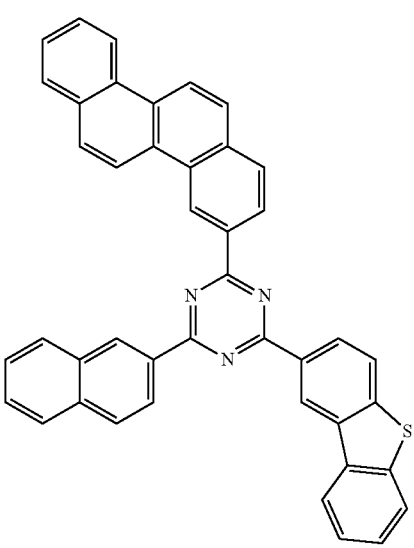
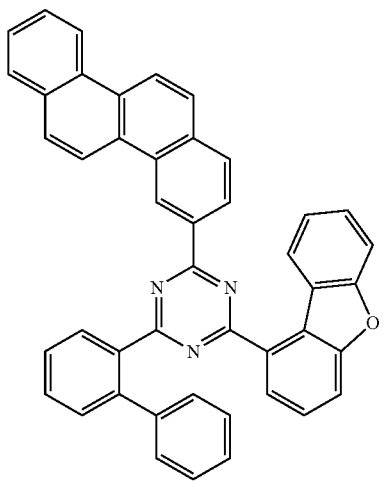

857
-continued
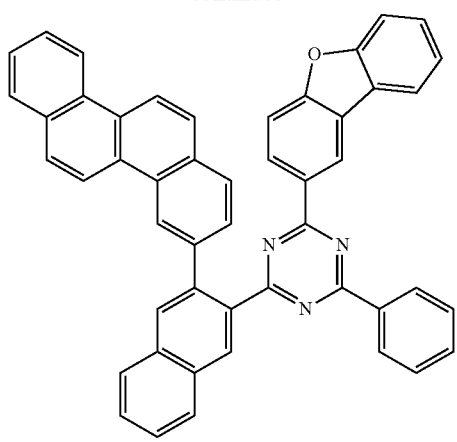
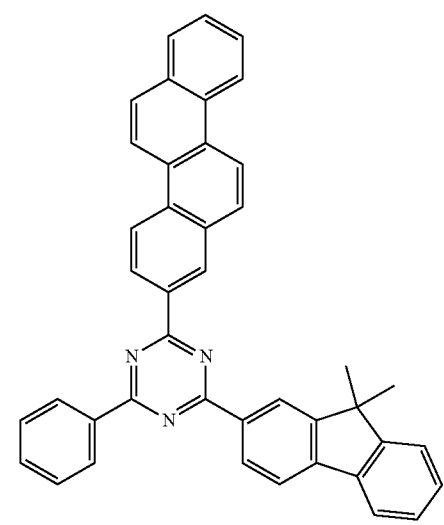
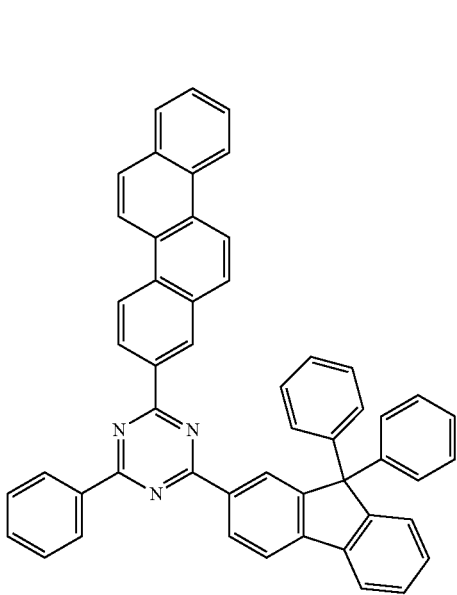
858
-continued
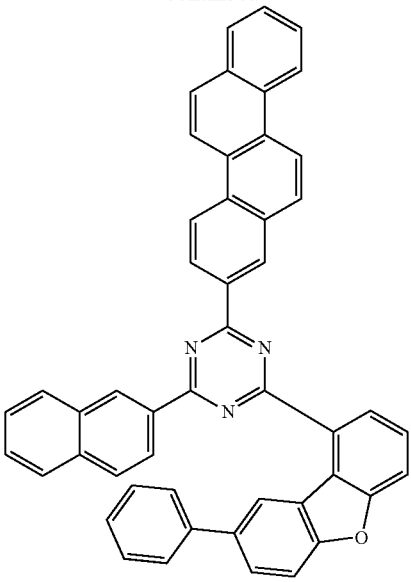
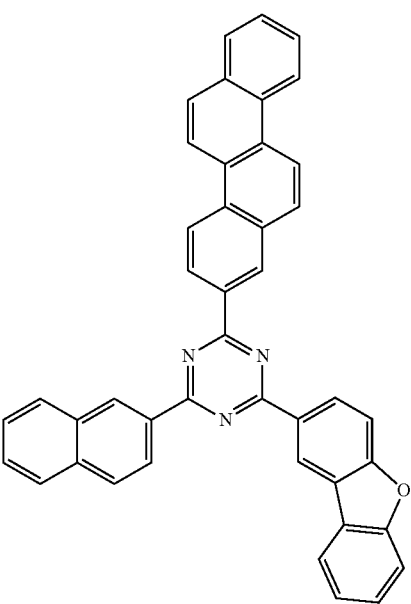

| 859 -continued | 860 -continued |
|---|---|
| 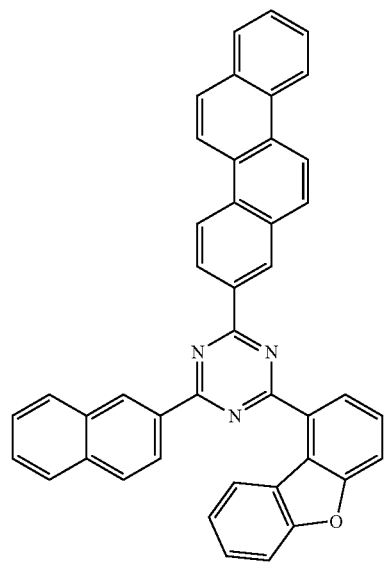 | 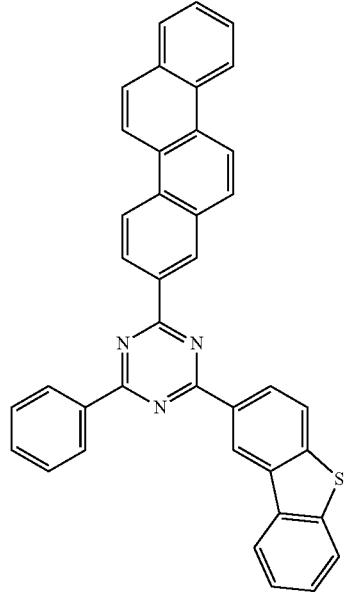 |
| 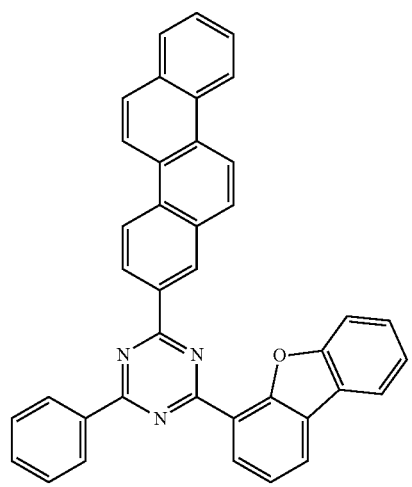 | 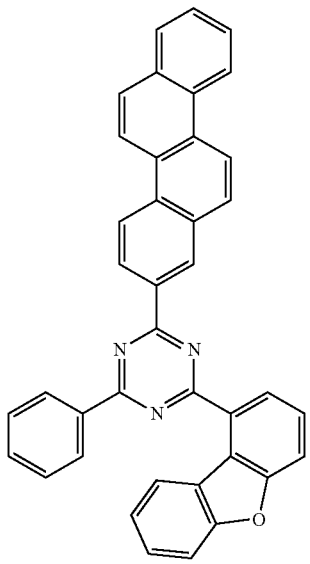 |
| 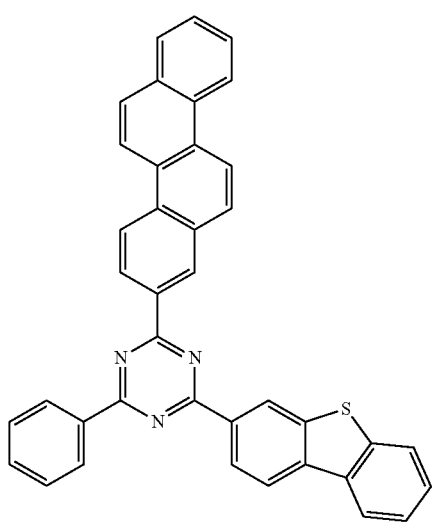 | 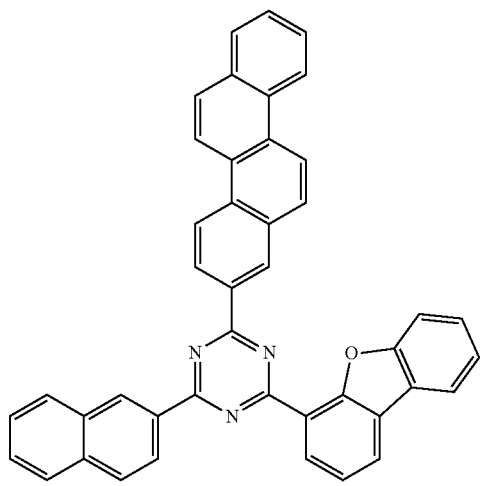 |

861
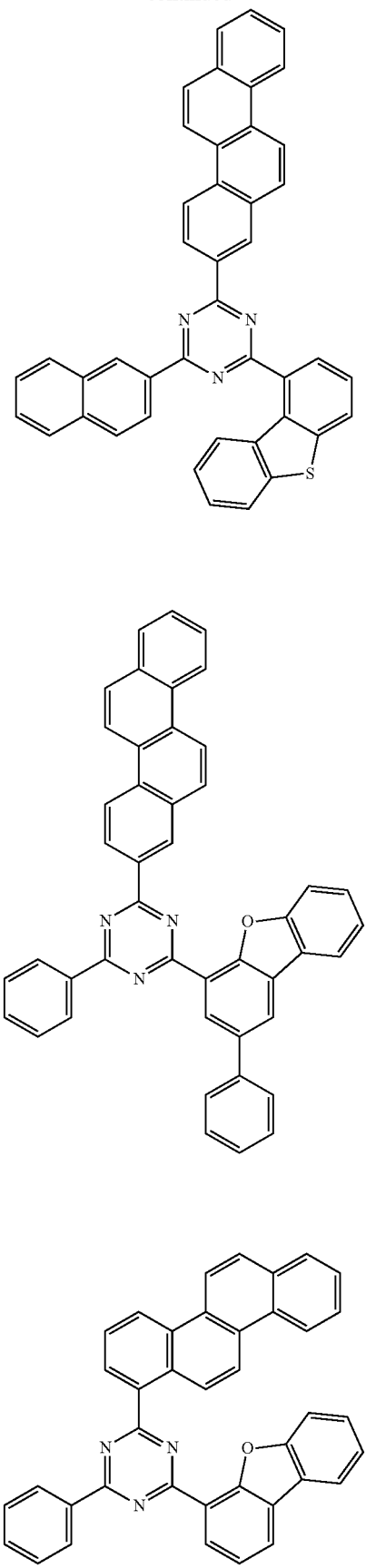
862
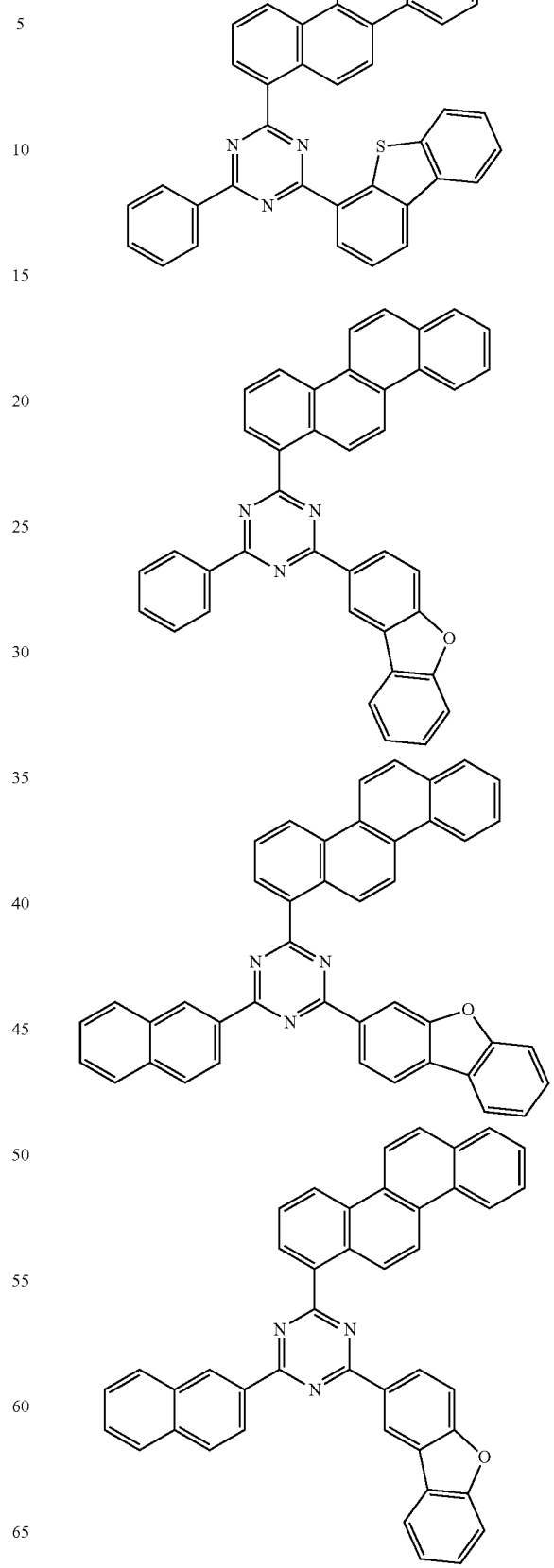

-continued
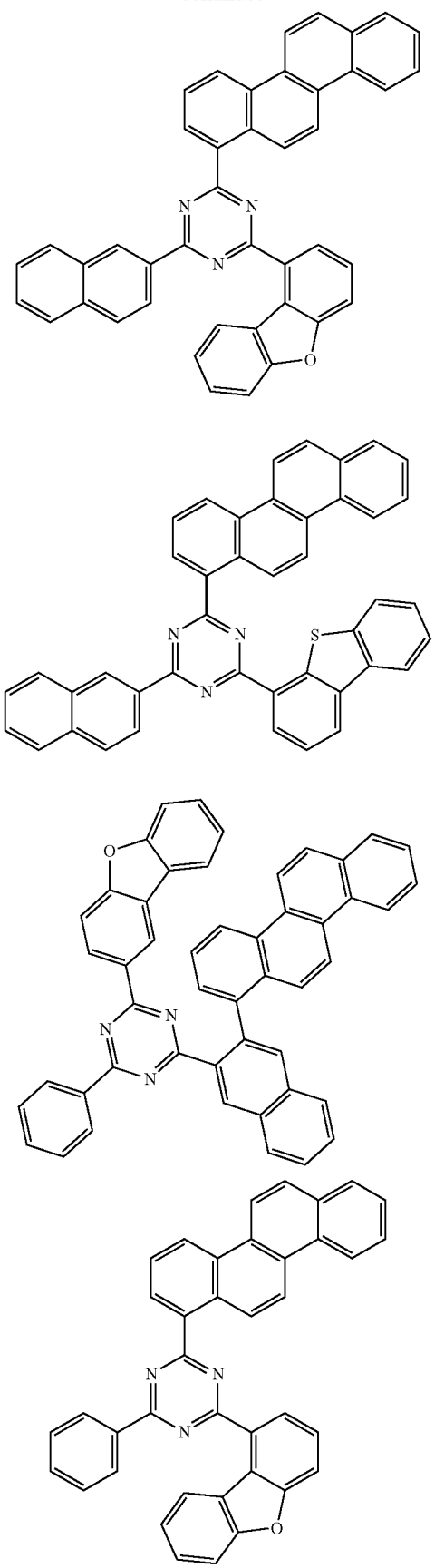
-continued
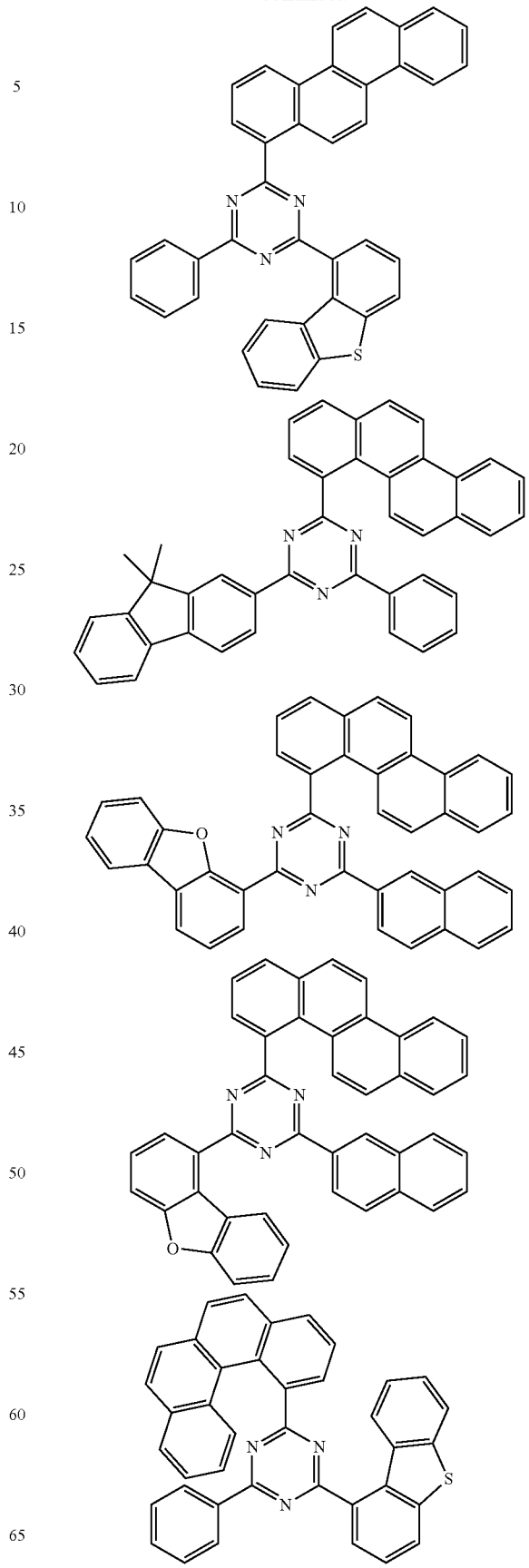

865
-continued
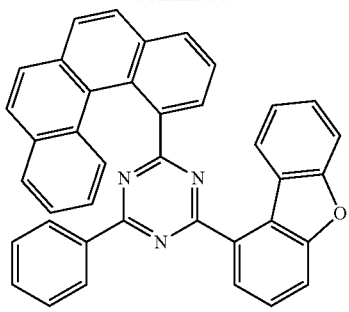
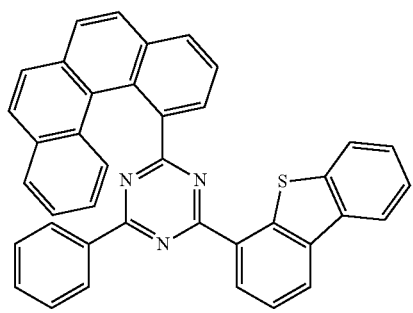
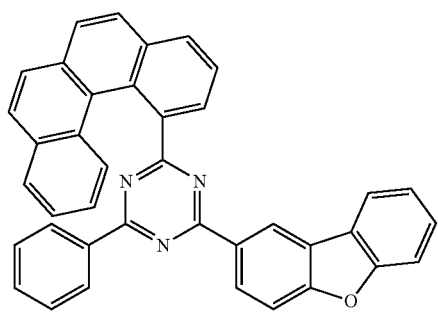
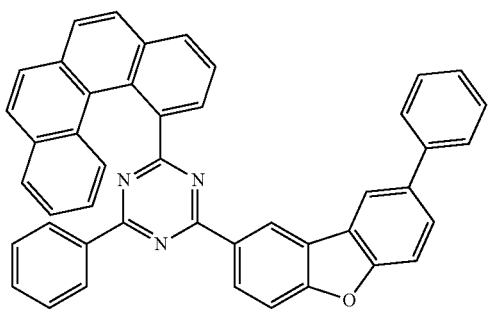
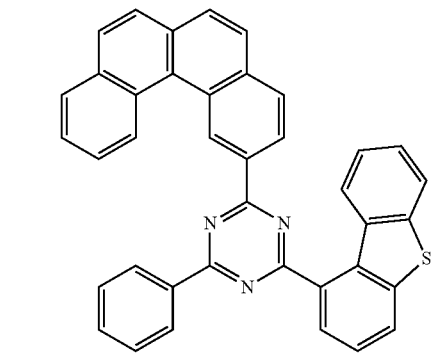
866
-continued
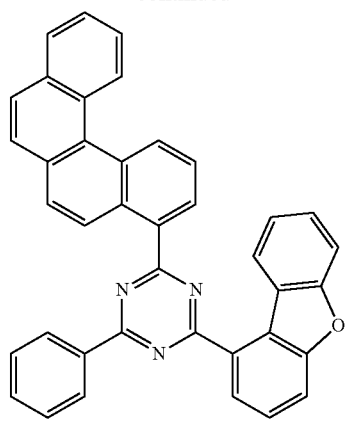
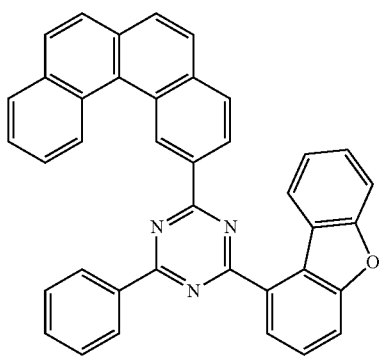
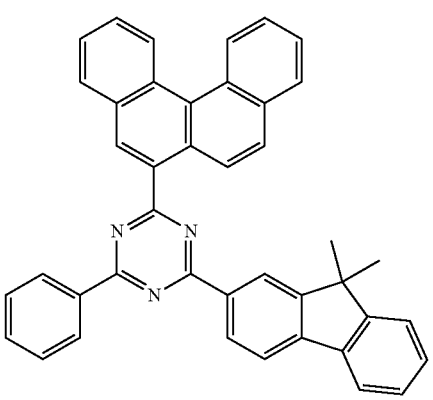
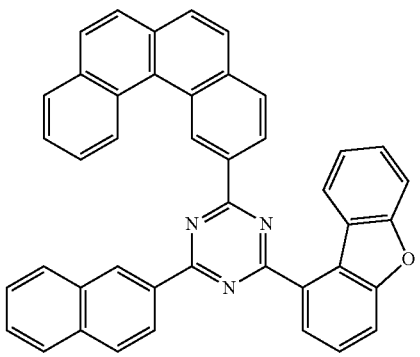

867
-continued
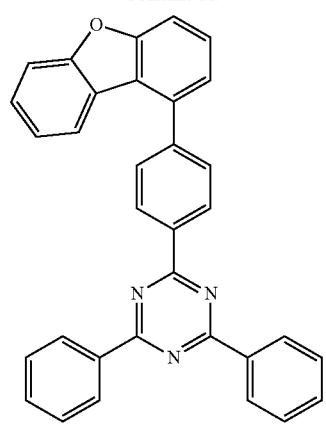
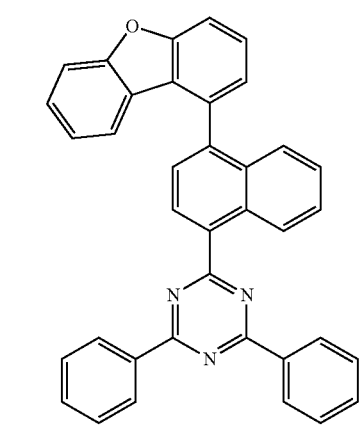
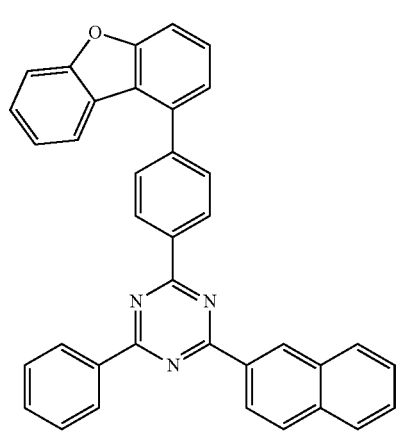
868
-continued
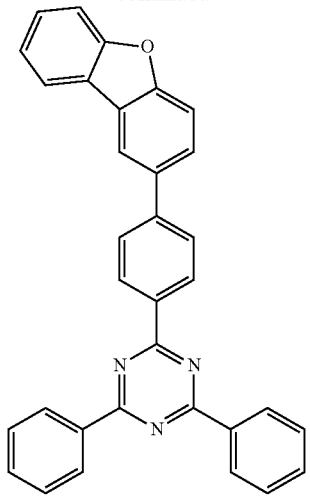
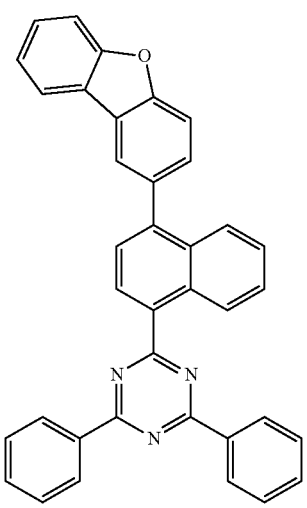
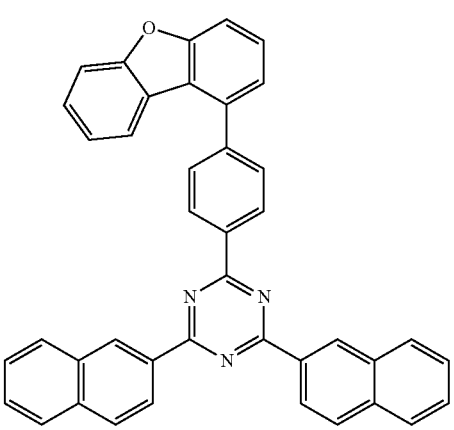

869
-continued
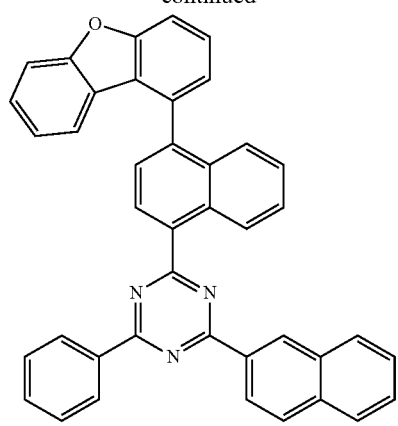
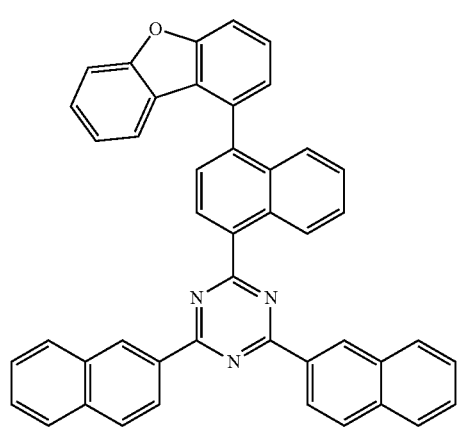
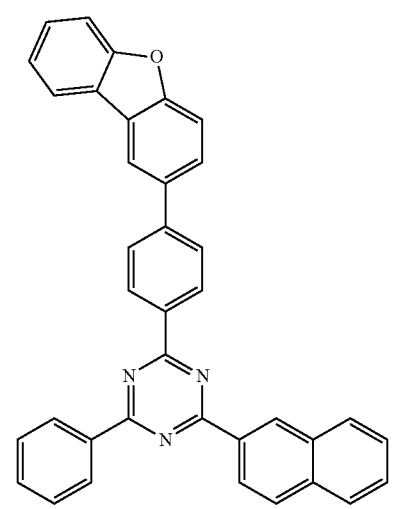
870
-continued
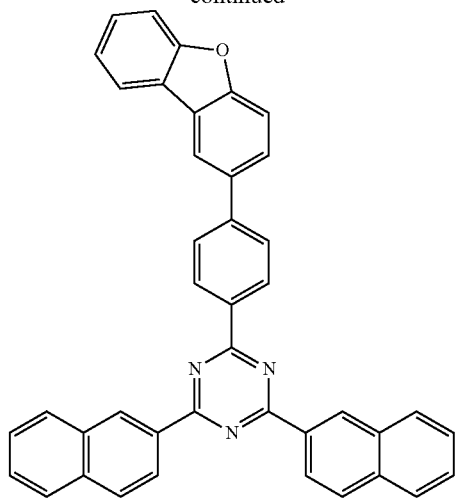
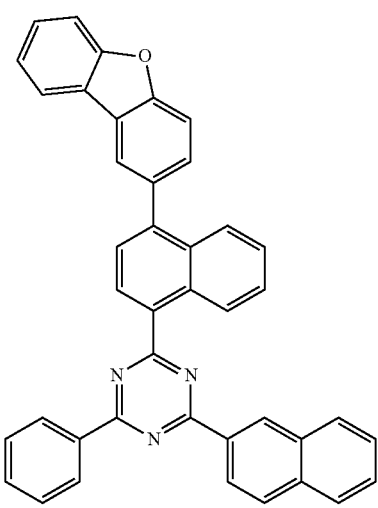
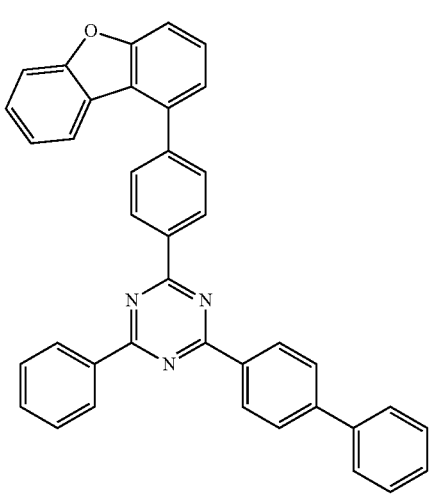

871
-continued
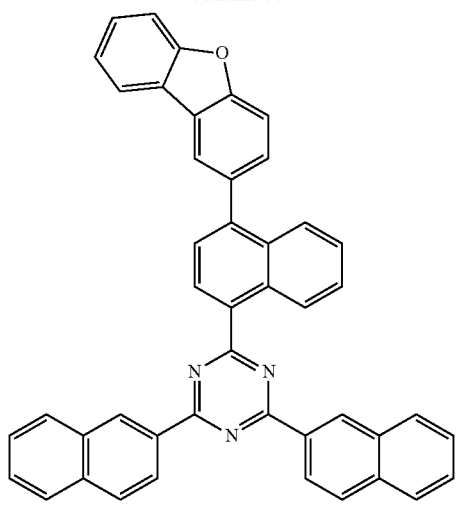
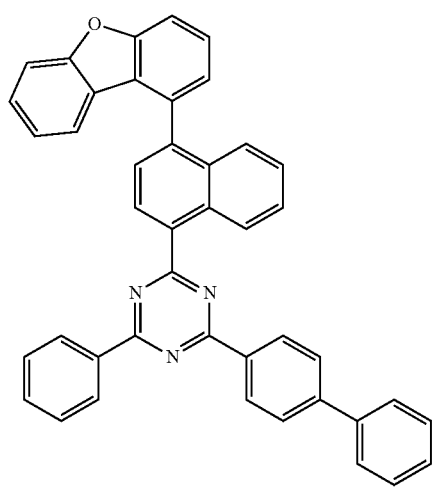
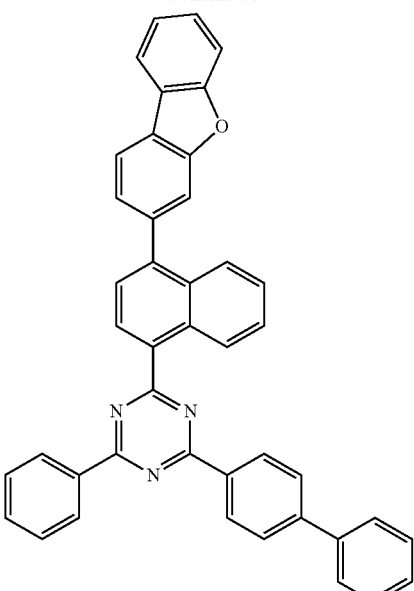
872
-continued
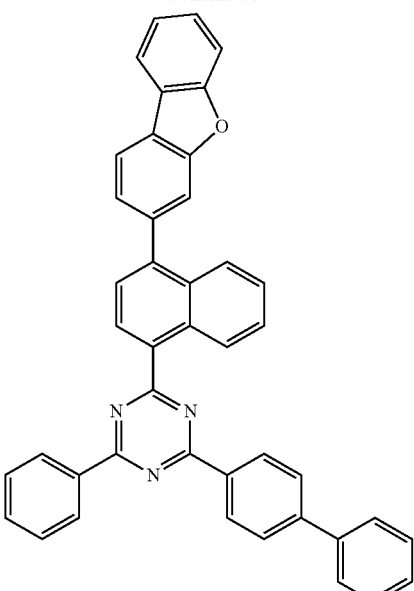
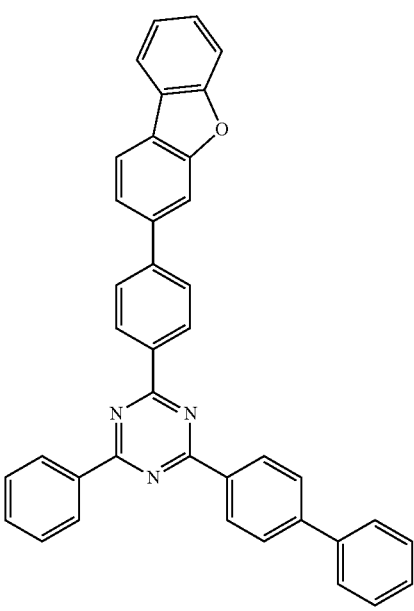 [SMILES: c1ccc(-c2ccc(-c3nc(-c4ccccc4)nc(-c4ccc(-c5ccc6c(c5)oc5ccccc56)c5ccccc45)n3)cc2)cc1]

873
-continued
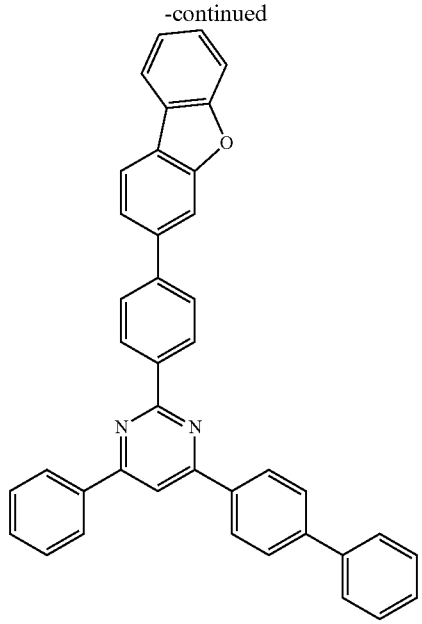
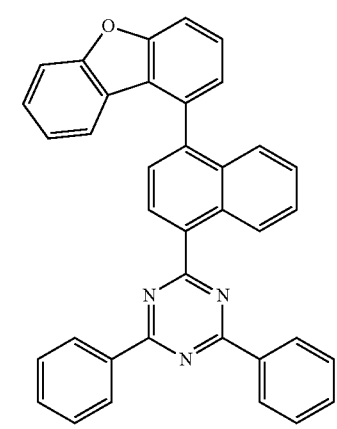
874
-continued
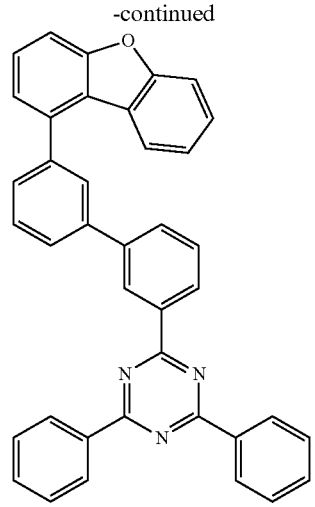
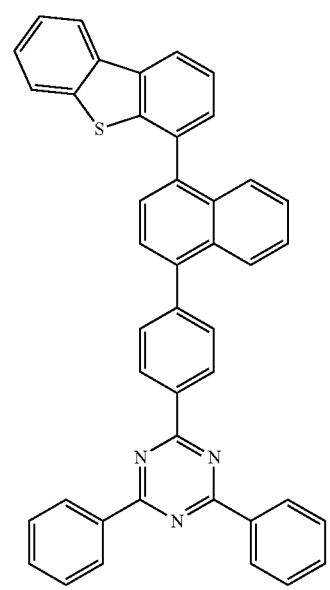
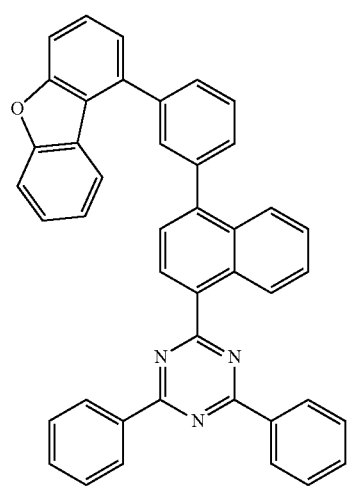
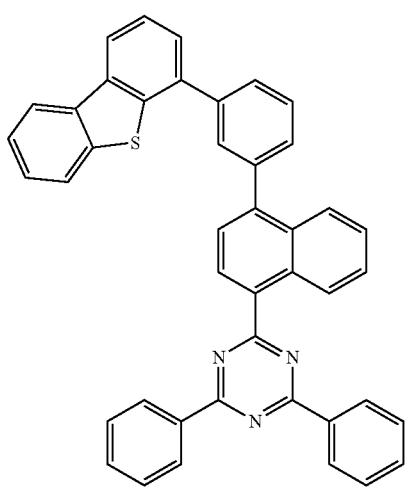

875
-continued
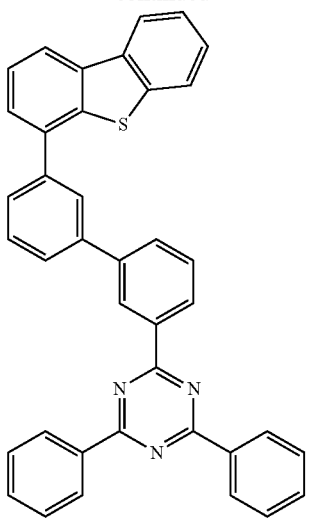
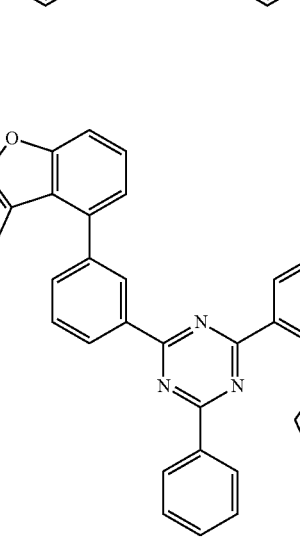
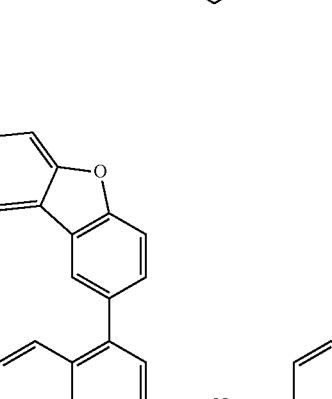
876
-continued
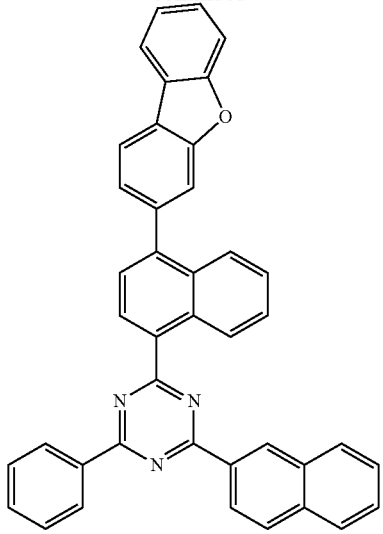
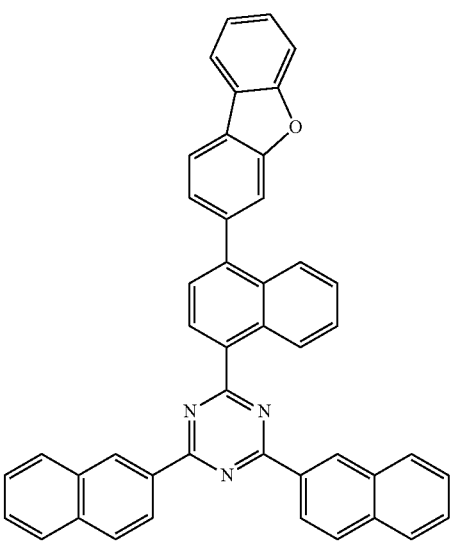
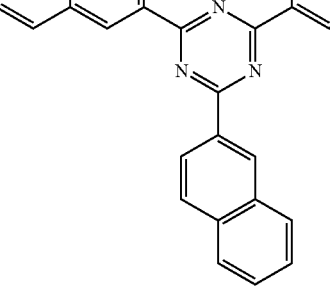
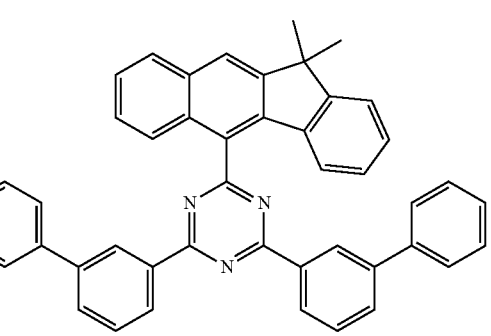

877
-continued
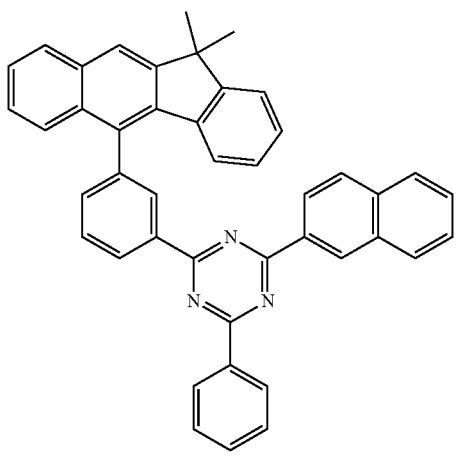
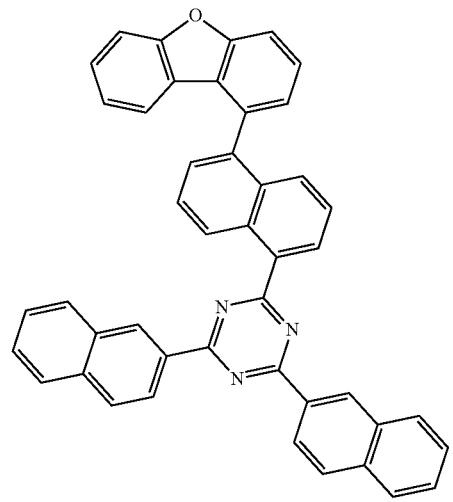
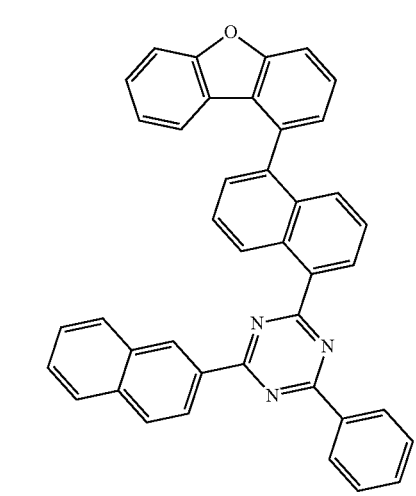
878
-continued
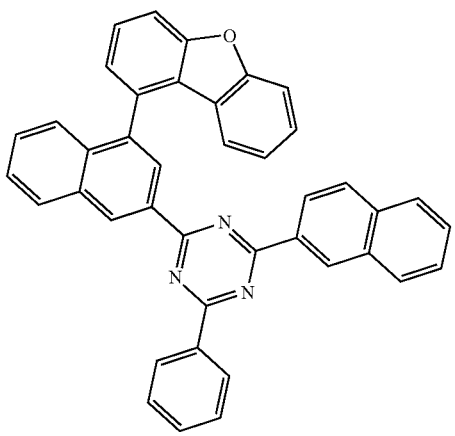
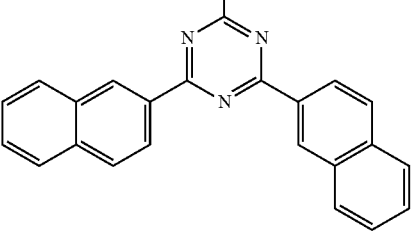
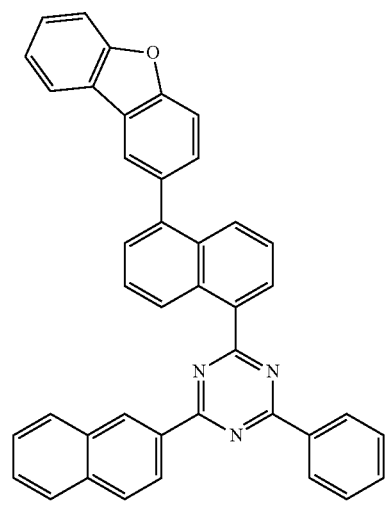

879
-continued
880
-continued
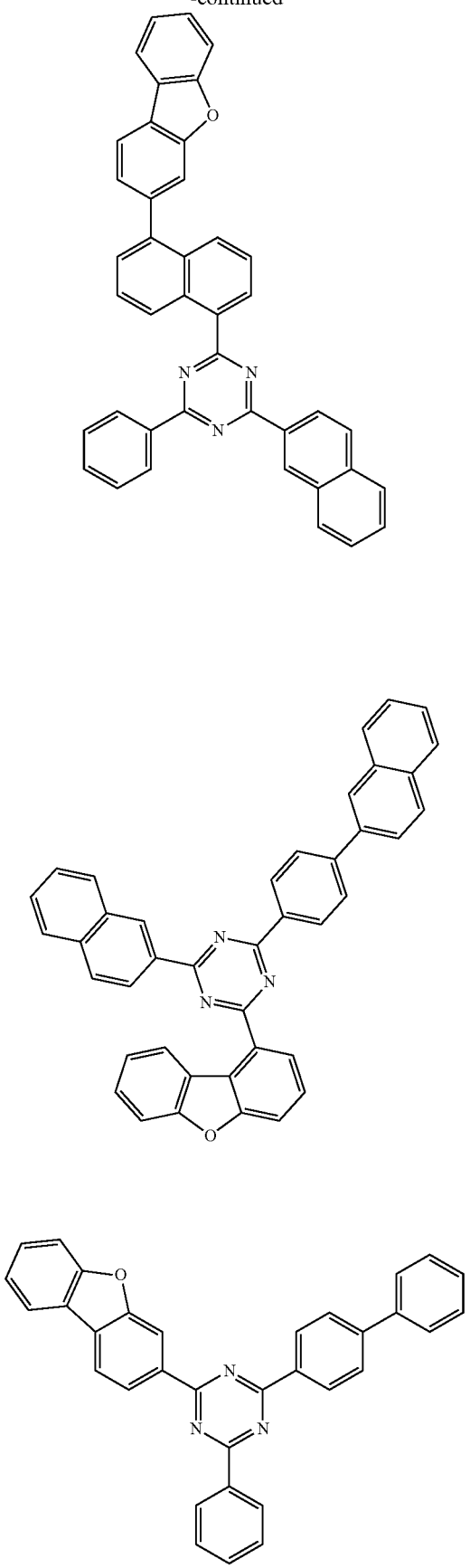
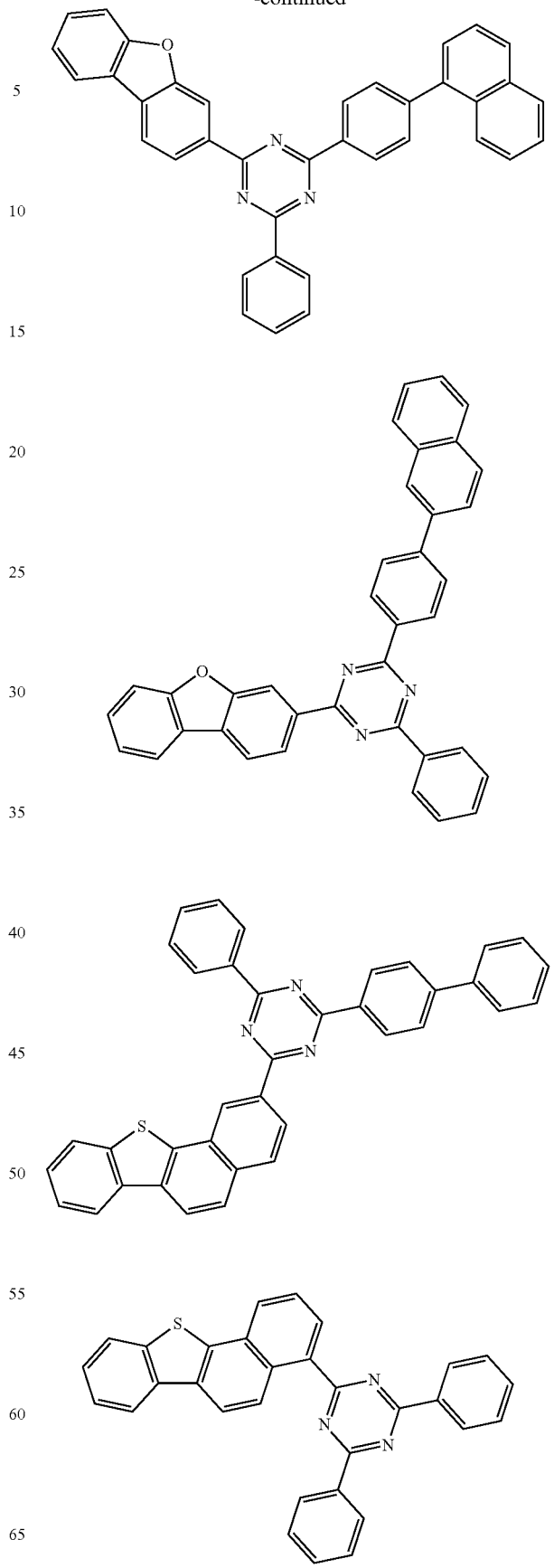

881
-continued
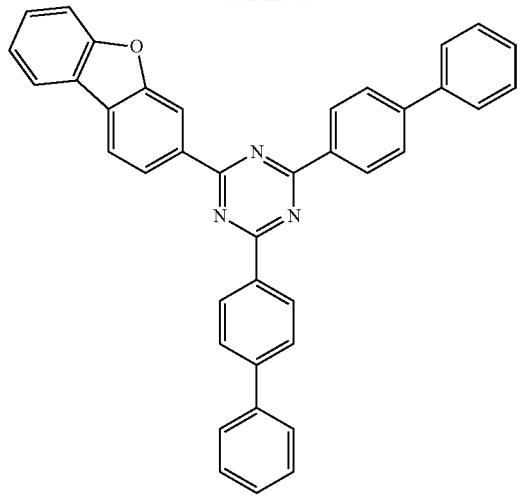
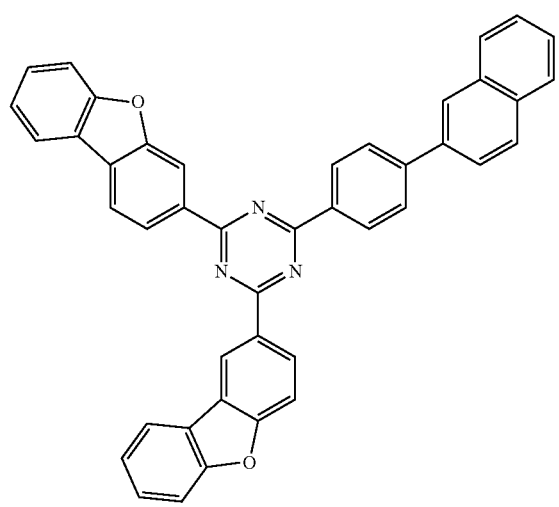
882
-continued
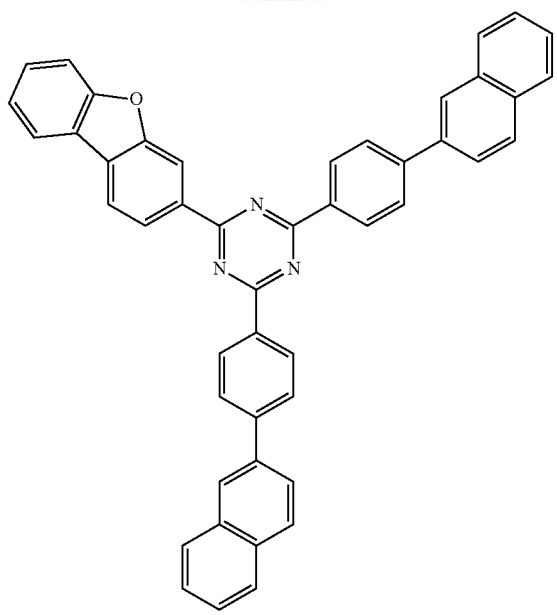
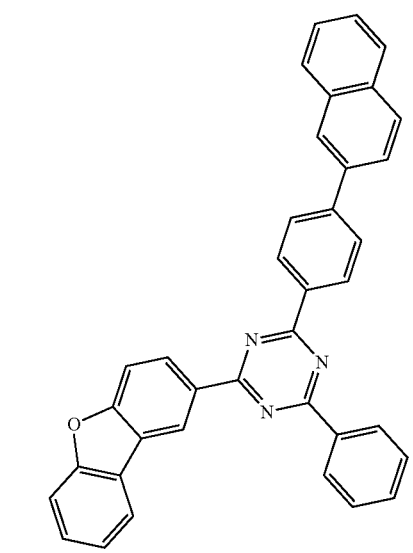
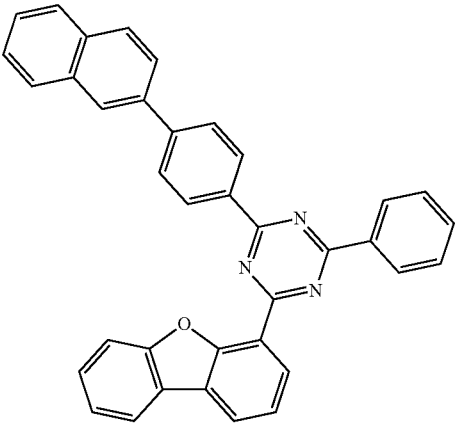

883
-continued
884
-continued
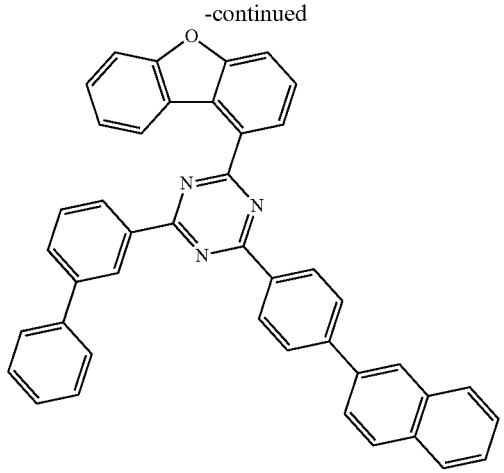
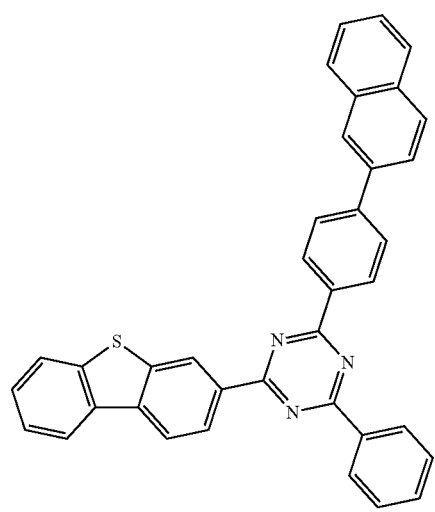
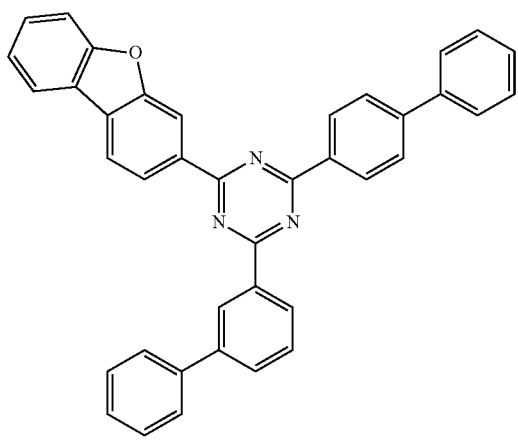
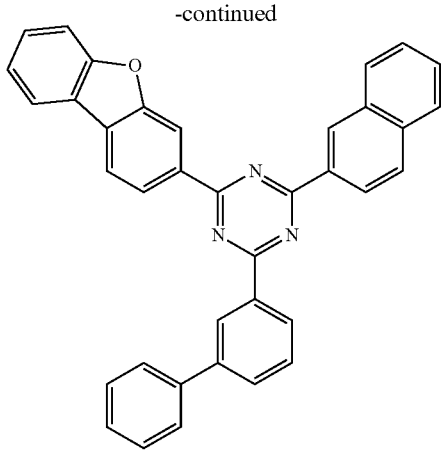
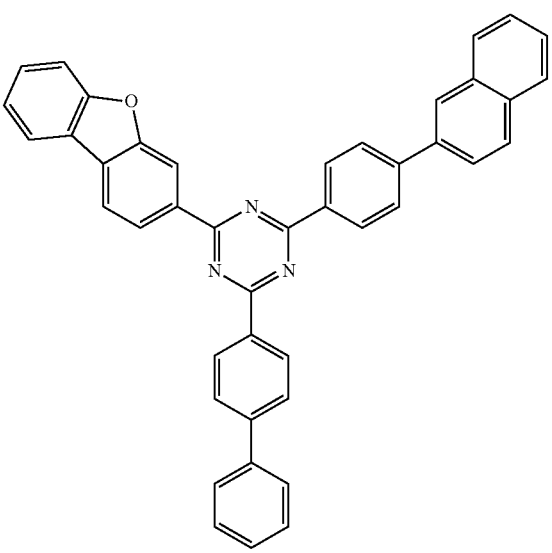

885
-continued
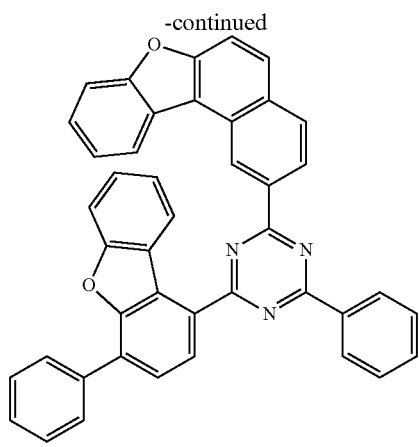
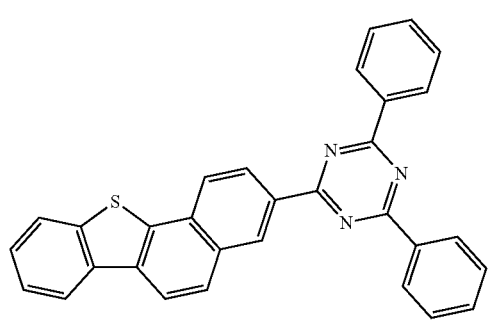
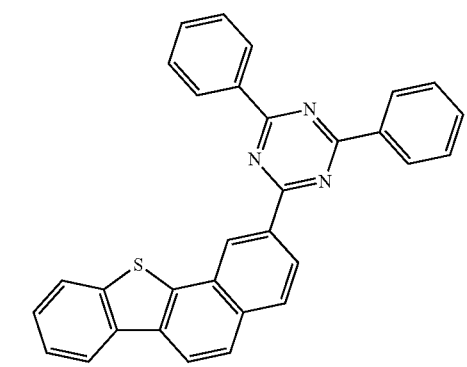
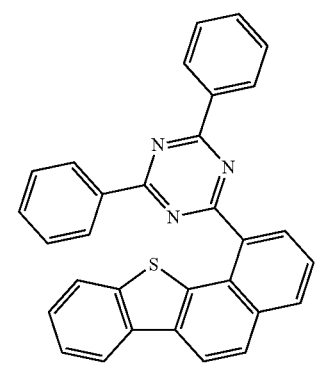
886
-continued
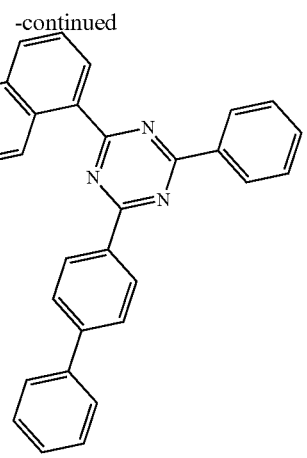
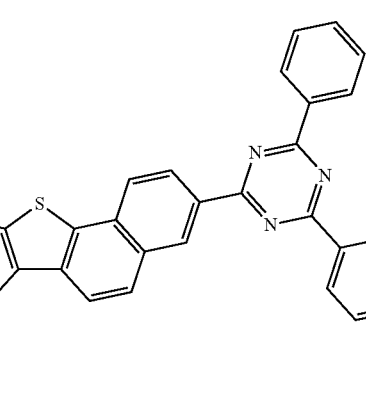
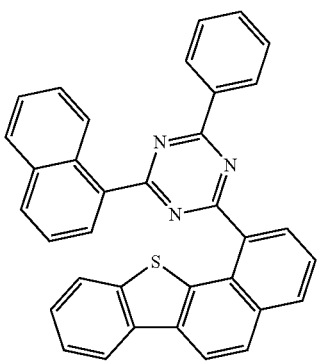
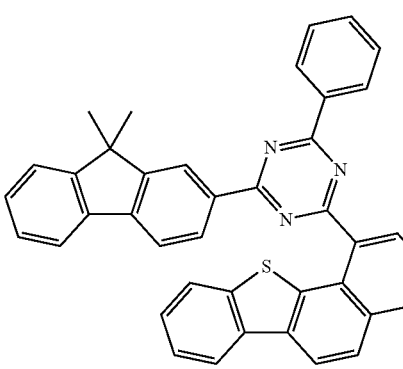

887
-continued
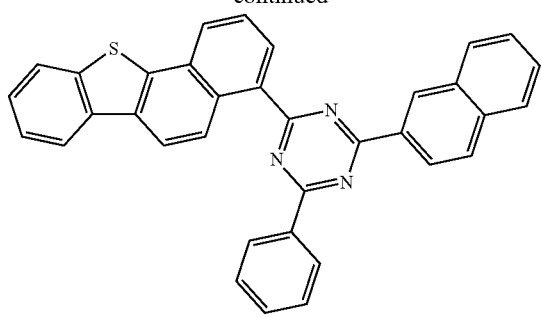
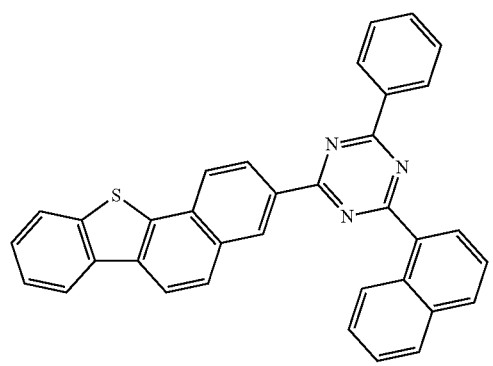
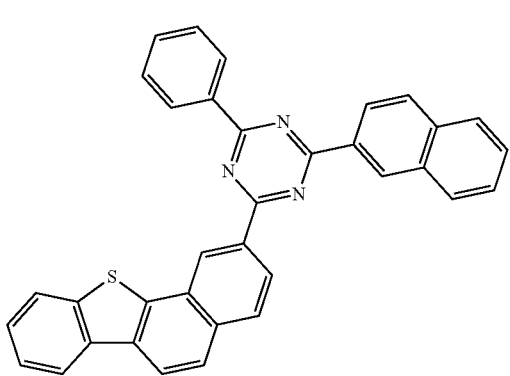
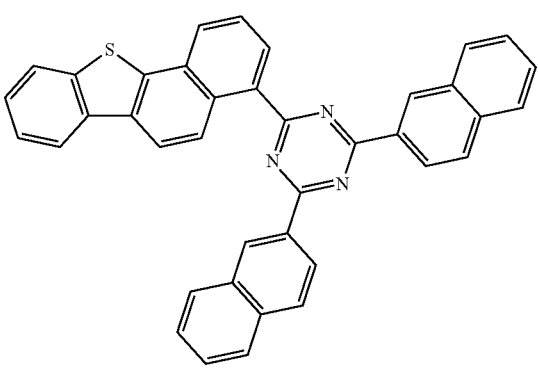
888
-continued
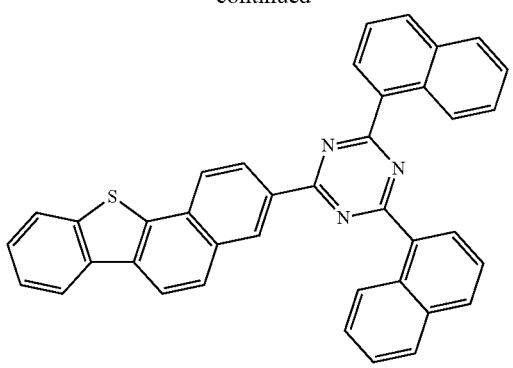
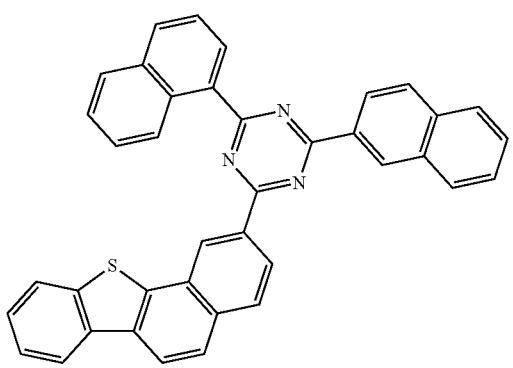
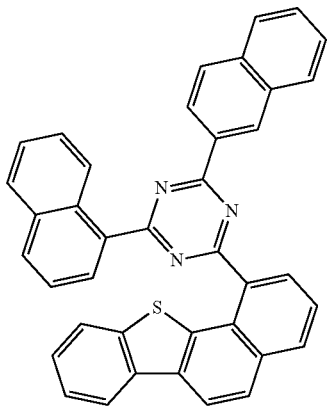
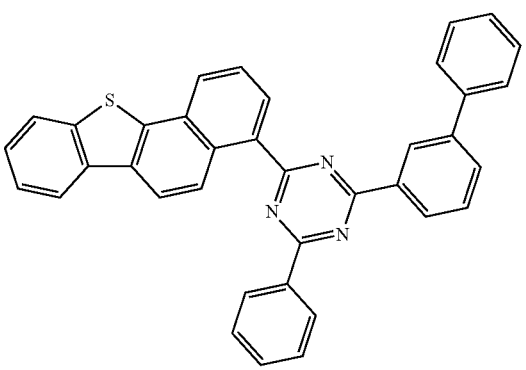

889
-continued
890
-continued
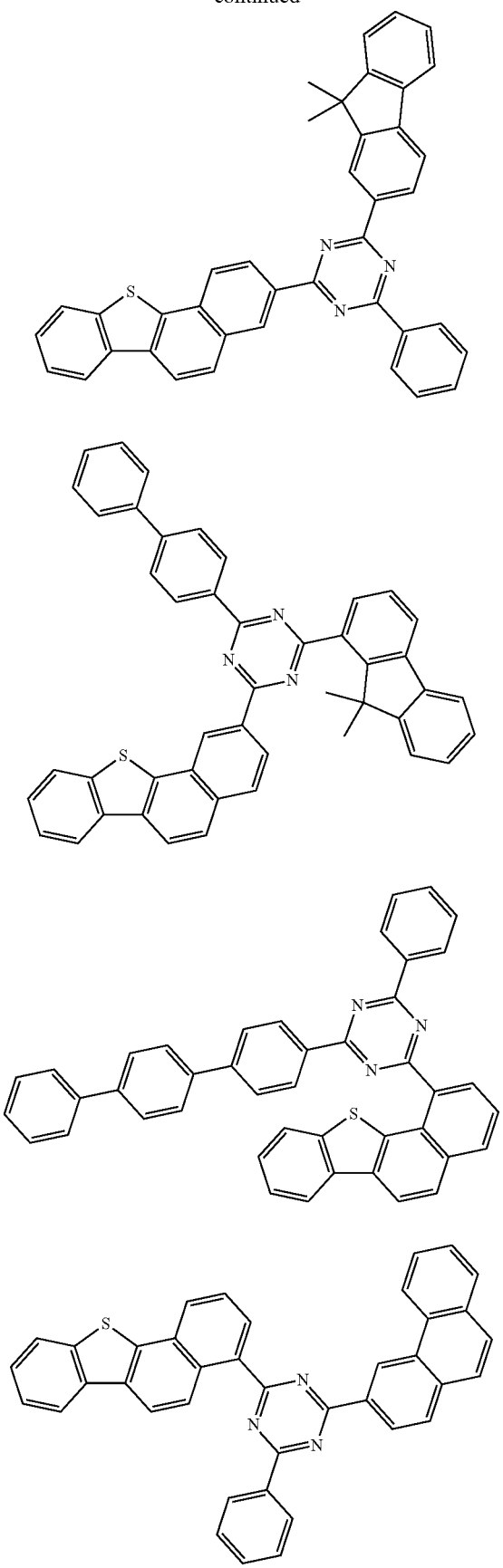
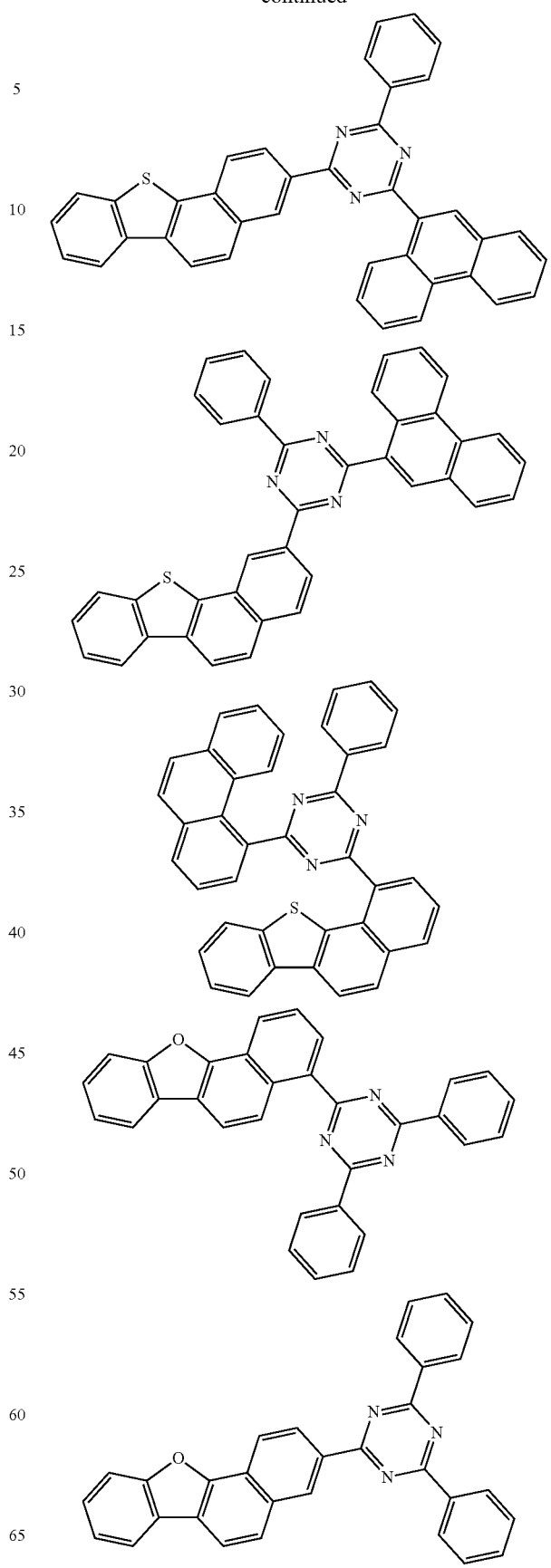

891
-continued
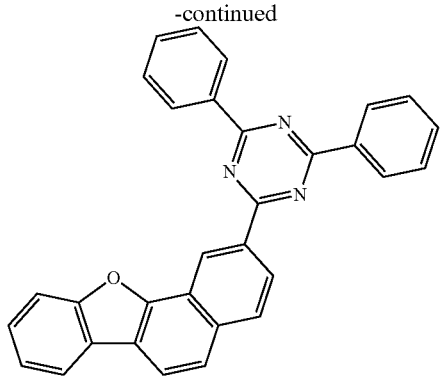
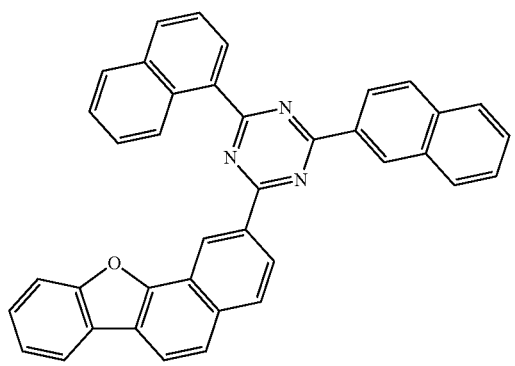
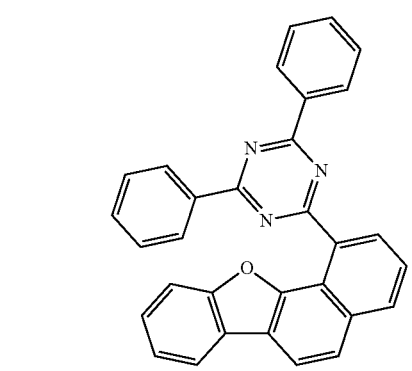
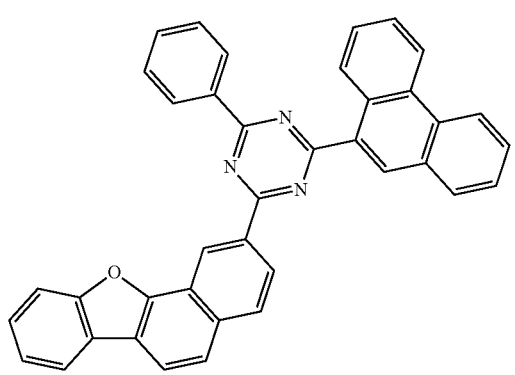
892
-continued
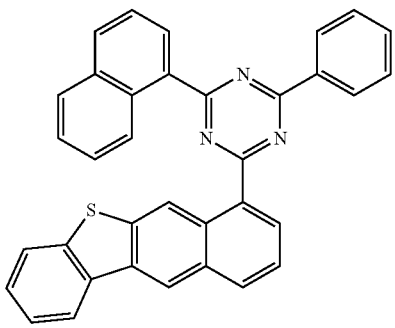
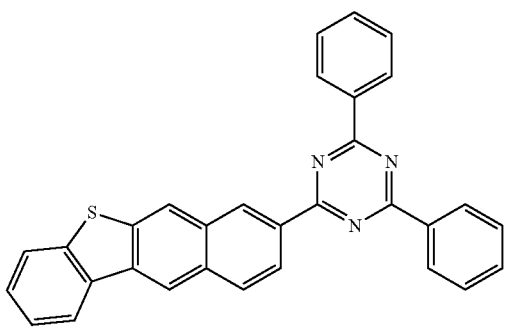
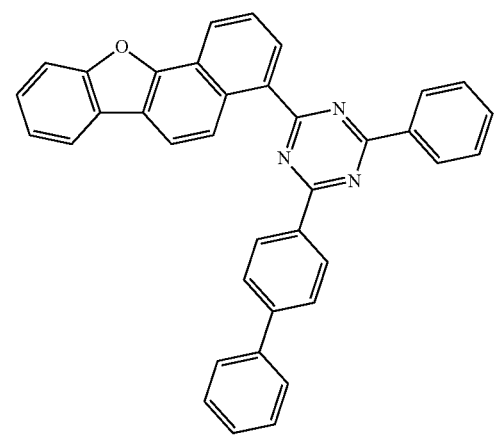
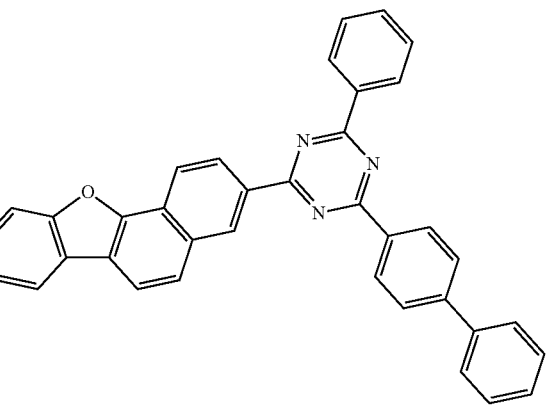

893
-continued
894
-continued
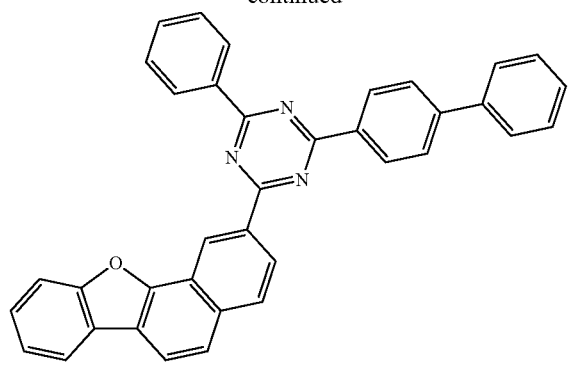
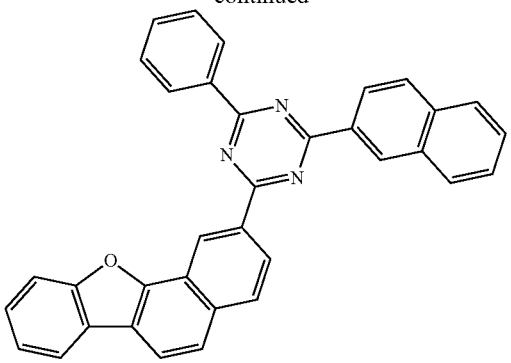
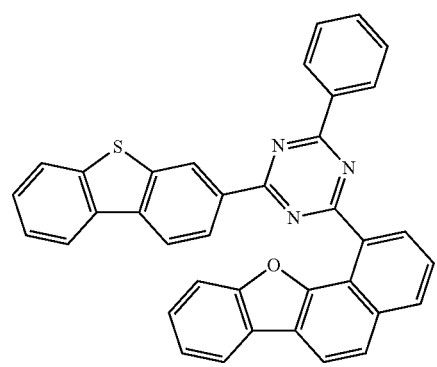
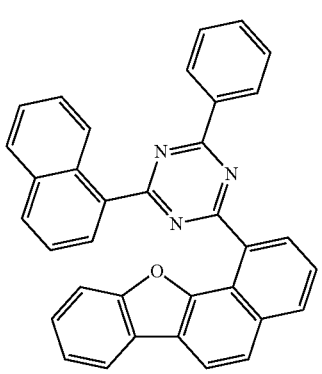
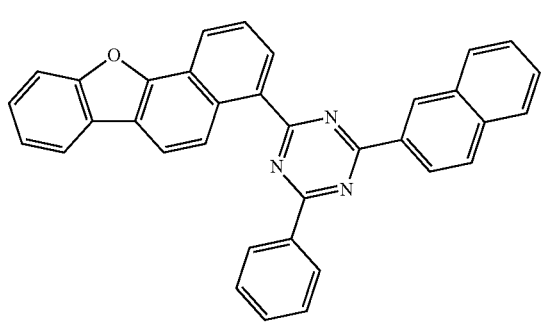
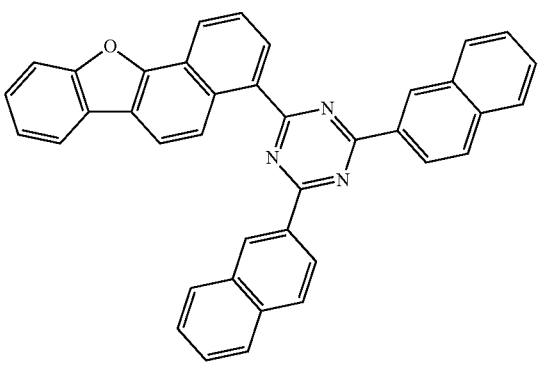
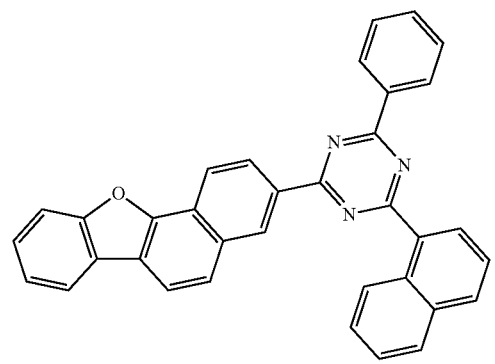
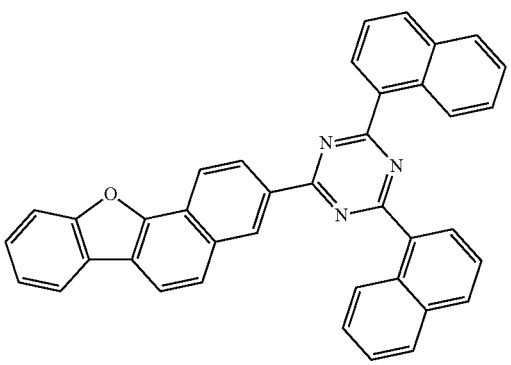

895
-continued
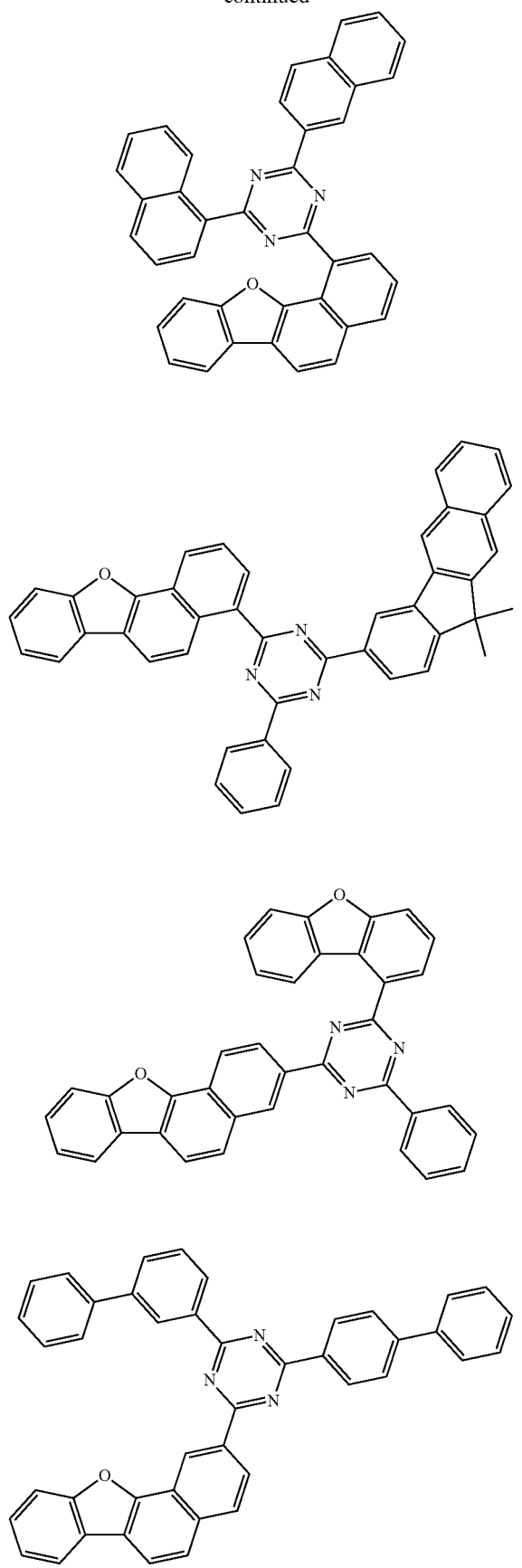
896
-continued
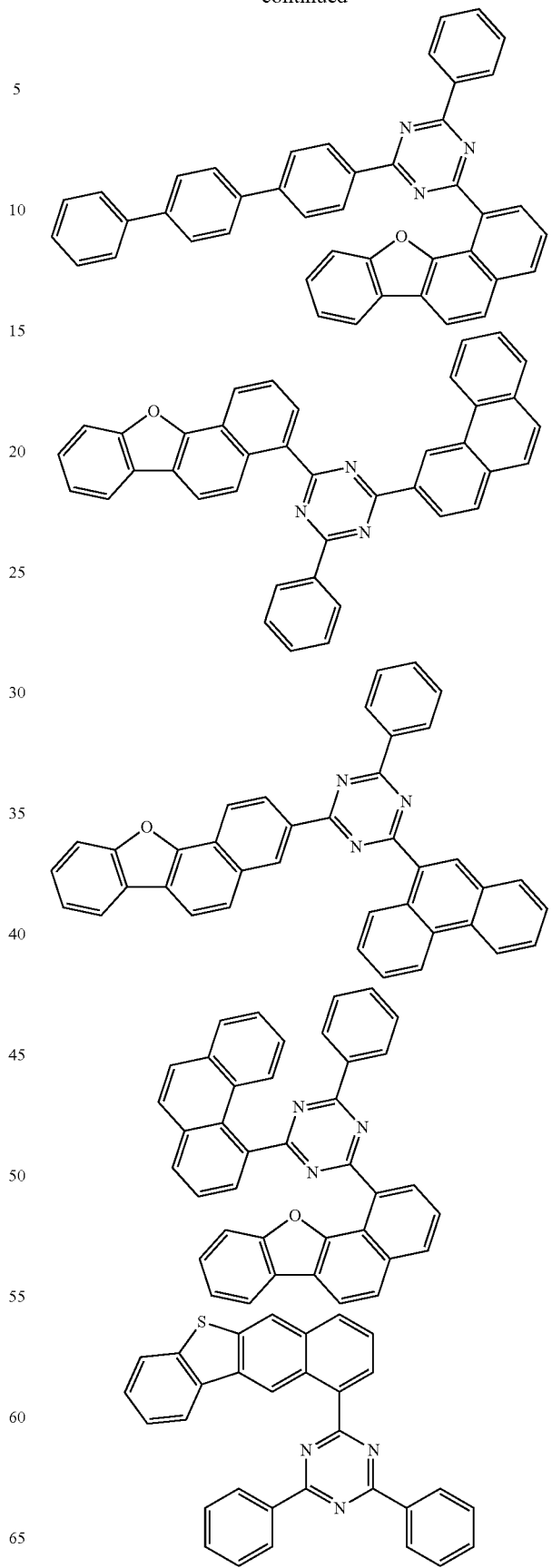

897
-continued
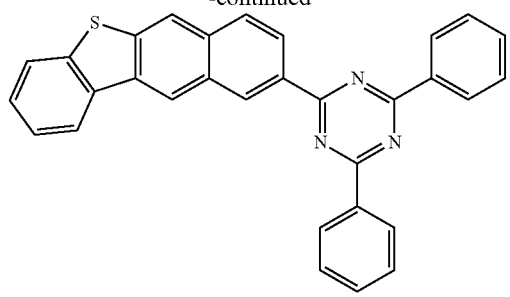
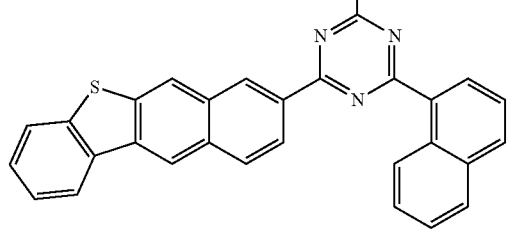
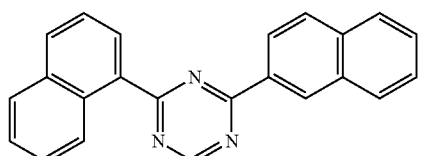
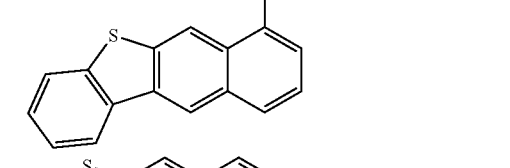
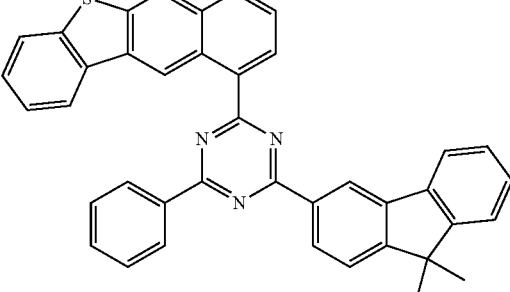
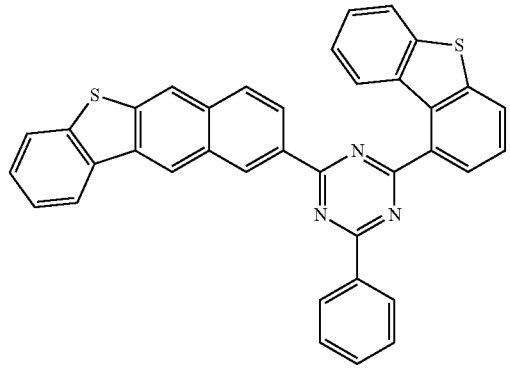
898
-continued
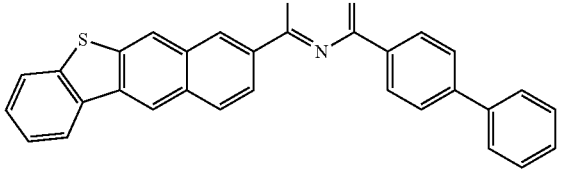
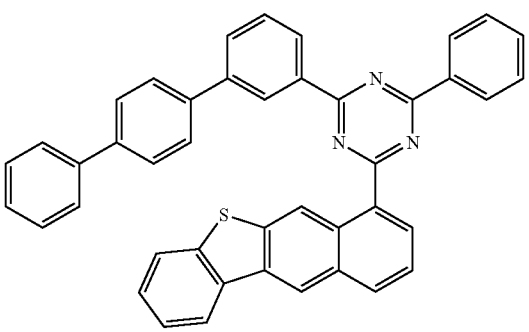
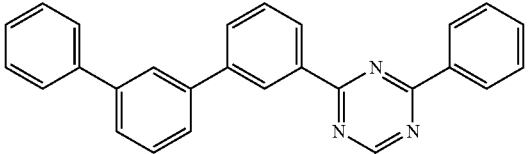
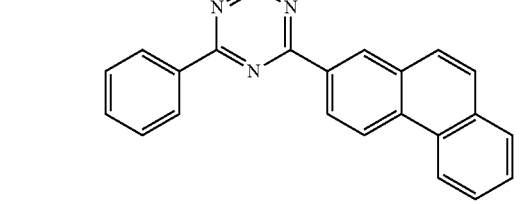

-continued

901
-continued
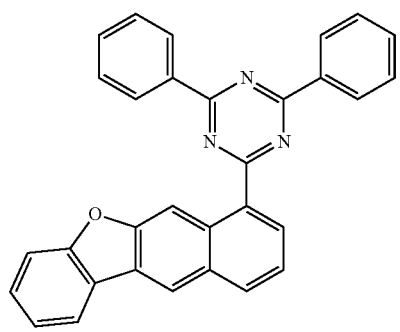
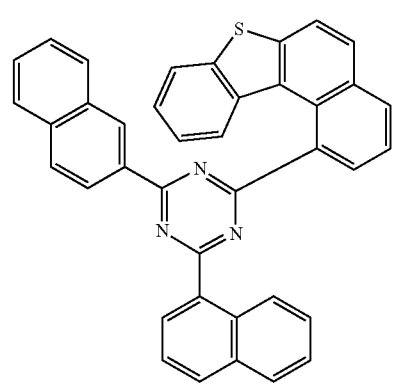
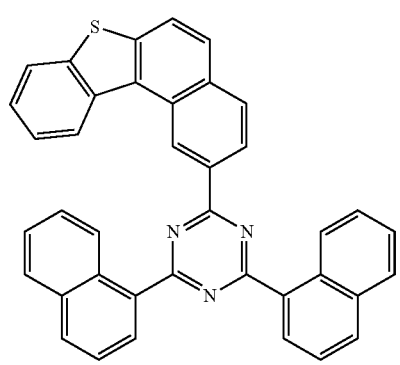
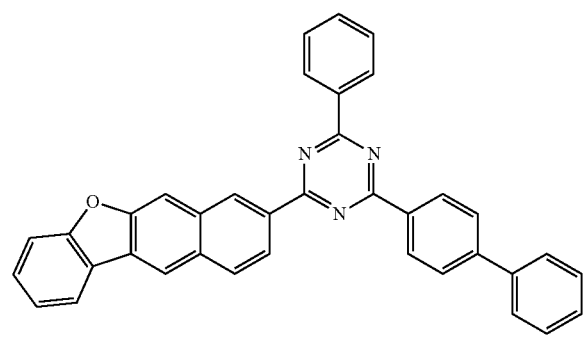
902
-continued
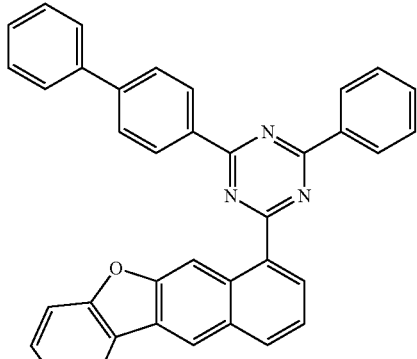
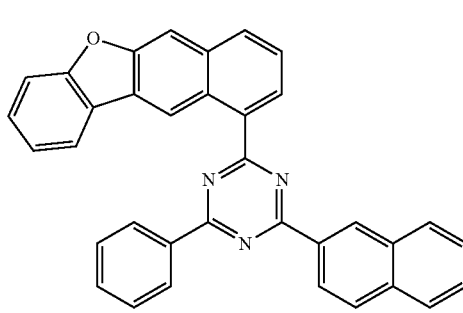
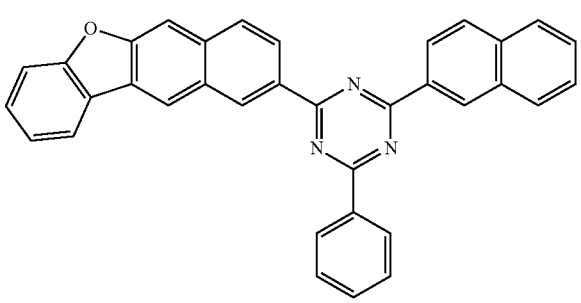
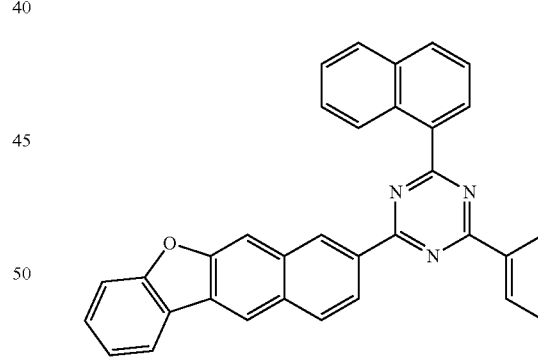
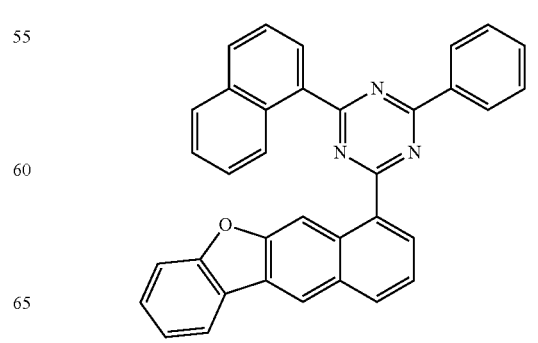

903
-continued
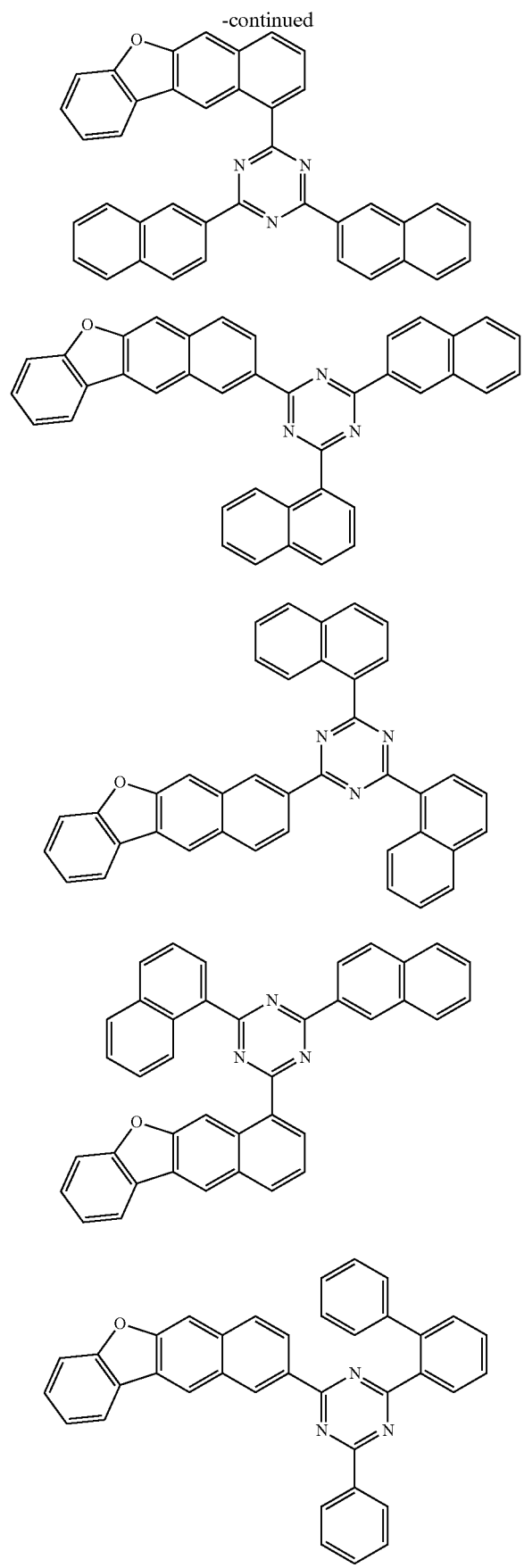
904
-continued
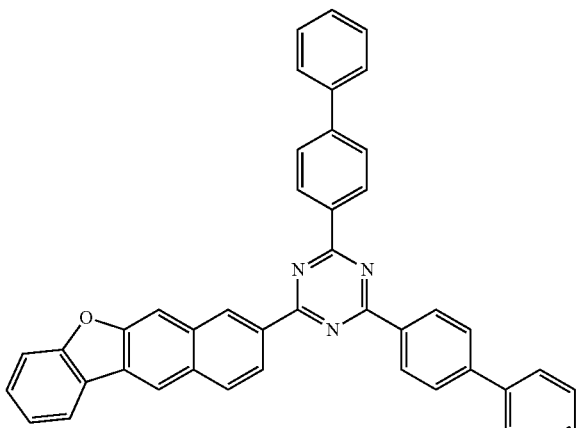
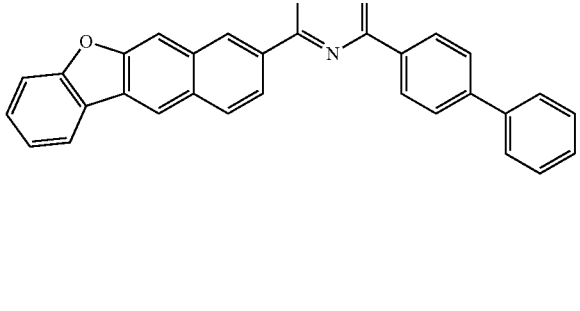
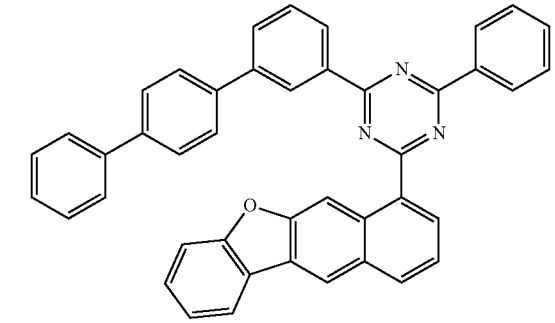
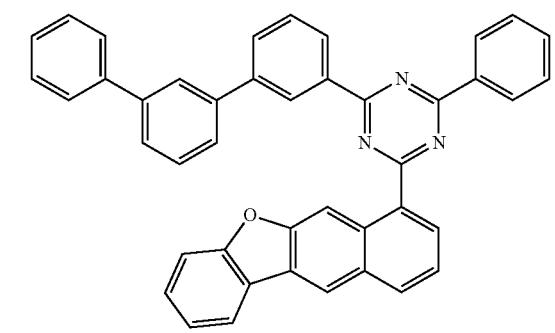
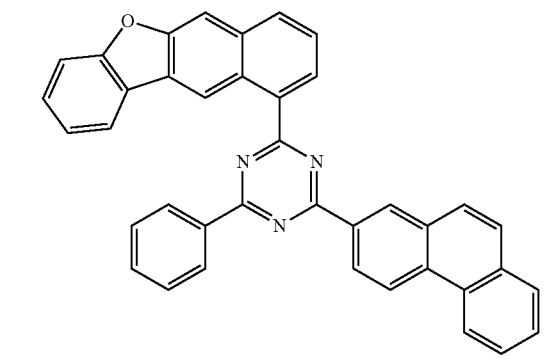

905
-continued
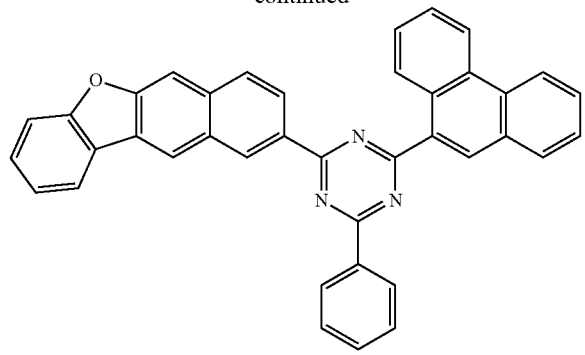
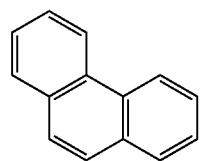
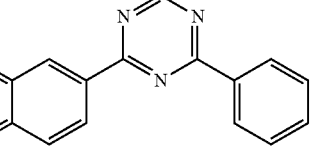
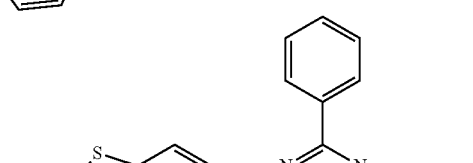
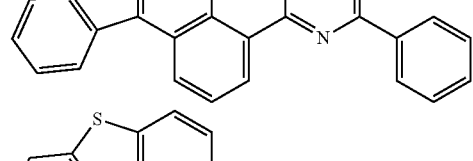
906
-continued
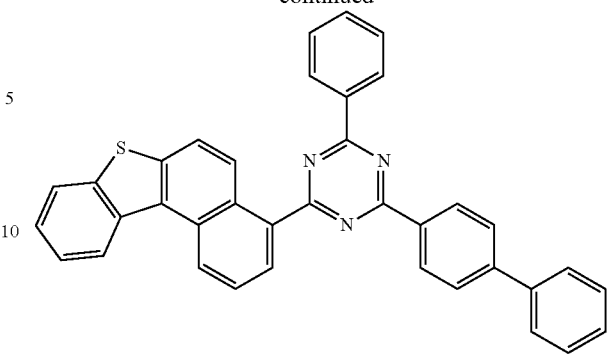
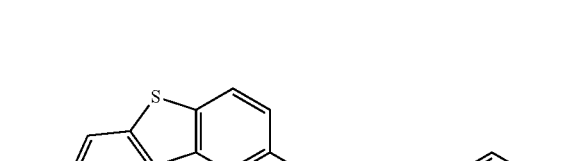
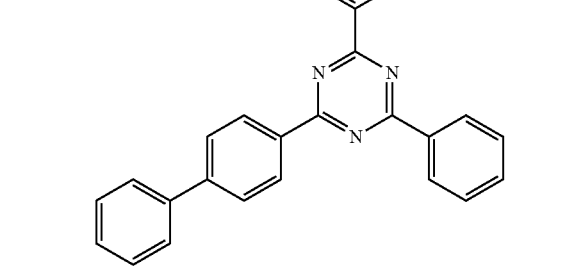

907
-continued
908
-continued
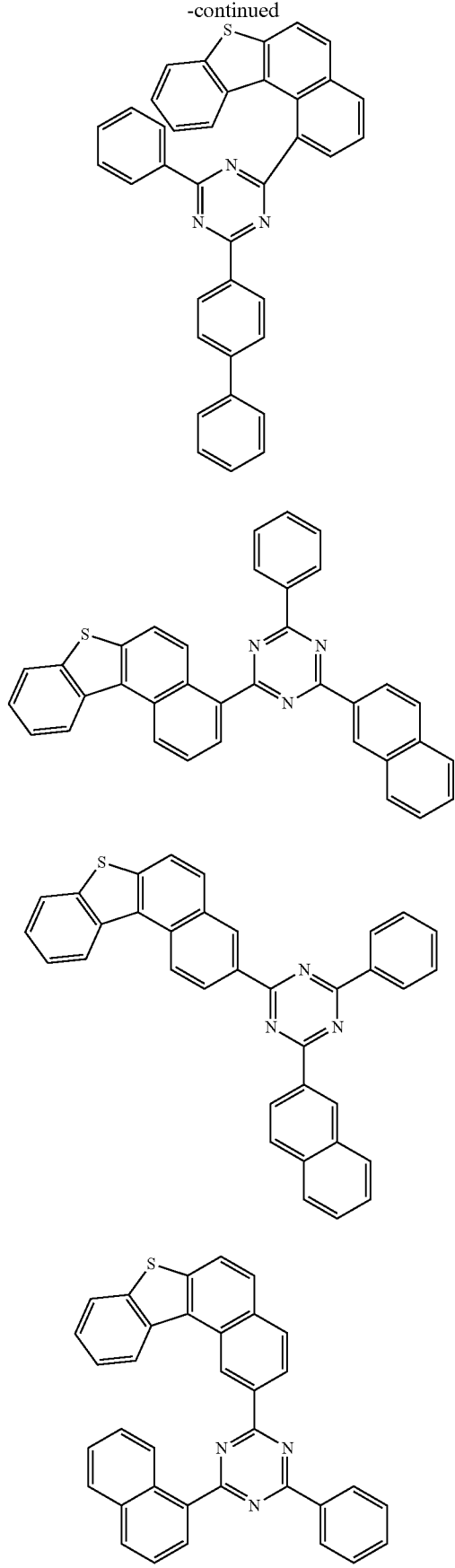
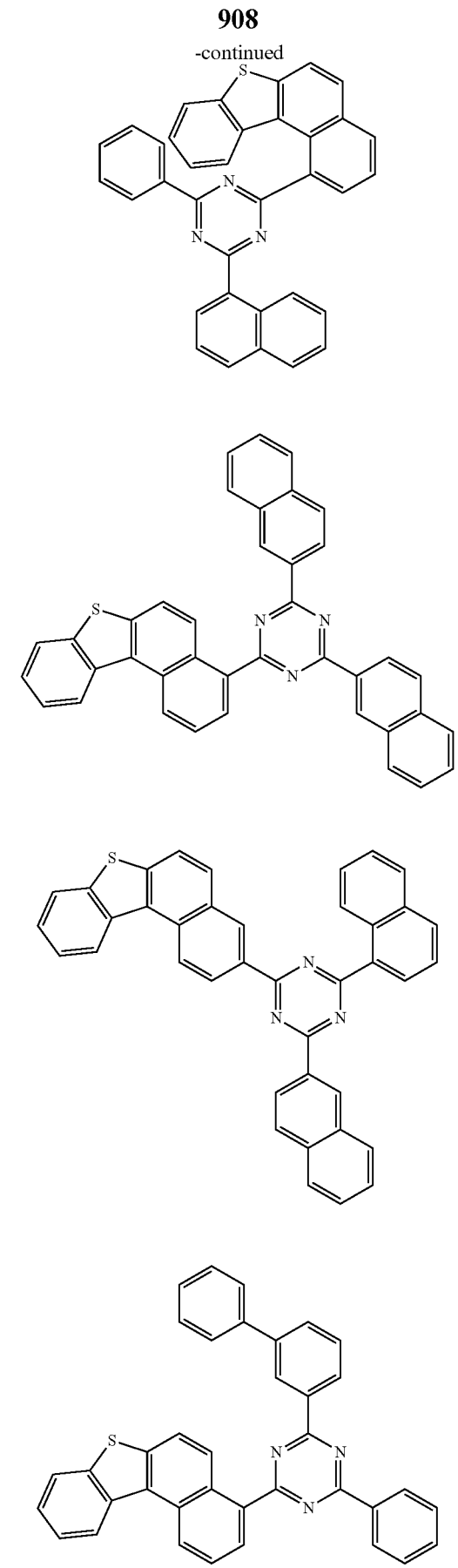

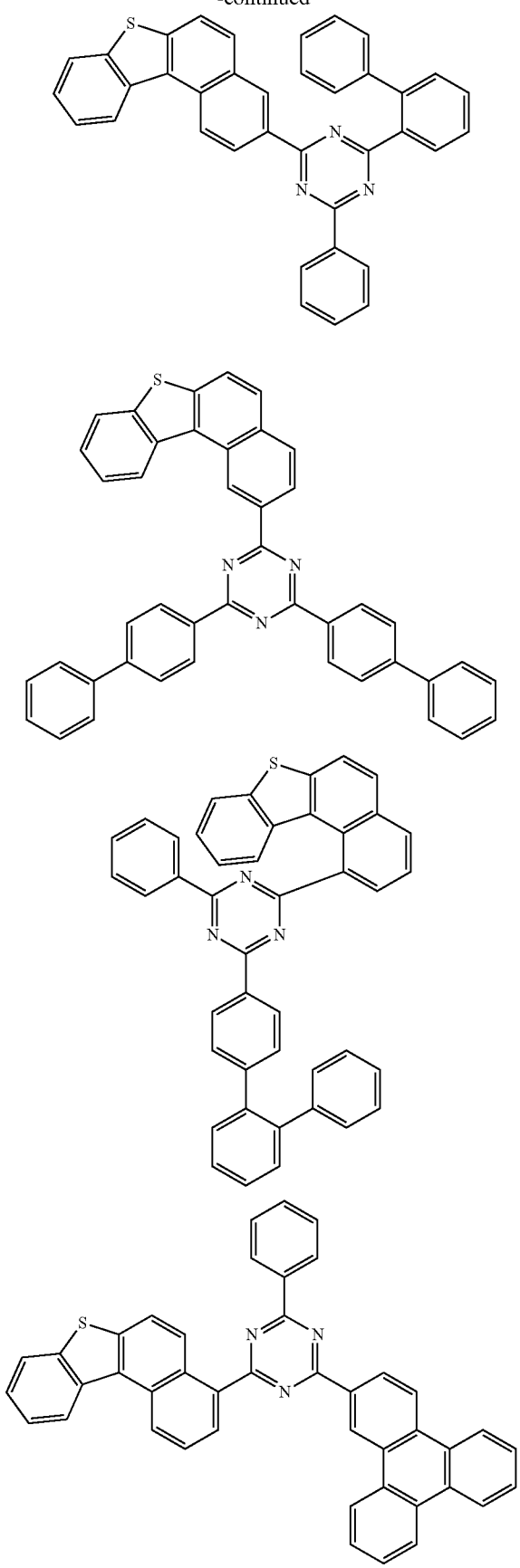

| 911 -continued | 912 -continued |
|---|---|
| 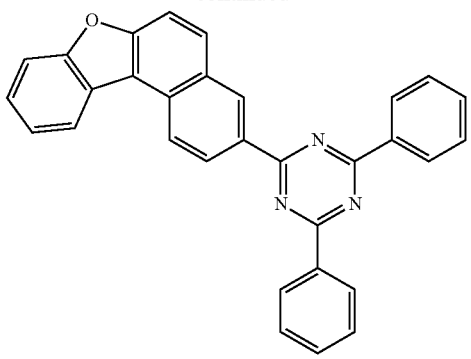 | 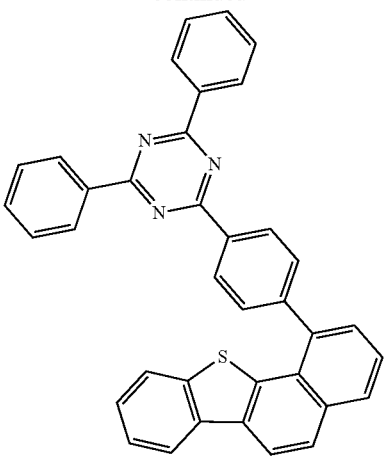 |
| 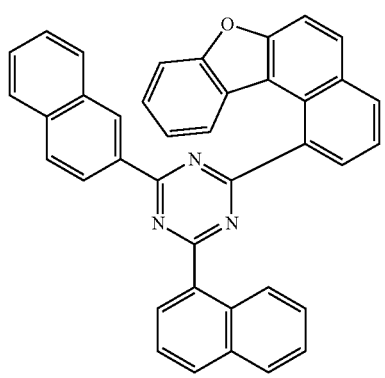 | 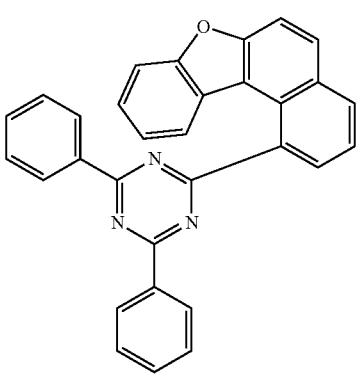 |
| 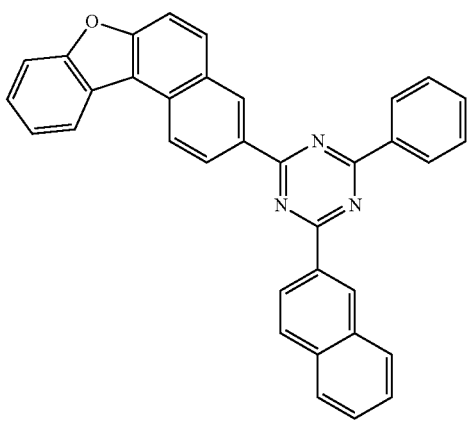 | 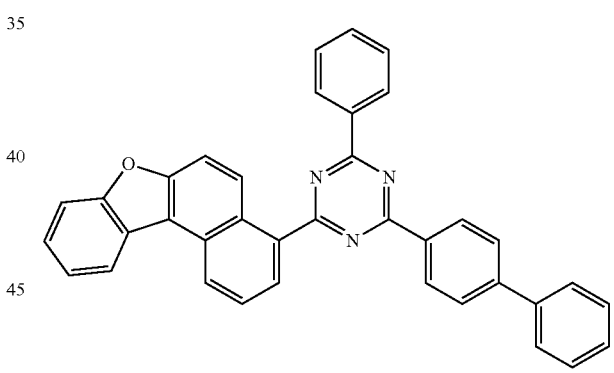 |
| 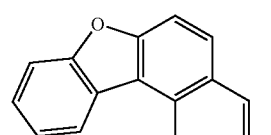 | 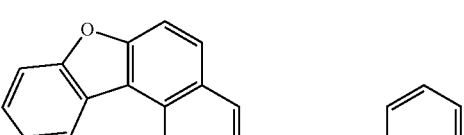 |
| 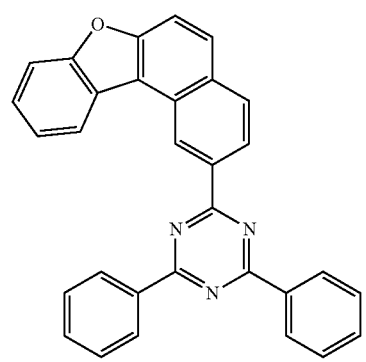 | |

913
-continued
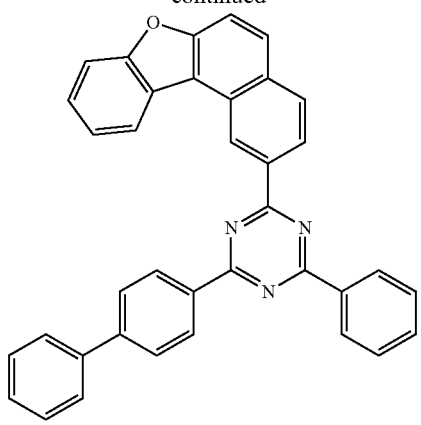
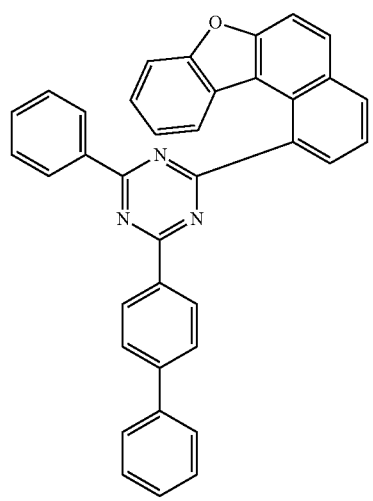
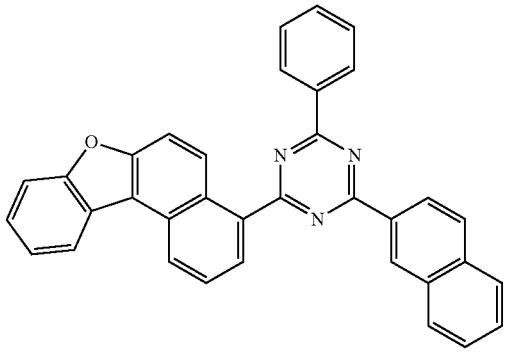
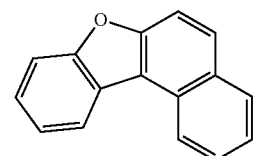
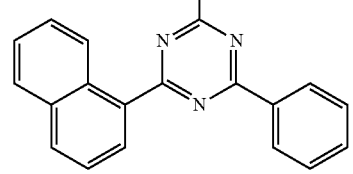
914
-continued
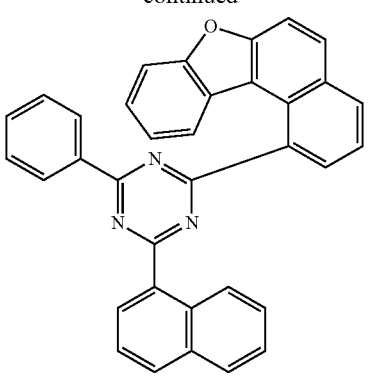
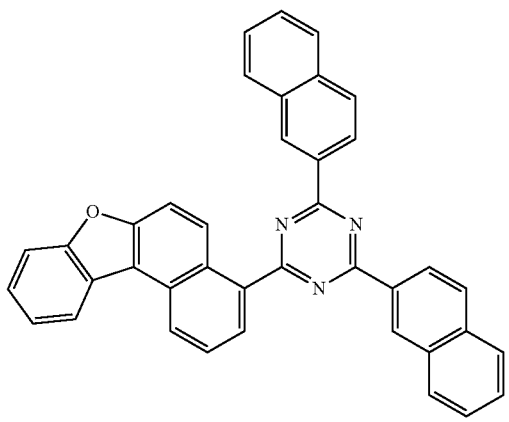
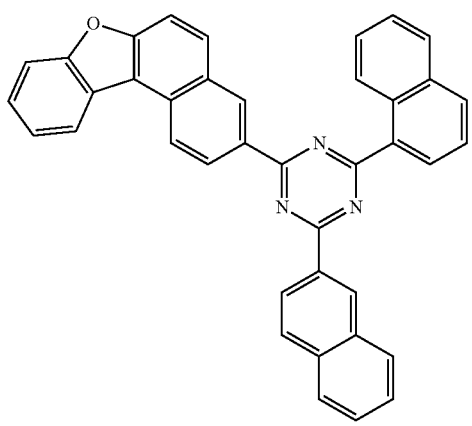
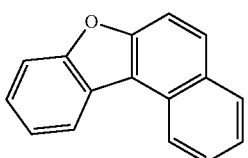
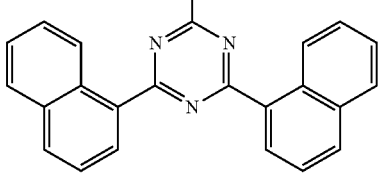

915
-continued
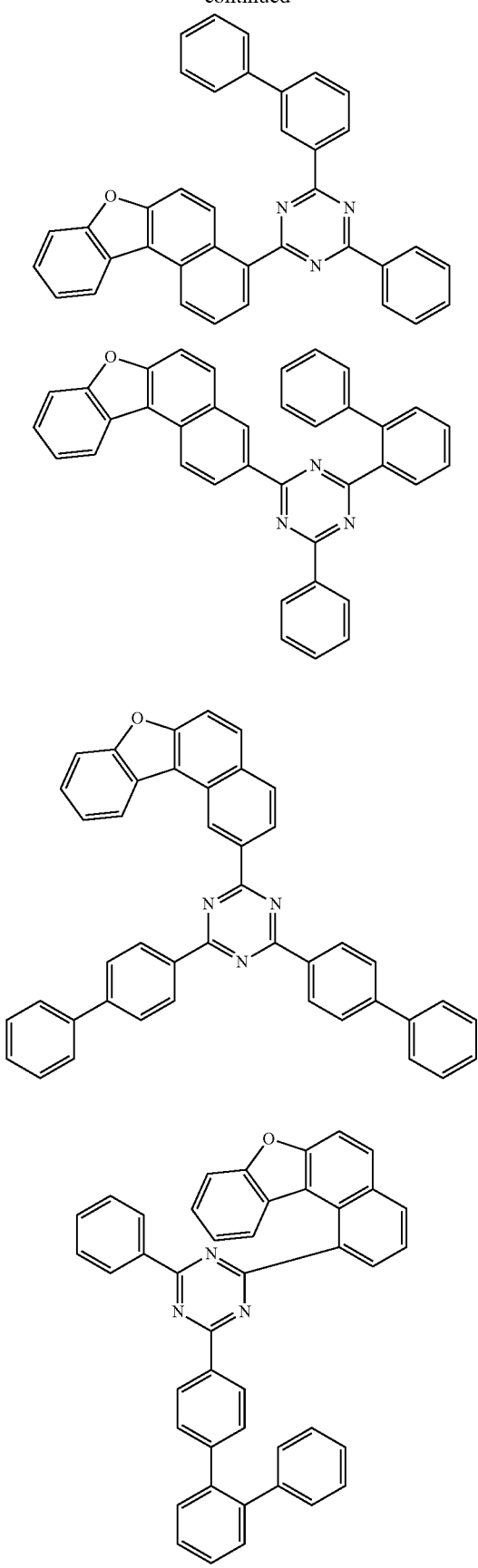
916
-continued
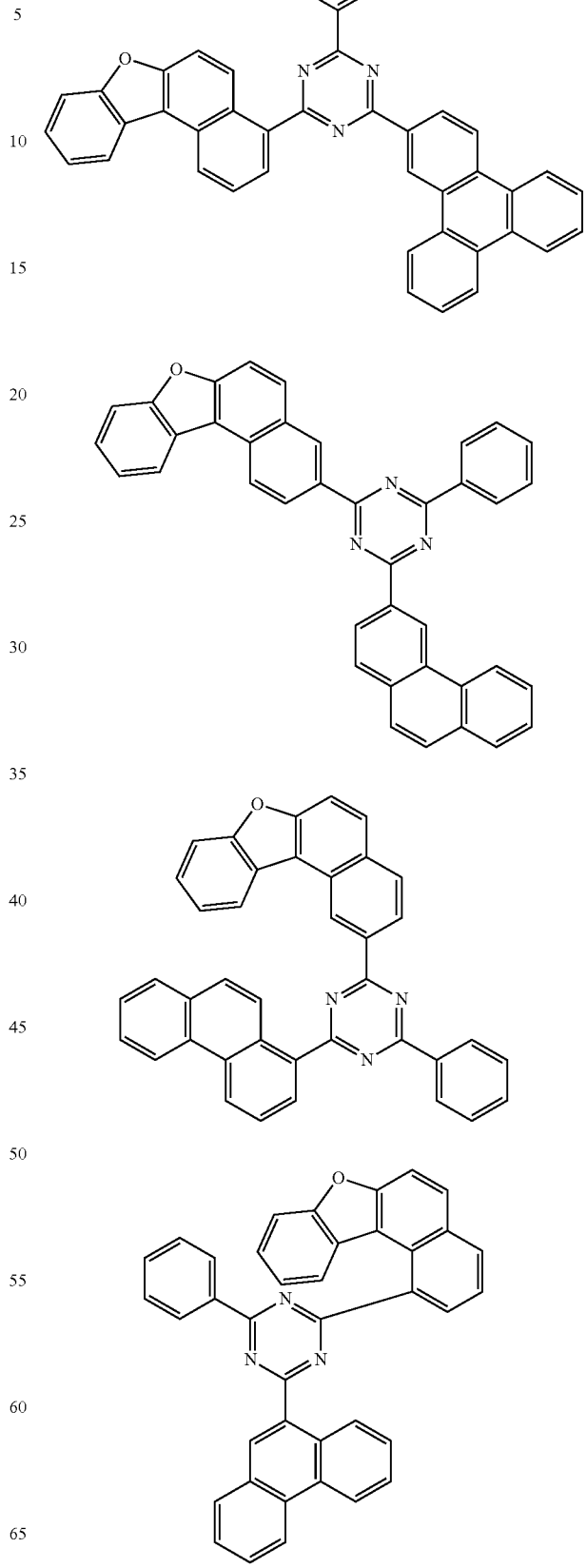

917
-continued
918
-continued
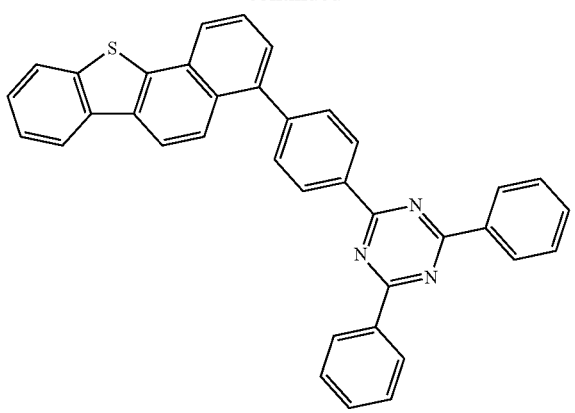
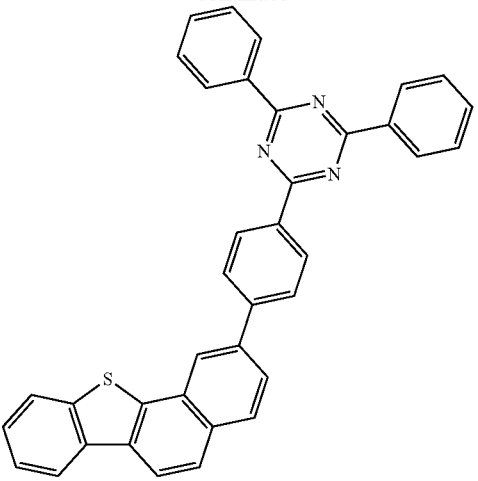
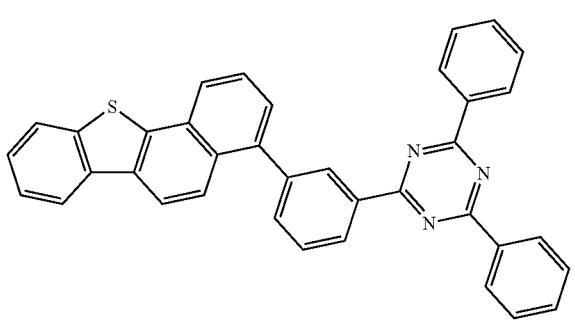
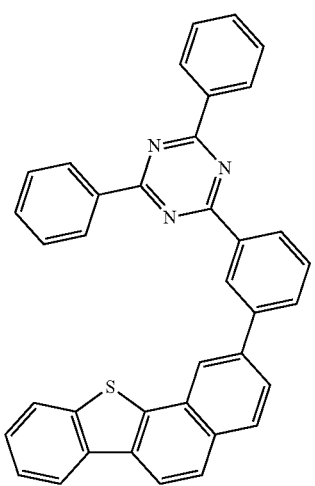
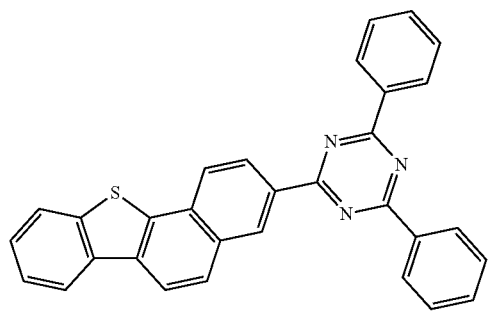
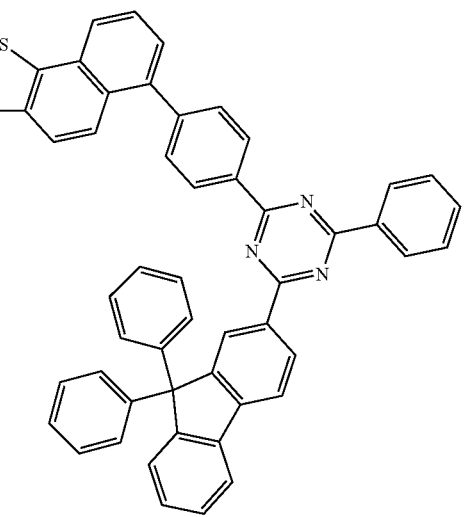
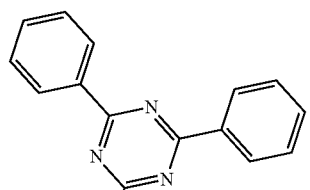

919
-continued
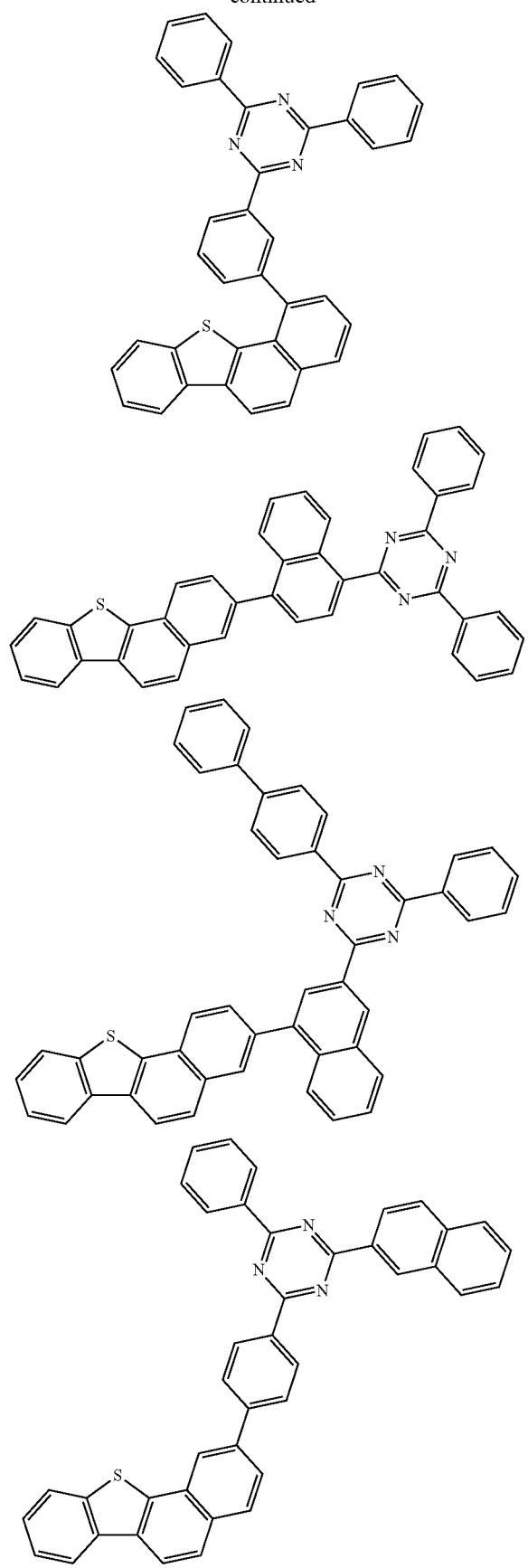
920
-continued
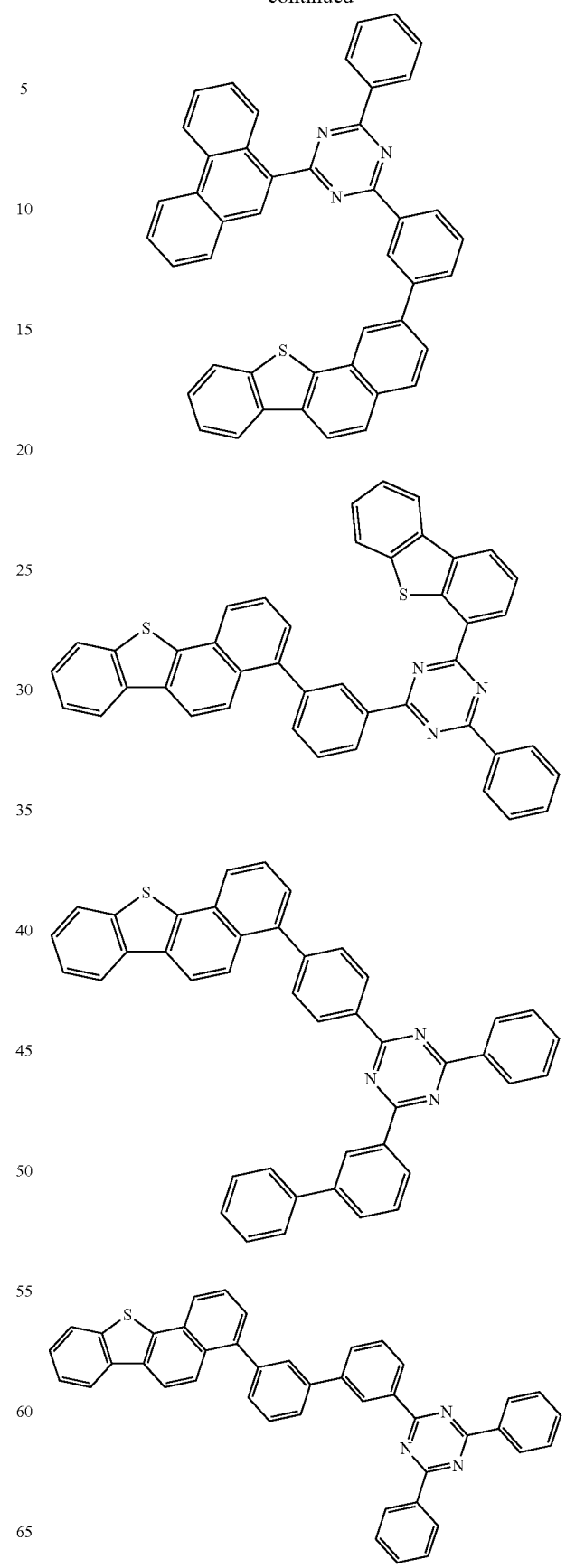

921
-continued
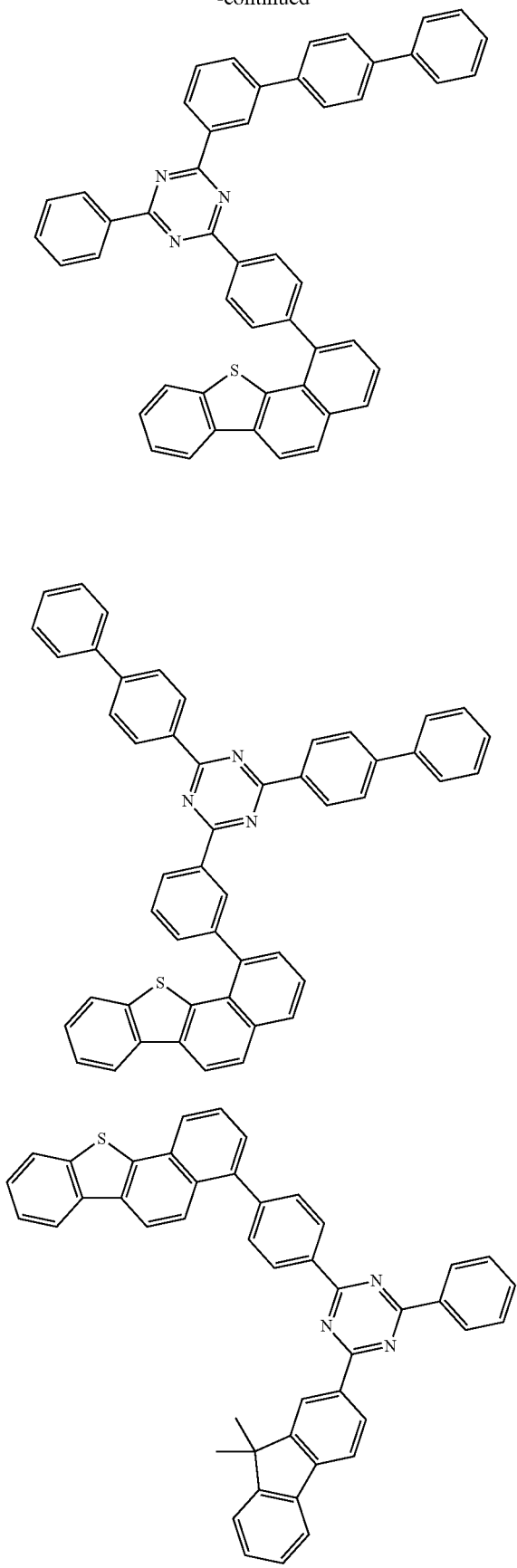
922
-continued
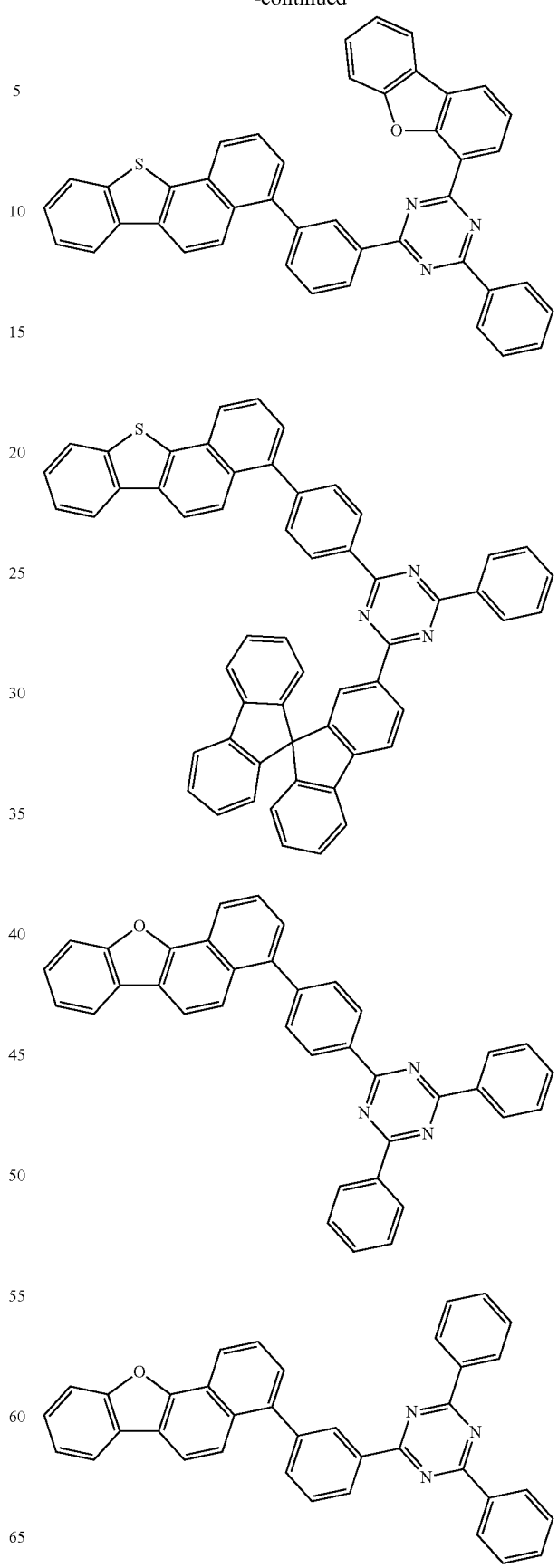

923
-continued
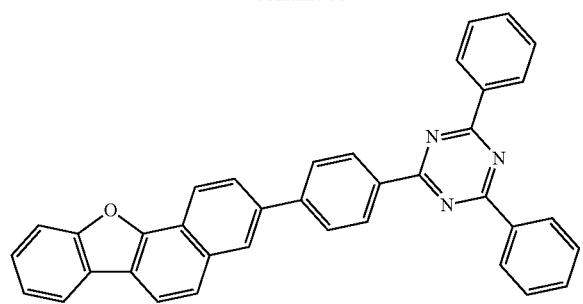
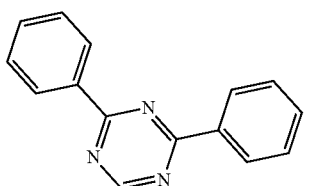
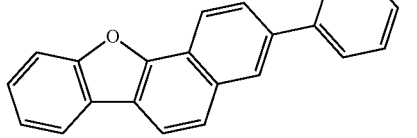
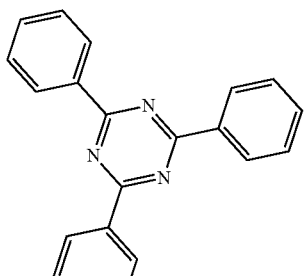
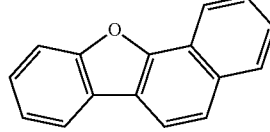
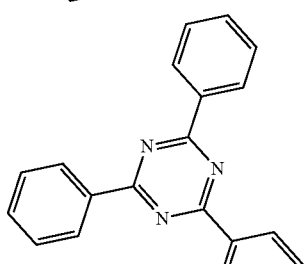
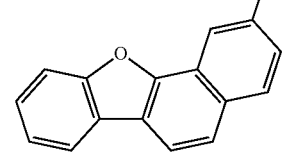
924
-continued
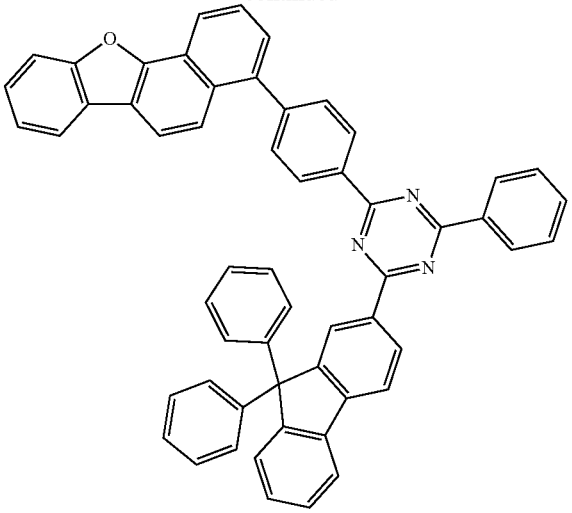 [SMILES: c1ccc(-c2nc(-c3ccc(-c4cccc5c4ccc4c6ccccc6oc54)cc3)nc(-c3ccc4c(c3)C(c3ccccc3)(c3ccccc3)c3ccccc3-4)n2)cc1]
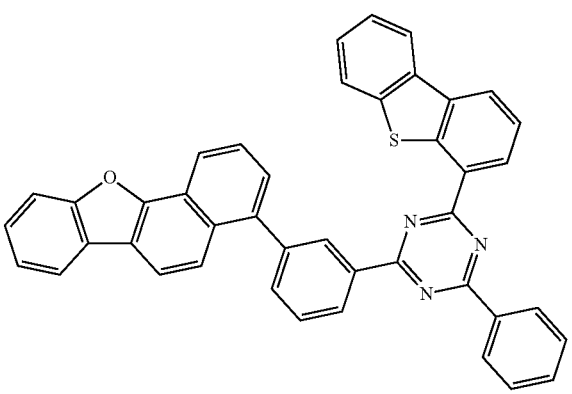
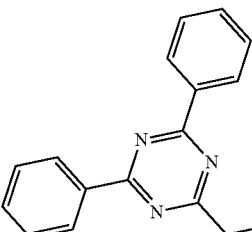
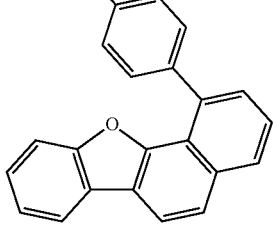

925
-continued
926
-continued
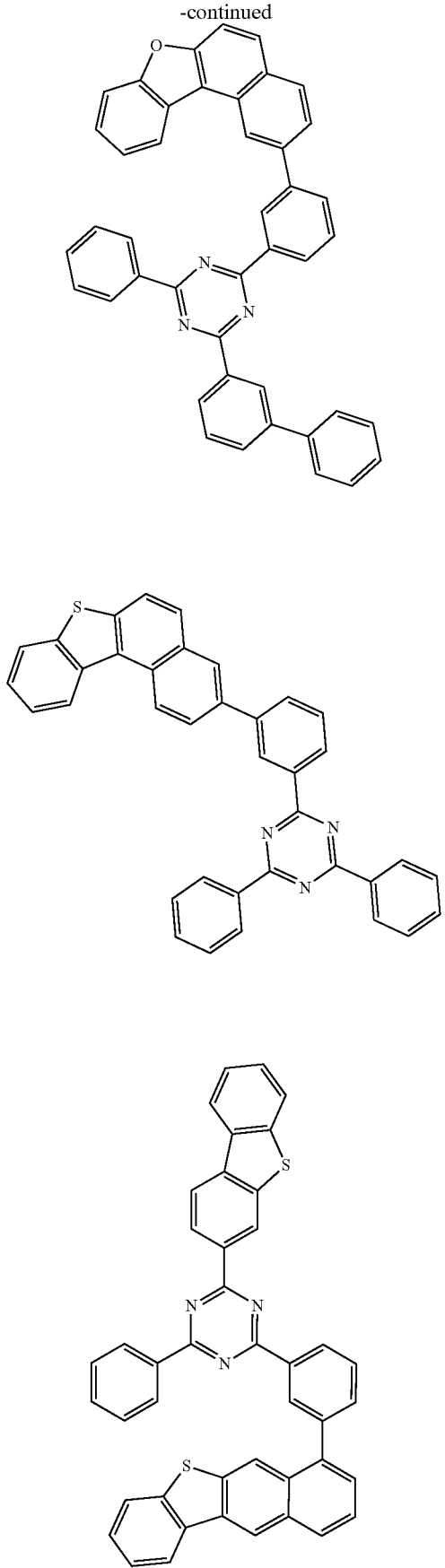
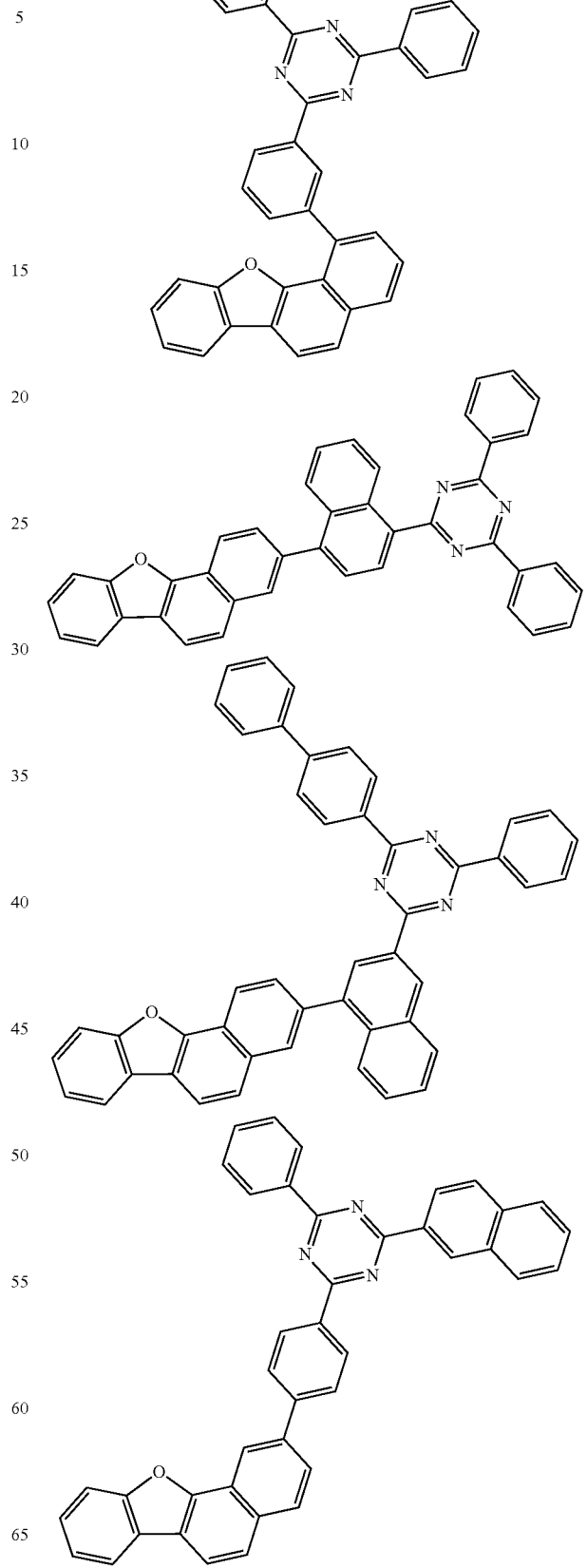

927
-continued
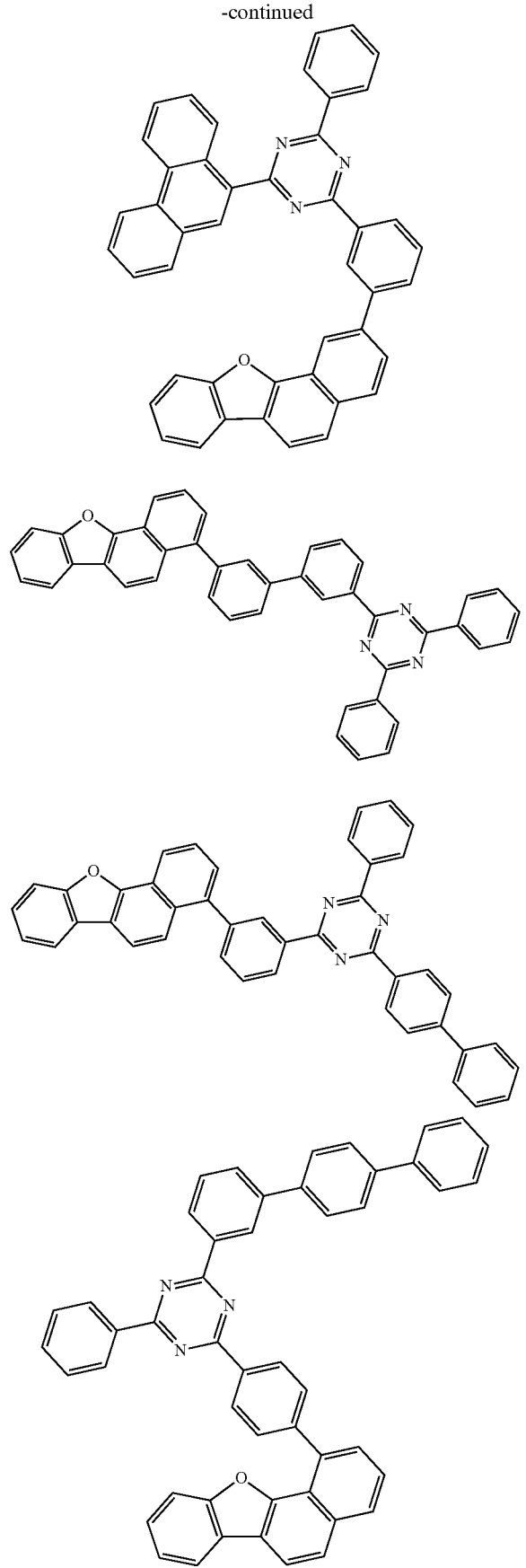
928
-continued
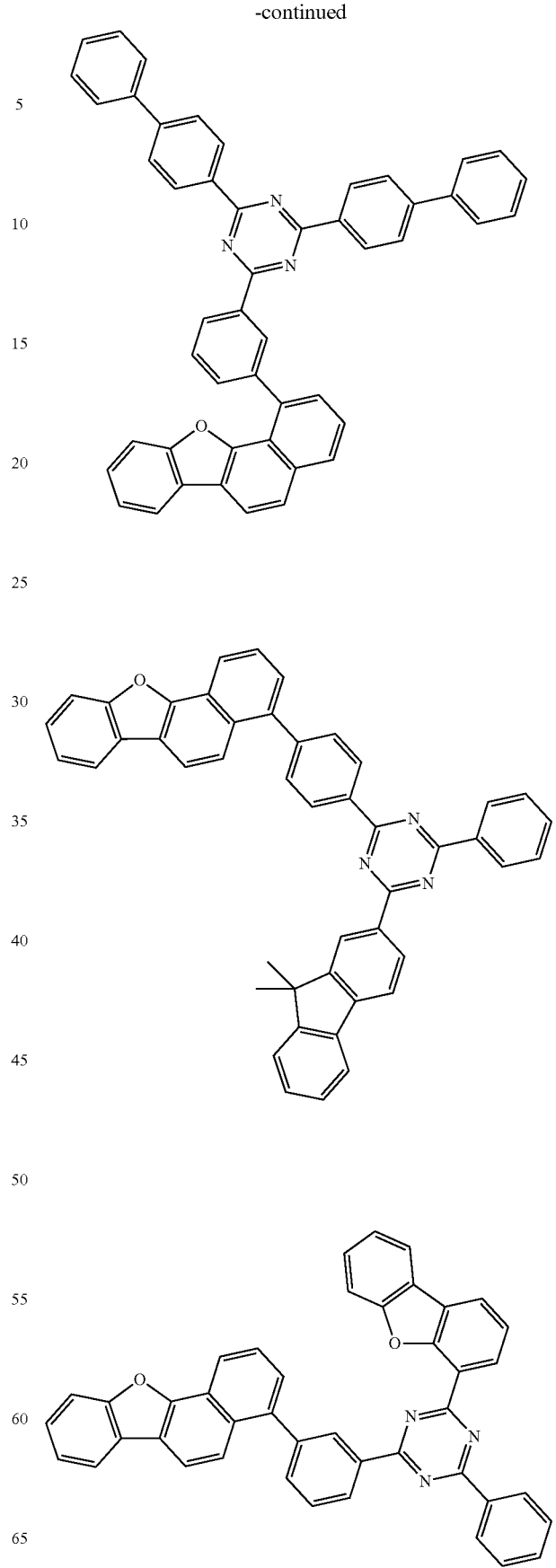

| 929 -continued | 930 -continued |
|---|---|
| 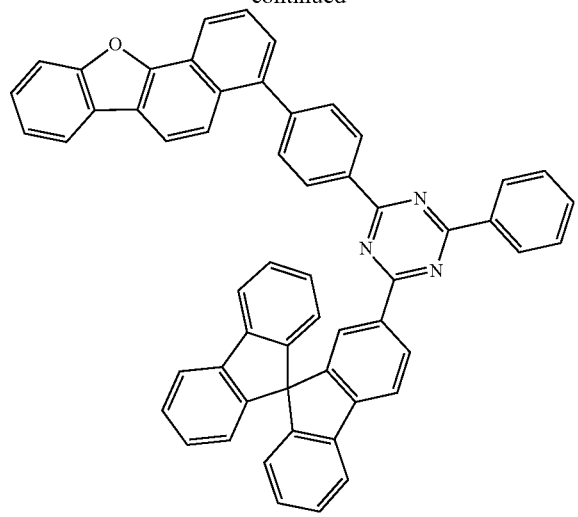 | 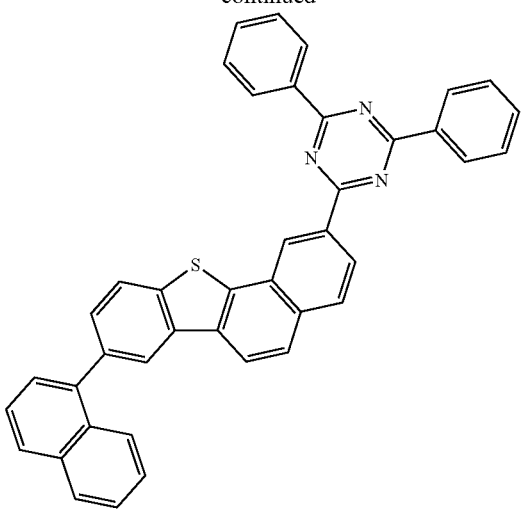 |
| 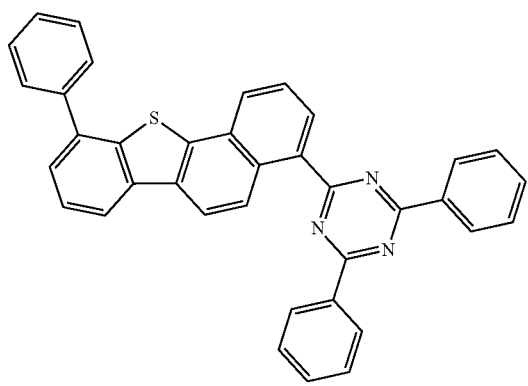 | 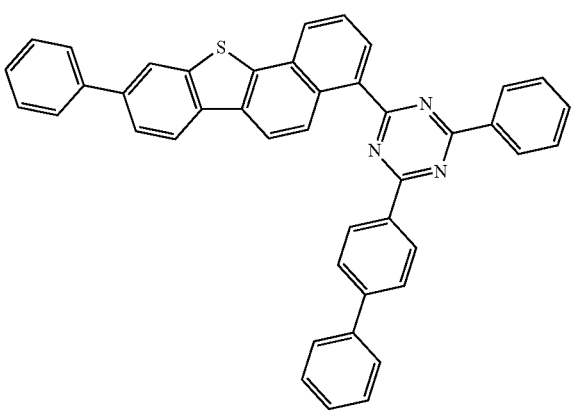 |
| 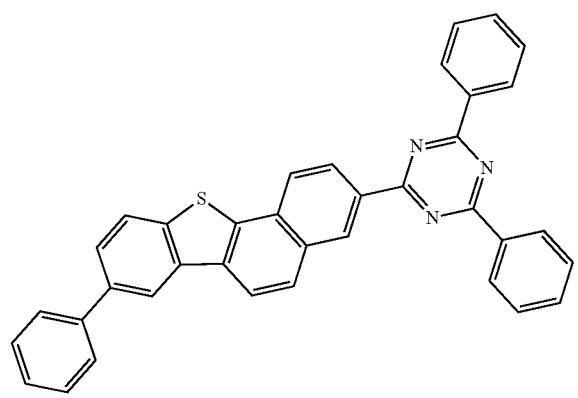 | 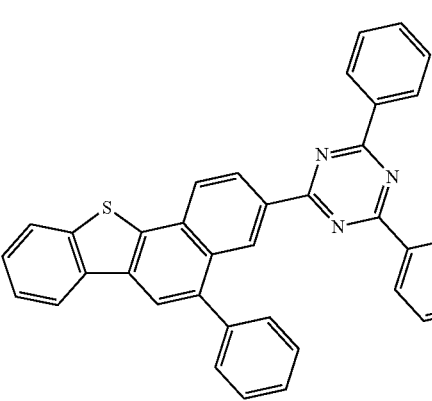 |
| | 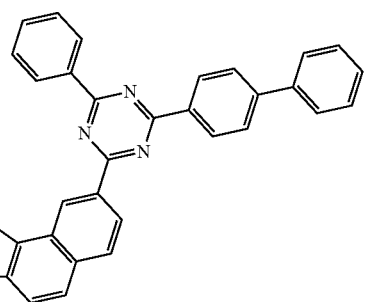 |

931
-continued
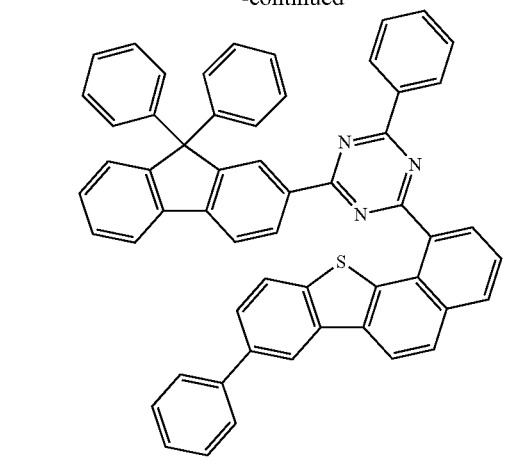
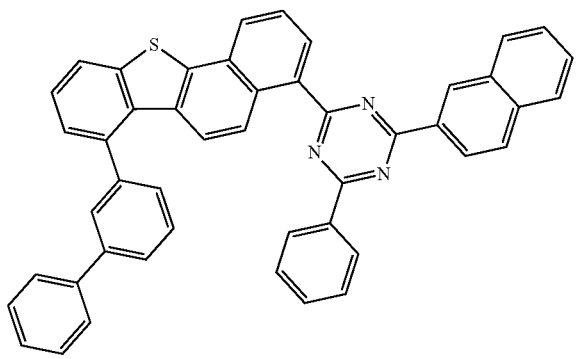
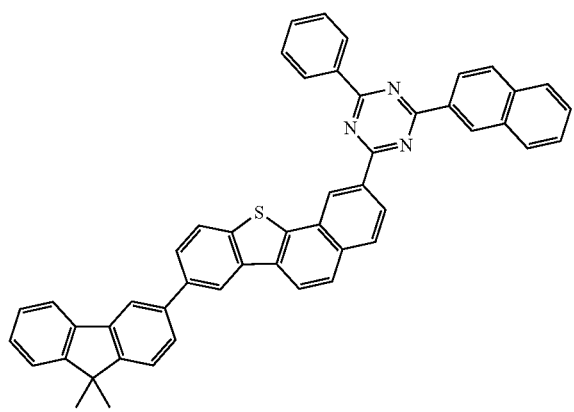
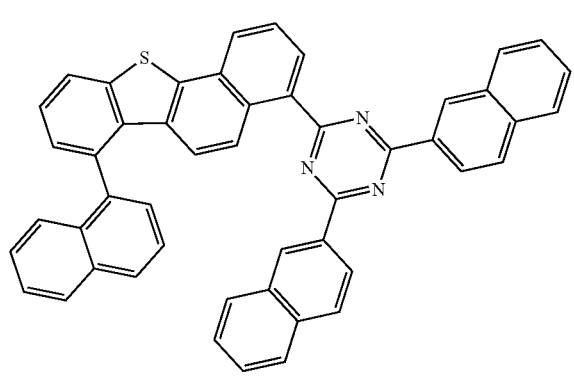
932
-continued
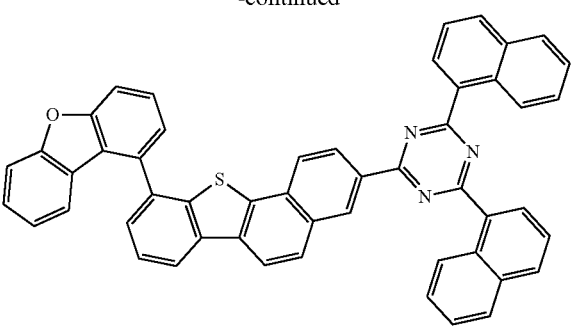
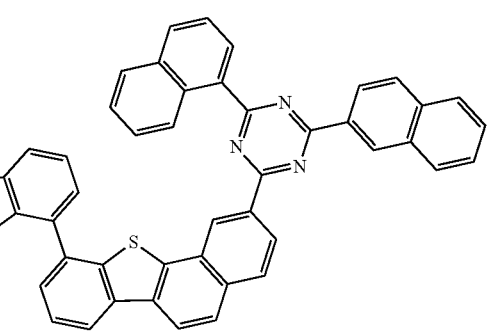
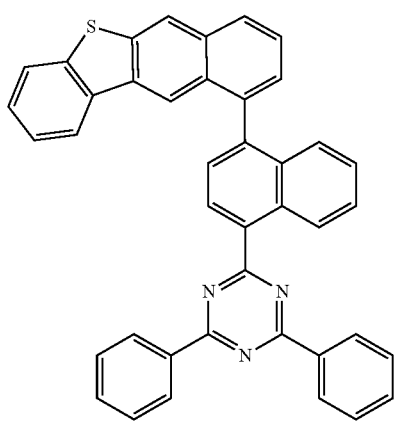
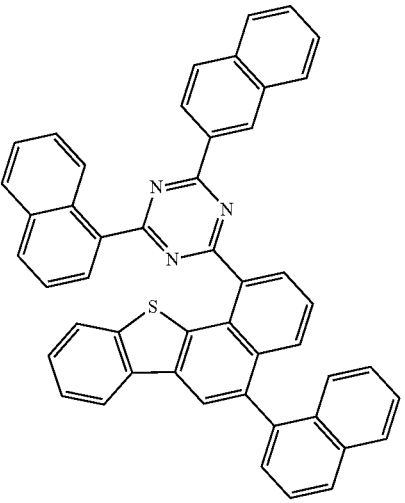

933
-continued
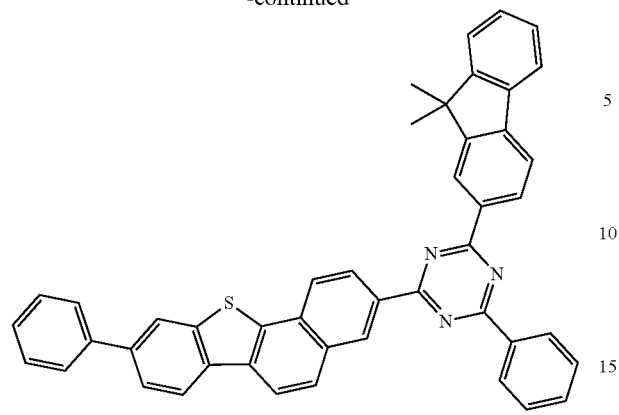
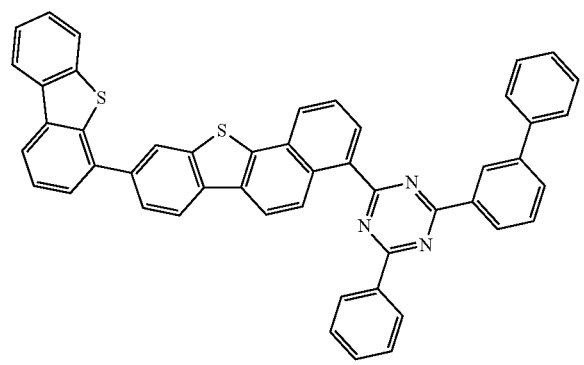
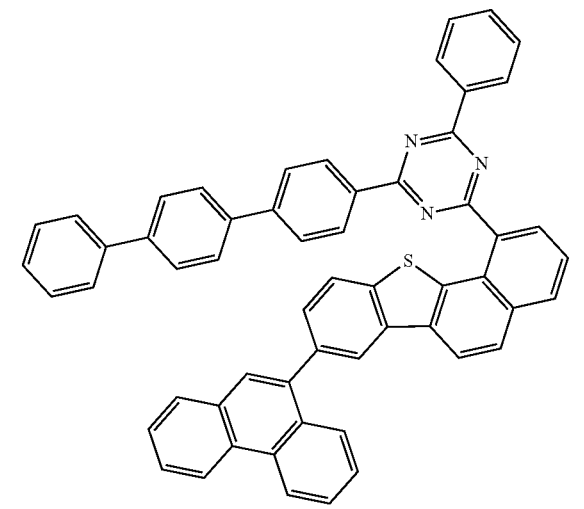
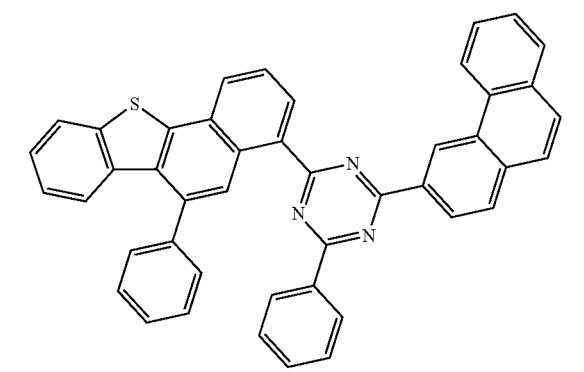
934
-continued
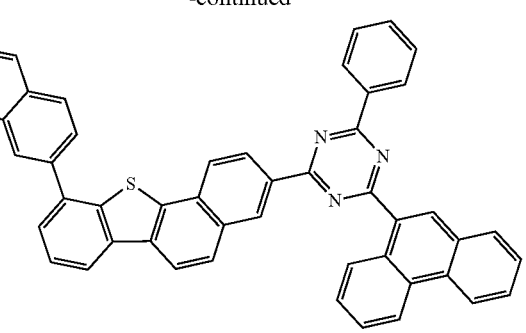
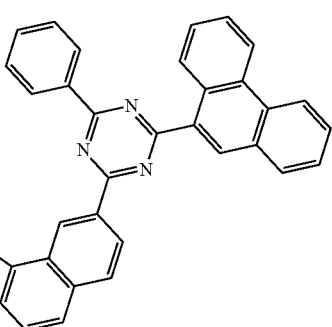
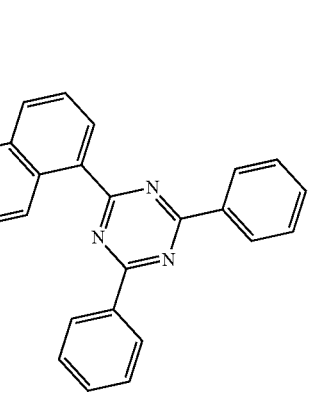
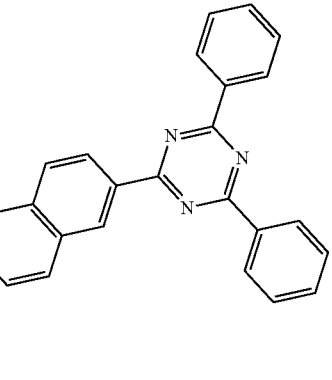

935
-continued
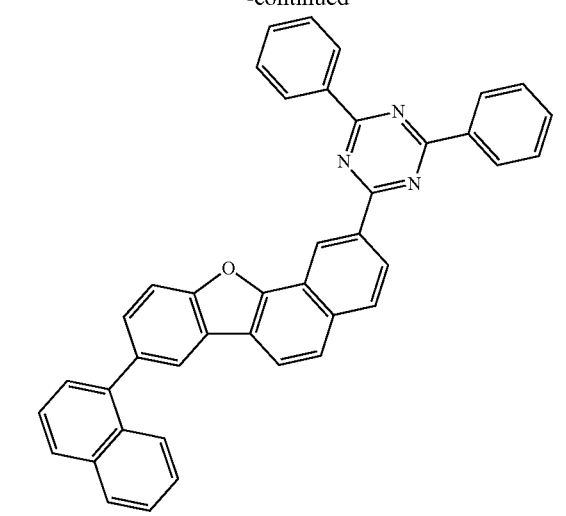
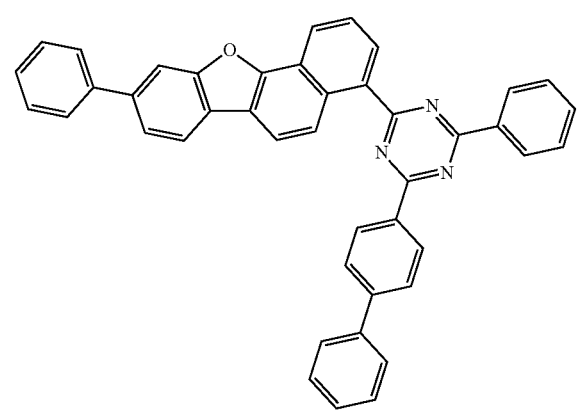
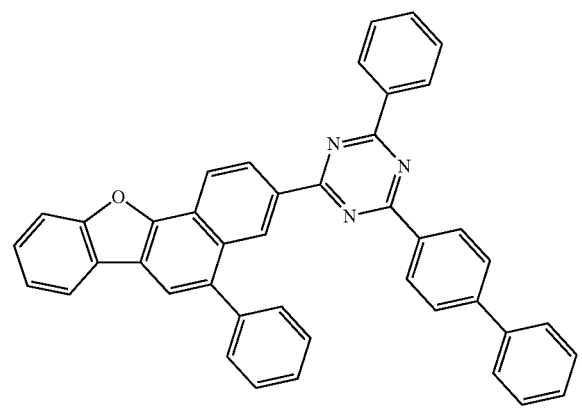
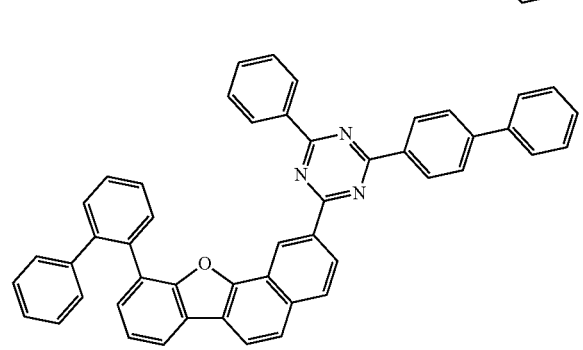
936
-continued
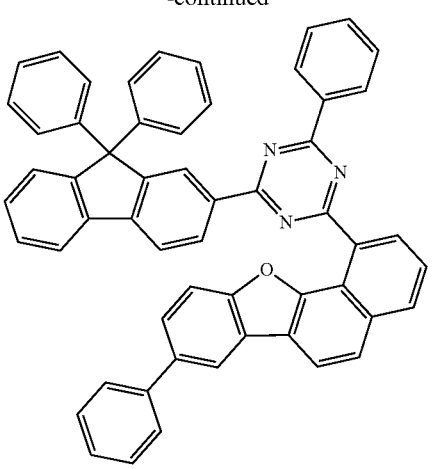
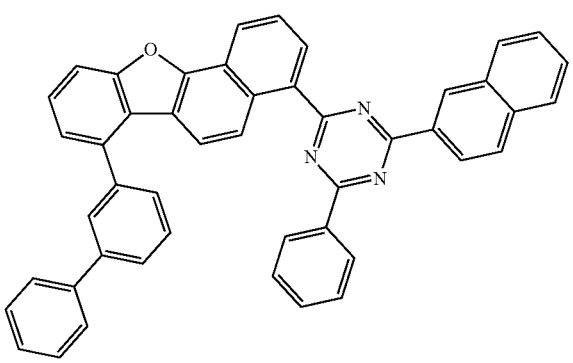
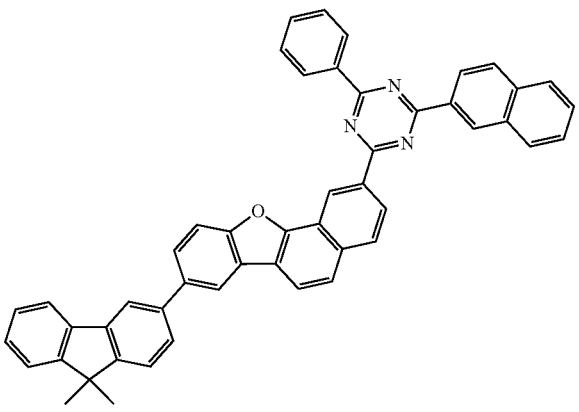
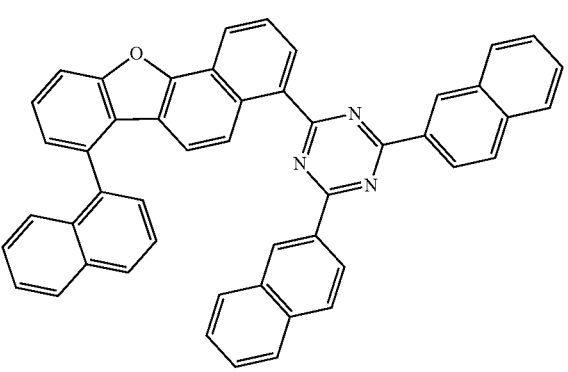

937
-continued
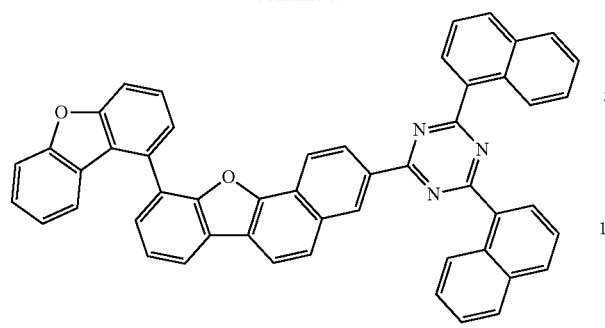
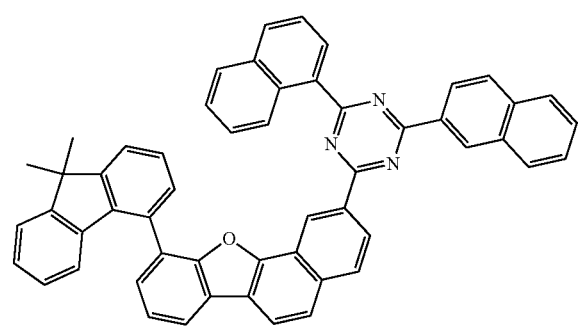
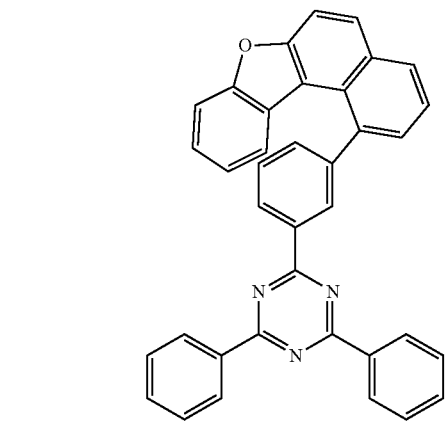
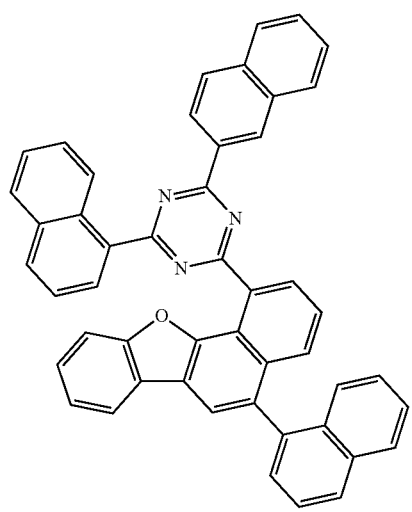
938
-continued
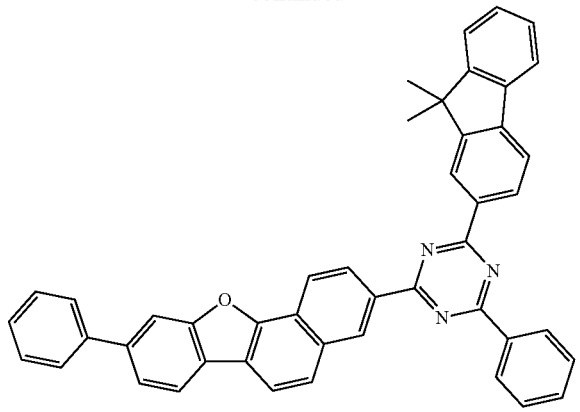
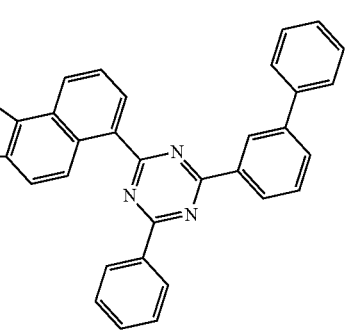
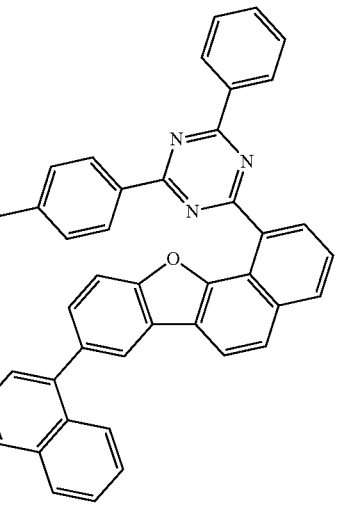
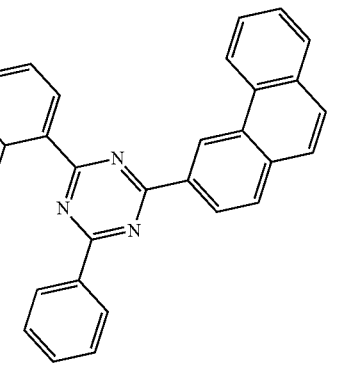

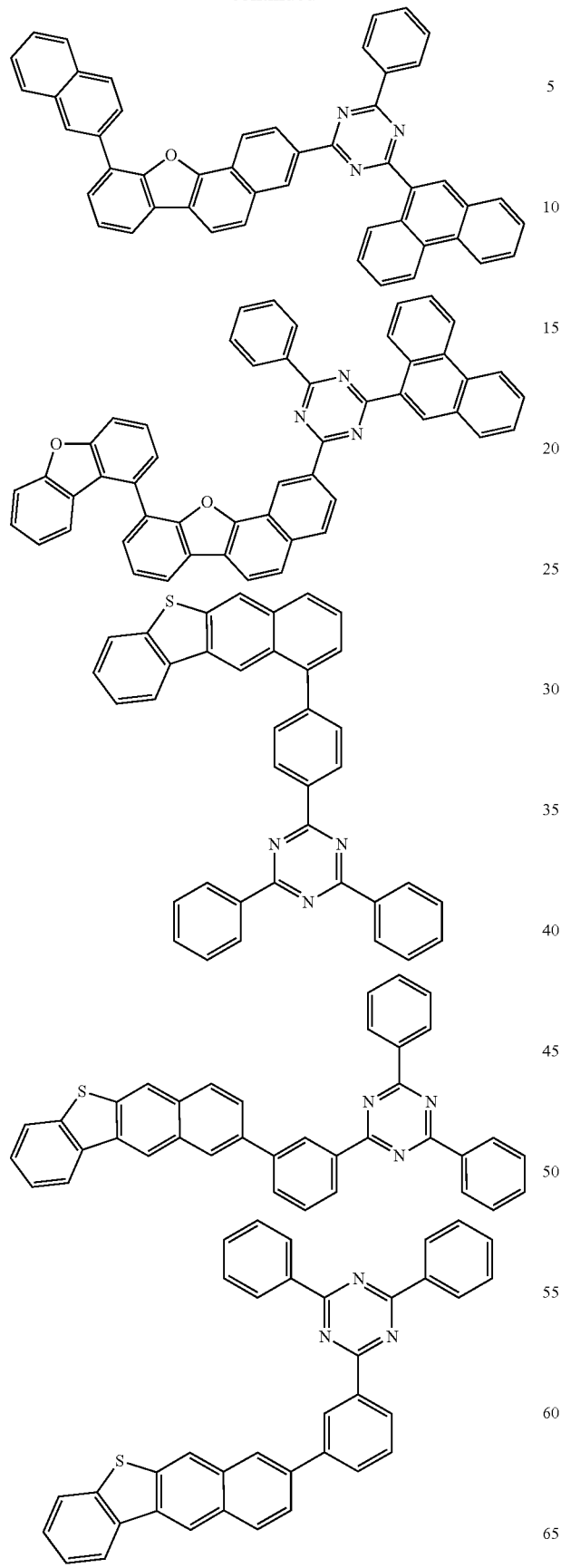

941
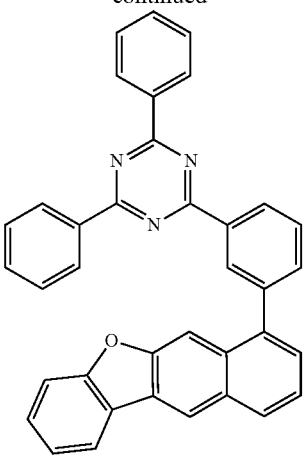
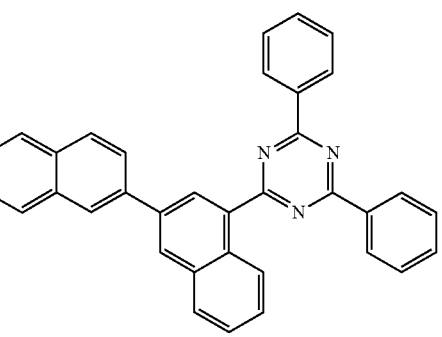
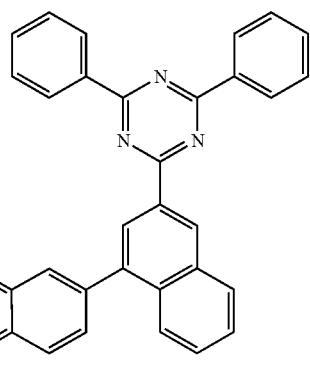
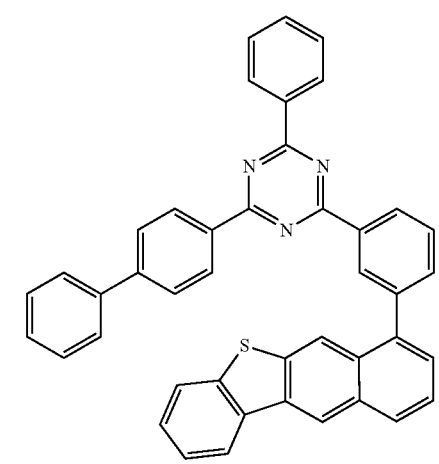
942
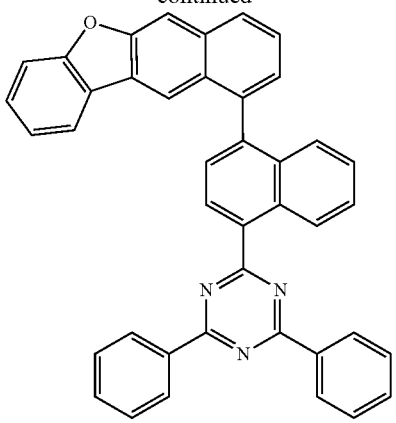
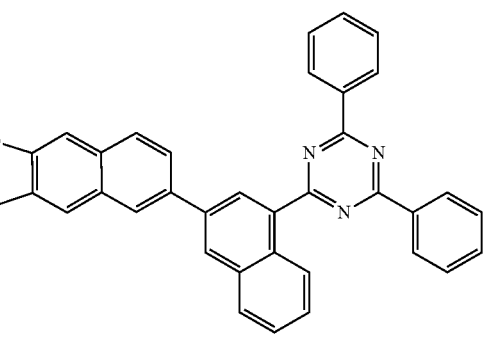
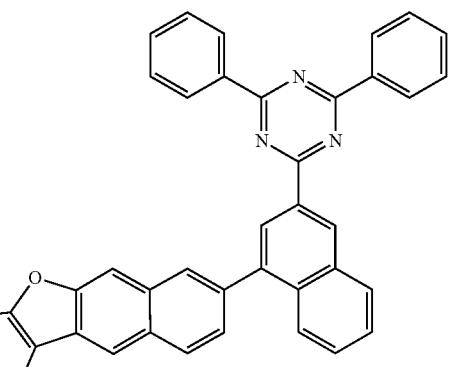
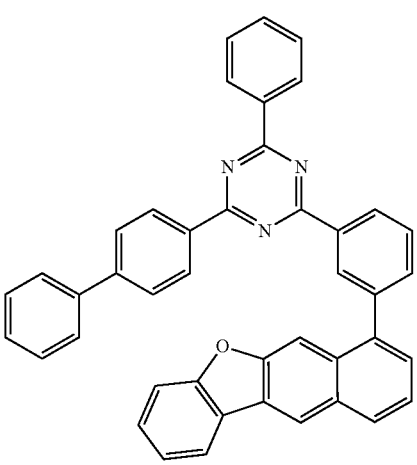

943
-continued
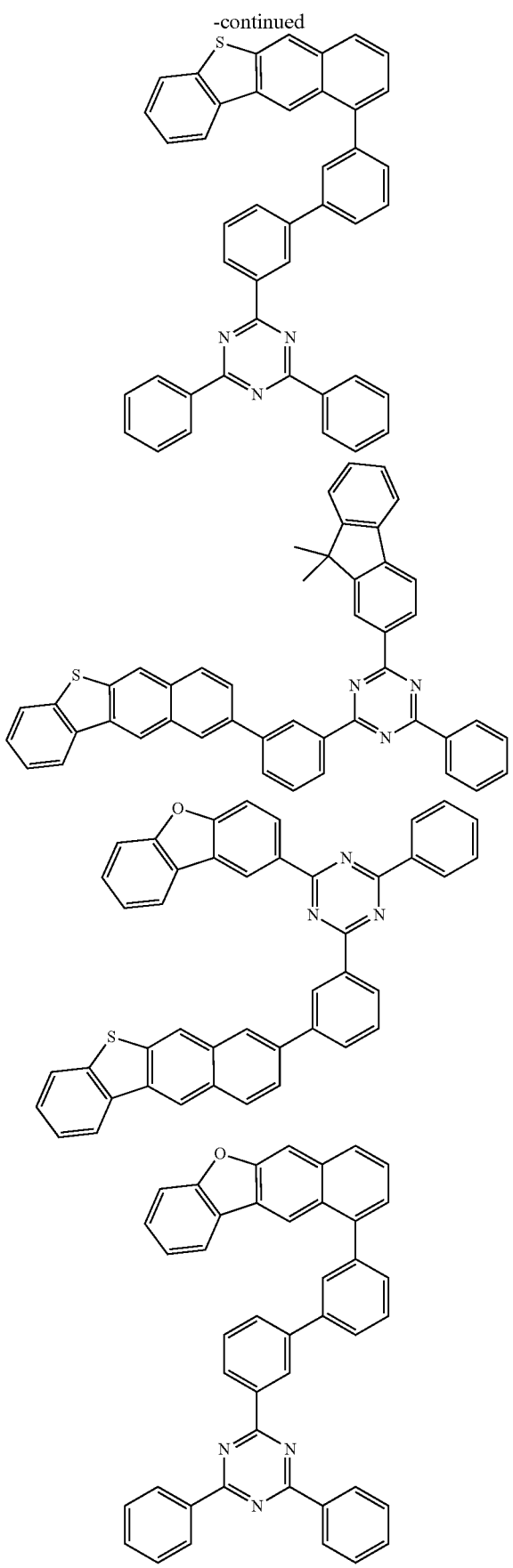
944
-continued
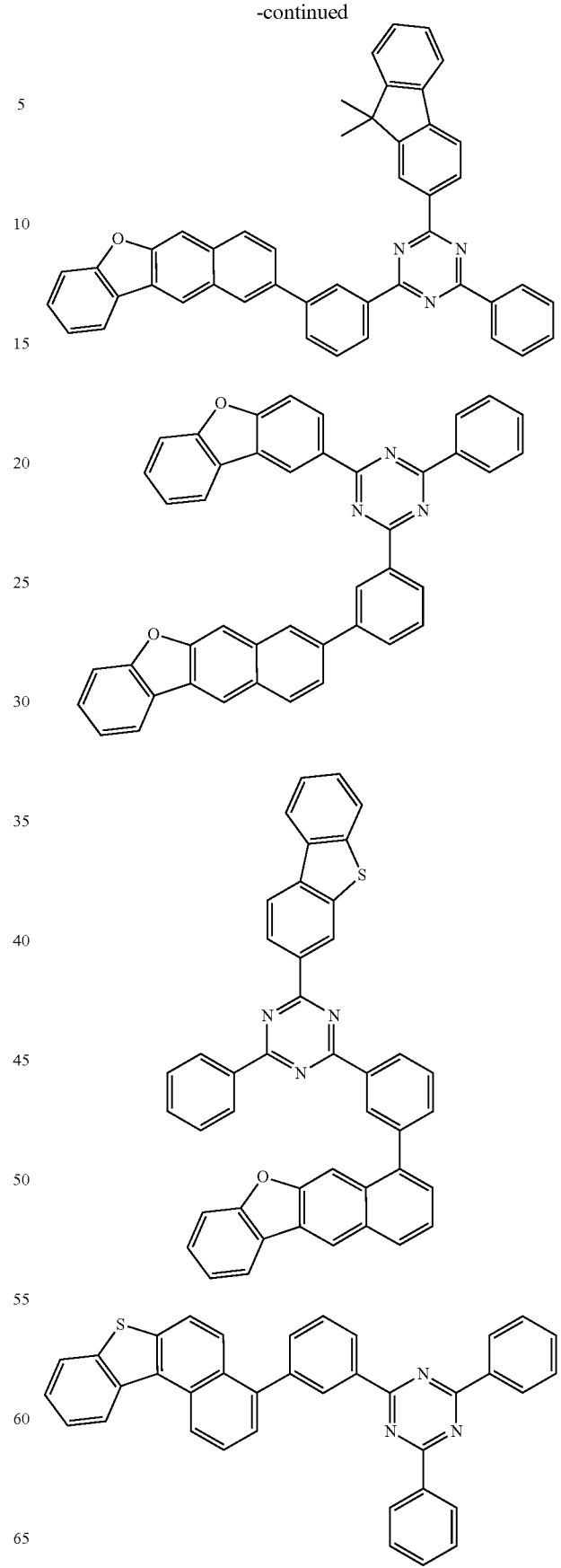

945
-continued
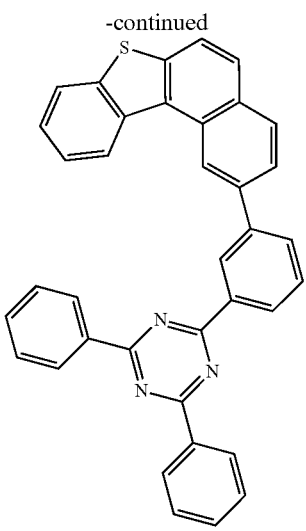
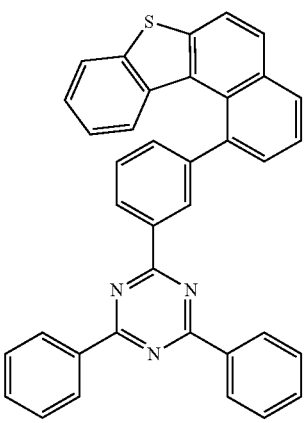
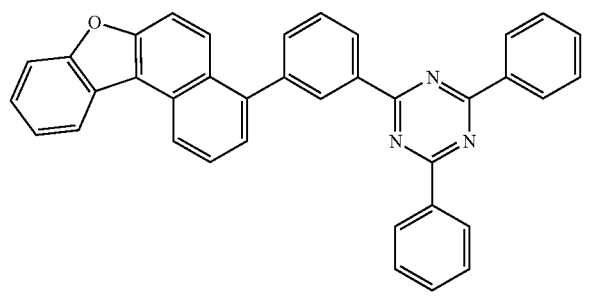
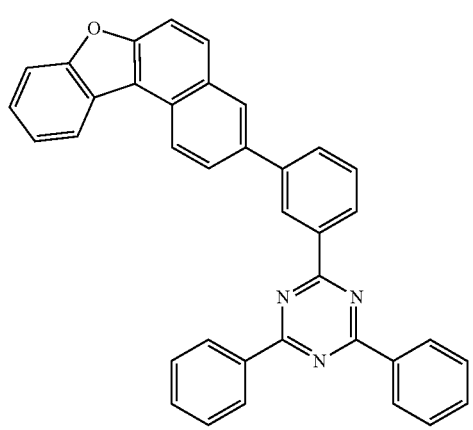
946
-continued
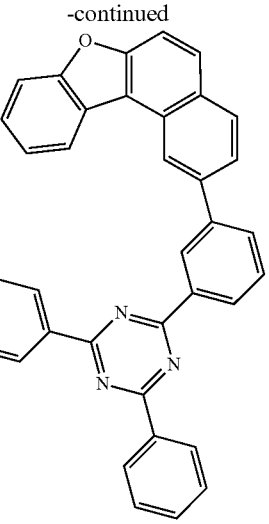
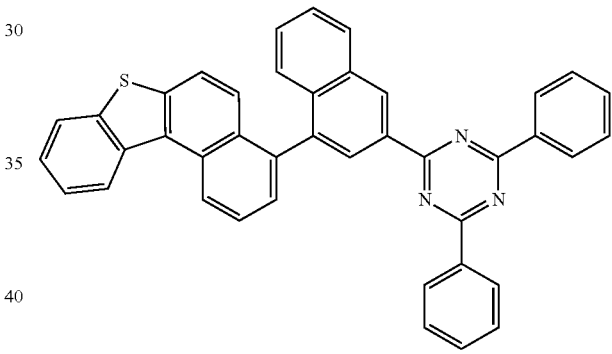
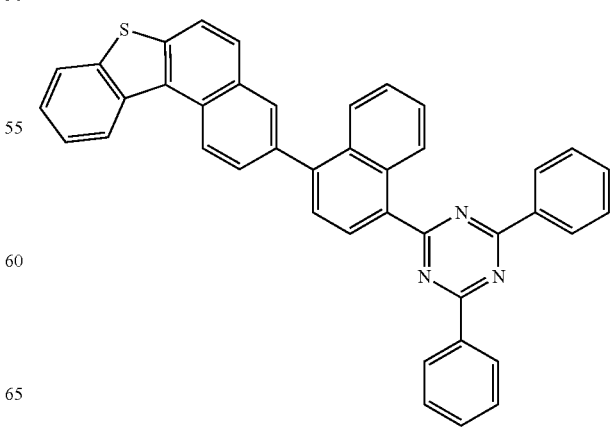

947
-continued
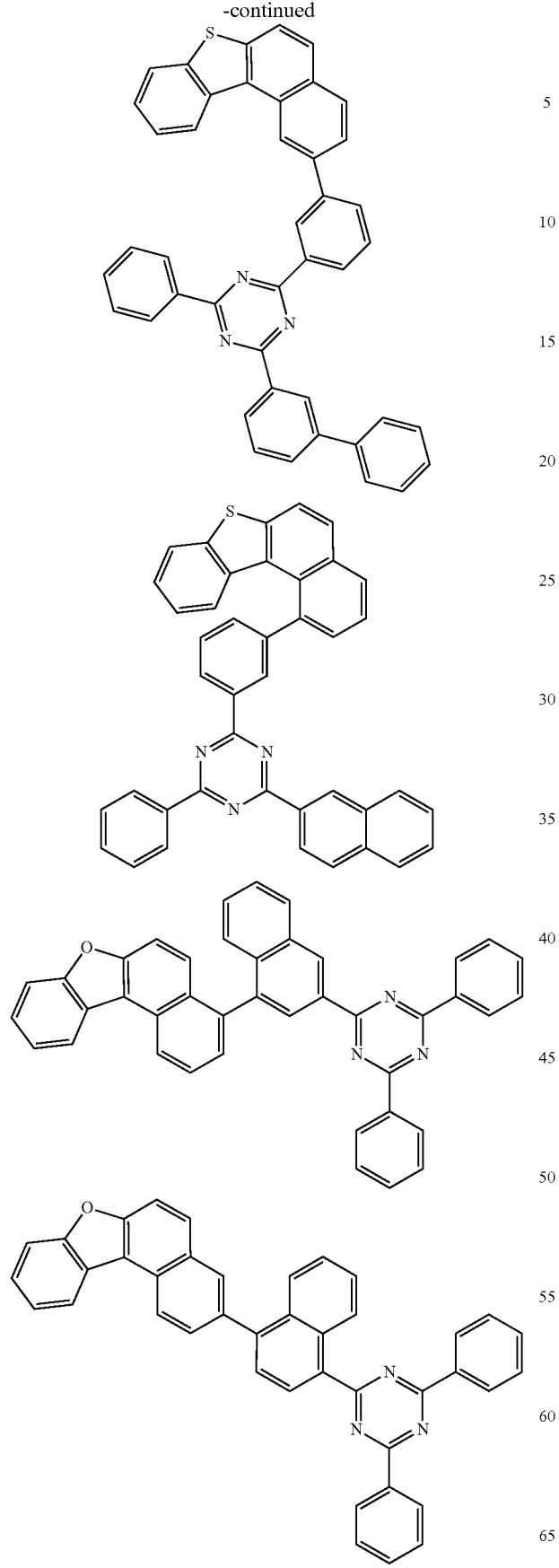
948
-continued
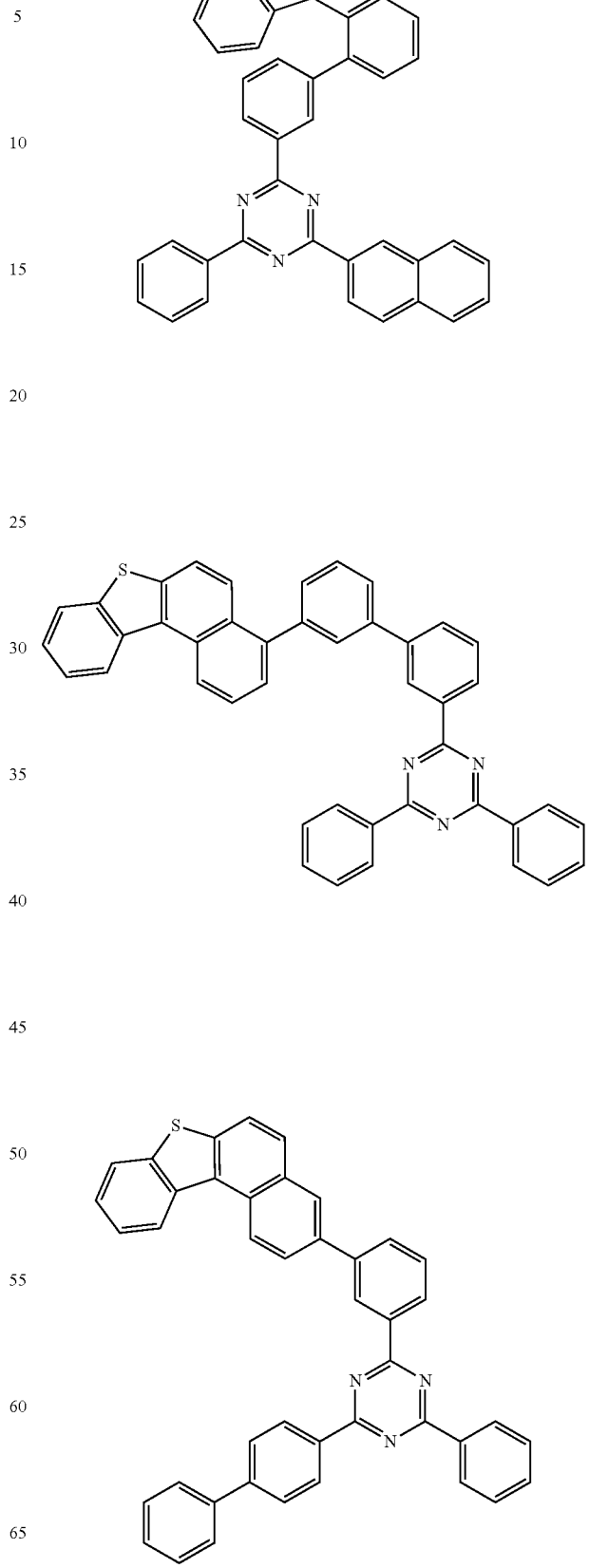

949
-continued
950
-continued
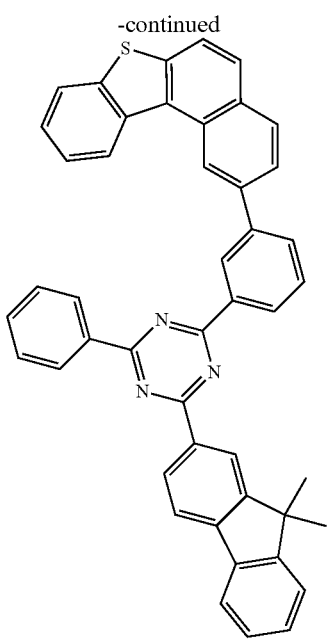
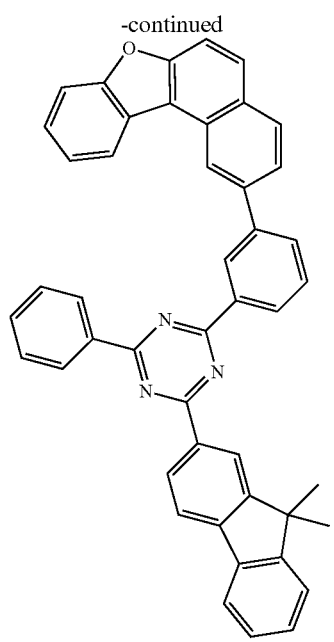
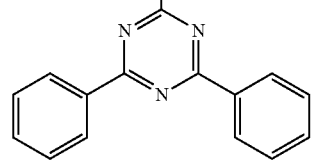
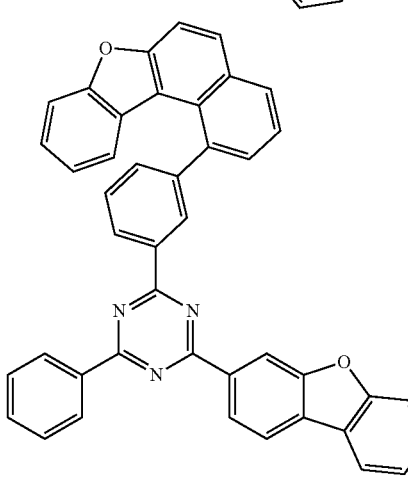
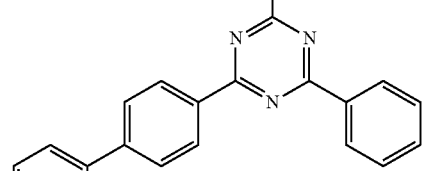
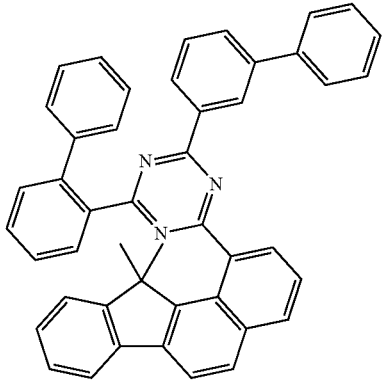

951
-continued
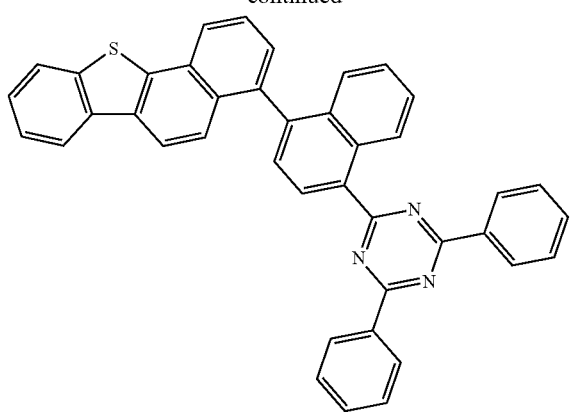
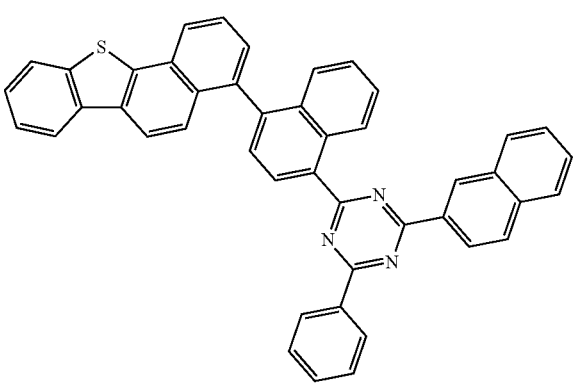
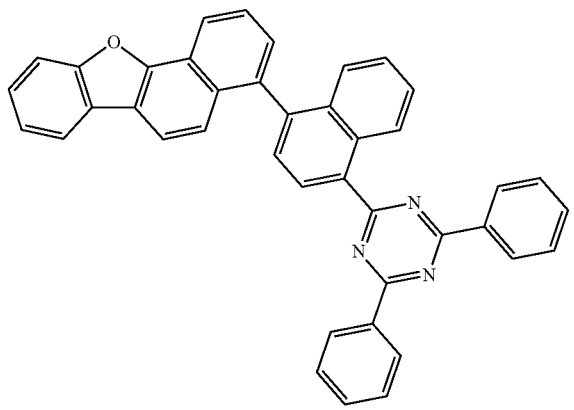
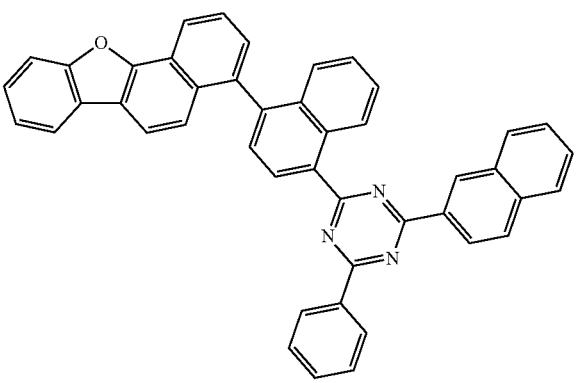
952
-continued
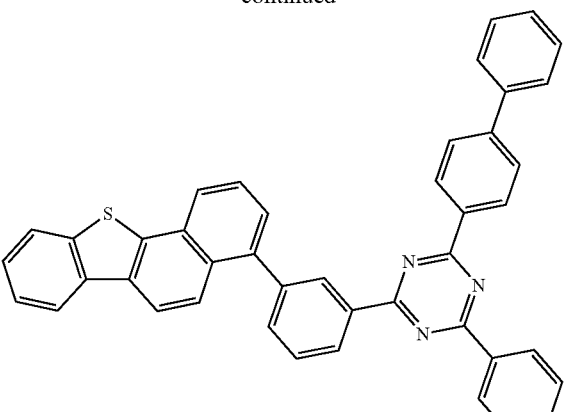
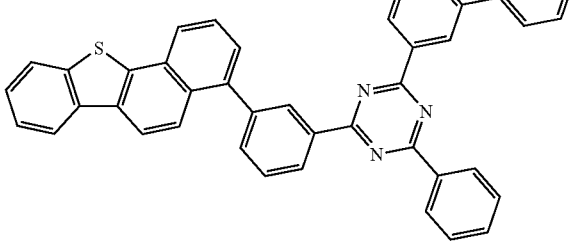
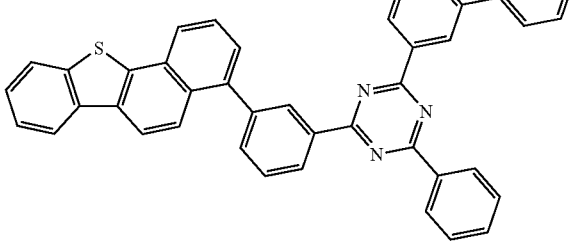
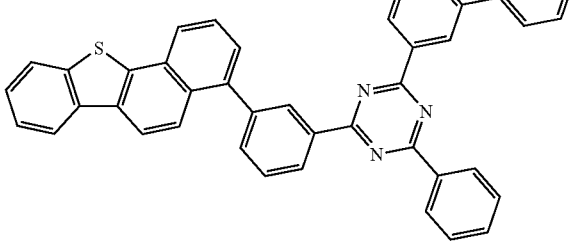
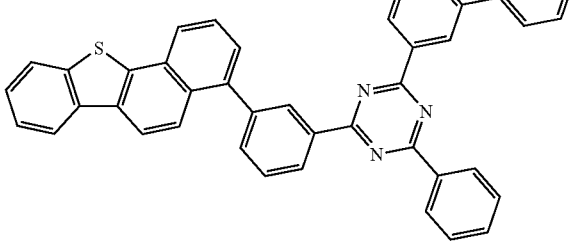

953
-continued
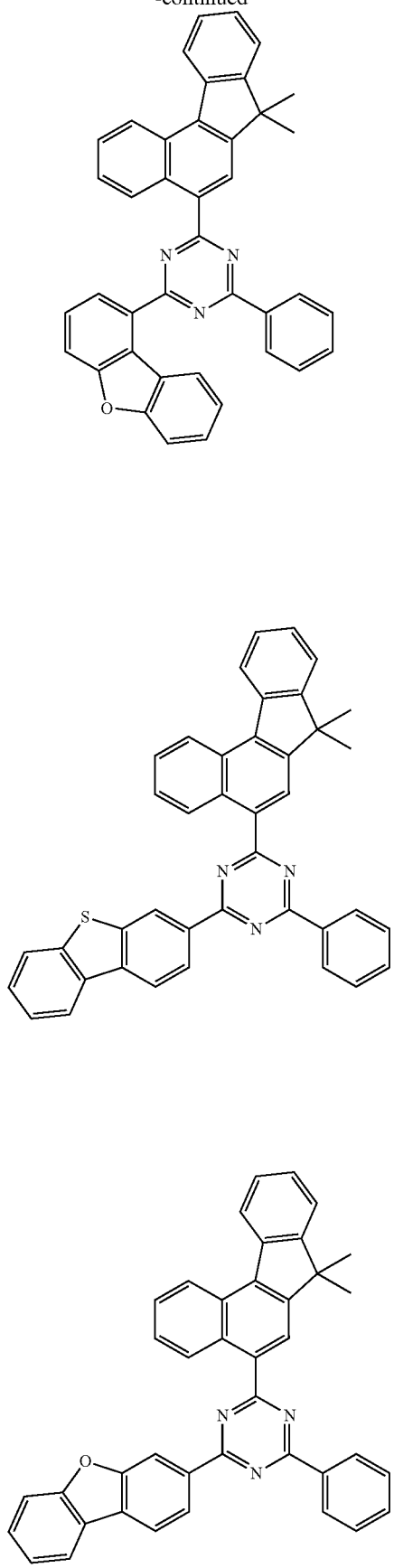
954
-continued
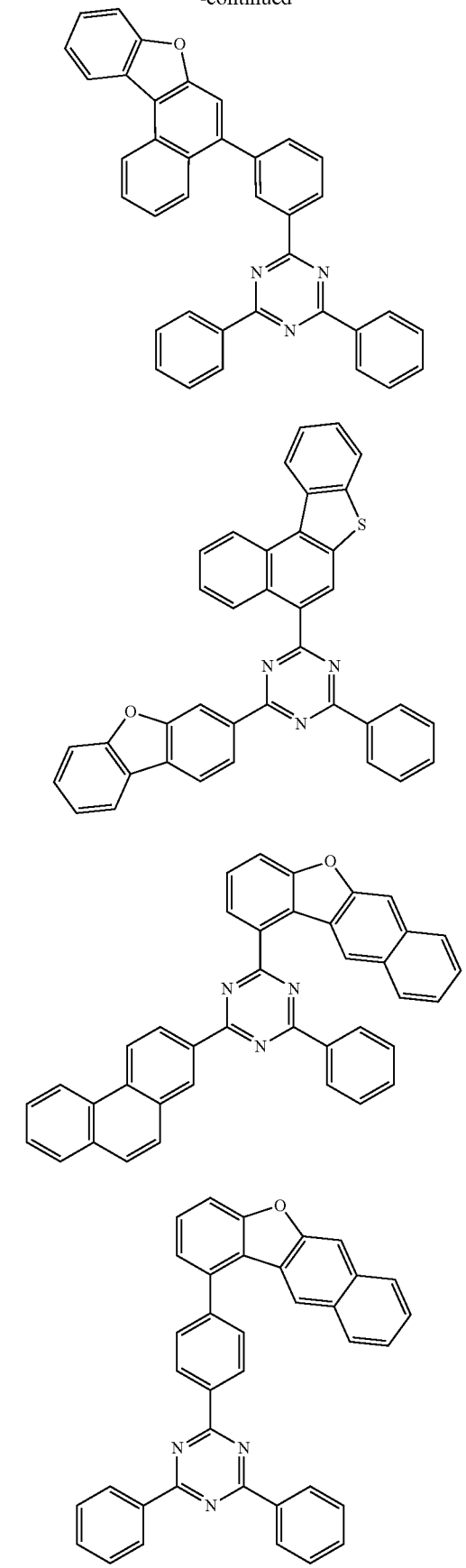

955
-continued
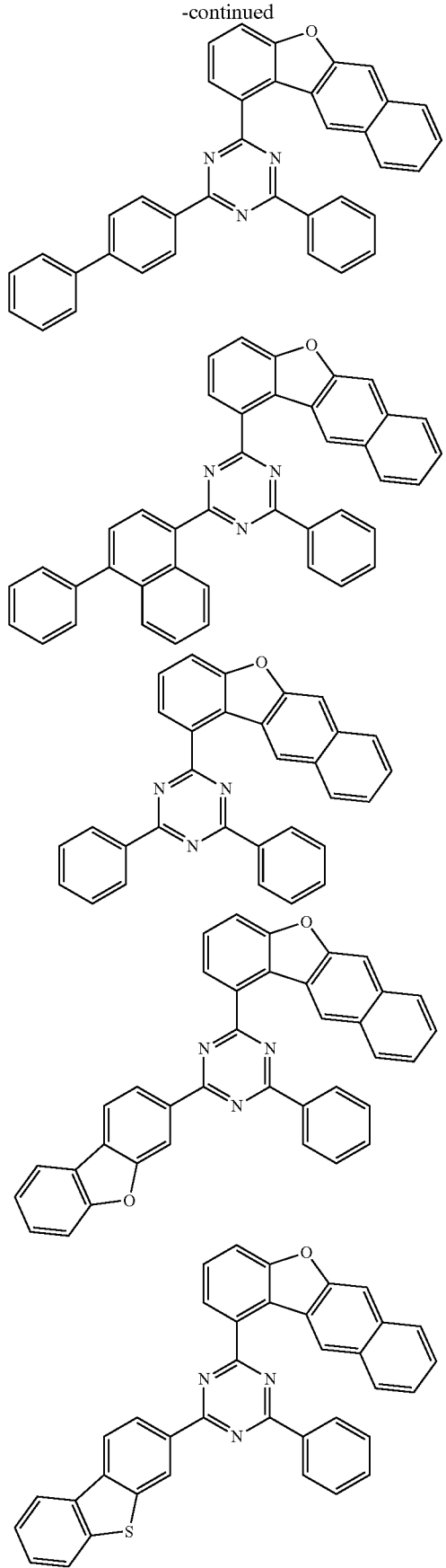
956
-continued
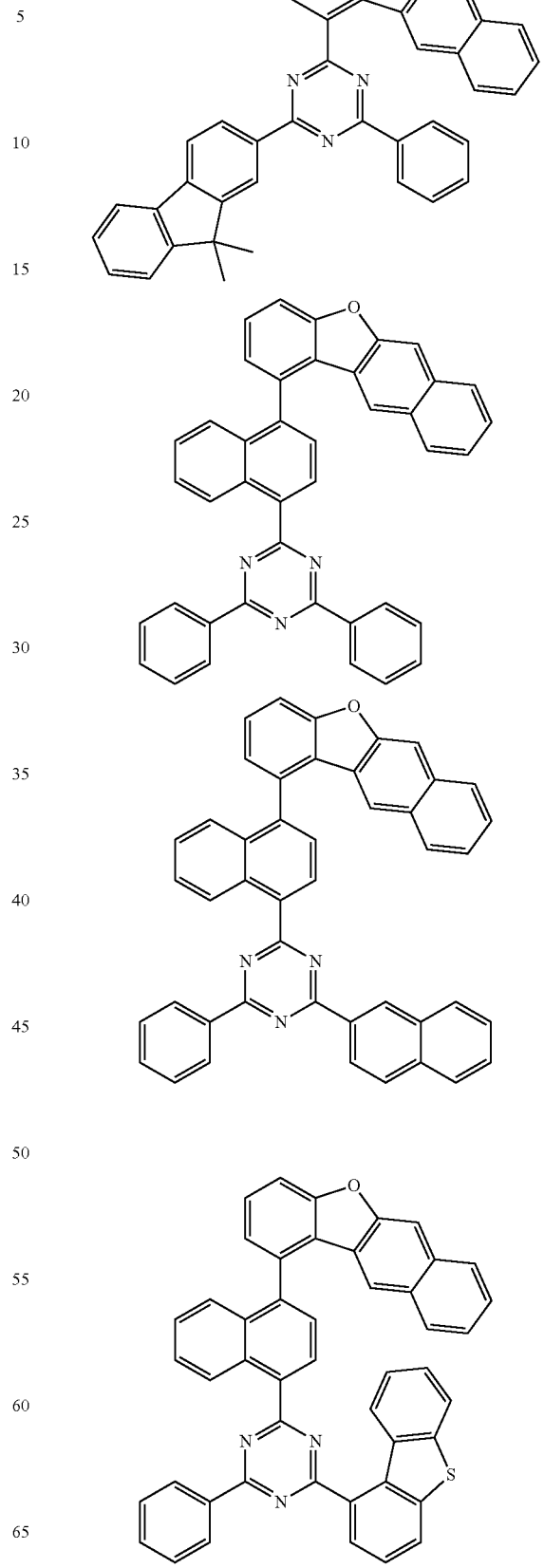

957
-continued

958
-continued

| 959 -continued | 960 -continued |
|---|---|
| 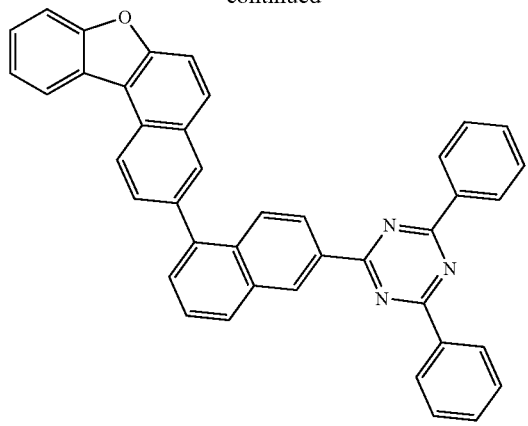 | 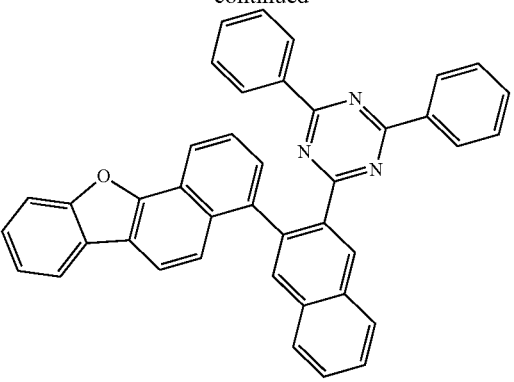 |
| 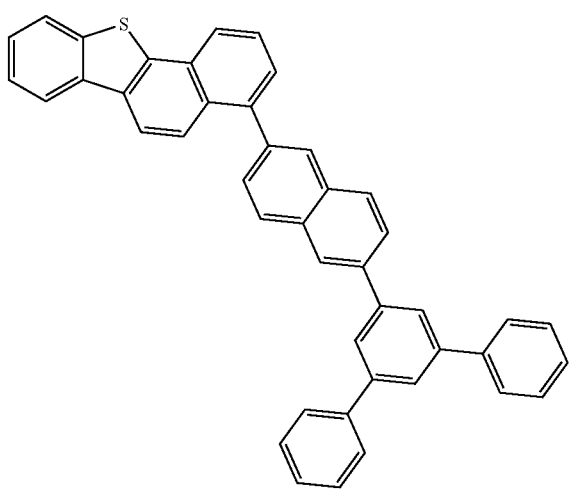 | 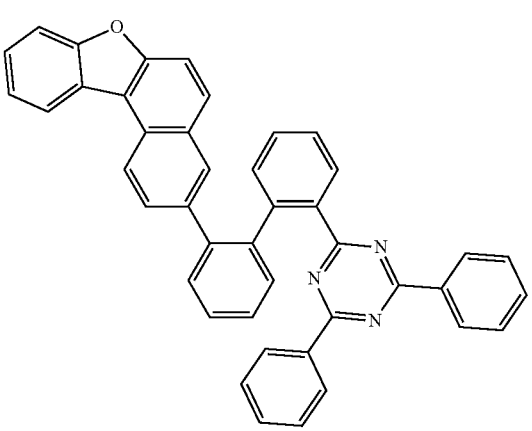 |
| 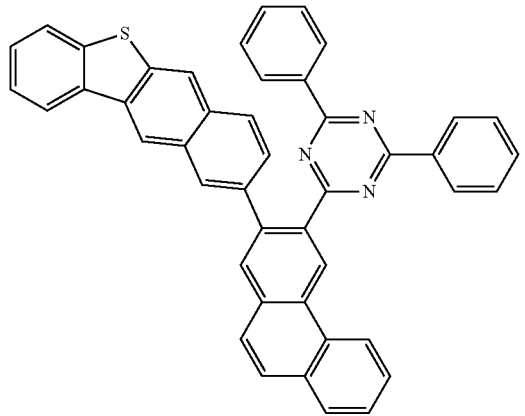 | 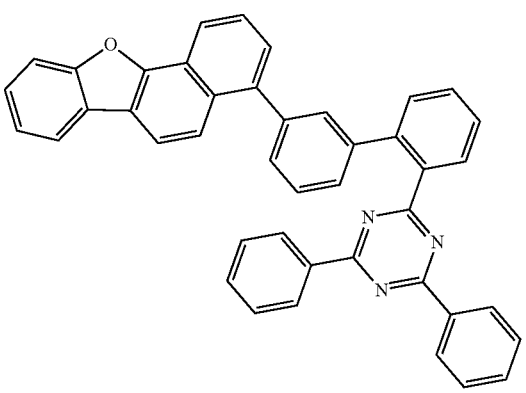 |
| 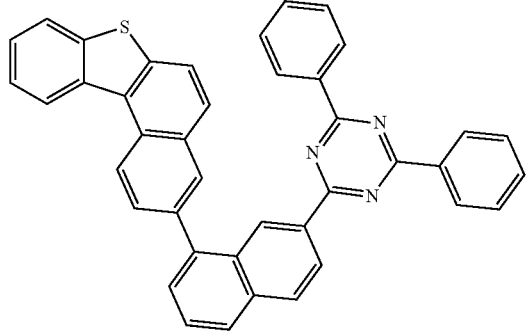 | |

961
-continued
962
-continued
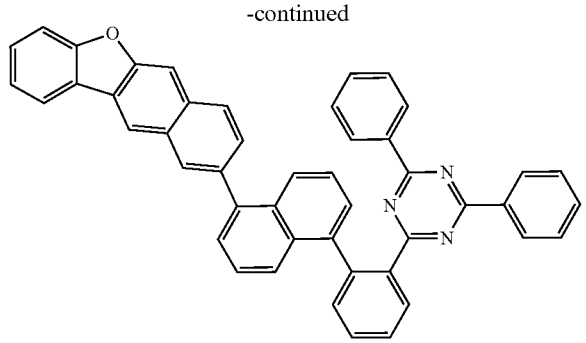
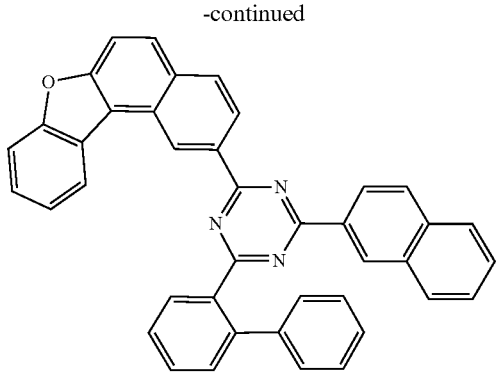
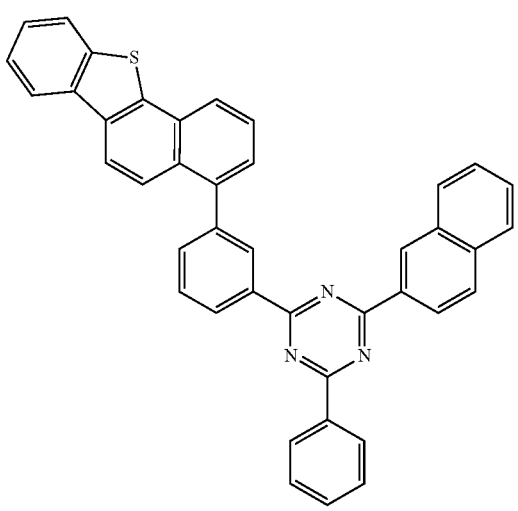
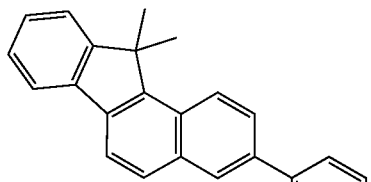
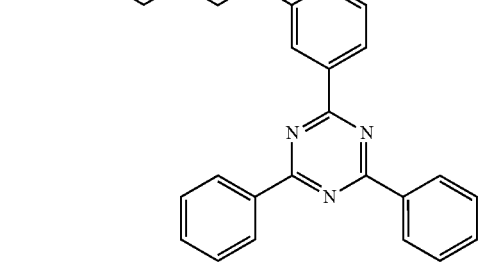
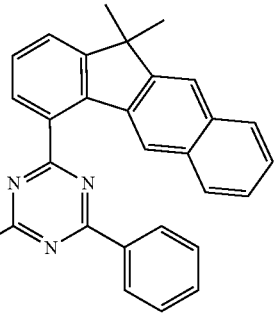

963
-continued
964
-continued
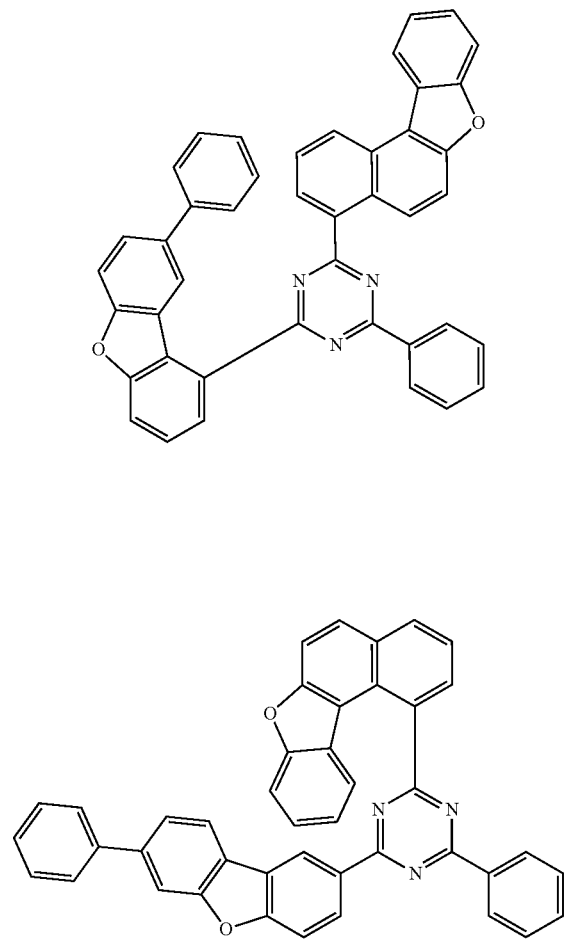
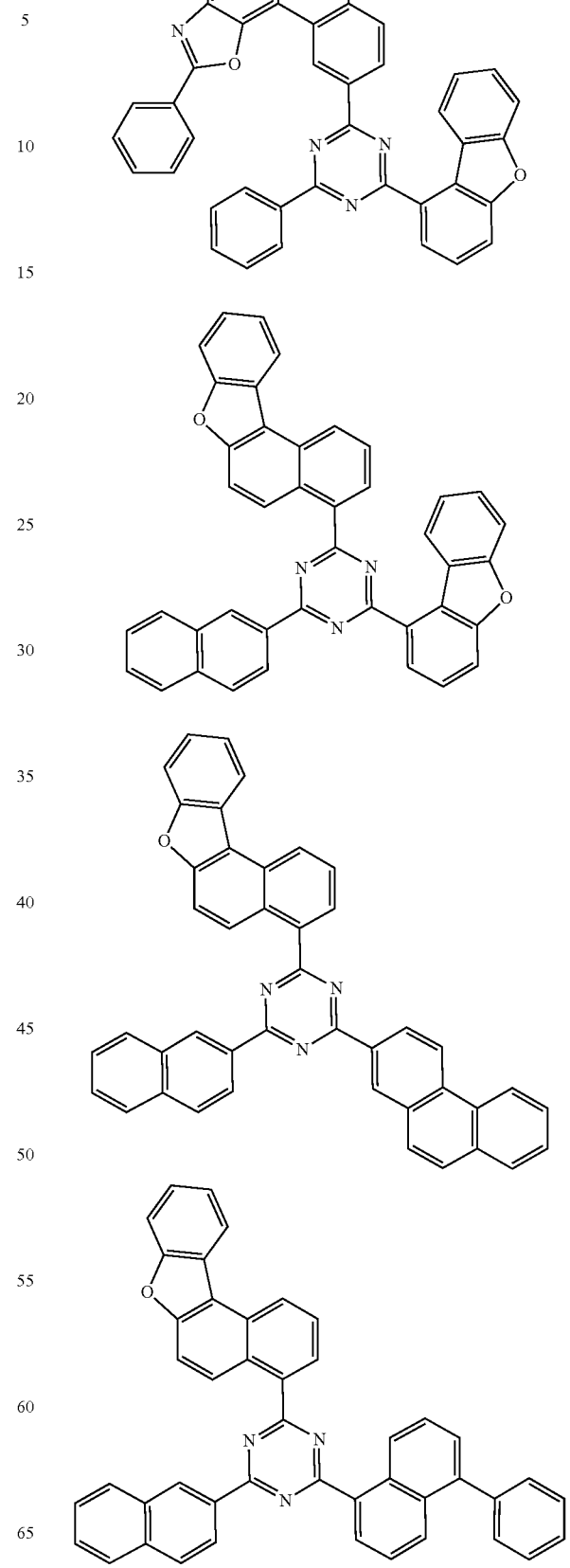

965
-continued
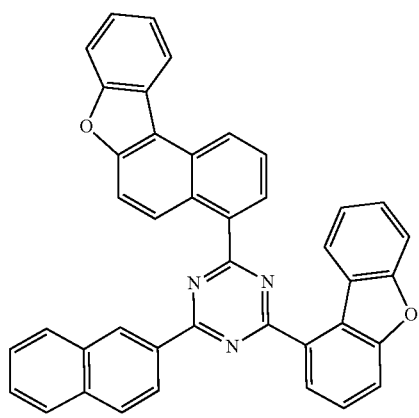
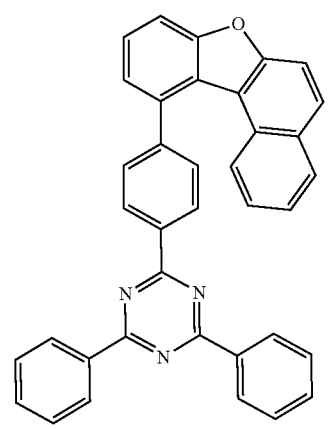
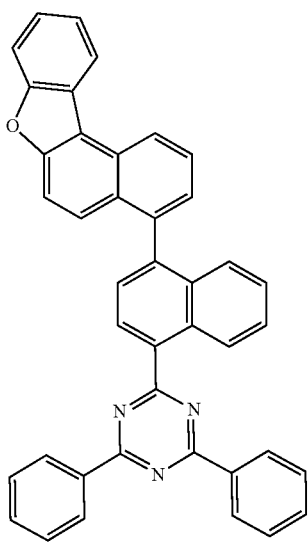
966
-continued
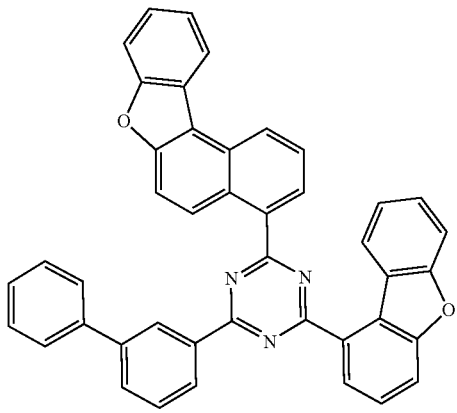
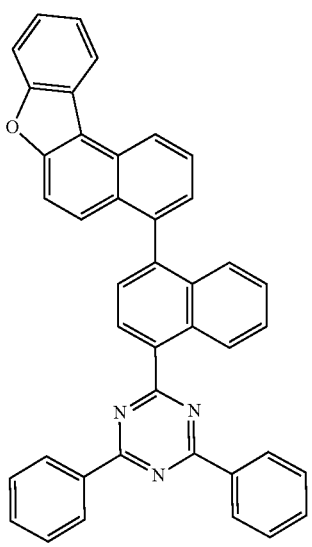
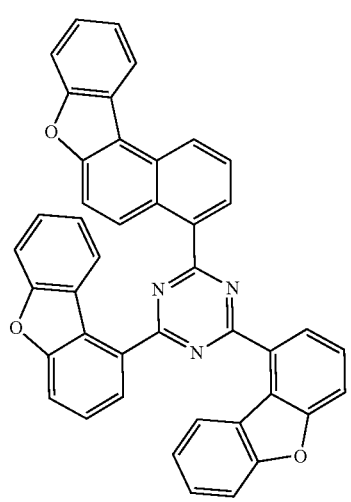

967
-continued
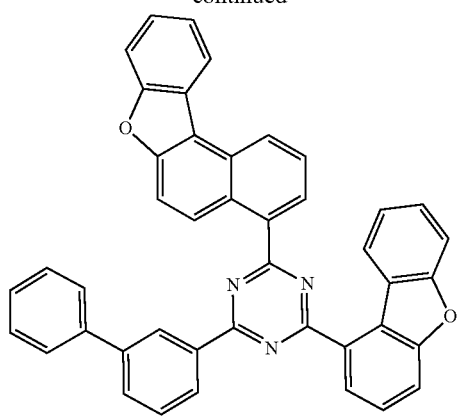
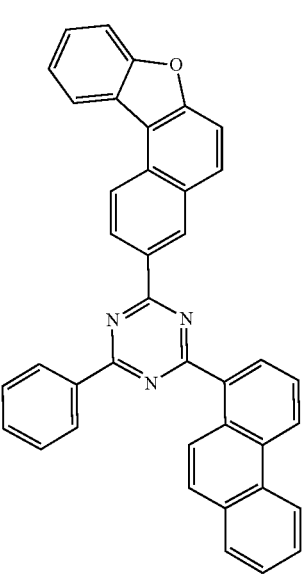
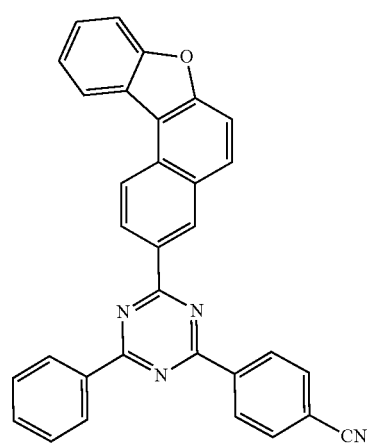
968
-continued
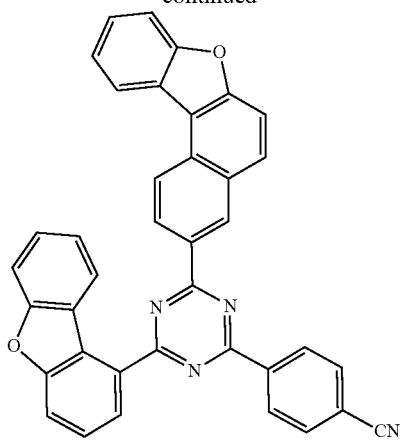
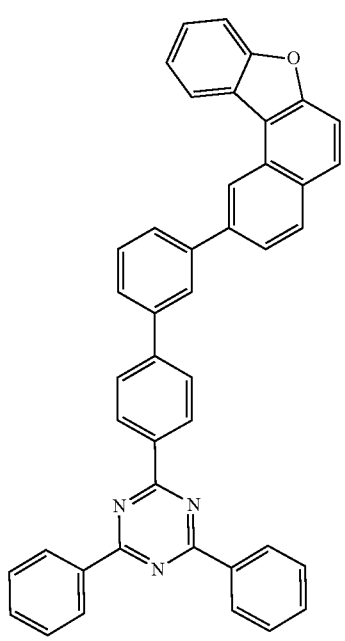

969 970
-continued -continued
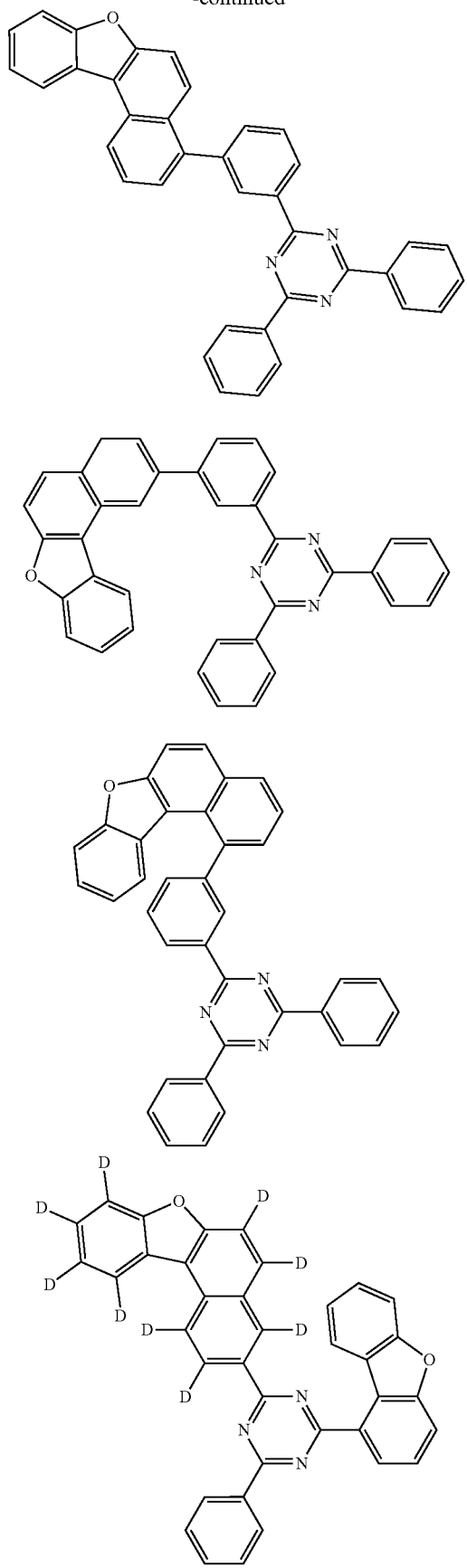

971
-continued
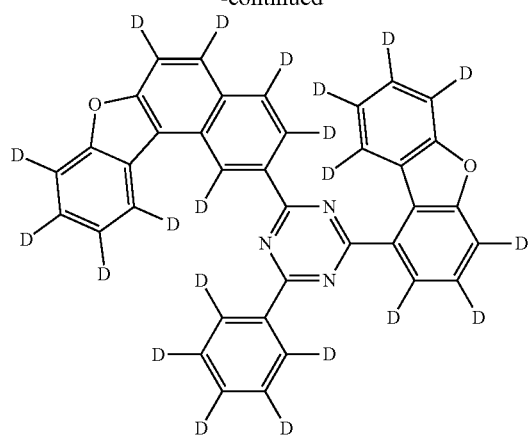
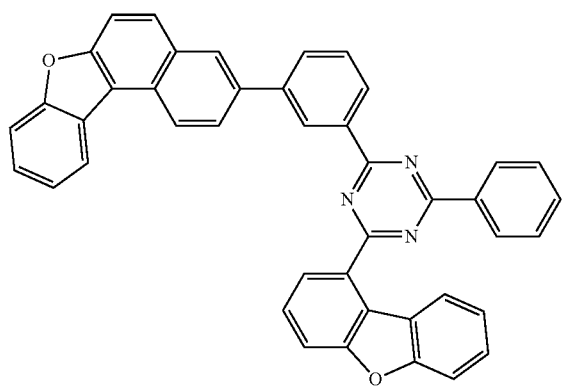
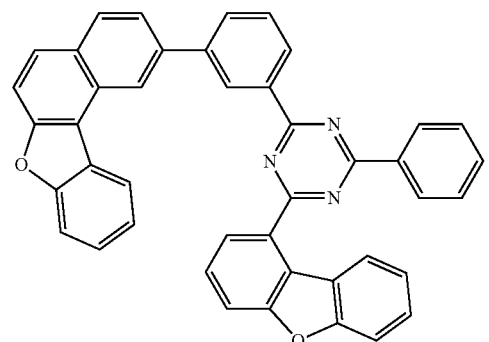
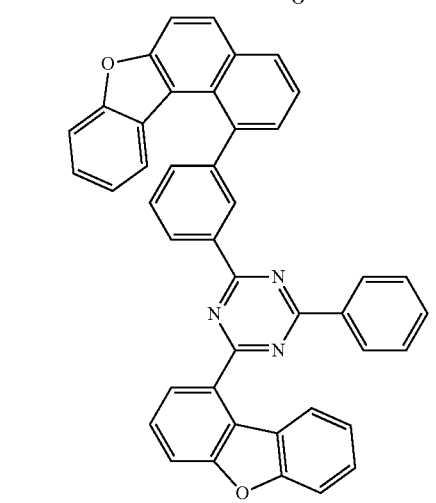
972
-continued
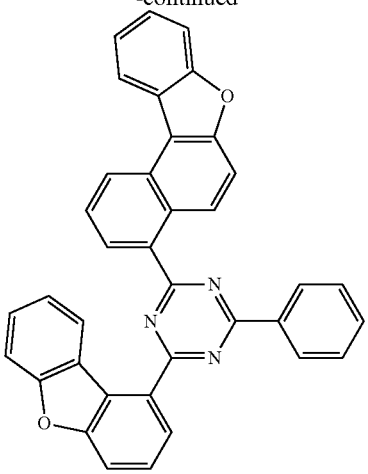
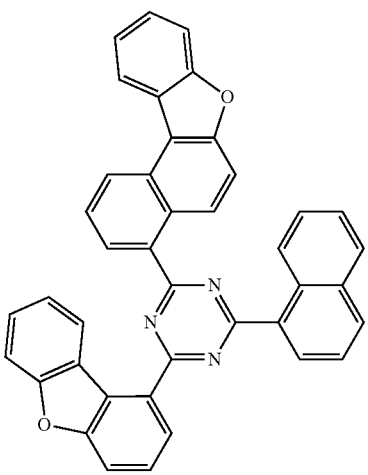
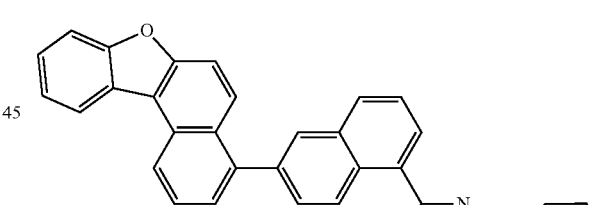
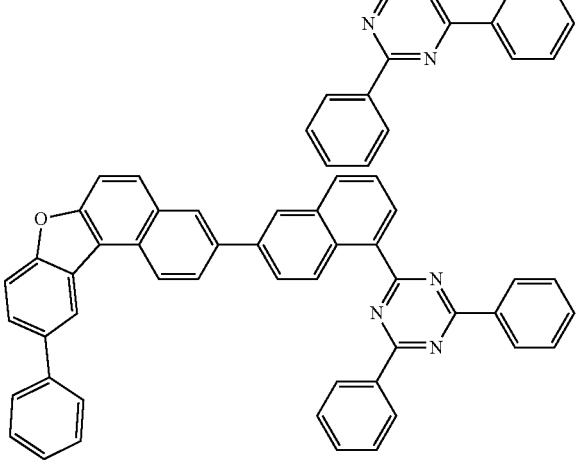

973
-continued
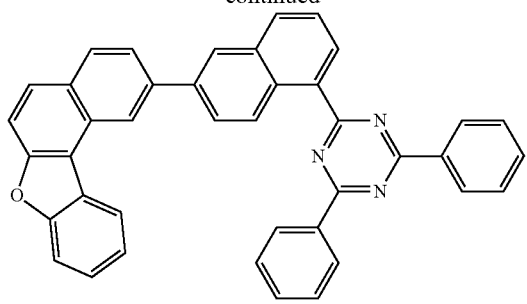
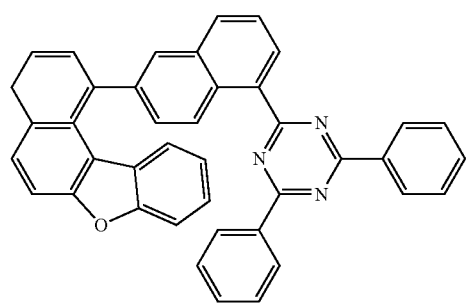
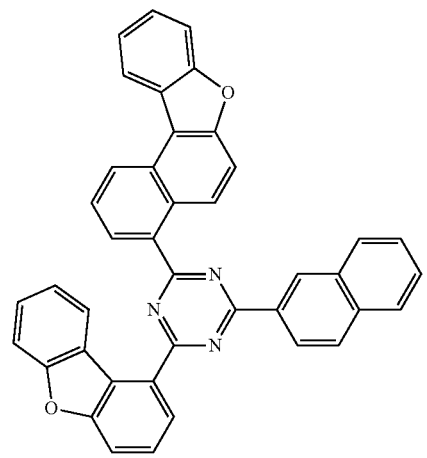
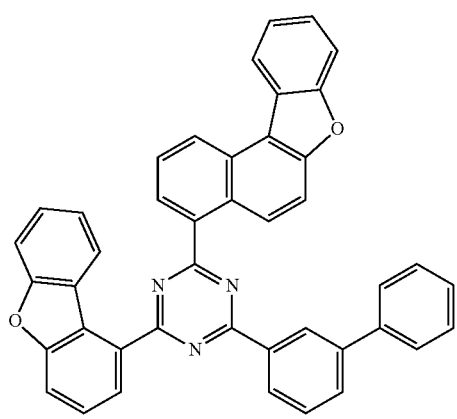
974
-continued
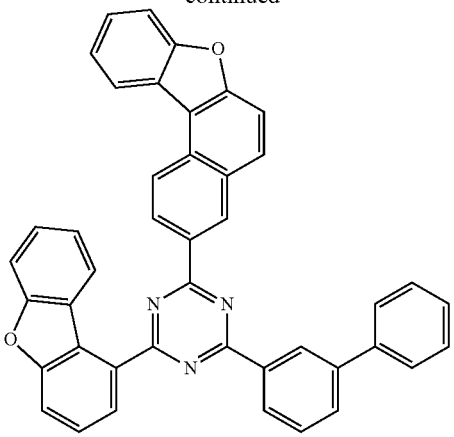
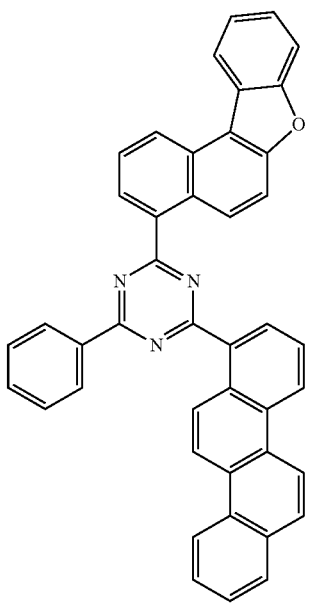
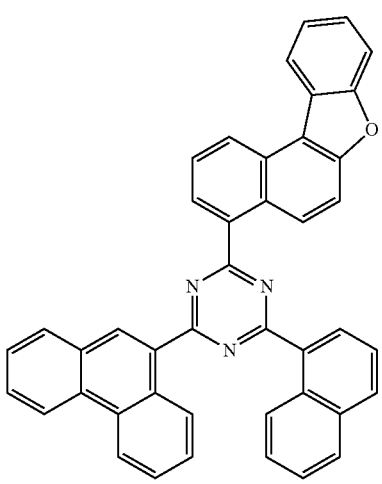

975
-continued
976
-continued
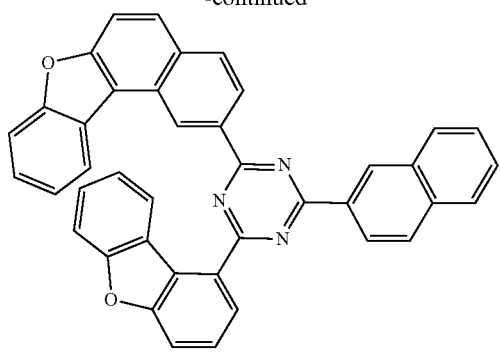
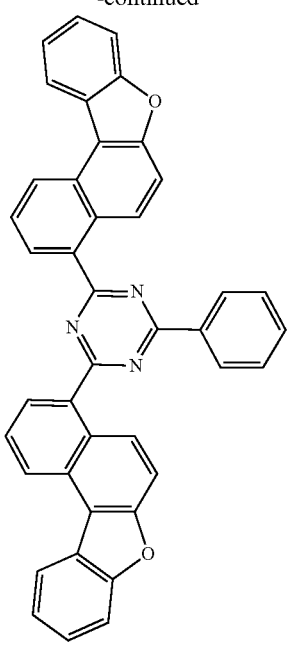
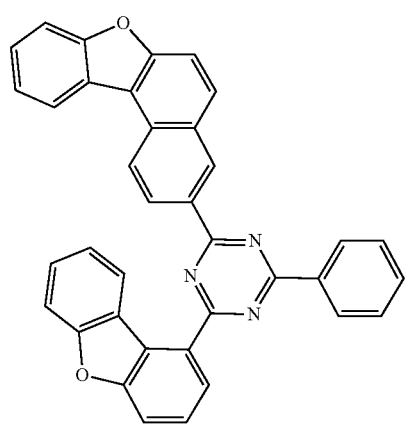
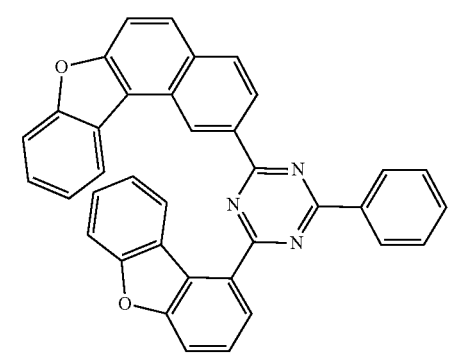
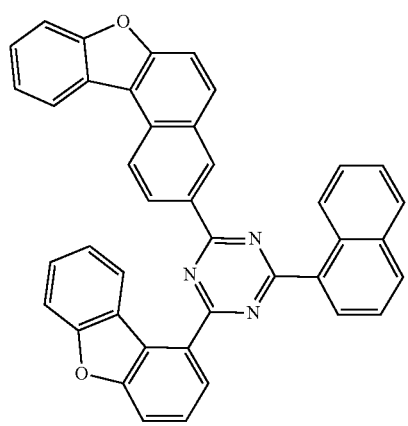
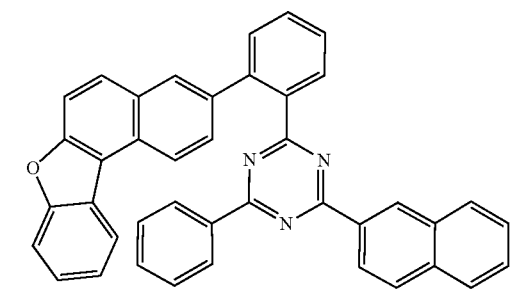
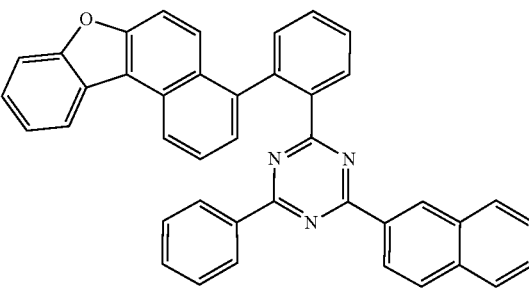

977
-continued
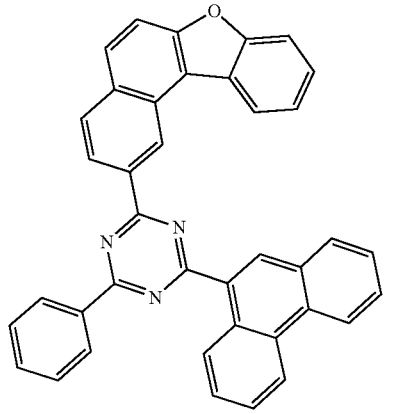
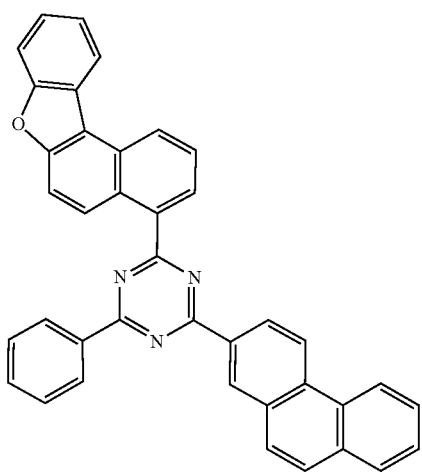
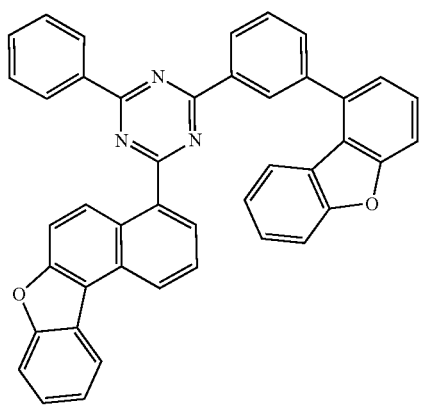
978
-continued
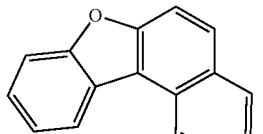
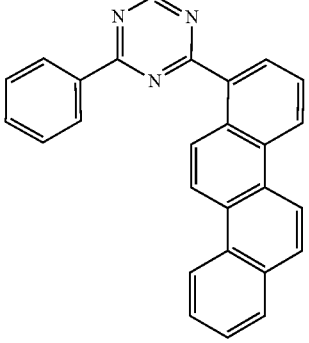
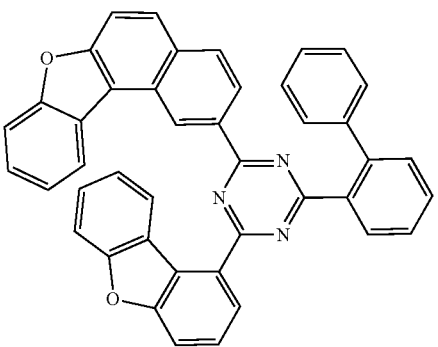
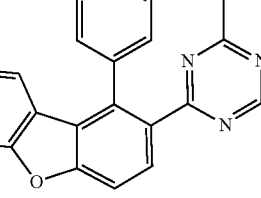

979
-continued
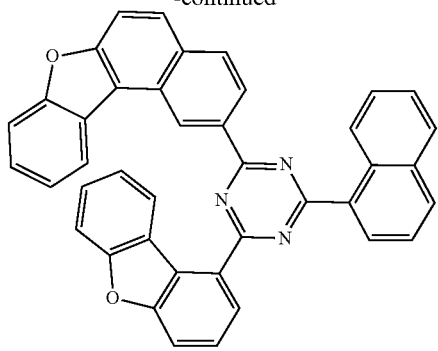
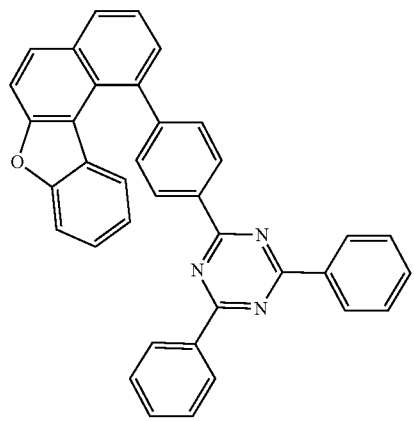
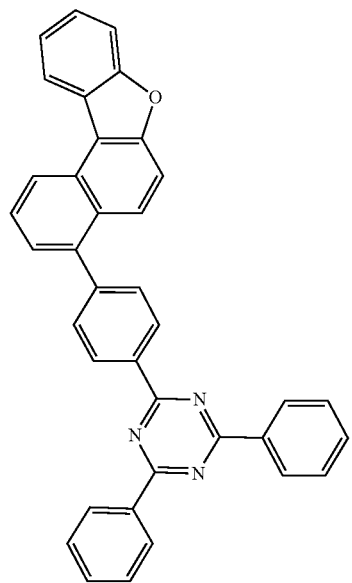
980
-continued
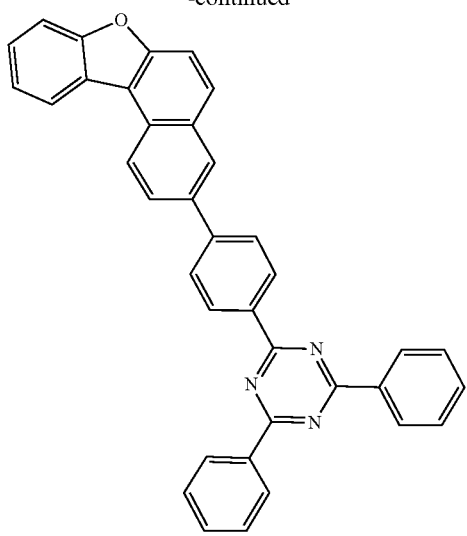
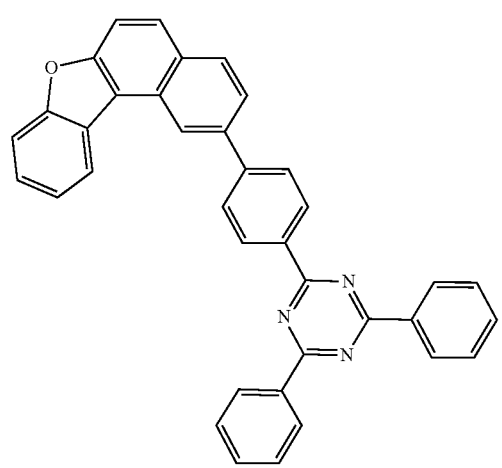
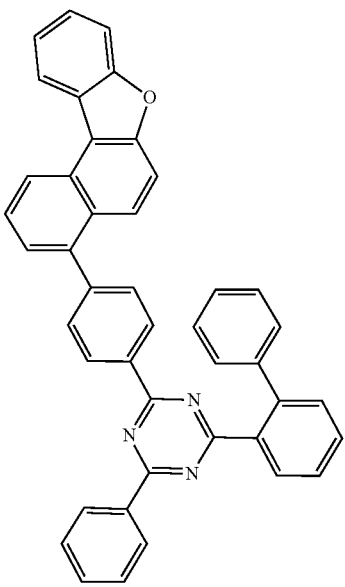

981
-continued
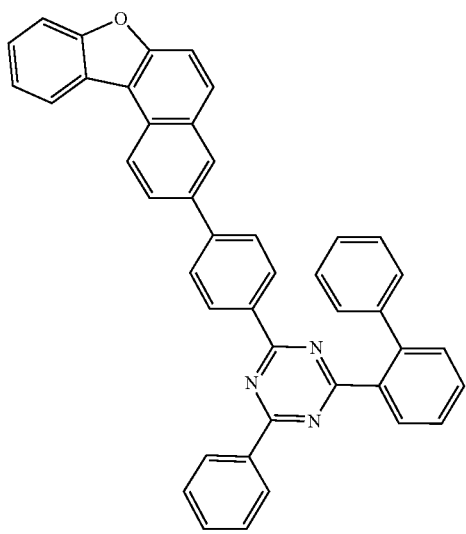
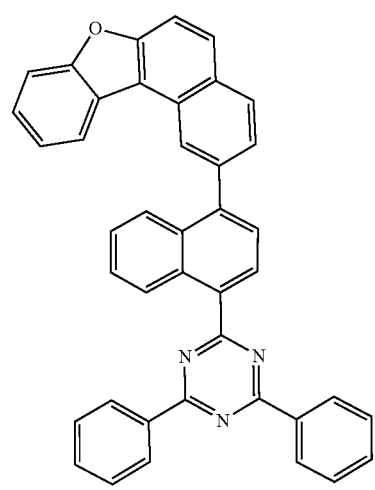
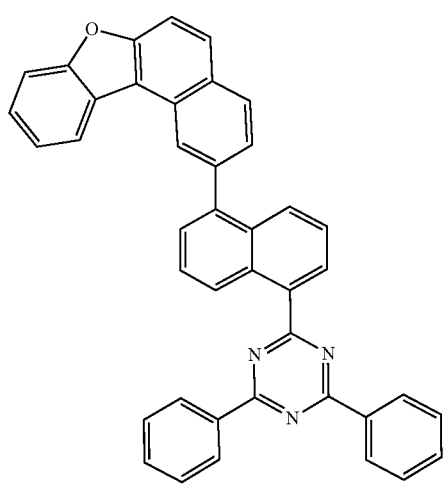
982
-continued
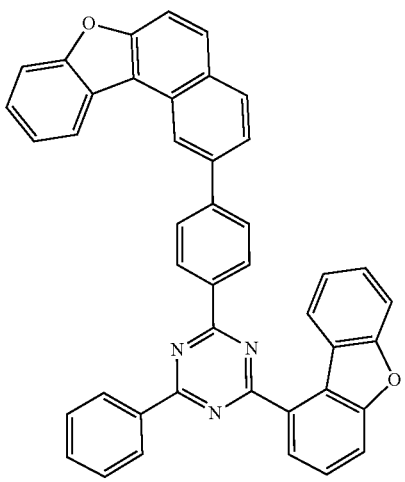
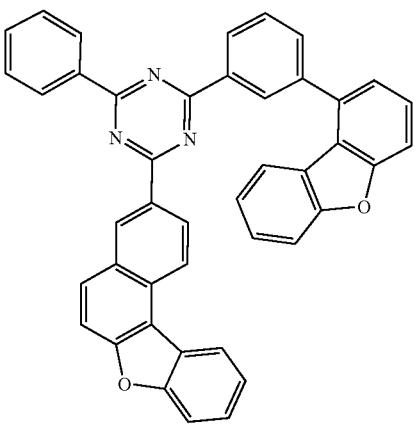
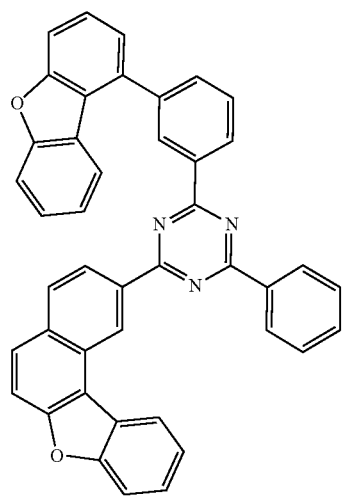

983
-continued
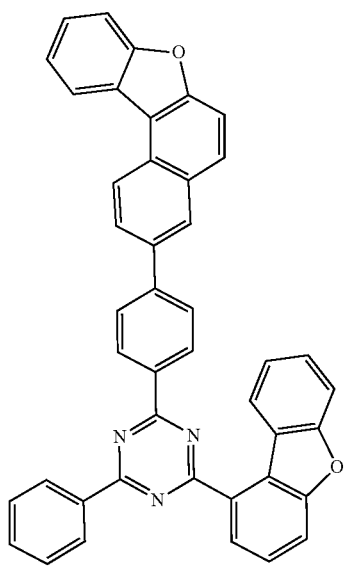
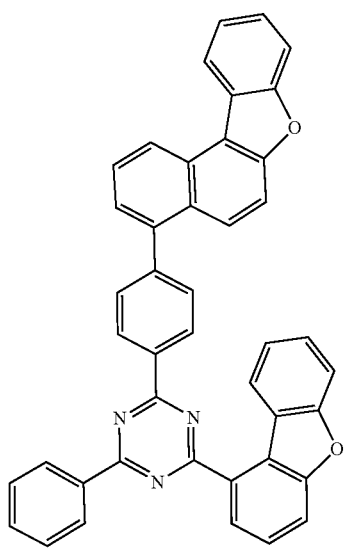
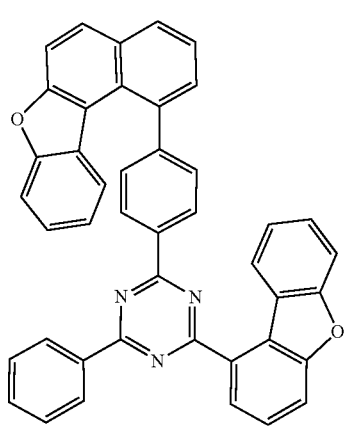
984
-continued
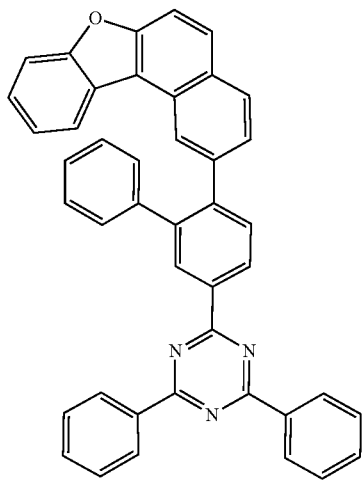
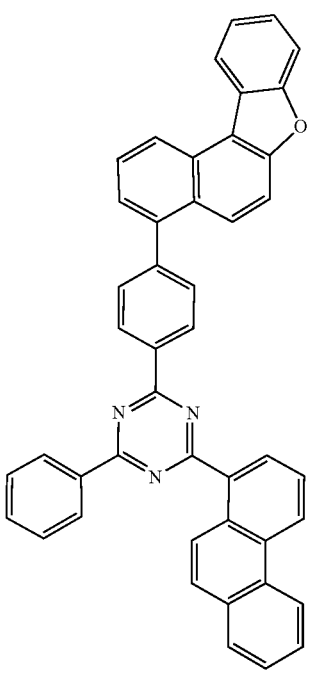
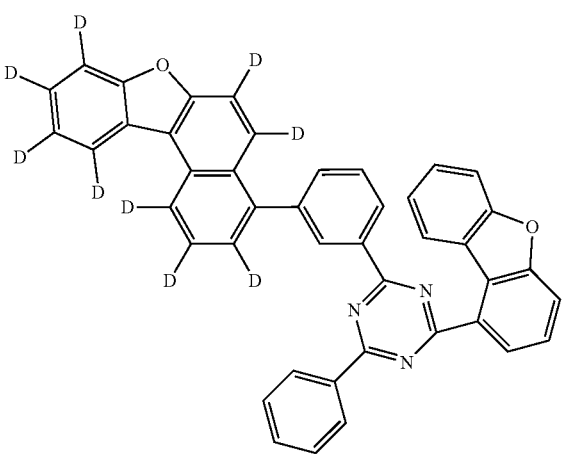

985
-continued
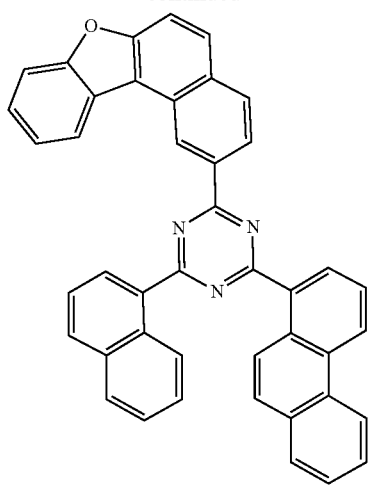
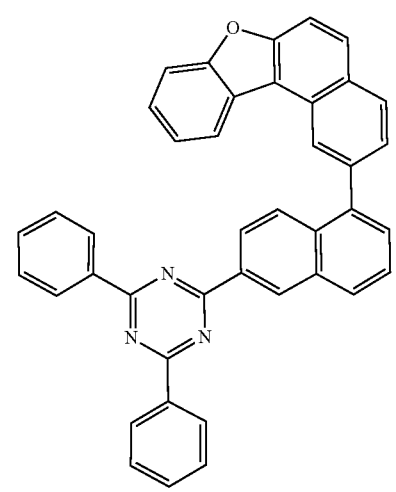
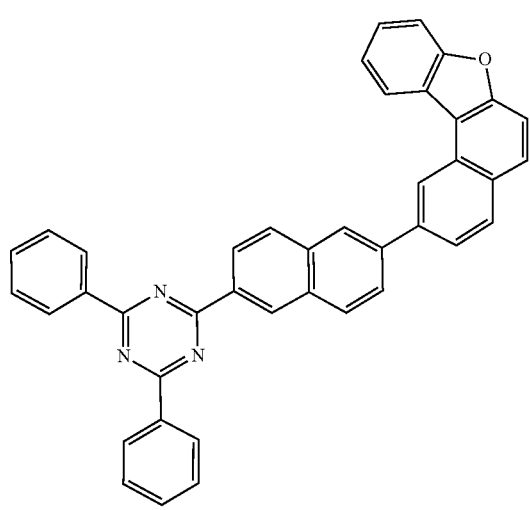
986
-continued
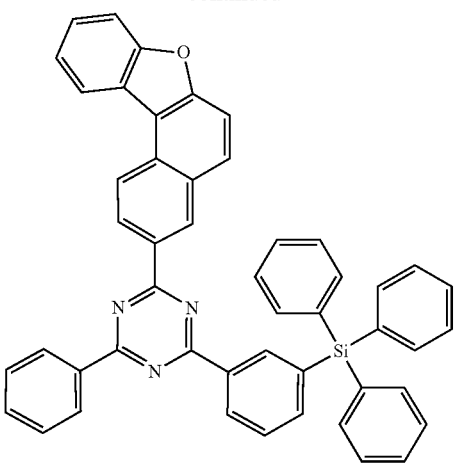
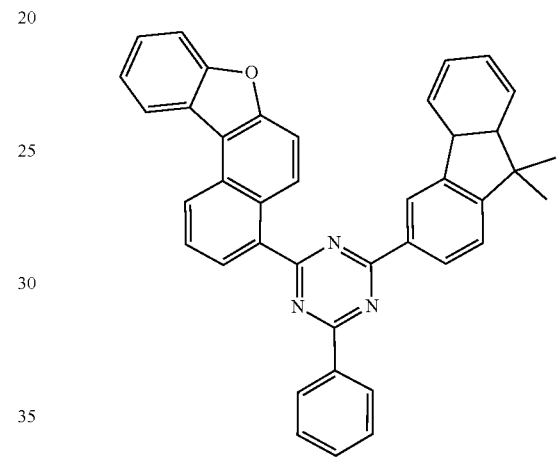
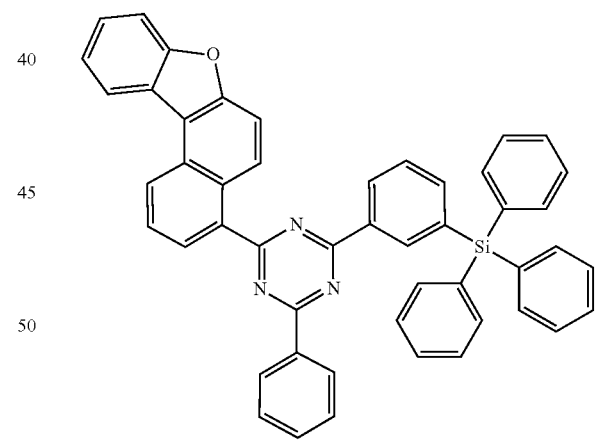
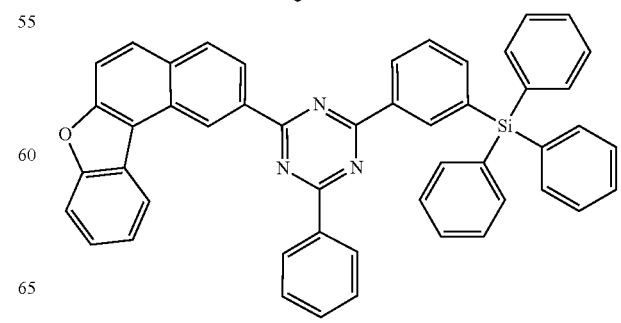

987
-continued
988
-continued
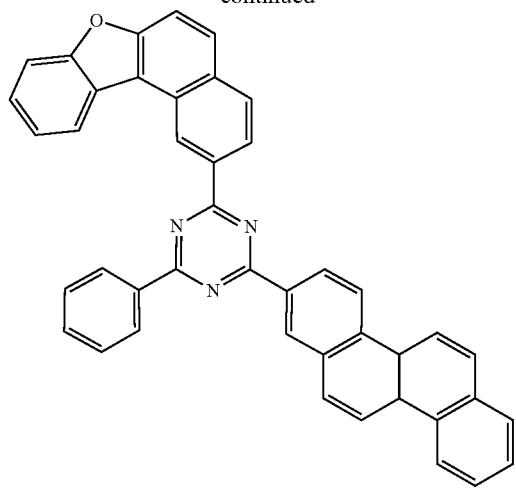
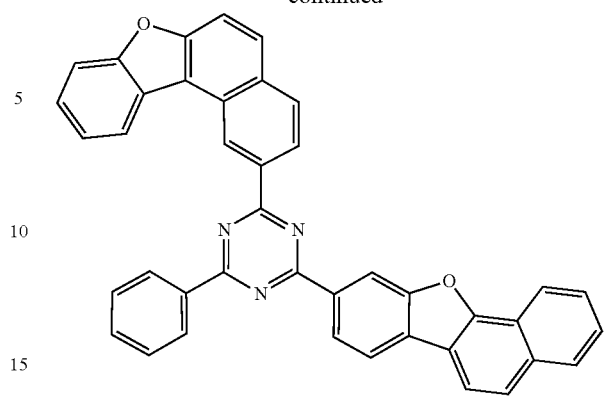
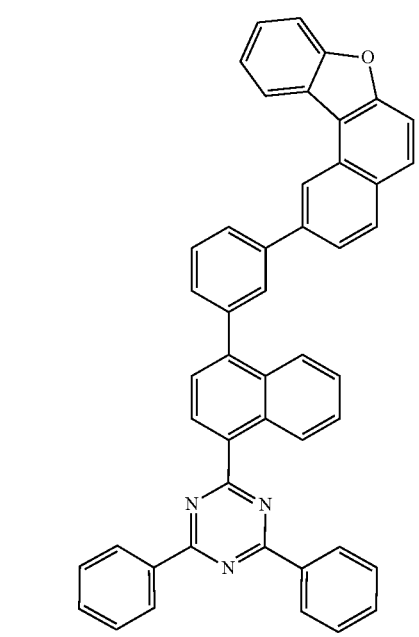
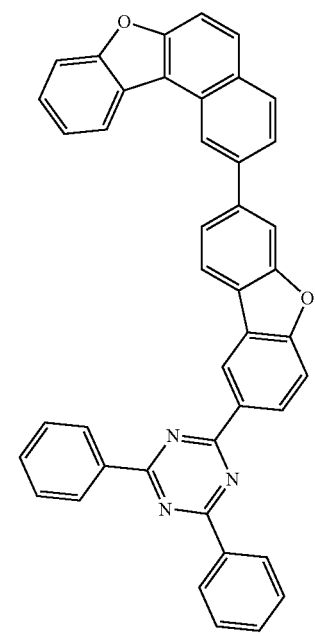

989
-continued
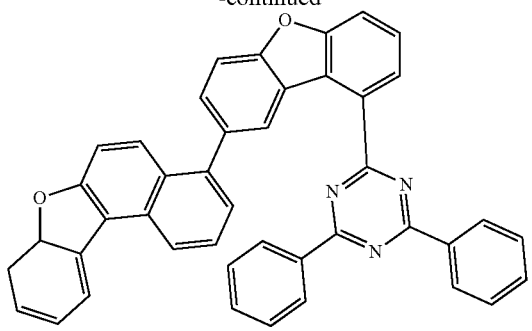
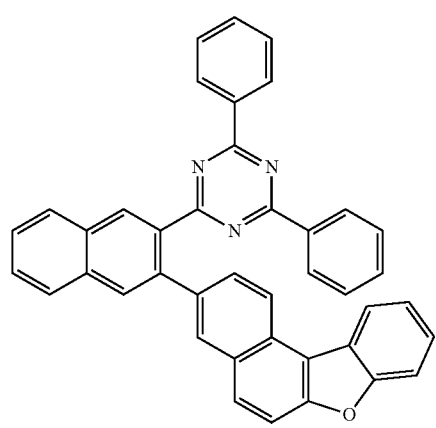
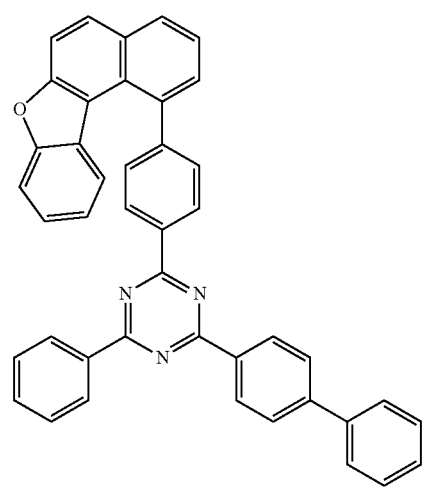
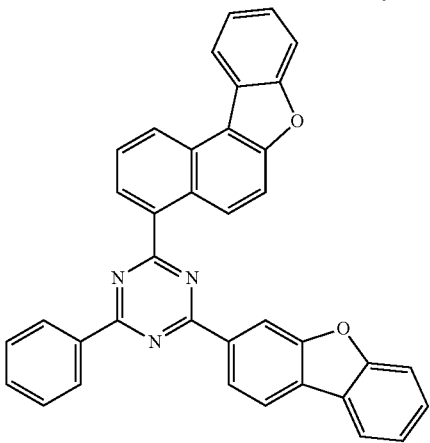
990
-continued
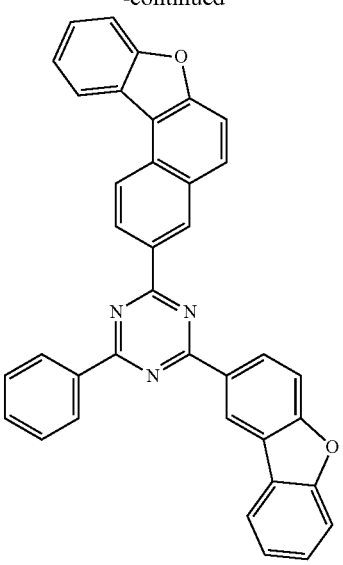
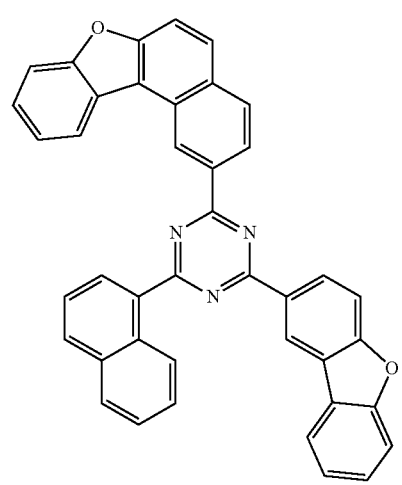
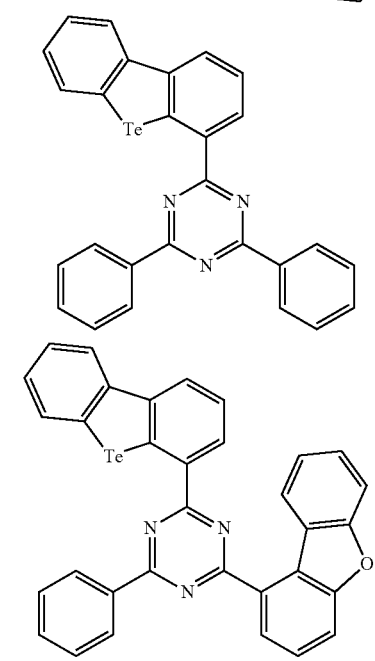

991
-continued
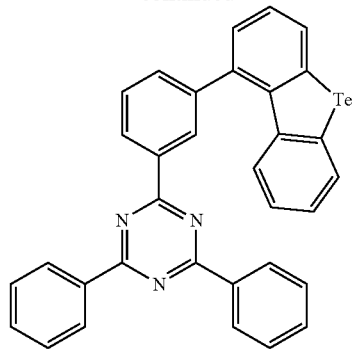
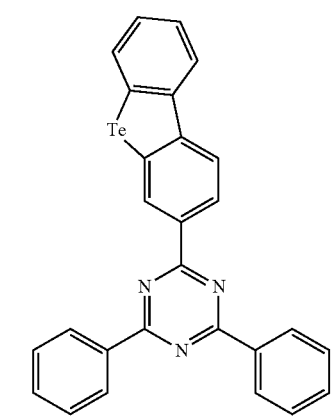
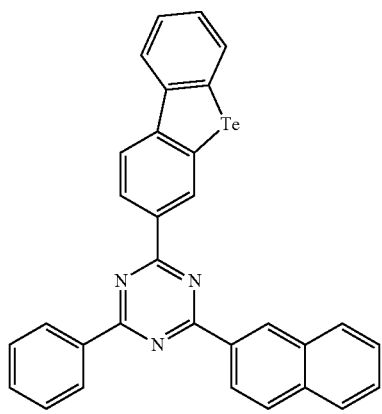
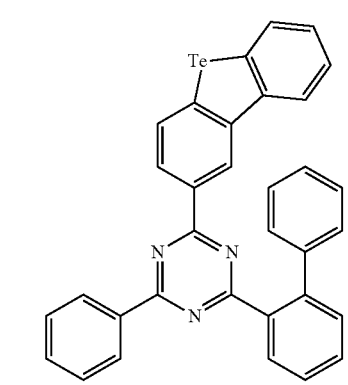
992
-continued
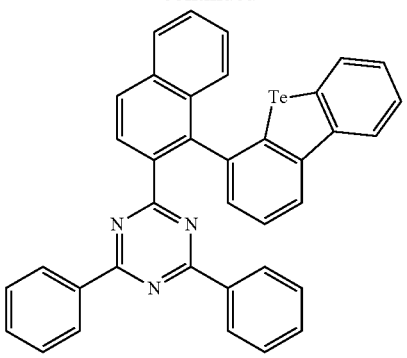
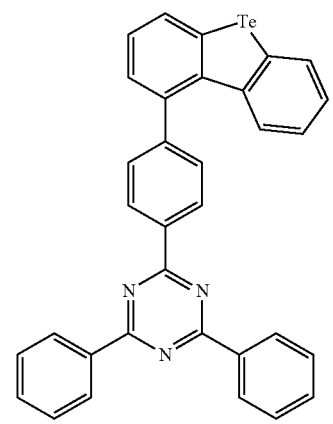
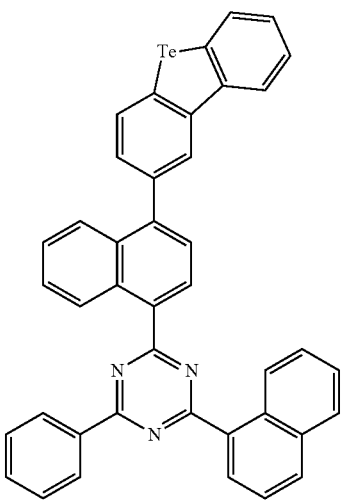
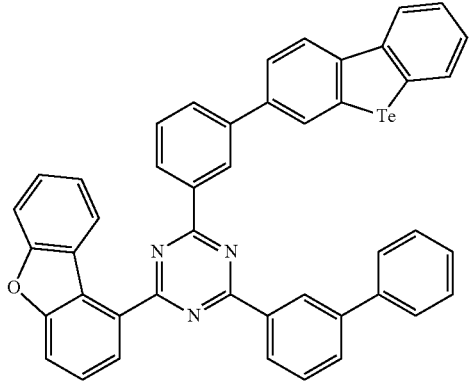

993
-continued
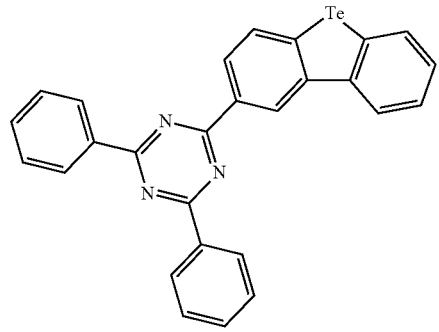
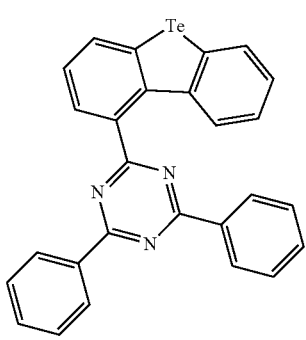
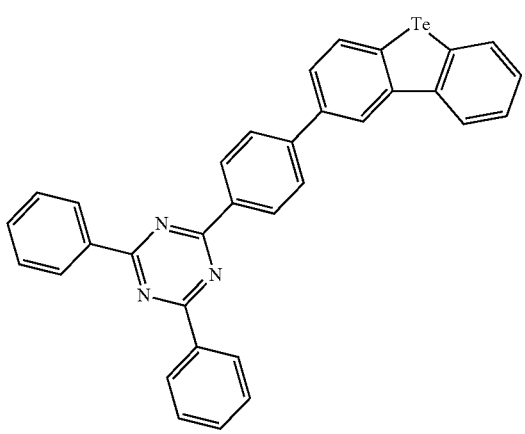
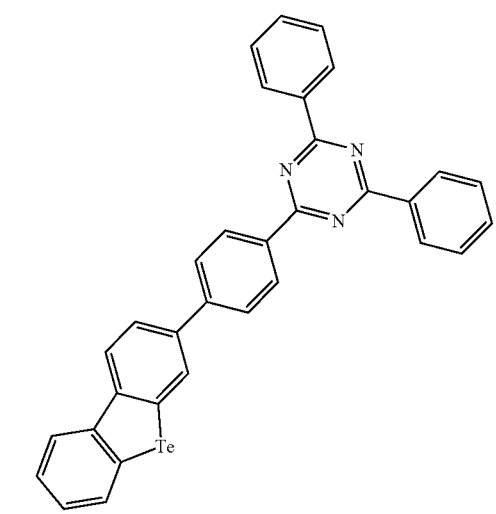
994
-continued
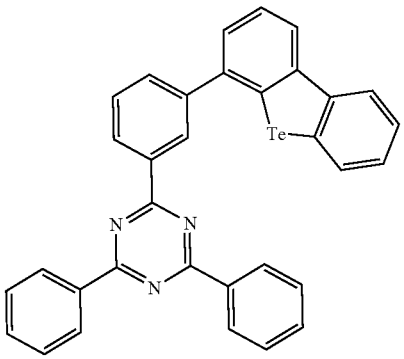
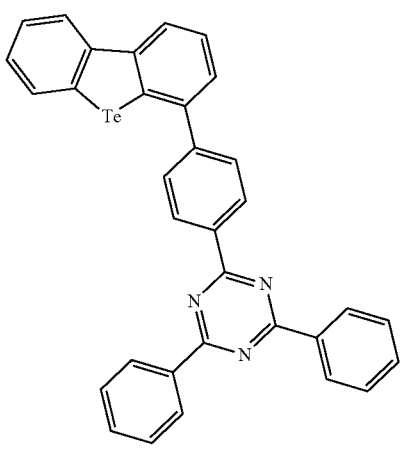
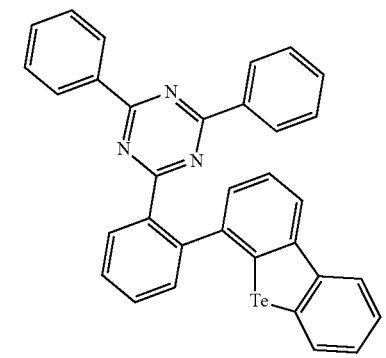
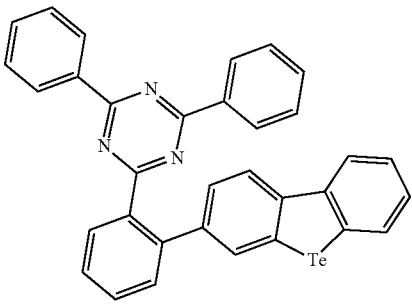

995
-continued
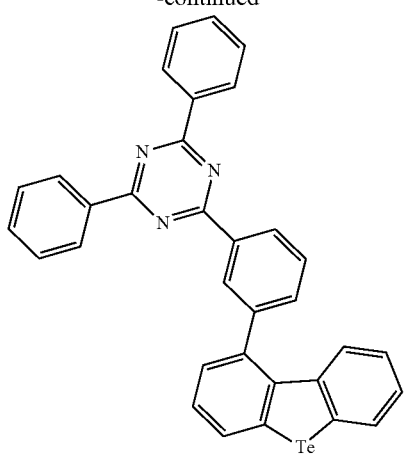
996
-continued
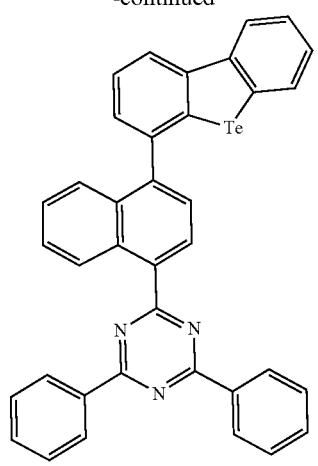
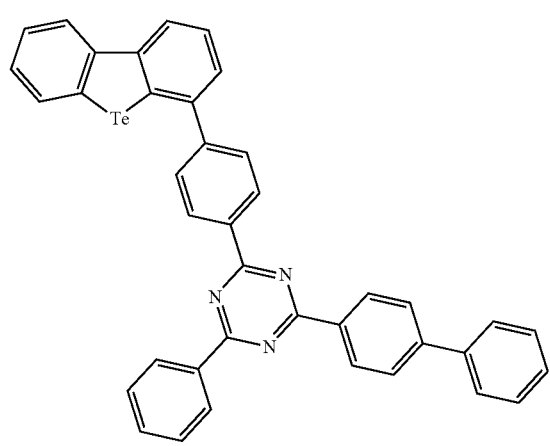
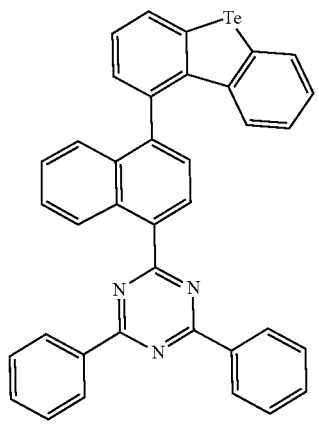
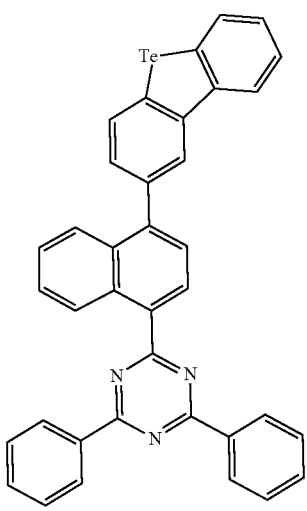
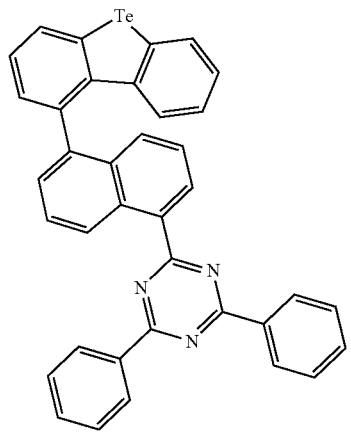

997
-continued
998
-continued
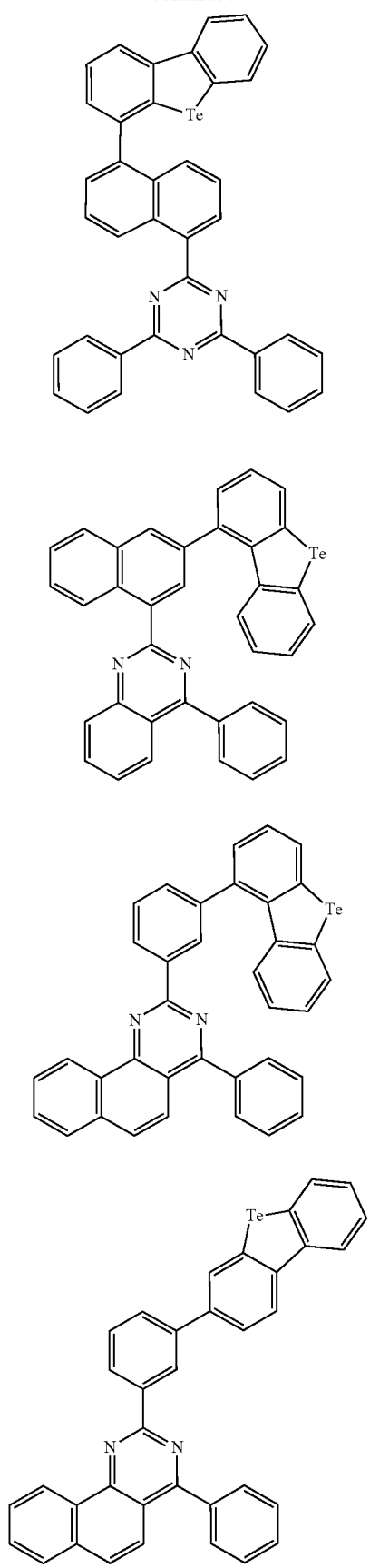
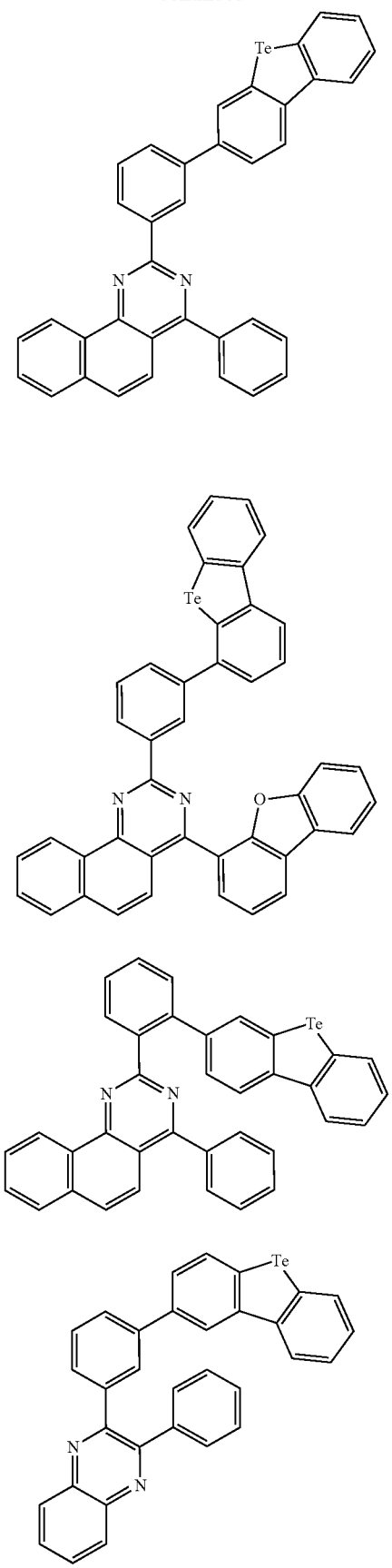

999
-continued
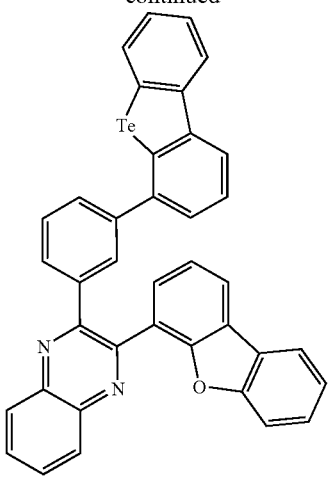
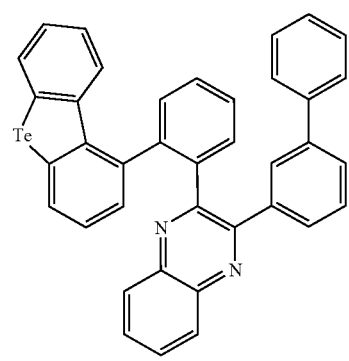
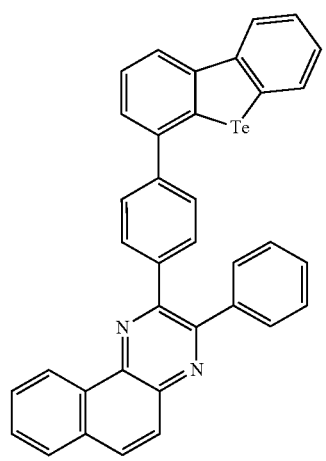
1000
-continued
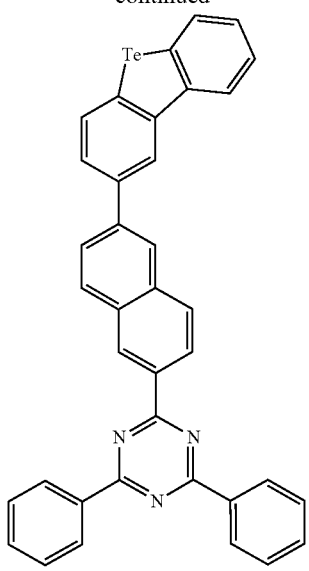
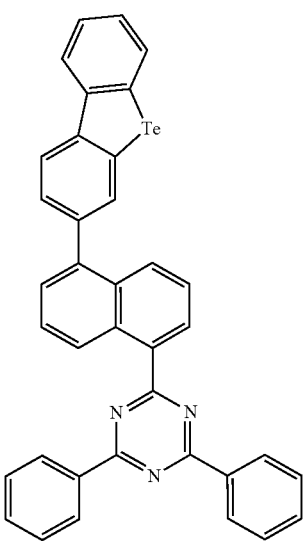
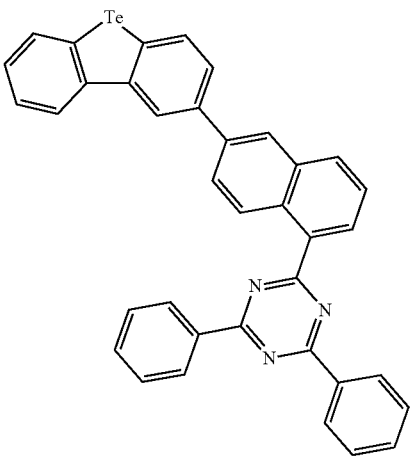

1001
-continued
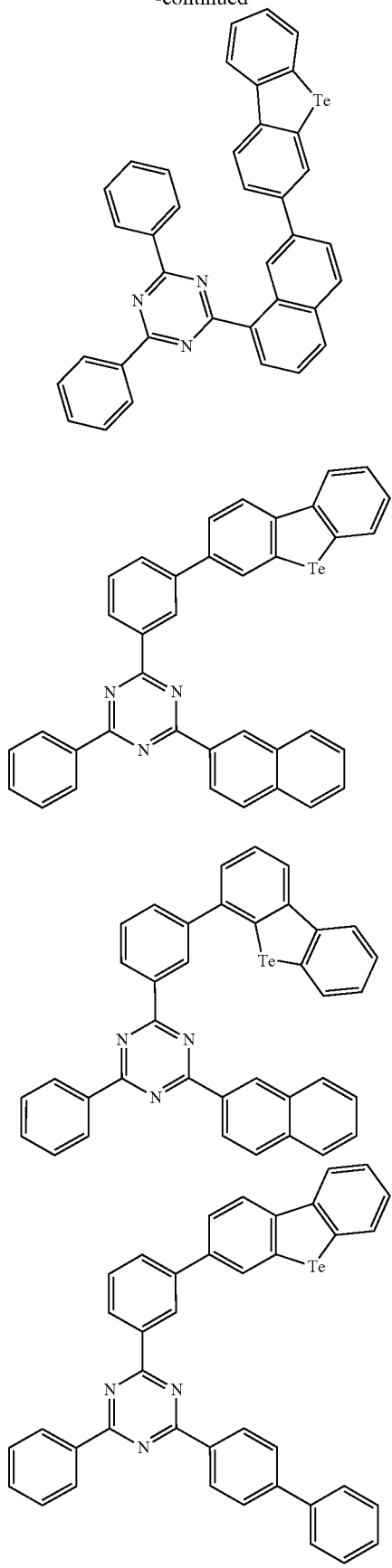
1002
-continued
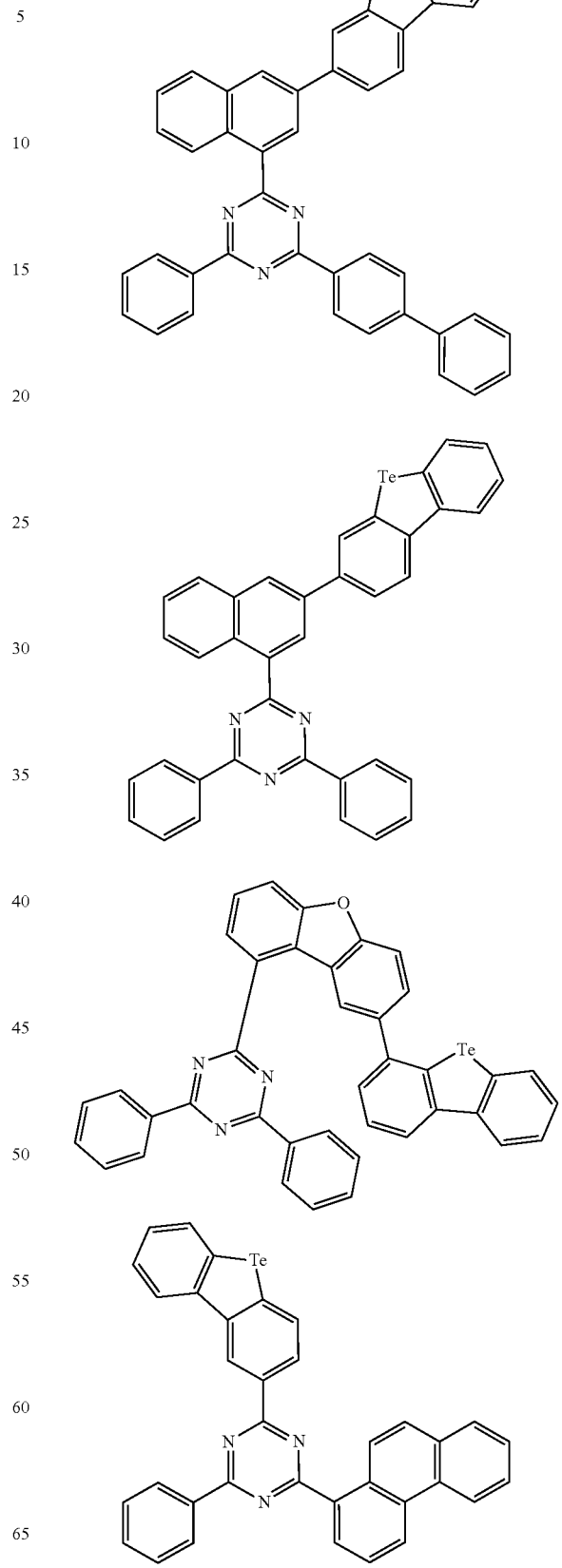

| 1003 -continued | 1004 -continued |
|---|---|
| 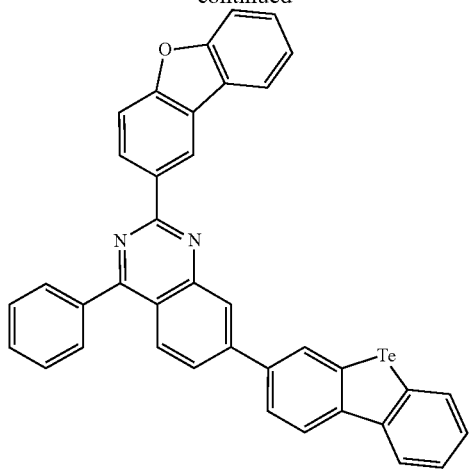 | 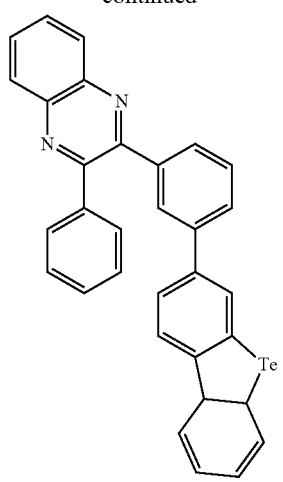 |
| 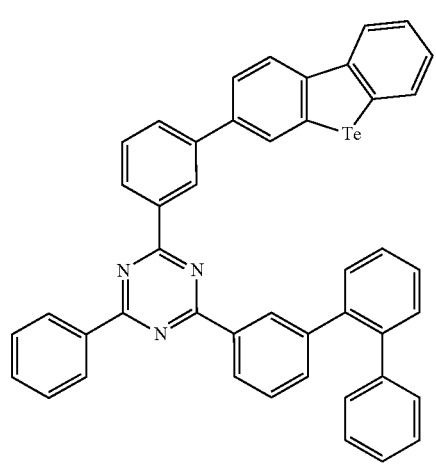 | 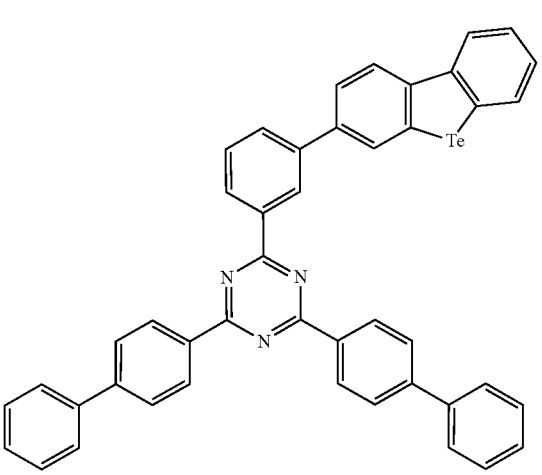 |
| 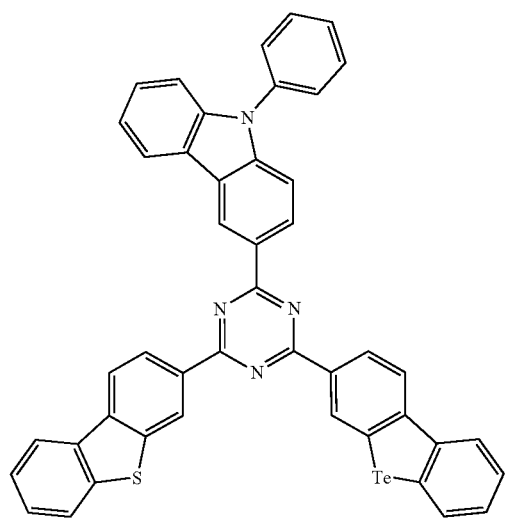 | 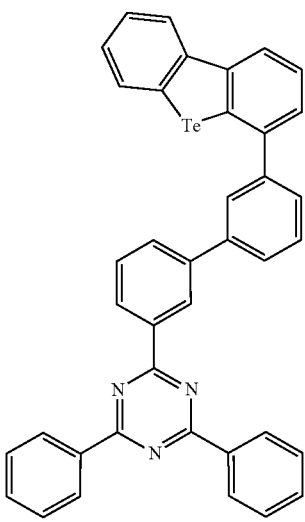 |

1005
-continued
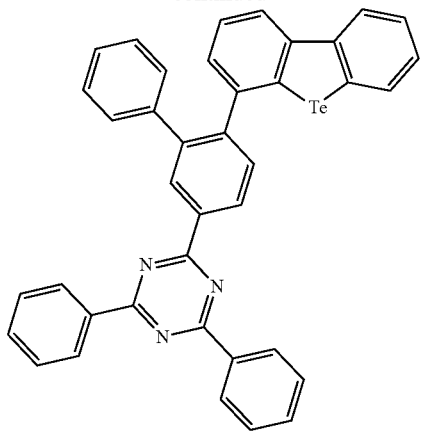
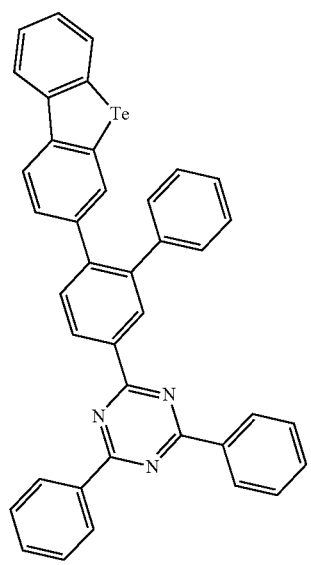
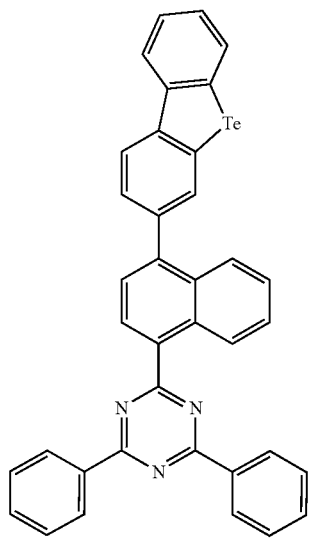
1006
-continued
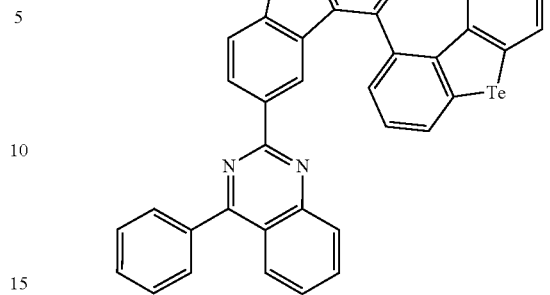
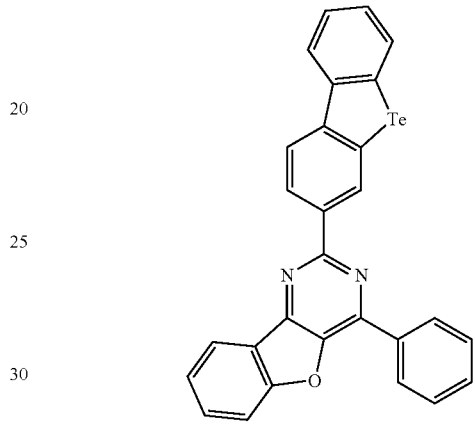
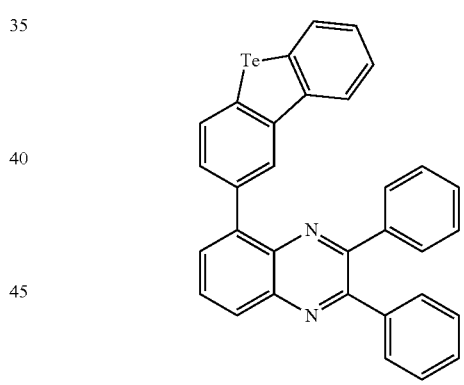
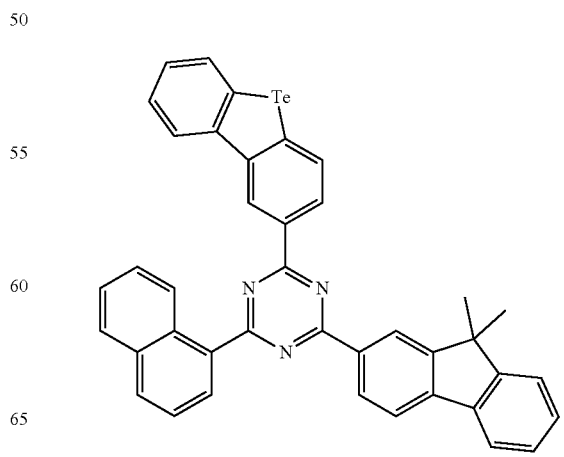

1007
-continued
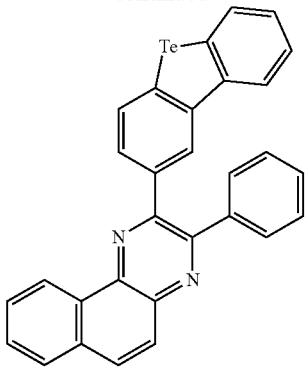
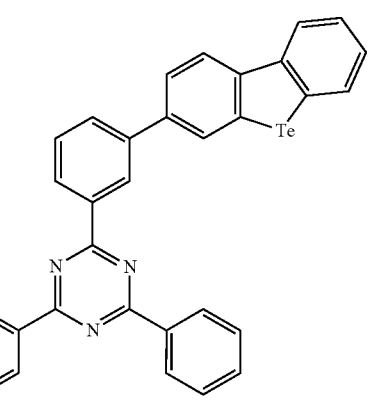
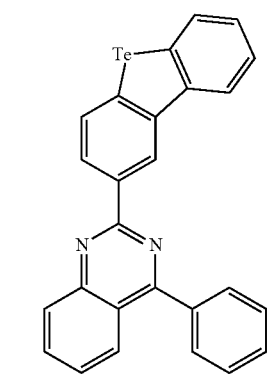
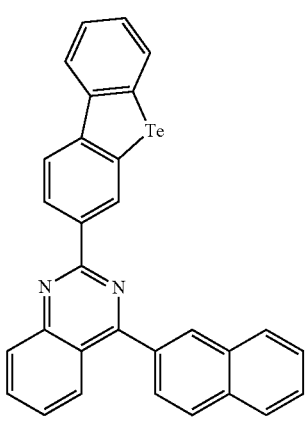
1008
-continued
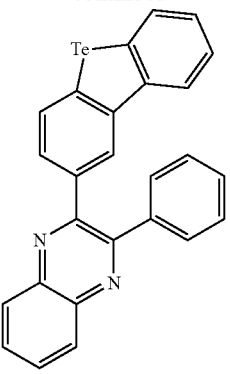
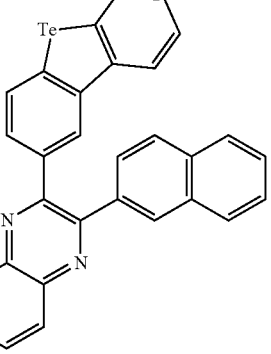
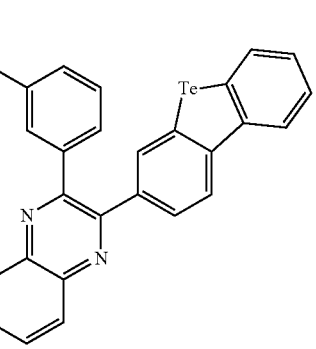
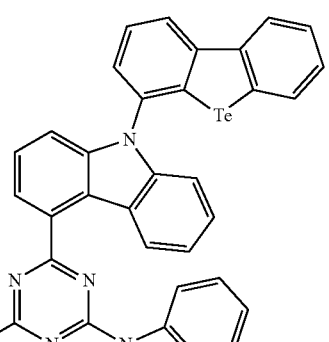

1009
-continued
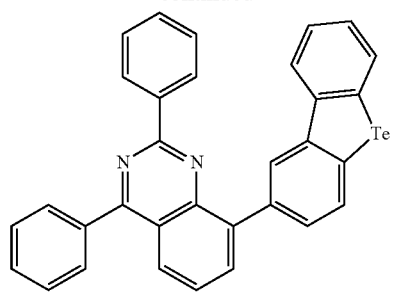
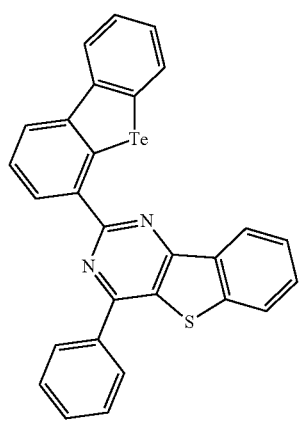
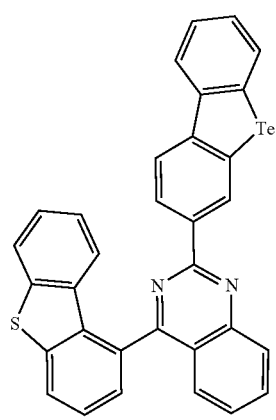
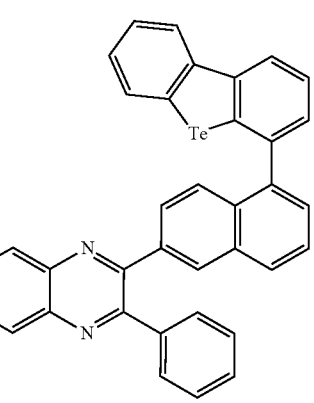
1010
-continued
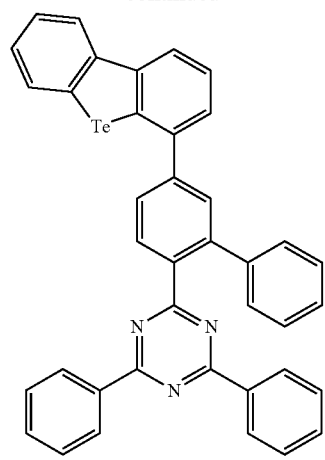
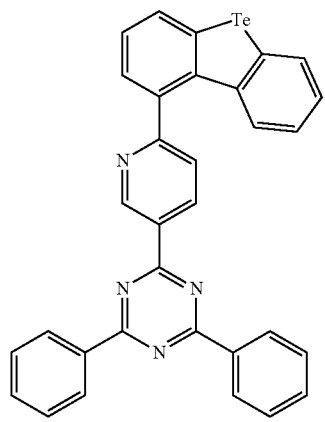
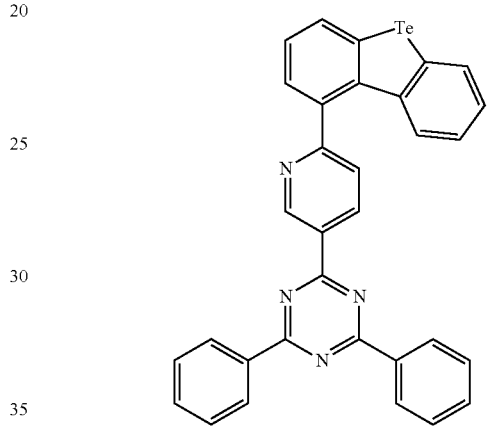
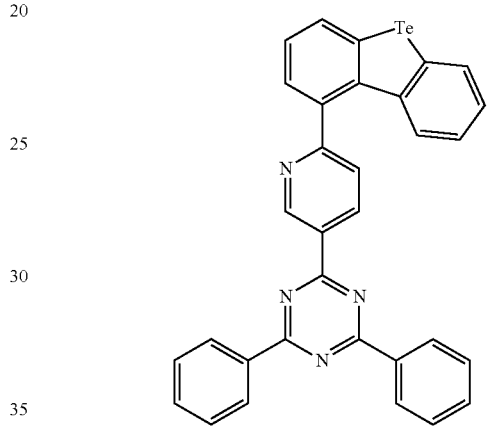

1011
-continued
1012
-continued
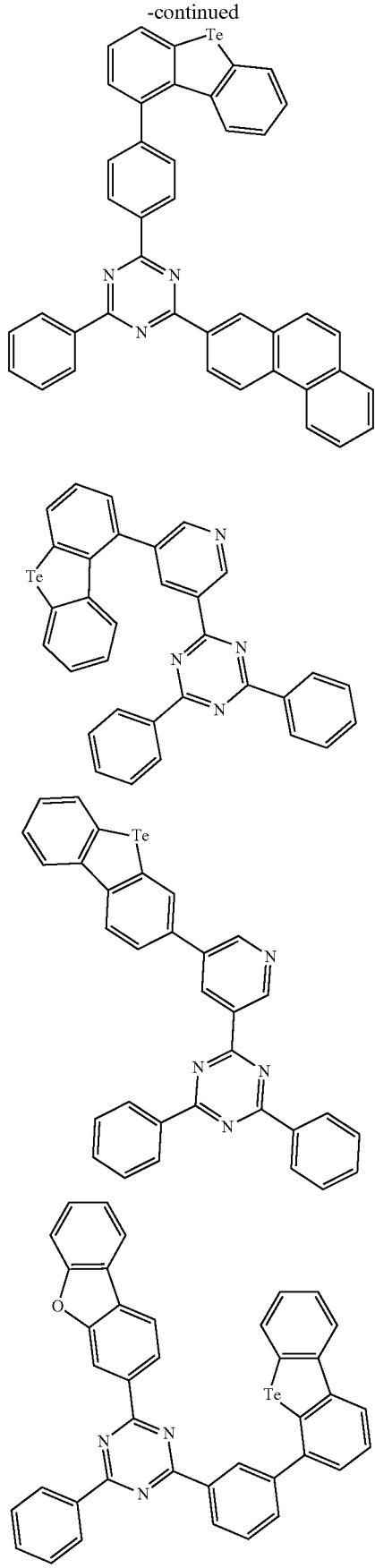
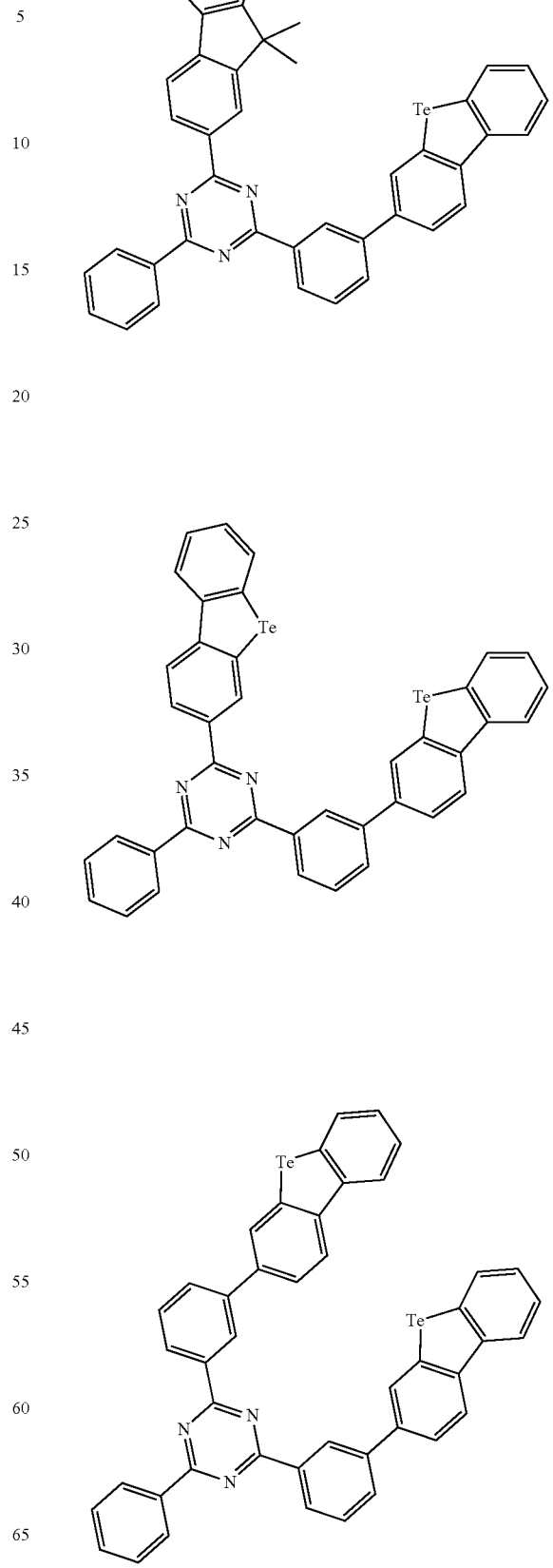

| 1013 -continued | 1014 -continued |
|---|---|
| 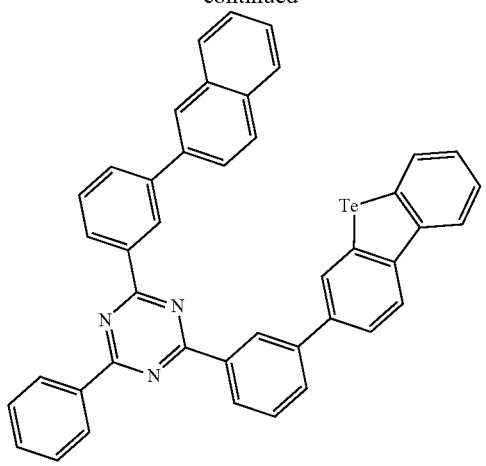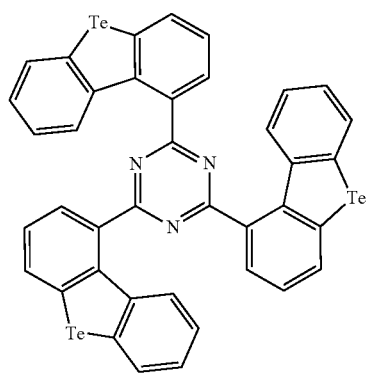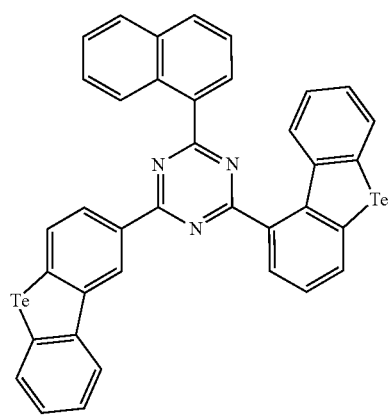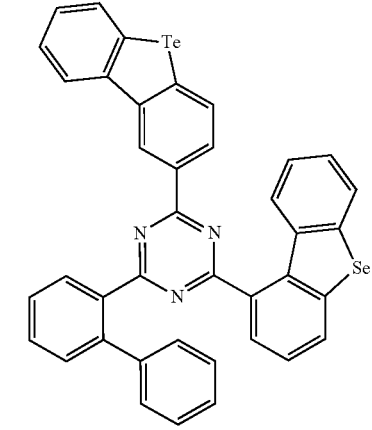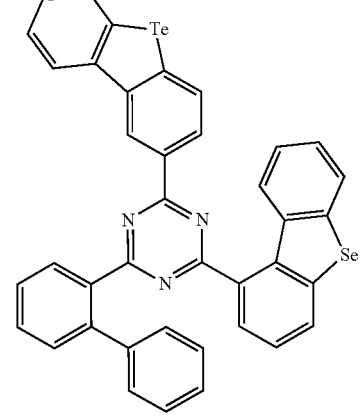 | 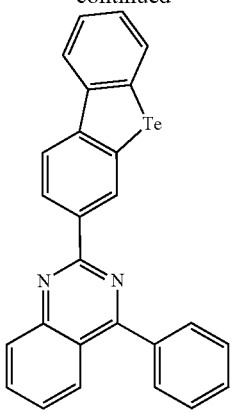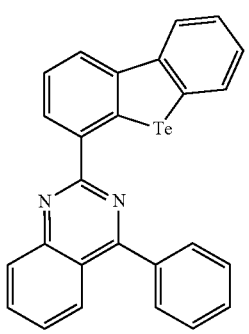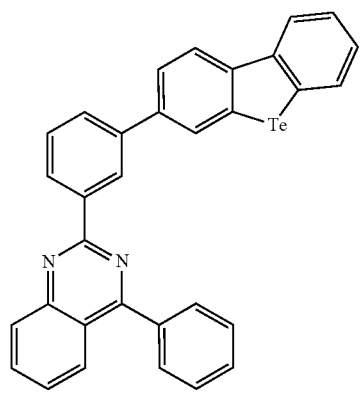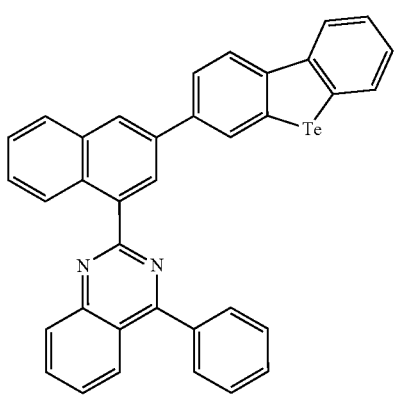 |

1015
-continued
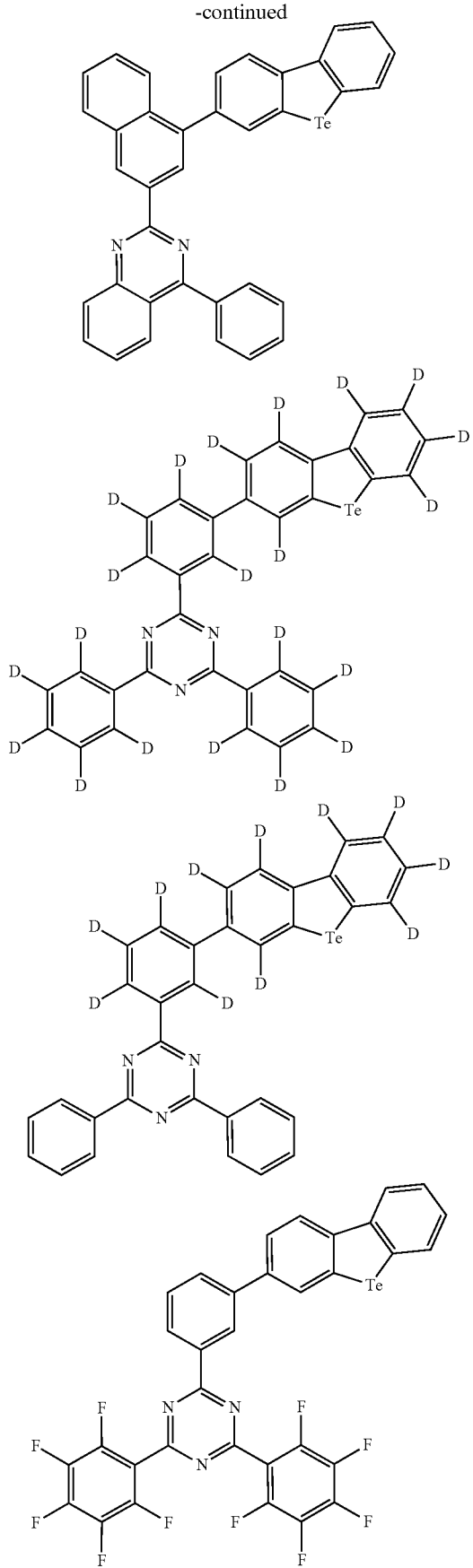
1016
-continued
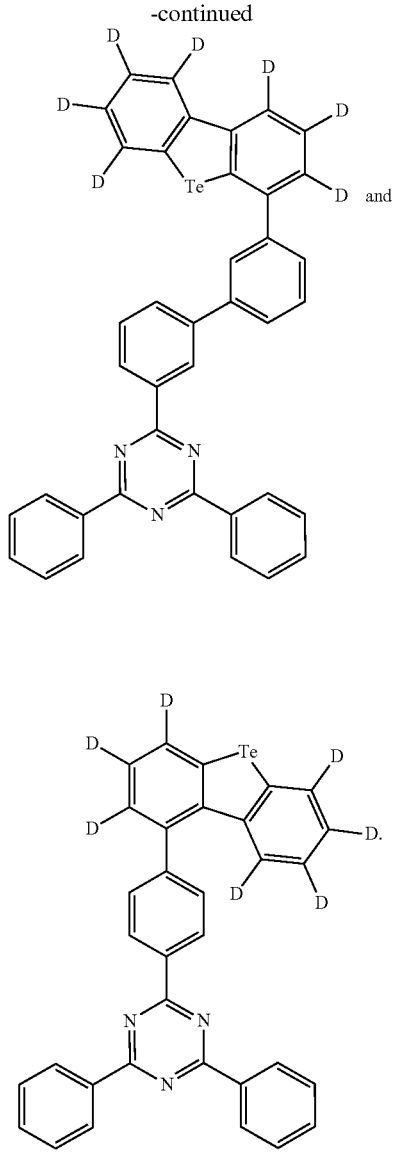
12. The organic electroluminescent material according to claim 8, wherein the compound represented by formula 15 is selected from the group consisting of the following:
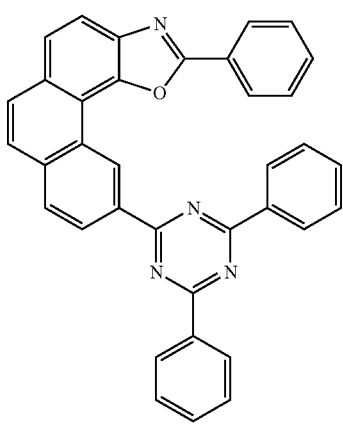

1017
-continued
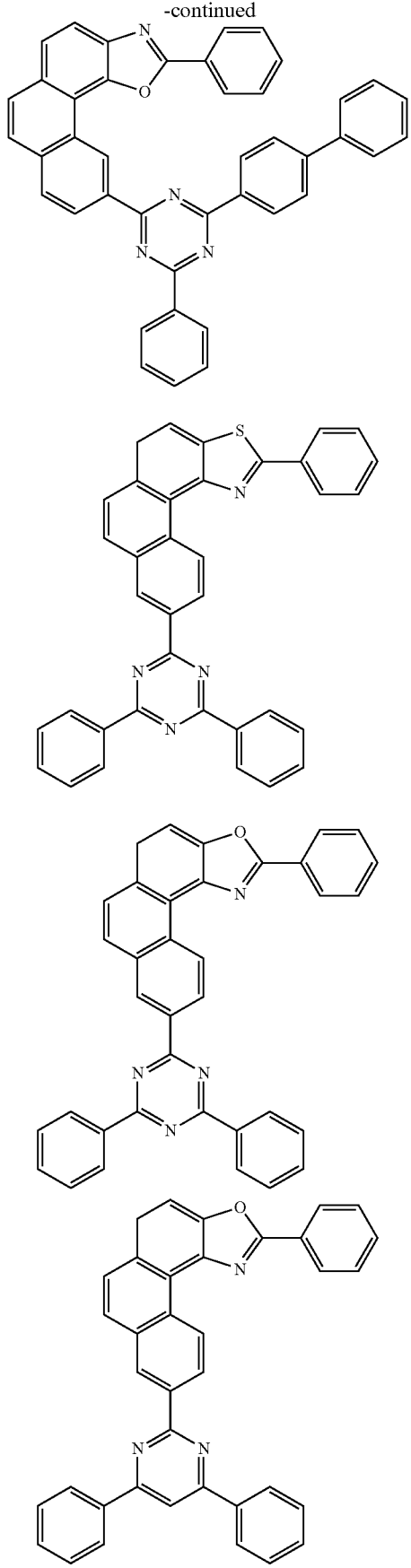
1018
-continued
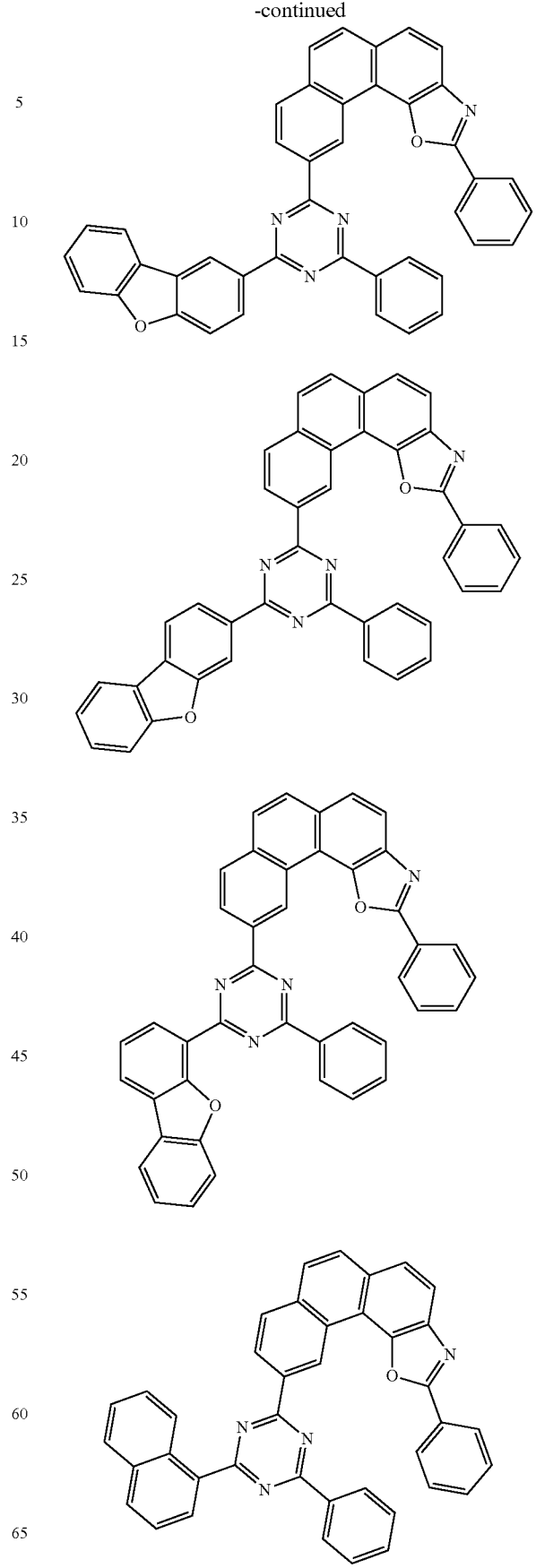

1019
-continued
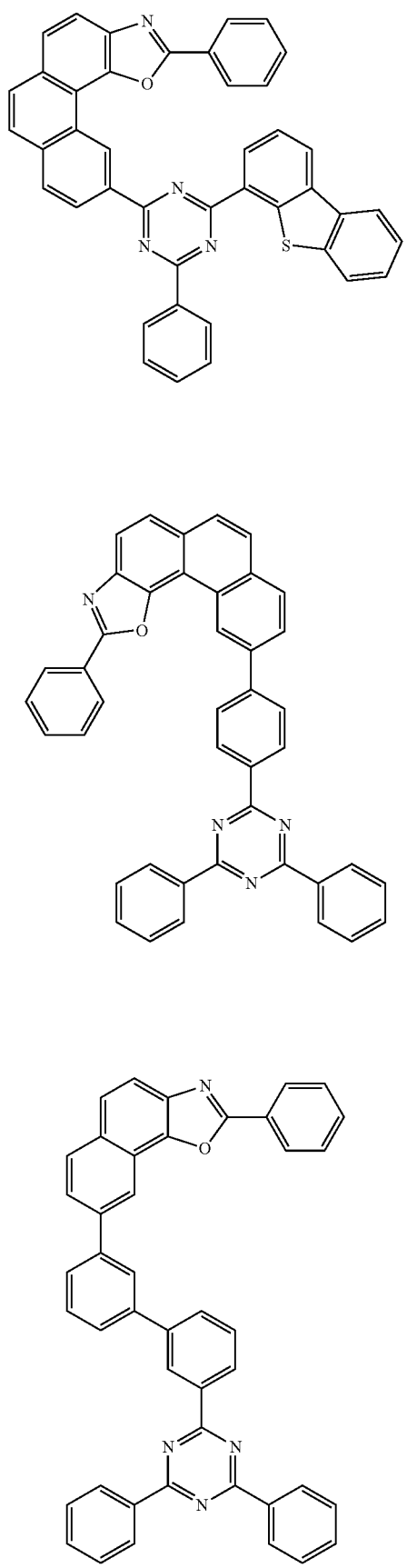
1020
-continued
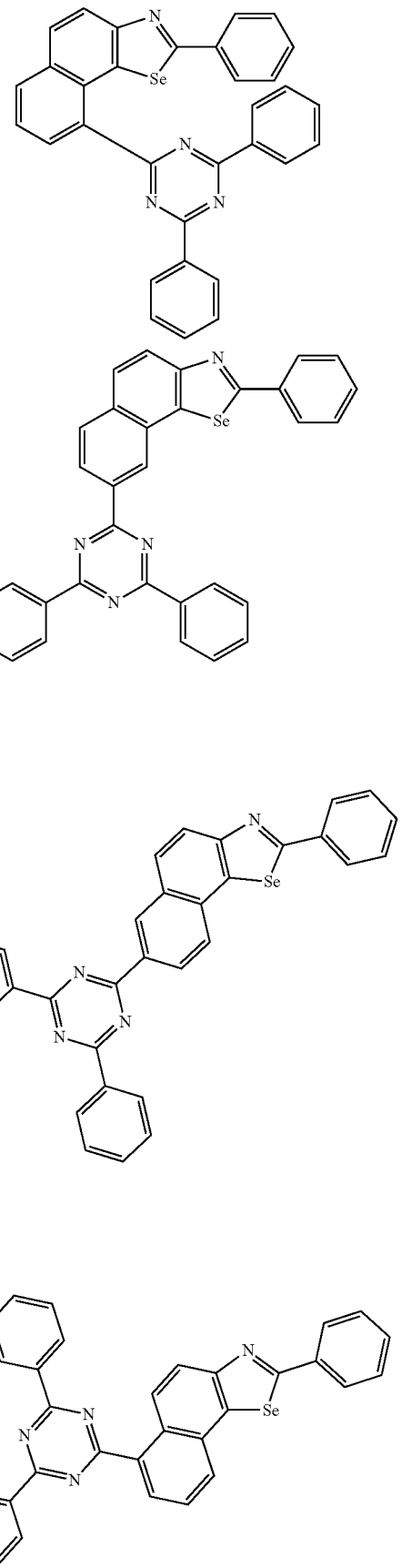

1021
-continued
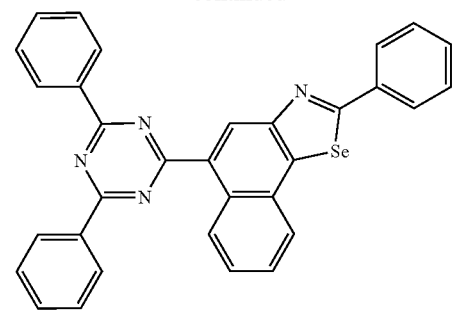
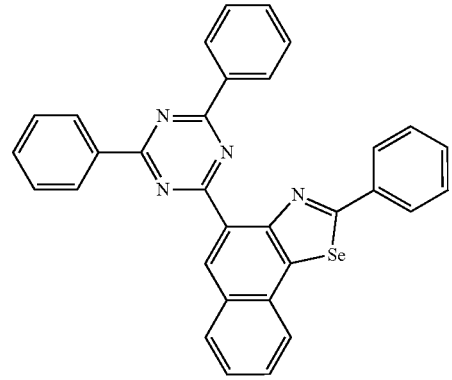
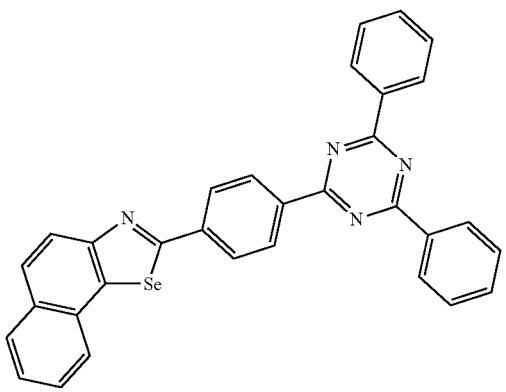
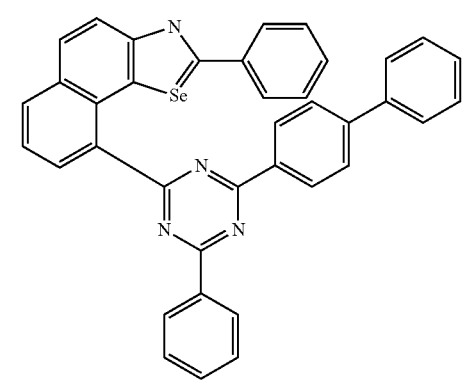
1022
-continued
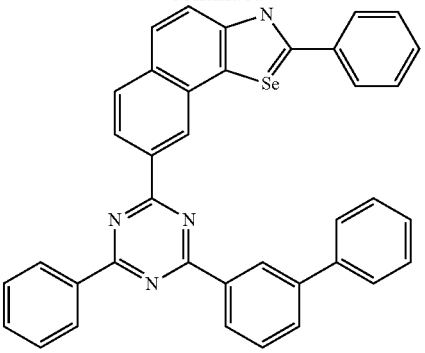
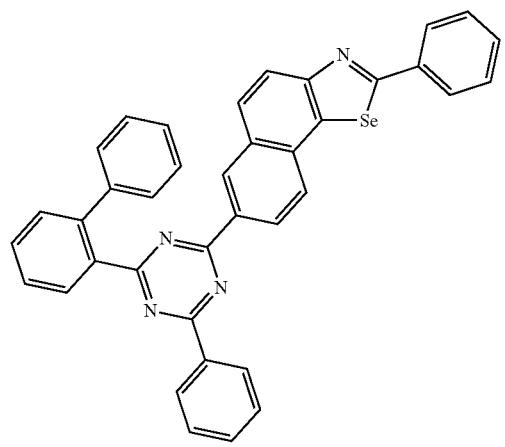
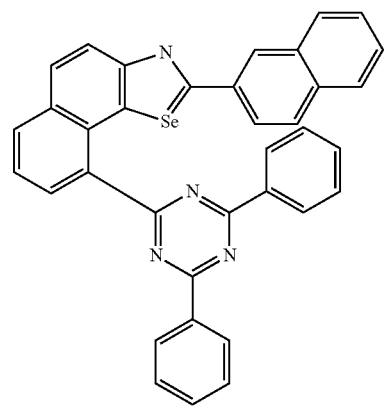
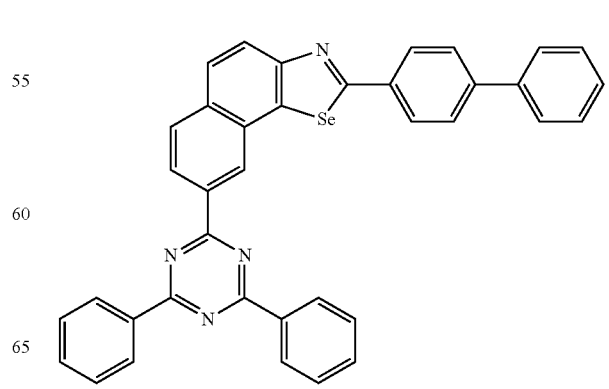

1023
-continued
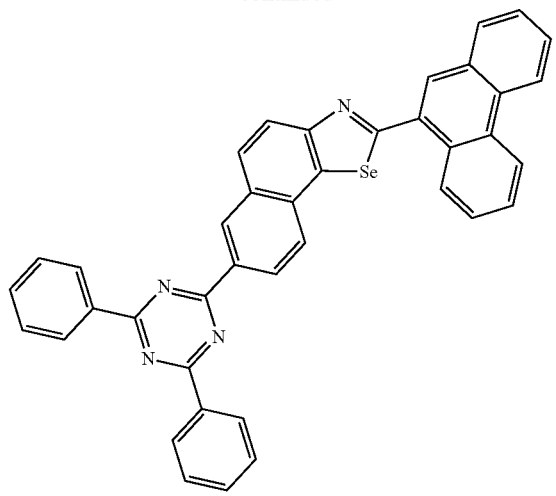
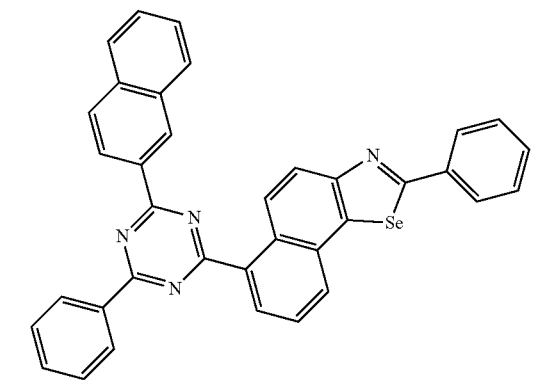
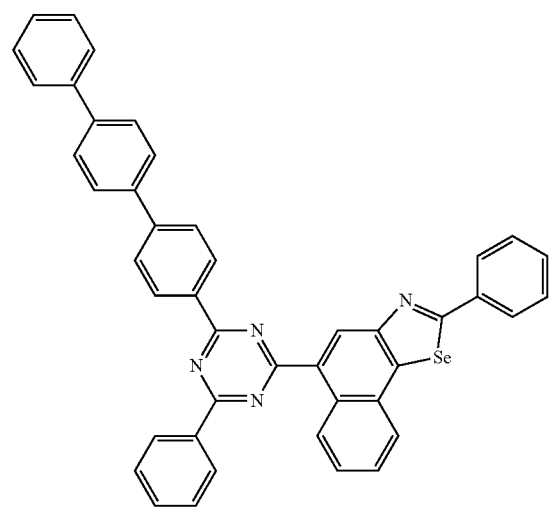
1024
-continued
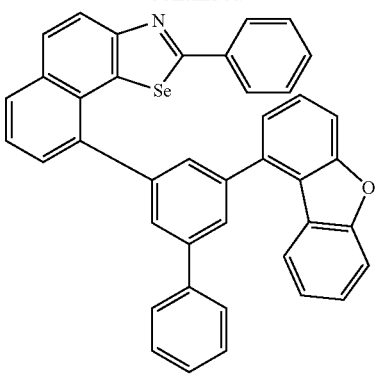
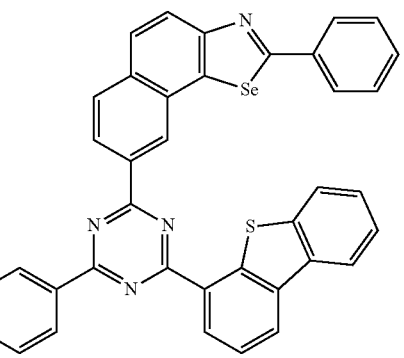
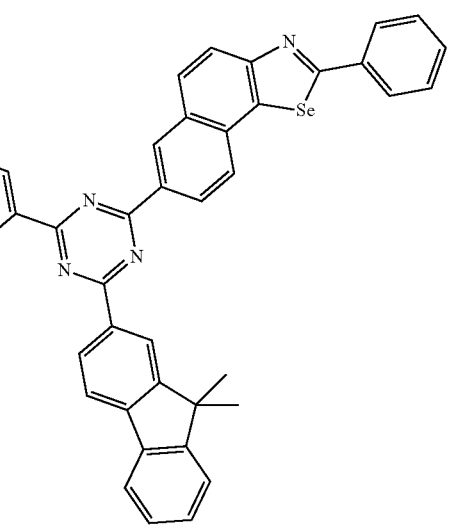
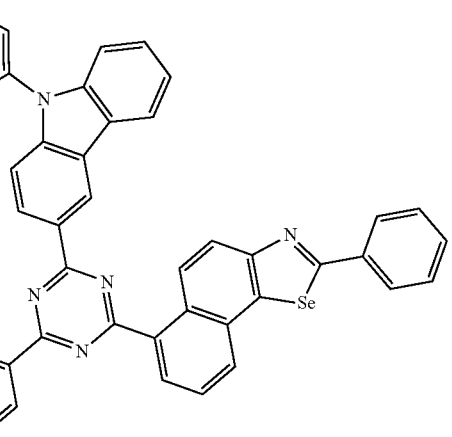

1025
-continued
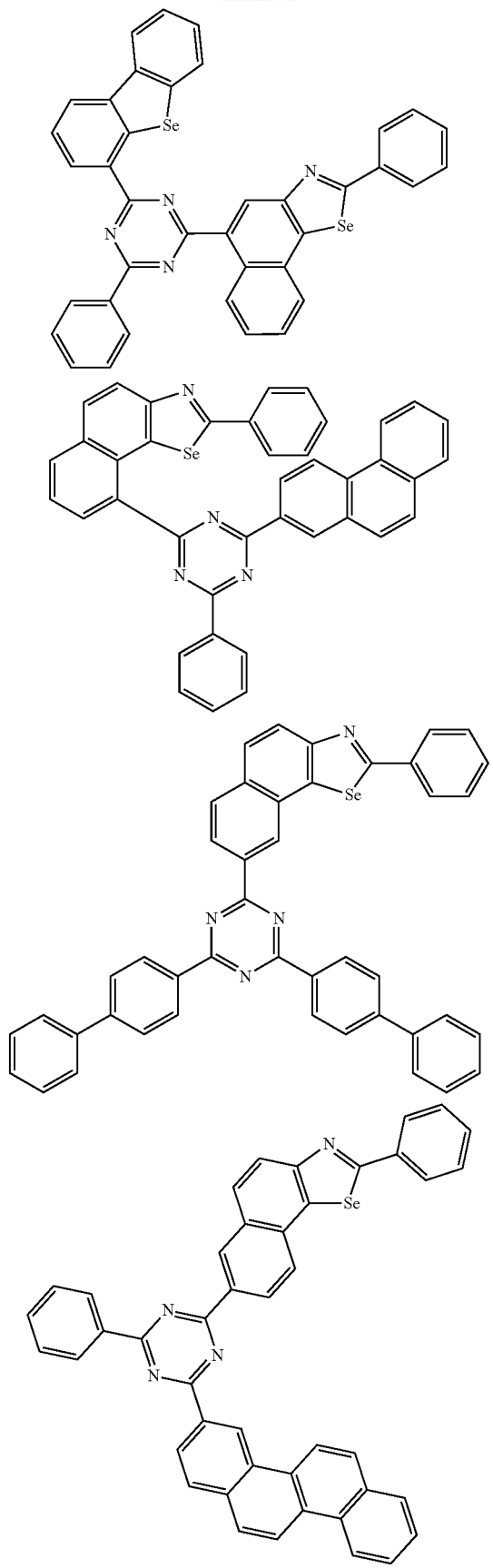
1026
-continued
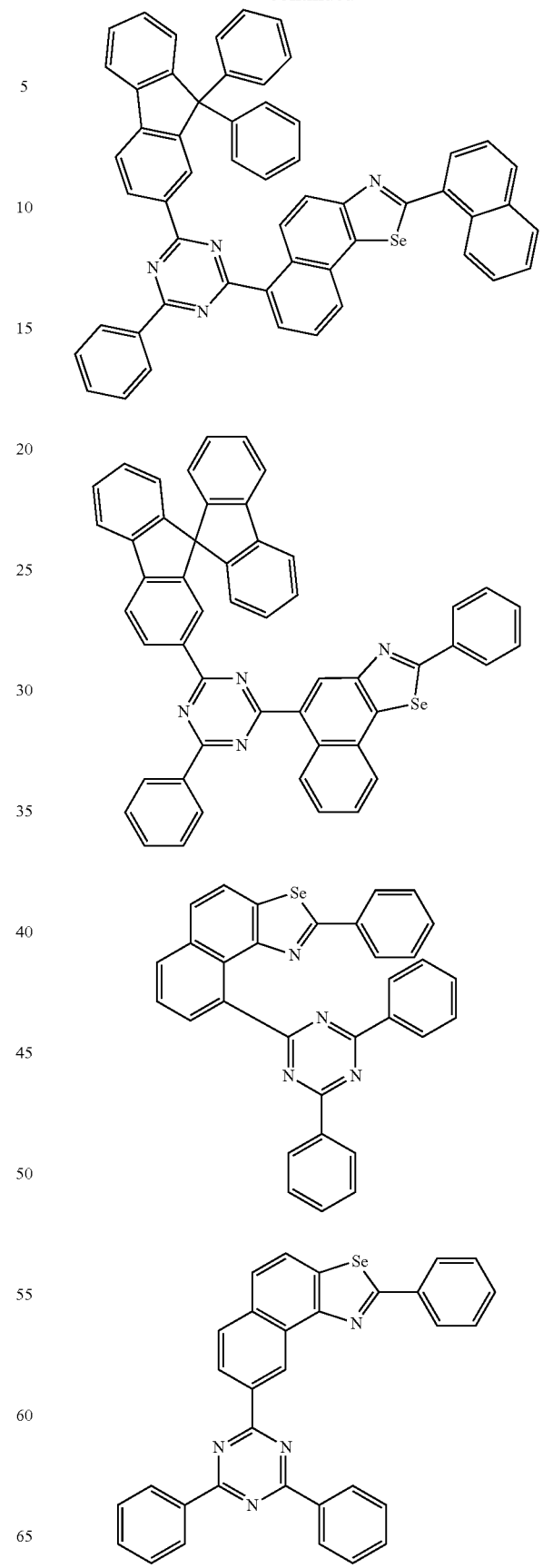

1027
-continued
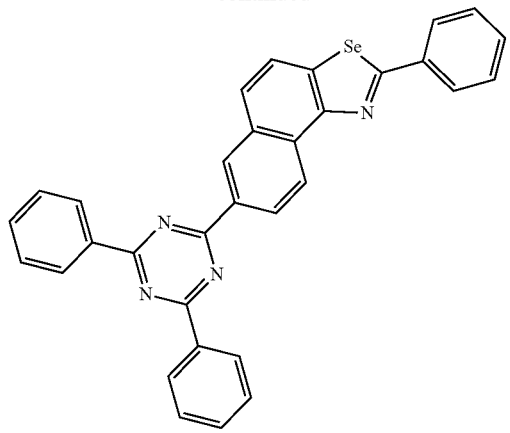
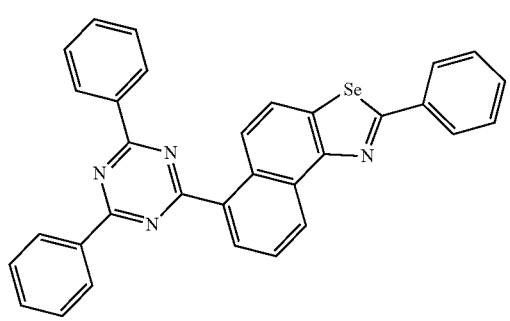
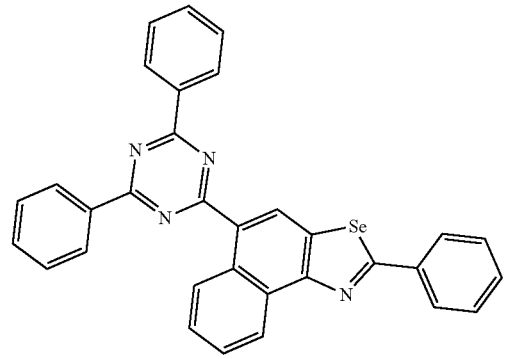
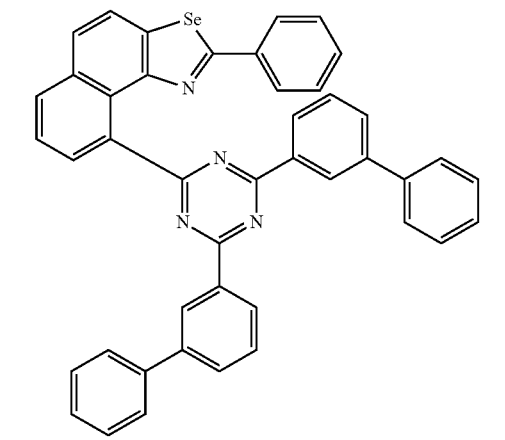
1028
-continued
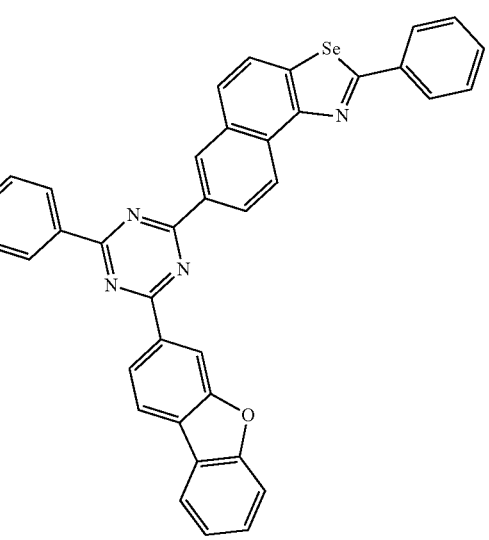
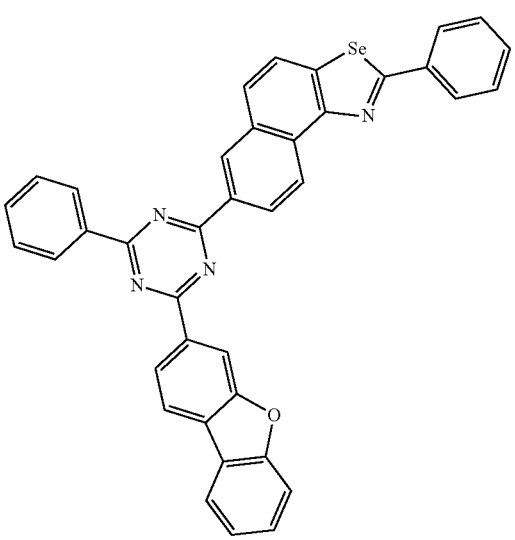
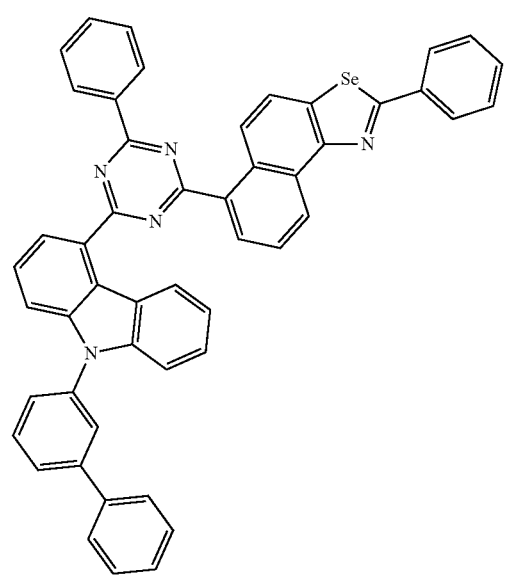

1029
-continued
1030
-continued
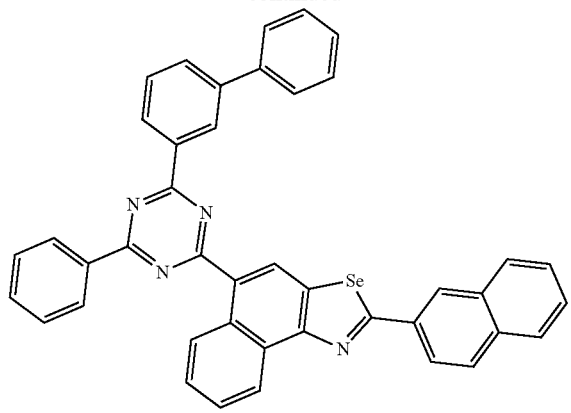
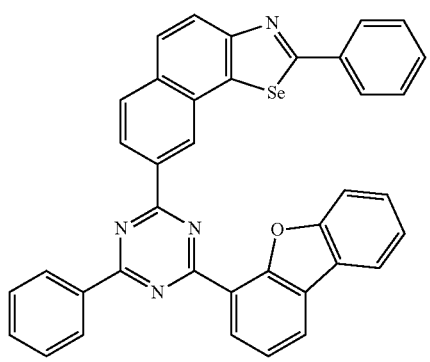
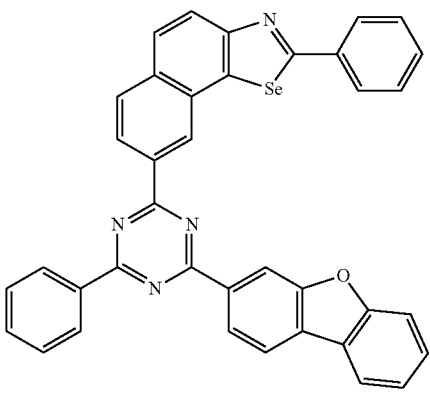
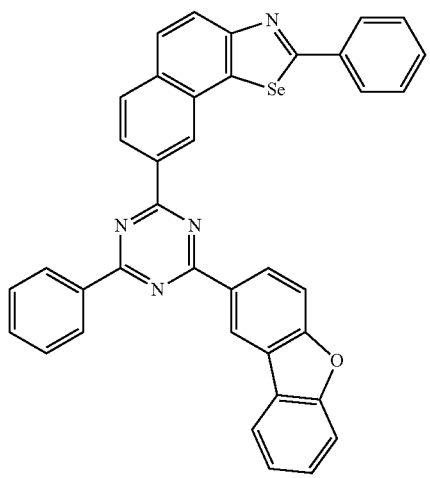
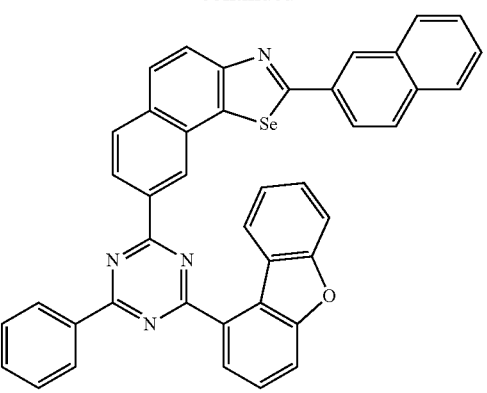
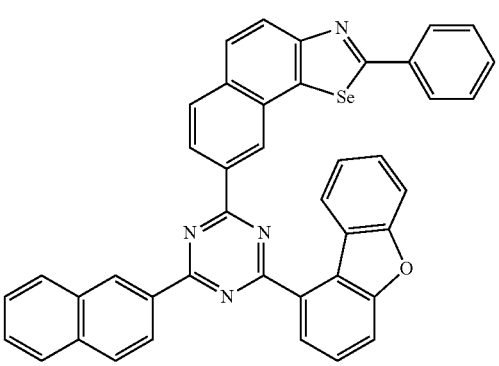
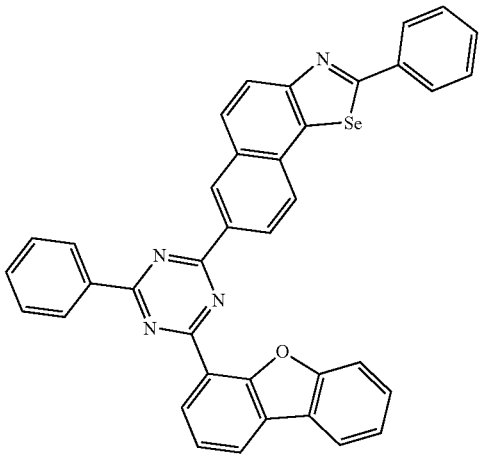

1031
-continued
1032
-continued
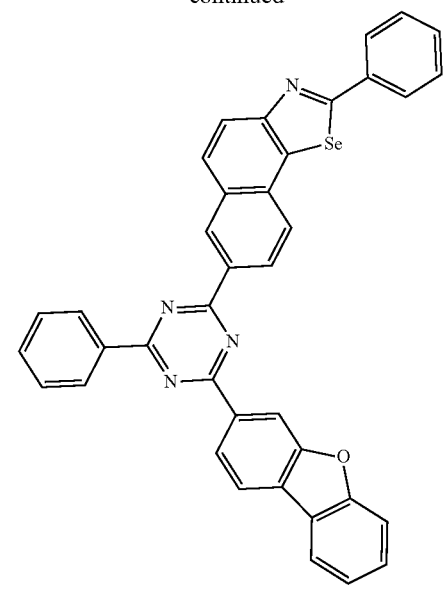
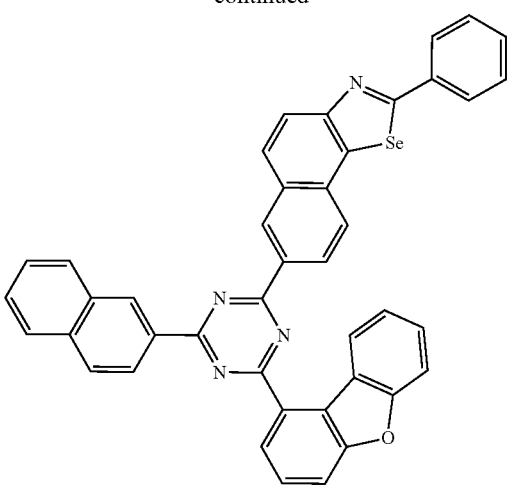
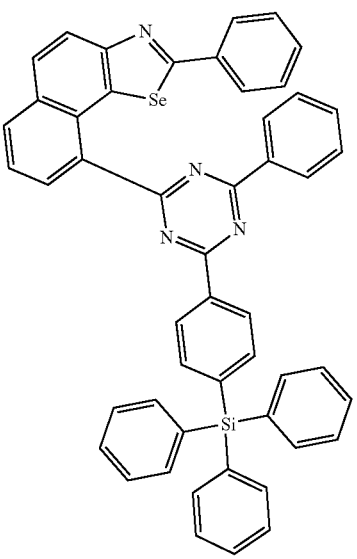
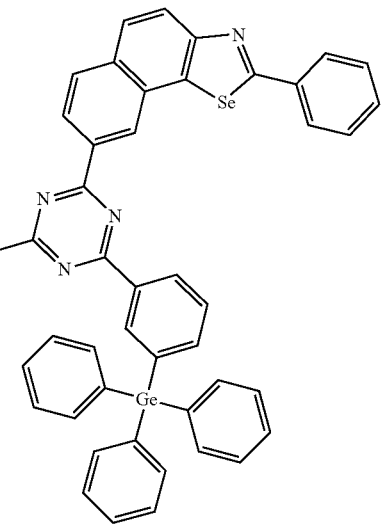

1033
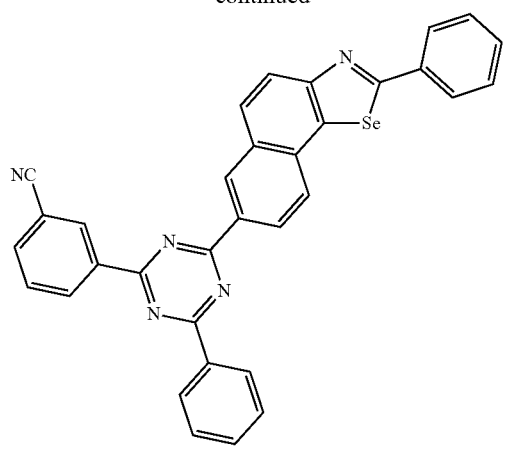
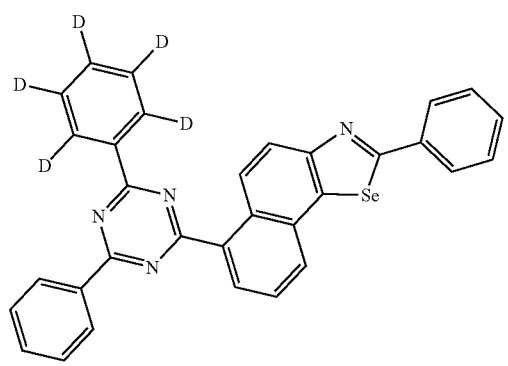
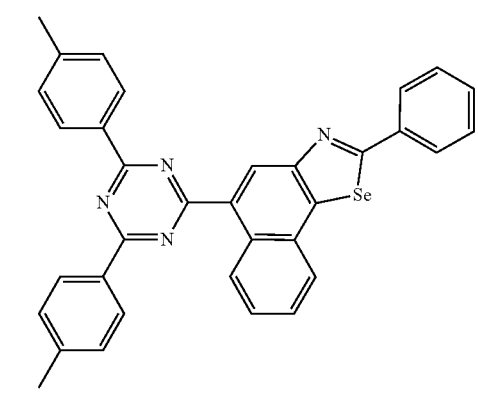
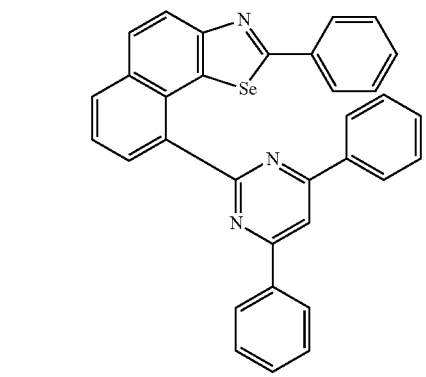
1034
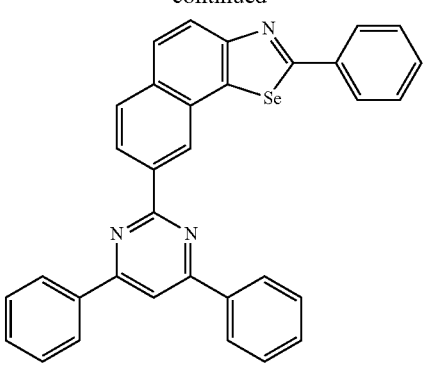
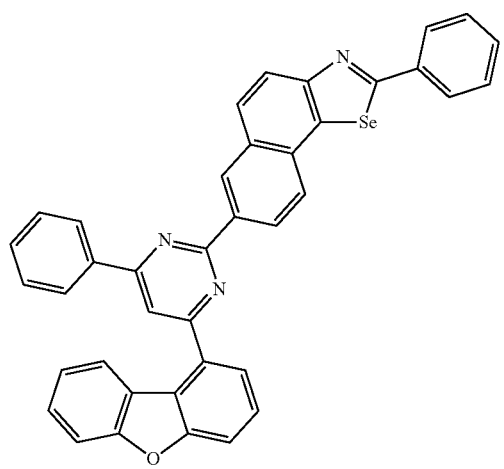
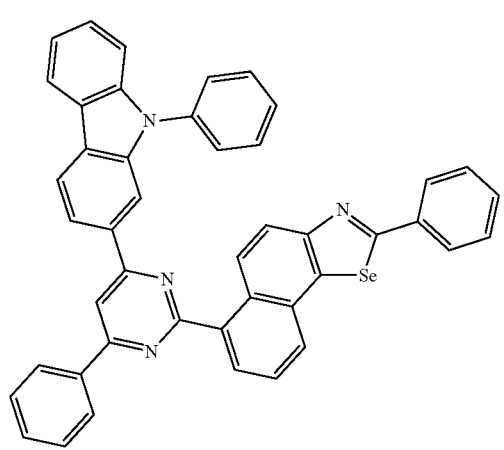

1035
-continued
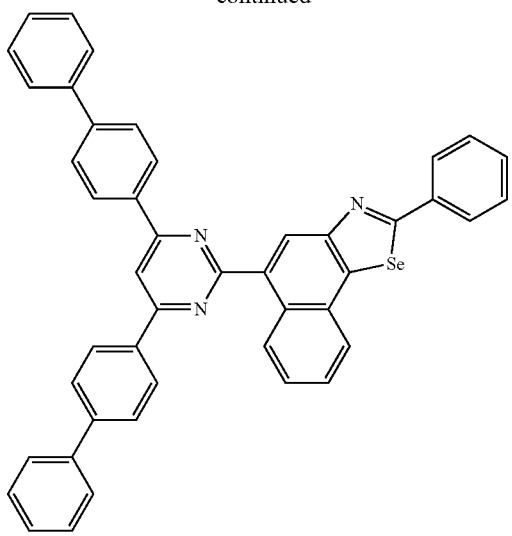
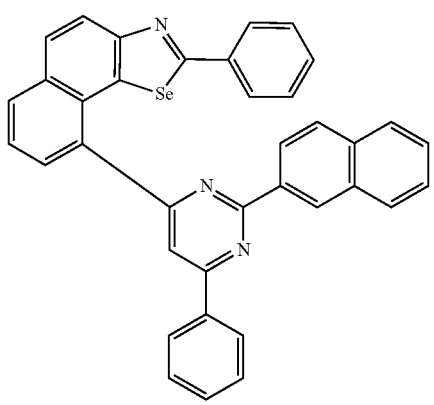
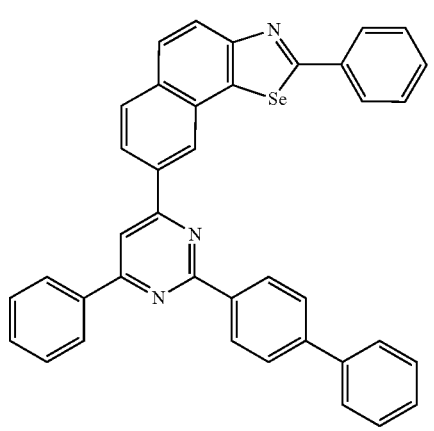
1036
-continued
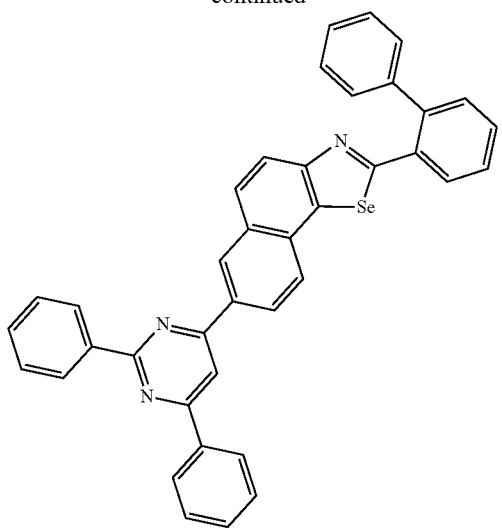

1037
-continued
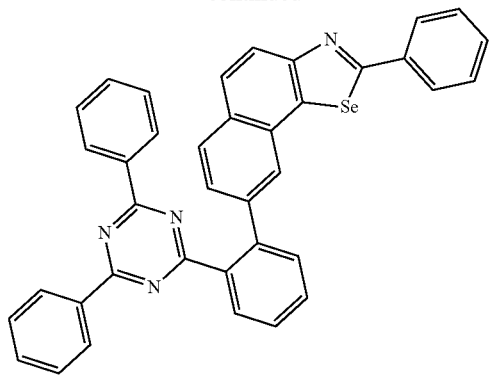
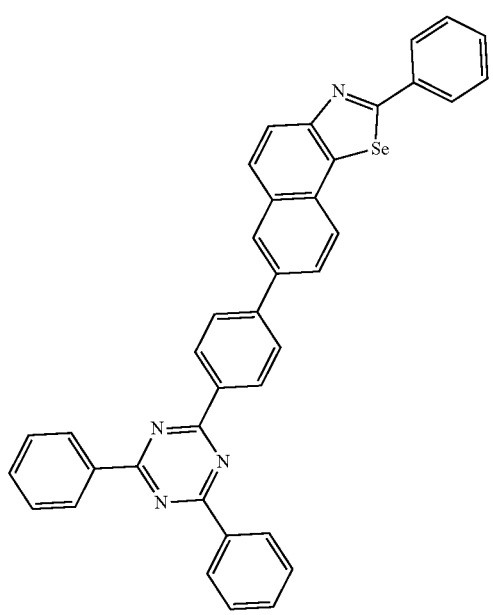
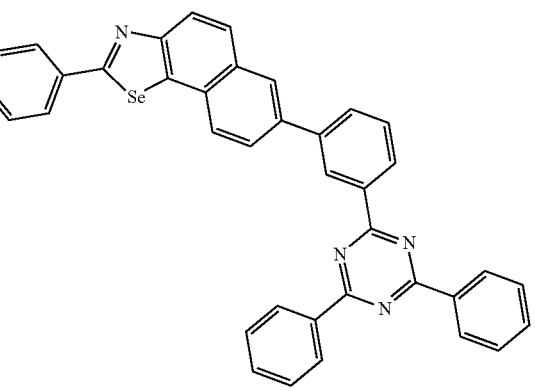
1038
-continued
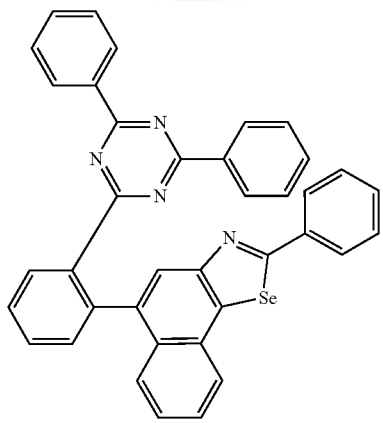
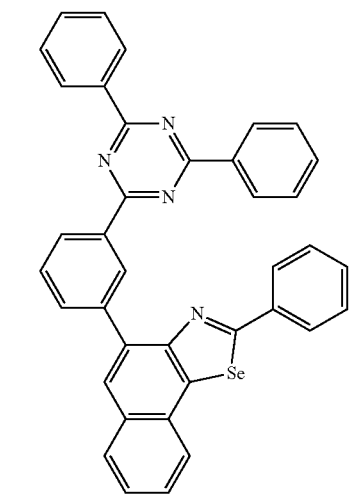
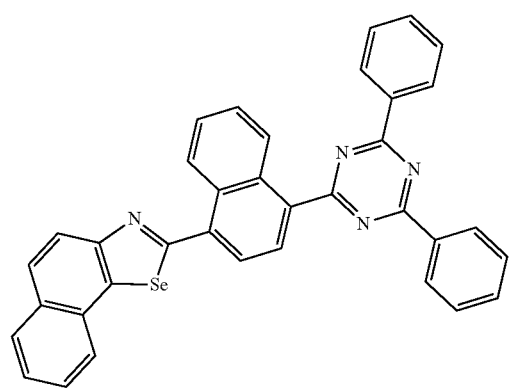

1039
-continued
1040
-continued
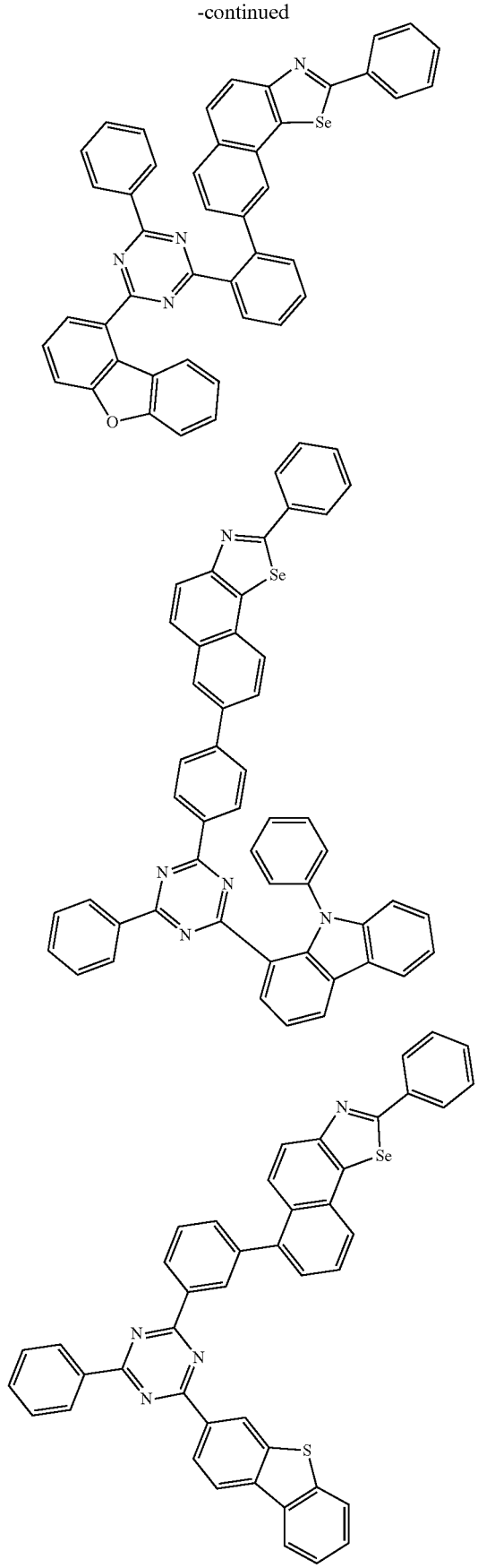
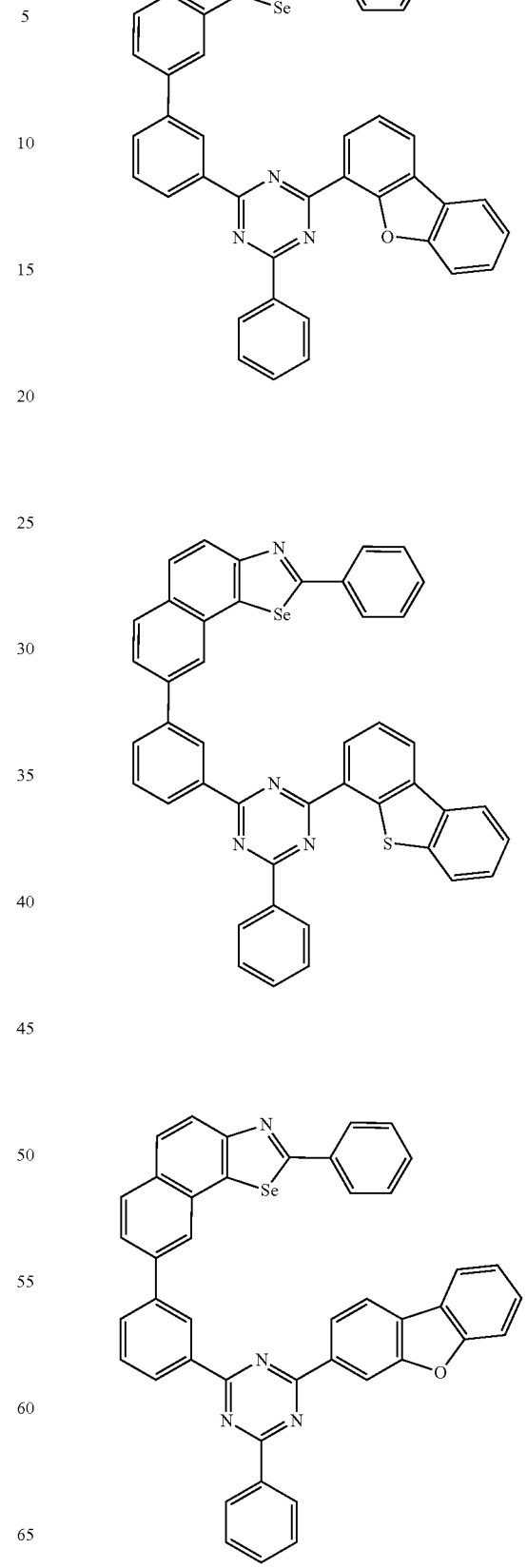

1041
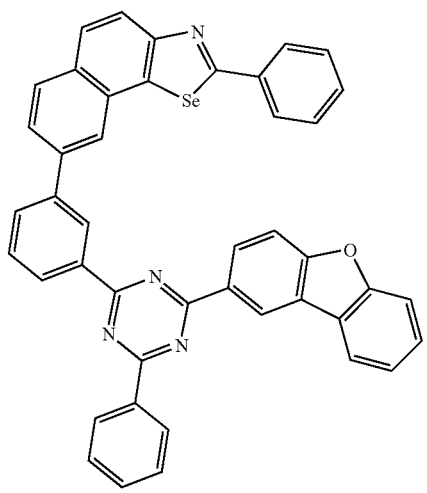
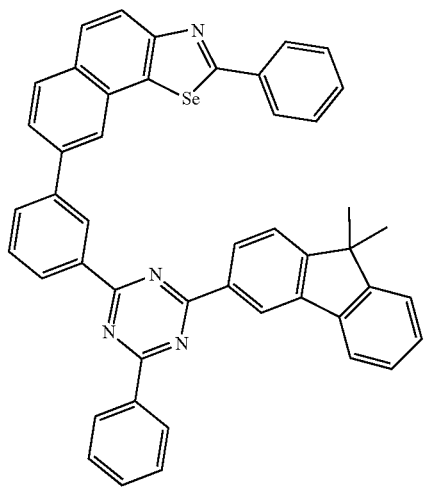
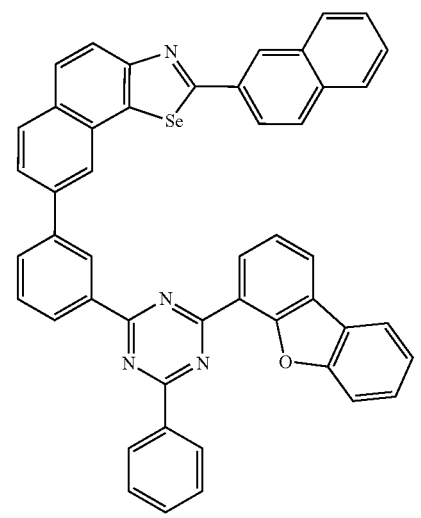
1042
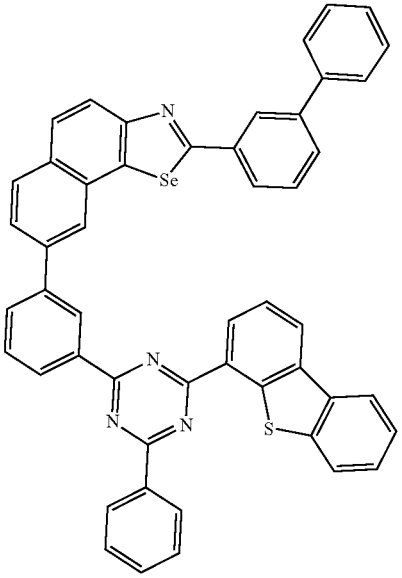
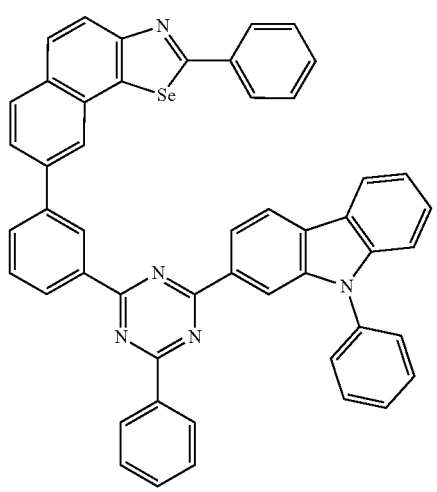
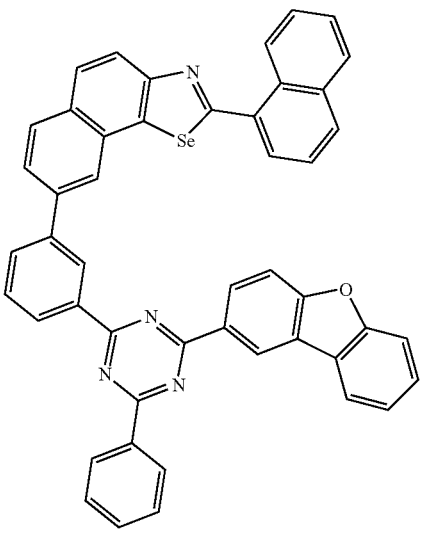

1043
-continued
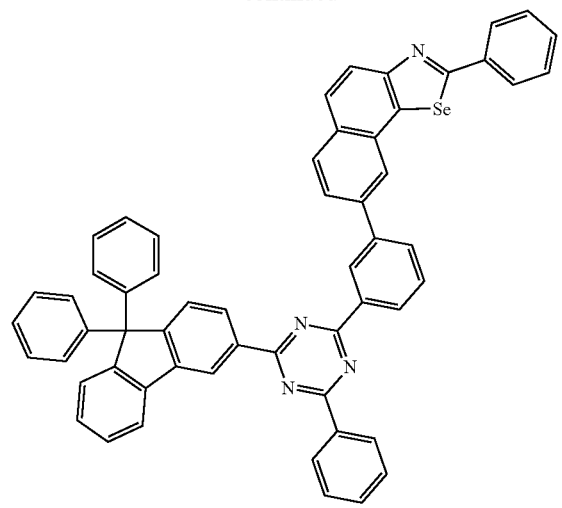
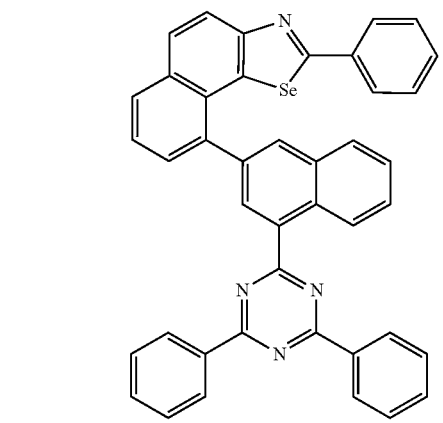
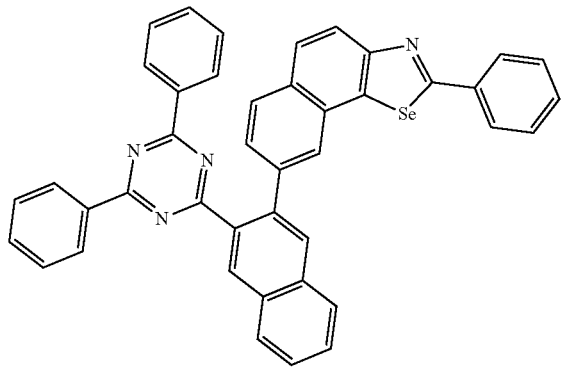
1044
-continued
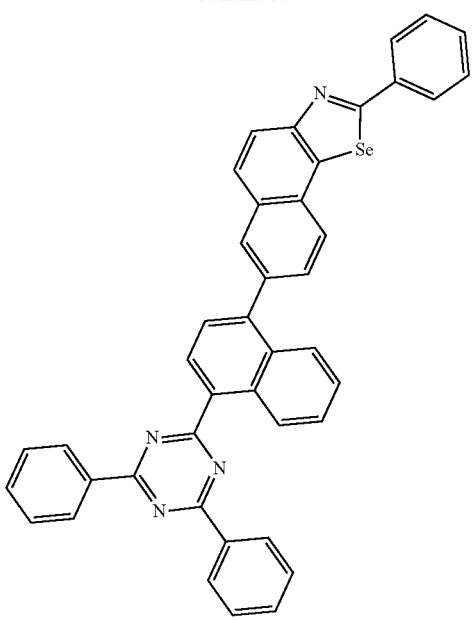
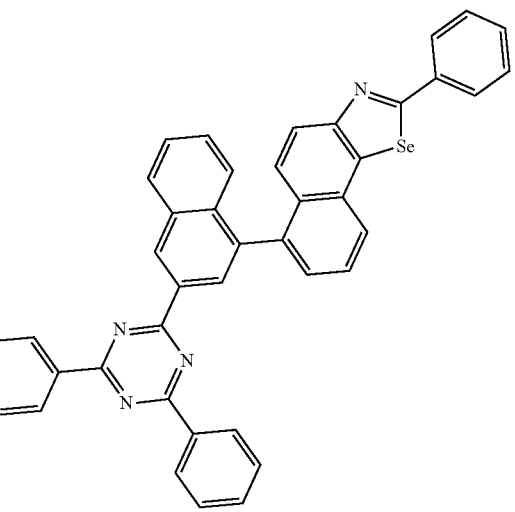
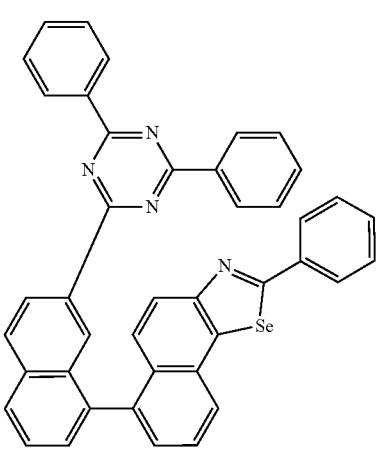

1045
-continued
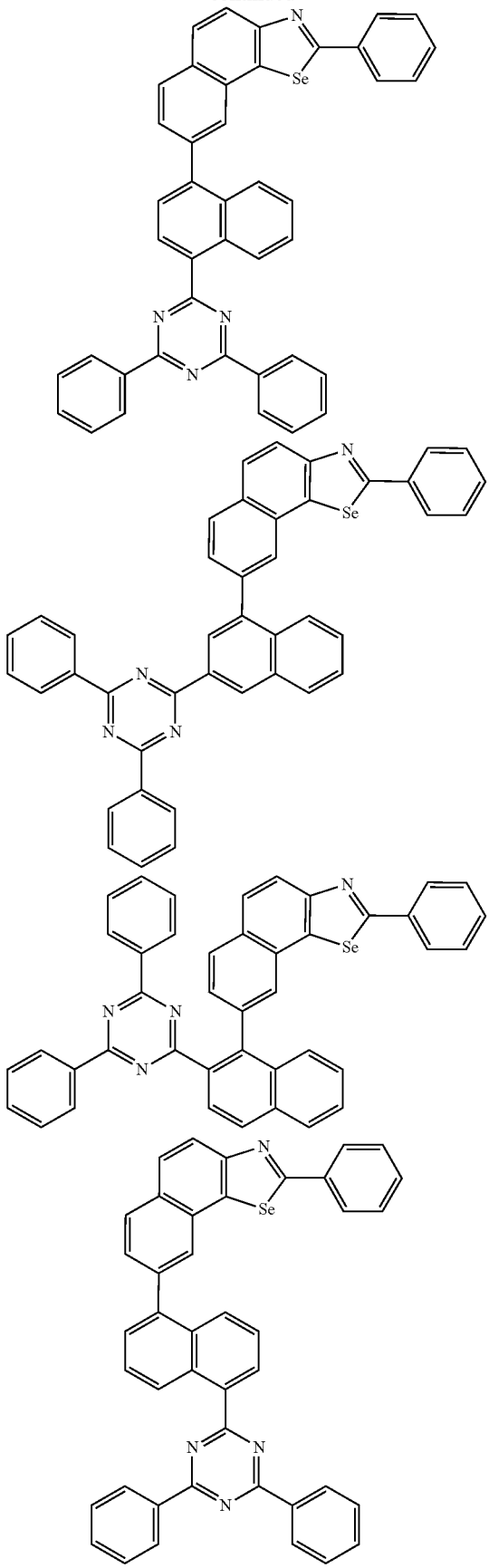
1046
-continued
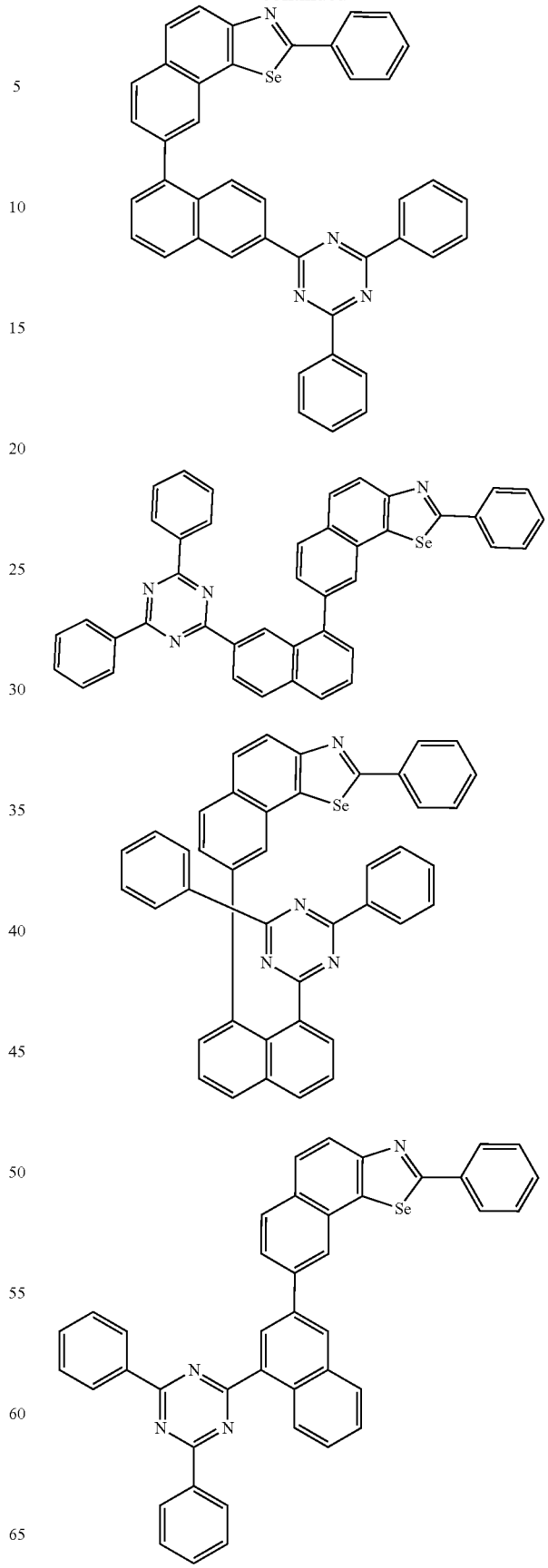

1047
-continued
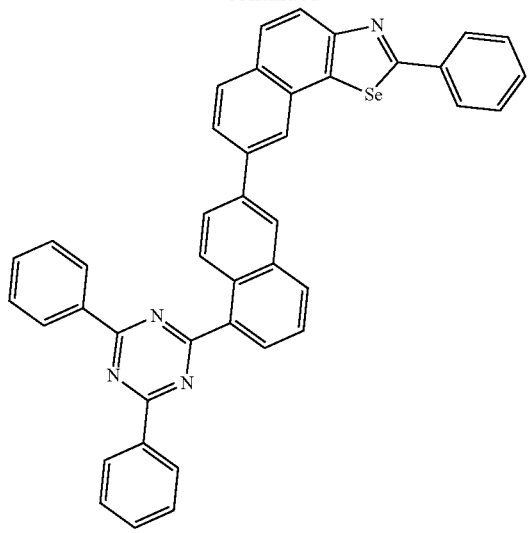
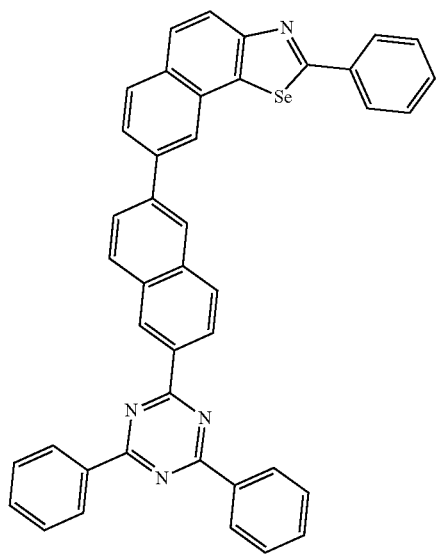
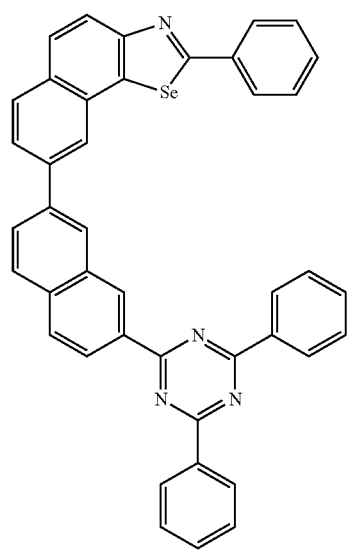
1048
-continued
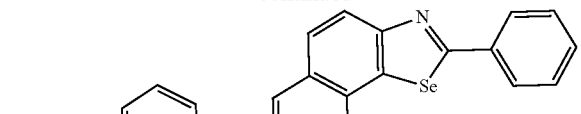
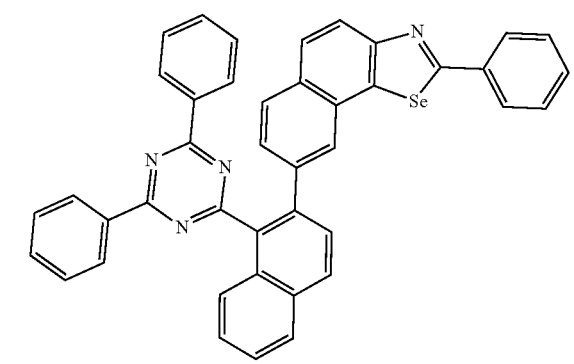
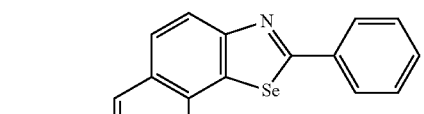
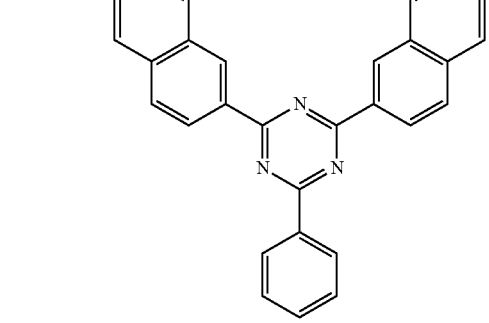

1049
-continued
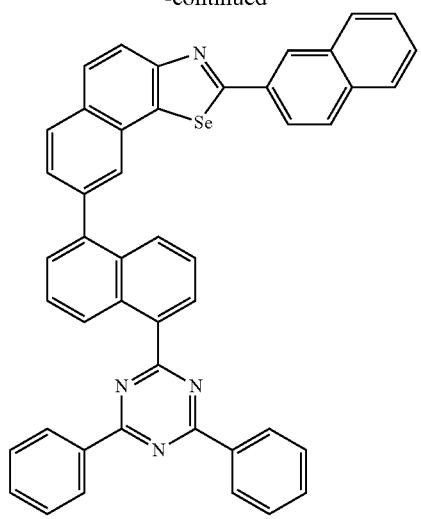
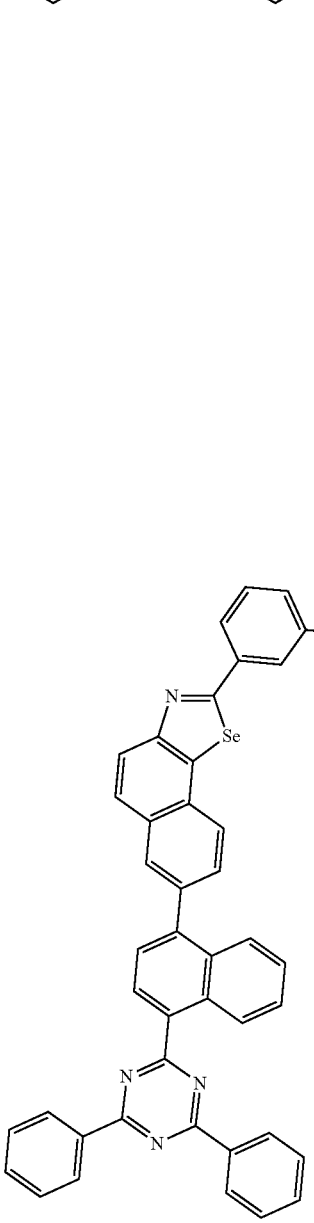
1050
-continued
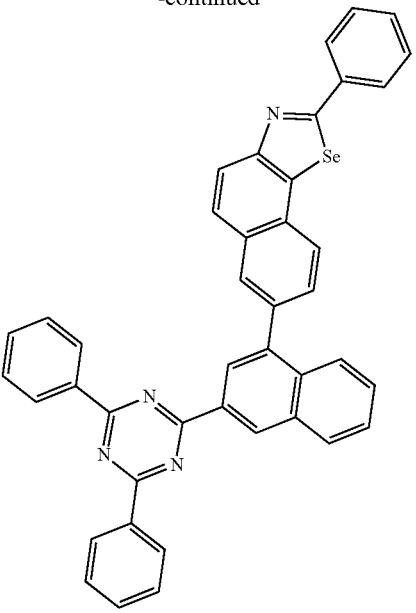
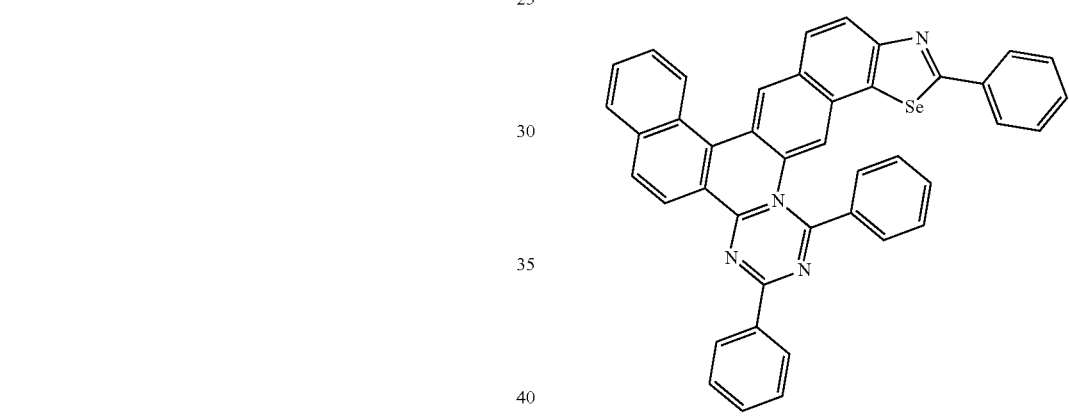
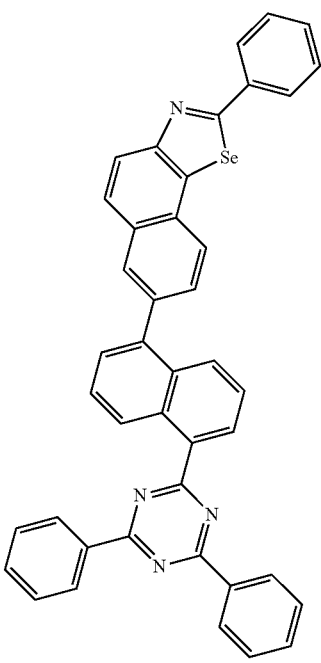

1051
-continued
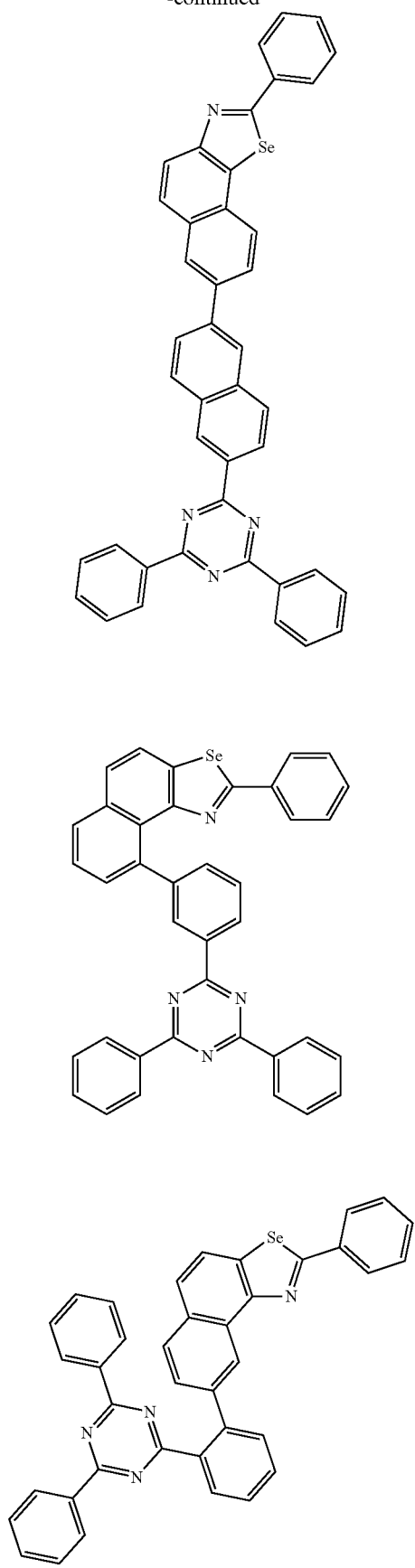
1052
-continued
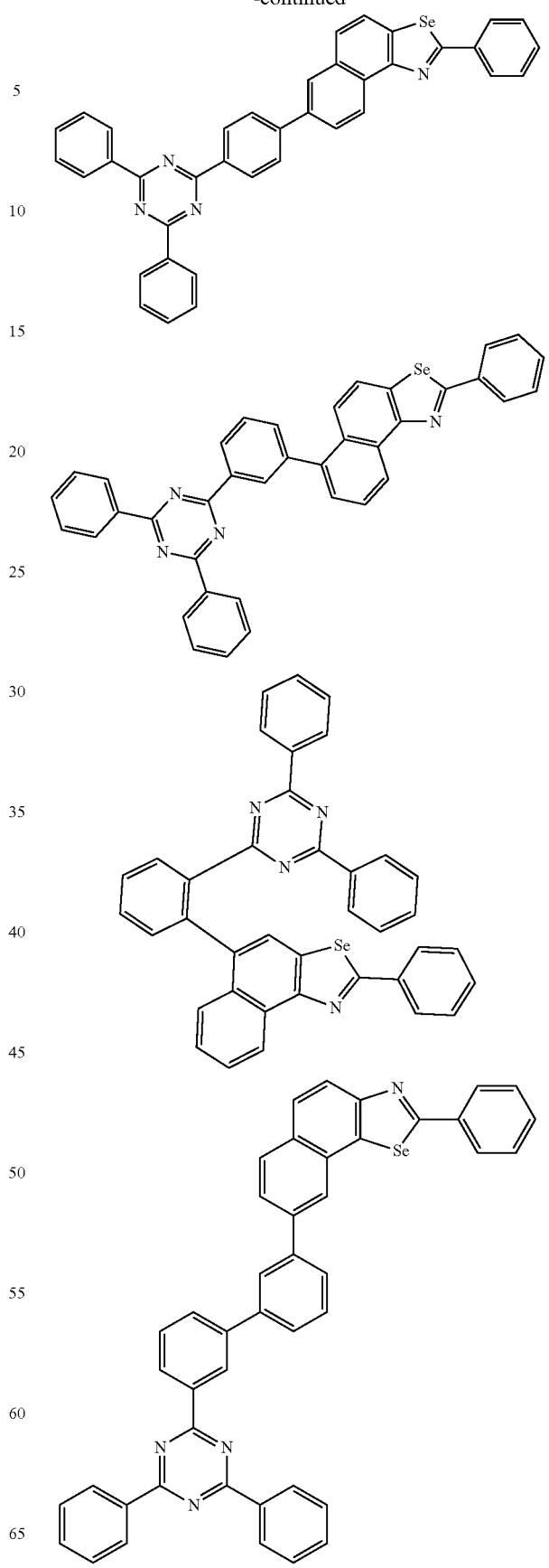

1053
-continued
1054
-continued
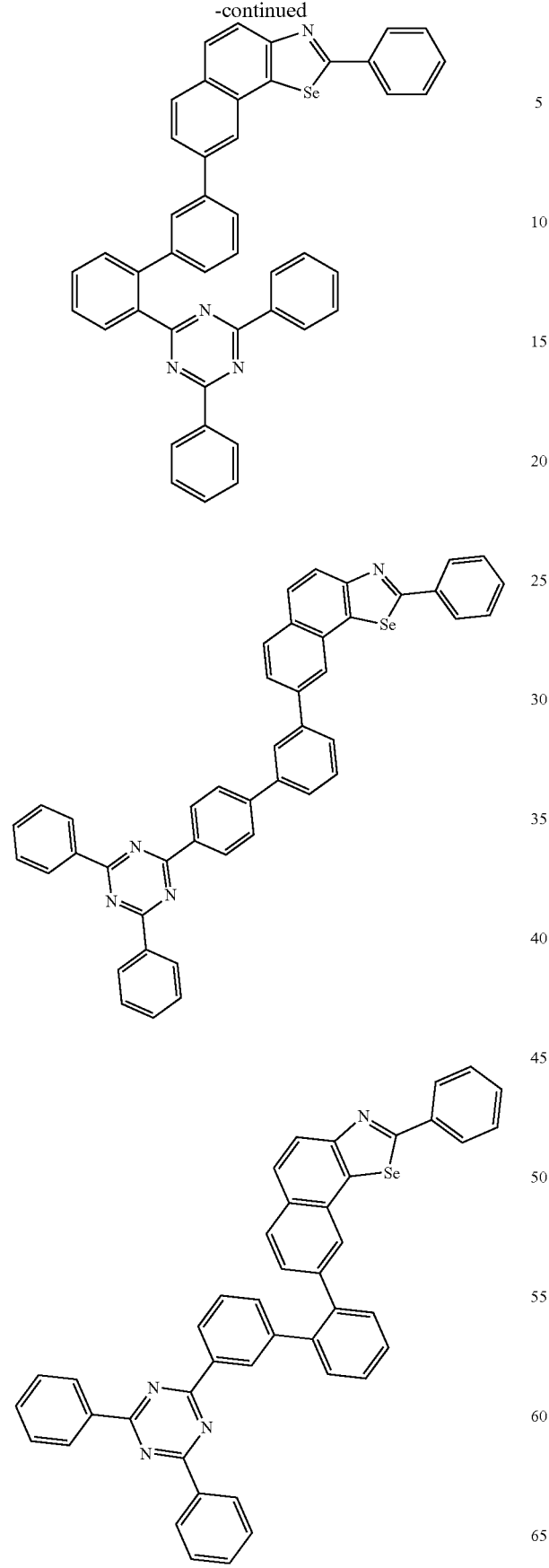

1055
-continued
1056
-continued
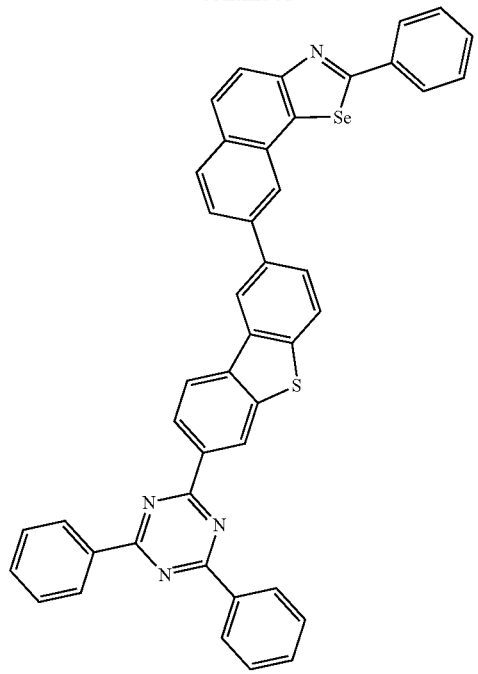
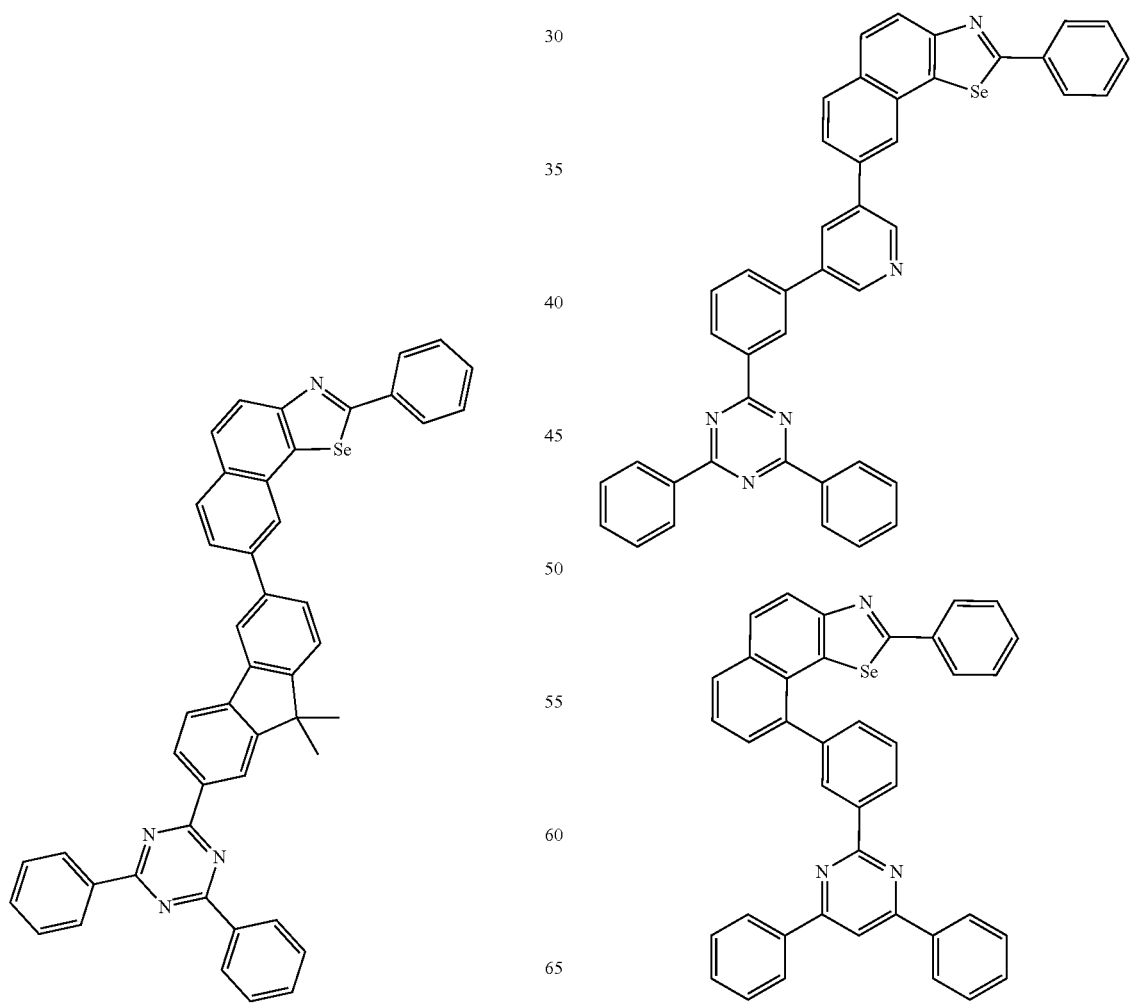

1057
-continued
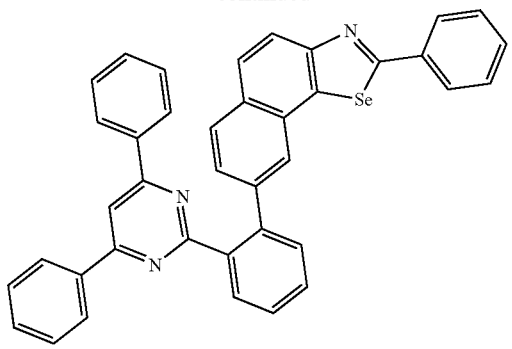
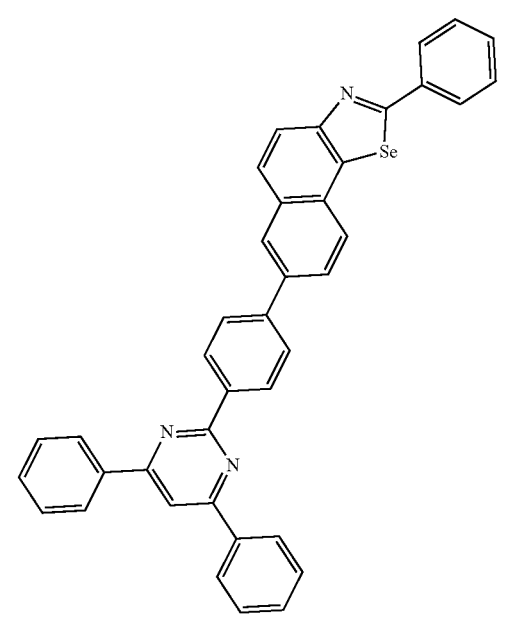
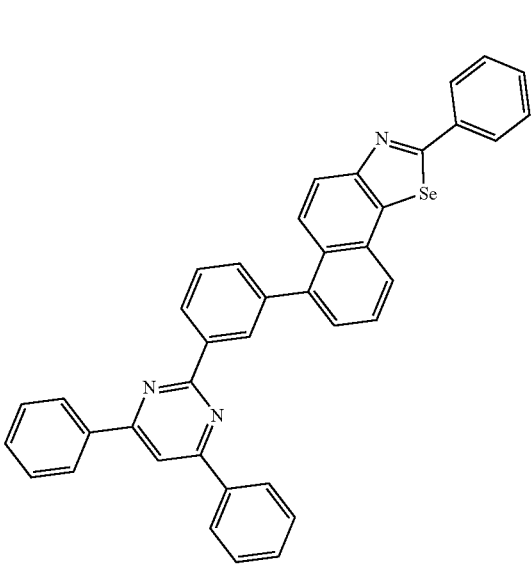
1058
-continued
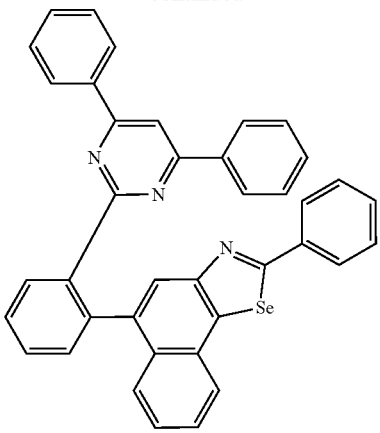
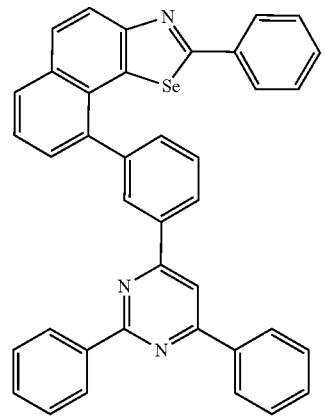
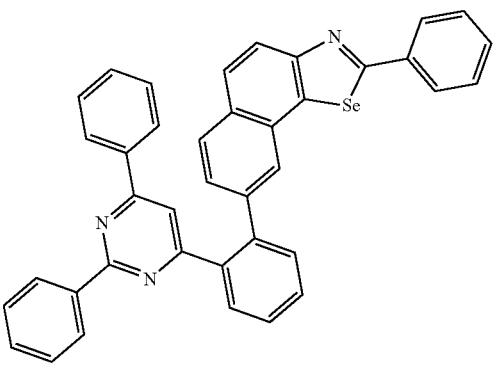

1059
-continued
1060
-continued
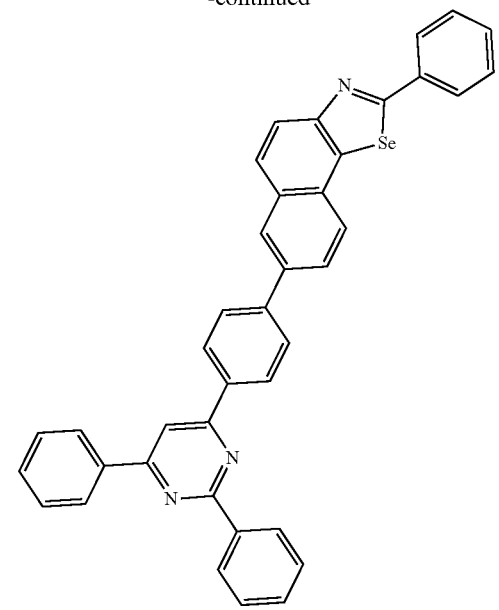
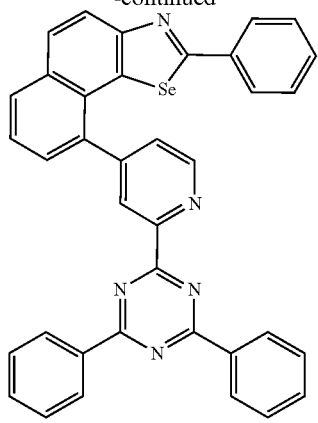
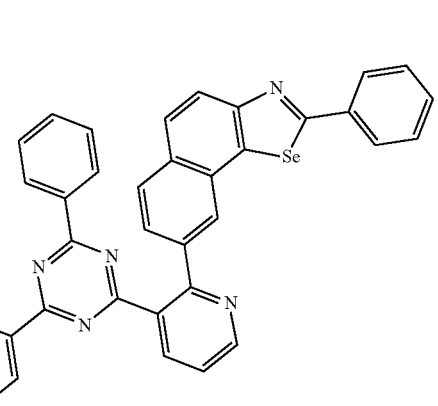
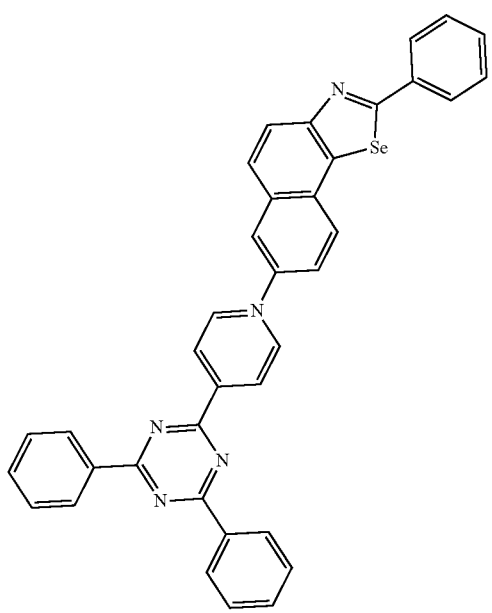

1061
-continued
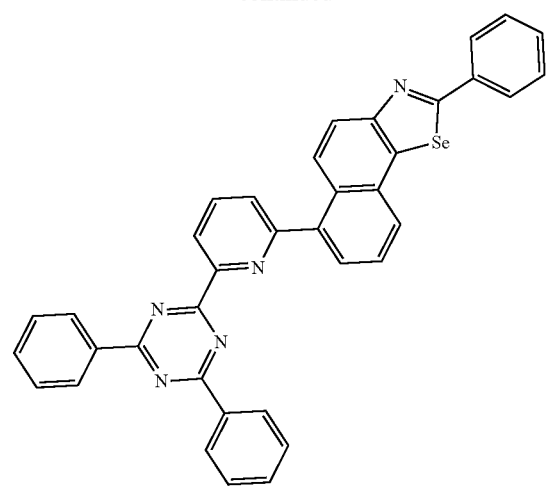
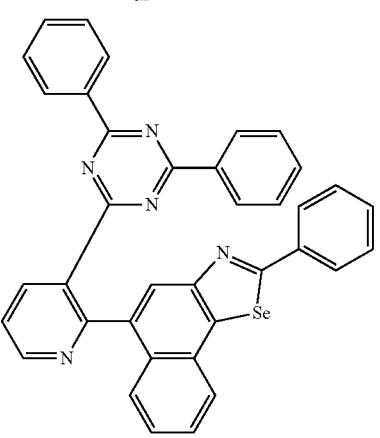
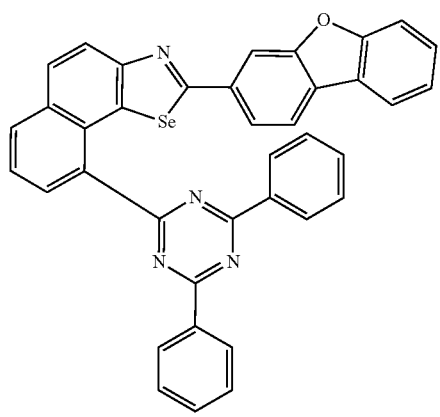
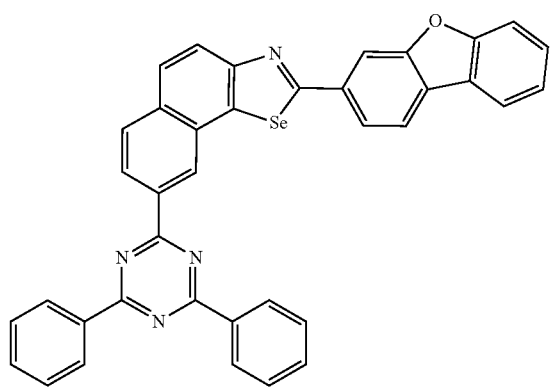
1062
-continued
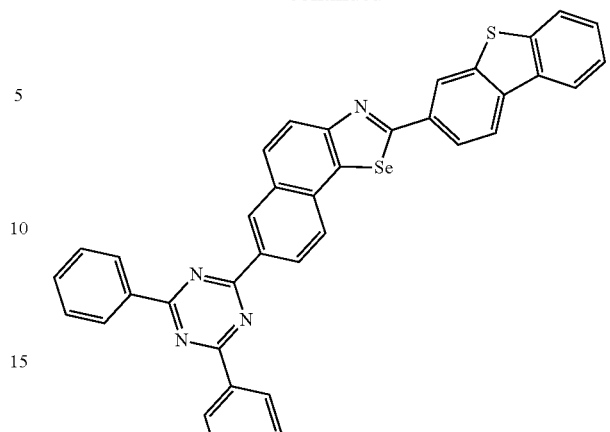
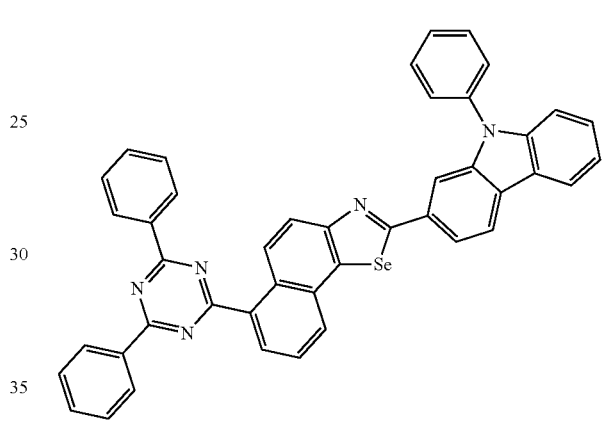
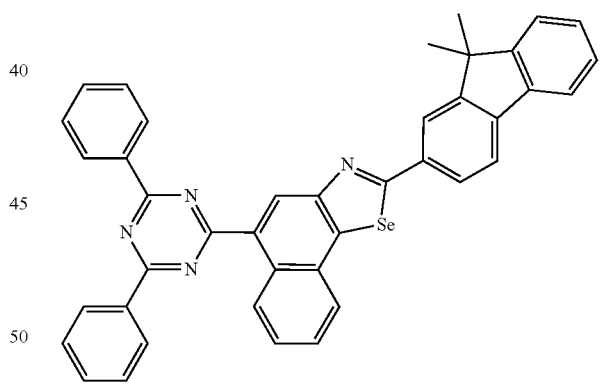
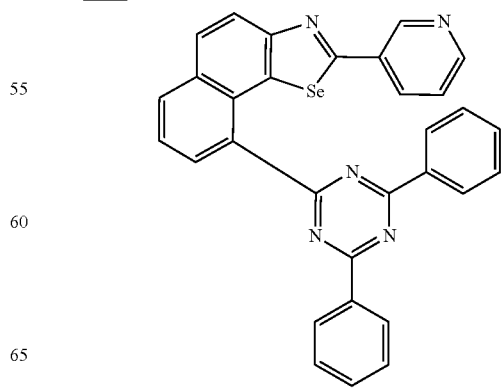

1063
-continued
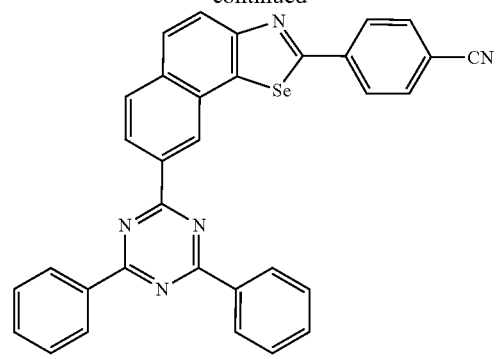
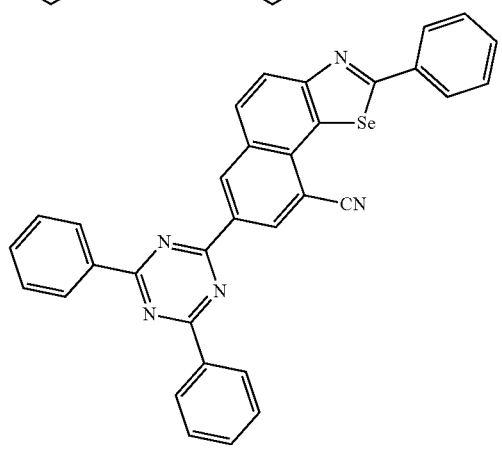
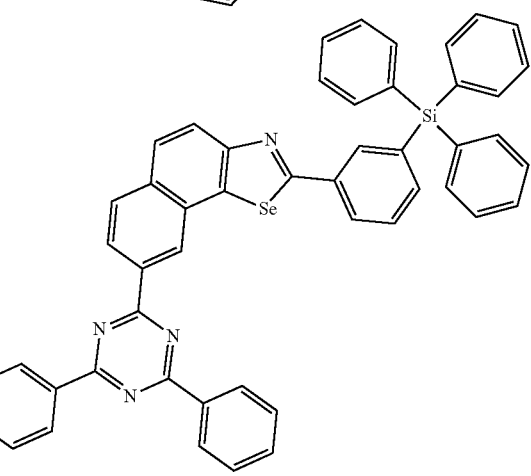
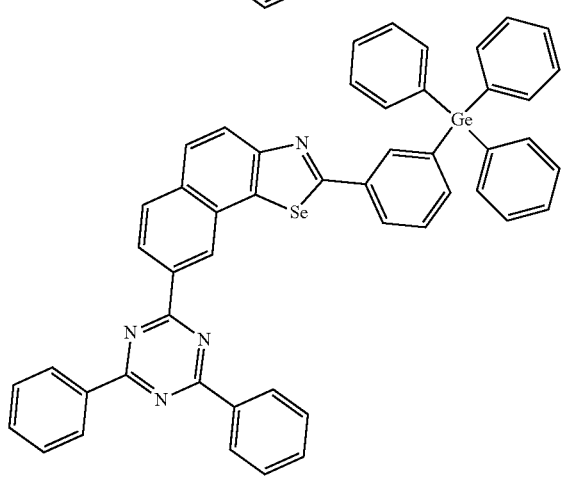
1064
-continued
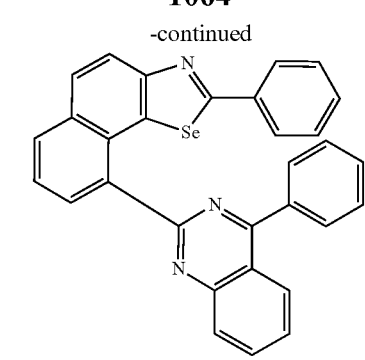
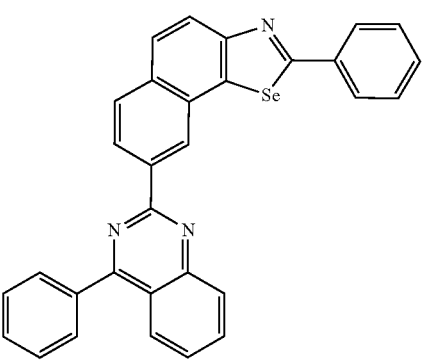
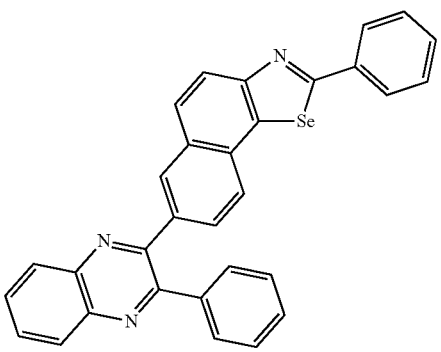
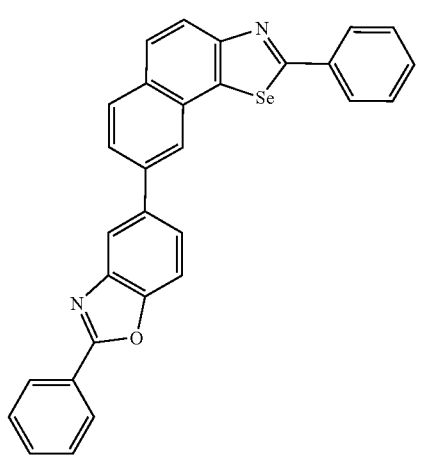

1065
-continued
1066
-continued
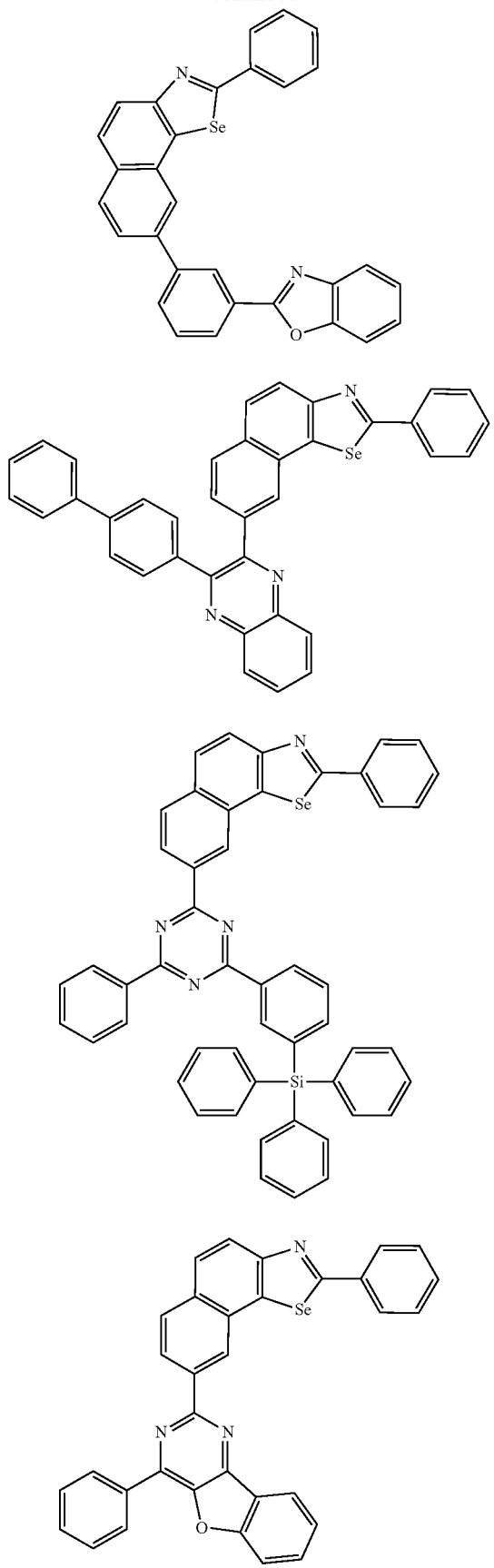
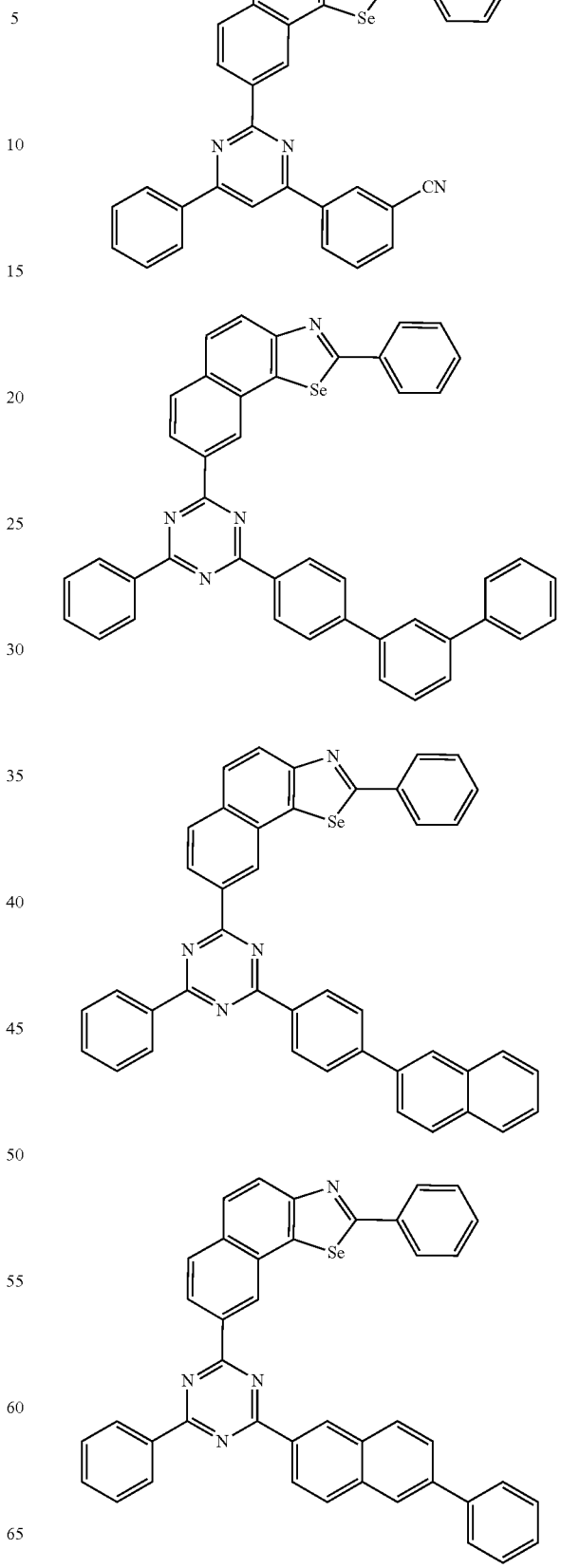

1067
-continued
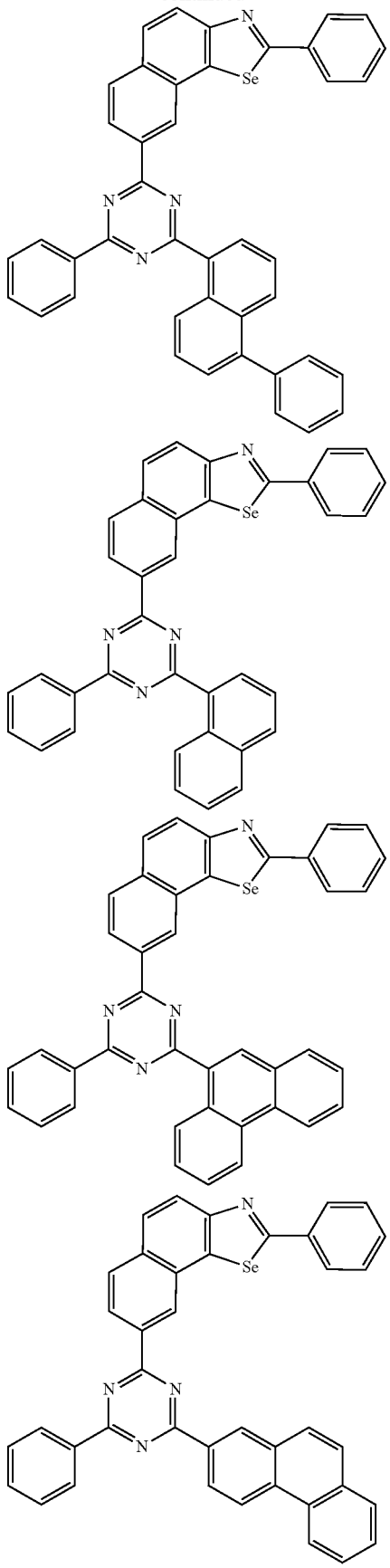
1068
-continued
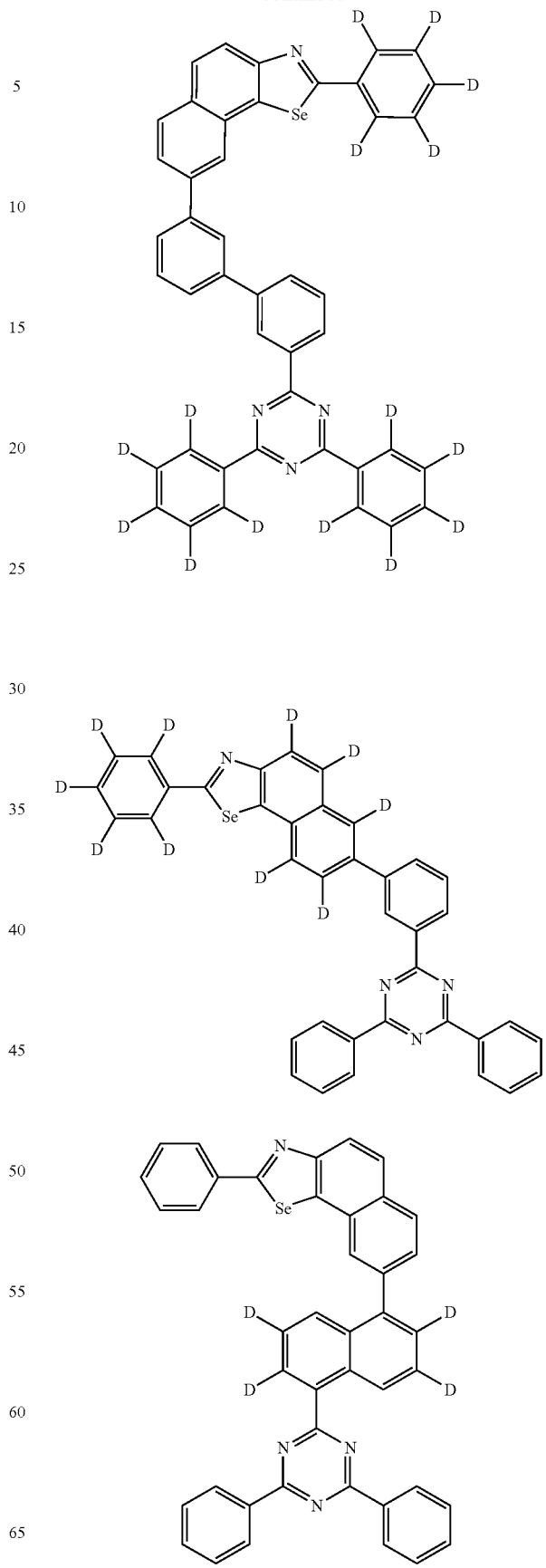

1069
-continued
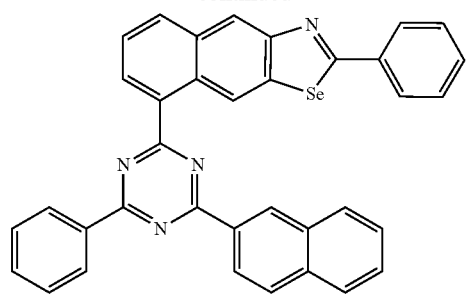
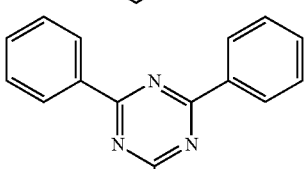
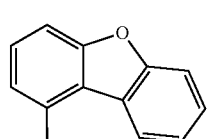
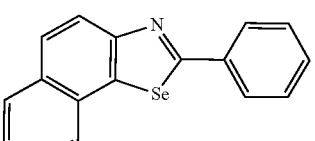
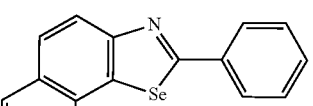
1070
-continued
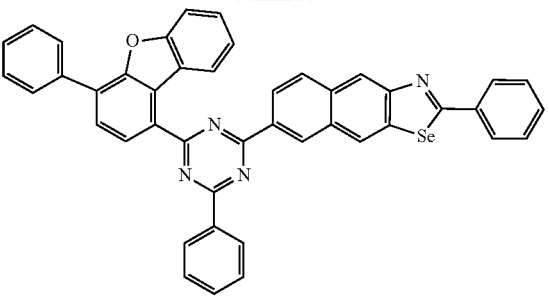
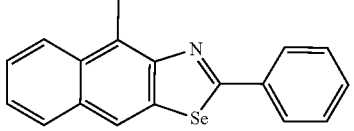
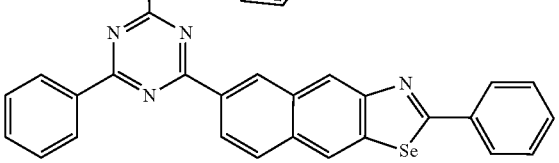
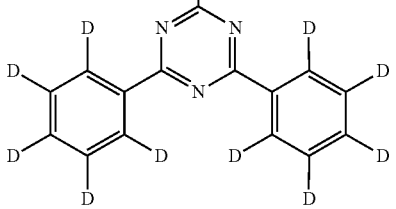
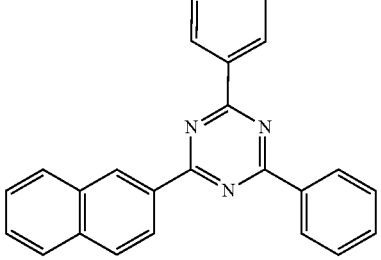

1071
-continued
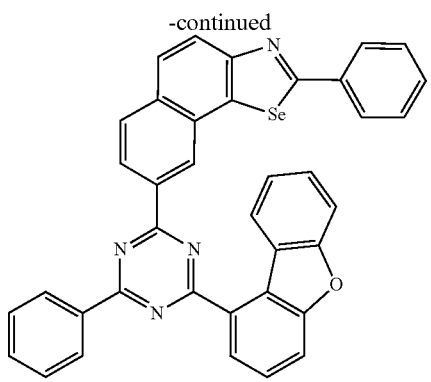
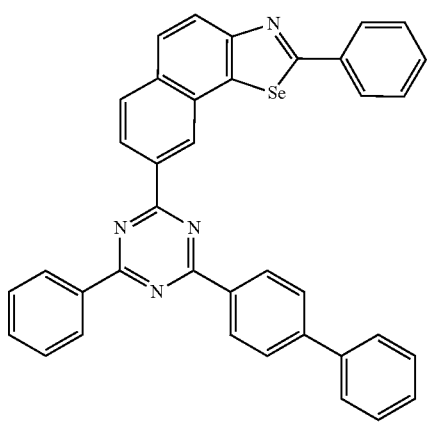
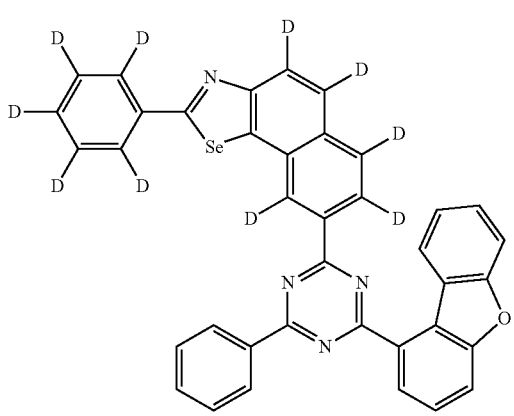
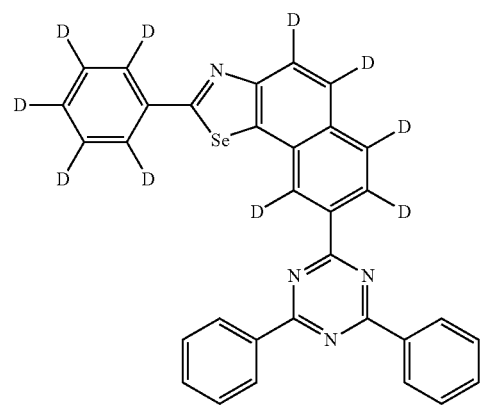
1072
-continued
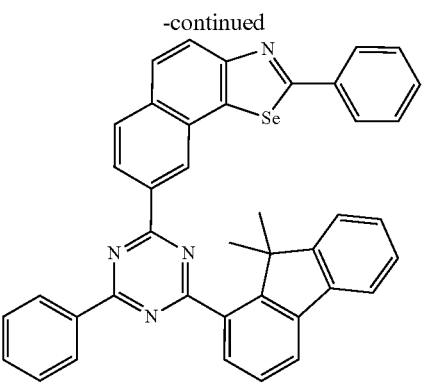
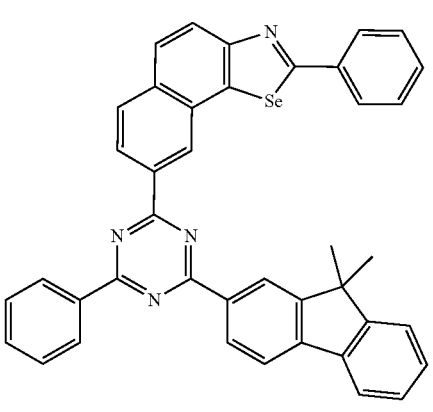
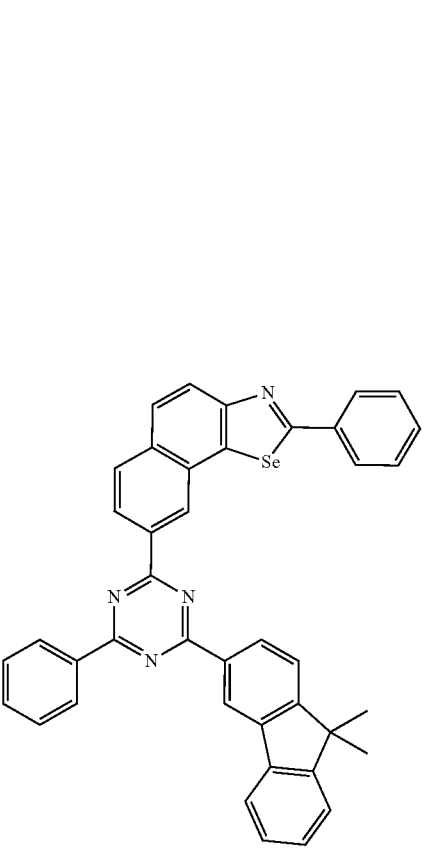

1073
-continued
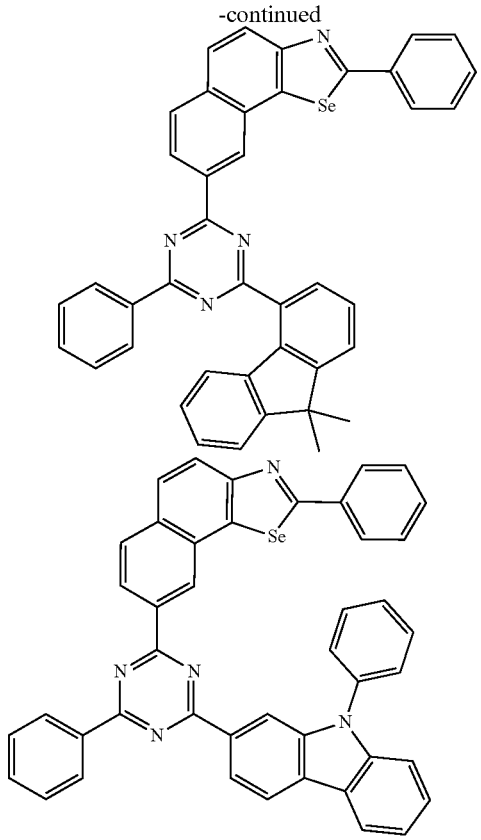
and
1074
-continued
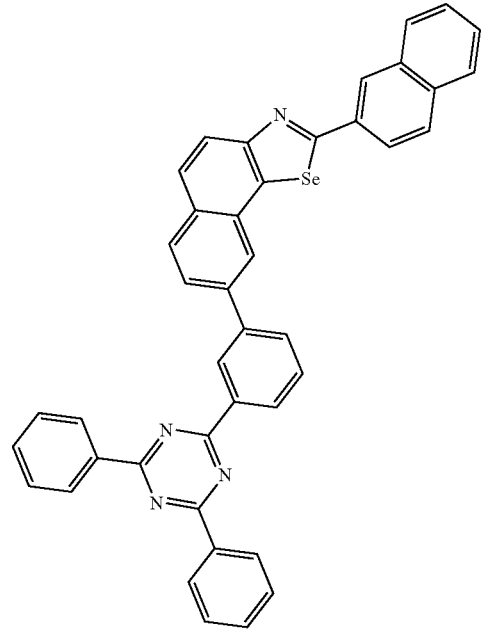
13. An organic electroluminescent device comprising the organic electroluminescent compound according to claim 1.
* * * * *